United States Patent
Lee et al.

(10) Patent No.: US 7,521,473 B2
(45) Date of Patent: Apr. 21, 2009

(54) INHIBITORS OF PROTEIN TYROSINE PHOSPHATASE 1B

(75) Inventors: Jinbo Lee, Acton, MA (US); Zhao-Kui Wan, Arlington, MA (US); Douglas P. Wilson, Ayer, MA (US); Bruce C. Follows, Littleton, MA (US); Steven J. Kirincich, Concord, MA (US); Michael J. Smith, Poland, OH (US); Jun-Jun Wu, Arlington, MA (US); Kenneth W. Foreman, Syosset, NY (US); David V. Erbe, Boston, MA (US); Yan-Ling Zhang, Lexington, MA (US); Weixin Xu, Acton, MA (US); Steve Y. Tam, Wellesley, MA (US)

(73) Assignee: Wyeth, Madison, NJ (US)

( * ) Notice: Subject to any disclaimer, the term of this patent is extended or adjusted under 35 U.S.C. 154(b) by 595 days.

(21) Appl. No.: 11/063,475

(22) Filed: Feb. 23, 2005

(65) Prior Publication Data

US 2005/0203087 A1 Sep. 15, 2005

Related U.S. Application Data

(60) Provisional application No. 60/547,049, filed on Feb. 25, 2004.

(51) Int. Cl.
*A61K 31/381* (2006.01)
*C07D 333/38* (2006.01)

(52) U.S. Cl. ............... 514/445; 514/252.13; 514/326; 514/444; 514/448; 544/379; 549/60; 549/64; 549/68; 549/71; 549/72; 546/213; 546/280.4

(58) Field of Classification Search ............... 546/213, 546/280.4; 549/64, 60, 68, 71, 72; 544/379; 514/252.13, 326, 444, 445, 448
See application file for complete search history.

(56) References Cited

U.S. PATENT DOCUMENTS

| | | | |
|---|---|---|---|
| 3,989,718 A | 11/1976 | Beck | |
| 4,119,727 A | 10/1978 | Beundia et al. | |
| 4,720,503 A | 1/1988 | Witzel et al. | |
| 4,847,386 A | 7/1989 | Barker et al. | |
| 4,877,440 A | 10/1989 | Christensen et al. | |
| 4,996,214 A | 2/1991 | Cousins et al. | |
| 5,021,449 A | 6/1991 | Fernandez et al. | |
| 5,389,620 A | 2/1995 | Ishikawa et al. | |
| 5,474,995 A | 12/1995 | Ducharme et al. | |
| 5,883,110 A | 3/1999 | Tang et al. | |
| 5,928,886 A | 7/1999 | Logan et al. | |
| 5,972,978 A | 10/1999 | Anderson et al. | |
| 6,103,708 A | 8/2000 | Dollings et al. | |
| 6,143,765 A | 11/2000 | Tang et al. | |
| 6,221,902 B1 | 4/2001 | Malamas et al. | |
| 6,225,329 B1 | 5/2001 | Richter et al. | |
| 6,248,764 B1 | 6/2001 | Dollings et al. | |
| 6,251,936 B1 | 6/2001 | Wrobel et al. | |
| 6,410,586 B1 | 6/2002 | Moller et al. | |
| 6,444,670 B2 | 9/2002 | Wrobel et al. | |
| 2002/0002187 A1 | 1/2002 | Wrobel et al. | |
| 2002/0002199 A1 | 1/2002 | Jeppeson et al. | |
| 2002/0035136 A1 | 3/2002 | Liu et al. | |
| 2002/0035272 A1 | 3/2002 | Dollings et al. | |
| 2002/0045605 A1 | 4/2002 | Kargman et al. | |
| 2002/0147196 A1 | 10/2002 | Quessy et al. | |
| 2002/0147197 A1 | 10/2002 | Newman et al. | |
| 2003/0013757 A1 | 1/2003 | Leser-Reiff et al. | |
| 2003/0018028 A1 | 1/2003 | Gwynne et al. | |
| 2003/0069267 A1 | 4/2003 | Moller et al. | |
| 2003/0073709 A1 | 4/2003 | Dollings et al. | |
| 2005/0203081 A1 | 9/2005 | Lee et al. | |

FOREIGN PATENT DOCUMENTS

| CA | 2027022 | 4/1991 |
|---|---|---|
| DE | 4014 006 A1 | 10/1990 |
| DE | 44 08005 | 2/1995 |
| DE | 44 24 788 | 6/1995 |
| DE | 44 43 641 A1 | 6/1996 |
| DE | 2719244 | 11/1997 |
| DE | 100/64823 | 6/2002 |
| EP | 0435 134 A2 | 7/1991 |
| EP | 0 590 885 | 4/1994 |
| EP | 701988 | 3/1996 |
| EP | 0747704 A2 | 12/1996 |
| EP | 903583 A2 | 3/1999 |
| EP | 1166792 | 1/2002 |
| JP | 09194476 | 7/1996 |

(Continued)

OTHER PUBLICATIONS

CAS Online, RN 41022-98-4, CA 82:72964 (1975).*

(Continued)

*Primary Examiner*—Bernard Dentz

(57) ABSTRACT

Protein tyrosine phosphatases (PTPases) such as PTP1B can play a role in regulating a wide variety of cellular responses such as insulin signaling. Substituted thiophene compounds such as, for example, 2-carboxyl, 3-carboxymethoxy, 5-aryl substituted thiophenes, can inhibit PTP1B and thereby induce greater insulin sensitivity. Accordingly, PTP1B inhibition can provide an alternate treatment for PTPase-mediated disorders such as diabetes.

59 Claims, No Drawings

FOREIGN PATENT DOCUMENTS

| | | |
|---|---|---|
| JP | 9-183960 | 7/1997 |
| JP | 10-287654 | 10/1998 |
| JP | 11-71368 | 3/1999 |
| JP | 2000-26421 | 1/2000 |
| WO | WO 91/04967 | 4/1991 |
| WO | WO 93/13664 | 7/1993 |
| WO | WO 95/00501 | 1/1995 |
| WO | 9602529 | 2/1996 |
| WO | WO 96 40113 | 12/1996 |
| WO | WO 97/03667 | 2/1997 |
| WO | WO 97 39748 | 10/1997 |
| WO | WO 97 40017 | 10/1997 |
| WO | WO 98 56376 | 12/1998 |
| WO | WO 99 46237 | 9/1999 |
| WO | WO 99/46244 | 9/1999 |
| WO | WO 99 46267 | 9/1999 |
| WO | WO 99/55668 | 11/1999 |
| WO | WO 00/04001 | 1/2000 |
| WO | WO 00/24722 | 5/2000 |
| WO | WO 00/27790 | 5/2000 |
| WO | WO 00/71118 | 11/2000 |
| WO | WO 00/76993 | 12/2000 |
| WO | WO 01 19831 | 3/2001 |
| WO | WO 02/04434 A1 | 1/2002 |
| WO | WO 02 04459 | 1/2002 |
| WO | WO 02/06268 | 1/2002 |
| WO | WO/02/18321 A2 | 3/2002 |
| WO | WO 03 006454 | 1/2003 |
| WO | WO 03 032916 | 4/2003 |
| WO | WO 03 041729 | 5/2003 |

OTHER PUBLICATIONS

CAS Online, RN 41022-07-5, CA78:136052 (1973).*
Banks et al. "The Synthesis . . . 4-ones." J. Chem Research (S) 1985, 386-387.
Banks et al. "Preparations and some Reactions of Substituted Thieno [3,4-b] furans." J. Chem Soc. Perkins, 1986 (12), 2223-2232.
Barker et al. "Nitration of methyl-3-hydroxy . . . of the products." J. Chem Research (S) 2001, 401-402.
Beck, James. "[1]Benzothieno[3,2-b] furan Derivatives." Journal of Heterocyclic Chemistry, 1975 (XII) 1037-1038.
Corral et al. "Reactions with . . . Derivatives." Communications, Oct. 1984, 847-850.
Svoboda et al. "Application of Magnesium Alkoxides to Syntheses of Benzoheterocyclic Compounds." Collection of Czechoslovak Chemical Communications, 1993 (58:3), 592-599.
Svoboda et al. "Synthesis of [1]Benzothieno[3,2-b]Furan-A New fused Benzoheterocyclic System." Collection of Czechoslovak Chemical Communications, 1993 (58:12), 2983-2986.
Database CAS on STN (Columbus, OH, USA), No. 39:8911, "Condensed aromatic nuclei. XI. Chemistry of thianaphthene and dibenzothiophene." Buu-Hoi et al. Ber. (1943) 76B, see RN 856353-78-1.
Database CAS on STN (Columbus, OH, USA), No. 68:10487:2 "Preparation of benzo[b]thiophene-3-propionic acid by a ring closure reaction." Sauter et al. Monatschefte fuer chemie (1968) 99(22) 715-20, see RN 18168-88-2.
Database CAS on STN (Columbus, OH, USA), No. 69:96370, "5,6-dimethoxy and 4,5,6-trimethoxybenzo[b]thien-3-ylaclamines." Sauter et al. Monantshefte 99(4)1515-20 (1968), see RN 19711-66-1.
Database CAS on STN (Columbus, OH, USA), No. 70:3701, "3-aminoalkyl-5-methlbenzo[b]thiophenes." Sauter et al. Monatschefte (1968) 99(5) 2095-9, see RN 20841-37-6.
Database CAS on STN (Columbus, OH, USA), No. 70:96663, "Condesed sulfur heterocycles . . . " Cagniant et al. Bull. De la Soc. Chim. de France (1969) (2) 596-600, see RN 221314-67-6, 22315-07-0, 22315-08-1, 22316-09-2, 22136-10-5.
Database CAS on STN (Columbus, OH, USA), No. 72:3410, "Synthesis on sulfer heterocyclics X . . . " Ind. J. Chem. (1969) 7(10) 948-51, see RN 24333-96-8.
Database CAS on STN (Columbus, OH, USA), No. 72:100559, "Dithiaaromatic system I . . . " Young et al. J. Org. Chem. (1970) 35(3) 816-21, see RN 22316-07-0.
Database CAS on STN (Columbus, OH, USA), No. 80:82746, "Condensed sulfer heterocycles . . . " Lepage et al. Bull. De la Coc. Chim. De France (1973) 11, pt. 2, 3107-9, see RN 51942-57-5, 51942-75-7, 51942-77-9.
Database CAS on STN (Columbus, OH, USA), No. 122:81383, "Morpholinylakylamino benzo[b]thiophencarboxamides . . . " Boschelli et al. US 5,350748, see RN 160383-16-4, 160383-22-2, 160383-23-3.
Database CAS on STN (Columbus, OH, USA), No. 124:56141, "Inhibition of E-selection, ICAM-1 and . . . " Boschelli et al. J. Med chem.. (1995) 38(22) 4597-614, see RN 160383-22-2, 160383-23-3.
Database CAS on STN (Columbus, OH, USA), No. 139:53023, "Preparation of heterocyclcyl amino . . . " Weaver et al. US 200311441, see RN 546114-94-7.
Database CAS on STN (Columbus, OH, USA), No. 84:59261, "Benzothieno[3,2-b]furan derivatives." Beck J. Het chem.. (1975) 1295, 1037-8, see RN 58108-07-9, 58108-08-0, 58108-09-1.
Database CAS on STN (Columbus, OH, USA), No. 124:117357, "Preparation of benzothieno . . . " Boschelli et al. WO 9524408 (1995), see RN 58108-08-0, 172832-20-1, 172832-22-3.
Database CAS on STN (Columbus, OH, USA), No. 119:72458, "Application of magnesium . . . " Svoboda et al. Col. Cze. Chem. Comm. (1993) 58(3), 592-9,see RN 14761-41-5.
International Search Report. PCT/US05/05722. Feb. 14, 2006.
Database CA on STN (Columbus, OH, USA), Accession No. 127:190640, "Preparation of thiophenealkanoic acids as pharmaceuticals for treatment of autoimmune diseases" Tomizawa et al., JP, A2, 09194476, 19970729, see RN 17754, e.g. 1998.
Database CA on STN (Columbus, OH, USA), Accession No. 140:128214, *Bioorganic & Medicinal Chemistry*, vol. 11, No. 22, pp. 4729-4742, (2003), see RN 17754, e.g. 1998.
Noguchi, T., et. al., *Bioorganic & Medicinal Chemistry*, vol. 11, No. 22, pp. 4729-4742, (2003).
Database CA on STN (Columbus, OH, USA), Accession No. 125:33493, WO 9602529 (1996), see RN 17754, e.g. 1998.
Database CAPLUS on STN (Columbus, OH, USA), Accession No. 1978:62047, Document No. 88:62047, "11-Deoxyprostaglandin F2 derivatives", Buendia et al., Ger. Offen. DE 2719244 19971117, see RN 65449-53-8, 65449-62-9, 65449-44-7, 65449-45-8, 65449-47-0, 65449-54-9, 65449-63-0, 65449-67-4, 63114-87-4, 63114-87-4 (1978).
Database CAS on STN (Columbus, OH, USA), No. 122:81383, "Morpholinylakylamino benzo[b]thiophencarboxamides . . . " Boschelli et al. US 5,350748, see RN 160383-16-4, 160383-22-2, 160383-23-3, Sep. 1994.
Database CAS on STN (Columbus, OH, USA), No. 139:53023, "Preparation of heterocyclcyl amino . . . " Weaver et al. US 200311441, see RN 546114-94-7, Jun. 2003.

* cited by examiner

INHIBITORS OF PROTEIN TYROSINE PHOSPHATASE 1B

CROSS REFERENCE TO RELATED APPLICATIONS

This application claims the benefit of U.S. Provisional Application No.: 60/547,049, filed on Feb. 25, 2004, which is incorporated herein by reference in its entirety.

TECHNICAL FIELD

This invention relates to inhibitors of protein tyrosine phosphatase 1B (PTP1B) and other protein tyrosine phosphatases (PTPases).

BACKGROUND

Protein tyrosine phosphatases (PTPases) are a large family of diverse molecules that can play an important role in modulating a wide variety of cellular responses. The PTPase family is divided into three major subclasses, classical PTPases, low molecular weight PTPases, and dual specificity PTPases. The classical PTPases can be further categorized into two classes, intracellular PTPases (e.g., PTP1B, TC-PTP, rat-brain PTPase, STEP, PTPMEG1, PTPH1, PTPD1, PTPD2, FAP-1/BAS, PTP1C/SH-PTP1/SHP-1 and PTP1D/Syp/SH-PTP2/SHP2) and receptor-type PTPases (e.g., CD45, LAR, PTPα, PTPβ, PTPδ, PTPε, PTPγ, SAP-1 and DEP-1). Dual specificity phosphatases have the ability to remove the phosphate group from both serine/threonine and tyrosine residues. Members of the PTPase family have been implicated as important modulators or regulators of a wide variety of cellular processes including insulin signaling, leptin signaling, T-cell activation and T-cell mediated signaling cascade, the growth of fibroblasts, platelet aggregation, and regulation of osteoblast proliferation.

SUMMARY

In general, compounds of formula (I); including pharmaceutically acceptable salts or pro-drugs of those compounds, inhibit PTP1B. Pharmaceutical compositions can include one or more compounds of formula (I) or pharmaceutically acceptable salts, or prodrugs of those compounds and a pharmaceutically acceptable carrier or excipient. In addition, PTPase-mediated disorders can be treated with and PTPases can be inhibited with compounds of formula (I) or pharmaceutically acceptable salts, or pro-drugs of those compounds.

In one aspect, this invention features compounds of formula (I):

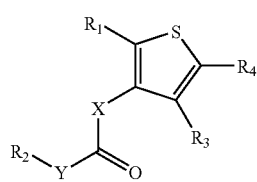

(I)

$R_1$ is $R_5$, $OR_5$, $C(O)OR_5$, $C(O)R_5$, or $C(O)NR_5R_6$.

$R_2$ is $R_5$.

X is —O—$C_{1-3}$alkylene-, —$NR_8$—$C_{1-3}$alkylene-, —S—$C_{1-3}$alkylene-, —SO—$C_{1-3}$alkylene-, —$SO_2$—$C_{1-3}$alkylene-, —$C_{1-4}$alkylene-, —$C_{2-4}$alkenylene-, or —$C_{2-4}$alkynylene-. Any of the alkylene, alkenylene or alkynylene groups can be optionally substituted with one or more halogen, oxo, imido, CN, $OCF_3$, OH, $NH_2$, $NO_2$, or Q.

Y is absent, —O—, or —$NR_6$—.

$R_3$ is H, halogen, CN, $CF_3$, $OCF_3$, alkyl, $C_{3-4}$cycloalkyl, $C_{1-3}$alkoxy, or aryl.

$R_4$ is A-B-E-D, where A is absent or arylene, heteroarylene, $C_{1-6}$alkylene, $C_{2-6}$ alkenyldiyl, or $C_{2-6}$alkynyl. Each A can be optionally substituted with one or more of $C_{1-6}$alkyl, $C_{2-6}$alkenyl, $C_{2-6}$alkynyl, halogen, CN, $OCF_3$, OH, $NH_2$, CHO, $NO_2$, or Q. Any of the alkyl, alkenyl or alkynyl groups is optionally substituted with one or more halogen, oxo, CN, $OCF_3$, OH, $NH_2$, $NO_2$, $N_3$, or Q. Each A can be optionally terminated with one or more arylene, alkylene, or alkenylene.

B is absent or —$NR_5$—, —$NR_7$—, —$N(R_5)CH_2$—, —$N(R_7)CH_2$—, —$N(R_9)$—, —$N(R_9)C(O)$—, —$N(R_9)C(O)C(R_{11})(R_{12})$—, —$N(R_9)C(O)C(O)$—, —$N(R_9)C(O)N(R_{10})$—, —$N(R_9)SO_2$—, —$N(R_9)SO_2C(R_{10})(R_{11})$—, —$N(R_9)(R_{10})C(R_{11})(R_{12})$—, —$N(R_9)C(R_{11})(R_{12})C(R_{13})(R_{14})$—, —O—, —O—$C(R_{11})(R_{12})$, —O—$C(R_{11})(R_{12})C(R_{13})(R_{14})$—, —$C(R_{11})(R_{12})$—O—, —$C(R_{11})(R_{12})$—O—$C(R_{13})(R_{14})$—, —$C(R_{11})(R_{12})N(R_9)$—, —$C(R_{11})(R_{12})N(R_9)C(R_{13})(R_{14})$—, —$C(R_{11})(R_{12})S$—, —$C(R_{11})(R_{12})SC(R_{13})(R_{14})$—, or —$C(R_{11})(R_{12})SO_2C(R_{13})(R_{14})$—.

E is absent or $C_{3-12}$cycloalkylene, 3- to 12-membered heterocycdiyl, arylene, $C_{1-12}$alkylene, $C_{2-12}$alkenylene, or $C_{2-12}$alkynylene, where each E is optionally substituted with one or more $C_{1-3}$ alkyl, $C_{1-3}$alkoxy, halogen, CN, OH, $NH_2$, or $NO_2$.

D is one or more H, halogen, OH, $NH_2$, CHO, CN, $NO_2$, $CF_3$, or Q.

When A, B, and E are absent, $R_1$ is C(O)OH or $C(O)OCH_3$, $R_2$ is H, and $R_3$ is H or chlorine, D is not H or chlorine; and when A, B, and E are absent, $R_1$ is C(O)OH or $C(O)OCH_3$, $R_2$ is H, and $R_3$ is H or bromine, D is not H or bromine.

Each Q, independently, is —$R_5$, —$R_7$, —$OR_5$, —$OR_7$, —$NR_5R_6$, —$NR_5R_7$, —$N^+R_5R_6R_8$, $S(O)_nR_5$, or —$S(O)_nR_7$, and n is 0, 1, or 2.

Each $R_5$, $R_6$, and $R_8$, independently, is H, $C_{1-12}$alkyl, $C_{2-12}$alkenyl, $C_{2-12}$alkynyl, $C_{3-12}$cycloalkyl, $C_{1-12}$alkoxy $C_{1-12}$ alkyl, cycloalkyl$C_{1-6}$alkyl, 3- to 8-membered heterocycyl, heterocycyl$C_{1-6}$alkyl, aryl, aryl$C_{1-6}$ alkyl, aryl$C_{2-6}$ alkenyl, or aryl$C_{2-6}$ alkynyl. Each $R_5$, $R_6$, and $R_8$ can be optionally substituted with one or more $R_9$, —$OR_9$, —$OC(O)OR_9$, —$C(O)R_9$, —$C(O)OR_9$, —$C(O)NR_9R_{10}$, —$SR_9$, —$S(O)R_9$, —$S(O)_2$ $R_9$, —$NR_9R_{10}$, —$N^+R_9R_{10}R_{11}$, —$NR_9C(O)R_{10}$, —$NC(O)NR_9R_{10}$, —$NR_9S(O)_2R_{10}$, oxo, halogen, CN, $OCF_3$, $CF_3$, OH, or $NO_2$.

$R_7$ is —$C(O)R_5$, —$C(O)OR_5$, —$C(O)NR_5R_6$, —$S(O)_2R_5$, —$S(O)R_5$, or —$S(O)_2NR_5R_6$.

Each $R_9$, $R_{10}$, $R_{11}$, $R_{12}$, $R_{13}$ and $R_{14}$ is, independently, H, $C_{1-12}$alkyl, $C_{2-12}$alkenyl, $C_{2-12}$alkynyl, $C_{3-12}$cycloalkyl, aryl, or aryl$C_{1-12}$alkyl. Any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

The compound of formula (I) can be a salt.

In another aspect, this invention features compounds of formula (I),

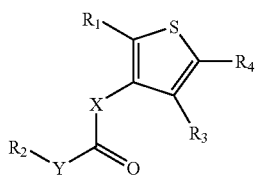

(I)

wherein R$_1$ is R$_5$, OR$_5$, C(O)OR$_5$, C(O)R$_5$, or C(O)NR$_5$R$_6$;
R$_2$ is R$_5$;
X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, —C$_{2-4}$alkynylene-; wherein any of the alkylene, alkenylene or alkynylene groups is optionally substituted with one or more halogen, oxo, imido, CN, OCF$_3$, OH, NH$_2$, NO$_2$, or Q;
Y is absent, —O—, or —NR$_6$—;
R$_3$ is F, Br, I, CN, CF$_3$, OCF$_3$, C$_{1-3}$alkyl, C$_{3-4}$cycloalkyl, C$_{1-3}$alkoxy, or aryl;
R$_4$ is A-B-E-D, where A is absent or arylene, heteroarylene, C$_{1-6}$alkylene, C$_{2-6}$ alkenyldiyl, or C$_{2-6}$alkynyl, each A being optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q; where any of the alkyl, alkenyl or alkynyl is optionally substituted with one or more halogen, oxo, CN, OCF$_3$, OH, NH$_2$, NO$_2$, N$_3$, or Q; and each A being optionally terminated with one or more arylene, alkylene, or alkenylene;
B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—;
E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$;
D is one or more F, Cl, I, OH, NH$_2$, CHO, CN, NO$_2$, CF$_3$, or Q;
each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, where n is 0, 1, or 2;
each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxyC$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$; and
R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

The compound of formula (I) can be a salt.

In a further aspect, this invention features compounds of formula (I),

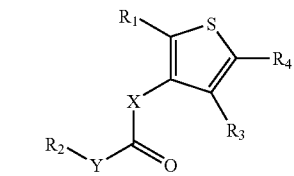

(I)

wherein R$_1$ is R$_5$, OR$_5$, C(O)OR$_5$, C(O)R$_5$, or C(O)NR$_5$R$_6$;
R$_2$ is R$_5$;
X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, —C$_{2-4}$alkynylene-; wherein any of the alkylene, alkenylene or alkynylene groups is optionally substituted with one or more halogen, oxo, imido, CN, OCF$_3$, OH, NH$_2$, NO$_2$, or Q;
Y is absent, —O—, or —NR$_6$—;
R$_3$ is F, Cl, I, CN, CF$_3$, OCF$_3$, C$_{1-3}$alkyl, C$_{3-4}$cycloalkyl, C$_{1-3}$alkoxy, or aryl;
R$_4$ is A-B-E-D, where A is absent or arylene, heteroarylene, C$_{1-6}$alkylene, C$_{2-6}$ alkenyldiyl, or C$_{2-6}$alkynyl, each A being optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q; where any of the alkyl, alkenyl or alkynyl is optionally substituted with one or more halogen, oxo, CN, OCF$_3$, OH, NH$_2$, NO$_2$, N$_3$, or Q; and each A being optionally terminated with one or more arylene, alkylene, or alkenylene;
B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_4$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—;
E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$;
D is one or more F, Br, I, OH, NH$_2$, CHO, CN, NO$_2$, CF$_3$, or Q;
each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, where n is 0, 1, or 2;
each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxyC$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$;

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

The compound of formula (I) can be a salt.

In one aspect, this invention features compounds of formula (I),

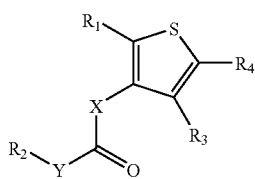

(I)

wherein R$_1$ is R$_5$, OR$_5$, C(O)OR$_5$, C(O)R$_5$, or C(O)NR$_5$R$_6$;
R$_2$ is R$_5$;

X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, —C$_{2-4}$alkynylene-; wherein any of the alkylene, alkenylene or alkynylene groups is optionally substituted with one or more halogen, oxo, imido, CN, OCF$_3$, OH, NH$_2$, NO$_2$, or Q;

Y is absent, —O—, or —N$_6$—;

R$_3$ is H, F, Cl, Br, I, CN, CF$_3$, OCF$_3$, C$_{1-3}$alkyl, C$_{3-4}$cycloalkyl, C$_{1-3}$alkoxy, or aryl;

R$_4$ is A-B-E-D, where A is absent or arylene, heteroarylene, C$_{1-6}$alkylene, C$_{2-6}$ alkenyldiyl, or C$_{2-6}$alkynyl, each A being optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q; where any of the alkyl, alkenyl or alkynyl is optionally substituted with one or more halogen, oxo, CN, OCF$_3$, OH, NH$_2$, NO$_2$, N$_3$, or Q; and each A being optionally terminated with one or more arylene, alkylene, or alkenylene;

B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—;

E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$;

D is one or more F, I, OH, NH$_2$, CHO, CN, NO$_2$, CF$_3$, or Q;

each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, where n is 0, 1, or 2;

each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-2}$alkoxy C$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$;

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$;

The compound of formula (I) can be a salt.

In another aspect, this invention features compounds of formula (I):

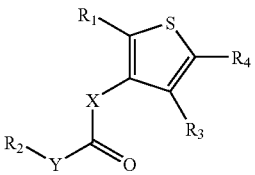

(I)

wherein R$_1$ is R$_5$, OR$_5$, C(O)OR$_5$, C(O)R$_5$, or C(O)NR$_5$R$_6$;
R$_2$ is R$_5$;

X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, —C$_{2-4}$alkynylene-; wherein any of the alkylene, alkenylene or alkynylene groups is optionally substituted with one or more halogen, oxo, imido, CN, OCF$_3$, OH, NH$_2$, NO$_2$, or Q;

Y is absent, —O—, or —NR$_6$—;

R$_3$ is F, I, CN, CF$_3$, OCF$_3$, C$_{1-3}$alkyl, C$_{3-4}$cycloalkyl, C$_{1-3}$alkoxy, or aryl;

R$_4$ is A-B-E-D, where A is absent or arylene, heteroarylene, C$_{1-6}$alkylene, C$_{2-6}$ alkenyldiyl, or C$_{2-6}$alkynyl, each A being optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q; where any of the alkyl, alkenyl or alkynyl is optionally substituted with one or more halogen, oxo, CN, OCF$_3$, OH, NH$_2$, NO$_2$, N$_3$, or Q; and each A being optionally terminated with one or more arylene, alkylene, or alkenylene;

B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—;

E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$;

D is one or more F, Cl, Br, I, OH, NH$_2$, CHO, CN, NO$_2$, CF$_3$, or Q;

each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$ R$_7$, where n is 0, 1, or 2;

each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxyC$_1$-

$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$—NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$;

R$_7$ is —C(O)R$_5$, —C(O)OR$_5$, —C(O)NR$_5$R$_5$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$;

The compound of formula (I) can be a salt.

In one aspect, a pharmaceutical composition includes at least one of the compounds of formula (I), or a pharmaceutically acceptable salt or prodrug thereof, and a pharmaceutically acceptable excipient or carrier. The compound can inhibit a PTPase such as PTP1B.

For the pharmaceutical composition, the compound of formula (I) can have the following structure.

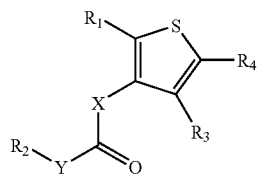

(I)

R$_1$ is R$_5$, OR$_5$, C(O)OR$_5$, C(O)R$_5$, or C(O)NR$_5$R$_6$.

R$_2$ is R$_5$.

X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, or —C$_{2-4}$alkynylene-. Any of the alkylene, alkenylene or alkynylene groups can be optionally substituted with one or more halogen, oxo, imido, CN, OCF$_3$, OH, NH$_2$, NO$_2$, or Q.

Y is absent, —O—, or —NR$_6$—.

R$_3$ is H, halogen, CN, CF$_3$, OCF$_3$, C$_{1-3}$alkyl, C$_{3-4}$cycloalkyl, C$_{1-3}$alkoxy, or aryl.

R$_4$ is A-B-E-D, where A is absent or arylene, heteroarylene, C$_{1-6}$alkylene, C$_{2-6}$ alkenyldiyl, or C$_{2-6}$alkynyl. Each A can be optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q. Any of the alkyl, alkenyl or alkynyl groups is optionally substituted with one or more halogen, oxo, CN, OCF$_3$, OH, NH$_2$, NO$_2$, N$_3$, or Q. Each A can be optionally terminated with one or more arylene, alkylene, or alkenylene.

B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(P$_{14}$)—, or —C(R$_{11}$)(R$_{12}$)SO$_2$C(R$_{13}$)(R$_{14}$)—.

E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$.

D is one or more H, halogen, OH, NH$_2$, CHO, CN, NO$_2$, CF$_3$, or Q.

Each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, and n is 0, 1, or 2.

Each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxy C$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl. Each R$_5$, R$_6$, and R$_8$ can be optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$ R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$.

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$.

Each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl. Any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

In one aspect, a method of treating a PTPase-mediated disorder or condition (e.g., a PTP1B-mediated disorder or condition) includes administering to a mammal (e.g., a human) a therapeutically effective amount of a 2-carboxyl, 3-carboxymethoxy, 5-aryl substituted thiophene or a pharmaceutically acceptable salt or prodrug thereof.

In another aspect, a method of treating a PTPase-mediated disorder or condition (e.g., a PTP1B-mediated disorder or condition) includes administering to a mammal (e.g., a human) a therapeutically effective amount of a compound of formula (I). In the method of treatment, the compound of formula (I) can have the following structure.

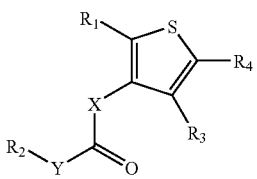

(I)

R$_1$ is R$_5$, OR$_5$, C(O)OR$_5$, C(O)R$_5$, or C(O)NR$_5$R$_6$.

R$_2$ is R$_5$.

X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, or —C$_{2-4}$alkynylene-. Any of the alkylene, alkenylene or alkynylene groups can be optionally substituted with one or more halogen, oxo, imido, CN, OCF$_3$, OH, NH$_2$, NO$_2$, or Q.

Y is absent, —O—, or —NR$_6$—.

R$_3$ is H, halogen, CN, CF$_3$, OCF$_3$, C$_{1-3}$alkyl, C$_{3-4}$cycloalkyl, C$_{1-3}$alkoxy, or aryl.

R$_4$ is A-B-E-D, where A is absent or arylene, heteroarylene, C$_{1-6}$alkylene, C$_{2-6}$ alkenyldiyl, or C$_{2-6}$alkynyl. Each A can be optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q. Any of the alkyl, alkenyl or alkynyl groups is optionally substituted with one or more halogen, oxo, CN, OCF$_3$, OH, NH$_2$, NO$_2$, N$_3$, or Q. Each A can be optionally terminated with one or more arylene, alkylene, or alkenylene.

B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—.

E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$.

D is one or more H, halogen, OH, NH$_2$, CHO, CN, NO$_2$, CF$_3$, or Q.

Each Q, independently, is —R$_5$, —R$_7$, —OR$_5$, —OR$_7$, —NR$_5$R$_6$, —NR$_5$R$_7$, —N$^+$R$_5$R$_6$, S(O)R$_5$, or —S(O)$_n$R$_7$, and n is 0, 1, or 2.

Each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxy C$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl. Each R$_5$, R$_6$, and R$_8$ can be optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$ R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$.

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$.

Each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl. Any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

In one aspect, a method of inhibiting a PTPase activity (e.g., a PTP1B activity) in a sample includes contacting the sample with an effective amount of a 2-carboxyl, 3-carboxymethoxy, 5-aryl substituted thiophene or a pharmaceutically acceptable salt or prodrug thereof.

In another aspect, a method of inhibiting a PTPase, such as PTP1B, includes contacting a sample with an effective amount of a compound of formula (I). In the method of inhibiting PTPase, the compound of formula (I) can have the following structure.

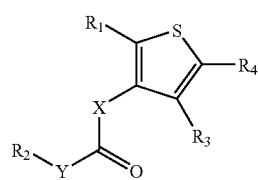

(I)

R$_1$ is R$_5$, OR$_5$, C(O)OR$_5$, C(O)R$_5$, or C(O)NR$_5$R$_6$.

R$_2$ is R$_5$R$_6$.

X is —O—C$_{1-3}$alkylene-, —NR$_8$—C$_{1-3}$alkylene-, —S—C$_{1-3}$alkylene-, —SO—C$_{1-3}$alkylene-, —SO$_2$—C$_{1-3}$alkylene-, —C$_{1-4}$alkylene-, —C$_{2-4}$alkenylene-, or —C$_{2-4}$alkynylene-. Any of the alkylene, alkenylene or alkynylene groups can be optionally substituted with one or more halogen, oxo, imido, CN, OCF$_3$, OH, NH$_2$, NO$_2$, or Q.

Y is absent, —O—, or —NR$_6$—.

R$_3$ is H, halogen, CN, CF$_3$, OCF$_3$, C$_{1-3}$alkyl, C$_{3-4}$cycloalkyl, C$_{1-3}$alkoxy, or aryl.

R$_4$ is A-B-E-D, where A is absent or arylene, heteroarylene, C$_{1-6}$alkylene, C$_{2-6}$ alkenyldiyl, or C$_{2-6}$alkynyl. Each A can be optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q. Any of the alkyl, alkenyl or alkynyl groups is optionally substituted with one or more halogen, oxo, CN, OCF$_3$, OH, NH$_2$, NO$_2$, N$_3$, or Q. Each A can be optionally terminated with one or more arylene, alkylene, or alkenylene.

B is absent or —NR$_5$—, —NR$_7$—, —N(R$_5$)CH$_2$—, —N(R$_7$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—.

E is absent or C$_{3-12}$cycloalkylene, 3-to 12-membered heterocycdiyl, arylene, C$_{1-12}$alkylene, C$_{2-12}$alkenylene, or C$_{2-12}$alkynylene, where each E is optionally substituted with one or more C$_{1-3}$ alkyl, C$_{1-3}$alkoxy, halogen, CN, OH, NH$_2$, or NO$_2$.

D is one or more H, halogen, OH, NH$_2$, CHO, CN, NO$_2$, CF$_3$, or Q.

Each Q, independently, is —R$_5$, —R$_7$, —OR$_5$, —OR$_7$, —NR$_5$R$_6$, —NR$_5$R$_7$, —N$^+$R$_6$R$_8$, S(O)$_n$R$_5$, or —S(O)$_n$R$_7$, and n is 0, 1, or 2.

Each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxy C$_{1-12}$ alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl. Each R$_5$, R$_6$, and R$_8$ can be optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$ R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$.

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$.

Each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl. Any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

In one aspect, the present invention relates to methods for testing PTP1B inhibitors.

A method of synthesizing a compound of formula (I) for the inhibition of a PTPase includes a step of alkylating a compound of formula (II) to form a compound of formula (III), the compound of formula (I) being:

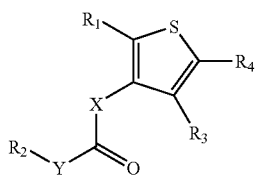

(I)

wherein $R_1$ is $R_5$, $OR_5$, $C(O)OR_5$, $C(O)R_5$, or $C(O)NR_5R_6$;
$R_2$ is $R_5$;

X is $-O-C_{1-3}$alkylene-, $-NR_8-C_{1-3}$alkylene-, $-S-C_{1-3}$alkylene-, $-SO-C_{1-3}$alkylene-, $-SO_2-C_{1-3}$alkylene-, $-C_{1-4}$alkylene-, $-C_{2-4}$alkenylene-, $-C_{2-4}$alkynylene-; wherein any of the alkylene, alkenylene or alkynylene groups is optionally substituted with one or more halogen, oxo, imido, CN, $OCF_3$, OH, $NH_2$, $NO_2$, or Q;

Y is absent, $-O-$, or $-NR_6-$;

$R_3$ is H, halogen, CN, $CF_3$, $OCF_3$, $C_{1-3}$alkyl, $C_{3-4}$cycloalkyl, $C_{1-3}$alkoxy, or aryl;

$R_4$ is A-B-E-D, where A is absent or arylene, heteroarylene, $C_{1-6}$alkylene, $C_{2-6}$ $C_{1-3}$alkenyldiyl, or $C_{2-6}$alkynyl, each A being optionally substituted with one or more of $C_{1-6}$alkyl, $C_{2-6}$alkenyl, $C_{2-6}$alkynyl, halogen, CN, $OCF_3$, OH, $NH_2$, CHO, $NO_2$, or Q; where any of the alkyl, alkenyl or alkynyl is optionally substituted with one or more halogen, oxo, CN, $OCF_3$, OH, $NH_2$, $NO_2$, $N_3$, or Q; and each A being optionally terminated with one or more arylene, alkylene, or alkenylene;

B is absent or $-NR_5-$, $-NR_7-$, $-N(R_5)CH_2-$, $-N(R_7)CH_2-$, $-N(R_9)-$, $-N(R_9)C(O)-$, $-N(R_9)C(O)C(R_{11})(R_{12})-$, $-N(R_9)C(O)C(O)-$, $-N(R_9)C(O)N(R_{10})-$, $-N(R_9)SO_2-$, $-N(R_9)SO_2C(R_{10})(R_{11})-$, $-N(R_9)(R_{10})C(R_{11})(R_{12})-$, $-N(R_9)C(R_{11})(R_{12})C(R_{13})(R_{14})-$, $-O-$, $-O-C(R_{11})(R_{12})$, $-O-C(R_{11})(R_{12})C(R_{13})(R_{14})-$, $-C(R_{11})(R_{12})-O-$, $-C(R_{11})(R_{12})-O-C(R_{13})(R_{14})-$, $-C(R_{11})(R_{12})N(R_9)-$, $-C(R_{11})(R_{12})N(R_9)C(R_{13})(R_{14})-$, $-C(R_{11})(R_{12})S-$, $-C(R_{11})(R_{12})SC(R_{13})(R_{14})-$, or $-C(R_{11})(R_{12})SO_2C(R_{13})(R_{14})-$;

E is absent or $C_{3-12}$cycloalkylene, 3- to 12-membered heterocycdiyl, arylene, $C_{1-12}$alkylene, $C_{2-12}$alkenylene, or $C_{2-12}$alkynylene, where each E is optionally substituted with one or more $C_{1-3}$alkyl, $C_{1-3}$alkoxy, halogen, CN, OH, $NH_2$, or $NO_2$;

D is one or more H, OH, $NH_2$, CHO, CN, $NO_2$, $CF_3$, or Q;

each Q, independently, is $-R_5$, $-R_7$, $-OR_5$, $-OR_7$, $-NR_5R_6$, $-NR_5R_7$, $-N^+R_5R_6R_8$, $S(O)_nR_5$, or $-S(O)_nR_7$, where n is 0, 1, or 2;

each $R_5$, $R_6$, and $R_9$, independently, is H, $C_{1-12}$alkyl, $C_{2-12}$alkenyl, $C_{2-12}$alkynyl, $C_{3-12}$cycloalkyl, $C_{1-2}$alkoxy $C_{1-12}$alkyl, cycloalkyl$C_{1-6}$alkyl, 3- to 8-membered heterocycyl, heterocycyl$C_{1-6}$alkyl, aryl, aryl$C_{1-6}$ alkyl, aryl$C_{2-6}$ alkenyl, or aryl$C_{2-6}$ alkynyl, where each $R_5$, $R_6$, and $R_8$ is optionally substituted with one or more $R_9$, $-OR_9$, $-OC(O)R_9$, $-C(O)R_9$, $-C(O)OR_9$, $-C(O)NR_9R_{10}$, $-SR_9$, $-S(O)R_9$, $-S(O)_2R_9$, $-NR_9R_{10}$, $-N^+R_9R_{10}R_{11}$, $-NR_9C(O)R_{10}$, $-NC(O)NR_9R_{10}$, $-NR_9S(O)_2R_{10}$, oxo, halogen, CN, $OCF_3$, $CF_3$, OH, or $NO_2$;

$R_7$ is $-C(O)R_5$, $-C(O)OR_5$, $-C(O)NR_5R_6$, $-S(O)_2R_5$, $-S(O)R_5$, or $-S(O)_2NR_5R_6$; and each $R_9$, $R_{10}$, $R_{11}$, $R_{12}$, $R_{13}$ and $R_{14}$ is, independently, H, $C_{1-12}$alkyl, $C_{2-12}$alkenyl, $C_{2-12}$alkynyl, $C_{3-12}$cycloalkyl, aryl, or aryl$C_{1-12}$alkyl; where any of the alkyl, alkenyl, alkynyl, cycloalkyl, aryl, or arylalkyl groups is optionally substituted with one or more halogen, oxo, CN, $OCF_3$, OH, $NH_2$, or $NO_2$.and wherein the compound of formula (II) is:

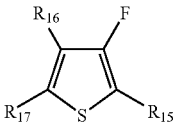

wherein $R_{15}$ is as defined for $R_1$, $R_{16}$ is as defined for $R_3$, and $R_{17}$ is as defined for $R_4$ in the compound of formula (I); and F is OH, $NH_2$, or $S(O)_2CF_3$;

and wherein the compound of formula (III) is defined as the compound of formula (II) except that F has been alkylated to form $O(C_{1-3}$alkyl$)C(O)YR_2$; $NR_5$ (alkyl)$C(O)YR_2$, $-S(C_{1-3}$alkyl$)C(O)YR_2$, $SO(C_{1-3}$alkyl$)C(O)YR_2$, or $SO_2$ $(C_{1-3}$alkyl$)C(O)YR_2$, where Y, $R_2$, and $R_5$ are as defined for the compound of formula (I).

The step of alkylating a compound of formula (II) can include contacting the compound of formula (II) with ZCHC(O)OC$_{1-6}$alkyl, in which Z is a halogen.

Embodiments can include one or more features.

$R_1$ can be $C(O)OR_5$ (e.g., $C(O)OH$, $C(O)OCH_3$, $C(O)OCH_2CH_3$, $C(O)OCH_2CH_2CH_3$, $C(O)OCH(CH_3)CH_3$, $C(O)OCH_2CH(CH_3)CH_3$, or benzyl ester).

$R_1$ can be $C(O)NR_5R_6$ (e.g., $C(O)NH_2$).

$R_2$ can be H, $CH_3$, $CH_2CH_3$, or $CH(CH_3)CH_3$.

X can be $-O-C_{1-3}$ alkylene- (e.g., $-O-CH_2-$, $-O-CH(CH_3)-$, $-O-CHF-$).

X can be $-N-C_{1-3}$ alkylene- (e.g., $-N-CH_2-$, $-N-CHF-$).

Y can be O.

$R_3$ can be H, halogen, CN, $CF_3$, $OCF_3$, $C_{1-3}$alkyl, $C_{3-4}$cycloalkyl, or $C_{1-3}$alkoxy. In certain embodiments, $R_3$ can be halogen, (e.g., fluorine, bromine, chlorine). In certain embodiments, $R_3$ can be H. In certain embodiments, $R_3$ can be $C_{1-3}$alkyl and can be optionally substituted with one or more halogen, oxo, imido, CN, $OCF_3$, OH, $NH_2$, $NO_2$, or Q (e.g., $CH_3$, $CF_3$).

A, B, and E can be absent and D can be H.

A, B, and E can be absent and D can be halogen.

A can be a 6-membered aryl group and B-E-D can be connected to A in a meta (C-3 or C-5) position relative to the connection between A and thiophene.

A can be a 5-membered aryl group and B-E-D can be connected to A at the C-3 or C4 position relative to the connection between A and thiophene.

A can be aryl optionally substituted with one or more $C_{1-6}$alkyl, $C_{2-6}$alkenyl, $C_{2-6}$alkynyl, halogen, CN, $OCF_3$, OH, $NH_2$, CHO, $NO_2$, Q, or B; where alkyl, alkenyl or alkynyl is optionally substituted with one or more halogen, oxo, CN, $OCF_3$, OH, $NH_2$, $NO_2$, $N_3$, Q, or B.

A can be phenyl optionally substituted with one or more $C_{1-6}$alkyl, $C_{2-6}$alkenyl, $C_{2-6}$alkynyl, halogen, CN, $OCF_3$, OH, $NH_2$, CHO, $NO_2$, Q, or B; where alkyl, alkenyl or alkynyl is optionally substituted with one or more halogen, oxo, CN, $OCF_3$, OH, $NH_2$, $NO_2$, $N_3$, Q, or B.

A can be phenyl and is substituted with $NR_5R_6$ or $NR_5R_7$.

A can be phenyl and is substituted with $NR_5R_7$, where $R_7$ is $C(O)R_5$, $C(O)OR_5$, $C(O)NR_5R_6$, or $S(O)_2R_5$.

A can be phenyl.

A can be naphthyl.

A can be thiophene, indole, benzofuran, or pyridine.

B can be —NR$_7$—, NR$_5$—, —NR$_5$CH$_2$—, NR$_7$CH$_2$—, —O—, —O—C(R$_{11}$)(R$_{12}$)—, or —C(R$_{11}$)(R$_{12}$)—O—.

B can be —NH—, —NHCH$_2$—, —NHC(O)CH$_2$—, —NHC(O)—, —O—, —CH$_2$—O—, or —O—CH$_2$—.

B can be —N(C(O)R$_5$)—, —N(C(O)OR$_5$)—, or —N(C(O)NHR$_5$)—.

E can be cyclopentdiyl, cyclohexdiyl, cycloheptdiyl, piperidindiyl, piperazindiyl, pyrrolidindiyl, tetrahydrofurandiyl, morpholindiyl, phenylene, pyridindiyl, pyrimidindiyl, thiophendiyl, furandiyl, imidazoldiyl, pyrroldiyl, benzimidazoldiyl, tetrahydrothiopyrandiyl, or tetrahydropyrandiyl, where E is optionally substituted with one or more C$_{1-3}$alkyl, C$_{1-3}$alkoxy, halogen, CN, OH, NH$_2$, or NO$_2$.

E can be piperidindiyl optionally substituted with one or more C$_{1-3}$alkyl, C$_{1-3}$alkoxy, halogen, CN, OH, NH$_2$, or NO$_2$.

D can be —SO$_2$R$_5$, —C(O)R$_5$, —OC(O)NR$_5$R$_6$, —OR$_5$, —C(O)OR$_5$, pyrimidinyl or pyridinyl.

R$_1$ can be C(O)OH, X can be —OCH$_2$—, Y can be O, and R$_2$ can be H.

R$_1$ can be C(O)OH, X can be —OCH$_2$—, Y can be O, R$_2$ can be H, and R$_3$ can be Br.

In certain embodiments, R$_1$ is C(O)OH, C(O)OCH$_3$, C(O)OCH$_2$CH$_3$, or C(O)NH$_2$. In other embodiments, R$_2$ is H, CH$_3$, CH$_2$CH$_3$, or t-butyl. In certain embodiments, X is —O—C$_{1-3}$alkyl-, —N—C$_{1-3}$ alkyl-, —S—C$_{1-3}$alkyl-, —SO—C$_{1-3}$alkyl-, or —SO$_2$—C$_{1-3}$alkyl-. In other embodiments, R$_3$ is H, F, Cl, Br, methyl, or CF$_3$.

In one embodiment, A is an aryl group substituted with B and may furthermore be optionally substituted with one or more of OH, NH$_2$, CHO, CN, NO$_2$, halogen, C$_1$-C$_4$ alkyl or Q; B can be absent or a 1-3 atom linker such as C$_1$-C$_3$ alkyl, C$_2$-C$_3$ alkenyl, NH, NHCO, NHCONH, NHSO$_2$, NHSO$_2$CH$_2$, NHCH$_2$, NHCH$_2$CH$_2$, O, OCH$_2$, OCH$_2$CH$_2$, CH$_2$O, CH$_2$OCH$_2$, CH$_2$NH, CH$_2$NHCH$_2$, CH$_2$S, CH$_2$SCH$_2$, or CH$_2$SO$_2$CH$_2$.

In the following examples, for the connection of B-E-D to A, it is shown that the meta positions (C-3 or C-5) relative to the connection between A and the thiophene ring are preferred when A is a 6-membered aryl group. When A is a 5-membered aryl group, the C-3 or C4 positions relative to the connection between A and the thiophene ring are preferred.

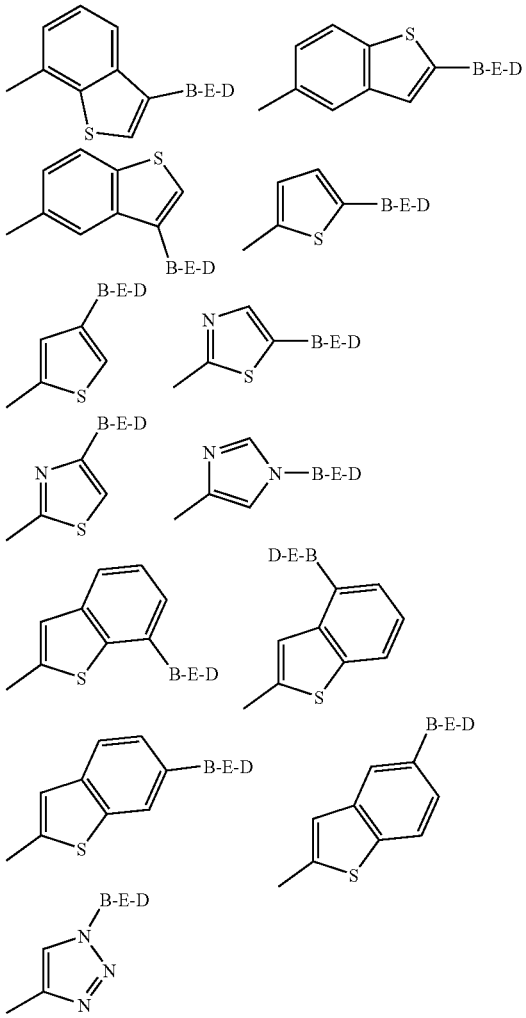

In another embodiment, E is absent or C$_{3-8}$cycloalkylene, C$_{3-8}$heterocycdiyl, arylene, C$_{1-6}$alkylene, C$_{2-6}$alkenylene, or C$_{2-6}$alkynylene, and is optionally substituted with one or more C$_{1-3}$ alkyl, C$_{1-3}$alkoxy, halogen, CN, OH, NH$_2$, or NO$_2$. In certain embodiments, E can be cyclopentdiyl, cyclohexdiyl, cycloheptdiyl, piperidindiyl, piperazindiyl, pyrrolidindiyl, tetrahydrofurandiyl, morpholindiyl, phenylene, pyridindiyl, pyrimidindiyl, thiophendiyl, furandiyl, imidazoldiyl, pyrroldiyl, benzimidazoldiyl, tetrahydrothiopyrandiyl, or tetrahydropyrandiyl.

In one embodiment, D is one or more H, halogen, OH, NH$_2$, CHO, CN, NO$_2$, CF$_3$, aryl, or Q. In certain embodiments, D is SO$_2$R$_7$, —C(O)R$_7$, —OC(O)NR$_5$R$_6$, —OR$_7$, —COOR$_7$, —C(O)NR$_5$R$_6$, —C(O)R$_7$, pyrimidinyl or pyridinyl.

In some embodiments, the compound can be selected from 3-carboxymethoxy-4-phenyl-thiophene-2-carboxylic acid, 3-carboxymethoxy-4-(3-trifluoromethyl-phenyl)-thiophene-2-carboxylic acid, 3-carboxymethoxy-4-(1H-indol-5-yl)-thiophene-2-carboxylic acid, 4-carboxymethoxy-[3,3']bithiophenyl-5-carboxylic acid, 4-bromo-3-carboxymethoxy-5-phenyl-thiophene-2-carboxylic acid, 5-(4-amino-phenyl)-4-bromo-3-carboxymethoxy-thiophene-2-carboxylic acid, 4-bromo-3-carboxymethoxy-5-(4-dimethylamino-phenyl)-thiophene-2-carboxylic acid, 5-(3-amino-phenyl)-4-bromo-3-carboxymethoxy-thiophene-2-carboxylic acid, 4-bromo-3-carboxymethoxy-5-naphthalen-2-yl-thiophene-2-carboxylic acid, 4-bromo-3-carboxymethoxy-5-(4-hydroxy-phenyl)-thiophene-2-carboxylic acid, 4-bromo-3-carboxymethoxy-5-(4-methoxy-phenyl)-thiophene-2-carboxylic acid, 3-carboxymethoxy-5-(4-trifluoromethoxy-phenyl)-thiophene-2-carboxylic acid, 4-bromo-3-carboxymethoxy-5-(4-hydroxymethyl-phenyl)-thiophene-2-carboxylic acid, 4-bromo-3-carboxymethoxy-5-(3-hydroxy-phenyl)-thiophene-2-carboxylic acid, 3-ethoxycarbonylmethoxy-4,5-bis-(3-hydroxy-phenyl)-thiophene-2-carboxylic acid methyl ester, 4-bromo-3-carboxymethoxy-5-(3-methoxy-phenyl)-thiophene-2-carboxylic acid, 4-bromo-3-carboxymethoxy-5-(4-fluoro-phenyl)-thiophene-2-carboxylic acid, 3-carboxymethoxy-5-o-tolyl-thiophene-2-carboxylic acid, 5-(4-acetylamino-phenyl)-4-bromo-3-carboxymethoxy-thiophene-2-carboxylic acid, 5-(4-benzoylamino-phenyl)-4-bromo-3-carboxymethoxy-thiophene-2-carboxylic acid, 4-bromo-3-carboxymethoxy-5-{4-[(pyridine-3-carbonyl)-amino]-phenyl}-thiophene-2-carboxylic acid, 4-bromo-3-carboxymethoxy-5-{4-[(furan-3-carbonyl)-amino]-phenyl}-thiophene-2-carboxylic acid, 4-bromo-3-carboxymethoxy-5-{4-[(furan-2-carbonyl)-amino]-phenyl}-thiophene-2-carboxylic acid, 4-[4-(3-bromo-5-carboxy-4-carboxymethoxy-thiophen-2-yl)-phenylcarbamoyl]-piperidine-1-carboxylic acid tert-butyl ester, 3-[4-(3-bromo-5-carboxy-4-carboxymethoxy-thiophen-2-yl)-phenylcarbamoyl]-piperidine-1-carboxylic acid tert-butyl ester, 4-bromo-3-carboxymethoxy-5-(4-methoxycarbonylamino-phenyl)-thiophene-2-carboxylic acid, 4-bromo-3-carboxymethoxy-5-[4-(3-isopropyl-ureido)-phenyl]-thiophene-2-carboxylic acid, 5-[4-(2-benzyloxy-acetylamino)-phenyl]-4-bromo-3-carboxymethoxy-thiophene-2-carboxylic acid, 4-bromo-5-[4-(2-tert-butoxycarbonylamino-acetylamino)-phenyl]-3-carboxymethoxy-thiophene-2-carboxylic acid, 5-[4-(2-amino-acetylamino)-phenyl]-4-bromo-3-carboxymethoxy-thiophene-2-carboxylic acid, 4-bromo-3-carboxymethoxy-5-[4-(oxalyl-amino)-phenyl]-thiophene-2-carboxylic acid, 4-bromo-5-[4-(2-carboxy-acetylamino)-phenyl]-3-carboxymethoxy-thiophene-2-carboxylic acid, 4-bromo-3-carboxymethoxy-5-(4-methanesulfonylamino-phenyl)-thiophene-2-carboxylic acid, 5-(4-benzenesulfonylamino-phenyl)-4-bromo-3-carboxymethoxy-thiophene-2-carboxylic acid, 4-bromo-3-carboxymethoxy-5-[4-(4-trifluoromethyl-benzenesulfonylamino)-phenyl]-thiophene-2-carboxylic acid, 4-bromo-3-carboxymethoxy-5-{4-[methyl-(4-trifluoromethyl-benzenesulfonyl)-amino]-phenyl}-thiophene-2-carboxylic acid, 4-bromo-3-carboxymethoxy-5-[4-(3-trifluoromethyl-benzenesulfonylamino)-phenyl]-thiophene-2-carboxylic acid, 4-bromo-3-carboxymethoxy-5-[4-(2-trifluoromethyl-benzenesulfonylamino)-phenyl]-thiophene-2-carboxylic acid, 4-bromo-3-carboxymethoxy-5-[4-(2,6-dichloro-benzenesulfonylamino)-phenyl]-thiophene-2-carboxylic acid, 4-bromo-3-carboxymethoxy-5-[4-(2,6-difluoro-benzenesulfonylamino)-phenyl]-thiophene-2-carboxylic acid, 4-bromo-3-carboxymethoxy-5-[4-(3,3,5,5-tetramethyl-cyclohexylamino)-phenyl]-thiophene-2-carboxylic acid, 3-carboxymethoxy-5-[4-(3,3,5,5-tetramethyl-cyclohexylamino)-phenyl]-thiophene-2-carboxylic acid, 5-[4-(benzenesulfonylamino-methyl)-phenyl]-4-bromo-3-carboxymethoxy-thiophene-2-carboxylic acid, 4-bromo-5-[4-(tert-butoxycarbonylamino-methyl)-phenyl]-3-carboxymethoxy-thiophene-2-carboxylic acid, 4-bromo-3-carboxymethoxy-5-[4-(ethanesulfonylamino-methyl)-phenyl]-thiophene-2-carboxylic acid, 5-[4-(acetylamino-methyl)-phenyl]-4-bromo-3-carboxymethoxy-thiophene-2-carboxylic acid, 4-bromo-3-carboxymethoxy-5-[4-(ethoxycarbonylamino-methyl)-phenyl]-thiophene-2-carboxylic acid, 4-bromo-3-carboxymethoxy-5-[4-(3-isopropyl-ureidomethyl)-phenyl]-thiophene-2-carboxylic acid, 5-(4-aminomethyl-phenyl)-4-bromo-3-carboxymethoxy-thiophene-2-carboxylic acid trifluoroacetic acid, 4-bromo-3-carboxymethoxy-5-(4-phenylcarbamoyl-phenyl)-thiophene-2-carboxylic acid, 4-bromo-3-carboxymethoxy-5-(4-formyl-phenyl)-thiophene-2-carboxylic acid, 4-bromo-3-carboxymethoxy-5-(4-isopropylcarbamoyl-phenyl)-thiophene-2-carboxylic acid, 4-bromo-5-[4-(1-carbamoyl-ethylcarbamoyl)-phenyl]-3-carboxymethoxy-thiophene-2-carboxylic acid, 4-bromo-3-carboxymethoxy-5-[4-(4-trifluoromethyl-phenylcarbamoyl)-phenyl]-thiophene-2-carboxylic acid, 4-bromo-3-carboxymethoxy-5-(3-propionylamino-phenyl)-thiophene-2-carboxylic acid, 4-bromo-5-(3-butyrylamino-phenyl)-3-carboxymethoxy-thiophene-2-carboxylic acid, 4-bromo-5-(3-butyrylamino-phenyl)-3-carboxymethoxy-thiophene-2-carboxylic acid, 4-bromo-3-carboxymethoxy-5-[3-(cyclohexanecarbonyl-amino)-phenyl]-thiophene-2-carboxylic acid, 4-bromo-3-carboxymethoxy-5-(3-hexanoylamino-phenyl)-thiophene-2-carboxylic acid, 4-bromo-3-carboxymethoxy-5-[3-(cyclopentanecarbonyl-amino)-phenyl]-thiophene-2-carboxylic acid, 4-[3-(3-bromo-5-carboxy-4-carboxymethoxy-thiophen-2-yl)-phenylcarbamoyl]-piperidine-1-carboxylic acid tert-butyl ester, 3-[3-(3-bromo-5-carboxy-4-carboxymethoxy-thiophen-2-yl)-phenylcarbamoyl]-piperidine-1-carboxylic acid tert-butyl ester, 4-bromo-3-carboxymethoxy-5-[3-(3,3,3-trifluoro-propionylamino)-phenyl]-thiophene-2-carboxylic acid, 5-(3-benzoylamino-phenyl)-4-bromo-3-carboxymethoxy-thiophene-2-carboxylic acid, 4-bromo-3-carboxymethoxy-5-{3-[(furan-2-carbonyl)-amino]-phenyl}-thiophene-2-carboxylic acid, 4-bromo-3-carboxymethoxy-5-{3-[(furan-3-carbonyl)-amino]-phenyl}-thiophene-2-carboxylic acid, 4-bromo-3-carboxymethoxy-5-[3-(2-trifluoromethyl-benzoylamino)-phenyl]-thiophene-2-carboxylic acid, 4-bromo-3-carboxymethoxy-5-[3-(2-fluoro-benzoylamino)-phenyl]-thiophene-2-carboxylic acid, 4-bromo-3-carboxymethoxy-5-[3-(3-fluoro-benzoylamino)-phenyl]-thiophene-2-carboxylic acid, 4-bromo-3-carboxymethoxy-5-{3-[(pyridine-3-carbonyl)-amino]-phenyl}-thiophene-2-carboxylic acid, 4-bromo-3-carboxymethoxy-5-[3-(4,4,4-trifluoro-butyrylamino)-phenyl]-thiophene-2-carboxylic acid, 4-bromo-3-carboxymethoxy-5-{3-[(2-hydroxy-pyridine-3-carbonyl)-amino]-phenyl}-thiophene-2-carboxylic acid, 4-bromo-3-carboxymethoxy-5-{3-[(pyridine-4-carbonyl)-amino]-phenyl}-thiophene-2-carboxylic acid, 4-bromo-3-carboxymethoxy-5-{3-[(quinoline-3-carbonyl)-amino]-phenyl}-thiophene-2-carboxylic acid, 4-bromo-3-carboxymethoxy-5-{3-[(pyridine-2-carbonyl)-amino]-phenyl}-thiophene-2-carboxylic acid, 4-bromo-3-carboxymethoxy-5-{3-[(1-oxy-pyridine-3-carbonyl)-amino]-phenyl}-thiophene-2-carboxylic acid, 4-bromo-3-carboxymethoxy-5-[3-(2-pyridin-2-yl-acetylamino)-phenyl]-thiophene-2-carboxylic acid, 4-bromo-3-carboxymethoxy-5-[3-(2-pyridin-3-yl-acetylamino)-phenyl]-thiophene-2-carboxylic acid, 4-bromo-3-carboxymethoxy-5-{3-[(pyrazine-2-carbonyl)-amino]-phenyl}-thiophene-2-carboxylic acid, 4-bromo-3-carboxymethoxy-5-[3-(2-pyridin-4-yl-acetylamino)-phenyl]-thiophene-2-carboxylic acid, 4-bromo-3-carboxymethoxy-5-{3-[(piperidine-4-carbonyl)-amino]-phenyl}-thiophene-2-carboxylic acid trifluoroacetic acid salt, 4-bromo-3-carboxymethoxy-5-[3-(cyclohexanecarbonyl-amino)-phenyl]-thiophene-2-carboxylic acid, 5-(3-acetylamino-phenyl)-4-bromo-3-carboxymethoxy-thiophene-2-carboxylic acid, 4-bromo-3-carboxymethoxy-5-(3-isobutyrylamino-phenyl)-thiophene-2-carboxylic acid, 4-bromo-3-carboxymethoxy-5-[3-(2,2,2-trifluoro-ethane-sulfonylamino)-phenyl]-thiophene-2-carboxylic acid, 5-(3-benzenesulfonylamino-phenyl)-4-bromo-3-car-boxymethoxy-thiophene-2-carboxylic acid, 4-bromo-3-carboxymethoxy-5-(3-ethanesulfonylamino-phenyl)-thiophene-2-carboxylic acid, 4-bromo-3 carboxymethoxy-5-(3-phenylmethanesulfonylamino-phenyl)-thiophene-2-carboxylic acid, 4-bromo-3-carboxymethoxy-5-[3-(4-trifluoromethyl-benzenesulfonylamino)-phenyl]-thiophene-2-carboxylic acid, 4-bromo-3-carboxymethoxy-5-[3-(4-trifluoromethoxy-benzenesulfonylamino)-phenyl]-thiophene-2-carboxylic acid, 4-bromo-3-carboxymethoxy-5-[3-(3-trifluoromethyl-benzenesulfonylamino)-phenyl]-thiophene-2-carboxylic acid, 4-bromo-3-carboxymethoxy-5-[3-(2-trifluoromethyl-benzenesulfonylamino)-phenyl]-thiophene-2-carboxylic acid, 4-bromo-3-carboxymethoxy-5-[3-(2-cyano-benzenesulfonylamino)-phenyl]-thiophene-2-carboxylic acid, 4-bromo-3-carboxymethoxy-5-[3-(4-methoxy-benzenesulfonylamino)-phenyl]-thiophene-2-carboxylic acid, 4-bromo-3-carboxymethoxy-5-[3-(4-cyano-benzenesulfonylamino)-phenyl]-thiophene-2-carboxylic acid, 4-bromo-3-carboxymethoxy-5-[3-(4-fluoro-benzene-sulfonylamino)-phenyl]-thiophene-2-carboxylic acid, 4-bromo-3-carboxymethoxy-5-(3-methoxycarbonylamino-phenyl)-thiophene-2-carboxylic acid, 4-bromo-3-car-boxymethoxy-5-[3-(3-isopropyl-ureido)-phenyl]-thiophene-2-carboxylic acid, 4-bromo-3-carboxymethoxy-5-[3-(3,3-diethyl-ureido)-phenyl]-thiophene-2-carboxylic acid, 5-(3-benzylamino-phenyl)-4-bromo-3-carboxymethoxy-thiophene-2-carboxylic acid, 4-bromo-3-carboxymethoxy-5-[3-(3-trifluoromethyl-benzylamino)-phenyl]-thiophene-2-carboxylic acid, 4-bromo-3-carboxymethoxy-5-[3-(2-trifluoromethyl-benzylamino)-phenyl]-thiophene-2-carboxylic acid, 4-bromo-3-carboxymethoxy-5-{3-[(furan-2-ylmethyl)-amino]-phenyl}-thiophene-2-carboxylic acid, 4-bromo-3-carboxymethoxy-5-{3-[(furan-3-ylmethyl)-amino]-phenyl}-thiophene-2-carboxylic acid, 4-bromo-3-carboxymethoxy-5-[3-(3-fluoro-benzylamino)-phenyl]-thiophene-2-carboxylic acid, 4-bromo-3-carboxymethoxy-5-[3-(3-cyano-benzylamino)-phenyl]-thiophene-2-carboxylic acid, 4-bromo-3-carboxymethoxy-5-{3-[(pyridin-3-ylmethyl)-amino]-phenyl}-thiophene-2-carboxylic acid, 4-bromo-3-carboxymethoxy-5-[3-(4-fluoro-benzylamino)-phenyl]-thiophene-2-carboxylic acid, 4-bromo-3-carboxymethoxy-5-[3-(4-trifluoromethyl-benzylamino)-phenyl]-thiophene-2-carboxylic acid, 4-bromo-3-carboxymethoxy-5-[3-(4-methoxy-benzylamino)-phenyl]-thiophene-2-carboxylic acid, 5-[3-(4-benzyloxy-benzylamino)-phenyl]-4-bromo-3-carboxymethoxy-thiophene-2-carboxylic acid, 4-bromo-3-carboxymethoxy-5-[3-(4-phenoxy-benzylamino)-phenyl]-thiophene-2-carboxylic acid, 4-bromo-3-carboxymethoxy-5-{3-[(naphthalen-2-ylmethyl)-amino]-phenyl}-thiophene-2-carboxylic acid, 4-bromo-5-[3-(3-carboxy-benzylamino)-phenyl]-3-carboxymethoxy-thiophene-2-carboxylic acid, 4-bromo-3-carboxymethoxy-5-[3-(3-trifluoromethoxy-ben-zylamino)-phenyl]-thiophene-2-carboxylic acid, 4-bromo-3-carboxymethoxy-5-[3-(2-trifluoromethoxy-benzylamino)-phenyl]-thiophene-2-carboxylic acid, 4-bromo-3-carboxymethoxy-5-[3-(2-hydroxy-benzylamino)-phenyl]-thiophene-2-carboxylic acid, 4-bromo-3-carboxymethoxy-5-[3-(4-methyl-benzylamino)-phenyl]-thiophene-2-carboxylic acid, 4-bromo-3-carboxymethoxy-5-[3-(4-chloro-benzylamino)-phenyl]-thiophene-2-carboxylic acid, 4-bromo-3-carboxymethoxy-5-[3-(4-isopropyl-benzy-lamino)-phenyl]-thiophene-2-carboxylic acid, 4-bromo-3-carboxymethoxy-5-[3-(3-nitro-benzylamino)-phenyl]-thiophene-2-carboxylic acid, 4-bromo-3-carboxymethoxy-5-[3-(3-methanesulfonylamino-benzylamino)-phenyl]-thiophene-2-carboxylic acid, 5-[3-(3-amino-benzylamino)-phenyl]-4-bromo-3-carboxymethoxy-thiophene-2-carboxylic acid, 5-[3-(3-acetylamino-benzylamino)-phenyl]-4-bromo-3-carboxymethoxy-thiophene-2-carboxylic acid, 4-bromo-3-carboxymethoxy-5-(3-cyclohexylamino-phenyl)-thiophene-2-carboxylic acid, 4-bromo-3-carboxymethoxy-5-(3-cyclopentylamino-phe-nyl)-thiophene-2-carboxylic acid, 5-[3-(1-acetyl-piperidin-4-ylamino)-phenyl]-4-bromo-3-carboxymethoxy-thiophene-2-carboxylic acid, 4-bromo-3-carboxymethoxy-5-(3-cycloheptylamino-phenyl)-thiophene-2-carboxylic acid, 5-[3-(bicyclo[3.3.1]non-9-ylamino)-phenyl]-4-bromo-3-carboxymethoxy-thiophene-2-carboxylic acid, 4-bromo-3-carboxymethoxy-5-[3-(4-ethyl-cyclohexylamino)-phe-nyl]-thiophene-2-carboxylic acid, 4-bromo-3-carboxymethoxy-5-[3-cis(4-phenyl-cyclohexylamino)-phenyl]-thiophene-2-carboxylic acid, 4-bromo-3-carboxymethoxy-5-[3-trans(4-phenyl-cyclohexylamino)-phenyl]-thiophene-2-carboxylic acid, 4-bromo-3-carboxymethoxy-5-[3-(1-cyclohexyl-ethylamino)-phenyl]-thiophene-2-carboxylic acid, 4-bromo-3-carboxymethoxy-5-[3-(3,3,5,5-tetramethyl-cyclohexylamino)-phenyl]-thiophene-2-carboxylic acid, 5-[3-(adamantan-2-ylamino)-phenyl]-4-bromo-3-carboxymethoxy-thiophene-2-carboxylic acid, 4-bromo-3-carboxymethoxy-5-[3-(tetrahydro-pyran-4-ylamino)-phenyl]-thiophene-2-carboxylic acid, 4-bromo-3-carboxymethoxy-5-[3-(cyclohexylmethyl-amino)-phenyl]-thiophene-2-carboxylic acid, 4-bromo-3-carboxymethoxy-5-[3-(1-methanesulfonyl-piperidin-4-ylamino)-phenyl]-thiophene-2-carboxylic acid, 4-bromo-3-carboxymethoxy-5-[3-(1-phenylmethanesulfo-nyl-piperidin-4-ylamino)-phenyl]-thiophene-2-carboxylic acid, 4-bromo-3-carboxymethoxy-5-[3-(1-ethanesulfonyl-piperidin-4-ylamino)-phenyl]-thiophene-2-carboxylic acid, 4-bromo-5-{3-[1-(butane-1-sulfonyl)-piperidin-4-ylamino]-phenyl}-3-carboxymethoxy-thiophene-2-carboxylic acid, 5-{3-[1-(3,5-bis-trifluoromethyl-phenylmethanesulfonyl)-piperidin-4-ylamino]-phenyl}-4-bromo-3-carboxymethoxy-thiophene-2-carboxylic acid, 4-bromo-3-carboxymethoxy-5-{3-[1-(propane-1-sulfonyl)-piperidin-4-ylamino]-phenyl}-thiophene-2-carboxylic acid, 4-bromo-3-carboxymethoxy-5-{3-[1-(3-trifluoromethyl-phenylmethanesulfonyl)-piperidin-4-ylamino]-phenyl}-thiophene-2-carboxylic acid, 4-bromo-3-carboxymethoxy-5-{3-[1-(4-fluoro-phenylmethanesulfonyl)-piperidin-4-ylamino]-phenyl}-thiophene-2-carboxylic acid, 4-bromo-3-carboxymethoxy-5-{3-[1-(4-trifluoromethyl-phenylmethanesulfonyl)-piperidin-4-ylamino]-phenyl}-thiophene-2-carboxylic acid, 4-bromo-3-carboxymethoxy-5-{3-[1-(naphthalene-1-sulfonyl)-piperidin-4-ylamino]-phenyl}-thiophene-2-carboxylic acid, 4-bromo-3-carboxymethoxy-5-{3-[1-(naphthalene-2-sulfonyl)-piperidin-4-ylamino]-phenyl}-thiophene-2-carboxylic acid, 4-bromo-3-carboxymethoxy-5-{3-[1-(2-nitro-phenyl-methanesulfonyl)-piperidin-4-ylamino]-phenyl}-thiophene-2-carboxylic acid, 4-bromo-3-carboxymethoxy-5-{3-[1-(4-chloro-phenylmethanesulfonyl)-piperidin-4-ylamino]-phenyl}-thiophene-2-carboxylic acid, 4-bromo-3-carboxymethoxy-5-{3-[1-(3,5-dichloro-phenylmethanesulfonyl)-piperidin-4-ylamino]-phenyl}-thiophene-2-carboxylic acid, 4-bromo-3-carboxymethoxy- 5-{3-[1-(3,4-dichloro-phenylmethanesulfonyl)-piperidin-4-ylamino]-phenyl}-thiophene-2-carboxylic acid, 4-bromo-3-carboxymethoxy-5-{3-[1-(3-nitro-phenylmethanesulfonyl)-piperidin-4-ylamino]-phenyl}-thiophene-2-carboxylic acid, 4-bromo-3-carboxymethoxy-5-{3-[1-(3-chloro-phenyl-methanesulfonyl)-piperidin-4-ylamino]-phenyl}-thiophene-2-carboxylic acid, 4-bromo-3-carboxymethoxy-5-{3-[1-(2-phenyl-ethanesulfonyl)-piperidin-4-ylamino]-phenyl}-thiophene-2-carboxylic acid, 4-bromo-3-carboxymethoxy-5-[3-(1-o-tolylmethanesulfonyl-piperidin-4-ylamino)-phenyl]-thiophene-2-carboxylic acid, 4-bromo-3-carboxymethoxy-5-[3-(1-m-tolylmethanesulfonyl-piperidin-4-ylamino)-phenyl]-thiophene-2-carboxylic acid, 4-bromo-3-carboxymethoxy-5-{3-[1-(2,6-dimethyl-phenyl-methanesulfonyl)-piperidin-4-ylamino]-phenyl}-thiophene-2-carboxylic acid, 4-bromo-3-carboxymethoxy-5-{3-[1-(2-imidazol-1-yl-ethanesulfonyl)-piperidin-4-ylamino]-phenyl}-thiophene-2-carboxylic acid, 4-bromo-3-carboxymethoxy-5-{3-[1-(2-pyrazol-1-yl-ethanesulfonyl)-piperidin-4-ylamino]-phenyl}-thiophene-2-carboxylic acid, 4-bromo-3-carboxymethoxy-5-{3-[1-(2-isopropoxy-ethane-sulfonyl)-piperidin-4-ylamino]-phenyl}-thiophene-2-carboxylic acid, 5-{3-[1-(2-amino-phenylmethanesulfonyl)-piperidin-4-ylamino]-phenyl}-4-bromo-3-carboxymethoxy-thiophene-2-carboxylic acid, 4-[3-(3-bromo-5-carboxy-4-carboxymethoxy-thiophen-2-yl)-phenylamino]-piperidine-1-carboxylic acid methyl ester, 5-[3-(1-benzoyl-piperidin-4-ylamino)-phenyl]-4-bromo-3-carboxymethoxy-thiophene-2-carboxylic acid, 4-bromo-3-carboxymethoxy-5-[3-(1-phenylacetyl-piperidin-4-ylamino)-phenyl]-thiophene-2-carboxylic acid, 5-{3-[3-benzyl-1-(1-benzylcarbamoyl-piperidin-4-yl)-ureido]-phenyl}4-bromo-3-carboxymethoxy-thiophene-2-carboxylic acid, 5-[3-(1-benzylcarbamoyl-piperidin-4-ylamino)-phenyl]-4-bromo-3-carboxymethoxy-thiophene-2-carboxylic acid, 4-bromo-3-carboxymethoxy-5-{3-[(1-methanesulfonyl-piperidin-4-ylmethyl)-amino]-phenyl}-thiophene-2-carboxylic acid, 4-bromo-3-carboxymethoxy-5-{3-[(1-ethanesulfonyl-piperidin-4-ylmethyl)-amino]-phenyl}-thiophene-2-carboxylic acid, 5-{3-[(1-benzenesulfonyl-piperidin-4-ylmethyl)-amino]-phenyl}4-bromo-3-carboxymethoxy-thiophene-2-carboxylic acid, 4-bromo-3-carboxymethoxy-5-{3-[(1-phenylmethanesulfonyl-piperidin-4-ylmethyl)-amino]-phenyl}-thiophene-2-carboxylic acid, 5-(3-{[1-(2-amino-phenylmethanesulfonyl)-piperidin-4-ylmethyl]-amino}-phenyl)-4-bromo-3-carboxymethoxy-thiophene-2-carboxylic acid, 4-{[3-(3-bromo-5-carboxy-4-carboxymethoxy-thiophen-2-yl)-phenylamino]-methyl}-piperidine-1-carboxylic acid methyl ester, 4-bromo-3-carboxymethoxy-5-{3-[(1-phenylcarbamoyl-piperidin-4-ylmethyl)-amino]-phenyl}-thiophene-2-carboxylic acid, 5-{3-[(1-benzylcarbamoyl-piperidin-4-ylmethyl)-amino]-phenyl}-4-bromo-3-carboxymethoxy-thiophene-2-carboxylic acid, 4-bromo-3-carboxymethoxy-5-{3-[(1-cyclohexylcarbamoyl-piperidin-4-ylmethyl)-amino]-phenyl}-thiophene-2-carboxylic acid, 4-bromo-3-carboxymethoxy-5-(3-{[1-(4-methoxy-phenylcarbamoyl)-piperidin-4-ylmethyl]-amino}-phenyl)-thiophene-2-carboxylic acid, 4-bromo-3-carboxymethoxy-5-(3-{[1-(4-cyano-phenylcarbamoyl)-piperidin-4-ylmethyl]-amino}-phenyl)-thiophene-2-carboxylic acid, 4-bromo-3-carboxymethoxy-5-{3-[(1-p-tolylcarbamoyl-piperidin-4-ylmethyl)-amino]-phenyl}-thiophene-2-carboxylic acid, 4-bromo-3-carboxymethoxy-5-(3-{[1-(3-methoxy-phenylcarbamoyl)-piperidin-4-ylmethyl]-amino}-phenyl)-thiophene-2-carboxylic acid, 4-bromo-3-carboxymethoxy-5-(3-{[1-(2-methoxy-phenylcarbamoyl)-piperidin-4-ylmethyl]-amino}-phenyl)-thiophene-2-carboxylic acid, 4-bromo-3-carboxymethoxy-5-(3-{[1-(3-chloro-phenylcarbamoyl)-piperidin-4-ylmethyl]-amino}-phenyl)-thiophene-2-carboxylic acid, 4-bromo-3-carboxymethoxy-5-(3-{[1-(2-chloro-phenylcarbamoyl)-piperidin-4-ylmethyl]-amino}-phenyl)-thiophene-2-carboxylic acid, 4-bromo-3-carboxymethoxy-5-{3-[(1-m-tolylcarbamoyl-piperidin-4-ylmethyl)-amino]-phenyl}-thiophene-2-carboxylic acid, 4-bromo-3-carboxymethoxy-5-{3-[(1-o-tolylcarbamoyl-piperidin-4-ylmethyl)-amino]-phenyl}-thiophene-2-carboxylic acid, 4-bromo-3-carboxymethoxy-5-(3-{[1-(2,6-dimethyl-phenylcarbamoyl)-piperidin-4-ylmethyl]-amino}-phenyl)-thiophene-2-carboxylic acid, 4-bromo-3-carboxymethoxy-5-(3-{[1-(2-trifluoromethyl-phenylcarbamoyl)-piperidin-4-ylmethyl]-amino}-phenyl)-thiophene-2-carboxylic acid, 4-bromo-3-carboxymethoxy-5-(3-{[1-(methyl-phenyl-carbamoyl)-piperidin-4-ylmethyl]-amino}-phenyl)-thiophene-2-carboxylic acid, 4-bromo-3-carboxymethoxy-5-(3-{[1-(2-methylsulfanyl-phenylcarbamoyl)-piperidin-4-ylmethyl]-amino}-phenyl)-thiophene-2-carboxylic acid, 4-bromo-3-carboxymethoxy-5-(3-{[1-(2,3-dimethyl-phenylcarbamoyl)-piperidin-4-ylmethyl]-amino}-phenyl)-thiophene-2-carboxylic acid, 4-{[3-(3-bromo-5-carboxy-4-carboxymethoxy-thiophen-2-yl)-phenylamino]-methyl}-piperidine-1-carboxylic acid tert-butyl ester, 4-bromo-3-carboxymethoxy-5-(3-cyclohexylmethoxy-phenyl)-thiophene-2-carboxylic acid, 5-[3-(3,5-bis-trifluoromethyl-benzyloxy)-phenyl]-4-bromo-3-carboxymethoxy-thiophene-2-carboxylic acid, 5-(3-benzyloxy-phenyl)-4-bromo-3-carboxymethoxy-thiophene-2-carboxylic acid, 4-bromo-3-carboxymethoxy-5-[3-(1-phenyl-ethoxy)-phenyl]-thiophene-2-carboxylic acid, 4-bromo-5-[3-(1-carboxy-ethoxy)-phenyl]-3-carboxymethoxy-thiophene-2-carboxylic acid, 4-bromo-3-carboxymethoxy-5-[3-(naphthalen-2-ylmethoxy)-phenyl]-thiophene-2-carboxylic acid, 4-bromo-3-carboxymethoxy-5-[3-(3-methyl-3,3a-dihydro-benzo[1,2,5]oxadiazol-5-ylmethoxy)-phenyl]-thiophene-2-carboxylic acid, 4-bromo-5-[3-(3-carboxy-benzyloxy)-phenyl]-3-carboxymethoxy-thiophene-2-carboxylic acid, 4-bromo-3-carboxymethoxy-5-[3-(3-trifluoromethoxy-benzyloxy)-phenyl]-thiophene-2-carboxylic acid, 4-[3-(3-bromo-5-carboxy-4-carboxymethoxy-thiophen-2-yl)-phenoxy]-piperidine-1-carboxylic acid tert-butyl ester, 4-bromo-3-carboxymethoxy-5-[3-(1-phenylcarbamoyl-piperidin-4-yloxy)-phenyl]-thiophene-2-carboxylic acid, 4-[3-(3-bromo-5-carboxy-4-carboxymethoxy-thiophen-2-yl)-phenoxy]-piperidine-1-carboxylic acid phenyl ester, 4-bromo-3-carboxymethoxy-5-[3-(1-phenylmethanesulfonyl-piperidin-4-yloxy)-phenyl]-thiophene-2-carboxylic acid, 4-[3-(3-bromo-5-carboxy-4-carboxymethoxy-thiophen-2-yl)-phenoxymethyl]-piperidine-1-carboxylic acid tert-butyl ester, 4-bromo-3-carboxymethoxy-5-[3-(1-methanesulfonyl-piperidin-4-ylmethoxy)-phenyl]-thiophene-2-carboxylic acid, 4-bromo-3-carboxymethoxy-5-[3-(1-phenylmethanesulfonyl-piperidin-4-ylmethoxy)-phenyl]-thiophene-2-carboxylic acid, 4-bromo-3-carboxymethoxy-5-{3-[1-(toluene-4-sulfonyl)-piperidin-4-ylmethoxy]-phenyl}-thiophene-2-carboxylic acid, 5-[3-(1-benzenesulfonyl-piperidin-4-ylmethoxy)-phenyl]-4-bromo-3-carboxymethoxy-thiophene-2-carboxylic acid, 4-[3-(3-bromo-5-carboxy-4-carboxymethoxy-thiophen-2-yl)-phenoxymethyl]-piperidine-1-carboxylic acid phenyl ester, 4-[3-(3-bromo-5-carboxy-4-carboxymethoxy-thiophen-2-yl)-phenoxymethyl]-piperidine-1-carboxylic acid methyl ester, 4-bromo-3-carboxymethoxy-5-[3-(1-ethylcarbamoyl-piperidin-4-ylmethoxy)-phenyl]-thiophene-2-carboxylic acid, 4-bromo-3-carboxymethoxy-5-[3-(1-phenylcarbamoyl-piperidin-4-ylmethoxy)-phenyl]-thiophene-2-carboxylic acid, 4-bromo-3-carboxymethoxy-5-{3-[1-(2-chloro-phenylcarbamoyl)-piperidin-4-ylmethoxy]-phenyl}-thiophene-2-carboxylic acid, 4-bromo-3-carboxymethoxy-5-[3-(1-o-tolyl-carbamoyl-piperidin-4-ylmethoxy)-phenyl]-thiophene-2-carboxylic acid, 4-bromo-3-carboxymethoxy-5-{3-[1-(2-methoxy-phenylcarbamoyl)-piperidin-4-ylmethoxy]-phenyl}-thiophene-2-carboxylic acid, 4-bromo-3-carboxymethoxy-5-{3-[1-(2-isopropyl-phenylcarbamoyl)-piperidin-4-ylmethoxy]-phenyl}-thiophene-2-carboxylic acid, 4-bromo-3-carboxymethoxy-5-{3-[1-(2-phenoxy-phenylcarbamoyl)-piperidin-4-ylmethoxy]-phenyl}-thiophene-2-carboxylic acid, 4-bromo-3-carboxymethoxy-5-{3-[1-(2,6-diethyl-phenylcarbamoyl)-piperidin-4-ylmethoxy]-phenyl}-t, 4-bromo-3-carboxymethoxy-5-{3-[1-(2,4,6-trimethyl-phenylcarbamoyl)-piperidin-4-ylmethoxy]-phenyl}-thiophene-2-carboxylic acid, 4-bromo-3-carboxymethoxy-5-{3-[1-(2-isopropyl-6-methyl-phenylcarbamoyl)-piperidin-4-ylmethoxy]-phenyl}-thiophene-2-carboxylic acid, 4-bromo-3-carboxymethoxy-5-{3-[1-(3-phenoxy-phenylcarbamoyl)-piperidin-4-ylmethoxy]-phenyl}-thiophene-2-carboxylic acid, 4-bromo-3-carboxymethoxy-5-{3-[1-(2,6-dimethyl-phenylcarbamoyl)-piperidin-4-ylmethoxy]-phenyl}-thiophene-2-carboxylic acid, 4-bromo-3-carboxymethoxy-5-{3-[1-(4-methyl-2-nitro-phenylcarbamoyl)-piperidin-4-ylmethoxy]-phenyl}-thiophene-2-carboxylic acid, 4-bromo-3-carboxymethoxy-5-{3-[1-(5-chloro-2-nitro-phenylcarbamoyl)-piperidin-4-ylmethoxy]-phenyl}-thiophene-2-carboxylic acid, 4-bromo-3-carboxymethoxy-5-{3-[1-(2-nitro-phenylcarbamoyl)-piperidin-4-ylmethoxy]-phenyl}-thiophene-2-carboxylic acid, 4-bromo-3-carboxymethoxy-5-(3-phenylaminomethyl-phenyl)-thiophene-2-carboxylic acid, 4-bromo-3-carboxymethoxy-5-{3-[(3-trifluoromethyl-phenylamino)-methyl]-phenyl}-thiophene-2-carboxylic acid, 4-bromo-3-carboxymethoxy-5-{3-[(3,4-difluoro-phenylamino)-methyl]-phenyl}-thiophene-2-carboxylic acid, 4-bromo-3-carboxymethoxy-5-(3-cyclohexylaminomethyl-phenyl)-thiophene-2-carboxylic acid, 4-bromo-3-carboxymethoxy-5-{3-[(3-nitro-phenylamino)-methyl]-phenyl}-thiophene-2-carboxylic acid, 4-bromo-5-{3-[(4-bromo-3-trifluoromethyl-phenylamino)-methyl]-phenyl}-3-carboxymethoxy-thiophene-2-carboxylic acid, 4-bromo-3-carboxymethoxy-5-{3-[(3,5-difluoro-phenylamino)-methyl]-phenyl}-thiophene-2-carboxylic acid, 4-bromo-3-carboxymethoxy-5-{3-[(3-fluoro-4-methyl-phenylamino)-methyl]-phenyl}-thiophene-2-carboxylic acid, 4-bromo-3-carboxymethoxy-5-{3-[(4-chloro-3-trifluoromethyl-phenylamino)-methyl]-phenyl}-thiophene-2-carboxylic acid, 4-bromo-3-carboxymethoxy-5-{3-[(4-methyl-3-nitro-phenylamino)-methyl]-phenyl}-thiophene-2-carboxylic acid, 5-{3-[(acetyl-cyclohexyl-amino)-methyl]-phenyl})-4-bromo-3-carboxymethoxy-thiophene-2-carboxylic acid, 4-bromo-3-carboxymethoxy-5-{3-[(cyclohexyl-methanesulfonyl-amino)-methyl]-phenyl}-thiophene-2-carboxylic acid, 4-bromo-3-carboxymethoxy-5-{3-[(cyclohexyl-methoxycarbonyl-amino)-methyl]-phenyl}-thiophene-2-carboxylic acid, 4-bromo-3-carboxymethoxy-5-[3-(1-cyclohexyl-3-ethyl-ureidomethyl)-phenyl]-thiophene-2-carboxylic acid, 5-(3-{[acetyl-(3,3,5,5-tetramethyl-cyclohexyl)-amino]-methyl}-phenyl)-4-bromo-3-carboxymethoxy-thiophene-2-carboxylic acid, 4-{acetyl-[3-(3-bromo-5-carboxy-4-carboxymethoxy-thiophen-2-yl)-benzyl]-amino}-piperidine-1-carboxylic acid ethyl ester, 4-bromo-3-carboxymethoxy-5-(4-methoxy-3-phenylaminomethyl-phenyl)-thiophene-2-carboxylic acid, 5-{3-[(acetyl-phenyl-amino)-methyl]-4-methoxy-phenyl}-4-bromo-3-carboxymethoxy-thiophene-2-carboxylic acid, 5-{3-[(3,5-bis-trifluoromethyl-phenylamino)-methyl]-4-methoxy-phenyl}-4-bromo-3-carboxymethoxy-thiophene-2-carboxylic acid, 4-bromo-3-carboxymethoxy-5-[3-(2-carboxy-vinyl)-4-methoxy-phenyl]-thiophene-2-carboxylic acid, 4-bromo-3-carboxymethoxy-5-{4-methoxy-3-[2-(2,2,2-trifluoro-ethyl-carbamoyl)-vinyl]-phenyl}-thiophene-2-carboxylic acid, 5-(3,4-bis-benzyloxy-phenyl)-4-bromo-3-(2-hydroxy-ethoxy)-thiophene-2-carboxylic acid, 5-(3-benzyloxy-4-hydroxy-phenyl)-4-bromo-3-(2-hydroxy-ethoxy)-thiophene-2-carboxylic acid, 5-(4-benzyloxy-3-hydroxy-phenyl)-4-bromo-3-(2-hydroxy-ethoxy)-thiophene-2-carboxylic acid, 4-bromo-3-methoxycarbonylmethoxy-5-phenyl-thiophene-2-carboxylic acid, 4-bromo-3-methoxycarbonylmethoxy-5-[3-(3,3,5,5-tetramethyl-cyclohexylamino)-phenyl]-thiophene-2-carboxylic acid, 4-bromo-3-methoxycarbonylmethoxy-5-[3-(1-phenylmethanesulfonyl-piperidin-4-ylamino)-phenyl]-thiophene-2-carboxylic acid, 4-bromo-3-carboxymethoxy-5-phenyl-thiophene-2-carboxylic acid methyl ester, 4-bromo-3-carboxymethoxy-5-{3-[1-(2-nitro-phenylmethanesulfonyl)-piperidin-4-ylamino]-phenyl}-thiophene-2-carboxylic acid methyl ester, 4-bromo-3-carboxymethoxy-5-{3-[1-(4-chloro-phenylmethanesulfonyl)-piperidin-4-ylamino]-phenyl}-thiophene-2-carboxylic acid methyl ester, 4-bromo-3-carboxymethoxy-5-{3-[1-(3,5-dichloro-phenylmethanesulfonyl)-piperidin-4-ylamino]-phenyl}-thiophene-2-carboxylic acid methyl ester, 4-bromo-3-carboxymethoxy-5-{3-[1-(3,4-dichloro-phenylmethanesulfonyl)-piperidin-4-ylamino]-phenyl}-thiophene-2-carboxylic acid methyl ester, 4-bromo-3-carboxymethoxy-5-(3-cyclohexylmethoxy-phenyl)-thiophene-2-carboxylic acid methyl ester, 4-bromo-3-carboxymethoxy-5-[3-(1-phenylmethanesulfonyl-piperidin-4-ylamino)-phenyl]-thiophene-2-carboxylic acid methyl ester, 4-bromo-3-carboxymethoxy-5-{3-[1-(3-trifluoromethyl-phenylmethanesulfonyl)-piperidin-4-ylamino]-phenyl}-thiophene-2-carboxylic acid methyl ester, 4-bromo-3-carboxymethoxy-5-{3-[1-(4-fluoro-phenylmethanesulfonyl)-piperidin-4-ylamino]-phenyl}-thiophene-2-carboxylic acid methyl ester, 4-bromo-3-carboxymethoxy-5-{3-[1-(4-trifluoromethyl-phenylmethanesulfonyl)-piperidin-4-ylamino]-phenyl}-thiophene-2-carboxylic acid methyl ester, 4-bromo-3-carboxymethoxy-5-[3-(3,3,5,5-tetramethyl-cyclohexylamino)-phenyl]-thiophene-2-carboxylic acid methyl ester, 5-{3-[(acetyl-cyclohexyl-amino)-methyl]-phenyl}4-bromo-3-carboxymethoxy-thiophene-2-carboxylic acid methyl ester, 3-carboxymethoxy-4-methyl-5-phenyl-thiophene-2-carboxylic acid, 5-bromo-3-carboxymethoxy-4-methyl-thiophene-2-carboxylic acid, 3-carboxymethoxy-4-methyl-thiophene-2-carboxylic acid, 3-carboxymethoxy-4-methyl-5-styryl-thiophene-2-carboxylic acid, 3-carboxymethoxy-5-(4-hydroxy-phenyl)-4-methyl-thiophene-2-carboxylic acid, 3-carboxymethoxy-4-methyl-5-[3-(pyridin-3-ylcarbamoyl)-phenyl]-thiophene-2-carboxylic acid, 3-carboxymethoxy-5-[4-(3-isopropyl-ureido)-phenyl]-4-methyl-thiophene-2-carboxylic acid, 5-(3-carboxymethanesulfonylamino-phenyl)-3-carboxymethoxy-4-methyl-thiophene-2-carboxylic acid, 5-(3-benzylamino-phenyl)-3-carboxymethoxy-4-methyl-thiophene-2-carboxylic acid, 3-carboxymethoxy-5-[3-(cyclohexylmethyl-amino)-phenyl]-4-methyl-thiophene-2-carboxylic acid, 3-carboxymethoxy-4-methyl-5-[3-(3-phenoxy-benzylamino)-phenyl]-thiophene-2-carboxylic acid, 5-[3-(3-bromo-benzylamino)-phenyl]-3-carboxymethoxy-4-methyl-thiophene-2-carboxylic acid, 3-carboxymethoxy-4-methyl-5-[3-(3-trifluoromethyl-benzylamino)-phenyl]-thiophene-2-carboxylic acid, 3-carboxymethoxy-5-[3-(cycloheptylmethyl-amino)-phenyl]-4-methyl-thiophene-2-carboxylic acid, 5-benzofuran-2-yl-4-bromo-3-carboxymethoxy-thiophene-2-carboxylic acid, 4,5-bis-benzofuran-2-yl-3-ethoxycarbonylmethoxy-thiophene-2-carboxylic acid methyl ester, 5-biphenyl-3-yl-4-bromo-3-carboxymethoxy-thiophene-2-carboxylic acid, 5-benzo[1,3]dioxol-5-yl-4-bromo-3-carboxymethoxy-thiophene-2-carboxylic acid, 4-bromo-3-carboxymethoxy-5-pyridin-4-yl-thiophene-2-carboxylic acid, 4-bromo-3-carboxymethoxy-5-[3-(4-trifluoromethyl-phenylcarbamoyl)-phenyl]-thiophene-2-carboxylic acid, 4-bromo-3-carboxymethoxy-5-naphthalen-1-yl-thiophene-2-carboxylic acid, 3-bromo-4-carboxymethoxy-[2,3]-bithiophenyl-5-carboxylic acid, 4-bromo-3-carboxymethoxy-5-pyridin-3-yl-thiophene-2-carboxylic acid, 3-bromo-4-carboxymethoxy-2'-formyl-[2,3]-bithiophenyl-5-carboxylic acid, 3-bromo-4-carboxymethoxy-2'-(isobutylamino-methyl)-[2,3]-bithiophenyl-5-carboxylic acid, 4-bromo-3-carboxymethoxy-5-{3-[(5-phenylcarbamoyl-thiophen-2-ylmethyl)-amino]-phenyl}-thiophene-2-carboxylic acid, 5-{3-[(5-benzylcarbamoyl-thiophen-2-ylmethyl)-amino]-phenyl}4-bromo-3-carboxymethoxy-thiophene-2-carboxylic acid, and 4-bromo-3-carboxymethoxy-5-{3-[(5-cyclohexylcarbamoyl-thiophen-2-ylmethyl)-amino]-phenyl}-thiophene-2-carboxylic acid.

In some embodiments, the compound can be selected from 4-bromo-3-(carboxymethoxy)-5-[3-(piperidin-4-ylamino)phenyl]thiophene-2-carboxylic acid, ({4-bromo-2-(methoxycarbonyl)-5-[3-(piperidin-4-ylamino)phenyl]thien-3-yl}oxy)acetic acid, methyl 4-bromo-3-(2-ethoxy-2-oxoethoxy)-5-(3-{[1-(5-nitropyridin-2-yl)piperidin-4-yl]amino)phenyl)thiophene-2-carboxylate, 4-bromo-3-(carboxymethoxy)-5-(3-{[1-(5-nitropyridin-2-yl)piperidin-4-yl]amino}phenyl)thiophene-2-carboxylic acid, 5-[3-({1-[5-(acetylamino)pyridin-2-yl]piperidin-4-yl}amino)phenyl]-4-bromo-3-(carboxymethoxy)thiophene-2-carboxylic acid, 4-bromo-3-(carboxymethoxy)-5-(3-{1-(5-{[(methylamino)carbonyl]amino}pyridin-2-yl)piperidin-4-yl]amino}phenyl)thiophene-2-carboxylic acid, 4-bromo-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid, 4-bromo-3-(carboxymethoxy)-5-{3-[(1-{5-[(methylsulfonyl)amino]pyridin-2-yl}piperidin-4-yl)amino]phenyl}thiophene-2-carboxylic acid, 3-(carboxymethoxy)-5-phenylthiophene-2-carboxylic acid, methyl 5-(3-{[1-(benzylsulfonyl)piperidin-4-yl]amino}phenyl)-4-bromo-3-{2-[(2-methylphenyl)amino]-2-oxoethoxy}thiophene-2-carboxylate, 5-(3-{[1-(benzylsulfonyl)piperidin-4-yl][(ethylamino)carbonyl]amino}phenyl)-4-bromo-3-(carboxymethoxy)thiophene-2-carboxylic acid, 4,5-dibromo-3-[carboxy(fluoro)methoxy]thiophene-2-carboxylic acid, {[5-phenyl-2-(2H-tetrazol-5-yl)thien-3-yl]oxy}acetic acid, {[5-[3-({[1-(anilinocarbonyl)piperidin-4-yl]methyl}amino)phenyl]-4-bromo-2-(methoxycarbonyl)thien-3-yl]oxy}acetic acid, 5-(3-{{[1-(anilinocarbonyl)piperidin-4-yl]methyl}[(ethylamino)carbonyl]amino}phenyl)-4-bromo-3-(carboxymethoxy)thiophene-2-carboxylic acid, 4-bromo-3-(carboxymethoxy)-5-{3-[(1-{[2-(trifluoromethoxy)phenyl]sulfonyl}piperidin-4-yl)amino]phenyl}thiophene-2-carboxylic acid, 4-bromo-3-(carboxymethoxy)-5-[3-({1-[(5-chloro-2-methoxyphenyl)sulfonyl]piperidin-4-yl}amino)phenyl]thiophene-2-carboxylic acid, 4-bromo-3-(carboxymethoxy)-5-[3-({1-[(3,5-dichloro-2-hydroxyphenyl)sulfonyl]piperidin-4-yl}amino)phenyl]thiophene-2-carboxylic acid, propyl 4-bromo-3-(2-tert-butoxy-2-oxoethoxy)-5-{3-[(3,3,5,5-tetramethylcyclohexyl)amino]phenyl}thiophene-2-carboxylate, [(4-bromo-2-(propoxycarbonyl)-5-{3-[(3,3,5,5-tetramethylcyclohexyl)amino]phenyl}thien-3-yl)oxy]acetic acid, 4-bromo-3-carboxymethoxy-5-{3-[1-(2-trifluoromethyl-phenylmethanesulfonyl)-piperidin-4-ylamino]-phenyl}-thiophene-2-carboxylic acid, 4-bromo-3-carboxymethoxy-5-[3-(indan-2-ylamino)-phenyl]-thiophene-2-carboxylic acid, 3-[3-(3-bromo-5-carboxy-4-carboxymethoxy-thiophen-2-yl)-phenylamino]-8-aza-bicyclo[3.2.1]octane-8-carboxylic acid ethyl ester, 4-bromo-3-carboxymethoxy-5-[3-(8-phenylmethanesulfonyl-8-aza-bicyclo[3.2.1]oct-3-ylamino)-phenyl]-thiophene-2-carboxylic acid, 5-(1-benzyl-1H-pyrazol-4-yl)-4-bromo-3-carboxymethoxy-thiophene-2-carboxylic acid; compound with methane, 5-{3-[1-(2-acetylamino-phenylmethanesulfonyl)-piperidin-4-ylamino]-phenyl}-4-bromo-3-carboxymethoxy-thiophene-2-carboxylic acid, 5-{3-[1-(2-acetylamino-phenylmethanesulfonyl)-piperidin-4-ylamino]-phenyl}-3-carboxymethoxy-thiophene-2-carboxylic acid, 4-bromo-3-carboxymethoxy-5-{3-[1-(2-methanesulfonylamino-phenylmethanesulfonyl)-piperidin-4-ylamino]-phenyl}-thiophene-2-carboxylic acid, 3-carboxymethoxy-5-{3-[1-(2-methanesulfonylamino-phenylmethanesulfonyl)-piperidin-4-ylamino]-phenyl}-thiophene-2-carboxylic acid, 4-bromo-3-carboxymethoxy-5-(3-{1-[2-(3-ethyl-ureido)-phenylmethanesulfonyl]-piperidin-4-ylamino}-phenyl)-thiophene-2-carboxylic acid, 3-carboxymethoxy-5-(3-{1-[2-(3-ethyl-ureido)-phenylmethanesulfonyl]-piperidin-4-ylamino}-phenyl)-thiophene-2-carboxylic acid, 4-bromo-3-carboxymethoxy-5-{3-[1-(2-chloromethanesulfonylamino-phenylmethanesulfonyl)-piperidin-4-ylamino]-phenyl}-thiophene-2-carboxylic acid, 5-{3-[(acetyl-isopropyl-amino)-methyl]-phenyl}4-bromo-3-carboxymethoxy-thiophene-2-carboxylic acid, 5-{3-[(acetyl-isobutyl-amino)-methyl]-phenyl)-4-bromo-3-carboxymethoxy-thiophene-2-carboxylic acid, 5-{3-[(acetyl-cyclohexylmethyl-amino)-methyl]-phenyl)}4-bromo-3-carboxymethoxy-thiophene-2-carboxylic acid, 5-{3-[(acetyl-p-tolyl-amino)-methyl]-phenyl}-4-bromo-3-carboxymethoxy-thiophene-2-carboxylic acid, 5-(3-{[acetyl-(4-tert-butyl-phenyl)-amino]-methyl}-phenyl)-4-bromo-3-carboxymethoxy-thiophene-2-carboxylic acid, 5-(3-{[acetyl-(4-trifluoromethyl-phenyl)-amino]-methyl}-phenyl)-4-bromo-3-carboxymethoxy-thiophene-2-carboxylic acid, 5-{3-[(acetyl-phenyl-amino)-methyl]-phenyl}-4-bromo-3-carboxymethoxy-thiophene-2-carboxylic acid, 5-{3-[(acetyl-cyclopropyl-amino)-methyl]-phenyl}-4-bromo-3-carboxymethoxy-thiophene-2-carboxylic acid, 5-(3-{[acetyl-(4-bromo-phenyl)-amino]-methyl}-phenyl)-4-bromo-3-carboxymethoxy-thiophene-2-carboxylic acid, 5-{3-[(acetyl-biphenyl-4-yl-amino)-methyl]-phenyl}-4-bromo-3-carboxymethoxy-thiophene-2-carboxylic acid, 5-(3-{[acetyl-(4-phenoxy-phenyl)-amino]-methyl}-phenyl)-4-bromo-3-carboxymethoxy-thiophene-2-carboxylic acid, 5-{3-[(acetyl-benzyl-amino)-methyl]-phenyl}-4-bromo-3-carboxymethoxy-thiophene-2-carboxylic acid, 5-(3-{[acetyl-(4-methoxy-benzyl)-amino]-methyl}-phenyl)-4-bromo-3-carboxymethoxy-thiophene-2-carboxylic acid, 5-{3-[(acetyl-biphenyl-4-ylmethyl-amino)-methyl]-phenyl}-4-bromo-3-carboxymethoxy-thiophene-2-carboxylic acid, 5-(3-{[acetyl-(4-chloro-phenyl)-amino]-methyl}-phenyl)-4-bromo-3-carboxymethoxy-thiophene-2-carboxylic acid, 5-(3-{[acetyl-(4-trifluoromethyl-phenyl)-amino]-methyl}-phenyl)-4-bromo-3-carboxymethoxy-thiophene-2-carboxylic acid, 5-(3-{[acetyl-(3,5-bis-trifluoromethyl-phenyl)-amino]-methyl}-phenyl)-4- bromo--carboxymethoxy-thiophene-2-carboxylic acid, 5-[3-({acetyl-[2-(4-chloro-phenyl)-ethyl]-amino}-methyl)-phenyl]-4-bromo-3-carboxymethoxy-thiophene-2-carboxylic acid, 4-bromo-3-carboxymethoxy-5-[3-(1,3-diisopropyl-ureido)-phenyl]-thiophene-2-carboxylic acid, 4-bromo-3-carboxymethoxy-5-{3-[1-(2,2-dimethyl-propyl)-3-isopropyl-ureido]-phenyl}-thiophene-2-carboxylic acid, 4-bromo-3-carboxymethoxy-5-[3-(1-isobutyl-3-isopropyl-ureido)-phenyl]-thiophene-2-carboxylic acid, 5-[3-(1-benzyl-3-isopropyl-ureido)-phenyl]-4-bromo-3-carboxymethoxy-thiophene-2-carboxylic acid, 4-bromo-3-carboxymethoxy-5-{3-[3-isopropyl-1-(4-trifluoromethyl-benzyl)-ureido]-phenyl}-thiophene-2-carboxylic acid, 4-bromo-5-{3-[1-(4-tert-butyl-benzyl)-3-isopropyl-ureido]-phenyl}-3-carboxymethoxy-thiophene-2-carboxylic acid, 5-[3-(acetyl-cyclohexylmethyl-amino)-phenyl]-4-bromo-3-carboxymethoxy-thiophene-2-carboxylic acid, 4-bromo-3-carboxymethoxy-5-{3-[cyclohexylmethyl-(3-methyl-butyryl)-amino]-phenyl}-thiophene-2-carboxylic acid, 4-bromo-3-carboxymethoxy-5-[3-(cyclohexanecarbonyl-cyclohexylmethyl-amino)-phenyl]-thiophene-2-carboxylic acid, 4-bromo-3-carboxymethoxy-5-[3-(cyclohexylmethyl-isobutyryl-amino)-phenyl]-thiophene-2-carboxylic acid, 4-bromo-3-carboxymethoxy-5-[3-(cyclohexylmethyl-methoxycarbonyl-amino)-phenyl]-thiophene-2-carboxylic acid, 3-carboxymethoxy-5-[3-(cyclohexylmethyl-methoxycarbonyl-amino)-phenyl]-4-methyl-thiophene-2-carboxylic acid, 3-carboxymethoxy-5-[3-(cyclohexylmethyl-isopropoxycarbonyl-amino)-phenyl]-4-methyl-thiophene-2-carboxylic acid, 5-[3-(bis-cyclohexylmethyl-amino)-phenyl]-3-carboxymethoxy-4-methyl-thiophene-2-carboxylic acid, 4-bromo-3-carboxymethoxy-5-[3-(1-cyclohexylmethyl-3-phenyl-ureido)-phenyl]-thiophene-2-carboxylic acid, 5-[3-(3-benzyl-1-cyclohexylmethyl-ureido)-phenyl]-4-bromo-3-carboxymethoxy-thiophene-2-carboxylic acid, 4-bromo-3-carboxymethoxy-5-{3-[1-cyclohexylmethyl-3-(4-ethyl-phenyl)-ureido]-phenyl}-thiophene-2-carboxylic acid, 4-bromo-3-carboxymethoxy-5-{3-[1-cyclohexylmethyl-3-(4-ethoxy-phenyl)-ureido]-phenyl}-thiophene-2-carboxylic acid, 4-bromo-3-carboxymethoxy-5-{3-[1-cyclohexylmethyl-3-(4-phenoxy-phenyl)-ureido]-phenyl}-thiophene-2-carboxylic acid, 4-bromo-3-carboxymethoxy-5-{3-[3-(2-cyano-phenyl)-1-cyclohexylmethyl-ureido]-phenyl}-thiophene-2-carboxylic acid, 4-bromo-3-carboxymethoxy-5-[3-(1-cyclohexylmethyl-3-thiophen-3-yl-ureido)-phenyl]-thiophene-2-carboxylic acid, 4-bromo-3-carboxymethoxy-5-{3-[1-cyclohexylmethyl-3-(3,5-dimethyl-isoxazol-4-yl)-ureido]-phenyl}-thiophene-2-carboxylic acid, 4-bromo-3-carboxymethoxy-5-{3-[1-cyclohexylmethyl-3-(5-methyl-3-phenyl-isoxazol-4-yl)-ureido]-phenyl}-thiophene-2-carboxylic acid, 4-bromo-3-carboxymethoxy-5-{3-[3-(4-carboxy-phenyl)-1-cyclohexylmethyl-ureido]-phenyl}-thiophene-2-carboxylic acid, 4-bromo-3-carboxymethoxy-5-[3-(1-cyclohexylmethyl-3-ethyl-ureido)-phenyl]-thiophene-2-carboxylic acid, 3-carboxymethoxy-5-[3-(1-cyclohexylmethyl-3-isopropyl-ureido)-phenyl]-4-methyl-thiophene-2-carboxylic acid, 3-carboxymethoxy-5-[3-(1-cyclohexyl-3-isopropyl-ureido)-phenyl]-4-methyl-thiophene-2-carboxylic acid, 3-carboxymethoxy-5-[3-(1-cyclohexylmethyl-3-phenyl-ureido)-phenyl]-4-methyl-thiophene-2-carboxylic acid, 5-[3-(3-benzyl-1-cyclohexylmethyl-ureido)-phenyl]-3-carboxymethoxy-4-methyl-thiophene-2-carboxylic acid, 5-[3-(3-benzyl-1-cyclohexyl-ureido)-phenyl]-3-carboxymethoxy-4-methyl-thiophene-2-carboxylic acid, 3-carboxymethoxy-5-[3-(1-cyclohexylmethyl-3-phenethyl-ureido)-phenyl]-4-methyl-thiophene-2-carboxylic acid, 3-carboxymethoxy-5-[3-(1-cyclohexylmethyl-3-phenethyl-ureido)-phenyl]-4-methyl-thiophene-2-carboxylic acid, 4-bromo-3-isopropoxycarbonylmethoxy-5-[3-(1-phenylmethanesulfonyl-piperidin-4-ylamino)-phenyl]-thiophene-2-carboxylic acid, 4-bromo-3-isobutoxycarbonylmethoxy-5-[3-(1-phenylmethanesulfonyl-piperidin-4-ylamino)-phenyl]-thiophene-2-carboxylic acid, 4-bromo-5-[3-(1-phenylmethanesulfonyl-piperidin-4-ylamino)-phenyl]-3-propoxycarbonylmethoxy-thiophene-2-carboxylic acid, 4-bromo-3-cyclopropylmethoxycarbonylmethoxy-5-[3-(1-phenylmethanesulfonyl-piperidin-4-ylamino)-phenyl]-thiophene-2-carboxylic acid, 3-benzyloxycarbonylmethoxy-4-bromo-5-[3-(1-phenylmethanesulfonyl-piperidin-4-ylamino)-phenyl]-thiophene-2-carboxylic acid, 4-bromo-3-cyclohexylmethoxycarbonylmethoxy-5-[3-(1-phenylmethanesulfonyl-piperidin-4-ylamino)-phenyl]-thiophene-2-carboxylic acid, 4-bromo-3-cyclohexyloxycarbonylmethoxy-5-[3-(1-phenylmethanesulfonyl-piperidin-4-ylamino)-phenyl]-thiophene-2-carboxylic acid, 4-bromo-3-carboxymethoxy-5-{3-[1-(2,3-dichloro-phenylmethanesulfonyl)-piperidin-4-ylamino]-phenyl}-thiophene-2-carboxylic acid, 4-bromo-5-{3-[1-(2,3-dichloro-phenylmethanesulfonyl)-piperidin-4-ylamino]-phenyl}-3-methoxycarbonylmethoxy-thiophene-2-carboxylic acid, 4-bromo-3-carboxymethoxy-5-{3-[1-(2,3-dichloro-phenylmethanesulfonyl)-piperidin-4-ylamino]-phenyl}-thiophene-2-carboxylic acid methyl ester, [4-bromo-5-(3-cyclohexylamino-phenyl)-2-(2H-tetrazol-5-yl)-thiophen-3-yloxy]-acetic acid, [4-bromo-5-[3-(cyclohexylmethyl-amino)-phenyl]-2-(2H-tetrazol-5-yl)-thiophen-3-yloxy]-acetic acid, [4-bromo-5-[3-(3,3,5,5-tetramethyl-cyclohexylamino)-phenyl]-2-(2H-tetrazol-5-yl)-thiophen-3-yloxy]-acetic acid, tetrazole/acid: [5-(3-[acetyl-(3,3,5,5-tetramethyl-cyclohexyl)-amino]-phenyl}-4-bromo-2-(2H-tetrazol-5-yl)-thiophen-3-yloxy]-acetic acid, [4-bromo-5-[3-(1-phenylmethanesulfonyl-piperidin-4-ylamino)-phenyl]-2-(2H-tetrazol-5-yl)-thiophen-3-yloxy]-acetic acid, 4-bromo-3-carboxymethoxy-5-[3-(1-phenylmethanesulfonyl-piperidin-4-ylamino)-phenyl]-thiophene-2-carboxylic acid methyl ester, ethanolamine salt, 4-bromo-3-carboxymethoxy-5-[3-(1-phenylmethanesulfonyl-piperidin-4-ylamino)-phenyl]-thiophene-2-carboxylic acid methyl ester, choline salt, 4-bromo-3-carboxymethoxy-5-[3-(1-phenylmethanesulfonyl-piperidin-4-ylamino)-phenyl]-thiophene-2-carboxylic acid methyl ester, sodium salt, {[2-[(benzyloxy)carbonyl]-5-(3-{[1-(benzylsulfonyl)piperidin-4-yl]amino}phenyl)-4-bromothien-3-yl]oxy}acetic acid, [(5-(3-{[1-(benzylsulfonyl)piperidin-4-yl]amino}phenyl)-4-bromo-2-{[(2-nitrobenzyl)oxy]carbonyl}thien-3-yl)oxy]acetic acid, [(5-(3-{[1-(benzylsulfonyl)piperidin-4-yl]amino}phenyl)-4-bromo-2-{[(2-nitrobenzyl)oxy]carbonyl}thien-3-yl)oxy]acetic acid, [(5-(3-{[1-(benzylsulfonyl)piperidin-4-yl]amino}phenyl)-4-bromo-2-{[(2-nitrobenzyl)oxy]carbonyl}thien-3-yl)oxy]acetic acid, ({5-(3-{[1-(benzylsulfonyl)piperidin-4-yl]amino}phenyl)-4-bromo-2-[(cyclohexylmethoxy)carbonyl]thien-3-yl}oxy)acetic acid, ({5-(3-{[1-(benzylsulfonyl)piperidin-4-yl]amino}phenyl)-4-bromo-2-[(cyclohexylmethoxy)carbonyl]thien-3-yl}oxy)acetic acid, 5-[3-(benzyloxycarbonyl-cyclohexyl-amino)-phenyl]-4-bromo-3-carboxymethoxy-thiophene-2-carboxylic acid, 5-[3-(benzyloxycarbonyl-cyclohexyl-amino)-phenyl]-4-bromo-3-carboxymethoxy-thiophene-2-carboxylic acid, 4-bromo-3-carboxymethoxy-5-[3-(cyclohexyl-propoxycarbonyl-amino)-phenyl]-thiophene-2-carboxylic acid, 4-bromo-3-carboxymethoxy-5-[3-(cyclohexyl-isopropoxycarbonyl-amino)-phenyl]- thiophene-2-carboxylic acid, 5-[3-(benzyloxycarbonyl-cyclohexylmethyl-amino)-phenyl]-4-bromo-3-carboxymethoxy-thiophene-2-carboxylic acid, 4-bromo-3-carboxymethoxy-5-[3-(cyclohexylmethyl-isopropoxycarbonyl-amino)-phenyl]-thiophene-2-carboxylic acid, 4-bromo-3-carboxymethoxy-5-[3-(cyclohexylmethyl-isopropoxycarbonyl-amino)-phenyl]-thiophene-2-carboxylic acid, 4-bromo-3-carboxymethoxy-5-[3-(cyclohexylmethyl-propoxycarbonyl-amino)-phenyl]-thiophene-2-carboxylic acid, 5-[3-(benzoyl-cyclohexylmethyl-amino)-phenyl]-4-bromo-3-carboxymethoxy-thiophene-2-carboxylic acid, 4-bromo-3-carboxymethoxy-5-[3-(cyclohexylmethyl-phenylacetyl-amino)-phenyl]-thiophene-2-carboxylic acid, 4-bromo-3-carboxymethoxy-5-{3-[cyclohexylmethyl-(4-methyl-pentanoyl)-amino]-phenyl}-thiophene-2-carboxylic acid methyl ester, 4-bromo-3-carboxymethoxy-5-{3-[1-(3-chloro-phenylmethanesulfonyl)-piperidin-4-ylamino]-phenyl}-thiophene-2-carboxylic acid methyl ester, 4-bromo-3-carboxymethoxy-5-{3-[1-(3-fluoro-phenylmethanesulfonyl)-piperidin-4-ylamino]-phenyl}-thiophene-2-carboxylic acid methyl ester, 4-bromo-3-carboxymethoxy-5-{3-[1-(2-chloro-phenylmethanesulfonyl)-piperidin-4-ylamino]-phenyl}-thiophene-2-carboxylic acid, 4-bromo-5-{3-[1-(2-chloro-phenylmethanesulfonyl)-piperidin-4-ylamino]-phenyl}-3-methoxycarbonylmethoxy-thiophene-2-carboxylic acid, 3-carboxymethoxy-5-{3-[1-(3-fluoro-phenylmethanesulfonyl)-piperidin-4-ylamino]-phenyl}-4-methyl-thiophene-2-carboxylic acid methyl ester, 3-carboxymethoxy-4-methyl-5-[3-(1-phenylmethanesulfonyl-piperidin-4-ylamino)-phenyl]-thiophene-2-carboxylic acid methyl ester, 3-carboxymethoxy-4-methyl-5-{3-[1-(2-trifluoromethyl-phenylmethanesulfonyl)-piperidin-4-ylamino]-phenyl}-thiophene-2-carboxylic acid methyl ester 3-carboxymethoxy-4-methyl-5-[3-(1-phenylmethanesulfonyl-piperidin-4-ylamino)-phenyl]-thiophene-2-carboxylic acid, 3-methoxycarbonylmethoxy-4-methyl-5-[3-(1-phenyl-methanesulfonyl-piperidin-4-ylamino)-phenyl]-thiophene-2-carboxylic acid, 3-carboxymethoxy-4-methyl-5-[3-(3,3,5,5-tetramethyl-cyclohexylamino)-phenyl]-thiophene-2-carboxylic acid methyl ester], 4,5-dibromo-3-(1-carboxy-ethoxy)-thiophene-2-carboxylic acid, [4,5-dibromo-2-(5-methyl-[1,2,4]oxadiazol-3-yl)-thiophen-3-yloxy]-acetic acid, [4,5-dibromo-2-(5-ethyl-[1,2,4]oxadiazol-3-yl)-thiophen-3-yloxy]-acetic acid, [4,5-dibromo-2-(5-isopropyl-[1,2,4]oxadiazol-3-yl)-thiophen-3-yloxy]-acetic acid, [4-bromo-5-[3-(1-phenylmethanesulfonyl-piperidin-4-ylamino)-phenyl]-2-(1H-tetrazol-5-yl)-thiophen-3-yloxy]-acetic acid, [4-bromo-5-[3-(1-phenylmethanesulfonyl-piperidin-4-ylamino)-phenyl]-2-(1H-tetrazol-5-yl)-thiophen-3-yloxy]-acetic acid isopropyl ester, [4-bromo-5-[3-(1-phenylmethanesulfonyl-piperidin-4-ylamino)-phenyl]-2-(1H-tetrazol-5-yl)-thiophen-3-yloxy]-acetic acid methyl ester, 4,5-dibromo-3-(isobutylcarbamoyl-methoxy)-thiophene-2-carboxylic acid methyl ester, 4,5-dibromo-3-(2-oxo-2-pyrrolidin-1-yl-ethoxy)-thiophene-2-carboxylic acid methyl ester, 4,5-dibromo-3-[(2-hydroxy-1-methyl-ethylcarbamoyl)-methoxy]-thiophene-2-carboxylic acid methyl ester, [4-bromo-5-[3-(1-phenylmethanesulfonyl-piperidin-4-ylamino)-phenyl]-2-(1H-tetrazol-5-yl)-thiophen-3-yloxy]-acetic acid methyl ester, 4,5-dibromo-3-(isobutylcarbamoyl-methoxy)-thiophene-2-carboxylic acid methyl ester, 4-[2-(4,5-dibromo-2-methoxycarbonyl-thiophen-3-yloxy)-acetyl]-piperazine-1-carboxylic acid tert-butyl ester, 4,5-dibromo-3-[(2-hydroxy-1-methyl-ethylcarbamoyl)-methoxy]-thiophene-2-carboxylic acid methyl ester, 4,5-dibromo-3-[(2-tert-butoxycarbonylamino-ethylcarbamoyl)-methoxy]-thiophene-2-carboxylic acid methyl ester, 3-[(2-amino-ethylcarbamoyl)-methoxy]-4,5-dibromo-thiophene-2-carboxylic acid methyl ester, 3-{[2-(4-Hydroxy-phenyl)-1-methoxycarbonyl-ethylcarbamoyl]-methoxy}-4-methyl-5-[3-(3,3,5,5-tetramethyl-cyclohexyl)-phenyl]-thiophene-2-carboxylic acid methyl ester, 1-(2-{2-methoxycarbonyl-4-methyl-5-[3-(3,3,5,5-tetramethyl-cyclohexyl)-phenyl]-thiophen-3-yloxy}-acetyl)-pyrrolidine-2-carboxylic acid methyl ester, 4-methyl-3-(2-oxo-2-pyrrolidin-1-yl-ethoxy)-5-[3-(3,3,5,5-tetramethyl-cyclohexyl)-phenyl]-thiophene-2-carboxylic acid methyl ester, 3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester, 3-[(1-methoxycarbonyl-2-methyl-propylcarbamoyl)-methoxy]-4-methyl-5-[3-(3,3,5,5-tetramethyl-cyclohexyl)-phenyl]-thiophene-2-carboxylic acid methyl ester, 3-[(1-methoxycarbonyl-3-methyl-butylcarbamoyl)-methoxy]-4-methyl-5-[3-(3,3,5,5-tetramethyl-cyclohexyl)-phenyl]-thiophene-2-carboxylic acid methyl ester, 3-[(1-methoxycarbonyl-2-phenyl-ethylcarbamoyl)-methoxy]-4-methyl-5-[3-(3,3,5,5-tetramethyl-cyclohexyl)-phenyl]-thiophene-2-carboxylic acid methyl ester, 3-[2-(2-carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester, 3-[(2-tert-butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester, 4-(2-{2-methoxycarbonyl-4-methyl-5-[3-(3,3,5,5-tetramethyl-cyclohexyl)-phenyl]-thiophen-3-yloxy}-acetyl)-piperazine-1-carboxylic acid tert-butyl ester, 3-[(2-amino-ethylcarbamoyl)-methoxy]-4-methyl-5-[3-(3,3,5,5-tetramethyl-cyclohexyl)-phenyl]-thiophene-2-carboxylic acid methyl ester, 4-methyl-3-(2-oxo-2-piperazin-1-yl-ethoxy)-5-[3-(3,3,5,5-tetramethyl-cyclohexyl)-phenyl]-thiophene-2-carboxylic acid methyl ester 4-bromo-5-[3-(1-phenylmethanesulfonyl-piperidin-4-yl)-phenyl]-3-(piperidin-4-yloxycarbonylmethoxy)-thiophene-2-carboxylic acid methyl ester, 4-bromo-3-methoxycarbonylmethoxy-5-[3-(1-phenylmethanesulfonyl-piperidin-4-yl)-phenyl]-thiophene-2-carboxylic acid, 2,2-dimethyl-propionyloxymethyl ester, 4-bromo-3-isopropoxycarbonylmethoxy-5-[3-(1-phenylmethanesulfonyl-piperidin-4-yl)-phenyl]-thiophene-2-carboxylic acid, 2,2-dimethyl-propionyloxymethyl ester 4-bromo-3-isopropoxycarbonylmethoxy-5-[3-(1-phenyl-methanesulfonyl-piperidin-4-yl)-phenyl]-thiophene-2-carboxylic acid acetoxymethyl ester, 4,5-dibromo-3-methoxycarbonylmethoxy-thiophene-2-carboxylic acid 2,2-dimethyl-propionyloxymethyl ester, [5-bromo-4-methyl-2-(1H-tetrazol-5-yl)-thiophen-3-yloxy]-acetic acid, [4-methyl-5-phenyl-2-(1H-tetrazol-5-yl)-thiophen-3-yloxy]-acetic acid, [5-bromo-4-methyl-2-(2-methyl-2H-tetrazol-5-yl)-thiophen-3-yloxy]-acetic acid, 3-carboxymethoxy-5-{3-[1-(3-chloro-benzenesulfonyl)-piperidin-4-ylamino]-phenyl}-4-methyl-thiophene-2-carboxylic acid, 3-carboxymethoxy-5-{3-[1-(2-chloro-benzenesulfonyl)-piperidin-4-ylamino]-phenyl}4-methyl-thiophene-2-carboxylic acid, 3-carboxymethoxy-4-methyl-5-{3-[1-(4-nitro-benzenesulfonyl)-piperidin-4-ylamino]-phenyl}-thiophene-2-carboxylic acid, 3-carboxymethoxy-5-{3-[1-(2-cyano-benzenesulfonyl)-piperidin-4-ylamino]-phenyl}14-methyl-thiophene-2-carboxylic acid, 3-carboxymethoxy-4-methyl-5-{3-[1-(4-trifluoromethyl-benzenesulfonyl)-piperidin-4-ylamino]-phenyl}-thiophene-2-carboxylic acid, 5-{3-[1-(4-carboxy-benzenesulfonyl)-piperidin-4-ylamino]-phenyl}-3-carboxymethoxy-4-methyl-thiophene-2-carboxylic acid, 3-carboxymethoxy-5-{3-[1-(2-cyano-benzenesulfonyl)-piperidin-4-ylamino]-phenyl}-4-methyl-thiophene-2-carboxylic acid, 3-carboxymethoxy-4-methyl-5-{3-[1-(4-trifluoromethyl-benzenesulfonyl)-piperidin-4-ylamino]-phenyl}-thiophene-2-carboxylic acid, 4-bromo-3-carboxymethoxy-5-[3-(1-cyclohexyl-3-methyl-ureido)-phenyl]-thiophene-2-carboxylic acid, 5-[3-(3-benzyl-1-cyclohexyl-ureido)-phenyl]-4-bromo-3-carboxymethoxy-thiophene-2-carboxylic acid, 4-bromo-3-tert-butoxycarbonylmethoxy-5-[3-(3,3,5,5-tetramethyl-cyclohexylamino)-phenyl]-thiophene-2-carboxylic acid methyl ester, 4-bromo-3-carboxymethoxy-5-{3-[3-methyl-1-(3,3,5,5-tetramethyl-cyclohexyl)-ureido]-phenyl}-thiophene-2-carboxylic acid, 4-bromo-3-carboxymethoxy-5-{3-[3-ethyl-1-(3,3,5,5-tetramethyl-cyclohexyl)-ureido]-phenyl}-thiophene-2-carboxylic acid, 4-bromo-3-carboxymethoxy-5-{3-[3-methyl-1-(3,3,5,5-tetramethyl-cyclohexyl)-ureido]-phenyl}-thiophene-2-carboxylic acid methyl ester, 4-bromo-3-ethoxycarbonylmethoxy-5-[3-(piperidin-4-ylamino)-phenyl]-thiophene-2-carboxylic acid methyl ester hydrochloride, 4-bromo-3-carboxymethoxy-5-{3-[1-(4-trifluoromethyl-pyrimidin-2-yl)-piperidin-4-ylamino]-phenyl}-thiophene-2-carboxylic acid, 4-bromo-3-carboxymethoxy-5-[3-(1-pyrimidin-2-yl-piperidin-4-ylamino)-phenyl]-thiophene-2-carboxylic acid, 4-bromo-3-carboxymethoxy-5-[3-(5'-trifluoromethyl-3,4,5,6-tetrahydro-2H-[1,2']bipyridinyl-4-ylamino)-phenyl]-thiophene-2-carboxylic acid, 4-bromo-3-ethoxycarbonylmethoxy-5-[3-(1-phenyl-methanesulfonyl-piperidin-4-ylamino)-phenyl]-thiophene-2-carboxylic acid ethyl ester, 4-bromo-5-[3-(1-phenyl-methanesulfonyl-piperidin-4-ylamino)-phenyl]-3-(o-tolylcarbamoyl-methoxy)-thiophene-2-carboxylic acid, {4-bromo-2-hydroxymethyl-5-[3-(1-phenylmethanesulfonyl-piperidin-4-ylamino)-phenyl]-thiophen-3-yloxy}-acetic acid, 3-carboxymethoxy-5-[3-(1-phenylmethanesulfonyl-piperidin-4-ylamino)-phenyl]-thiophene-2-carboxylic acid, 4-bromo-3-carboxymethoxy-5-(3-{1-[3-(3-ethyl-ureido)-phenylmethanesulfonyl]-piperidin-4-ylamino}-phenyl)-thiophene-2-carboxylic acid, [2-(2-{4-bromo-2-methoxycarbonyl-5-[3-(1-phenylmethanesulfonyl-piperidin-4-ylamino)-phenyl]-thiophen-3-yloxy}-acetoxy)-ethyl]-trimethyl-ammonium chloride, 4-bromo-3-cyclohexylcarbamoylmethoxy-5-[3-(1-phenylmethanesulfonyl-piperidin-4-ylamino)-phenyl]-thiophene-2-carboxylic acid methyl ester, (4,5-dibromo-2-hydroxymethyl-thiophen-3-yloxy)-acetic acid, 5-[3-(acetyl-cyclohexyl-amino)-phenyl]-4-bromo-3-carboxymethoxy-thiophene-2-carboxylic acid, 5-[3-(acetyl-cyclohexyl-amino)-phenyl]-4-bromo-3-carboxymethoxy-thiophene-2-carboxylic acid methyl ester, 5-[3-(benzoyl-cyclohexyl-amino)-phenyl]-4-bromo-3-carboxymethoxy-thiophene-2-carboxylic acid, 5-[3-(benzoyl-cyclohexyl-amino)-phenyl]-4-bromo-3-carboxymethoxy-thiophene-2-carboxylic acid methyl ester, 4-bromo-3-carboxymethoxy-5-{3-[cyclohexyl-(3-phenyl-acryloyl)-amino]-phenyl}-thiophene-2-carboxylic acid methyl ester, 4-bromo-3-carboxymethoxy-5-[3-(cyclohexanecarbonyl-cyclohexyl-amino)-phenyl]-thiophene-2-carboxylic acid methyl ester, 5-{3-[benzoyl-(3,3,5,5-tetramethyl-cyclohexyl)-amino]-phenyl}-4-bromo-3-carboxymethoxy-thiophene-2-carboxylic acid, 4-bromo-3-carboxymethoxy-5-[3-(1-phenylmethanesulfonyl-piperidin-4-ylamino)-phenyl]-thiophene-2-carboxylic acid methyl ester (Hydrochloride Salt), 4-bromo-3-[(carbamoylmethyl-carbamoyl)-methoxy]-5-[3-(3,3,5,5-tetramethyl-cyclohexylamino)-phenyl]-thiophene-2-carboxylic acid methyl ester, 4-bromo-3-[(1-carbamoyl-ethylcarbamoyl)-methoxy]-5-[3-(3,3,5,5-tetramethyl-cyclohexylamino)-phenyl]-thiophene-2-carboxylic acid methyl ester, 4-bromo-3-[(ethoxycarbonylmethyl-carbamoyl)-methoxy]-5-[3-(3,3,5,5-tetramethyl-cyclohexylamino)-phenyl]-thiophene-2-carboxylic acid methyl ester, 4-bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 4-bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 3-{[(benzylcarbamoyl-methyl)-carbamoyl]-methoxy}-4-bromo-5-[3-(3,3,5,5-tetramethylcyclohexylamino)-phenyl]-thiophene-2-carboxylic acid methyl ester, 4-bromo-3-carboxymethoxy-5-{3-[1-(3-methanesulfonylamino-phenylmethanesulfonyl)-piperidin-4-ylamino]-phenyl}-thiophene-2-carboxylic acid, 5-{3-[1-(3-acetylamino-phenylmethanesulfonyl)-piperidin-4-ylamino]-phenyl}-4-bromo-3-carboxymethoxy-thiophene-2-carboxylic acid, {[4-bromo-5-(3-methoxyphenyl)-2-(morpholin-4-ylcarbonyl)thien-3-yl]oxy}acetic acid, {[5-(1,3-benzodioxol-5-yl)-4-bromo-2-(morpholin-4-ylcarbonyl)thien-3-yl]oxy}acetic acid, {[3-bromo-5-(morpholin-4-ylcarbonyl)-2,3'-bithien-4-yl]oxy}acetic acid, {[4-bromo-2-(morpholin-4-ylcarbonyl)-5-phenylthien-3-yl]oxy}acetic acid, [(4,5-dibromo-2-{[(2-hydroxy-1,1-dimethylethyl)amino]carbonyl}thien-3-yl)oxy]acetic acid, ({4,5-dibromo-2-[(dimethylamino)carbonyl]thien-3-yl}oxy)acetic acid, ({4,5-dibromo-2-[(diethylamino)carbonyl]thien-3-yl}oxy)acetic acid, ({4,5-dibromo-2-[(1,3-thiazol-2-ylamino)carbonyl]thien-3-yl}oxy)acetic acid, [4,5-dibromo-2-(2H-pyrazol-3-ylcarbamoyl)-thiophen-3-yloxy]-acetic acid, {[4,5-dibromo-2-(morpholin-4-ylcarbonyl)thien-3-yl]oxy}acetic acid, [(4,5-dibromo-2-{[(2R,6S)-2,6-dimethylmorpholin-4-yl]carbonyl}thien-3-yl)oxy]acetic acid, {[4,5-dibromo-2-(thiomorpholin-4-ylcarbonyl)thien-3-yl]oxy}acetic acid, {[2-(anilinocarbonyl)-4,5-dibromothien-3-yl]oxy}acetic acid, {[4,5-dibromo-2-(piperidin-1-ylcarbonyl)thien-3-yl]oxy}acetic acid, {[4,5-dibromo-2-(4,4-dimethyl-4,5-dihydro-1,3-oxazol-2-yl)thien-3-yl]oxy}acetic acid, {[5-(3-{[1-(benzylsulfonyl)piperidin-4-yl]amino}phenyl)-4-bromo-2-(morpholin-4-ylcarbonyl)thien-3-yl]oxy}acetic acid, [(4-bromo-2-(morpholin-4-ylcarbonyl)-5-{3-[(3,3,5,5-tetramethylcyclohexyl)amino]phenyl}thien-3-yl)oxy]acetic acid, 4-bromo-5-(3-{[1-(butylsulfonyl)piperidin-4-yl]amino}phenyl)-3-(2-methoxy-2-oxoethoxy)thiophene-2-carboxylic acid, 4-bromo-5-(3-{[1-(ethylsulfonyl)piperidin-4-yllamino}phenyl)-3-(2-methoxy-2-oxoethoxy)thiophene-2-carboxylic acid, 4-bromo-5-(3-{[1-(isopropylsulfonyl)piperidin-4-yl]amino}phenyl)-3-(2-methoxy-2-oxoethoxy)thiophene-2-carboxylic acid, 5-{3-[acetyl(3,3,5,5-tetramethylcyclohexyl)amino]phenyl}-4-bromo-3-(2-methoxy-2-oxoethoxy)thiophene-2-carboxylic acid, [4-bromo-5-[3-(cyclohexylamino)phenyl]-2-(methoxycarbonyl)thien-3-yl]oxyacetic acid, {[5-(3-{[1-(benzylsulfonyl)piperidin-4-yl]aminophenyl)-4-bromo-2-(ethoxycarbonyl)thien-3-yl]oxy}acetic acid, {[5-(3-{[1-(benzylsulfonyl)piperidin-4-yl]amino}phenyl)-4-bromo-2-(isopropoxycarbonyl)thien-3-yl]oxy}acetic acid, ({5-(3-{[1-(benzylsulfonyl)piperidin-4-yl]amino}phenyl)-4-bromo-2-[(cyclohexyloxy)carbonyl]thien-3-yl}oxy)acetic acid, {[4-bromo-2-(ethoxycarbonyl)-5-(3-{[1-(phenylsulfonyl)piperidin-4-yl]amino)phenyl)thien-3-yl]oxy}acetic acid, [4-bromo-2-(methoxycarbonyl)-5-(3-{[1-(phenylsulfonyl)piperidin-4-yl]amino}phenyl)thien-3-yl]oxyacetic acid, [(4-bromo-2-(ethoxycarbonyl)-5-{3-[(3,3,5,5-tetramethylcyclohexyl)amino]phenyl}thien-3-yl)oxy]acetic acid, and {[4,5-dibromo-2-(methoxyacetyl)thien-3-yl]oxy}acetic acid.

In some embodiments, the compound can be selected from 3-(carboxymethoxy)-4-phenylthiophene-2-carboxylic acid, 3-(carboxymethoxy)-4-(1H-indol-5-yl)thiophene-2-carboxylic acid, 4-bromo-3-(carboxymethoxy)-5-phenylthiophene-2-carboxylic acid, 4-bromo-3-(carboxymethoxy)-5-[4-(dimethylamino)phenyl]thiophene-2-carboxylic acid, 5-(4-aminophenyl)-4-bromo-3-(carboxymethoxy) thiophene-2-carboxylic acid, 4-(carboxymethoxy)-3,3'-bithiophene-5-carboxylic acid, 5-[4-(acetylamino)phenyl]-4-bromo-3-(carboxymethoxy)thiophene-2-carboxylic acid, 5-(3-aminophenyl)-4-bromo-3-(carboxymethoxy) thiophene-2-carboxylic acid, 3-(carboxymethoxy)-4-[3-(trifluoromethyl)phenyl]thiophene-2-carboxylic acid, 4-bromo-3-(carboxymethoxy)-5-(1-naphthyl)thiophene-2-carboxylic acid, 4-bromo-3-(carboxymethoxy)-5-(2-naphthyl) thiophene-2-carboxylic acid, 3-(carboxymethoxy)-4,5-diphenylthiophene-2-carboxylic acid, {[2-(2H-tetraazol-5-yl)thieno[2,3-b]pyridin-3-yl]oxy}acetic acid, 5-[3-(acetylamino)phenyl]-4-bromo-3-(carboxymethoxy) thiophene-2-carboxylic acid, 4-bromo-3-(carboxymethoxy)-5-[3-(isobutyrylamino)phenyl]thiophene-2-carboxylic acid, 4-bromo-3-(carboxymethoxy)-5-[3-(propionylamino)phenyl]thiophene-2-carboxylic acid, 4-bromo-5-[3-(butyrylamino)phenyl]-3-(carboxymethoxy)thiophene-2-carboxylic acid, 4-bromo-3-(carboxymethoxy)-5-{3-[(cyclohexylcarbonyl)amino]phenyl}thiophene-2-carboxylic acid, 4-bromo-3-(carboxymethoxy)-5-(4-hydroxyphenyl)thiophene-2-carboxylic acid, 4-bromo-3-(carboxymethoxy)-5-{4-[(methoxycarbonyl)amino] phenyl}thiophene-2-carboxylic acid, 5-[4-(benzoylamino) phenyl]-4-bromo-3-(carboxymethoxy)thiophene-2-carboxylic acid, 4-bromo-3-(carboxymethoxy)-5-[3-(hexanoylamino)phenyl]thiophene-2-carboxylic acid, 4-bromo-3-(carboxymethoxy)-5-{3-[(cyclopentylcarbonyl) amino]phenyl}thiophene-2-carboxylic acid, 4-bromo-3-(carboxymethoxy)-5-{3-[(methoxycarbonyl)amino] phenyl}thiophene-2-carboxylic acid, 4-bromo-3-(carboxymethoxy)-5-(3-{[(2,2,2-trifluoroethyl)sulfonyl] amino}phenyl)thiophene-2-carboxylic acid, 5-(1,1'-biphenyl-3-yl)-4-bromo-3-(carboxymethoxy)thiophene-2-carboxylic acid, 4-bromo-3-(carboxymethoxy)-5-(3-{[(isopropylamino)carbonyl]amino}phenyl)thiophene-2-carboxylic acid, 4-bromo-3-(carboxymethoxy)-5-(4-fluorophenyl)thiophene-2-carboxylic acid, 3-bromo-4-(carboxymethoxy)-2,3'-bithiophene-5-carboxylic acid, 5-(4-{[(benzyloxy)acetyl]amino}phenyl)-4-bromo-3-(carboxymethoxy)thiophene-2-carboxylic acid, 5-(1,3-benzodioxol-5-yl)-4-bromo-3-(carboxymethoxy)thiophene-2-carboxylic acid, 4-bromo-5-(4-{[(tert-butoxycarbonyl) amino]methyl}phenyl)-3-(carboxymethoxy)thiophene-2-carboxylic acid, 4-bromo-3-(carboxymethoxy)-5-(3-{[(diethylamino)carbonyl]amino}phenyl)thiophene-2-carboxylic acid, 4-bromo-3-(carboxymethoxy)-5-(3-hydroxyphenyl)thiophene-2-carboxylic acid, 4-bromo-3-(carboxymethoxy)-5-(3-methoxyphenyl)thiophene-2-carboxylic acid, 4-bromo-5-[3-({[1-(tert-butoxycarbonyl) piperidin-4-yl]carbonyl}amino)phenyl]-3-(carboxymethoxy)thiophene-2-carboxylic acid, 4-bromo-5-[3-({[1-(tert-butoxycarbonyl)piperidin-3-yl] carbonyl}amino)phenyl]-3-(carboxymethoxy)thiophene-2-carboxylic acid, 4-bromo-3-(carboxymethoxy)-5-{4-[(methylsulfonyl)amino]phenyl}thiophene-2-carboxylic acid, carboxylic acid, 4-bromo-3-(carboxymethoxy)-5-[4-({ [4-(trifluoromethyl)phenyl]sulfonyl}amino)phenyl] thiophene-2-carboxylic acid, 4-bromo-5-(4-{[N-(tert-butoxycarbonyl)glycyl]amino}phenyl)-3-(carboxymethoxy) thiophene-2-carboxylic acid, 4-bromo-3-(carboxymethoxy)-5-[(hydroxymethyl)phenyl]thiophene-2-carboxylic acid, 4-bromo-3-(carboxymethoxy)-5-{3-[(piperidin-4-ylcarbonyl)amino]phenyl}thiophene-2-carboxylic acid, 4-bromo-3-(carboxymethoxy)-5-{3-[(piperidin-3-ylcarbonyl)amino] phenyl}thiophene-2-carboxylic acid, 5-(1-benzofuran-2-yl)-4-bromo-3-(carboxymethoxy)thiophene-2-carboxylic acid, 4-bromo-3-(carboxymethoxy)-5-(4-{[(phenylsulfonyl) amino]methyl}phenyl)thiophene-2-carboxylic acid, 4-bromo-3-(carboxymethoxy)-5-(4-methoxyphenyl) thiophene-2-carboxylic acid, 3-(carboxymethoxy)-5-[4-(trifluoromethoxy)phenyl]thiophene-2-carboxylic acid, 4-bromo-3-(carboxymethoxy)-5-(4-{[(ethylsulfonyl)amino] methyl}phenyl)thiophene-2-carboxylic acid, 5-{4-[(acetylamino)methyl]phenyl)}4-bromo-3-(carboxymethoxy) thiophene-2-carboxylic acid, 4-bromo-3-(carboxymethoxy)-5-(4-{[(ethoxycarbonyl)amino]methyl}phenyl)thiophene-2-carboxylic acid, 4-bromo-3-(carboxymethoxy)-5-[4-({ [(isopropylamino)carbonyl]amino}methyl)phenyl] thiophene-2-carboxylic acid, 4-bromo-3-(carboxymethoxy)-5-{3-[(phenylsulfonyl)amino]phenyl}thiophene-2-carboxylic acid, 5-[4-(aminomethyl)phenyl]-4-bromo-3-(carboxymethoxy)thiophene-2-carboxylic acid, 4-bromo-3-(carboxymethoxy)-5-pyridin-3-ylthiophene-2-carboxylic acid, 4-bromo-5-{4-[(carboxycarbonyl)amino]phenyl}-3-(carboxymethoxy)thiophene-2-carboxylic acid, 4-bromo-3-(carboxymethoxy)-5-{3-[(ethylsulfonyl)amino] phenyl}thiophene-2-carboxylic acid, 3-(carboxymethoxy)-5-(2-methylphenyl)thiophene-2-carboxylic acid, 4-bromo-3-(carboxymethoxy)-5-{3-[(3,3,3-trifluoropropanoyl)amino] phenyl}thiophene-2-carboxylic acid, 5-{3-[(benzylsulfonyl) amino]phenyl})-4-bromo-3-(carboxymethoxy)thiophene-2-carboxylic acid, 4-bromo-3-(carboxymethoxy)-5-(4-{ [(isopropylamino)carbonyl]amino}phenyl)thiophene-2-carboxylic acid, 4-bromo-3-(carboxymethoxy)-5-{4-[(pyridin-3-ylcarbonyl)amino]phenyl}thiophene-2-carboxylic acid, 4-bromo-3-(carboxymethoxy)-5-(4-formylphenyl)thiophene-2-carboxylic acid, 3-bromo-4-(carboxymethoxy)-2'-formyl-2,3'-bithiophene-5-carboxylic acid, 4-bromo-3-(carboxymethoxy)-5-[3-({[4-(trifluoromethyl)phenyl]sulfonyl}amino)phenyl]thiophene-2-carboxylic acid, 4-bromo-3-(carboxymethoxy)-5-[3-({[4-(trifluoromethoxy)phenyl]sulfonyl}amino)phenyl]thiophene-2-carboxylic acid, 4-bromo-3-(carboxymethoxy)-5-{3-[(3,3,3-(trifluoromethyl)phenyl]sulfonyl}amino)phenyl]thiophene-2-carboxylic acid, 4-bromo-3-(carboxymethoxy)-5-[4-(glycylamino)phenyl]thiophene-2-carboxylic acid, 4-bromo-3-(carboxymethoxy)-5-{4-[(phenylsulfonyl) amino]phenyl}thiophene-2-carboxylic acid, 4-bromo-3-(carboxymethoxy)-5-[4-(methyl {[4-(trifluoromethyl)phenyl]sulfonyl}amino)phenyl]thiophene-2-carboxylic acid, 5-[4-(anilinocarbonyl)phenyl]-4-bromo-3-(carboxymethoxy)thiophene-2-carboxylic acid, 4-bromo-3-(carboxymethoxy)-5-[3-({[2-(trifluoromethyl)phenyl] sulfonyl}amino)phenyl]thiophene-2-carboxylic acid, 3-bromo-4-(carboxymethoxy)-2'-[(isobutylamino)methyl]-2,3'-bithiophene-5-carboxylic acid, 4-bromo-3-(carboxymethoxy)-5-(3-{[(2-cyanophenyl)sulfonyl] amino}phenyl)thiophene-2-carboxylic acid, 4-bromo-3-(carboxymethoxy)-5-(3-{[(4-methoxyphenyl)sulfonyl] amino}phenyl)thiophene-2-carboxylic acid, 4-bromo-3-(carboxymethoxy)-5-(3-{[(4-cyanophenyl)sulfonyl] amino}phenyl)thiophene-2-carboxylic acid, 4-bromo-3-(carboxymethoxy)-5-{4-[(isopropylamino)carbonyl] phenyl}thiophene-2-carboxylic acid, 5-[3-(benzylamino) phenyl]-4-bromo-3-(carboxymethoxy)thiophene-2-carboxylic acid, 5-[4-({[(1S)-2-amino-1-methyl-2-oxoethyl] amino}carbonyl)phenyl]-4-bromo-3-, (carboxymethoxy) thiophene-2-carboxylic acid, 5-[3-(benzoylamino)phenyl]-4-bromo-3-(carboxymethoxy)thiophene-2-carboxylic acid, 4-bromo-3-(carboxymethoxy)-5-(4-{[(2,6-difluorophenyl)

sulfonyl]amino}phenyl)thiophene-2-carboxylic acid, 4-bromo-3-(carboxymethoxy)-5-(4-{[(2,6-dichlorophenyl)sulfonyl]amino}phenyl)thiophene-2-carboxylic acid, 5-[3-(anilinomethyl)-4-bromo-3-(carboxymethoxy)thiophene-2-carboxylic acid, 4-bromo-3-(carboxymethoxy)-5-[3-(1-phenylethoxy)phenyl]thiophene-2-carboxylic acid, 4-bromo-3-(carboxymethoxy)-5-[4-({[4-(trifluoromethyl)phenyl]amino}carbonyl)phenyl]thiophene-2-carboxylic acid, 4-bromo-3-(carboxymethoxy)-5-[3-(2-furoylamino)phenyl]thiophene-2-carboxylic acid, 4-bromo-3-(carboxymethoxy)-5-[3-(3-furoylamino)phenyl]thiophene-2-carboxylic acid, 4-bromo-3-(carboxymethoxy)-5-(3-formyl-4-methoxyphenyl)thiophene-2-carboxylic acid, 4-bromo-3-(carboxymethoxy)-5-[4-({[2-(trifluoromethyl)phenyl]sulfonyl}amino)phenyl]thiophene-2-carboxylic acid, 4-bromo-3-(carboxymethoxy)-5-[4-({[3-(trifluoromethyl)phenyl]sulfonyl}amino)phenyl]thiophene-2-carboxylic acid, 4-bromo-3-(carboxymethoxy)-5-(3-{[(4-3-(carboxymethoxy)-4-methylthiophene-2-carboxylic acid, 3-(carboxymethoxy)-4-methylthiophene-2-carboxylic acid, 4-bromo-3-(carboxymethoxy)-5-(3-{[2-(trifluoromethyl)benzoyl]amino}phenyl)thiophene-2-carboxylic acid, 4-bromo-3-(carboxymethoxy)-5-(3-{[3-(trifluoromethyl)benzyl]amino}phenyl)thiophene-2-carboxylic acid, 4-bromo-3-(carboxymethoxy)-5-(3-{[2-(trifluoromethyl)benzyl]amino}phenyl)thiophene-2-carboxylic acid, 5-[3-(benzyloxy)phenyl]-4-bromo-3-(carboxymethoxy)thiophene-2-carboxylic acid, 4-bromo-5-[3-(1-carboxymethoxy)phenyl]-3-(carboxymethoxy)thiophene-2-carboxylic acid, 4-bromo-3-(carboxymethoxy)-5-{3-[(2-fluorobenzyl)amino]phenyl}thiophene-2-carboxylic acid, 4-bromo-3-(carboxymethoxy)-5-[3-({[3-(trifluoromethyl)phenyl]amino}methyl)phenyl]thiophene-2-carboxylic acid, 4-bromo-3-(carboxymethoxy)-5-(3-{[(3,4-difluorophenyl)amino]methyl}phenyl)thiophene-2-carboxylic acid, 4-bromo-3-(carboxymethoxy)-5-{3-[(2-furylmethyl)amino]phenyl}thiophene-2-carboxylic acid, 4-bromo-3-(carboxymethoxy)-5-{3-[(cyclohexylamino)methyl]phenyl}thiophene-2-carboxylic acid, 5-bromo-3-(carboxymethoxy)-4-methylthiophene-2-carboxylic acid, 4-bromo-3-(carboxymethoxy)-5-(3-{[(3-nitrophenyl)amino]methyl}phenyl)thiophene-2 carboxylic acid, 4-bromo-5-[3-({[4-bromo-3-(trifluoromethyl)phenyl]amino}methyl)phenyl]-3-(carboxymethoxy)thiophene-2-carboxylic acid, 5-[3-(anilinomethyl)-4-methoxyphenyl]-4-bromo-3-(carboxymethoxy)thiophene-2-carboxylic acid, 4-bromo-5-{3-[(E)-2-carboxyethenyl]-4-methoxyphenyl}-3-(carboxymethoxy)thiophene-2-carboxylic acid, 4-bromo-3-(carboxymethoxy)-5-{3-[(3-furylmethyl)amino]phenyl}thiophene-2-carboxylic acid, 4-bromo-3-(carboxymethoxy)-5-{3-[(3-fluorobenzyl)amino]phenyl}thiophene-2-carboxylic acid, 4-bromo-3-(carboxymethoxy)-5-{3-[(2-fluorobenzoyl)amino]phenyl}thiophene-2-carboxylic acid, 4-bromo-3-(carboxymethoxy)-5-{3-[(3-fluorobenzoyl)amino]phenyl}thiophene-2-carboxylic acid, 4-bromo-3-(carboxymethoxy)-5-(3-{[(3,5-difluorophenyl)amino]methyl}phenyl)thiophene-2-carboxylic acid, 4-bromo-3-(carboxymethoxy)-5-(3-{[(3-fluoro-4-methylphenyl)amino]methyl}phenyl)thiophene-2-carboxylic acid, 4-bromo-3-(carboxymethoxy)-5-{3-[(3-cyanobenzyl)amino]phenyl}thiophene-2-carboxylic acid, 4-bromo-3-(carboxymethoxy)-5-{3-[(pyridin-3-ylcarbonyl)amino]phenyl}thiophene-2-carboxylic acid, 4-bromo-3-(carboxymethoxy)-5-{3-[(cyclohexylmethyl)amino]phenyl}thiophene-2-carboxylic acid, carboxylic acid, 4-bromo-3-(carboxymethoxy)-5-{3-[(pyridin-3-ylmethyl)amino]phenyl}thiophene-2-carboxylic acid, carboxylic acid, 4-bromo-3-(carboxymethoxy)-5-[3-(cyclohexylamino)phenyl]thiophene-2-carboxylic acid, acid, 4-bromo-3-(carboxymethoxy)-5-(1H-indol-5-yl)thiophene-2-carboxylic acid, 4-bromo-5-{4-[(carboxyacetyl)amino]phenyl}-3-(carboxymethoxy)thiophene-2-carboxylic acid, 4-bromo-3-(carboxymethoxy)-5-[3-({[4-chloro-3-(trifluoromethyl)phenyl]amino}methyl)phenyl]thiophene-2-carboxylic acid, 4-bromo-3-(carboxymethoxy)-5-(3-{[(4-methyl-3-nitrophenyl)amino]methyl}phenyl)thiophene-2-carboxylic acid, 4-bromo-3-(carboxymethoxy)-5-{3-[(4,4,4-trifluorobutanoyl)amino]phenyl}thiophene-2-carboxylic acid, 4-bromo-3-(carboxymethoxy)-5-{3-[(4-fluorobenzyl)amino]phenyl}thiophene-2-carboxylic acid, 4-bromo-3-(carboxymethoxy)-5-[4-(3-furoylamino)phenyl]thiophene-2-carboxylic acid, 5-[3-({[3,5-bis(trifluoromethyl)phenyl]amino}methyl)-4-methoxyphenyl]-4-bromo-3-(carboxymethoxy)thiophene-2-carboxylic acid, 4-bromo-3-(carboxymethoxy)-5-[3-({[4-(trifluoromethyl)phenyl]amino}carbonyl)phenyl]thiophene-2-carboxylic acid, 4-bromo-3-(carboxymethoxy)-5-(3-{[4-(trifluoromethyl)benzyl]amino}phenyl)thiophene-2-carboxylic acid, 4-bromo-3-(carboxymethoxy)-5-{3-[(4-methoxybenzyl)amino]phenyl}thiophene-2-carboxylic acid, 4-bromo-3-(carboxymethoxy)-5-[4-(2-furoylamino)phenyl]thiophene-2-carboxylic acid, 4-bromo-5-[4-({[1-(tert-butoxycarbonyl)piperidin-4-yl]carbonyl}amino)phenyl]-3-(carboxymethoxy)thiophene-2-carboxylic acid, 4-bromo-5-[4-({[1-(tert-butoxycarbonyl)piperidin-3-yl]carbonyl}amino)phenyl]-3-(carboxymethoxy)thiophene-2-carboxylic acid, 5-(3-{[4-(benzyloxy)benzyl]amino}phenyl)-4-bromo-3-(carboxymethoxy)thiophene-2-carboxylic acid, 4-bromo-3-(carboxymethoxy)-5-{3-[(4-phenoxybenzyl)amino]phenyl}thiophene-2-carboxylic acid, 4-bromo-3-(carboxymethoxy)-5-(4-methoxy-3-{(1E)-3-oxo-3-[(2,2,2-trifluoroethyl)amino]prop-1-enyl}phenyl)thiophene-2-carboxylic acid, 4-bromo-3-(carboxymethoxy)-5-[3-(2-naphthylmethoxy)phenyl]thiophene-2-carboxylic acid, 5-[3-(2,1,3-benzoxadiazol-5-ylmethoxy)phenyl]-4-bromo-3-(carboxymethoxy)thiophene-2-carboxylic acid, 4-bromo-3-(carboxymethoxy)-5-(3-{[(2-hydroxypyridin-3-yl)carbonyl]amino}phenyl)thiophene-2-carboxylic acid, 3-(carboxymethoxy)-4-methyl-5-phenylthiophene-2-carboxylic acid, 4-bromo-3-(carboxymethoxy)-5-[3-(isonicotinoylamino)phenyl]thiophene-2-carboxylic acid, 4-bromo-3-(carboxymethoxy)-5-{3-[(quinolin-3-ylcarbonyl)amino]phenyl}thiophene-2-carboxylic acid, 5-[3-(benzylamino)phenyl]-3-(carboxymethoxy)-4-methylthiophene-2-carboxylic acid, 3-(carboxymethoxy)-5-{3-[(cyclohexylmethyl)amino]phenyl}-4-methylthiophene-2-carboxylic acid, 4-bromo-3-(carboxymethoxy)-5-{3-[(pyridin-2-ylcarbonyl)amino}phenyl}thiophene-2-carboxylic acid, 4-bromo-3-(carboxymethoxy)-5-{3-[(2-naphthylmethyl)amino]phenyl}thiophene-2-carboxylic acid, 4-bromo-3-(carboxymethoxy)-5-(3-{[(1-oxidopyridin-3-yl)carbonyl]amino}phenyl)thiophene-2-carboxylic acid, 3-(carboxymethoxy)-4-methyl-5-{3-[(pyridin-3-ylcarbonyl)amino]phenyl}thiophene-2-carboxylic acid, 3-(carboxymethoxy)-5-(3-{[(carboxymethyl)sulfonyl]amino}phenyl)-4-methylthiophene-2-carboxylic acid, 4-bromo-3-(carboxymethoxy)-5-{3-[(pyridin-2-ylacetyl)amino]phenyl}thiophene-2-carboxylic acid, 4-bromo-3-(carboxymethoxy)-5-{3-[(pyridin-3-ylacetyl)amino]phenyl}thiophene-2-carboxylic acid, 4-bromo-5-{3-[(3-carboxybenzyl)amino]phenyl}-3-(carboxymethoxy)thiophene-2-carboxylic acid, 4-bromo-3-(carboxymethoxy)-5-{3-[(pyrazin-2-ylcarbonyl)amino]phenyl}thiophene-2- carboxylic acid, 4-bromo-3-(carboxymethoxy)-5-(3-{[3-(trifluoromethoxy)benzyl]amino}phenyl)thiophene-2-carboxylic acid, 4-bromo-3-(carboxymethoxy)-5-(3-{[2-(trifluoromethoxy)benzyl]amino}phenyl)thiophene-2-carboxylic acid, 4-bromo-3-(carboxymethoxy)-5-{3-[(2-hydroxybenzyl)amino]phenyl}thiophene-2-carboxylic acid, 4-bromo-5-{3-[(3-carboxybenzyl)oxy]phenyl}-3-(carboxymethoxy)thiophene-2-carboxylic acid, 4-bromo-3-(carboxymethoxy)-5-{3-[(4-methylbenzyl)amino]phenyl}thiophene-2-carboxylic acid, 4-bromo-3-(carboxymethoxy)-5-{3-[(pyridin-4-ylacetyl)amino]phenyl}thiophene-2-carboxylic acid, 4-bromo-3-(carboxymethoxy)-5-{3-[(4-chlorobenzyl)amino]phenyl}thiophene-2-carboxylic acid, 4-bromo-3-(carboxymethoxy)-5-(3-{[3-(trifluoromethoxy)benzyl]oxy}phenyl)thiophene-2-carboxylic acid, 4-bromo-3-(carboxymethoxy)-5-[3-cyclopentylamino)phenyl]thiophene-2-carboxylic acid, 4-bromo-3-(carboxymethoxy)-5-{3-[(4-isopropylbenzyl)amino]phenyl}thiophene-2-carboxylic acid, 5-{3-[(1-acetylpiperidin-4-yl)amino]phenyl}4-bromo-3-(carboxymethoxy)thiophene-2-carboxylic acid, 5-[4-(benzyloxy)phenyl]-4-bromo-3-(carboxymethoxy)thiophene-2-carboxylic acid, 4-bromo-3-(carboxymethoxy)-5-[3-(5-fluoro-1H-benzimidazol-2-yl)phenyl]thiophene-2-carboxylic acid, 4-bromo-3-(carboxymethoxy)-5-[3-(cycloheptylamino)phenyl]thiophene-2-carboxylic acid, 5-[3-(bicyclo[3.3.1]non-9-ylamino)phenyl]-4-bromo-3-(carboxymethoxy)thiophene-2-carboxylic acid, 5-(anilinocarbonyl)-3-(carboxymethoxy)thiophene-2-carboxylic acid, 4-bromo-3-(carboxymethoxy)-5-{3-[(4-ethylcyclohexyl)amino]phenyl}thiophene-2-carboxylic acid, 3-(carboxymethoxy)-5-(4-hydroxyphenyl)-4-methylthiophene-2-carboxylic acid, 4-bromo-3-(carboxymethoxy)-5-{3-[(4-phenylcyclohexyl)amino]phenyl}thiophene-2-carboxylic acid, 4-bromo-3-(carboxymethoxy)-5-{3-[(4-phenylcyclohexyl)amino]phenyl}thiophene-2-carboxylic acid, 4-bromo-3-(carboxymethoxy)-5-[2-(hydroxymethyl)phenyl]thiophene-2-carboxylic acid, 3-(carboxymethoxy)-5-(4-{[(isopropylamino)carbonyl]aminophenyl)-4-methylthiophene-2-carboxylic acid, 5-[3,4-bis(benzyloxy)phenyl]-4-bromo-3-(carboxymethoxy)thiophene-2-carboxylic acid, 5-[3-(benzyloxy)-4-hydroxyphenyl]-4-bromo-3-(carboxymethoxy)thiophene-2-carboxylic acid, 5-[4-(benzyloxy)-3-hydroxyphenyl]-4-bromo-3-(carboxymethoxy)thiophene-2-carboxylic acid, 2-{3-[3-bromo-5-carboxy-4-(carboxymethoxy)thien-2-yl]phenyl}-1H-benzimidazole-5-carboxylic acid, carboxylic acid, 3-(carboxymethoxy)thiophene-2-carboxylic acid, 4-bromo-3-(carboxymethoxy)-5-[3-(cyclohexylmethoxy)phenyl]thiophene-2-carboxylic acid, 4-bromo-3-(carboxymethoxy)-5-pyridin-4-ylthiophene-2-carboxylic acid, 4-bromo-3-(carboxymethoxy)-5-{3-[(1-cyclohexylethyl)amino]phenyl}thiophene-2-carboxylic acid, 4-bromo-3-(carboxymethoxy)-5-(3-{[1-(methoxycarbonyl)piperidin-4-yl]amino}phenyl)thiophene-2-carboxylic acid, 4-bromo-3-(carboxymethoxy)-5-{3-[(3,3,5,5-tetramethylcyclohexyl)amino]phenyl}thiophene-2-carboxylic acid, 5-[3-(2-adamantylamino)phenyl]-4-bromo-3-(carboxymethoxy)thiophene-2-carboxylic acid, 3-(carboxymethoxy)-4-methyl-5-{3-[(3-phenoxybenzyl)amino]phenyl}thiophene-2-carboxylic acid, 5-{3-[(3-bromobenzyl)amino]phenyl}-3-(carboxymethoxy)-4-methylthiophene-2-carboxylic acid, 3-(carboxymethoxy)-4-methyl-5-(3-{[3-(trifluoromethyl)benzyl]amino}phenyl)thiophene-2-carboxylic acid, 5-[3-({[(benzylamino)carbonyl]{1-[(benzylamino)carbonyl]piperidin-4-yl}amino)phenyl]-4-bromo-3-(carboxymethoxy) thiophene-2-carboxylic acid, 5-[3-([1-[(benzylamino)carbonyl]piperidin-4-yl}amino)phenyl]-4-bromo-3-(carboxymethoxy)thiophene-2-carboxylic acid, 4-bromo-3-(carboxymethoxy)-5-(3-[(3-nitrobenzyl)amino]phenyl}thiophene-2-carboxylic acid, 4-bromo-3-(carboxymethoxy)-5-(3-{[1-(methylsulfonyl)piperidin-4-yl]amino}phenyl)thiophene-2-carboxylic acid, 4-bromo-3-(carboxymethoxy)-5-[3-([3-[(methylsulfonyl)amino]benzyl}amino)phenyl]thiophene-2-carboxylic acid, 5-(3-{[3-(acetylamino)benzyl]amino}phenyl)-4-bromo-3-(carboxymethoxy)thiophene-2-carboxylic acid, 5-(3-[(3-aminobenzyl)amino]phenyl)}4-bromo-3-(carboxymethoxy)thiophene-2-carboxylic acid, 4-bromo-3-(carboxymethoxy)-5-[3-(tetrahydro-2H-pyran-4-ylamino)phenyl]thiophene-2-carboxylic acid, 5-(3-{[acetyl(cyclohexyl)amino]methyl}phenyl)-4-bromo-3-(carboxymethoxy)thiophene-2-carboxylic acid, 4-bromo-3-(carboxymethoxy)-5-(3-{[1-(phenylsulfonyl)piperidin-4-yl]amino}phenyl)thiophene-2-carboxylic acid, 5-(3-{[3,5-bis(trifluoromethyl)benzyl]oxy}phenyl)-4-bromo-3-(carboxymethoxy)thiophene-2-carboxylic acid, 4-bromo-5-[3-({[1-(tert-butoxycarbonyl)piperidin-4-yl]methyl}amino)phenyl]-3-(carboxymethoxy)thiophene-2-carboxylic acid, 5-(3-{[1-(benzylsulfonyl)piperidin-4-yl]amino}phenyl)-4-bromo-3-(carboxymethoxy)thiophene-2-carboxylic acid, 4-bromo-3-(carboxymethoxy)-5-(3-{[1-(ethylsulfonyl)piperidin-4-yl]methyl}amino)phenyl]thiophene-2-carboxylic acid, yl]methyl}amino)phenyl]thiophene-2-carboxylic acid, 4-bromo-3-(carboxymethoxy)-5-[3-({[1-(methylsulfonyl)piperidin-4-yl]methyl}amino)phenyl]thiophene-2-carboxylic acid, 4-bromo-3-(carboxymethoxy)-5-[3-({[1-(ethylsulfonyl)piperidin-4-yl]methyl}amino)phenyl]thiophene-2-carboxylic acid, 5-{3-[acetyl(benzyl)amino]phenyl}-4-bromo-3-(carboxymethoxy)thiophene-2-carboxylic acid, 4-bromo-3-(carboxymethoxy)-5-[3-({[1-(phenylsulfonyl)piperidin-4-yl]methyl}amino)phenyl]thiophene-2-carboxylic acid, 5-[3-({[1-(benzylsulfonyl)piperidin-4-yl]methyl}amino)phenyl]-4-bromo-3-(carboxymethoxy)thiophene-2-carboxylic acid, 4-bromo-3-(carboxymethoxy)-5-(3-{[1-(isopropylsulfonyl)piperidin-4-yl]amino}phenyl)thiophene-2-carboxylic acid, 5-{3-[acetyl(3,3,5,5-tetramethylcyclohexyl)amino]phenyl}-4-bromo-3-(carboxymethoxy)thiophene-2-carboxylic acid, 4-bromo-3-(carboxymethoxy)-5-[3-({[1-(methoxycarbonyl)piperidin-4-yl]methyl}amino)phenyl]thiophene-2-carboxylic acid, 4-bromo-3-(carboxymethoxy)-5-(3-{[1-(phenylacetyl)piperidin-4-yl]amino}phenyl)thiophene-2-carboxylic acid, 5-{3-[(1-benzoylpiperidin-4-yl)amino]phenyl}-4-bromo-3-(carboxymethoxy)thiophene-2-carboxylic acid, 5-(3-{[acetyl(phenyl)amino]methyl}-4-methoxyphenyl)-4-bromo-3-(carboxymethoxy)thiophene-2-carboxylic acid, 4-bromo-3-(carboxymethoxy)-5-{4-[(3,3,5,5-tetramethylcyclohexyl)amino]phenyl}thiophene-2-carboxylic acid, 5-(3-{[acetyl(3,3,5,5-tetramethylcyclohexyl)amino]methyl}phenyl)-4-bromo-3-(carboxymethoxy)thiophene-2-carboxylic acid, 3-(carboxymethoxy)-4-methyl-5-{3-[(3,3,5,5-tetramethylcyclohexyl)amino]phenyl}thiophene-2-carboxylic acid, 3-(carboxymethoxy)-5-[3-(cycloheptylamino)phenyl]-4-methylthiophene-2-carboxylic acid, 4-bromo-5-(3-{[1-(tert-butoxycarbonyl)piperidin-4-yl]methoxy}phenyl)-3-(carboxymethoxy)thiophene-2-carboxylic acid, 4-bromo-5-(3-{[1-(butylsulfonyl)piperidin-4-yl]amino}phenyl)-3-(carboxymethoxy)thiophene-2-carboxylic acid, 3-(carboxymethoxy)-5-{4-[(3,3,5,5-tetramethylcyclohexyl)amino]phenyl}thiophene-2-carboxylic acid, 5-[3-({acetyl[1-(ethoxycarbonyl)piperidin-4-yl]amino}methyl)phenyl]-4-bromo-3-(carboxymethoxy)thiophene-2-carboxylic acid, 5-{3-[(1-{[3,5-bis(trifluoromethyl)benzyl]sulfonyl}piperidin-4-yl)amino]phenyl}-4-bromo-3-(carboxymethoxy)thiophene-2-carboxylic acid, 4-bromo-3-(carboxymethoxy)-5-(3-{[1-(propylsulfonyl)piperidin-4-yl]amino}phenyl)thiophene-2-carboxylic acid, 4-bromo-3-(carboxymethoxy)-5-(3-{[1-(1-naphthylsulfonyl)piperidin-4-,yl]amino}phenyl)thiophene-2-carboxylic acid, 4-bromo-3-(carboxymethoxy)-5-(3-{[1-(2-naphthylsulfonyl)piperidin-4-yl]amino}phenyl)thiophene-2-carboxylic acid, 4-bromo-3-(carboxymethoxy)-5-[3-({1-[(2-nitrobenzyl)sulfonyl]piperidin-4-yl}amino)phenyl]thiophene-2-carboxylic acid, 2-[(4,5-dibromo-2-carboxythien-3-yl)oxy]malonic acid, 5-(3-{[1-(benzylsulfonyl)piperidin-4-yl]methoxy}phenyl)-4-bromo-3-(carboxymethoxy)thiophene-2-carboxylic acid, 4-bromo-3-(carboxymethoxy)-5-{3-[(1-{[3-(trifluoromethyl)benzyl]sulfonyl}piperidin-4-yl)amino]phenyl}thiophene-2-carboxylic acid, 4-bromo-3-(carboxymethoxy)-5-[3-({1-[(4-fluorobenzyl)sulfonyl]piperidin-4-yl}amino)phenyl]thiophene-2-carboxylic acid, 4-bromo-3-(carboxymethoxy)-5-{3-[(1-{[4-(trifluoromethyl)benzyl]sulfonyl}piperidin-4-yl)amino]phenyl}thiophene-2-carboxylic acid, 4-bromo-3-(carboxymethoxy)-5-[3-({1-[(4-chlorobenzyl)sulfonyl]piperidin-4-yl}amino)phenyl]thiophene-2-carboxylic acid, 4-bromo-3-(carboxymethoxy)-5-[3-({1-[(3,5-dichlorobenzyl)sulfonyl]piperidin-4-yl}amino)phenyl]thiophene-2-carboxylic acid, 4-bromo-3-(carboxymethoxy)-5-[3-({1-[(3,4-dichlorobenzyl)sulfonyl]piperidin-4-yl}amino)phenyl]thiophene-2-carboxylic acid, 5-[3-({[1-(anilinocarbonyl)piperidin-4-yl]methyl}amino)phenyl]-4-bromo-3-(carboxymethoxy)thiophene-2-carboxylic acid, 4-bromo-3-(carboxymethoxy)-5-[3-({1-[(3-nitrobenzyl)sulfonyl]piperidin-4-yl}amino)phenyl]thiophene-2-carboxylic acid, 4-bromo-3-(carboxymethoxy)-5-[3-({1-[(3-chlorobenzyl)sulfonyl]piperidin-4-yl}amino)phenyl]thiophene-2-carboxylic acid, 4-bromo-3-(carboxymethoxy)-5-[3-({1-[(4-methylphenyl)sulfonyl]piperidin-4-yl}methoxy)phenyl]thiophene-2-carboxylic acid, 4-bromo-3-(carboxymethoxy)-5-[3-({1-[(2-phenylethyl)sulfonyl]piperidin-4-yl}amino)phenyl]thiophene-2-carboxylic acid, 5-{3-[({1-[(benzylamino)carbonyl]piperidin-4-yl}methyl)amino]phenyl}-4-bromo-3-(carboxymethoxy)thiophene-2-carboxylic acid, 4-bromo-3-(carboxymethoxy)-5-{3-[({1-[(cyclohexylamino)carbonyl]piperidin-4-yl}methyl)amino]phenyl}thiophene-2-carboxylic acid, 5-(3-{[1-(benzylsulfonyl)piperidin-4-yl]amino}phenyl)-3-(carboxymethoxy)thiophene-2-carboxylic acid, 4-bromo-5-(3-{[1-(tert-butoxycarbonyl)piperidin-4-yl]oxy}phenyl)-3-(carboxymethoxy)thiophene-2-carboxylic acid, 4-bromo-3-(carboxymethoxy)-5-(3-{[cyclohexyl(methylsulfonyl)amino]methyl}phenyl)thiophene-2-carboxylic acid, 4-bromo-3-(carboxymethoxy)-5-(3-{[cyclohexyl(methoxycarbonyl)amino]methyl}phenyl)thiophene-2-carboxylic acid, 4-bromo-3-(carboxymethoxy)-5-[3-({cyclohexyl[(ethylamino)carbonyl]amino}methyl)phenyl]thiophene-2-carboxylic acid, 4-bromo-3-(carboxymethoxy)-5-(3-{[(1-{[(4-methoxyphenyl)amino]carbonyl}piperidin-4-yl)methyl]amino}phenyl)thiophene-2-carboxylic acid, 4-bromo-3-(carboxymethoxy)-5-(3-{[(1-{[(4-cyanophenyl)amino]carbonyl}piperidin-4-yl)methyl]amino}phenyl)thiophene-2-carboxylic acid, 4-bromo-3-(carboxymethoxy)-5-(3-{[(1-{[(4-methylphenyl)amino]carbonyl}piperidin-4-yl)methyl]amino}phenyl)thiophene-2-carboxylic acid, 4-bromo-3-(carboxymethoxy)-5-(3-{[1-(phenylsulfonyl)piperidin-4-yl]methoxy}phenyl)thiophene-2-carboxylic acid, 4-bromo-3-(carboxymethoxy)-5-(3-{[(1-{[(2-methoxyphenyl)amino]carbonyl}piperidin-4-yl)methyl]amino}phenyl)thiophene-2-carboxylic acid, 4-bromo-3-(carboxymethoxy)-5-(3-{[(1-{[(3-chlorophenyl)amino]carbonyl}piperidin-4-yl)methyl]amino}phenyl)thiophene-2-carboxylic acid, 4-bromo-3-(carboxymethoxy)-5-(3-{[(1-{[(2-chlorophenyl)amino]carbonyl}piperidin-4-yl)methyl]amino}phenyl)thiophene-2-carboxylic acid, 4-bromo-3-(carboxymethoxy)-5-(3-{[1-(methylsulfonyl)piperidin-4-yl]methoxy}phenyl)thiophene-2-carboxylic acid, 4-bromo-3-(carboxymethoxy)-5-[3-(hydroxymethyl)phenyl]thiophene-2-carboxylic acid, 5-(3-{[1-(anilinocarbonyl)piperidin-4-yl]oxy}phenyl)-4-bromo-3-(carboxymethoxy)thiophene-2-carboxylic acid, 4-bromo-3-(carboxymethoxy)-5-(3-{[1-(phenoxycarbonyl)piperidin-4-yl]oxy}phenyl)thiophene-2-carboxylic acid, 5-(3-{[1-(benzylsulfonyl)piperidin-4-yl]oxy}phenyl)-4-bromo-3-(carboxymethoxy)thiophene-2-carboxylic acid, 5-(3-{[1-(anilinocarbonyl)piperidin-4-yl]methoxy}phenyl)-4-bromo-3-(carboxymethoxy)thiophene-2-carboxylic acid, 4-bromo-3-(carboxymethoxy)-5-[3-({1-[(ethylamino)carbonyl]piperidin-4-yl}methoxy)phenyl]thiophene-2-carboxylic acid, 4-bromo-3-(carboxymethoxy)-5-[3-({1-[(2-methylbenzyl)sulfonyl]piperidin-4-yl}amino)phenyl]thiophene-2-carboxylic acid, 4-bromo-3-(carboxymethoxy)-5-[3-({1-[(3-methylbenzyl)sulfonyl]piperidin-4-yl}amino)phenyl]thiophene-2-carboxylic acid, 4-bromo-3-(carboxymethoxy)-5-(3-{[(1-{[(3-methoxyphenyl)amino]carbonyl}piperidin-4-yl)methyl]amino}phenyl)thiophene-2-carboxylic acid, 4-bromo-3-(carboxymethoxy)-5-(3-{[(1-{[(3-methylphenyl)amino]carbonyl}piperidin-4-yl)methyl]amino}phenyl)thiophene-2-carboxylic acid, 4-bromo-3-(carboxymethoxy)-5-(3-{[(1-{[(2-methylphenyl)amino]carbonyl}piperidin-4-yl)methyl]amino}phenyl)thiophene-2-carboxylic acid, 4-bromo-3-(carboxymethoxy)-5-(3-{[1-(methoxycarbonyl)piperidin-4-yl]methoxy}phenyl)thiophene-2-carboxylic acid, 4-bromo-3-(carboxymethoxy)-5-(3-{[1-(phenoxycarbonyl)piperidin-4-yl]methoxy}phenyl)thiophene-2-carboxylic acid, 4-bromo-3-(carboxymethoxy)-5-{3-[(1-{[(2-chlorophenyl)amino]carbonyl}piperidin-4-yl)methoxy]phenyl}thiophene-2-carboxylic acid, 4-bromo-3-(carboxymethoxy)-5-{3-[(1-{[(2-methylphenyl)amino]carbonyl}piperidin-4-yl)methoxy]phenyl}thiophene-2-carboxylic acid, 4-yl)methoxy]phenyl}thiophene-2-carboxylic acid, 4-bromo-3-(carboxymethoxy)-5-{3-[(1-{[(2-methoxyphenyl)amino]carbonyl}piperidin-4-yl)methoxy]phenyl}thiophene-2-carboxylic acid, 4-yl)methoxy]phenyl}thiophene-2-carboxylic acid, 4-bromo-3-(carboxymethoxy)-5-{3-[(1-{[(2-isopropylphenyl)amino]carbonyl}piperidin-4-yl)methoxy]phenyl}thiophene-2-carboxylic acid, 4-bromo-3-(carboxymethoxy)-5-{3-[(1-{[(2,6-diethylphenyl)amino]carbonyl}piperidin-4-yl)methoxy]phenyl}thiophene-2-carboxylic acid, 4-bromo-3-(carboxymethoxy)-5-[3-({1-[(mesitylamino)carbonyl]piperidin-4-yl}methoxy)phenyl]thiophene-2-carboxylic acid, 4-bromo-3-(carboxymethoxy)-5-{3-[(1-{[(2-isopropyl-6-methylphenyl)amino]carbonyl}piperidin-4-yl)methoxy]phenyl}thiophene-2-carboxylic acid, 4-bromo-3-(carboxymethoxy)-5-{3-[(1-{[(2-phenoxyphenyl)amino]carbonyl}piperidin-4-yl)methoxy]phenyl}thiophene-2-carboxylic acid, 4-bromo-3-(carboxymethoxy)-5-[3-({1-[(2,6-dimethylbenzyl)sulfonyl]piperidin-4-yl}amino)phenyl]thiophene-2-carboxylic acid, 4-bromo-3-(carboxymethoxy)-5-(3-{[(1-{[(2,6-dimethylphenyl)amino]carbonyl}piperidin-4-yl)methyl]amino}phenyl)thiophene-2-carboxylic acid, 4-bromo-3-(carboxymethoxy)-5-[3-({[1-({[2-(trifluoromethyl)phenyl]amino}carbonyl)piperidin-4-yl]methyl}amino)phenyl]thiophene-2-carboxylic acid, 4-bromo-3-(carboxymethoxy)-5-(3-{[(1-{[methyl(phenyl)

amino]carbonyl}piperidin-4-(methylthio)phenyl]
amino}carbonyl)piperidin-4-yl]methyl}amino)phenyl]
thiophene-2-carboxylic acid, 4-bromo-3-(carboxymethoxy)-5-[3-({[1-({[2-(methylthio)phenyl]amino}carbonyl)
piperidin-4-yl]methyl}amino)phenyl]thiophene-2-carboxylic acid, 4-bromo-3-(carboxymethoxy)-5-{3-[(1-{[(2,6-dimethylphenyl)amino]carbonyl}piperidin-4-yl)
methoxy]phenyl}thiophene-2-carboxylic acid, 4-bromo-3-(carboxymethoxy)-5-(3-{[(1-{[(2,3-dimethylphenyl)amino]carbonyl}piperidin-4-yl)methyl]amino}phenyl)thiophene-2-carboxylic acid, 5-(3-{[1-(anilinocarbonyl)piperidin-4-yl]amino}phenyl)-4-bromo-3-(carboxymethoxy)thiophene-2-carboxylic acid, 4-bromo-3-(carboxymethoxy)-5-{3-[(1-{[(3-phenoxyphenyl)amino]carbonyl}piperidin-4-yl)
methoxy]phenyl}thiophene-2-carboxylic acid, {[5-{3-[acetyl(3,3,5,5-tetramethylcyclohexyl)amino]phenyl}-2-(2H-tetrazol-5-yl)thien-3-yl]oxy}acetic acid, 4-bromo-3-(carboxymethoxy)-5-{3-[(1-{[(4-methyl-2-nitrophenyl)
amino]carbonyl}piperidin-4-yl)methoxy]phenyl}thiophene-2-carboxylic acid, 4-bromo-3-(carboxymethoxy)-5-{3-[(1-{[(5-chloro-2-nitrophenyl)amino]carbonyl}piperidin-4-yl)
methoxy]phenyl}thiophene-2-carboxylic acid, 4-bromo-3-(carboxymethoxy)-5-{3-[(1-{[(2-nitrophenyl)amino]
carbonyl}piperidin-4-yl)methoxy]phenyl}thiophene-2-carboxylic acid, 4-bromo-3-(carboxymethoxy)-5-{3-[(1-{[2-(1H-imidazol-1-yl)ethyl]sulfonyl}piperidin-4-yl)amino]
phenyl}thiophene-2-carboxylic acid, 5-[3-({[5-(anilinocarbonyl)thien-2-yl]methyl}amino)phenyl]-4-bromo-3-(carboxymethoxy)thiophene-2-carboxylic acid, 5-{3-[({5-[(benzylamino)carbonyl]thien-2-yl}methyl)
amino]phenyl}-4-bromo-3-(carboxymethoxy)thiophene-2-carboxylic acid, 4-bromo-3-(carboxymethoxy)-5-{3-[({5-[(cyclohexylamino)carbonyl]thien-2-yl}methyl)amino]
phenyl}thiophene-2-carboxylic acid, 5-{3-[({1-[(2-aminobenzyl)sulfonyl]piperidin-4-yl}methyl)amino]
phenyl}-4-bromo-3-(carboxymethoxy)thiophene-2-carboxylic acid, 4-bromo-3-(carboxymethoxy)-5-{3-[(1-{[2-(1H-pyrazol-1-yl)ethyl]sulfonyl}piperidin-4-yl)amino]
phenyl}thiophene-2-carboxylic acid, {[4,5-dibromo-2-(1H-tetrazol-5-yl)thien-3-yl]oxy}acetic acid, 4-bromo-5-{4-[(4-tert-butylbenzoyl)amino]phenyl}-3-(carboxymethoxy)
thiophene-2-carboxylic acid, 4-bromo-3-(carboxymethoxy)-5-[3-({1-[(2-isopropoxyethyl)sulfonyl]piperidin-4-yl}amino)phenyl]thiophene-2-carboxylic acid, 4-bromo-3-(carboxymethoxy)-5-{4-[(phenylacetyl)amino]
phenyl}thiophene-2-carboxylic acid, 5-[3-({t[1-(benzylsulfonyl)piperidin-3-yl]carbonyl}amino)phenyl]-4-bromo-3-(carboxymethoxy)thiophene-2-carboxylic acid, 5-[3-({1-[(2-aminobenzyl)sulfonyl]piperidin-4-yl}amino)
phenyl]-4-bromo-3-(carboxymethoxy)thiophene-2-carboxylic acid, 4-bromo-5-(3-{[1-({2-[(2-carboxybenzoyl)
amino]ethyl}sulfonyl)piperidin-4-yl]amino}phenyl)-3-(carboxymethoxy)thiophene-2-carboxylic acid, {[4-bromo-5-phenyl-2-(2H-tetrazol-5-yl)thien-3-yl]oxy}acetic acid, {[4-methyl-5-phenyl-2-(2H-tetrazol-5-yl)thien-3-yl]
oxy}acetic acid, {[5-bromo-4-methyl-2-(2H-tetrazol-5-yl)
thien-3-yl]oxy}acetic acid, {[5-bromo-4-methyl-2-(2-methyl-2H-tetrazol-5-yl)thien-3-yl]oxy}acetic acid, {[5-(3-{[1-(benzylsulfonyl)piperidin-4-yl]amino}phenyl)-4-bromo-2-(2H-tetrazol-5-yl)thien-3-yl]oxy}acetic acid, {[5-{3-[acetyl
(3,3,5,5-tetramethylcyclohexyl)amino]phenyl}-4-bromo-2-(2H-tetrazol-5-yl)thien-3-yl]oxy}acetic acid, {[4-bromo-5-{3-[(cyclohexylmethyl)amino]phenyl}-2-(2H-tetrazol-5-yl)
thien-3-yl]oxy}acetic acid, {[4-bromo-5-{3-[(3,3,5,5-tetramethylcyclohexyl)amino]phenyl}-2-(2H-tetrazol-5-yl)
thien-3-yl]oxy}acetic acid, {[4-bromo-5-[3-(cyclohexylamino)phenyl]-2-(2H-tetrazol-5-yl)thien-3-yl]
oxy}acetic acid, tetrazol-5-yl)thien-3-yl]oxy}acetic {[4-bromo-5-(3-{[1-(tert-butoxycarbonyl)piperidin-4-yl]
oxy}phenyl)-2-(2H-, {[5-(3-{[1-(benzylsulfonyl)piperidin-4-yl]oxy}phenyl)-4-bromo-2-(2H-tetrazol-5-yl)thien-3-yl]
oxy}acetic acid, 4-bromo-3-(carboxymethoxy)-5-[3-({1-[(cyclohexylmethyl)sulfonyl]piperidin-4-yl}amino)phenyl]
thiophene-2-carboxylic acid, 4-bromo-3-(carboxymethoxy)-5-{3-[[(methylamino)carbonyl](3,3,5,5-tetramethylcyclohexyl)amino]phenyl}thiophene-2-carboxylic acid, 5-(3-{[cis-4-(benzyloxy)cyclohexyl]
amino}phenyl)-4-bromo-3-(carboxymethoxy)thiophene-2-carboxylic acid, 5-(3-{[trans-4-(benzyloxy)cyclohexyl]
aminophenyl)-4-bromo-3-(carboxymethoxy)thiophene-2-carboxylic acid, 4-bromo-3-(carboxymethoxy)-5-[3-({[1-(phenylacetyl)piperidin-4-yl]methyl}amino)phenyl]
thiophene-2-carboxylic acid, 4-bromo-3-(carboxymethoxy)-5-{3-[(1-{[2-(trifluoromethyl)benzyl]sulfonyl}piperidin-4-yl)amino]phenyl}thiophene-2-carboxylic acid, 4-bromo-3-(carboxymethoxy)-5-[3-({1-[(2-chlorobenzyl)sulfonyl]
piperidin-4-yl}amino)phenyl]thiophene-2-carboxylic acid, 5-(3-{[1-(benzylsulfonyl)piperidin-4-yl]amino}phenyl)-3-(carboxymethoxy)-4-methylthiophene-2-carboxylic acid, 4-bromo-3-(carboxymethoxy)-5-[3-({1-[(2,3-dichlorobenzyl)sulfonyl]piperidin-4-yl}amino)phenyl]thiophene-2-carboxylic acid, methyl {[5-(3-{[1-(benzylsulfonyl)piperidin-4-yl]amino}phenyl)-4-bromo-2-(1H-tetrazol-5-yl)thien-3-yl]
oxy}acetate, 4-bromo-3-(carboxymethoxy)-5-[3-(piperidin-4-ylamino)phenyl]thiophene-2-carboxylic acid, 4-bromo-3-(carboxymethoxy)-5-{3-[(1-pyrimidin-2-ylpiperidin-4-yl)
amino]phenyl}thiophene-2-carboxylic acid, 4-bromo-3-(carboxymethoxy)-5-[3-([(pyridin-4-ylmethyl)sulfonyl]{1-[(pyridin-4-ylmethyl)sulfonyl]piperidin-4-yl}amino)
phenyl]thiophene-2-carboxylic acid, 4-bromo-3-(carboxymethoxy)-5-[3-({1-[5-(trifluoromethyl)pyridin-2-yl]piperidin-4-yl}amino)phenyl]thiophene-2-carboxylic
acid, 4-bromo-3-(carboxymethoxy)-5-[3-({1-[4-(trifluoromethyl)pyrimidin-2-yl]piperidin-4-yl}amino)phenyl]
thiophene-2-carboxylic acid, 4-bromo-3-(carboxymethoxy)-5-(3-{[1-(5-nitropyridin-2-yl)piperidin-4-yl]amino}phenyl)
thiophene-2-carboxylic acid, {[4-bromo-5-(3-{[1-(methylsulfonyl)piperidin-4-yl]oxy}phenyl)-2-(1H-tetrazol-5-yl)thien-3-yl]oxy}acetic acid, 5-[3-({1-[(benzylamino)
carbonyl]piperidin-4-yl}methoxy)phenyl]-4-bromo-3-(carboxymethoxy)thiophene-2-carboxylic acid, 4-bromo-3-(carboxymethoxy)-5-[3-({1-[(cyclohexylamino)carbonyl]
piperidin-4-yl}methoxy)phenyl]thiophene-2-carboxylic acid, 4-bromo-3-(carboxymethoxy)-5-{3-[(cyclohexylmethyl)(methylsulfonyl)amino]phenyl}thiophene-2-carboxylic acid, 4-bromo-3-(carboxymethoxy)-5-{3-[[(ethylamino)
carbonyl](3,3,5,5-tetramethylcyclohexyl)amino]
phenyl}thiophene-2-carboxylic acid, 5-[3-({1-[5-(acetylamino)pyridin-2-yl]piperidin-4-yl}amino)phenyl]-4-bromo-3-(carboxymethoxy)thiophene-2-carboxylic acid, isopropyl {[5-(3-{[1-(benzylsulfonyl)piperidin-4-yl]
amino}phenyl)-4-bromo-2-(2H-tetrazol-5-yl)thien-3-yl]
oxy}acetate, 4-bromo-3-(carboxymethoxy)-5-[3-(2,3-dihydro-1H-inden-2-ylamino)phenyl]thiophene-2-carboxylic acid, 4-bromo-3-(carboxymethoxy)-5-(3-{[8-(ethoxycarbonyl)-8-azabicyclo[3.2.1]oct-3-yl]amino}phenyl)thiophene-2-carboxylic acid, 4-bromo-3-(carboxymethoxy)-5-(3-{[1-(5-{[(methylamino)carbonyl]amino}pyridin-2-yl)piperidin-4-yl]amino}phenyl)thiophene-2-carboxylic acid, 4-bromo-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid, 4-bromo-3-(carboxymethoxy)-5-{3-[(1-{5-[(methylsulfonyl)amino]
pyridin-2-yl}piperidin-4-yl)amino]phenyl}thiophene-2- carboxylic acid, 5-(1-benzyl-1H-pyrazol-4-yl)-4-bromo-3-(carboxymethoxy)thiophene-2-carboxylic acid, 5-{3-[(1-{[2-(acetylamino)benzyl]sulfonyl}piperidin-4-yl)amino]phenyl}-4-bromo-3-(carboxymethoxy)thiophene-2-carboxylic acid, 4-bromo-3-(carboxymethoxy)-5-(3-{[1-({2-[(methylsulfonyl)amino]benzyl}sulfonyl)piperidin-4-yl]amino}phenyl)thiophene-2-carboxylic acid, 4-bromo-3-(carboxymethoxy)-5-[3-([1-[(2-{[(ethylamino)carbonyl]amino}benzyl)sulfonyl]piperidin-4-yl}amino)phenyl]thiophene-2-carboxylic acid, 5-{3-[(1-{[2-(acetylamino)benzyl]sulfonyl}piperidin-4-yl)amino]phenyl}-3-(carboxymethoxy)thiophene-2-carboxylic acid, 3-(carboxymethoxy)-5-[3-({1-[(2-{[(ethylamino)carbonyl]amino}benzyl)sulfonyl]piperidin-4-yl}amino)phenyl]thiophene-2-carboxylic acid, 5-{3-[[(benzylamino)carbonyl](cyclohexyl)amino]phenyl}-4-bromo-3-(carboxymethoxy)thiophene-2-carboxylic acid, 4-bromo-3-(carboxymethoxy)-5-(3-{cyclohexyl[(methylamino)carbonyl]amino}phenyl)thiophene-2-carboxylic acid, 3-(carboxymethoxy)-5-phenylthiophene-2-carboxylic acid, 4-bromo-3-(carboxymethoxy)-5-[3-({1-[(3-{[(ethylamino)carbonyl]amino}benzyl)sulfonyl]piperidin-4-yl}amino)phenyl]thiophene-2-carboxylic acid, 4-bromo-3-(carboxymethoxy)-5-[3-({1-[(2-{[(chloromethyl)sulfonyl]amino}benzyl)sulfonyl]piperidin-4-yl}amino)phenyl]thiophene-2-carboxylic acid, 3-(carboxymethoxy)-5-(3-{[1-({2-[(methylsulfonyl)amino]benzyl}sulfonyl)piperidin-4-yl]amino}phenyl)thiophene-2-carboxylic acid, 5-(3-{[2-(benzylsulfonyl)-2-azabicyclo[2.2.2]oct-5-yl]amino}phenyl)-4-bromo-3-(carboxymethoxy)thiophene-2-carboxylic acid, 5-{3-[(1-{[3-(acetylamino)benzyl]sulfonyl}piperidin-4-yl)amino]phenyl}-4-bromo-3-(carboxymethoxy)thiophene-2-carboxylic acid, 4-bromo-3-(carboxymethoxy)-5-(3-{[1-({3-[(methylsulfonyl)amino]benzyl}sulfonyl)piperidin-4-yl]amino}phenyl)thiophene-2-carboxylic acid, 4-bromo-3-(carboxymethoxy)-5-{3-[(2,2,6,6-tetramethyltetrahydro-2H-pyran-4-yl)amino]phenyl}thiophene-2-carboxylic acid, 4-bromo-3-(carboxymethoxy)-5-(3-{(cyclohexylmethyl)[(ethylamino)carbonyl]amino}phenyl)thiophene-2-carboxylic acid, 4,5-dibromo-3-(1-carboxymethoxy)thiophene-2-carboxylic acid, 4-bromo-3-(carboxymethoxy)-5-(3-{cyclohexyl[(cyclohexylamino)carbonyl]amino}phenyl)thiophene-2-carboxylic acid, 5-{3-[(anilinocarbonyl)(cyclohexyl)amino]phenyl}-4-bromo-3-(carboxymethoxy)thiophene-2-carboxylic acid, 4-bromo-3-(carboxymethoxy)-5-[3-(cyclohexyl{[(2-phenylethyl)amino]carbonyl}amino)phenyl]thiophene-2-carboxylic acid, 4-bromo-3-(carboxymethoxy)-5-[3-(cyclohexyl {[(4-ethoxyphenyl)amino]carbonyl}amino)phenyl]thiophene-2-carboxylic acid, 4-bromo-3-(carboxymethoxy)-5-(3-{cyclohexyl[(isopropylamino)carbonyl]aminophenyl)thiophene-2-carboxylic acid, 4-bromo-3-(carboxymethoxy)-5-(3-{cyclohexyl[(propylamino)carbonyl]amino}phenyl)thiophene-2-carboxylic acid, 4-bromo-3-(carboxymethoxy)-5-[3-(cyclohexyl {[(4-phenoxyphenyl)amino]carbonyl}amino)phenyl]thiophene-2-carboxylic acid, 5-(3-{[acetyl(isopropyl)amino]methyl}phenyl)-4-bromo-3-(carboxymethoxy)thiophene-2-carboxylic acid, 5-(3-{[acetyl(isobutyl)amino]methyl}phenyl)-4-bromo-3-(carboxymethoxy)thiophene-2-carboxylic acid, 5-(3-{[acetyl(cyclohexylmethyl)amino]methyl}phenyl)-4-bromo-3-(carboxymethoxy)thiophene-2-carboxylic acid, 5-(3-{[acetyl(4-methylphenyl)amino]methyl}phenyl)-4-bromo-3-(carboxymethoxy)thiophene-2-carboxylic acid, 5-(3-{[acetyl(4-tert-butylphenyl)amino]methylphenyl)-4-bromo-3-(carboxymethoxy)thiophene-2-carboxylic acid, 5-[3-({acetyl[4-(trifluoromethyl)phenyl]aminomethyl)phenyl]-4-bromo-3-(carboxymethoxy)thiophene-2-carboxylic acid, 5-(3-{[acetyl(phenyl)amino]methyl}phenyl)-4-bromo-3-(carboxymethoxy)thiophene-2-carboxylic acid, 5-(3-{[acetyl(cyclopropyl)amino]methyl}phenyl)-4-bromo-3-(carboxymethoxy)thiophene-2-carboxylic acid, 5-(3-{[acetyl(4-bromophenyl)amino]methyl}phenyl)-4-bromo-3-(carboxymethoxy)thiophene-2-carboxylic acid, 5-(3-{[acetyl(1,1'-biphenyl-4-yl)amino]methyl}phenyl)-4-bromo-3-(carboxymethoxy)thiophene-2-carboxylic acid, 5-(3-{[acetyl(4-phenoxyphenyl)amino]methyl}phenyl)-4-bromo-3-(carboxymethoxy)thiophene-2-carboxylic acid, 5-(3-{[acetyl(benzyl)amino]methyl}phenyl)-4-bromo-3-(carboxymethoxy)thiophene-2-carboxylic acid, 5-(3-{[acetyl(4-methoxybenzyl)amino]methyl}phenyl)-4-bromo-3-(carboxymethoxy)thiophene-2-carboxylic acid, 5-(3-{[acetyl(1,1'-biphenyl-4-ylmethyl)amino]methyl}phenyl)-4-bromo-3-(carboxymethoxy)thiophene-2-carboxylic acid, 5-(3-{[acetyl(4-chlorobenzyl)amino]methyl}phenyl)-4-bromo-3-(carboxymethoxy)thiophene-2-carboxylic acid, (carboxymethoxy)thiophene-2-carboxylic acid, 5-[3-({acetyl[4-(trifluoromethyl)benzyl]amino}methyl)phenyl]-4-bromo-3-(carboxymethoxy)thiophene-2-carboxylic acid, 5-[3-({acetyl[3,5-bis(trifluoromethyl)benzyl]amino}methyl)phenyl]-4-bromo-3-(carboxymethoxy)thiophene-2-carboxylic acid, 5-[3-({acetyl[2-(4-chlorophenyl)ethyl]aminomethyl)phenyl]-4-bromo-3-(carboxymethoxy)thiophene-2-carboxylic acid, 4-bromo-3-(carboxymethoxy)-5-[3-(cyclohexyl{[(2-thien-3-ylethyl)amino]carbonyl}amino)phenyl]thiophene-2-carboxylic acid, 4-bromo-3-(carboxymethoxy)-5-(3-{cyclohexyl[(thien-3-ylamino)carbonyl]amino}phenyl)thiophene-2-carboxylic acid, 4-bromo-3-(carboxymethoxy)-5-[3-(cyclohexyl {[(3,5-dimethylisoxazol-4-yl)amino]carbonyl}amino)phenyl]thiophene-2-carboxylic acid, 4-bromo-5-{3-[({[2-(5-bromo-2-methoxyphenyl)ethyl]amino}carbonyl)(cyclohexyl)amino]phenyl}-3-(carboxymethoxy)thiophene-2-carboxylic acid, 4-bromo-5-{3-[{[(2-carboxyethyl)amino]carbonyl}(cyclohexyl)amino]phenyl}-3-(carboxymethoxy)thiophene-2-carboxylic acid (non-preferred name), 4-bromo-3-(carboxymethoxy)-5-{3-[{[(4-carboxyphenyl)amino]carbonyl}(cyclohexyl)amino]phenyl}thiophene-2-carboxylic acid, 4-bromo-3-(carboxymethoxy)-5-{3-[{[(5-carboxypentyl)amino]carbonyl}(cyclohexyl)amino]phenyl}thiophene-2-carboxylic acid, 4-bromo-3-(carboxymethoxy)-5-{3-[{[(3-,5-{3-[[(benzylamino)carbonyl](ethyl)amino]phenyl}-4-bromo-3-(carboxymethoxy)thiophene-2-carboxylic acid, 5-(3-{[1-(benzylsulfonyl)piperidin-4-yl][(ethylamino)carbonyl]amino}phenyl)-4-bromo-3-(carboxymethoxy)thiophene-2-carboxylic acid, 5-{3-[(anilinocarbonyl)(cyclohexylmethyl)amino]phenyl}-4-bromo-3-(carboxymethoxy)thiophene-2-carboxylic acid, 5-{3-[[(benzylamino)carbonyl](cyclohexylmethyl)amino]phenyl}-4-bromo-3-(carboxymethoxy)thiophene-2-carboxylic acid, 4-bromo-3-(carboxymethoxy)-5-[3-((cyclohexylmethyl){[(4-ethylphenyl)amino]carbonyl}amino)phenyl]thiophene-2-carboxylic acid, 4-bromo-3-(carboxymethoxy)-5-[3-((cyclohexylmethyl){[(4-ethoxyphenyl)amino]carbonyl}amino)phenyl]thiophene-2-carboxylic acid, 4-bromo-3-(carboxymethoxy)-5-[3-((cyclohexylmethyl){[(4-phenoxyphenyl)amino]carbonyl}amino)phenyl]thiophene-2-carboxylic acid, 4-bromo-3-(carboxymethoxy)-5-[3-(cyclohexyl {[(3-methyl-5-phenylisoxazol-4-yl)amino]carbonyl}amino)phenyl]thiophene-2-carboxylic acid, 4,5-dibromo-3-[carboxy(fluoro)methoxy]thiophene-2-carboxylic acid, 4-bromo-3-(carboxymethoxy)-5-{3-[{[(2- cyanophenyl)amino]carbonyl}(cyclohexylmethyl)amino]phenyl}thiophene-2-carboxylic acid, 4-bromo-3-(carboxymethoxy)-5-(3-{(cyclohexylmethyl)[(thien-3-ylamino)carbonyl]amino}phenyl)thiophene-2-carboxylic acid, 4-bromo-3-(carboxymethoxy)-5-[3-((cyclohexylmethyl){[(5-methyl-3-phenylisoxazol-4-yl)amino]carbonyl}amino)phenyl]thiophene-2-carboxylic acid, 4-bromo-3-(carboxymethoxy)-5-[3-((cyclohexylmethyl){[(3,5-dimethylisoxazol-4-yl)amino]carbonyl}amino)phenyl]thiophene-2-carboxylic acid, 5-{3-[bis(cyclohexylmethyl)amino]phenyl)}4-bromo-3-(carboxymethoxy)thiophene-2-carboxylic acid, {[5-phenyl-2-(2H-tetrazol-5-yl)thien-3-yl]oxy}acetic acid, carboxyphenyl)amino]carbonyl}(cyclohexylmethyl)amino]phenyl}thiophene-2-carboxylic acid, 3-(carboxymethoxy)-4-methyl-5-(phenylethynyl)thiophene-2-carboxylic acid, 5-(3-{benzyl[(isopropylamino)carbonyl]amino}phenyl)-4-bromo-3-(carboxymethoxy)thiophene-2-carboxylic acid, 4-bromo-3-(carboxymethoxy)-5-(3-{[(isopropylamino)carbonyl][4-(trifluoromethyl)benzyl]amino}phenyl)thiophene-2-carboxylic acid, 4-bromo-5-(3-{(4-tert-butylbenzyl)[(isopropylamino)carbonyl]amino}phenyl)-3-(carboxymethoxy)thiophene-2-carboxylic acid, 4-bromo-3-(carboxymethoxy)-5-(3-{isopropyl[(isopropylamino)carbonyl]aminophenyl)thiophene-2-carboxylic acid, 5-{3-[acetyl(cyclohexyl)amino]phenyl}4-bromo-3-(carboxymethoxy)thiophene-2-carboxylic acid, and 5-{3-[benzoyl(cyclohexyl)amino]phenyl}-4-bromo-3-(carboxymethoxy)thiophene-2-carboxylic acid.

In some embodiments, the compound can be selected from 3-carboxymethoxy-4-phenyl-thiophene-2-carboxylic acid, 3-carboxymethoxy-4-(3-trifluoromethyl-phenyl)-thiophene-2-carboxylic acid, 3-carboxymethoxy-4-(1H-indol-5-yl)-thiophene-2-carboxylic acid, 4-carboxymethoxy-[3,3']bithiophenyl-5-carboxylic acid, 4-chloro-3-carboxymethoxy-5-phenyl-thiophene-2-carboxylic acid, 5-(4-amino-phenyl)-4-chloro-3-carboxymethoxy-thiophene-2-carboxylic acid, 4-chloro-3-carboxymethoxy-5-(4-dimethylamino-phenyl)-thiophene-2-carboxylic acid, 5-(3-amino-phenyl)-4-chloro-3-carboxymethoxy-thiophene-2-carboxylic acid, 4-chloro-3-carboxymethoxy-5-naphthalen-2-yl-thiophene-2-carboxylic acid, 4-chloro-3-carboxymethoxy-5-(4-hydroxy-phenyl)-thiophene-2-carboxylic acid, 4-chloro-3-carboxymethoxy-5-(4-methoxy-phenyl)-thiophene-2-carboxylic acid, 3-carboxymethoxy-5-(4-trifluoromethoxy-phenyl)-thiophene-2-carboxylic acid, 4-chloro-3-carboxymethoxy-5-(4-hydroxymethyl-phenyl)-thiophene-2-carboxylic acid, 4-chloro-3-carboxymethoxy-5-(3-hydroxy-phenyl)-thiophene-2-carboxylic acid, 3-ethoxycarbonylmethoxy-4,5-bis-(3-hydroxy-phenyl)-thiophene-2-carboxylic acid methyl ester, 4-chloro-3-carboxymethoxy-5-(3-methoxy-phenyl)-thiophene-2-carboxylic acid, 4-chloro-3-carboxymethoxy-5-(4-fluoro-phenyl)-thiophene-2-carboxylic acid, 3-carboxymethoxy-5-o-tolyl-thiophene-2-carboxylic acid, 5-(4-acetylamino-phenyl)-4-chloro-3-carboxymethoxy-thiophene-2-carboxylic acid, 5-(4-benzoylamino-phenyl)-4-chloro-3-carboxymethoxy-thiophene-2-carboxylic acid, 4-chloro-3-carboxymethoxy-5-{4-[(pyridine-3-carbonyl)-amino]-phenyl}-thiophene-2-carboxylic acid, 4-chloro-3-carboxymethoxy-5-{4-[(furan-3-carbonyl)-amino]-phenyl}-thiophene-2-carboxylic acid, 4-chloro-3-carboxymethoxy-5-{4-[(furan-2-carbonyl)-amino]-phenyl}-thiophene-2-carboxylic acid, 4-[4-(3-bromo-5-carboxy-4-carboxymethoxy-thiophen-2-yl)-phenylcarbamoyl]-piperidine-1-carboxylic acid tert-butyl ester, 3-[4-(3-bromo-5-carboxy-4-carboxymethoxy-thiophen-2-yl)-phenylcarbamoyl]-piperidine-1-carboxylic acid tert-butyl ester, 4-chloro-3-carboxymethoxy-5-(4-methoxycarbonylamino-phenyl)-thiophene-2-carboxylic acid, 4-chloro-3-carboxymethoxy-5-[4-(3-isopropyl-ureido)-phenyl]-thiophene-2-carboxylic acid, 5-[4-(2-benzyloxy-acetylamino)-phenyl]-4-chloro-3-carboxymethoxy-thiophene-2-carboxylic acid, 4-chloro-5-[4-(2-tert-butoxycarbonylamino-acetylamino)-phenyl]-3-carboxymethoxy-thiophene-2-carboxylic acid, 5-[4-(2-amino-acetylamino)-phenyl]-4-chloro-3-carboxymethoxy-thiophene-2-carboxylic acid, 4-chloro-3-carboxymethoxy-5-[4-(oxalyl-amino)-phenyl]-thiophene-2-carboxylic acid, 4-chloro-5-[4-(2-carboxy-acetylamino)-phenyl]-3-carboxymethoxy-thiophene-2-carboxylic acid, 4-chloro-3-carboxymethoxy-5-(4-methanesulfonylamino-phenyl)-thiophene-2-carboxylic acid, 5-(4-benzenesulfonylamino-phenyl)-4-chloro-3-carboxymethoxy-thiophene-2-carboxylic acid, 4-chloro-3-carboxymethoxy-5-[4-(4-trifluoromethyl-benzenesulfonylamino)-phenyl]-thiophene-2-carboxylic acid, 4-chloro-3-carboxymethoxy-5-{4-[methyl-(4-trifluoromethyl-benzenesulfonyl)-amino]-phenyl}-thiophene-2-carboxylic acid, 4-chloro-3-carboxymethoxy-5-[4-(3-trifluoromethyl-benzenesulfonylamino)-phenyl]-thiophene-2-carboxylic acid, 4-chloro-3-carboxymethoxy-5-[4-(2-trifluoromethyl-benzenesulfonylamino)-phenyl]-thiophene-2-carboxylic acid, 4-chloro-3-carboxymethoxy-5-[4-(2,6-dichloro-benzenesulfonylamino)-phenyl]-thiophene-2-carboxylic acid, 4-chloro-3-carboxymethoxy-5-[4-(2,6-difluoro-benzenesulfonylamino)-phenyl]-thiophene-2-carboxylic acid, 4-chloro-3-carboxymethoxy-5-[4-(3,3,5,5-tetramethyl-cyclohexylamino)-phenyl]-thiophene-2-carboxylic acid, 3-carboxymethoxy-5-[4-(3,3,5,5-tetramethyl-cyclohexylamino)-phenyl]-thiophene-2-carboxylic acid, 5-[4-(benzenesulfonylamino-methyl)-phenyl]-4-chloro-3-carboxymethoxy-thiophene-2-carboxylic acid, 4-chloro-5-[4-(tert-butoxycarbonylamino-methyl)-phenyl]-3-carboxymethoxy-thiophene-2-carboxylic acid, 4-chloro-3-carboxymethoxy-5-[4-(ethanesulfonylamino-methyl)-phenyl]-thiophene-2-carboxylic acid, 5-[4-(acetylamino-methyl)-phenyl]-4-chloro-3-carboxymethoxy-thiophene-2-carboxylic acid, 4-chloro-3-carboxymethoxy-5-[4-(ethoxycarbonylamino-methyl)-phenyl]-thiophene-2-carboxylic acid, 4-chloro-3-carboxymethoxy-5-[4-(3-isopropyl-ureidomethyl)-phenyl]-thiophene-2-carboxylic acid, 5-(4-aminomethyl-phenyl)-4-chloro-3-carboxymethoxy-thiophene-2-carboxylic acid trifluoroacetic acid, 4-chloro-3-carboxymethoxy-5-(4-phenylcarbamoyl-phenyl)-thiophene-2-carboxylic acid, 4-chloro-3-carboxymethoxy-5-(4-formyl-phenyl)-thiophene-2-carboxylic acid, 4-chloro-3-carboxymethoxy-5-(4-isopropylcarbamoyl-phenyl)-thiophene-2-carboxylic acid, 4-chloro-5-[4-(1-carbamoyl-ethylcarbamoyl)-phenyl]-3-carboxymethoxy-thiophene-2-carboxylic acid, 4-chloro-3-carboxymethoxy-5-[4-(4-trifluoromethyl-phenylcarbamoyl)-phenyl]-thiophene-2-carboxylic acid, 4-chloro-3-carboxymethoxy-5-(3-propionylamino-phenyl)-thiophene-2-carboxylic acid, 4-chloro-5-(3-butyrylamino-phenyl)-3-carboxymethoxy-thiophene-2-carboxylic acid, 4-chloro-5-(3-butyrylamino-phenyl)-3-carboxymethoxy-thiophene-2-carboxylic acid, 4-chloro-3-carboxymethoxy-5-[3-(cyclohexanecarbonyl-amino)-phenyl]-thiophene-2-carboxylic acid, 4-chloro-3-carboxymethoxy-5-(3-hexanoylamino-phenyl)-thiophene-2-carboxylic acid, 4-chloro-3-carboxymethoxy-5-[3-(cyclopentanecarbonyl-amino)-phenyl]-thiophene-2-carboxylic acid, 4-[3-(3-bromo-5-carboxy-4-carboxymethoxy-thiophen-2-yl)-phenylcarbamoyl]-piperidine-1-carboxylic acid tert-butyl ester, 3-[3-(3-bromo- 5-carboxy-4-carboxymethoxy-thiophen-2-yl)-phenylcarbamoyl]-piperidine-1-carboxylic acid tert-butyl ester, 4-chloro-3-carboxymethoxy-5-[3-(3,3,3-trifluoro-propionylamino)-phenyl]-thiophene-2-carboxylic acid, 5-(3-benzoylamino-phenyl)-4-chloro-3-carboxymethoxy-thiophene-2-carboxylic acid, 4-chloro-3-carboxymethoxy-5-{3-[(furan-2-carbonyl)-amino]-phenyl}-thiophene-2-carboxylic acid, 4-chloro-3-carboxymethoxy-5-{3-[(furan-3-carbonyl)-amino]-phenyl}-thiophene-2-carboxylic acid, 4-chloro-3-carboxymethoxy-5-[3-(2-trifluoromethyl-benzoylamino)-phenyl]-thiophene-2-carboxylic acid, 4-chloro-3-carboxymethoxy-5-[3-(2-fluoro-benzoylamino)-phenyl]-thiophene-2-carboxylic acid, 4-chloro-3-carboxymethoxy-5-[3-(3-fluoro-benzoylamino)-phenyl]-thiophene-2-carboxylic acid, 4-chloro-3-carboxymethoxy-5-{3-[(pyridine-3-carbonyl)-amino]-phenyl}-thiophene-2-carboxylic acid, 4-chloro-3-carboxymethoxy-5-[3-(4,4,4-trifluoro-butyrylamino)-phenyl]-thiophene-2-carboxylic acid, 4-chloro-3-carboxymethoxy-5-{3-[(2-hydroxy-pyridine-3-carbonyl)-amino]-phenyl}-thiophene-2-carboxylic acid, 4-chloro-3-carboxymethoxy-5-{3-[(pyridine-4-carbonyl)-amino]-phenyl}-thiophene-2-carboxylic acid, 4-chloro-3-carboxymethoxy-5-{3-[(quinoline-3-carbonyl)-amino]-phenyl}-thiophene-2-carboxylic acid, 4-chloro-3-carboxymethoxy-5-{3-[(pyridine-2-carbonyl)-amino]-phenyl}-thiophene-2-carboxylic acid, 4-chloro-3-carboxymethoxy-5-{3-[(1-oxy-pyridine-3-carbonyl)-amino]-phenyl}-thiophene-2-carboxylic acid, 4-chloro-3-carboxymethoxy-5-[3-(2-pyridin-2-yl-acetylamino)-phenyl]-thiophene-2-carboxylic acid, 4-chloro-3-carboxymethoxy-5-[3-(2-pyridin-3-yl-acetylamino)-phenyl]-thiophene-2-carboxylic acid, 4-chloro-3-carboxymethoxy-5-{3-[(pyrazine-2-carbonyl)-amino]-phenyl}-thiophene-2-carboxylic acid, 4-chloro-3-carboxymethoxy-5-[3-(2-pyridin-4-yl-acetylamino)-phenyl]-thiophene-2-carboxylic acid, 4-chloro-3-carboxymethoxy-5-{3-[(piperidine-4-carbonyl)-amino]-phenyl}-thiophene-2-carboxylic acid trifluoroacetic acid salt, 4-chloro-3-carboxymethoxy-5-[3-(cyclohexanecarbonyl-amino)-phenyl]-thiophene-2-carboxylic acid, 5-(3-acetylamino-phenyl)-4-chloro-3-carboxymethoxy-thiophene-2-carboxylic acid, 4-chloro-3-carboxymethoxy-5-(3-isobutyrylamino-phenyl)-thiophene-2-carboxylic acid, 4-chloro-3-carboxymethoxy-5-[3-(2,2,2-trifluoro-ethanesulfonylamino)-phenyl]-thiophene-2-carboxylic acid, 5-(3-benzenesulfonylamino-phenyl)-4-chloro-3-carboxymethoxy-thiophene-2-carboxylic acid, 4-chloro-3-carboxymethoxy-5-(3-ethanesulfonylamino-phenyl)-thiophene-2-carboxylic acid, 4-chloro-3-carboxymethoxy-5-(3-phenylmethanesulfonylamino-phenyl)-thiophene-2-carboxylic acid, 4-chloro-3-carboxymethoxy-5-[3-(4-trifluoromethyl-benzenesulfonylamino)-phenyl]-thiophene-2-carboxylic acid, 4-chloro-3-carboxymethoxy-5-[3-(4-trifluoromethoxy-benzenesulfonylamino)-phenyl]-thiophene-2-carboxylic acid, 4-chloro-3-carboxymethoxy-5-[3-(3-trifluoromethyl-benzenesulfonylamino)-phenyl]-thiophene-2-carboxylic acid, 4-chloro-3-carboxymethoxy-5-[3-(2-trifluoromethyl-benzenesulfonylamino)-phenyl]-thiophene-2-carboxylic acid, 4-chloro-3-carboxymethoxy-5-[3-(2-cyano-benzenesulfonylamino)-phenyl]-thiophene-2-carboxylic acid, 4-chloro-3-carboxymethoxy-5-[3-(4-methoxy-benzenesulfonylamino)-phenyl]-thiophene-2-carboxylic acid, 4-chloro-3-carboxymethoxy-5-[3-(4-cyano-benzenesulfonylamino)-phenyl]-thiophene-2-carboxylic acid, 4-chloro-3-carboxymethoxy-5-[3-(4-fluoro-benzenesulfonylamino)-phenyl]-thiophene-2-carboxylic acid, 4-chloro-3-carboxymethoxy-5-(3-methoxycarbonylamino-phenyl)-thiophene-2-carboxylic acid, 4-chloro-3-carboxymethoxy-5-[3-(3-isopropyl-ureido)-phenyl]-thiophene-2-carboxylic acid, 4-chloro-3-carboxymethoxy-5-[3-(3,3-diethyl-ureido)-phenyl]-thiophene-2-carboxylic acid, 5-(3-benzylamino-phenyl)-4-chloro-3-carboxymethoxy-thiophene-2-carboxylic acid, 4-chloro-3-carboxymethoxy-5-[3-(3-trifluoromethyl-benzylamino)-phenyl]-thiophene-2-carboxylic acid, 4-chloro-3-carboxymethoxy-5-[3-(2-trifluoromethyl-benzylamino)-phenyl]-thiophene-2-carboxylic acid, 4-chloro-3-carboxymethoxy-5-{3-[(furan-2-ylmethyl)-amino]-phenyl}-thiophene-2-carboxylic acid, 4-chloro-3-carboxymethoxy-5-{3-[(furan-3-ylmethyl)-amino]-phenyl}-thiophene-2-carboxylic acid, 4-chloro-3-carboxymethoxy-5-[3-(3-fluoro-benzylamino)-phenyl]-thiophene-2-carboxylic acid, 4-chloro-3-carboxymethoxy-5-[3-(3-cyano-benzylamino)-phenyl]-thiophene-2-carboxylic acid, 4-chloro-3-carboxymethoxy-5-{3-[(pyridin-3-ylmethyl)-amino]-phenyl}-thiophene-2-carboxylic acid, 4-chloro-3-carboxymethoxy-5-[3-(4-fluoro-benzylamino)-phenyl]-thiophene-2-carboxylic acid, 4-chloro-3-carboxymethoxy-5-[3-(4-trifluoromethyl-benzylamino)-phenyl]-thiophene-2-carboxylic acid, 4-chloro-3-carboxymethoxy-5-[3-(4-methoxy-benzylamino)-phenyl]-thiophene-2-carboxylic acid, 5-[3-(4-benzyloxy-benzylamino)-phenyl]-4-chloro-3-carboxymethoxy-thiophene-2-carboxylic acid, 4-chloro-3-carboxymethoxy-5-[3-(4-phenoxy-benzylamino)-phenyl]-thiophene-2-carboxylic acid, 4-chloro-3-carboxymethoxy-5-{3-[(naphthalen-2-ylmethyl)-amino]-phenyl}-thiophene-2-carboxylic acid, 4-chloro-5-[3-(3-carboxy-benzylamino)-phenyl]-3-carboxymethoxy-thiophene-2-carboxylic acid, 4-chloro-3-carboxymethoxy-5-[3-(3-trifluoromethoxy-benzylamino)-phenyl]-thiophene-2-carboxylic acid, 4-chloro-3-carboxymethoxy-5-[3-(2-trifluoromethoxy-benzylamino)-phenyl]-thiophene-2-carboxylic acid, 4-chloro-3-carboxymethoxy-5-[3-(2-hydroxy-benzylamino)-phenyl]-thiophene-2-carboxylic acid, 4-chloro-3-carboxymethoxy-5-[3-(4-methyl-benzylamino)-phenyl]-thiophene-2-carboxylic acid, 4-chloro-3-carboxymethoxy-5-[3-(4-chloro-benzylamino)-phenyl]-thiophene-2-carboxylic acid, 4-chloro-3-carboxymethoxy-5-[3-(4-isopropyl-benzylamino)-phenyl]-thiophene-2-carboxylic acid, 4-chloro-3-carboxymethoxy-5-[3-(3-nitro-benzylamino)-phenyl]-thiophene-2-carboxylic acid, 4-chloro-3-carboxymethoxy-5-[3-(3-methanesulfonylamino-benzylamino)-phenyl]-thiophene-2-carboxylic acid, 5-[3-(3-amino-benzylamino)-phenyl]-4-chloro-3-carboxymethoxy-thiophene-2-carboxylic acid, 5-[3-(3-acetylamino-benzylamino)-phenyl]-4-chloro-3-carboxymethoxy-thiophene-2-carboxylic acid, 4-chloro-3-carboxymethoxy-5-(3-cyclohexylamino-phenyl)-thiophene-2-carboxylic acid, 4-chloro-3-carboxymethoxy-5-(3-cyclopentylamino-phenyl)-thiophene-2-carboxylic acid, 5-[3-(1-acetyl-piperidin-4-ylamino)-phenyl]-4-chloro-3-carboxymethoxy-thiophene-2-carboxylic acid, 4-chloro-3-carboxymethoxy-5-(3-cycloheptylamino-phenyl)-thiophene-2-carboxylic acid, 5-[3-(bicyclo[3.3.1]non-9-ylamino)-phenyl]-4-chloro-3-carboxymethoxy-thiophene-2-carboxylic acid, 4-chloro-3-carboxymethoxy-5-[3-(4-ethyl-cyclohexylamino)-phenyl]-thiophene-2-carboxylic acid, 4-chloro-3-carboxymethoxy-5-[3-cis(4-phenyl-cyclohexylamino)-phenyl]-thiophene-2-carboxylic acid, 4-chloro-3-carboxymethoxy-5-[3-trans(4-phenyl-cyclohexylamino)-phenyl]-thiophene-2-carboxylic acid, 4-chloro-3-carboxymethoxy-5-[3-(1-cyclohexyl-ethylamino)-phenyl]-thiophene-2-carboxylic acid, 4-chloro-3-carboxymethoxy-5-[3-(3,3,5,5-tetramethyl-cyclohexylamino)-phenyl]-thiophene-2-carboxylic acid, 5-[3-(adamantan-2-ylamino)-phenyl]-4-chloro-3- carboxymethoxy-thiophene-2-carboxylic acid, 4-chloro-3-carboxymethoxy-5-[3-(tetrahydro-pyran-4-ylamino)-phenyl]-thiophene-2-carboxylic acid, 4-chloro-3-carboxymethoxy-5-[3-(cyclohexylmethyl-amino)-phenyl]-thiophene-2-carboxylic acid, 4-chloro-3-carboxymethoxy-5-[3-(1-methanesulfonyl-piperidin-4-ylamino)-phenyl]-thiophene-2-carboxylic acid, 4-chloro-3-carboxymethoxy-5-[3-(1-phenylmethanesulfonyl-piperidin-4-ylamino)-phenyl]-thiophene-2-carboxylic acid, 4-chloro-3-carboxymethoxy-5-[3-(1-ethanesulfonyl-piperidin-4-ylamino)-phenyl]-thiophene-2-carboxylic acid, 4-chloro-5-{3-[1-(butane-1-sulfonyl)-piperidin-4-ylamino]-phenyl}-3-carboxymethoxy-thiophene-2-carboxylic acid, 5-{3-[1-(3,5-bis-trifluoromethyl-phenylmethanesulfonyl)-piperidin-4-ylamino]-phenyl}-4-chloro-3-carboxymethoxy-thiophene-2-carboxylic acid, 4-chloro-3-carboxymethoxy-5-{3-[1-(propane-1-sulfonyl)-piperidin-4-ylamino]-phenyl}-thiophene-2-carboxylic acid, 4-chloro-3-carboxymethoxy-5-{3-[1-(3-trifluoromethyl-phenylmethanesulfonyl)-piperidin-4-ylamino]-phenyl}-thiophene-2-carboxylic acid, 4-chloro-3-carboxymethoxy-5-{3-[1-(4-fluoro-phenyl-methanesulfonyl)-piperidin-4-ylamino]-phenyl}-thiophene-2-carboxylic acid, 4-chloro-3-carboxymethoxy-5-{3-[1-(4-trifluoromethyl-phenylmethanesulfonyl)-piperidin-4-ylamino]-phenyl}-thiophene-2-carboxylic acid, 4-chloro-3-carboxymethoxy-5-{3-[1-(naphthalene-1-sulfonyl)-piperidin-4-ylamino]-phenyl}-thiophene-2-carboxylic acid, 4-chloro-3-carboxymethoxy-5-{3-[1-(naphthalene-2-sulfonyl)-piperidin-4-ylamino]-phenyl}-thiophene-2-carboxylic acid, 4-chloro-3-carboxymethoxy-5-{3-[1-(2-nitro-phenyl-methanesulfonyl)-piperidin-4-ylamino]-phenyl}-thiophene-2-carboxylic acid, 4-chloro-3-carboxymethoxy-5-{3-[1-(4-chloro-phenylmethanesulfonyl)-piperidin-4-ylamino]-phenyl}-thiophene-2-carboxylic acid, 4-chloro-3-carboxymethoxy-5-{3-[1-(3,5-dichloro-phenylmethanesulfonyl)-piperidin-4-ylamino]-phenyl}-thiophene-2-carboxylic acid, 4-chloro-3-carboxymethoxy-5-{3-[1-(3,4-dichloro-phenylmethanesulfonyl)-piperidin-4-ylamino]-phenyl}-thiophene-2-carboxylic acid, 4-chloro-3-carboxymethoxy-5-{3-[1-(3-nitro-phenylmethanesulfonyl)-piperidin-4-ylamino]-phenyl}-thiophene-2-carboxylic acid, 4-chloro-3-carboxymethoxy-5-{3-[1-(3-chloro-phenyl-methanesulfonyl)-piperidin-4-ylamino]-phenyl}-thiophene-2-carboxylic acid, 4-chloro-3-carboxymethoxy-5-{3-[1-(2-phenyl-ethanesulfonyl)-piperidin-4-ylamino]-phenyl}-thiophene-2-carboxylic acid, 4-chloro-3-carboxymethoxy-5-[3-(1-o-tolylmethanesulfonyl-piperidin-4-ylamino)-phenyl]-thiophene-2-carboxylic acid, 4-chloro-3-carboxymethoxy-5-[3-(1-m-tolylmethanesulfonyl-piperidin-4-ylamino)-phenyl]-thiophene-2-carboxylic acid, 4-chloro-3-carboxymethoxy-5-{3-[1-(2,6-dimethyl-phenyl-methanesulfonyl)-piperidin-4-ylamino]-phenyl}-thiophene-2-carboxylic acid, 4-chloro-3-carboxymethoxy-5-{3-[1-(2-imidazol-1-yl-ethanesulfonyl)-piperidin-4-ylamino]-phenyl}-thiophene-2-carboxylic acid, 4-chloro-3-carboxymethoxy-5-{3-[1-(2-pyrazol-1-yl-ethanesulfonyl)-piperidin-4-ylamino]-phenyl}-thiophene-2-carboxylic acid, 4-chloro-3-carboxymethoxy-5-{3-[1-(2-isopropoxy-ethanesulfonyl)-piperidin-4-ylamino]-phenyl}-thiophene-2-carboxylic acid, 5-{3-[1-(2-amino-phenylmethanesulfonyl)-piperidin-4-ylamino]-phenyl}-4-chloro-3-carboxymethoxy-thiophene-2-carboxylic acid, 4-[3-(3-bromo-5-carboxy-4-carboxymethoxy-thiophen-2-yl)-phenylamino]-piperidine-1-carboxylic acid methyl ester, 5-[3-(1-benzoyl-piperidin-4-ylamino)-phenyl]-4-chloro-3-carboxymethoxy-thiophene-2-carboxylic acid, 4-chloro-3-carboxymethoxy-5-[3-(1-phenylacetyl-piperidin-4-ylamino)-phenyl]-thiophene-2-carboxylic acid, 5-{3-[3-benzyl-1-(1-benzylcarbamoyl-piperidin-4-yl)-ureido]-phenyl}-4-chloro-3-carboxymethoxy-thiophene-2-carboxylic acid, 5-[3-(1-benzylcarbamoyl-piperidin-4-ylamino)-phenyl]-4-chloro-3-carboxymethoxy-thiophene-2-carboxylic acid, 4-chloro-3-carboxymethoxy-5-{3-[(1-methanesulfonyl-piperidin-4-ylmethyl)-amino]-phenyl}-thiophene-2-carboxylic acid, 4-chloro-3-carboxymethoxy-5-{3-[(1-ethanesulfonyl-piperidin-4-ylmethyl)-amino]-phenyl}-thiophene-2-carboxylic acid, 5-{3-[(1-benzenesulfonyl-piperidin-4-ylmethyl)-amino]-phenyl}4-chloro-3-carboxymethoxy-thiophene-2-carboxylic acid, 4-chloro-3-carboxymethoxy-5-{3-[(1-phenyl-methanesulfonyl-piperidin-4-ylmethyl)-amino]-phenyl}-thiophene-2-carboxylic acid, 5-(3-{[1-(2-amino-phenylmethanesulfonyl)-piperidin-4-ylmethyl]-amino}-phenyl)-4-chloro-3-carboxymethoxy-thiophene-2-carboxylic acid, 4-{[3-(3-bromo-5-carboxy-4-carboxymethoxy-thiophen-2-yl)-phenylamino]-methyl}-piperidine-1-carboxylic acid methyl ester, 4-chloro-3-carboxymethoxy-5-{3-[(1-phenylcarbamoyl-piperidin-4-ylmethyl)-amino]-phenyl}-thiophene-2-carboxylic acid, 5-{3-[(1-benzylcarbamoyl-piperidin-4-ylmethyl)-amino]-phenyl}-4-chloro-3-carboxymethoxy-thiophene-2-carboxylic acid, 4-chloro-3-carboxymethoxy-5-{3-[(1-cyclohexylcarbamoyl-piperidin-4-ylmethyl)-amino]-phenyl}-thiophene-2-carboxylic acid, 4-chloro-3-carboxymethoxy-5-(3-{[1-(4-methoxy-phenylcarbamoyl)-piperidin-4-ylmethyl]-amino}-phenyl)-thiophene-2-carboxylic acid, 4-chloro-3-carboxymethoxy-5-(3-{[1-(4-cyano-phenylcarbamoyl)-piperidin-4-ylmethyl]-amino}-phenyl)-thiophene-2-carboxylic acid, 4-chloro-3-carboxymethoxy-5-{3-[(1-p-tolylcarbamoyl-piperidin-4-ylmethyl)-amino]-phenyl}-thiophene-2-carboxylic acid, 4-chloro-3-carboxymethoxy-5-(3-{[1-(3-methoxy-phenylcarbamoyl)-piperidin-4-ylmethyl]-amino}-phenyl)-thiophene-2-carboxylic acid, 4-chloro-3-carboxymethoxy-5-(3-{[1-(2-methoxy-phenylcarbamoyl)-piperidin-4-ylmethyl]-amino}-phenyl)-thiophene-2-carboxylic acid, 4-chloro-3-carboxymethoxy-5-(3-{[1-(3-chloro-phenylcarbamoyl)-piperidin-4-ylmethyl]-amino}-phenyl)-thiophene-2-carboxylic acid, 4-chloro-3-carboxymethoxy-5-(3-{[1-(2-chloro-phenylcarbamoyl)-piperidin-4-ylmethyl]-amino}-phenyl)-thiophene-2-carboxylic acid, 4-chloro-3-carboxymethoxy-5-{3-[(1-m-tolylcarbamoyl-piperidin-4-ylmethyl)-amino]-phenyl}-thiophene-2-carboxylic acid, 4-chloro-3-carboxymethoxy-5-{3-[(1-o-tolylcarbamoyl-piperidin-4-ylmethyl)-amino]-phenyl}-thiophene-2-carboxylic acid, 4-chloro-3-carboxymethoxy-5-(3-{[1-(2,6-dimethyl-phenylcarbamoyl)-piperidin-4-ylmethyl]-amino}-phenyl)-thiophene-2-carboxylic acid, 4-chloro-3-carboxymethoxy-5-(3-{[1-(2-trifluoromethyl-phenylcarbamoyl)-piperidin-4-ylmethyl]-amino}-phenyl)-thiophene-2-carboxylic acid, 4-chloro-3-carboxymethoxy-5-(3-{[1-(methyl-phenyl-carbamoyl)-piperidin-4-ylmethyl]-amino}-phenyl)-thiophene-2-carboxylic acid, 4-chloro-3-carboxymethoxy-5-(3-{[1-(2-methylsulfanyl-phenylcarbamoyl)-piperidin-4-ylmethyl]-amino}-phenyl)-thiophene-2-carboxylic acid, 4-chloro-3-carboxymethoxy-5-(3-{[1-(2,3-dimethyl-phenylcarbamoyl)-piperidin-4-ylmethyl]-amino}-phenyl)-thiophene-2-carboxylic acid, 4-{[3-(3-bromo-5-carboxy-4-carboxymethoxy-thiophen-2-yl)-phenylamino]-methyl}-piperidine-1-carboxylic acid tert-butyl ester, 4-chloro-3-carboxymethoxy-5-(3-cyclohexylmethoxy-phenyl)-thiophene-2-carboxylic acid, 5-[3-(3,5-bis-trifluoromethyl-benzyloxy)-phenyl]-4-chloro-3-carboxymethoxy-thiophene-2-carboxylic acid, 5-(3-benzyloxy-phenyl)-4-chloro-3-carboxymethoxy-thiophene-2-carboxylic acid, 4-chloro-3-carboxymethoxy-5-[3-(1-phenyl-ethoxy)-phenyl]-thiophene-2-carboxylic acid, 4-chloro-5-[3-(1-carboxy-ethoxy)-phenyl]-3-carboxymethoxy-thiophene-2-carboxylic acid, 4-chloro-3-carboxymethoxy-5-[3-(naphthalen-2-yl-methoxy)-phenyl]-thiophene-2-carboxylic acid, 4-chloro-3-carboxymethoxy-5-[3-(3-methyl-3,3a-dihydro-benzo[1,2,5]oxadiazol-5-ylmethoxy)-phenyl]-thiophene-2-carboxylic acid, 4-chloro-5-[3-(3-carboxy-benzyloxy)-phenyl]-3-carboxymethoxy-thiophene-2-carboxylic acid, 4-chloro-3-carboxymethoxy-5-[3-(3-trifluoromethoxy-benzyloxy)-phenyl]-thiophene-2-carboxylic acid, 4-[3-(3-bromo-5-carboxy-4-carboxymethoxy-thiophen-2-yl)-phenoxy]-piperidine-1-carboxylic acid tert-butyl ester, 4-chloro-3-carboxymethoxy-5-[3-(1-phenylcarbamoyl-piperidin-4-yloxy)-phenyl]-thiophene-2-carboxylic acid, 4-[3-(3-bromo-5-carboxy-4-carboxymethoxy-thiophen-2-yl)-phenoxy]-piperidine-1-carboxylic acid phenyl ester, 4-chloro-3-carboxymethoxy-5-[3-(1-phenylmethanesulfonyl-piperidin-4-yloxy)-phenyl]-thiophene-2-carboxylic acid, 4-[3-(3-bromo-5-carboxy-4-carboxymethoxy-thiophen-2-yl)-phenoxymethyl]-piperidine-1-carboxylic acid tert-butyl ester, 4-chloro-3-carboxymethoxy-5-[3-(1-methanesulfonyl-piperidin-4-ylmethoxy)-phenyl]-thiophene-2-carboxylic acid, 4-chloro-3-carboxymethoxy-5-[3-(1-phenylmethanesulfonyl-piperidin-4-ylmethoxy)-phenyl]-thiophene-2-carboxylic acid, 4-chloro-3-carboxymethoxy-5-{3-[1-(toluene-4-sulfonyl)-piperidin-4-ylmethoxy]-phenyl}-thiophene-2-carboxylic acid, 5-[3-(1-benzenesulfonyl-piperidin-4-ylmethoxy)-phenyl]-4-chloro-3-carboxymethoxy-thiophene-2-carboxylic acid, 4-[3-(3-bromo-5-carboxy-4-carboxymethoxy-thiophen-2-yl)-phenoxymethyl]-piperidine-1-carboxylic acid phenyl ester, 4-[3-(3-bromo-5-carboxy-4-carboxymethoxy-thiophen-2-yl)-phenoxymethyl]-piperidine-1-carboxylic acid methyl ester, 4-chloro-3-carboxymethoxy-5-[3-(1-ethylcarbamoyl-piperidin-4-ylmethoxy)-phenyl]-thiophene-2-carboxylic acid, 4-chloro-3-carboxymethoxy-5-[3-(1-phenylcarbamoyl-piperidin-4-ylmethoxy)-phenyl]-thiophene-2-carboxylic acid, 4-chloro-3-carboxymethoxy-5-{3-[1-(2-chloro-phenylcarbamoyl)-piperidin-4-ylmethoxy]-phenyl}-thiophene-2-carboxylic acid, 4-chloro-3-carboxymethoxy-5-[3-(1-o-tolyl-carbamoyl-piperidin-4-ylmethoxy)-phenyl]-thiophene-2-carboxylic acid, 4-chloro-3-carboxymethoxy-5-{3-[1-(2-methoxy-phenylcarbamoyl)-piperidin-4-ylmethoxy]-phenyl}-thiophene-2-carboxylic acid, 4-chloro-3-carboxymethoxy-5-{3-[1-(2-isopropyl-phenylcarbamoyl)-piperidin-4-ylmethoxy]-phenyl}-thiophene-2-carboxylic acid, 4-chloro-3-carboxymethoxy-5-{3-[1-(2-phenoxy-phenylcarbamoyl)-piperidin-4-ylmethoxy]-phenyl}-thiophene-2-carboxylic acid, 4-chloro-3-carboxymethoxy-5-{3-[1-(2,6-diethyl-phenylcarbamoyl)-piperidin-4-ylmethoxy]-phenyl}-t, 4-chloro-3-carboxymethoxy-5-{3-[1-(2,4,6-trimethyl-phenylcarbamoyl)-piperidin-4-ylmethoxy]-phenyl}-thiophene-2-carboxylic acid, 4-chloro-3-carboxymethoxy-5-{3-[1-(2-isopropyl-6-methyl-phenylcarbamoyl)-piperidin-4-ylmethoxy]-phenyl}-thiophene-2-carboxylic acid, 4-chloro-3-carboxymethoxy-5-{3-[1-(3-phenoxy-phenylcarbamoyl)-piperidin-4-ylmethoxy]-phenyl}-thiophene-2-carboxylic acid, 4-chloro-3-carboxymethoxy-5-{3-[1-(2,6-dimethyl-phenylcarbamoyl)-piperidin-4-ylmethoxy]-phenyl}-thiophene-2-carboxylic acid, 4-chloro-3-carboxymethoxy-5-{3-[1-(4-methyl-2-nitro-phenylcarbamoyl)-piperidin-4-ylmethoxy]-phenyl}-thiophene-2-carboxylic acid, 4-chloro-3-carboxymethoxy-5-{3-[1-(5-chloro-2-nitro-phenylcarbamoyl)-piperidin-4-ylmethoxy]-phenyl}-thiophene-2-carboxylic acid, 4-chloro-3-carboxymethoxy-5-{3-[1-(2-nitro-phenylcarbamoyl)-piperidin-4-ylmethoxy]-phenyl}-thiophene-2-carboxylic acid, 4-chloro-3-carboxymethoxy-5-(3-phenylaminomethyl-phenyl)-thiophene-2-carboxylic acid, 4-chloro-3-carboxymethoxy-5-{3-[(3-trifluoromethyl-phenylamino)-methyl]-phenyl}-thiophene-2-carboxylic acid, 4-chloro-3-carboxymethoxy-5-{3-[(3,4-difluoro-phenylamino)-methyl]-phenyl}-thiophene-2-carboxylic acid, 4-chloro-3-carboxymethoxy-5-(3-cyclohexylaminomethyl-phenyl)-thiophene-2-carboxylic acid, 4-chloro-3-carboxymethoxy-5-{3-[(3-nitro-phenylamino)-methyl]-phenyl}-thiophene-2-carboxylic acid, 4-chloro-5-{3-[(4-chloro-3-trifluoromethyl-phenylamino)-methyl]-phenyl}-3-carboxymethoxy-thiophene-2-carboxylic acid, 4-chloro-3-carboxymethoxy-5-{3-[(3,5-difluoro-phenylamino)-methyl]-phenyl}-thiophene-2-carboxylic acid, 4-chloro-3-carboxymethoxy-5-{3-[(3-fluoro-4-methyl-phenylamino)-methyl]-phenyl}-thiophene-2-carboxylic acid, 4-chloro-3-carboxymethoxy-5-{3-[(4-chloro-3-trifluoromethyl-phenylamino)-methyl]-phenyl}-thiophene-2-carboxylic acid, 4-chloro-3-carboxymethoxy-5-{3-[(4-methyl-3-nitro-phenylamino)-methyl]-phenyl}-thiophene-2-carboxylic acid, 5-{3-[(acetyl-cyclohexyl-amino)-methyl]-phenyl})-4-chloro-3-carboxymethoxy-thiophene-2-carboxylic acid, 4-chloro-3-carboxymethoxy-5-{3-[(cyclohexyl-methanesulfonyl-amino)-methyl]-phenyl}-thiophene-2-carboxylic acid, 4-chloro-3-carboxymethoxy-5-{3-[(cyclohexyl-methoxycarbonyl-amino)-methyl]-phenyl)-thiophene-2-carboxylic acid, 4-chloro-3-carboxymethoxy-5-[3-(1-cyclohexyl-3-ethyl-ureidomethyl)-phenyl]-thiophene-2-carboxylic acid, 5-(3-{[acetyl-(3,3,5,5-tetramethyl-cyclohexyl)-amino]-methyl}-phenyl)-4-chloro-3-carboxymethoxy-thiophene-2-carboxylic acid, 4-{acetyl-[3-(3-bromo-5-carboxy-4-carboxymethoxy-thiophen-2-yl)-benzyl]-amino}-piperidine-1-carboxylic acid ethyl ester, 4-chloro-3-carboxymethoxy-5-(4-methoxy-3-phenylaminomethyl-phenyl)-thiophene-2-carboxylic acid, 5-{3-[(acetyl-phenyl-amino)-methyl]-4-methoxy-phenyl}-4-chloro-3-carboxymethoxy-thiophene-2-carboxylic acid, 5-{3-[(3,5-bis-trifluoromethyl-phenylamino)-methyl]-4-methoxy-phenyl}-4-chloro-3-carboxymethoxy-thiophene-2-carboxylic acid, 4-chloro-3-carboxymethoxy-5-[3-(2-carboxy-vinyl)-4-methoxy-phenyl]-thiophene-2-carboxylic acid, 4-chloro-3-carboxymethoxy-5-{4-methoxy-3-[2-(2,2,2-trifluoro-ethylcarbamoyl)-vinyl]-phenyl}-thiophene-2-carboxylic acid, 5-(3,4-bis-benzyloxy-phenyl)-4-chloro-3-(2-hydroxy-ethoxy)-thiophene-2-carboxylic acid, 5-(3-benzyloxy-4-hydroxy-phenyl)-4-chloro-3-(2-hydroxy-ethoxy)-thiophene-2-carboxylic acid, 5-(4-benzyloxy-3-hydroxy-phenyl)-4-chloro-3-(2-hydroxy-ethoxy)-thiophene-2-carboxylic acid, 4-chloro-3-methoxycarbonylmethoxy-5-phenyl-thiophene-2-carboxylic acid, 4-chloro-3-methoxycarbonylmethoxy-5-[3-(3,3,5,5-tetramethyl-cyclohexylamino)-phenyl]-thiophene-2-carboxylic acid, 4-chloro-3-methoxycarbonylmethoxy-5-[3-(1-phenylmethanesulfonyl-piperidin-4-ylamino)-phenyl]-thiophene-2-carboxylic acid, 4-chloro-3-carboxymethoxy-5-phenyl-thiophene-2-carboxylic acid methyl ester, 4-chloro-3-carboxymethoxy-5-{3-[1-(2-nitro-phenylmethanesulfonyl)-piperidin-4-ylamino]-phenyl}-thiophene-2-carboxylic acid methyl ester, 4-chloro-3-carboxymethoxy-5-{3-[1-(4-chloro-phenylmethanesulfonyl)-piperidin-4-ylamino]-phenyl}-thiophene-2-carboxylic acid methyl ester, 4-chloro-3-carboxymethoxy-5-{3-[1-(3,5-dichloro-phenylmethanesulfonyl)-piperidin-4-ylamino]-phenyl}-thiophene-2-carboxylic acid methyl ester, 4-chloro-3-carboxymethoxy-5-{3-[1-(3,4-dichloro-phenylmethanesulfonyl)-piperidin-4-ylamino]-phenyl}- thiophene-2-carboxylic acid methyl ester, 4-chloro-3-carboxymethoxy-5-(3-cyclohexylmethoxy-phenyl)-thiophene-2-carboxylic acid methyl ester, 4-chloro-3-carboxymethoxy-5-[3-(1-phenylmethanesulfonyl-piperidin-4-ylamino)-phenyl]-thiophene-2-carboxylic acid methyl ester, 4-chloro-3-carboxymethoxy-5-{3-[1-(3-trifluoromethyl-phenylmethanesulfonyl)-piperidin-4-ylamino]-phenyl}-thiophene-2-carboxylic acid methyl ester, 4-chloro-3-carboxymethoxy-5-{3-[1-(4-fluoro-phenylmethanesulfonyl)-piperidin-4-ylamino]-phenyl}-thiophene-2-carboxylic acid methyl ester, 4-chloro-3-carboxymethoxy-5-{3-[1-(4-trifluoromethyl-phenylmethanesulfonyl)-piperidin-4-ylamino]-phenyl}-thiophene-2-carboxylic acid methyl ester, 4-chloro-3-carboxymethoxy-5-[3-(3,3,5,5-tetramethyl-cyclohexylamino)-phenyl]-thiophene-2-carboxylic acid methyl ester, 5-{3-[(acetyl-cyclohexyl-amino)-methyl]-phenyl}-4-chloro-3-carboxymethoxy-thiophene-2-carboxylic acid methyl ester, 3-carboxymethoxy-4-methyl-5-phenyl-thiophene-2-carboxylic acid, 5-bromo-3-carboxymethoxy-4-methyl-thiophene-2-carboxylic acid, 3-carboxymethoxy-4-methyl-thiophene-2-carboxylic acid, 3-carboxymethoxy-4-methyl-5-styryl-thiophene-2-carboxylic acid, 3-carboxymethoxy-5-(4-hydroxy-phenyl)-4-methyl-thiophene-2-carboxylic acid, 3-carboxymethoxy-4-methyl-5-[3-(pyridin-3-ylcarbamoyl)-phenyl]-thiophene-2-carboxylic acid, 3-carboxymethoxy-5-[4-(3-isopropyl-ureido)-phenyl]-4-methyl-thiophene-2-carboxylic acid, 5-(3-carboxymethanesulfonylamino-phenyl)-3-carboxymethoxy-4-methyl-thiophene-2-carboxylic acid, 5-(3-benzylamino-phenyl)-3-carboxymethoxy-4-methyl-thiophene-2-carboxylic acid, 3-carboxymethoxy-5-[3-(cyclohexylmethyl-amino)-phenyl]-4-methyl-thiophene-2-carboxylic acid, 3-carboxymethoxy-4-methyl-5-[3-(3-phenoxy-benzylamino)-phenyl]-thiophene-2-carboxylic acid, 5-[3-(3-bromo-benzylamino)-phenyl]-3-carboxymethoxy-4-methyl-thiophene-2-carboxylic acid, 3-carboxymethoxy-4-methyl-5-[3-(3-trifluoromethyl-benzylamino)-phenyl]-thiophene-2-carboxylic acid, 3-carboxymethoxy-5-[3-(cycloheptylmethyl-amino)-phenyl]-4-methyl-thiophene-2-carboxylic acid, 5-benzofuran-2-yl-4-chloro-3-carboxymethoxy-thiophene-2-carboxylic acid, 4,5-bis-benzofuran-2-yl-3-ethoxycarbonylmethoxy-thiophene-2-carboxylic acid methyl ester, 5-biphenyl-3-yl-4-chloro-3-carboxymethoxy-thiophene-2-carboxylic acid, 5-benzo[1,3]dioxol-5-yl-4-chloro-3-carboxymethoxy-thiophene-2-carboxylic acid, 4-chloro-3-carboxymethoxy-5-pyridin-4-yl-thiophene-2-carboxylic acid, 4-chloro-3-carboxymethoxy-5-[3-(4-trifluoromethyl-phenylcarbamoyl)-phenyl]-thiophene-2-carboxylic acid, 4-chloro-3-carboxymethoxy-5-naphthalen-1-yl-thiophene-2-carboxylic acid, 3-bromo-4-carboxymethoxy-[2,3]-bithiophenyl-5-carboxylic acid, 4-chloro-3-carboxymethoxy-5-pyridin-3-yl-thiophene-2-carboxylic acid, 3-bromo-4-carboxymethoxy-2'-formyl-[2,3]-bithiophenyl-5-carboxylic acid, 3-bromo-4-carboxymethoxy-2'-(isobutylamino-methyl)-[2,3]-bithiophenyl-5-carboxylic acid, 4-chloro-3-carboxymethoxy-5-{3-[(5-phenylcarbamoyl-thiophen-2-ylmethyl)-amino]-phenyl}-thiophene-2-carboxylic acid, 5-{3-[(5-benzylcarbamoyl-thiophen-2-ylmethyl)-amino]-phenyl}-4-chloro-3-carboxymethoxy-thiophene-2-carboxylic acid, and 4-chloro-3-carboxymethoxy-5-{3-[(5-cyclohexylcarbamoyl-thiophen-2-ylmethyl)-amino]-phenyl}-thiophene-2-carboxylic acid.

In some embodiments, the compound can be selected from 4-chloro-3-(carboxymethoxy)-5-[3-(piperidin-4-ylamino)phenyl]thiophene-2-carboxylic acid, ({4-chloro-2-(methoxycarbonyl)-5-[3-(piperidin-4-ylamino)phenyl]thien-3-yl}oxy)acetic acid, methyl 4-chloro-3-(2-ethoxy-2-oxoethoxy)-5-(3-{[1-(5-nitropyridin-2-yl)piperidin-4-yl]aminophenyl)thiophene-2-carboxylate, 4-chloro-3-(carboxymethoxy)-5-(3-{[1-(5-nitropyridin-2-yl)piperidin-4-yl]amino}phenyl)thiophene-2-carboxylic acid, 5-[3-({1-[5-(acetylamino)pyridin-2-yl]piperidin-4-yl}amino)phenyl]-4-chloro-3-(carboxymethoxy)thiophene-2-carboxylic acid, 4-chloro-3-(carboxymethoxy)-5-(3-{[1-(5-{[(methylamino)carbonyl]amino}pyridin-2-yl)piperidin-4-yl]amino}phenyl)thiophene-2-carboxylic acid, 4-chloro-3-(carboxymethoxy)-5-(3-{[(methylamino)carbonyl][1-(5-{[(methylamino)carbonyl]amino}pyridin-2-yl)piperidin-4-yl]aminophenyl)thiophene-2-carboxylic acid, 4-chloro-3-(carboxymethoxy)-5-{3-[(1-{5-[(methylsulfonyl)amino]pyridin-2-yl}piperidin-4-yl)amino]phenyl}thiophene-2-carboxylic acid, 3-(carboxymethoxy)-5-phenylthiophene-2-carboxylic acid, methyl 5-(3-{[1-(benzylsulfonyl)piperidin-4-yl]amino}phenyl)-4-chloro-3-{2-[(2-methylphenyl)amino]-2-oxoethoxy}thiophene-2-carboxylate, 5-(3-{[1-(benzylsulfonyl)piperidin-4-yl][(ethylamino)carbonyl]amino}phenyl)-4-chloro-3-(carboxymethoxy)thiophene-2-carboxylic acid, 4,5-dibromo-3-[carboxy(fluoro)methoxy]thiophene-2-carboxylic acid, {[5-phenyl-2-(2H-tetrazol-5-yl)thien-3-yl]oxy}acetic acid, {[5-[3-({[1-(anilinocarbonyl)piperidin-4-yl]methyl}amino)phenyl]-4-chloro-2-(methoxycarbonyl)thien-3-yl]oxy}acetic acid, 5-(3-{{[1-(anilinocarbonyl)piperidin-4-yl]methyl}[(ethylamino)carbonyl]amino}phenyl)-4-chloro-3-(carboxymethoxy)thiophene-2-carboxylic acid 4-chloro-3-(carboxymethoxy)-5-{3-[(1-{[2-(trifluoromethoxy)phenyl]sulfonyl}piperidin-4-yl)amino]phenyl}thiophene-2-carboxylic acid, 4-chloro-3-(carboxymethoxy)-5-[3-({1-[(5-chloro-2-methoxyphenyl)sulfonyl]piperidin-4-yl}amino)phenyl]thiophene-2-carboxylic acid, 4-chloro-3-(carboxymethoxy)-5-[3-({1-[(3,5-dichloro-2-hydroxyphenyl)sulfonyl]piperidin-4-yl}amino)phenyl]thiophene-2-carboxylic acid, propyl 4-chloro-3-(2-tert-butoxy-2-oxoethoxy)-5-{3-[(3,3,5,5-tetramethylcyclohexyl)amino]phenyl}thiophene-2-carboxylate, [(4-chloro-2-(propoxycarbonyl)-5-{3-[(3,3,5,5-tetramethylcyclohexyl)amino]phenyl}thien-3-yl)oxy]acetic acid, 4-chloro-3-carboxymethoxy-5-{3-[1-(2-trifluoromethyl-phenylmethanesulfonyl)-piperidin-4-ylamino]-phenyl}-thiophene-2-carboxylic acid, 4-chloro-3-carboxymethoxy-5-[3-(indan-2-ylamino)-phenyl]-thiophene-2-carboxylic acid, 3-[3-(3-bromo-5-carboxy-4-carboxymethoxy-thiophen-2-yl)-phenylamino]-8-aza-bicyclo[3.2.1]octane-8-carboxylic acid ethyl ester, 4-chloro-3-carboxymethoxy-5-[3-(8-phenylmethanesulfonyl-8-aza-bicyclo[3.2.1]oct-3-ylamino)-phenyl]-thiophene-2-carboxylic acid, 5-(1-benzyl-1H-pyrazol-4-yl)-4-chloro-3-carboxymethoxy-thiophene-2-carboxylic acid; compound with methane, 5-{3-[1-(2-acetylamino-phenylmethanesulfonyl)-piperidin-4-ylamino]-phenyl}-4-chloro-3-carboxymethoxy-thiophene-2-carboxylic acid, 5-{3-[1-(2-acetylamino-phenylmethanesulfonyl)-piperidin-4-ylamino]-phenyl}-3-carboxymethoxy-thiophene-2-carboxylic acid, 4-chloro-3-carboxymethoxy-5-{3-[1-(2-methanesulfonylamino-phenylmethanesulfonyl)-piperidin-4-ylamino]-phenyl}-thiophene-2-carboxylic acid, 3-carboxymethoxy-5-{3-[1-(2-methanesulfonylamino-phenylmethanesulfonyl)-piperidin-4-ylamino]-phenyl}-thiophene-2-carboxylic acid 4-chloro-3-carboxymethoxy-5-(3-{1-[2-(3-ethyl-ureido)-phenylmethanesulfonyl]-piperidin-4-ylamino}-phenyl)-thiophene-2-carboxylic acid, 3-carboxymethoxy-5-(3-{1-[2-(3-ethyl-ureido)-phenylmethanesulfonyl]-piperidin-4-ylamino}-phenyl)-thiophene-2-carboxylic acid, 4-chloro-3- carboxymethoxy-5-{3-[1-(2-chloromethanesulfonylamino-phenylmethanesulfonyl)-piperidin-4-ylamino]-phenyl}-thiophene-2-carboxylic acid, 5-{3-[(acetyl-isopropyl-amino)-methyl]-phenyl}-4-chloro-3-carboxymethoxy-thiophene-2-carboxylic acid, 5-{3-[(acetyl-isobutyl-amino)-methyl]-phenyl}-4-chloro-3-carboxymethoxy-thiophene-2-carboxylic acid, 5-{3-[(acetyl-cyclohexylmethyl-amino)-methyl]-phenyl}4-chloro-3-carboxymethoxy-thiophene-2-carboxylic acid, 5-{3-[(acetyl-p-tolyl-amino)-methyl]-phenyl}-4-chloro-3-carboxymethoxy-thiophene-2-carboxylic acid, 5-(3-{[acetyl-(4-tert-butyl-phenyl)-amino]-methyl}-phenyl)-4-chloro-3-carboxymethoxy-thiophene-2-carboxylic acid, 5-(3-{[acetyl-(4-trifluoromethyl-phenyl)-amino]-methyl}-phenyl)-4-chloro-3-carboxymethoxy-thiophene-2-carboxylic acid, 5-{3-[(acetyl-phenyl-amino)-methyl]-phenyl}-4-chloro-3-carboxymethoxy-thiophene-2-carboxylic acid, 5-{3-[(acetyl-cyclopropyl-amino)-methyl]-phenyl}-4-chloro-3-carboxymethoxy-thiophene-2-carboxylic acid, 5-(3-{[acetyl-(4-chloro-phenyl)-amino]-methyl}-phenyl)-4-chloro-3-carboxymethoxy-thiophene-2-carboxylic acid, 5-{3-[(acetyl-biphenyl-4-yl-amino)-methyl]-phenyl}-4-chloro-3-carboxymethoxy-thiophene-2-carboxylic acid, 5-(3-{[acetyl-(4-phenoxy-phenyl)-amino]-methyl}-phenyl)-4-chloro-3-carboxymethoxy-thiophene-2-carboxylic acid, 5-{3-[(acetyl-benzyl-amino)-methyl]-phenyl}-4-chloro-3-carboxymethoxy-thiophene-2-carboxylic acid 5-(3-{[acetyl-(4-methoxy-benzyl)-amino]-methyl}-phenyl)-4-chloro-3-carboxymethoxy-thiophene-2-carboxylic acid, 5-{3-[(acetyl-biphenyl-4-ylmethyl-amino)-methyl]-phenyl}-4-chloro-3-carboxymethoxy-thiophene-2-carboxylic acid, 5-(3-{[acetyl-(4-chloro-phenyl)-amino]-methyl}-phenyl)-4-chloro-3-carboxymethoxy-thiophene-2-carboxylic acid, 5-(3-{[acetyl-(4-trifluoromethyl-phenyl)-amino]-methyl}-phenyl)-4-chloro-3-carboxymethoxy-thiophene-2-carboxylic acid, 5-(3-{[acetyl-(3,5-bis-trifluoromethyl-phenyl)-amino]-methyl}-phenyl)-4-chloro--carboxymethoxy-thiophene-2-carboxylic acid, 5-[3-({acetyl-[2-(4-chloro-phenyl)-ethyl]-amino}-methyl)-phenyl]-4-chloro-3-carboxymethoxy-thiophene-2-carboxylic acid, 4-chloro-3-carboxymethoxy-5-[3-(1,3-diisopropyl-ureido)-phenyl]-thiophene-2-carboxylic acid, 4-chloro-3-carboxymethoxy-5-{3-[1-(2,2-dimethyl-propyl)-3-isopropyl-ureido]-phenyl}-thiophene-2-carboxylic acid, 4-chloro-3-carboxymethoxy-5-[3-(1-isobutyl-3-isopropyl-ureido)-phenyl]-thiophene-2-carboxylic acid, 5-[3-(1-benzyl-3-isopropyl-ureido)-phenyl]-4-chloro-3-carboxymethoxy-thiophene-2-carboxylic acid, 4-chloro-3-carboxymethoxy-5-{3-[3-isopropyl-1-(4-trifluoromethyl-benzyl)-ureido]-phenyl}-thiophene-2-carboxylic acid, 4-chloro-5-{3-[1-(4-tert-butyl-benzyl)-3-isopropyl-ureido]-phenyl}-3-carboxymethoxy-thiophene-2-carboxylic acid, 5-[3-(acetyl-cyclohexylmethyl-amino)-phenyl]-4-chloro-3-carboxymethoxy-thiophene-2-carboxylic acid, 4-chloro-3-carboxymethoxy-5-{3-[cyclohexylmethyl-(3-methyl-butyryl)-amino]-phenyl}-thiophene-2-carboxylic acid, 4-chloro-3-carboxymethoxy-5-[3-(cyclohexanecarbonyl-cyclohexylmethyl-amino)-phenyl]-thiophene-2-carboxylic acid, 4-chloro-3-carboxymethoxy-5-[3-(cyclohexylmethyl-isobutyryl-amino)-phenyl]-thiophene-2-carboxylic acid, 4-chloro-3-carboxymethoxy-5-[3-(cyclohexylmethyl-methoxycarbonyl-amino)-phenyl]-thiophene-2-carboxylic acid, 3-carboxymethoxy-5-[3-(cyclohexylmethyl-methoxycarbonyl-amino)-phenyl]-4-methyl-thiophene-2-carboxylic acid, 3-carboxymethoxy-5-[3-(cyclohexylmethyl-isopropoxycarbonyl-amino)-phenyl]-4-methyl-thiophene-2-carboxylic acid, 5-[3-(bis-cyclohexylmethyl-amino)-phenyl]-3-carboxymethoxy-4-methyl-thiophene-2-carboxylic acid, 4-chloro-3-carboxymethoxy-5-[3-(1-cyclohexylmethyl-3-phenyl-ureido)-phenyl]-thiophene-2-carboxylic acid, 5-[3-(3-benzyl-1-cyclohexylmethyl-ureido)-phenyl]-4-chloro-3-carboxymethoxy-thiophene-2-carboxylic acid, 4-chloro-3-carboxymethoxy-5-{3-[1-cyclohexylmethyl-3-(4-ethyl-phenyl)-ureido]-phenyl}-thiophene-2-carboxylic acid, 4-chloro-3-carboxymethoxy-5-{3-[1-cyclohexylmethyl-3-(4-ethoxy-phenyl)-ureido]-phenyl}-thiophene-2-carboxylic acid, 4-chloro-3-carboxymethoxy-5-{3-[1-cyclohexylmethyl-3-(4-phenoxy-phenyl)-ureido]-phenyl}-thiophene-2-carboxylic acid, 4-chloro-3-carboxymethoxy-5-{3-[3-(2-cyano-phenyl)-1-cyclohexylmethyl-ureido]-phenyl}-thiophene-2-carboxylic acid, 4-chloro-3-carboxymethoxy-5-[3-(1-cyclohexylmethyl-3-thiophen-3-yl-ureido)-phenyl]-thiophene-2-carboxylic acid, 4-chloro-3-carboxymethoxy-5-{3-[1-cyclohexylmethyl-3-(3,5-dimethyl-isoxazol-4-yl)-ureido]-phenyl}-thiophene-2-carboxylic acid, 4-chloro-3-carboxymethoxy-5-{3-[1-cyclohexylmethyl-3-(5-methyl-3-phenyl-isoxazol-4-yl)-ureido]-phenyl}-thiophene-2-carboxylic acid, 4-chloro-3-carboxymethoxy-5-{3-[3-(4-carboxy-phenyl)-1-cyclohexylmethyl-ureido]-phenyl}-thiophene-2-carboxylic acid, 4-chloro-3-carboxymethoxy-5-[3-(1-cyclohexylmethyl-3-ethyl-ureido)-phenyl]-thiophene-2-carboxylic acid, 3-carboxymethoxy-5-[3-(1-cyclohexylmethyl-3-isopropyl-ureido)-phenyl]-4-methyl-thiophene-2-carboxylic acid, 3-carboxymethoxy-5-[3-(1-cyclohexyl-3-isopropyl-ureido)-phenyl]-4-methyl-thiophene-2-carboxylic acid, 3-carboxymethoxy-5-[3-(1-cyclohexylmethyl-3-phenyl-ureido)-phenyl]-4-methyl-thiophene-2-carboxylic acid, 5-[3-(3-benzyl-1-cyclohexylmethyl-ureido)-phenyl]-3-carboxymethoxy-4-methyl-thiophene-2-carboxylic acid, 5-[3-(3-benzyl-1-cyclohexyl-ureido)-phenyl]-3-carboxymethoxy-4-methyl-thiophene-2-carboxylic acid, 3-carboxymethoxy-5-[3-(1-cyclohexylmethyl-3-phenethyl-ureido)-phenyl]-4-methyl-thiophene-2-carboxylic acid, 3-carboxymethoxy-5-[3-(1-cyclohexylmethyl-3-phenethyl-ureido)-phenyl]-4-methyl-thiophene-2-carboxylic acid, 4-chloro-3-isopropoxycarbonylmethoxy-5-[3-(1-phenylmethanesulfonyl-piperidin-4-ylamino)-phenyl]-thiophene-2-carboxylic acid, 4-chloro-3-isobutoxycarbonylmethoxy-5-[3-(1-phenylmethanesulfonyl-piperidin-4-ylamino)-phenyl]-thiophene-2-carboxylic acid, 4-chloro-5-[3-(1-phenylmethanesulfonyl-piperidin-4-ylamino)-phenyl]-3-propoxycarbonylmethoxy-thiophene-2-carboxylic acid, 4-chloro-3-cyclopropylmethoxycarbonylmethoxy-5-[3-(1-phenylmethanesulfonyl-piperidin-4-ylamino)-phenyl]-thiophene-2-carboxylic acid, 3-benzyloxycarbonylmethoxy-4-chloro-5-[3-(1-phenylmethanesulfonyl-piperidin-4-ylamino)-phenyl]-thiophene-2-carboxylic acid, 4-chloro-3-cyclohexylmethoxycarbonylmethoxy-5-[3-(1-phenylmethanesulfonyl-piperidin-4-ylamino)-phenyl]-thiophene-2-carboxylic acid, 4-chloro-3-cyclohexyloxycarbonylmethoxy-5-[3-(1-phenylmethanesulfonyl-piperidin-4-ylamino)-phenyl]-thiophene-2-carboxylic acid, 4-chloro-3-carboxymethoxy-5-{3-[1-(2,3-dichloro-phenylmethanesulfonyl)-piperidin-4-ylamino]-phenyl}-thiophene-2-carboxylic acid, 4-chloro-5-{3-[1-(2,3-dichloro-phenylmethanesulfonyl)-piperidin-4-ylamino]-phenyl}-3-methoxycarbonylmethoxy-thiophene-2-carboxylic acid, 4-chloro-3-carboxymethoxy-5-{3-[1-(2,3-dichloro-phenylmethanesulfonyl)-piperidin-4-ylamino]-phenyl}-thiophene-2-carboxylic acid methyl ester, [4-chloro-5-(3-cyclohexylamino-phenyl)-2-(2H-tetrazol-5-yl)-thiophen-3-yloxy]-acetic acid, [4-chloro-5-[3-(cyclohexylmethyl-amino)-phenyl]-2-(2H-tetrazol-5-yl)- thiophen-3-yloxy]-acetic acid, [4-chloro-5-[3-(3,3,5,5-tetramethyl-cyclohexylamino)-phenyl]-2-(2H-tetrazol-5-yl)-thiophen-3-yloxy]-acetic acid, tetrazole/acid: [5-(3-[acetyl-(3,3,5,5-tetramethyl-cyclohexyl)-amino]-4-chloro-2-(2H-tetrazol-5-yl)-thiophen-3-yloxy]-acetic acid, [4-chloro-5-[3-(1-phenylmethanesulfonyl-piperidin-4-ylamino)-phenyl]-2-(2H-tetrazol-5-yl)-thiophen-3-yloxy]-acetic acid, 4-chloro-3-carboxymethoxy-5-[3-(1-phenyl-methanesulfonyl-piperidin-4-ylamino)-phenyl]-thiophene-2-carboxylic acid methyl ester, ethanolamine salt, 4-chloro-3-carboxymethoxy-5-[3-(1-phenylmethanesulfonyl-piperidin-4-ylamino)-phenyl]-thiophene-2-carboxylic acid methyl ester, choline salt, 4-chloro-3-carboxymethoxy-5-[3-(1-phenylmethanesulfonyl-piperidin-4-ylamino)-phenyl]-thiophene-2-carboxylic acid methyl ester, sodium salt, {[2-[(benzyloxy)carbonyl]-5-(3-{[1-(benzylsulfonyl)piperidin-4-yl]amino}phenyl)-4-chlorothien-3-yl]oxy}acetic acid, [(5-(3-{[1-(benzylsulfonyl)piperidin-4-yl]amino}phenyl)-4-chloro-2-{[(2-nitrobenzyl)oxy]carbonyl}thien-3-yl)oxy]acetic acid, [(5-(3-{[1-(benzylsulfonyl)piperidin-4-yl]amino}phenyl)-4-chloro-2-{[(2-nitrobenzyl)oxy]carbonyl}thien-3-yl)oxy]acetic acid, [(5-(3-{[1-(benzylsulfonyl)piperidin-4-yl]amino}phenyl)-4-chloro-2-{[(2-nitrobenzyl)oxy]carbonyl}thien-3-yl)oxy]acetic acid, ({5-(3-{[1-(benzylsulfonyl)piperidin-4-yl]amino}phenyl)-4-chloro-2-[(cyclohexylmethoxy)carbonyl]thien-3-yl}oxy)acetic acid, ({5-(3-{[1-(benzylsulfonyl)piperidin-4-yl]amino}phenyl)-4-chloro-2-[(cyclohexylmethoxy)carbonyl]thien-3-yl}oxy)acetic acid, 5-[3-(benzyloxycarbonyl-cyclohexyl-amino)-phenyl]-4-chloro-3-carboxymethoxy-thiophene-2-carboxylic acid, 5-[3-(benzyloxycarbonyl-cyclohexyl-amino)-phenyl]-4-chloro-3-carboxymethoxy-thiophene-2-carboxylic acid, 4-chloro-3-carboxymethoxy-5-[3-(cyclohexyl-propoxycarbonyl-amino)-phenyl]-thiophene-2-carboxylic acid, 4-chloro-3-carboxymethoxy-5-[3-(cyclohexyl-isopropoxycarbonyl-amino)-phenyl]-thiophene-2-carboxylic acid, 5-[3-(benzyloxycarbonyl-cyclohexylmethyl-amino)-phenyl]-4-chloro-3-carboxymethoxy-thiophene-2-carboxylic acid, 4-chloro-3-carboxymethoxy-5-[3-(cyclohexylmethyl-isopropoxycarbonyl-amino)-phenyl]-thiophene-2-carboxylic acid, 4-chloro-3-carboxymethoxy-5-[3-(cyclohexylmethyl-isopropoxycarbonyl-amino)-phenyl]-thiophene-2-carboxylic acid, 4-chloro-3-carboxymethoxy-5-[3-(cyclohexylmethyl-propoxycarbonyl-amino)-phenyl]-thiophene-2-carboxylic acid, 5-[3-(benzoyl-cyclohexylmethyl-amino)-phenyl]-4-chloro-3-carboxymethoxy-thiophene-2-carboxylic acid, 4-chloro-3-carboxymethoxy-5-[3-(cyclohexylmethyl-phenylacetyl-amino)-phenyl]-thiophene-2-carboxylic acid, 4-chloro-3-carboxymethoxy-5-{3-[cyclohexylmethyl-(4-methyl-pentanoyl)-amino]-phenyl}-thiophene-2-carboxylic acid methyl ester, 4-chloro-3-carboxymethoxy-5-{3-[1-(3-chloro-phenylmethanesulfonyl)-piperidin-4-ylamino]-phenyl}-thiophene-2-carboxylic acid methyl ester, 4-chloro-3-carboxymethoxy-5-{3-[1-(3-fluoro-phenylmethanesulfonyl)-piperidin-4-ylamino]-phenyl}-thiophene-2-carboxylic acid methyl ester, 4-chloro-3-carboxymethoxy-5-{3-[1-(2-chloro-phenylmethanesulfonyl)-piperidin-4-ylamino]-phenyl}-thiophene-2-carboxylic acid, 4-chloro-5-{3-[1-(2-chloro-phenylmethanesulfonyl)-piperidin-4-ylamino]-phenyl}-3-methoxycarbonylmethoxy-thiophene-2-carboxylic acid, 3-methoxycarbonylmethoxy-5-{3-[1-(3-fluoro-phenylmethanesulfonyl)-piperidin-4-ylamino]-phenyl}4-methyl-thiophene-2-carboxylic acid methyl ester, 3-carboxymethoxy-4-methyl-5-[3-(1-phenylmethanesulfonyl-piperidin-4-ylamino)-phenyl]-thiophene-2-carboxylic acid methyl ester, 3-carboxymethoxy-4-methyl-5-{3-[1-(2-trifluoromethyl-phenylmethanesulfonyl)-piperidin-4-ylamino]-phenyl}-thiophene-2-carboxylic acid methyl ester 3-carboxymethoxy-4-methyl-5-[3-(1-phenylmethanesulfonyl-piperidin-4-ylamino)-phenyl]-thiophene-2-carboxylic acid, 3-methoxycarbonylmethoxy-4-methyl-5-[3-(1-phenyl-methanesulfonyl-piperidin-4-ylamino)-phenyl]-thiophene-2-carboxylic acid, 3-carboxymethoxy-4-methyl-5-[3-(3,3,5,5-tetramethyl-cyclohexylamino)-phenyl]-thiophene-2-carboxylic acid methyl ester], 4,5-dibromo-3-(1-carboxy-ethoxy)-thiophene-2-carboxylic acid, [4,5-dibromo-2-(5-methyl-[1,2,4]oxadiazol-3-yl)-thiophen-3-yloxy]-acetic acid, [4,5-dibromo-2-(5-ethyl-[1,2,4]oxadiazol-3-yl)-thiophen-3-yloxy]-acetic acid, [4,5-dibromo-2-(5-isopropyl-[1,2,4]oxadiazol-3-yl)-thiophen-3-yloxy]-acetic acid, [4-chloro-5-[3-(1-phenylmethanesulfonyl-piperidin-4-ylamino)-phenyl]-2-(1H-tetrazol-5-yl)-thiophen-3-yloxy]-acetic acid, [4-chloro-5-[3-(1-phenylmethanesulfonyl-piperidin-4-ylamino)-phenyl]-2-(1H-tetrazol-5-yl)-thiophen-3-yloxy]-acetic acid isopropyl ester, [4-chloro-5-[3-(1-phenylmethanesulfonyl-piperidin-4-ylamino)-phenyl]-2-(1H-tetrazol-5-yl)-thiophen-3-yloxy]-acetic acid methyl ester, 4,5-dibromo-3-(isobutylcarbamoyl-methoxy)-thiophene-2-carboxylic acid methyl ester, 4,5-dibromo-3-(2-oxo-2-pyrrolidin-1-yl-ethoxy)-thiophene-2-carboxylic acid methyl ester, 4,5-dibromo-3-[(2-hydroxy-1-methyl-ethylcarbamoyl)-methoxy]-thiophene-2-carboxylic acid methyl ester, [4-chloro-5-[3-(1-phenylmethanesulfonyl-piperidin-4-ylamino)-phenyl]-2-(1H-tetrazol-5-yl)-thiophen-3-yloxy]-acetic acid methyl ester, 4,5-dibromo-3-(isobutylcarbamoyl-methoxy)-thiophene-2-carboxylic acid methyl ester, 4-[2-(4,5-dibromo-2-methoxycarbonyl-thiophen-3-yloxy)-acetyl]-piperazine-1-carboxylic acid tert-butyl ester, 4,5-dibromo-3-[(2-hydroxy-1-methyl-ethylcarbamoyl)-methoxy]-thiophene-2-carboxylic acid methyl ester, 4,5-dibromo-3-[(2-tert-butoxycarbonylamino-ethylcarbamoyl)-methoxy]-thiophene-2-carboxylic acid methyl ester, 3-[(2-amino-ethylcarbamoyl)-methoxy]-4,5-dibromo-thiophene-2-carboxylic acid methyl ester, 3-{[2-(4-Hydroxy-phenyl)-1-methoxycarbonyl-ethylcarbamoyl]-methoxy}-4-methyl-5-[3-(3,3,5,5-tetramethyl-cyclohexyl)-phenyl]-thiophene-2-carboxylic acid methyl ester, 1-(2-{2-methoxycarbonyl-4-methyl-5-[3-(3,3,5,5-tetramethyl-cyclohexyl)-phenyl]-thiophen-3-yloxy}-acetyl)-pyrrolidine-2-carboxylic acid methyl ester, 4-methyl-3-(2-oxo-2-pyrrolidin-1-yl-ethoxy)-5-[3-(3,3,5,5-tetramethyl-cyclohexyl)-phenyl]-thiophene-2-carboxylic acid methyl ester, 3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester, 3-[(1-methoxycarbonyl-2-methyl-propylcarbamoyl)-methoxy]-4-methyl-5-[3-(3,3,5,5-tetramethyl-cyclohexyl)-phenyl]-thiophene-2-carboxylic acid methyl ester, 3-[(1-methoxycarbonyl-3-methyl-butylcarbamoyl)-methoxy]-4-methyl-5-[3-(3,3,5,5-tetramethyl-cyclohexyl)-phenyl]-thiophene-2-carboxylic acid methyl ester, 3-[(1-methoxycarbonyl-2-phenyl-ethylcarbamoyl)-methoxy]-4-methyl-5-[3-(3,3,5,5-tetramethyl-cyclohexyl)-phenyl]-thiophene-2-carboxylic acid methyl ester, 3-[2-(2-carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester, 3-[(2-tert-butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester, 4-(2-{2-methoxycarbonyl-4-methyl-5-[3-(3,3,5,5-tetramethyl-cyclohexyl)-phenyl]-thiophen-3-yloxy}-acetyl)-piperazine- 1-carboxylic acid tert-butyl ester, 3-[(2-aminoethylcarbamoyl)-methoxy]-4-methyl-5-[3-(3,3,5,5-tetramethyl-cyclohexyl)-phenyl]-thiophene-2-carboxylic acid methyl ester, 4-methyl-3-(2-oxo-2-piperazin-1-yl-ethoxy)-5-[3-(3,3,5,5-tetramethyl-cyclohexyl)-phenyl]-thiophene-2-carboxylic acid methyl ester 4-chloro-5-[3-(1-phenylmethanesulfonyl-piperidin-4-yl)-phenyl]-3-(piperidin-4-yloxycarbonylmethoxy)-thiophene-2-carboxylic acid methyl ester, 4-chloro-3-methoxycarbonylmethoxy-5-[3-(1-phenylmethanesulfonyl-piperidin-4-yl)-phenyl]-thiophene-2-carboxylic acid 2,2-dimethyl-propionyloxymethyl ester, 4-chloro-3-isopropoxycarbonylmethoxy-5-[3-(1-phenylmethanesulfonyl-piperidin-4-yl)-phenyl]-thiophene-2-carboxylic acid 2,2-dimethyl-propionyloxymethyl ester 4-chloro-3-isopropoxycarbonylmethoxy-5-[3-(1-phenyl-methanesulfonyl-piperidin-4-yl)-phenyl]-thiophene-2-carboxylic acid acetoxymethyl ester, 4,5-dibromo-3-methoxycarbonylmethoxy-thiophene-2-carboxylic acid 2,2-dimethyl-propionyloxymethyl ester, [5-bromo-4-methyl-2-(1H-tetrazol-5-yl)-thiophen-3-yloxy]-acetic acid, [4-methyl-5-phenyl-2-(1H-tetrazol-5-yl)-thiophen-3-yloxy]-acetic acid, [5-bromo-4-methyl-2-(2-methyl-2H-tetrazol-5-yl)-thiophen-3-yloxy]-acetic acid, 3-carboxymethoxy-5-{3-[1-(3-chloro-benzenesulfonyl)-piperidin-4-ylamino]-phenyl}-4-methyl-thiophene-2-carboxylic acid, 3-carboxymethoxy-5-{3-[1-(2-chloro-benzenesulfonyl)-piperidin-4-ylamino]-phenyl}4-methyl-thiophene-2-carboxylic acid, 3-carboxymethoxy-4-methyl-5-{3-[1-(4-nitro-benzenesulfonyl)-piperidin-4-ylamino]-phenyl}-thiophene-2-carboxylic acid, 3-carboxymethoxy-5-{3-[1-(2-cyano-benzenesulfonyl)-piperidin-4-ylamino]-phenyl}-4-methyl-thiophene-2-carboxylic acid, 3-carboxymethoxy-4-methyl-5-{3-[1-(4-trifluoromethyl-benzenesulfonyl)-piperidin-4-ylamino]-phenyl}-thiophene-2-carboxylic acid, 5-{3-[1-(4-carboxy-benzenesulfonyl)-piperidin-4-ylamino]-phenyl}-3-carboxymethoxy-4-methyl-thiophene-2-carboxylic acid, 3-carboxymethoxy-5-{3-[1-(2-cyano-benzenesulfonyl)-piperidin-4-ylamino]-phenyl}-4-methyl-thiophene-2-carboxylic acid, 3-carboxymethoxy-4-methyl-5-{3-[1-(4-trifluoromethyl-benzenesulfonyl)-piperidin-4-ylamino]-phenyl}-thiophene-2-carboxylic acid, 4-chloro-3-carboxymethoxy-5-[3-(1-cyclohexyl-3-methyl-ureido)-phenyl]-thiophene-2-carboxylic acid, 5-[3-(3-benzyl-1-cyclohexyl-ureido)-phenyl]-4-chloro-3-carboxymethoxy-thiophene-2-carboxylic acid, 4-chloro-3-tert-butoxycarbonylmethoxy-5-[3-(3,3,5,5-tetramethyl-cyclohexylamino)-phenyl]-thiophene-2-carboxylic acid methyl ester, 4-chloro-3-carboxymethoxy-5-{3-[3-methyl-1-(3,3,5,5-tetramethyl-cyclohexyl)-ureido]-phenyl}-thiophene-2-carboxylic acid, 4-chloro-3-carboxymethoxy-5-{3-[3-ethyl-1-(3,3,5,5-tetramethyl-cyclohexyl)-ureido]-phenyl}-thiophene-2-carboxylic acid, 4-chloro-3-carboxymethoxy-5-{3-[3-methyl-1-(3,3,5,5-tetramethyl-cyclohexyl)-ureido]-phenyl}-thiophene-2-carboxylic acid methyl ester, 4-chloro-3-ethoxycarbonylmethoxy-5-[3-(piperidin-4-ylamino)-phenyl]-thiophene-2-carboxylic acid methyl ester hydrochloride, 4-chloro-3-carboxymethoxy-5-{3-[1-(4-trifluoromethyl-pyrimidin-2-yl)-piperidin-4-ylamino]-phenyl}-thiophene-2-carboxylic acid, 4-chloro-3-carboxymethoxy-5-[3-(1-pyrimidin-2-yl-piperidin-4-ylamino)-phenyl]-thiophene-2-carboxylic acid, 4-chloro-3-carboxymethoxy-5-[3-(5'-trifluoromethyl-3,4,5,6-tetrahydro-2H-[1,2']bipyridinyl-4-ylamino)-phenyl]-thiophene-2-carboxylic acid, 4-chloro-3-ethoxycarbonylmethoxy-5-[3-(1-phenylmethanesulfonyl-piperidin-4-ylamino)-phenyl]-thiophene-2-carboxylic acid ethyl ester, 4-chloro-5-[3-(1-phenylmethanesulfonyl-piperidin-4-ylamino)-phenyl]-3-(o-tolylcarbamoyl-methoxy)-thiophene-2-carboxylic acid, {4-chloro-2-hydroxymethyl-5-[3-(1-phenylmethanesulfonyl-piperidin-4-ylamino)-phenyl]-thiophen-3-yloxy}-acetic acid, 3-carboxymethoxy-5-[3-(1-phenylmethanesulfonyl-piperidin-4-ylamino)-phenyl]-thiophene-2-carboxylic acid, 4-chloro-3-carboxymethoxy-5-(3-{1-[3-(3-ethyl-ureido)-phenylmethanesulfonyl]-piperidin-4-ylamino}-phenyl)-thiophene-2-carboxylic acid, [2-(2-{4-chloro-2-methoxycarbonyl-5-[3-(1-phenylmethanesulfonyl-piperidin-4-ylamino)-phenyl]-thiophen-3-yloxy}-acetoxy)-ethyl]-trimethyl-ammonium chloride, 4-chloro-3-cyclohexylcarbamoylmethoxy-5-[3-(1-phenylmethanesulfonyl-piperidin-4-ylamino)-phenyl]-thiophene-2-carboxylic acid methyl ester, (4,5-dibromo-2-hydroxymethyl-thiophen-3-yloxy)-acetic acid, 5-[3-(acetyl-cyclohexyl-amino)-phenyl]-4-chloro-3-carboxymethoxy-thiophene-2-carboxylic acid, 5-[3-(acetyl-cyclohexyl-amino)-phenyl]-4-chloro-3-carboxymethoxy-thiophene-2-carboxylic acid methyl ester, 5-[3-(benzoyl-cyclohexyl-amino)-phenyl]-4-chloro-3-carboxymethoxy-thiophene-2-carboxylic acid, 5-[3-(benzoyl-cyclohexyl-amino)-phenyl]-4-chloro-3-carboxymethoxy-thiophene-2-carboxylic acid methyl ester, 4-chloro-3-carboxymethoxy-5-{3-[cyclohexyl-(3-phenyl-acryloyl)-amino]-phenyl}-thiophene-2-carboxylic acid methyl ester, 4-chloro-3-carboxymethoxy-5-[3-(cyclohexanecarbonyl-cyclohexyl-amino)-phenyl]-thiophene-2-carboxylic acid methyl ester, 5-{3-[benzoyl-(3,3,5,5-tetramethyl-cyclohexyl)-amino]-phenyl}4-chloro-3-carboxymethoxy-thiophene-2-carboxylic acid, 4-chloro-3-carboxymethoxy-5-[3-(1-phenylmethanesulfonyl-piperidin-4-ylamino)-phenyl]-thiophene-2-carboxylic acid methyl ester (Hydrochloride Salt), 4-chloro-3-[(carbamoylmethyl-carbamoyl)-methoxy]-5-[3-(3,3,5,5-tetramethyl-cyclohexylamino)-phenyl]-thiophene-2-carboxylic acid methyl ester, 4-chloro-3-[(1-carbamoyl-ethylcarbamoyl)-methoxy]-5-[3-(3,3,5,5-tetramethyl-cyclohexylamino)-phenyl]-thiophene-2-carboxylic acid methyl ester, 4-chloro-3-[(ethoxycarbonylmethyl-carbamoyl)-methoxy]-5-[3-(3,3,5,5-tetramethyl-cyclohexylamino)-phenyl]-thiophene-2-carboxylic acid methyl ester, 4-chloro-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 4-chloro-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 3-{[(benzylcarbamoyl-methyl)-carbamoyl]-methoxy}-4-chloro-5-[3-(3,3,5,5-tetramethylcyclohexylamino)-phenyl]-thiophene-2-carboxylic acid methyl ester, 4-chloro-3-carboxymethoxy-5-{3-[1-(3-methanesulfonylamino-phenylmethanesulfonyl)-piperidin-4-ylamino]-phenyl}-thiophene-2-carboxylic acid, 5-{3-[1-(3-acetylamino-phenylmethanesulfonyl)-piperidin-4-ylamino]-phenyl}4-chloro-3-carboxymethoxy-thiophene-2-carboxylic acid, {[4-chloro-5-(3-methoxyphenyl)-2-(morpholin-4-ylcarbonyl)thien-3-yl]oxy}acetic acid, {[5-(1,3-benzodioxol-5-yl)-4-chloro-2-(morpholin-4-ylcarbonyl)thien-3-yl]oxy}acetic acid, {[3-bromo-5-(morpholin-4-ylcarbonyl)-2,3'-bithien-4-yl]oxy}acetic acid, {[4-chloro-2-(morpholin-4-ylcarbonyl)-5-phenylthien-3-yl]oxy}acetic acid, [(4,5-dibromo-2-{[(2-hydroxy-1,1-dimethylethyl)amino]carbonyl}thien-3-yl)oxy]acetic acid, ({4,5-dibromo-2-[(dimethylamino)carbonyl]thien-3-yl}oxy)acetic acid, ({4,5-dibromo-2-[(diethylamino)carbonyl]thien-3-yl}oxy)acetic acid, ({4,5-dibromo-2-[(1,3-thiazol-2-ylamino)carbonyl]thien-3-yl}oxy)acetic acid, 4,5-dibromo-2-(2H-pyrazol-3-ylcarbamoyl)-thiophen-3-yloxy]-acetic acid, {[4,5-dibromo-2-(morpholin-4-ylcarbonyl)thien-3-yl]oxy}acetic acid, [(4,5-dibromo-2-{[(2R,6S)-2,6-dimethylmorpholin-4-yl]carbonyl}thien-3-yl)oxy]acetic acid, {[4,5-dibromo-2-(thiomorpholin-4-ylcarbonyl)thien-3-yl]oxy}acetic acid, {[2-(anilinocarbonyl)-4,5-dibromothien-3-yl]oxy}acetic acid, {[4,5-dibromo-2-(piperidin-1-ylcarbonyl)thien-3-yl]oxy}acetic acid, {[4,5-dibromo-2-(4,4-dimethyl-4,5-dihydro-1,3-oxazol-2-yl)thien-3-yl]oxy}acetic acid, {[5-(3-{[1-(benzylsulfonyl)piperidin-4-yl]aminophenyl)-4-chloro-2-(morpholin-4-ylcarbonyl)thien-3-yl]oxy}acetic acid, [(4-chloro-2-(morpholin-4-ylcarbonyl)-5-{3-[(3,3,5,5-tetramethylcyclohexyl)amino]phenyl}thien-3-yl)oxy]acetic acid, 4-chloro-5-(3-{[1-(butylsulfonyl)piperidin-4-yl]amino}phenyl)-3-(2-methoxy-2-oxoethoxy)thiophene-2-carboxylic acid, 4-chloro-5-(3-{[1-(ethylsulfonyl)piperidin-4-yl]amino}phenyl)-3-(2-methoxy-2-oxoethoxy)thiophene-2-carboxylic acid, 4-chloro-5-(3-{[1-(isopropylsulfonyl)piperidin-4-yl]amino}phenyl)-3-(2-methoxy-2-oxoethoxy)thiophene-2-carboxylic acid, 5-{3-[acetyl(3,3,5,5-tetramethylcyclohexyl)amino}phenyl}-4-chloro-3-(2-methoxy-2-oxoethoxy)thiophene-2-carboxylic acid, [4-chloro-5-[3-(cyclohexylamino)phenyl]-2-(methoxycarbonyl)thien-3-yl]oxyacetic acid, {[5-(3-{[1-(benzylsulfonyl)piperidin-4-yl]aminophenyl)-4-chloro-2-(ethoxycarbonyl)thien-3-yl]oxy}acetic acid, {[5-(3-{[1-(benzylsulfonyl)piperidin-4-yl]amino}phenyl)-4-chloro-2-(isopropoxycarbonyl)thien-3-yl]oxy}acetic acid, ({5-(3-{[1-(benzylsulfonyl)piperidin-4-yl]amino}phenyl)-4-chloro-2-[(cyclohexyloxy)carbonyl]thien-3-yl}oxy)acetic acid, {[4-chloro-2-(ethoxycarbonyl)-5-(3-{[1-(phenylsulfonyl)piperidin-4-yl]amino}phenyl)thien-3-yl]oxy}acetic acid, [4-chloro-2-(methoxycarbonyl)-5-(3-{[1-(phenylsulfonyl)piperidin-4-yl]amino}phenyl)thien-3-yl]oxyacetic acid, [(4-chloro-2-(ethoxycarbonyl)-5-{3-[(3,3,5,5-tetramethylcyclohexyl)amino]phenyl}thien-3-yl)oxy]acetic acid, and {[4,5-dibromo-2-(methoxyacetyl)thien-3-yl]oxy}acetic acid.

In some embodiments, the compound can be selected from 3-(carboxymethoxy)-4-phenylthiophene-2-carboxylic acid, 3-(carboxymethoxy)-4-(1H-indol-5-yl)thiophene-2-carboxylic acid, 4-chloro-3-(carboxymethoxy)-5-phenylthiophene-2-carboxylic acid, 4-chloro-3-(carboxymethoxy)-5-[4-(dimethylamino)phenyl]thiophene-2-carboxylic acid, 5-(4-aminophenyl)-4-chloro-3-(carboxymethoxy)thiophene-2-carboxylic acid, 4-(carboxymethoxy)-3,3'-bithiophene-5-carboxylic acid, 5-[4-(acetylamino)phenyl]-4-chloro-3-(carboxymethoxy)thiophene-2-carboxylic acid, 5-(3-aminophenyl)-4-chloro-3-(carboxymethoxy)thiophene-2-carboxylic acid, 3-(carboxymethoxy)-4-[3-(trifluoromethyl)phenyl]thiophene-2-carboxylic acid, 4-chloro-3-(carboxymethoxy)-5-(1-naphthyl)thiophene-2-carboxylic acid, 4-chloro-3-(carboxymethoxy)-5-(2-naphthyl)thiophene-2-carboxylic acid, 3-(carboxymethoxy)-4,5-diphenylthiophene-2-carboxylic acid, {[2-(2H-tetraazol-5-yl)thieno[2,3-b]pyridin-3-yl]oxy}acetic acid, 5-[3-(acetylamino)phenyl]-4-chloro-3-(carboxymethoxy)thiophene-2-carboxylic acid, 4-chloro-3-(carboxymethoxy)-5-[3-(isobutyrylamino)phenyl]thiophene-2-carboxylic acid, 4-chloro-3-(carboxymethoxy)-5-[3-(propionylamino)phenyl]thiophene-2-carboxylic acid, 4-chloro-5-[3-(butyrylamino)phenyl]-3-(carboxymethoxy)thiophene-2-carboxylic acid, 4-chloro-3-(carboxymethoxy)-5-{3-[(cyclohexylcarbonyl)amino]phenyl}thiophene-2-carboxylic acid, 4-chloro-3-(carboxymethoxy)-5-(4-hydroxyphenyl)thiophene-2-carboxylic acid, 4-chloro-3-(carboxymethoxy)-5-{4-[(methoxycarbonyl)amino]phenyl}thiophene-2-carboxylic acid, 5-[4-(benzoylamino)phenyl]-4-chloro-3-(carboxymethoxy)thiophene-2-carboxylic acid, 4-chloro-3-(carboxymethoxy)-5-[3-(hexanoylamino)phenyl]thiophene-2-carboxylic acid, 4-chloro-3-(carboxymethoxy)-5-{3-[(cyclopentylcarbonyl)amino]phenyl}thiophene-2-carboxylic acid, 4-chloro-3-(carboxymethoxy)-5-{3-[(methoxycarbonyl)amino]phenyl}thiophene-2-carboxylic acid, 4-chloro-3-(carboxymethoxy)-5-(3-{[(2,2,2-trifluoroethyl)sulfonyl]amino}phenyl)thiophene-2-carboxylic acid, 5-(1,1'-biphenyl-3-yl)-4-chloro-3-(carboxymethoxy)thiophene-2-carboxylic acid, 4-chloro-3-(carboxymethoxy)-5-(3-{[(isopropylamino)carbonyl]amino}phenyl)thiophene-2-carboxylic acid, 4-chloro-3-(carboxymethoxy)-5-(4-fluorophenyl)thiophene-2-carboxylic acid, 3-bromo-4-(carboxymethoxy)-2,3'-bithiophene-5-carboxylic acid, 5-(4-{[(benzyloxy)acetyl]amino}phenyl)-4-chloro-3-(carboxymethoxy)thiophene-2-carboxylic acid, 5-(1,3-benzodioxol-5-yl)-4-chloro-3-(carboxymethoxy)thiophene-2-carboxylic acid, 4-chloro-5-(4-{[(tert-butoxycarbonyl)amino]methyl}phenyl)-3-(carboxymethoxy)thiophene-2-carboxylic acid, 4-chloro-3-(carboxymethoxy)-5-(3-{[(diethylamino)carbonyl]amino}phenyl)thiophene-2-carboxylic acid, 4-chloro-3-(carboxymethoxy)-5-(3-hydroxyphenyl)thiophene-2-carboxylic acid, 4-chloro-3-(carboxymethoxy)-5-(3-methoxyphenyl)thiophene-2-carboxylic acid, 4-chloro-5-[3-({[1-(tert-butoxycarbonyl)piperidin-4-yl]carbonyl}amino)phenyl]-3-(carboxymethoxy)thiophene-2-carboxylic acid, 4-chloro-5-[3-({[1-(tert-butoxycarbonyl)piperidin-3-yl]carbonyl}amino)phenyl]-3-(carboxymethoxy)thiophene-2-carboxylic acid, 4-chloro-3-(carboxymethoxy)-5-{4-[(methylsulfonyl)amino]phenyl}thiophene-2-carboxylic acid, carboxylic acid, 4-chloro-3-(carboxymethoxy)-5-[4-({[4-(trifluoromethyl)phenyl]sulfonyl}amino)phenyl]thiophene-2-carboxylic acid, 4-chloro-5-(4-{[N-(tert-butoxycarbonyl)glycyl]amino}phenyl)-3-(carboxymethoxy)thiophene-2-carboxylic acid, 4-chloro-3-(carboxymethoxy)-5-[4-(hydroxymethyl)phenyl]thiophene-2-carboxylic acid, 4-chloro-3-(carboxymethoxy)-5-{3-[(piperidin-4-ylcarbonyl)amino]phenyl}thiophene-2-carboxylic acid, 4-chloro-3-(carboxymethoxy)-5-{3-[(piperidin-3-ylcarbonyl)amino]phenyl}thiophene-2-carboxylic acid, 5-(1-benzofuran-2-yl)-4-chloro-3-(carboxymethoxy)thiophene-2-carboxylic acid, 4-chloro-3-(carboxymethoxy)-5-(4-{[(phenylsulfonyl)amino]methyl}phenyl)thiophene-2-carboxylic acid, 4-chloro-3-(carboxymethoxy)-5-(4-methoxyphenyl)thiophene-2-carboxylic acid, 3-(carboxymethoxy)-5-[4-(trifluoromethoxy)phenyl]thiophene-2-carboxylic acid, 4-chloro-3-(carboxymethoxy)-5-(4-{[(ethylsulfonyl)amino]methyl}phenyl)thiophene-2-carboxylic acid, 5-{4-[(acetylamino)methyl]phenyl}-4-chloro-3-(carboxymethoxy)thiophene-2-carboxylic acid, 4-chloro-3-(carboxymethoxy)-5-(4-{[(ethoxycarbonyl)amino]methyl}phenyl)thiophene-2-carboxylic acid, 4-chloro-3-(carboxymethoxy)-5-[4-({[(isopropylamino)carbonyl]amino}methyl)phenyl]thiophene-2-carboxylic acid, 4-chloro-3-(carboxymethoxy)-5-{3-[(phenylsulfonyl)amino]phenyl}thiophene-2-carboxylic acid, 5-[4-(aminomethyl)phenyl]-4-chloro-3-(carboxymethoxy)thiophene-2-carboxylic acid, 4-chloro-3-(carboxymethoxy)-5-pyridin-3-ylthiophene-2-carboxylic acid, 4-chloro-5-{4-[(carboxycarbonyl)amino]phenyl}-3-(carboxymethoxy)thiophene-2-carboxylic acid, 4-chloro-3-(carboxymethoxy)-5-{3-[(ethylsulfonyl)amino]phenyl}thiophene-2-carboxylic acid, 3-(carboxymethoxy)-5-(2-methylphenyl)thiophene-2-carboxylic acid, 4-chloro-3-(carboxymethoxy)-5-{3-[(3,3,3-trifluoropropanoyl)amino]phenyl}thiophene-2-carboxylic acid, 5-{3-[(benzylsulfonyl)amino]phenyl}4-chloro-3-(carboxymethoxy)thiophene-2-carboxylic acid, 4-chloro-3-(carboxymethoxy)-5-(4-{

[(isopropylamino)carbonyl]amino}phenyl)thiophene-2-carboxylic acid, 4-chloro-3-(carboxymethoxy)-5-{4-[(pyridin-3-ylcarbonyl)amino]phenyl}thiophene-2-carboxylic acid, 4-chloro-3-(carboxymethoxy)-5-(4-formylphenyl)thiophene-2-carboxylic acid, 3-bromo-4-(carboxymethoxy)-2'-formyl-2,3'-bithiophene-5-carboxylic acid, 4-chloro-3-(carboxymethoxy)-5-[3-({[4-(trifluoromethyl)phenyl]sulfonyl}amino)phenyl]thiophene-2-carboxylic acid, 4-chloro-3-(carboxymethoxy)-5-[3-({[4-(trifluoromethoxy)phenyl]sulfonyl}amino)phenyl]thiophene-2-carboxylic acid, 4-chloro-3-(carboxymethoxy)-5-{3-[(3,3,3-trifluoromethyl)phenyl]sulfonyl}amino]phenyl]thiophene-2-carboxylic acid, 4-chloro-3-(carboxymethoxy)-5-[4-(glycylamino)phenyl]thiophene-2-carboxylic acid, 4-chloro-3-(carboxymethoxy)-5-{4-[(phenylsulfonyl)amino]phenyl}thiophene-2-carboxylic acid, 4-chloro-3-(carboxymethoxy)-5-[4-(methyl {4-(trifluoromethyl)phenyl]sulfonyl}amino)phenyl]thiophene-2-carboxylic acid, 5-[4-(anilinocarbonyl)phenyl]-4-chloro-3-(carboxymethoxy)thiophene-2-carboxylic acid, 4-chloro-3-(carboxymethoxy)-5-[3-({[2-(trifluoromethyl)phenyl]sulfonyl}amino)phenyl]thiophene-2-carboxylic acid, 3-bromo-4-(carboxymethoxy)-2'-[(isobutylamino)methyl]-2,3'-bithiophene-5-carboxylic acid, 4-chloro-3-(carboxymethoxy)-5-(3-{[(2-cyanophenyl)sulfonyl]amino}phenyl)thiophene-2-carboxylic acid, 4-chloro-3-(carboxymethoxy)-5-(3-{[(4-methoxyphenyl)sulfonyl]amino}phenyl)thiophene-2-carboxylic acid, 4-chloro-3-(carboxymethoxy)-5-(3-{[(4-cyanophenyl)sulfonyl]amino}phenyl)thiophene-2-carboxylic acid, 4-chloro-3-(carboxymethoxy)-5-{4-[(isopropylamino)carbonyl]phenyl}thiophene-2-carboxylic acid, 5-[3-(benzylamino)phenyl]-4-chloro-3-(carboxymethoxy)thiophene-2-carboxylic acid, 5-[4-({[(1S)-2-amino-1-methyl-2-oxoethyl]amino}carbonyl)phenyl]-4-chloro-3-, (carboxymethoxy) thiophene-2-carboxylic acid, 5-[3-(benzoylamino)phenyl]-4-chloro-3-(carboxymethoxy)thiophene-2-carboxylic acid, 4-chloro-3-(carboxymethoxy)-5-(4-{[(2,6-difluorophenyl)sulfonyl]amino)phenyl)thiophene-2-carboxylic acid, 4-chloro-3-(carboxymethoxy)-5-(4-{[(2,6-dichlorophenyl)sulfonyl]amino}phenyl)thiophene-2-carboxylic acid, 5-[3-(anilinomethyl)phenyl]-4-chloro-3-(carboxymethoxy)thiophene-2-carboxylic acid, 4-chloro-3-(carboxymethoxy)-5-[3-(1-phenylethoxy)phenyl]thiophene-2-carboxylic acid, 4-chloro-3-(carboxymethoxy)-5-[4-({[4-(trifluoromethyl)phenyl]amino}carbonyl)phenyl]thiophene-2-carboxylic acid, 4-chloro-3-(carboxymethoxy)-5-[3-(2-furoylamino)phenyl]thiophene-2-carboxylic acid, 4-chloro-3-(carboxymethoxy)-5-[3-(3-furoylamino)phenyl]thiophene-2-carboxylic acid, 4-chloro-3-(carboxymethoxy)-5-(3-formyl-4-methoxyphenyl)thiophene-2-carboxylic acid, 4-chloro-3-(carboxymethoxy)-5-[4-({[2-(trifluoromethyl)phenyl]sulfonyl}amino)phenyl]thiophene-2-carboxylic acid, 4-chloro-3-(carboxymethoxy)-5-[4-({[3-(trifluoromethyl)phenyl]sulfonyl}amino)phenyl]thiophene-2-carboxylic acid, 4-chloro-3-(carboxymethoxy)-5-(3-{[(4-3-(carboxymethoxy)-4-methylthiophene-2-carboxylic acid, 3-(carboxymethoxy)-4-methylthiophene-2-carboxylic acid, 4-chloro-3-(carboxymethoxy)-5-(3-{[2-(trifluoromethyl)benzoyl]amino}phenyl)thiophene-2-carboxylic acid, 4-chloro-3-(carboxymethoxy)-5-(3-{[3-(trifluoromethyl)benzoyl]amino}phenyl)thiophene-2-carboxylic acid, 4-chloro-3-(carboxymethoxy)-5-(3-{[2-(trifluoromethyl)benzoyl]amino}phenyl)thiophene-2-carboxylic acid, 5-[3-(benzyloxy)phenyl]-4-chloro-3-(carboxymethoxy)thiophene-2-carboxylic acid, 4-chloro-5-[3-(1-carboxymethoxy)phenyl]-3-(carboxymethoxy)thiophene-2-carboxylic acid, 4-chloro-3-(carboxymethoxy)-5-{3-[(2-fluorobenzyl)amino]phenyl}thiophene-2-carboxylic acid, 4-chloro-3-(carboxymethoxy)-5-[3-({[3-(trifluoromethyl)phenyl]amino}methyl)phenyl]thiophene-2-carboxylic acid, 4-chloro-3-(carboxymethoxy)-5-(3-{[(3,4-difluorophenyl)amino]methyl}phenyl)thiophene-2-carboxylic acid, 4-chloro-3-(carboxymethoxy)-5-{3-[(2-furylmethyl)amino]phenyl}thiophene-2-carboxylic acid, 4-chloro-3-(carboxymethoxy)-5-{3-[(cyclohexylamino)methyl]phenyl}thiophene-2-carboxylic acid, 5-bromo-3-(carboxymethoxy)-4-methylthiophene-2-carboxylic acid, 4-chloro-3-(carboxymethoxy)-5-(3-{[(3-nitrophenyl)amino]methyl}phenyl)thiophene-2 carboxylic acid, 4-chloro-5-[3-({[4-chloro-3-(trifluoromethyl)phenyl]amino}methyl)phenyl]-3-(carboxymethoxy)thiophene-2-carboxylic acid, 5-[3-(anilinomethyl)-4-methoxyphenyl]-4-chloro-3-(carboxymethoxy)thiophene-2-carboxylic acid, 4-chloro-5-{3-[(E)-2-carboxyethenyl]-4-methoxyphenyl}-3-(carboxymethoxy)thiophene-2-carboxylic acid, 4-chloro-3-(carboxymethoxy)-5-{3-[(3-furylmethyl)amino]phenyl}thiophene-2-carboxylic acid, 4-chloro-3-(carboxymethoxy)-5-{3-[(3-fluorobenzyl)amino]phenyl}thiophene-2-carboxylic acid, 4-chloro-3-(carboxymethoxy)-5-{3-[(2-fluorobenzoyl)amino]phenyl}thiophene-2-carboxylic acid, 4-chloro-3-(carboxymethoxy)-5-{3-[(3-fluorobenzoyl)amino]phenyl}thiophene-2-carboxylic acid, 4-chloro-3-(carboxymethoxy)-5-(3-{[(3,5-difluorophenyl)amino]methyl}phenyl)thiophene-2-carboxylic acid, 4-chloro-3-(carboxymethoxy)-5-(3-{[(3-fluoro-4-methylphenyl)amino]methyl}phenyl)thiophene-2-carboxylic acid, 4-chloro-3-(carboxymethoxy)-5-{3-[(3-cyanobenzyl)amino]phenyl}thiophene-2-carboxylic acid, 4-chloro-3-(carboxymethoxy)-5-{3-[(pyridin-3-ylcarbonyl)amino]phenyl}thiophene-2-carboxylic acid, carboxylic acid, 4-chloro-3-(carboxymethoxy)-5-{3-[(cyclohexylmethyl)amino]phenyl}thiophene-2-carboxylic acid, carboxylic acid, 4-chloro-3-(carboxymethoxy)-5-{3-[(pyridin-3-ylmethyl)amino}phenyl}thiophene-2-carboxylic acid, carboxylic acid, 4-chloro-3-(carboxymethoxy)-5-[3-(cyclohexylamino)phenyl]thiophene-2-carboxylic acid, acid, 4-chloro-3-(carboxymethoxy)-5-(1H-indol-5-yl)thiophene-2-carboxylic acid, 4-chloro-5-{4-[(carboxyacetyl)amino]phenyl}-3-(carboxymethoxy)thiophene-2-carboxylic acid, 4-chloro-3-(carboxymethoxy)-5-[3-({[4-chloro-3-(trifluoromethyl)phenyl]amino}methyl)phenyl]thiophene-2-carboxylic acid, 4-chloro-3-(carboxymethoxy)-5-(3-{[(4-methyl-3-nitrophenyl)amino]methyl}phenyl)thiophene-2-carboxylic acid, 4-chloro-3-(carboxymethoxy)-5-{3-[(4,4,4-trifluorobutanoyl)amino]phenyl}thiophene-2-carboxylic acid, 4-chloro-3-(carboxymethoxy)-5-{3-[(4-fluorobenzyl)amino]phenyl}thiophene-2-carboxylic acid, 4-chloro-3-(carboxymethoxy)-5-[4-(3-furoylamino)phenyl]thiophene-2-carboxylic acid, 5-[3-({[3,5-bis(trifluoromethyl)phenyl]amino}methyl)-4-methoxyphenyl]-4-chloro-3-(carboxymethoxy)thiophene-2-carboxylic acid, 4-chloro-3-(carboxymethoxy)-5-[3-({[4-(trifluoromethyl)phenyl]amino}carbonyl)phenyl]thiophene-2-carboxylic acid, 4-chloro-3-(carboxymethoxy)-5-(3-{[4-(trifluoromethyl)benzyl]amino}phenyl)thiophene-2-carboxylic acid, 4-chloro-3-(carboxymethoxy)-5-{3-[(4-methoxybenzyl)amino]phenyl}thiophene-2-carboxylic acid, 4-chloro-3-(carboxymethoxy)-5-[4-(2-furoylamino)phenyl]thiophene-2-carboxylic acid, 4-chloro-5-[4-({[1-(tert-butoxycarbonyl)piperidin-4-yl]carbonyl}amino)phenyl]-3-(carboxymethoxy)thiophene-2-carboxylic acid, 4-chloro-5-[4-({[1-(tert-butoxycarbonyl)piperidin-3-yl]

carbonyl}amino)phenyl]-3-(carboxymethoxy)thiophene-2-carboxylic acid, 5-(3-{[4-(benzyloxy)benzyl]amino}phenyl)-4-chloro-3-(carboxymethoxy)thiophene-2-carboxylic acid, 4-chloro-3-(carboxymethoxy)-5-{3-[(4-phenoxybenzyl)amino]phenyl}thiophene-2-carboxylic acid, 4-chloro-3-(carboxymethoxy)-5-(4-methoxy-3-{(1E)-3-oxo-3-[(2,2,2-trifluoroethyl)amino]prop-1-enyl}phenyl)thiophene-2-carboxylic acid, 4-chloro-3-(carboxymethoxy)-5-[3-(2-naphthylmethoxy)phenyl]thiophene-2-carboxylic acid, 5-[3-(2,1,3-benzoxadiazol-5-ylmethoxy)phenyl]-4-chloro-3-(carboxymethoxy)thiophene-2-carboxylic acid, 4-chloro-3-(carboxymethoxy)-5-(3-{[(2-hydroxypyridin-3-yl)carbonyl]amino}phenyl)thiophene-2-carboxylic acid, 3-(carboxymethoxy)-4-methyl-5-phenylthiophene-2-carboxylic acid, 4-chloro-3-(carboxymethoxy)-5-[3-(isonicotinoylamino)phenyl]thiophene-2-carboxylic acid, 4-chloro-3-(carboxymethoxy)-5-{3-[(quinolin-3-ylcarbonyl)amino]phenyl}thiophene-2-carboxylic acid, 5-[3-(benzylamino)phenyl]-3-(carboxymethoxy)-4-methylthiophene-2-carboxylic acid, 3-(carboxymethoxy)-5-{3-[(cyclohexylmethyl)amino]phenyl)}4-methylthiophene-2-carboxylic acid, 4-chloro-3-(carboxymethoxy)-5-{3-[(pyridin-2-ylcarbonyl)amino]phenyl}thiophene-2-carboxylic acid, 4-chloro-3-(carboxymethoxy)-5-{3-[(2-naphthylmethyl)amino]phenyl}thiophene-2-carboxylic acid, 4-chloro-3-(carboxymethoxy)-5-(3-{[(1-oxidopyridin-3-yl)carbonyl]amino}phenyl)thiophene-2-carboxylic acid, 3-(carboxymethoxy)-4-methyl-5-{3-[(pyridin-3-ylcarbonyl)amino]phenyl}thiophene-2-carboxylic acid, 3-(carboxymethoxy)-5-(3-{[(carboxymethyl)sulfonyl]amino}phenyl)-4-methylthiophene-2-carboxylic acid, 4-chloro-3-(carboxymethoxy)-5-{3-[(pyridin-2-ylacetyl)amino]phenyl}thiophene-2-carboxylic acid, 4-chloro-3-(carboxymethoxy)-5-{3-[(pyridin-3-ylacetyl)amino]phenyl}thiophene-2-carboxylic acid, 4-chloro-5-{3-[(3-carboxybenzyl)amino]phenyl}-3-(carboxymethoxy)thiophene-2-carboxylic acid, 4-chloro-3-(carboxymethoxy)-5-{3-[(pyrazin-2-ylcarbonyl)amino]phenyl}thiophene-2-carboxylic acid, 4-chloro-3-(carboxymethoxy)-5-(3-{[3-(trifluoromethoxy)benzyl]amino}phenyl)thiophene-2-carboxylic acid, 4-chloro-3-(carboxymethoxy)-5-(3-{[2-(trifluoromethoxy)benzyl]amino}phenyl)thiophene-2-carboxylic acid, 4-chloro-3-(carboxymethoxy)-5-{3-[(2-hydroxybenzyl)amino]phenyl}thiophene-2-carboxylic acid, 4-chloro-5-{3-[(3-carboxybenzyl)oxy]phenyl}-3-(carboxymethoxy)thiophene-2-carboxylic acid, 4-chloro-3-(carboxymethoxy)-5-{3-[(4-methylbenzyl)amino]phenyl}thiophene-2-carboxylic acid, 4-chloro-3-(carboxymethoxy)-5-{3-[(pyridin-4-ylacetyl)amino]phenyl}thiophene-2-carboxylic acid, 4-chloro-3-(carboxymethoxy)-5-{3-[(4-chlorobenzyl)amino]phenyl}thiophene-2-carboxylic acid, 4-chloro-3-(carboxymethoxy)-5-(3-{[3-(trifluoromethoxy)benzyl]oxy}phenyl)thiophene-2-carboxylic acid, 4-chloro-3-(carboxymethoxy)-5-[3-(cyclopentylamino)phenyl]thiophene-2-carboxylic acid, 4-chloro-3-(carboxymethoxy)-5-{3-[(4-isopropylbenzyl)amino]phenyl}thiophene-2-carboxylic acid, 5-{3-[(1-acetylpiperidin-4-yl)amino]phenyl)}4-chloro-3-(carboxymethoxy)thiophene-2-carboxylic acid, 5-[4-(benzyloxy)phenyl]-4-chloro-3-(carboxymethoxy)thiophene-2-carboxylic acid, 4-chloro-3-(carboxymethoxy)-5-[3-(5-fluoro-1H-benzimidazol-2-yl)phenyl]thiophene-2-carboxylic acid, 4-chloro-3-(carboxymethoxy)-5-[3-(cycloheptylamino)phenyl]thiophene-2-carboxylic acid, 5-[3-(bicyclo[3.3.1]non-9-ylamino)phenyl]-4-chloro-3-(carboxymethoxy)thiophene-2-carboxylic acid, 5-(anilinocarbonyl)-3-(carboxymethoxy)thiophene-2-carboxylic acid, 4-chloro-3-(carboxymethoxy)-5-{3-[(4-ethylcyclohexyl)amino]phenyl}thiophene-2-carboxylic acid, 3-(carboxymethoxy)-5-(4-hydroxyphenyl)-4-methylthiophene-2-carboxylic acid, 4-chloro-3-(carboxymethoxy)-5-{3-[(4-phenylcyclohexyl)amino]phenyl}thiophene-2-carboxylic acid, 4-chloro-3-(carboxymethoxy)-5-{3-[(4-phenylcyclohexyl)amino]phenyl}thiophene-2-carboxylic acid, 4-chloro-3-(carboxymethoxy)-5-[2-(hydroxymethyl)phenyl]thiophene-2-carboxylic acid, 3-(carboxymethoxy)-5-(4-{[(isopropylamino)carbonyl]aminophenyl)-4-methylthiophene-2-carboxylic acid, 5-[3,4-bis(benzyloxy)phenyl]-4-chloro-3-(carboxymethoxy)thiophene-2-carboxylic acid, 5-[3-(benzyloxy)-4-hydroxyphenyl]-4-chloro-3-(carboxymethoxy)thiophene-2-carboxylic acid, 5-[4-(benzyloxy)-3-hydroxyphenyl]-4-chloro-3-(carboxymethoxy)thiophene-2-carboxylic acid, 2-{3-[3-bromo-5-carboxy-4-(carboxymethoxy)thien-2-yl]phenyl}-1H-benzimidazole-5-carboxylic acid, carboxylic acid, 3-(carboxymethoxy)thiophene-2-carboxylic acid, 4-chloro-3-(carboxymethoxy)-5-[3-(cyclohexylmethoxy)phenyl]thiophene-2-carboxylic acid, 4-chloro-3-(carboxymethoxy)-5-pyridin-4-ylthiophene-2-carboxylic acid, 4-chloro-3-(carboxymethoxy)-5-{3-[(1-cyclohexylethyl)amino]phenyl}thiophene-2-carboxylic acid, 4-chloro-3-(carboxymethoxy)-5-(3-{[1-(methoxycarbonyl)piperidin-4-yl]amino}phenyl)thiophene-2-carboxylic acid, 4-chloro-3-(carboxymethoxy)-5-{3-[(3,3,5,5-tetramethylcyclohexyl)amino]phenyl}thiophene-2-carboxylic acid, 5-[3-(2-adamantylamino)phenyl]-4-chloro-3-(carboxymethoxy)thiophene-2-carboxylic acid, 3-(carboxymethoxy)-4-methyl-5-{3-[(3-phenoxybenzyl)amino]phenyl}thiophene-2-carboxylic acid, 5-{3-[(3-bromobenzyl)amino}phenyl}-3-(carboxymethoxy)-4-methylthiophene-2-carboxylic acid, 3-(carboxymethoxy)-4-methyl-5-(3-{[3-(trifluoromethyl)benzyl]amino}phenyl)thiophene-2-carboxylic acid, 5-[3-([(benzylamino)carbonyl]{1-[(benzylamino)carbonyl]piperidin-4-yl}amino)phenyl]-4-chloro-3-(carboxymethoxy)thiophene-2-carboxylic acid, 5-[3-({1-[(benzylamino)carbonyl]piperidin-4-yl}amino)phenyl]-4-chloro-3-(carboxymethoxy)thiophene-2-carboxylic acid, 4-chloro-3-(carboxymethoxy)-5-{3-[(3-nitrobenzyl)amino]phenyl}thiophene-2-carboxylic acid, 4-chloro-3-(carboxymethoxy)-5-(3-{[1-(methylsulfonyl)piperidin-4-yl]amino}phenyl)thiophene-2-carboxylic acid, 4-chloro-3-(carboxymethoxy)-5-[3-({3-[(methylsulfonyl)amino]benzyl}amino)phenyl]thiophene-2-carboxylic acid, 5-(3-{[3-(acetylamino)benzyl]amino}phenyl)-4-chloro-3-(carboxymethoxy)thiophene-2-carboxylic acid, 5-{3-[(3-aminobenzyl)amino]phenyl}-4-chloro-3-(carboxymethoxy)thiophene-2-carboxylic acid, 4-chloro-3-(carboxymethoxy)-5-[3-(tetrahydro-2H-pyran-4-ylamino)phenyl]thiophene-2-carboxylic acid, 5-(3-{[acetyl(cyclohexyl)amino]methyl}phenyl)-4-chloro-3-(carboxymethoxy)thiophene-2-carboxylic acid, 4-chloro-3-(carboxymethoxy)-5-(3-{[1-(phenylsulfonyl)piperidin-4-yl]amino}phenyl)thiophene-2-carboxylic acid, 5-(3-{[3,5-bis(trifluoromethyl)benzyl]oxy}phenyl)-4-chloro-3-(carboxymethoxy)thiophene-2-carboxylic acid, 4-chloro-5-[3-({[1-(tert-butoxycarbonyl)piperidin-4-yl]methyl}amino)phenyl]-3-(carboxymethoxy)thiophene-2-carboxylic acid, 5-(3-{[1-(benzylsulfonyl)piperidin-4-yl]amino}phenyl)-4-chloro-3-(carboxymethoxy)thiophene-2-carboxylic acid, 4-chloro-3-(carboxymethoxy)-5-(3-{[1-(ethylsulfonyl)piperidin-4-yl]methyl}amino)phenyl]thiophene-2-carboxylic acid, 4-chloro-3-(carboxymethoxy)-5-[3-({[1-(methylsulfonyl)

piperidin-4-yl]methyl}amino)phenyl]thiophene-2-carboxylic acid, 4-chloro-3-(carboxymethoxy)-5-[3-({[1-(ethylsulfonyl)piperidin-4-yl]methyl}amino)phenyl]thiophene-2-carboxylic acid, 5-{3-[acetyl(benzyl)amino]phenyl}4-chloro-3-(carboxymethoxy)thiophene-2-carboxylic acid, 4-chloro-3-(carboxymethoxy)-5-[3-({[1-(phenylsulfonyl)piperidin-4-yl]methyl}amino)phenyl]thiophene-2-carboxylic acid, 5-[3-({[1-(benzylsulfonyl)piperidin-4-yl] methyl}amino)phenyl]-4-chloro-3-(carboxymethoxy) thiophene-2-carboxylic acid, 4-chloro-3-(carboxymethoxy)-5-(3-{[1-(isopropylsulfonyl)piperidin-4-yl]amino}phenyl) thiophene-2-carboxylic acid, 5-{3-[acetyl(3,3,5,5-tetramethylcyclohexyl)amino]phenyll}4-chloro-3-(carboxymethoxy)thiophene-2-carboxylic acid, 4-chloro-3-(carboxymethoxy)-5-[3-({[1-(methoxycarbonyl)piperidin-4-yl]methyl}amino)phenyl]thiophene-2-carboxylic acid, 4-chloro-3-(carboxymethoxy)-5-(3-{[1-(phenylacetyl)piperidin-4-yl]amino}phenyl)thiophene-2-carboxylic acid, 5-[3-[(1-benzoylpiperidin-4-yl)amino]phenyl]4-chloro-3-(carboxymethoxy)thiophene-2-carboxylic acid, 5-(3-{[acetyl(phenyl)amino]methyl}-4-methoxyphenyl)-4-chloro-3-(carboxymethoxy)thiophene-2-carboxylic acid, 4-chloro-3-(carboxymethoxy)-5-{4-[(3,3,5,5-tetramethylcyclohexyl)amino]phenyl}thiophene-2-carboxylic acid, 5-(3-{[acetyl(3,3,5,5-tetramethylcyclohexyl)amino]methyl}phenyl)-4-chloro-3-(carboxymethoxy)thiophene-2-carboxylic acid, 3-(carboxymethoxy)-4-methyl-5-{3-[(3,3,5,5-tetramethylcyclohexyl)amino]phenyl}thiophene-2-carboxylic acid, 3-(carboxymethoxy)-5-[3-(cycloheptylamino)phenyl]-4-methylthiophene-2-carboxylic acid, 4-chloro-5-(3-{[1-(tert-butoxycarbonyl)piperidin-4-yl]methoxy}phenyl)-3-(carboxymethoxy)thiophene-2-carboxylic acid, 4-chloro-5-(3-{[1-(butylsulfonyl)piperidin-4-yl]amino}phenyl)-3-(carboxymethoxy)thiophene-2-carboxylic acid, 3-(carboxymethoxy)-5-{4-[(3,3,5,5-tetramethylcyclohexyl)amino]phenyl}thiophene-2-carboxylic acid, 5-[3-({acetyl[1-(ethoxycarbonyl)piperidin-4-yl]amino}methyl)phenyl]-4-chloro-3-(carboxymethoxy)thiophene-2-carboxylic acid, 5-{3-[(1-{[3,5-bis(trifluoromethyl)benzyl] sulfonyl}piperidin-4-yl)amino]phenyl}-4-chloro-3-(carboxymethoxy)thiophene-2-carboxylic acid, 4-chloro-3-(carboxymethoxy)-5-(3-{[1-(propylsulfonyl)piperidin-4-yl] amino}phenyl)thiophene-2-carboxylic acid, 4-chloro-3-(carboxymethoxy)-5-(3-{[1-(1-naphthylsulfonyl)piperidin-4-, yl]amino}phenyl)thiophene-2-carboxylic acid, 4-chloro-3-(carboxymethoxy)-5-(3-{[1-(2-naphthylsulfonyl) piperidin-4-yl]amino}phenyl)thiophene-2-carboxylic acid, 4-chloro-3-(carboxymethoxy)-5-[3-({1-[(2-nitrobenzyl)sulfonyl]piperidin-4-yl}amino)phenyl]thiophene-2-carboxylic acid, 2-[(4,5-dibromo-2-carboxythien-3-yl)oxy]malonic acid, 5-(3-{[1-(benzylsulfonyl)piperidin-4-yl] methoxy}phenyl)-4-chloro-3-(carboxymethoxy)thiophene-2-carboxylic acid, 4-chloro-3-(carboxymethoxy)-5-{3-[(1-{[3-(trifluoromethyl)benzyl]sulfonyl}piperidin-4-yl)amino] phenyl}thiophene-2-carboxylic acid, 4-chloro-3-(carboxymethoxy)-5-[3-({1-[(4-fluorobenzyl)sulfonyl] piperidin-4-yl}amino)phenyl]thiophene-2-carboxylic acid, 4-chloro-3-(carboxymethoxy)-5-{3-[(1-{[4-(trifluoromethyl)benzyl]sulfonyl}piperidin-4-yl)amino] phenyl}thiophene-2-carboxylic acid, 4-chloro-3-(carboxymethoxy)-5-[3-({1-[(4-chlorobenzyl)sulfonyl] piperidin-4-yl}amino)phenyl]thiophene-2-carboxylic acid, 4-chloro-3-(carboxymethoxy)-5-[3-({1-[(3,5-dichlorobenzyl)sulfonyl]piperidin-4-yl}amino)phenyl]thiophene-2-carboxylic acid, 4-chloro-3-(carboxymethoxy)-5-[3-({1-[(3,4-dichlorobenzyl)sulfonyl]piperidin-4-yl}amino)phenyl] thiophene-2-carboxylic acid, 5-[3-({[1-(anilinocarbonyl) piperidin-4-yl]methyl}amino)phenyl]-4-chloro-3-(carboxymethoxy)thiophene-2-carboxylic acid, 4-chloro-3-(carboxymethoxy)-5-[3-({1-[(3-nitrobenzyl)sulfonyl] piperidin-4-yl}amino)phenyl]thiophene-2-carboxylic acid, 4-chloro-3-(carboxymethoxy)-5-[3-({1-[(3-chlorobenzyl) sulfonyl]piperidin-4-yl}amino)phenyl]thiophene-2-carboxylic acid, 4-chloro-3-(carboxymethoxy)-5-[3-({1-[(4-methylphenyl)sulfonyl]piperidin-4-yl}methoxy)phenyl] thiophene-2-carboxylic acid, 4-chloro-3-(carboxymethoxy)-5-[3-({1-[(2-phenylethyl)sulfonyl]piperidin-4-yl}amino) phenyl]thiophene-2-carboxylic acid, 5-{3-[({1-[(benzylamino)carbonyl]piperidin-4-yl}methyl)amino] phenyl}-4-chloro-3-(carboxymethoxy)thiophene-2-carboxylic acid, 4-chloro-3-(carboxymethoxy)-5-{3-[({1-[(cyclohexylamino)carbonyl]piperidin-4-yl}methyl)amino] phenyl}thiophene-2-carboxylic acid, 5-(3-{[1-(benzylsulfonyl)piperidin-4-yl]amino}phenyl)-3-(carboxymethoxy)thiophene-2-carboxylic acid, 4-chloro-5-(3-{[1-(tert-butoxycarbonyl)piperidin-4-yl]oxy}phenyl)-3-(carboxymethoxy)thiophene-2-carboxylic acid, 4-chloro-3-(carboxymethoxy)-5-(3-{[cyclohexyl(methylsulfonyl) amino]methyl}phenyl)thiophene-2-carboxylic acid, 4-chloro-3-(carboxymethoxy)-5-(3-{[cyclohexyl(methoxycarbonyl)amino]methyl}phenyl)thiophene-2-carboxylic acid, 4-chloro-3-(carboxymethoxy)-5-[3-({cyclohexyl [(ethylamino)carbonyl]amino}methyl)phenyl]thiophene-2-carboxylic acid, 4-chloro-3-(carboxymethoxy)-5-(3-{[(1-{[(4-methoxyphenyl)amino]carbonyl}piperidin-4-yl)methyl] aamino}phenyl)thiophene-2-carboxylic acid, 4-chloro-3-(carboxymethoxy)-5-(3-{[(1-{[(4-cyanophenyl)amino] carbonyl}piperidin-4-yl)methyl]amino}phenyl)thiophene-2-carboxylic acid, 4-chloro-3-(carboxymethoxy)-5-(3-{[(1-{[(4-methylphenyl)amino]carbonyl}piperidin-4-yl)methyl] amino}phenyl)thiophene-2-carboxylic acid, 4-chloro-3-(carboxymethoxy)-5-(3-{[1-(phenylsulfonyl)piperidin-4-yl] methoxy}phenyl)thiophene-2-carboxylic acid, 4-chloro-3-(carboxymethoxy)-5-(3-{[(1-{[(2-methoxyphenyl)amino] carbonyl}piperidin-4-yl)methyl]amino}phenyl)thiophene-2-carboxylic acid, 4-chloro-3-(carboxymethoxy)-5-(3-{[(1-{[(3-chlorophenyl)amino]carbonyl}piperidin-4-yl)methyl] aminophenyl)thiophene-2-carboxylic acid, 4-chloro-3-(carboxymethoxy)-5-(3-{[(1-{[(2-chlorophenyl)amino] carbonyl}piperidin-4-yl)methyl]amino}phenyl)thiophene-2-carboxylic acid, 4-chloro-3-(carboxymethoxy)-5-(3-{[1-(methylsulfonyl)piperidin-4-yl]methoxy}phenyl)thiophene-2-carboxylic acid, 4-chloro-3-(carboxymethoxy)-5-[3-(hydroxymethyl)phenyl]thiophene-2-carboxylic acid, 5-(3-{[1-(anilinocarbonyl)piperidin-4-yl]oxy}phenyl)-4-chloro-3-(carboxymethoxy)thiophene-2-carboxylic acid, 4-chloro-3-(carboxymethoxy)-5-(3-{[1-(phenoxycarbonyl)piperidin-4-yl]oxy}phenyl)thiophene-2-carboxylic acid, 5-(3-{[1-(benzylsulfonyl)piperidin-4-yl]oxy}phenyl)-4-chloro-3-(carboxymethoxy)thiophene-2-carboxylic acid, 5-(3-{[1-(anilinocarbonyl)piperidin-4-yl]methoxy}phenyl)-4-chloro-3-(carboxymethoxy)thiophene-2-carboxylic acid, (carboxymethoxy)thiophene-2-carboxylic acid, 4-chloro-3-(carboxymethoxy)-5-[3-({1-[(ethylamino)carbonyl]piperidin-4-yl}methoxy)phenyl]thiophene-2-carboxylic acid, 4-chloro-3-(carboxymethoxy)-5-[3-({1-[(2-methylbenzyl) sulfonyl]piperidin-4-yl}amino)phenyl]thiophene-2-carboxylic acid, 4-chloro-3-(carboxymethoxy)-5-[3-({1-[(3-methylbenzyl)sulfonyl]piperidin-4-yl}amino)phenyl] thiophene-2-carboxylic acid, 4-chloro-3-(carboxymethoxy)-5-(3-{[(1-{[(3-methoxyphenyl)amino]carbonyl}piperidin-4-yl)methyl]amino}phenyl)thiophene-2-carboxylic acid, 4-chloro-3-(carboxymethoxy)-5-(3-{[(1-{[(3-methylphenyl)amino]carbonyl}piperidin-4-yl)methyl]amino}phenyl)

thiophene-2-carboxylic acid, 4-chloro-3-(carboxymethoxy)-5-(3-{[(1-{[(2-methylphenyl)amino]carbonyl}piperidin-4-yl)methyl]armino}phenyl)thiophene-2-carboxylic acid, 4-chloro-3-(carboxymethoxy)-5-(3-{[1-(methoxycarbonyl)piperidin-4-yl]methoxy}phenyl)thiophene-2-carboxylic acid, 4-chloro-3-(carboxymethoxy)-5-(3-{[1-(phenoxycarbonyl)piperidin-4-yl]methoxy}phenyl)thiophene-2-carboxylic acid, 4-chloro-3-(carboxymethoxy)-5-{3-[(1-{[(2-chlorophenyl)amino]carbonyl}piperidin-4-yl)methoxy]phenyl}thiophene-2-carboxylic acid, 4-chloro-3-(carboxymethoxy)-5-{3-[(1-{[(2-methylphenyl)amino]carbonyl}piperidin-4-yl)methoxy]phenyl}thiophene-2-carboxylic acid, 4-yl)methoxy]phenyl}thiophene-2-carboxylic acid, 4-chloro-3-(carboxymethoxy)-5-{3-[(1-{[(2-methoxyphenyl)amino]carbonyl}piperidin-4-yl)methoxy]phenyl}thiophene-2-carboxylic acid, 4-yl)methoxy]phenyl}thiophene-2-carboxylic acid, 4-chloro-3-(carboxymethoxy)-5-{3-[(1-{[(2-isopropylphenyl)amino]carbonyl}piperidin-4-yl)methoxy]phenyl}thiophene-2-carboxylic acid, 4-chloro-3-(carboxymethoxy)-5-{3-[(1-{[(2,6-diethylphenyl)amino]carbonyl}piperidin-4-yl)methoxy]phenyl}thiophene-2-carboxylic acid, 4-chloro-3-(carboxymethoxy)-5-[3-({1-[(mesitylamino)carbonyl]piperidin-4-yl}methoxy)phenyl]thiophene-2-carboxylic acid, 4-chloro-3-(carboxymethoxy)-5-{3-[(1-{[(2-isopropyl-6-methylphenyl)amino]carbonyl}piperidin-4-yl)methoxy]phenyl}thiophene-2-carboxylic acid, 4-chloro-3-(carboxymethoxy)-5-{3-[(1-{[(2-phenoxyphenyl)amino]carbonyl}piperidin-4-yl)methoxy]phenyl}thiophene-2-carboxylic acid, 4-chloro-3-(carboxymethoxy)-5-[3-({1-[(2,6-dimethylbenzyl)sulfonyl]piperidin-4-yl}amino)phenyl]thiophene-2-carboxylic acid, 4-chloro-3-(carboxymethoxy)-5-(3-{[(1-{[(2,6-dimethylphenyl)amino]carbonyl}piperidin-4-yl)methyl]amino}phenyl)thiophene-2-carboxylic acid, 4-chloro-3-(carboxymethoxy)-5-[3-({[1-({[2-(trifluoromethyl)phenyl]amino}carbonyl)piperidin-4-yl]methyl}amino)phenyl]thiophene-2-carboxylic acid, 4-chloro-3-(carboxymethoxy)-5-(3-{[(1-{[methyl(phenyl)amino]carbonyl}piperidin-4-(methylthio)phenyl]amino}carbonyl)piperidin-4-yl]methyl}amino)phenyl]thiophene-2-carboxylic acid, 4-chloro-3-(carboxymethoxy)-5-[3-({[1-({[2-(methylthio)phenyl]amino}carbonyl)piperidin-4-yl]methyl}amino)phenyl]thiophene-2-carboxylic acid, 4-chloro-3-(carboxymethoxy)-5-{3-[(1-{[(2,6-dimethylphenyl)amino]carbonyl}piperidin-4-yl)methoxy]phenyl}thiophene-2-carboxylic acid, 4-chloro-3-(carboxymethoxy)-5-(3-{[(1-{[(2,3-dimethylphenyl)amino]carbonyl}piperidin-4-yl)methyl]amino}phenyl)thiophene-2-carboxylic acid, 5-(3-{[1-(anilinocarbonyl)piperidin-4-yl]amino}phenyl)-4-chloro-3-(carboxymethoxy)thiophene-2-carboxylic acid, 4-chloro-3-(carboxymethoxy)-5-{3-[(1-{[(3-phenoxyphenyl)amino]carbonyl}piperidin-4-yl)methoxy]phenyl}thiophene-2-carboxylic acid, {5-{3-[acetyl(3,3,5,5-tetramethylcyclohexyl)amino]phenyl}-2-(2H-tetrazol-5-yl)thien-3-yl]oxy}acetic acid, 4-chloro-3-(carboxymethoxy)-5-{3-[(1-{[(4-methyl-2-nitrophenyl)amino]carbonyl}piperidin-4-yl)methoxy]phenyl}thiophene-2-carboxylic acid, 4-chloro-3-(carboxymethoxy)-5-{3-[(1-{[(5-chloro-2-nitrophenyl)amino]carbonyl}piperidin-4-yl)methoxy]phenyl}thiophene-2-carboxylic acid, 4-chloro-3-(carboxymethoxy)-5-{3-[(1-{[(2-nitrophenyl)amino]carbonyl}piperidin-4-yl)methoxy]phenyl}thiophene-2-carboxylic acid, 4-chloro-3-(carboxymethoxy)-5-{3-[(1-{[2-(1H-imidazol-1-yl)ethyl]sulfonyl}piperidin-4-yl)amino]phenyl}thiophene-2-carboxylic acid, 5-[3-({[5-(anilinocarbonyl)thien-2-yl]methyl}amino)phenyl]-4-chloro-3-(carboxymethoxy)thiophene-2-carboxylic acid, 5-{3-[({5-[(benzylamino)carbonyl]thien-2-yl}methyl)amino]phenyl}-4-chloro-3-(carboxymethoxy)thiophene-2-carboxylic acid, 4-chloro-3-(carboxymethoxy)-5-{3-[({5-[(cyclohexylamino)carbonyl]thien-2-yl}methyl)amino]phenyl}thiophene-2-carboxylic acid, 5-{3-[({1-[(2-aminobenzyl)sulfonyl]piperidin-4-yl}methyl)amino]phenyl}-4-chloro-3-(carboxymethoxy)thiophene-2-carboxylic acid, 4-chloro-3-(carboxymethoxy)-5-{3-[(1-{[2-(1H-pyrazol-1-yl)ethyl]sulfonyl}piperidin-4-yl)amino]phenyl}thiophene-2-carboxylic acid, {[4,5-dibromo-2-(1H-tetrazol-5-yl)thien-3-yl]oxy}acetic acid, 4-chloro-5-{4-[(4-tert-butylbenzoyl)amino]phenyl}-3-(carboxymethoxy)thiophene-2-carboxylic acid, 4-chloro-3-(carboxymethoxy)-5-[3-({1-[(2-isopropoxyethyl)sulfonyl]piperidin-4-yl}amino)phenyl]thiophene-2-carboxylic acid, 4-chloro-3-(carboxymethoxy)-5-{4-[(phenylacetyl)amino]phenyl}thiophene-2-carboxylic acid, 5-[3-({[1-(benzylsulfonyl)piperidin-3-yl]carbonyl}amino)phenyl]-4-chloro-3-(carboxymethoxy)thiophene-2-carboxylic acid, 5-[3-({1-[(2-aminobenzyl)sulfonyl]piperidin-4-yl}amino)phenyl]-4-chloro-3-(carboxymethoxy)thiophene-2-carboxylic acid, 4-chloro-5-(3-{[1-({2-[(2-carboxybenzoyl)amino]ethyl}sulfonyl)piperidin-4-yl]amino}phenyl)-3-(carboxymethoxy)thiophene-2-carboxylic acid, {[4-chloro-5-phenyl-2-(2H-tetrazol-5-yl)thien-3-yl]oxy}acetic acid, {[4-methyl-5-phenyl-2-(2H-tetrazol-5-yl)thien-3-yl]oxy}acetic acid, {[5-bromo-4-methyl-2-(2H-tetrazol-5-yl)thien-3-yl]oxy}acetic acid, {[5-bromo-4-methyl-2-(2-methyl-2H-tetrazol-5-yl)thien-3-yl]oxy}acetic acid, {[5-(3-{[1-(benzylsulfonyl)piperidin-4-yl]amino}phenyl)-4-chloro-2-(2H-tetrazol-5-yl)thien-3-yl]oxy}acetic acid, {[5-{3-[acetyl(3,3,5,5-tetramethylcyclohexyl)amino]phenyl}-4-chloro-2-(2H-tetrazol-5-yl)thien-3-yl]oxy}acetic acid, {[4-chloro-5-{3-[(cyclohexylmethyl)amino]phenyl}-2-(2H-tetrazol-5-yl)thien-3-yl]oxy}acetic acid, {[4-chloro-5-{3-[(3,3,5,5-tetramethylcyclohexyl)amino]phenyl}-2-(2H-tetrazol-5-yl)thien-3-yl]oxy}acetic acid, {[4-chloro-5-[3-(cyclohexylamino)phenyl]-2-(2H-tetrazol-5-yl)thien-3-yl]oxy}acetic acid, tetrazol-5-yl)thien-3-yl]oxy}acetic acid {[4-chloro-5-(3-{[1-(tert-butoxycarbonyl)piperidin-4-yl]oxy}phenyl)-2-(2H-, {[5-(3-{[1-(benzylsulfonyl)piperidin-4-yl]oxy}phenyl)-4-chloro-2-(2H-tetrazol-5-yl)thien-3-yl]oxy}acetic acid, 4-chloro-3-(carboxymethoxy)-5-[3-({1-[(cyclohexylmethyl)sulfonyl]piperidin-4-yl}amino)phenyl]thiophene-2-carboxylic acid, 4-chloro-3-(carboxymethoxy)-5-{3-[[(methylamino)carbonyl](3,3,5,5-tetramethylcyclohexyl)amino]phenyl}thiophene-2-carboxylic acid, 5-(3-{[cis-4-(benzyloxy)cyclohexyl]amino}phenyl)-4-chloro-3-(carboxymethoxy)thiophene-2-carboxylic acid, 5-(3-{[trans-4-(benzyloxy)cyclohexyl]aminophenyl)-4-chloro-3-(carboxymethoxy)thiophene-2-carboxylic acid, 4-chloro-3-(carboxymethoxy)-5-[3-({[1-(phenylacetyl)piperidin-4-yl]methyl}amino)phenyl]thiophene-2-carboxylic acid, 4-chloro-3-(carboxymethoxy)-5-{3-[(1-{[2-(trifluoromethyl)benzyl]sulfonyl}piperidin-4-yl)amino]phenyl}thiophene-2-carboxylic acid, 4-chloro-3-(carboxymethoxy)-5-[3-({1-[(2-chlorobenzyl)sulfonyl]piperidin-4-yl}amino)phenyl]thiophene-2-carboxylic acid, 5-(3-{[1-(benzylsulfonyl)piperidin-4-yl]amino}phenyl)-3-(carboxymethoxy)-4-methylthiophene-2-carboxylic acid, 4-chloro-3-(carboxymethoxy)-5-[3-({1-[(2,3-dichlorobenzyl)sulfonyl]piperidin-4-yl}amino)phenyl]thiophene-2-carboxylic acid, methyl {[5-(3-{[1-(benzylsulfonyl)piperidin-4-yl]amino}phenyl)-4-chloro-2-(1H-tetrazol-5-yl)thien-3-yl]oxy}acetate, 4-chloro-3-(carboxymethoxy)-5-[3-(piperidin-4-ylamino)phenyl]thiophene-2-carboxylic acid, 4-chloro-3-(carboxymethoxy)-5-{3-[(1-pyrimidin-2-ylpiperidin-4-yl)

amino]phenyl}thiophene-2-carboxylic acid, 4-chloro-3-(carboxymethoxy)-5-[3-([(pyridin-4-ylmethyl)sulfonyl]{1-[(pyridin-4-ylmethyl)sulfonyl]piperidin-4-yl}amino)phenyl]thiophene-2-carboxylic acid, 4-chloro-3-(carboxymethoxy)-5-[3-({1-[5-(trifluoromethyl)pyridin-2-yl]piperidin-4-yl}amino)phenyl]thiophene-2-carboxylic acid, 4-chloro-3-(carboxymethoxy)-5-[3-({1-[4-(trifluoromethyl)pyrimidin-2-yl]piperidin-4-yl}amino)phenyl]thiophene-2-carboxylic acid, 4-chloro-3-(carboxymethoxy)-5-(3-{[1-(5-nitropyridin-2-yl)piperidin-4-yl]amino}phenyl)thiophene-2-carboxylic acid, {[4-chloro-5-(3-{[1-(methylsulfonyl)piperidin-4-yl]oxy}phenyl)-2-(1H-tetrazol-5-yl)thien-3-yl]oxy}acetic acid, 5-[3-({1-[(benzylamino)carbonyl]piperidin-4-yl}methoxy)phenyl]-4-chloro-3-(carboxymethoxy)thiophene-2-carboxylic acid, 4-chloro-3-(carboxymethoxy)-5-[3-({1-[(cyclohexylamino)carbonyl]piperidin-4-yl}methoxy)phenyl]thiophene-2-carboxylic acid, 4-chloro-3-(carboxymethoxy)-5-{3-[(cyclohexylmethyl)(methylsulfonyl)amino]phenyl}thiophene-2-carboxylic acid, 4-chloro-3-(carboxymethoxy)-5-{3-[[(ethylamino)carbonyl](3,3,5,5-tetramethylcyclohexyl)amino]phenyl}thiophene-2-carboxylic acid, 5-[3-({1-[5-(acetylamino)pyridin-2-yl]piperidin-4-yl}amino)phenyl]-4-chloro-3-(carboxymethoxy)thiophene-2-carboxylic acid, isopropyl {[5-(3-{[1-(benzylsulfonyl)piperidin-4-yl]amino}phenyl)-4-chloro-2-(2H-tetrazol-5-yl)thien-3-yl]oxy}acetate, 4-chloro-3-(carboxymethoxy)-5-[3-(2,3-dihydro-1H-inden-2-ylamino)phenyl]thiophene-2-carboxylic acid, 4-chloro-3-(carboxymethoxy)-5-(3-{[8-(ethoxycarbonyl)-8-azabicyclo[3.2.1]oct-3-yl]amino}phenyl)thiophene-2-carboxylic acid, 4-chloro-3-(carboxymethoxy)-5-(3-{[1-(5-{[(methylamino)carbonyl]amino}pyridin-2-yl)piperidin-4-yl]amino}phenyl)thiophene-2-carboxylic acid, 4-chloro-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid, 4-chloro-3-(carboxymethoxy)-5-{3-[(1-{5-[(methylsulfonyl)amino]pyridin-2-yl}piperidin-4-yl)amino]phenyl}thiophene-2-carboxylic acid, 5-(1-benzyl-1H-pyrazol-4-yl)-4-chloro-3-(carboxymethoxy)thiophene-2-carboxylic acid, 5-{3-[(1-{[2-(acetylamino)benzyl]sulfonyl}piperidin-4-yl)amino]phenyl}-4-chloro-3-(carboxymethoxy)thiophene-2-carboxylic acid, 4-chloro-3-(carboxymethoxy)-5-(3-{[1-({2-[(methylsulfonyl)amino]benzyl}sulfonyl)piperidin-4-yl]amino}phenyl)thiophene-2-carboxylic acid, 4-chloro-3-(carboxymethoxy)-5-[3-({1-[(2-{[(ethylamino)carbonyl]amino}benzyl)sulfonyl]piperidin-4-yl}amino)phenyl]thiophene-2-carboxylic acid, 5-{3-[(1-{[2-(acetylamino)benzyl]sulfonyl}piperidin-4-yl)amino]phenyl}-3-(carboxymethoxy)thiophene-2-carboxylic acid, 3-(carboxymethoxy)-5-[3-({1-[(2-{[(ethylamino)carbonyl]amino}benzyl)sulfonyl]piperidin-4-yl}amino)phenyl]thiophene-2-carboxylic acid, 5-{3-[[(benzylamino)carbonyl](cyclohexyl)amino]phenyl}-4-chloro-3-(carboxymethoxy)thiophene-2-carboxylic acid, 4-chloro-3-(carboxymethoxy)-5-(3-{cyclohexyl[(methylamino)carbonyl]aminophenyl)thiophene-2-carboxylic acid, 3-(carboxymethoxy)-5-phenylthiophene-2-carboxylic acid, 4-chloro-3-(carboxymethoxy)-5-[3-({1-[(3-{[(ethylamino)carbonyl]amino}benzyl)sulfonyl]piperidin-4-yl}amino)phenyl]thiophene-2-carboxylic acid, 4-chloro-3-(carboxymethoxy)-5-[3-({1-[(2-{[(chloromethyl)sulfonyl]amino}benzyl)sulfonyl]piperidin-4-yl}amino)phenyl]thiophene-2-carboxylic acid, 3-(carboxymethoxy)-5-[3-{[1-({2-[(methylsulfonyl)amino]benzyl}sulfonyl)piperidin-4-yl]amino}phenyl]thiophene-2-carboxylic acid, 5-(3-{[2-(benzylsulfonyl)-2-azabicyclo[2.2.2]oct-5-yl]amino}phenyl)-4-chloro-3-(carboxymethoxy)thiophene-2-carboxylic acid, 5-{3-[(1-{[3-(acetylamino)benzyl]sulfonyl}piperidin-4-yl)amino]phenyl}-4-chloro-3-(carboxymethoxy)thiophene-2-carboxylic acid, 4-chloro-3-(carboxymethoxy)-5-(3-{[1-({3-[(methylsulfonyl)amino]benzyl}sulfonyl)piperidin-4-yl]amino}phenyl)thiophene-2-carboxylic acid, 4-chloro-3-(carboxymethoxy)-5-{3-[(2,2,6,6-tetramethyltetrahydro-2H-pyran-4-yl)amino]phenyl}thiophene-2-carboxylic acid, 4-chloro-3-(carboxymethoxy)-5-(3-{(cyclohexylmethyl)[(ethylamino)carbonyl]amino}phenyl)thiophene-2-carboxylic acid, 4,5-dibromo-3-(1-carboxymethoxy)thiophene-2-carboxylic acid, 4-chloro-3-(carboxymethoxy)-5-(3-{cyclohexyl[(cyclohexylamino)carbonyl]amino}phenyl)thiophene-2-carboxylic acid, 5-{3-[(anilinocarbonyl)(cyclohexyl)amino]phenyl}-4-chloro-3-(carboxymethoxy)thiophene-2-carboxylic acid, 4-chloro-3-(carboxymethoxy)-5-[3-(cyclohexyl{[(2-phenylethyl)amino]carbonyl}amino)phenyl]thiophene-2-carboxylic acid, 4-chloro-3-(carboxymethoxy)-5-[3-(cyclohexyl {[(4-ethoxyphenyl)amino]carbonyl}amino)phenyl]thiophene-2-carboxylic acid, 4-chloro-3-(carboxymethoxy)-5-(3-{cyclohexyl[(isopropylamino)carbonyl]aminophenyl)thiophene-2-carboxylic acid, 4-chloro-3-(carboxymethoxy)-5-(3-{cyclohexyl[(propylamino)carbonyl]amino}phenyl)thiophene-2-carboxylic acid, 4-chloro-3-(carboxymethoxy)-5-[3-(cyclohexyl {[(4-phenoxyphenyl)amino]carbonyl}amino)phenyl]thiophene-2-carboxylic acid, 5-(3-{[acetyl(isopropyl)amino]methyl}phenyl)-4-chloro-3-(carboxymethoxy)thiophene-2-carboxylic acid, 5-(3-{[acetyl(isobutyl)amino]methylphenyl)-4-chloro-3-(carboxymethoxy)thiophene-2-carboxylic acid, 5-(3-{[acetyl(cyclohexylmethyl)amino]methyl}phenyl)-4-chloro-3-(carboxymethoxy)thiophene-2-carboxylic acid, 5-(3-{[acetyl(4-methylphenyl)amino]methyl}phenyl)-4-chloro-3-(carboxymethoxy)thiophene-2-carboxylic acid, 5-(3-{[acetyl(4-tert-butylphenyl)amino]methyl}phenyl)-4-chloro-3-(carboxymethoxy)thiophene-2-carboxylic acid, 5-[3-({acetyl[4-(trifluoromethyl)phenyl]amino}methyl)phenyl]-4-chloro-3-(carboxymethoxy)thiophene-2-carboxylic acid, 5-(3-{[acetyl(phenyl)amino]methyl}phenyl)-4-chloro-3-(carboxymethoxy)thiophene-2-carboxylic acid, 5-(3-{[acetyl(cyclopropyl)amino]methyl}phenyl)-4-chloro-3-(carboxymethoxy)thiophene-2-carboxylic acid, 5-(3-{[acetyl(4-chlorophenyl)amino]methyl}phenyl)-4-chloro-3-(carboxymethoxy)thiophene-2-carboxylic acid, 5-(3-{[acetyl(1,1'-biphenyl-4-yl)amino]methyl}phenyl)-4-chloro-3-(carboxymethoxy)thiophene-2-carboxylic acid, 5-(3-{[acetyl(4-phenoxyphenyl)amino]methyl}phenyl)-4-chloro-3-(carboxymethoxy)thiophene-2-carboxylic acid, 5-(3-{[acetyl(benzyl)amino]methyl}phenyl)-4-chloro-3-(carboxymethoxy)thiophene-2-carboxylic acid, 5-(3-{[acetyl(4-methoxybenzyl)amino]methyl}phenyl)-4-chloro-3-(carboxymethoxy)thiophene-2-carboxylic acid, 5-(3-{[acetyl(1,1'-biphenyl-4-ylmethyl)amino]methyl}phenyl)-4-chloro-3-(carboxymethoxy)thiophene-2-carboxylic acid, 5-(3-{[acetyl(4-chlorobenzyl)amino]methyl}phenyl)-4-chloro-3-(carboxymethoxy)thiophene-2-carboxylic acid, (carboxymethoxy)thiophene-2-carboxylic acid, 5-[3-({acetyl[4-(trifluoromethyl)benzyl]amino}methyl)phenyl]-4-chloro-3-(carboxymethoxy)thiophene-2-carboxylic acid, 5-[3-({acetyl[3,5-bis(trifluoromethyl)benzyl]amino}methyl)phenyl]-4-chloro-3-(carboxymethoxy)thiophene-2-carboxylic acid, 5-[3-({acetyl[2-(4-chlorophenyl)ethyl]amino}methyl)phenyl]-4-chloro-3-(carboxymethoxy)thiophene-2-carboxylic acid, 4-chloro-3-(carboxymethoxy)-5-[3-(cyclohexyl{[(2-thien-3-ylethyl)

amino]carbonyl}amino)phenyl]thiophene-2-carboxylic acid, 4-chloro-3-(carboxymethoxy)-5-(3-{cyclohexyl[(thien-3-ylamino)carbonyl]aminophenyl)thiophene-2-carboxylic acid, 4-chloro-3-(carboxymethoxy)-5-[3-(cyclohexyl{[(3,5-dimethylisoxazol-4-yl)amino]carbonyl}amino)phenyl]thiophene-2-carboxylic acid, 4-chloro-5-{3-[({[2-(5-bromo-2-methoxyphenyl)ethyl]amino}carbonyl)(cyclohexyl)amino]phenyl}-3-(carboxymethoxy)thiophene-2-carboxylic acid, 4-chloro-5-{3-[{[(2-carboxyethyl)amino]carbonyl}(cyclohexyl)amino}phenyl}-3-(carboxymethoxy)thiophene-2-carboxylic acid (non-preferred name), 4-chloro-3-(carboxymethoxy)-5-{3-[{[(4-carboxyphenyl)amino]carbonyl}(cyclohexyl)amino]phenyl}thiophene-2-carboxylic acid, 4-chloro-3-(carboxymethoxy)-5-{3-[{[(5-carboxypentyl)amino]carbonyl}(cyclohexyl)amino]phenyl}thiophene-2-carboxylic acid, 4-chloro-3-(carboxymethoxy)-5-{3-[{[(3-,5-{3-[[(benzylamino)carbonyl](ethyl)amino]phenyl}-4-chloro-3-(carboxymethoxy)thiophene-2-carboxylic acid, 5-(3-{[1-(benzylsulfonyl)piperidin-4-yl][(ethylamino)carbonyl]amino}phenyl)-4-chloro-3-(carboxymethoxy)thiophene-2-carboxylic acid, 5-{3-[(anilinocarbonyl)(cyclohexylmethyl)amino]phenyl}-4-chloro-3-(carboxymethoxy)thiophene-2-carboxylic acid, 5-{3-[[(benzylamino)carbonyl](cyclohexylmethyl)amino]phenyl}-4-chloro-3-(carboxymethoxy)thiophene-2-carboxylic acid, 4-chloro-3-(carboxymethoxy)-5-[3-((cyclohexylmethyl){[(4-ethylphenyl)amino]carbonyl}amino)phenyl]thiophene-2-carboxylic acid, 4-chloro-3-(carboxymethoxy)-5-[3-((cyclohexylmethyl){[(4-ethoxyphenyl)amino]carbonyl}amino)phenyl]thiophene-2-carboxylic acid, 4-chloro-3-(carboxymethoxy)-5-[3-((cyclohexylmethyl){[(4-phenoxyphenyl)amino]carbonyl}amino)phenyl]thiophene-2-carboxylic acid, 4-chloro-3-(carboxymethoxy)-5-[3-(cyclohexyl{[(3-methyl-5-phenylisoxazol-4-yl)amino]carbonyl}amino)phenyl]thiophene-2-carboxylic acid, 4,5-dibromo-3-[carboxy(fluoro)methoxy]thiophene-2-carboxylic acid, 4-chloro-3-(carboxymethoxy)-5-{3-[{[(2-cyanophenyl)amino]carbonyl}(cyclohexylmethyl)amino]phenyl}thiophene-2-carboxylic acid, 4-chloro-3-(carboxymethoxy)-5-(3-{(cyclohexylmethyl)[(thien-3-ylamino)carbonyl]amino}phenyl)thiophene-2-carboxylic acid, 4-chloro-3-(carboxymethoxy)-5-[3-((cyclohexylmethyl){[(5-methyl-3-phenylisoxazol-4-yl)amino]carbonyl}amino)phenyl]thiophene-2-carboxylic acid, 4-chloro-3-(carboxymethoxy)-5-[3-((cyclohexylmethyl){[(3,5-dimethylisoxazol-4-yl)amino]carbonyl}amino)phenyl]thiophene-2-carboxylic acid, 5-{3-[bis(cyclohexylmethyl)amino]phenyl})-4-chloro-3-(carboxymethoxy)thiophene-2-carboxylic acid, {[5-phenyl-2-(2H-tetrazol-5-yl)thien-3-yl]oxy}acetic acid, carboxyphenyl)amino]carbonyl}(cyclohexylmethyl)amino]phenyl}thiophene-2-carboxylic acid, 3-(carboxymethoxy)-4-methyl-5-(phenylethynyl)thiophene-2-carboxylic acid, 5-(3-{benzyl[(isopropylamino)carbonyl]aminophenyl)-4-chloro-3-(carboxymethoxy)thiophene-2-carboxylic acid, 4-chloro-3-(carboxymethoxy)-5-(3-{[(isopropylamino)carbonyl][4-(trifluoromethyl)benzyl]amino}phenyl)thiophene-2-carboxylic acid, 4-chloro-5-(3-{(4-tert-butylbenzyl)[(isopropylamino)carbonyl]amino}phenyl)-3-(carboxymethoxy)thiophene-2-carboxylic acid, 4-chloro-3-(carboxymethoxy)-5-(3-{isopropyl[(isopropylamino)carbonyl]amino}phenyl)thiophene-2-carboxylic acid, 5-{3-[acetyl(cyclohexyl)amino]phenyl})4-chloro-3-(carboxymethoxy)thiophene-2-carboxylic acid, and 5-{3-[benzoyl(cyclohexyl)amino]phenyl}-4-chloro-3-(carboxymethoxy)thiophene-2-carboxylic acid.

In some embodiments, the compound can be selected from 3-carboxymethoxy-4-phenyl-thiophene-2-carboxylic acid, 3-carboxymethoxy-4-(3-trifluoromethyl-phenyl)-thiophene-2-carboxylic acid, 3-carboxymethoxy-4-(1H-indol-5-yl)-thiophene-2-carboxylic acid, 4-carboxymethoxy-[3,3']bithiophenyl-5-carboxylic acid, 4-methyl-3-carboxymethoxy-5-phenyl-thiophene-2-carboxylic acid, 5-(4-amino-phenyl)-4-methyl-3-carboxymethoxy-thiophene-2-carboxylic acid, 4-methyl-3-carboxymethoxy-5-(4-dimethylamino-phenyl)-thiophene-2-carboxylic acid, 5-(3-amino-phenyl)-4-methyl-3-carboxymethoxy-thiophene-2-carboxylic acid, 4-methyl-3-carboxymethoxy-5-naphthalen-2-yl-thiophene-2-carboxylic acid, 4-methyl-3-carboxymethoxy-5-(4-hydroxy-phenyl)-thiophene-2-carboxylic acid, 4-methyl-3-carboxymethoxy-5-(4-methoxy-phenyl)-thiophene-2-carboxylic acid, 3-carboxymethoxy-5-(4-trifluoromethoxy-phenyl)-thiophene-2-carboxylic acid, 4-methyl-3-carboxymethoxy-5-(4-hydroxymethyl-phenyl)-thiophene-2-carboxylic acid, 4-methyl-3-carboxymethoxy-5-(3-hydroxy-phenyl)-thiophene-2-carboxylic acid, 3-ethoxycarbonylmethoxy-4,5-bis-(3-hydroxy-phenyl)-thiophene-2-carboxylic acid methyl ester, 4-methyl-3-carboxymethoxy-5-(3-methoxy-phenyl)-thiophene-2-carboxylic acid, 4-methyl-3-carboxymethoxy-5-(4-fluoro-phenyl)-thiophene-2-carboxylic acid, 3-carboxymethoxy-5-o-tolyl-thiophene-2-carboxylic acid, 5-(4-acetylamino-phenyl)-4-methyl-3-carboxymethoxy-thiophene-2-carboxylic acid, 5-(4-benzoylamino-phenyl)-4-methyl-3-carboxymethoxy-thiophene-2-carboxylic acid, 4-methyl-3-carboxymethoxy-5-{4-[(pyridine-3-carbonyl)-amino]-phenyl}-thiophene-2-carboxylic acid, 4-methyl-3-carboxymethoxy-5-{4-[(furan-3-carbonyl)-amino]-phenyl}-thiophene-2-carboxylic acid, 4-methyl-3-carboxymethoxy-5-{4-[(furan-2-carbonyl)-amino]-phenyl}-thiophene-2-carboxylic acid, 4-[4-(3-bromo-5-carboxy-4-carboxymethoxy-thiophen-2-yl)-phenylcarbamoyl]-piperidine-1-carboxylic acid tert-butyl ester, 3-[4-(3-bromo-5-carboxy-4-carboxymethoxy-thiophen-2-yl)-phenylcarbamoyl]-piperidine-1-carboxylic acid tert-butyl ester, 4-methyl-3-carboxymethoxy-5-(4-methoxycarbonylamino-phenyl)-thiophene-2-carboxylic acid, 4-methyl-3-carboxymethoxy-5-[4-(3-isopropyl-ureido)-phenyl]-thiophene-2-carboxylic acid, 5-[4-(2-benzyloxy-acetylamino)-phenyl]-4-methyl-3-carboxymethoxy-thiophene-2-carboxylic acid, 4-methyl-5-[4-(2-tert-butoxycarbonylamino-acetylamino)-phenyl]-3-carboxymethoxy-thiophene-2-carboxylic acid, 5-[4-(2-amino-acetylamino)-phenyl]-4-methyl-3-carboxymethoxy-thiophene-2-carboxylic acid, 4-methyl-3-carboxymethoxy-5-[4-(oxalyl-amino)-phenyl]-thiophene-2-carboxylic acid, 4-methyl-5-[4-(2-carboxy-acetylamino)-phenyl]-3-carboxymethoxy-thiophene-2-carboxylic acid, 4-methyl-3-carboxymethoxy-5-(4-methanesulfonylamino-phenyl)-thiophene-2-carboxylic acid, 5-(4-benzenesulfonylamino-phenyl)-4-methyl-3-carboxymethoxy-thiophene-2-carboxylic acid, 4-methyl-3-carboxymethoxy-5-[4-(4-trifluoromethyl-benzenesulfonylamino)-phenyl]-thiophene-2-carboxylic acid, 4-methyl-3-carboxymethoxy-5-{4-[methyl-(4-trifluoromethyl-benzenesulfonyl)-amino]-phenyl}-thiophene-2-carboxylic acid, 4-methyl-3-carboxymethoxy-5-[4-(3-trifluoromethyl-benzenesulfonylamino)-phenyl]-thiophene-2-carboxylic acid, 4-methyl-3-carboxymethoxy-5-[4-(2-trifluoromethyl-benzenesulfonylamino)-phenyl]-thiophene-2-carboxylic acid, 4-methyl-3-carboxymethoxy-5-[4-(2,6-dichloro-benzenesulfonylamino)-phenyl]-thiophene-2-carboxylic acid, 4-methyl-3-carboxymethoxy-5-[4-(2,6-difluoro-benzenesulfonylamino)-phenyl]-thiophene-2-carboxylic acid, 4-methyl-3-carboxymethoxy-5-[4-(3,3,5,5-tetramethyl-cyclohexylamino)-phenyl]-thiophene-2-carboxylic acid, 3-carboxymethoxy-5-[4-(3,3,5,5-tetramethyl-cyclohexylamino)-phenyl]-thiophene-2-carboxylic acid, 5-[4-(benzenesulfonylamino-methyl)-phenyl]-4-methyl-3-carboxymethoxy-thiophene-2-carboxylic acid, 4-methyl-5-[4-(tert-butoxycarbonylamino-methyl)-phenyl]-3-carboxymethoxy-thiophene-2-carboxylic acid, 4-methyl-3-carboxymethoxy-5-[4-(ethanesulfonylamino-methyl)-phenyl]-thiophene-2-carboxylic acid, 5-[4-(acetylamino-methyl)-phenyl]-4-methyl-3-carboxymethoxy-thiophene-2-carboxylic acid, 4-methyl-3-carboxymethoxy-5-[4-(ethoxycarbonylamino-methyl)-phenyl]-thiophene-2-carboxylic acid, 4-methyl-3-carboxymethoxy-5-[4-(3-isopropyl-ureidomethyl)-phenyl]-thiophene-2-carboxylic acid, 5-(4-aminomethyl-phenyl)-4-methyl-3-carboxymethoxy-thiophene-2-carboxylic acid trifluoroacetic acid, 4-methyl-3-carboxymethoxy-5-(4-phenylcarbamoyl-phenyl)-thiophene-2-carboxylic acid, 4-methyl-3-carboxymethoxy-5-(4-formyl-phenyl)-thiophene-2-carboxylic acid, 4-methyl-3-carboxymethoxy-5-(4-isopropylcarbamoyl-phenyl)-thiophene-2-carboxylic acid, 4-methyl-5-[4-(1-carbamoyl-ethylcarbamoyl)-phenyl]-3-carboxymethoxy-thiophene-2-carboxylic acid, 4-methyl-3-carboxymethoxy-5-[4-(4-trifluoromethyl-phenylcarbamoyl)-phenyl]-thiophene-2-carboxylic acid, 4-methyl-3-carboxymethoxy-5-(3-propionylamino-phenyl)-thiophene-2-carboxylic acid, 4-methyl-5-(3-butyrylamino-phenyl)-3-carboxymethoxy-thiophene-2-carboxylic acid, 4-methyl-5-(3-butyrylamino-phenyl)-3-carboxymethoxy-thiophene-2-carboxylic acid, 4-methyl-3-carboxymethoxy-5-[3-(cyclohexanecarbonyl-amino)-phenyl]-thiophene-2-carboxylic acid, 4-methyl-3-carboxymethoxy-5-(3-hexanoylamino-phenyl)-thiophene-2-carboxylic acid, 4-methyl-3-carboxymethoxy-5-[3-(cyclopentanecarbonyl-amino)-phenyl]-thiophene-2-carboxylic acid, 4-[3-(3-bromo-5-carboxy-4-carboxymethoxy-thiophen-2-yl)-phenylcarbamoyl]-piperidine-1-carboxylic acid tert-butyl ester, 3-[3-(3-bromo-5-carboxy-4-carboxymethoxy-thiophen-2-yl)-phenylcarbamoyl]-piperidine-1-carboxylic acid tert-butyl ester, 4-methyl-3-carboxymethoxy-5-[3-(3,3,3-trifluoro-propionylamino)-phenyl]-thiophene-2-carboxylic acid, 5-(3-benzoylamino-phenyl)-4-methyl-3-carboxymethoxy-thiophene-2-carboxylic acid, 4-methyl-3-carboxymethoxy-5-{3-[(furan-2-carbonyl)-amino]-phenyl}-thiophene-2-carboxylic acid, 4-methyl-3-carboxymethoxy-5-{3-[(furan-3-carbonyl)-amino]-phenyl}-thiophene-2-carboxylic acid, 4-methyl-3-carboxymethoxy-5-[3-(2-trifluoromethyl-benzoylamino)-phenyl]-thiophene-2-carboxylic acid, 4-methyl-3-carboxymethoxy-5-[3-(2-fluoro-benzoylamino)-phenyl]-thiophene-2-carboxylic acid, 4-methyl-3-carboxymethoxy-5-[3-(3-fluoro-benzoylamino)-phenyl]-thiophene-2-carboxylic acid, 4-methyl-3-carboxymethoxy-5-{3-[(pyridine-3-carbonyl)-amino]-phenyl}-thiophene-2-carboxylic acid, 4-methyl-3-carboxymethoxy-5-[3-(4,4,4-trifluoro-butyrylamino)-phenyl]-thiophene-2-carboxylic acid, 4-methyl-3-carboxymethoxy-5-{3-[(2-hydroxy-pyridine-3-carbonyl)-amino]-phenyl}-thiophene-2-carboxylic acid, 4-methyl-3-carboxymethoxy-5-{3-[(pyridine-4-carbonyl)-amino]-phenyl}-thiophene-2-carboxylic acid, 4-methyl-3-carboxymethoxy-5-{3-[(quinoline-3-carbonyl)-amino]-phenyl}-thiophene-2-carboxylic acid, 4-methyl-3-carboxymethoxy-5-{3-[(pyridine-2-carbonyl)-amino]-phenyl}-thiophene-2-carboxylic acid, 4-methyl-3-carboxymethoxy-5-{3-[(1-oxy-pyridine-3-carbonyl)-amino]-phenyl}-thiophene-2-carboxylic acid, 4-methyl-3-carboxymethoxy-5-[3-(2-pyridin-2-yl-acetylamino)-phenyl]-thiophene-2-carboxylic acid, 4-methyl-3-carboxymethoxy-5-[3-(2-pyridin-3-yl-acetylamino)-phenyl]-thiophene-2-carboxylic acid, 4-methyl-3-carboxymethoxy-5-{3-[(pyrazine-2-carbonyl)-amino]-phenyl}-thiophene-2-carboxylic acid, 4-methyl-3-carboxymethoxy-5-[3-(2-pyridin-4-yl-acetylamino)-phenyl]-thiophene-2-carboxylic acid, 4-methyl-3-carboxymethoxy-5-{3-[(piperidine-4-carbonyl)-amino]-phenyl}-thiophene-2-carboxylic acid trifluoroacetic acid salt, 4-methyl-3-carboxymethoxy-5-[3-(cyclohexanecarbonyl-amino)-phenyl]-thiophene-2-carboxylic acid, 5-(3-acetylamino-phenyl)-4-methyl-3-carboxymethoxy-thiophene-2-carboxylic acid, 4-methyl-3-carboxymethoxy-5-(3-isobutyrylamino-phenyl)-thiophene-2-carboxylic acid, 4-methyl-3-carboxymethoxy-5-[3-(2,2,2-trifluoro-ethanesulfonylamino)-phenyl]-thiophene-2-carboxylic acid, 5-(3-benzenesulfonylamino-phenyl)-4-methyl-3-carboxymethoxy-thiophene-2-carboxylic acid, 4-methyl-3-carboxymethoxy-5-(3-ethanesulfonylamino-phenyl)-thiophene-2-carboxylic acid, 4-methyl-3-carboxymethoxy-5-(3-phenylmethanesulfonylamino-phenyl)-thiophene-2-carboxylic acid, 4-methyl-3-carboxymethoxy-5-[3-(4-trifluoromethyl-benzenesulfonylamino)-phenyl]-thiophene-2-carboxylic acid, 4-methyl-3-carboxymethoxy-5-[3-(4-trifluoromethoxy-benzenesulfonylamino)-phenyl]-thiophene-2-carboxylic acid, 4-methyl-3-carboxymethoxy-5-[3-(3-trifluoromethyl-benzenesulfonylamino)-phenyl]-thiophene-2-carboxylic acid, 4-methyl-3-carboxymethoxy-5-[3-(2-trifluoromethyl-benzenesulfonylamino)-phenyl]-thiophene-2-carboxylic acid, 4-methyl-3-carboxymethoxy-5-[3-(2-cyano-benzenesulfonylamino)-phenyl]-thiophene-2-carboxylic acid, 4-methyl-3-carboxymethoxy-5-[3-(4-methoxy-benzenesulfonylamino)-phenyl]-thiophene-2-carboxylic acid, 4-methyl-3-carboxymethoxy-5-[3-(4-cyano-benzenesulfonylamino)-phenyl]-thiophene-2-carboxylic acid, 4-methyl-3-carboxymethoxy-5-[3-(4-fluoro-benzenesulfonylamino)-phenyl]-thiophene-2-carboxylic acid, 4-methyl-3-carboxymethoxy-5-(3-methoxycarbonylamino-phenyl)-thiophene-2-carboxylic acid, 4-methyl-3-carboxymethoxy-5-[3-(3-isopropyl-ureido)-phenyl]-thiophene-2-carboxylic acid, 4-methyl-3-carboxymethoxy-5-[3-(3,3-diethyl-ureido)-phenyl]-thiophene-2-carboxylic acid, 5-(3-benzylamino-phenyl)-4-methyl-3-carboxymethoxy-thiophene-2-carboxylic acid, 4-methyl-3-carboxymethoxy-5-[3-(3-trifluoromethyl-benzylamino)-phenyl]-thiophene-2-carboxylic acid, 4-methyl-3-carboxymethoxy-5-[3-(2-trifluoromethyl-benzylamino)-phenyl]-thiophene-2-carboxylic acid, 4-methyl-3-carboxymethoxy-5-{3-[(furan-2-ylmethyl)-amino]-phenyl}-thiophene-2-carboxylic acid, 4-methyl-3-carboxymethoxy-5-{3-[(furan-3-ylmethyl)-amino]-phenyl}-thiophene-2-carboxylic acid, 4-methyl-3-carboxymethoxy-5-[3-(3-fluoro-benzylamino)-phenyl]-thiophene-2-carboxylic acid, 4-methyl-3-carboxymethoxy-5-[3-(3-cyano-benzylamino)-phenyl]-thiophene-2-carboxylic acid, 4-methyl-3-carboxymethoxy-5-{3-[(pyridin-3-ylmethyl)-amino]-phenyl}-thiophene-2-carboxylic acid, 4-methyl-3-carboxymethoxy-5-[3-(4-fluoro-benzylamino)-phenyl]-thiophene-2-carboxylic acid, 4-methyl-3-carboxymethoxy-5-[3-(4-trifluoromethyl-benzylamino)-phenyl]-thiophene-2-carboxylic acid, 4-methyl-3-carboxymethoxy-5-[3-(4-methoxy-benzylamino)-phenyl]-thiophene-2-carboxylic acid, 5-[3-(4-benzyloxy-benzylamino)-phenyl]-4-methyl-3-carboxymethoxy-thiophene-2-carboxylic acid, 4-methyl-3-carboxymethoxy-5-[3-(4-phenoxy-benzylamino)-phenyl]-thiophene-2-carboxylic acid, 4-methyl-3-carboxymethoxy-5-{3-

[(naphthalen-2-ylmethyl)-amino]-phenyl}-thiophene-2-carboxylic acid, 4-methyl-5-[3-(3-carboxy-benzylamino)-phenyl]-3-carboxymethoxy-thiophene-2-carboxylic acid, 4-methyl-3-carboxymethoxy-5-[3-(3-trifluoromethoxy-benzylamino)-phenyl]-thiophene-2-carboxylic acid, 4-methyl-3-carboxymethoxy-5-[3-(2-trifluoromethoxy-benzylamino)-phenyl]-thiophene-2-carboxylic acid, 4-methyl-3-carboxymethoxy-5-[3-(2-hydroxy-benzylamino)-phenyl]-thiophene-2-carboxylic acid, 4-methyl-3-carboxymethoxy-5-[3-(4-methyl-benzylamino)-phenyl]-thiophene-2-carboxylic acid, 4-methyl-3-carboxymethoxy-5-[3-(4-chloro-benzylamino)-phenyl]-thiophene-2-carboxylic acid, 4-methyl-3-carboxymethoxy-5-[3-(4-isopropyl-benzylamino)-phenyl]-thiophene-2-carboxylic acid, 4-methyl-3-carboxymethoxy-5-[3-(3-nitro-benzylamino)-phenyl]-thiophene-2-carboxylic acid, 4-methyl-3-carboxymethoxy-5-[3-(3-methanesulfonylamino-benzylamino)-phenyl]-thiophene-2-carboxylic acid, 5-[3-(3-amino-benzylamino)-phenyl]-4-methyl-3-carboxymethoxy-thiophene-2-carboxylic acid, 5-[3-(3-acetylamino-benzylamino)-phenyl]-4-methyl-3-carboxymethoxy-thiophene-2-carboxylic acid, 4-methyl-3-carboxymethoxy-5-(3-cyclohexylamino-phenyl)-thiophene-2-carboxylic acid, 4-methyl-3-carboxymethoxy-5-(3-cyclopentylamino-phenyl)-thiophene-2-carboxylic acid, 5-[3-(1-acetyl-piperidin-4-ylamino)-phenyl]-4-methyl-3-carboxymethoxy-thiophene-2-carboxylic acid, 4-methyl-3-carboxymethoxy-5-(3-cycloheptylamino-phenyl)-thiophene-2-carboxylic acid, 5-[3-(bicyclo[3.3.1]non-9-ylamino)-phenyl]-4-methyl-3-carboxymethoxy-thiophene-2-carboxylic acid, 4-methyl-3-carboxymethoxy-5-[3-(4-ethyl-cyclohexylamino)-phenyl]-thiophene-2-carboxylic acid, 4-methyl-3-carboxymethoxy-5-[3-cis(4-phenyl-cyclohexylamino)-phenyl]-thiophene-2-carboxylic acid, 4-methyl-3-carboxymethoxy-5-[3-trans(4-phenyl-cyclohexylamino)-phenyl]-thiophene-2-carboxylic acid, 4-methyl-3-carboxymethoxy-5-[3-(1-cyclohexyl-ethylamino)-phenyl]-thiophene-2-carboxylic acid, 4-methyl-3-carboxymethoxy-5-[3-(3,3,5,5-tetramethyl-cyclohexylamino)-phenyl]-thiophene-2-carboxylic acid, 5-[3-(adamantan-2-ylamino)-phenyl]-4-methyl-3-carboxymethoxy-thiophene-2-carboxylic acid, 4-methyl-3-carboxymethoxy-5-[3-(tetrahydro-pyran-4-ylamino)-phenyl]-thiophene-2-carboxylic acid, 4-methyl-3-carboxymethoxy-5-[3-(cyclohexylmethyl-amino)-phenyl]-thiophene-2-carboxylic acid, 4-methyl-3-carboxymethoxy-5-[3-(1-methanesulfonyl-piperidin-4-ylamino)-phenyl]-thiophene-2-carboxylic acid, 4-methyl-3-carboxymethoxy-5-[3-(1-phenylmethanesulfonyl-piperidin-4-ylamino)-phenyl]-thiophene-2-carboxylic acid, 4-methyl-3-carboxymethoxy-5-[3-(1-ethanesulfonyl-piperidin-4-ylamino)-phenyl]-thiophene-2-carboxylic acid, 4-methyl-5-{3-[1-(butane-1-sulfonyl)-piperidin-4-ylamino]-phenyl}-3-carboxymethoxy-thiophene-2-carboxylic acid, 5-{3-[1-(3,5-bis-trifluoromethyl-phenylmethanesulfonyl)-piperidin-4-ylamino]-phenyl}-4-methyl-3-carboxymethoxy-thiophene-2-carboxylic acid, 4-methyl-3-carboxymethoxy-5-{3-[1-(propane-1-sulfonyl)-piperidin-4-ylamino]-phenyl}-thiophene-2-carboxylic acid, 4-methyl-3-carboxymethoxy-5-{3-[1-(trifluoromethyl-phenylmethanesulfonyl)-piperidin-4-ylamino]-phenyl}-thiophene-2-carboxylic acid, 4-methyl-3-carboxymethoxy-5-{3-[1-(4-fluoro-phenyl-methanesulfonyl)-piperidin-4-ylamino]-phenyl}-thiophene-2-carboxylic acid, 4-methyl-3-carboxymethoxy-5-{3-[1-(4-trifluoromethyl-phenylmethanesulfonyl)-piperidin-4-ylamino]-phenyl}-thiophene-2-carboxylic acid, 4-methyl-3-carboxymethoxy-5-{3-[1-(naphthalene-1-sulfonyl)-piperidin-4-ylamino]-phenyl}-thiophene-2-carboxylic acid, 4-methyl-3-carboxymethoxy-5-{3-[1-(naphthalene-2-sulfonyl)-piperidin-4-ylamino]-phenyl}-thiophene-2-carboxylic acid, 4-methyl-3-carboxymethoxy-5-{3-[1-(2-nitro-phenyl-methanesulfonyl)-piperidin-4-ylamino]-phenyl}-thiophene-2-carboxylic acid, 4-methyl-3-carboxymethoxy-5-{3-[1-(4-chloro-phenylmethanesulfonyl)-piperidin-4-ylamino]-phenyl}-thiophene-2-carboxylic acid, 4-methyl-3-carboxymethoxy-5-{3-[1-(3,5-dichloro-phenylmethanesulfonyl)-piperidin-4-ylamino]-phenyl}-thiophene-2-carboxylic acid, 4-methyl-3-carboxymethoxy-5-{3-[1-(3,4-dichloro-phenylmethanesulfonyl)-piperidin-4-ylamino]-phenyl}-thiophene-2-carboxylic acid, 4-methyl-3-carboxymethoxy-5-{3-[1-(3-nitro-phenylmethanesulfonyl)-piperidin-4-ylamino]-phenyl}-thiophene-2-carboxylic acid, 4-methyl-3-carboxymethoxy-5-{3-[1-(3-chloro-phenyl-methanesulfonyl)-piperidin-4-ylamino]-phenyl}-thiophene-2-carboxylic acid, 4-methyl-3-carboxymethoxy-5-{3-[1-(2-phenyl-ethanesulfonyl)-piperidin-4-ylamino]-phenyl}-thiophene-2-carboxylic acid, 4-methyl-3-carboxymethoxy-5-[3-(1-o-tolylmethanesulfonyl-piperidin-4-ylamino)-phenyl]-thiophene-2-carboxylic acid, 4-methyl-3-carboxymethoxy-5-[3-(1-m-tolylmethanesulfonyl-piperidin-4-ylamino)-phenyl]-thiophene-2-carboxylic acid, 4-methyl-3-carboxymethoxy-5-{3-[1-(2,6-dimethyl-phenyl-methanesulfonyl)-piperidin-4-ylamino]-phenyl}-thiophene-2-carboxylic acid, 4-methyl-3-carboxymethoxy-5-{3-[1-(2-imidazol-1-yl-ethanesulfonyl)-piperidin-4-ylamino]-phenyl}-thiophene-2-carboxylic acid, 4-methyl-3-carboxymethoxy-5-{3-[1-(2-pyrazol-1-yl-ethanesulfonyl)-piperidin-4-ylamino]-phenyl}-thiophene-2-carboxylic acid, 4-methyl-3-carboxymethoxy-5-{3-[1-(2-isopropoxy-ethanesulfonyl)-piperidin-4-ylamino]-phenyl}-thiophene-2-carboxylic acid, 5-{3-[1-(2-amino-phenylmethanesulfonyl)-piperidin-4-ylamino]-phenyl}-4-methyl-3-carboxymethoxy-thiophene-2-carboxylic acid, 4-[3-(3-bromo-5-carboxy-4-carboxymethoxy-thiophen-2-yl)-phenylamino]-piperidine-1-carboxylic acid methyl ester, 5-[3-(1-benzoyl-piperidin-4-ylamino)-phenyl]-4-methyl-3-carboxymethoxy-thiophene-2-carboxylic acid, 4-methyl-3-carboxymethoxy-5-[3-(1-phenylacetyl-piperidin-4-ylamino)-phenyl]-thiophene-2-carboxylic acid, 5-{3-[3-benzyl-1-(1-benzylcarbamoyl-piperidin-4-yl)-ureido]-phenyl}-4-methyl-3-carboxymethoxy-thiophene-2-carboxylic acid, 5-[3-(1-benzylcarbamoyl-piperidin-4-ylamino)-phenyl]-4-methyl-3-carboxymethoxy-thiophene-2-carboxylic acid, 4-methyl-3-carboxymethoxy-5-{3-[(1-methanesulfonyl-piperidin-4-ylmethyl)-amino]-phenyl}-thiophene-2-carboxylic acid, 4-methyl-3-carboxymethoxy-5-{3-[(1-ethanesulfonyl-piperidin-4-ylmethyl)-amino]-phenyl}-thiophene-2-carboxylic acid, 5-{3-[(1-benzenesulfonyl-piperidin-4-ylmethyl)-amino]-phenyl}4-methyl-3-carboxymethoxy-thiophene-2-carboxylic acid, 4-methyl-3-carboxymethoxy-5-{3-[(1-phenylmethanesulfonyl-piperidin-4-ylmethyl)-amino]-phenyl}-thiophene-2-carboxylic acid, 5-(3-{[1-(2-amino-phenylmethanesulfonyl)-piperidin-4-ylmethyl]-amino}-phenyl)-4-methyl-3-carboxymethoxy-thiophene-2-carboxylic acid, 4-{[3-(3-bromo-5-carboxy-4-carboxymethoxy-thiophen-2-yl)-phenylamino]-methyl}-piperidine-1-carboxylic acid methyl ester, 4-methyl-3-carboxymethoxy-5-{3-[(1-phenylcarbamoyl-piperidin-4-ylmethyl)-amino]-phenyl}-thiophene-2-carboxylic acid, 5-{3-[(1-benzylcarbamoyl-piperidin-4-ylmethyl)-amino]-phenyl}-4-methyl-3-carboxymethoxy-thiophene-2-carboxylic acid, 4-methyl-3-carboxymethoxy-5-{3-[(1-cyclohexylcarbamoyl-piperidin-4-ylmethyl)-amino]-phenyl}-thiophene-2-carboxylic acid, 4-methyl-3- carboxymethoxy-5-(3-{[1-(4-methoxy-phenylcarbamoyl)-piperidin-4-ylmethyl]-amino}-phenyl)-thiophene-2-carboxylic acid, 4-methyl-3-carboxymethoxy-5-(3-{[1-(4-cyano-phenylcarbamoyl)-piperidin-4-ylmethyl]-amino}-phenyl)-thiophene-2-carboxylic acid, 4-methyl-3-carboxymethoxy-5-{3-[(1-p-tolylcarbamoyl-piperidin-4-ylmethyl)-amino]-phenyl}-thiophene-2-carboxylic acid, 4-methyl-3-carboxymethoxy-5-(3-{[1-(3-methoxy-phenylcarbamoyl)-piperidin-4-ylmethyl]-amino}-phenyl)-thiophene-2-carboxylic acid, 4-methyl-3-carboxymethoxy-5-(3-{[1-(2-methoxy-phenylcarbamoyl)-piperidin-4-ylmethyl]-amino}-phenyl)-thiophene-2-carboxylic acid, 4-methyl-3-carboxymethoxy-5-(3-{[1-(3-chloro-phenylcarbamoyl)-piperidin-4-ylmethyl]-amino}-phenyl)-thiophene-2-carboxylic acid, 4-methyl-3-carboxymethoxy-5-(3-{[1-(2-chloro-phenylcarbamoyl)-piperidin-4-ylmethyl]-amino}-phenyl)-thiophene-2-carboxylic acid, 4-methyl-3-carboxymethoxy-5-{3-[(1-m-tolylcarbamoyl-piperidin-4-ylmethyl)-amino]-phenyl}-thiophene-2-carboxylic acid, 4-methyl-3-carboxymethoxy-5-{3-[(1-o-tolylcarbamoyl-piperidin-4-ylmethyl)-amino]-phenyl}-thiophene-2-carboxylic acid, 4-methyl-3-carboxymethoxy-5-(3-{[1-(2,6-dimethyl-phenylcarbamoyl)-piperidin-4-ylmethyl]-amino}-phenyl)-thiophene-2-carboxylic acid, 4-methyl-3-carboxymethoxy-5-(3-{[1-(2-trifluoromethyl-phenylcarbamoyl)-piperidin-4-ylmethyl]-amino}-phenyl)-thiophene-2-carboxylic acid, 4-methyl-3-carboxymethoxy-5-(3-{[1-(methyl-phenyl-carbamoyl)-piperidin-4-ylmethyl]-amino}-phenyl)-thiophene-2-carboxylic acid, 4-methyl-3-carboxymethoxy-5-(3-{[1-(2-methylsulfanyl-phenylcarbamoyl)-piperidin-4-ylmethyl]-amino}-phenyl)-thiophene-2-carboxylic acid, 4-methyl-3-carboxymethoxy-5-(3-{[1-(2,3-dimethyl-phenylcarbamoyl)-piperidin-4-ylmethyl]-amino}-phenyl)-thiophene-2-carboxylic acid, 4-{[3-(3-bromo-5-carboxy-4-carboxymethoxy-thiophen-2-yl)-phenylamino]-methyl}-piperidine-1-carboxylic acid tert-butyl ester, 4-methyl-3-carboxymethoxy-5-(3-cyclohexylmethoxy-phenyl)-thiophene-2-carboxylic acid, 5-[3-(3,5-bis-trifluoromethyl-benzyloxy)-phenyl]-4-methyl-3-carboxymethoxy-thiophene-2-carboxylic acid, 5-(3-benzyloxy-phenyl)-4-methyl-3-carboxymethoxy-thiophene-2-carboxylic acid, 4-methyl-3-carboxymethoxy-5-[3-(1-phenyl-ethoxy)-phenyl]-thiophene-2-carboxylic acid, 4-methyl-5-[3-(1-carboxy-ethoxy)-phenyl]-3-carboxymethoxy-thiophene-2-carboxylic acid, 4-methyl-3-carboxymethoxy-5-[3-(naphthalen-2-ylmethoxy)-phenyl]-thiophene-2-carboxylic acid, 4-methyl-3-carboxymethoxy-5-[3-(3-methyl-3,3a-dihydro-benzo[1,2,5]oxadiazol-5-ylmethoxy)-phenyl]-thiophene-2-carboxylic acid, 4-methyl-5-[3-(3-carboxy-benzyloxy)-phenyl]-3-carboxymethoxy-thiophene-2-carboxylic acid, 4-methyl-3-carboxymethoxy-5-[3-(3-trifluoromethoxy-benzyloxy)-phenyl]-thiophene-2-carboxylic acid, 4-[3-(3-bromo-5-carboxy-4-carboxymethoxy-thiophen-2-yl)-phenoxy]-piperidine-1-carboxylic acid tert-butyl ester, 4-methyl-3-carboxymethoxy-5-[3-(1-phenylcarbamoyl-piperidin-4-yloxy)-phenyl]-thiophene-2-carboxylic acid, 4-[3-(3-bromo-5-carboxy-4-carboxymethoxy-thiophen-2-yl)-phenoxy]-piperidine-1-carboxylic acid phenyl ester, 4-methyl-3-carboxymethoxy-5-[3-(1-phenylmethanesulfonyl-piperidin-4-yloxy)-phenyl]-thiophene-2-carboxylic acid, 4-[3-(3-bromo-5-carboxy-4-carboxymethoxy-thiophen-2-yl)-phenoxymethyl]-piperidine-1-carboxylic acid tert-butyl ester, 4-methyl-3-carboxymethoxy-5-[3-(1-methanesulfonyl-piperidin-4-ylmethoxy)-phenyl]-thiophene-2-carboxylic acid, 4-methyl-3-carboxymethoxy-5-[3-(1-phenyl-methanesulfonyl-piperidin-4-ylmethoxy)-phenyl]-thiophene-2-carboxylic acid, 4-methyl-3-carboxymethoxy-5-{3-[1-(toluene-4-sulfonyl)-piperidin-4-ylmethoxy]-phenyl}-thiophene-2-carboxylic acid, 5-[3-(1-benzenesulfonyl-piperidin-4-ylmethoxy)-phenyl]-4-methyl-3-carboxymethoxy-thiophene-2-carboxylic acid, 4-[3-(3-bromo-5-carboxy-4-carboxymethoxy-thiophen-2-yl)-phenoxymethyl]-piperidine-1-carboxylic acid phenyl ester, 4-[3-(3-bromo-5-carboxy-4-carboxymethoxy-thiophen-2-yl)-phenoxymethyl]-piperidine-1-carboxylic acid methyl ester, 4-methyl-3-carboxymethoxy-5-[3-(1-ethylcarbamoyl-piperidin-4-ylmethoxy)-phenyl]-thiophene-2-carboxylic acid, 4-methyl-3-carboxymethoxy-5-[3-(1-phenylcarbamoyl-piperidin-4-ylmethoxy)-phenyl]-thiophene-2-carboxylic acid, 4-methyl-3-carboxymethoxy-5-{3-[1-(2-chloro-phenylcarbamoyl)-piperidin-4-ylmethoxy]-phenyl}-thiophene-2-carboxylic acid, 4-methyl-3-carboxymethoxy-5-[3-(1-o-tolylcarbamoyl-piperidin-4-ylmethoxy)-phenyl]-thiophene-2-carboxylic acid, 4-methyl-3-carboxymethoxy-5-{3-[1-(2-methoxy-phenylcarbamoyl)-piperidin-4-ylmethoxy]-phenyl}-thiophene-2-carboxylic acid, 4-methyl-3-carboxymethoxy-5-{3-[1-(2-isopropyl-phenylcarbamoyl)-piperidin-4-ylmethoxy]-phenyl}-thiophene-2-carboxylic acid, 4-methyl-3-carboxymethoxy-5-{3-[1-(2-phenoxy-phenylcarbamoyl)-piperidin-4-ylmethoxy]-phenyl}-thiophene-2-carboxylic acid, 4-methyl-3-carboxymethoxy-5-{3-[1-(2,6-diethyl-phenylcarbamoyl)-piperidin-4-ylmethoxy]-phenyl}-t, 4-methyl-3-carboxymethoxy-5-{3-[1-(2,4,6-trimethyl-phenylcarbamoyl)-piperidin-4-ylmethoxy]-phenyl}-thiophene-2-carboxylic acid, 4-methyl-3-carboxymethoxy-5-{3-[1-(2-isopropyl-6-methyl-phenylcarbamoyl)-piperidin-4-ylmethoxy]-phenyl}-thiophene-2-carboxylic acid, 4-methyl-3-carboxymethoxy-5-{3-[1-(3-phenoxy-phenylcarbamoyl)-piperidin-4-ylmethoxy]-phenyl}-thiophene-2-carboxylic acid, 4-methyl-3-carboxymethoxy-5-{3-[1-(2,6-dimethyl-phenylcarbamoyl)-piperidin-4-ylmethoxy]-phenyl}-thiophene-2-carboxylic acid, 4-methyl-3-carboxymethoxy-5-{3-[1-(4-methyl-2-nitro-phenylcarbamoyl)-piperidin-4-ylmethoxy]-phenyl}-thiophene-2-carboxylic acid, 4-methyl-3-carboxymethoxy-5-{3-[1-(5-chloro-2-nitro-phenylcarbamoyl)-piperidin-4-ylmethoxy]-phenyl}-thiophene-2-carboxylic acid, 4-methyl-3-carboxymethoxy-5-{3-[1-(2-nitro-phenylcarbamoyl)-piperidin-4-ylmethoxy]-phenyl}-thiophene-2-carboxylic acid, 4-methyl-3-carboxymethoxy-5-(3-phenylaminomethyl-phenyl)-thiophene-2-carboxylic acid, 4-methyl-3-carboxymethoxy-5-{3-[(3-trifluoromethyl-phenylamino)-methyl]-phenyl}-thiophene-2-carboxylic acid, 4-methyl-3-carboxymethoxy-5-{3-[(3,4-difluoro-phenylamino)-methyl]-phenyl}-thiophene-2-carboxylic acid, 4-methyl-3-carboxymethoxy-5-(3-cyclohexylaminomethyl-phenyl)-thiophene-2-carboxylic acid, 4-methyl-3-carboxymethoxy-5-{3-[(3-nitro-phenylamino)-methyl]-phenyl}-thiophene-2-carboxylic acid, 4-methyl-5-{3-[(4-methyl-3-trifluoromethyl-phenylamino)-methyl]-phenyl}-3-carboxymethoxy-thiophene-2-carboxylic acid, 4-methyl-3-carboxymethoxy-5-{3-[(3,5-difluoro-phenylamino)-methyl]-phenyl}-thiophene-2-carboxylic acid, 4-methyl-3-carboxymethoxy-5-{3-[(3-fluoro-4-methyl-phenylamino)-methyl]-phenyl}-thiophene-2-carboxylic acid, 4-methyl-3-carboxymethoxy-5-{3-[(4-chloro-3-trifluoromethyl-phenylamino)-methyl]-phenyl}-thiophene-2-carboxylic acid, 4-methyl-3-carboxymethoxy-5-{3-[(4-methyl-3-nitro-phenylamino)-methyl]-phenyl}-thiophene-2-carboxylic acid, 5-{3-[(acetyl-cyclohexyl-amino)-methyl]-phenyl}-4-methyl-3-carboxymethoxy-thiophene-2-carboxylic acid, 4-methyl-3-carboxymethoxy-5-{3-[(cyclohexyl-methanesulfonyl-amino)-methyl]-phenyl}-thiophene-2-carboxylic acid, 4-methyl-3-carboxymethoxy-5-{3-[(cyclohexyl-methoxycarbonyl-amino)-methyl]-phenyl}-thiophene-2-carboxylic acid, 4-methyl-3-carboxymethoxy-5-[3-(1-cyclohexyl-3-ethyl-ureidomethyl)-phenyl]-thiophene-2-carboxylic acid, 5-(3-{[acetyl-(3,3,5,5-tetramethyl-cyclohexyl)-amino]-methyl}-phenyl)-4-methyl-3-carboxymethoxy-thiophene-2-carboxylic acid, 4-{acetyl-[3-(3-bromo-5-carboxy-4-carboxymethoxy-thiophen-2-yl)-benzyl]-amino}-piperidine-1-carboxylic acid ethyl ester, 4-methyl-3-carboxymethoxy-5-(4-methoxy-3-phenylaminomethyl-phenyl)-thiophene-2-carboxylic acid, 5-{3-[(acetyl-phenyl-amino)-methyl]-4-methoxy-phenyl}-4-methyl-3-carboxymethoxy-thiophene-2-carboxylic acid, 5-{3-[(3,5-bis-trifluoromethyl-phenylamino)-methyl]-4-methoxy-phenyl}-4-methyl-3-carboxymethoxy-thiophene-2-carboxylic acid, 4-methyl-3-carboxymethoxy-5-[3-(2-carboxy-vinyl)-4-methoxy-phenyl]-thiophene-2-carboxylic acid, 4-methyl-3-carboxymethoxy-5-{4-methoxy-3-[2-(2,2,2-trifluoro-ethylcarbamoyl)-vinyl]-phenyl}-thiophene-2-carboxylic acid, 5-(3,4-bis-benzyloxy-phenyl)-4-methyl-3-(2-hydroxy-ethoxy)-thiophene-2-carboxylic acid, 5-(3-benzyloxy-4-hydroxy-phenyl)-4-methyl-3-(2-hydroxy-ethoxy)-thiophene-2-carboxylic acid, 5-(4-benzyloxy-3-hydroxy-phenyl)-4-methyl-3-(2-hydroxy-ethoxy)-thiophene-2-carboxylic acid, 4-methyl-3-methoxycarbonylmethoxy-5-phenyl-thiophene-2-carboxylic acid, 4-methyl-3-methoxycarbonylmethoxy-5-[3-(3,3,5,5-tetramethyl-cyclohexylamino)-phenyl]-thiophene-2-carboxylic acid, 4-methyl-3-methoxycarbonylmethoxy-5-[3-(1-phenylmethanesulfonyl-piperidin-4-ylamino)-phenyl]-thiophene-2-carboxylic acid, 4-methyl-3-carboxymethoxy-5-phenyl-thiophene-2-carboxylic acid methyl ester, 4-methyl-3-carboxymethoxy-5-{3-[1-(2-nitro-phenylmethanesulfonyl)-piperidin-4-ylamino]-phenyl}-thiophene-2-carboxylic acid methyl ester, 4-methyl-3-carboxymethoxy-5-{3-[1-(4-chloro-phenyl-methanesulfonyl)-piperidin-4-ylamino]-phenyl}-thiophene-2-carboxylic acid methyl ester, 4-methyl-3-carboxymethoxy-5-{3-[1-(3,5-dichloro-phenylmethanesulfonyl)-piperidin-4-ylamino]-phenyl}-thiophene-2-carboxylic acid methyl ester, 4-methyl-3-carboxymethoxy-5-{3-[1-(3,4-dichloro-phenylmethanesulfonyl)-piperidin-4-ylamino]-phenyl}-thiophene-2-carboxylic acid methyl ester, 4-methyl-3-carboxymethoxy-5-(3-cyclohexylmethoxy-phenyl)-thiophene-2-carboxylic acid methyl ester, 4-methyl-3-carboxymethoxy-5-[3-(1-phenylmethanesulfonyl-piperidin-4-ylamino)-phenyl]-thiophene-2-carboxylic acid methyl ester, 4-methyl-3-carboxymethoxy-5-{3-[1-(3-trifluoromethyl-phenylmethanesulfonyl)-piperidin-4-ylamino]-phenyl}-thiophene-2-carboxylic acid methyl ester, 4-methyl-3-carboxymethoxy-5-{3-[1-(4-fluoro-phenylmethanesulfonyl)-piperidin-4-ylamino]-phenyl}-thiophene-2-carboxylic acid methyl ester, 4-methyl-3-carboxymethoxy-5-{3-[1-(4-trifluoromethyl-phenylmethanesulfonyl)-piperidin-4-ylamino]-phenyl}-thiophene-2-carboxylic acid methyl ester, 4-methyl-3-carboxymethoxy-5-[3-(3,3,5,5-tetramethyl-cyclohexylamino)-phenyl]-thiophene-2-carboxylic acid methyl ester, 5-{3-[(acetyl-cyclohexyl-amino)-methyl]-phenyl}-4-methyl-3-carboxymethoxy-thiophene-2-carboxylic acid methyl ester, 3-carboxymethoxy-4-methyl-5-phenyl-thiophene-2-carboxylic acid, 5-bromo-3-carboxymethoxy-4-methyl-thiophene-2-carboxylic acid, 3-carboxymethoxy-4-methyl-thiophene-2-carboxylic acid, 3-carboxymethoxy-4-methyl-5-styryl-thiophene-2-carboxylic acid, 3-carboxymethoxy-5-(4-hydroxy-phenyl)-4-methyl-thiophene-2-carboxylic acid, 3-carboxymethoxy-4-methyl-5-[3-(pyridin-3-ylcarbamoyl)-phenyl]-thiophene-2-carboxylic acid, 3-carboxymethoxy-5-[4-(3-isopropyl-ureido)-phenyl]-4-methyl-thiophene-2-carboxylic acid, 5-(3-carboxymethanesulfonylamino-phenyl)-3-carboxymethoxy-4-methyl-thiophene-2-carboxylic acid, 5-(3-benzylamino-phenyl)-3-carboxymethoxy-4-methyl-thiophene-2-carboxylic acid, 3-carboxymethoxy-5-[3-(cyclohexylmethyl-amino)-phenyl]-4-methyl-thiophene-2-carboxylic acid, 3-carboxymethoxy-4-methyl-5-[3-(3-phenoxy-benzylamino)-phenyl]-thiophene-2-carboxylic acid, 5-[3-(3-bromo-benzylamino)-phenyl]-3-carboxymethoxy-4-methyl-thiophene-2-carboxylic acid, 3-carboxymethoxy-4-methyl-5-[3-(3-trifluoromethyl-benzylamino)-phenyl]-thiophene-2-carboxylic acid, 3-carboxymethoxy-5-[3-(cycloheptylmethyl-amino)-phenyl]-4-methyl-thiophene-2-carboxylic acid, 5-benzofuran-2-yl-4-methyl-3-carboxymethoxy-thiophene-2-carboxylic acid, 4,5-bis-benzofuran-2-yl-3-ethoxycarbonylmethoxy-thiophene-2-carboxylic acid methyl ester, 5-biphenyl-3-yl-4-methyl-3-carboxymethoxy-thiophene-2-carboxylic acid, 5-benzo[1,3]dioxol-5-yl-4-methyl-3-carboxymethoxy-thiophene-2-carboxylic acid, 4-methyl-3-carboxymethoxy-5-pyridin-4-yl-thiophene-2-carboxylic acid, 4-methyl-3-carboxymethoxy-5-[3-(4-trifluoromethyl-phenylcarbamoyl)-phenyl]-thiophene-2-carboxylic acid, 4-methyl-3-carboxymethoxy-5-naphthalen-1-yl-thiophene-2-carboxylic acid, 3-bromo-4-carboxymethoxy-[2,3]-bithiophenyl-5-carboxylic acid, 4-methyl-3-carboxymethoxy-5-pyridin-3-yl-thiophene-2-carboxylic acid, 3-bromo-4-carboxymethoxy-2'-formyl-[2,3]-bithiophenyl-5-carboxylic acid, 3-bromo-4-carboxymethoxy-2'-(isobutylamino-methyl)-[2,3]-bithiophenyl-5-carboxylic acid, 4-methyl-3-carboxymethoxy-5-{3-[(5-phenylcarbamoyl-thiophen-2-ylmethyl)-amino]-phenyl}-thiophene-2-carboxylic acid, 5-{3-[(5-benzylcarbamoyl-thiophen-2-ylmethyl)-amino]-phenyl)}4-methyl-3-carboxymethoxy-thiophene-2-carboxylic acid, and 4-methyl-3-carboxymethoxy-5-{3-[(5-cyclohexylcarbamoyl-thiophen-2-ylmethyl)-amino]-phenyl}-thiophene-2-carboxylic acid.

In some embodiments, the compound can be selected from 4-methyl-3-(carboxymethoxy)-5-[3-(piperidin-4-ylamino)phenyl]thiophene-2-carboxylic acid, ({4-methyl-2-(methoxycarbonyl)-5-[3-(piperidin-4-ylamino)phenyl]thien-3-yl}oxy)acetic acid, methyl 4-methyl-3-(2-ethoxy-2-oxoethoxy)-5-(3-{[1-(5-nitropyridin-2-yl)piperidin-4-yl]aminophenyl)thiophene-2-carboxylate, 4-methyl-3-(carboxymethoxy)-5-(3-{[1-(5-nitropyridin-2-yl)piperidin-4-yl]amino}phenyl)thiophene-2-carboxylic acid, 5-[3-({1-[5-(acetylamino)pyridin-2-yl]piperidin-4-yl}amino)phenyl]-4-methyl-3-(carboxymethoxy)thiophene-2-carboxylic acid, 4-methyl-3-(carboxymethoxy)-5-(3-{[1-(5-{[(methylamino)carbonyl]amino}pyridin-2-yl)piperidin-4-yl]amino}phenyl)thiophene-2-carboxylic acid, 4-methyl-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid, 4-methyl-3-(carboxymethoxy)-5-{3-[(1-{5-[(methylsulfonyl)amino]pyridin-2-yl}piperidin-4-yl)amino]phenyl}thiophene-2-carboxylic acid, 3-(carboxymethoxy)-5-phenylthiophene-2-carboxylic acid, methyl 5-(3-{[1-(benzylsulfonyl)piperidin-4-yl]amino}phenyl)-4-methyl-3-{2-[(2-methylphenyl)amino]-2-oxoethoxy}thiophene-2-carboxylate, 5-(3-{[1-(benzylsulfonyl)piperidin-4-yl][(ethylamino)carbonyl]amino}phenyl)-4-methyl-3-(carboxymethoxy)thiophene-2-carboxylic acid, 4,5-dibromo-3-[carboxy(fluoro)methoxy]

thiophene-2-carboxylic acid, {[5-phenyl-2-(2H-tetrazol-5-yl)thien-3-yl]oxy}acetic acid, {5-[3-({[1-(anilinocarbonyl)piperidin-4-yl]methyl}amino)phenyl]-4-methyl-2-(methoxycarbonyl)thien-3-yl]oxy}acetic acid, 5-(3-{{[1-(anilinocarbonyl)piperidin-4-yl]methyl}[(ethylamino)carbonyl]aminophenyl)-4-methyl-3-(carboxymethoxy)thiophene-2-carboxylic acid 4-methyl-3-(carboxymethoxy)-5-{3-[(1-{[2-(trifluoromethoxy)phenyl]sulfonyl}piperidin-4-yl)amino]phenyl}thiophene-2-carboxylic acid, 4-methyl-3-(carboxymethoxy)-5-[3-({1-[(5-chloro-2-methoxyphenyl)sulfonyl]piperidin-4-yl}amino)phenyl]thiophene-2-carboxylic acid, 4-methyl-3-(carboxymethoxy)-5-[3-({1-[(3,5-dichloro-2-hydroxyphenyl)sulfonyl]piperidin-4-yl}amino)phenyl]thiophene-2-carboxylic acid, propyl 4-methyl-3-(2-tert-butoxy-2-oxoethoxy)-5-{3-[(3,3,5,5-tetramethylcyclohexyl)amino]phenyl}thiophene-2-carboxylate, [(4-methyl-2-(propoxycarbonyl)-5-{3-[(3,3,5,5-tetramethylcyclohexyl)amino]phenyl}thien-3-yl)oxy]acetic acid, 4-methyl-3-carboxymethoxy-5-{3-[1-(2-trifluoromethyl-phenylmethanesulfonyl)-piperidin-4-ylamino]-phenyl}-thiophene-2-carboxylic acid, 4-methyl-3-carboxymethoxy-5-[3-(indan-2-ylamino)-phenyl]-thiophene-2-carboxylic acid, 3-[3-(3-bromo-5-carboxy-4-carboxymethoxy-thiophen-2-yl)-phenylamino]-8-aza-bicyclo[3.2.1]octane-8-carboxylic acid ethyl ester, 4-methyl-3-carboxymethoxy-5-[3-(8-phenylmethanesulfonyl-8-aza-bicyclo[3.2.1]oct-3-ylamino)-phenyl]-thiophene-2-carboxylic acid, 5-(1-benzyl-1H-pyrazol-4-yl)-4-methyl-3-carboxymethoxy-thiophene-2-carboxylic acid; compound with methane, 5-{3-[1-(2-acetylamino-phenylmethanesulfonyl)-piperidin-4-ylamino]-phenyl}-4-methyl-3-carboxymethoxy-thiophene-2-carboxylic acid, 5-{3-[1-(2-acetylamino-phenylmethanesulfonyl)-piperidin-4-ylamino]-phenyl}-3-carboxymethoxy-thiophene-2-carboxylic acid, 4-methyl-3-carboxymethoxy-5-{3-[1-(2-methanesulfonylamino-phenylmethanesulfonyl)-piperidin-4-ylamino]-phenyl}-thiophene-2-carboxylic acid, 3-carboxymethoxy-5-{3-[1-(2-methanesulfonylamino-phenylmethanesulfonyl)-piperidin-4-ylamino]-phenyl}-thiophene-2-carboxylic acid 4-methyl-3-carboxymethoxy-5-(3-{1-[2-(3-ethyl-ureido)-phenylmethanesulfonyl]-piperidin-4-ylamino}-phenyl)-thiophene-2-carboxylic acid, 3-carboxymethoxy-5-(3-{1-[2-(3-ethyl-ureido)-phenylmethanesulfonyl]-piperidin-4-ylamino}-phenyl)-thiophene-2-carboxylic acid, 4-methyl-3-carboxymethoxy-5-{3-[1-(2-chloromethanesulfonylamino-phenylmethanesulfonyl)-piperidin-4-ylamino]-phenyl}-thiophene-2-carboxylic acid, 5-{3-[(acetyl-isopropyl-amino)-methyl]-phenyl})-4-methyl-3-carboxymethoxy-thiophene-2-carboxylic acid, 5-{3-[(acetyl-isobutyl-amino)-methyl]-phenyl})-4-methyl-3-carboxymethoxy-thiophene-2-carboxylic acid, 5-{3-[(acetyl-cyclohexylmethyl-amino)-methyl]-phenyl}-4-methyl-3-carboxymethoxy-thiophene-2-carboxylic acid, 5-{3-[(acetyl-p-tolyl-amino)-methyl]-phenyl}-4-methyl-3-carboxymethoxy-thiophene-2-carboxylic acid, 5-(3-{[acetyl-(4-tert-butyl-phenyl)-amino]-methyl}-phenyl)-4-methyl-3-carboxymethoxy-thiophene-2-carboxylic acid, 5-(3-{[acetyl-(4-trifluoromethyl-phenyl)-amino]-methyl}-phenyl)-4-methyl-3-carboxymethoxy-thiophene-2-carboxylic acid, 5-{3-[(acetyl-phenyl-amino)-methyl]-phenyl}-4-methyl-3-carboxymethoxy-thiophene-2-carboxylic acid, 5-{3-[(acetyl-cyclopropyl-amino)-methyl]-phenyl})-4-methyl-3-carboxymethoxy-thiophene-2-carboxylic acid, 5-(3-{[acetyl-(4-methyl-phenyl)-amino]-methyl}-phenyl)-4-methyl-3-carboxymethoxy-thiophene-2-carboxylic acid, 5-{3-[(acetyl-biphenyl-4-yl-amino)-methyl]-phenyl}-4-methyl-3-carboxymethoxy-thiophene-2-carboxylic acid, 5-(3-{[acetyl-(4-phenoxy-phenyl)-amino]-methyl}-phenyl)-4-methyl-3-carboxymethoxy-thiophene-2-carboxylic acid, 5-{3-[(acetyl-benzyl-amino)-methyl]-phenyl}-4-methyl-3-carboxymethoxy-thiophene-2-carboxylic acid 5-(3-{[acetyl-(4-methoxy-benzyl)-amino]-methyl}-phenyl)-4-methyl-3-carboxymethoxy-thiophene-2-carboxylic acid, 5-{3-[(acetyl-biphenyl-4-ylmethyl-amino)-methyl]-phenyl}4-methyl-3-carboxymethoxy-thiophene-2-carboxylic acid, 5-(3-{[acetyl-(4-chloro-phenyl)-amino]-methyl}-phenyl)-4-methyl-3-carboxymethoxy-thiophene-2-carboxylic acid, 5-(3-{[acetyl-(4-trifluoromethyl-phenyl)-amino]-methyl}-phenyl)-4-methyl-3-carboxymethoxy-thiophene-2-carboxylic acid, 5-(3-{[acetyl-(3,5-bis-trifluoromethyl-phenyl)-amino]-methyl}-phenyl)-4-methyl--carboxymethoxy-thiophene-2-carboxylic acid, 5-[3-({acetyl-[2-(4-chloro-phenyl)-ethyl]-amino}-methyl)-phenyl]-4-methyl-3-carboxymethoxy-thiophene-2-carboxylic acid, 4-methyl-3-carboxymethoxy-5-[3-(1,3-diisopropyl-ureido)-phenyl]-thiophene-2-carboxylic acid, 4-methyl-3-carboxymethoxy-5-{3-[1-(2,2-dimethyl-propyl)-3-isopropyl-ureido]-phenyl}-thiophene-2-carboxylic acid, 4-methyl-3-carboxymethoxy-5-[3-(1-isobutyl-3-isopropyl-ureido)-phenyl]-thiophene-2-carboxylic acid, 5-[3-(1-benzyl-3-isopropyl-ureido)-phenyl]-4-methyl-3-carboxymethoxy-thiophene-2-carboxylic acid, 4-methyl-3-carboxymethoxy-5-{3-[3-isopropyl-1-(4-trifluoromethyl-benzyl)-ureido]-phenyl}-thiophene-2-carboxylic acid, 4-methyl-5-{3-[1-(4-tert-butyl-benzyl)-3-isopropyl-ureido]-phenyl}-3-carboxymethoxy-thiophene-2-carboxylic acid, 5-[3-(acetyl-cyclohexylmethyl-amino)-phenyl]-4-methyl-3-carboxymethoxy-thiophene-2-carboxylic acid, 4-methyl-3-carboxymethoxy-5-{3-[cyclohexylmethyl-(3-methyl-butyryl)-amino]-phenyl}-thiophene-2-carboxylic acid, 4-methyl-3-carboxymethoxy-5-[3-(cyclohexanecarbonyl-cyclohexylmethyl-amino)-phenyl]-thiophene-2-carboxylic acid, 4-methyl-3-carboxymethoxy-5-[3-(cyclohexylmethyl-isobutyryl-amino)-phenyl]-thiophene-2-carboxylic acid, 4-methyl-3-carboxymethoxy-5-[3-(cyclohexylmethyl-methoxycarbonyl-amino)-phenyl]-thiophene-2-carboxylic acid, 3-carboxymethoxy-5-[3-(cyclohexylmethyl-methoxycarbonyl-amino)-phenyl]-4-methyl-thiophene-2-carboxylic acid, 3-carboxymethoxy-5-[3-(cyclohexylmethyl-isopropoxycarbonyl-amino)-phenyl]-4-methyl-thiophene-2-carboxylic acid, 5-[3-(bis-cyclohexylmethyl-amino)-phenyl]-3-carboxymethoxy-4-methyl-thiophene-2-carboxylic acid, 4-methyl-3-carboxymethoxy-5-[3-(1-cyclohexylmethyl-3-phenyl-ureido)-phenyl]-thiophene-2-carboxylic acid, 5-[3-(3-benzyl-1-cyclohexylmethyl-ureido)-phenyl]-4-methyl-3-carboxymethoxy-thiophene-2-carboxylic acid, 4-methyl-3-carboxymethoxy-5-{3-[1-cyclohexylmethyl-3-(4-ethyl-phenyl)-ureido]-phenyl}-thiophene-2-carboxylic acid, 4-methyl-3-carboxymethoxy-5-{3-[1-cyclohexylmethyl-3-(4-ethoxy-phenyl)-ureido]-phenyl}-thiophene-2-carboxylic acid, 4-methyl-3-carboxymethoxy-5-{3-[1-cyclohexylmethyl-3-(4-phenoxy-phenyl)-ureido]-phenyl}-thiophene-2-carboxylic acid, 4-methyl-3-carboxymethoxy-5-{3-[3-(2-cyano-phenyl)-1-cyclohexylmethyl-ureido]-phenyl}-thiophene-2-carboxylic acid, 4-methyl-3-carboxymethoxy-5-[3-(1-cyclohexylmethyl-3-thiophen-3-yl-ureido)-phenyl]-thiophene-2-carboxylic acid, 4-methyl-3-carboxymethoxy-5-{3-[1-cyclohexylmethyl-3-(3,5-dimethyl-isoxazol-4-yl)-ureido]-phenyl}-thiophene-2-carboxylic acid, 4-methyl-3-carboxymethoxy-5-{3-[1-cyclohexylmethyl-3-(5-methyl-3-phenyl-isoxazol-4-yl)-ureido]-phenyl}-thiophene-2-carboxylic acid, 4-methyl-3-carboxymethoxy-5-{3-[3-(4-carboxy-phenyl)-1-cyclohexylmethyl-ureido]-phenyl}-thiophene-2-carboxylic acid, 4-methyl-3-carboxymethoxy-5-[3-(1-cyclohexylmethyl-3-ethyl-ureido)-phenyl]- thiophene-2-carboxylic acid, 3-carboxymethoxy-5-[3-(1-cyclohexylmethyl-3-isopropyl-ureido)-phenyl]-4-methyl-thiophene-2-carboxylic acid, 3-carboxymethoxy-5-[3-(1-cyclohexyl-3-isopropyl-ureido)-phenyl]-4-methyl-thiophene-2-carboxylic acid, 3-carboxymethoxy-5-[3-(1-cyclohexylmethyl-3-phenyl-ureido)-phenyl]-4-methyl-thiophene-2-carboxylic acid, 5-[3-(3-benzyl-1-cyclohexylmethyl-ureido)-phenyl]-3-carboxymethoxy-4-methyl-thiophene-2-carboxylic acid, 5-[3-(3-benzyl-1-cyclohexyl-ureido)-phenyl]-3-carboxymethoxy-4-methyl-thiophene-2-carboxylic acid, 3-carboxymethoxy-5-[3-(1-cyclohexylmethyl-3-phenethyl-ureido)-phenyl]-4-methyl-thiophene-2-carboxylic acid, 3-carboxymethoxy-5-[3-(1-cyclohexylmethyl-3-phenethyl-ureido)-phenyl]-4-methyl-thiophene-2-carboxylic acid, 4-methyl-3-isopropoxycarbonylmethoxy-5-[3-(1-phenylmethanesulfonyl-piperidin-4-ylamino)-phenyl]-thiophene-2-carboxylic acid, 4-methyl-3-isobutoxycarbonylmethoxy-5-[3-(1-phenylmethanesulfonyl-piperidin-4-ylamino)-phenyl]-thiophene-2-carboxylic acid, 4-methyl-5-[3-(1-phenylmethanesulfonyl-piperidin-4-ylamino)-phenyl]-3-propoxycarbonylmethoxy-thiophene-2-carboxylic acid, 4-methyl-3-cyclopropylmethoxycarbonylmethoxy-5-[3-(1-phenylmethanesulfonyl-piperidin-4-ylamino)-phenyl]-thiophene-2-carboxylic acid, 3-benzyloxycarbonylmethoxy-4-methyl-5-[3-(1-phenylmethanesulfonyl-piperidin-4-ylamino)-phenyl]-thiophene-2-carboxylic acid, 4-methyl-3-cyclohexylmethoxycarbonylmethoxy-5-[3-(1-phenylmethanesulfonyl-piperidin-4-ylamino)-phenyl]-thiophene-2-carboxylic acid, 4-methyl-3-cyclohexyloxycarbonylmethoxy-5-[3-(1-phenylmethanesulfonyl-piperidin-4-ylamino)-phenyl]-thiophene-2-carboxylic acid, 4-methyl-3-carboxymethoxy-5-{3-[1-(2,3-dichloro-phenylmethanesulfonyl)-piperidin-4-ylamino]-phenyl}-thiophene-2-carboxylic acid, 4-methyl-5-{3-[1-(2,3-dichloro-phenylmethanesulfonyl)-piperidin-4-ylamino]-phenyl}-3-methoxycarbonylmethoxy-thiophene-2-carboxylic acid, 4-methyl-3-carboxymethoxy-5-{3-[1-(2,3-dichloro-phenylmethanesulfonyl)-piperidin-4-ylamino]-phenyl}-thiophene-2-carboxylic acid methyl ester, [4-methyl-5-(3-cyclohexylamino-phenyl)-2-(2H-tetrazol-5-yl)-thiophen-3-yloxy]-acetic acid, [4-methyl-5-[3-(cyclohexylmethyl-amino)-phenyl]-2-(2H-tetrazol-5-yl)-thiophen-3-yloxy]-acetic acid, [4-methyl-5-[3-(3,3,5,5-tetramethyl-cyclohexylamino)-phenyl]-2-(2H-tetrazol-5-yl)-thiophen-3-yloxy]-acetic acid, tetrazole/acid: [5-{3-[acetyl-(3,3,5,5-tetramethyl-cyclohexyl)-amino]-phenyl}-4-methyl-2-(2H-tetrazol-5-yl)-thiophen-3-yloxy]-acetic acid, [4-methyl-5-[3-(1-phenylmethanesulfonyl-piperidin-4-ylamino)-phenyl]-2-(2H-tetrazol-5-yl)-thiophen-3-yloxy]-acetic acid, 4-methyl-3-carboxymethoxy-5-[3-(1-phenylmethanesulfonyl-piperidin-4-ylamino)-phenyl]-thiophene-2-carboxylic acid methyl ester, ethanolamine salt, 4-methyl-3-carboxymethoxy-5-[3-(1-phenylmethanesulfonyl-piperidin-4-ylamino)-phenyl]-thiophene-2-carboxylic acid methyl ester, choline salt, 4-methyl-3-carboxymethoxy-5-[3-(1-phenylmethanesulfonyl-piperidin-4-ylamino)-phenyl]-thiophene-2-carboxylic acid methyl ester, sodium salt, {[2-[(benzyloxy)carbonyl]-5-(3-{[1-(benzylsulfonyl)piperidin-4-yl]amino}phenyl)-4-methylthien-3-yl]oxy}acetic acid, [(5-(3-{[1-(benzylsulfonyl)piperidin-4-yl]amino}phenyl)-4-methyl-2-{[(2-nitrobenzyl)oxy]carbonyl}thien-3-yl)oxy] acetic acid, [(5-(3-{[1-(benzylsulfonyl)piperidin-4-yl] amino}phenyl)-4-methyl-2-{[(2-nitrobenzyl)oxy] carbonyl}thien-3-yl)oxy]acetic acid, [(5-(3-{[1-(benzylsulfonyl)piperidin-4-yl]amino}phenyl)-4-methyl-2-{[(2-nitrobenzyl)oxy]carbonyl}thien-3-yl)oxy]acetic acid, ({5-(3-{[1-(benzylsulfonyl)piperidin-4-yl]amino}phenyl)-4-methyl-2-[(cyclohexylmethoxy)carbonyl]thien-3-yl}oxy) acetic acid, ({5-(3-{[1-(benzylsulfonyl)piperidin-4-yl] amino}phenyl)-4-methyl-2-[(cyclohexylmethoxy)carbonyl] thien-3-yl}oxy)acetic acid, 5-[3-(benzyloxycarbonyl-cyclohexyl-amino)-phenyl]-4-methyl-3-carboxymethoxy-thiophene-2-carboxylic acid, 5-[3-(benzyloxycarbonyl-cyclohexyl-amino)-phenyl]-4-methyl-3-carboxymethoxy-thiophene-2-carboxylic acid, 4-methyl-3-carboxymethoxy-5-[3-(cyclohexyl-propoxycarbonyl-amino)-phenyl]-thiophene-2-carboxylic acid, 4-methyl-3-carboxymethoxy-5-[3-(cyclohexyl-isopropoxycarbonyl-amino)-phenyl]-thiophene-2-carboxylic acid, 5-[3-(benzyloxycarbonyl-cyclohexylmethyl-amino)-phenyl]-4-methyl-3-carboxymethoxy-thiophene-2-carboxylic acid, 4-methyl-3-carboxymethoxy-5-[3-(cyclohexylmethyl-isopropoxycarbonyl-amino)-phenyl]-thiophene-2-carboxylic acid, 4-methyl-3-carboxymethoxy-5-[3-(cyclohexylmethyl-isopropoxycarbonyl-amino)-phenyl]-thiophene-2-carboxylic acid, 4-methyl-3-carboxymethoxy-5-[3-(cyclohexylmethyl-propoxycarbonyl-amino)-phenyl]-thiophene-2-carboxylic acid, 5-[3-(benzoyl-cyclohexylmethyl-amino)-phenyl]-4-methyl-3-carboxymethoxy-thiophene-2-carboxylic acid, 4-methyl-3-carboxymethoxy-5-[3-(cyclohexylmethyl-phenylacetyl-amino)-phenyl]-thiophene-2-carboxylic acid, 4-methyl-3-carboxymethoxy-5-{3-[cyclohexylmethyl-(4-methyl-pentanoyl)-amino]-phenyl}-thiophene-2-carboxylic acid methyl ester, 4-methyl-3-carboxymethoxy-5-{3-[1-(3-chloro-phenylmethanesulfonyl)-piperidin-4-ylamino]-phenyl}-thiophene-2-carboxylic acid methyl ester, 4-methyl-3-carboxymethoxy-5-{3-[1-(3-fluoro-phenylmethanesulfonyl)-piperidin-4-ylamino]-phenyl}-thiophene-2-carboxylic acid methyl ester, 4-methyl-3-carboxymethoxy-5-{3-[1-(2-chloro-phenylmethanesulfonyl)-piperidin-4-ylamino]-phenyl}-thiophene-2-carboxylic acid, 4-methyl-5-{3-[1-(2-chloro-phenylmethanesulfonyl)-piperidin-4-ylamino]-phenyl}-3-methoxycarbonylmethoxy-thiophene-2-carboxylic acid, 3-carboxymethoxy-5-{3-[1-(3-fluoro-phenylmethanesulfonyl)-piperidin-4-ylamino]-phenyl}-4-methyl-thiophene-2-carboxylic acid methyl ester, 3-carboxymethoxy-4-methyl-5-[3-(1-phenylmethanesulfonyl-piperidin-4-ylamino)-phenyl]-thiophene-2-carboxylic acid methyl ester, 3-carboxymethoxy-4-methyl-5-{3-[1-(2-trifluoromethyl-phenylmethanesulfonyl)-piperidin-4-ylamino]-phenyl}-thiophene-2-carboxylic acid methyl ester 3-carboxymethoxy-4-methyl-5-[3-(1-phenylmethanesulfonyl-piperidin-4-ylamino)-phenyl]-thiophene-2-carboxylic acid, 3-methoxycarbonylmethoxy-4-methyl-5-[3-(1-phenyl-methanesulfonyl-piperidin-4-ylamino)-phenyl]-thiophene-2-carboxylic acid, 3-carboxymethoxy-4-methyl-5-[3-(3,3,5,5-tetramethyl-cyclohexylamino)-phenyl]-thiophene-2-carboxylic acid methyl ester], 4,5-dibromo-3-(1-carboxy-ethoxy)-thiophene-2-carboxylic acid, [4,5-dibromo-2-(5-methyl-[1,2,4]oxadiazol-3-yl)-thiophen-3-yloxy]-acetic acid, [4,5-dibromo-2-(5-ethyl-[1,2,4]oxadiazol-3-yl)-thiophen-3-yloxy]-acetic acid, [4,5-dibromo-2-(5-isopropyl-[1,2,4]oxadiazol-3-yl)-thiophen-3-yloxy]-acetic acid, [4-methyl-5-[3-(1-phenylmethanesulfonyl-piperidin-4-ylamino)-phenyl]-2-(1H-tetrazol-5-yl)-thiophen-3-yloxy]-acetic acid, [4-methyl-5-[3-(1-phenylmethanesulfonyl-piperidin-4-ylamino)-phenyl]-2-(1H-tetrazol-5-yl)-thiophen-3-yloxy]-acetic acid isopropyl ester, [4-methyl-5-[3-(1-phenylmethanesulfonyl-piperidin-4-ylamino)-phenyl]-2-(1H-tetrazol-5-yl)-thiophen-3-yloxy]-acetic acid methyl ester, 4,5-dibromo-3-(isobutylcarbamoyl-methoxy)-thiophene-2-carboxylic acid methyl ester, 4,5-dibromo-3-(2-oxo-2-pyrrolidin-1-yl-ethoxy)-thiophene-2-carboxylic acid methyl ester, 4,5-dibromo-3-[(2-hydroxy-1-methyl-ethylcarbamoyl)-methoxy]-thiophene-2-carboxylic acid methyl ester, [4-methyl-5-[3-(1-phenylmethanesulfonyl-piperidin-4-ylamino)-phenyl]-2-(1H-tetrazol-5-yl)-thiophen-3-yloxy]-acetic acid methyl ester, 4,5-dibromo-3-(isobutylcarbamoyl-methoxy)-thiophene-2-carboxylic acid methyl ester, 4-[2-(4,5-dibromo-2-methoxycarbonyl-thiophen-3-yloxy)-acetyl]-piperazine-1-carboxylic acid tert-butyl ester, 4,5-dibromo-3-[(2-hydroxy-1-methyl-ethylcarbamoyl)-methoxy]-thiophene-2-carboxylic acid methyl ester, 4,5-dibromo-3-[(2-tert-butoxycarbonylamino-ethylcarbamoyl)-methoxy]-thiophene-2-carboxylic acid methyl ester, 3-[(2-amino-ethylcarbamoyl)-methoxy]-4,5-dibromo-thiophene-2-carboxylic acid methyl ester, 3-{[2-(4-Hydroxy-phenyl)-1-methoxycarbonyl-ethylcarbamoyl]-methoxy})-4-methyl-5-[3-(3,3,5,5-tetramethyl-cyclohexyl)-phenyl]-thiophene-2-carboxylic acid methyl ester, 1-(2-{2-methoxycarbonyl-4-methyl-5-[3-(3,3,5,5-tetramethyl-cyclohexyl)-phenyl]-thiophen-3-yloxy}-acetyl)-pyrrolidine-2-carboxylic acid methyl ester, 4-methyl-3-(2-oxo-2-pyrrolidin-1-yl-ethoxy)-5-[3-(3,3,5,5-tetramethyl-cyclohexyl)-phenyl]-thiophene-2-carboxylic acid methyl ester, 3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester, 3-[(1-methoxycarbonyl-2-methyl-propylcarbamoyl)-methoxy]-4-methyl-5-[3-(3,3,5,5-tetramethyl-cyclohexyl)-phenyl]-thiophene-2-carboxylic acid methyl ester, 3-[(1-methoxycarbonyl-3-methyl-butylcarbamoyl)-methoxy]-4-methyl-5-[3-(3,3,5,5-tetramethyl-cyclohexyl)-phenyl]-thiophene-2-carboxylic acid methyl ester, 3-[(1-methoxycarbonyl-2-phenyl-ethylcarbamoyl)-methoxy]-4-methyl-5-[3-(3,3,5,5-tetramethyl-cyclohexyl)-phenyl]-thiophene-2-carboxylic acid methyl ester, 3-[2-(2-carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester, 3-[(2-tert-butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester, 4-(2-{2-methoxycarbonyl-4-methyl-5-[3-(3,3,5,5-tetramethyl-cyclohexyl)-phenyl]-thiophen-3-yloxy}-acetyl)-piperazine-1-carboxylic acid tert-butyl ester, 3-[(2-amino-ethylcarbamoyl)-methoxy]-4-methyl-5-[3-(3,3,5,5-tetramethyl-cyclohexyl)-phenyl]-thiophene-2-carboxylic acid methyl ester, 4-methyl-3-(2-oxo-2-piperazin-1-yl-ethoxy)-5-[3-(3,3,5,5-tetramethyl-cyclohexyl)-phenyl]-thiophene-2-carboxylic acid methyl ester 4-methyl-5-[3-(1-phenylmethanesulfonyl-piperidin-4-yl)-phenyl]-3-(piperidin-4-yloxycarbonylmethoxy)-thiophene-2-carboxylic acid methyl ester, 4-methyl-3-methoxycarbonylmethoxy-5-[3-(1-phenylmethanesulfonyl-piperidin-4-yl)-phenyl]-thiophene-2-carboxylic acid 2,2-dimethyl-propionyloxymethyl ester, 4-methyl-3-isopropoxycarbonylmethoxy-5-[3-(1-phenylmethanesulfonyl-piperidin-4-yl)-phenyl]-thiophene-2-carboxylic acid 2,2-dimethyl-propionyloxymethyl ester 4-methyl-3-isopropoxycarbonylmethoxy-5-[3-(1-phenylmethanesulfonyl-piperidin-4-yl)-phenyl]-thiophene-2-carboxylic acid acetoxymethyl ester, 4,5-dibromo-3-methoxycarbonylmethoxy-thiophene-2-carboxylic acid 2,2-dimethyl-propionyloxymethyl ester, [5-bromo-4-methyl-2-(1H-tetrazol-5-yl)-thiophen-3-yloxy]-acetic acid, [4-methyl-5-phenyl-2-(1H-tetrazol-5-yl)-thiophen-3-yloxy]-acetic acid, [5-bromo-4-methyl-2-(2-methyl-2H-tetrazol-5-yl)-thiophen-3-yloxy]-acetic acid, 3-carboxymethoxy-5-{3-[1-(3-chloro-benzenesulfonyl)-piperidin-4-ylamino]-phenyl}-4-methyl-thiophene-2-carboxylic acid, 3-carboxymethoxy-5-{3-[1-(2-chloro-benzenesulfonyl)-piperidin-4-ylamino]-phenyl)}4-methyl-thiophene-2-carboxylic acid, 3-carboxymethoxy-4-methyl-5-{3-[1-(4-nitro-benzenesulfonyl)-piperidin-4-ylamino]-phenyl}-thiophene-2-carboxylic acid, 3-carboxymethoxy-5-{3-[1-(2-cyano-benzenesulfonyl)-piperidin-4-ylamino]-phenyl}-4-methyl-thiophene-2-carboxylic acid, 3-carboxymethoxy-4-methyl-5-{3-[1-(4-trifluoromethyl-benzenesulfonyl)-piperidin-4-ylamino]-phenyl}-thiophene-2-carboxylic acid, 5-{3-[1-(4-carboxy-benzenesulfonyl)-piperidin-4-ylamino]-phenyl}-3-carboxymethoxy-4-methyl-thiophene-2-carboxylic acid, 3-carboxymethoxy-5-{3-[1-(2-cyano-benzenesulfonyl)-piperidin-4-ylamino]-phenyl}-4-methyl-thiophene-2-carboxylic acid, 3-carboxymethoxy-4-methyl-5-{3-[1-(4-trifluoromethyl-benzenesulfonyl)-piperidin-4-ylamino]-phenyl}-thiophene-2-carboxylic acid, 4-methyl-3-carboxymethoxy-5-[3-(1-cyclohexyl-3-methyl-ureido)-phenyl]-thiophene-2-carboxylic acid, 5-[3-(3-benzyl-1-cyclohexyl-ureido)-phenyl]-4-methyl-3-carboxymethoxy-thiophene-2-carboxylic acid, 4-methyl-3-tert-butoxycarbonylmethoxy-5-[3-(3,3,5,5-tetramethyl-cyclohexylamino)-phenyl]-thiophene-2-carboxylic acid methyl ester, 4-methyl-3-carboxymethoxy-5-(3-[3-methyl-1-(3,3,5,5-tetramethyl-cyclohexyl)-ureido]-phenyl}-thiophene-2-carboxylic acid, 4-methyl-3-carboxymethoxy-5-{3-[3-ethyl-1-(3,3,5,5-tetramethyl-cyclohexyl)-ureido]-phenyl}-thiophene-2-carboxylic acid, 4-methyl-3-carboxymethoxy-5-{3-[3-methyl-1-(3,3,5,5-tetramethyl-cyclohexyl)-ureido]-phenyl}-thiophene-2-carboxylic acid methyl ester, 4-methyl-3-ethoxycarbonylmethoxy-5-[3-(piperidin-4-ylamino)-phenyl]-thiophene-2-carboxylic acid methyl ester hydrochloride, 4-methyl-3-carboxymethoxy-5-{3-[1-(4-trifluoromethyl-pyrimidin-2-yl)-piperidin-4-ylamino]-phenyl}-thiophene-2-carboxylic acid, 4-methyl-3-carboxymethoxy-5-[3-(1-pyrimidin-2-yl-piperidin-4-ylamino)-phenyl]-thiophene-2-carboxylic acid, 4-methyl-3-carboxymethoxy-5-[3-(5'-trifluoromethyl-3,4,5,6-tetrahydro-2H-[1,2'] bipyridinyl-4-ylamino)-phenyl]-thiophene-2-carboxylic acid, 4-methyl-3-ethoxycarbonylmethoxy-5-[3-(1-phenylmethanesulfonyl-piperidin-4-ylamino)-phenyl]-thiophene-2-carboxylic acid ethyl ester, 4-methyl-5-[3-(1-phenylmethanesulfonyl-piperidin-4-ylamino)-phenyl]-3-(o-tolylcarbamoyl-methoxy)-thiophene-2-carboxylic acid, {4-methyl-2-hydroxymethyl-5-[3-(1-phenylmethanesulfonyl-piperidin-4-ylamino)-phenyl]-thiophen-3-yloxy}-acetic acid, 3-carboxymethoxy-5-[3-(1-phenylmethanesulfonyl-piperidin-4-ylamino)-phenyl]-thiophene-2-carboxylic acid, 4-methyl-3-carboxymethoxy-5-(3-{1-[3-(3-ethyl-ureido)-phenylmethanesulfonyl]-piperidin-4-ylamino}-phenyl)-thiophene-2-carboxylic acid, [2-(2-{4-methyl-2-methoxycarbonyl-5-[3-(1-phenylmethanesulfonyl-piperidin-4-ylamino)-phenyl]-thiophen-3-yloxy}-acetoxy)-ethyl]-trimethyl-ammonium chloride, 4-methyl-3-cyclohexylcarbamoylmethoxy-5-[3-(1-phenylmethanesulfonyl-piperidin-4-ylamino)-phenyl]-thiophene-2-carboxylic acid methyl ester, (4,5-dibromo-2-hydroxymethyl-thiophen-3-yloxy)-acetic acid, 5-[3-(acetyl-cyclohexyl-amino)-phenyl]-4-methyl-3-carboxymethoxy-thiophene-2-carboxylic acid, 5-[3-(acetyl-cyclohexyl-amino)-phenyl]-4-methyl-3-carboxymethoxy-thiophene-2-carboxylic acid methyl ester, 5-[3-(benzoyl-cyclohexyl-amino)-phenyl]-4-methyl-3-carboxymethoxy-thiophene-2-carboxylic acid, 5-[3-(benzoyl-cyclohexyl-amino)-phenyl]-4-methyl-3-carboxymethoxy-thiophene-2-carboxylic acid methyl ester, 4-methyl-3-carboxymethoxy-5-{3-[cyclohexyl-(3-phenyl-acryloyl)-amino]-phenyl}-thiophene-2-carboxylic acid methyl ester, 4-methyl-3-carboxymethoxy-5-[3-(cyclohexanecarbonyl-cyclohexyl-amino)-phenyl]-thiophene-2-carboxylic acid methyl ester, 5-{3-[benzoyl-(3,3,5,5-tetramethyl-cyclohexyl)-amino]-phenyl}-4-methyl-3-carboxymethoxy-thiophene-2-carboxylic acid, 4-methyl-3-carboxymethoxy-5-[3-(1-phenylmethanesulfonyl-piperidin-4-ylamino)-phenyl]-thiophene-2-carboxylic acid methyl ester (Hydrochloride Salt), 4-methyl-3-[(carbamoylmethyl-carbamoyl)-methoxy]-5-[3-(3,3,5,5-tetramethyl-cyclohexylamino)-phenyl]-thiophene-2-carboxylic acid methyl ester, 4-methyl-3-[(1-carbamoyl-ethylcarbamoyl)-methoxy]-5-[3-(3,3,5,5-tetramethyl-cyclohexylamino)-phenyl]-thiophene-2-carboxylic acid methyl ester, 4-methyl-3-[(ethoxycarbonylmethyl-carbamoyl)-methoxy]-5-[3-(3,3,5,5-tetramethyl-cyclohexylamino)-phenyl]-thiophene-2-carboxylic acid methyl ester, 4-methyl-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 4-methyl-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 3-{[(benzylcarbamoyl-methyl)-carbamoyl]-methoxy}-4-methyl-5-[3-(3,3,5,5-tetramethylcyclohexylamino)-phenyl]-thiophene-2-carboxylic acid methyl ester, 4-methyl-3-carboxymethoxy-5-{3-[1-(3-methanesulfonylamino-phenylmethanesulfonyl)-piperidin-4-ylamino]-phenyl}-thiophene-2-carboxylic acid, 5-{3-[1-(3-acetylamino-phenylmethanesulfonyl)-piperidin-4-ylamino]-phenyl}-4-methyl-3-carboxymethoxy-thiophene-2-carboxylic acid, {[4-methyl-5-(3-methoxyphenyl)-2-(morpholin-4-ylcarbonyl)thien-3-yl]oxy}acetic acid, {[5-(1,3-benzodioxol-5-yl)-4-methyl-2-(morpholin-4-ylcarbonyl)thien-3-yl]oxy}acetic acid, {[3-bromo-5-(morpholin-4-ylcarbonyl)-2,3'-bithien-4-yl]oxy}acetic acid, {[4-methyl-2-(morpholin-4-ylcarbonyl)-5-phenylthien-3-yl]oxy}acetic acid, [(4,5-dibromo-2-{[(2-hydroxy-1,1-dimethylethyl)amino]carbonyl}thien-3-yl)oxy]acetic acid, ({4,5-dibromo-2-[(dimethylamino)carbonyl]thien-3-yl}oxy)acetic acid, ({4,5-dibromo-2-[(diethylamino)carbonyl]thien-3-yl}oxy)acetic acid, ({4,5-dibromo-2-[(1,3-thiazol-2-ylamino)carbonyl]thien-3-yl}oxy)acetic acid, [4,5-dibromo-2-(2H-pyrazol-3-ylcarbamoyl)-thiophen-3-yloxy]-acetic acid, {[4,5-dibromo-2-(morpholin-4-ylcarbonyl)thien-3-yl]oxy}acetic acid, [(4,5-dibromo-2-{[(2R,6S)-2,6-dimethylmorpholin-4-yl]carbonyl}thien-3-yl)oxy]acetic acid, {[4,5-dibromo-2-(thiomorpholin-4-ylcarbonyl)thien-3-yl]oxy}acetic acid, {[2-(anilinocarbonyl)-4,5-dibromothien-3-yl]oxy}acetic acid, {[4,5-dibromo-2-(piperidin-1-ylcarbonyl)thien-3-yl]oxy}acetic acid, {[4,5-dibromo-2-(4,4-dimethyl-4,5-dihydro-1,3-oxazol-2-yl)thien-3-yl]oxy}acetic acid, {[5-(3-{[1-(benzylsulfonyl)piperidin-4-yl]amino}phenyl)-4-methyl-2-(morpholin-4-ylcarbonyl)thien-3-yl]oxy}acetic acid, [(4-methyl-2-(morpholin-4-ylcarbonyl)-5-{3-[(3,3,5,5-tetramethylcyclohexyl)amino]phenyl}thien-3-yl)oxy]acetic acid, 4-methyl-5-(3-{[1-(butylsulfonyl)piperidin-4-yl]amino}phenyl)-3-(2-methoxy-2-oxoethoxy)thiophene-2-carboxylic acid, 4-methyl-5-(3-{[1-(ethylsulfonyl)piperidin-4-yl]amino}phenyl)-3-(2-methoxy-2-oxoethoxy)thiophene-2-carboxylic acid, 4-methyl-5-(3-{[1-(isopropylsulfonyl)piperidin-4-yl]amino}phenyl)-3-(2-methoxy-2-oxoethoxy)thiophene-2-carboxylic acid, 5-{3-[acetyl(3,3,5,5-tetramethylcyclohexyl)amino]phenyl}-4-methyl-3-(2-methoxy-2-oxoethoxy)thiophene-2-carboxylic acid, [4-methyl-5-[3-(cyclohexylamino)phenyl]-2-(methoxycarbonyl)thien-3-yl]oxyacetic acid, {[5-(3-{[1-(benzylsulfonyl)piperidin-4-yl]amino}phenyl)-4-methyl-2-(ethoxycarbonyl)thien-3-yl]oxy}acetic acid, {[5-(3-{[1-(benzylsulfonyl)piperidin-4-yl]amino}phenyl)-4-methyl-2-(isopropoxycarbonyl)thien-3-yl]oxy}acetic acid, ({5-(3-{[1-(benzylsulfonyl)piperidin-4-yl]amino}phenyl)-4-methyl-2-[(cyclohexyloxy)carbonyl]thien-3-yl}oxy)acetic acid, {[4-methyl-2-(ethoxycarbonyl)-5-(3-{[1-(phenylsulfonyl)piperidin-4-yl]amino}phenyl)thien-3-yl]oxy}acetic acid, [4-methyl-2-(methoxycarbonyl)-5-(3-{[1-(phenylsulfonyl)piperidin-4-yl]amino}phenyl)thien-3-yl]oxyacetic acid, [(4-methyl-2-(ethoxycarbonyl)-5-{3-[(3,3,5,5-tetramethylcyclohexyl)amino]phenyl}thien-3-yl)oxy]acetic acid, and {[4,5-dibromo-2-(methoxyacetyl)thien-3-yl]oxy}acetic acid.

In some embodiments, the compound can be selected from the group consisting of 3-(carboxymethoxy)-4-phenylthiophene-2-carboxylic acid, 3-(carboxymethoxy)-4-(1H-indol-5-yl)thiophene-2-carboxylic acid, 4-methyl-3-(carboxymethoxy)-5-phenylthiophene-2-carboxylic acid, 4-methyl-3-(carboxymethoxy)-5-[4-(dimethylamino)phenyl]thiophene-2-carboxylic acid, 5-(4-aminophenyl)-4-methyl-3-(carboxymethoxy)thiophene-2-carboxylic acid, 4-(carboxymethoxy)-3,3'-bithiophene-5-carboxylic acid, 5-[4-(acetylamino)phenyl]-4-methyl-3-(carboxymethoxy)thiophene-2-carboxylic acid, 5-(3-aminophenyl)-4-methyl-3-(carboxymethoxy)thiophene-2-carboxylic acid, 3-(carboxymethoxy)-4-[3-(trifluoromethyl)phenyl]thiophene-2-carboxylic acid, 4-methyl-3-(carboxymethoxy)-5-(1-naphthyl)thiophene-2-carboxylic acid, 4-methyl-3-(carboxymethoxy)-5-(2-naphthyl)thiophene-2-carboxylic acid, 3-(carboxymethoxy)-4,5-diphenylthiophene-2-carboxylic acid, {[2-(2H-tetraazol-5-yl)thieno[2,3-b]pyridin-3-yl]oxy}acetic acid, 5-[3-(acetylamino)phenyl]-4-methyl-3-(carboxymethoxy)thiophene-2-carboxylic acid, 4-methyl-3-(carboxymethoxy)-5-[3-(isobutyrylamino)phenyl]thiophene-2-carboxylic acid, 4-methyl-3-(carboxymethoxy)-5-[3-(propionylamino)phenyl]thiophene-2-carboxylic acid, 4-methyl-5-[3-(butyrylamino)phenyl]-3-(carboxymethoxy)thiophene-2-carboxylic acid, 4-methyl-3-(carboxymethoxy)-5-{3-[(cyclohexylcarbonyl)amino]phenyl}thiophene-2-carboxylic acid, 4-methyl-3-(carboxymethoxy)-5-(4-hydroxyphenyl)thiophene-2-carboxylic acid, 4-methyl-3-(carboxymethoxy)-5-{4-[(methoxycarbonyl)amino]phenyl}thiophene-2-carboxylic acid, 5-[4-(benzoylamino)phenyl]-4-methyl-3-(carboxymethoxy)thiophene-2-carboxylic acid, 4-methyl-3-(carboxymethoxy)-5-[3-(hexanoylamino)phenyl]thiophene-2-carboxylic acid, 4-methyl-3-(carboxymethoxy)-5-{3-[(cyclopentylcarbonyl)amino]phenyl}thiophene-2-carboxylic acid, 4-methyl-3-(carboxymethoxy)-5-{3-[(methoxycarbonyl)amino]phenyl}thiophene-2-carboxylic acid, 4-methyl-3-(carboxymethoxy)-5-(3-{[(2,2,2-trifluoroethyl)sulfonyl]amino}phenyl)thiophene-2-carboxylic acid, 5-(1,1'-biphenyl-3-yl)-4-methyl-3-(carboxymethoxy)thiophene-2-carboxylic acid, 4-methyl-3-(carboxymethoxy)-5-(3-{[(isopropylamino)carbonyl]amino}phenyl)thiophene-2-carboxylic acid, 4-methyl-3-(carboxymethoxy)-5-(4-fluorophenyl)thiophene-2-carboxylic acid, 3-bromo-4-(carboxymethoxy)-2,3'-bithiophene-5-carboxylic acid, 5-(4-{[(benzyloxy)acetyl]amino}phenyl)-4-methyl-3-(carboxymethoxy)thiophene-2-carboxylic acid, 5-(1,3-benzodioxol-5-yl)-4-methyl-3-(carboxymethoxy)thiophene-2-carboxylic acid, 4-methyl-5-(4-{[(tert-butoxycarbonyl)amino]methyl}phenyl)-3-(carboxymethoxy)thiophene-2-carboxylic acid, 4-methyl-3-(carboxymethoxy)-5-(3-{[(diethylamino)carbonyl]amino}phenyl)thiophene-2-carboxylic acid, 4-methyl-3-(carboxymethoxy)-5-(3-hydroxyphenyl)thiophene-2- carboxylic acid, 4-methyl-3-(carboxymethoxy)-5-(3-methoxyphenyl)thiophene-2-carboxylic acid, 4-methyl-5-[3-({[1-(tert-butoxycarbonyl)piperidin-4-yl]carbonyl}amino)phenyl]-3-(carboxymethoxy)thiophene-2-carboxylic acid, 4-methyl-5-[3-({[1-(tert-butoxycarbonyl)piperidin-3-yl]carbonyl}amino)phenyl]-3-(carboxymethoxy)thiophene-2-carboxylic acid, 4-methyl-3-(carboxymethoxy)-5-{4-[(methylsulfonyl)amino]phenyl}thiophene-2-carboxylic acid, carboxylic acid, 4-methyl-3-(carboxymethoxy)-5-[4-({[4-(trifluoromethyl)phenyl]sulfonyl}amino)phenyl]thiophene-2-carboxylic acid, 4-methyl-5-(4-{[N-(tert-butoxycarbonyl)glycyl]amino}phenyl)-3-(carboxymethoxy)thiophene-2-carboxylic acid, 4-methyl-3-(carboxymethoxy)-5-[4-(hydroxymethyl)phenyl]thiophene-2 -carboxylic acid, 4-methyl-3-(carboxymethoxy)-5-{3-[(piperidin-4-ylcarbonyl)amino]phenyl}thiophene-2-carboxylic acid, 4-methyl-3-(carboxymethoxy)-5-{3-[(piperidin-3-ylcarbonyl)amino]phenyl}thiophene-2-carboxylic acid, 5-(1-benzofuran-2-yl)-4-methyl-3-(carboxymethoxy)thiophene-2-carboxylic acid, 4-methyl-3-(carboxymethoxy)-5-(4-{[(phenylsulfonyl)amino]methyl}phenyl)thiophene-2-carboxylic acid, 4-methyl-3-(carboxymethoxy)-5-(4-methoxyphenyl)thiophene-2-carboxylic acid, 3-(carboxymethoxy)-5-[4-(trifluoromethoxy)phenyl]thiophene-2-carboxylic acid, 4-methyl-3-(carboxymethoxy)-5-(4-{[(ethylsulfonyl)amino]methyl}phenyl)thiophene-2-carboxylic acid, 5-{4-[(acetylamino)methyl]phenyl]4-methyl-3-(carboxymethoxy)thiophene-2-carboxylic acid, 4-methyl-3-(carboxymethoxy)-5-(4-{[(ethoxycarbonyl)amino]methyl}phenyl)thiophene-2-carboxylic acid, 4-methyl-3-(carboxymethoxy)-5-[4-({[(isopropylamino)carbonyl]amino}methyl)phenyl]thiophene-2-carboxylic acid, 4-methyl-3-(carboxymethoxy)-5-{3-[(phenylsulfonyl)amino]phenyl}thiophene-2-carboxylic acid, 5-[4-(aminomethyl)phenyl]-4-methyl-3-(carboxymethoxy)thiophene-2-carboxylic acid, 4-methyl-3-(carboxymethoxy)-5-pyridin-3-ylthiophene-2-carboxylic acid, 4-methyl-5-{4-[(carboxycarbonyl)amino]phenyl}-3-(carboxymethoxy)thiophene-2-carboxylic acid, 4-methyl-3-(carboxymethoxy)-5-{3-[(ethylsulfonyl)amino]phenyl}thiophene-2-carboxylic acid, 3-(carboxymethoxy)-5-(2-methylphenyl)thiophene-2-carboxylic acid, 4-methyl-3-(carboxymethoxy)-5-{3-[(3,3,3-trifluoropropanoyl)amino]phenyl}thiophene-2-carboxylic acid, 5-{3-[(benzylsulfonyl)amino]phenyl)}4-methyl-3-(carboxymethoxy)thiophene-2-carboxylic acid, 4-methyl-3-(carboxymethoxy)-5-(4-{[(isopropylamino)carbonyl]amino}phenyl)thiophene-2-carboxylic acid, 4-methyl-3-(carboxymethoxy)-5-{4-[(pyridin-3-ylcarbonyl)amino]phenyl}thiophene-2-carboxylic acid, 4-methyl-3-(carboxymethoxy)-5-(4-formylphenyl)thiophene-2-carboxylic acid, 3-bromo-4-(carboxymethoxy)-2'-formyl-2,3'-bithiophene-5-carboxylic acid, 4-methyl-3-(carboxymethoxy)-5-[3-({[4-(trifluoromethyl)phenyl]sulfonyl}amino)phenyl]thiophene-2-carboxylic acid, 4-methyl-3-(carboxymethoxy)-5-[3-({[4-(trifluoromethoxy)phenyl]sulfonyl}amino)phenyl]thiophene-2-carboxylic acid, 4-methyl-3-(carboxymethoxy)-5-{3-[(3,3,3-(trifluoromethyl)phenyl]sulfonyl}amino)phenyl]thiophene-2-carboxylic acid, 4-methyl-3-(carboxymethoxy)-5-[4-(glycylamino)phenyl]thiophene-2-carboxylic acid, 4-methyl-3-(carboxymethoxy)-5-{4-[(phenylsulfonyl)amino]phenyl}thiophene-2-carboxylic acid, 4-methyl-3-(carboxymethoxy)-5-[4-(methyl {[4-(trifluoromethyl)phenyl]sulfonyl}amino)phenyl]thiophene-2-carboxylic acid, 5-[4-(anilinocarbonyl)phenyl]-4-methyl-3-(carboxymethoxy)thiophene-2-carboxylic acid, 4-methyl-3-(carboxymethoxy)-5-[3-({[2-(trifluoromethyl)phenyl]sulfonyl}amino)phenyl]thiophene-2-carboxylic acid, 3-bromo-4-(carboxymethoxy)-2'-[(isobutylamino)methyl]-2,3'-bithiophene-5-carboxylic acid, 4-methyl-3-(carboxymethoxy)-5-(3-{[(2-cyanophenyl)sulfonyl]amino}phenyl)thiophene-2-carboxylic acid, 4-methyl-3-(carboxymethoxy)-5-(3-{[(4-methoxyphenyl)sulfonyl]amino}phenyl)thiophene-2-carboxylic acid, 4-methyl-3-(carboxymethoxy)-5-(3-{[(4-cyanophenyl)sulfonyl]amino}phenyl)thiophene-2-carboxylic acid, 4-methyl-3-(carboxymethoxy)-5-{4-[(isopropylamino)carbonyl]phenyl}thiophene-2-carboxylic acid, 5-[3-(benzylamino)phenyl]-4-methyl-3-(carboxymethoxy)thiophene-2-carboxylic acid, 5-[4-({[(1S)-2-amino-1-methyl-2-oxoethyl]amino}carbonyl)phenyl]-4-methyl-3-, (carboxymethoxy)thiophene-2-carboxylic acid, 5-[3-(benzoylamino)phenyl]-4-methyl-3-(carboxymethoxy)thiophene-2-carboxylic acid, 4-methyl-3-(carboxymethoxy)-5-(4-{[(2,6-difluorophenyl)sulfonyl]amino}phenyl)thiophene-2-carboxylic acid, 4-methyl-3-(carboxymethoxy)-5-(4-{[(2,6-dichlorophenyl)sulfonyl]amino}phenyl)thiophene-2-carboxylic acid, 5-[3-(anilinomethyl)phenyl]-4-methyl-3-(carboxymethoxy)thiophene-2-carboxylic acid, 4-methyl-3-(carboxymethoxy)-5-[3-(1-phenylethoxy)phenyl]thiophene-2-carboxylic acid, 4-methyl-3-(carboxymethoxy)-5-[4-({[4-(trifluoromethyl)phenyl]amino}carbonyl)phenyl]thiophene-2-carboxylic acid, 4-methyl-3-(carboxymethoxy)-5-[3-(2-furoylamino)phenyl]thiophene-2-carboxylic acid, 4-methyl-3-(carboxymethoxy)-5-[3-(3-furoylamino)phenyl]thiophene-2-carboxylic acid, 4-methyl-3-(carboxymethoxy)-5-(3-formyl-4-methoxyphenyl)thiophene-2-carboxylic acid, 4-methyl-3-(carboxymethoxy)-5-[4-({[2-(trifluoromethyl)phenyl]sulfonyl}amino)phenyl]thiophene-2-carboxylic acid, 4-methyl-3-(carboxymethoxy)-5-[4-({[3-(trifluoromethyl)phenyl]sulfonyl}amino)phenyl]thiophene-2-carboxylic acid, 4-methyl-3-(carboxymethoxy)-5-{3-[(4-3-(carboxymethoxy)-4-methylthiophene-2-carboxylic acid, 3-(carboxymethoxy)-4-methylthiophene-2-carboxylic acid, 4-methyl-3-(carboxymethoxy)-5-(3-{[2-(trifluoromethyl)benzoyl]amino}phenyl)thiophene-2-carboxylic acid, 4-methyl-3-(carboxymethoxy)-5-(3-{[3-(trifluoromethyl)benzyl]amino}phenyl)thiophene-2-carboxylic acid, 4-methyl-3-(carboxymethoxy)-5-(3-{[2-(trifluoromethyl)benzyl]amino}phenyl)thiophene-2-carboxylic acid, 5-[3-(benzyloxy)phenyl]-4-methyl-3-(carboxymethoxy)thiophene-2-carboxylic acid, 4-methyl-5-[3-(1-carboxymethoxy)phenyl]-3-(carboxymethoxy)thiophene-2-carboxylic acid, 4-methyl-3-(carboxymethoxy)-5-{3-[(2-fluorobenzyl)amino]phenyl}thiophene-2-carboxylic acid, 4-methyl-3-(carboxymethoxy)-5-[3-({[3-(trifluoromethyl)phenyl]amino}methyl)phenyl]thiophene-2-carboxylic acid, 4-methyl-3-(carboxymethoxy)-5-(3-{[(3,4-difluorophenyl)amino]methyl}phenyl)thiophene-2-carboxylic acid, 4-methyl-3-(carboxymethoxy)-5-{3-[(2-furylmethyl)amino]phenyl}thiophene-2-carboxylic acid, 4-methyl-3-(carboxymethoxy)-5-{3-[(cyclohexylamino)methyl]phenyl thiophene-2-carboxylic acid, 5-bromo-3-(carboxymethoxy)-4-methylthiophene-2-carboxylic acid, 4-methyl-3 -(carboxymethoxy)-5-(3-{[(3-nitrophenyl)amino]methyl}phenyl)thiophene-2 carboxylic acid, 4-methyl-5-[3-({[4-methyl-3-(trifluoromethyl)phenyl]amino}methyl)phenyl]-3-(carboxymethoxy)thiophene-2-carboxylic acid, 5-[3-(anilinomethyl)-4-methoxyphenyl]-4-methyl-3-(carboxymethoxy)thiophene-2-carboxylic acid, 4-methyl-5-{3-[(E)-2-carboxyethenyl]-4-methoxyphenyl}-3-(carboxymethoxy)thiophene-2-carboxylic acid, 4-methyl-3-(carboxymethoxy)-5-{3-[(3-furylmethyl)amino]phenyl}thiophene-2-carboxylic acid, 4-methyl-3-(carboxymethoxy)-5-{3-[(3-fluorobenzyl)amino]phenyl}thiophene-2-carboxylic acid, 4-methyl-3-(carboxymethoxy)-5-{3-[(2-fluorobenzoyl)amino]phenyl}thiophene-2-carboxylic acid, 4-methyl-3-(carboxymethoxy)-5-(3-[(3-fluorobenzoyl)amino]phenyl}thiophene-2-carboxylic acid, 4-methyl-3-(carboxymethoxy)-5-(3-{[(3,5-difluorophenyl)amino]methyl}phenyl)thiophene-2-carboxylic acid, 4-methyl-3-(carboxymethoxy)-5-(3-{[(3-fluoro-4-methylphenyl)amino]methyl}phenyl)thiophene-2-carboxylic acid, 4-methyl-3-(carboxymethoxy)-5-{3-[(3-cyanobenzyl)amino]phenyl}thiophene-2-carboxylic acid, 4-methyl-3-(carboxymethoxy)-5-{3-[(pyridin-3-ylcarbonyl)amino]phenyl}thiophene-2-carboxylic acid, carboxylic acid, 4-methyl-3-(carboxymethoxy)-5-{3-[(cyclohexylmethyl)amino]phenyl}thiophene-2-carboxylic acid, carboxylic acid, 4-methyl-3-(carboxymethoxy)-5-{3-[(pyridin-3-ylmethyl)amino]phenyl}thiophene-2-carboxylic acid, carboxylic acid, 4-methyl-3-(carboxymethoxy)-5-[3-(cyclohexylamino)phenyl]thiophene-2-carboxylic acid, acid, 4-methyl-3-(carboxymethoxy)-5-(1H-indol-5-yl)thiophene-2-carboxylic acid, 4-methyl-5-{4-[(carboxyacetyl)amino]phenyl}-3-(carboxymethoxy)thiophene-2-carboxylic acid, 4-methyl-3-(carboxymethoxy)-5-[3-({[4-chloro-3-(trifluoromethyl)phenyl]amino}methyl)phenyl]thiophene-2-carboxylic acid, 4-methyl-3-(carboxymethoxy)-5-(3-{[(4-methyl-3-nitrophenyl)amino]methyl}phenyl)thiophene-2-carboxylic acid, 4-methyl-3-(carboxymethoxy)-5-{3-[(4,4,4-trifluorobutanoyl)amino]phenyl}thiophene-2-carboxylic acid, 4-methyl-3-(carboxymethoxy)-5-{3-[(4-fluorobenzyl)amino]phenyl}thiophene-2-carboxylic acid, 4-methyl-3-(carboxymethoxy)-5-[4-(3-furoylamino)phenyl]thiophene-2-carboxylic acid, 5-[3-({[3,5-bis(trifluoromethyl)phenyl]amino}methyl)-4-methoxyphenyl]-4-methyl-3-(carboxymethoxy)thiophene-2-carboxylic acid, 4-methyl-3-(carboxymethoxy)-5-[3-({[4-(trifluoromethyl)phenyl]amino}carbonyl)phenyl]thiophene-2-carboxylic acid, 4-methyl-3-(carboxymethoxy)-5-(3-{[4-(trifluoromethyl)benzyl]amino}phenyl)thiophene-2-carboxylic acid, 4-methyl-3-(carboxymethoxy)-5-{3-[(4-methoxybenzyl)amino]phenyl}thiophene-2-carboxylic acid, 4-methyl-3-(carboxymethoxy)-5-[4-(2-furoylamino)phenyl]thiophene-2-carboxylic acid, 4-methyl-5-[4-({[1-(tert-butoxycarbonyl)piperidin-4-yl]carbonyl}amino)phenyl]-3-(carboxymethoxy)thiophene-2-carboxylic acid, 4-methyl-5-[4-({[1-(tert-butoxycarbonyl)piperidin-3-yl]carbonyl}amino)phenyl]-3-(carboxymethoxy)thiophene-2-carboxylic acid, 5-(3-{[4-(benzyloxy)benzyl]amino}phenyl)-4-methyl-3-(carboxymethoxy)thiophene-2-carboxylic acid, 4-methyl-3-(carboxymethoxy)-5-{3-[(4-phenoxybenzyl)amino]phenyl}thiophene-2-carboxylic acid, 4-methyl-3-(carboxymethoxy)-5-(4-methoxy-3-{(1E)-3-oxo-3-[(2,2,2-trifluoroethyl)amino]prop-1-enyl}phenyl)thiophene-2-carboxylic acid, 4-methyl-3-(carboxymethoxy)-5-[3-(2-naphthylmethoxy)phenyl]thiophene-2-carboxylic acid, 5-[3-(2,1,3-benzoxadiazol-5-ylmethoxy)phenyl]-4-methyl-3-(carboxymethoxy)thiophene-2-carboxylic acid, 4-methyl-3-(carboxymethoxy)-5-(3-{[(2-hydroxypyridin-3-yl)carbonyl]amino}phenyl)thiophene-2-carboxylic acid, 3-(carboxymethoxy)-4-methyl-5-phenylthiophene-2-carboxylic acid, 4-methyl-3-(carboxymethoxy)-5-[3-(isonicotinoylamino)phenyl]thiophene-2-carboxylic acid, 4-methyl-3-(carboxymethoxy)-5-{3-[(quinolin-3-ylcarbonyl)amino]phenyl}thiophene-2-carboxylic acid, 5-[3-(benzylamino)phenyl]-3-(carboxymethoxy)-4-methylthiophene-2-carboxylic acid, 3-(carboxymethoxy)-5-{3-[(cyclohexylmethyl)amino]phenyl}4-methylthiophene-2-carboxylic acid, 4-methyl-3-(carboxymethoxy)-5-{3-[(pyridin-2-ylcarbonyl)amino]phenyl}thiophene-2-carboxylic acid, 4-methyl-3-(carboxymethoxy)-5-{3-[(2-naphthylmethyl)amino]phenyl}thiophene-2-carboxylic acid, 4-methyl-3-(carboxymethoxy)-5-(3-{[(1-oxidopyridin-3-yl)carbonyl]amino}phenyl)thiophene-2-carboxylic acid, 3-(carboxymethoxy)-4-methyl-5-{3-[(pyridin-3-ylcarbonyl)amino]phenyl}thiophene-2-carboxylic acid, 3-(carboxymethoxy)-5-(3-{[(carboxymethyl)sulfonyl]amino}phenyl)-4-methylthiophene-2-carboxylic acid, 4-methyl-3-(carboxymethoxy)-5-{3-[(pyridin-2-ylacetyl)amino]phenyl}thiophene-2-carboxylic acid, 4-methyl-3-(carboxymethoxy)-5-{3-[(pyridin-3-ylacetyl)amino]phenyl}thiophene-2-carboxylic acid, 4-methyl-5-{3-[(3-carboxybenzyl)amino]phenyl}-3-(carboxymethoxy)thiophene-2-carboxylic acid, 4-methyl-3-(carboxymethoxy)-5-{3-[(pyrazin-2-ylcarbonyl)amino]phenyl}thiophene-2-carboxylic acid, 4-methyl-3-(carboxymethoxy)-5-(3-{[3-(trifluoromethoxy)benzyl]amino}phenyl)thiophene-2-carboxylic acid, 4-methyl-3-(carboxymethoxy)-5-(3-{[2-(trifluoromethoxy)benzyl]amino}phenyl)thiophene-2-carboxylic acid, 4-methyl-3-(carboxymethoxy)-5-{3-[(2-hydroxybenzyl)amino]phenyl}thiophene-2-carboxylic acid, 4-methyl-5-{3-[(3-carboxybenzyl)oxy]phenyl}-3-(carboxymethoxy)thiophene-2-carboxylic acid, 4-methyl-3-(carboxymethoxy)-5-{3-[(4-methylbenzyl)amino]phenyl}thiophene-2-carboxylic acid, 4-methyl-3-(carboxymethoxy)-5-{3-[(pyridin-4-ylacetyl)amino]phenyl}thiophene-2-carboxylic acid, 4-methyl-3-(carboxymethoxy)-5-{3-[(4-chlorobenzyl)amino]phenyl}thiophene-2-carboxylic acid, 4-methyl-3-(carboxymethoxy)-5-(3-{[3-(trifluoromethoxy)benzyl]oxy}phenyl)thiophene-2-carboxylic acid, 4-methyl-3-(carboxymethoxy)-5-[3-cyclopentylamino)phenyl]thiophene-2-carboxylic acid, 4-methyl-3-(carboxymethoxy)-5-{3-[(4-isopropylbenzyl)amino]phenyl}thiophene-2-carboxylic acid, 5-{3-[(1-acetylpiperidin-4-yl)amino]phenyl}-4-methyl-3-(carboxymethoxy)thiophene-2-carboxylic acid, 5-[4-(benzyloxy)phenyl]-4-methyl-3-(carboxymethoxy)thiophene-2-carboxylic acid, 4-methyl-3-(carboxymethoxy)-5-[3-(5-fluoro-1H-benzimidazol-2-yl)phenyl]thiophene-2-carboxylic acid, 4-methyl-3-(carboxymethoxy)-5-[3-(cycloheptylamino)phenyl]thiophene-2-carboxylic acid, 5-[3-(bicyclo[3.3.1]non-9-ylamino)phenyl]-4-methyl-3-(carboxymethoxy)thiophene-2-carboxylic acid, 5-(anilinocarbonyl)-3-(carboxymethoxy)thiophene-2-carboxylic acid, 4-methyl-3-(carboxymethoxy)-5-{3-[(4-ethylcyclohexyl)amino]phenyl}thiophene-2-carboxylic acid, 3-(carboxymethoxy)-5-(4-hydroxyphenyl)-4-methylthiophene-2-carboxylic acid, 4-methyl-3-(carboxymethoxy)-5-{3-[(4-phenylcyclohexyl)amino]phenyl}thiophene-2-carboxylic acid, 4-methyl-3-(carboxymethoxy)-5-{3-[(4-phenylcyclohexyl)amino]phenyl}thiophene-2-carboxylic acid, 4-methyl-3-(carboxymethoxy)-5-[2-(hydroxymethyl)phenyl]thiophene-2-carboxylic acid, 3-(carboxymethoxy)-5-(4-{[(isopropylamino)carbonyl]amino}phenyl)-4-methylthiophene-2-carboxylic acid, 5-[3,4-bis(benzyloxy)phenyl]-4-methyl-3-(carboxymethoxy)thiophene-2-carboxylic acid, 5-[3-(benzyloxy)-4-hydroxyphenyl]-4-methyl-3-(carboxymethoxy)thiophene-2-carboxylic acid, 5-[4-(benzyloxy)-3-hydroxyphenyl]-4-methyl-3-(carboxymethoxy)thiophene-2-carboxylic acid, 2-{3-[3-bromo-5-carboxy-4-(carboxymethoxy)thien-2-yl]phenyl}-1H-benzimidazole-5-carboxylic acid, carboxylic acid, 3-(carboxymethoxy)thiophene-2-carboxylic acid, 4-methyl-3-(carboxymethoxy)-5-[3-(cyclohexylmethoxy)phenyl]thiophene-2-carboxylic acid, 4-methyl-3-(carboxymethoxy)-5-pyridin-4-ylthiophene-2-carboxylic acid, 4-methyl-3-(carboxymethoxy)-5-{3-[(1-cyclohexylethyl)amino]phenyl}thiophene-2-carboxylic acid, 4-methyl-3-(carboxymethoxy)-5-(3-{[1-(methoxycarbonyl)piperidin-4-yl]amino}phenyl)thiophene-2-carboxylic acid, 4-methyl-3-(carboxymethoxy)-5-{3-[(3,3,5,5-tetramethylcyclohexyl)amino]phenyl}thiophene-2-carboxylic acid, 5-[3-(2-adamantylamino)phenyl]-4-methyl-3-(carboxymethoxy)thiophene-2-carboxylic acid, 3-(carboxymethoxy)-4-methyl-5-{3-[(3-phenoxybenzyl)amino]phenyl}thiophene-2-carboxylic acid, 5-{3-[(3-bromobenzyl)amino]phenyl}-3-(carboxymethoxy)-4-methylthiophene-2-carboxylic acid, 3-(carboxymethoxy)-4-methyl-5-(3-{[3-(trifluoromethyl)benzyl]amino}phenyl)thiophene-2-carboxylic acid, 5-[3-([(benzylamino)carbonyl]{1-[(benzylamino)carbonyl]piperidin-4-yl}amino)phenyl]-4-methyl-3-(carboxymethoxy)thiophene-2-carboxylic acid, 5-[3-({1-[(benzylamino)carbonyl]piperidin-4-yl}amino)phenyl]-4-methyl-3-(carboxymethoxy)thiophene-2-carboxylic acid, 4-methyl-3-(carboxymethoxy)-5-{3-[(3-nitrobenzyl)amino]phenyl}thiophene-2-carboxylic acid, 4-methyl-3-(carboxymethoxy)-5-(3-{[1-(methylsulfonyl)piperidin-4-yl]amino}phenyl)thiophene-2-carboxylic acid, 4-methyl-3-(carboxymethoxy)-5-[3-({3-[(methylsulfonyl)amino]benzyl}amino)phenyl]thiophene-2-carboxylic acid, 5-(3-{[3-(acetylamino)benzyl]amino}phenyl)-4-methyl-3-(carboxymethoxy)thiophene-2-carboxylic acid, 5-{3-[(3-aminobenzyl)amino]phenyl}-4-methyl-3-(carboxymethoxy)thiophene-2-carboxylic acid, 4-methyl-3-(carboxymethoxy)-5-[3-(tetrahydro-2H-pyran-4-ylamino)phenyl]thiophene-2-carboxylic acid, 5-(3-{[acetyl(cyclohexyl)amino]methyl}phenyl)-4-methyl-3-(carboxymethoxy)thiophene-2-carboxylic acid, 4-methyl-3-(carboxymethoxy)-5-(3-{[1-(phenylsulfonyl)piperidin-4-yl]amino}phenyl)thiophene-2-carboxylic acid, 5-(3-{[3,5-bis(trifluoromethyl)benzyl]oxy}phenyl)-4-methyl-3-(carboxymethoxy)thiophene-2-carboxylic acid, 4-methyl-5-[3-({[1-(tert-butoxycarbonyl)piperidin-4-yl]methyl}amino)phenyl]-3-(carboxymethoxy)thiophene-2-carboxylic acid, 5-(3-{[1-(benzylsulfonyl)piperidin-4-yl]amino}phenyl)-4-methyl-3-(carboxymethoxy)thiophene-2-carboxylic acid, 4-methyl-3-(carboxymethoxy)-5-(3-{[1-(ethylsulfonyl)piperidin-4-yl]methyl}amino)phenyl]thiophene-2-carboxylic acid, yl]methyl}amino)phenyl]thiophene-2-carboxylic acid, 4-methyl-3-(carboxymethoxy)-5-[3-({[1-(methylsulfonyl)piperidin-4-yl]methyl}amino)phenyl]thiophene-2-carboxylic acid, 4-methyl-3-(carboxymethoxy)-5-[3-({[1-(ethylsulfonyl)piperidin-4-yl]methyl}amino)phenyl]thiophene-2-carboxylic acid, 5-{3-[acetyl(benzyl)amino]phenyl}-4-methyl-3-(carboxymethoxy)thiophene-2-carboxylic acid, 4-methyl-3-(carboxymethoxy)-5-[3-({[1-(phenylsulfonyl)piperidin-4-yl]methyl}amino)phenyl]thiophene-2-carboxylic acid, 5-[3-({[1-(benzylsulfonyl)piperidin-4-yl]methyl}amino)phenyl]-4-methyl-3-(carboxymethoxy)thiophene-2-carboxylic acid, 4-methyl-3-(carboxymethoxy)-5-(3-{[1-(isopropylsulfonyl)piperidin-4-yl]amino}phenyl)thiophene-2-carboxylic acid, 5-{3-[acetyl(3,3,5,5-tetramethylcyclohexyl)amino]phenyl}-4-methyl-3-(carboxymethoxy)thiophene-2-carboxylic acid, 4-methyl-3-(carboxymethoxy)-5-[3-({[1-(methoxycarbonyl)piperidin-4-yl]methyl}amino)phenyl]thiophene-2-carboxylic acid, 4-methyl-3-(carboxymethoxy)-5-(3-{[1-(phenylacetyl)piperidin-4-yl]amino}phenyl)thiophene-2-carboxylic acid, 5-{3-[(1-benzoylpiperidin-4-yl)amino]phenyl}-4-methyl-3-(carboxymethoxy)thiophene-2-carboxylic acid, 5-(3-{[acetyl(phenyl)amino]methyl}-4-methoxyphenyl)-4-methyl-3-(carboxymethoxy)thiophene-2-carboxylic acid, 4-methyl-3-(carboxymethoxy)-5-{4-[(3,3,5,5-tetramethylcyclohexyl)amino]phenyl}thiophene-2-carboxylic acid, 5-(3-{[acetyl(3,3,5,5-tetramethylcyclohexyl)amino]methyl}phenyl)-4-methyl-3-(carboxymethoxy)thiophene-2-carboxylic acid, 3-(carboxymethoxy)-4-methyl-5-{3-[(3,3,5,5-tetramethylcyclohexyl)amino]phenyl}thiophene-2-carboxylic acid, 3-(carboxymethoxy)-5-[3-(cycloheptylamino)phenyl]-4-methylthiophene-2-carboxylic acid, 4-methyl-5-(3-{[1-(tert-butoxycarbonyl)piperidin-4-yl]methoxy}phenyl)-3-(carboxymethoxy)thiophene-2-carboxylic acid, 4-methyl-5-(3-{[1-(butylsulfonyl)piperidin-4-yl]amino}phenyl)-3-(carboxymethoxy)thiophene-2-carboxylic acid, 3-(carboxymethoxy)-5-{4-[(3,3,5,5-tetramethylcyclohexyl)amino]phenyl}thiophene-2-carboxylic acid, 5-[3-({acetyl[1-(ethoxycarbonyl)piperidin-4-yl]amino}methyl)phenyl]-4-methyl-3-(carboxymethoxy)thiophene-2-carboxylic acid, 5-{3-[(1-{[3,5-bis(trifluoromethyl)benzyl]sulfonyl}piperidin-4-yl)amino]phenyl}-4-methyl-3-(carboxymethoxy)thiophene-2-carboxylic acid, 4-methyl-3-(carboxymethoxy)-5-(3-{[1-(propylsulfonyl)piperidin-4-yl]amino}phenyl)thiophene-2-carboxylic acid, 4-methyl-3-(carboxymethoxy)-5-(3-{[1-(1-naphthylsulfonyl)piperidin-4-,yl]amino}phenyl)thiophene-2-carboxylic acid, 4-methyl-3-(carboxymethoxy)-5-(3-{[1-(2-naphthylsulfonyl)piperidin-4-yl]amino}phenyl)thiophene-2-carboxylic acid, 4-methyl-3-(carboxymethoxy)-5-[3-({1-[(2-nitrobenzyl)sulfonyl]piperidin-4-yl}amino)phenyl]thiophene-2-carboxylic acid, 2-[(4,5-dibromo-2-carboxythien-3-yl)oxy]malonic acid, 5-(3-{[1-(benzylsulfonyl)piperidin-4-yl]methoxy}phenyl)-4-methyl-3-(carboxymethoxy)thiophene-2-carboxylic acid, 4-methyl-3-(carboxymethoxy)-5-{3-[(1-{[3-(trifluoromethyl)benzyl]sulfonyl}piperidin-4-yl)amino]phenyl}thiophene-2-carboxylic acid, 4-methyl-3-(carboxymethoxy)-5-[3-({1-[(4-fluorobenzyl)sulfonyl]piperidin-4-yl}amino)phenyl]thiophene-2-carboxylic acid, 4-methyl-3-(carboxymethoxy)-5-{3-[(1-{[4-(trifluoromethyl)benzyl]sulfonyl}piperidin-4-yl)amino]phenyl}thiophene-2-carboxylic acid, 4-methyl-3-(carboxymethoxy)-5-[3-({1-[(4-chlorobenzyl)sulfonyl]piperidin-4-yl}amino)phenyl]thiophene-2-carboxylic acid, 4-methyl-3-(carboxymethoxy)-5-[3-({1-[(3,5-dichlorobenzyl)sulfonyl]piperidin-4-yl}amino)phenyl]thiophene-2-carboxylic acid, 4-methyl-3-(carboxymethoxy)-5-[3-({1-[(3,4-dichlorobenzyl)sulfonyl]piperidin-4-yl}amino)phenyl]thiophene-2-carboxylic acid, 5-[3-({[1-(anilinocarbonyl)piperidin-4-yl]methyl}amino)phenyl]-4-methyl-3-(carboxymethoxy)thiophene-2-carboxylic acid, 4-methyl-3-(carboxymethoxy)-5-[3-({1-[(3-nitrobenzyl)sulfonyl]piperidin-4-yl}amino)phenyl]thiophene-2-carboxylic acid, 4-methyl-3-(carboxymethoxy)-5-[3-({1-[(3-chlorobenzyl)sulfonyl]piperidin-4-yl}amino)phenyl]thiophene-2-carboxylic acid, 4-methyl-3-(carboxymethoxy)-5-[3-({1-[(4-methylphenyl)sulfonyl]piperidin-4-yl}methoxy)phenyl]thiophene-2-carboxylic acid, 4-methyl-3-(carboxymethoxy)-5-[3-({1-[(2-phenylethyl)sulfonyl]piperidin-4-yl}amino)phenyl]thiophene-2-carboxylic acid, 5-{3-[({1-[(benzylamino)carbonyl]piperidin-4-yl}methyl)amino]phenyl}-4-methyl-3-(carboxymethoxy)thiophene-2-carboxylic acid, 4-methyl-3-(carboxymethoxy)-5-{3-[({1-

[(cyclohexylamino)carbonyl]piperidin-4-yl}methyl)amino]phenyl}thiophene-2-carboxylic acid, 5-(3-[1-(benzylsulfonyl)piperidin-4-yl]amino}phenyl)-3-(carboxymethoxy)thiophene-2-carboxylic acid, 4-methyl-5-(3-{[1-(tert-butoxycarbonyl)piperidin-4-yl]oxy}phenyl)-3-(carboxymethoxy)thiophene-2-carboxylic acid, 4-methyl-3-(carboxymethoxy)-5-(3 -{[cyclohexyl(methylsulfonyl)amino]methyl}phenyl)thiophene-2-carboxylic acid, 4-methyl-3-(carboxymethoxy)-5-(3-{[cyclohexyl(methoxycarbonyl)amino]methyl}phenyl)thiophene-2-carboxylic acid, 4-methyl-3-(carboxymethoxy)-5-[3-({cyclohexyl[(ethylamino)carbonyl]amino}methyl)phenyl]thiophene-2-carboxylic acid, 4-methyl-3-(carboxymethoxy)-5-(3-{[(1-{[(4-methoxyphenyl)amino]carbonyl}piperidin-4-yl)methyl]amino}phenyl)thiophene-2-carboxylic acid, 4-methyl-3-(carboxymethoxy)-5-(3-{[(1-{[(4-cyanophenyl)amino]carbonyl}piperidin-4-yl)methyl]amino}phenyl)thiophene-2-carboxylic acid, 4-methyl-3-(carboxymethoxy)-5-(3-{[(1-{t[(4-methylphenyl)amino]carbonyl piperidin-4-yl)methyl]amino}phenyl)thiophene-2-carboxylic acid, 4-methyl-3-(carboxymethoxy)-5-(3-{[1-(phenylsulfonyl)piperidin-4-yl]methoxy}phenyl)thiophene-2-carboxylic acid, 4-methyl-3-(carboxymethoxy)-5-(3-{[(1-{[(2-methoxyphenyl)amino]carbonyl}piperidin-4-yl)methyl]amino)phenyl)thiophene-2-carboxylic acid, 4-methyl-3-(carboxymethoxy)-5-(3-{[(1-{[(3-chlorophenyl)amino]carbonyl}piperidin-4-yl)methyl]amino}phenyl)thiophene-2-carboxylic acid, 4-methyl-3-(carboxymethoxy)-5-(3-{[(1-{[(2-chlorophenyl)amino]carbonyl}piperidin-4-yl)methyl]amino}phenyl)thiophene-2-carboxylic acid, 4-methyl-3-(carboxymethoxy)-5-(3-{[1-(methylsulfonyl)piperidin-4-yl]methoxy}phenyl)thiophene-2-carboxylic acid, 4-methyl-3-(carboxymethoxy)-5-[3-(hydroxymethyl)phenyl]thiophene-2-carboxylic acid, 5-(3-{[1-(anilinocarbonyl)piperidin-4-yl]oxy}phenyl)-4-methyl-3-(carboxymethoxy)thiophene-2-carboxylic acid, 4-methyl-3-(carboxymethoxy)-5-(3-{[1-(phenoxycarbonyl)piperidin-4-yl]oxy}phenyl)thiophene-2-carboxylic acid, 5-(3-{[1-(benzylsulfonyl)piperidin-4-yl]oxy}phenyl)-4-methyl-3-(carboxymethoxy)thiophene-2-carboxylic acid, 5-(3-{[1-(anilinocarbonyl)piperidin-4-yl]methoxy}phenyl)-4-methyl-3-(carboxymethoxy)thiophene-2-carboxylic acid, (carboxymethoxy)thiophene-2-carboxylic acid, 4-methyl-3-(carboxymethoxy)-5-[3-({1-[(ethylamino)carbonyl]piperidin-4-yl}methoxy)phenyl]thiophene-2-carboxylic acid, 4-methyl-3-(carboxymethoxy)-5-[3-({1-[(2-methylbenzyl)sulfonyl]piperidin-4-yl}amino)phenyl]thiophene-2-carboxylic acid, 4-methyl-3-(carboxymethoxy)-5-[3-({1-[(3-methylbenzyl)sulfonyl]piperidin-4-yl}amino)phenyl]thiophene-2-carboxylic acid, 4-methyl-3-(carboxymethoxy)-5-(3-{[(1-{[(3-methoxyphenyl)amino]carbonyl}piperidin-4-yl)methyl]amino}phenyl)thiophene-2-carboxylic acid, 4-methyl-3-(carboxymethoxy)-5-(3-{[(1-{[(3-methylphenyl)amino]carbonyl}piperidin-4-yl)methyl]amino}phenyl)thiophene-2-carboxylic acid, 4-methyl-3-(carboxymethoxy)-5-(3-{[(1-{[(2-methylphenyl)amino]carbonyl}piperidin-4-yl)methyl]amino}phenyl)thiophene-2-carboxylic acid, 4-methyl-3-(carboxymethoxy)-5-(3-{[1-(methoxycarbonyl)piperidin-4-yl]methoxy}phenyl)thiophene-2-carboxylic acid, 4-methyl-3-(carboxymethoxy)-5-(3-{[1-(phenoxycarbonyl)piperidin-4-yl]methoxy}phenyl)thiophene-2-carboxylic acid, 4-methyl-3-(carboxymethoxy)-5-{3-[1-{[(2-chlorophenyl)amino]carbonyl}piperidin-4-yl)methoxy]phenyl}thiophene-2-carboxylic acid, 4-methyl-3-(carboxymethoxy)-5-{3-[(1-{[(2-methylphenyl)amino]carbonyl}piperidin-4-yl)methoxy]phenyl}thiophene-2-carboxylic acid, 4-methyl-3-(carboxymethoxy)-5-{3-[(1-{[(2-methoxyphenyl)amino]carbonyl}piperidin-4-yl)methoxy]phenyl}thiophene-2-carboxylic acid, 4-yl)methoxy]phenyl}thiophene-2-carboxylic acid, 4-methyl-3-(carboxymethoxy)-5-{3-[(1-{[(2-isopropylphenyl)amino]carbonyl}piperidin-4-yl)methoxy]phenyl}thiophene-2-carboxylic acid, 4-methyl-3-(carboxymethoxy)-5-{3-[(1-{[(2,6-diethylphenyl)amino]carbonyl}piperidin-4-yl)methoxy]phenyl}thiophene-2-carboxylic acid, 4-methyl-3-(carboxymethoxy)-5-[3-({1-[(mesitylamino)carbonyl]piperidin-4-yl}methoxy)phenyl]thiophene-2-carboxylic acid, 4-methyl-3-(carboxymethoxy)-5-{3-[(1-{[(2-isopropyl-6-methylphenyl)amino]carbonyl}piperidin-4-yl)methoxy]phenyl}thiophene-2-carboxylic acid, 4-methyl-3-(carboxymethoxy)-5-{3-[(1-{[(2-phenoxyphenyl)amino]carbonyl}piperidin-4-yl)methoxy]phenyl}thiophene-2-carboxylic acid, 4-methyl-3-(carboxymethoxy)-5-[3-({1-[(2,6-dimethylbenzyl)sulfonyl]piperidin-4-yl}amino)phenyl]thiophene-2-carboxylic acid, 4-methyl-3-(carboxymethoxy)-5-(3-{[(1-{[(2,6-dimethylphenyl)amino]carbonyl}piperidin-4-yl)methyl]amino}phenyl)thiophene-2-carboxylic acid, 4-methyl-3-(carboxymethoxy)-5-[3-({[1-({[2-(trifluoromethyl)phenyl]amino}carbonyl)piperidin-4-yl]methyl}amino)phenyl]thiophene-2-carboxylic acid, 4-methyl-3-(carboxymethoxy)-5-(3-{[(1-{[methyl(phenyl)amino]carbonyl}piperidin-4-(methylthio)phenyl]amino}carbonyl)piperidin-4-yl]methyl}amino)phenyl]thiophene-2-carboxylic acid, 4-methyl-3-(carboxymethoxy)-5-[3-({[1-({[2-(methylthio)phenyl]amino}carbonyl)piperidin-4-yl]methyl}amino)phenyl]thiophene-2-carboxylic acid, 4-methyl-3-(carboxymethoxy)-5-{3-[(1-{[(2,6-dimethylphenyl)amino]carbonyl}piperidin-4-yl)methoxy]phenyl}thiophene-2-carboxylic acid, 4-methyl-3-(carboxymethoxy)-5-(3-{[(1-{[(2,3-dimethylphenyl)amino]carbonyl}piperidin-4-yl)methyl]amino}phenyl)thiophene-2-carboxylic acid, 5-(3-{[1-(anilinocarbonyl)piperidin-4-yl]amino}phenyl)-4-methyl-3-(carboxymethoxy)thiophene-2-carboxylic acid, 4-methyl-3-(carboxymethoxy)-5-{3-[(1-{[(3-phenoxyphenyl)amino]carbonyl}piperidin-4-yl)methoxy]phenyl}thiophene-2-carboxylic acid, {[5-{3-[acetyl(3,3,5,5-tetramethylcyclohexyl)amino]phenyl}-2-(2H-tetrazol-5-yl)thien-3-yl]oxy}acetic acid, 4-methyl-3-(carboxymethoxy)-5-{3-[(1-{[(4-methyl-2-nitrophenyl)amino]carbonyl}piperidin-4-yl)methoxy]phenyl}thiophene-2-carboxylic acid, 4-methyl-3-(carboxymethoxy)-5-{3-[(1-{[(5-chloro-2-nitrophenyl)amino]carbonyl}piperidin-4-yl)methoxy]phenyl}thiophene-2-carboxylic acid, 4-methyl-3-(carboxymethoxy)-5-{3-[(1 {[(2-nitrophenyl)amino]carbonyl}piperidin-4 -yl)methoxy]phenyl}thiophene-2-carboxylic acid, 4-methyl-3-(carboxymethoxy)-5-{3-[(1-{[2-(1H-imidazol-1-yl)ethyl]sulfonyl}piperidin-4-yl)amino]phenyl}thiophene-2-carboxylic acid, 5-[3-({[5-(anilinocarbonyl)thien-2-yl]methyl}amino)phenyl]-4-methyl-3-(carboxymethoxy)thiophene-2-carboxylic acid, 5-{3-[({5-[(benzylamino)carbonyl]thien-2-yl}methyl)amino]phenyl}-4-methyl-3-(carboxymethoxy)thiophene-2-carboxylic acid, 4-methyl-3-(carboxymethoxy)-5-{3-[({5-[(cyclohexylamino)carbonyl]thien-2-yl}methyl)amino]phenyl}thiophene-2-carboxylic acid, 5-{3-[({1-[(2-aminobenzyl)sulfonyl]piperidin-4-yl}methyl)amino]phenyl}-4-methyl-3-(carboxymethoxy)thiophene-2-carboxylic acid, 4-methyl-3-(carboxymethoxy)-5-{3-[(1-{[2-(1H-pyrazol-1-yl)ethyl]sulfonyl}piperidin-4-yl)amino]phenyl}thiophene-2-carboxylic acid, {[4,5-dibromo-2-(1H-tetrazol-5-yl)thien-3-yl]oxy}acetic acid, 4-methyl-5-{4-[(4-tert-butylbenzoyl)amino]phenyl}-3-(carboxymethoxy)

thiophene-2-carboxylic acid, 4-methyl-3-(carboxymethoxy)-5-[3-({1-[(2-isopropoxyethyl)sulfonyl]piperidin-4-yl}amino)phenyl]thiophene-2-carboxylic acid, 4-methyl-3-(carboxymethoxy)-5-{4-[(phenylacetyl)amino]phenyl}thiophene-2-carboxylic acid, 5-[3-({[1-(benzylsulfonyl)piperidin-3-yl]carbonyl}amino)phenyl]-4-methyl-3-(carboxymethoxy)thiophene-2-carboxylic acid, 5-[3-({1-[(2-aminobenzyl)sulfonyl]piperidin-4-yl}amino)phenyl]-4-methyl-3-(carboxymethoxy)thiophene-2-carboxylic acid, 4-methyl-5-(3-{[1-({2-[(2-carboxybenzoyl)amino]ethyl}sulfonyl)piperidin-4-yl]amino}phenyl)-3-(carboxymethoxy)thiophene-2-carboxylic acid, {[4-methyl-5-phenyl-2-(2H-tetrazol-5-yl)thien-3-yl]oxy}acetic acid, {[4-methyl-5-phenyl-2-(2H-tetrazol-5-yl)thien-3-yl]oxy}acetic acid, {[5-bromo-4-methyl-2-(2H-tetrazol-5-yl)thien-3-yl]oxy}acetic acid, {[5-bromo-4-methyl-2-(2-methyl-2H-tetrazol-5-yl)thien-3-yl]oxy}acetic acid, {[5-(3-{[1-(benzylsulfonyl)piperidin-4-yl]amino}phenyl)-4-methyl-2-(2H-tetrazol-5-yl)thien-3-yl]oxy}acetic acid, {[5-{3-[acetyl(3,3,5,5-tetramethylcyclohexyl)amino]phenyl}-4-methyl-2-(2H-tetrazol-5-yl)thien-3-yl]oxy}acetic acid, [4-methyl-5-{3-[(cyclohexylmethyl)amino]phenyl}-2-(2H-tetrazol-5-yl)thien-3-yl]oxy}acetic acid, {[4-methyl-5-{3-[(3,3,5,5-tetramethylcyclohexyl)amino]phenyl}-2-(2H-tetrazol-5-yl)thien-3-yl]oxy}acetic acid, {[4-methyl-5-[3-(cyclohexylamino)phenyl]-2-(2H-tetrazol-5-yl)thien-3-yl]oxy}acetic acid, tetrazol-5-yl)thien-3-yl]oxy}acetic acid {[4-methyl-5-(3-{[1-(tert-butoxycarbonyl)piperidin-4-yl]oxy}phenyl)-2-(2H-, {[5-(3-{[1-(benzylsulfonyl)piperidin-4-yl]oxy}phenyl)-4-methyl-2-(2H-tetrazol-5-yl)thien-3-yl]oxy}acetic acid, 4-methyl-3-(carboxymethoxy)-5-[3-({1-[(cyclohexylmethyl)sulfonyl]piperidin-4-yl}amino)phenyl]thiophene-2-carboxylic acid, 4-methyl-3-(carboxymethoxy)-5-{3-[[(methylamino)carbonyl](3,3,5,5-tetramethylcyclohexyl)aminolphenyl}thiophene-2-carboxylic acid, 5-(3-{[cis-4-(benzyloxy)cyclohexyl]amino}phenyl)-4-methyl-3-(carboxymethoxy)thiophene-2-carboxylic acid, 5 -(3-{[trans-4-(benzyloxy)cyclohexyl]amino}phenyl)-4-methyl-3-(carboxymethoxy)thiophene-2-carboxylic acid, 4-methyl-3-(carboxymethoxy)-5-[3-({[1-(phenylacetyl)piperidin-4-yl]methyl}amino)phenyl]thiophene-2-carboxylic acid, 4-methyl-3-(carboxymethoxy)-5-{3-[(1-[2-(trifluoromethyl)benzyl]sulfonyl}piperidin-4-yl)amino]phenyl}thiophene-2-carboxylic acid, 4-methyl-3-(carboxymethoxy)-5-[3-({1-[(2-chlorobenzyl)sulfonyl]piperidin-4-yl}amino)phenyl]thiophene-2-carboxylic acid, 5-(3-{[1-(benzylsulfonyl)piperidin-4-yl]amino}phenyl)-3-(carboxymethoxy)-4-methylthiophene-2-carboxylic acid, 4-methyl-3-(carboxymethoxy)-5-[3-({1-[(2,3-dichlorobenzyl)sulfonyl]piperidin-4-yl}amino)phenyl]thiophene-2-carboxylic acid, methyl {[5-(3-{[1-(benzylsulfonyl)piperidin-4-yl]amino}phenyl)-4-methyl-2-(1H-tetrazol-5-yl)thien-3-yl]oxy}acetate, 4-methyl-3-(carboxymethoxy)-5-[3-(piperidin-4-ylamino)phenyl]thiophene-2-carboxylic acid, 4-methyl-3-(carboxymethoxy)-5-{3-[(1-pyrimidin-2-ylpiperidin-4-yl)amino]phenyl}thiophene-2-carboxylic acid, 4-methyl-3-(carboxymethoxy)-5-[3-([(pyridin-4-ylmethyl)sulfonyl]{1-[(pyridin-4-ylmethyl)sulfonyl]piperidin-4-yl}amino)phenyl]thiophene-2-carboxylic acid, 4-methyl-3-(carboxymethoxy)-5-[3-({1-[5-(trifluoromethyl)pyridin-2-yl]piperidin-4-yl}amino)phenyl]thiophene-2-carboxylic acid, 4-methyl-3-(carboxymethoxy)-5-[3-({1-[4-(trifluoromethyl)pyrimidin-2-yl]piperidin-4-yl}amino)phenyl]thiophene-2-carboxylic acid, 4-methyl-3-(carboxymethoxy)-5-(3-{[1-(5-nitropyridin-2-yl)piperidin-4-yl]amino}phenyl)thiophene-2-carboxylic acid, {[4-methyl-5-(3-{[1-(methylsulfonyl)piperidin-4-yl]oxy}phenyl)-2-(1H-tetrazol-5-yl)thien-3-yl]oxy}acetic acid, 5-[3-({1-[(benzylamino)carbonyl]piperidin-4-yl}methoxy)phenyl]-4-methyl-3-(carboxymethoxy)thiophene-2-carboxylic acid, 4-methyl-3-(carboxymethoxy)-5-[3-({1-[(cyclohexylamino)carbonyl]piperidin-4-yl}methoxy)phenyl]thiophene-2-carboxylic acid, 4-methyl-3-(carboxymethoxy)-5-{3-[(cyclohexylmethyl)(methylsulfonyl)amino]phenyl}thiophene-2-carboxylic acid, 4-methyl-3-(carboxymethoxy)-5-{3-[[(ethylamino)carbonyl](3,3,5,5-tetramethylcyclohexyl)amino]phenyl}thiophene-2-carboxylic acid, 5-[3-({1-[5-(acetylamino)pyridin-2-yl]piperidin-4-yl}amino)phenyl]-4-methyl-3-(carboxymethoxy)thiophene-2-carboxylic acid, isopropyl {[5-(3-{[1-(benzylsulfonyl)piperidin-4-yl]amino}phenyl)-4-methyl-2-(2H-tetrazol-5-yl)thien-3-yl]oxy}acetate, 4-methyl-3-(carboxymethoxy)-5-[3-(2,3-dihydro-1H-inden-2-ylamino)phenyl]thiophene-2-carboxylic acid, 4-methyl-3-(carboxymethoxy)-5-(3-{[8-(ethoxycarbonyl)-8-azabicyclo[3.2.1]oct-3-yl]amino}phenyl)thiophene-2-carboxylic acid, 4-methyl-3-(carboxymethoxy)-5-(3-{[1-(5-{[(methylamino)carbonyl]amino}pyridin-2-yl)piperidin-4-yl]amino}phenyl)thiophene-2-carboxylic acid, 4-methyl-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid, 4-methyl-3-(carboxymethoxy)-5-{3-[(1-{5-[(methylsulfonyl)amino]pyridin-2-yl}piperidin-4-yl)amino]phenyl}thiophene-2-carboxylic acid, 5-(1-benzyl-1H-pyrazol-4-yl)-4-methyl-3-(carboxymethoxy)thiophene-2-carboxylic acid, 5-{3-[(1-{[2-(acetylamino)benzyl]sulfonyl}piperidin-4-yl)amino]phenyl}-4-methyl-3-(carboxymethoxy)thiophene-2-carboxylic acid, 4-methyl-3-(carboxymethoxy)-5-(3-{[1-({2-[(methylsulfonyl)amino]benzyl}sulfonyl)piperidin-4-yl]amino}phenyl)thiophene-2-carboxylic acid, 4-methyl-3-(carboxymethoxy)-5-[3-({1-[(2-{[(ethylamino)carbonyl]amino}benzyl)sulfonyl]piperidin-4-yl}amino)phenyl]thiophene-2-carboxylic acid, 5-{3-[(1-{[2-(acetylamino)benzyl]sulfonyl}piperidin-4-yl)amino]phenyl}-3-(carboxymethoxy)thiophene-2-carboxylic acid, 3-(carboxymethoxy)-5-[3-({1-[(2-{[(ethylamino)carbonyl]amino}benzyl)sulfonyl]piperidin-4-yl}amino)phenyl]thiophene-2-carboxylic acid, 5-{3-[[(benzylamino)carbonyl](cyclohexyl)amino]phenyl}-4-methyl-3-(carboxymethoxy)thiophene-2-carboxylic acid, 4-methyl-3-(carboxymethoxy)-5-(3-{cyclohexyl[(methylamino)carbonyl]amino}phenyl)thiophene-2-carboxylic acid, 3-(carboxymethoxy)-5-phenylthiophene-2-carboxylic acid, 4-methyl-3-(carboxymethoxy)-5-[3-({1-[(3-{[(ethylamino)carbonyl]amino}benzyl)sulfonyl]piperidin-4-yl}amino)phenyl]thiophene-2-carboxylic acid, 4-methyl-3-(carboxymethoxy)-5-[3-({1-[(2-{[(chloromethyl)sulfonyl]amino}benzyl)sulfonyl]piperidin-4-yl}amino)phenyl]thiophene-2-carboxylic acid, 3-(carboxymethoxy)-5-(3-{[1-({2-[(methylsulfonyl)amino]benzyl}sulfonyl)piperidin-4-yl]amino}phenyl)thiophene-2-carboxylic acid, 5-(3-{[2-(benzylsulfonyl)-2-azabicyclo[2.2.2]oct-5-yl]amino}phenyl)-4-methyl-3-(carboxymethoxy)thiophene-2-carboxylic acid, 5-{3-[(1-{[3-(acetylamino)benzyl]sulfonyl}piperidin-4-yl)amino]phenyl})4-methyl-3-(carboxymethoxy)thiophene-2-carboxylic acid, 4-methyl-3-(carboxymethoxy)-5-{3-[1-({3-[(methylsulfonyl)amino]benzyl}sulfonyl)piperidin-4-yl]amino}phenyl)thiophene-2-carboxylic acid, 4-methyl-3-(carboxymethoxy)-5-{3-[(2,2,6,6-tetramethyltetrahydro-2H-pyran-4-yl)amino]phenyl}thiophene-2-carboxylic acid, 4-methyl-3-(carboxymethoxy)-5-(3-{(cyclohexylmethyl)[(ethylamino)carbonyl]amino}phenyl)thiophene-2-carboxylic acid, 4,5- dibromo-3-(1-carboxymethoxy)thiophene-2-carboxylic acid, 4-methyl-3-(carboxymethoxy)-5-(3-{cyclohexyl [(cyclohexylamino)carbonyl]amino}phenyl)thiophene-2-carboxylic acid, 5-{3-[(anilinocarbonyl)(cyclohexyl)amino]phenyl}-4-methyl-3-(carboxymethoxy)thiophene-2-carboxylic acid, 4-methyl-3-(carboxymethoxy)-5-[3-(cyclohexyl{[(2-phenylethyl)amino]carbonyl}amino)phenyl]thiophene-2-carboxylic acid, 4-methyl-3-(carboxymethoxy)-5-[3-(cyclohexyl{[(4-ethoxyphenyl)amino]carbonyl}amino)phenyl]thiophene-2-carboxylic acid, 4-methyl-3-(carboxymethoxy)-5-(3-{cyclohexyl[(isopropylamino)carbonyl]amino}phenyl)thiophene-2-carboxylic acid, 4-methyl-3-(carboxymethoxy)-5-(3-{cyclohexyl[(propylamino)carbonyl]amino}phenyl)thiophene-2-carboxylic acid, 4-methyl-3-(carboxymethoxy)-5-[3-(cyclohexyl{[(4-phenoxyphenyl)amino]carbonyl}amino)phenyl]thiophene-2-carboxylic acid, 5-(3-{[acetyl(isopropyl)amino]methyl}phenyl)-4-methyl-3-(carboxymethoxy)thiophene-2-carboxylic acid, 5-(3-{[acetyl(isobutyl)amino]methyl}phenyl)-4-methyl-3-(carboxymethoxy)thiophene-2-carboxylic acid, 5-(3-{[acetyl(cyclohexylmethyl)amino]methyl}phenyl)-4-methyl-3-(carboxymethoxy)thiophene-2-carboxylic acid, 5-(3-{[acetyl(4-methylphenyl)amino]methyl}phenyl)-4-methyl-3-(carboxymethoxy)thiophene-2-carboxylic acid, 5-(3-{[acetyl(4-tert-butylphenyl)amino]methyl}phenyl)-4-methyl-3-(carboxymethoxy)thiophene-2-carboxylic acid, 5-[3-({acetyl[4-(trifluoromethyl)phenyl]amino}methyl)phenyl]-4-methyl-3-(carboxymethoxy)thiophene-2-carboxylic acid, 5-(3-{[acetyl(phenyl)amino]methyl}phenyl)-4-methyl-3-(carboxymethoxy)thiophene-2-carboxylic acid, 5-(3-{[acetyl(cyclopropyl)amino]methyl}phenyl)-4-methyl-3-(carboxymethoxy)thiophene-2-carboxylic acid, 5-(3-{[acetyl(4-methylphenyl)amino]methyl}phenyl)-4-methyl-3-(carboxymethoxy)thiophene-2-carboxylic acid, 5-(3-{[acetyl(1,1'-biphenyl-4-yl)amino]methyl}phenyl)-4-methyl-3-(carboxymethoxy)thiophene-2-carboxylic acid, 5-(3-{[acetyl(4-phenoxyphenyl)amino]methyl}phenyl)-4-methyl-3-(carboxymethoxy)thiophene-2-carboxylic acid, 5-(3-{[acetyl(benzyl)amino]methyl}phenyl)-4-methyl-3-(carboxymethoxy)thiophene-2-carboxylic acid, 5-(3-{[acetyl(4-methoxybenzyl)amino]methyl}phenyl)-4-methyl-3-(carboxymethoxy)thiophene-2-carboxylic acid, 5-(3-{[acetyl(1,1'-biphenyl-4-ylmethyl)amino]methyl}phenyl)-4-methyl-3-(carboxymethoxy)thiophene-2-carboxylic acid, 5-(3-{[acetyl(4-chlorobenzyl)amino]methyl}phenyl)-4-methyl-3-(carboxymethoxy)thiophene-2-carboxylic acid, (carboxymethoxy)thiophene-2-carboxylic acid, 5-[3-({acetyl[4-(trifluoromethyl)benzyl]amino}methyl)phenyl]-4-methyl-3-(carboxymethoxy)thiophene-2-carboxylic acid, 5-[3-({acetyl[3,5-bis(trifluoromethyl)benzyl]amino}methyl)phenyl]-4-methyl-3-(carboxymethoxy)thiophene-2-carboxylic acid, 5-[3-({acetyl[2-(4-chlorophenyl)ethyl]amino}methyl)phenyl]-4-methyl-3-(carboxymethoxy)thiophene-2-carboxylic acid, 4-methyl-3-(carboxymethoxy)-5-[3-(cyclohexyl{[(2-thien-3-ylethyl)amino]carbonyl}amino)phenyl]thiophene-2-carboxylic acid, 4-methyl-3-(carboxymethoxy)-5-(3-{cyclohexyl[(thien-3-ylamino)carbonyl]amino}phenyl)thiophene-2-carboxylic acid, 4-methyl-3-(carboxymethoxy)-5-[3-(cyclohexyl{[(3,5-dimethylisoxazol-4-yl)amino]carbonyl}amino)phenyl]thiophene-2-carboxylic acid, 4-methyl-5-{3-[({[2-(5-bromo-2-methoxyphenyl)ethyl]amino}carbonyl)(cyclohexyl)amino]phenyl}-3-(carboxymethoxy)thiophene-2-carboxylic acid, 4-methyl-5-{3-[{[(2-carboxyethyl)amino]carbonyl}(cyclohexyl)amino]phenyl}-3-(carboxymethoxy)thiophene-2-carboxylic acid (non-preferred name), 4-methyl-3-(carboxymethoxy)-5-{3-[{[(4-carboxyphenyl)amino]carbonyl}(cyclohexyl)amino]phenyl}thiophene-2-carboxylic acid, 4-methyl-3-(carboxymethoxy)-5-{3-[{[(5-carboxypentyl)amino]carbonyl}(cyclohexyl)amino]phenyl}thiophene-2-carboxylic acid, 4-methyl-3-(carboxymethoxy)-5-{3-[([(3-,5-{3-[[(benzylamino)carbonyl](ethyl)amino]phenyl]-4-methyl-3-(carboxymethoxy)thiophene-2-carboxylic acid, 5-(3-{[1-(benzylsulfonyl)piperidin-4-yl][(ethylamino)carbonyl]amino}phenyl)-4-methyl-3-(carboxymethoxy)thiophene-2-carboxylic acid, 5-{3-[(anilinocarbonyl)(cyclohexylmethyl)amino]phenyl}-4-methyl-3-(carboxymethoxy)thiophene-2-carboxylic acid, 5-{3-[[(benzylamino)carbonyl](cyclohexylmethyl)amino]phenyl}-4-methyl-3-(carboxymethoxy)thiophene-2-carboxylic acid, 4-methyl-3-(carboxymethoxy)-5-[3-((cyclohexylmethyl){[(4-ethylphenyl)amino]carbonyl}amino)phenyl]thiophene-2-carboxylic acid, 4-methyl-3-(carboxymethoxy)-5-[3-((cyclohexylmethyl){[(4-ethoxyphenyl)amino]carbonyl}amino)phenyl]thiophene-2-carboxylic acid, 4-methyl-3-(carboxymethoxy)-5-[3-((cyclohexylmethyl){[(4-phenoxyphenyl)amino]carbonyl}amino)phenyl]thiophene-2-carboxylic acid, 4-methyl-3-(carboxymethoxy)-5-[3-(cyclohexyl{[(3-methyl-5-phenylisoxazol-4-yl)amino]carbonyl}amino)phenyl]thiophene-2-carboxylic acid, 4,5-dibromo-3-[carboxy(fluoro)methoxy]thiophene-2-carboxylic acid, 4-methyl-3-(carboxymethoxy)-5-{3-[{[(2-cyanophenyl)amino]carbonyl}(cyclohexylmethyl)amino]phenyl}thiophene-2-carboxylic acid, 4-methyl-3-(carboxymethoxy)-5-(3-{(cyclohexylmethyl)[(thien-3-ylamino)carbonyl]amino}phenyl)thiophene-2-carboxylic acid, 4-methyl-3-(carboxymethoxy)-5-[3-((cyclohexylmethyl){[(5-methyl-3-phenylisoxazol-4-yl)amino]carbonyl}amino)phenyl]thiophene-2-carboxylic acid, 4-methyl-3-(carboxymethoxy)-5-[3-((cyclohexylmethyl){[(3,5-dimethylisoxazol-4-yl)amino]carbonyl}amino)phenyl]thiophene-2-carboxylic acid, 5-{3-[bis(cyclohexylmethyl)amino]phenyl}-4-methyl-3-(carboxymethoxy)thiophene-2-carboxylic acid, {[5-phenyl-2-(2H-tetrazol-5-yl)thien-3-yl]oxy}acetic acid, carboxyphenyl)amino]carbonyl}(cyclohexylmethyl)amino]phenyl}thiophene-2-carboxylic acid, 3-(carboxymethoxy)-4-methyl-5-(phenylethynyl)thiophene-2-carboxylic acid, 5-(3-{benzyl[(isopropylamino)carbonyl]amino}phenyl)-4-methyl-3-(carboxymethoxy)thiophene-2-carboxylic acid, 4-methyl-3-(carboxymethoxy)-5-(3-{[(isopropylamino)carbonyl][4-(trifluoromethyl)benzyl]amino}phenyl)thiophene-2-carboxylic acid, 4-methyl-5-(3-{(4-tert-butylbenzyl)[(isopropylamino)carbonyl]amino}phenyl)-3-(carboxymethoxy)thiophene-2-carboxylic acid, 4-methyl-3-(carboxymethoxy)-5-(3-{isopropyl[(isopropylamino)carbonyl]aminophenyl)thiophene-2-carboxylic acid, 5-{3-[acetyl(cyclohexyl)amino]phenyl}-4-methyl-3-(carboxymethoxy)thiophene-2-carboxylic acid, and 5-{3-[benzoyl(cyclohexyl)amino]phenyl}-4-methyl-3-(carboxymethoxy)thiophene-2-carboxylic acid.

"Alkyl" refers to hydrocarbon chains that can contain 1 to 10 (preferably 1 to 6; more preferably 1 to 4) carbon atoms. Examples of alkyl include, but are not limited to, methyl, ethyl, propyl, butyl, pentyl, hexyl, heptyl, isopropyl, isobutyl, tert-butyl, isopentyl, neopentyl, octyl, or nonyl.

"Alkenyl" refers to a straight or branched hydrocarbon chain containing one or more (preferably 14; more preferably 1-2) double bonds and can contain 2 to 10 carbon atoms.

Examples of alkenyl include vinyl, allyl, isopropenyl, pentenyl, hexenyl, heptenyl, 1-propenyl, 2-butenyl, or 2-methyl-2-butenyl.

"Alkynyl" refers to a straight or branched hydrocarbon chain containing one or more (preferably 14; more preferably 1-2) triple bonds and can contain 2 to 10 carbon atoms. Examples of alkynyl include ethynyl, propargyl, 3-methyl-1-pentynyl, or 2-heptynyl.

"Cycloalkyl" refers to saturated or partly saturated monocyclic or polycyclic carbocyclic rings. Each ring can have from 3 to 10 carbon atoms. The term also can include a monocyclic or polycyclic ring fused to an aryl group or a heterocyclic group. Examples of cycloalkyl include cyclopropyl, cyclobutyl, cyclopentyl, cyclohexyl, cycloheptyl, cyclohexenyl, or cyclopentenyl.

"Heterocyclyl", "heterocycle", or "heterocyclic" refers to a saturated or partially saturated monocyclic or polycyclic ring system containing at least one heteroatom selected from N, O and S (including SO and $SO_2$). Each of the rings can have from 3 to 10 atoms, except where defined otherwise. Examples of this definition include tetrahydrofuran, piperazine, piperidine, tetrahydropyran, morpholine, pyrrolidine, or tetrahydrothiophene.

The term "aryl" means monocyclic-, polycyclic, biaryl or heterocyclic aromatic rings. Each ring can contain 5 to 6 atoms. The term also may describe one of the foregoing aromatic rings fused to a cycloalkyl or heterocyclic group. "Heterocyclic aromatic" and "heteroaryl" means a monocyclic or polycyclic aromatic rings containing at least one heteroatom selected from N, O and S (including SO and $SO_2$) in the perimeter of the ring. Each ring can contain 5 to 6 atoms. Examples of aryl include phenyl, naphthyl, biphenyl, indanyl, indenyl, tetrahydronaphthyl, dihydrobenzopyranyl, fluorenyl, pyrrolyl, pyrazolyl, imidazolyl, triazolyl, oxazolyl, isoxazolyl, oxadiazolyl, thiazoyl, thiadiazolyl, isothiazolyl, thienyl, thiophenyl, triazinyl, furanyl, pyridyl, tetrazolyl, pyrimidinyl, pyridazinyl, quinolyl, isoquinolyl, 2,3-dihydrobenzofuranyl, benzothiophenyl, 2,3-dihydrobenzothiophenyl, furo(2,3-b)pyridyl, isoquinolyl, dibenzofuran, benzisoxazolyl, benzoxazolyl, benzothiazolyl, benzimidazolyl, benzofuranyl, 4,5,6,7-tetrahydro-benzo[b]thiophenyl, indolyl, isoindolyl, 1,3-dihydro-isoindolyl, indazolyl, carbazolyl, 5H-dibenz[b,f]azepine, 10,11-dihydro-5H-dibenz[b,f]azepine, phenylpyridyl, phenylpyrimidinyl, phenylpyrazinyl, or phenypyridazinyl.

"Alkoxy" or alkyloxy" means an alkyl group as defined above having the indicated number of carbon atoms attached through an oxygen bridge. Examples include methoxy, ethoxy, or propyloxy. "Alkenyloxy" and "alkynyloxy" are similarly defined for alkenyl and alkynyl groups, respectively.

"Aryloxy" means an aryl group as defined above attached through an oxygen bridge. Examples include phenoxy or naphthyloxy. "Cycloalkyloxy" and "heterocyclyloxy" are similiarly defined for cycloalkyl and heterocyclic groups, respectively.

Additional terms are similarly defined, following the convention that the last group in the term is the attachment point, unless is defined otherwise. For example, "arylalkenyl" represents an aryl group as defined above attached through an alkenyl group.

A salt of any of the compounds of formula (I) can be prepared. For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, and maleate. A compound of this invention may also form a pharmaceutically acceptable salt when a compound of this invention having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts; or ammonium salts or salts of organic bases such as morpholine, ethanol amine, choline, piperidine, pyridine, dimethylamine, or diethylamine salts. It should be recognized that a compound of the invention can contain chiral carbon atoms. In other words, it may have optical isomers or diastereoisomers.

An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). An effective amount of a compound described herein can range from about 0.01-100 mg/kg, and more preferably from about 1-10 mg/kg. Effective doses will also vary, as recognized by those skilled in the art, dependent on route of administration, excipient usage, and the possibility of co-usage, pre-treatment, or post-treatment, with other therapeutic treatments.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. Because some of the compounds described herein can have limited water solubility, a solubilizing agent can be included in the composition to improve the solubility of the compound. For example, the compounds can be solubilized in polyethoxylated castor oil (Cremophor EL®) and may further contain other solvents, e.g., ethanol.

A compound described herein can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound described herein with a solid carrier and a lubricant. Examples of solid carriers include starch and sugar bentonite. The compound can also be administered in a form of a hard shell tablet or a capsule containing a binder, e.g., lactose or mannitol, a conventional filler, and a tableting agent.

Inhibition of a PTPase may be determined by measuring turnover of various substrates, from small, phosphorylated organic compounds to endogenous phospho-peptides.

McCain D F, Zhang Z Y: *Assays for protein-tyrosine phosphatases*. Methods Enzymol. (2002) 345: 507-518. Typical inhibition (Ki) values for the compounds disclosed herein ranged from 200 micromolar up to 1 nanomolar, and more preferably from 1 micromolar to 1 nanomolar.

Some disorders or physiological conditions may be mediated by inhibition of a PTPase. A disorder or physiological condition that is mediated by PTPase refers to a disorder or condition wherein PTPase plays a role in either triggering the onset of the condition, or where inhibition of a particular PTPase affects signaling in such a way as to improve the condition. Examples of such disorders include, but are not limited to, type 1 and type 2 diabetes, obesity, cancer, autoimmune diseases, allergic disorders, acute and chronic inflammation, metabolic syndrome, and osteoporosis. Inhibitors of a specific PTPase can have therapeutic benefits in treating such disorders.

Protein tyrosine phosphatase 1B (PTP1B), a ~50 kd intracelluar PTPase abundant in various human tissues, has been studied for its potential role as a negative regulator of insulin signaling. Some studies have shown that PTP1B is a negative regulator of insulin signaling. Mice deficient in PTP1B were healthy and showed increased insulin sensitivity and resistance to diet-induced obesity. These mice had lower glucose, insulin and triglyceride levels as well as improved insulin sensitivity as measured by glucose and insulin tolerance tests. Importantly, PTP1B has also been implicated in attenuation of leptin receptor signaling. PTP1B deficient mice were shown to be more sensitive to leptin, which may explain in part their resistance to weight gain when placed on a high fat diet. Thus, the main target tissues for PTP1B inhibition appear to be insulin action in muscle and liver, as well as leptin signaling in the brain, while the commercial diabetes drugs, the peroxisome proliferative activated receptor-gamma (PPAR-γ) agonist class of insulin sensitizers, target adipose tissue. Thus inhibition of PTP1B provides a unique target for regulating a variety of cellular responses important to human diseases related to obesity and type 2 diabetes.

The details of one or more embodiments are set forth in the accompanying drawings and the description below. Other features, objects, and advantages will be apparent from the description and drawings, and from the claims.

DETAILED DESCRIPTION

Most of the compounds of the current invention may be prepared according to the following general synthetic scheme from commercially available starting materials, materials prepared as described in literature procedures, or new intermediates described in the schemes and experimental procedures. This general scheme covers many of the examples. More detailed synthetic methods are also set forth below.

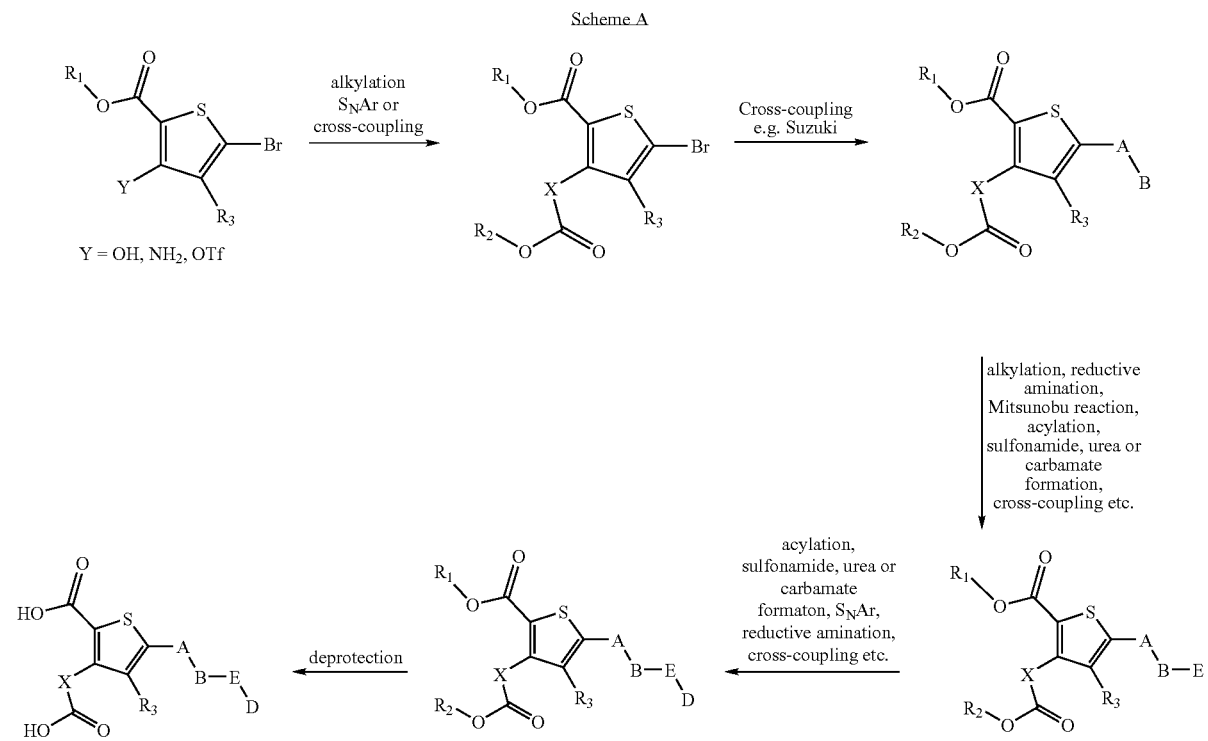

Scheme A

In Scheme A, an electronegative 3-substituent of thiophene can be alkylated or cross-coupled to form an alkyl carboxylate or carboxylic acid at that position. An "A" aryl group, optionally substituted with a "B" 1-3 atom linker group, can be cross-coupled with the 5-position of the thiophene. The "B" group can be substituted with a "E" spacer group by means of alkylation, reductive amination, or other appropriate methods. (Michael B. Smith and Jerry March, March's Advanced Organic Chemistry Reactions, Mechanisms, and Structure (5th ed. 2001)). The "E" group can be cross-coupled with a "D" end group by any appropriate method. Protective groups on the carboxylates at the 2- and 3-thiophene positions can be removed by hydrolysis.

Scheme 1

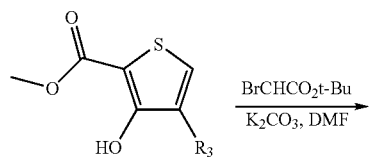

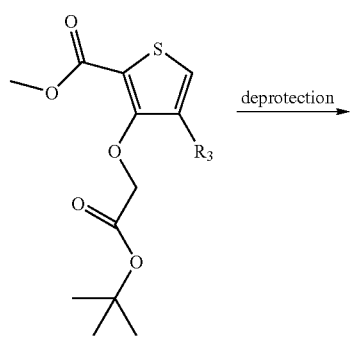

In Scheme 1, the 3-hydroxy substituent of a substituted thiophene is alkylated to form a hydroxy-acetic acid tert-butyl ester substituent at the 3-position of thiophene. That substituent is hydrolyzed to form a carboxymethoxy substituent at the 3-position of thiophene. A carboxylate at the 2-position of the thiophene can also be hydrolyzed to a carboxylic acid.

Scheme 2

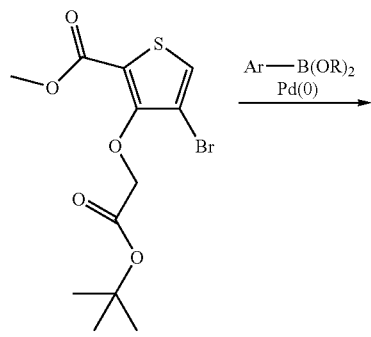

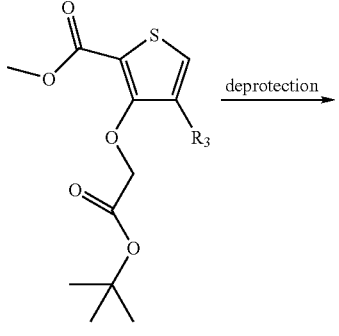

In Scheme 2, a halogen 4-substituent of a thiophene is converted to a $R_3$ substituent such as aryl by treatment with Ar—B(OR)$_2$ and Pd catalyst. The resultant compound can be hydrolyzed at the 2- and/or 3-positions to form terminal carboxylic acids at those positions.

Scheme 3

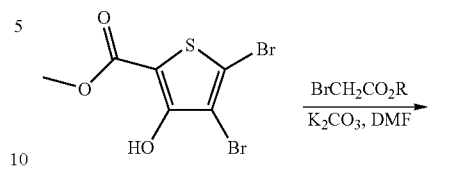

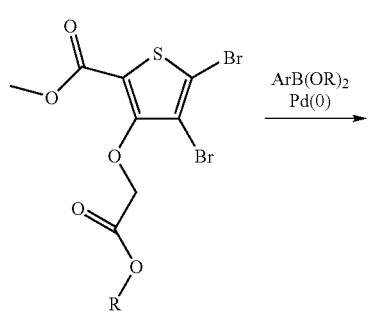

R = Et, t-Bu

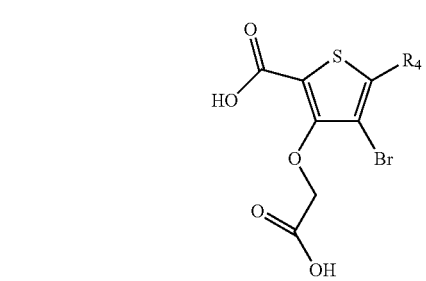

In Scheme 3, a thiophene substituted at the 3-position with hydroxy is alkylated to form a 2-alkoxy-2-oxoethoxy substituent at the 3-position. A halogen substituent at the 5-position on thiophene can be converted to an $R_4$ group, and the resulting compound can be hydrolyzed to form terminal carboxylic acids on the 2- and 3-thiophene substituents.

Scheme 4

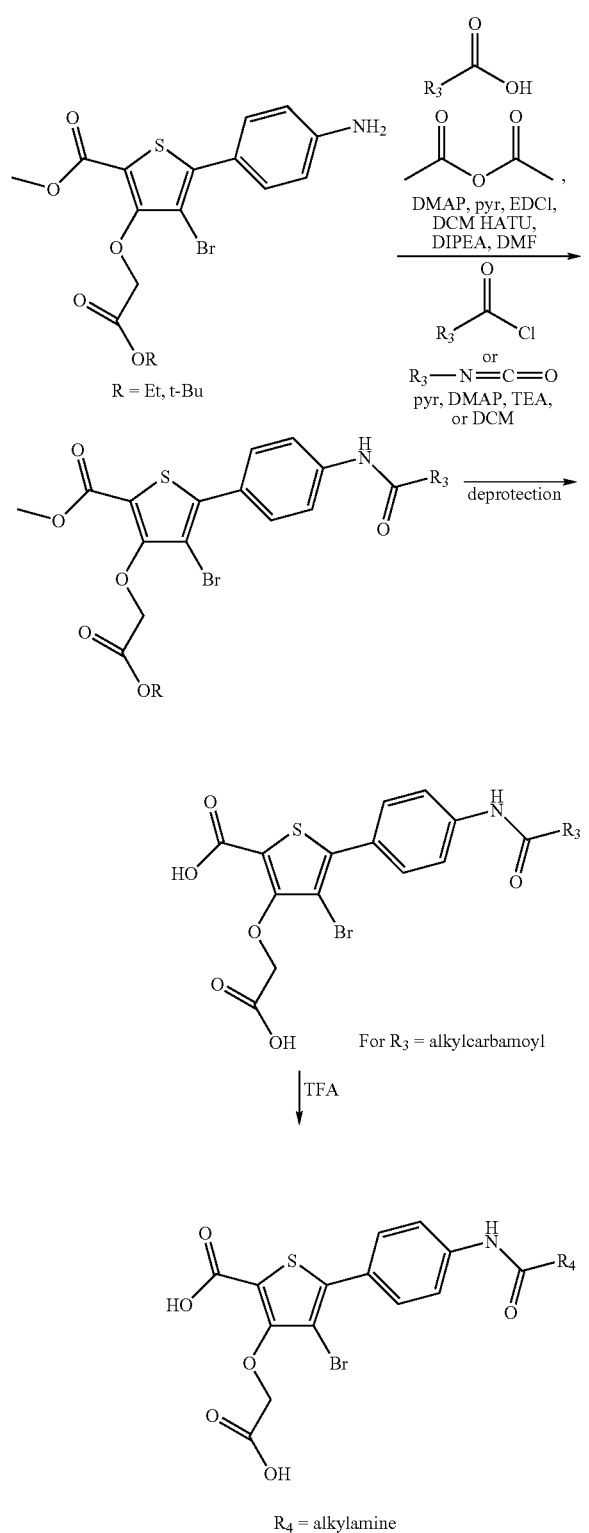

Scheme 5

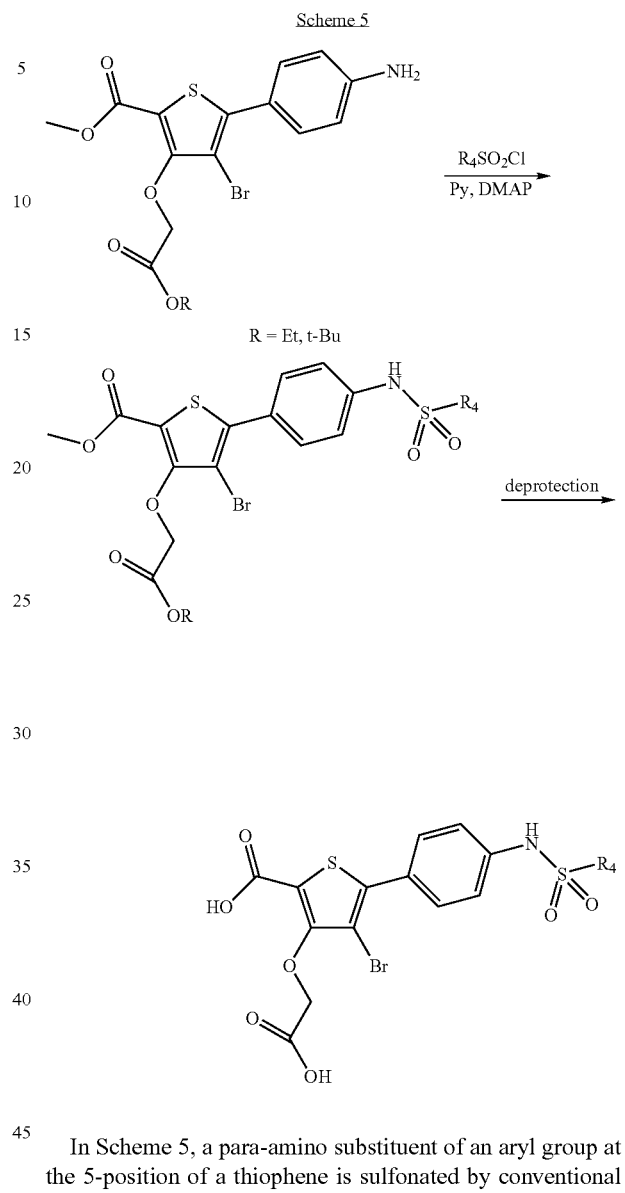

In Scheme 5, a para-amino substituent of an aryl group at the 5-position of a thiophene is sulfonated by conventional methods. The resulting compound can be hydrolyzed to form terminal carboxylic acids on the 2- and 3-thiophene substituents.

Scheme 6

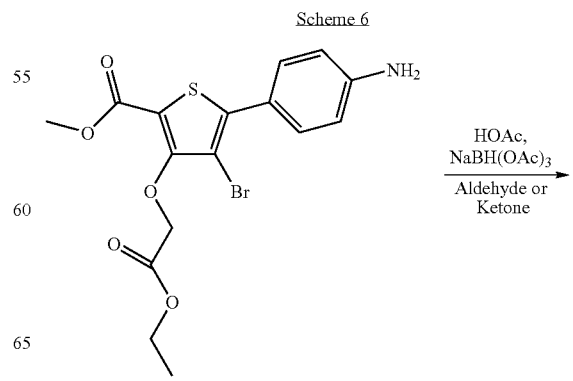

In Scheme 4, an amino substituent on an aryl group at the 5-position of a thiophene is acylated by conventional methods. The resulting compound can be hydrolyzed to form terminal carboxylic acids on the 2- and 3-thiophene substituents. In step three, the $R_3$ substituent can be hydrolyzed.

-continued

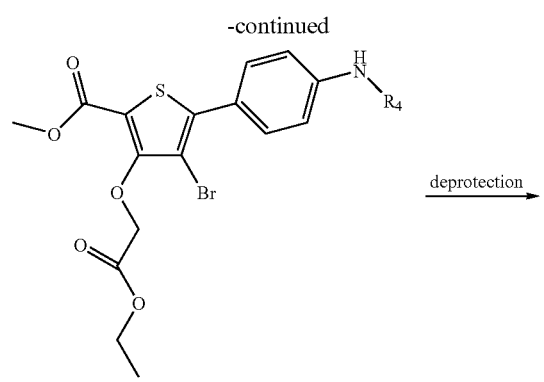

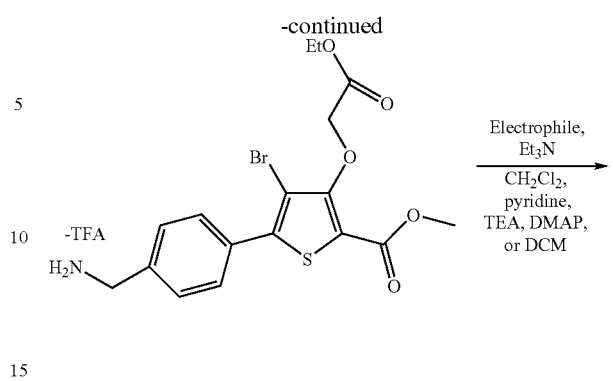

In Scheme 6, an amino substituent of an aryl group at the 5-position of a thiophene is substituted, such as by an alkyl group, by conventional methods. The resulting compound can be hydrolyzed to form terminal carboxylic acids on the 2- and 3-thiophene substituents.

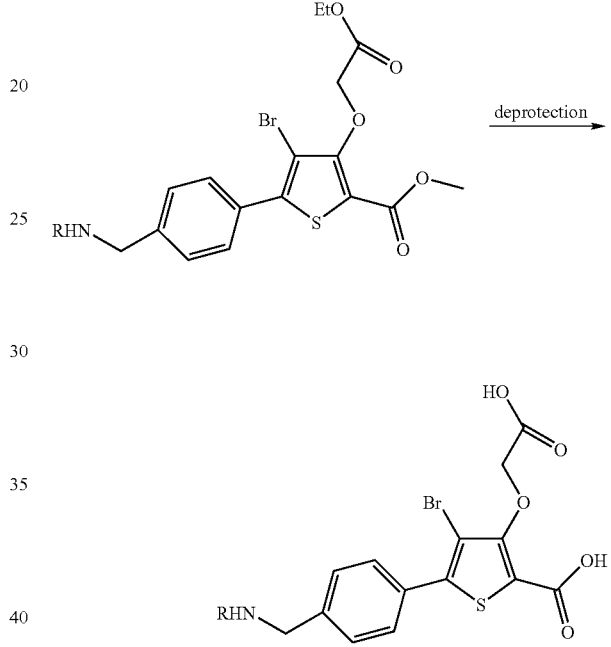

In the first step of Scheme 7, a halogen substituent at the 5-thiophene position is substituted with a protected aminomethylarylene such as tert-butyloxycarbonyl (BOC) aminomethylarylene as shown. The resultant BOC group is removed under acid conditions to give an amine in the second step, and then substituted with an R substituent such as alkyl in the third step. The resulting compound can be hydrolyzed to form terminal carboxylic acids on the 2- and 3-thiophene substituents in the fourth step.

Scheme 7

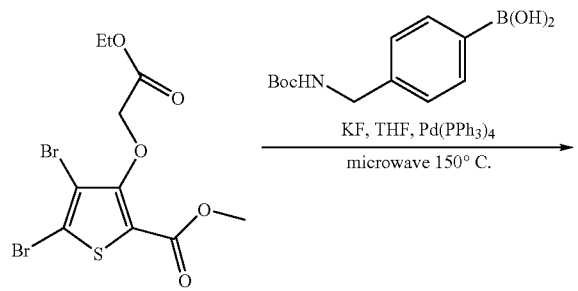

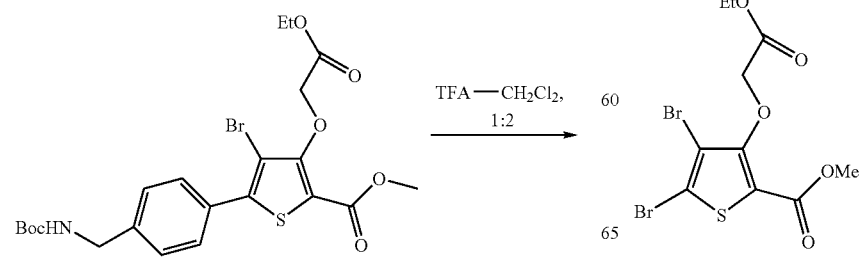

Scheme 8

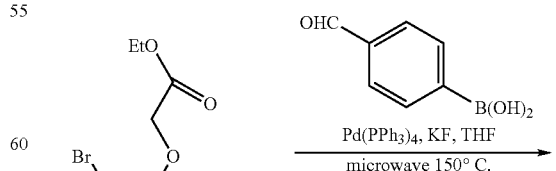

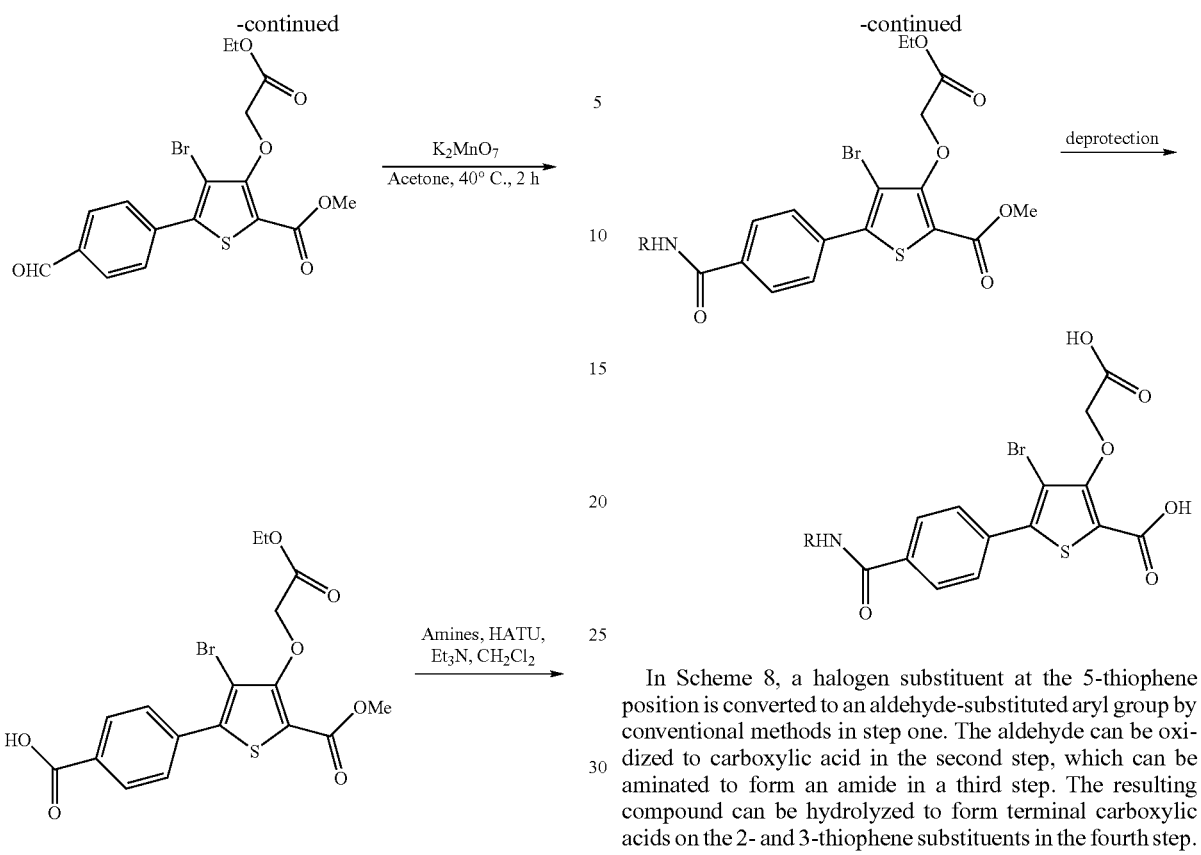

In Scheme 8, a halogen substituent at the 5-thiophene position is converted to an aldehyde-substituted aryl group by conventional methods in step one. The aldehyde can be oxidized to carboxylic acid in the second step, which can be aminated to form an amide in a third step. The resulting compound can be hydrolyzed to form terminal carboxylic acids on the 2- and 3-thiophene substituents in the fourth step.

Scheme 9

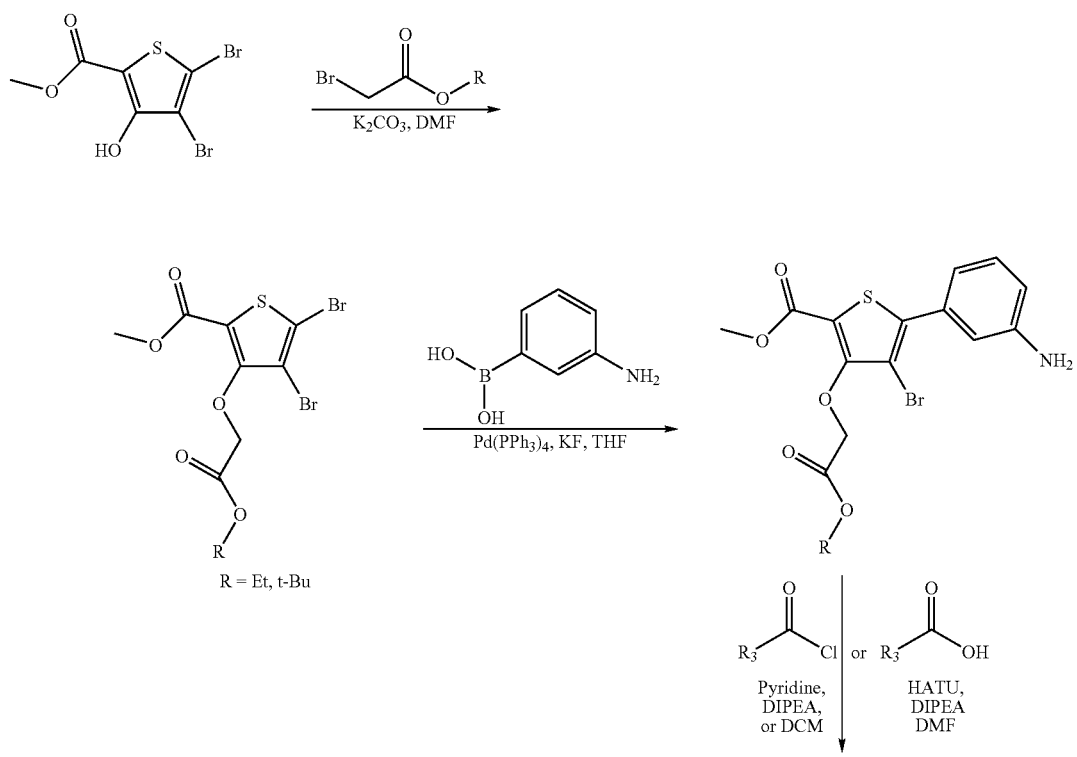

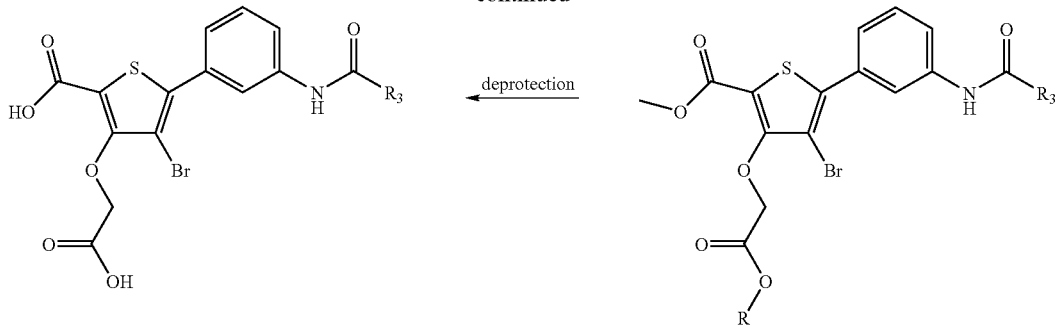

-continued

In step one of Scheme 9, a 3-hydroxy substituent of thiophene is alkylated to form a 2-alkoxy-2-ethoxy substituent at the 3-position. A 5-halogen substituent can be converted to an amino-substituted aryl group by conventional methods in the second step, which can be acylated to form an amide in the third step. The resulting compound can be hydrolyzed to form terminal carboxylic acids on the 2- and 3-thiophene substituents in the fourth step.

methods. The resulting compound can be hydrolyzed to form terminal carboxylic acids on the 2- and 3-thiophene substituents.

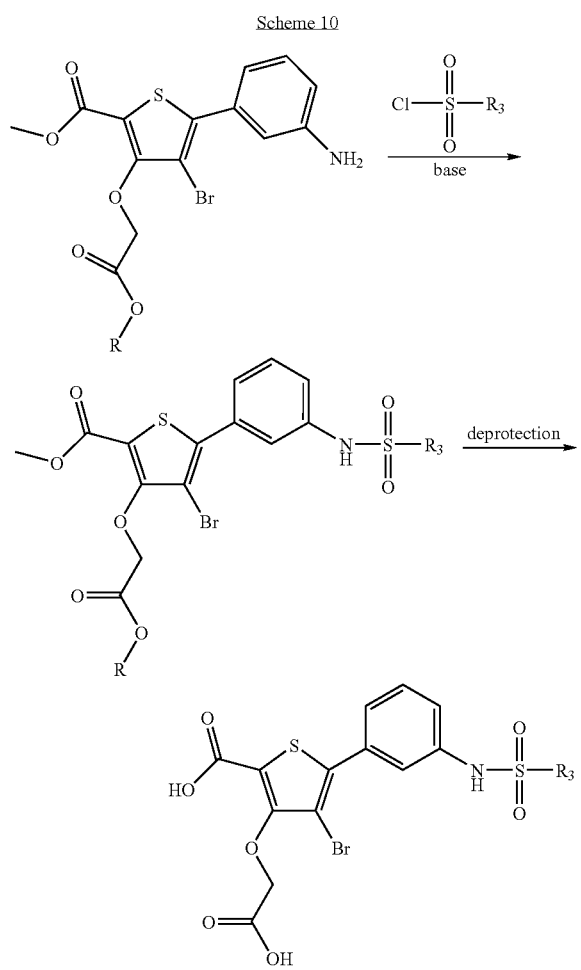

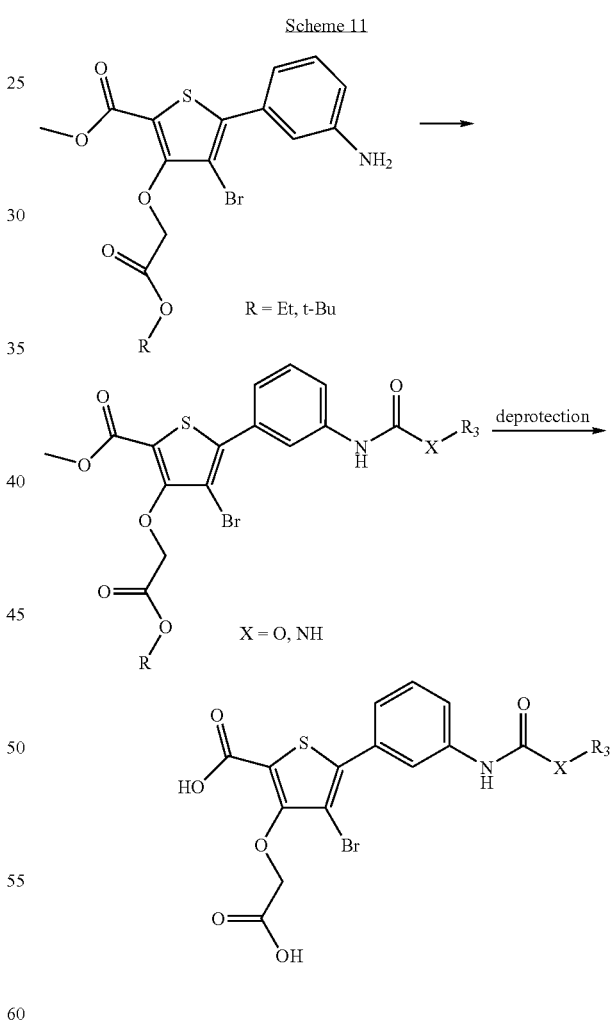

In Scheme 10, a meta-amino substituent on an aryl group at the 5-position on thiophene is sulfonated by conventional In Scheme 11, an amino substituent on an aryl group at the 5-position on thiophene is converted to a functional group such as alkoxycarbonylamino (after reaction with alkylchloroformate) or ureido (after reaction with alkylisocynate). The resulting compound can be hydrolyzed to form terminal carboxylic acids on the 2- and 3-thiophene substituents.

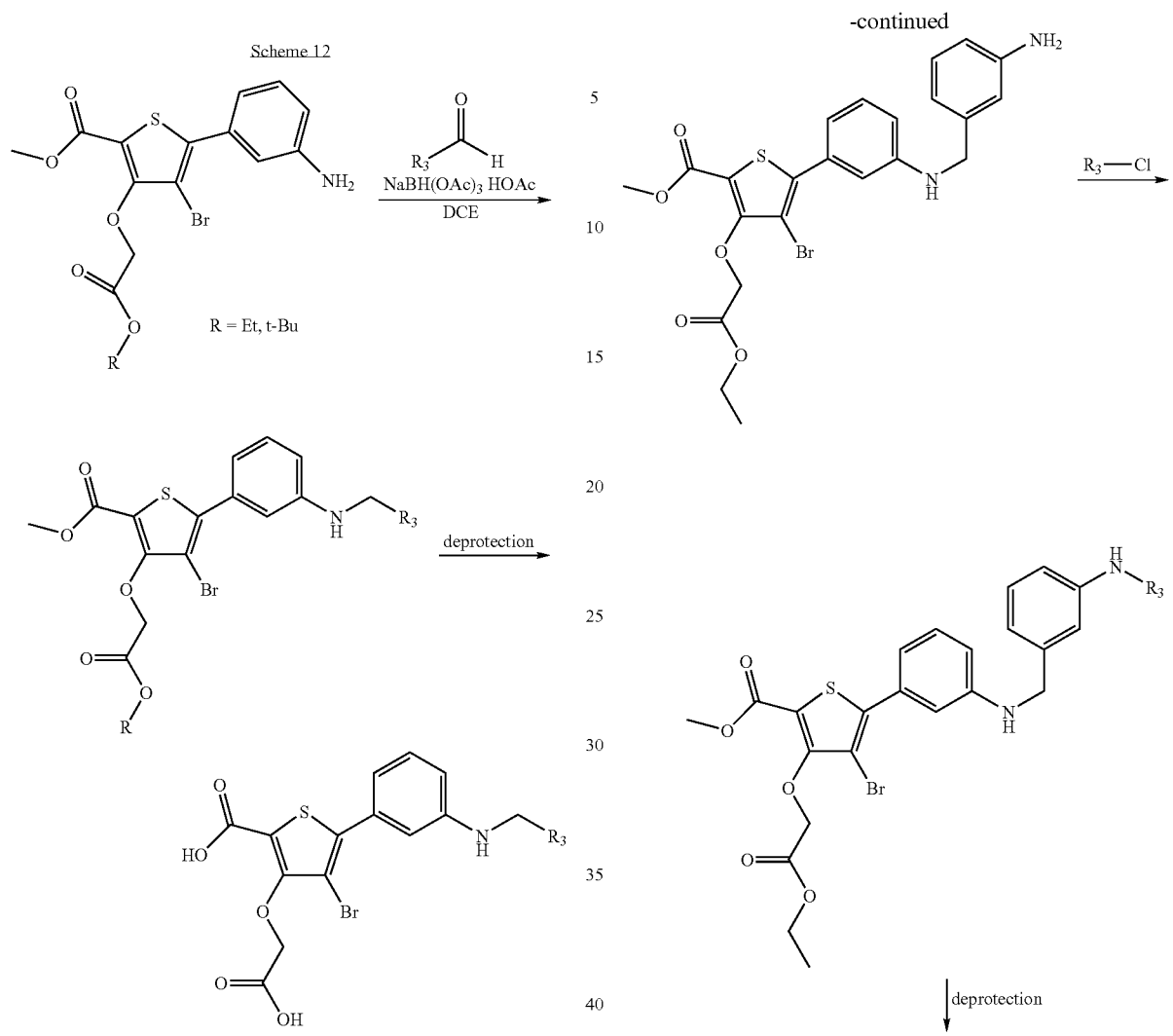

In Scheme 12, an amino substituent on an aryl group at the 5-position of thiophene is alkylated with an optionally substituted alkyl group by conventional methods. The resulting compound can be hydrolyzed to form terminal carboxylic acids on the 2- and 3-thiophene substituents.

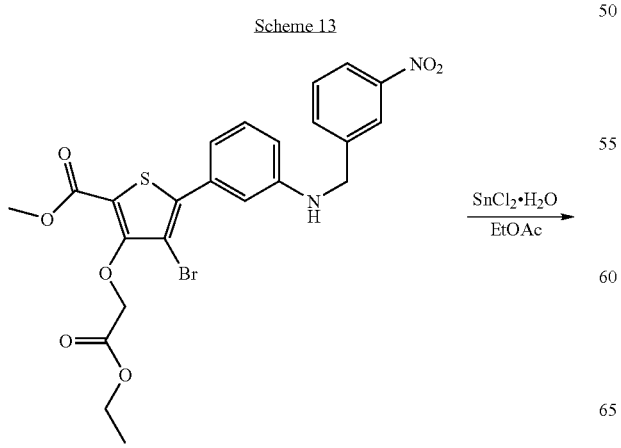

In the first step of Scheme 13, a nitro substituent of an aryl group (attached by a linker to the 5-position of a thiophene) is reduced to an amine. The amine can be substituted by a group such as sulfonyl or acyl by conventional methods. The resulting compound can be hydrolyzed to form terminal carboxylic acids on the 2- and 3-thiophene substituents.

Scheme 14

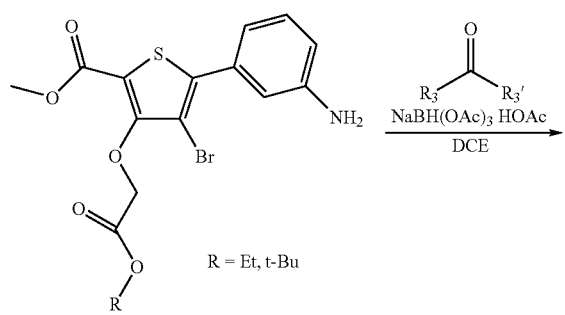

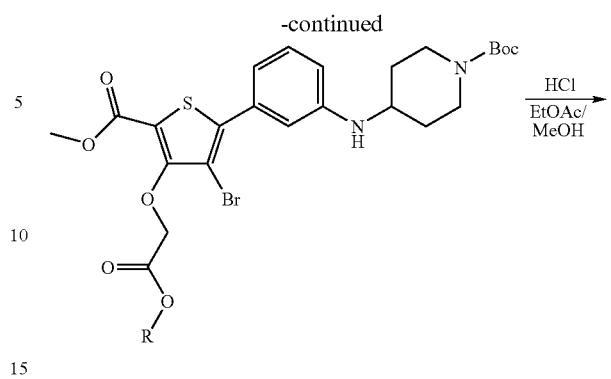

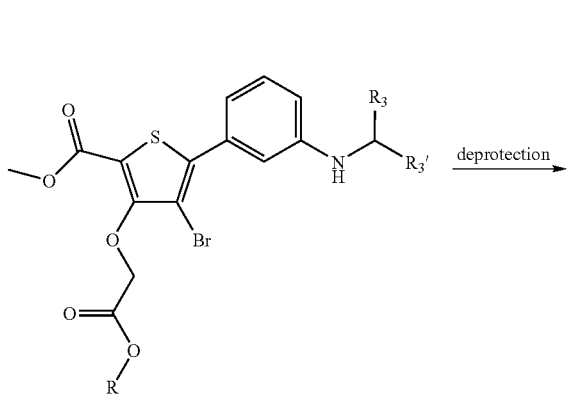

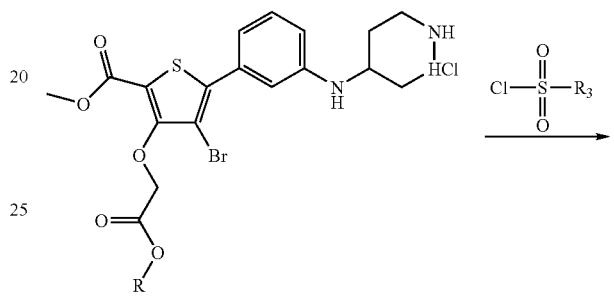

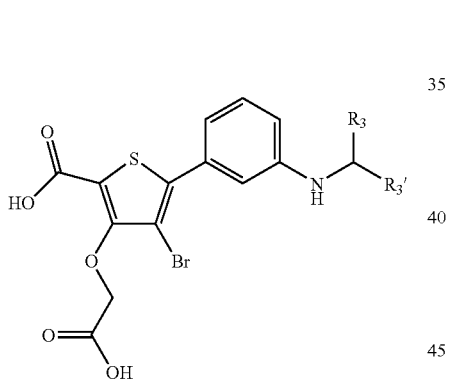

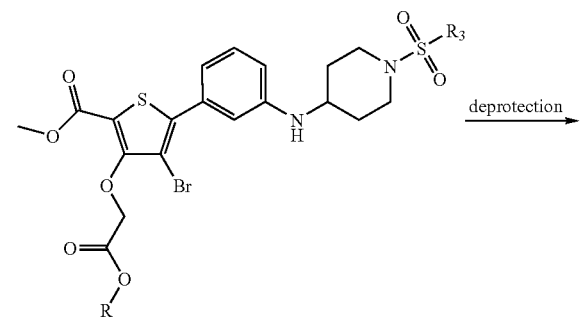

In Scheme 14, an amine substituent of an aryl group at the 5-position of thiophene is alkylated by conventional methods. The resulting compound can be hydrolyzed to form terminal carboxylic acids on the 2- and 3-thiophene substituents.

Scheme 15

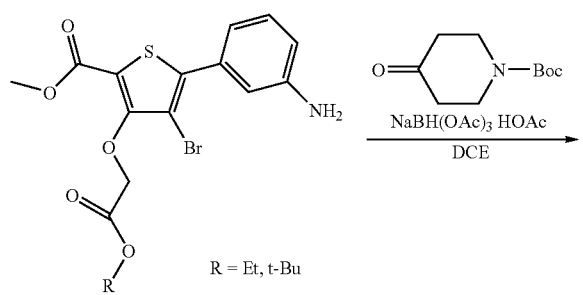

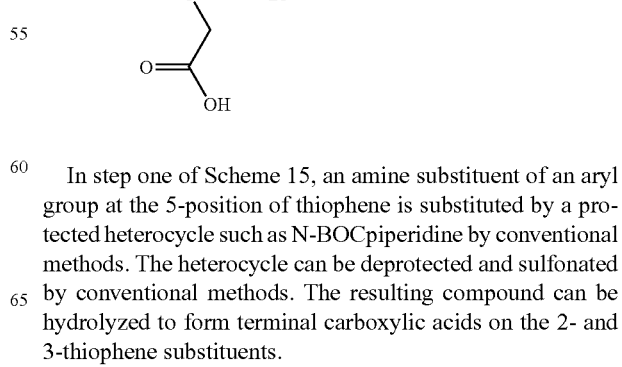

In step one of Scheme 15, an amine substituent of an aryl group at the 5-position of thiophene is substituted by a protected heterocycle such as N-BOCpiperidine by conventional methods. The heterocycle can be deprotected and sulfonated by conventional methods. The resulting compound can be hydrolyzed to form terminal carboxylic acids on the 2- and 3-thiophene substituents.

Scheme 16

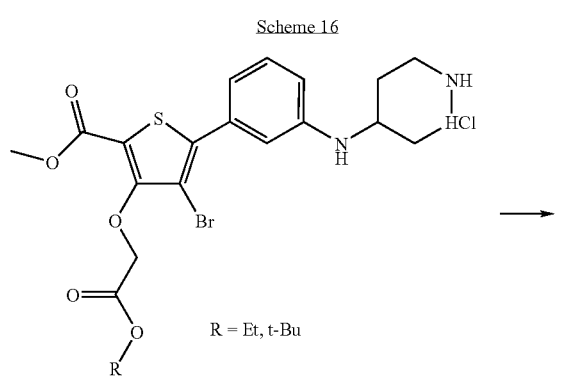

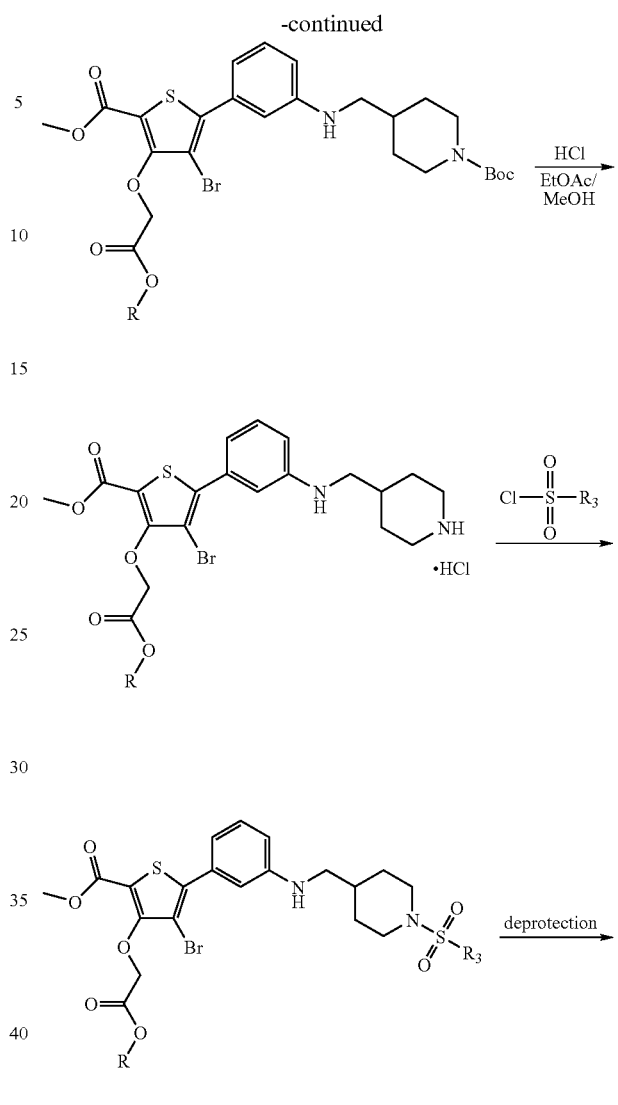

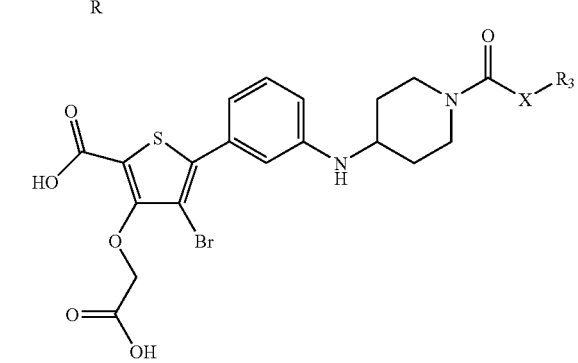

In Scheme 16, an amine of a heterocycle such as piperidine (the piperidine being attached through an arylene linker to the 5-position of thiophene) is converted to an aminoacyl compound such as an amide, oxycarbonylamine, or ureido by conventional methods. The resulting compound can be hydrolyzed to form terminal carboxylic acids on the 2- and 3-thiophene substituents.

Scheme 17

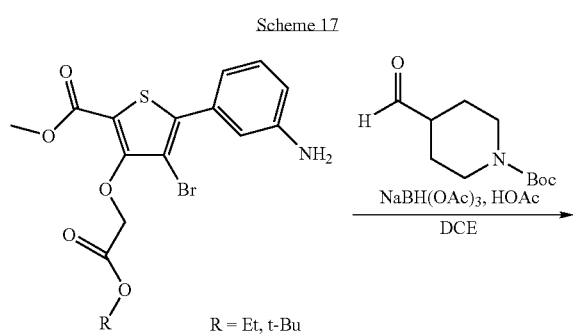

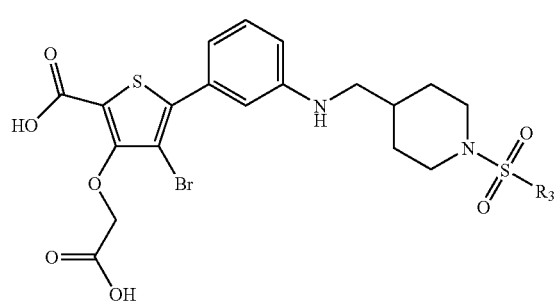

In the first step of Scheme 17, the amine of an aminoaryl 5-thiophene substituent is alkylated with a compound such as a protected alkylheterocycle. The protection group can be removed by hydrolysis in step two, and the amine of the heterocycle sulfonated in step three. In step four, the resulting compound can be hydrolyzed to form terminal carboxylic acids on the 2- and 3-thiophene substituents.

Scheme 18

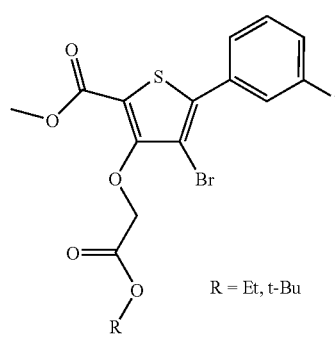

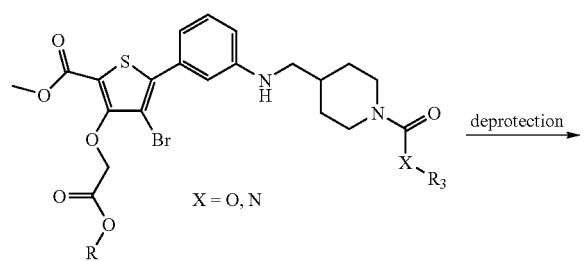

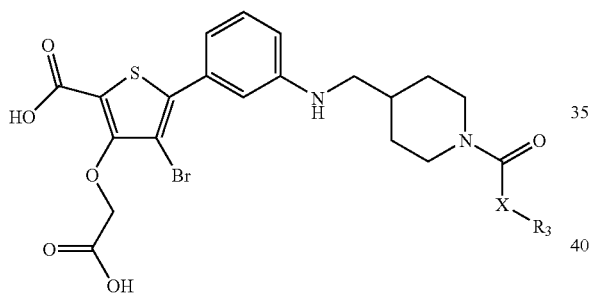

Scheme 19

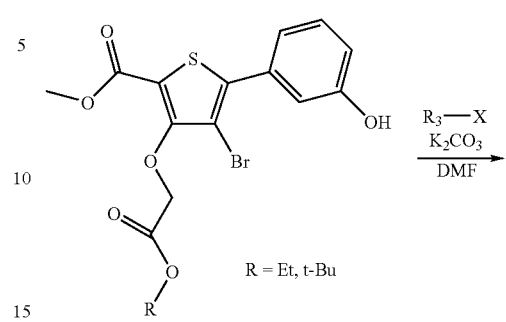

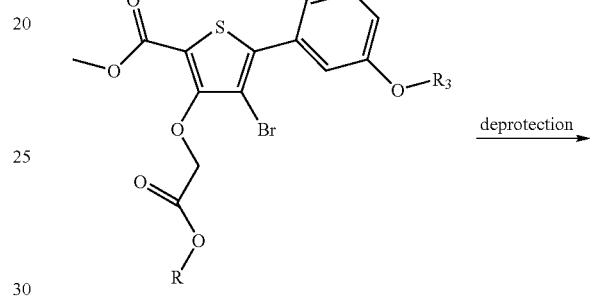

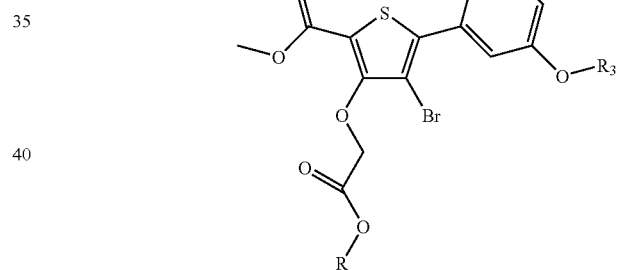

In Scheme 18, an amino group of a heterocycle (attached via an alkylarylene linker to the 5-position of thiophene) is converted to a functional group such as alkoxycarbonylamino (after reaction with alkylchloroformate) or ureido (after reaction with isocynate). The resulting compound can be hydrolyzed to form terminal carboxylic acids on the 2- and 3-thiophene substituents.

In Scheme 19, the hydroxyl of a hydroxyl-substituted aryl group at the 5-position of thiophene is alkylated by conventional methods. The resulting compound can be hydrolyzed to form terminal carboxylic acids on the 2- and 3-thiophene substituents.

Scheme 20

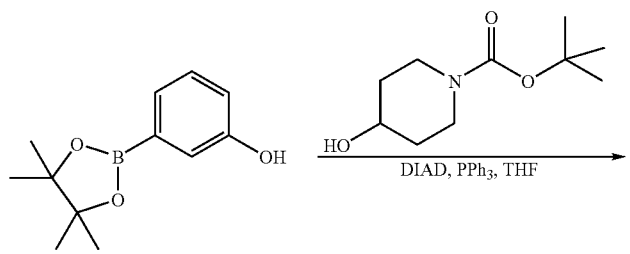

123 124
-continued
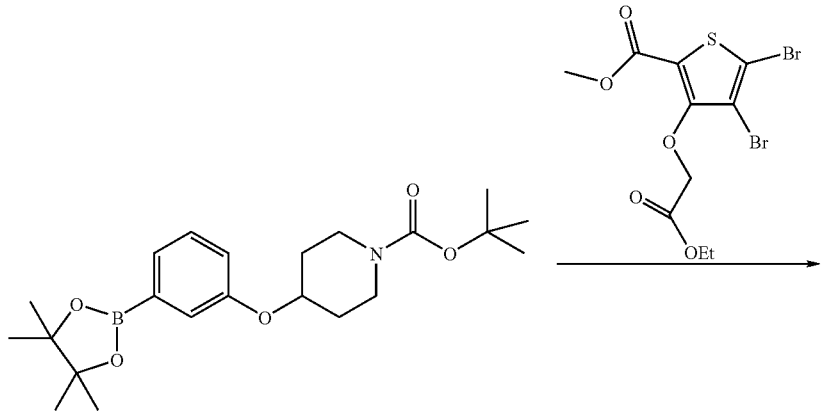
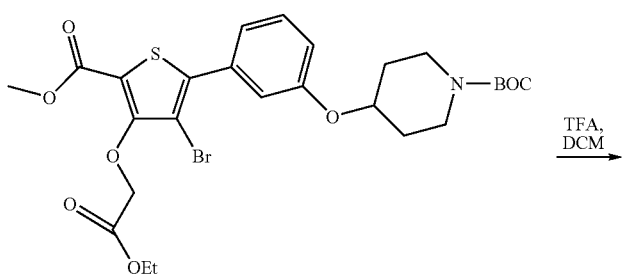
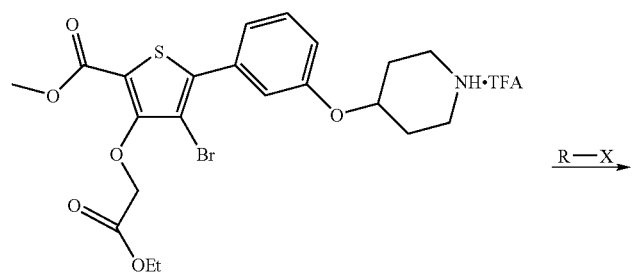
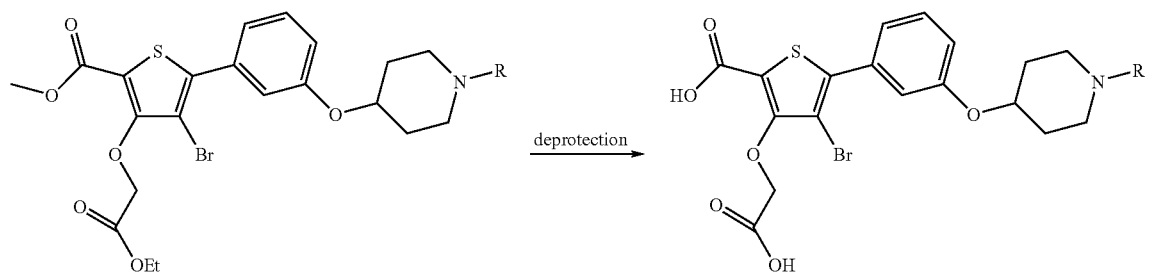

In the first step of Scheme 20, the hydroxy group of a substituted arylhydroxyl group is alkylated with a group such as a protected heterocycle to form an alkoxyaryl. The other aryl substituent, such as 4,4,5,5-tetramethyl-[1,3,2]dioxaborolan2-yl, can be reacted with a 5-halogen substituted thiophene to form an aryl substituent at the 5-thiophene position. Any protection groups on the heterocycle can be hydrolyzed and substituted with a group such as carboxylate or sulfonyl. The resulting compound can be hydrolyzed to form terminal carboxylic acids on the 2- and 3-thiophene substituents.

-continued

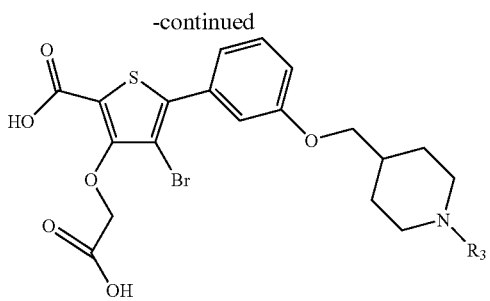

In the first step of Scheme 21, the hydroxy substituent of an arylhydroxy group (the aryl being attached to a thiophene at the 5-position) is alkylated such as by an alkylheterocycle as shown. Any protection groups on the heterocycle can be removed by hydrolysis, and the resulting unprotected amine can be substituted with a group such as a carbonyl or sulfonyl. The resulting compound can be hydrolyzed to form terminal carboxylic acids on the 2- and 3-thiophene substituents.

Scheme 21

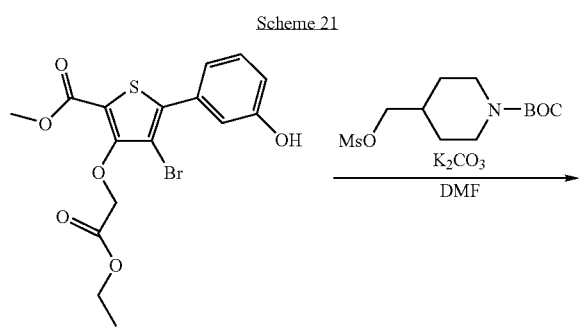

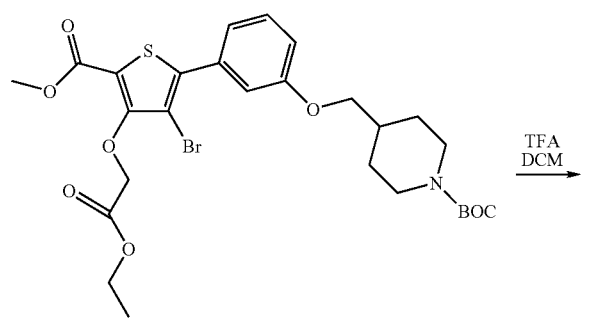

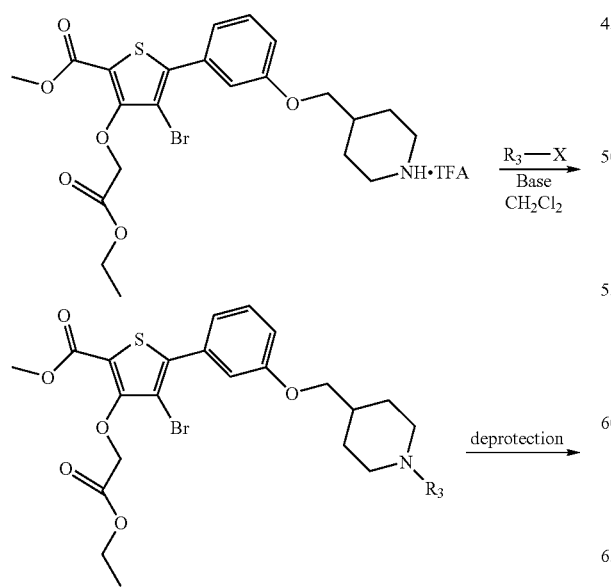

Scheme 22

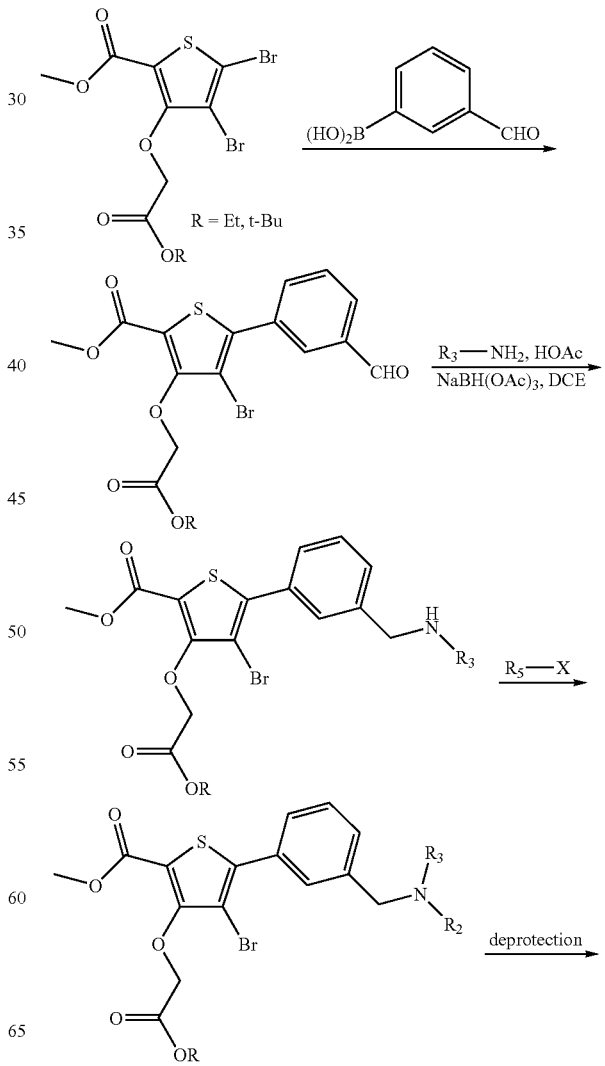

-continued

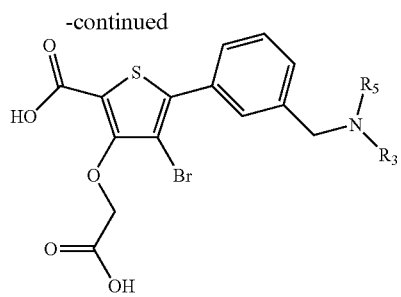

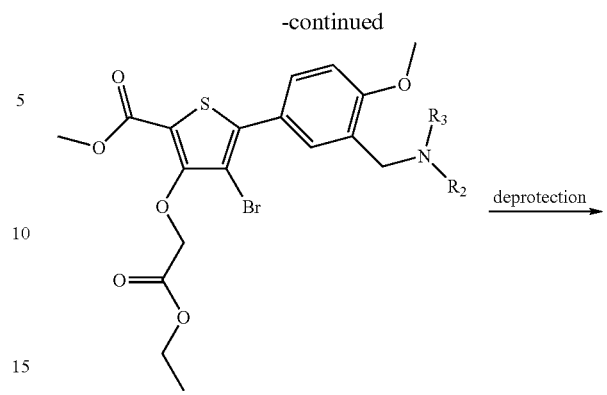

In the first step of Scheme 22, a halogen at the 5-position of thiophene is substituted with an aldehyde-substituted arylene group. The aldehyde can be reduced and converted to a secondary amine. The secondary amine can be substituted with a group such as carboxyl, sulfonyl, or ureido. The resulting compound can be hydrolyzed to form terminal carboxylic acids on the 2- and 3-thiophene substituents.

Scheme 23

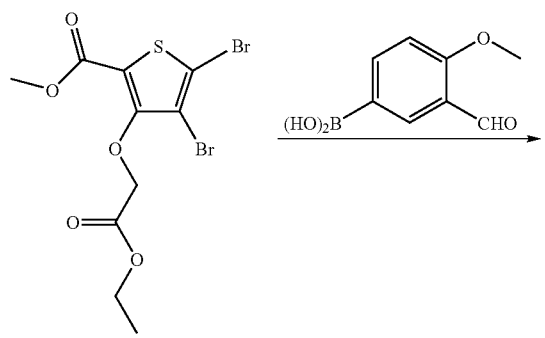

In the first step of Scheme 23, a halogen at the 5-position of a thiophene can be arylated with an aldehyde substituted aryl group. The aldehyde can be aminated to form a secondary amine, which can be substituted with a group such as carbonyl, sulfonyl, or ureido. The resulting compound can be hydrolyzed to form terminal carboxylic acids on the 2- and 3-thiophene substituents.

Scheme 24

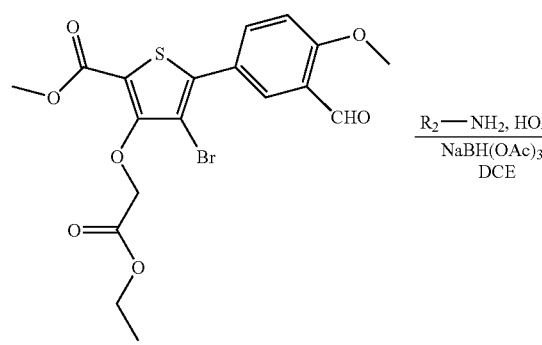

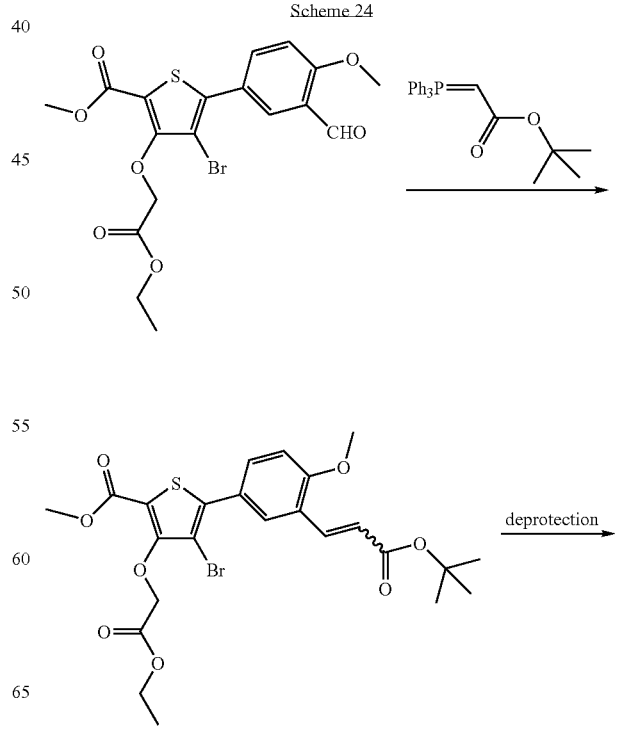

-continued

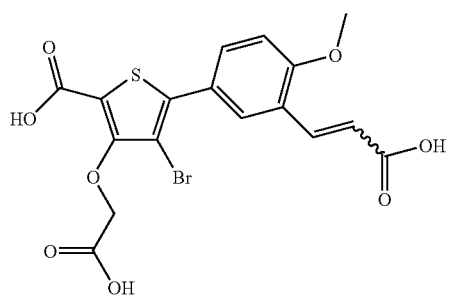

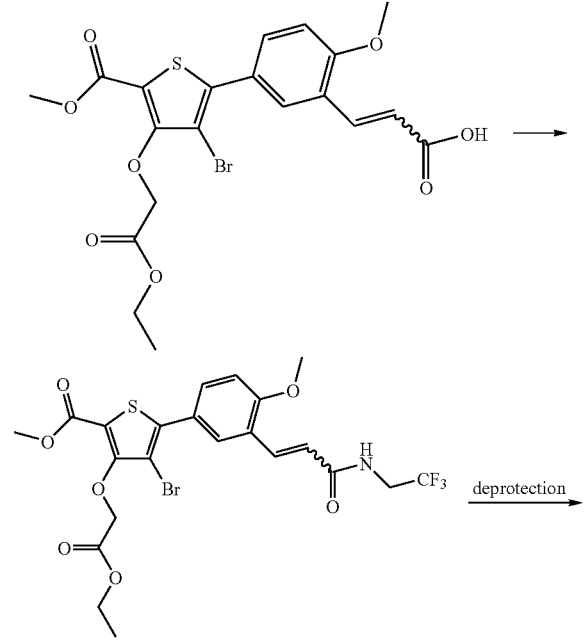

In the first step of Scheme 24, an aldehyde substituent of an aryl group (the aryl group being attached to thiophene at the 5-position) is converted to a carboxylate substituted alkene as shown. The carboxylate, as well as carboxylate substituents on the 2- and 3-positions of thiophene, can be hydrolyzed to form terminal carboxylic acids.

Scheme 25

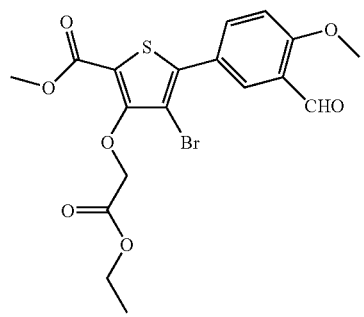 

In Scheme 25, an aldehyde substituent of an aryl group (the aryl group being attached to thiophene at the 5-position) is converted to a carboxylic acid substituted alkene as shown. The carboxylic acid can be converted to an amide. The resulting compound can be hydrolyzed to form terminal carboxylic acids on the 2- and 3-thiophene substituents.

Scheme 26

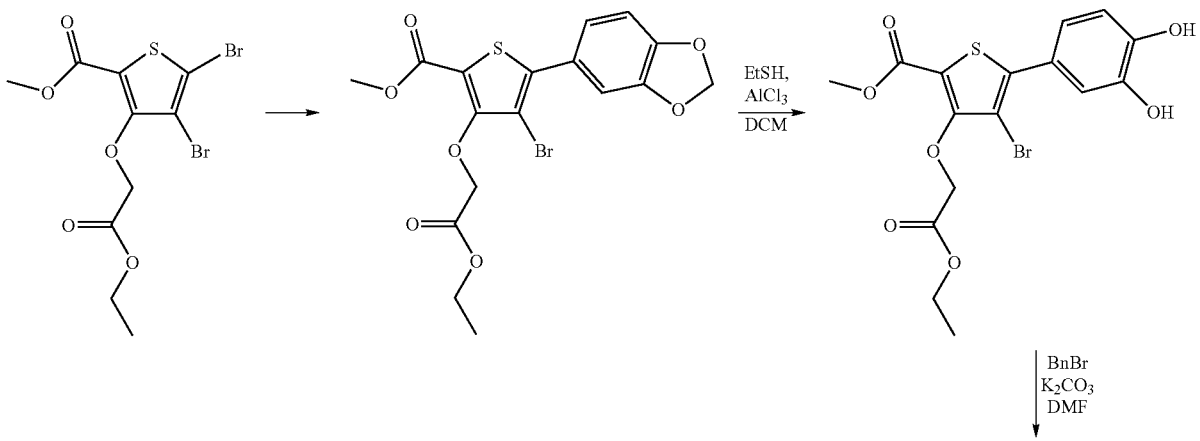

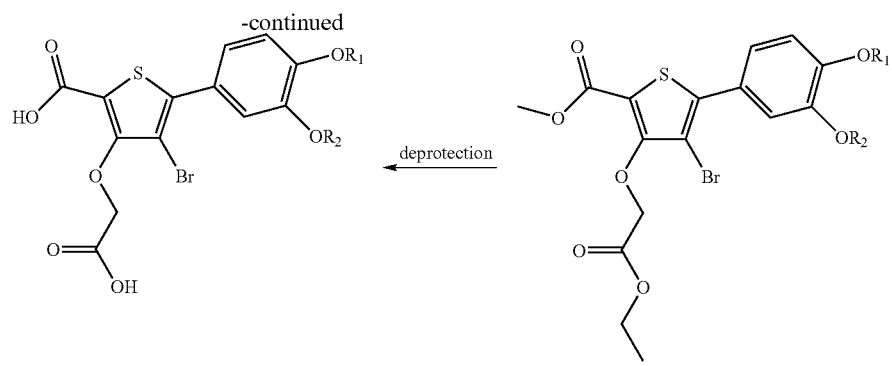

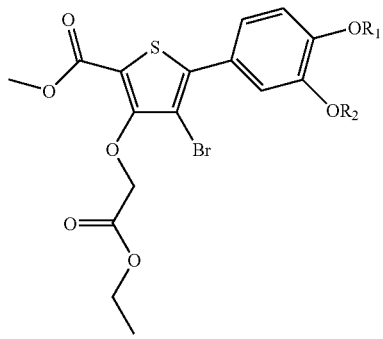

In the first step of Scheme 26, a halogen at the 5-position of thiophene is substituted with benzodioxol substituent. The dioxol can be converted to the dihydroxy product as shown, and each hydroxy group substituted with a group such as benzyl. The resulting compound can be hydrolyzed to form terminal carboxylic acids on the 2- and 3-thiophene substituents.

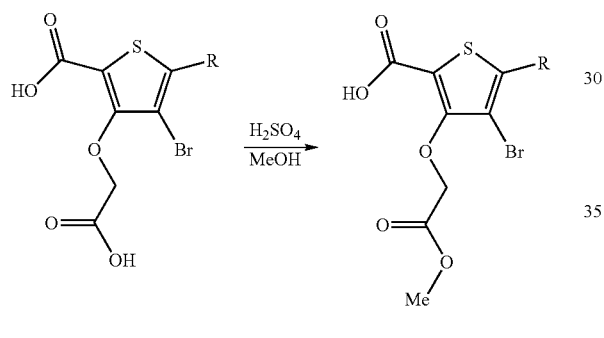

In Scheme 27, a carboxymethoxy substituent at the 3-position of thiophene is alkylated to form an alkoxy-2-oxoethoxy substituent.

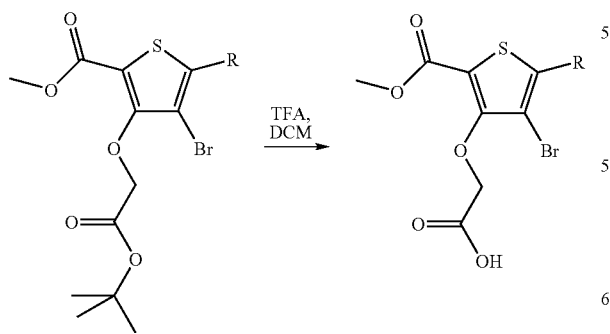

In Scheme 28, an alkxoy-2-oxoethoxy substituent at the 3-position of thiophene is selectively hydrolyzed to a terminal carboxylic acid. A carboxylate at the 2-position of thiophene remains protected.

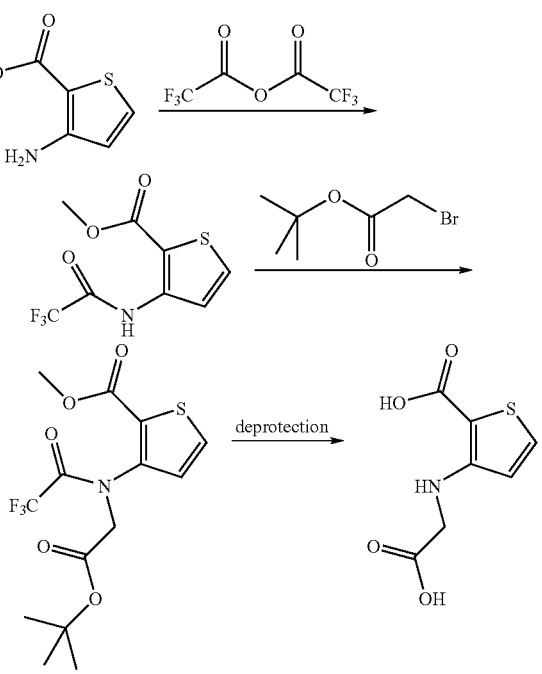

In Scheme 29, an amine substituent at the 3-position of thiophene is substituted to form an amide. The nitrogen of the amide can be alkylated with an alkyl carboxylate. The resulting compound can be hydrolyzed to form terminal carboxylic acids on the 2- and 3-thiophene substituents.

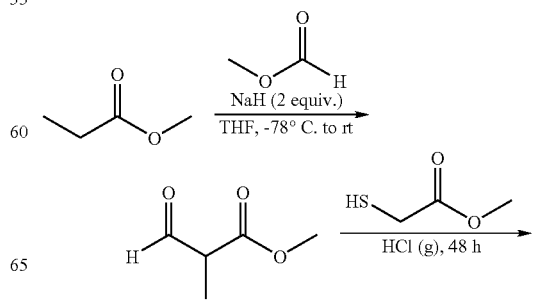

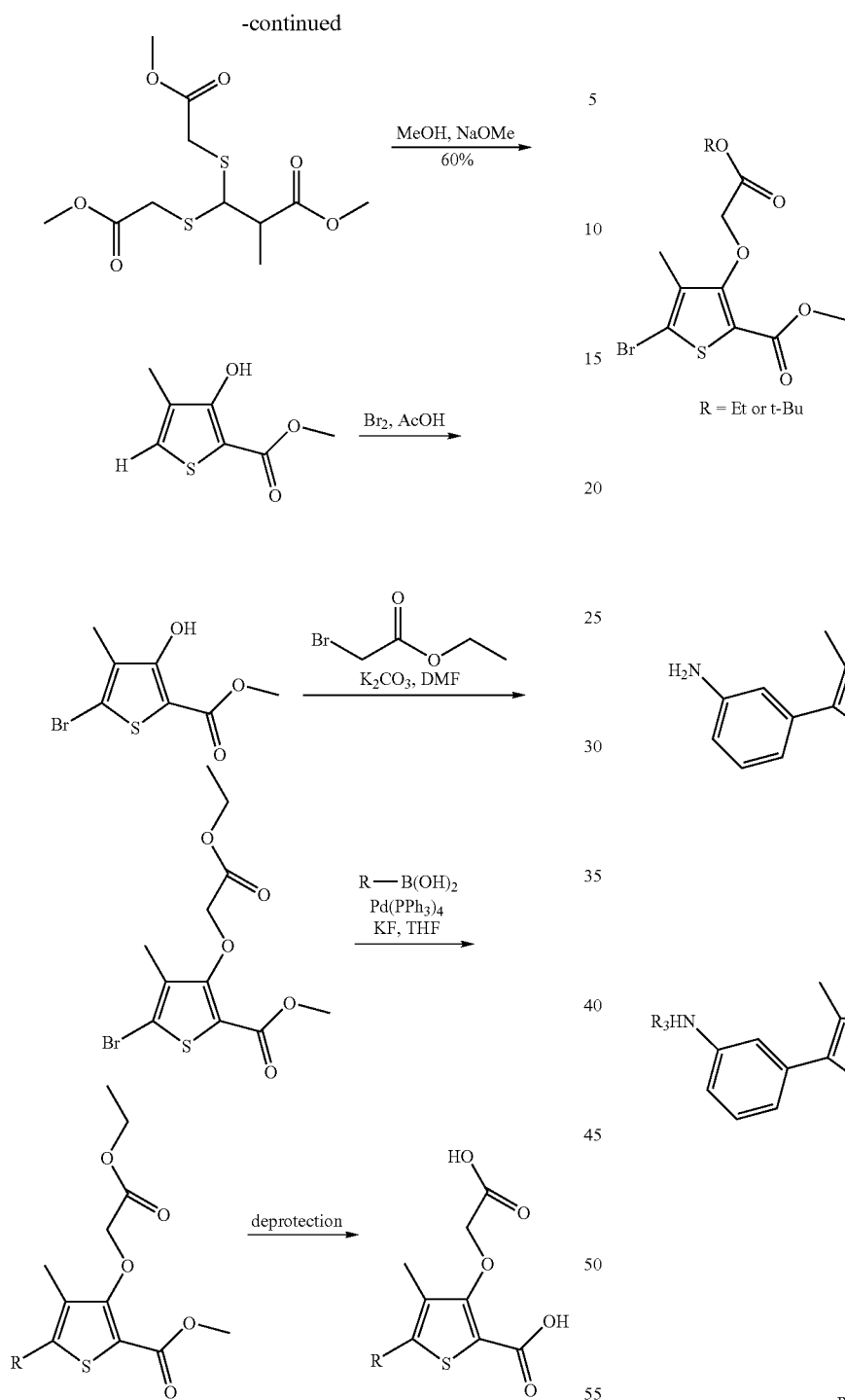
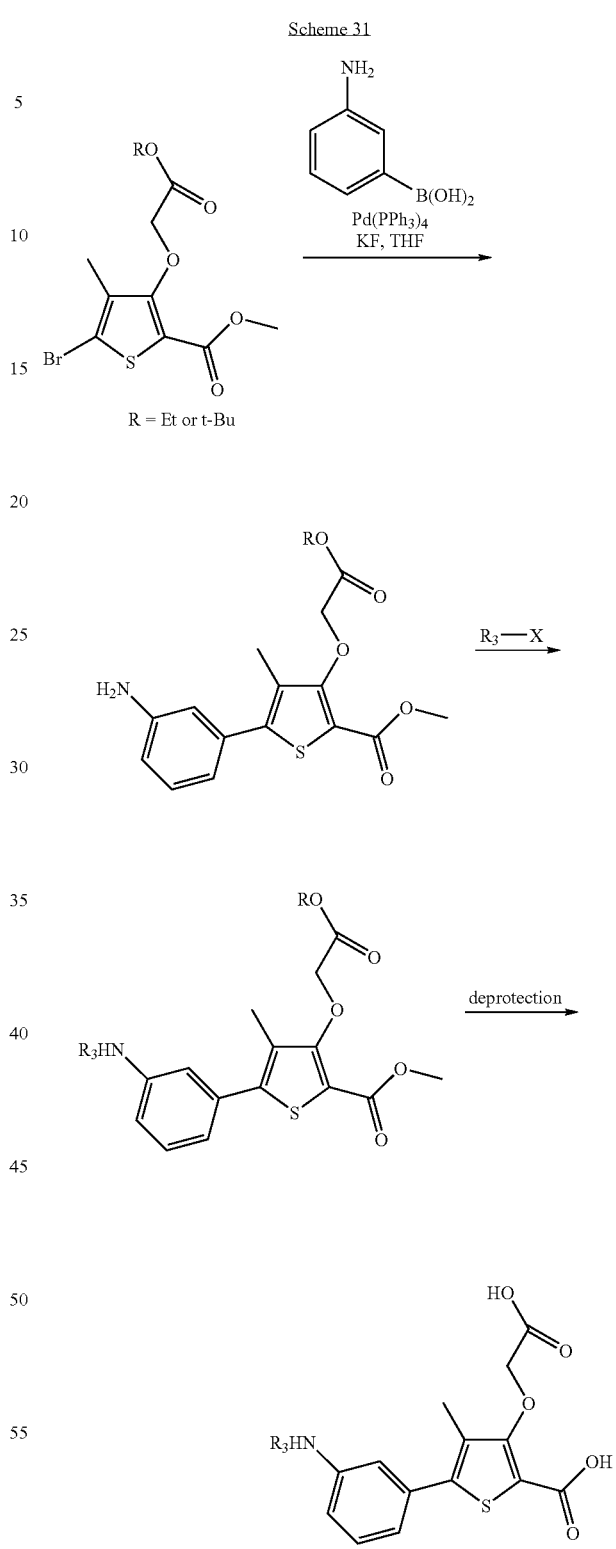

Scheme 31

In Scheme 30, an alkyl ester is converted to 2-alkyl-3-oxo-propionic acid alkyl ester as shown. The oxo group can be substituted to a dithioalkylcarboxylate as shown, which can be cyclized to form a 2-carboxylate, 3-hydroxy, 4-alkyl thiophene. The 5-thiophene position can be brominated. The 3-hydroxy substituent can be substituted to form 2-alkoxy-2-oxoethoxy. The 5-bromo substituent can be substituted with groups such as arylene, and the resulting compound can be hydrolyzed to form terminal carboxylic acids on the 2- and 3-thiophene substituents.

In Scheme 31, a halogen at the 5-position of thiophene is substituted with an amine-substituted arylene. The amino group can be substituted with a group such as acyl or sulfonyl, and the resulting compound can be hydrolyzed to form terminal carboxylic acids on the 2- and 3-thiophene substituents.

Scheme 32

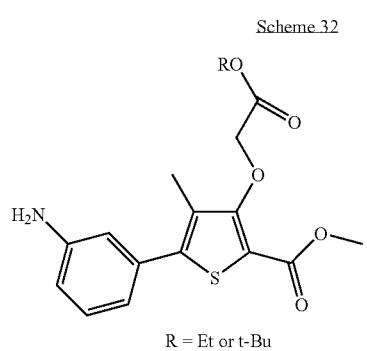

R = Et or t-Bu

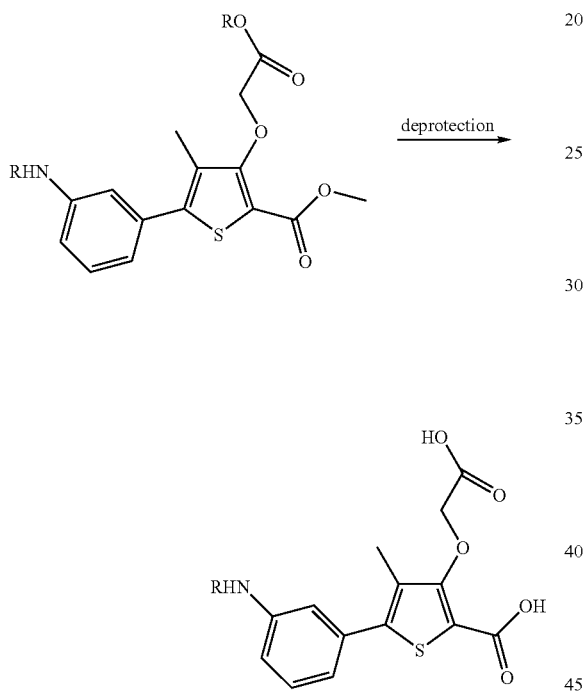

In Scheme 32, an amino substituent on an arylene (the arylene being on the 5-position of thiophene) can be substituted with a group such as alkyl or arylalkyl. The resulting compound can be hydrolyzed to form terminal carboxylic acids on the 2- and 3-thiophene substituents.

Scheme 33

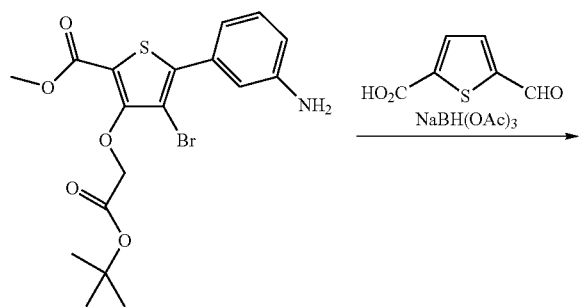

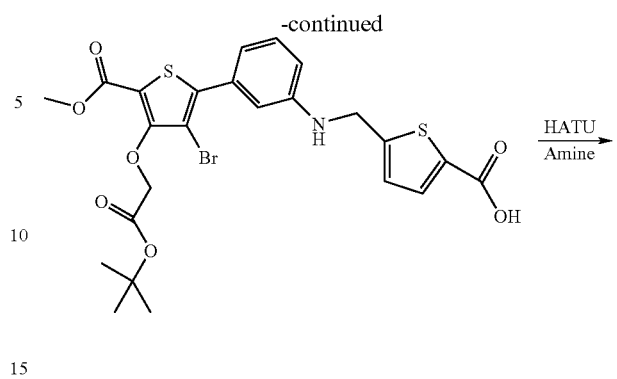

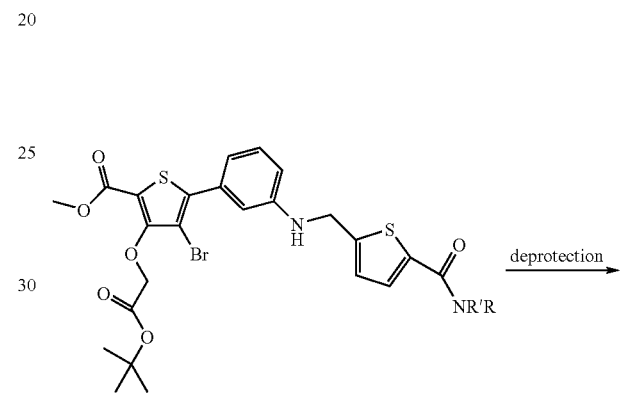

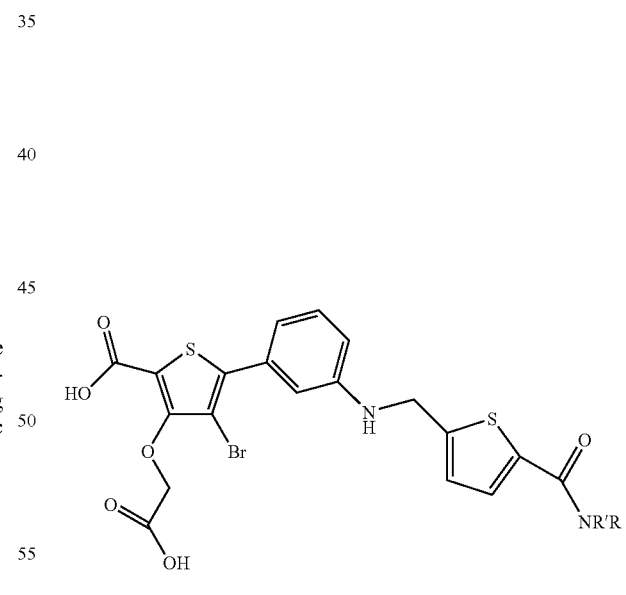

In Scheme 33, an amino substituent on an arylene (the arylene being on the 5-position of thiophene) is substituted through an alkyl linker to a substituted heterocyclic group such as thiophene carboxylic acid. The carboxylic acid substituent of that thiophene can be converted to an amide by conventional methods, and the resulting compound can be hydrolyzed to form terminal carboxylic acids on the 2- and 3-thiophene substituents.

137 138
Scheme 34
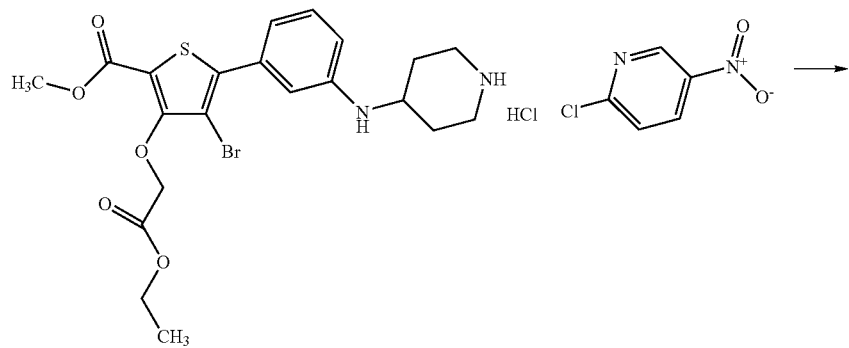
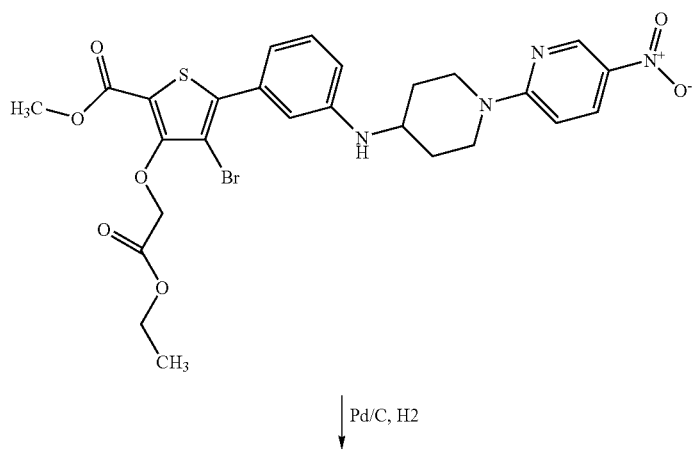
Pd/C, H2
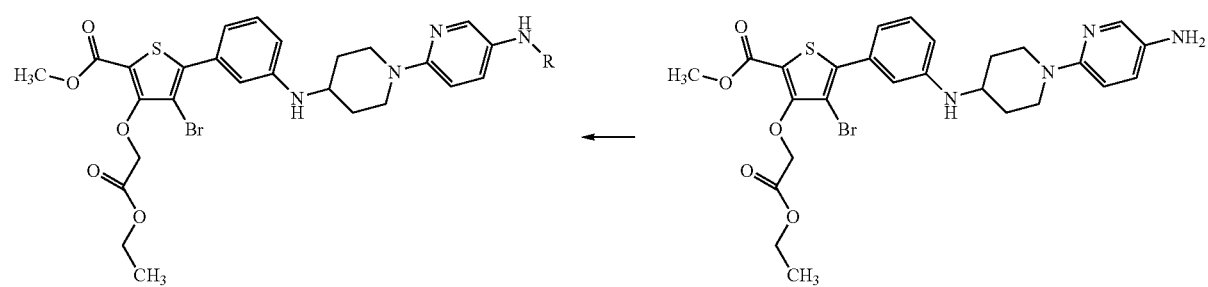

In Scheme 34, a pyridine substituent (attached to an aminophenyl group at the 5-position of thiophene) is substituted with nitropyridine. The nitro group is reduced to an amine, which can be substituted with another group such as acyl or sulfonyl.

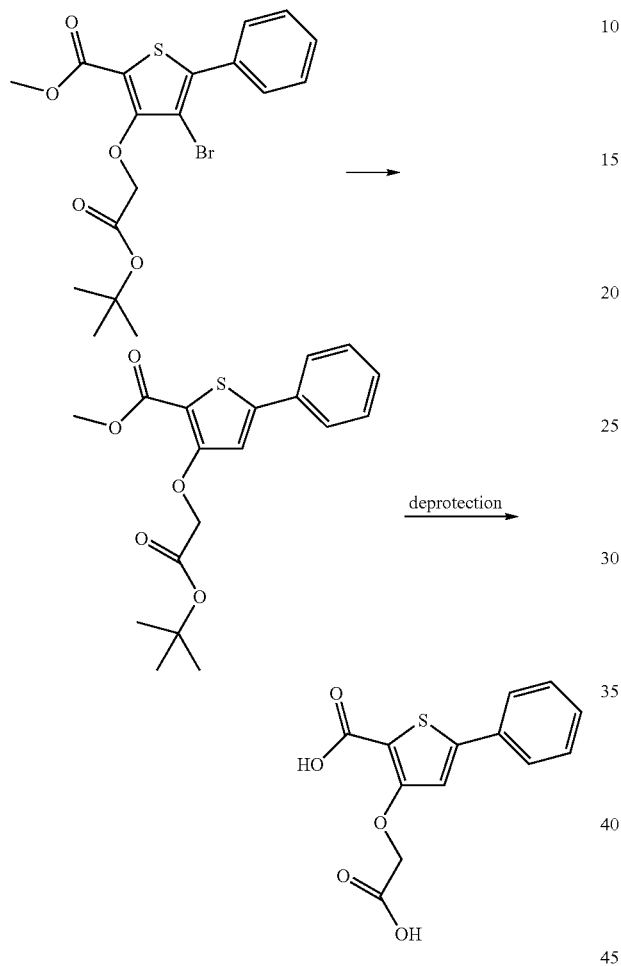

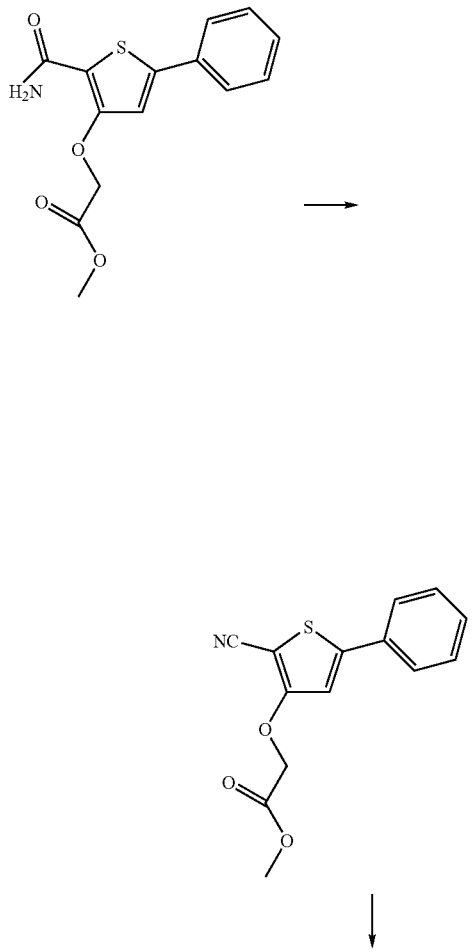

In Scheme 35, a bromine substituent at the 4-thiophene position is removed by conventional methods. Esters in the resulting compound can be hydrolyzed to form terminal carboxylic acids on the 2- and 3-thiophene substituents.

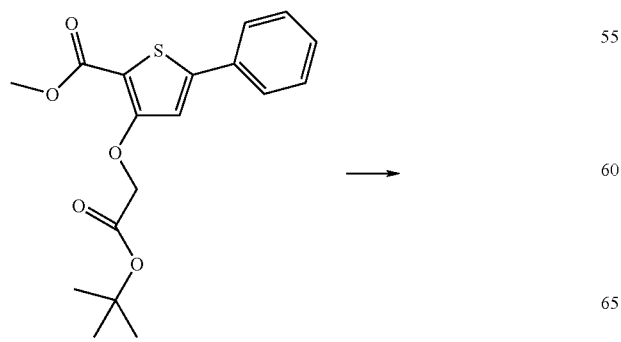

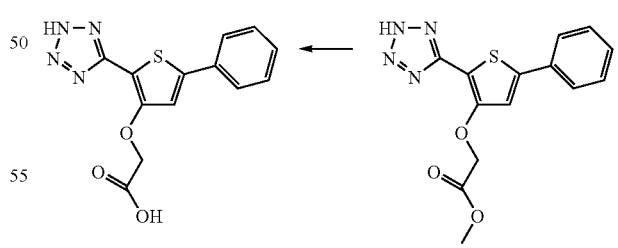

In Scheme 36, an amide is formed from an ester at the 2-thiophene position. The amide can be reacted with a cyanuric halide to form a cyano substituent at that position, which can in turn be reacted with an azide to form a tetrazole unit. An ester at the 3-position of the thiophene can be hydrolyzed to a carboxylic acid.

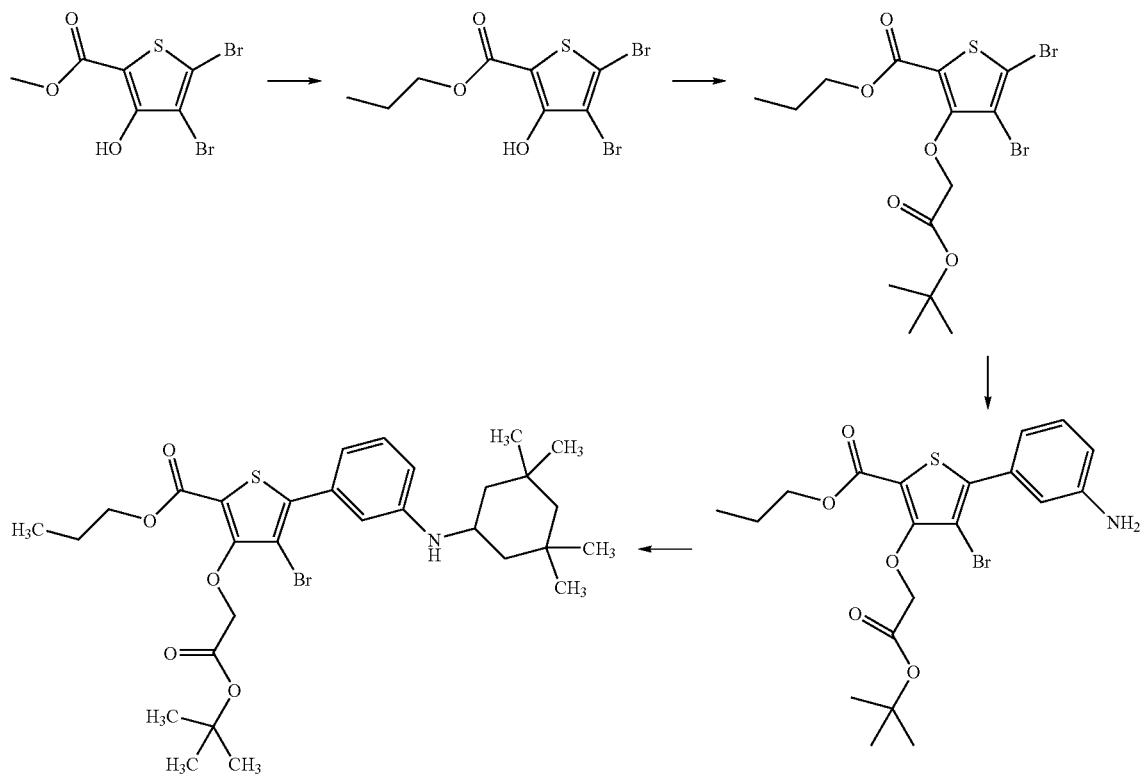

In Scheme 37, a methyl ester is converted to a propyl ester at the 2-thiophene position. A hydroxyl group at the 3-position is then substituted with 2-alkoxy-2-oxoethoxy. A bromine at the 5-thiophene position can be substituted with an aminophenyl group via a coupling reaction. The amine group can be further substituted with an alkyl group such as tetramethyl cyclohexane.

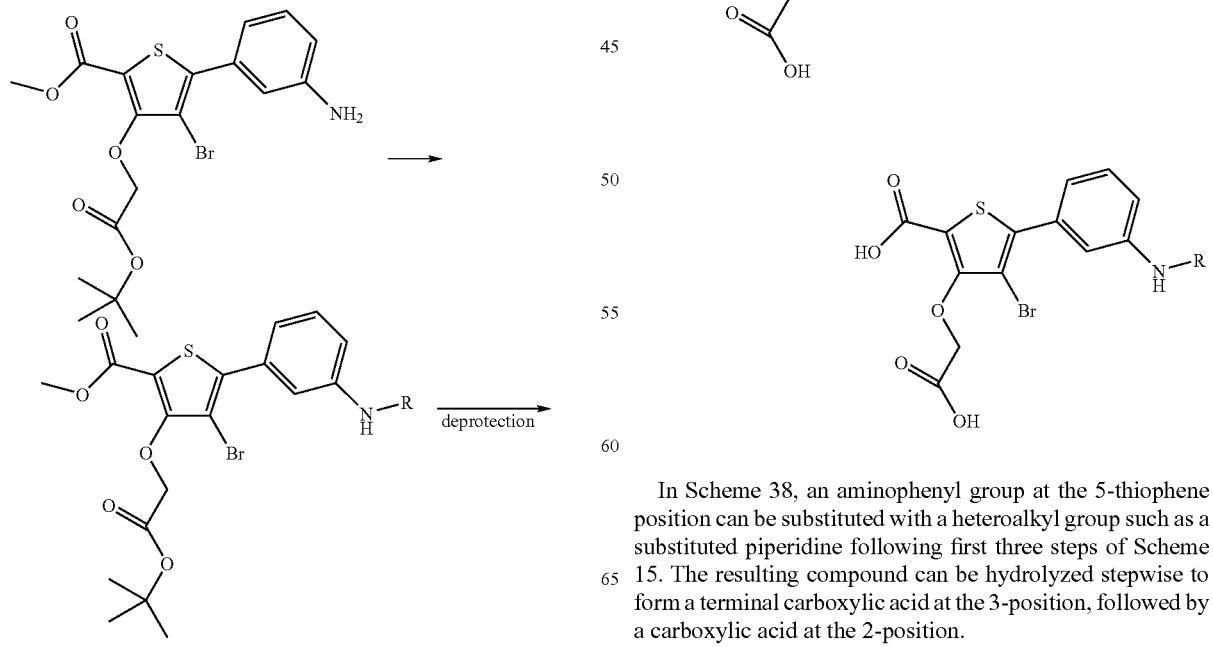

In Scheme 38, an aminophenyl group at the 5-thiophene position can be substituted with a heteroalkyl group such as a substituted piperidine following first three steps of Scheme 15. The resulting compound can be hydrolyzed stepwise to form a terminal carboxylic acid at the 3-position, followed by a carboxylic acid at the 2-position.

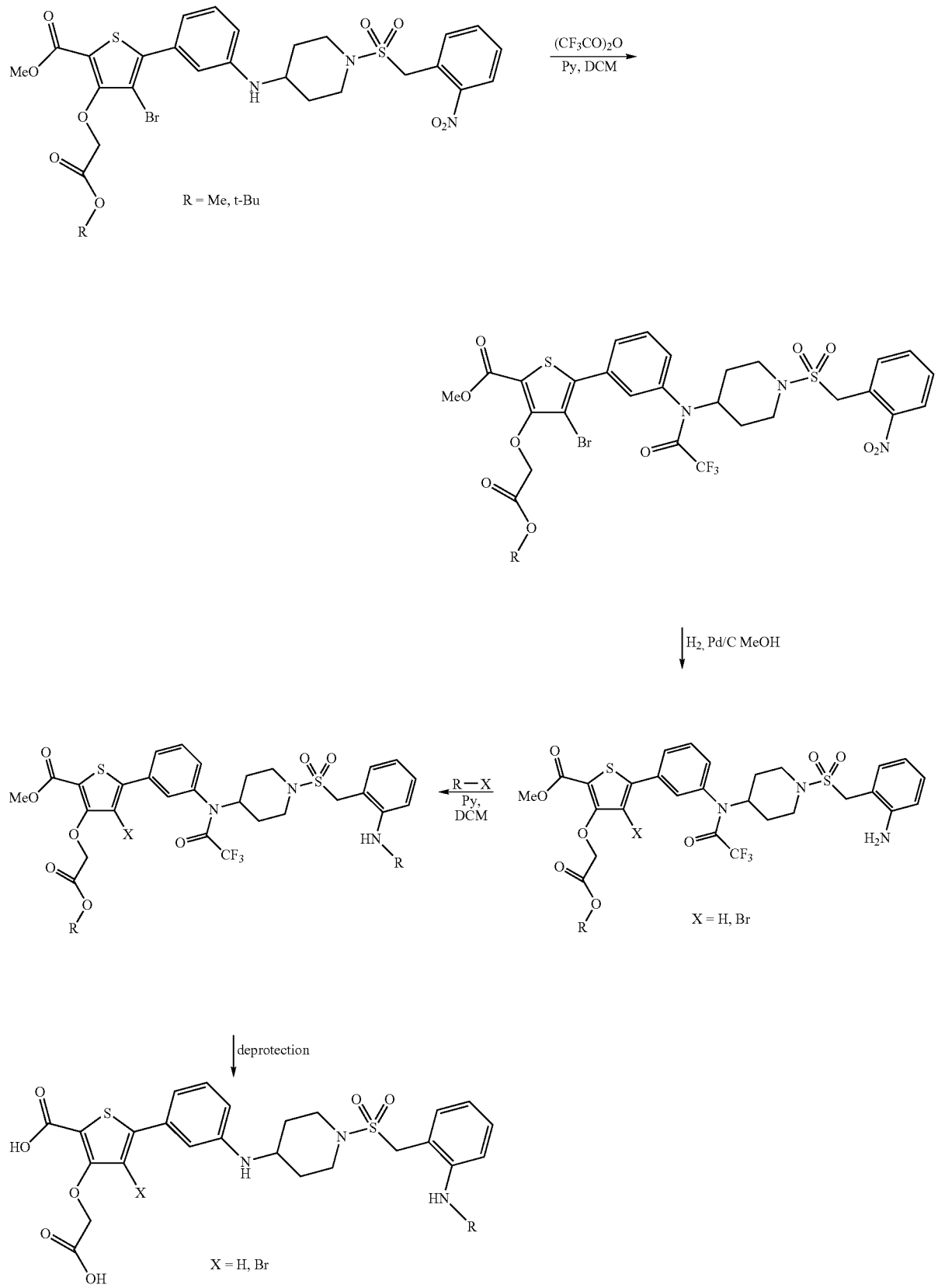

In Scheme 39, a disubstituted amine linking a phenyl group at the 5-thiophene position to a substituted piperidine is acylated to a tertiary amine with trifluoroacetic anhydride. A terminal nitro group is reduced to an amine, and the resulting amine can be substituted with a group such as acyl. The compound can be hydrolyzed to form carboxylic acids at the 2- and 3-thiophene positions.

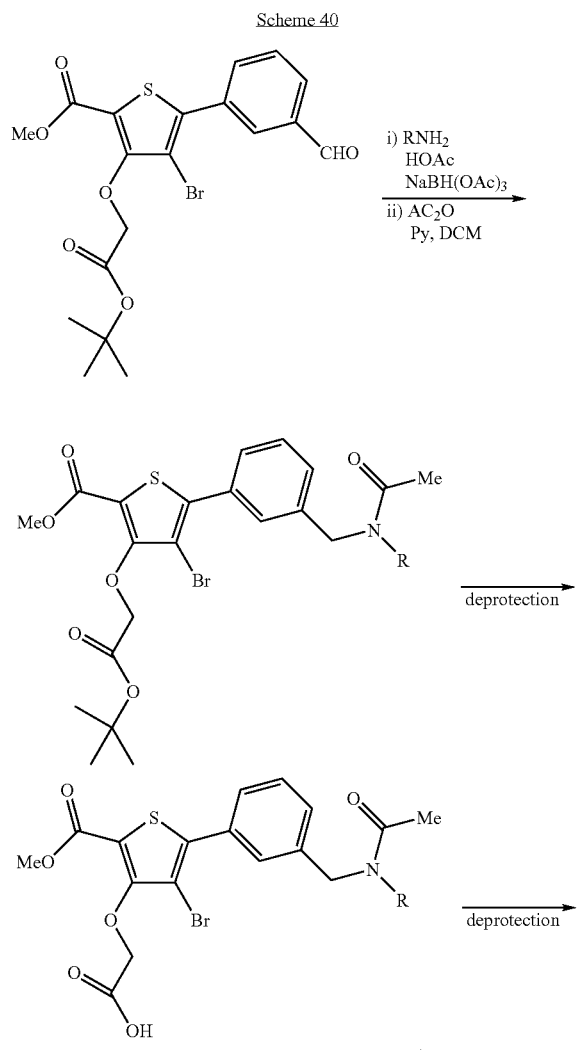

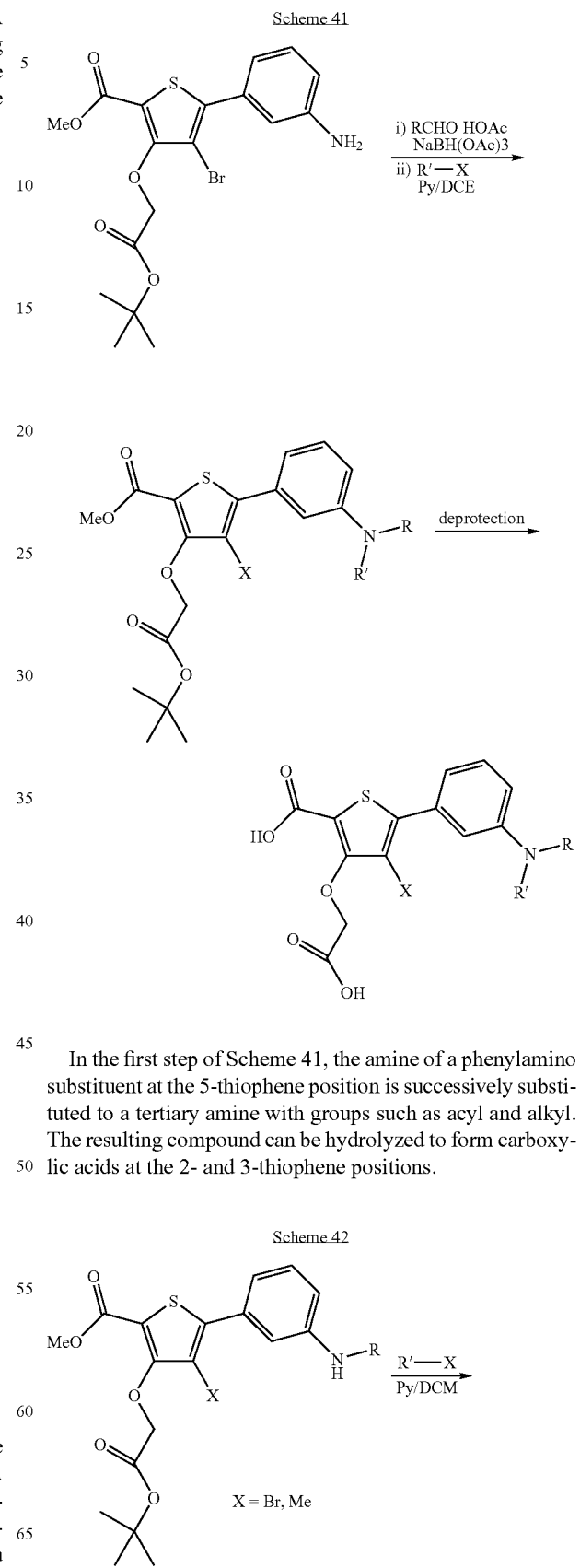

In Scheme 40, a benzaldehyde substituent at the 5-thiophene position is reduced as shown to an acyl amine. A t-butoxy protective group can be hydrolyzed to the corresponding terminal carboxylic acid at the 3-thiophene position, followed by hydrolysis of the ester at the 2-position to a carboxylic acid.

In the first step of Scheme 41, the amine of a phenylamino substituent at the 5-thiophene position is successively substituted to a tertiary amine with groups such as acyl and alkyl. The resulting compound can be hydrolyzed to form carboxylic acids at the 2- and 3-thiophene positions.

-continued

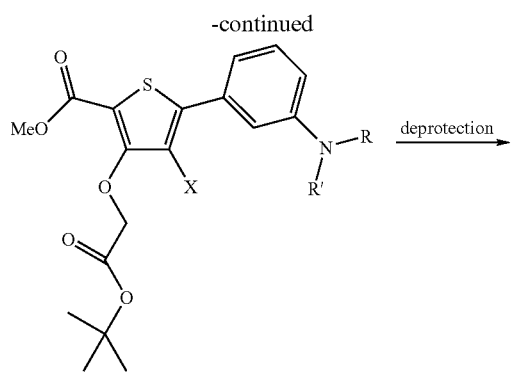

-continued

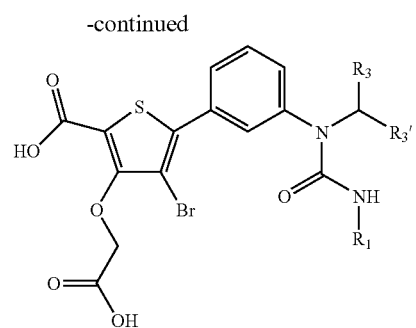

In Scheme 43, a secondary amine on a phenyl substituent at the 5-thiophene position is further substituted, such as by an amide, as shown. The resulting compound can be hydrolyzed to form carboxylic acids at the 2- and 3-thiophene positions.

In Scheme 42, an secondary amine on a phenyl substituent at the 5-thiophene position is further substituted, such as by an acyl group, as shown. The resulting compound can be hydrolyzed to form carboxylic acids at the 2- and 3-thiophene positions.

Scheme 44

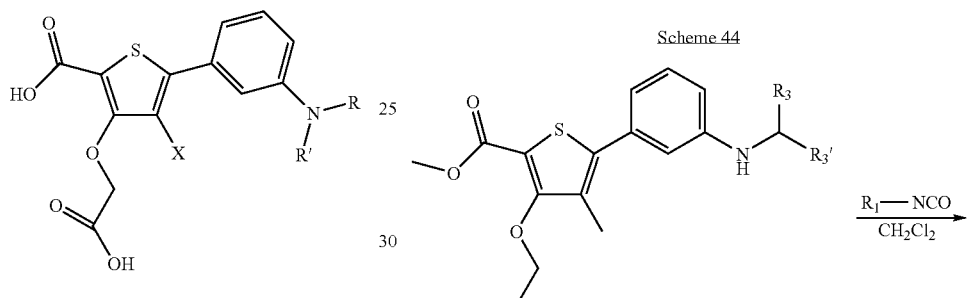

Scheme 43

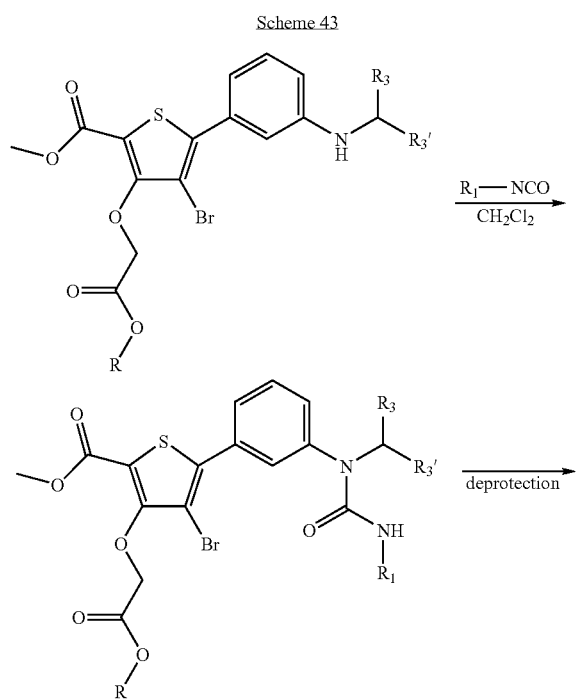

In Scheme 44, a secondary amine on a phenyl substituent at the 5-thiophene position is further substituted, such as by an amide, as shown. A methyl group is at the 4-thiophene position. The resulting compound can be hydrolyzed to form carboxylic acids at the 2- and 3-thiophene positions.

Scheme 45

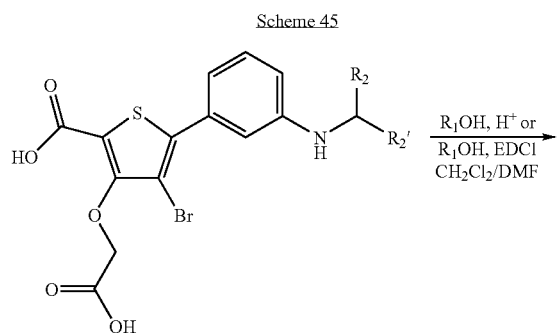

In Scheme 45, the 3-carboxymethoxy thiophene substituent is substituted with another group such as alkyl under acidic conditions.

Scheme 46

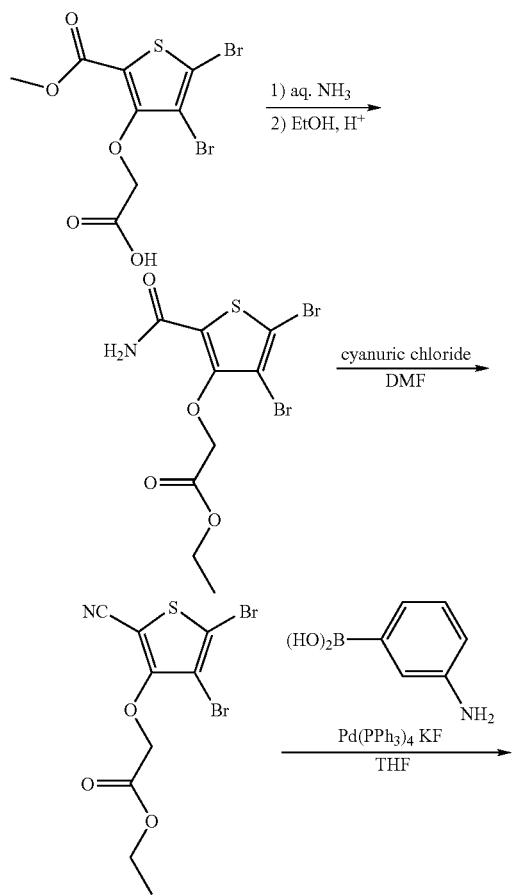

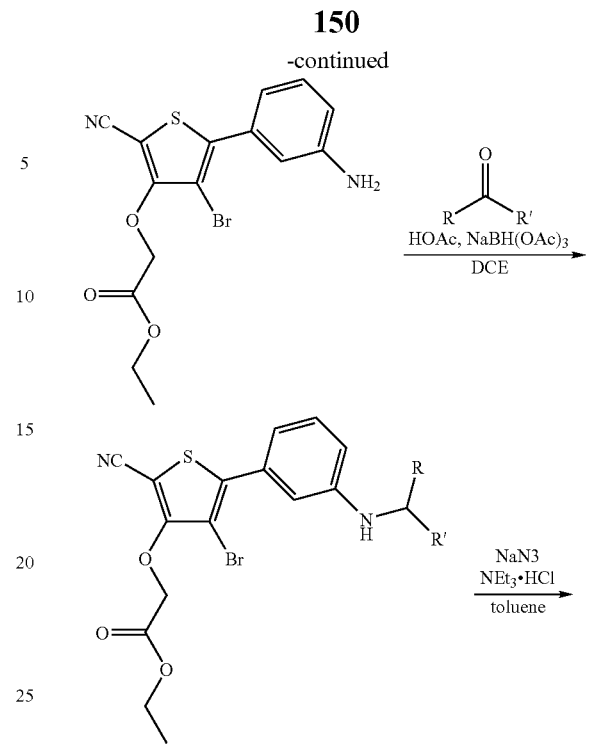

In the first step of Scheme 46, a methyl ester substituent at the 2-thiophene position is treated with amine to form an amide, while a 3-carboxymethoxy substituent is protected by treatment with an alkanol. In the second step, the amide is transformed to a cyano group. In step three, a bromine substituent at the 5-thiophene position is substituted with an amino phenyl group, which can be further substituted at the amine position in step four. In step five, the resultant compound can be treated with sodium azide to form a tetrazole at the 2-thiophene position. In step six, the alkyl protective group at the 3-thiophene position can be hydrolyzed to form a 3-carboxymethoxy group.

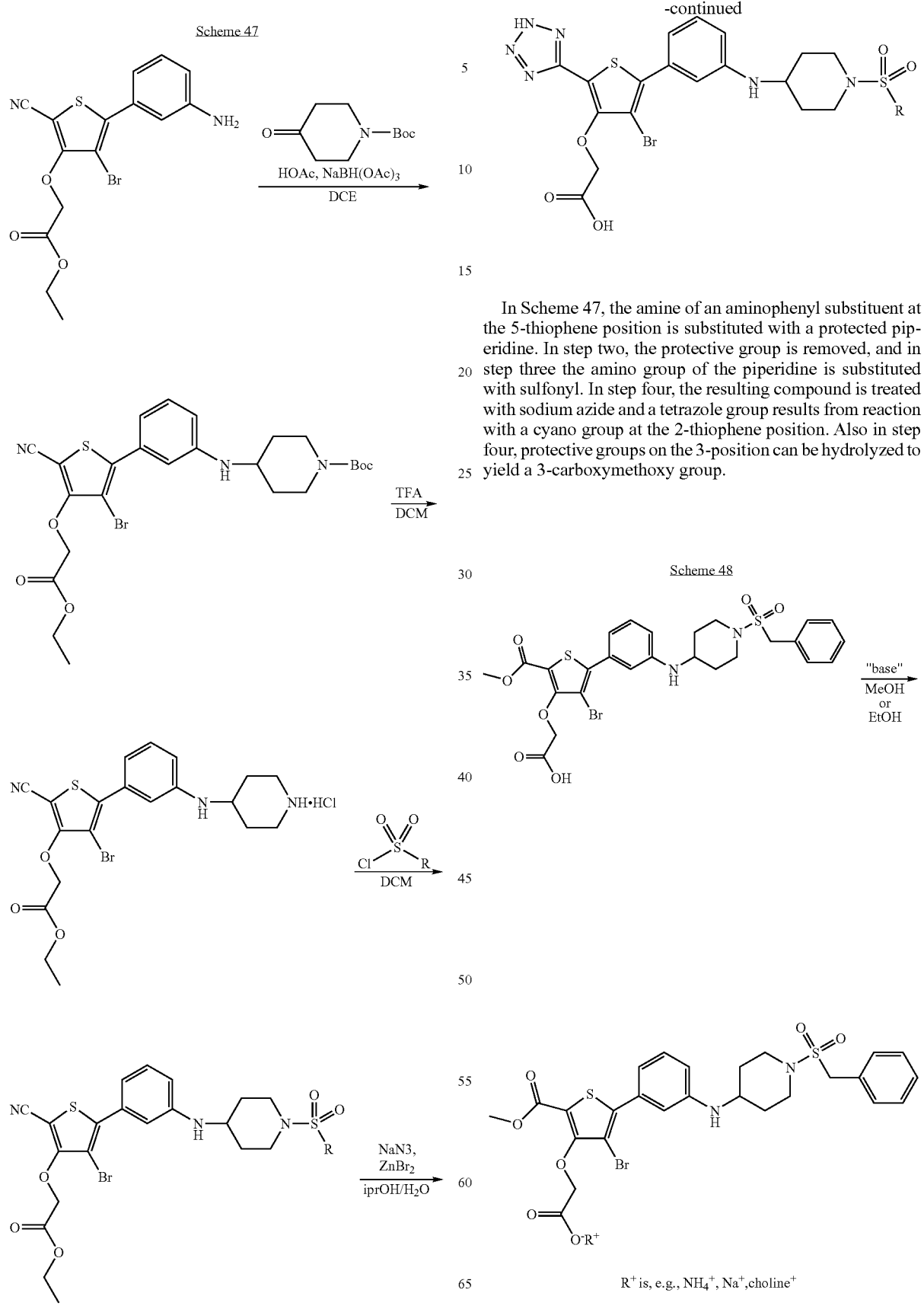

In Scheme 47, the amine of an aminophenyl substituent at the 5-thiophene position is substituted with a protected piperidine. In step two, the protective group is removed, and in step three the amino group of the piperidine is substituted with sulfonyl. In step four, the resulting compound is treated with sodium azide and a tetrazole group results from reaction with a cyano group at the 2-thiophene position. Also in step four, protective groups on the 3-position can be hydrolyzed to yield a 3-carboxymethoxy group.

$R^+$ is, e.g., $NH_4^+$, $Na^+$, choline$^+$

In Scheme 48, a 3-carboxymethoxy thiophene substituent is treated with base to yield a salt.
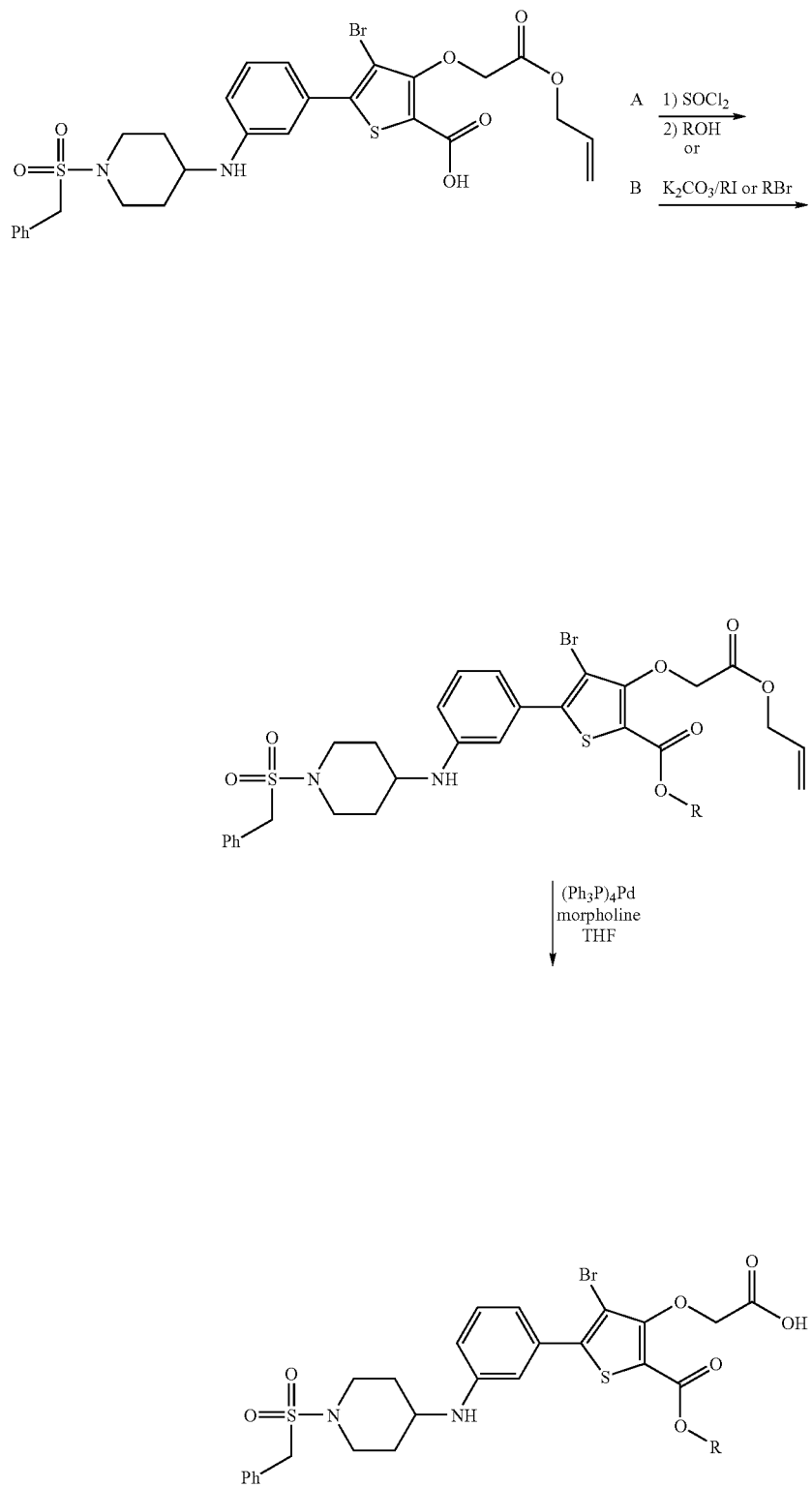

In Scheme 49, a 2-carboxylic acid thiophene group is substituted with a group such as an aryl alkyl group following treatment with sulfonyl chloride. In step 2, the compound can be deprotected at the 3-position to yield a 3-carboxymethoxy substituent.
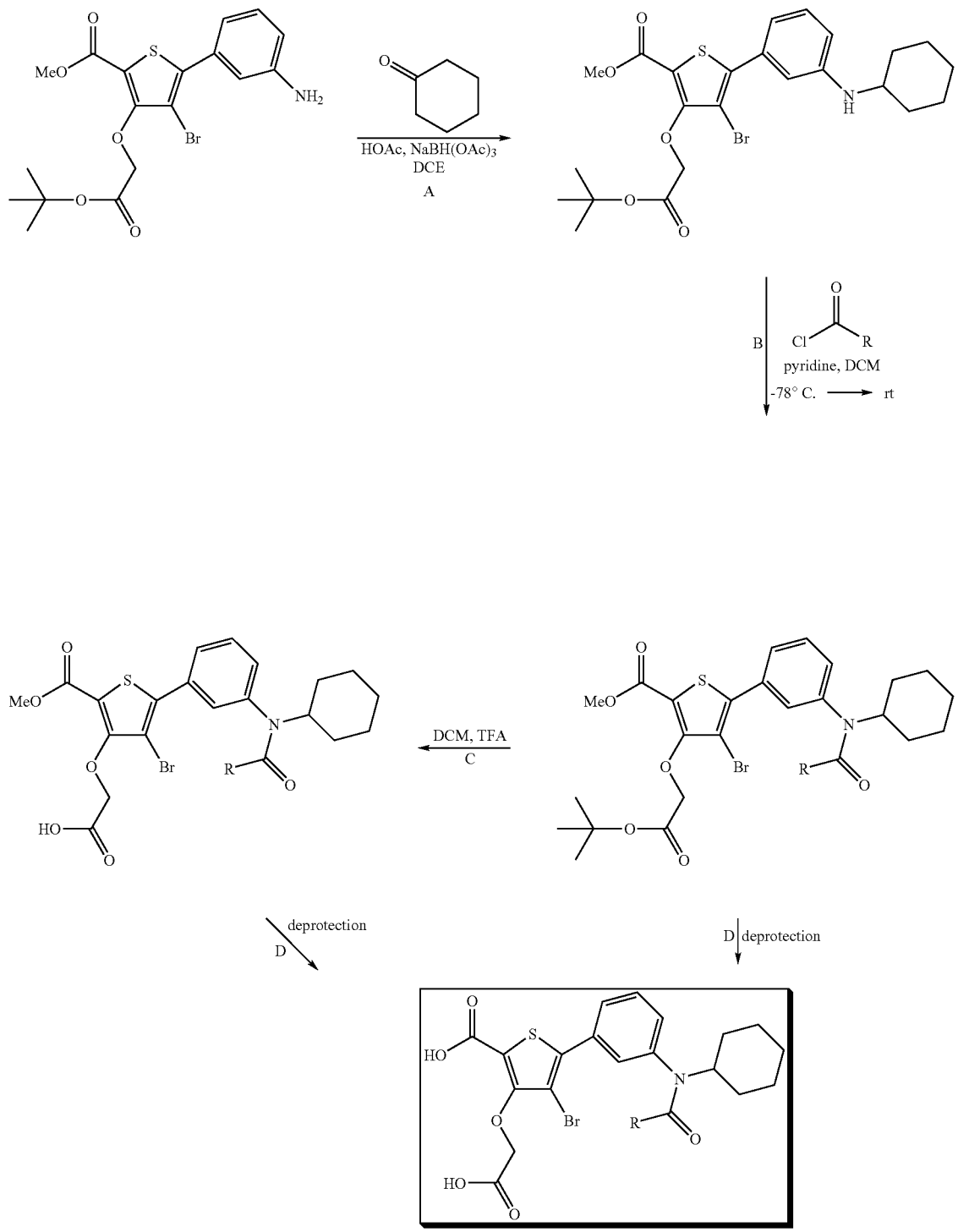
Scheme 50

In Scheme 50, the amine group of an aminophenyl 5-thiophene substituent undergoes reductive amination with cyclohexanone to yield a disubstituted amine. The amine can be treated with acyl chloride to afford an amide. The resulting compound can either be selectively deprotected first at the 3-carboxy position and then at the 2-thiophene position to yield terminal carboxylic acids at both those positions, or it can be deprotected simultaneously at both positions, as shown.

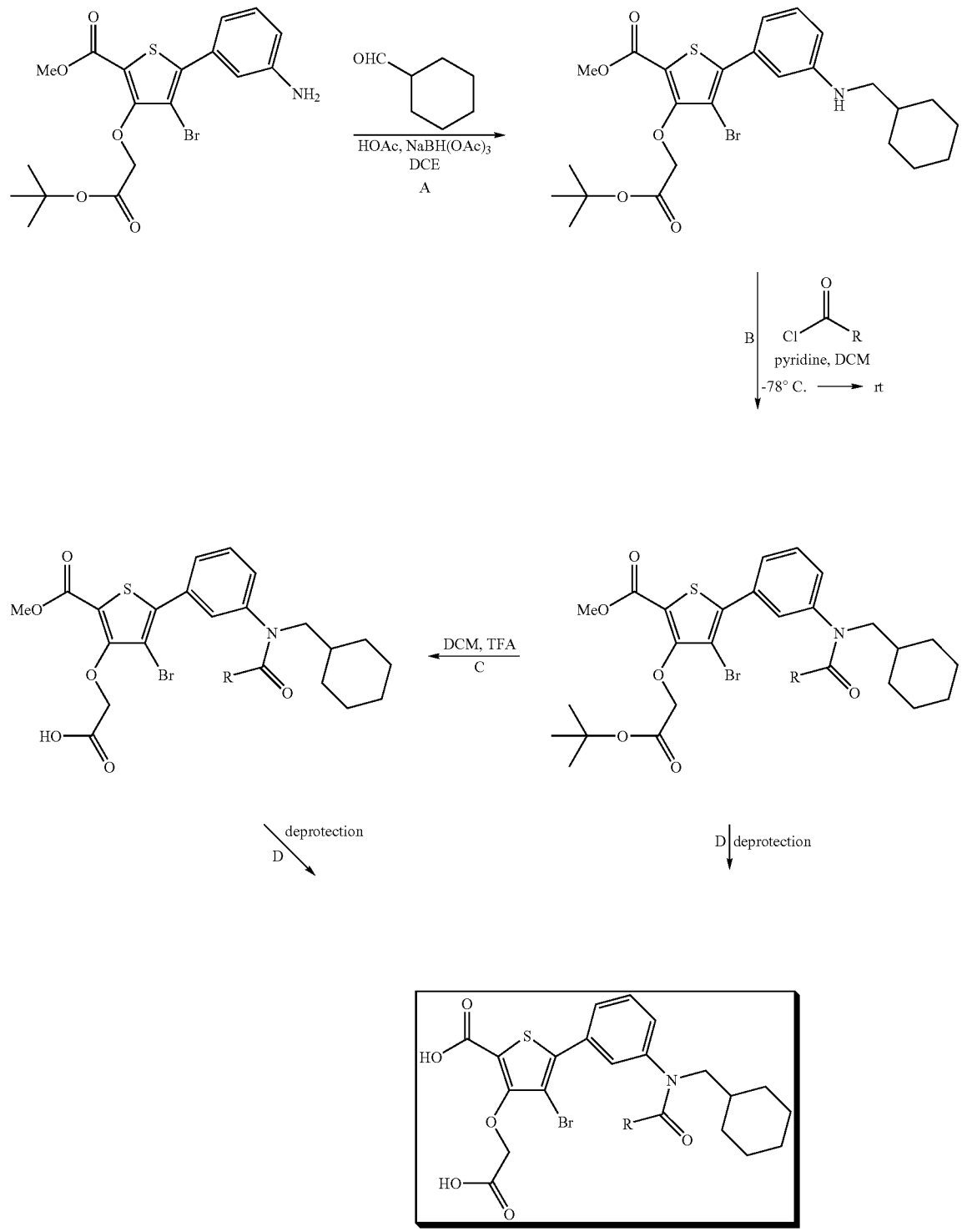

Scheme 51

In Scheme 51, the amine group of an aminophenyl 5-thiophene substituent undergoes reductive amination with cyclohexanecarbaldehyde to yield a disubstituted amine. The amine can be treated with acyl chloride to afford an amide. The resulting compound can either be selectively deprotected first at the 3-carboxy position and then at the 2-thiophene position to yield terminal carboxylic acids at both those positions, or it can be deprotected simultaneously at both positions, as shown.

Scheme 52

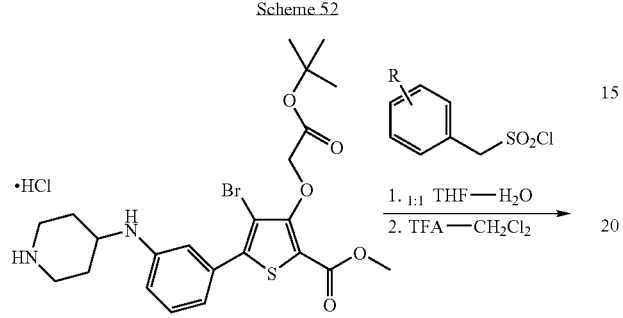

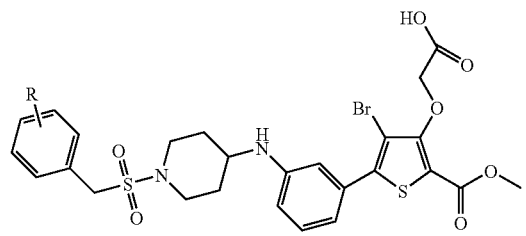

-continued

In Scheme 52, the amine of a piperidine substituent (ultimately attached to the 5-thiophene position via aminophenylene) is sulfonated with an arylalkyl sulfonyl substituent. A protective group on the 3-thiophene substituent can be hydrolyzed to a 3-carboxymethoxy substituent.

Scheme 53

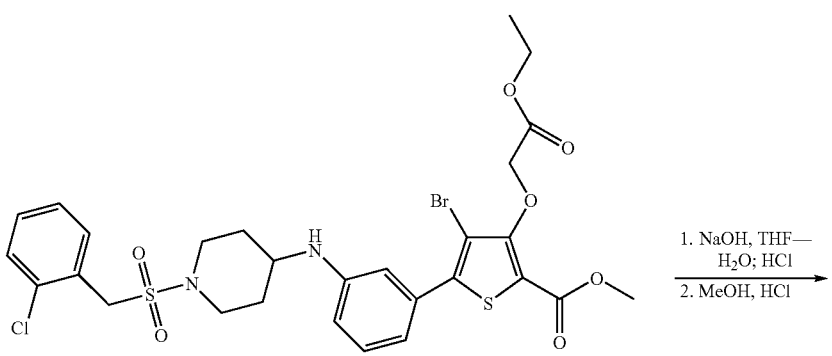

1. NaOH, THF—H$_2$O; HCl
2. MeOH, HCl

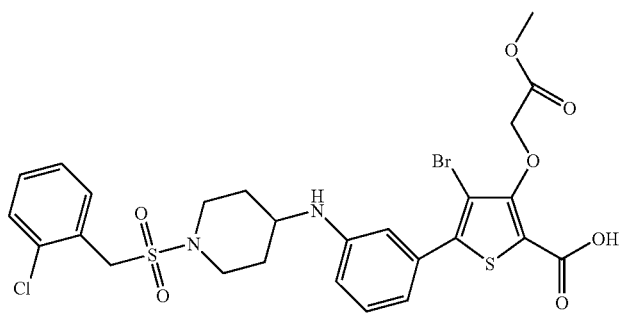

In Scheme 53, an alkoxycarboxymethoxy substituent at the 3-thiophene position is deprotected, and can subsequently be substituted with an alkyl group such as methyl following treatment with methanol. An alkyl ester at the 2-thiophene position is hydrolyzed to yield a carboxylic acid.

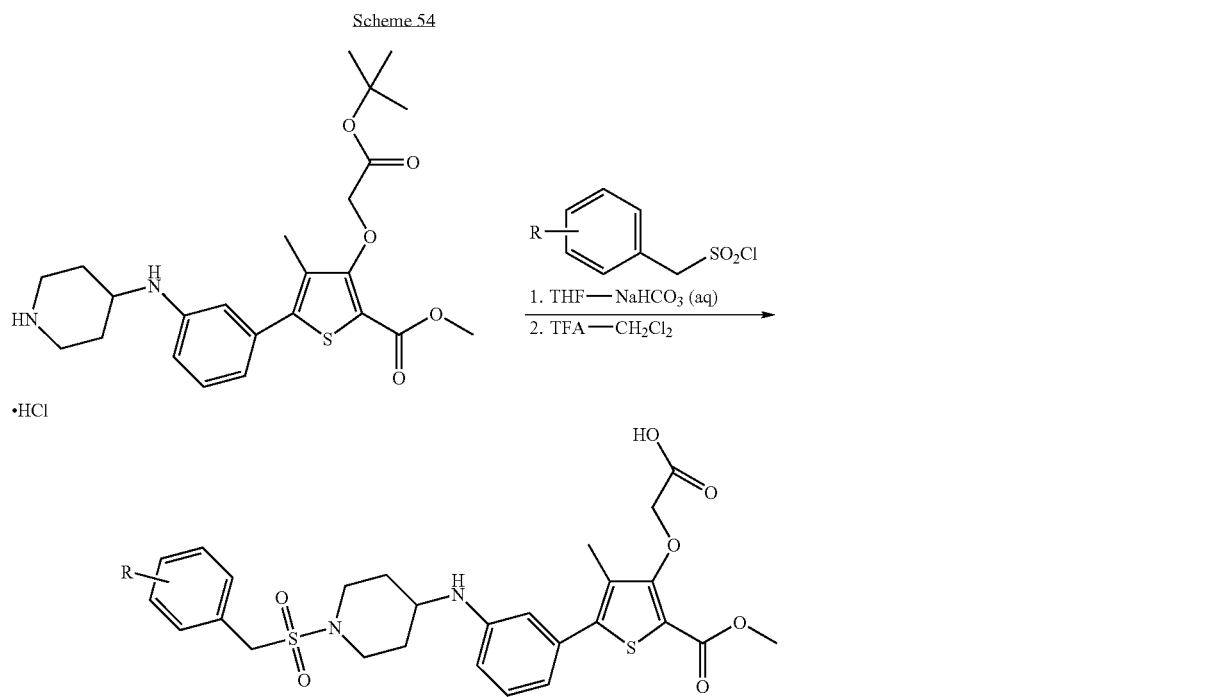

In Scheme 54, as in Scheme 52, the amine of a piperidine substituent (ultimately attached to the 5-thiophene position via aminophenylene) is sulfonated with an arylalkyl sulfonyl substituent. A protective group on the 3-thiophene substituent can be hydrolyzed to a 3-carboxymethoxy substituent. The thiophene is substituted with an alkyl group at the 4-position.

In Scheme 55, a hydroxyl group at the 3-thiophene position is substituted under basic conditions to form a 1-carboxyethoxy substituent. A methyl ester at the 2-thiophene position can be hydrolyzed to a carboxylic acid.

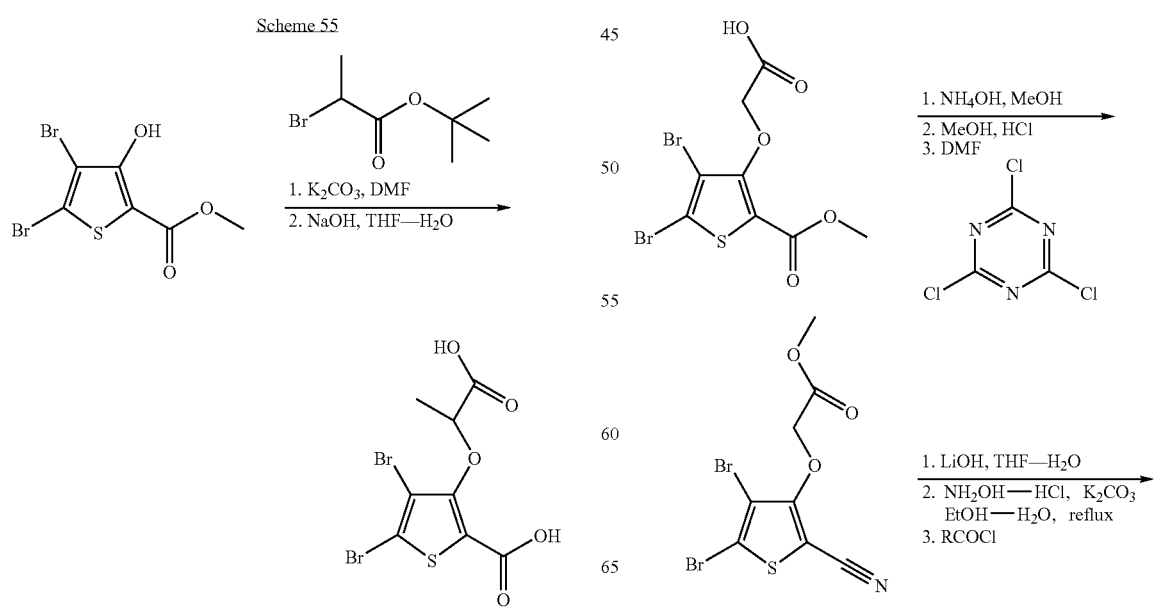

-continued

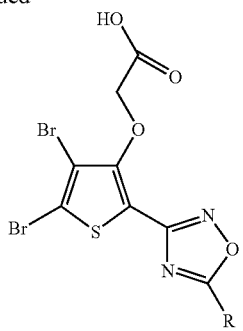

In Scheme 56, a 2-thiophene methyl ester is treated with ammonia to afford a 2-carbamoyl substituent. The resulting compound can be acidified in the presence of methanol to yield a methyl ester on the 3-carboxymethoxy substituent. In the third step, the resulting compound reacts with cyanuric chloride to form a 2-cyano substituent. It is further hydrolyzed to the 3-carboxymethoxy substituent in step four. In steps five and six, the 2-cyano substituent reacts with hydroxylamine hydrochloride to form 2-N-hydroxycarbamimidoyl, which can be treated with an anhydride such as acetic anhydride to form an oxadiazole substituent.

Scheme 57

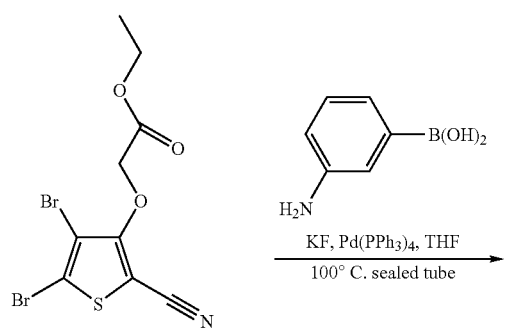

KF, Pd(PPh$_3$)$_4$, THF
100° C. sealed tube

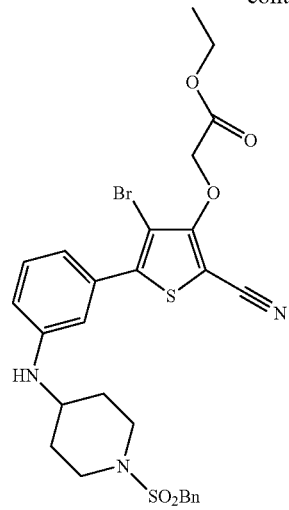

1. NaN$_3$, ZnBr$_2$, i-PrOH⁻
   H$_2$O, heat
2. ROH, HCl

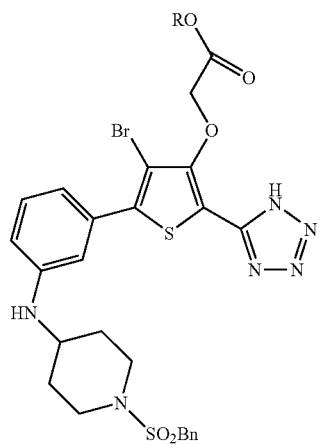

In Scheme 57, a 5-bromothiophene substituent reacts with an aminoaryl boronic acid to form a 5-aminophenyl substituent on thiophene. In step two, the amine of the amino phenyl group is sulfonated, and in step three, a 2-cyano substituent reacts with sodium azide to form a 2-tetrazole thiophene. In step four, a protective group on the 3-thiophene substituent is hydrolyzed in the presence of an alkanol to afford an alkyl ester.

Scheme 58

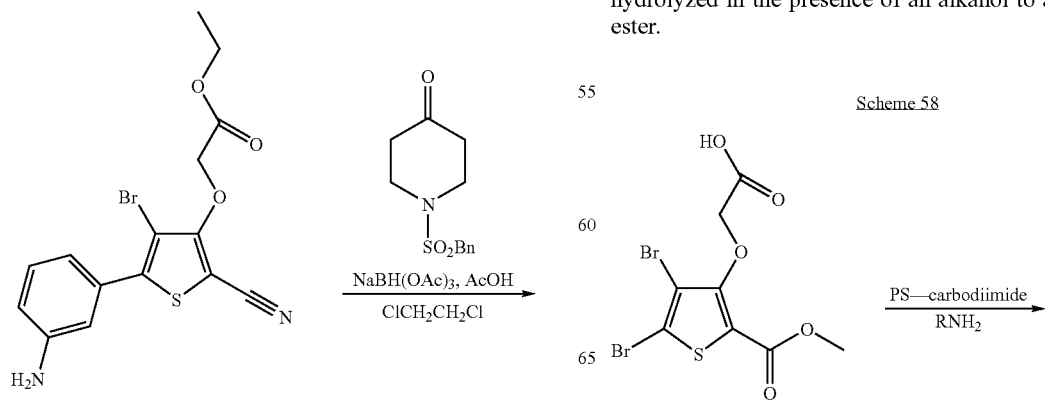

PS—carbodiimide
RNH$_2$

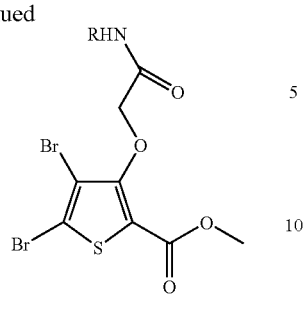
In Scheme 58, a 3-carboxymethoxy substituent reacts with an amine in the presence of PS-carbodiimide to form an amide.
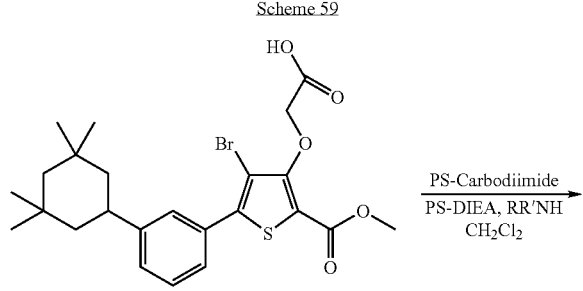
In Scheme 59, a 3-carboxymethoxy substituent reacts with a secondary amine in the presence of PS-carbodiimide to form an amide.
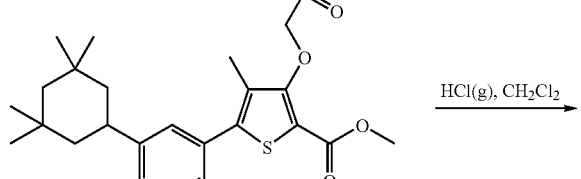
In Scheme 60, a carbamoyl substituent is hydrolyzed to yield a terminal amine substituent on the 3-thiophene position.
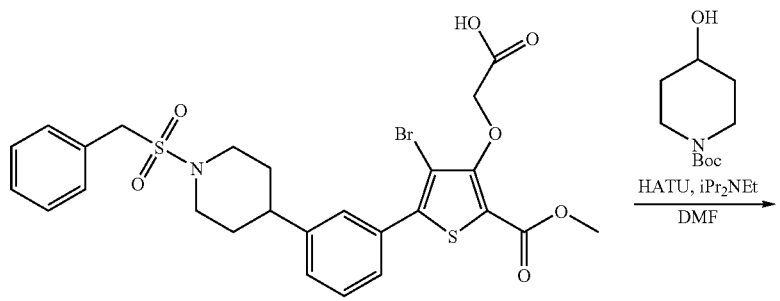

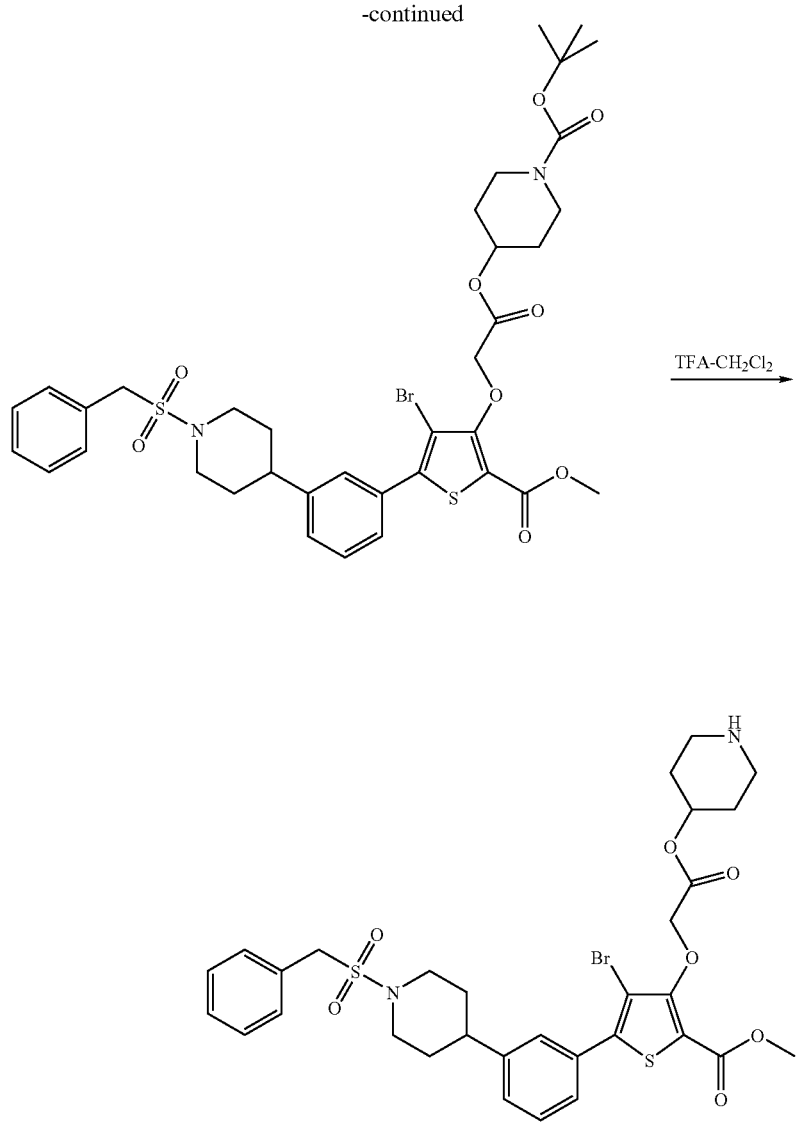
In Scheme 61, a 3-thiophene carboxymethoxy substituent reacts with a hydroxypiperidine carboxylic acid ester to form a piperidine carboxylic acid ester. The piperidine can be hydrolyzed to yield a piperidinyloxycarbonylmethoxy substituent at the 3-position.
Scheme 62
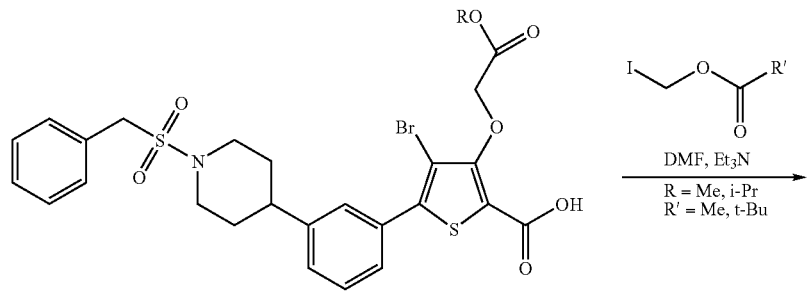

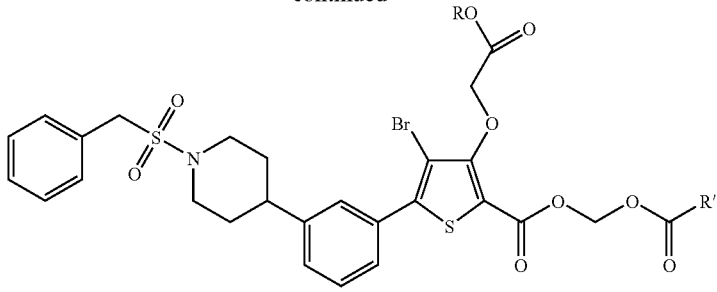

In Scheme 62, a 2-thiophene carboxylic acid substituent reacts with an iodyl alkyl ester reagent to yield a diester on the 2-thiophene position, as shown.

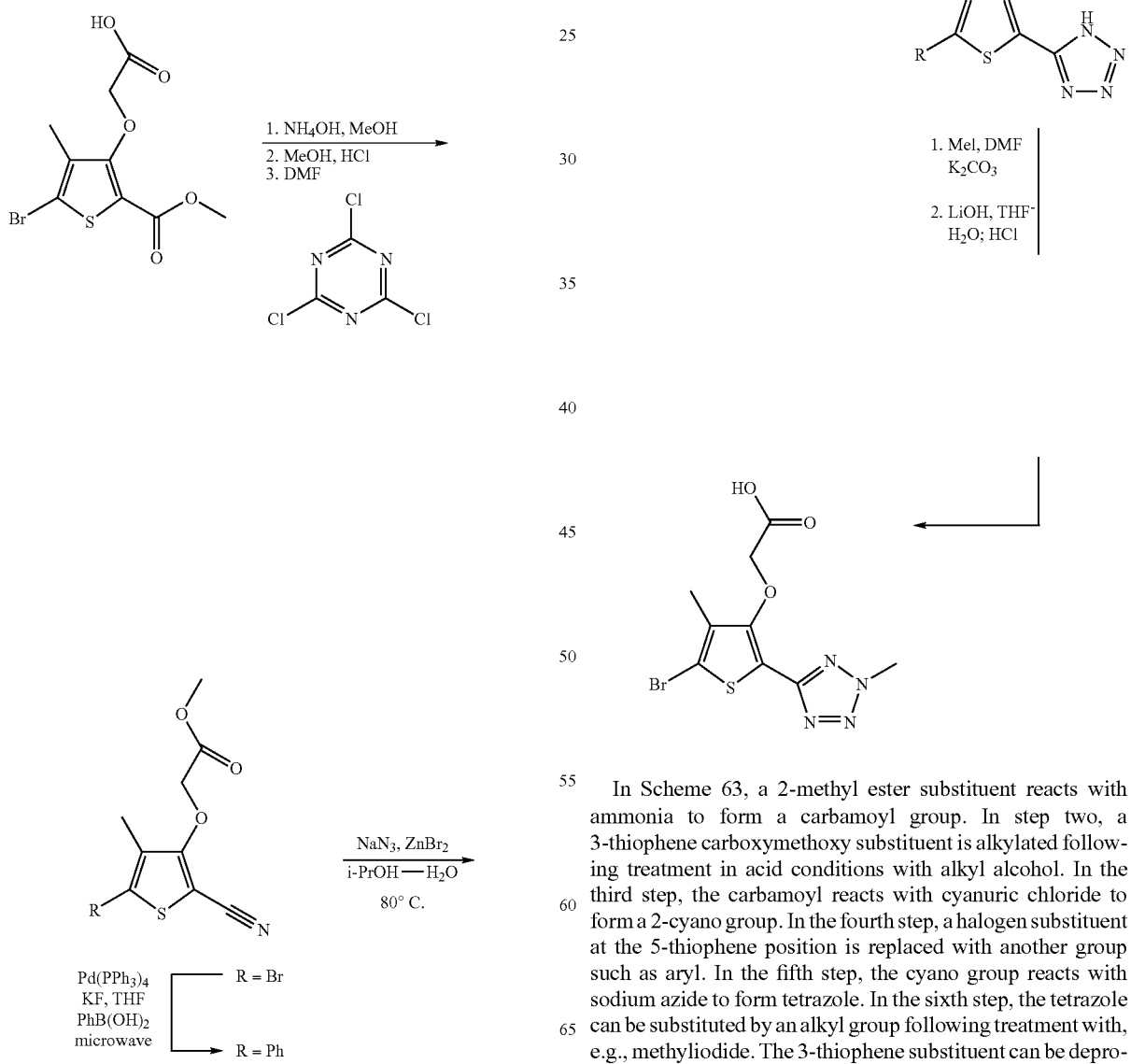

In Scheme 63, a 2-methyl ester substituent reacts with ammonia to form a carbamoyl group. In step two, a 3-thiophene carboxymethoxy substituent is alkylated following treatment in acid conditions with alkyl alcohol. In the third step, the carbamoyl reacts with cyanuric chloride to form a 2-cyano group. In the fourth step, a halogen substituent at the 5-thiophene position is replaced with another group such as aryl. In the fifth step, the cyano group reacts with sodium azide to form tetrazole. In the sixth step, the tetrazole can be substituted by an alkyl group following treatment with, e.g., methyliodide. The 3-thiophene substituent can be deprotected to form 3-carboxymethoxy in the seventh step.

Scheme 64
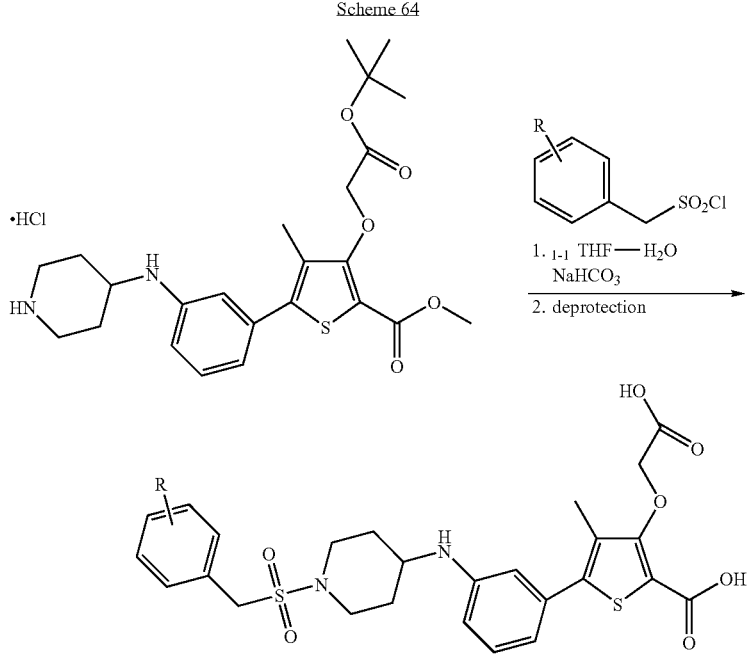
In Scheme 64, the amine group of a piperidine (ultimately attached to the 5-thiophene position through aminoarylene) is sulfonated. Protective groups on the 2- and 3-thiophene positions can be hydrolyzed to yield terminal carboxylic acids.
Scheme 65
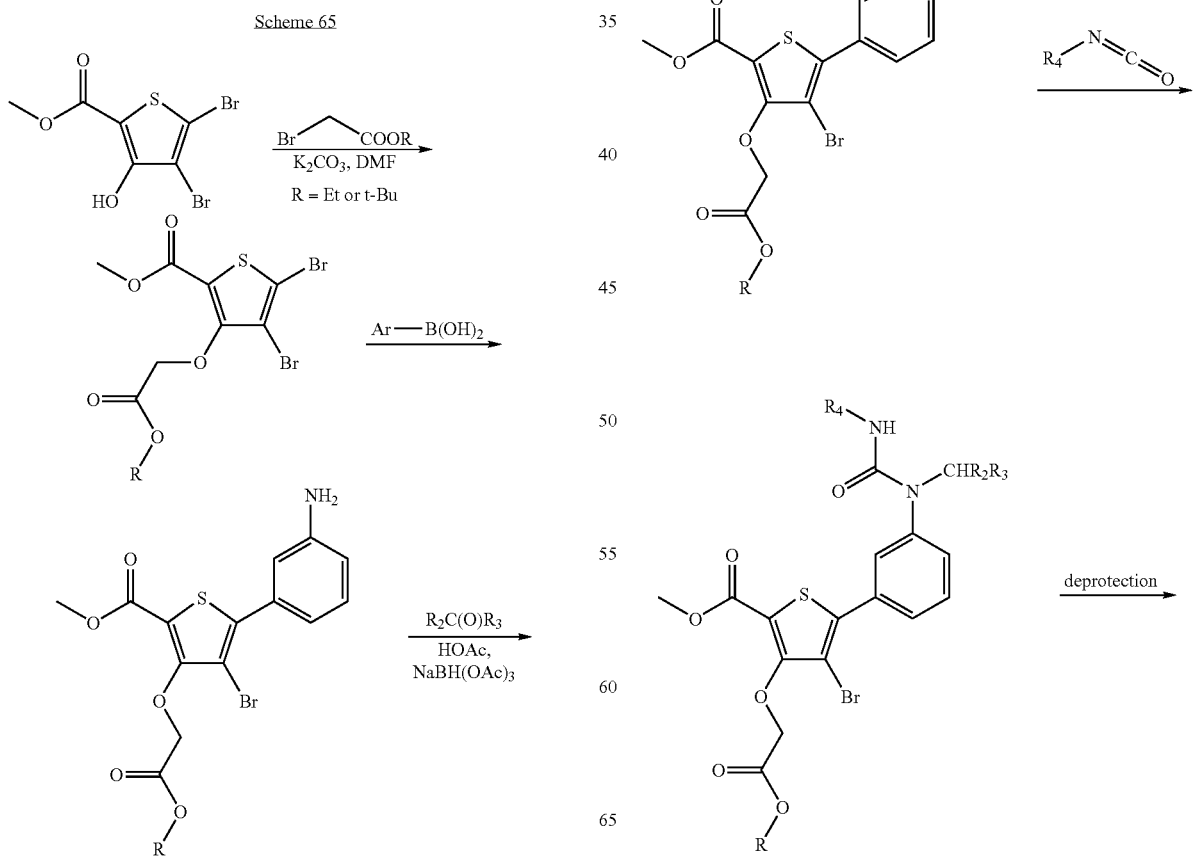

-continued

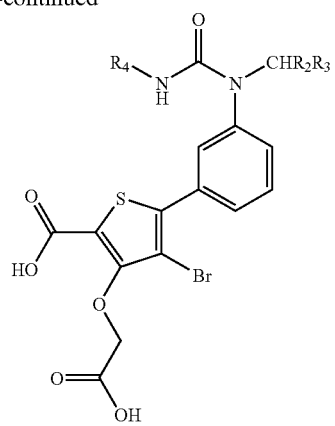

In Scheme 65, a 3-thiophene hydroxyl group reacts with an alkyl ester halide to form an alkoxycarbonylmethoxy substituent. In the second step, an aminobenzene boronic acid reacts with a 5-thiophene bromine substituent to form an aminophenyl substituent. In the third step, the amine group of the aminophenyl substituent reacts with a ketone and forms a secondary amine. The resulting compound reacts with a substituted isocyanate to form a substituted ureido compound in the fourth step. Protective groups on the 2- and 3-thiophene positions can be hydrolyzed to yield terminal carboxylic acids in the fifth step.

Scheme 66

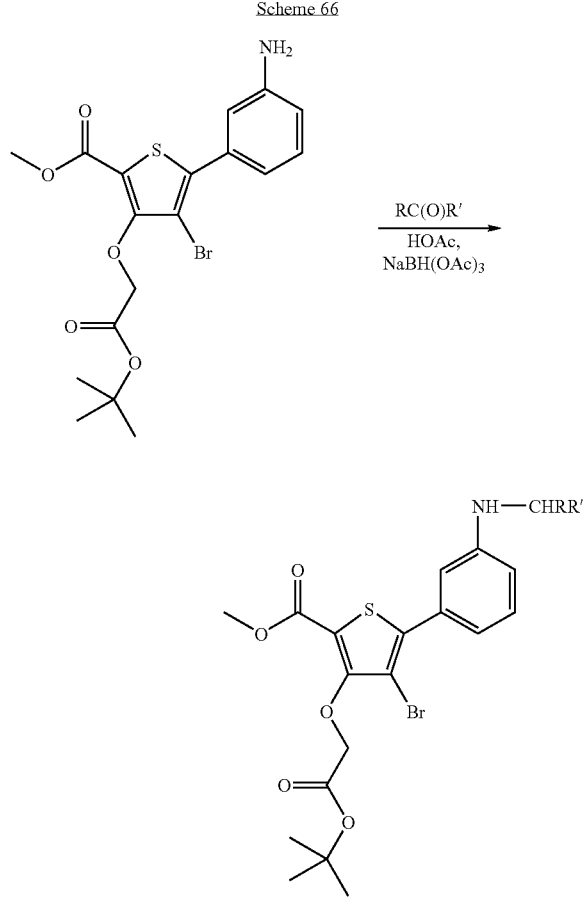

In Scheme 66, the amine group of an aminophenyl substituent at the 5-thiophene position reacts with a ketone and forms a secondary amine, as shown.

Scheme 67

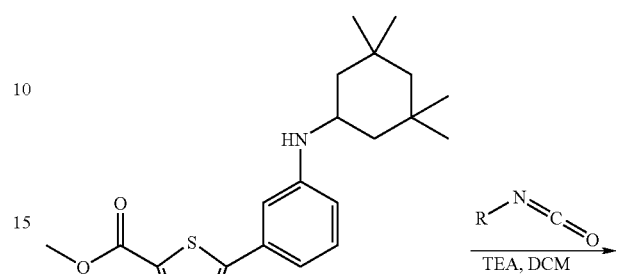

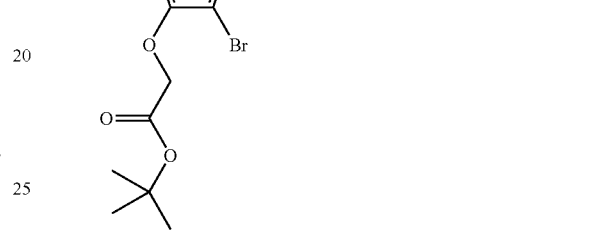

In Scheme 67, a secondary amine attached to a 5-phenyl thiophene substituent reacts with a substituted isocyanate to form a substituted ureido group. Protective groups on the 2- and 3-thiophene substituents can be hydrolyzed to form terminal carboxylic acids.

Scheme 68

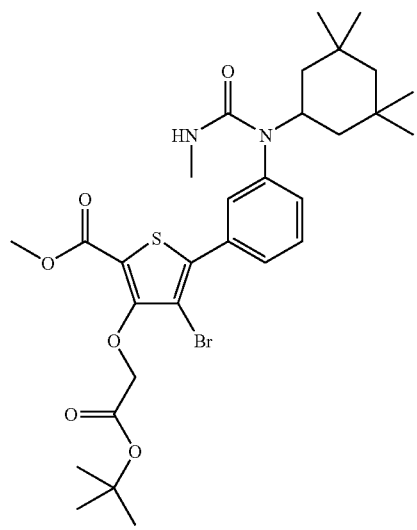

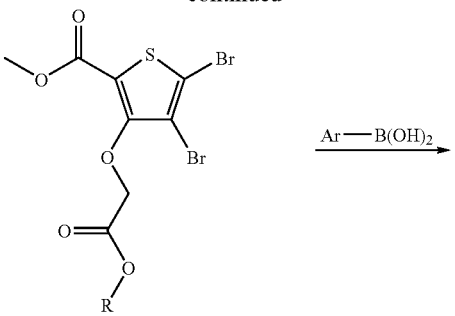

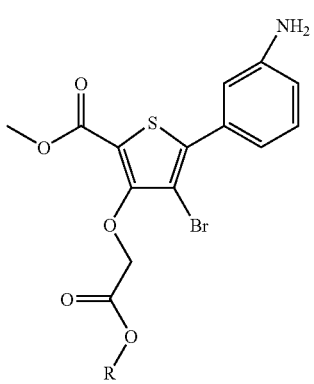

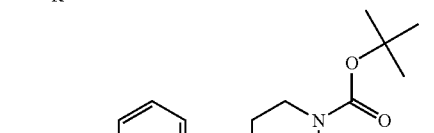

In Scheme 68, a protective group on the 3-thiophene substituent is selectively hydrolyzed to yield a 3-carboxymethoxy substituent.

Scheme 69

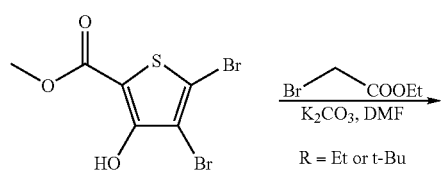

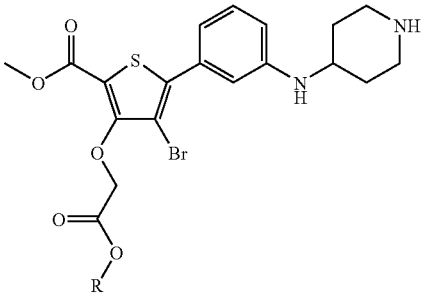

In Scheme 69, a 3-thiophene hydroxyl group reacts with an alkyl ester halide to form an alkoxycarbonylmethoxy substituent. A halogen substituent at the 5-thiophene position reacts with an aryl boronic acid to yield an aminophenyl 5-substituent in step two. In step three, the amino group reacts with a ketone and forms a secondary amine. A terminal piperidine carboxylic acid ester group can be hydrolyzed to yield a hydrochloric acid piperidine salt in step four.

177

Scheme 70

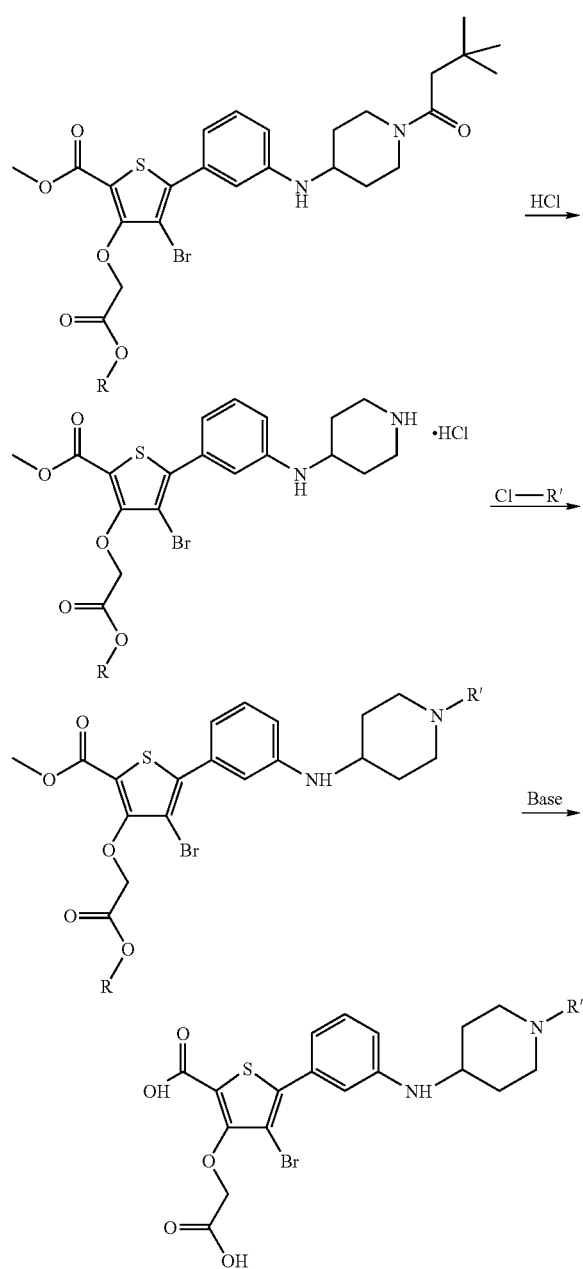

178

In Scheme 70, the amine of an aminophenyl group at the 5-thiophene position reacts with a ketone to yield a secondary amine. The resulting piperidine carboxylic acid ester can be hydrolyzed to a piperidine hydrochloric acid salt. In step three, the amine salt can react with a chloride such as pyrimidine chloride to form a substituted piperidine. In step four, protective groups on the 2- and 3-thiophene positions are hydrolyzed to form terminal carboxylic acids.

Scheme 71

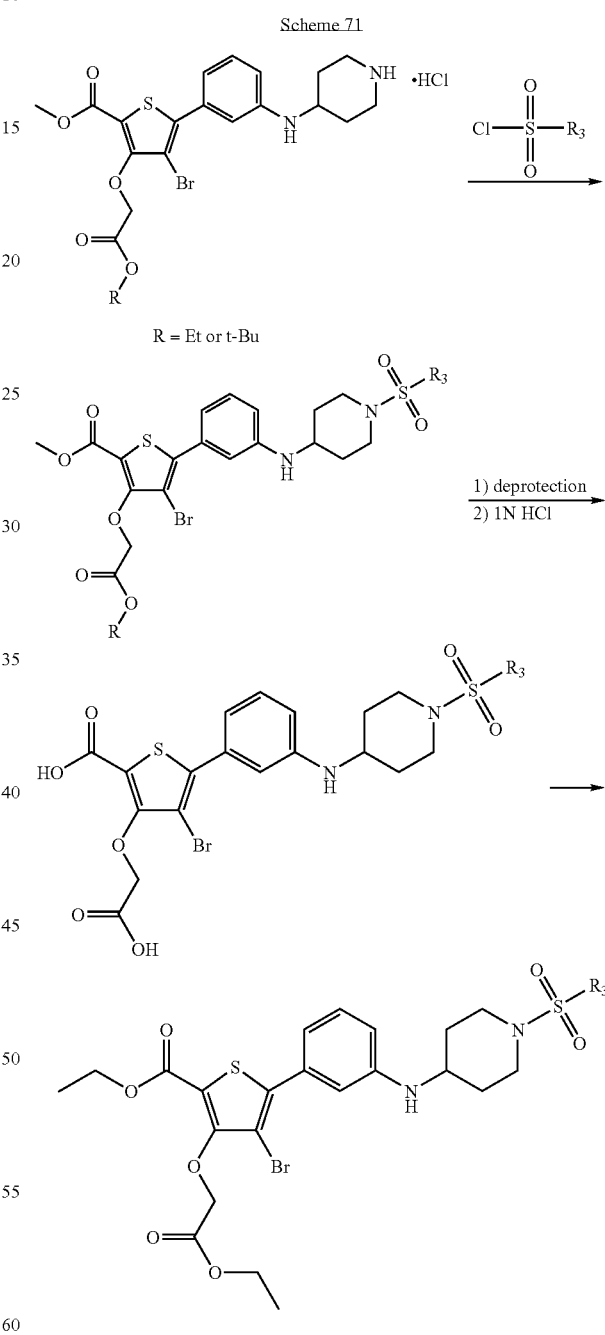

In Scheme 71, a piperidine hydrochloric acid salt is sulfonated in step one. Protective groups on the 2- and 3-thiophene positions are hydrolyzed to terminal carboxylic acids in step two. In step three, reaction with an alkyl halide affords terminal carboxylic acid alkyl esters at the 2- and 3-thiophene positions.

In Scheme 72, a 3-carboxymethoxy thiophene substituent reacts with an amine to form an amide.

Scheme 72

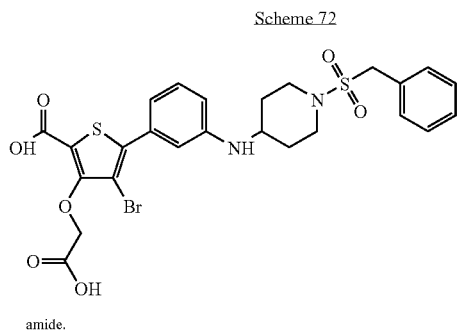

amide.

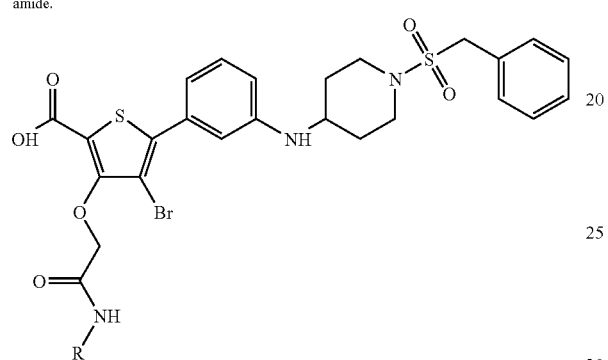

Scheme 73

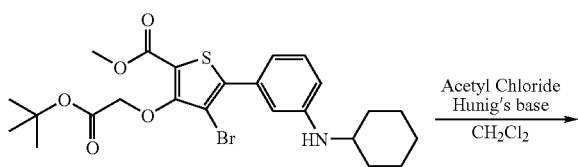

-continued

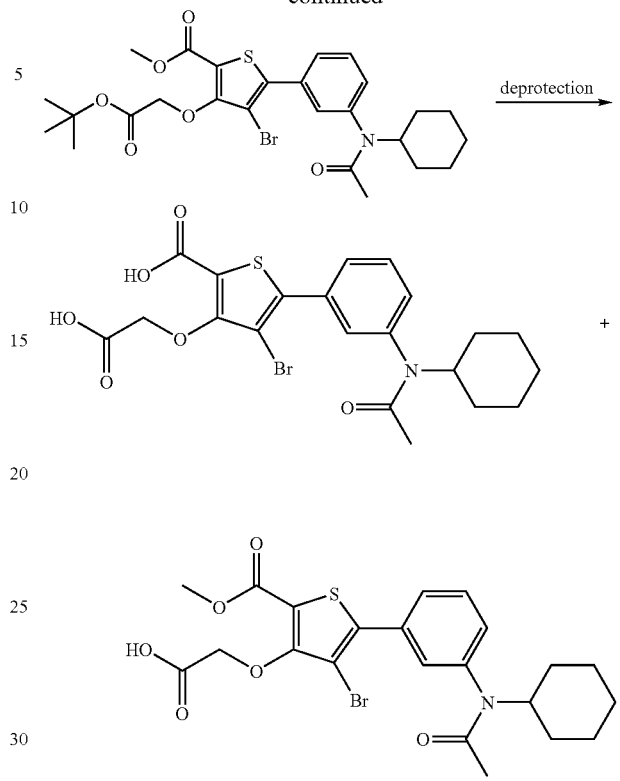

In Scheme 73, a cyclohexyl aminophenyl substituent at the 5-thiophene position reacts with acetyl chloride to form acetyl cyclohexyl aminophenyl. The resulting compound is hydrolyzed to yield two products, one with terminal carboxylic acids at both the 2- and 3-thiophene positions, and one that has only been hydrolyzed at the 3-thiophene position to the 3-carboxymethoxy group.

Scheme 74

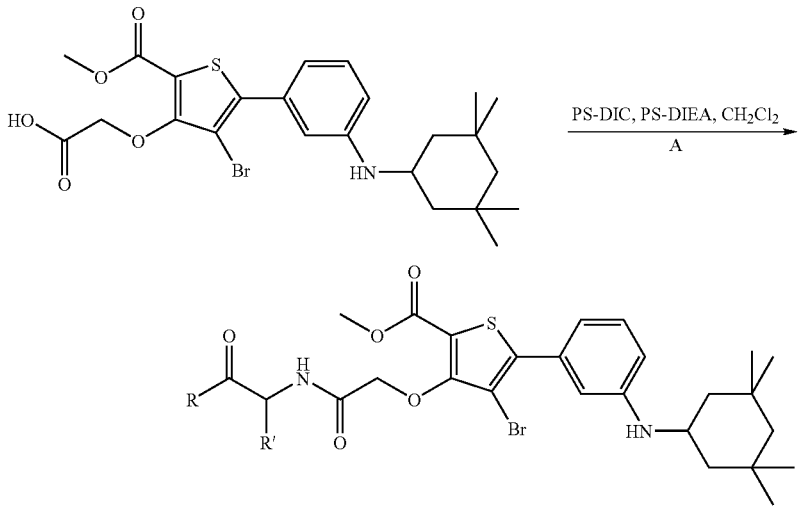

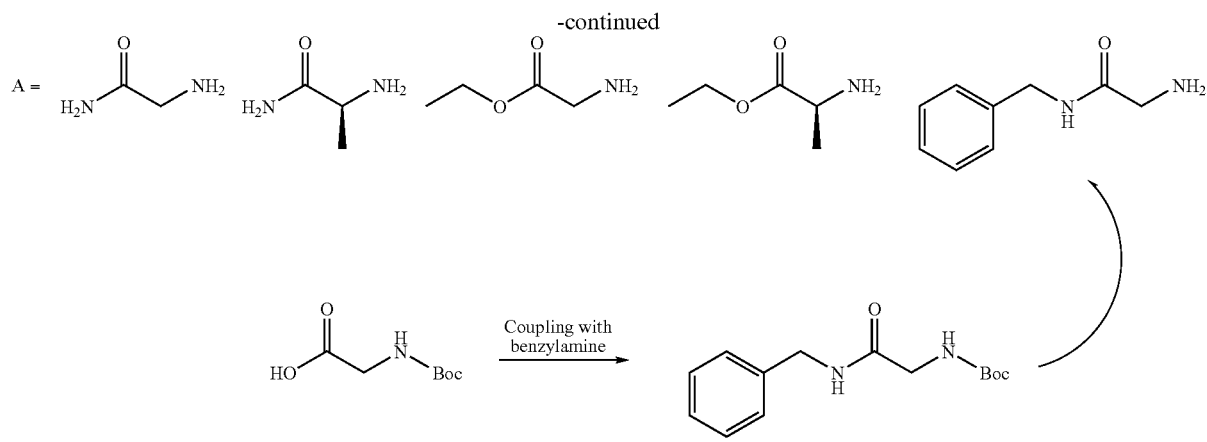
In Scheme 74, a 3-thiophene carboxymethoxy substituent is substituted with an amine to form an amide as shown.
Scheme 75
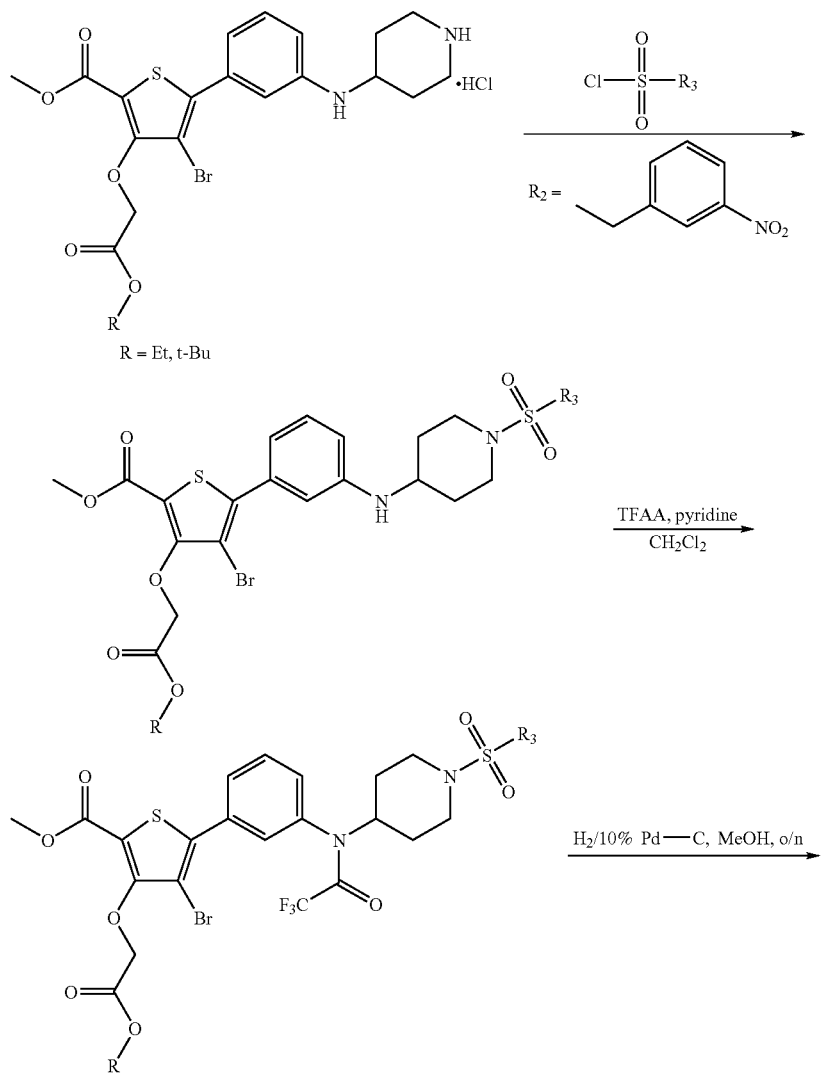

-continued
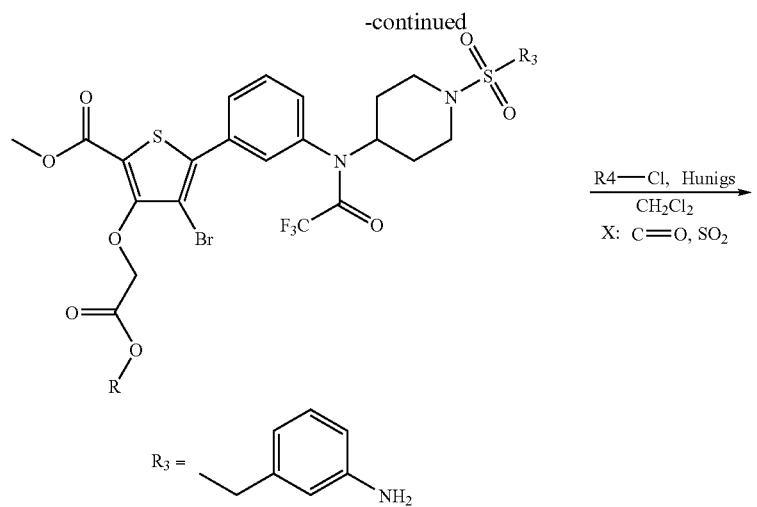
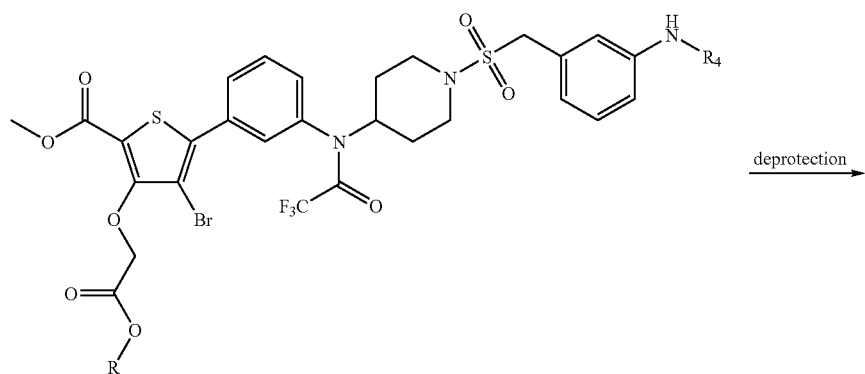
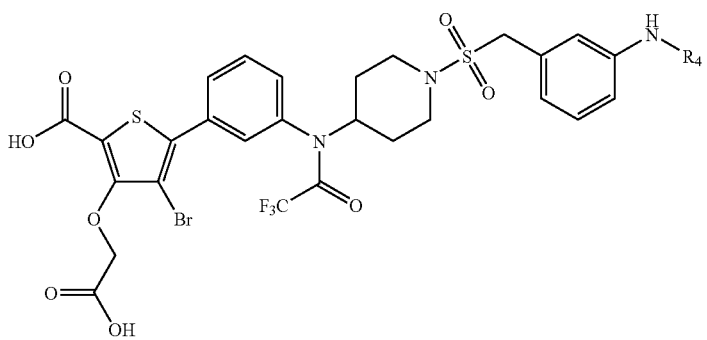

In Scheme 75, the amine of a piperidine group (attached to the 5-thiophene position via aminophenyl) is sulfonated with an aryl nitro group. The amine of the aminophenyl group reacts with trifluoroaceticanhydride to form trifluoro acetyl amide. In step three, the nitro group on the sulfonyl substituent is reduced to an amine. The amine can be substituted to form an amide or aminosulfonyl group in step four. In the fifth step, the 2- and 3-thiophene substituents are hydrolyzed to terminal carboxylic acids, and the trifluoromethyl acetyl amide is hydrolyzed to an amine.

Scheme 76

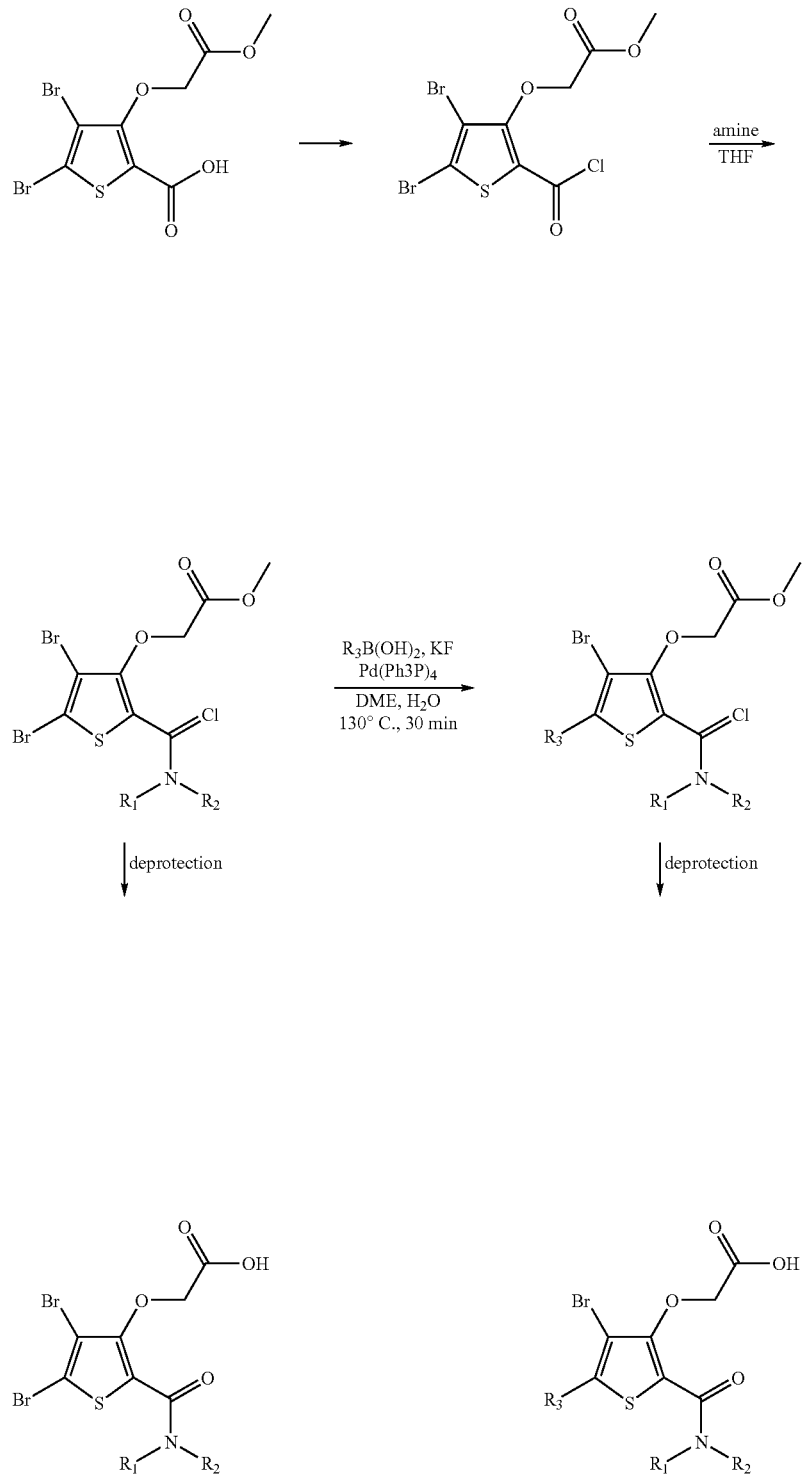

In the first step of Scheme 76, a carboxylic acid is converted to an acid chloride following conventional methods. In step two, the acid chloride thiophene substituent reacts with an amine to form an amide. In step three, a 5-halogen substituent can be substituted, such as by an aryl group, as shown. The resulting compound is hydrolyzed to form the 3-carboxymethoxy substituent in step four.

Scheme 77

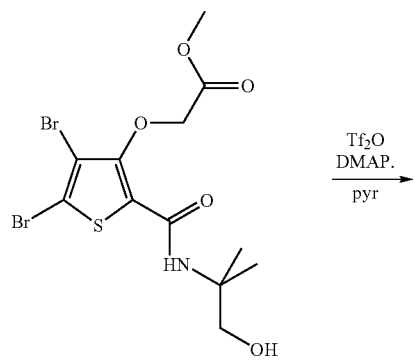
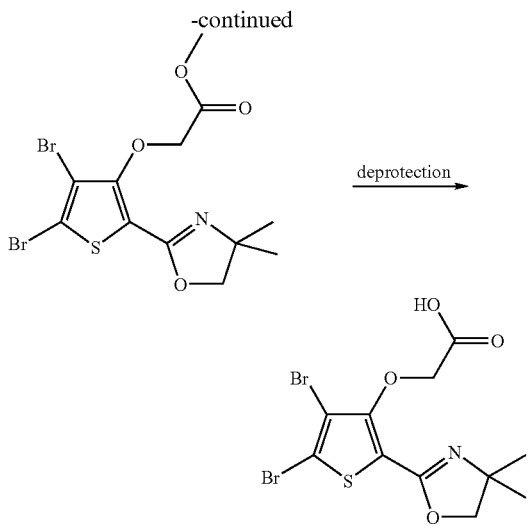

In Scheme 77, a 2-thiophene hydroxy alkyl amide substituent is cyclized to form a dimethyl dihydro oxazole at that position. The 3-thiophene substituent is hydrolyzed to afford 3-carboxymethoxy.

Scheme 78

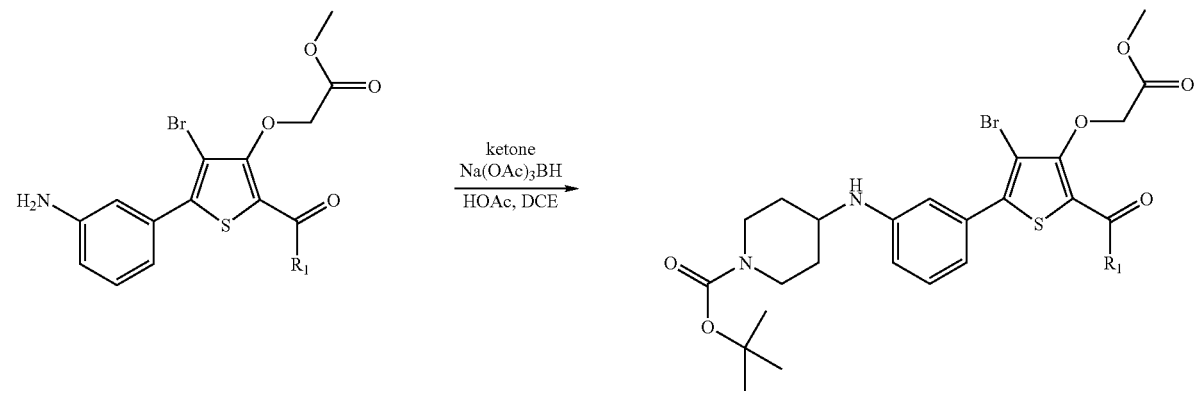
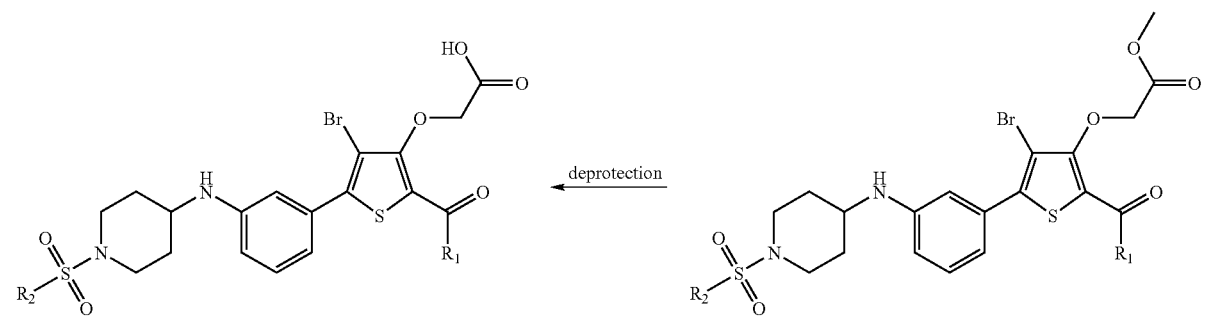

In Scheme 78, the amine of an aminophenyl 5-thiophene group reacts with a ketone to form a secondary piperidine amine as shown. The amine of the piperidine is sulfonated, and the 3-thiophene substituent is hydrolyzed to afford 3-carboxymethoxy.

Scheme 79

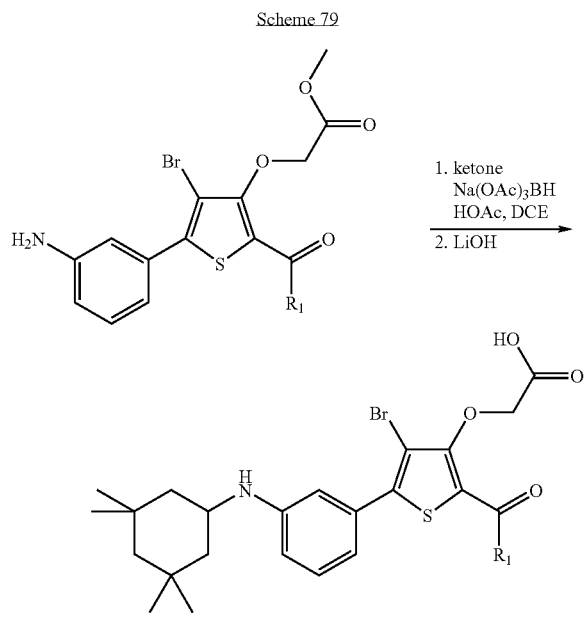

In Scheme 79, the amine of an aminophenyl 5-thiophene group reacts with a ketone to form a secondary amine. The 3-thiophene substituent is hydrolyzed to afford 3-carboxymethoxy.

Scheme 80

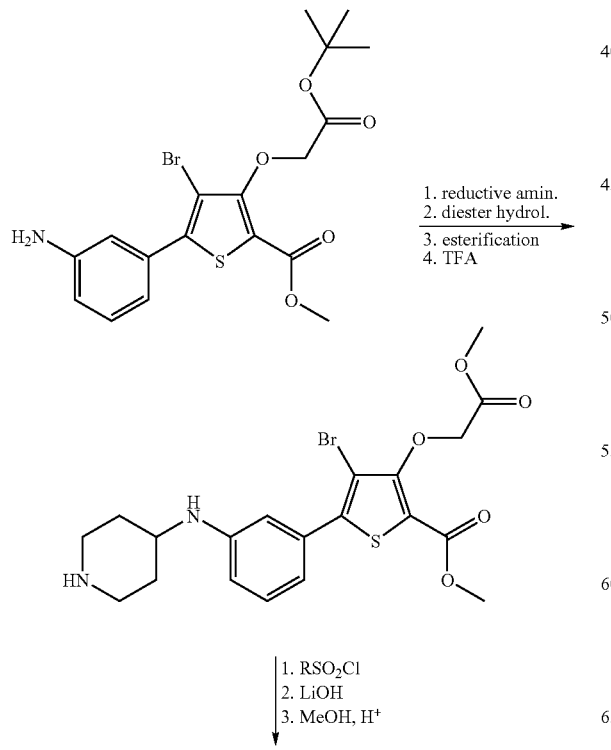

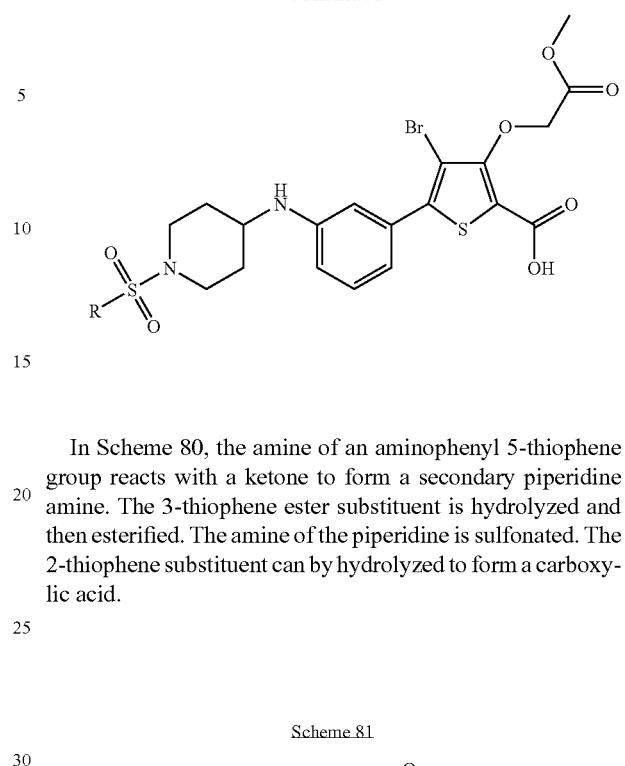

In Scheme 80, the amine of an aminophenyl 5-thiophene group reacts with a ketone to form a secondary piperidine amine. The 3-thiophene ester substituent is hydrolyzed and then esterified. The amine of the piperidine is sulfonated. The 2-thiophene substituent can by hydrolyzed to form a carboxylic acid.

Scheme 81

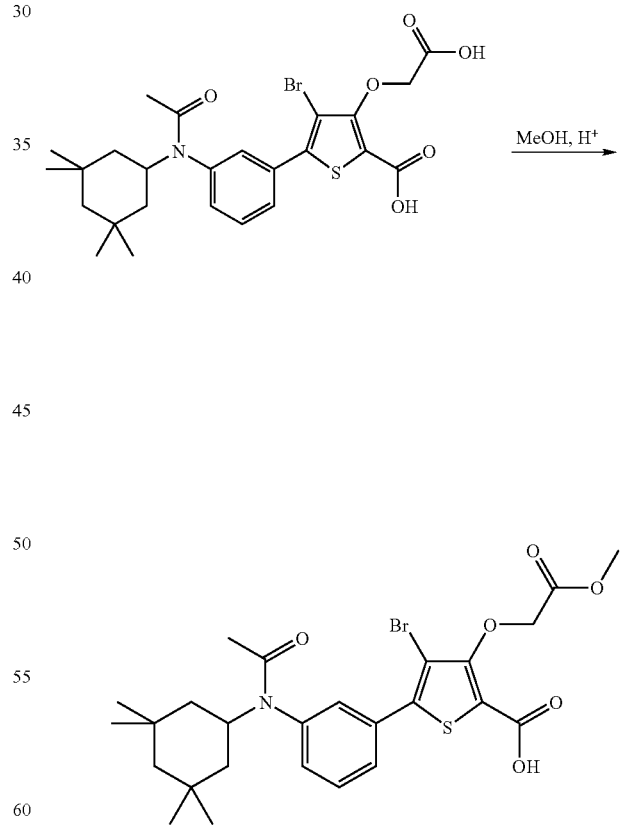

In Scheme 81, a 3-carboxymethoxy substituent is hydrolyzed in the presence of methanol to yield 3-2-methoxy-2-oxoethoxy.

Scheme 82
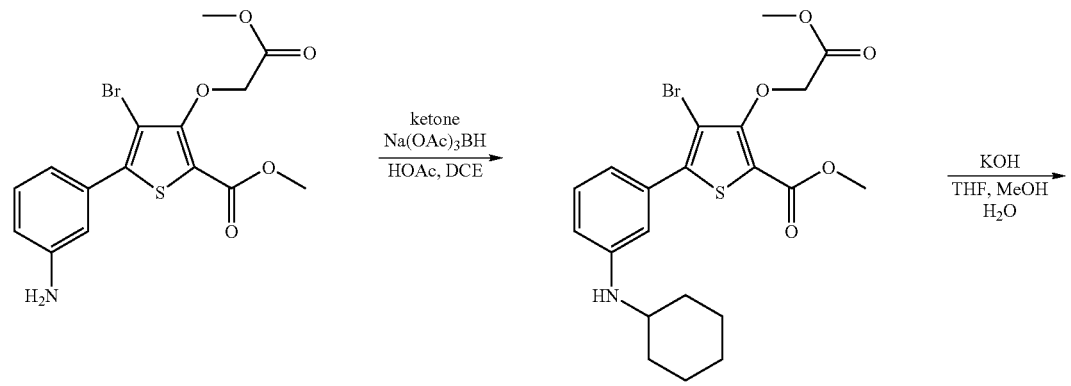
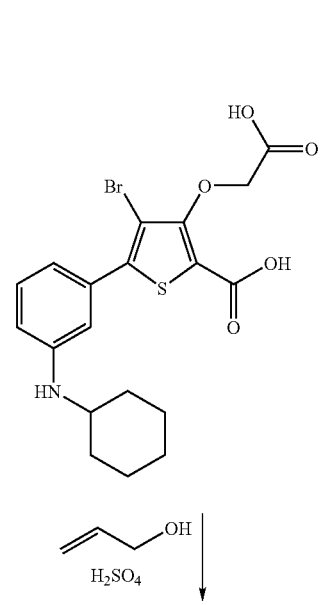
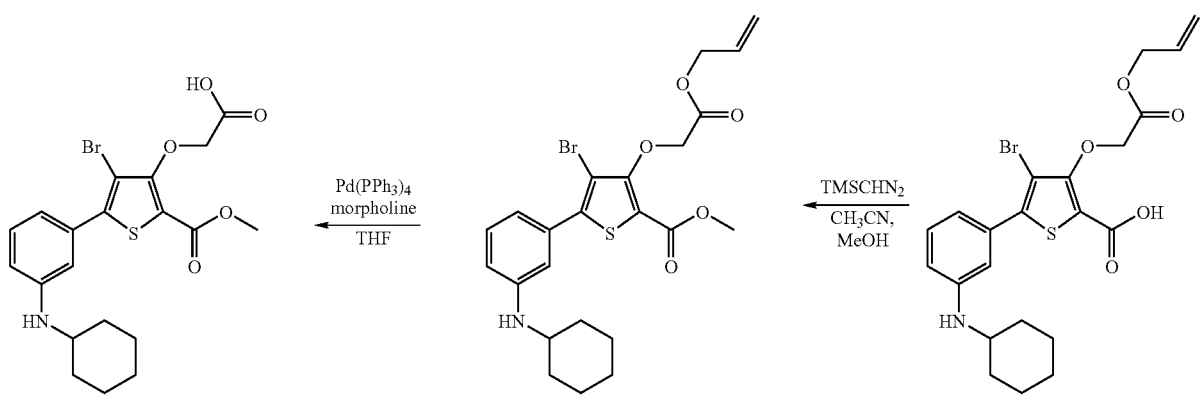

In Scheme 82, the amine of an aminophenyl 5-thiophene group reacts with a ketone to form a secondary amine. The 2- and 3-thiophene substituents are hydrolyzed to form terminal carboxylic acids. The resulting 3-carboxymethoxy group reacts with a hydroxy alkene to form an alkene ester. The 2-carboxylic acid group forms a methyl ester. In the final step, the alkene ester 3-substituent is hydrolyzed to 3-carboxymethoxy.

Scheme 83

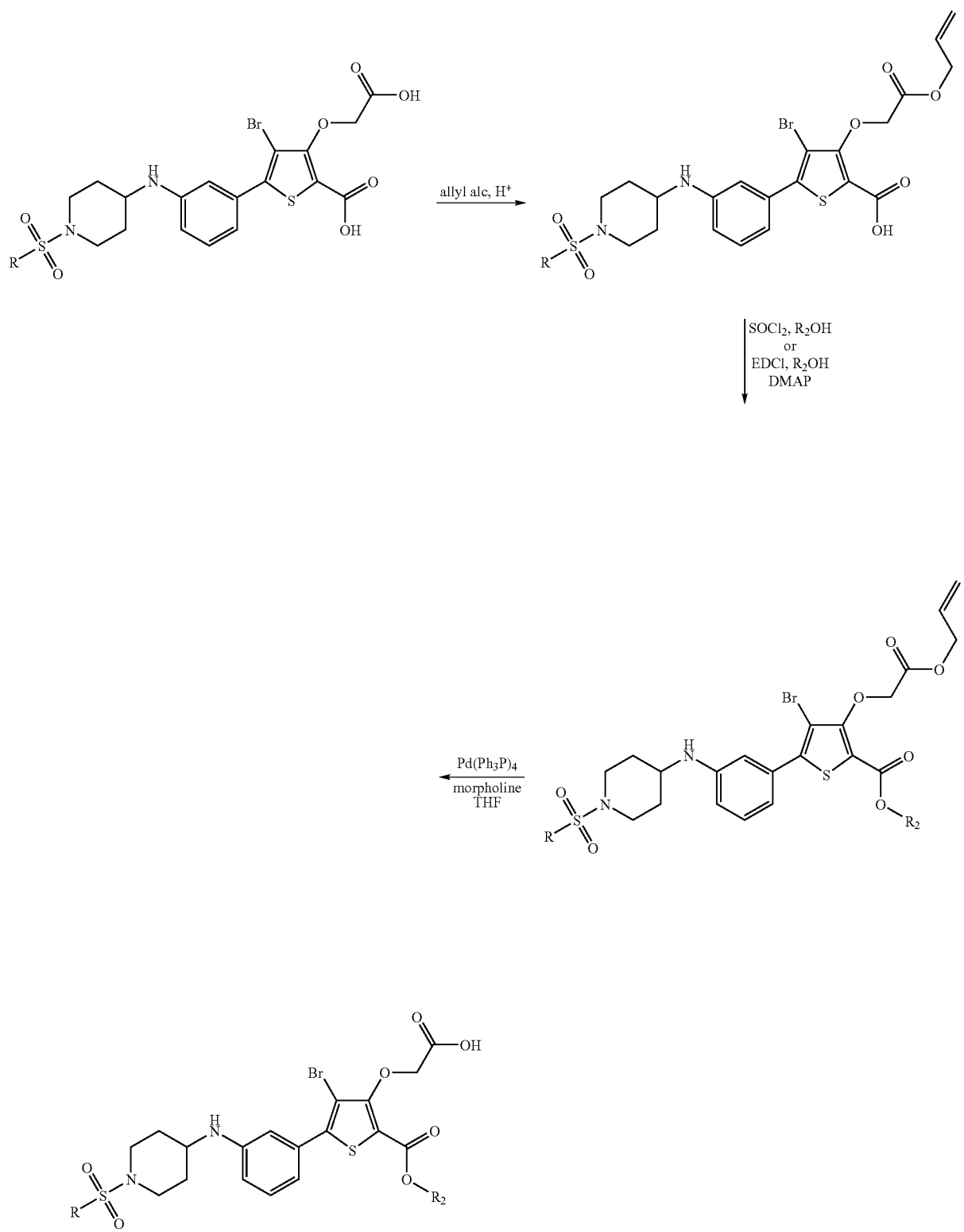

In Scheme 83, a 3-carboxymethoxy group reacts with a hydroxy alkene to form an alkene ester. The X 2-carboxylic acid group is substituted to form an ester. The 3-substituent is hydrolyzed to a 3-carboxymethoxy group.
Scheme 84
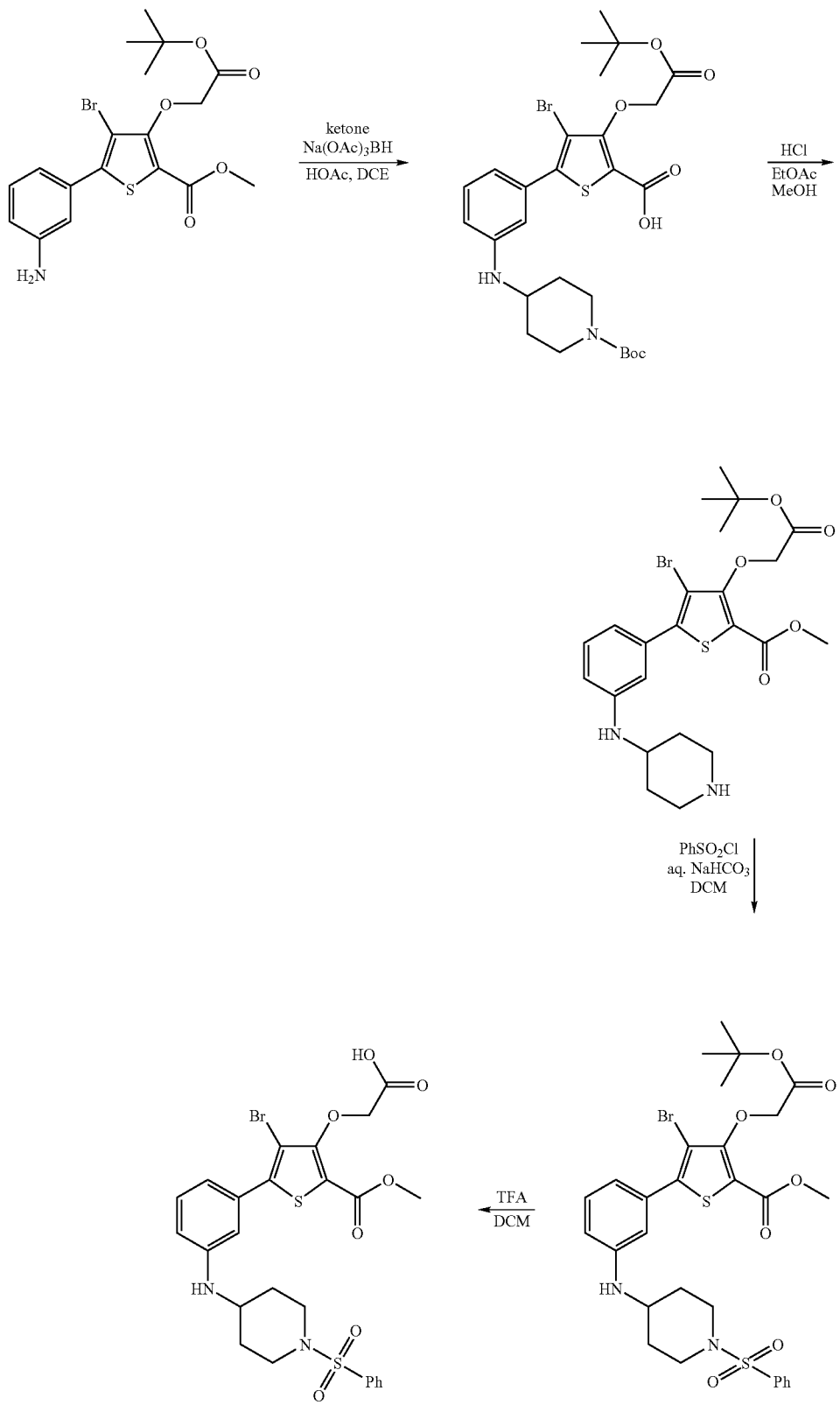

In Scheme 84, the amine of an aminophenyl 5-thiophene substituent reacts with a ketone to form a secondary piperidine amine. Any protective group on the piperidine amine is hydrolyzed, and the resulting amine is sulfonated. The 3-thiophene substituent can be hydrolyzed (selectively over a 2-alkyl ester substituent) to afford 3-carboxymethoxy.

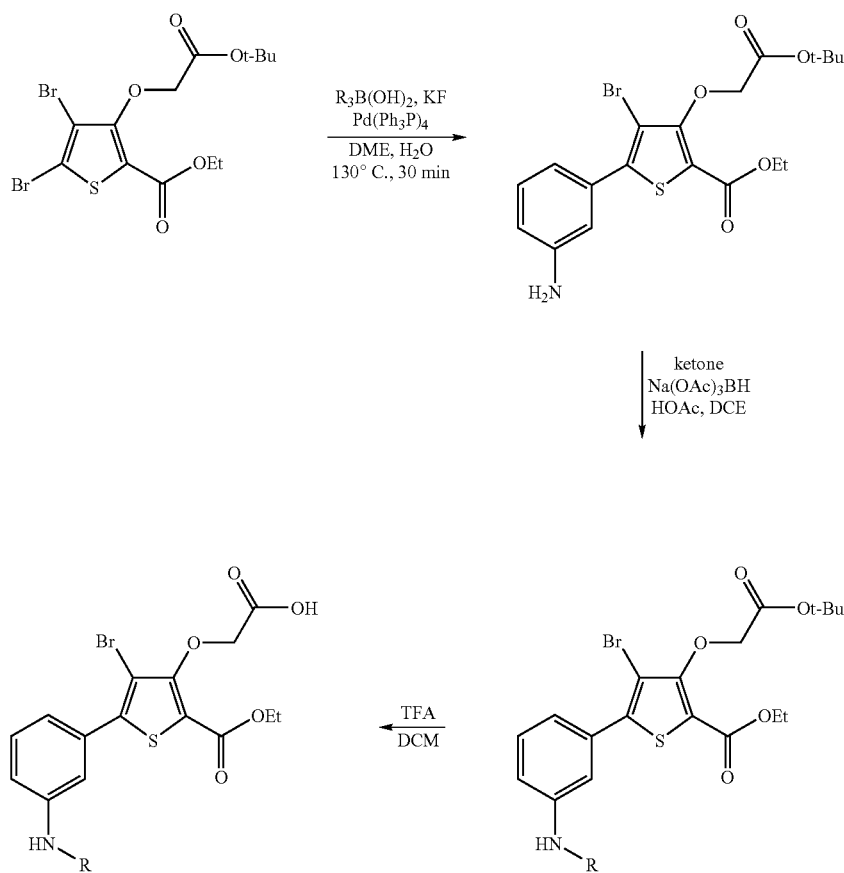

Scheme 85

In Scheme 85, a 5-halogen thiophene substituent is substituted with an aminophenyl group. The amine group reacts with a ketone to form a secondary amine. A protective group on the 3-substituent is hydrolyzed (selectively over a 2-alkyl ester substituent) to form 3-carboxymethoxy.

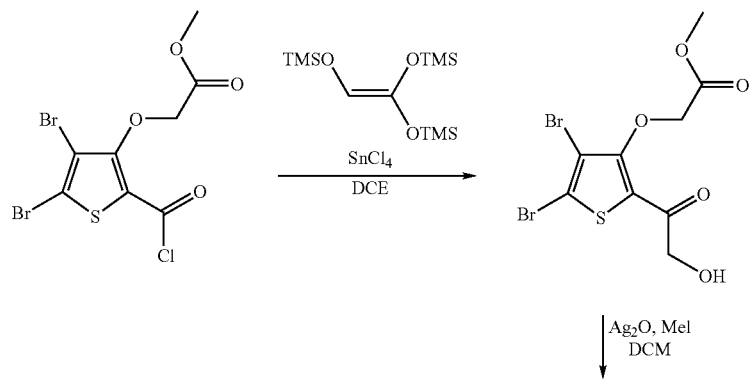

Scheme 86

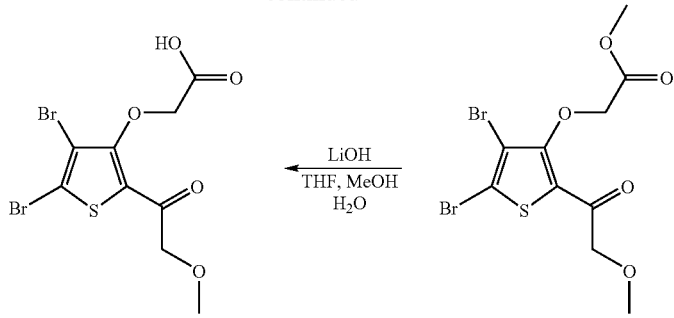

In Scheme 86, a 2-acylhalide thiophene substituent forms a hydroxyacetyl group as shown. The hydroxy group reacts with an alkyl halide to form an alkoxyacetyl group. A protective group on the 3-substituent can be hydrolyzed to form 3-carboxymethoxy.

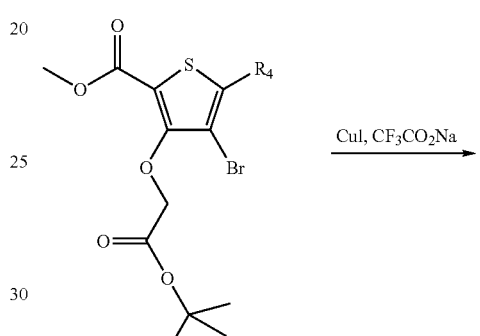

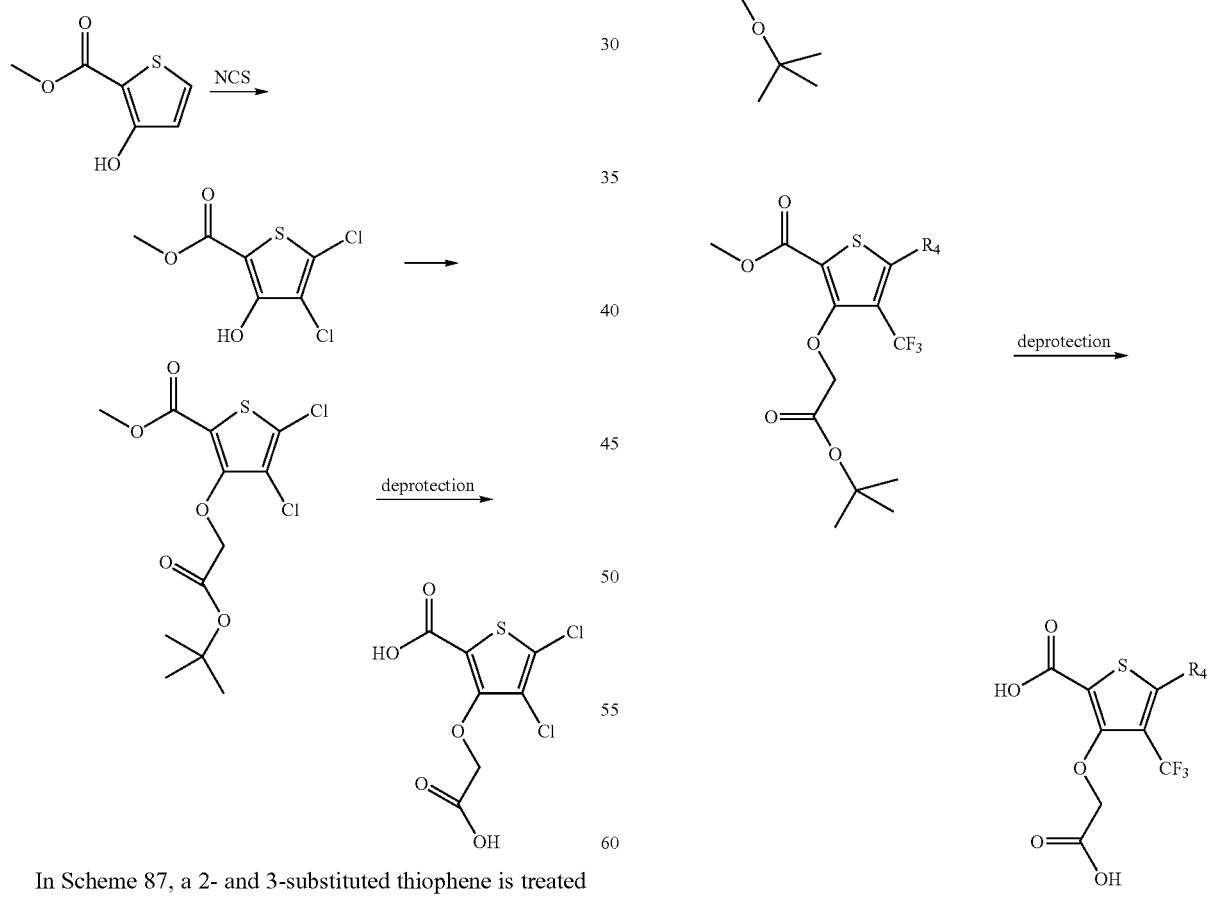

In Scheme 87, a 2- and 3-substituted thiophene is treated with a halogenating agent such as N-chlorosuccinimide to afford a 4- and 5-halogenated thiophene. A 3-hydroxy substituent is alkylated to form a 2-alkoxy-2-oxoethoxy group. Protective groups on the 2- and 3-thiophene positions are hydrolyzed to form terminal carboxylic acids.

In Scheme 88, a 4-halogen thiophene group is substituted with trifluoromethane. Protective groups on the 2- and 3-thiophene positions are hydrolyzed to form terminal carboxylic acids.

Scheme 89
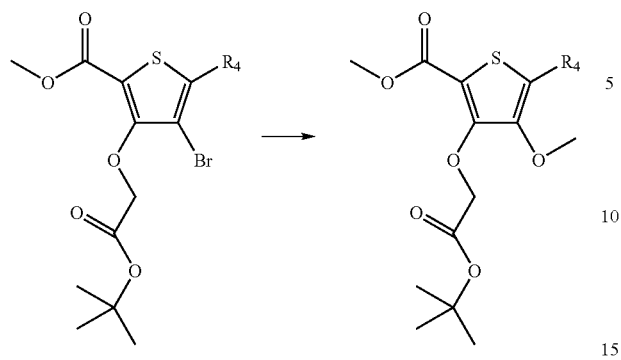
In Scheme 89, a 4-halogen thiophene group is substituted with an alkoxy group.
Scheme 90
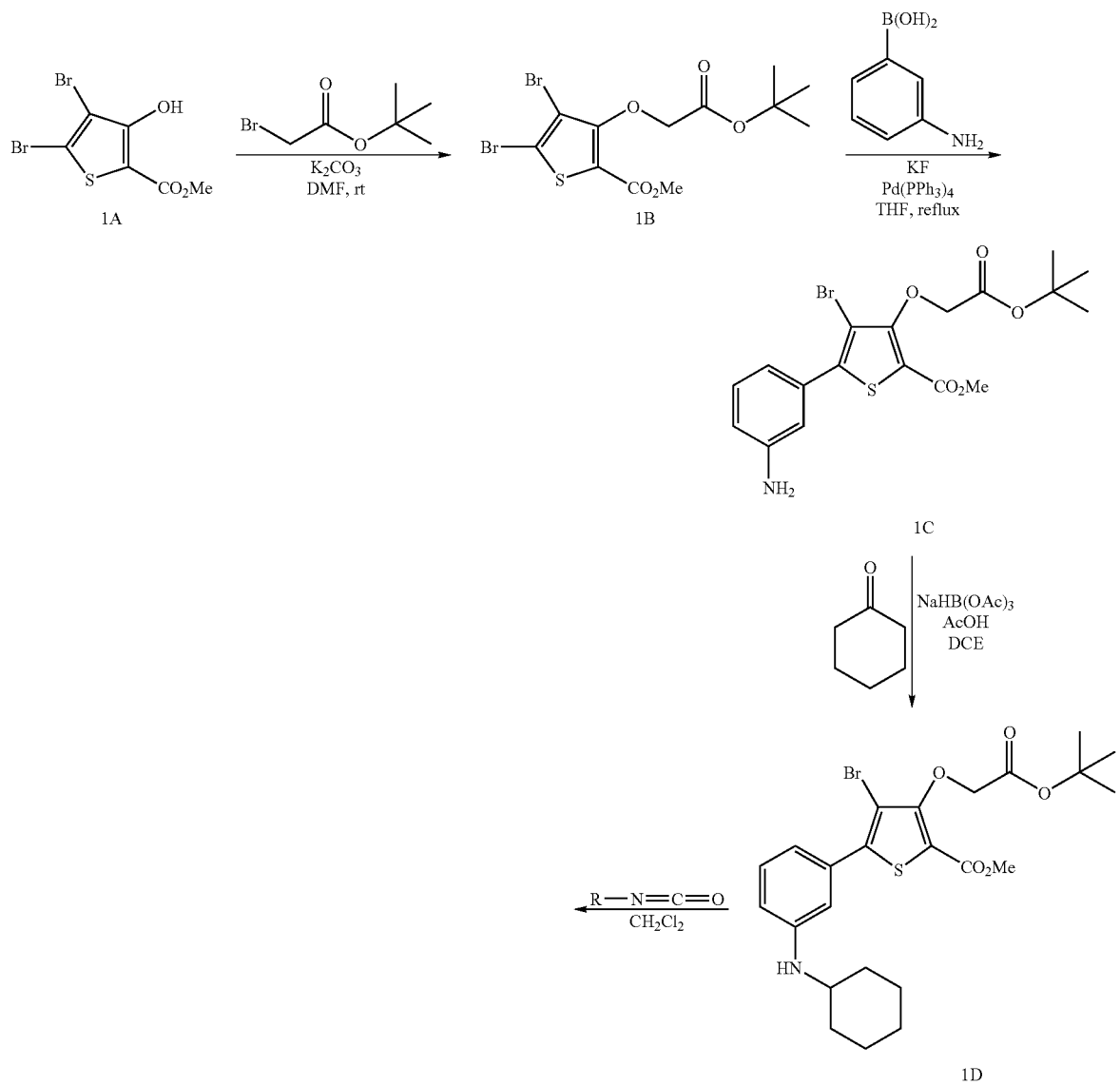

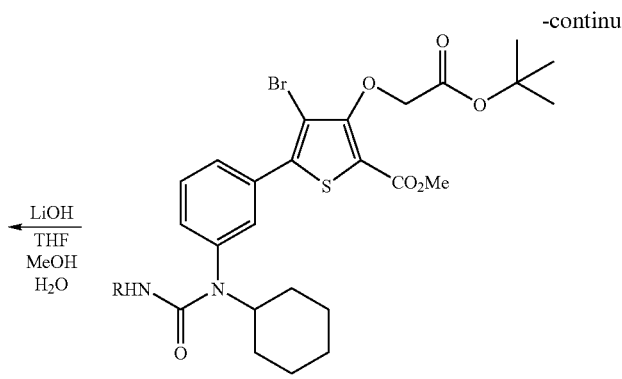

1F

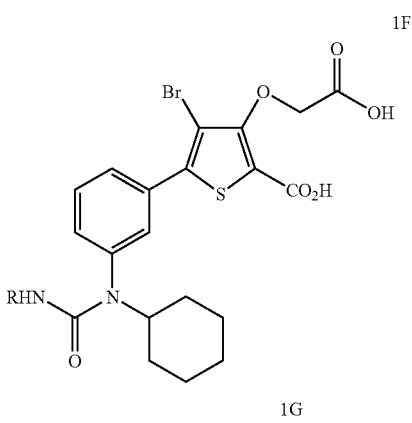

1G

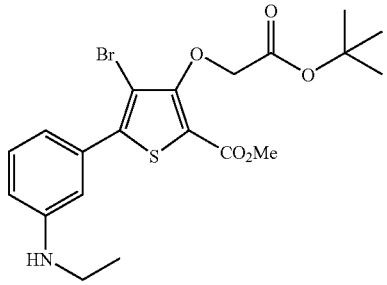

1E

Some compounds of formula (I) are set forth below:

4-Bromo-3-carboxymethoxy-thiophene-2-carboxylic acid, 4-Bromo-3-carboxymethoxy-5-phenyl-thiophene-2-carboxylic acid, 5-(4-Amino-phenyl)-4-bromo-3-carboxymethoxy-thiophene-2-carboxylic acid, 5-(3-Amino-phenyl)-4-bromo-3-carboxymethoxy-thiophene-2-carboxylic acid, 4-Bromo-3-methoxycarbonylmethoxy-5-[3-(3,3,5,5-tetramethyl-cyclohexylamino)-phenyl]-thiophene-2-carboxylic acid, 4-Bromo-3-carboxymethoxy-5-[3-(2,2,2-trifluoro-ethanesulfonylamino)-phenyl]-thiophene-2-carboxylic acid, 4-Bromo-3-carboxymethoxy-5-[3-(1-phenyl-ethoxy)-phenyl]-thiophene-2-carboxylic acid, 4-Bromo-3-carboxymethoxy-5-[3-(1-phenylmethanesulfonyl-piperidin-4-ylamino)-phenyl]-thiophene-2-carboxylic acid, 5-(3-Benzylamino-phenyl)-4-bromo-3-carboxymethoxy-thiophene-2-carboxylic acid, 5-(4-Acetylamino-phenyl)-4-bromo-3-carboxymethoxy-thiophene-2-carboxylic acid, 3-Carboxymethoxy-4-methyl-5-phenyl-thiophene-2-carboxylic acid, 4-Bromo-3-carboxymethoxy-5-[3-(1-o-tolylmethanesulfonyl-piperidin-4-ylamino)-phenyl]-thiophene-2-carboxylic acid, 5-(3-Benzyloxy-4-hydroxy-phenyl)-4-bromo-3-(2-hydroxy-ethoxy)-thiophene-2-carboxylic acid, 4,5-Dibromo-3-methoxycarbonylmethoxy-thiophene-2-carboxylic acid, 4-Bromo-3-carboxymethoxy-5-naphthalen-1-yl-thiophene-2-carboxylic acid, 4-Bromo-3-carboxymethoxy-5-[3-(3,3-diethyl-ureido)-phenyl]-thiophene-2-carboxylic acid, 4-Bromo-3-carboxymethoxy-5-{3-[(piperidine-4-carbonyl)-amino]-phenyl}-thiophene-2-carboxylic acid trifluoroacetic acid salt, 4-Bromo-3-carboxymethoxy-5-[3-(cyclohexanecarbonyl-amino)-phenyl]-thiophene-2-carboxylic acid, 3-Carboxymethoxy-5-(4-trifluoromethoxy-phenyl)-thiophene-2-carboxylic acid, 5-(4-Aminomethyl-phenyl)-4-bromo-3-carboxymethoxy-thiophene-2-carboxylic acid trifluoroacetic acid, 3-Bromo-4-carboxymethoxy-2'-formyl-[2,3]-bithiophenyl-5-carboxylic acid, 3-Bromo-4-carboxymethoxy-2'-(isobutylamino-methyl)-[2,3]-bithiophenyl-5-carboxylic acid, 3-Carboxymethoxy-4-methyl-thiophene-2-carboxylic acid, 5-Bromo-3-carboxymethoxy-4-methyl-thiophene-2-carboxylic acid, (2-Propionyl-thiophen-3-ylamino)-acetic acid, 3-Carboxymethoxy-thiophene-2-carboxylic acid, 4-Bromo-3-carboxymethoxy-5-phenyl-thiophene-2-carboxylic acid methyl ester, 4-Bromo-3-carboxymethoxy-5-[3-(3,3,5,5-tetramethyl-cyclohexylamino)-phenyl]-thiophene-2-carboxylic acid methyl ester, 5-{3-[(Acetyl-phenyl-amino)-methyl]-4-methoxy-phenyl}-4-bromo-3-carboxymethoxy-thiophene-2-carboxylic acid, 4-Bromo-3-carboxymethoxy-5-{3-[1-(3-trifluoromethyl-phenylmethanesulfonyl)-piperidin-4-ylamino]-phenyl}-thiophene-2-carboxylic acid methyl ester, 4-Bromo-3-carboxymethoxy-5-{3-[1-(4-fluoro-phenyl-methanesulfonyl)-piperidin-4-ylamino]-phenyl}-thiophene-2-carboxylic acid methyl ester, 5-{3-[(Acetyl-cyclohexyl-amino)-methyl]-phenyl}-4-bromo-3-carboxymethoxy-thiophene-2-carboxylic acid methyl ester, 4-Bromo-3-carboxymethoxy-5-{3-[1-(4-chloro-phenylmethanesulfonyl)-piperidin-4-ylamino]-phenyl}-thiophene-2-carboxylic acid methyl ester, 4,5-Dibromo-3-methoxycarbonylmethoxy-thiophene-2-carboxylic acid, 4-Bromo-3-methoxycarbonylmethoxy-5-phenyl-thiophene-2-carboxylic acid, 4-Bromo-3-(carboxymethoxy)-5-[3-(piperidin-4-ylamino)phenyl]thiophene-2-carboxylic acid, ({4-Bromo-2-(methoxycarbonyl)-5-[3-(piperidin-4-ylamino)phenyl]thien-3-yl}oxy)acetic acid, Methyl 4-bromo-3-(2-ethoxy-2-oxoethoxy)-5-(3-{[1-(5-nitropyridin-2-yl)piperidin-4-yl]amino}phenyl)thiophene-2-carboxylate, 4-Bromo-3 -(carboxymethoxy)-5-(3-{[1-(5-nitropyridin-2-yl)piperidin-4-yl]amino}phenyl)thiophene-2-carboxylic acid, 5-[3-({1-[5-(Acetylamino)pyridin-2-yl]piperidin-4-yl}amino)phenyl]-4-bromo-3-(carboxymethoxy)thiophene-2-carboxylic acid, 4-Bromo-3-(carboxymethoxy)-5-(3-{[1-(5-{[(methylamino)carbonyl]amino}pyridin-2-yl)piperidin-4-yl]amino}phenyl)thiophene-2-carboxylic acid, 4-Bromo-3-(carboxymethoxy)-5-(3-{[(methylamino)carbonyl][1-(5-{[(methylamino)carbonyl]amino}pyridin-2-yl)piperidin-4-yl]amino phenyl)thiophene-2-carboxylic acid, 4-Bromo-3-(carboxymethoxy)-5-{3-[(1-{5-[(methylsulfonyl)amino]pyridin-2-yl}piperidin-4-yl)amino]phenyl}thiophene-2-carboxylic acid, 3-(Carboxymethoxy)-5-phenylthiophene-2-carboxylic acid, Methyl 5-(3-{[1-(benzylsulfonyl)piperidin-4-yl]amino}phenyl)-4-bromo-3-{2-[(2-methylphenyl)amino]-2-oxoethoxy}thiophene-2-carboxylate, 5-(3-{[1-(Benzylsulfonyl)piperidin-4-yl][(ethylamino)carbonyl]amino}phenyl)-4-bromo-3-(carboxymethoxy)thiophene-2-carboxylic acid, 4,5-Dibromo-3-[carboxy(fluoro)methoxy]thiophene-2-carboxylic acid, {[5-Phenyl-2-(2H-tetrazol-5-yl)thien-3-yl]oxy}acetic acid, {[5-[3-({[1-(Anilinocarbonyl)piperidin-4-yl]methyl}amino)phenyl]-4-bromo-2-(methoxycarbonyl)thien-3-yl]oxy}acetic acid, 5-(3-{{[1-(Anilinocarbonyl)piperidin-4-yl]methyl}[(ethylamino)carbonyl]amino}phenyl)-4-bromo-3-(carboxymethoxy)thiophene-2-carboxylic acid, 4-Bromo-3-(carboxymethoxy)-5-{3-[(1-{[2-(trifluoromethoxy)phenyl]sulfonyl}piperidin-4-yl)amino]phenyl}thiophene-2-carboxylic acid, 4-Bromo-3-(carboxymethoxy)-5-[3-({1-[(5-chloro-2-methoxyphenyl)sulfonyl]piperidin-4-yl}amino)phenyl]thiophene-2-carboxylic acid, 4-Bromo-3-(carboxymethoxy)-5-[3-({1-[(3,5-dichloro-2-hydroxyphenyl)sulfonyl]piperidin-4-yl}amino)phenyl]thiophene-2-carboxylic acid, Propyl 4-bromo-3-(2-tert-butoxy-2-oxoethoxy)-5-{3-[(3,3,5,5-tetramethylcyclohexyl)amino]phenyl}thiophene-2-carboxylate, [(4-Bromo-2-(propoxycarbonyl)-5-{3-[(3,3,5,5-tetramethylcyclohexyl)amino]phenyl}thien-3-yl)oxy]acetic acid, 4-Bromo-3-carboxymethoxy-5-{3-[1-(2-trifluoromethyl-phenylmethanesulfonyl)-piperidin-4-ylamino]-phenyl}-thiophene-2-carboxylic acid, 4-Bromo-3-carboxymethoxy-5-[3-(indan-2-ylamino)-phenyl]-thiophene-2-carboxylic acid, 3-[3-(3-Bromo-5-carboxy-4-carboxymethoxy-thiophen-2-yl)-phenylamino]-8-aza-bicyclo[3.2.1]octane-8-carboxylic acid ethyl ester, 4-Bromo-3-carboxymethoxy-5-[3-(8-phenylmethanesulfonyl-8-aza-bicyclo[3.2.1]oct-3-ylamino)-phenyl]-thiophene-2-carboxylic acid, 5-(1-Benzyl-1H-pyrazol-4-yl)-4-bromo-3-carboxymethoxy-thiophene-2-carboxylic acid; compound with methane, 5-{3-[1-(2-Acetylamino-phenylmethanesulfonyl)-piperidin-4-ylamino]-phenyl}-4-bromo-3-carboxymethoxy-thiophene-2-carboxylic acid, 5-{3-[1-(2-Acetylamino-phenylmethanesulfonyl)-piperidin-4-ylamino]-phenyl}-3-carboxymethoxy-thiophene-2-carboxylic acid, 4-Bromo-3-carboxymethoxy-5-(3-[1-(2-methanesulfonylamino-phenylmethanesulfonyl)-piperidin-4-ylamino]-phenyl}-thiophene-2-carboxylic acid, 3-Carboxymethoxy-5-{3-[1-(2-methanesulfonylamino-phenylmethanesulfonyl)-piperidin-4-ylamino]-phenyl}-thiophene-2-carboxylic acid, 4-Bromo-3-carboxymethoxy-5-(3-{1-[2-(3-ethyl-ureido)-phenylmethanesulfonyl]-piperidin-4-ylamino}-phenyl)-thiophene-2-carboxylic acid, 3-Carboxymethoxy-5-(3-{1-[2-(3-ethyl-ureido)-phenylmethanesulfonyl]-piperidin-4-ylamino}-phenyl)-thiophene-2-carboxylic acid, 4-Bromo-3-carboxymethoxy-5-{3-[1-(2-chloromethanesulfonylamino-phenylmethanesulfonyl)-piperidin-4-ylamino]-phenyl}-thiophene-2-carboxylic acid, 5-{3-[(Acetyl-isopropyl-amino)-methyl]-phenyl}-4-bromo-3-carboxymethoxy-thiophene-2-carboxylic acid, 5-{3-[(Acetyl-isobutyl-amino)-methyl]-phenyl}-4-bromo-3-carboxymethoxy-thiophene-2-carboxylic acid, 5-{3-[(Acetyl-cyclohexylmethyl-amino)-methyl]-phenyl}4-bromo-3-carboxymethoxy-thiophene-2-carboxylic acid, 5-{3-[(Acetyl-p-tolyl-amino)-methyl]-phenyl}-4-bromo-3-carboxymethoxy-thiophene-2-carboxylic acid, 5-(3-{[Acetyl-(4-tert-butyl-phenyl)-amino]-methyl}-phenyl)-4-bromo-3-carboxymethoxy-thiophene-2-carboxylic acid, 5-(3-{[Acetyl-(4-trifluoromethyl-phenyl)-amino]-methyl}-phenyl)-4-bromo-3-carboxymethoxy-thiophene-2-carboxylic acid, 5-{3-[(Acetyl-phenyl-amino)-methyl]-pheny}-4-bromo-3-carboxymethoxy-thiophene-2-carboxylic acid, 5-{3-[(Acetyl-cyclopropyl-amino)-methyl]-phenyl)}4-bromo-3-carboxymethoxy-thiophene-2-carboxylic acid, 5-(3-{[Acetyl-(4-bromo-phenyl)-amino]-methyl}-phenyl)-4-bromo-3-carboxymethoxy-thiophene-2-carboxylic acid, 5-{3-[(Acetyl-biphenyl-4-yl-amino)-methyl]-phenyl}-4-bromo-3-carboxymethoxy-thiophene-2-carboxylic acid, 5-(3-{[Acetyl-(4-phenoxy-phenyl)-amino]-methyl}-phenyl)-4-bromo-3-carboxymethoxy-thiophene-2-carboxylic acid, 5-{3-[(Acetyl-benzyl-amino)-methyl]-phenyl}-4-bromo-3-carboxymethoxy-thiophene-2-carboxylic acid, 5-(3-{[Acetyl-(4-methoxy-benzyl)-amino]-methyl}-phenyl)-4-bromo-3-carboxymethoxy-thiophene-2-carboxylic acid, 5-{3-[(Acetyl-biphenyl-4-ylmethyl-amino)-methyl]-phenyl}-4-bromo-3-carboxymethoxy-thiophene-2-carboxylic acid, 5-(3-{[Acetyl-(4-chloro-phenyl)-amino]-methyl}-phenyl)-4-bromo-3-carboxymethoxy-thiophene-2-carboxylic acid, 5-(3-{[Acetyl-(4-trifluoromethyl-phenyl)-amino]-methyl}-phenyl)-4-bromo-3-carboxymethoxy-thiophene-2-carboxylic acid, 5-(3-{[Acetyl-(3,5-bis-trifluoromethyl-phenyl)-amino]-methyl}-phenyl)-4-bromo--carboxymethoxy-thiophene-2-carboxylic acid, 5-[3-({Acetyl-[2-(4-chloro-phenyl)-ethyl]-amino}-methyl)-phenyl]-4-bromo-3-carboxymethoxy-thiophene-2-carboxylic acid, 4-Bromo-3-carboxymethoxy-5-[3-(1,3-diisopropyl-ureido)-phenyl]-thiophene-2-carboxylic acid, 4-Bromo-3-carboxymethoxy-5-{3-[1-(2,2-dimethyl-propyl)-3-isopropyl-ureido]-phenyl}-thiophene-2-carboxylic acid, 4-Bromo-3-carboxymethoxy-5-[3-(1-isobutyl-3-isopropyl-ureido)-phenyl]-thiophene-2-carboxylic acid, 5-[3-(1-Benzyl-3-isopropyl-ureido)-phenyl]-4-bromo-3-carboxymethoxy-thiophene-2-carboxylic acid, 4-Bromo-3- carboxymethoxy-5-{3-[3-isopropyl-1-(4-trifluoromethyl-benzyl)-ureido]-phenyl}-thiophene-2-carboxylic acid, 4-Bromo-5-{3-[1-(4-tert-butyl-benzyl)-3-isopropyl-ureido]-phenyl}-3-carboxymethoxy-thiophene-2-carboxylic acid, 5-[3-(Acetyl-cyclohexylmethyl-amino)-phenyl]-4-bromo-3-carboxymethoxy-thiophene-2-carboxylic acid, 4-Bromo-3-carboxymethoxy-5-{3-[cyclohexylmethyl-(3-methyl-butyryl)-amino]-phenyl}-thiophene-2-carboxylic acid, 4-Bromo-3-carboxymethoxy-5-[3-(cyclohexanecarbonyl-cyclohexyl methyl-amino)-phenyl]-thiophene-2-carboxylic acid, 4-Bromo-3-carboxymethoxy-5-[3-(cyclohexylmethyl-isobutyryl-amino)-phenyl]-thiophene-2-carboxylic acid, 4-Bromo-3-carboxymethoxy-5-[3-(cyclohexylmethyl-methoxycarbonyl-amino)-phenyl]-thiophene-2-carboxylic acid, 3-Carboxymethoxy-5-[3-(cyclohexylmethyl-methoxycarbonyl-amino)-phenyl]-4-methyl-thiophene-2-carboxylic acid, 3-Carboxymethoxy-5-[3-(cyclohexylmethyl-isopropoxycarbonyl-amino)-phenyl]-4-methyl-thiophene-2-carboxylic acid, 5-[3-(Bis-cyclohexylmethyl-amino)-phenyl]-3-carboxymethoxy-4-methyl-thiophene-2-carboxylic acid, 4-Bromo-3-carboxymethoxy-5-[3-(1-cyclohexylmethyl-3-phenyl-ureido)-phenyl]-thiophene-2-carboxylic acid, 5-[3-(3-Benzyl-1-cyclohexylmethyl-ureido)-phenyl]-4-bromo-3-carboxymethoxy-thiophene-2-carboxylic acid, 4-Bromo-3-carboxymethoxy-5-{3-[1-cyclohexylmethyl-3-(4-ethyl-phenyl)-ureido]-phenyl}-thiophene-2-carboxylic acid, 4-Bromo-3-carboxymethoxy-5-{3-[1-cyclohexylmethyl-3-(4-ethoxy-phenyl)-ureido]-phenyl}-thiophene-2-carboxylic acid, 4-Bromo-3-carboxymethoxy-5-{3-[1-cyclohexylmethyl-3-(4-phenoxy-phenyl)-ureido]-phenyl}-thiophene-2-carboxylic acid, 4-Bromo-3-carboxymethoxy-5-{3-[3-(2-cyano-phenyl)-1-cyclohexylmethyl-ureido]-phenyl}-thiophene-2-carboxylic acid, 4-Bromo-3-carboxymethoxy-5-[3-(1-cyclohexylmethyl-3-thiophen-3-yl-ureido)-phenyl]-thiophene-2-carboxylic acid, 4-Bromo-3-carboxymethoxy-5-{3-[1-cyclohexylmethyl-3-(3,5-dimethyl-isoxazol-4-yl)-ureido]-phenyl}-thiophene-2-carboxylic acid, 4-Bromo-3-carboxymethoxy-5-{3-[1-cyclohexylmethyl-3-(5-methyl-3-phenyl-isoxazol-4-yl)-ureido]-phenyl}-thiophene-2-carboxylic acid, 4-Bromo-3-carboxymethoxy-5-{3-[3-(4-carboxy-phenyl)-1-cyclohexylmethyl-ureido]-phenyl}-thiophene-2-carboxylic acid, 4-Bromo-3-carboxymethoxy-5-[3-(1-cyclohexylmethyl-3-ethyl-ureido)-phenyl]-thiophene-2-carboxylic acid, 3-Carboxymethoxy-5-[3-(1-cyclohexylmethyl-3-isopropyl-ureido)-phenyl]-4-methyl-thiophene-2-carboxylic acid, 3-Carboxymethoxy-5-[3-(1-cyclohexyl-3-isopropyl-ureido)-phenyl]-4-methyl-thiophene-2-carboxylic acid, 3-Carboxymethoxy-5-[3-(1-cyclohexylmethyl-3-phenyl-ureido)-phenyl]-4-methyl-thiophene-2-carboxylic acid, 5-[3-(3-Benzyl-1-cyclohexylmethyl-ureido)-phenyl]-3-carboxymethoxy-4-methyl-thiophene-2-carboxylic acid, 5-[3-(3-Benzyl-1-cyclohexyl-ureido)-phenyl]-3-carboxymethoxy-4-methyl-thiophene-2-carboxylic acid, 3-Carboxymethoxy-5-[3-(1-cyclohexylmethyl-3-phenethyl-ureido)-phenyl]-4-methyl-thiophene-2-carboxylic acid, 3-Carboxymethoxy-5-[3-(1-cyclohexylmethyl-3-phenethyl-ureido)-phenyl]-4-methyl-thiophene-2-carboxylic acid, 4-Bromo-3-isopropoxycarbonylmethoxy-5-[3-(1-phenylmethanesulfonyl-piperidin-4-ylamino)-phenyl]-thiophene-2-carboxylic acid, 4-Bromo-3-isobutoxycarbonylmethoxy-5-[3-(1-phenylmethanesulfonyl-piperidin-4-ylamino)-phenyl]-thiophene-2-carboxylic acid, 4-Bromo-5-[3-(1-phenylmethanesulfonyl-piperidin-4-ylamino)-phenyl]-3-propoxycarbonylmethoxy-thiophene-2-carboxylic acid, 4-Bromo-3-cyclopropylmethoxycarbonylmethoxy-5-[3-(1-phenylmethanesulfonyl-piperidin-4-ylamino)-phenyl]-thiophene-2-carboxylic acid, 3-Benzyloxycarbonylmethoxy-4-bromo-5-[3-(1-phenylmethanesulfonyl-piperidin-4-ylamino)-phenyl]-thiophene-2-carboxylic acid, 4-Bromo-3-cyclohexylmethoxycarbonylmethoxy-5-[3-(1-phenylmethanesulfonyl-piperidin-4-ylamino)-phenyl]-thiophene-2-carboxylic acid, 4-Bromo-3-cyclohexyloxycarbonylmethoxy-5-[3-(1-phenylmethanesulfonyl-piperidin-4-ylamino)-phenyl]-thiophene-2-carboxylic acid, 4-Bromo-3-carboxymethoxy-5-{3-[1-(2,3-dichloro-phenylmethanesulfonyl)-piperidin-4-ylamino]-phenyl}-thiophene-2-carboxylic acid, 4-Bromo-5-{3-[1-(2,3-dichloro-phenylmethanesulfonyl)-piperidin-4-ylamino]-phenyl}-3-methoxycarbonylmethoxy-thiophene-2-carboxylic acid, 4-Bromo-3-carboxymethoxy-5-{3-[1-(2,3-dichloro-phenylmethanesulfonyl)-piperidin-4-ylamino]-phenyl}-thiophene-2-carboxylic acid methyl ester, [4-Bromo-5-(3-cyclohexylamino-phenyl)-2-(2H-tetrazol-5-yl)-thiophen-3-yloxy]-acetic acid, [4-Bromo-5-[3-(cyclohexylmethyl-amino)-phenyl]-2-(2H-tetrazol-5-yl)-thiophen-3-yloxy]-acetic acid, [4-Bromo-5-[3-(3,3,5,5-tetramethyl-cyclohexylamino)-phenyl]-2-(2H-tetrazol-5-yl)-thiophen-3-yloxy]-acetic acid, Tetrazole/acid: [5-{3-[Acetyl-(3,3,5,5-tetramethyl-cyclohexyl)-amino]-phenyl}-4-bromo-2-(2H-tetrazol-5-yl)-thiophen-3-yloxy]-acetic acid, [4-Bromo-5-[3-(1-phenylmethanesulfonyl-piperidin-4-ylamino)-phenyl]-2-(2H-tetrazol-5-yl)-thiophen-3-yloxy]-acetic acid, 4-Bromo-3-carboxymethoxy-5-[3-(1-phenylmethanesulfonyl-piperidin-4-ylamino)-phenyl]-thiophene-2-carboxylic acid methyl ester, ethanolamine salt, 4-Bromo-3-carboxymethoxy-5-[3-(1-phenylmethanesulfonyl-piperidin-4-ylamino)-phenyl]-thiophene-2-carboxylic acid methyl ester, choline salt, 4-Bromo-3-carboxymethoxy-5-[3-(1-phenylmethanesulfonyl-piperidin-4-ylamino)-phenyl]-thiophene-2-carboxylic acid methyl ester, sodium salt, {[2-[(Benzyloxy)carbonyl]-5-(3-{[1-(benzylsulfonyl)piperidin-4-yl]amino}phenyl)-4-bromothien-3-yl]oxy}acetic acid, [(5-(3-{[1-(benzylsulfonyl)piperidin-4-yl]amino}phenyl)-4-bromo-2-{[(2-nitrobenzyl)oxy]carbonyl}thien-3-yl)oxy] acetic acid, [(5-(3-{[1-(Benzylsulfonyl)piperidin-4-yl]amino}phenyl)-4-bromo-2-{[(2-nitrobenzyl)oxy]carbonyl}thien-3-yl)oxy]acetic acid, [(5-(3-[1-(Benzylsulfonyl)piperidin-4-yl]amino}phenyl)-4-bromo-2-{[(2-nitrobenzyl)oxy]carbonyl}thien-3-yl)oxy]acetic acid, ({5-(3-{[1-(benzylsulfonyl)piperidin-4-yl]amino}phenyl)-4-bromo-2-[(cyclohexylmethoxy)carbonyl]thien-3-yl}oxy) acetic acid, ({5-(3-{[1-(Benzylsulfonyl)piperidin-4-yl]amino}phenyl)-4-bromo-2-[(cyclohexylmethoxy)carbonyl]thien-3-yl}oxy)acetic acid, 5-[3-(Benzyloxycarbonyl-cyclohexyl-amino)-phenyl]-4-bromo-3-carboxymethoxy-thiophene-2-carboxylic acid, 5-[3-(Benzyloxycarbonyl-cyclohexyl-amino)-phenyl]-4-bromo-3-carboxymethoxy-thiophene-2-carboxylic acid, 4-Bromo-3-carboxymethoxy-5-[3-(cyclohexyl-propoxycarbonyl-amino)-phenyl]-thiophene-2-carboxylic acid, 4-Bromo-3-carboxymethoxy-5-[3-(cyclohexyl-isopropoxycarbonyl-amino)-phenyl]-thiophene-2-carboxylic acid, 5-[3-(Benzyloxycarbonyl-cyclohexylmethyl-amino)-phenyl]-4-bromo-3-carboxymethoxy-thiophene-2-carboxylic acid, 4-Bromo-3-carboxymethoxy-5-[3-(cyclohexylmethyl-isopropoxycarbonyl-amino)-phenyl]-thiophene-2-carboxylic acid, 4-Bromo-3-carboxymethoxy-5-[3-(cyclohexylmethyl-isopropoxycarbonyl-amino)-phenyl]-thiophene-2-carboxylic acid, 4-Bromo-3-carboxymethoxy-5-[3-(cyclohexylmethyl-propoxycarbonyl-amino)-phenyl]-thiophene-2-carboxylic acid, 5-[3-(Benzoyl-cyclohexylmethyl-amino)-phenyl]-4-bromo-3- carboxymethoxy-thiophene-2-carboxylic acid, 4-Bromo-3-carboxymethoxy-5-[3-(cyclohexylmethyl-phenylacetyl-amino)-phenyl]-thiophene-2-carboxylic acid, 4-Bromo-3-carboxymethoxy-5-{3-[cyclohexylmethyl-(4-methyl-pentanoyl)-amino]-phenyl}-thiophene-2-carboxylic acid methyl ester, 4-Bromo-3-carboxymethoxy-5-{3-[1-(3-chloro-phenylmethanesulfonyl)-piperidin-4-ylamino]-phenyl}-thiophene-2-carboxylic acid methyl ester, 4-Bromo-3-carboxymethoxy-5-{3-[1-(3-fluoro-phenylmethanesulfonyl)-piperidin-4-ylamino]-phenyl}-thiophene-2-carboxylic acid methyl ester, 4-Bromo-3-carboxymethoxy-5-{3-[1-(2-chloro-phenylmethanesulfonyl)-piperidin-4-ylamino]-phenyl}-thiophene-2-carboxylic acid, 4-Bromo-5-{3-[1-(2-chloro-phenylmethanesulfonyl)-piperidin-4-ylamino]-phenyl}-3-methoxycarbonylmethoxy-thiophene-2-carboxylic acid, 3-Carboxymethoxy-5-{3-[1-(3-fluoro-phenylmethanesulfonyl)-piperidin-4-ylamino]-phenyl}-4-methyl-thiophene-2-carboxylic acid methyl ester, 3-Carboxymethoxy-4-methyl-5-[3-(1-phenylmethanesulfonyl-piperidin-4-ylamino)-phenyl]-thiophene-2-carboxylic acid methyl ester, 3-Carboxymethoxy-4-methyl-5-{3-[1-(2-trifluoromethyl-phenylmethanesulfonyl)-piperidin-4-ylamino]-phenyl}-thiophene-2-carboxylic acid methyl ester, 3-Carboxymethoxy-4-methyl-5-[3-(1-phenylmethanesulfonyl-piperidin-4-ylamino)-phenyl]-thiophene-2-carboxylic acid, 3-Methoxycarbonylmethoxy-4-methyl-5-[3-(1-phenyl-methanesulfonyl-piperidin-4-ylamino)-phenyl]-thiophene-2-carboxylic acid, 3-carboxymethoxy-4-methyl-5-[3-(3,3,5,5-tetramethyl-cyclohexylamino)-phenyl]-thiophene-2-carboxylic acid methyl ester], 4,5-Dibromo-3-(1-carboxy-ethoxy)-thiophene-2-carboxylic acid, [4,5-Dibromo-2-(5-methyl-[1,2,4]oxadiazol-3-yl)-thiophen-3-yloxy]-acetic acid, [4,5-Dibromo-2-(5-ethyl-[1,2,4]oxadiazol-3-yl)-thiophen-3-yloxy]-acetic acid, [4,5-Dibromo-2-(5-isopropyl-[1,2,4]oxadiazol-3-yl)-thiophen-3-yloxy]-acetic acid, [4-Bromo-5-[3-(1-phenylmethanesulfonyl-piperidin-4-ylamino)-phenyl]-2-(1H-tetrazol-5-yl)-thiophen-3-yloxy]-acetic acid, [4-Bromo-5-[3-(1 -phenylmethanesulfonyl-piperidin-4-ylamino)-phenyl]-2-(1H-tetrazol-5-yl)-thiophen-3-yloxy]-acetic acid isopropyl ester, [4-Bromo-5-[3-(1-phenylmethanesulfonyl-piperidin-4-ylamino)-phenyl]-2-(1H-tetrazol-5-yl)-thiophen-3-yloxy]-acetic acid methyl ester, 4,5-Dibromo-3-(isobutylcarbamoyl-methoxy)-thiophene-2-carboxylic acid methyl ester, 4,5-Dibromo-3-(2-oxo-2-pyrrolidin-1-yl-ethoxy)-thiophene-2-carboxylic acid methyl ester, 4,5-Dibromo-3-[(2-hydroxy-1-methyl-ethylcarbamoyl)-methoxy]-thiophene-2-carboxylic acid methyl ester, [4-Bromo-5-[3-(1-phenylmethanesulfonyl-piperidin-4-ylamino)-phenyl]-2-(1H-tetrazol-5-yl)-thiophen-3-yloxy]-acetic acid methyl ester, 4,5-Dibromo-3-(isobutylcarbamoyl-methoxy)-thiophene-2-carboxylic acid methyl ester, 4-[2-(4,5-Dibromo-2-methoxycarbonyl-thiophen-3-yloxy)-acetyl]-piperazine-1-carboxylic acid tert-butyl ester, 4,5-Dibromo-3-[(2-hydroxy-1-methyl-ethylcarbamoyl)-methoxy]-thiophene-2-carboxylic acid methyl ester, 4,5-Dibromo-3-[(2-tert-butoxycarbonylamino-ethylcarbamoyl)-methoxy]-thiophene-2-carboxylic acid methyl ester, 3-[(2-Amino-ethylcarbamoyl)-methoxy]-4,5-dibromo-thiophene-2-carboxylic acid methyl ester, 3-{[2-(4-Hydroxy-phenyl)-1-methoxycarbonyl-ethylcarbamoyl]-methoxy}-4-methyl-5-[3-(3,3,5,5-tetramethyl-cyclohexyl)-phenyl]-thiophene-2-carboxylic acid methyl ester, 1-(2-{2-Methoxycarbonyl-4-methyl-5-[3-(3,3,5,5-tetramethyl-cyclohexyl)-phenyl]-thiophen-3-yloxy}-acetyl)-pyrrolidine-2-carboxylic acid methyl ester, 4-Methyl-3-(2-oxo-2-pyrrolidin-1-yl-ethoxy)-5-[3-(3,3,5,5-tetramethyl-cyclohexyl)-phenyl]-thiophene-2-carboxylic acid methyl ester, 3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester, 3-[(1-Methoxycarbonyl-2-methyl-propylcarbamoyl)-methoxy]-4-methyl-5-[3-(3,3,5,5-tetramethyl-cyclohexyl)-phenyl]-thiophene-2-carboxylic acid methyl ester, 3-[(1-Methoxycarbonyl-3-methyl-butylcarbamoyl)-methoxy]-4-methyl-5-[3-(3,3,5,5-tetramethyl-cyclohexyl)-phenyl]-thiophene-2-carboxylic acid methyl ester, 3-[(1-Methoxycarbonyl-2-phenyl-ethylcarbamoyl)-methoxy]-4-methyl-5-[3-(3,3,5,5-tetramethyl-cyclohexyl)-phenyl]-thiophene-2-carboxylic acid methyl ester, 3-[2-(2-Carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester, 3-[(2-tert-Butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester, 4-(2-{2-Methoxycarbonyl-4-methyl-5-[3-(3,3,5,5-tetramethyl-cyclohexyl)-phenyl]-thiophen-3-yloxy}-acetyl)-piperazine-1-carboxylic acid tert-butyl ester, 3-[(2-Amino-ethylcarbamoyl)-methoxy]-4-methyl-5-[3-(3,3,5,5-tetramethyl-cyclohexyl)-phenyl]-thiophene-2-carboxylic acid methyl ester, 4-Methyl-3-(2-oxo-2-piperazin-1-yl-ethoxy)-5-[3-(3,3,5,5-tetramethyl-cyclohexyl)-phenyl]-thiophene-2-carboxylic acid methyl ester, 4-Bromo-5-[3-(1-phenylmethanesulfonyl-piperidin-4-yl)-phenyl]-3-(piperidin-4-yloxycarbonylmethoxy)-thiophene-2-carboxylic acid methyl ester, 4-Bromo-3-methoxycarbonylmethoxy-5-[3-(1-phenylmethanesulfonyl-piperidin-4-yl)-phenyl]-thiophene-2-carboxylic acid 2,2-dimethyl-propionyloxymethyl ester, 4-Bromo-3-isopropoxycarbonylmethoxy-5-[3-(1-phenylmethanesulfonyl-piperidin-4-yl)-phenyl]-thiophene-2-carboxylic acid 2,2-dimethyl-propionyloxymethyl ester, 4-Bromo-3-isopropoxycarbonylmethoxy-5-[3-(1-phenylmethanesulfonyl-piperidin-4-yl)-phenyl]-thiophene-2-carboxylic acid acetoxymethyl ester, 4,5-Dibromo-3-methoxycarbonylmethoxy-thiophene-2-carboxylic acid 2,2-dimethyl-propionyloxymethyl ester, [5-Bromo-4-methyl-2-(1H-tetrazol-5-yl)-thiophen-3-yloxy]-acetic acid, [4-Methyl-5-phenyl-2-(1H-tetrazol-5-yl)-thiophen-3-yloxy]-acetic acid, [5-Bromo-4-methyl-2-(2-methyl-2H-tetrazol-5-yl)-thiophen-3-yloxy]-acetic acid, 3-Carboxymethoxy-5-{3-[1-(3-chloro-benzenesulfonyl)-piperidin-4-ylamino]-phenyl}-4-methyl-thiophene-2-carboxylic acid, 3-Carboxymethoxy-5-{3-[1-(2-chloro-benzenesulfonyl)-piperidin-4-ylamino]-phenyl}-4-methyl-thiophene-2-carboxylic acid, 3-carboxymethoxy-4-methyl-5-{3-[1-(4-nitro-benzenesulfonyl)-piperidin-4-ylamino]-phenyl}-thiophene-2-carboxylic acid, 3-Carboxymethoxy-5-{3-[1-(2-cyano-benzenesulfonyl)-piperidin-4-ylamino]-phenyl}-4-methyl-thiophene-2-carboxylic acid, 3-Carboxymethoxy-4-methyl-5-{3-[1-(4-trifluoromethyl-benzenesulfonyl)-piperidin-4-ylamino]-phenyl}-thiophene-2-carboxylic acid, 5-{3-[1-(4-Carboxy-benzenesulfonyl)-piperidin-4-ylamino]-phenyl}-3-carboxymethoxy-4-methyl-thiophene-2-carboxylic acid, 3-Carboxymethoxy-5-{3-[1-(2-cyano-benzenesulfonyl)-piperidin-4-ylamino]-phenyl}-4-methyl-thiophene-2-carboxylic acid, 3-Carboxymethoxy-4-methyl-5-{3-[1-(4-trifluoromethyl-benzenesulfonyl)-piperidin-4-ylamino]-phenyl}-thiophene-2-carboxylic acid, 4-Bromo-3-carboxymethoxy-5-[3-(1-cyclohexyl-3-methylureido)-phenyl]-thiophene-2-carboxylic acid, 5-[3-(3-Benzyl-1-cyclohexyl-ureido)-phenyl]-4-bromo-3-carboxymethoxy-thiophene-2-carboxylic acid, 4-Bromo-3-tert-butoxycarbonylmethoxy-5-[3-(3,3,5,5-tetramethyl-cyclohexylamino)-phenyl]-thiophene-2-carboxylic acid methyl ester, 4-Bromo-3-carboxymethoxy-5-{3-[3-methyl-1-(3,3,5,5-tetramethyl-cyclohexyl)-ureido]-phenyl}-thiophene-2-carboxylic acid, 4-Bromo-3-carboxymethoxy-5-{3-[3-ethyl-1-(3,3,5,5-tetramethyl-cyclohexyl)-ureido]-phenyl}-thiophene-2-carboxylic acid, 4-Bromo-3-carboxymethoxy-5-{3-[3-methyl-1-(3,3,5,5-tetramethyl-cyclohexyl)-ureido]-phenyl}-thiophene-2-carboxylic acid methyl ester, 4-Bromo-3-ethoxycarbonylmethoxy-5-[3-(piperidin-4-ylamino)-phenyl]-thiophene-2-carboxylic acid methyl ester hydrochloride, 4-Bromo-3-carboxymethoxy-5-{3-[1-(4-trifluoromethyl-pyrimidin-2-yl)-piperidin-4-ylamino]-phenyl}-thiophene-2-carboxylic acid, 4-Bromo-3-carboxymethoxy-5-[3-(1-pyrimidin-2-yl-piperidin-4-ylamino)-phenyl]-thiophene-2-carboxylic acid, 4-Bromo-3-carboxymethoxy-5-[3-(5'-trifluoromethyl-3,4,5,6-tetrahydro-2H-[1,2']bipyridinyl-4-ylamino)-phenyl]-thiophene-2-carboxylic acid, 4-Bromo-3-ethoxycarbonylmethoxy-5-[3-(1-phenylmethanesulfonyl-piperidin-4-ylamino)-phenyl]-thiophene-2-carboxylic acid ethyl ester, 4-Bromo-5-[3-(1-phenylmethanesulfonyl-piperidin-4-ylamino)-phenyl]-3-(o-tolylcarbamoyl-methoxy)-thiophene-2-carboxylic acid, {4-Bromo-2-hydroxymethyl-5-[3-(1-phenylmethanesulfonyl-piperidin-4-ylamino)-phenyl]-thiophen-3-yloxy}-acetic acid, 3-Carboxymethoxy-5-[3-(1-phenylmethanesulfonyl-piperidin-4-ylamino)-phenyl]-thiophene-2-carboxylic acid, 4-Bromo-3-carboxymethoxy-5-(3-{1-[3-(3-ethyl-ureido)-phenylmethanesulfonyl]-piperidin-4-ylamino}-phenyl)-thiophene-2-carboxylic acid, [2-(2-{4-Bromo-2-methoxycarbonyl-5-[3-(1-phenylmethanesulfonyl-piperidin-4-ylamino)-phenyl]-thiophen-3-yloxy}-acetoxy)-ethyl]-trimethyl-ammonium chloride, 4-Bromo-3-cyclohexylcarbamoylmethoxy-5-[3-(1-phenylmethanesulfonyl-piperidin-4-ylamino)-phenyl]-thiophene-2-carboxylic acid methyl ester, (4,5-Dibromo-2-hydroxymethyl-thiophen-3-yloxy)-acetic acid, 5-[3-(Acetyl-cyclohexyl-amino)-phenyl]-4-bromo-3-carboxymethoxy-thiophene-2-carboxylic acid, 5-[3-(Acetyl-cyclohexyl-amino)-phenyl]-4-bromo-3-carboxymethoxy-thiophene-2-carboxylic acid methyl ester, 5-[3-(Benzoyl-cyclohexyl-amino)-phenyl]-4-bromo-3-carboxymethoxy-thiophene-2-carboxylic acid, 5-[3-(Benzoyl-cyclohexyl-amino)-phenyl]-4-bromo-3-carboxymethoxy-thiophene-2-carboxylic acid methyl ester, 4-Bromo-3-carboxymethoxy-5-{3-[cyclohexyl-(3-phenyl-acryloyl)-amino]-phenyl}-thiophene-2-carboxylic acid methyl ester, 4-Bromo-3-carboxymethoxy-5-[3-(cyclohexanecarbonyl-cyclohexyl-amino)-phenyl]-thiophene-2-carboxylic acid methyl ester, 5-{3-[Benzoyl-(3,3,5,5-tetramethyl-cyclohexyl)-amino]-phenyl}-4-bromo-3-carboxymethoxy-thiophene-2-carboxylic acid, 4-Bromo-3-carboxymethoxy-5-[3-(1-phenylmethanesulfonyl-piperidin-4-ylamino)-phenyl]-thiophene-2-carboxylic acid methyl ester (Hydrochloride Salt), 4-Bromo-3-[(carbamoylmethyl-carbamoyl)-methoxy]-5-[3-(3,3,5,5-tetramethyl-cyclohexylamino)-phenyl]-thiophene-2-carboxylic acid methyl ester, 4-Bromo-3-[(1-carbamoyl-ethylcarbamoyl)-methoxy]-5-[3-(3,3,5,5-tetramethyl-cyclohexylamino)-phenyl]-thiophene-2-carboxylic acid methyl ester, 4-Bromo-3-[(ethoxycarbonylmethyl-carbamoyl)-methoxy]-5-[3-(3,3,5,5-tetramethyl-cyclohexylamino)-phenyl]-thiophene-2-carboxylic acid methyl ester, 4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester, 3-{[(Benzylcarbamoyl-methyl)-carbamoyl]-methoxy}-4-bromo-5-[3-(3,3,5,5-tetramethylcyclohexylamino)-phenyl]-thiophene-2-carboxylic acid methyl ester, 4-Bromo-3-carboxymethoxy-5-{3-[1-(3-methanesulfonylamino-phenylmethanesulfonyl)-piperidin-4-ylamino]-phenyl}-thiophene-2-carboxylic acid, 5-{3-[1-(3-Acetylamino-phenylmethanesulfonyl)-piperidin-4-ylamino]-phenyl}-4-bromo-3-carboxymethoxy-thiophene-2-carboxylic acid, {[4-Bromo-5-(3-methoxyphenyl)-2-(morpholin-4-ylcarbonyl)thien-3-yl]oxy}acetic acid, {[5-(1,3-Benzodioxol-5-yl)-4-bromo-2-(morpholin-4-ylcarbonyl)thien-3-yl]oxy}acetic acid, {[3-Bromo-5-(morpholin-4-ylcarbonyl)-2,3'-bithien-4-yl]oxy}acetic acid, {[4-Bromo-2-(morpholin-4-ylcarbonyl)-5-phenylthien-3-yl]oxy}acetic acid, [(4,5-Dibromo-2-{[(2-hydroxy-1,1-dimethylethyl)amino]carbonyl}thien-3-yl)oxy]acetic acid, ({4,5-Dibromo-2-[(dimethylamino)carbonyl]thien-3-yl}oxy)acetic acid, ({4,5-dibromo-2-[(diethylamino)carbonyl]thien-3-yl}oxy)acetic acid, ({4,5-dibromo-2-[(1,3-thiazol-2-ylamino)carbonyl]thien-3-yl}oxy)acetic acid, [4,5-Dibromo-2-(2H-pyrazol-3-ylcarbamoyl)-thiophen-3-yloxy]-acetic acid, {[4,5-dibromo-2-(morpholin-4-ylcarbonyl)thien-3-yl]oxy}acetic acid, [(4,5-Dibromo-2-{[(2R,6S)-2,6-dimethylmorpholin-4-yl]carbonyl}thien-3-yl)oxy]acetic acid, {[4,5-Dibromo-2-(thiomorpholin-4-ylcarbonyl)thien-3-yl]oxy}acetic acid, {[2-(Anilinocarbonyl)-4,5-dibromothien-3-yl]oxy}acetic acid, {[4,5-Dibromo-2-(piperidin-1-ylcarbonyl)thien-3-yl]oxy}acetic acid, {[4,5-Dibromo-2-(4,4-dimethyl-4,5-dihydro-1,3-oxazol-2-yl)thien-3-yl]oxy}acetic acid, {[5-(3-{[1-(Benzylsulfonyl)piperidin-4-ylamino}phenyl)-4-bromo-2-(morpholin-4-ylcarbonyl)thien-3-yl]oxy}acetic acid, [(4-Bromo-2-(morpholin-4-ylcarbonyl)-5-{3-[(3,3,5,5-tetramethylcyclohexyl)amino]phenyl}thien-3-yl)oxy]acetic acid, 4-Bromo-5-(3-{[1-(butylsulfonyl)piperidin-4-yl]amino}phenyl)-3-(2-methoxy-2-oxoethoxy)thiophene-2-carboxylic acid, 4-Bromo-5-(3-{[1-(ethylsulfonyl)piperidin-4-yl]amino}phenyl)-3-(2-methoxy-2-oxoethoxy)thiophene-2-carboxylic acid, 4-Bromo-5-(3-{[1-(isopropylsulfonyl)piperidin-4-yl]amino}phenyl)-3-(2-methoxy-2-oxoethoxy)thiophene-2-carboxylic acid, 5-{3-[Acetyl(3,3,5,5-tetramethylcyclohexyl)amino]phenyl}-4-bromo-3-(2-methoxy-2-oxoethoxy)thiophene-2-carboxylic acid, [4-Bromo-5-[3-(cyclohexylamino)phenyl]-2-(methoxycarbonyl)thien-3-yl]oxyacetic acid, {[5-(3-{[1-(Benzylsulfonyl)piperidin-4-yl]amino}phenyl)-4-bromo-2-(ethoxycarbonyl)thien-3-yl]oxy}acetic acid, {[5-(3-{[1-(Benzylsulfonyl)piperidin-4-yl]amino}phenyl)-4-bromo-2-(isopropoxycarbonyl)thien-3-yl]oxy}acetic acid, ({5-(3-{[1-(Benzylsulfonyl)piperidin-4-yl]amino}phenyl)-4-bromo-2-[(cyclohexyloxy)carbonyl]thien-3-yl}oxy)acetic acid, {[4-Bromo-2-(ethoxycarbonyl)-5-(3-{[1-(phenylsulfonyl)piperidin-4-yl]amino}phenyl)thien-3-yl]oxy}acetic acid, [4-Bromo-2-(methoxycarbonyl)-5-(3-{[1-(phenylsulfonyl)piperidin-4-yl]amino}phenyl)thien-3-yl]oxyacetic acid, [(4-bromo-2-(ethoxycarbonyl)-5-(3-[(3,3,5,5-tetramethylcyclohexyl)amino]phenyl}thien-3-yl)oxy]acetic acid, and {[4,5-Dibromo-2-(methoxyacetyl)thien-3-yl]oxy}acetic acid.

These and other compounds of formula (I) were prepared according to the following detailed schemes from commercially available starting materials, intermediates prepared using literature procedures, or novel intermediates described in the schemes and experimental procedures.

EXAMPLE 1

4-Bromo-3-carboxymethoxy-thiophene-2-carboxylic acid

The first step of Scheme 1: To a solution of 4-bromo-3-hydroxy-thiophene-2-carboxylic acid methyl ester (2.37 g, 10 mmol) in DMF (20 mL) was added tert-butyl bromoacetate (1.77 mL, 12 mmol) and $K_2CO_3$ (2.76 g, 20 mmol). The resultant reaction mixture was stirred at room temperature overnight, diluted with EtOAc and washed with aq. $NH_4Cl$. The aqueous layer was extracted with EtOAc. The combined organic layer was dried over $MgSO_4$, and the crude product was purified on $SiO_2$ gel column eluted with EtOAc/Hexanes (1/10 to 1/8) to give 4-bromo-3-tert-butoxycarbonylmethoxy-thiophene-2-carboxylic acid methyl ester as a colorless crystalline (2.97 g, 85%).

$^1$H NMR (400 MHz, CHLOROFORM-D) δ ppm 1.49 (s, 9 H) 3.86 (s, 3 H) 4.80 (s, 2 H) 7.39 (s, 1 H).

The second step of Scheme 1: To a solution of 4-bromo-3-tert-butoxycarbonylmethoxy-thiophene-2-carboxylic acid methyl ester (431.1 mg, 1.225 mmol) in THF (2 mL)/$H_2O$ (2 mL) was added 5 eq of LiOH (65 mg, 2.2 mmol). The resultant reaction mixture was stirred at room temperature overnight, and concentrated under vacuum to remove THF. The aqueous solution was acidified with 10% aqueous HCl solution to pH 1. The precipitate was collected by filtration, washed with $H_2O$, and dried under vacuum to give 4-bromo-3-carboxymethoxy-thiophene-2-carboxylic acid as a white solid (261.2 mg, 77%).

EXAMPLE 2

3-Carboxymethoxy-thiophene-2-carboxylic acid

3-Carboxymethoxy-thiophene-2-carboxylic acid was prepared according procedures similar to that for Example 1.

3-tert-Butoxycarbonylmethoxy-thiophene-2-carboxylic acid methyl ester (796 mg, 99%) was prepared as a white solid according to procedures in the first step of Scheme 1 for Example 1, using 3-hydroxy-thiophene-2-carboxylic acid methyl ester (480 mg, 3.0 mmol) as the starting material.

3-Carboxymethoxy-thiophene-2-carboxylic acid (154 mg, 64%) was prepared as a white solid following similar procedures described in the second step of Scheme 1 of Example 1. The product was extracted with EtOAc after acidification with aqueous HCl, and the crude product was recrystallized with hexanes/EtOAc, using 3-tert-butoxycarbonylmethoxy-thiophene-2-carboxylic acid methyl ester (320 mg, 1.19 mmol) as the starting material.

EXAMPLE 3

3-Carboxymethoxy-4-phenyl-thiophene-2-carboxylic acid

4-Bromo-3-tert-butoxycarbonylmethoxy-thiophene-2-carboxylic acid methyl ester was prepared according to procedures in the second step of Scheme 1 of Example 1.

The first step of Scheme 2: 4-Bromo-3-tert-butoxycarbonylmethoxy-thiophene-2-carboxylic acid methyl ester (70.2 mg, 0.2 mmol), $PhB(OH)_2$ (36.6 mg, 0.3 mmol), $Pd(OAc)_2$ (2.2 mg, 0.01 mmole), KF (34.9 mg, 0.6 mmol) and 0.1 eq of biphenyl-2-yl-di-tert-butyl-phosphane (6 mg, 0.02 mmol) in THF (1 mL) were mixed in a sealed tube. After purging with $N_2$, anhydrous THF was added and the tube was sealed. The resultant reaction mixture was stirred at room temperature overnight and then heated to 50° C. for 6 h. The precipitate was removed by filtering through a pad of Celite and washed with EtOAc. The filtrate was concentrated and loaded to a silica gel column and eluted with Hexanes/EtOAc (10/1) to give 3-tert-butoxycarbonylmethoxy-4-phenyl-thiophene-2-carboxylic acid methyl ester (45.3 mg, 65%).

$^1$H NMR (400 MHz, CHLOROFORM-D) δ ppm 1.35 (m, 9 H) 3.82 (m, 3 H) 4.47 (m, 2 H) 7.34 (m, 5 H).

3-Carboxymethoxy-4-phenyl-thiophene-2-carboxylic acid (27 mg, 78%) was synthesized from 3-tert-butoxycarbonylmethoxy-4-phenyl-thiophene-2-carboxylic acid methyl ester (43.2 mg, 0.124 mmol) and LiOH (6.6 mg, 0.273 mmol) in THF (1 mL)/$H_2O$ (1 mL) according to procedures in the second step of Scheme 2 of Example 1.

$^1$H NMR (400 MHz, DMSO-D6) δ ppm 4.47 (m, 2 H) 7.25 (m, 1 H) 7.32 (m, 2 H) 7.54 (m, 2 H) 7.62 (m, 1 H).

EXAMPLE 4

3-Carboxymethoxy-4-(3-trifluoromethyl-phenyl)-thiophene-2-carboxylic acid 3-tert-butoxycarbonylmethoxy-4-(3-trifluoromethyl-phenyl)thiophene-2-carboxylic acid methyl ester was synthesized according to procedures in the first step of Scheme 2 of Example 3, using 4-bromo-3-tert-butoxycarbonylmethoxy-thiophene-2-carboxylic acid methyl ester and 3-trifluoromethylphenyl boronic acid as starting materials.

$^1$H NMR (400 MHz, CHLOROFORM-D) δ ppm 1.19 (s, 9 H) 4.44 (s, 3 H) 7.05 (s, 2 H) 7.33 (d, J=7.58 Hz, 1 H) 7.38 (m, 1 H) 7.67 (d, J=8.08 Hz, 1 H) 7.69 (s, 1 H).

3-Carboxymethoxy-4-(3-trifluoromethyl-phenyl)-thiophene-2-carboxylic acid (5.2 mg, 39%) was synthesized according to procedures in the second step of Scheme 2 of Example 3, using 3-tert-butoxycarbonylmethoxy-4-(3-trifluoromethyl-phenyl)thiophene-2-carboxylic acid methyl ester (16 mg, 0.038 mmol) and LiOH (6 mg, 0.25 mmol) as starting materials.

$^1$H NMR (400 MHz, DMSO-D6) δ ppm 4.84 (s, 2 H) 7.67 (m, 2 H) 7.98 (d, J=7.83 Hz, 1 H) 8.10 (s, 1 H) 8.14 (s, 1 H).

EXAMPLE 5

3-Carboxymethoxy-4-(1H-indol-5-yl)-thiophene-2-carboxylic acid 3-tert-Butoxycarbonylmethoxy-4-(1H-indol-5-yl)thiophene-2-carboxylic acid methyl ester was synthesized according to the procedures in the first step of Scheme 2 of Example 3, using 4-bromo-3-tert-butoxycarbonylmethoxy-thiophene-2-carboxylic acid methyl ester (1B) and 5-indolyl boronic acid as starting materials.

$^1$H NMR (400 MHz, CHLOROFORM-D) δ ppm 1.40 (m, 9 H) 3.89 (m, 3 H) 4.48 (m, 2 H) 6.60 (t, J=2.53 Hz, 1 H) 7.25 (t, J=2.78 Hz, 1 H) 7.42 (m, 2 H) 7.48 (dd, J=1.77 8.59 Hz, 1 H) 7.90 (d, J=0.76 Hz, 1 H) 8.24 (s, 1 H).

3-Carboxymethoxy-4-(1H-indol-5-yl)thiophene-2-carboxylic acid was synthesized according to the procedures in the second step of Scheme 2 of Example 3, using 3-tert-butoxycarbonylmethoxy-4-(1H-ino-5-yl)-thiophene-2-carboxylic acid methyl ester (70.9 mg, 0.18 mmol) and LiOH (9.7 mg) as starting materials. After hydrolysis, the product was extracted with EtOAc and dried over $MgSO_4$. The solvent was removed and the crude product was recrystallized with Hexanes/EtOAc to give 3-carboxymethoxy-4-(1H-indol-5-yl)thiophene-2-carboxylic acid as a white foamy solid.

$^1$H NMR (400 MHz, CD3OD) δ ppm 4.37 (s, 2 H) 6.40 (dd, J=1.01, 3.29 Hz, 1 H) 7.17 (d, J=3.03 Hz, 1 H) 7.26 (dd, J=1.77, 8.34 Hz, 1 H) 7.34 (dt, J=0.77, 8.34 Hz, 1 H) 7.5 (s, 1 H) 7.72 (dd, J=0.77, 1.77 Hz, 1 H).

EXAMPLE 6

4-Carboxymethoxy-[3,3']bithiophenyl-5-carboxylic acid 4-tert-butoxycarbonylmethoxy-[3,3']bithiophenyl-5-carboxylic acid methyl ester was synthesized according to procedures in the first step of Scheme 2 of Example 3, using 4-bromo-3-tert-butoxycarbonylmethoxy-thiophene-2-carboxylic acid methyl ester and 3-thiophenyl boronic acid as starting materials.

4-Carboxymethoxy-[3,3']bithiophenyl-5-carboxylic acid was synthesized according to procedures in the second step of Scheme 2 of Example 3, using 4-tert-butoxycarbonylmethoxy-[3,3']bithiophenyl-5-carboxylic acid methyl ester and LiOH as starting materials.

$^1$H NMR (400 MHz, DMSO-D6) δ ppm 4.86 (s, 2 H) 7.60 (s, 1 H) 7.60 (s, 1 H) 8.05 (s, 1 H) 8.11 (t, J=2.02 Hz, 1 H).

EXAMPLE 7

4,5-Dibromo-3-carboxymethoxy-thiophene-2-carboxylic acid

The first step of Scheme 3: 4,5-Dibromo-3-tert-butoxycarbonylmethoxyl-thiophene-2-carboxylic acid methyl ester (4.31 g, 95%) was prepared from 4,5-dibromo-3-hydroxy-thiophene-2-carboxylic acid methyl ester (3.17 g, 10 mmol), tert-butyl bromoacetate (1.77 mL, 12 mmol) and K$_2$CO$_3$ (2.76 g, 20 mmol) according to procedures in the first step of Scheme 1 of Example 1.

$^1$H NMR (400 MHz, CHLOROFORM-D) δ ppm 1.42 (s, 9 H) 3.78 (s, 3 H) 4.75 (s, 2 H).

4,5-Dibromo-3-ethoxycarbonylmethoxy-thiophene-2-carboxylic acid methyl ester was synthesized using the following procedures: To a 150 mL DMF solution of 4,5-dibromo-3-hydroxy-thiophene-2-carboxylic acid methyl ester (20 g, 63.1 mmol) were added potassium carbonate (13.07 g, 94.7 mmol) and ethyl bromoacetate (10.5 mL, 94.7 mmol). The resulting suspension was stirred at 50° C. overnight. The reaction mixture was cooled to room temperature, followed by addition of 200 mL of Et$_2$O. The mixture was filtered through a pad of celite to remove any solid materials. Solvents were evaporated under reduced pressure and the solids were dissolved in CH$_2$Cl$_2$ and loaded on a pad of silica. Elution with 1/6 EtOAc/hexane gave of 4,5-dibromo-3-ethoxycarbonylmethoxy-thiophene-2-carboxylic acid methyl ester (24.9 g, 99%) as a white solid.

$^1$H NMR (400 MHz, CHLOROFORM-D) δ ppm 1.30 (t, J=7.07 Hz, 3 H) 3.85 (s, 3 H) 4.27 (q, J=7.07 Hz, 2 H) 4.90 (s, 2 H).

The third step of Scheme 3: 4,5-Dibromo-3-carboxymethoxy-thiophene-2-carboxylic acid (67 mg, 93%) was made in a similar way as described in the first step of Scheme 1 of Example 1, using 4,5-dibromo-3-ethoxycarbonylmethoxy-thiophene-2-carboxylic acid methyl ester (86.2 mg, 0.2 mmol) and LiOH (11 mg, 0.44 mmol) as starting materials.

$^1$H NMR (400 MHz, DMSO-D6) δ ppm 4.92 (s, 2 H).

EXAMPLE 8

4-Bromo-3-carboxymethoxy-5-phenyl-thiophene-2-carboxylic acid

The second step of Scheme 3: 4-Bromo-3-tert-butoxycarbonylmethoxy-5-phenyl-thiophene-2-carboxylic acid methyl ester was synthesized according to procedures in the first step of Scheme 2 of Example 3, using 4,5-dibromo-3-tert-butoxycarbonylmethoxyl-thiophene-2-carboxylic acid methyl ester, phenyl boronic acid, KF, biphenyl-2-yl-di-tert-butyl-phosphane and Pd(OAc)$_2$ as starting materials.

$^1$H NMR (400 MHz, CHLOROFORM-D) δ ppm 1.43 (m, 9 H) 3.80 (m, 3 H) 4.77 (m, 2 H) 7.37 (m, 3 H) 7.59 (m, 2 H).

The third step of Scheme 3: 4-Bromo-3-carboxymethoxy-5-phenyl-thiophene-2-carboxylic acid (35.9 mg, 90%) was synthesized according to procedures in the second step of Scheme 1 of Example 1, using 4-bromo-3-tert-butoxycarbonylmethoxy-5-phenyl-thiophene-2-carboxylic acid methyl ester (54 mg, 0.126 mmol) and LiOH (7 mg, 0.28 mmol) as starting materials.

$^1$H NMR (400 MHz, DMSO-D6) δ ppm 4.89 (s, 2 H) 7.53 (m, 3 H) 7.68 (m, 2 H).

EXAMPLE 9

5-(4-Amino-phenyl)-4-bromo-3-carboxymethoxy-thiophene-2-carboxylic acid

The second step of Scheme 3: 4,5-Dibromo-3-tert-butoxycarbonylmethoxyl-thiophene-2-carboxylic acid methyl ester (130 mg, 0.3 mmol), 4-(4,4,5,5-tetramethyl-1,3,2-dioxaborolan-2-yl)aniline (98.6 mg, 0.45 mmol), K$_2$CO$_3$ (124.2 mg, 0.9 mmol) and Pd(PPh$_3$)$_4$ (17.3 mg, 0.015 mmol) in THF (4 mL) were mixed in a sealed tube. After purging with N$_2$, anhydrous THF was added and the tube was sealed. The resultant reaction mixture was stirred at 100° C. overnight. The precipitate was removed by filtering through a pad of Celite and washed with EtOAc. The filtrate was concentrated and loaded to a silica gel column and eluted with Hexanes/EtOAc (10/1) to give 5-(4-amino-phenyl)-4-bromo-3-tert-butoxycarbonylmethoxy-thiophene-2-carboxylic acid methyl ester (92.7 mg, 70%).

$^1$H NMR (400 MHz, CHLOROFORM-D) δ ppm 1.44 (m, 9 H) 3.79 (s, 3 H) 4.73 (s, 2 H) 6.67 (d, J=8.59 Hz, 2 H) 7.43 (d, J=8.34 Hz, 2 H).

The third step of Scheme 3: 5-(4-Amino-phenyl)-4-bromo-3-carboxymethoxy-thiophene-2-carboxylic acid was synthesized from 5-(4-amino-phenyl)-4-bromo-3-tert-butoxycarbonylmethoxy-thiophene-2-carboxylic acid methyl ester according to the procedure in the second step of Scheme 1 of Example 1 as a light gray solid.

$^1$H NMR (400 MHz, DMSO-D6) δ ppm 4.84 (s, 2 H) 5.66 (s, 2 H) 6.65 (m, 2 H) 7.39 (m, 2 H).

EXAMPLE 10

4-Bromo-3-carboxymethoxy-5-(4-dimethylamino-phenyl)-thiophene-2-carboxylic acid

The second step of Scheme 3: 4-Bromo-3-tert-butoxycarbonylmethoxy-5-(4-dimethylamino-phenyl)-thiophene-2-carboxylic acid methyl ester (34.2 mg, 24%) was synthesized according to procedures in the second step of Scheme 3 of Example 9, using 4,5-dibromo-3-tert-butoxycarbonylmethoxyl-thiophene-2-carboxylic acid methyl ester (130 mg, 0.3 mmol), 4-(4,4,5,5-tetramethyl-1,3,2-dioxaborolan-2-yl) aniline (98.6 mg, 0.45 mmol), $K_2CO_3$ (124.2 mg, 0.9 mmol) and $Pd(PPh_3)_4$ (17.3 mg, 0.015 mmol) as starting materials.

$^1$H NMR (400 MHz, CHLOROFORM-D) δ ppm 1.43 (s, 9 H) 2.96 (s, 6 H) 3.79 (s, 3 H) 4.74 (s, 2 H) 6.73 (d, J=8.84 Hz, 2 H) 7.54 (d, J=8.84 Hz, 2 H).

The third step of Scheme 3: 4-Bromo-3-carboxymethoxy-5-(4-dimethylamino-phenyl)-thiophene-2-carboxylic acid was synthesized from 4-bromo-3-tert-butoxycarbonyl-methoxy-5-(4-dimethylamino-phenyl)-thiophene-2-carboxylic acid methyl ester according to procedures in the second step of Scheme 1 of Example 1 as a yellow solid.

$^1$H NMR (400 MHz, DMSO-D6) δ ppm 2.98 (s, 6 H) 4.86 (s, 2 H) 6.81 (d, J=9.10 Hz, 2 H) 7.54 (d, J=9.0 Hz, 2 H).

EXAMPLE 11

5-(3-Amino-phenyl)-4-bromo-3-carboxymethoxy-thiophene-2-carboxylic acid

The second step of Scheme 3: 5-(3-Amino-phenyl)-4-bromo-3-tert-butoxycarbonylmethoxy-thiophene-2-carboxylic acid methyl ester (51 mg, 38%) was synthesized according to procedures in the second step of Scheme 3 of Example 9, using 4,5-dibromo-3-tert-butoxycarbonyl-methoxyl-thiophene-2-carboxylic acid methyl ester (130 mg, 0.3 mmol), 3-aminophenyl boronic acid (66 mg, 0.42 mmol), $K_2CO_3$ (124.2 mg, 0.9 mmol) and $Pd(PPh_3)_4$ (17.3 mg, 0.015 mmol) as starting materials.

$^1$H NMR (400 MHz, CHLOROFORM-D) δ ppm 1.50 (s, 9 H) 3.79 (br, s, 2 H) 3.87 (s, 3 H) 4.82 (s, 2 H) 6.75 (dd, J=7.96, 2.15 Hz, 1 H) 6.96 (t, J=2.02 Hz, 1 H) 7.03 (d, J=7.58 Hz, 1 H) 7.23 (t, J=7.83 Hz, 1 H) 7.26 (s, 1 H).

5-(3-Amino-phenyl)-4-bromo-3-ethoxycarbonyl-methoxy-thiophene-2-carboxylic acid methyl ester (905 mg, 73%) was synthesized according to procedures similar to that in the second step of Example 7, using 4,5-dibromo-3-tert-butoxycarbonylmethoxyl-thiophene-2-carboxylic acid methyl ester (1.2 g, 3.0 mmol), 3-aminophenyl boronic acid (511.5 mg, 3.3 mmol), KF (696 mg, 12 mmol) and $Pd(PPh_3)_4$ (173.3 mg, 0.15 mmol) as starting materials.

The third step of Scheme 3: 5-(3-Amino-phenyl)-4-bromo-3-carboxymethoxy-thiophene-2-carboxylic acid (9.5 mg, 71%) was synthesized from 5-(3-amino-phenyl)-4-bromo-3-tert-butoxycarbonylmethoxy-thiophene-2-carboxylic acid methyl ester (16 mg, 0.036 mmol) with excess of LiOH similar to that in the second step of Scheme 1 of Example 1.

$^1$H NMR (400 MHz, DMSO-D6) δ ppm 4.88 (s, 2 H) 6.75 (d, J=7.07 Hz, 1 H) 6.88 (d, J=7.07 Hz, 1 H) 6.94 (s, 1 H) 7.20 (t, J=8.08 Hz, 1 H).

EXAMPLE 12

4-Bromo-3-carboxymethoxy-5-naphthalen-2-yl-thiophene-2-carboxylic acid

The second step of Scheme 3: 4-Bromo-3-tert-butoxycarbonylmethoxy-5-naphthalen-2-yl-thiophene-2-carboxylic acid methyl ester was synthesized according to procedures in the second step of Scheme 3 of Example 9, using 4,5-dibromo-3-tert-butoxycarbonylmethoxyl-thiophene-2-carboxylic acid methyl ester as the starting material.

$^1$H NMR (400 MHz, CHLOROFORM-D) δ ppm 1.52 (s, 9 H) 3.90 (s, 3 H) 4.86 (s, 2 H) 7.55 (m, 2 H) 7.76 (dd, J=8.59, 1.77 Hz, 1 H) 7.90 (m, 3 H) 8.16 (d, J=1.52 Hz, 1 H).

The third step of Scheme 3: 4-Bromo-3-carboxymethoxy-5-naphthalen-2-yl-thiophene-2-carboxylic acid (41.5 mg, 99+%) was synthesized according to procedures in the second step of Scheme 1 of Example 1, using 4-bromo-3-tert-butoxycarbonylmethoxy-5-naphthalen-2-yl-thiophene-2-carboxylic acid methyl ester (49 mg) and excess of LiOH as the starting materials.

$^1$H NMR (400 MHz, DMSO-D6) δ ppm 4.93 (m, 2 H) 7.62 (m, 2 H) 7.80 (dd, J=8.46, 1.89 Hz, 1 H) 8.00 (d, J=9.10 Hz, 1 H) 8.06 (t, J=7.71 Hz, 1 H) 8.28 (d, J=1.77 Hz, 1H).

EXAMPLE 13

4-Bromo-3-carboxymethoxy-5-(4-hydroxy-phenyl)-thiophene-2-carboxylic acid

The second step of Scheme 3: 4-Bromo-3-tert-butoxycarbonylmethoxy-5-(4-hydroxy-phenyl)-thiophene-2-carboxylic acid methyl ester (48.1 mg, 36%) was prepared according to procedures similar to that in the second step of Scheme 3 of Example 9, using 4,5-dibromo-3-tert-butoxycarbonyl-methoxyl-thiophene-2-carboxylic acid methyl ester (130 mg, 0.3 mmol), 4-(4,4,5,5-tetramethyl-1,3,2-dioxaborolan-2-yl) phenol (99 mg, 0.45 mmol), $Pd(PPh_3)_4$ (17.3 mg, 0.015 mmol) and $K_2CO_3$ (124.2 mg, 0.9 mmol) as starting materials. The reaction was run in $THF/H_2O$ (3/1, 3 mL) in microwave oven at 150° C. for 15 min.

$^1$H NMR (400 MHz, CHLOROFORM-D) δ ppm 1.51 (s, 9 H) 3.87 (s, 3 H) 4.82 (s, 2 H) 6.91 (m, 2 H) 7.55 (m, 2 H)

The third step of Scheme 3: 4-Bromo-3-carboxymethoxy-5-(4-hydroxyl-phenyl)-thiophene-2-carboxylic acid (19.5 mg, 99+%) was prepared according to procedures in the second step of Scheme 1 of Example 1, using 4-bromo-3-tert-butoxycarbonylmethoxy-5-(4-hydroxy-phenyl)-thiophene-2-carboxylic acid methyl ester (24 mg) and LiOH (10 mg, excess) as the starting materials.

$^1$H NMR (400 MHz, DMSO-D6) δ ppm 4.85 (s, 2 H) 6.89 (d, J=8.84 Hz, 2 H) 7.51 (d, J=8.59 Hz, 2 H) 9.99 (s, 1 H).

EXAMPLE 14

4-Bromo-3-carboxymethoxy-5-(4-methoxy-phenyl)-thiophene-2-carboxylic acid

The second step of Scheme 3: 4-Bromo-3-tert-butoxycarbonylmethoxy-5-(4-hydroxy-phenyl)-thiophene-2-carboxylic acid methyl ester (52 mg, 38%) was prepared according to procedures in the second step of Scheme 3 of Example 13, using 4,5-dibromo-3-tert-butoxycarbonylmethoxyl-thiophene-2-carboxylic acid methyl ester (130 mg, 0.3 mmol), 4-methoxybenzeneboronic acid (68 mg, 0.45 mmol), $Pd(PPh_3)_4$ (17.3 mg, 0.015 mmol) and $K_2CO_3$ (124.2 mg, 0.9 mmol) as starting materials. The reaction was run in $THF/H_2O$ (3/1, 3 mL) in microwave oven at 150° C. for 20 min.

$^1$H NMR (400 MHz, CHLOROFORM-D) δ ppm 1.50 (s, 9 H) 3.86 (s, 3 H (CH2+OH)) 3.87 (s, 3 H) 4.82 (s, 2 H) 6.98 (m, 2 H) 7.61 (m, 2 H).

The third step of Scheme 3: 4-Bromo-3-carboxymethoxy-5-(4-methoxy-phenyl)-thiophene-2-carboxylic acid (41.5 mg, 96%) was prepared according to procedures in the second step of Scheme 1 of Example 1, using 4-bromo-3-tert-butoxycarbonylmethoxy-5-(4-hydroxy-phenyl)-thiophene-2-carboxylic acid methyl ester (51 mg, 0.11 mmol) and LiOH (excess) as the starting materials.

$^1$H NMR (400 MHz, DMSO-D6) δ ppm 3.82 (s, 3 H) 4.88 (s, 2 H) 7.09 (m, 2 H) 7.63 (m, 2 H).

EXAMPLE 15

3-Carboxymethoxy-5-(4-trifluoromethoxy-phenyl)-thiophene-2-carboxylic acid

The second step Scheme 3: 3-Ethoxycarbonylmethoxy-5-(4-trifluoromethoxy-phenyl)-thiophene-2-carboxylic acid methyl ester (11 mg) was obtained according to procedures in the second step of Scheme 3 of Example 13, using 4,5-dibromo-3-tert-butoxycarbonylmethoxyl-thiophene-2-carboxylic acid methyl ester (130 mg, 0.3 mmol), 4-methoxybenzeneboronic acid (68 mg, 0.45 mmol), Pd(PPh$_3$)$_4$ (17.3 mg, 0.015 mmol) and K$_2$CO$_3$ (124.2 mg, 0.9 mmol) as starting materials. The reaction was run in THF/H$_2$O (3/1, 3 mL) in microwave oven at 150° C. for 45 min.

$^1$H NMR (400 MHz, CHLOROFORM-D) δ ppm 1.48 (s, 9 H) 3.88 (s, 3 H) 4.71 (s, 2 H) 6.91 (s, 1 H) 7.26 (m, 2 H) 7.59 (m, 2 H).

The third step of Scheme 3: 3-Carboxymethoxy-5-(4-trifluoromethoxy-phenyl)-thiophene-2-carboxylic acid (9.7 mg, 99%) was prepared as a white solid according to procedures in the step of Scheme 1 of Example 1, using 3-ethoxycarbonylmethoxy-5-(4-trifluoromethoxy-phenyl)-thiophene-2-carboxylic acid methyl ester (11 mg) as the starting material.

$^1$H NMR (400 MHz, DMSO-D6) δ ppm 4.89 (s, 2 H) 7.46 (dd, J=8.84, 0.76 Hz, 2 H) 7.55 (s, 1 H) 7.86 (m, 2 H).

EXAMPLE 16

4-Bromo-3-carboxymethoxy-5-(4-hydroxymethyl-phenyl)-thiophene-2-carboxylic acid The second step of Scheme 3: 4-Bromo-3-tert-butoxycarbonylmethoxy-5-(4-hydroxymethyl-phenyl)-thiophene-2-carboxylic acid methyl ester (53 mg, 39%) was prepared according to procedures in the second step of Scheme 3 of Example 13, except using 4-(hydroxymethyl)phenylboronic acid (68.4 mg, 0.45 mmol) as one of the coupling partners.

$^1$H NMR (400 MHz, CHLOROFORM-D) δ ppm 1.51 (s, 9 H) 3.88 (s, 3 H) 4.77 (d, J=6.06 Hz, 2 H) 4.83 (s, 2 H) 7.47 (m, 2 H) 7.66 (m, 1 H).

The third step of Scheme 3: 4-Bromo-3-carboxymethoxy-5-(4-hydroxymethyl-phenyl)-thiophene-2-carboxylic acid (38 mg, 90%) was prepared as a white solid according to procedures in the second step of Scheme 1 of Example 1, using 4-bromo-3-tert-butoxycarbonylmethoxy-5-(4-hydroxymethyl-phenyl)-thiophene-2-carboxylic acid methyl ester (50 mg, 0.11 mmol) and LiOH (excess) as the starting materials.

$^1$H NMR (400 MHz, DMSO-D6) δ ppm 4.56 (s, 2 H) 4.88 (s, 2 H) 7.46 (m, 2 H) 7.63 (m, 2 H).

EXAMPLE 17

4-Bromo-3-carboxymethoxy-5-(3-hydroxy-phenyl)-thiophene-2-carboxylic acid

The second step of Scheme 3: To a microwave test tube (Personal Chemistry) of 4,5-dibromo-3-ethoxycarbonylmethoxy-thiophene-2-carboxylic acid methyl ester (500 mg, 1.24 mmol), tetrakis(triphenylphosphine)palladium(0) (143 mg, 0.12 mmol), KF (216 mg, 3.74 mmol) and 3-hydroxyphenylboronic acid (171 mg, 1.24 mmol) under nitrogen were added 4 mL DME and 1 mL H$_2$O. The reaction mixture was stirred at 150° C. in a Personal Chemistry microwave for 20 minutes. The reaction mixture was extracted twice with EtOAc (2×20 mL). The organic fractions were combined and dried over anhydrous Na$_2$SO$_4$. Solvents were evaporated under reduced pressure. The crude material was purified by silica gel chromatography using a gradient of EtOAc/hexane (10 to 40%) as eluent. Pure fractions were collected and evaporation of solvent gave 334 mg (65%) of 4-bromo-3-ethoxycarbonylmethoxy-5-(3-hydroxy-phenyl)-thiophene-2-carboxylic acid methyl ester as a white solid.

$^1$H NMR (400 MHz, CHLOROFORM-D) δ ppm 1.32 (t, J=7.20 Hz, 3 H) 3.85 (s, 3 H) 4.30 (q, J=7.07 Hz, 2 H) 4.89 (s, 2 H) 6.04 (s, 1 H) 7.18 (m, 2 H) 7.30 (m, 1 H).

ESI-MS: m/e=437.42 [M+Na]$^+$, 413.36 [M−H]$^−$.

The third step of Scheme 3: 4-Bromo-3-carboxymethoxy-5-(3-hydroxy-phenyl)-thiophene-2-carboxylic acid was prepared following the procedure in the second step of Scheme 1 of Example 1. 4-bromo-3-ethoxycarbonylmethoxy-5-(3-hydroxy-phenyl)-thiophene-2-carboxylic acid methyl ester (39 mg, 0.09 mmol) was hydrolyzed to give 26 mg (73%) of 4-bromo-3-carboxymethoxy-5-(3-hydroxy-phenyl)-thiophene-2-carboxylic acid as a white solid.

$^1$H NMR (400 MHz, DMSO-D6) δ ppm 4.88 (s, 2 H) 6.89 (m, 1 H) 7.07 (m, 2 H) 7.32 (t, J=8.08 Hz, 1 H) 9.84 (s, 1 H).

ESI-MS: m/e=371.06 [M−H]$^−$.

EXAMPLE 18

3-Ethoxycarbonylmethoxy-4,5-bis-(3-hydroxy-phenyl)-thiophene-2-carboxylic acid methyl ester The second step of Scheme 3: 3-Ethoxycarbonylmethoxy-4,5-bis-(3-hydroxy-phenyl)-thiophene-2-carboxylic acid methyl ester was a side product (22 mg, 21%) in the second step of Scheme 3 of Example 17.

$^1$H NMR (400 MHz, CHLOROFORM-D) δ ppm 0.88 (t, 3 H) 3.85 (s, 3 H) 4.16 (q, 2 H) 4.47 (s, 2 H) 6.62 (m, 1 H) 6.67 (d, J=7.58 Hz, 1 H) 6.78 (m, 3 H) 6.91 (m, 1 H) 7.11 (m, 2 H).

ESI-MS: m/e=429.56 [M+H]$^+$, 427.51 [M−H]$^−$.

EXAMPLE 19

4-Bromo-3-carboxymethoxy-5-(3-methoxy-phenyl)-thiophene-2-carboxylic acid

The second step of Scheme 3: 4-Bromo-3-ethoxycarbonylmethoxy-5-(3-methoxy-phenyl)-thiophene-2-carboxylic acid methyl ester (38 mg, 59%) was synthesized according to procedures in the second step of Scheme 3 of Example 17, except using 3-methoxyphenylboronic acid as the coupling partner in the Suzuki reaction.

$^1$H NMR (400 MHz, CHLOROFORM-D) δ ppm 1.33 (m, 3 H) 3.86 (s, 3 H) 3.88 (s, 3 H) 4.30 (q, J=7.16 Hz, 2 H) 4.92 (s, 2 H) 6.98 (m, 1 H) 7.22 (m, 2 H) 7.37 (m, 1 H).

ESI-MS: m/e=429.45 [M+H]$^+$.

The third step of Scheme 3: 4-Bromo-3-ethoxycarbonylmethoxy-5-(3-methoxy-phenyl)-thiophene-2-carboxylic acid methyl ester (38 mg, 0.088 mmol) was hydrolyzed according to procedures in the second step of Scheme 1 of Example 1 to give 4-bromo-3-carboxymethoxy-5-(3-methoxy-phenyl)-thiophene-2-carboxylic acid (25 mg, 71%) as a white solid.

¹H NMR (400 MHz, DMSO-D6) δ ppm 3.82 (s, 3 H) 4.88 (s, 2 H) 7.08 (dd, J=8.34, 2.27 Hz, 1 H) 7.22 (m, 2 H) 7.45 (t, J=7.96 Hz, 1 H).
ESI-MS: m/e=341.07 [M–CO$_2$]⁻.

EXAMPLE 20

4-Bromo-3-carboxymethoxy-5-(4-fluoro-phenyl)-thiophene-2-carboxylic acid

The second step of Scheme 3: 4-Bromo-3-ethoxycarbonylmethoxy-5-(4-fluoro-phenyl)-thiophene-2-carboxylic acid methyl ester (25 mg, 48%) was synthesized according to procedures in the second step of Scheme 3 of Example 17, except using 4-fluoro-phenylboronic acid as the coupling partner in the Suzuki reaction.
¹H NMR (400 MHz, CHLOROFORM-D) δ ppm 1.31 (t, 3 H) 3.88 (s, 3 H) 4.29 (q, J=7.07 Hz, 2 H) 4.92 (s, 2 H) 7.16 (m, 2 H) 7.64 (m, 2 H).
ESI-MS: m/e=439.39 [M+Na]⁺.
The third step of Scheme 3: 4-Bromo-3-ethoxycarbonylmethoxy-5-(4-fluoro-phenyl)-thiophene-2-carboxylic acid methyl ester (25 mg, 0.060 mmol) was hydrolyzed according to procedures in the second step of Scheme 1 of Example 1 to give 4-bromo-3-carboxymethoxy-5-(4-fluoro-phenyl)-thiophene-2-carboxylic acid (15 mg, 67%) as a white solid.
¹H NMR (400 MHz, DMSO-D6) δ ppm 4.89 (s, 2 H) 7.39 (t, J=8.84 Hz, 2 H) 7.71 (m, 2 H).
ESI-MS: m/e=397.27 [M+Na]⁺.

EXAMPLE 21

3-Carboxymethoxy-5-o-tolyl-thiophene-2-carboxylic acid

The second step of Scheme 3: 3-Ethoxycarbonylmethoxy-5-o-tolyl-thiophene-2-carboxylic acid methyl ester (29 mg, 35%) was synthesized according to procedures in the second step of Scheme 3 of Example 17, except using o-tolylboronic acid as the coupling partner in the Suzuki reaction.
¹H NMR (400 MHz, CHLOROFORM-D) δ ppm 1.28 (m, 3 H) 2.41 (s, 3 H) 3.87 (s, 3 H) 4.26 (q, J=7.07 Hz, 2 H) 4.79 (s, 2 H) 6.72 (s, 1 H) 7.27 (m, 3 H) 7.36 (d, J=7.58 Hz, 1 H).
ESI-MS: m/e=335.4 [M+H]⁺.
The third step of Scheme 3: 3-Ethoxycarbonylmethoxy-5-o-tolyl-thiophene-2-carboxylic acid methyl ester (23 mg, 0.069 mmol) was hydrolyzed according to procedures in the second step of Scheme 1 of Example 1 to give 3-carboxymethoxy-5-o-tolyl-thiophene-2-carboxylic acid (14 mg, 68%) as a white solid.
¹H NMR (400 MHz, DMSO-D6) δ ppm 2.40 (s, 3 H) 4.86 (s, 2 H) 7.10 (s, 1 H) 7.33 (m, 3 H) 7.41 (d, J=7.33 Hz, 1 H).
ESI-MS: m/e=315.30 [M+Na]⁺.

EXAMPLE 22

5-(4-Acetylamino-phenyl)-4-bromo-3-carboxymethoxy-thiophene-2-carboxylic acid The first step of Scheme 4: 5-(4-amino-phenyl)-4-bromo-3-tert-butoxycarbonylmethoxy-5-phenyl-thiophene-2-carboxylic acid methyl ester (12 mg) was treated with excess of acetic anhydride in pyridine in presence of catalytic amount of DMAP. The resultant reaction mixture was stirred at room temperature until the disappearance of the starting material as monitored by TLC. The solvent was removed and the crude product was purified via silica gel column chromatography to give 5-(4-acetylamino-phenyl)-4-bromo-3-tert-butoxycarbonymethoxy-thiphene-2-carboxylic acid methyl ester (13.5 mg, 99+%).
¹H NMR (400 MHz, CHLOROFORM-D) δ ppm 1.49 (s, 9 H) 2.21 (s, 3 H) 3.87 (s, 3 H) 4.83 (s, 2 H) 7.30 (br, s, 1 H) 7.62 (m, 4 H).
The second step of Scheme 4: 5-(4-Acetylamino-phenyl)-4-bromo-3-carboxymethoxy-thiophene-2-carboxylic acid (7.3 mg, 63%) was prepared as a white solid according to procedures in the second step of Scheme 1 of Example 1, using 5-(4-acetylamino-phenyl)-4-bromo-3-tert-butoxycarbonymethoxy-thiphene-2-carboxylic acid methyl ester (13.5 mg) as starting material.

EXAMPLE 23

5-(4-Benzoylamino-phenyl)-4-bromo-3-carboxymethoxy-thiophene-2-carboxylic acid The first step of Scheme 4: To a solution of 5-(4-amino-phenyl)-4-bromo-3-tert-butoxycarbonylmethoxy-5-phenyl-thiophene-2-carboxylic acid methyl ester (23 mg, 0.052 mmol) in DCM was added benzoyl chloride (2-3 eq), DMAP (cat. Amount), and Et$_3$N (5-10 eq.) at −20° C. The cooling bath was removed and the resultant reaction mixture was stirred at room temperature until the disappearance of the starting material as monitored by TLC before it was quenched by addition of aq. NaHCO$_3$. The organic layer was separated and the aqueous layer was extracted with DCM. The combined organic layer was dried with MgSO$_4$, and the crude product was purified via silica gel chromatography to give 5-(4-benzoylamino-phenyl)-4-bromo-3-tert-butoxycarbonylmethoxy-thiophene-2-carboxylic acid methyl ester (28 mg, 99+%).
¹H NMR (400 MHz, CHLOROFORM-D) δ ppm 1.50 (s, 9 H) 3.87 (s, 3 H) 4.82 (s, 2 H) 7.27 (m, 2 H) 7.35 (m, 2 H) 7.47 (m, 1 H) 7.68 (m, 2 H) 7.75 (m, 2 H).
The second step of Scheme 4: 5-(4-Benzoylamino-phenyl)-4-bromo-3-carboxymethoxy-thiophene-2-carboxylic acid (17.9 mg, 73%) was prepared as a white solid according to procedures in the second step of Scheme 1 of Example 1, using 5-(4-benzoylamino-phenyl)-4-bromo-3-tert-butoxycarbonylmethoxy-thiophene-2-carboxylic acid methyl ester (28 mg, 0.051 mmol) as the starting material.
¹H NMR (400 MHz, DMSO-D6) δ ppm 4.89 (s, 2 H) 7.58 (m, 3 H) 7.70 (d, J=8.59 Hz, 2 H) 7.96 (m, 4 H) 10.49 (s, 1 H).

EXAMPLE 24

4-Bromo-3-carboxymethoxy-5-{4-[(pyridine-3-carbonyl)-amino]-phenyl}-thiophene-2-carboxylic acid The first step of Scheme 4: 4-Bromo-3-ethoxycarbonylmethoxy-5-{4-[pyridine-3-carbonyl)-amino]-phenyl}-thiophene-2-carboxylic acid methyl ester (43 mg, 82%) was prepared according to procedures in the first step of Scheme 4 of Example 23, using 5-(4-amino-phenyl)-4-bromo-3-ethoxycarbonylmethoxy-thiophene-2-carboxylic acid methyl ester (40 mg, 0.1 mmol) as the starting material.
¹H NMR (400 MHz, CHLOROFORM-D) δ ppm 1.32 (t, J=7.20 Hz, 3 H) 3.88 (s, 3 H) 4.30 (q, J=7.24 Hz, 2 H) 4.92 (s, 2 H) 5.30 (s, 1 H) 7.48 (ddd, J=7.83, 4.80, 0.76 Hz, 1 H) 7.71 (m, 2 H) 7.77 (m, 2 H) 8.02 (s, 1 H) 8.24 (m, 1 H) 8.81 (dd, J=4.93, 1.64 Hz, 1 H) 9.12 (dd, J=2.40, 0.63 Hz, 1 H).
The second step of Scheme 4: 4-Bromo-3-carboxymethoxy-5-{4-[(pyridine-3-carbonyl)-amino]-phenyl}-thiophene-2-carboxylic acid (26 mg, 71%) was prepared as a white solid according to procedures in the second step of Scheme 1 of Example 1, using 4-bromo-3-ethoxycarbonyl-methoxy-5-{4-[pyridine-3-carbonyl)-amino]-phenyl}-thiophene-2-carboxylic acid methyl ester (40 mg) as the starting material.

$^1$H NMR (400 MHz, DMSO-D6) δ ppm 4.89 (s, 2 H) 7.59 (m, 1 H) 7.70 (m, 2 H) 7.93 (m, 2 H) 8.31 (m, 1 H) 8.78 (m, 1 H) 9.12 (m, 1 H).

EXAMPLE 25

4-Bromo-3-carboxymethoxy-5-{4-[(furan-3-carbonyl)-amino]-phenyl}-thiophene-2-carboxylic acid The first step of Scheme 4: To a solution of 5-(4-aminophenyl)-4-bromo-3-ethoxycarbonylmethoxy-5-phenyl-thiophene-2-carboxylic acid methyl ester (45 mg, 0.1 mmol) in $CH_2Cl_2$ was added furan-3-carboxylic acid (2 eq.) and EDCI (3 eq.). The resultant reaction mixture was stirred at room temperature until the disappearance of the starting material as monitored by TLC. The crude reaction mixture was concentrated and directly subjected to column purification on CombiFlash-sq 16× to give 4-bromo-3-ethoxycarbonylmethoxy-5-{4-[(furan-3-carbonyl)-amino]-phenyl]}-thiophene-2-carboxylic acid methyl ester (36 mg, 70%).

$^1$H NMR (400 MHz, CHLOROFORM-D) δ ppm 1.32 (t, J=7.07 Hz, 3 H) 3.88 (s, 3 H) 4.30 (q, J=7.07 Hz, 2 H) 4.92 (s, 2 H) 6.74 (dd, J=1.89, 0.88 Hz, 1 H) 7.49 (s, 1 H) 7.52 (m, 1 H) 7.70 (m, 4 H) 8.07 (dd, J=1.52, 0.76 Hz, 1 H).

The second step of Scheme 4: 4-Bromo-3carbonyl-methoxy-5-{4-[(furan-3-carbonyl)-amino]-phenyl]}-thiophene-2-carboxylic acid (11 mg) was prepared as a white solid according to procedures in the second step of Scheme 1 of Example 1, using 4-bromo-3-ethoxycarbonylmethoxy-5-{4-[(furan-3-carbonyl)-amino]-phenyl]}-thiophene-2-carboxylic acid methyl ester (34 mg) as the starting material.

$^1$H NMR (400 MHz, DMSO-D6) δ ppm 4.87 (s, 2 H) 7.03 (dd, J=1.77, 0.76 Hz, 1 H) 7.68 (m, 2 H) 7.82 (t, J=1.77 Hz, 1 H) 7.89 (m, 2 H) 8.44 (dd, J=1.52, 1.01 Hz, 1 H) 10.19 (s, 1 H).

EXAMPLE 26

4-Bromo-3-carboxymethoxy-5-{4-[(furan-2-carbonyl)-amino]-phenyl}-thiophene-2-carboxylic acid The first step of Scheme 4: 4-Bromo-3-ethoxycarbonyl-methoxy-5-{4-[(furan-2-carbonyl)-amino]-phenyl]}-thiophene-2-carboxylic acid methyl ester (39 mg, 77%) was prepared according to procedures in the first step of Scheme 4 of Example 23, using 5-(4-amino-phenyl)-4-bromo-3-ethoxycarbonylmethoxy-thiophene-2-carboxylic acid methyl ester (45 mg, 0.1 mmol) as the starting material.

$^1$H NMR (400 MHz, CHLOROFORM-D) δ ppm 1.32 (t, J=7.07 Hz, 3 H) 3.88 (s, 3 H) 4.30 (q, J=7.16 Hz, 2 H) 4.92 (s, 2 H) 6.59 (dd, J=3.54, 1.77 Hz, 1 H) 7.28 (dd, J=3.54, 0.76 Hz, 1 H) 7.55 (dd, J=1.77, 0.76 Hz, 1 H) 7.69 (m, 2 H) 7.77 (m, 2 H) 8.17 (s, 1 H).

The second step of Scheme 4: 4-Bromo-3-carbonyl-methoxy-5-{4-[(furan-2-carbonyl)-amino]-phenyl]}-thiophene-2-carboxylic acid (33 mg, 97%) was prepared as a white solid according to procedures in the second step of Scheme 1 of Example 1, using 4-bromo-3-ethoxycarbonyl-methoxy-5-{4-[(furan-2-carbonyl)-amino]-phenyl]}-thiophene-2-carboxylic acid methyl ester (39 mg, 0.073 mmol) as the starting material.

$^1$H NMR (400 MHz, DMSO-D6) δ ppm 4.89 (s, 2 H) 6.73 (dd, J=3.54, 1.77 Hz, 1 H) 7.39 (d, J=3.54 Hz, 1 H) 7.68 (d, J=9.10 Hz, 2 H) 7.92 (d, J=8.84 Hz, 2 H) 7.97 (d, J=1.77 Hz, 1 H) 10.43 (s, 1 H).

EXAMPLE 27

4-[4-(3-Bromo-5-carboxy-4-carboxymethoxy-thiophen-2-yl)-phenylcarbamoyl]-piperidine-1-carboxylic acid tert-butyl ester The first step of Scheme 4: 4-[4-(3-Bromo-4-ethoxycarbonylmethoxy-5-methoxycarbonyl-thiophen-2-yl)-phenylcarbamoyl]-piperidine-1-carboxylic acid tert-butyl ester (38 mg, 60%) was prepared according to procedures in the first step of Scheme 4 of Example 25, using 5-(4-amino-phenyl)-4-bromo-3-ethoxycarbonylmethoxy-thiophene-2-carboxylic acid methyl ester (45 mg, 0.1 mmol) as the starting material.

$^1$H NMR (400 MHz, CHLOROFORM-D) δ ppm 1.32 (t, J=7.20 Hz, 3 H) 1.47 (s, 9 H) 1.76 (m, 2 H) 1.92 (m, 2 H) 2.42 (m, 1 H) 2.81 (m, 2 H) 3.87 (s, 3 H) 4.20 (m, 2 H) 4.29 (q, J=7.07 Hz, 2 H) 4.91 (s, 2 H) 7.64 (m, 4 H).

The second step of Scheme 4: 4-[4-(3-Bromo-5-carboxy-4-carboxylmethoxy-thiophen-2-yl)-phenylcarbamoyl]-piperidine-1-carboxylic acid (9 mg, 29%) was prepared as a white solid according to procedures in the second step of Scheme 1 of Example 1, using 4-[4-(3-bromo-4-ethoxycarbonylmethoxy-5-methoxycarbonyl-thiophen-2-yl)-phenyl-carbamoyl]-piperidine-1-carboxylic acid tert-butyl ester (34 mg, 0.054 mmol) as the starting material.

$^1$H NMR (400 MHz, DMSO-D6) δ ppm 1.41 (s, 9 H) 1.49 (m, 2 H) 1.77 (m, 2 H) 2.53 (m, 1 H) 2.79 (m, 2 H) 4.00 (m, 2 H) 4.87 (s, 2 H) 7.63 (m, 2 H) 7.75 (m, 2 H) 10.18 (s, 1 H).

EXAMPLE 28

3-[4-(3-Bromo-5-carboxy-4-carboxymethoxy-thiophen-2-yl)-phenylcarbamoyl]-piperidine-1-carboxylic acid tert-butyl ester The first step of Scheme 4: 3-[4-(3-Bromo-4-ethoxycarbonylmethoxy-5-methoxycarbonyl-thiophen-2-yl)-phenylcarbamoyl]-piperidine-1-carboxylic acid tert-butyl ester (38 mg, 60%) was prepared according to procedures in the first step of Scheme 4 of Example 25, using 5-(4-amino-phenyl)-4-bromo-3-ethoxycarbonylmethoxy-thiophene-2-carboxylic acid methyl ester (45 mg, 0.11 mmol) as the starting material.

$^1$H NMR (400 MHz, CHLOROFORM-D) δ ppm 1.32 (t, J=7.07 Hz, 3 H) 1.48 (s, 9 H) 1.58 (m, 2 H) 1.91 (m, 2 H) 2.19 (m, 1 H) 2.55 (m, 2 H) 3.73 (m, 2 H) 3.87 (s, 3 H) 4.29 (q, J=7.16 Hz, 2 H) 4.91 (s, 2 H) 7.63 (m, 2 H) 7.71 (m, 2 H).

The second step of Scheme 4: 3-[4-(3-Bromo-5-carboxy-4-carboxylmethoxy-thiophen-2-yl)-phenylcarbamoyl]-piperidine-1-carboxylic acid (23.5 mg, 76%) was prepared as a white solid according to procedures in the second step of Scheme 1 of Example 1, using 3-[4-(3-bromo-4-ethoxycarbonylmethoxy-5-methoxycarbonyl-thiophen-2-yl)-phenyl-carbamoyl]-piperidine-1-carboxylic acid tert-butyl ester (34 mg, 0.054 mmol) as the starting material.

$^1$H NMR (400 MHz, DMSO-D6) δ ppm 1.30 (m, 2 H) 1.40 (s, 9 H) 1.69 (m, 3 H) 1.95 (dd, J=9.73, 3.16 Hz, 1 H) 2.46 (m, 1 H) 2.77 (m, 1 H) 3.87 (dd, J=13.77, 6.69 Hz, 1 H) 4.81 (s, 2 H) 7.62 (m, 2 H) 7.74 (m, 2 H) 10.25 (s, 1 H).

EXAMPLE 29

4-Bromo-3-carboxymethoxy-5-(4-methoxycarbonylamino-phenyl)-thiophene-2-carboxylic acid The first step of Scheme 4: 4-Bromo-3-tert-butoxycarbonylmethoxy-5-(4-methoxycarbonylamino-phenyl)-thiophene-2-carboxylic acid methyl ester (16.5 mg, 63%) was prepared according to procedures in the first step of Scheme 4 of Example 23, using 5-(4-amino-phenyl)-4-bromo-3-tert-butoxycarbonylmethoxy-thiophene-2-carboxylic acid methyl ester (23 mg, 0.05 mmol) as the starting material.

$^1$H NMR (400 MHz, CHLOROFORM-D) δ ppm 1.50 (s, 9 H) 3.81 (s, 3 H) 3.87 (s, 3 H) 4.82 (s, 2 H) 6.71 (d, J=1.26 Hz, 2 H) 7.49 (m, 2 H) 7.63 (m, 2 H).

The second step of Scheme 4: 4-Bromo-3-carbonylmethoxy-5-(4-methoxycarbonylamino-phenyl)-thiophene-2-carboxylic acid was prepared according to procedures in the second step of Scheme 1 of Example 1, from 4-bromo-3-tert-butoxycarbonylmethoxy-5-(4-methoxycarbonylamino-phenyl)-thiophene-2-carboxylic acid methyl ester.

$^1$H NMR (400 MHz, CD3OD) δ ppm 3.75 (s, 3 H) 4.83 (s, 2 H) 7.58 (m, 4 H).

EXAMPLE 30

4-Bromo-3-carboxymethoxy-5-[4-(3-isopropyl-ureido)-phenyl]-thiophene-2-carboxylic acid The first step of Scheme 4: To a solution of 5-(4-amino-phenyl)-4-bromo-3-ethoxycarbonylmethoxy-thiophene-2-carboxylic acid methyl ester (40 mg, 0.097 mmol) in DCM (2 mL) and pyridine (1 mL) was added isopropyl isocyanate (0.1 mL). The resultant reaction mixture was stirred at room temperature overnight. The solvent was removed under vacuum and the crude product was purified on CombiFlash column to give 4-bromo-3-ethoxycarbonylmethoxy-5-[4-(3-isopropyl-ureido)-phenyl]-thiophene-2-carboxylic acid methyl ester (45 mg, 93%).

$^1$H NMR (400 MHz, CHLOROFORM-D) δ ppm 1.21 (d, J=6.57 Hz, 6 H) 1.32 (t, J=7.07 Hz, 3 H) 3.87 (s, 3 H) 4.01 (m, 1 H) 4.30 (q, J=7.24 Hz, 2 H) 4.68 (d, J=7.58 Hz, 1 H) 4.90 (s, 2 H) 6.55 (s, 1 H) 7.41 (m, 2 H) 7.58 (m, 2 H).

The second step of Scheme 4: 4-Bromo-3-carboxymethoxy-5-[4-(3-isopropyl-ureido)-phenyl]-thiophene-2-carboxylic acid (38.5 mg, 68%) was prepared as a white solid according to procedures in the second step of Scheme 1 of Example 1, using 4-bromo-3-ethoxycarbonylmethoxy-5-[4-(3-isopropyl-ureido)-phenyl]-thiophene-2-carboxylic acid methyl ester (42 mg) as the starting material.

$^1$H NMR (400 MHz, DMSO-D6) δ ppm 1.11 (d, J=6.57 Hz, 6 H) 3.77 (ddd, J=20.53, 6.51, 6.32 Hz, 1 H) 4.87 (s, 2 H) 6.12 (d, J=7.58 Hz, 1 H) 7.54 (m, 4 H) 8.60 (s, 1 H).

EXAMPLE 31

5-[4-(2-Benzyloxy-acetylamino)-phenyl]-4-bromo-3-carboxymethoxy-thiophene-2-carboxylic acid The first step of Scheme 4: 5-[4-(2-Benzyloxy-acetylamino)-phenyl]-4-bromo-3-tert-butoxycarbonylmethoxy-thiophene-2-carboxylic acid methyl ester (36 mg, 61%) was prepared according to procedures in the first step of Scheme 4 of Example 23, using 5-(4-amino-phenyl)-4-bromo-3-tert-butoxycarbonylmethoxy-5-phenyl-thiophene-2-carboxylic acid methyl ester (44 mg, 0.1 mmol) as the starting material.

$^1$H NMR (400 MHz, CHLOROFORM-D) δ ppm 1.50 (s, 9 H) 3.87 (s, 3 H) 4.13 (s, 2 H) 4.68 (s, 2 H) 4.82 (s, 2 H) 7.26 (s, 2 H) 7.39 (m, 5 H) 7.65 (s, 3 H).

The second step of Scheme 4: 5-[4-(2-Benzyloxy-acetylamino)-phenyl]-4-bromo-3-carboxymethoxy-thiophene-2-carboxylic acid (25.8 mg, 86%) was prepared as a white solid according to procedures in the second step of Scheme 1 of Example 1 from 5-[4-(2-benzyloxy-acetylamino)-phenyl]-4-bromo-3-tert-butoxycarbonylmethoxy-thiophene-2-carboxylic acid methyl ester (34 mg, 0.0576 mmol).

$^1$H NMR (400 MHz, Solvent) δ ppm 4.02 (s, 2 H) 4.60 (s, 2 H) 7.28 (m, 5 H) 7.56 (m, 2 H) 7.65 (m, 2 H).

EXAMPLE 32

4-Bromo-5-[4-(2-tert-butoxycarbonylamino-acetylamino)-phenyl]-3-carboxymethoxy-thiophene-2-carboxylic acid The first step of Scheme 4: 4-Bromo-5-[4-(2-tert-butoxycarbonylamino-acetylamino)-phenyl]-3-tert-butoxycarbonylmethoxy-thiophene-2-carboxylic acid methyl ester (60 mg, 100%) was prepared according to procedures in the first step of Scheme 4 of Example 25, 5-(4-amino-phenyl)-4-bromo-3-tert-butoxycarbonylmethoxy-5-phenyl-thiophene-2-carboxylic acid methyl ester (45 mg, 0.1 mmol) as the starting material.

$^1$H NMR (400 MHz, CHLOROFORM-D) δ ppm 1.49 (s, 9 H) 1.50 (s, 9 H) 3.87 (s, 2 H) 3.95 (d, J=6.06 Hz, 2 H) 4.82 (s, 2 H) 5.3 (br, s, 1 H) 7.62 (m, 4 H).

The second step of Scheme 4: 4-Bromo-5-[4-(2-tert-butoxycarbonylamino-acetylamino)-phenyl]-3-carbonylmethoxy-thiophene-2-carboxylic acid (52.9 mg, 90%) was prepared as a white solid according to procedures in the second step of Scheme 1 of Example 1, using 4-bromo-5-[4-(2-tert-butoxycarbonylamino-acetylamino)-phenyl]-3-tert-butoxycarbonylmethoxy-thiophene-2-carboxylic acid methyl ester (59.8 mg, 0.1 mmol) as the starting material.

$^1$H NMR (400 MHz, DMSO-D6) δ ppm 1.40 (s, 9 H) 3.75 (d, J=5.81 Hz, 2 H) 4.85 (s, 2 H) 7.09 (t, J=6.06 Hz, 1 H) 7.64 (m, 2 H) 7.73 (m, 2 H) 10.19 (s, 1 H).

EXAMPLE 33

5-[4-(2-Amino-acetylamino)-phenyl]-4-bromo-3-carboxymethoxy-thiophene-2-carboxylic acid The third step of Scheme 4: 5-[4-(2-Amino-acetylamino)-phenyl]-4-bromo-3-carboxymethoxy-thiophene-2-carboxylic acid (28.3 mg as TFA salt) was synthesized as following: To a solution of 4-bromo-5-[4-(2-tert-butoxycarbonylamino-acetylamino)-phenyl]-3-carbonylmethoxy-thiophene-2-carboxylic acid (23 mg) in DCM (2 mL) and HOAc (0.5 mL) was added TFA (2 drops) at room temperature. The reaction mixture was stirred at room temperature for 5 h, then the solvent was removed. The crude product was triturated with EtOAc to give 5-[4-(2-amino-acetylamino)-phenyl]-4-bromo-3-carboxymethoxy-thiophene-2-carboxylic acid as a light yellow solid.

$^1$H NMR (400 MHz, DMSO-D6) δ ppm 4.62 (br, s, 4 H: CH2+NH2) 4.72 (s, 2 H) 6.80 (s, 1 H) 7.63 (m, 2 H) 7.71 (m, 2 H).

EXAMPLE 34

4-Bromo-3-carboxymethoxy-5-[4-(oxalyl-amino)-phenyl]-thiophene-2-carboxylic acid The first step of Scheme 4: 4-Bromo-3-ethoxycarbonylmethoxy-5-[4-methoxyoxalyl-amino)-phenyl]-thiophene-2-carboxylic acid methyl ester (40 mg, 83%) was prepared according to procedures in the first step of Scheme 4 of Example 23, using 5-(4-amino-phenyl)-4-bromo-3-ethoxycarbonylmethoxy-thiophene-2-carboxylic acid methyl ester (40 mg, 0.097 mmol) as the starting material.

$^1$H NMR (400 MHz, CHLOROFORM-D) δ ppm 1.32 (t, J=7.20 Hz, 3 H) 3.88 (s, 3 H) 4.00 (s, 3 H) 4.30 (q, J=7.24 Hz, 2 H) 4.92 (s, 2 H) 7.74 (m, 4 H).

The second step of Scheme 4: 4-Bromo-3-carboxymethoxy-5-[4-(oxalyl-amino)-phenyl]-thiophene-2-carboxylic acid was prepared as a white solid (16 mg, 72%) from 4-bromo-3-ethoxycarbonylmethoxy-5-[4-methoxyoxalyl-amino)-phenyl]-thiophene-2-carboxylic acid methyl ester (25 mg, 0.5 mmol) according to procedures in the second step of Scheme 1 of Example 1.

$^1$H NMR (400 MHz, DMSO-D6) δ ppm 4.88 (s, 2 H) 5.75 (s, 2 H) 7.68 (d, J=8.59 Hz, 2 H) 7.92 (d, J=8.84 Hz, 2 H) 10.96 (s, 1 H).

EXAMPLE 35

4-Bromo-5-[4-(2-carboxy-acetylamino)-phenyl]-3-carboxymethoxy-thiophene-2-carboxylic acid The first step of Scheme 4: 4-Bromo-5-[4-(2-ethoxycarbonyl-acetylamino)-phenyl]3-ethoxycarbonylmethoxy-thiophene-2-carboxylic acid methyl ester was prepared from using 4-bromo-3-ethoxycarbonylmethoxy-5-(4-methoxycarbonylamino-phenyl)-thiophene-2-carboxylic acid methyl ester according to procedures in the first step of Scheme 4 of Example 25.

$^1$H NMR (400 MHz, CHLOROFORM-D) δ ppm 1.33 (m, 6 H) 3.50 (s, 2 H) 3.88 (s, 3 H) 4.29 (m, 4 H) 4.91 (s, 2 H) 7.66 (m, 4 H) 9.47 (br, s, 1 H).

The second step of Scheme 4: 4-Bromo-5-[4-(2-carboxyacetylamino)-phenyl]-3-carboxymethoxy-thiophene-2-carboxylic acid was synthesized as a yellowish solid according to procedures in the second step of Scheme 1 of Example 1 from 4-bromo-5-[4-(2-ethoxycarbonyl-acetylamino)-phenyl]3-ethoxycarbonylmethoxy-thiophene-2-carboxylic acid methyl ester.

$^1$H NMR (400 MHz, DMSO-D6) δ ppm 3.39 (s, 1 H) 4.85 (s, 2 H) 7.65 (d, J=8.84 Hz, 2 H) 7.73 (d, J=8.84 Hz, 2 H) 10.39 (s, 1 H).

EXAMPLE 36

4-Bromo-3-carboxymethoxy-5-(4-methanesulfonylamino-phenyl)-thiophene-2-carboxylic acid The first step of Scheme 5: To a solution of 5-(4-aminophenyl)-4-bromo-3-tert-butoxycarbonylmethoxy-5-phenyl-thiophene-2-carboxylic acid methyl ester (44 mg, 0.1 mmol) in DCM was added methanesulfonyl chloride (2-5 eq.), Et$_3$N (3-6 eq.), and DMAP (catalytic amount) at 0° C. The resultant solution was stirred at room temperature until TLC showed the disappearance of the starting material. The solvent was removed under vacuum, and the crude product was purified on CombiFlash column to give 4-bromo-3-tert-butoxycarbonylmethoxy-5-(4-methanesulfonylaminophenyl)-thiophene-2-carboxylic acid methyl ester (39 mg, 75%).

$^1$H NMR (400 MHz, CHLOROFORM-D) δ ppm 1.51 (s, 9 H) 3.88 (s, 3 H) 4.83 (s, 2 H) 6.64 (br, s, 1 H) 7.29 (m, 2 H) 7.67 (m, 2 H).

The second step of Scheme 5: 4-Bromo-3-carboxymethoxy-5-(4-methanesulfonylamino-phenyl)-thiophene-2-carboxylic acid was prepared as a white solid (28 mg, 92%) according to procedures in the step of the second step of Scheme 1 of Example 1, using 4-bromo-3-tert-butoxycarbonylmethoxy-5-(4-methanesulfonylamino-phenyl)-thiophene-2-carboxylic acid methyl ester (39 mg, 0.065 mmol) as the starting material.

$^1$H NMR (400 MHz, DMSO-D6) δ ppm 3.09 (s, 3 H) 4.88 (s, 2 H) 7.33 (m, 2 H) 7.66 (m, 2 H) 10.14 (s, 1 H).

EXAMPLE 37

5-(4-Benzenesulfonylamino-phenyl)-4-bromo-3-carboxymethoxy-thiophene-2-carboxylic acid The first step of Scheme 5: 4-Bromo-3-tert-butoxycarbonylmethoxy-5-(4-methanesulfonylamino-phenyl)-thiophene-2-carboxylic acid methyl ester (39 mg, 75%) was prepared according to first step of Example 36, using 5-(4-amino-phenyl)-4-bromo-3-tert-butoxycarbonylmethoxy-5-phenyl-thiophene-2-carboxylic acid methyl ester (44 mg, 0.1 mmol) as the starting material.

$^1$H NMR (400 MHz, CHLOROFORM-D) δ ppm 1.51 (s, 9 H) 3.88 (s, 3 H) 4.83 (s, 2 H) 6.64 (br, s, 1 H) 7.29 (m, 2 H) 7.67 (m, 2 H).

The second step of Scheme 5: 5-(4-Benzenesulfonylamino-phenyl)-4-bromo-3-carboxymethoxy-thiophene-2-carboxylic acid was prepared as a white solid (28 mg, 92%) according to the second step of Example 1 using 4-bromo-3-tert-butoxycarbonylmethoxy-5-(4-methanesulfonylamino-phenyl)-thiophene-2-carboxylic acid methyl ester (39 mg, 0.065 mmol) as the starting material.

$^1$H NMR (400 MHz, DMSO-D6) δ ppm 4.85 (s, 2 H) 7.23 (m, 2 H) 7.60 (m, 5 H) 7.84 (m, 2 H) 10.72 (s, 1 H).

EXAMPLE 38

4-Bromo-3-carboxymethoxy-5-[4-(4-trifluoromethyl-benzenesulfonylamino)-phenyl]-thiophene-2-carboxylic acid The first step of Scheme 5: 4-Bromo-3-tert-butoxycarbonylmethoxy-5-[4-(4-trifluormethyl-benzenesulfonylamino-phenyl)-thiophene-2-carboxylic acid methyl ester (64 mg, 98%) was prepared according to procedures in the first step of Scheme 5 of Example 36, using 5-(4-amino-phenyl)-4-bromo-3-tert-butoxycarbonylmethoxy-5-phenyl-thiophene-2-carboxylic acid methyl ester (45 mg, 0.1 mmol) as the starting material.

$^1$H NMR (400 MHz, CHLOROFORM-D) δ ppm 1.51 (s, 9 H) 3.90 (s, 2 H) 4.86 (s, 2 H) 7.12 (m, 2 H) 7.75 (m, 2 H) 7.87 (m, 2 H) 8.13 (m, 2 H).

The second step of Scheme 5: 4-Bromo-3-carbonylmethoxy-5-[4-(4-trifluormethyl-benzenesulfonylamino-phenyl)-thiophene-2-carboxylic acid, was prepared as a white solid (34.6 mg, recrystallized, 64%) according to procedures in the second step of Scheme 1 of Example 1, using 4-bromo-3-tert-butoxycarbonylmethoxy-5-[4-(4-trifluormethyl-benzenesulfonylamino-phenyl)-thiophene-2-carboxylic acid methyl ester (61 mg, 0.094 mmol) as the starting material.

¹H NMR (400 MHz, DMSO-D6) δ ppm 4.83 (s, 2 H) 7.24 (m, 2 H) 7.59 (m, 2 H) 8.02 (m, 4 H) 10.94 (s, 1 H).

EXAMPLE 39

4-Bromo-3-carboxymethoxy-5-{4-[methyl-(4-trifluoromethyl-benzenesulfonyl)-amino]-phenyl}-thiophene-2-carboxylic acid 4-Bromo-3-carboxymethoxy-5-{4-[methyl-(4-trifluoromethyl-benzenesulfonyl)-amino]-phenyl}-thiophene-2-carboxylic acid was synthesized according to the following procedures: Treatment of 4-bromo-3-carbonylmethoxy-5-[4-(4-trifluormethyl-benzenesulfonylamino-phenyl)-thiophene-2-carboxylic acid (20 mg) with excess of MeI (0.1 mL) in DMF in presence of K₂CO₃ gave 4-bromo-3-ethoxycarbonylmethoxy-5-{4-[methyl-(4-trifluoromethyl-benzenesulfonyl)-amino]-phenyl}-thiophene-2-carboxylic acid methyl ester (16 mg, 75%).

The second step of Scheme 5: 4-Bromo-3-ethoxycarbonylmethoxy-5-{4-[methyl-(4-trifluoromethyl-benzenesulfonyl)-amino]-phenyl}-thiophene-2-carboxylic acid methyl ester (16 mg) was hydrolyzed with excess of LiOH according to procedures in the second step of Scheme 1 of Example 1 to give 4-bromo-3-carboxymethoxy-5-{4-[methyl-(4-trifluoromethyl-benzenesulfonyl)-amino]-phenyl)-thiophene-2-carboxylic acid as a white solid (8.7 mg, 57%).

¹H NMR (400 MHz, DMSO-D6) δ ppm 3.23 (s, 3 H) 4.88 (s, 2 H) 7.33 (d, J=8.84 Hz, 2 H) 7.70 (d, J=8.59 Hz, 2 H) 7.79 (d, J=8.84 Hz, 2 H) 8.01 (d, J=8.08 Hz, 2 H).

EXAMPLE 40

4-Bromo-3-carboxymethoxy-5-[4-(3-trifluoromethyl-benzenesulfonylamino)-phenyl]-thiophene-2-carboxylic acid The first step of Scheme 5: To a solution of 5-(4-aminophenyl)-4-bromo-3-ethoxycarbonylmethoxy-5-phenyl-thiophene-2-carboxylic acid methyl ester in pyridine was added 3-trifluormethyl-benzenesulfonyl chloride (2-5 eq.), and DMAP (catalytic amount). The resultant solution was stirred at room temperature until TLC shows the disappearance of the starting material. The solvent was removed under vacuum, and the crude product was purified on CombiFlash column to give 4-bromo-3-ethoxycarboxymethoxy-5-[4-(3-trifluormethyl-benzenesulfonylamino-phenyl)-thiophene-2-carboxylic acid methyl.

¹H NMR (400 MHz, CHLOROFORM-D) δ ppm 1.31 (t, J=7.20 Hz, 3 H) 3.87 (s, 3 H) 4.29 (q, J=7.07 Hz, 2 H) 4.91 (s, 2 H) 6.91 (s, 1 H) 7.17 (m, 2 H) 7.58 (m, 2 H) 7.63 (t, J=7.96 Hz, 1 H) 7.83 (d, J=7.83 Hz, 1 H) 7.99 (d, J=7.83 Hz) 8.09 (s, 1 H).

The second step of Scheme 5: 4-Bromo-3-carboxymethoxy-5-[4-(3-trifluormethyl-benzenesulfonylamino)-phenyl]-thiophene-2-carboxylic acid, was prepared as a white according to procedures in the second step of Scheme 1 of Example 1, using 4-bromo-3-ethoxycarboxymethoxy-5-[4-(3-trifluormethyl-benzenesulfonylamino-phenyl)-thiophene-2-carboxylic acid methyl ester as the starting material.

¹H NMR (400 MHz, DMSO-D6) δ ppm 4.86 (s, 2 H) 7.24 (m, 2 H) 7.24 (m, 2 H) 7.59 (m, 2 H) 7.85 (t, J=8.21 Hz, 1 H) 8.06 (dd, J=4.30, 1.52 Hz, 2 H) 8.11 (d, J=8.84 Hz, 1 H) 10.84 (s, 1 H).

EXAMPLE 41

4-Bromo-3-carboxymethoxy-5-[4-(2-trifluoromethyl-benzenesulfonylamino)-phenyl]-thiophene-2-carboxylic acid The first step of Scheme 5: 4-Bromo-3-ethoxycarboxymethoxy-5-[4-(2-trifluoromethyl-benzenesulfonylamino-phenyl)-thiophene-2-carboxylic acid methyl ester was prepared according to procedures in the first step of Scheme 5 of Example 40, using 5-(4-amino-phenyl)-4-bromo-3-ethoxycarbonylmethoxy-5-phenyl-thiophene-2-carboxylic acid methyl ester as the starting material.

¹H NMR (400 MHz, CHLOROFORM-D) δ ppm 3.87 (t, J=7.24 Hz, 3 H) 4.28 (q, J=7.24 Hz, 2 H) 4.90 (s, 2 H) 6.84 (s, 1 H) 7.17 (m, 2 H) 7.55 (m, 2 H) 7.67 (m, 2 H) 7.90 (d, J=7.58 Hz, 1 H) 8.12 (d, J=7.07 Hz, 1 H).

The second step of Scheme 5: 4-Bromo-3-carboxymethoxy-5-[4-(2-trifluoromethyl-benzenesulfonylamino)-phenyl]-thiophene-2-carboxylic acid, was prepared as a white according to procedures in the second step of Scheme 1 of Example 1, using 4-bromo-3-ethoxycarboxymethoxy-5-[4-(2-trifluormethyl-benzenesulfonylamino-phenyl)-thiophene-2-carboxylic acid methyl ester as the starting material.

¹H NMR (400 MHz, DMSO-D6) δ ppm 4.00 (s, 3 H) 4.89 (s, 2 H) 7.42 (d, J=8.59 Hz, 1 H) 7.95 (d, J=2.53 Hz, 1 H) 7.98 (m, 1 H) 10.38 (s, 1 H).

EXAMPLE 42

4-Bromo-3-carboxymethoxy-5-[4-(2,6-dichloro-benzenesulfonylamino)-phenll]-thiophene-2-carboxylic acid The first step of Scheme 5: 4-Bromo-5-[4-(2,6-dichloro-benzenesulfonylamino)-phenyl]-3-ethoxycarbonylmethoxy-thiophene-2-carboxylic acid methyl ester was prepared according to procedures in the first step of Scheme 5 of Example 40, using 5-(4-amino-phenyl)-4-bromo-3-ethoxycarbonylmethoxy-5-phenyl-thiophene-2-carboxylic acid methyl ester as the starting material.

¹H NMR (400 MHz, CHLOROFORM-D) δ ppm 1.32 (t, J=7.07 Hz, 3 H) 3.88 (s, 3 H) 4.29 (q, J=7.16 Hz, 2 H) 4.93 (s, 2 H) 7.42 (m, 8 H) 7.59 (m, 2 H).

The second step of Scheme 5: 4-Bromo-3-carboxymethoxy-5-[4-(2,6-dichloro-benzenesulfonylamino)-phenyl]-thiophene-2-carboxylic acid, was prepared as a white solid according to procedures in the second step of Scheme 1 of Example 1, using 4-bromo-5-[4-(2,6-dichloro-benzenesulfonylamino)-phenyl]-3-ethoxycarbonylmethoxy-thiophene-2-carboxylic acid methyl ester as the starting material.

¹H NMR (400 MHz, DMSO-D6) δ ppm 4.85 (s, 2 H) 7.21 (m, 2 H) 7.58 (m, 3 H) 7.67 (m, 2 H) 11.26 (s, 1 H).

EXAMPLE 43

4-Bromo-3-carboxymethoxy-5-[4-(2,6-difluoro-benzenesulfonylamino)-phenyl]-thiophene-2-carboxylic acid The first step of Scheme 5: 4-Bromo-5-[4-(2,6-difluoro-benzenesulfonylamino)-phenyl]-3-ethoxycarbonylmethoxy-thiophene-2-carboxylic acid methyl ester was prepared according to procedures in the first step of Scheme 5 of Example 40, using 5-(4-amino-phenyl)-4-bromo-3-ethoxycarbonylmethoxy-5-phenyl-thiophene-2-carboxylic acid methyl ester as the starting material.

$^1$H NMR (400 MHz, CHLOROFORM-D) δ ppm 1.33 (t, J=7.20 Hz, 3 H) 3.89 (s, 3 H) 4.30 (q, J=7.16 Hz, 2 H) 7.07 (t, J=8.46 Hz, 4 H) 7.46 (d, J=8.59 Hz, 2 H) 7.65 (m, 2 H) 7.74 (m, 2 H).

The second step of Scheme 5: 4-Bromo-3-carboxymethoxy-5-[4-(2,6-difluoro-benzenesulfonylamino)-phenyl]-thiophene-2-carboxylic acid, was prepared as a white solid according to procedures in the first step of Scheme 1 of Example 1, using 4-bromo-5-[4-(2,6-difluoro-benzenesulfonylamino)-phenyl]-3-ethoxycarbonylmethoxy-thiophene-2-carboxylic acid methyl ester as the starting material.

$^1$H NMR (400 MHz, DMSO-D6) δ ppm 4.84 (s, 2 H) 7.30 (m, 5 H) 7.61 (d, J=8.84 Hz, 2 H).

EXAMPLE 44

4-Bromo-3-carboxymethoxy-5-[4-(3,3,5,5-tetramethyl-cyclohexylamino)-phenyl]-thiophene-2-carboxylic acid The first step of Scheme 6: To a solution 5-(4-amino-phenyl)-4-bromo-3-ethoxycarbonylmethoxy-thiophene-2-carboxylic acid methyl ester (115 mg, 0.278 mmol) and 3,3,5,5-tetramethyl-cyclohexanone (0.15 mL, 0.87 mmol) in DCE was added HOAc (0.043 mL, 0.87 mmol) at room temperature. The resultant mixture was stirred at the same temperature for 5 min, NaBH(OAc)$_3$ (155 mg, 0.87 mmol) was added in one portion. After vigorously stirring overnight, the reaction mixture was quenched with aq. NaHCO3, extracted with DCM. The combined organic layer was dried over MgSO4 and concentrated. The crude product was purified on CombiFlash column eluted with EtOAc to give 4-bromo-3-ethoxycarbonylmethoxy-5-[4-(3,3,5,5-tetramethyl-cyclohexylamino)-phenyl]-thiophene-2-carboxylic acid methyl ester (80 mg, 52%) as a colorless oil.

The second step of Scheme 6: 4-Bromo-3-carboxymethoxy-5-[4-(3,3,5,5-tetramethyl-cyclohexylamino)-phenyl]-thiophene-2-carboxylic acid (31 mg, 73%) was prepared as a white solid according to procedures in the second step of Scheme 1 of Example 1, using 4-bromo-3-ethoxycarbonylmethoxy-5-[4-(3,3,5,5-tetramethyl-cyclohexylamino)-phenyl]-thiophene-2-carboxylic acid methyl ester (31 mg, 0.056 mmol) as the starting material.

EXAMPLE 45

3-Carboxymethoxy-5-[4-(3,3,5,5-tetramethyl-cyclohexylamino)-phenyl]-thiophene-2-carboxylic acid 3-Ethoxycarbonylmethoxy-5-[4-(3,3,5,5-tetramethyl-cyclohexylamino)-phenyl]-thiophene-2-carboxylic acid methyl ester was prepared as follow: To a solution of 4-bromo-3-ethoxycarbonylmethoxy-5-[4-(3,3,5,5-tetramethyl-cyclohexylamino)-phenyl]-thiophene-2-carboxylic acid methyl ester (12 mg, 0.0265 mmol) in MeOH (2 mL) was added Pd/C (20 mg). The resultant mixture was stirred under H$_2$ balloon at room temperature overnight. The precipitate was removed by filtering through a pad of Celite, the crude product was purified on CombiFlash column to give 3-ethoxycarbonylmethoxy-5-[4-(3,3,5,5-tetramethyl-cyclohexylamino)-phenyl]-thiophene-2-carboxylic acid methyl ester (9.5 mg, 92%).

The second step of Scheme 6: 3-Carboxymethoxy-5-[4-(3,3,5,5-tetramethyl-cyclohexylamino)-phenyl]-thiophene-2-carboxylic acid (7.5 mg, 87%) was prepared as a light yellow solid according to procedures in the second step of Scheme 1 of Example 1, using 3-ethoxycarbonylmethoxy-5-[4-(3,3,5,5-tetramethyl-cyclohexylamino)-phenyl]-thiophene-2-carboxylic acid methyl ester (9.5 mg, 0.02 mmol) as the starting material.

EXAMPLE 46

5-[4-(Benzenesulfonylamino-methyl)-phenyl]-4-bromo-3-carboxymethoxy-thiophene-2-carboxylic acid The first step of Scheme 7: To a microwave tube was added 4-benzyl-carbamic acid tert-butyl ester boronic acid (75 mg, 0.3 mmol), 4,5-Dibromo-3-ethoxycarbonylmethoxy-thiophene-2-carboxylic acid methyl ester (80 mg, 0.2 mmol), potassium fluoride (46 mg, 0.8 mmol) and tetrakis(triphenylphosphine)palladium(0) (35 mg, 0.03 mmol). The vessel was purged with argon and then diluted with THF (2 mL). The reaction was heated in the microwave at 150° C. for 40 minutes. The reaction was diluted with ethyl acetate (10 mL) and filtered through a layer of silica gel. Purification of the material by CombiFlash column chromatography eluting with a 10-35% ethyl acetate-hexane gradient to yield 61 mg of 4-Bromo-5-[4-(tert-butoxycarbonylamino-methyl)-phenyl]-3-ethoxycarbonylmethoxy-thiophene-2-carboxylic acid methyl ester as a white solid (58%).

$^1$H NMR (400 MHz, CHLOROFORM-D) δ ppm 1.32 (t, J=7.07 Hz, 3 H) 1.47 (s, 9 H) 3.88 (s, 3 H) 4.30 (q, J=7.16 Hz, 2 H) 4.37 (d, J=5.81 Hz, 2 H) 4.91 (s, 2 H) 7.38 (d, J=8.34 Hz, 3 H) 7.63 (m, 2 H).

The second step of Scheme 7: A solution of 4-bromo-5-[4-(tert-butoxycarbonylamino-methyl)-phenyl]-3-ethoxycarbonylmethoxy-thiophene-2-carboxylic acid methyl ester (306 mg, 0.58 mmol) in TFA (2 mL) and dichloromethane (4 mL) was stirred at room temperature for 1 hour. The solvent was removed under reduced pressure to give 314 mg of 5-(4-aminomethyl-phenyl)-4-bromo-3-ethoxycarbonylmethoxy-thiophene-2-carboxylic acid methyl ester trifluoroacetic acid as a light brown oil (99%).

$^1$H NMR (400 MHz, CHLOROFORM-D) δ ppm 1.32 (t, J=7.07 Hz, 3 H) 1.47 (s, 9 H) 3.88 (s, 3 H) 4.30 (q, J=7.16 Hz, 2 H) 4.37 (d, J=5.81 Hz, 2 H) 4.91 (s, 2 H) 7.38 (d, J=8.34 Hz, 2 H) 7.63 (m, 2 H).

The third step of Scheme 7: To a solution of 5-(4-aminomethyl-phenyl)-4-bromo-3-ethoxycarbonylmethoxy-thiophene-2-carboxylic acid methyl ester trifluoroacetic acid (53 mg, 0.1 mmol) and triethylamine (56 mL, 0.4 mmol) in dichloromethane (1.5 mL) was added phenylsulfonyl chloride (19 μL, 0.15 mmol). After 3 hours, the reaction was quenched with saturated aqueous sodium bicarbonate (10 mL) and extracted with ethyl acetate (2×30 mL). The organic layer was dried over magnesium sulfate and filtered. The solvent was removed under reduced pressure and the material was purified by CombiFlash column chromatography eluting with a 20-50% ethyl acetate-hexane gradient to give 40 mg of 5-[4-(Benzenesulfonylamino-methyl)-phenyl]-4-bromo-3-ethoxycarbonylmethoxy-thiophene-2-carboxylic acid methyl ester as a white solid (70%).

$^1$H NMR (400 MHz, CHLOROFORM-D) δ ppm 1.32 (t, J=7.20 Hz, 3 H) 3.88 (s, 3 H) 4.22 (d, J=6.32 Hz, 2 H) 4.29 (q, J=7.16 Hz, 2 H) 4.84 (t, J=6.19 Hz, 1 H) 4.91 (s, 2 H) 7.29 (d, J=8.59 Hz, 2 H) 7.56 (m, 5 H) 7.87 (m, 2 H).

The fourth step of Scheme 7: The procedure of the second step of Scheme 1 of Example 1 afforded 5.0 mg of 5-[4-(benzenesulfonylamino-methyl)-phenyl]-4-bromo-3-carboxymethoxy-thiophene-2-carboxylic acid (99%).

$^1$H NMR (400 MHz, DMSO-D6) δ ppm 4.06 (d, J=6.32 Hz, 2 H) 4.80 (s, 2 H) 7.36 (m, J=8.34 Hz, 2 H) 7.58 (m, 5 H) 7.79 (m, 2 H) 8.25 (m, J=6.06 Hz, 1 H).

EXAMPLE 47

4-Bromo-5-[4-(tert-butoxycarbonylamino-methyl)-phenyl]-3-carboxymethoxy-thiophene-2-carboxylic acid 4-Bromo-5-[4-(tert-butoxycarbonylamino-methyl)-phenyl]-3-carboxymethoxy-thiophene-2-carboxylic acid was prepared according to procedures in Example 46 to give 6.8 mg of 4-bromo-5-[4-(tert-butoxycarbonylamino-methyl)-phenyl]-3-carboxymethoxy-thiophene-2-carboxylic acid (70%).

$^1$H NMR (400 MHz, Solvent) δ ppm 3.35 (s, 9 H) 4.29 (s, 2 H) 4.87 (s, 2 H) 7.39 (d, J=8.34 Hz, 1 H) 7.63 (d, J=8.34 Hz, 1 H).

EXAMPLE 48

4-Bromo-3-carboxymethoxy-5-[4-(ethanesulfonylamino-methyl)-phenyl]-thiophene-2-carboxylic acid The intermediate compound, 4-Bromo-5-[4-(ethanesulfonylamino-methyl)-phenyl]-3-ethoxycarbonylmethoxy-thiophene-2-carboxylic acid methyl ester, was prepared following the procedure in the first and second steps of Scheme 7. In the third step of Scheme 7, 5-(4-aminomethyl-phenyl)-4-bromo-3-ethoxycarbonylmethoxy-thiophene-2-carboxylic acid methyl ester trifluoroacetic acid (55 mg, 0.10 mmol) and ethyl sulfonylchloride (14 µL, 0.15 mmol) in pyridine (1 mL) was stirred at room temperature for 3 hours. The reaction was diluted with ethyl acetate (50 mL) and washed with 1N HCl (10 mL). The organic layer was dried over magnesium sulfate and filtered. The solvent was removed under reduced pressure and the material was purified by combi-flash column chromatography eluting with a 20-50% ethyl acetate-hexane gradient to give 12 mg of 4-Bromo-5-[4-(ethanesulfonylamino-methyl)-phenyl]-3-ethoxycarbonylmethoxy-thiophene-2-carboxylic acid methyl ester as a white solid (23%).

$^1$H NMR (400 MHz, CHLOROFORM-D) δ ppm 1.32 (t, J=7.07 Hz, 3 H) 1.37 (t, J=7.33 Hz, 3 H) 3.03 (q, J=7.33 Hz, 2 H) 3.88 (s, 3 H) 4.29 (q, J=7.16 Hz, 2 H) 4.37 (d, J=6.06 Hz, 2 H) 4.57 (d, J=5.81 Hz, 1 H) 4.92 (s, 2 H) 7.45 (d, J=8.59 Hz, 2 H) 7.67 (m, 2 H).

The fourth step of Scheme 7: The procedure of the second step of Scheme 1 of Example 1 afforded 9.7 mg (65%) of 4-bromo-3-carboxymethoxy-5-[4-(ethanesulfonylamino-methyl)-phenyl]-thiophene-2-carboxylic acid as a light brown powder.

$^1$H NMR (400 MHz, DMSO-D6) δ ppm 1.19 (t, J=7.33 Hz, 3 H) 3.00 (q, J=7.33 Hz, 2 H) 4.20 (d, J=6.32 Hz, 2 H) 4.82 (s, 2 H) 7.49 (d, J=8.34 Hz, 2 H) 7.65 (d, J=8.34 Hz, 2 H) 7.71 (t, J=6.32 Hz, 1 H).

EXAMPLE 49

5-[4-(Acetylamino-methyl)phenyl]-4-bromo-3-carboxymethoxy-thiophene-2-carboxylic acid The intermediate, 5-[4-(acetylamino-methyl)-phenyl]-4-bromo-3-ethoxycarbonylmethoxy-thiophene-2-carboxylic acid methyl ester, was prepared following the procedure in the first and second steps of Scheme 7. In the third step of Scheme 7, a stirred solution of 5-(4-aminomethyl-phenyl)-4-bromo-3-ethoxycarbonylmethoxy-thiophene-2-carboxylic acid methyl ester trifluoroacetic acid (45 mg, 0.08 mmol) and triethylamine (45 µL, 0.16 mmol) and dimethylaminopyridine (5 mg, 0.05 mmol) in dichloromethane (2 mL) was treated with acetic anhydride (15 µL, 0.16 mmol). After 18 hours, the solvent was removed under reduced pressure. The material was purified by combi-flash column chromatography eluting with a 20-50% ethyl acetate-hexane gradient to give 25 mg of 5-[4-(acetylamino-methyl)-phenyl]-4-bromo-3-ethoxycarbonylmethoxy-thiophene-2-carboxylic acid methyl ester as a white powder (66%).

$^1$H NMR (400 MHz, CHLOROFORM-D) δ ppm 1.32 (t, J=7.07 Hz, 3 H) 2.06 (s, 3 H) 3.88 (s, 3 H) 4.29 (q, J=7.16 Hz, 2 H) 4.49 (d, J=5.81 Hz, 2 H) 4.92 (s, 2 H) 7.38 (d, J=8.59 Hz, 2 H) 7.63 (m, 2 H).

The fourth step of Scheme 7: 5-[4-(Acetylamino-methyl)-phenyl]-4-bromo-3-carboxymethoxy-thiophene-2-carboxylic acid was prepared following the procedure in the second step of Scheme 1 of Example 1 to give 25 mg of 5-[4-(acetylamino-methyl)-phenyl]-4-bromo-3-carboxymethoxy-thiophene-2-carboxylic acid as a light brown solid.

$^1$H NMR (400 MHz, DMSO-D6) δ ppm 1.89 (s, 3 H) 4.30 (d, J=6.06 Hz, 2 H) 4.86 (s, 2 H) 7.39 (d, J=8.34 Hz, 2 H) 7.62 (d, J=8.08 Hz, 2 H) 8.42 (s, 1 H).

EXAMPLE 50

4-Bromo-3-carboxymethoxy-5-[4-(ethoxycarbonylamino-methyl)-phenyl]-thiophene-2-carboxylic acid The intermediate, 4-bromo-5-[4-(ethoxycarbonylamino-methyl)-phenyl]-3-ethoxycarbonylmethoxy-thiophene-2-carboxylic acid methyl ester, was prepared following the procedure in the first and second steps of Scheme 7. In the third step of Scheme 7, a stirred solution of 5-(4-aminomethyl-phenyl)-4-bromo-3-ethoxycarbonylmethoxy-thiophene-2-carboxylic acid methyl ester trifluoroacetic acid (52 mg, 0.1 mmol), triethylamine (53 mL, 0.4 mmol), dimethylaminopyridine (5 mg, 0.05 mmol) and ethyl chloroformate (96 mL, 1.0 mmol) in N,N-dimethylformamide (3 mL) were stirred at 60° C. for 3 hours and then stirred at room temperature for 18 hours. The solvent was removed under reduced pressure. The material was purified by combi-flash column chromatography to give 44 mg of 4-Bromo-5-[4-(ethoxycarbonylamino-methyl)-phenyl]-3-ethoxycarbonylmethoxy-thiophene-2-carboxylic acid methyl ester as an orange solid (93%).

$^1$H NMR (400 MHz, CHLOROFORM-D) δ ppm 1.27 (t, J=7.20 Hz, 3 H) 1.32 (t, J=7.07 Hz, 3 H) 3.88 (s, 3 H) 4.17 (d, J=7.07 Hz, 2 H) 4.29 (q, J=7.16 Hz, 2 H) 4.42 (d, J=6.06 Hz, 2 H) 4.91 (s, 2 H) 7.39 (d, J=8.34 Hz, 2 H) 7.63 (m, 2 H).

The fourth step of Scheme 7: The procedure in the second step of Scheme 1 of Example 1 afforded 21 mg of 4-bromo-3-carboxymethoxy-5-[4-(ethoxycarbonylamino-methyl)-phenyl]-thiophene-2-carboxylic acid as a light brown powder.

¹H NMR (400 MHz, DMSO-D6) δ ppm 1.18 (t, J=7.07 Hz, 3 H) 4.01 (m, 2 H) 4.23 (d, J=5.81 Hz, 2 H) 4.84 (s, 2 H) 7.39 (d, J=8.34 Hz, 2 H) 7.62 (d, J=8.08 Hz, 2 H) 7.72 (t, J=4.29 Hz, 1 H).

EXAMPLE 51

4-Bromo-3-carboxymethoxy-5-[4-(3-isopropyl-ureidomethyl)-phenyl]-thiophene-2-carboxylic acid The intermediate, 4-bromo-3-ethoxycarbonylmethoxy-5-[4-(3-isopropyl-ureidomethyl)-phenyl]-thiophene-2-carboxylic acid, was prepared following the procedure in the first and second steps of Scheme 7. In the third step of Scheme 7, a stirred solution of 5-(4-aminomethyl-phenyl)-4-bromo-3-ethoxycarbonylmethoxy-thiophene-2-carboxylic acid methyl ester trifluoroacetic acid (52 mg, 0.1 mmol) and pyridine (49 μL, 0.6 mmol) in dichloromethane (1 mL) was treated with isopropyl isocyanate (14 μL, 0.14 mmol). The reaction was heated at 50° C. for 3 hours and then stirred at room temperature for 18 hours. The solvent was removed under reduced pressure. The material was purified by combi-flash column chromatography eluting with a 20-50% ethyl acetate-hexane gradient to give 58 mg of 4-Bromo-3-ethoxycarbonylmethoxy-5-[4-(3-isopropyl-ureidomethyl)-phenyl]-thiophene-2-carboxylic acid methyl ester as a white solid (99%).

¹H NMR (400 MHz, CHLOROFORM-D) δ ppm 1.16 (m, 6 H) 1.32 (t, J=7.20 Hz, 2 H) 3.88 (s, 3 H) 3.90 (s, 1 H) 4.18 (d, J=7.83 Hz, 1 H) 4.29 (q, J=7.24 Hz, 2 H) 4.43 (d, J=5.81 Hz, 2 H) 4.62 (s, 1 H) 4.90 (s, 2 H) 7.38 (d, J=8.59 Hz, 2 H) 7.61 (d, J=8.34 Hz, 2 H). The fourth step of Scheme 7: The procedure of the second step of Scheme 1 of Example 1 afforded 9.3 mg of 4-Bromo-3-carboxymethoxy-5-[4-(3-isopropyl-ureidomethyl)-phenyl]-thiophene-2-carboxylic acid as a white solid (70%).

¹H NMR (400 MHz, DMSO-D6) δ ppm 1.04 (d, J=6.32 Hz, 6 H) 3.69 (m, 1 H) 4.24 (d, J=5.81 Hz, 2 H) 4.77 (s, 2 H) 5.87 (d, J=7.83 Hz, 1 H) 6.32 (t, J=5.94 Hz, 1 H) 7.37 (d, J=8.59 Hz, 2 H) 7.60 (m, 2 H).

EXAMPLE 52

5-(4-Aminomethyl-phenyl)-4-bromo-3-carboxymethoxy-thiophene-2-carboxylic acid trifluoroacetic acid To 4-bromo-5-[4-(tert-butoxycarbonylamino-methyl)-phenyl]-3-carboxymethoxy-thiophene-2-carboxylic acid in dichloromethane was added trifluoroacetic acid. After 2 hours, the solvent was removed under reduced pressure to give 4 mg of 5-(4-aminomethyl-phenyl)-4-bromo-3-carboxymethoxy-thiophene-2-carboxylic acid trifluoroacetic acid as an off white solid.

¹H NMR (400 MHz, Solvent) δ ppm 4.19 (s, 2 H) 4.90 (s, 2 H) 7.59 (d, J=8.34 Hz, 2 H) 7.76 (d, J=8.34 Hz, 2 H).

EXAMPLE 53

4-Bromo-3-carboxymethoxy-5-(4-phenylcarbamoyl-phenyl)-thiophene-2-carboxylic acid The first step of Scheme 8: 4-Bromo-3-ethoxycarbonyl-methoxy-5-(4-formyl-phenyl)-thiophene-2-carboxylic acid methyl ester was prepared according to the procedure in the second step of Scheme 7 of Example 46 to give 137 mg (52%) of 4-Bromo-3-ethoxycarbonylmethoxy-5-(4-formyl-phenyl)-thiophene-2-carboxylic acid methyl ester as a white solid.

¹H NMR (400 MHz, CHLOROFORM-D) δ ppm 1.19 (t, J=7.07 Hz, 3 H) 3.91 (s, 3 H) 4.12 (d, J=7.07 Hz, 2 H) 4.72 (s, 2 H) 7.35 (d, J=8.34 Hz, 2 H) 7.78 (d, J=8.34 Hz, 2 H) 9.98 (s, 1 H).

The second step of Scheme 8: To 4-bromo-3-ethoxycarbonylmethoxy-5-(4-formyl-phenyl)-thiophene-2-carboxylic acid methyl ester (301 mg, 0.70 mmol) in acetone (7 mL) was added potassium permanganate (123 mg, 0.80 mmol). The reaction was heated at reflux for 3 hours and then cooled to room temperature. The mixture was diluted with dichloromethane (150 mL) and washed with 0.5 N HCl (50 mL). The aqueous layer was back extracted with dichloromethane (50 mL). The organic layers were combined and dried over magnesium sulfate. The solids were removed by filtration and the solvent was removed under reduced pressure to give 175 mg (56%) of 4-bromo-5-(4-carboxy-phenyl)-3-ethoxycarbonylmethoxy-thiophene-2-carboxylic acid methyl ester as a tan oil.

¹H NMR (400 MHz, DMSO-D6) δ ppm 1.22 (t, J=7.20 Hz, 3 H) 3.83 (s, 3 H) 4.18 (q, J=7.07 Hz, 2 H) 4.98 (s, 2 H) 7.83 (d, J=8.59. Hz, 2 H) 8.08 (d, J=8.59 Hz, 2 H).

The third step of Scheme 8: To 4-bromo-5-(4-carboxy-phenyl)-3-ethoxycarbonylmethoxy-thiophene-2-carboxylic acid methyl ester, triethylamine and aniline in N,N-dimethylformamide was added HATU. The reaction was stirred for 18 hours at ambient temperature. The reaction was diluted with ethyl acetate. The organic layer was washed with 0.5 N HCl, saturated aqueous sodium bicarbonate and dried over magnesium sulfate. The solution was filtered and the solvent was removed under reduced pressure. The material was purified by combi-flash column chromatography eluting with a 0-5% methanol-dichloromethane gradient to give 48 mg (99%) of 4-Bromo-3-ethoxycarbonylmethoxy-5-(4-phenyl-carbamoyl-phenyl)-thiophene-2-carboxylic acid methyl ester as an off-white solid.

¹H NMR (400 MHz, DMSO-D6) δ ppm 1.23 (t, J=7.07 Hz, 3 H) 3.83 (s, 3 H) 4.19 (q, J=7.07 Hz, 2 H) 4.99 (s, 2 H) 7.12 (s, 1 H) 7.37 (m, 2 H) 7.79 (d, J=7.58 Hz, 2 H) 7.85 (m, 2 H) 8.08 (m, 2 H).

The fourth step of Scheme 8: The compound was prepared following the procedure in the second step of Scheme 1 of Example 1 to give 25 mg (60%) of 4-bromo-3-carboxymethoxy-5-(4-phenylcarbamoyl-phenyl)-thiophene-2-carboxylic acid as a light brown solid.

¹H NMR (400 MHz, DMSO-D6) δ ppm 4.89 (s, 2 H) 7.12 (t, J=7.45 Hz, 1 H) 7.37 (m, 2 H) 7.80 (m, 2 H) 7.84 (m, 2 H) 8.08 (m, 2 H) 10.40 (s, 1 H).

EXAMPLE 54

4-Bromo-3-carboxymethoxy-5-(4-formyl-phenyl)-thiophene-2-carboxylic acid

The fourth step of Scheme 8: 4-Bromo-3-ethoxycarbonyl-methoxy-5-(4-formyl-phenyl)-thiophene-2-carboxylic acid methyl ester was subjected to the conditions outlined in the second step of Scheme 1 of Example 1 to provide 10 mg (17%) of 4-Bromo-3-carboxymethoxy-5-(4-formyl-phenyl)-thiophene-2-carboxylic acid as a light brown solid.

¹H NMR (400 MHz, Solvent) δ ppm 4.76 (s, 2 H) 7.89 (d, J=8.34 Hz, 2 H) 8.01 (m, 2 H) 10.04 (s, 1 H).

EXAMPLE 55

4-Bromo-3-carboxymethoxy-5-(4-isopropylcarbamoyl-phenyl)-thiophene-2-carboxylic acid The third step of Scheme 8: 4-Bromo-5-(4-carboxy-phenyl)-3-ethoxycarbonylmethoxy-thiophene-2-carboxylic acid methyl ester was subjected to the conditions (except that isopropylamine was used as the starting material) described in the third step of Scheme 8 of Example 53 to give 39 mg (99%) of 4-Bromo-3-ethoxycarbonylmethoxy-5-(4-isopropylcarbamoyl-phenyl)-thiophene-2-carboxylic acid methyl ester as an off-white solid.

¹H NMR (400 MHz, CHLOROFORM-D) δ ppm 1.29 (d, J=6.57 Hz, 6 H) 1.32 (m, 3 H) 3.59 (m, 1 H) 3.89 (s, 3 H) 4.29 (d, J=7.33 Hz, 2 H) 4.93 (s, 2 H) 5.96 (d, J=7.83 Hz, 1 H) 7.73 (d, J=8.59 Hz, 2 H) 7.83 (s, 2 H).

The fourth step of Scheme 8: The procedures of the second step of Scheme 1 of Example 1 afforded 27 mg (74%) of 4-bromo-3-carboxymethoxy-5-(4-isopropylcarbamoyl-phenyl)-thiophene-2-carboxylic acid as a light yellow powder.

¹H NMR (400 MHz, DMSO-D6) δ ppm 1.16 (m, 6 H) 4.12 (s, 1 H) 4.90 (s, 2 H) 7.76 (m, 2 H) 7.96 (d, J=8.34 Hz, 2 H) 8.38 (s, 1 H).

EXAMPLE 56

4-Bromo-5-[4-(1-carbamoyl-ethylcarbamoyl)phenyl]-3-carboxymethoxy-thiophene-2-carboxylic acid The third step of Scheme 8: 4-Bromo-5-[4-(1-carbamoyl-ethylcarbamoyl)-phenyl]-3-ethoxycarbonylmethoxy-thiophene-2-carboxylic acid methyl ester (46 mg, 99%) was prepared according to the procedure in the third step of Scheme 8 of Example 53 an off white solid.

The fourth step of Scheme 8: The procedures outlined in the second step of Scheme 1 of Example 1 afforded 24 mg (57%) of 4-Bromo-5-[4-(1-carbamoyl-ethylcarbamoyl)-phenyl]-3-carboxymethoxy-thiophene-2-carboxylic acid as a white powder.

¹H NMR (400 MHz, DMSO-D6) δ ppm 1.34 (d, 3 H), 4.35-4.50 (m, 1 H), 4.85-4.93 (m, 2 H), 6.97-7.05 (m, 1 H), 7.37-7.42 (m, 1 H), 7.78 (d, 2 H), 8.01 (d, 2 H), 8.58 (d, 1 H). ESI-MS: m/e=472 [M+H]⁺.

EXAMPLE 57

4-Bromo-3-carboxymethoxy-5-[4-(4-trifluoromethyl-phenylcarbamoyl)-phenyl]-thiophene-2-carboxylic acid The third step of Scheme 8: 4-Bromo-3-carboxymethoxy-5-[4-(4-trifluoromethyl-phenylcarbamoyl)-phenyl]-thiophene-2-carboxylic acid (33 mg, 51%) was prepared according to the procedure in the third step of Scheme 8 of Example 53 as an off white solid.

¹H NMR (400 MHz, CHLOROFORM-D) δ ppm 1.32 (t, J=7.20 Hz, 3 H) 3.89 (s, 3 H) 4.29 (t, J=7.07 Hz, 2 H) 4.94 (s, 2 H) 7.65 (d, J=8.59 Hz, 2 H) 7.81 (m, 4 H) 7.97 (d, J=8.59 Hz, 2 H) 8.06 (m, 1 H).

The fourth step of Scheme 8: The procedures in the second step of Scheme 1 of Example 1 afforded 22 mg (72%) of 4-Bromo-3-carboxymethoxy-5-[4-(4-trifluoromethyl-phenylcarbamoyl)-phenyl]-thiophene-2-carboxylic acid as a white powder.

¹H NMR (400 MHz, DMSO-D6) δ ppm 4.91 (s, 2 H) 7.75 (d, J=8.84 Hz, 2 H) 7.86 (m, 2 H) 8.03 (d, J=8.59 Hz, 2 H) 8.10 (m, 2 H) 10.73 (s, 1 H).

EXAMPLE 58

4-Bromo-3-carboxymethoxy-5-(3-propionylaminophenyl)-thiophene-2-carboxylic acid

The first step of Scheme 9: To a 500 mL DMF solution of 4,5-dibromo-3-hydroxy-thiophene-2-carboxylic acid methyl ester (39.62 g, 125 mmol) were added potassium carbonate (34.55 g, 250 mmol) and tert-butyl bromoacetate (18.5 mL, 125 mmol) and the mixture was allowed to stir at room temperature overnight. The reaction mixture was filtered through celite to remove excess potassium carbonate and the filtrate was concentrated on the rotary evaporator. The resulting residue was dissolved in ethyl acetate (400 mL), washed with $H_2O$ (300 mL), brine, and dried over $MgSO_4$. Evaporation yielded 47.54 g (88%) of 4,5-dibromo-3-ethoxycarbonylmethoxy-thiophene-2-carboxylic acid methyl ester a reddish oil that crystallized on standing.

¹H NMR (400 MHz, CHLOROFORM-D) δ ppm 1.48 (s, 9 H) 3.85 (s, 3 H) 4.90 (s, 2 H).

The second step of Scheme 9: A 150 mL heavy-walled pressure vessel was charged with 4,5-dibromo-3-ethoxycarbonylmethoxy-thiophene-2-carboxylic acid methyl ester (6.45 g, 15.0 mmol), 3-aminophenylboronic acid (2.79 g, 18.0 mmol), Pd(PPh₃)₄ (867 mg, 5 mol %), and potassium fluoride (2.61 g, 45.0 mmol). 75 mL of THF was then added and the mixture purged with argon. The reaction vessel was capped and heated to 100° C. After 5 hours, TLC of the reaction mixture indicated complete consumption of 4,5-dibromo-3-ethoxycarbonylmethoxy-thiophene-2-carboxylic acid methyl ester. The reaction mixture was diluted with ether (250 mL), washed with saturated sodium bicarbonate solution, brine, and dried over $MgSO_4$. Evaporation yielded 8.53 g of an orange semisolid. This procedure was performed a second time and the crude products combined to give a total of 16.21 g of an orange semisolid. The crude product was purified by chromatography on silica gel using a gradient of hexane/EtOAc (10 to 30%) as eluent. Pure fractions were combined and evaporated to give 9.75 g (73%) of 5-(3-amino-phenyl)-4-bromo-3-ethoxycarbonylmethoxy-thiophene-2-carboxylic acid methyl ester as an off-white solid.

¹H NMR (400 MHz, CHLOROFORM-D) δ ppm 1.50 (s, 9 H) 3.79 (s, 1 H) 3.87 (s, 3 H) 4.81 (s, 2 H) 6.74 (m, 1 H) 6.96 (m, 1 H) 7.03 (ddd, J=7.96, 1.39, 1.01 Hz, 1 H) 7.23 (t, J=8.08 Hz, 1 H).

ESI-MS: m/e=442 [M+H]⁺.

The third step of Scheme 9: To a 1.5 mL $CH_2Cl_2$ solution of 5-(3-amino-phenyl)-4-bromo-3-ethoxycarbonylmethoxy-thiophene-2-carboxylic acid methyl ester (44 mg, 0.1 mmol) were added diisopropylethyl amine (27 μL, 0.15 mmol) and propionyl chloride (11 μL, 0.12 mmol) and the reaction mixture stirred at room temperature for 1 hour. TLC indicates complete consumption of the starting material. The reaction mixture was diluted with $CH_2Cl_2$ and washed with dilute aqueous HCl, saturated bicarbonate solution, brine, and dried over $MgSO_4$. 45 mg (90%) of 4-bromo-3-ethoxycarbonylmethoxy-5-(3-propionylamino-phenyl)-thiophene-2-carboxylic acid methyl ester was obtained as a yellow oil.

¹H NMR (400 MHz, CHLOROFORM-D) δ ppm 1.26 (t, J=7.58 Hz, 3 H) 1.51 (s, 9 H) 2.43 (q, J=7.58 Hz, 2 H) 3.87 (s, 3 H) 4.82 (s, 2 H) 7.38 (m, 2 H) 7.43 (s, 1 H) 7.63 (m, 1 H) 7.83 (s, 1 H).

The fourth step of Scheme 9: 4-Bromo-3-ethoxycarbonylmethoxy-5-(3-propionylamino-phenyl)-thiophene-2-carboxylic acid methyl ester (45 mg, 9.0×10⁻⁵ mmol) was dissolved in 1.5 mL of a 2:1 mixture of THF:H₂O and LiOH.H₂O (11 mg, 0.27 mmol) was added and the mixture stirred at room temperature overnight. The reaction mixture was then evaporated and the residue re-dissolved in 2-3 mL of H₂O. The mixture was acidified dropwise with 1N HCl while stirring. A solid emerged that was filtered, washed with water, and vacuum oven-dried to give 32 mg (83%) 4-bromo-3-carboxymethoxy-5-(3-propionylamino-phenyl)-thiophene-2-carboxylic acid as an off-white solid.

¹H NMR (400 MHz, DMSO-D6) δ ppm 1.09 (t, J=7.58 Hz, 3 H) 2.34 (m, 2 H) 4.89 (s, 2 H) 7.33 (s, 1 H) 7.44 (t, J=7.83 Hz, 1 H) 7.67 (s, 1 H) 8.03 (s, 1 H) 10.08 (s, 1 H).
ESI-MS: m/e=426 [M–H]⁻.

EXAMPLE 59

4-Bromo-5-(3-butyrylamino-phenyl)-3-carboxymethoxy-thiophene-2-carboxylic acid

The third step of Scheme 9: 4-Bromo-3-tert-butoxycarbonylmethoxy-5-(3-butyrylamino-phenyl)-thiophene-2-carboxylic acid methyl ester was obtained in 99% yield as an orange oil according to the procedure in the third of Scheme 9 of Example 58, using 5-(3-amino-phenyl)-4-bromo-3-tert-butoxycarbonylmethoxy-thiophene-2-carboxylic acid methyl ester as the starting material.

¹H NMR (400 MHz, CHLOROFORM-D) δ ppm 1.01 (m, 3 H) 1.01 (m, 3 H) 1.78 (m, 2 H) 2.38 (t, J=7.33 Hz, 2 H) 4.82 (s, 2 H) 7.40 (m, 3 H) 7.64 (m, 1 H) 7.83 (s, 1 H).

The fourth step of Scheme 9: 4-Bromo-3-tert-butoxycarbonylmethoxy-5-(3-butyrylamino-phenyl)-thiophene-2-carboxylic acid methyl ester was hydrolyzed under the same conditions as that in the fourth step of Scheme 9 of Example 58, but the compound was extracted with ethyl acetate, washed with brine and dried over MgSO₄. Evaporation afforded 25 mg (56%) 4-bromo-5-(3-butyrylamino-phenyl)-3-carboxymethoxy-thiophene-2-carboxylic acid compound as a pale orange solid.

¹H NMR (400 MHz, DMSO-D6) δ ppm 0.92 (t, J=7.45 Hz, 3 H) 1.62 (m, 2 H) 2.31 (t, J=7.33 Hz, 2 H) 4.90 (s, 2 H) 7.33 (d, J=8.34 Hz, 1 H) 7.44 (t, J=7.96 Hz, 1 H) 7.68 (m, 1 H) 8.03 (m, 1 H) 10.09 (s, 1 H).
ESI-MS: m/e=440 [M–H]⁻.

EXAMPLE 60

4-Bromo-3-carboxymethoxy-5-[3-(cyclohexanecarbonyl-amino)-phenyl]-thiophene-2-carboxylic acid The third step of Scheme 9: 4-Bromo-3-tert-butoxycarbonylmethoxy-5-[3-(cyclohexanecarbonyl-amino)-phenyl]-thiophene-2-carboxylic acid methyl ester was obtained in 85% yield as a pale yellow oil according to the procedure in the third step of Scheme 9 of Example 58, using 5-(3-amino-phenyl)-4-bromo-3-tert-butoxycarbonylmethoxy-thiophene-2-carboxylic acid methyl ester as the starting material.

¹H NMR (400 MHz, CHLOROFORM-D) δ ppm 1.29 (m, 6 H) 1.51 (m, 9 H) 1.86 (m, 2 H) 1.97 (d, J=13.39 Hz, 2 H) 2.26 (m, J=3.54 Hz, 1 H) 3.87 (s, 3 H) 4.82 (s, 2 H) 7.30 (s, 1 H) 7.39 (m, 2 H) 7.63 (m, J=3.54 Hz, 1 H) 7.85 (s, 1 H).

The fourth step of Scheme 9: 4-Bromo-3-tert-butoxycarbonylmethoxy-5-[3-(cyclohexanecarbonyl-amino)-phenyl]-thiophene-2-carboxylic acid methyl ester was hydrolyzed as in the fourth step of Scheme 9 of Example 58 to give 66 mg (77%) of 4-bromo-3-carboxymethoxy-5-[3-(cyclohexanecarbonyl-amino)-phenyl]-thiophene-2-carboxylic acid as an off-white solid.

¹H NMR (400 MHz, DMSO-D6) δ ppm 1.29 (m, 6 H) 1.77 (m, 4 H) 4.88 (s, 2 H) 7.32 (d, J=7.83 Hz, 1 H) 7.43 (t, J=7.96 Hz, 1 H) 7.69 (d, J=8.84 Hz, 1 H) 8.03 (s, 1 H) 10.02 (s, 1 H).
ESI-MS: m/e=480 [M–H]⁻.

EXAMPLE 61

4-Bromo-3-carboxymethoxy-5-(3-hexanoylamino-phenyl)-thiophene-2-carboxylic acid

The third step of Scheme 9: 4-Bromo-3-tert-butoxycarbonylmethoxy-5-(3-hexanoylamino-phenyl)-thiophene-2-carboxylic acid methyl ester was obtained in 93% yield as a pale yellow oil according to the procedure in the third step of Scheme of 9 of Example 58, using 5-(3-amino-phenyl)-4-bromo-3-tert-butoxycarbonylmethoxy-thiophene-2-carboxylic acid methyl ester as the starting material.

¹H NMR (400 MHz, CHLOROFORM-D) δ ppm 0.91 (m, 3 H) 1.35 (m, 2 H) 1.51 (s, 9 H) 1.74 (m, 2 H) 2.38 (m, 2 H) 2.44 (t, J=7.45 Hz, 2 H) 3.87 (s, 3 H) 4.82 (s, 2 H) 7.39 (m, 3 H) 7.64 (m, 1 H) 7.82 (s, 1 H).

The fourth step of Scheme of 9: 4-Bromo-3-tert-butoxycarbonylmethoxy-5-(3-hexanoylamino-phenyl)-thiophene-2-carboxylic acid methyl ester was hydrolyzed as in the fourth step of Scheme 9 of Example 58 to give 52% of 4-bromo-3-carboxymethoxy-5-(3-hexanoylamino-phenyl)-thiophene-2-carboxylic acid as a pink solid.

¹H NMR (400 MHz, DMSO-D6) δ ppm 0.88 (t, J=6.69 Hz, 3 H) 1.30 (d, J=3.03 Hz, 5 H) 1.61 (d, J=7.33 Hz, 2 H) 2.32 (m, 2 H) 4.90 (s, 2 H) 7.34 (s, 1 H) 7.44 (t, J=7.83 Hz, 1 H) 7.67 (s, 1 H) 8.02 (s, 1 H).
SI-MS: m/e=468 [M–H]⁻.

EXAMPLE 62

4-Bromo-3-carboxymethoxy-5-[3-(cyclopentanecarbonyl-amino)-phenyl]-thiophene-2-carboxylic acid The third step of Scheme 9: To a 1.5 mL DMF solution of 5-(3-amino-phenyl)-4-bromo-3-tert-butoxycarbonylmethoxy-thiophene-2-carboxylic acid methyl ester were added cyclopentane carboxylic acid (14 mL, 0.12 mmol), HATU (43 mg, 0.11 mmol), and diisopropylethyl amine (40 mL, 0.22 mmol) and the resulting mixture was heated to 60° C. overnight. The reaction mixture was diluted with water and extracted with EtOAc (2×25 mL). Combined organic phases were combined and washed with dilute aqueous HCl, dilute aqueous NaOH, brine, and dried over MgSO₄. They were then filtered and evaporated to give a yellow oil. The crude product was purified by chromatography on silica gel using a gradient of hexane/EtOAc (0 to 25%) as eluent. Pure fractions were combined and evaporated to give 47 mg (79%) of 4-bromo-3-tert-butoxycarbonylmethoxy-5-[3-(cyclopentanecarbonyl-amino)-phenyl]-thiophene-2-carboxylic acid methyl ester as a colorless oil.

¹H NMR (400 MHz, CHLOROFORM-D) δ ppm 1.51 (s, 9 H) 1.63 (m, 2 H) 1.80 (m, 4 H) 1.92 (m, 4 H) 2.71 (m, 1 H) 3.87 (s, 3 H) 4.82 (s, 2 H) 7.36 (m, 1 H) 7.38 (m, 2 H) 7.63 (m, 1 H) 7.85 (s, 1 H)

The fourth step of Scheme 9: 4-Bromo-3-tert-butoxycarbonylmethoxy-5-[3-(cyclopentanecarbonyl-amino)-phenyl]-thiophene-2-carboxylic acid methyl ester was hydrolyzed as in the fourth step of Scheme 9 of Example 58 to give 34 mg (83%) of 4-bromo-3-carboxymethoxy-5-[3-(cyclopentanecarbonyl-amino)-phenyl]-thiophene-2-carboxylic acid as an off-white solid.

$^1$H NMR (400 MHz, DMSO-D6) δ ppm 1.56 (m, 2 H) 1.70 (m, 4 H) 2.79 (m, 1 H) 4.88 (d, J=10.61 Hz, 2 H) 7.33 (d, J=8.34 Hz, 1 H) 7.44 (t, J=7.96 Hz, 1 H) 7.69 (d, J=8.34 Hz, 1 H) 7.69 (m, 1 H) 8.04 (m, J=1.77, 1.77 Hz, 1 H) 10.09 (s, 1 H).

SI-MS: m/e=466 [M−H]$^-$.

EXAMPLE 63

4-[3-(3-Bromo-5-carboxy-4-carboxymethoxy-thiophen-2-yl)-phenylcarbamoyl]-piperidine-1-carboxylic acid tert-butyl ester The third step of Scheme 9: 4-[3-(3-Bromo-4-tert-butoxycarbonylmethoxy-5-methoxycarbonyl-thiophen-2-yl)-phenylcarbamoyl]-piperidine-1-carboxylic acid tert-butyl ester was prepared in 90% yield as a colorless oil according to the procedure in the third step of Scheme 9 of Example 62, using 5-(3-amino-phenyl)-4-bromo-3-tert-butoxycarbonylmethoxy-thiophene-2-carboxylic acid methyl ester as the starting material.

$^1$H NMR (400 MHz, CHLOROFORM-D) δ ppm 1.32 (m, 3 H) 1.47 (s, 9 H) 1.76 (m, 2 H) 1.91 (m, 2 H) 2.42 (m, 1 H) 2.79 (m, 4 H) 3.87 (s, 3 H) 4.29 (q, J=7.16 Hz, 2 H) 4.90 (s, 2 H) 7.39 (m, 2 H) 7.48 (s, 1 H) 7.64 (m, 1 H) 7.84 (s, 1 H).

The fourth step of Scheme 9: 4-[3-(3-Bromo-4-tert-butoxycarbonylmethoxy-5-methoxycarbonyl-thiophen-2-yl)-phenylcarbamoyl]-piperidine-1-carboxylic acid tert-butyl ester was hydrolyzed as in the fourth step of Scheme 9 of Example 58 to give 85% yield of 4-[3-(3-bromo-5-carboxy-4-carboxymethoxy-thiophen-2-yl)-phenylcarbamoyl]-piperidine-1-carboxylic acid tert-butyl ester as a white solid.

$^1$H NMR (400 MHz, DMSO-D6) δ ppm 1.41 (s, 9 H) 1.50 (m, 2 H) 1.80 (m, 2 H) 2.54 (m, 2 H) 2.78 (m, 2 H) 4.00 (m, 1 H) 4.89 (s, 2 H) 7.34 (d, J=7.83 Hz, 1 H) 7.44 (t, J=7.96 Hz, 1 H) 7.69 (d, J=9.10 Hz, 1 H) 8.03 (d, J=1.77 Hz, 1 H) 10.15 (s, 1 H).

ESI-MS: m/e=581 [M−H]$^-$.

EXAMPLE 64

3-[3-(3-Bromo-5-carboxy-4-carboxymethoxy-thiophen-2-yl)-phenylcarbamoyl]-piperidine-1-carboxylic acid tert-butyl ester The third step of Scheme 9: 3-[3-(3-Bromo-4-tert-butoxycarbonylmethoxy-5-methoxycarbonyl-thiophen-2-yl)-phenylcarbamoyl]-piperidine-1-carboxylic acid tert-butyl ester was obtained in 78% yield as a colorless oil according to the procedure in the third step of Scheme 9 of Example 62, using 5-(3-amino-phenyl)-4-bromo-3-tert-butoxycarbonylmethoxy-thiophene-2-carboxylic acid methyl ester as the starting material.

$^1$H NMR (400 MHz, CHLOROFORM-D) δ ppm 1.32 (t, J=7.20 Hz, 3 H) 1.47 (s, 9 H) 1.54 (m, 4 H) 1.71 (s, 2 H) 1.93 (m, 2 H) 2.54 (m, 1 H) 3.87 (s, 3 H) 4.30 (q, J=7.24 Hz, 2 H) 4.90 (s, 2 H) 7.40 (m, 2 H) 7.64 (m, 1 H) 7.98 (s, 1 H).

The fourth step of Scheme 9: 3-[3-(3-Bromo-4-tert-butoxycarbonylmethoxy-5-methoxycarbonyl-thiophen-2-yl)-phenylcarbamoyl]-piperidine-1-carboxylic acid tert-butyl ester was hydrolyzed as in the fourth step of Scheme 9 of Example 58 to give 3-[3-(3-bromo-5-carboxy-4-carboxymethoxy-thiophen-2-yl)-phenylcarbamoyl]-piperidine-1-carboxylic acid tert-butyl ester in 85% yield as a white solid.

$^1$H NMR (400 MHz, DMSO-D6) δ ppm 1.39 (s, 9 H) 1.70 (m, 2 H) 1.95 (d, J=13.89 Hz, 2 H) 2.78 (t, J=13.39 Hz, 2 H) 3.93 (m, 3 H) 4.89 (s, 2 H) 7.34 (d, J=7.83 Hz, 1 H) 7.45 (t, J=7.96 Hz, 1 H) 7.69 (d, J=8.59 Hz, 1 H) 8.03 (s, 1 H) 10.23 (s, 1 H).

ESI-MS: m/e=581 [M−H]$^-$.

EXAMPLE 65

4-Bromo-3-carboxymethoxy-5-[3-(3,3,3-trifluoro-propionylamino)-phenyl]-thiophene-2-carboxylic acid The third step of Scheme 9: 4-Bromo-3-ethoxycarbonylmethoxy-5-[3-(3,3,3-trifluoro-propionylamino)-phenyl]-thiophene-2-carboxylic acid methyl ester was obtained in 76% yield as a colorless oil according to the procedure in the third step of Scheme 9 of Example 62, using 5-(3-amino-phenyl)-4-bromo-3-tert-butoxycarbonylmethoxy-thiophene-2-carboxylic acid methyl ester as the starting material.

$^1$H NMR (400 MHz, CHLOROFORM-D) δ ppm 1.33 (t, J=7.20 Hz, 3 H) 3.32 (q, J=10.36 Hz, 2 H) 3.84 (s, 3 H) 4.30 (q, J=7.07 Hz, 2 H) 4.88 (s, 2 H) 7.40 (m, 2 H) 7.69 (m, 1 H) 7.75 (s, 1 H) 8.03 (s, 1 H).

The fourth step of Scheme 9: 4-Bromo-3-ethoxycarbonylmethoxy-5-[3-(3,3,3-trifluoro-propionylamino)-phenyl]-thiophene-2-carboxylic acid methyl ester was hydrolyzed as in the fourth step of Scheme 9 of Example 58 to give 4-bromo-3-carboxymethoxy-5-[3-(3,3,3-trifluoro-propionylamino)-phenyl]-thiophene-2-carboxylic acid in 43% yield as a pale yellow solid.

$^1$H NMR (400 MHz, DMSO-D6) δ ppm 3.38 (s, 2 H) 4.90 (s, 2 H) 7.36 (m, 1 H) 7.47 (t, J=7.96 Hz, 1 H) 7.67 (dd, J=8.08, 1.01 Hz, 1 H) 8.00 (t, J=1.77 Hz, 1 H) 10.37 (s, 1 H).

EXAMPLE 66

5-(3-Benzoylamino-phenyl)-4-bromo-3-carboxymethoxy-thiophene-2-carboxylic acid

The third step of Scheme 9: To a 1 mL pyridine solution of 5-(3-amino-phenyl)-4-bromo-3-ethoxycarbonylmethoxy-thiophene-2-carboxylic acid methyl ester (36 mg, 0.087 mmol) was added benzoyl chloride (14 µL, 0.12 mmol) and the reaction mixture was allowed to stir at room temperature for 3 hours. TLC indicated a complete reaction. Diluted with 8-10 mL 2N HCl and extracted with EtOAc. The organic layer was washed with saturated sodium bicarbonate solution, brine and dried over MgSO$_4$. Evaporation gave the crude product which was chromatographed on silica gel using a gradient of hexane/EtOAc (5 to 35%) as eluent. Pure fractions were combined and evaporated to give 27 mg (60%) 5-(3-benzoylamino-phenyl)-4-bromo-3-ethoxycarbonylmethoxy-thiophene-2-carboxylic acid methyl ester as a colorless glassy solid.

$^1$H NMR (400 MHz, CHLOROFORM-D) δ ppm 1.32 (t, J=7.07 Hz, 3 H) 3.88 (s, 3 H) 4.29 (q, J=7.16 Hz, 2 H) 4.91 (s, 2 H) 7.48 (m, 4 H) 7.56 (m, 1 H) 7.76 (m, 1 H) 7.89 (m, 2 H) 7.98 (m, 2 H).

The fourth step of Scheme 9: 5-(3-Benzoylamino-phenyl)-4-bromo-3-ethoxycarbonylmethoxy-thiophene-2-carboxylic acid methyl ester was hydrolyzed as in the fourth step of Scheme 9 of Example 58 to give 27 mg (100%) of 5-(3-benzoylamino-phenyl)-4-bromo-3-carboxymethoxy-thiophene-2-carboxylic acid as a pale yellow solid.

$^1$H NMR (400 MHz, DMSO-D6) δ ppm 4.90 (s, 2 H) 7.42 (m, 1 H) 7.53 (m, 3 H) 7.61 (m, 1 H) 7.91 (m, 1 H) 7.97 (m, 2 H) 8.21 (t, J=1.77 Hz, 1 H) 10.46 (s, 1 H).

ESI-MS: m/e=474 [M–H]$^-$.

EXAMPLE 67

4-Bromo-3-carboxymethoxy-5-{3-[(furan-2-carbonyl)-amino]-phenyl}-thiophene-2-carboxylic acid The third step of Scheme 9: 4-Bromo-3-ethoxycarbonyl-methoxy-5-{3-[(furan-2-carbonyl)-amino]-phenyl}-thiophene-2-carboxylic acid methyl ester was obtained in 90% yield as a colorless solid according to the procedure in the third step of Scheme 9 of Example 66, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.20 Hz, 3 H) 3.88 (s, 3 H) 4.30 (q, J=7.24 Hz, 2 H) 4.92 (s, 2 H) 6.58 (dd, J=3.41, 1.64 Hz, 1 H) 7.27 (m, 1 H) 7.45 (m, 2 H) 7.54 (d, J=1.01 Hz, 1 H) 7.75 (m, 1 H) 8.01 (m, 1 H) 8.18 (s, 1 H).

The fourth step of Scheme 9: 4-Bromo-3-ethoxycarbonyl-methoxy-5-{3-[(furan-2-carbonyl)-amino]-phenyl}-thiophene-2-carboxylic acid methyl ester was hydrolyzed as in the fourth step of Scheme 9 of Example 58 to give 4-bromo-3-carboxymethoxy-5-{3-[(furan-2-carbonyl)-amino]-phenyl}-thiophene-2-carboxylic acid in 19% yield as an off-white solid.

$^1$H NMR (400 MHz, DMSO-D6) δ ppm 4.86 (s, 2 H) 6.73 (dd, J=3.54, 1.77 Hz, 1 H) 7.37 (d, J=3.28 Hz, 1 H) 7.41 (d, J=6.82 Hz, 1 H) 7.50 (t, J=7.96 Hz, 1 H) 7.89 (d, J=8.08 Hz, 1 H) 7.97 (d, J=1.01 Hz, 1 H) 8.16 (s, 1 H) 10.40 (s, 1 H).

ESI-MS: m/e=464 [M–H]$^-$.

EXAMPLE 68

4-Bromo-3-carboxymethoxy-5-{3-[(furan-3-carbonyl)-amino]-phenyl}-thiophene-2-carboxylic acid The third step of Scheme 9: 4-Bromo-3-ethoxycarbonyl-methoxy-5-{3-[(furan-3-carbonyl)-amino]-phenyl}-thiophene-2-carboxylic acid methyl ester was obtained in 66% as a colorless glassy solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.07 Hz, 3 H) 3.87 (s, 3 H) 4.29 (q, J=7.24 Hz, 2 H) 4.92 (s, 2 H) 6.78 (m, 1 H) 7.42 (m, 2 H) 7.50 (t, J=1.64 Hz, 1 H) 7.72 (m, 1 H) 7.76 (s, 1 H) 7.90 (m, 1 H) 8.09 (dd, J=1.39, 0.88 Hz, 1 H).

The fourth step of Scheme 9: 4-Bromo-3-ethoxycarbonyl-methoxy-5-{3-[(furan-3-carbonyl)-amino]-phenyl}-thiophene-2-carboxylic acid methyl ester was hydrolyzed as in the fourth step of Scheme 9 of Example 58 to give 38% of 4-bromo-3-carboxymethoxy-5-{3-[(furan-3-carbonyl)-amino]-phenyl}-thiophene-2-carboxylic acid as a pale yellow solid.

$^1$H NMR (400 MHz, DMSO-D6) δ ppm 4.82 (s, 2 H) 7.02 (m, 1 H) 7.39 (m, 1 H) 7.50 (t, J=7.83 Hz, 1 H) 7.82 (m, 1 H) 7.85 (dd, J=2.02, 1.01 Hz, 1 H) 8.10 (d, J=1.52 Hz, 1 H) 8.41 (dd, J=1.52, 0.76 Hz, 1 H) 10.12 (s, 1 H).

ESI-MS: m/e=464 [M–H]$^-$.

EXAMPLE 69

4-Bromo-3-carboxymethoxy-5-[3-(2-trifluoromethyl-benzoylamino)-phenyl]-thiophene-2-carboxylic acid The third step of Scheme 9: 4-Bromo-3-ethoxycarbonyl-methoxy-5-[3-(2-trifluoromethyl-benzoylamino)-phenyl]-thiophene-2-carboxylic acid methyl ester was obtained in 89% yield as a colorless glassy solid according to the procedure in the third step of Scheme 9 of Example 66, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.31 (t, J=7.20 Hz, 3 H) 3.87 (s, 3 H) 4.27 (q, J=7.07 Hz, 2 H) 4.90 (s, 2 H) 7.47 (t, J=4.55 Hz, 2 H) 7.68 (m, 6 H) 7.89 (s, 1 H)

The fourth step of Scheme 9: 4-Bromo-3-ethoxycarbonyl-methoxy-5-[3-(2-trifluoromethyl-benzoylamino)-phenyl]-thiophene-2-carboxylic acid methyl ester was hydrolyzed as in the fourth step of Scheme 9 of Example 58 in 45% yield to give 4-bromo-3-carboxymethoxy-5-[3-(2-trifluoromethyl-benzoylamino)-phenyl]-thiophene-2-carboxylic acid as a white solid.

$^1$H NMR (400 MHz, DMSO-D6) δ ppm 4.70 (s, 2 H) 7.40 (d, J=8.08 Hz, 1 H) 7.50 (t, J=7.83 Hz, 1 H) 7.75 (m, 2 H) 7.82 (m, 2 H) 7.87 (d, J=7.58 Hz, 1 H) 8.00 (s, 1 H) 10.79 (s, 1 H).

ESI-MS: m/e=542 [M–H]$^-$.

EXAMPLE 70

4-Bromo-3-carboxymethoxy-5-[3-(2-fluoro-benzoylamino)-phenyl]-thiophene-2-carboxylic acid The third step of Scheme 9: 4-Bromo-3-ethoxycarbonyl-methoxy-5-[3-(2-fluoro-benzoylamino)-phenyl]-thiophene-2-carboxylic acid methyl ester was obtained in 73% yield as a colorless glassy solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.33 (t, J=7.07 Hz, 3 H) 3.88 (s, 3 H) 4.30 (q, J=7.16 Hz, 2 H) 4.92 (s, 2 H) 7.20 (m, 1 H) 7.33 (m, 1 H) 7.46 (m, 2 H) 7.55 (m, 1 H) 7.74 (m, 1 H) 8.03 (s, 1 H) 8.18 (td, J=7.96, 2.02 Hz, 1 H) 8.55 (d, J=15.92 Hz, 1 H).

The fourth step of Scheme 9: 4-Bromo-3-ethoxycarbonyl-methoxy-5-[3-(2-fluoro-benzoylamino)-phenyl]-thiophene-2-carboxylic acid methyl ester was hydrolyzed as in the fourth step of Scheme 9 of Example 58 to give 4-bromo-3-carboxymethoxy-5-[3-(2-fluoro-benzoylamino)-phenyl]-thiophene-2-carboxylic acid in 75% yield as a white solid.

$^1$H NMR (400 MHz, DMSO-D6) δ ppm 4.91 (s, 2 H) 7.38 (m, 3 H) 7.52 (t, J=7.96 Hz, 1 H) 7.60 (m, 1 H) 7.70 (m, 1 H) 7.83 (d, J=8.34 Hz, 1 H) 8.15 (s, 1 H) 10.66 (s, 1 H).

ESI-MS: n/e=492 [M–H]$^-$.

EXAMPLE 71

4-Bromo-3-carboxymethoxy-5-[3-(3-fluoro-benzoylamino)-phenyl]-thiophene-2-carboxylic acid The third step of Scheme 9: 4-Bromo-3-ethoxycarbonylmethoxy-5-[3-(3-fluoro-benzoylamino)-phenyl]-thiophene-2-carboxylic acid methyl ester was obtained in 75% yield as a pale yellow solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.07 Hz, 3 H) 3.87 (s, 3 H) 4.29 (q, J=7.24 Hz, 2 H) 4.91 (s, 2 H) 7.26 (m, 1 H) 7.45 (m, 3 H) 7.62 (m, 1 H) 7.67 (m, 1 H) 7.76 (m, 1 H) 7.95 (s, 1 H) 8.08 (s, 1 H).

The fourth step of Scheme 9: 4-Bromo-3-ethoxycarbonylmethoxy-5-[3-(3-fluoro-benzoylamino)-phenyl]-thiophene-2-carboxylic acid methyl ester was hydrolyzed as in the fourth step of Scheme 9 of Example 58 to give 4-bromo-3-carboxymethoxy-5-[3-(3-uoro-benzoylamino)-phenyl]-thiophene-2-carboxylic acid in 81% yield as a pale yellow solid.

$^1$H NMR (400 MHz, DMSO-D6) δ ppm 4.90 (s, 2 H) 7.49 (m, 3 H) 7.61 (m, 1 H) 7.80 (m, 1 H) 7.84 (d, J=7.83 Hz, 1 H) 7.91 (dd, J=8.08, 1.01 Hz, 1 H) 8.19 (m, 1 H) 10.52 (s, 1 H).

ESI-MS: m/e=492 [M−H]$^-$.

EXAMPLE 72

4-Bromo-3-carboxymethoxy-5-{3-[(pyridine-3-carbonyl)-amino]-phenyl}-thiophene-2-carboxylic acid The third step of Scheme 9: 4-Bromo-3-ethoxycarbonylmethoxy-5-{3-[(pyridine-3-carbonyl)-amino]-phenyl}-thiophene-2-carboxylic acid methyl ester was obtained in 75% yield as a white solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.20 Hz, 3 H) 3.88 (s, 3 H) 4.29 (q, J=7.07 Hz, 2 H) 4.92 (s, 2 H) 7.47 (m, 3 H) 7.77 (m, 1 H) 7.98 (m, 1 H) 8.09 (s, 1 H) 8.24 (m, 1 H) 8.80 (dd, J=4.80, 1.52 Hz, 2 H) 9.13 (d, J=1.52 Hz, 1 H).

The fourth step of Scheme 9: 4-Bromo-3-ethoxycarbonylmethoxy-5-{3-[(pyridine-3-carbonyl)-amino]-phenyl}-thiophene-2-carboxylic acid methyl ester was hydrolyzed as in the fourth step of Scheme 9 of Example 58 to give 4-bromo-3-carboxymethoxy-5-{3-[(pyridine-3-carbonyl)-amino]-phenyl}-thiophene-2-carboxylic acid in 81% yield as a yellow solid.

$^1$H NMR (400 MHz, DMSO-D6) δ ppm 4.89 (s, 2 H) 7.44 (m, 1 H) 7.53 (t, J=7.96 Hz, 1 H) 7.59 (dd, J=8.08, 5.05 Hz, 1 H) 7.90 (m, 1 H) 8.19 (t, J=1.77 Hz, 1 H) 8.32 (m, 1 H) 8.79 (d, J=3.79 Hz, 1 H) 9.13 (s, 1 H) 10.65 (s, 1 H).

EXAMPLE 73

4-Bromo-3-carboxymethoxy-5-[3-(4,4,4-trifluoro-butyrylamino)-phenyl]-thiophene-2-carboxylic acid The third step of Scheme 9: 4-Bromo-3-ethoxycarbonylmethoxy-5-[3-(4,4,4-trifluoro-butyrylamino)-phenyl]-thiophene-2-carboxylic acid methyl ester was obtained in 76% yield as a colorless glassy solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (m, 3 H) 2.62 (m, 4 H) 3.84 (s, 3 H) 4.30 (q, J=7.07 Hz, 2 H) 4.89 (s, 2 H) 7.38 (m, 2 H) 7.66 (m, 1 H) 7.77 (d, J=5.31 Hz, 2 H).

The fourth step of Scheme 9: 4-Bromo-3-ethoxycarbonylmethoxy-5-[3-(4,4,4-trifluoro-butyrylamino)-phenyl]-thiophene-2-carboxylic acid methyl ester was hydrolyzed as in the fourth step of Scheme 9 of Example 59 to give 4-bromo-3-carboxymethoxy-5-[3-(4,4,4-trifluoro-butyrylamino)-phenyl]-thiophene-2-carboxylic acid in 90% yield as a white solid.

$^1$H NMR (400 MHz, DMSO-D6) δ ppm 2.61 (m, 4 H) 4.90 (s, 2 H) 7.36 (d, J=7.83 Hz, 1 H) 7.47 (t, J=7.96 Hz, 1 H) 7.66 (dd, J=8.97, 1.14 Hz, 1 H) 8.02 (s, 1 H) 10.31 (s, 1 H).

ESI-MS: m/e=494 [M−H]$^-$.

EXAMPLE 74

4-Bromo-3-carboxymethoxy-5-{3-[(2-hydroxy-pyridine-3-carbonyl)-amino]-phenyl}-thiophene-2-carboxylic acid The third step of Scheme 9: To a 1.5 mL DMF solution of 5-(3-amino-phenyl)-4-bromo-3-ethoxycarbonylmethoxy-thiophene-2-carboxylic acid methyl ester were added 2-hydroxynicotinic acid (21 mg, 0.15 mmol), HATU (46 mg, 0.12 mmol), and diisopropylethyl amine (40 μL, 0.22 mmol). The resulting mixture was heated to 60° C. for 3 hours until TLC showed reaction had gone to completion. The reaction mixture was diluted with water and extracted with $CH_2Cl_2$ (2×25 mL). The organic phases were combined and washed with dilute aqueous HCl, saturated sodium bicarbonate solution, and dried over $MgSO_4$. They were then filtered and evaporated to give a pale yellow semisolid, which was triturated with 5 mL of 1:1 $CH_2Cl_2$:Hexane. The product was filtered and washed with hexane to give 36 mg (67%) 4-bromo-3-ethoxycarbonylmethoxy-5-{3-[(2-hydroxy-pyridine-3-carbonyl)-amino]-phenyl}-thiophene-2-carboxylic acid methyl ester as a white solid.

$^1$H NMR (400 MHz, DMSO-D6) δ ppm 1.23 (t, J=7.07 Hz, 3 H) 3.83 (s, 3 H) 4.19 (q, J=7.07 Hz, 2 H) 4.98 (s, 2 H) 6.60 (t, J=6.82 Hz, 1 H) 7.42 (m, 1 H) 7.53 (t, J=7.83 Hz, 1 H) 7.68 (m, 1 H) 7.84 (m, 1 H) 8.22 (t, J=1.89 Hz, 1 H) 8.48 (dd, J=7.20, 2.15 Hz, 1 H) 12.37 (s, 1 H) 12.80 (s, 1 H).

The fourth step of Scheme 9: 4-Bromo-3-ethoxycarbonylmethoxy-5-{3-[(2-hydroxy-pyridine-3-carbonyl)-amino]-phenyl}-thiophene-2-carboxylic acid methyl ester was hydrolyzed as that in the fourth step of Scheme 9 of Example 58 to give 22 mg (69%) of 4-bromo-3-carboxymethoxy-5-{3-[(2-hydroxy-pyridine-3-carbonyl)-amino]-phenyl}-thiophene-2-carboxylic acid as a white solid.

$^1$H NMR (400 MHz, DMSO-D6) δ ppm 4.67 (s, 2 H) 6.59 (t, J=6.69 Hz, 1 H) 7.37 (d, J=7.83 Hz, 1 H) 7.49 (t, J=7.96 Hz, 1 H) 7.67 (m, 1 H) 7.83 (m, 1 H) 8.10 (s, 1 H) 8.48 (dd, J=7.20, 2.15 Hz, 1 H) 12.34 (s, 1 H) 12.80 (s, 1 H).

ESI-MS: m/e=491 [M−H]$^-$.

EXAMPLE 75

4-Bromo-3-carboxymethoxy-5-{3-[(pyridine-4-carbonyl)-amino]-phenyl}-thiophene-2-carboxylic acid The third step of Scheme 9: 4-Bromo-3-ethoxycarbonylmethoxy-5-{3-[(pyridine-4-carbonyl)-amino]-phenyl}-thiophene-2-carboxylic acid methyl ester was obtained in 60% yield as a colorless glassy solid according to the procedure in the third step of Scheme 9 of Example 66, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.31 (t, J=7.20 Hz, 3 H) 3.86 (s, 3 H) 4.28 (q, J=7.24 Hz, 2 H) 4.91 (s, 2 H) 7.46 (m, 2 H) 7.78 (m, 3 H) 7.96 (s, 1 H) 8.35 (s, 1 H) 8.79 (m, 1 H).

The fourth step of Scheme 9: 4-Bromo-3-ethoxycarbonylmethoxy-5-{3-[(pyridine-4-carbonyl)-amino]-phenyl}-thiophene-2-carboxylic acid methyl ester was hydrolyzed as that in the fourth step of Scheme 9 of Example 58 to give 4-bromo-3-carboxymethoxy-5-{3-[(pyridine-4-carbonyl)-amino]-phenyl}-thiophene-2-carboxylic acid in 87% yield as a yellow solid.

$^1$H NMR (400 MHz, DMSO-D6) δ ppm 4.91 (s, 2 H) 7.46 (d, J=8.08 Hz, 1 H) 7.55 (t, J=7.96 Hz, 1 H) 7.90 (m, 3 H) 8.20 (s, 1 H) 8.82 (s, 1 H) 10.71 (s, 1 H)

EXAMPLE 76

4-Bromo-3-carboxymethoxy-5-{3-[(quinoline-3-carbonyl)-amino]-phenyl}-thiophene-2-carboxylic acid The third step of Scheme 9: 4-Bromo-3-ethoxycarbonylmethoxy-5-{3-[(quinoline-3-carbonyl)-amino]-phenyl}-thiophene-2-carboxylic acid methyl ester in 75% yield as an off-white solid according to the procedure in the third step of Scheme 9 of Example 74, using 5-(3-amino-phenyl)-4-bromo-3-ethoxycarbonylmethoxy-thiophene-2-carboxylic acid methyl ester as the starting material.

$^1$H NMR (400 MHz, DMSO-D6) δ ppm 1.23 (t, J=7.07 Hz, 3 H) 3.83 (s, 3 H) 4.19 (q, J=7.16 Hz, 2 H) 5.00 (s, 2 H) 7.48 (d, J=8.08 Hz, 1 H) 7.58 (t, J=7.96 Hz, 1 H) 7.75 (t, J=7.45 Hz, 1 H) 7.92 (m, 1 H) 8.15 (m, 1 H) 8.28 (s, 1 H) 8.99 (d, J=1.77 Hz, 1 H) 9.38 (d, J=2.27 Hz, 1 H) 10.84 (s, 1 H)

The fourth step of Scheme 9: 4-Bromo-3-ethoxycarbonylmethoxy-5-{3-[(quinoline-3-carbonyl)-amino]-phenyl}-thiophene-2-carboxylic acid methyl ester was hydrolyzed as that in the fourth step of Scheme 9 of Example 58 to give 4-bromo-3-carboxymethoxy-5-{3-[(quinoline-3-carbonyl)-amino]-phenyl}-thiophene-2-carboxylic acid in 81% yield as an orange solid.

$^1$H NMR (400 MHz, DMSO-D6) δ ppm 4.93 (s, 2 H) 7.47 (d, J=8.08 Hz, 1 H) 7.57 (t, J=8.08 Hz, 1 H) 7.75 (t, J=7.71 Hz, 1 H) 7.95 (m, 2 H) 8.15 (m, 2 H) 8.26 (s, 1 H) 9.03 (s, 1 H) 9.40 (d, J=1.77 Hz, 1 H) 10.85 (s, 1 H).

EXAMPLE 77

4-Bromo-3-carboxymethoxy-5-{3-[(pyridine-2-carbonyl)-amino]-phenyl}-thiophene-2-carboxylic acid The third step of Scheme 9: 4-Bromo-3-ethoxycarbonylmethoxy-5-{3-[(pyridine-2-carbonyl)-amino]-phenyl}-thiophene-2-carboxylic acid methyl ester was obtained in 65% yield as a pale yellow solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.33 (t, J=7.07 Hz, 3 H) 3.88 (s, 3 H) 4.30 (q, J=7.07 Hz, 2 H) 4.93 (s, 2 H) 7.46 (m, 1 H) 7.51 (m, 2 H) 7.93 (td, J=7.71, 1.77 Hz, 2 H) 8.15 (t, J=1.77 Hz, 1 H) 8.31 (m, 1 H) 8.64 (m, J=3.79 Hz, 1 H) 10.14 (s, 1 H).

The fourth step of Scheme 9: 4-Bromo-3-ethoxycarbonylmethoxy-5-{3-[(pyridine-2-carbonyl)-amino]-phenyl}-thiophene-2-carboxylic acid methyl ester was hydrolyzed as in the fourth step of Scheme 9 of Example 58 to give 4-bromo-3-carboxymethoxy-5-{3-[(pyridine-2-carbonyl)-amino]-phenyl}-thiophene-2-carboxylic acid in 92% yield as an off-white solid.

$^1$H NMR (400 MHz, DMSO-D6) δ ppm 4.91 (s, 2 H) 7.45 (d, J=7.58 Hz, 1 H) 7.53 (t, J=7.83 Hz, 1 H) 8.02 (d, J=9.35 Hz, 1 H) 8.09 (m, 1 H) 8.18 (d, J=7.58 Hz, 1 H) 8.38 (s, 1 H) 8.77 (d, J=4.29 Hz, 1 H) 10.90 (s, 1 H).

ESI-MS: m/e=475 [M−H]$^-$.

EXAMPLE 78

4-Bromo-3-carboxymethoxy-5-{3-[(1-oxy-pyridine-3-carbonyl)-amino]-phenyl}-thiophene-2-carboxylic acid The third step of Scheme 9: To a 1.5 mL DMF solution of 5-(3-amino-phenyl)-4-bromo-3-ethoxycarbonylmethoxy-thiophene-2-carboxylic acid methyl ester were added nicotinic acid N-oxide (21 mg, 0.15 mmol), HATU (46 mg, 0.12 mmol), and diisopropylethyl amine (40 μL, 0.22 mmol) and the resulting mixture was heated to 60° C. overnight, then cooled to room temperature. 20 mL water and 1 mL 1N HCl were added. The mixture was stirred at room temperature for 30 minutes, then filtered, washed with water and vacuum-oven dried to give 43 mg (77%) of 4-bromo-3-ethoxycarbonylmethoxy-5-{3-[(1-oxy-pyridine-3-carbonyl)-amino]-phenyl}-thiophene-2-carboxylic acid methyl ester as an off-white solid.

$^1$H NMR (400 MHz, DMSO-D6) δ ppm 1.23 (t, J=7.20 Hz, 3 H) 3.83 (s, 3 H) 4.18 (q, J=7.07 Hz, 2 H) 4.99 (s, 2 H) 7.47 (m, 1 H) 7.55 (m, 1 H) 7.60 (m, 1 H) 7.83 (d, J=8.08 Hz, 1 H) 7.88 (m, 1 H) 8.19 (t, J=1.77 Hz, 1 H) 8.42 (m, 1 H) 8.75 (t, J=1.39 Hz, 1 H) 10.68 (s, 1 H).

The fourth step of Scheme 9: 4-Bromo-3-ethoxycarbonylmethoxy-5-{3-[(1-oxy-pyridine-3-carbonyl)-amino]-phenyl}-thiophene-2-carboxylic acid methyl ester was hydrolyzed as in the fourth step of Scheme 9 of Example 58 to give 4-bromo-3-carboxymethoxy-5-{3-[(1-oxy-pyridine-3-carbonyl)-amino]-phenyl}-thiophene-2-carboxylic acid in 71% yield as a tan-colored solid.

$^1$H NMR (400 MHz, DMSO-D6) δ ppm 4.91 (s, 2 H) 7.46 (d, J=7.83 Hz, 1 H) 7.57 (m, 2 H) 7.83 (d, J=8.08 Hz, 1 H) 7.89 (d, J=8.59 Hz, 1 H) 8.16 (s, 1 H) 8.42 (d, J=6.32 Hz, 1 H) 8.76 (s, 1 H) 10.67 (s, 1 H).

ESI-MS: m/e=491 [M−H]$^-$.

EXAMPLE 79

4-Bromo-3-carboxymethoxy-5-[3-(2-pyridin-2-yl-acetylamino)-phenyl]-thiophene-2-carboxylic acid The third step of Scheme 9: 4-Bromo-3-ethoxycarbonylmethoxy-5-[3-(2-pyridin-2-yl-acetylamino)-phenyl]-thiophene-2-carboxylic acid methyl ester was obtained in 77% yield as a pale yellow solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.20 Hz, 3 H) 3.87 (s, 3 H) 3.90 (s, 2 H) 4.30 (q, J=7.16 Hz, 2 H) 4.90 (s, 2 H) 7.27 (m, 1 H) 7.31 (d, J=7.83 Hz, 1 H) 7.38 (m, 2 H) 7.66 (dt, J=7.39, 1.99 Hz, 1 H) 7.72 (td, J=7.71, 1.77 Hz, 1 H) 7.89 (m, 1 H) 8.63 (d, J=5.81 Hz, 1 H) 10.13 (s, 1 H).

The fourth step of Scheme 9: 4-Bromo-3-ethoxycarbonyl-methoxy-5-[3-(2-pyridin-2-yl-acetylamino)-phenyl]-thiophene-2-carboxylic acid methyl ester was hydrolyzed as in the fourth step of Scheme 9 of Example 58 to give 4-bromo-3-carboxymethoxy-5-[3-(2-pyridin-2-yl-acetylamino)-phenyl]-thiophene-2-carboxylic acid in 84% yield as a yellow solid.

$^1$H NMR (400 MHz, DMSO-D6) δ ppm 3.89 (s, 2 H) 4.89 (s, 2 H) 7.29 (m, 1 H) 7.35 (d, J=7.58 Hz, 1 H) 7.45 (m, 2 H) 7.70 (d, J=8.08 Hz, 1 H) 7.78 (m, 1 H) 8.05 (s, 1 H) 8.52 (d, J=4.04 Hz, 1 H) 10.48 (s, 1 H).

ESI-MS: m/e=445 [M–CO$_2$]$^-$.

EXAMPLE 80

4-Bromo-3-carboxymethoxy-5-[3-(2-pyridin-3-yl-acetylamino)-phenyl]-thiophene-2-carboxylic acid The third step of Scheme 9: 4-Bromo-3-ethoxycarbonyl-methoxy-5-[3-(2-pyridin-3-yl-acetylamino)-phenyl]-thiophene-2-carboxylic acid methyl ester was obtained in 52% yield as a pale yellow glassy solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.07 Hz, 3 H) 3.75 (s, 2 H) 3.85 (s, 3 H) 4.29 (d, J=7.07 Hz, 2 H) 4.89 (s, 2 H) 7.32 (dd, J=7.83, 4.80 Hz, 1 H) 7.38 (d, J=5.31 Hz, 2 H) 7.61 (m, 1 H) 7.77 (m, 2 H) 7.95 (s, 1 H) 8.56 (m, 2 H).

The fourth step of Scheme 9: 4-Bromo-3-ethoxycarbonyl-methoxy-5-[3-(2-pyridin-3-yl-acetylamino)-phenyl]-thiophene-2-carboxylic acid methyl ester was hydrolyzed as in the fourth step of Scheme 9 of Example 58 to give 4-bromo-3-carboxymethoxy-5-[3-(2-pyridin-3-yl-acetylamino)-phenyl]-thiophene-2-carboxylic acid in 82% yield as a pale yellow solid.

$^1$H NMR (400 MHz, DMSO-D6) δ ppm 3.75 (s, 2 H) 4.89 (s, 2 H) 7.38 (m, 2 H) 7.46 (t, J=8.08 Hz, 1 H) 7.68 (d, J=8.84 Hz, 1 H) 7.78 (d, J=8.08 Hz, 1 H) 8.02 (s, 1 H) 8.51 (m, 2 H) 10.47 (s, 1 H).

ESI-MS: m/e=445 [M–CO2]$^-$.

EXAMPLE 81

4-Bromo-3-carboxymethoxy-5-{3-[(pyrazine-2-carbonyl)-amino]-phenyl}-thiophene-2-carboxylic acid The third step of Scheme 9: 4-Bromo-3-ethoxycarbonyl-methoxy-5-{3-[(pyrazine-2-carbonyl)-amino]-phenyl}-thiophene-2-carboxylic acid methyl ester was obtained in 42% yield as a white solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.33 (t, J=7.20 Hz, 3 H) 3.89 (s, 3 H) 4.30 (q, J=7.07 Hz, 2 H) 4.93 (s, 2 H) 7.49 (m, 2 H) 7.86 (m, 1 H) 8.13 (s, 1 H) 8.62 1 H) 8.84 (d, J=2.27 Hz, 1 H) 9.53 (s, 1 H) 9.77 (s, 1 H).

The fourth step of Scheme 9: 4-Bromo-3-ethoxycarbonyl-methoxy-5-{3-[(pyrazine-2-carbonyl)-amino]-phenyl}-thiophene-2-carboxylic acid methyl ester was hydrolyzed as in the fourth step of Scheme 9 of Example 58 to obtain a tan-colored solid that was not pure by NMR. The compound was purified by preparative HPLC to give 8 mg (22%) of 4-bromo-3-carboxymethoxy-5-{3-[(pyrazine-2-carbonyl)-amino]-phenyl}-thiophene-2-carboxylic acid as an off-white solid.

$^1$H NMR (400 MHz, DMSO-D6) δ ppm 4.77 (s, 2 H) 7.45 (d, J=7.58 Hz, 1 H) 7.53 (t, J=7.83 Hz, 1 H) 8.02 (d, J=7.58 Hz, 1 H) 8.31 (s, 1 H) 8.84 (s, 1 H) 8.95 (s, 1 H) 9.32 (s, 1 H) 10.99 (s, 1 H).

ESI-MS: m/e=478 [M+H]$^+$.

EXAMPLE 82

4-Bromo-3-carboxymethoxy-5-[3-(2-pyridin-4-yl-acetylamino)-phenyl]-thiophene-2-carboxylic acid The third step of Scheme 9: 4-Bromo-3-ethoxycarbonyl-methoxy-5-[3-(2-pyridin-4-yl-acetylamino)-phenyl]-thiophene-2-carboxylic acid methyl ester was obtained in 47% yield as a colorless glassy solid according to the procedure in the third step of Scheme 9 of Example 62, using 5-(3-amino-phenyl)-4-bromo-3-ethoxycarbonylmethoxy-thiophene-2-carboxylic acid methyl ester as the starting material.

$^1$H NMR (400 MHz, CHLOROFORM-D) δ ppm 1.32 (t, J=7.20 Hz, 3 H) 3.75 (s, 2 H) 3.85 (s, 3 H) 4.29 (q, J=7.24 Hz, 2 H) 4.89 (s, 2 H) 7.30 (d, J=5.31 Hz, 2 H) 7.38 (m, 2 H) 7.61 (m, 1 H) 7.78 (s, 1 H) 7.90 (s, 1 H) 8.59 (s, 2 H).

The fourth step of Scheme 9: 4-Bromo-3-ethoxycarbonyl-methoxy-5-[3-(2-pyridin-4-yl-acetylamino)-phenyl]-thiophene-2-carboxylic acid methyl ester was hydrolyzed as in the fourth step of Scheme 9 of Example 58 to give 4-bromo-3-carboxymethoxy-5-[3-(2-pyridin-4-yl-acetylamino)-phenyl]-thiophene-2-carboxylic acid in 74% yield as a yellow solid.

$^1$H NMR (400 MHz, DMSO-D6) δ ppm 3.78 (s, 2 H) 4.89 (s, 2 H) 7.36 (m, 1 H) 7.42 (d, J=6.06 Hz, 2 H) 7.47 (t, J=7.96 Hz, 1 H) 7.68 (m, 1 H) 8.02 (t, J=1.77 Hz, 1 H) 8.55 (m, 2 H) 10.50 (s, 1 H).

EXAMPLE 83

4-Bromo-3-carboxymethoxy-5-{3-[(piperidine-4-carbonyl)-amino]-phenyl}-thiophene-2-carboxylic acid trifluoroacetic acid salt 4-[3-(3-Bromo-5-carboxy-4-carboxymethoxy-thiophen-2-yl)-phenylcarbamoyl]-piperidine-1-carboxylic acid tert-butyl ester (for preparation, see Example 63) was dissolved in 1 mL CH$_2$Cl$_2$ and trifluoroacetic acid (1 mL) was added and the mixture was allowed to stir at room temperature for 90 minutes. Evaporate the reaction mixture and co-evaporate twice with CH$_2$Cl$_2$ and vacuum-oven dry to give 26 mg (78%) of 4-bromo-3-carboxymethoxy-5-{3-[(piperidine-4-carbonyl)-amino]-phenyl}-thiophene-2-carboxylic acid trifluoroacetic acid salt as a pale gray solid.

$^1$H NMR (400 MHz, DMSO-D6) δ ppm 1.82 (m, 2 H) 1.98 (m, 2 H) 2.66 (m, 1 H) 2.94 (m, 2 H) 3.36 (m, 2 H) 4.91 (s, 2 H) 7.37 (m, 1 H) 7.46 (m, 1 H) 7.70 (m, 1 H) 8.03 (s, 1 H) 8.58 (m, 1 H) 10.26 (s, 1 H).

ESI-MS: m/e=439 [M–CO$_2$]$^-$

EXAMPLE 84

4-Bromo-3-carboxymethoxy-5-[3-(cyclohexanecarbonyl-amino)-phenyl-thiophene-2-carboxylic acid 3-[3-(3-Bromo-5-carboxy-4-carboxymethoxy-thiophen-2-yl)-phenylcarbamoyl]-piperidine-1-carboxylic acid tert-butyl ester (for preparation see Example 64) was treated with trifluoroacetic acid as in Example 83 to give 4-bromo-3-carboxymethoxy-5-[3-(cyclohexanecarbonyl-amino)-phenyl]-thiophene-2-carboxylic acid in 64% yield as a pale yellow solid.

$^1$H NMR (400 MHz, DMSO-D6) δ ppm 1.67 (m, 2 H) 1.85 (m, 1 H) 2.05 (m, 1 H) 2.83 (dd, J=9.98, 3.16 Hz, 1 H) 2.94 (m, 1 H) 3.10 (m, 1 H) 3.19 (m, 1 H) 3.35 (m, 1 H) 4.91 (s, 2 H) 7.38 (d, J=7.83 Hz, 1 H) 7.48 (t, J=8.08 Hz, 1 H) 7.67 (d, J=8.59 Hz, 1 H) 8.04 (s, 1 H) 8.57 (s, 1 H) 10.40 (s, 1 H).

ESI-MS: m/e=439 [M−CO$_2$]$^-$.

EXAMPLE 85

5-(3-Acetylamino-phenyl)-4-bromo-3-carboxymethoxy-thiophene-2-carboxylic acid

The third step of Scheme 9: 5-(3-acetylamino-phenyl)-4-bromo-3-tert-butoxycarbonylmethoxy-thiophene-2-carboxylic acid methyl ester (11 mg, 99+%) was prepared according to the procedure in the first step of Scheme 4 of Example 22, using 5-(3-amino-phenyl)-4-bromo-3-tert-butoxycarbonylmethoxy-thiophene-2-carboxylic acid methyl ester (10 mg, 0.023 mmol) as the starting material.

$^1$H NMR (400 MHz, CHLOROFORM-D) δ ppm 1.50 (s, 9 H) 2.35 (s, 3 H) 3.88 (s, 3 H) 4.84 (s, 2 H) 7.23 (ddd, J=7.89, 2.08, 1.14 Hz, 1 H) 7.51 (t, J=1.89 Hz, 1 H) 7.57 (t, J=7.83 Hz, 1 H) 7.68 (m, 1 H).

The fourth step of Scheme 9: 5-(3-Acetylamino-phenyl)-4-bromo-3-carbonylmethoxy-thiophene-2-carboxylic acid (5.3 mg, 86%) was prepared as a white solid according to the procedure in the second step of Scheme 1 of Example 1 using 5-(3-acetylamino-phenyl)-4-bromo-3-tert-butoxycarbonylmethoxy-thiophene-2-carboxylic acid methyl ester (7.2 mg) as the starting material.

$^1$H NMR (400 MHz, DMSO-D6) δ ppm 2.07 (s, 3 H) 4.89 (s, 2 H) 7.33 (m, 1 H) 7.44 (t, J=8.08 Hz, 1 H) 7.66 (m, 1 H) 8.00 (t, J=1.64 Hz, 1 H).

EXAMPLE 86

4-Bromo-3-carboxymethoxy-5-(3-isobutyrylaminophenyl)-thiophene-2-carboxylic acid The third step of Scheme 9: 5-(3-Isobutyrylamino-phenyl)-4-bromo-3-tert-butoxycarbonylmethoxy-thiophene-2-carboxylic acid methyl ester (13.9 mg, 99+%) was prepared according to the procedure in the first step of Scheme 4 of Example 22, using 5-(3-amino-phenyl)-4-bromo-3-tert-butoxycarbonylmethoxy-thiophene-2-carboxylic acid methyl ester (12 mg, 0.027 mmol) as the starting material.

The fourth step of Scheme 9: 5-(3-Isobutyrylamino-phenyl)-4-bromo-3-carbonylmethoxy-thiophene-2-carboxylic acid (8.9 mg, 75%) was prepared as a white solid according to the procedure in the second step of Scheme 1 of Example 1, using 5-(3-isobutyrylamino-phenyl)-4-bromo-3-tert-butoxycarbonylmethoxy-thiophene-2-carboxylic acid methyl ester (13.8 mg, 0.027 mmol) as the starting material.

$^1$H NMR (400 MHz, DMSO-D6) δ ppm 1.11 (d, J=6.82 Hz, 6 H) 2.61 (m, 1 H) 4.90 (s, 2 H) 7.33 (m, 1 H) 7.44 (t, J=7.83 Hz, 1 H) 7.69 (m, 1 H) 8.04 (t, J=1.89 Hz, 1 H) 10.05 (s, 1 H).

EXAMPLE 87

4-Bromo-3-carboxymethoxy-5-[3-(2,2,2-trifluoro-ethanesulfonylamino)-phenyl-4-thiophene-2-carboxylic acid The first step of Scheme 10: To a 1.5 mL CH$_2$Cl$_2$ solution of 5-(3-amino-phenyl)-4-bromo-3-tert-butoxycarbonylmethoxy-thiophene-2-carboxylic acid methyl ester (41 mg, 0.093 mmol) was added diisopropylethylamine (30 µL, 0.17 mmol) and 2,2,2-trifluoroethanesulfonyl chloride (15 µL, 0.14 mmol) and the reaction mixture was allowed to stir at room temperature overnight. The reaction mixture was then diluted with CH$_2$Cl$_2$ and washed with dilute aqueous HCl, saturated sodium bicarbonate solution, and dried over MgSO$_4$. Filtration and evaporation gave the crude product which was then purified by chromatography on silica gel using a gradient of EtOAc/hexane (0 to 25%) as eluent. Pure fractions were combined and evaporated to give 21 mg (38%) 4-bromo-3-tert-butoxycarbonylmethoxy-5-[3-(2,2,2-trifluoro-ethanesulfonylamino)-phenyl]-thiophene-2-carboxylic acid methyl ester as a colorless oil.

$^1$H NMR (400 MHz, CHLOROFORM-D) δ ppm 1.51 (s, 9 H) 3.88 (m, 5 H) 4.81 (s, 2 H) 7.37 (ddd, J=7.71, 1.89, 1.77 Hz, 1 H) 7.47 (t, J=7.71 Hz, 1 H) 7.51 (m, 1 H) 7.59 (d, J=2.02 Hz, 1 H)

The second step of Scheme 10: 4-Bromo-3-tert-butoxycarbonylmethoxy-5-[3-(2,2,2-trifluoro-ethanesulfonylamino)-phenyl]-thiophene-2-carboxylic acid methyl ester (21 mg, 3.6×10$^{-5}$ mmole) was dissolved in 1.5 mL of a 2:1 THF:H$_2$O mixture. LiOH.H$_2$O (8 mg, 0.18 mmole) was then added and the reaction mixture was stirred at room temperature overnight. The solvents were evaporated and the residue re-dissolved in 2-3 mL water. It was acidified with 1N HCl dropwise while stirring. A flocculent solid emerged that was too fine to filter effectively. It was extracted with EtOAc, and the organic layer was washed with brine and dried over MgSO$_4$. Filtration and evaporation gave 13 mg (70%) of 4-bromo-3-carboxymethoxy-5-[3-(2,2,2-trifluoro-ethanesulfonylamino)-phenyl]-thiophene-2-carboxylic acid as an off-white solid.

$^1$H NMR (400 MHz, DMSO-D6) δ ppm 4.63 (q, J=9.85 Hz, 2 H) 4.90 (s, 2 H) 7.34 (d, J=8.34 Hz, 1 H) 7.44 (d, J=7.58 Hz, 1 H) 7.52 (m, 2 H) 10.73 (s, 1 H).

ESI-MS: m/e=516 [M−H]$^-$.

EXAMPLE 88

5-(3-Benzenesulfonylamino-phenyl)-4-bromo-3-carboxymethoxy-thiophene-2-carboxylic acid The first step of Scheme 10: To a 1 mL pyridine solution of 5-(3-amino-phenyl)-4-bromo-3-ethoxycarbonylmethoxy-thiophene-2-carboxylic acid methyl ester (30 mg, 0.072 mmole) was added benzenesulfonyl chloride and the reaction mixture was allowed to stir at room temperature overnight. The reaction mixture was then diluted with 15 mL 1N HCl and extracted with EtOAc. The organic layer was washed with dilute aqueous HCl, saturated sodium bicarbonate solution, brine, and dried over MgSO$_4$. Filtration and evaporation gave the crude product which was purified by preparative TLC (35% EtOAc/Hexanes). The product band was isolated to give 20 mg (50%) 5-(3-benzenesulfonylamino-phenyl)-4-bromo-3-ethoxycarbonylmethoxy-thiophene-2-carboxylic acid methyl ester as a yellow oil.

$^1$H NMR (400 MHz, CHLOROFORM-D) δ ppm 1.32 (t, J=7.07 Hz, 2 H) 3.87 (s, 3 H) 4.30 (q, J=7.07 Hz, 2 H) 4.89 (s, 2 H) 7.06 (s, 1 H) 7.19 (dt, J=7.39, 1.99 Hz, 1 H) 7.32 (d, J=8.59 Hz, 1 H) 7.35 (m, 1 H) 7.37 (t, J=1.77 Hz, 1 H) 7.46 (m, 2 H) 7.55 (m, 1 H) 7.83 (m, 1 H).

The second step of Scheme 10: 5-(3-Benzenesulfonylamino-phenyl)-4-bromo-3-ethoxycarbonylmethoxy-thiophene-2-carboxylic acid methyl ester (20 mg, 0.036 mmole) was dissolved in 1.5 mL of a 2:1 THF:$H_2O$ mixture. LiOH.$H_2O$ (8 mg, 0.18 mmole) was then added and the reaction mixture was stirred at room temperature overnight. The solvents were evaporated and the residue re-dissolved in 2-3 mL water. The mixture was acidified with 1N HCl dropwise while stirring. A solid emerged that was filtered, washed with water and vacuum-oven dried to give 15 mg (81%) of 5-(3-benzenesulfonylamino-phenyl)-4-bromo-3-carboxymethoxy-thiophene-2-carboxylic acid as an off-white solid.

$^1$H NMR (400 MHz, Solvent) δ ppm 4.81 (s, 2 H) 7.12 (m, 1 H) 7.23 (m, 2 H) 7.30 (m, 1 H) 7.40 (m, 2 H) 7.48 (m, 1 H) 7.71 (m, 2 H).

EXAMPLE 89

4-Bromo-3-carboxymethoxy-5-(3-ethanesulfonylamino-phenyl)-thiophene-2-carboxylic acid The first step of Scheme 10: Following the procedure in the first step of Scheme 10 of Example 88, 4-bromo-5-(3-ethanesulfonylamino-phenyl)-3-ethoxycarbonylmethoxy-thiophene-2-carboxylic acid methyl ester was obtained in 71% yield as a pale yellow oil.

$^1$H NMR (400 MHz, CHLOROFORM-D) δ ppm 1.32 (t, J=7.07 Hz, 3 H) 1.41 (t, J=7.33 Hz, 3 H) 3.20 (q, J=7.41 Hz, 2 H) 3.88 (s, 3 H) 4.30 (q, J=7.07 Hz, 2 H) 4.92 (s, 2 H) 6.71 (s, 1 H) 7.30 (m, 1 H) 7.43 (m, 2 H) 7.54 (m, 1 H).

The second step of Scheme 10: 4-Bromo-5-(3-ethanesulfonylamino-phenyl)-3-ethoxycarbonylmethoxy-thiophene-2-carboxylic acid methyl ester was hydrolyzed according to the procedure in the second step of Scheme 10 of Example 87 to give 4-bromo-3-carboxymethoxy-5-(3-ethanesulfonylamino-phenyl)-thiophene-2-carboxylic acid in 93% yield as a colorless glassy solid.

$^1$H NMR (400 MHz, DMSO-D6) δ ppm 1.21 (t, J=7.33 Hz, 3 H) 3.16 (q, J=7.33 Hz, 2 H) 4.90 (s, 2 H) 7.34 (m, 2 H) 7.48 (t, J=7.83 Hz, 1 H) 7.55 (s, 1 H) 10.08 (s, 1 H).

ESI-MS: m/e=462 [M−H]$^−$.

EXAMPLE 90

4-Bromo-3-carboxymethoxy-5-(3-phenylmethanesulfonylamino-phenyl)-thiophene-2-carboxylic acid The first step of Scheme 10: 4-Bromo-3-ethoxycarbonylmethoxy-5-(3-phenylmethanesulfonylamino-phenyl)-thiophene-2-carboxylic acid methyl ester was obtained in 79% yield as a colorless glassy solid, following the procedure in the first step of Scheme 10 of Example 88 except that it was purified by chromatography on silica gel using a gradient of EtOAc/hexane (10 to 30%) as eluent.

$^1$H NMR (400 MHz, CHLOROFORM-D) δ ppm 1.33 (m, 3 H) 3.89 (s, 3 H) 4.30 (q, J=7.16 Hz, 2 H) 4.41 (s, 2 H) 4.93 (s, 2 H) 6.55 (s, 1 H) 7.20 (m, 1 H) 7.29 (m, 2 H) 7.35 (m, 3 H) 7.43 (m, 3 H).

The second step of Scheme 10: 4-Bromo-3-ethoxycarbonylmethoxy-5-(3-phenylmethanesulfonylamino-phenyl)-thiophene-2-carboxylic acid methyl ester was hydrolyzed according to the procedure in the second step of Scheme 10 of Example 87 to give 4-bromo-3-carboxymethoxy-5-(3-phenylmethanesulfonylamino-phenyl)-thiophene-2-carboxylic acid in 68% yield as a pale yellow solid.

$^1$H NMR (400 MHz, DMSO-D6) δ ppm 4.54 (s, 2 H) 4.91 (s, 2 H) 7.28 (m, 3 H) 7.34 (m, 4 H) 7.47 (m, 2 H) 10.13 (s, 1 H).

EXAMPLE 91

4-Bromo-3-carboxymethoxy-5-[3-(4-trifluoromethyl-benzenesulfonylamino)-phenyl]-thiophene-2-carboxylic acid The first step of Scheme 10: 4-Bromo-3-ethoxycarbonylmethoxy-5-[3-(4-trifluoromethyl-benzenesulfonylamino)-phenyl]-thiophene-2-carboxylic acid methyl ester was obtained in 42% yield as a colorless oil, following the procedure in the first step of Scheme 10 of Example 88 except that it was purified by chromatography on silica gel using a gradient of EtOAc/hexane (5 to 30%) as eluent.

$^1$H NMR (400 MHz, CHLOROFORM-D) δ ppm 1.32 (t, J=7.20 Hz, 3 H) 3.86 (s, 3 H) 4.30 (q, J=7.07 Hz, 2 H) 4.89 (s, 2 H) 7.23 (m, 1 H) 7.39 (m, 3 H) 7.74 (d, J=8.34 Hz, 2 H) 7.95 (d, J=8.34 Hz, 2 H).

The second step of Scheme 10: 4-Bromo-3-ethoxycarbonylmethoxy-5-[3-(4-trifluoromethyl-benzenesulfonylamino)-phenyl]-thiophene-2-carboxylic acid methyl ester was hydrolyzed according to the procedure in the second step of Scheme 10 of Example 87 to give 4-bromo-3-carboxymethoxy-5-[3-(4-trifluoromethyl-benzenesulfonylamino)-phenyl]-thiophene-2-carboxylic acid in >99% yield as a colorless glassy solid.

$^1$H NMR (400 MHz, DMSO-D6) δ ppm 4.88 (s, 2 H) 7.24 (m, 1 H) 7.34 (m, 1 H) 7.42 (m, 2 H) 7.99 (s, 4 H) 10.80 (s, 1 H).

ESI-MS: m/e=434 [M−$CO_2$]$^−$.

EXAMPLE 92

4-Bromo-3-carboxymethoxy-5-[3-(4-trifluoromethoxy-benzenesulfonylamino)-phenyl]-thiophene-2-carboxylic acid The first step of Scheme 10: 4-Bromo-3-ethoxycarbonylmethoxy-5-[3-(4-trifluoromethoxy-benzenesulfonylamino)-phenyl]-thiophene-2-carboxylic acid methyl ester was obtained in 70% yield as a colorless glassy solid, following the procedure in the first step of Scheme 10 of Example 88.

$^1$H NMR (400 MHz, CHLOROFORM-D) δ ppm 1.32 (t, J=7.07 Hz, 3 H) 3.87 (s, 3 H) 4.30 (q, J=7.24 Hz, 2 H) 4.90 (s, 2 H) 7.20 (m, 1 H) 7.29 (m, 2 H) 7.39 (m, 3 H) 7.87 (m, 2 H).

The second step of Scheme 10: 4-Bromo-3-ethoxycarbonylmethoxy-5-[3-(4-trifluoromethoxy-benzenesulfonylamino)-phenyl]-thiophene-2-carboxylic acid methyl ester was hydrolyzed according to the procedure in the second step of Scheme 10 of Example 87 to give 4-bromo-3-carboxymethoxy-5-[3-(4-trifluoromethoxy-benzenesulfonylamino)-phenyl]-thiophene-2-carboxylic acid in 67% yield as a pale yellow solid.

$^1$H NMR (400 MHz, DMSO-D6) δ ppm 4.88 (s, 2 H) 7.23 (m, 1 H) 7.33 (d, J=8.59 Hz, 1 H) 7.42 (m, 2 H) 7.59 (d, J=8.08 Hz, 2 H) 7.92 (m, 2 H) 10.70 (s, 1 H).

ESI-MS: m/e=550 [M−$CO_2$]$^−$.

EXAMPLE 93

4-Bromo-3-carboxymethoxy-5-[3-(3-trifluoromethyl-benzenesulfonylamino)-phenyl]-thiophene-2-carboxylic acid The first step of Scheme 10: 4-Bromo-3-ethoxycarbonylmethoxy-5-[3-(3-trifluoromethyl-benzenesulfonylamino)-phenyl]-thiophene-2-carboxylic acid methyl ester was obtained in 82% yield as a colorless glassy solid, following the procedure in the first step of Scheme 10 of Example 88.

$^1$H NMR (400 MHz, CHLOROFORM-D) δ ppm 1.32 (t, J=7.07 Hz, 3 H) 3.86 (s, 3 H) 4.30 (q, J=7.24 Hz, 2 H) 4.89 (s, 2 H) 7.14 (s, 1 H) 7.22 (m, 1 H) 7.38 (m, 3 H) 7.61 (t, J=7.83 Hz, 1 H) 7.81 (d, J=7.83 Hz, 1 H) 7.99 (d, J=7.83 Hz, 1 H) 8.09 (s, 1 H).

The second step of Scheme 10: 4-Bromo-3-ethoxycarbonylmethoxy-5-[3-(3-trifluoromethyl-benzenesulfonylamino)-phenyl]-thiophene-2-carboxylic acid methyl ester was hydrolyzed according to the procedure in the second step of Scheme 10 of Example 87 to give 4-bromo-3-carboxymethoxy-5-[3-(3-trifluoromethyl-benzenesulfonylamino)-phenyl]-thiophene-2-carboxylic acid in 84% yield as a pale yellow solid.

$^1$H NMR (400 MHz, DMSO-D6) δ ppm 4.88 (s, 2 H) 7.23 (m, 1 H) 7.35 (m, 1 H) 7.42 (m, 2 H) 7.84 (t, J=7.71 Hz, 1 H) 8.05 (m, 3 H) 10.72 (s, 1 H).

ESI-MS: m/e=534 [M−CO$_2$]$^-$.

EXAMPLE 94

4-Bromo-3-carboxymethoxy-5-[3-(2-trifluoromethyl-benzenesulfonylamino)-phenyl]-thiophene-2 carboxylic acid The first step of Scheme 10: 4-Bromo-3-ethoxycarbonylmethoxy-5-[3-(2-trifluoromethyl-benzenesulfonylamino)-phenyl]-thiophene-2-carboxylic acid methyl ester was obtained in 80% yield as a yellow oil, following the procedure in the first step of Scheme 10 of Example 88.

$^1$H NMR (400 MHz, CHLOROFORM-D) δ ppm 1.32 (t, J=7.20 Hz, 3 H) 3.88 (s, 3 H) 4.29 (q, J=7.24 Hz, 2 H) 4.90 (s, 2 H) 6.80 (s, 1 H) 7.17 (m, 1 H) 7.35 (m, 3 H) 7.61 (td, J=7.77, 1.14 Hz, 1 H) 7.68 (t, J=7.71 Hz, 1 H) 7.89 (d, J=7.07 Hz, 1 H) 8.09 (d, J=7.33 Hz, 1 H).

The second step of Scheme 10: 4-Bromo-3-ethoxycarbonylmethoxy-5-[3-(2-trifluoromethyl-benzenesulfonylamino)-phenyl]-thiophene-2-carboxylic acid methyl ester was hydrolyzed according to the procedure in the second step of Scheme 10 of Example 87 to give 4-bromo-3-carboxymethoxy-5-[3-(2-trifluoromethyl-benzenesulfonylamino)-phenyl]-thiophene-2-carboxylic acid in 83% yield as a white solid.

$^1$H NMR (400 MHz, DMSO-D6) δ ppm 4.88 (s, 2 H) 7.22 (m, 1 H) 7.32 (d, J=8.08 Hz, 1 H) 7.42 (m, 2 H) 7.88 (m, 2 H) 8.02 (dd, J=7.71, 1.39 Hz, 1 H) 8.13 (d, J=7.58 Hz, 1 H) 11.00 (s, 1 H).

ESI-MS: m/e=578 [M−H]$^-$.

EXAMPLE 95

4-Bromo-3-carboxymethoxy-5-[3-(2-cyano-benzenesulfonylamino)-phenyl]-thiophene-2-carboxylic acid The first step of Scheme 10: 4-Bromo-5-[3-(2-cyano-benzenesulfonylamino)-phenyl]-3-ethoxycarbonylmethoxy-thiophene-2-carboxylic acid methyl ester was obtained in 43% yield as a colorless glassy solid, following the procedure in the first step of Scheme 10 of Example 88 except that it was purified by chromatography on silica gel using a gradient of EtOAc/hexane (10 to 40%) as eluent.

$^1$H NMR (400 MHz, CHLOROFORM-D) δ ppm 1.32 (t, J=7.20 Hz, 3 H) 3.88 (s, 3 H) 4.29 (q, J=7.16 Hz, 2 H) 4.90 (s, 2 H) 7.25 (dt, J=7.39, 2.12 Hz, 1 H) 7.36 (m, 2 H) 7.46 (m, 2 H) 7.67 (td, J=7.58, 1.52 Hz, 1 H) 7.73 (td, J=7.77, 1.64 Hz, 1 H) 7.86 (m, 1 H) 8.16 (dd, J=7.83, 1.26 Hz, 1 H).

The second step of Scheme 10: 4-Bromo-5-[3-(2-cyano-benzenesulfonylamino)-phenyl]-3-ethoxycarbonylmethoxy-thiophene-2-carboxylic acid methyl ester was hydrolyzed according to the procedure in the second step of Scheme 10 of Example 88 to give 4-bromo-3-carboxymethoxy-5-[3-(2-cyano-benzenesulfonylamino)-phenyl]-thiophene-2-carboxylic acid in 87% yield as a white solid.

$^1$H NMR (400 MHz, DMSO-D6) δ ppm 4.86 (s, 2 H) 7.23 (m, 1 H) 7.39 (m, 2 H) 7.84 (m, 2 H) 7.93 (m, 2 H) 8.10 (m, 2 H) 11.10 (s, 1 H).

ESI-MS: m/e=535 [M−H]$^-$.

EXAMPLE 96

4-Bromo-3-carboxymethoxy-5-[3-(4-methoxy-benzenesulfonylamino)-phenll]-thiophene-2-carboxylic acid The first step of Scheme 10: 4-Bromo-3-ethoxycarbonylmethoxy-5-[3-(4-methoxy-benzenesulfonylamino)-phenyl]-thiophene-2-carboxylic acid methyl ester was obtained in 92% yield as a colorless glassy solid, following the procedure in the first step of Scheme 10 of Example 88 except that it was purified by chromatography on silica gel using a gradient of EtOAc/hexane (10 to 40%) as eluent.

$^1$H NMR (400 MHz, CHLOROFORM-D) δ ppm 1.32 (t, J=7.07 Hz, 3 H) 3.83 (s, 3 H) 3.87 (s, 3 H) 4.29 (q, J=7.24 Hz, 2 H) 4.90 (s, 2 H) 6.88 (s, 1 H) 6.91 (m, 2 H) 7.18 (m, 1 H) 7.35 (m, 3 H) 7.76 (m, 2 H).

The second step of Scheme 10: 4-Bromo-3-ethoxycarbonylmethoxy-5-[3-(4-methoxy-benzenesulfonylamino)-phenyl]-thiophene-2-carboxylic acid methyl ester was hydrolyzed as according to the procedure in the second step of Scheme 10 of Example 87 to give 4-bromo-3-carboxymethoxy-5-[3-(4-methoxy-benzenesulfonylamino)-phenyl]-thiophene-2-carboxylic acid in 93% yield as a pale yellow solid.

$^1$H NMR (400 MHz, DMSO-D6) δ ppm 3.79 (s, 3 H) 4.89 (s, 2 H) 7.08 (m, 2 H) 7.20 (m, 1 H) 7.30 (m, 1 H) 7.37 (d, J=7.83 Hz, 1 H) 7.41 (t, J=2.02 Hz, 1 H) 7.73 (m, 2 H) 10.43 (s, 1 H).

ESI-MS: m/e=540 [M−H]$^-$.

EXAMPLE 97

4-Bromo-3-carboxymethoxy-5-[3-(4-cyano-benzenesulfonylamino)-phenyl]-thiophene-2-carbocylic acid The first step of Scheme 10: 4-Bromo-5-[3-(4-cyano-benzenesulfonylamino)-phenyl]-3-ethoxycarbonylmethoxy-thiophene-2-carboxylic acid methyl ester was obtained in 62% yield as a colorless glassy solid, following the procedure in the first step of Scheme 10 of Example 88 except that it was purified by chromatography on silica gel using a gradient of EtOAc/hexane (10 to 40%) as eluent.

$^1$H NMR (400 MHz, CHLOROFORM-D) δ ppm 1.33 (m, 3 H) 3.86 (s, 3 H) 4.31 (m, 2 H) 4.90 (d, J=3.54 Hz, 2 H) 7.25 (m, 2 H) 7.38 (m, 3 H) 7.77 (m, 2 H) 7.93 (m, 2 H).

The second step of Scheme 10: 4-Bromo-5-[3-(4-cyano-benzenesulfonylamino)-phenyl]-3-ethoxycarbonylmethoxy-thiophene-2-carboxylic acid methyl ester was hydrolyzed according to the procedure in the second step of Scheme 10 of Example 87 to give 4-bromo-3-carboxymethoxy-5-[3-(4-cyano-benzenesulfonylamino)-phenyl]-thiophene-2-carboxylic acid in 98% yield as a white solid.

$^1$H NMR (400 MHz, MeOD) δ ppm 4.79 (s, 2 H) 7.12 (m, 1 H) 7.28 (d, J=5.05 Hz, 2 H) 7.32 (s, 1 H) 7.79 (d, J=8.59 Hz, 2 H) 7.85 (d, J=8.62 Hz, 2 H).

EXAMPLE 98

4-Bromo-3-carboxymethoxy-5-[3-(4-fluoro-benzenesulfonylamino)-phenyl]-thiophene-2-carboxylic acid The first step of Scheme 10: 4-Bromo-3-ethoxycarbonylmethoxy-5-[3-(4-fluoro-benzenesulfonylamino)-phenyl]-thiophene-2-carboxylic acid methyl ester was obtained in 86% yield as a colorless glassy solid, following the procedure in the first step of Example 88.

$^1$H NMR (400 MHz, CHLOROFORM-D) δ ppm 1.32 (t, J=7.20 Hz, 3 H) 3.87 (s, 3 H) 4.30 (q, J=7.07 Hz, 2 H) 4.90 (s, 2 H) 7.14 (m, 3 H) 7.20 (m, 1 H) 7.37 (m, 3 H) 7.85 (m, 2 H).

The second step of Scheme 10: 4-Bromo-3-ethoxycarbonylmethoxy-5-[3-(4-fluoro-benzenesulfonylamino)-phenyl]-thiophene-2-carboxylic acid methyl ester was hydrolyzed according to the procedure in the second step of Scheme 10 of Example 87 to give 4-bromo-3-carboxymethoxy-5-[3-(4-fluoro-benzenesulfonylamino)-phenyl]-thiophene-2-carboxylic acid in 96% yield as a white solid.

$^1$H NMR (400 MHz, DMSO-D6) δ ppm 4.89 (s, 2 H) 7.21 (m, 1 H) 7.32 (m, 1 H) 7.42 (m, 4 H) 7.86 (m, 2 H) 10.61 (s, 1 H).

ESI-MS: m/e=484 [M−CO$_2$]$^-$.

EXAMPLE 99

4-Bromo-3-carboxymethoxy-5-(3-methoxycarbonylamino-phenyl)-thiophene-2-carboxylic acid The first step of Scheme 11: To a 1.5 mL CH$_2$Cl$_2$ solution of 5-(3-amino-phenyl)-4-bromo-3-tert-butoxycarbonylmethoxy-thiophene-2-carboxylic acid methyl ester (42 mg, 0.095 mmole) was added diisopropylethylamine (34 µL, 0.19 mmole) followed by methyl chloroformate (13 µL, 0.17 mmole) and the reaction mixture was allowed to stir at room temperature overnight. The reaction mixture was diluted with CH$_2$Cl$_2$ and washed with dilute aqueous HCl, saturated sodium bicarbonate, and dried over MgSO$_4$. Filtration and evaporation gave 40 mg (84%) 4-bromo-3-tert-butoxycarbonylmethoxy-5-(3-methoxycarbonylamino-phenyl)-thiophene-2-carboxylic acid methyl ester as a pale yellow oil.

$^1$H NMR (400 MHz, CHLOROFORM-D) δ ppm 1.51 (s, 9 H) 3.80 (s, 3 H) 3.87 (s, 3 H) 4.82 (s, 2 H) 6.77 (s, 1 H) 7.35 (dt, J=7.64, 1.61 Hz, 1 H) 7.39 (t, J=7.83 Hz, 1 H) 7.47 (m, 1 H) 7.73 (s, 1 H).

The second step of Scheme 11: 4-Bromo-3-tert-butoxycarbonylmethoxy-5-(3-methoxycarbonylamino-phenyl)-thiophene-2-carboxylic acid methyl ester (40 mg, 7.9×10$^{-5}$ mmole) was dissolved in 1.5 mL of a 2:1 mixture of THF:H$_2$O. LiOH.H$_2$O (10 mg, 0.24 mmole) was added and the mixture stirred at room temperature overnight. The solvent was evaporated and the residue re-dissolved in 2-3 mL water and acidified dropwise with 1N HCl while stirring. A gelatinous solid emerged that could not be conveniently filtered. It was extracted with EtOAc and the organic layer was washed with brine and dried over MgSO$_4$. Filtration and evaporation gave 4-bromo-3-carboxymethoxy-5-(3-methoxycarbonylamino-phenyl)-thiophene-2-carboxylic acid in 26% yield as an off-white solid.

$^1$H NMR (400 MHz, DMSO-D6) δ ppm 3.69 (s, 3 H) 4.89 (s, 2 H) 7.29 (m, 1 H) 7.43 (t, J=7.96 Hz, 1 H) 7.55 (d, J=9.60 Hz, 1 H) 7.86 (s, 1 H) 9.90 (s, 1 H).

ESI-MS: m/e=428 [M−H]$^-$.

EXAMPLE 100

4-Bromo-3-carboxymethoxy-5-[3-(3-isopropyl-ureido)-phenyl]-thiophene-2-carboxylic acid The first step of Scheme 11: To a 1 mL DMF solution of 5-(3-amino-phenyl)-4-bromo-3-tert-butoxycarbonylmethoxy-thiophene-2-carboxylic acid methyl ester (35 mg, 0.079 mmole) was added isopropyl isocyanate (38 µL, 0.4 mmole) and the reaction mixture was heated to 60° C. overnight. The reaction mixture was then cooled to room temperature and diluted with water and extracted with EtOAc. The organic phase was washed with water, brine, and dried over MgSO$_4$. It was filtered and evaporated to obtain the crude product which was then purified by chromatography on silica gel using a gradient of hexane/EtOAc (0 to 30%) as eluent. Pure fractions were combined and evaporated to give 21 mg (50%) 4-bromo-3-tert-butoxycarbonylmethoxy-5-[3-(3-isopropyl-ureido)-phenyl]-thiophene-2-carboxylic acid methyl ester as a pale yellow oil.

$^1$H NMR (400 MHz, CHLOROFORM-D) δ ppm 1.08 (d, J=6.57 Hz, 6 H) 1.44 (s, 9 H) 3.75 (s, 3 H) 3.93 (m, 1 H) 4.70 (s, 2 H) 5.13 (d, J=7.58 Hz, 1 H) 7.14 (m, 2 H) 7.20 (t, J=7.83 Hz, 1 H) 7.40 (m, 2 H).

The second step of Scheme 11: 4-Bromo-3-tert-butoxycarbonylmethoxy-5-(3-methoxycarbonylamino-phenyl)-thiophene-2-carboxylic acid methyl ester (21 mg, 4.0×10$^{-5}$ mmole) was dissolved in 1.5 mL of a 2:1 mixture of THF:H$_2$O. LiOH.H$_2$O (8.5 mg, 0.2 mmole) was added and the mixture stirred at room temperature overnight. The solvent was evaporated and the residue re-dissolved in 2-3 mL water and acidified dropwise with 1N HCl while stirring. A solid emerged that was filtered, washed with water and vacuum-oven dried to give 4-bromo-3-carboxymethoxy-5-[3-(3-isopropyl-ureido)-phenyl]-thiophene-2-carboxylic acid in 77% yield as a white solid.

$^1$H NMR (400 MHz, DMSO-D6) δ ppm 1.10 (d, J=6.57 Hz, 6 H) 3.75 (m, 1 H) 4.88 (s, 2 H) 6.07 (d, J=7.83 Hz, 1 H) 7.18 (dd, J=6.19, 1.64 Hz, 1 H) 7.35 (t, J=7.83 Hz, 1 H) 7.42 (m, 1 H) 7.81 (t, J=1.77 Hz, 1 H) 8.54 (s, 1 H).

ESI-MS: m/e=455 [M−H]$^-$.

EXAMPLE 101

4-Bromo-3-carboxymethoxy-5-[3-(3,3-diethyl-ureido)-phenyl]-thiophene-2-carboxylic acid The first step of Scheme 11: To a 1.5 mL CH$_2$Cl$_2$ solution of 5-(3-amino-phenyl)-4-bromo-3-tert-butoxycarbonylmethoxy-thiophene-2-carboxylic acid methyl ester (54 mg, 0.12 mmole) was added diisopropylethylamine (32 µL, 0.18 mmole) followed by diethylcarbamoyl chloride (38 µL, 0.14 mmole) and the reaction mixture was allowed to stir at room temperature for 36 hours. The reaction mixture was diluted with CH$_2$Cl$_2$, washed with dilute aqueous HCl, saturated sodium bicarbonate solution, and dried over MgSO$_4$. Filtration and evaporation gave the crude product, which was purified by preparative TLC (30% EtOAc/Hex). The product band was isolated to give 31 mg (20%) of 4-bromo-3-tert-butoxycarbonylmethoxy-5-[3-(3,3-diethyl-ureido)-phenyl]-thiophene-2-carboxylic acid methyl ester as a pale yellow oil.

$^1$H NMR (400 MHz, CHLOROFORM-D) δ ppm 1.17 (t, J=7.20 Hz, 6 H) 1.44 (s, 9 H) 3.33 (q, J=7.24 Hz, 4 H) 3.80 (s, 3 H) 4.74 (s, 2 H) 6.30 (s, 1 H) 7.24 (m, 1 H) 7.29 (t, J=7.83 Hz, 1 H) 7.43 (m, 1 H) 7.61 (t, J=1.89 Hz, 1 H).

The second step of Scheme 11: 4-Bromo-3-tert-butoxycarbonylmethoxy-5-[3-(3,3-diethyl-ureido)-phenyl]-thiophene-2-carboxylic acid methyl ester was hydrolyzed according the procedure in the second step of Scheme 11 of Example 100 to give 4-bromo-3-carboxymethoxy-5-[3-(3,3-diethyl-ureido)-phenyl]-thiophene-2-carboxylic acid in 71% yield as a pale yellow solid.

$^1$H NMR (400 MHz, DMSO-D6) δ ppm 1.10 (t, J=7.07 Hz, 6 H) 3.36 (m, 4 H) 4.88 (s, 2 H) 7.25 (m, 1 H) 7.37 (t, J=7.96 Hz, 1 H) 7.63 (m, 1 H) 7.88 (t, J=1.89 Hz, 1 H) 8.36 (s, 1 H).

ESI-MS: m/e=469 [M−H]$^-$.

EXAMPLE 102

5-(3-Benzylamino-phenyl)-4-bromo-3-carboxymethoxy-thiophene-2-carboxylic acid

The first step of Scheme 12: To a 2 mL DCE solution of 5-(3-amino-phenyl)-4-bromo-3-ethoxycarbonylmethoxy-thiophene-2-carboxylic acid methyl ester (83 mg, 0.2 mmol) was added benzaldehyde (24 μL, 0.24 mmol) followed by acetic acid (20 μL, 0.3 mmol) and sodium triacetoxyborohydride (106 mg, 0.5 mmol). The resulting reaction mixture was allowed to stir at room temperature overnight. The reaction mixture was then diluted with $CH_2Cl_2$ and washed with saturated sodium bicarbonate solution and dried over $MgSO_4$. It was then filtered and evaporated to obtain the crude product, which was then purified by chromatography on silica gel using a gradient of hexane/EtOAc (5 to 25%) as eluent. Pure fractions were combined and evaporated to give 65 mg (64%) 5-(3-benzylamino-phenyl)-4-bromo-3-ethoxycarbonyl-methoxy-thiophene-2-carboxylic acid methyl ester as a yellow solid.

$^1$H NMR (400 MHz, CHLOROFORM-D) δ ppm 1.31 (t, J=7.07 Hz, 3 H) 3.86 (s, 3 H) 4.24 (s, 1 H) 4.29 (q, J=7.16 Hz, 2 H) 4.37 (s, 2 H) 4.88 (s, 2 H) 6.70 (m, 1 H) 6.92 (m, 1 H) 6.97 (dd, J=7.58, 1.01 Hz, 1 H) 7.23 (t, J=7.83 Hz, 1 H) 7.29 (m, 1 H) 7.37 (m, 4 H).

The second step of Scheme 12: 5-(3-Benzylamino-phenyl)-4-bromo-3-ethoxycarbonylmethoxy-thiophene-2-carboxylic acid methyl ester (40 mg, 7.9×110 mmol) was dissolved in 1.5 mL of a 2:1 mixture of THF:$H_2O$ and LiOH.$H_2O$ (17 mg, 0.4 mmol) was added and the mixture stirred at room temperature overnight. The reaction mixture was then evaporated and the residue re-dissolved in 2-3 mL of $H_2O$. The solution was acidified dropwise with 1N HCl while stirring. A solid emerged that was filtered, washed with water, and vacuum oven-dried to give 28 mg (77%) of 5-(3-benzylamino-phenyl)-4-bromo-3-carboxymethoxy-thiophene-2-carboxylic acid as a pale yellow solid.

$^1$H NMR (400 MHz, DMSO-D6) δ ppm 4.31 (s, 2 H) 4.85 (s, 2 H) 6.70 (d, J=8.84 Hz, 1 H) 6.79 (d, J=7.07 Hz, 1 H) 6.83 (s, 1 H) 7.20 (m, 2 H) 7.35 (m, 4 H).

ESI-MS: m/e=460 [N−H]$^-$.

EXAMPLE 103

4-Bromo-3-carboxymethoxy-5-[3-(3-trifluoromethyl-benzylamino)-phenyl]-thiophene-2-carboxylic acid The first step of Scheme 12: 4-Bromo-3-ethoxycarbonyl-methoxy-5-[3-(3-trifluoromethyl-benzylamino)-phenyl]-thiophene-2-carboxylic acid methyl ester was obtained in 75% yield as a yellow oil, following the procedure in the first step of Scheme 12 of Example 102.

$^1$H NMR (400 MHz, CHLOROFORM-D) δ ppm 1.31 (t, J=7.07 Hz, 3 H) 3.86 (s, 3 H) 4.29 (q, J=7.24 Hz, 2 H) 4.34 (s, 1 H) 4.45 (s, 2 H) 4.88 (s, 2 H) 6.69 (m, 1 H) 6.89 (m, 1 H) 6.99 (m, 1 H) 7.24 (m, 1 H) 7.47 (t, J=7.71 Hz, 1 H) 7.56 (m, 2 H) 7.65 (s, 1 H).

The second step of Scheme 12: 4-Bromo-3-ethoxycarbonylmethoxy-5-[3-(3-trifluoromethyl-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(3-trifluoromethyl-benzylamino)-phenyl]-thiophene-2-carboxylic acid in 45% yield as a pale yellow solid.

$^1$H NMR (400 MHz, DMSO-D6) δ ppm 4.42 (s, 2 H) 4.84 (s, 2 H) 6.71 (d, J=1.52 Hz, 2 H) 6.81 (m, 2 H) 7.19 (t, J=7.96 Hz, 1 H) 7.59 (m, 2 H) 7.69 (d, J=6.82 Hz, 1 H) 7.73 (s, 1 H).

ESI-MS: m/e=528 [M−H]$^-$.

EXAMPLE 104

4-Bromo-3-carboxymethoxy-5-[3-(2-trifluoromethyl-benzylamino)-phenyl]-thiophene-2-carboxylic acid The first step of Scheme 12: 4-Bromo-3-ethoxycarbonyl-methoxy-5-[3-(2-trifluoromethyl-benzylamino)-phenyl]-thiophene-2-carboxylic acid methyl ester was obtained in 75% yield as a white solid, following the procedure in the first step of Scheme 12 of Example 102.

$^1$H NMR (400 MHz, CHLOROFORM-D) δ ppm 1.31 (t, J=7.20 Hz, 3 H) 3.86 (s, 3 H) 4.29 (q, J=7.16 Hz, 2 H) 0.00 (none, 1 H) 4.61 (s, 2 H) 4.88 (s, 2 H) 6.66 (m, 1 H) 6.88 (m, 1 H) 6.97 (m, 1 H) 7.23 (t, J=7.83 Hz, 1 H) 7.37 (t, J=7.58 Hz, 1 H) 7.50 (t, J=7.33 Hz, 1 H) 7.63 (d, J=7.83 Hz, 1 H) 7.69 (d, J=7.83 Hz, 1 H).

The second step of Scheme 12: 4-Bromo-3-ethoxycarbonylmethoxy-5-[3-(2-trifluoromethyl-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(2-trifluoromethyl-benzylamino)-phenyl]-thiophene-2-carboxylic acid in 83% yield as a pale yellow solid.

$^1$H NMR (400 MHz, DMSO-D6) δ ppm 4.49 (s, 2 H) 4.84 (s, 2 H) 6.66 (dd, J=7.96, 1.64 Hz, 1 H) 6.79 (m, 2 H) 7.20 (t, J=7.96 Hz, 1 H) 7.46 (t, J=6.82 Hz, 1 H) 7.63 (m, 2 H) 7.75 (d, J=7.83 Hz, 1 H).

ESI-MS: m/e=528 [M−H]$^-$.

EXAMPLE 105

4-Bromo-3-carboxymethoxy-5-[3-(2-fluoro-benzylamino)-phenyl]-thiophene-2-carboxylic acid The first step of Scheme 12: 4-Bromo-3-ethoxycarbonyl-methoxy-5-[3-(2-fluoro-benzylamino)-phenyl]-thiophene-2-carboxylic acid methyl ester was obtained in 88% yield as a yellow oil that crystallizes on standing, following the procedure in the first step of Scheme 12 of Example 102.

¹H NMR (400 MHz, CHLOROFORM-D) δ ppm 1.31 (t, J=7.20 Hz, 3 H) 3.87 (s, 3 H) 4.29 (q, J=7.24 Hz, 2 H) 4.44 (s, 2 H) 4.88 (s, 2 H) 6.92 (m, 1 H) 6.97 (dd, J=7.96, 1.39 Hz, 1 H ) 7.09 (m, 2 H) 7.26 (m, 2 H) 7.39 (td, J=7.58, 1.52 Hz, 2 H).

The second step of Scheme 12: 4-Bromo-3-ethoxycarbonylmethoxy-5-[3-(2-fluoro-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(2-fluoro-benzylamino)-phenyl]-thiophene-2-carboxylic acid in 73% yield as a yellow solid.

¹H NMR (400 MHz, DMSO-D6) δ ppm 4.35 (s, 2 H) 4.85 (s, 2 H) 6.71 (d, J=9.60 Hz, 1 H) 6.83 (m, 2 H) 7.18 (m, 3 H) 7.30 (m, 1 H) 7.41 (m, 1 H).

ESI-MS: m/e=478 [M−H]⁻.

EXAMPLE 106

4-Bromo-3-carboxymethoxy-5-{3-[(furan-2-ylmethyl)-amino]-phenyl}-thiophene-2-carboxylic acid The first step of Scheme 12: 4-Bromo-3-ethoxycarbonylmethoxy-5-{3-[(furan-2-ylmethyl)-amino]-phenyl}-thiophene-2-carboxylic acid methyl ester was prepared in 66% yield as a pale yellow oil, following the procedure in the first step of Scheme 12 of Example 102.

¹H NMR (400 MHz, CHLOROFORM-D) δ ppm 1.32 (t, J=7.07 Hz, 3 H) 3.87 (s, 3 H) 4.29 (q, J=7.24 Hz, 2 H) 4.36 (s, 2 H) 4.90 (s, 2 H) 6.27 (d, J=3.28 Hz, 1 H) 6.33 (dd, J=3.28, 1.77 Hz, 1 H) 6.74 (m, 1 H) 6.95 (m, 1 H) 7.00 (m, 1 H) 7.25 (m, 1 H) 7.38 (dd, J=1.77, 0.76 Hz, 1 H).

The second step of Scheme 12: 4-Bromo-3-ethoxycarbonylmethoxy-5-{3-[(furan-2-ylmethyl)-amino]-phenyl}-thiophene-2-carboxylic acid methyl ester was hydrolyzed according to the procedure in the second step of Scheme 12 of Example 102 to give 4-bromo-3-carboxymethoxy-5-(3-[(furan-2-ylmethyl)-amino]-phenyl}-thiophene-2-carboxylic acid in 74% yield as an off-white solid.

¹H NMR (400 MHz, DMSO-D6) δ ppm 4.29 (s, 2 H) 4.86 (s, 2 H) 6.32 (d, J=3.03 Hz, 1 H) 6.39 (dd, J=3.03, 1.77 Hz, 1 H) 6.76 (dd, J=8.21, 1.64 Hz, 1 H) 6.83 (d, J=7.58 Hz, 1 H) 6.90 (t, J=1.89 Hz, 1 H) 7.20 (t, J=7.96 Hz, 1 H) 7.58 (s, 1 H).

ESI-MS: m/e=450 [M−H]⁻.

EXAMPLE 107

4-Bromo-3-carboxymethoxy-5-{3-[(furan-3-ylmethyl)-amino]-phenyl}-thiophene-2-carboxylic acid The first step of Scheme 12: 4-Bromo-3-ethoxycarbonylmethoxy-5-{3-[(furan-3-ylmethyl)-amino]-phenyl}-thiophene-2-carboxylic acid methyl ester was obtained in 42% yield as a yellow oil, following the procedure in the first step of Scheme 12 of Example 102.

¹H NMR (400 MHz, CHLOROFORM-D) δ ppm 1.32 (t, J=7.07 Hz, 3 H) 3.87 (s, 3 H) 4.21 (s, 2 H) 4.29 (q, J=7.16 Hz, 2 H) 4.90 (s, 2 H) 6.43 (d, J=1.01 Hz, 1 H) 6.72 (m, 1 H) 6.93 (m, 1 H) 6.99 (m, 1 H) 6.99 (m, 1 H) 7.25 (m, 1 H) 7.41 (m, 1 H).

The second step of Scheme 12: 4-Bromo-3-ethoxycarbonylmethoxy-5-{3-[(furan-3-ylmethyl)-amino]-phenyl}-thiophene-2-carboxylic acid methyl ester was hydrolyzed according to the procedure in the second step of Scheme 12 of Example 102 to give 4-bromo-3-carboxymethoxy-5-{3-[(furan-3-ylmethyl)-amino]-phenyl}-thiophene-2-carboxylic acid in 58% yield as a pale yellow solid.

¹H NMR (400 MHz, DMSO-D6) δ ppm 4.12 (s, 2 H) 4.86 (s, 2 H) 6.49 (d, J=1.77 Hz, 1 H) 6.74 (m, 1 H) 6.82 (d, J=7.58 Hz, 1 H) 6.88 (t, J=1.89 Hz, 1 H) 7.20 (m, 1 H) 7.60 (t, J=1.77 Hz, 1 H) 7.62 (s, 1 H).

ESI-MS: m/e=450 [M−H]⁻.

EXAMPLE 108

4-Bromo-3-carboxymethoxy-5-[3-(3-fluoro-benzylamino)-phenyl]-thiophene-2-carboxylic acid The first step of Scheme 12: 4-Bromo-3-ethoxycarbonylmethoxy-5-[3-(3-fluoro-benzylamino)-phenyl]-thiophene-2-carboxylic acid methyl ester was obtained in 80% yield as a colorless solid, following the procedure in the first step of Scheme 12 of Example 102.

¹H NMR (400 MHz, CHLOROFORM-D) δ ppm 1.31 (t, J=7.20 Hz, 3 H) 3.86 (s, 3 H) 4.29 (q, J=7.16 Hz, 2 H) 4.38 (s, 2 H) 4.88 (s, 2 H) 6.68 (m, 1 H) 6.89 (m, 1 H) 6.96 (m, 2 H) 7.09 (m, 1 H) 7.15 (d, J=7.58 Hz, 1 H) 7.23 (t, J=7.96 Hz, 1 H) 7.31 (m, 1 H).

The second step of Scheme 12: 4-Bromo-3-ethoxycarbonylmethoxy-5-[3-(3-fluoro-benzylamino)-phenyl]-thiophene-2-carboxylic acid methyl ester was hydrolyzed according to the procedure in Step the second step of Scheme 12 of Example 102 to give 4-bromo-3-carboxymethoxy-5-[3-(3-fluoro-benzylamino)-phenyl]-thiophene-2-carboxylic acid in 83% yield as a yellow solid.

¹H NMR (400 MHz, DMSO-D6) δ ppm 4.34 (s, 2 H) 4.84 (s, 2 H) 6.69 (m, 1 H) 6.81 (m, 2 H) 7.05 (t, J=8.59 Hz, 1 H) 7.20 (m, 3 H) 7.37 (m, 1 H).

ESI-MS: m/e=478 [M−H]⁻.

EXAMPLE 109

4-Bromo-3-carboxymethoxy-5-[3-(3-cyano-benzylamino)phenyl]-thiophene-2-carboxylic acid The first step of Scheme 12: 4-Bromo-5-[3-(3-cyano-benzylamino)-phenyl]-3-ethoxycarbonylmethoxy-thiophene-2-carboxylic acid methyl ester was obtained in 81% yield as a tan colored oil that crystallized on standing, following the procedure in the first step of Scheme 12 of Example 102.

¹H NMR (400 MHz, CHLOROFORM-D) δ ppm 1.31 (t, J=7.20 Hz, 3 H) 3.87 (s, 3 H) 4.29 (q, J=7.07 Hz, 2 H) 4.44 (s, 2 H) 4.88 (s, 2 H) 6.66 (m, 1 H) 6.86 (m, 1 H) 6.99 (dd, J=6.44, 1.39 Hz, 1 H) 7.24 (t, J=7.96 Hz, 1 H) 7.46 (m, 1 H) 7.57 (m, 1 H) 7.62 (d, J=8.34 Hz, 1 H) 7.68 (d, J=1.52 Hz, 1 H).

The second step of Scheme 12: 4-Bromo-5-[3-(3-cyano-benzylamino)-phenyl]-3-ethoxycarbonylmethoxy-thiophene-2-carboxylic acid methyl ester was hydrolyzed according to the procedure in the second step of Scheme 12 of Example 102 to give 4-bromo-3-carboxymethoxy-5-[3-(3-cyano-benzylamino)-phenyl]-thiophene-2-carboxylic acid in 91% yield as a yellow solid.

¹H NMR (400 MHz, DMSO-D6) δ ppm 4.38 (s, 2 H) 4.85 (s, 2 H) 6.71 (m, 1 H) 6.81 (m, 2 H) 7.19 (t, J=8.21 Hz, 1 H) 7.56 (t, J=7.71 Hz, 1 H) 7.72 (d, J=7.83 Hz, 2 H) 7.81 (s, 1 H).

ESI-MS: m/e=485 [M−H]⁻.

EXAMPLE 110

4-Bromo-3-carboxymethoxy-5-{3-[(pyridin-3-ylmethyl)-amino]-phenyl}-thiophene-2-carboxylic acid The first step of Scheme 12: 4-Bromo-3-ethoxycarbonylmethoxy-5-{3-[(pyridin-3-ylmethyl)-amino]-phenyl}-thiophene-2-carboxylic acid methyl ester was obtained in 57% yield as a pale yellow solid, following the procedure in the first step of Scheme 12 of Example 102.

$^1$H NMR (400 MHz, CHLOROFORM-D) δ ppm 1.31 (t, J=7.20 Hz, 3 H) 3.87 (s, 3 H) 4.29 (q, J=7.16 Hz, 2 H) 4.42 (d, J=5.31 Hz, 2 H) 4.88 (s, 2 H) 6.70 (m, 1 H) 6.91 (m, 1 H) 6.99 (m, 1 H) 7.24 (m, 1 H) 7.29 (m, 1 H) 7.71 (m, 1 H) 8.54 (dd, J=4.80, 1.52 Hz, 1 H) 8.65 (d, J=1.77 Hz, 1 H).

The second step of Scheme 12: 4-Bromo-3-ethoxycarbonylmethoxy-5-{3-[(pyridin-3-ylmethyl)-amino]-phenyl}-thiophene-2-carboxylic acid methyl ester was hydrolyzed according to the procedure in the second step of Scheme 12 of Example 102 to give 4-bromo-3-carboxymethoxy-5-{3-[(pyridin-3-ylmethyl)-amino]-phenyl}-thiophene-2-carboxylic acid in 91% yield as a pale yellow solid.

$^1$H NMR (400 MHz, DMSO-D6) δ ppm 4.36 (s, 2 H) 4.84 (s, 2 H) 6.72 (d, J=7.83 Hz, 1 H) 6.83 (m, 2 H) 7.19 (t, J=7.96 Hz, 1 H) 7.38 (dd, J=7.58, 4.55 Hz, 1 H) 7.79 (d, J=7.83 Hz, 1 H) 8.46 (s, 1 H) 8.61 (s, 1 H).

EXAMPLE 111

4-Bromo-3-carboxymethoxy-5-[3-(4-fluoro-benzylamino)-phenyl]-thiophene-2-carboxylic acid The first step of Scheme 12: 4-Bromo-3-ethoxycarbonylmethoxy-5-[3-(4-fluoro-benzylamino)-phenyl]-thiophene-2-carboxylic acid methyl ester was obtained in 77% yield as a colorless glass, following the procedure in the first step of Scheme 12 of Example 102.

$^1$H NMR (400 MHz, CHLOROFORM-D) δ ppm 1.31 (t, J=7.20 Hz, 3 H) 3.87 (s, 3 H) 4.22 (s, 1 H) 4.29 (q, J=7.16 Hz, 2 H) 4.34 (s, 2 H) 4.89 (s, 2 H) 6.68 (m, 1 H) 6.90 (m, 1 H) 6.97 (m, 1 H) 7.04 (m, 2 H) 7.23 (t, J=7.96 Hz, 1 H) 7.35 (m, 2 H).

The second step of Scheme 12: 4-Bromo-3-ethoxycarbonylmethoxy-5-[3-(4-fluoro-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(4-fluoro-benzylamino)-phenyl]-thiophene-2-carboxylic acid in 76% yield as a pale yellow solid.

$^1$H NMR (400 MHz, DMSO-D6) δ ppm 4.29 (s, 2 H) 4.85 (s, 2 H) 6.69 (dd, J=8.21, 1.39 Hz, 1 H) 6.81 (m, 2 H) 7.16 (m, 3 H) 7.40 (dd, J=8.46, 5.68 Hz, 2 H).

ESI-MS: m/e=478 [M−H]$^-$.

EXAMPLE 112

4-Bromo-3-carboxymethoxy-5-[3-(4-trifluoromethyl-benzylamino)-phenyl]-thiophene-2-carboxylic acid The first step of Scheme 12: 4-Bromo-3-ethoxycarbonylmethoxy-5-[3-(4-trifluoromethyl-benzylamino)-phenyl]-thiophene-2-carboxylic acid methyl ester was obtained in 56% yield as pale yellow crystalline solid, following the procedure in the first step of Scheme 12 of Example 102.

$^1$H NMR (400 MHz, CHLOROFORM-D) δ ppm 1.31 (t, J=7.20 Hz, 3 H) 3.86 (s, 3 H) 4.29 (q, J=7.07 Hz, 2 H) 4.46 (s, 2 H) 4.88 (s, 2 H) 6.67 (dd, J=7.71, 1.89 Hz, 1 H) 6.88 (m, 1 H) 6.98 (d, J=8.08 Hz, 1 H) 7.23 (t, J=7.83 Hz, 1 H) 7.50 (d, J=8.08 Hz, 2 H) 7.61 (d, J=8.34 Hz, 2 H).

The second step of Scheme 12: 4-Bromo-3-ethoxycarbonylmethoxy-5-[3-(4-trifluoromethyl-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(4-trifluoromethyl-benzylamino)-phenyl]-thiophene-2-carboxylic acid in 88% yield as a pale yellow solid.

$^1$H NMR (400 MHz, DMSO-D6) δ ppm 4.43 (s, 2 H) 4.85 (s, 2 H) 6.68 (m, 1 H) 6.80 (m, 2 H) 7.18 (t, J=8.08 Hz, 1 H) 7.59 (d, J=8.08 Hz, 2 H) 7.70 (d, J=7.83 Hz, 2 H).

ESI-MS: m/e=478 [M−H]$^-$.

EXAMPLE 113

4-Bromo-3-carboxymethoxy-5-[3-(4-methoxy-benzylamino)phenyl]-thiophene-2-carboxylic acid The first step of Scheme 12: 4-Bromo-3-ethoxycarbonylmethoxy-5-[3-(4-methoxy-benzylamino)-phenyl]-thiophene-2-carboxylic acid methyl ester was prepared in 78% yield as a pale yellow glassy solid, following the procedure in the first step of Scheme 12 of Example 102.

$^1$H NMR (400 MHz, CHLOROFORM-D) δ ppm 1.31 (t, J=7.20 Hz, 3 H) 3.86 (s, 3 H) 4.14 (s, 1 H) 4.29 (q, J=7.24 Hz, 2 H) 4.89 (s, 3 H) 5.06 (s, 2 H) 5.07 (s, 2 H) 6.91 (m, 1 H) 6.96 (m, 2 H) 7.23 (t, J=7.96 Hz, 1 H) 7.37 (m, 4 H).

The second step of Scheme 12: 4-Bromo-3-ethoxycarbonylmethoxy-5-[3-(4-methoxy-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(4-methoxy-benzylamino)-phenyl]-thiophene-2-carboxylic acid in 76% yield as a pale yellow solid.

$^1$H NMR (400 MHz, DMSO-D6) δ ppm 3.72 (s, 3 H) 4.23 (s, 2 H) 4.86 (s, 2 H) 6.69 (dd, J=8.08, 1.52 Hz, 1 H) 6.79 (d, J=7.58 Hz, 1 H) 6.84 (t, J=1.89 Hz, 1 H) 6.89 (d, J=8.59 Hz, 2 H) 7.17 (t, J=7.83 Hz, 1 H) 7.29 (d, J=8.84 Hz, 2 H).

ESI-MS: m/e=490 [M−H]$^-$.

EXAMPLE 114

5-[3-(4-Benzyloxy-benzylamino)-phenyl]-4-bromo-3-carboxymethoxy-thiophene-2-carboxylic acid The first step of Scheme 12: 5-[3-(4-Benzyloxy-benzylamino)-phenyl]-4-bromo-3-ethoxycarbonylmethoxy-thiophene-2-carboxylic acid methyl ester was obtained in 57% yield as a pale yellow glassy solid, following the procedure in the first step of Scheme 12 of Example 102.

$^1$H NMR (400 MHz, CHLOROFORM-D) δ ppm 1.31 (t, J=7.20 Hz, 3 H) 3.86 (s, 3 H) 4.14 (s, 1 H) 4.29 (m, 4 H) 4.89 (s, 2 H) 5.06 (s, 2 H) 6.69 (dd, J=7.71, 1.89 Hz, 1 H) 6.91 (m, 1 H) 6.96 (m, 3 H) 7.23 (t, J=7.96 Hz, 1 H) 7.29 (d, J=8.84 Hz, 2 H) 7.37 (m, 5 H).

The second step of Scheme 12: 5-[3-(4-Benzyloxy-benzylamino)-phenyl]-4-bromo-3-ethoxycarbonylmethoxy-thiophene-2-carboxylic acid methyl ester was hydrolyzed according to the procedure in the second step of Scheme 12 of Example 102 to give 5-[3-(4-benzyloxy-benzylamino)-phenyl]-4-bromo-3-carboxymethoxy-thiophene-2-carboxylic acid in quantitative yield as a pale yellow solid.

¹H NMR (400 MHz, DMSO-D6) δ ppm 4.22 (s, 2 H) 4.85 (s, 2 H) 5.07 (s, 2 H) 6.69 (dd, J=8.08, 1.52 Hz, 1 H) 6.78 (d, J=7.83 Hz, 1 H) 6.83 (s, 1 H) 6.97 (d, J=8.59 Hz, 2 H) 7.16 (t, J=7.83 Hz, 1 H) 7.31 (m, 3 H) 7.40 (m, 4 H).

ESI-MS: m/e=556 [M−H]⁻.

EXAMPLE 115

4-Bromo-3-carboxymethoxy-5-[3-(4-phenoxy-benzylamino)-phenyl]-thiophene-2-carboxylic acid The first step of Scheme 12: 4-Bromo-3-ethoxycarbonylmethoxy-5-[3-(4-phenoxy-benzylamino)-phenyl]-thiophene-2-carboxylic acid methyl ester was obtained in 80% yield as a yellow glassy solid, following the procedure in the first step of Scheme 12 of Example 102.

¹H NMR (400 MHz, CHLOROFORM-D) δ ppm 1.32 (t, J=7.07 Hz, 3 H) 3.86 (s, 3 H) 4.21 (s, 1 H) 4.28 (t, J=7.07 Hz, 2 H) 4.34 (s, 2 H) 4.89 (s, 2 H) 6.70 (m, 1 H) 6.92 (m, 1 H) 6.97 (m, 1 H) 7.00 (m, 4 H) 7.10 (m, 1 H) 7.24 (t, J=7.83 Hz, 1 H) 7.33 (m, 4 H).

The second step of Scheme 12: 4-Bromo-3-ethoxycarbonylmethoxy-5-[3-(4-phenoxy-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(4-phenoxy-benzylamino)-phenyl]-thiophene-2-carboxylic acid in 95% yield as a pale yellow solid.

¹H NMR (400 MHz, DMSO-D6) δ ppm 4.29 (s, 2 H) 4.86 (s, 2 H) 6.72 (dd, J=7.71, 1.89 Hz, 1 H) 6.79 (m, 1 H) 6.83 (t, J=1.77 Hz, 1 H) 6.98 (m, 4 H) 7.11 (m, 1 H) 7.18 (t, J=7.96 Hz, 1 H) 7.38 (m, 4 H).

ESI-MS: m/e=552 [M−H]⁻.

EXAMPLE 116

4-Bromo-3-carboxymethoxy-5-{3-[(naphthalen-2-ylmethyl)-amino]-phenyl}-thiophene-2-carboxylic acid The first step of Scheme 12: 4-Bromo-3-ethoxycarbonylmethoxy-5-{3-[(naphthalen-2-ylmethyl)-amino]-phenyl}-thiophene-2-carboxylic acid methyl ester was obtained in 65% yield as a pale yellow glassy solid, following the procedure in the first step of Scheme 12 of Example 102.

¹H NMR (400 MHz, CHLOROFORM-D) δ ppm 1.30 (t, J=7.07 Hz, 3 H) 3.86 (s, 3 H) 4.28 (q, J=7.07 Hz, 2 H) 4.54 (s, 2 H) 4.87 (s, 2 H) 6.74 (m, 1 H) 6.97 (m, 2 H) 7.23 (m, 1 H) 7.48 (m, 3 H) 7.83 (m, 4 H).

The second step of Scheme 12: 4-Bromo-3-ethoxycarbonylmethoxy-5-{3-[(naphthalen-2-ylmethyl)-amino]-phenyl}-thiophene-2-carboxylic acid methyl ester was hydrolyzed according to the procedure in the second step of Scheme 12 of Example 102 to give 4-bromo-3-carboxymethoxy-5-{3-[(naphthalen-2-ylmethyl)-amino]-phenyl}-thiophene-2-carboxylic acid in 96% yield as a pale yellow solid.

¹H NMR (400 MHz, DMSO-D6) δ ppm 4.48 (s, 2 H) 4.84 (s, 2 H) 6.74 (dd, J=8.21, 1.64 Hz, 1 H) 6.79 (d, J=8.34 Hz, 1 H) 6.90 (t, J=2.02 Hz, 1 H) 7.17 (t, J=7.83 Hz, 1 H) 7.47 (m, 2 H) 7.54 (dd, J=8.46, 1.64 Hz, 1 H) 7.88 (m, 4 H).

ESI-MS: m/e=510 [M−H]⁻.

EXAMPLE 117

4-Bromo-5-[3-(3-carboxy-benzylamino)phenyl]-3-carbomethoxy-thiophene-2-carboxylic acid The first step of Scheme 12: 4-Bromo-5-[3-(3-carboxy-benzylamino)-phenyl]-3-ethoxycarbonylmethoxy-thiophene-2-carboxylic acid methyl ester was obtained in 60% yield as an off-white solid, following the procedure in the first step of Scheme 12 of Example 102.

¹H NMR (400 MHz, DMSO-D6) δ ppm 1.21 (t, J=7.07 Hz, 3 H) 3.80 (s, 3 H) 4.17 (q, J=7.24 Hz, 2 H) 4.38 (d, J=6.06 Hz, 2 H) 4.92 (s, 2 H) 6.73 (m, 2 H) 6.81 (m, 2 H) 7.19 (t, J=7.83 Hz, 1 H) 7.46 (t, J=7.58 Hz, 1 H) 7.62 (d, J=7.58 Hz, 1 H) 7.81 (d, J=7.58 Hz, 1 H) 7.97 (s, 1 H).

The second step of Scheme 12: 4-Bromo-5-[3-(3-carboxy-benzylamino)-phenyl]-3-ethoxycarbonylmethoxy-thiophene-2-carboxylic acid methyl ester was hydrolyzed according to the procedure in the second step of Scheme 12 of Example 102 to give 4-bromo-5-[3-(3-carboxy-benzylamino)-phenyl]-3-carboxymethoxy-thiophene-2-carboxylic acid in 72% yield as a tan-colored solid.

¹H NMR (400 MHz, DMSO-D6) δ ppm 4.38 (s, 2 H) 4.84 (s, 2 H) 6.70 (dd, J=7.96, 1.89 Hz, 2 H) 6.79 (d, J=8.08 Hz, 1 H) 6.84 (s, 1 H) 7.18 (t, J=7.96 Hz, 1 H) 7.46 (t, J=7.71 Hz, 1 H) 7.62 (d, J=8.08 Hz, 1 H) 7.81 (d, J=7.33 Hz, 1 H) 7.97 (s, 1 H).

ESI-MS: m/e=504 [M−H]⁻.

EXAMPLE 118

4-Bromo-3-carboxymethoxy-5-[3-(3-trifluoromethoxy-benzylamino)-phenyl]-thiophene-2-carboxylic acid The first step of Scheme 12: 4-Bromo-3-ethoxycarbonylmethoxy-5-[3-(3-trifluoromethoxy-benzylamino)-phenyl]-thiophene-2-carboxylic acid methyl ester was obtained in 68% yield as a white solid, following the procedure in the first step of Scheme 12 of Example 102.

¹H NMR (400 MHz, CHLOROFORM-D) δ ppm 1.31 (m, 3 H) 3.86 (s, 3 H) 4.29 (m, 3 H) 4.41 (d, J=4.55 Hz, 2 H) 4.88 (s, 2 H) 6.68 (m, 1 H) 6.89 (m, 1 H) 6.98 (dd, J=6.82, 1.77 Hz, 1 H) 7.13 (m, 1 H) 7.24 (m, 2 H) 7.32 (d, J=7.58 Hz, 1 H) 7.37 (t, J=7.83 Hz, 1 H).

The second step of Scheme 12: 4-Bromo-3-ethoxycarbonylmethoxy-5-[3-(3-trifluoromethoxy-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(3-trifluoromethoxy-benzylamino)-phenyl]-thiophene-2-carboxylic acid in 67% yield as a pale yellow solid.

¹H NMR (400 MHz, DMSO-D6) δ ppm 4.38 (s, 2 H) 4.85 (s, 2 H) 6.71 (m, 1 H) 6.81 (m, 2 H) 7.18 (m, 2 H) 7.34 (s, 1 H) 7.41 (d, J=7.83 Hz, 1 H) 7.47 (t, J=7.83 Hz, 1 H).

ESI-MS: m/e=544 [M−H]⁻.

EXAMPLE 119

4-Bromo-3-carboethoxy-5-[3-(2-trifluoromethoxy-benzylamino)-phenyl]-thiophene-2-carboxylic acid The first step of Scheme 12: 4-Bromo-3-ethoxycarbonylmethoxy-5-[3-(2-trifluoromethoxy-benzylamino)-phenyl]-thiophene-2-carboxylic acid methyl ester was obtained in 59% yield as a white solid, following the procedure in the first step of Scheme 12 of Example 102.

¹H NMR (400 MHz, CHLOROFORM-D) δ ppm 1.31 (t, J=7.20 Hz, 3 H) 3.86 (s, 3 H) 4.29 (q, J=7.16 Hz, 2 H) 4.48 (d, J=5.31 Hz, 2 H) 4.88 (s, 2 H) 6.67 (dd, J=8.08, 1.52 Hz, 1 H) 6.89 (m, 1 H) 6.97 (d, J=7.58 Hz, 1 H) 7.26 (m, 4 H) 7.48 (d, J=7.33 Hz, 1 H).

The second step of Scheme 12: 4-Bromo-3-ethoxycarbonylmethoxy-5-[3-(2-trifluoromethoxy-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(2-trifluoromethoxy-benzylamino)-phenyl]-thiophene-2-carboxylic acid in 50% yield as a pale yellow solid.

¹H NMR (400 MHz, DMSO-D6) δ ppm 4.38 (s, 2 H) 4.84 (s, 2 H) 6.67 (dd, J=8.21, 1.64 Hz, 1 H) 6.80 (m, 2 H) 7.20 (m, 1 H) 7.37 (m, 3 H) 7.48 (m, 1 H).

ESI-MS: m/e=544 [M−H]⁻.

EXAMPLE 120

4-Bromo-3-carboxymethoxy-5-[3-(2-hydroxy-benzylamino)-phenyl]-thiophene-2-carboxylic acid The first step of Scheme 12: 4-Bromo-3-ethoxycarbonylmethoxy-5-[3-(2-hydroxy-benzylamino)-phenyl]-thiophene-2-carboxylic acid methyl ester was obtained in 36% yield as a pale yellow solid, following the procedure in the first step of Scheme 12 of Example 102.

¹H NMR (400 MHz, CHLOROFORM-D) δ ppm 1.32 (t, J=7.20 Hz, 3 H) 3.87 (s, 3 H) 4.29 (q, J=7.07 Hz, 2 H) 4.45 (s, 2 H) 4.89 (s, 2 H) 6.89 (m, 3 H) 7.15 (m, 2 H) 7.21 (m, 2 H) 7.30 (t, J=8.08 Hz, 1 H) 7.84 (s, 1 H)

The second step of Scheme-12: 4-Bromo-3-ethoxycarbonylmethoxy-5-[3-(2-hydroxy-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(2-hydroxy-benzylamino)-phenyl]-thiophene-2-carboxylic acid in 84% yield as an off-white solid.

¹H NMR (400 MHz, CHLOROFORM-D) δ ppm 1.32 (t, J=7.20 Hz, 3 H) 3.87 (s, 3 H) 4.29 (q, J=7.07 Hz, 2 H) 4.45 (s, 2 H) 4.89 (s, 2 H) 6.89 (m, 3 H) 7.15 (m, 2 H) 7.21 (m, 2 H) 7.30 (t, J=8.08 Hz, 1 H) 7.84 (s, 1 H).

EXAMPLE 121

4-Bromo-3-carboxymethoxy-5-[3-(4-methyl-benzylamino)-phenyl]-thiophene-2-carboxylic acid The first step of Scheme 12: 4-Bromo-3-ethoxycarbonylmethoxy-5-[3-(4-methyl-benzylamino)-phenyl]-thiophene-2-carboxylic acid methyl ester was obtained in 71% yield as a pale yellow glassy solid, following the procedure in the first step of Scheme 12 of Example 102.

¹H NMR (400 MHz, CHLOROFORM-D) δ ppm 1.31 (t, J=7.20 Hz, 3 H) 2.34 (s, 3 H) 3.86 (s, 3 H) 4.17 (s, 1 H) 4.29 (m, 4 H) 4.88 (s, 2 H) 6.68 (m, 1 H) 6.91 (m, 1 H) 6.96 (d, J=7.58 Hz, 1 H) 7.16 (d, J=7.83 Hz, 2 H) 7.24 (m, 3 H).

The second step of Scheme 12: 4-Bromo-3-ethoxycarbonylmethoxy-5-[3-(4-methyl-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(4-methyl-benzylamino)-phenyl]-thiophene-2-carboxylic acid in 95% yield as a pale yellow solid.

¹H NMR (400 MHz, DMSO-D6) δ ppm 2.27 (s, 3 H) 4.25 (s, 2 H) 4.85 (s, 2 H) 6.68 (dd, J=8.08, 1.77 Hz, 1 H) 6.78 (d, J=8.34 Hz, 1 H) 6.83 (m, 1 H) 7.15 (m, 3 H) 7.25 (d, J=8.08 Hz, 2 H).

EXAMPLE 122

4-Bromo-3-carboxymethoxy-5-[3-(4-chloro-benzylamino)-phenyl]-thiophene-2-carboxylic acid The first step of Scheme 12: 4-Bromo-5-[3-(4-chloro-benzylamino)-phenyl]-3-ethoxycarbonylmethoxy-thiophene-2-carboxylic acid methyl ester was obtained in 70% yield as a pale yellow solid, following the procedure in the first step of Scheme 12 of Example 102.

¹H NMR (400 MHz, CHLOROFORM-D) δ ppm 1.31 (t, J=7.07 Hz, 3 H) 3.87 (s, 3 H) 4.29 (q, J=7.24 Hz, 2 H) 4.35 (s, 2 H) 4.89 (s, 2 H) 6.67 (m, 1 H) 6.89 (m, 1 H) 6.98 (m, 1 H) 7.23 (t, J=7.96 Hz, 1 H) 7.31 (s, 4 H).

The second step of Scheme 12: 4-Bromo-5-[3-(4-chloro-benzylamino)-phenyl]-3-ethoxycarbonylmethoxy-thiophene-2-carboxylic acid methyl ester was hydrolyzed according to the procedure in the second step of Scheme 12 of Example 102 to give 4-bromo-3-carboxymethoxy-5-[3-(4-chloro-benzylamino)-phenyl]-thiophene-2-carboxylic acid in 71% yield as a pale yellow solid.

¹H NMR (400 MHz, DMSO-D6) δ ppm 4.31 (s, 2 H) 4.85 (s, 2 H) 6.68 (m, 1 H) 6.80 (m, 2 H) 7.17 (t, J=7.83 Hz, 1 H) 7.39 (s, 4 H).

EXAMPLE 123

4-Bromo-3-carboxymethoxy-5-[3-(4-isopropyl-benzylamino)-phenyl]-thiophene-2-carboxylic acid The first step of Scheme 12: 4-Bromo-3-ethoxycarbonylmethoxy-5-[3-(4-isopropyl-benzylamino)-phenyl]-thiophene-2-carboxylic acid methyl ester was obtained in 55% yield as a pale yellow glassy solid, following the procedure in the first step of Scheme 12 of Example 102.

¹H NMR (400 MHz, CHLOROFORM-D) δ ppm 1.25 (d, J=6.82 Hz, 6 H) 1.31 (t, J=7.20 Hz, 3 H) 2.91 (m, 1 H) 3.85 (d, J=6.82 Hz, 3 H) 4.18 (s, 1 H) 4.30 (m, 4 H) 4.89 (m, 2 H) 6.70 (m, 1 H) 6.91 (m, 1 H) 6.96 (dd, J=7.58, 1.01 Hz, 1 H) 7.23 (m, 3 H) 7.31 (m, 2 H).

The second step of Scheme 12: 4-Bromo-3-ethoxycarbonylmethoxy-5-[3-(4-isopropyl-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(4-isopropyl-benzylamino)-phenyl]-thiophene-2-carboxylic acid in 43% yield as an off-white solid.

¹H NMR (400 MHz, DMSO-D6) δ ppm 1.18 (d, J=7.07 Hz, 6 H) 2.85 (m, 1 H) 4.25 (s, 2 H) 4.85 (s, 2 H) 6.70 (dd, J=8.34, 1.52 Hz, 1 H) 6.78 (d, J=7.07 Hz, 1 H) 6.82 (t, J=1.77 Hz, 1 H) 7.17 (m, 3 H) 7.29 (m, 2 H).

ESI-MS: m/e=502 [M−H]⁻.

EXAMPLE 124

4-Bromo-3-carboxymethoxy-5-[3-(3-nitro-benzylamino)-phenyl]-thiophene-2-carboxylic acid The first step of Scheme 12: 4-Bromo-3-ethoxycarbonylmethoxy-5-[3-(3-nitro-benzylamino)-phenyl]-thiophene-2-carboxylic acid methyl ester was purified by recrystallization from EtOH to give 68% yield of the methyl ester as a pale yellow crystalline solid, following the procedure in the first step of Scheme 12 of Example 102.

¹H NMR (400 MHz, CHLOROFORM-D) δ ppm 1.31 (t, J=7.20 Hz, 3 H) 3.86 (s, 3 H) 4.29 (q, J=7.16 Hz, 2 H) 4.42 (t, J=5.94 Hz, 1 H) 4.51 (d, J=5.81 Hz, 2 H) 4.88 (s, 2 H) 6.68 (m, 1 H) 6.88 (m, 1 H) 7.00 (dd, J=6.69, 1.64 Hz, 1 H) 7.24 (m, 1 H) 7.53 (t, J=7.96 Hz, 1 H) 7.73 (d, J=8.34 Hz, 1 H) 8.14 (m, 1 H) 8.26 (s, 1 H).

The second step of Scheme 12: 4-Bromo-3-ethoxycarbonylmethoxy-5-[3-(3-nitro-benzylamino)-phenyl]-thiophene-2-carboxylic acid methyl ester was hydrolyzed according to the procedure in the second step of Scheme 12 of Example 102 to give 4-bromo-3-carboxymethoxy-5-[3-(3-nitro-benzylamino)-phenyl]-thiophene-2-carboxylic acid in 69% yield as a pale yellow solid.

$^1$H NMR (400 MHz, DMSO-D6) δ ppm 4.48 (d, J=4.04 Hz, 2 H) 4.84 (s, 2 H) 6.72 (dd, J=7.96, 1.89 Hz, 1 H) 6.82 (m, 2 H) 7.19 (t, J=7.83 Hz, 1 H) 7.64 (t, J=7.96 Hz, 1 H) 7.85 (d, J=7.58 Hz, 1 H) 8.10 (d, J=7.83 Hz, 1 H) 8.24 (s, 1 H).

ESI-MS: m/e=507 [M+H]$^+$.

EXAMPLE 125

4-Bromo-3-carboxymethoxy-5-[3-(3-methanesulfonylamino-benzylamino)-phenyl]-thiophene-2-carboxylic acid The first step of Scheme 13: To a 6 mL ethyl acetate suspension of 4-bromo-3-ethoxycarbonylmethoxy-5-[3-(3-nitro-benzylamino)-phenyl]-thiophene-2-carboxylic acid methyl ester (340 mg, 0.62 mmole) was added tin dichloride dihydrate (698 mg, 3.1 mmole) and the mixture was heated to reflux until TLC shows disappearance of starting material. The mixture was then cooled to room temperature and washed with saturated sodium bicarbonate solution, brine and dried over MgSO$_4$. Filtration and evaporation gave 304 mg (94%) 5-[3-(3-amino-benzylamino)-phenyl]-4-bromo-3-ethoxycarbonylmethoxy-thiophene-2-carboxylic acid methyl ester as a yellow semisolid.

$^1$H NMR (400 MHz, CHLOROFORM-D) δ ppm 1.32 (t, J=7.20 Hz, 3 H) 3.87 (s, 3 H) 4.29 (m, 4 H) 4.88 (s, 2 H) 6.60 (m, 1 H) 6.69 (m, 2 H) 6.76 (d, J=8.08 Hz, 1 H) 6.91 (m, 1 H) 6.96 (m, 1 H) 7.13 (t, J=7.71 Hz, 1 H) 7.23 (t, J=7.83 Hz, 1 H).

The second step of Scheme 13: To a 1 mL pyridine of 5-[3-(3-amino-benzylamino)-phenyl]-4-bromo-3-ethoxycarbonylmethoxy-thiophene-2-carboxylic acid methyl ester (52 mg, 0.1 mmole) was added methanesulfonylchloride (9 μL, 0.12 mmole) and the reaction mixture was allowed to stir 4 hours at room temperature. 15 mL 1N HCl was then added and extracted with EtOAc. The organic layer was washed with brine and dried over MgSO$_4$. Filtration and evaporation gave the crude product which was then purified by chromatography on silica gel using a gradient of EtOAc/hexane (15 to 60%) as eluent. Pure fractions were combined and evaporated to give 40 mg (67%) of 4-bromo-3-ethoxycarbonylmethoxy-5-[3-(3-methanesulfonylamino-benzylamino)-phenyl]-thiophene-2-carboxylic acid methyl ester as a colorless glassy solid.

$^1$H NMR (400 MHz, CHLOROFORM-D) δ ppm 1.31 (t, J=7.20 Hz, 3 H) 2.95 (s, 3 H) 3.86 (s, 3 H) 4.29 (q, J=7.07 Hz, 2 H) 4.39 (s, 2 H) 4.88 (s, 2 H) 6.59 (s, 1 H) 6.69 (m, 1 H) 6.86 (m, 1 H) 6.96 (m, 1 H) 7.12 (m, 1 H) 7.21 (m, 3 H) 7.33 (t, J=7.83 Hz, 1 H).

The third step of Scheme 13: 4-Bromo-3-ethoxycarbonylmethoxy-5-[3-(3-methanesulfonylamino-benzylamino)-phenyl]-thiophene-2-carboxylic acid methyl ester (40 mg, 6.7×10$^{-5}$ mmol) was dissolved in 1.5 mL of a 2:1 mixture of THF:H$_2$O and LiOH.H$_2$O (14 mg, 0.33 mmol) was added and the mixture stirred at room temperature overnight. The reaction mixture was then evaporated and the residue re-dissolved in 2-3 mL of H$_2$O. It was acidified dropwise with 1N HCl while stirring. A solid emerged that was filtered, washed with water, and vacuum oven-dried to give 27 mg (73%) of 4-bromo-3-carboxymethoxy-5-[3-(3-methanesulfonylamino-benzylamino)-phenyl]-thiophene-2-carboxylic acid as a pale yellow solid.

$^1$H NMR (400 MHz, DMSO-D6) δ ppm 2.92 (s, 3 H) 4.29 (s, 2 H) 4.84 (s, 2 H) 6.69 (dd, J=8.97, 1.64 Hz, 1 H) 6.79 (m, 2 H) 7.09 (m, 2 H) 7.17 (t, J=7.96 Hz, 1 H) 7.22 (s, 1 H) 7.29 (t, J=7.83 Hz, 1 H) 9.71 (s, 1 H).

ESI-MS: m/e=553 [M−H]$^-$.

EXAMPLE 126

5-[3-(3-Amino-benzylamino)-phenyl]-4-bromo-3-carboxymethoxy-thiophene-2-carboxylic acid The third step of Scheme 13: 5-[3-(3-Amino-benzylamino)-phenyl]-4-bromo-3-ethoxycarbonylmethoxy-thiophene-2-carboxylic acid methyl ester was hydrolyzed according to the procedure in the third step of Scheme 13 of Example 125 to give 5-[3-(3-amino-benzylamino)-phenyl]-4-bromo-3-carboxymethoxy-thiophene-2-carboxylic acid in 32% yield as a tan colored solid.

$^1$H NMR (400 MHz, DMSO-D6) δ ppm 4.14 (s, 2 H) 4.79 (s, 2 H) 6.42 (m, 1 H) 6.51 (d, J=7.58 Hz, 1 H) 6.57 (s, 1 H) 6.66 (m, 1 H) 6.77 (d, J=7.83 Hz, 1 H) 6.82 (d, J=1.77 Hz, 1 H) 6.96 (t, J=7.71 Hz, 1 H) 7.16 (t, J=8.08 Hz, 1 H).

ESI-MS: m/e=432 [M−CO$_2$]$^+$.

EXAMPLE 127

5-[3-(3-Acetylamino-benzylamino)-phenyl]-4-bromo-3-carboxymethoxy-thiophene-2-carboxylic acid The second step of Scheme 13: To a 1 mL pyridine solution of 5-[3-(3-amino-benzylamino)-phenyl]-4-bromo-3-ethoxycarbonylmethoxy-thiophene-2-carboxylic acid methyl ester (51 mg, 0.1 mmole) was added acetyl chloride (9 μL, 0.12 mmole) and the reaction mixture was stirred at room temperature overnight. 15 mL 1N HCl was added and the mixture extracted with EtOAc. The organic layer was washed with saturated bicarbonate solution, brine and dried over MgSO$_4$. Filtration and evaporation gave the crude product which was then purified by chromatography on silica gel using a gradient of EtOAc/hexane (15 to 60%) as eluent. Pure fractions were combined and evaporated to give 17 mg (30%) of 5-[3-(3-acetylamino-benzylamino)-phenyl]-4-bromo-3-ethoxycarbonylmethoxy-thiophene-2-carboxylic acid methyl ester as a pale yellow glassy solid.

$^1$H NMR (400 MHz, CHLOROFORM-D) δ ppm 1.31 (t, J=7.20 Hz, 3 H) 2.16 (s, 3 H) 3.86 (s, 3 H) 4.29 (q, J=7.16 Hz, 2 H) 4.35 (s, 2 H) 4.88 (s, 2 H) 6.67 (dd, J=7.83, 2.02 Hz, 1 H) 6.88 (m, 1 H) 6.96 (m, 1 H) 7.12 (d, J=7.83 Hz, 1 H) 7.22 (t, J=7.96 Hz, 1 H) 7.29 (t, J=7.83 Hz, 1 H) 7.43 (d, J=7.83 Hz, 1 H) 7.51 (s, 1 H).

The third step of Scheme 13: 5-[3-(3-Acetylamino-benzylamino)-phenyl]-4-bromo-3-ethoxycarbonylmethoxy-thiophene-2-carboxylic acid methyl ester was hydrolyzed according to the procedure in the third step of Scheme 13 of Example 125 to give 5-[3-(3-acetylamino-benzylamino)-phenyl]-4-bromo-3-carboxymethoxy-thiophene-2-carboxylic acid in 77% yield as a pale yellow solid.

¹H NMR (400 MHz, DMSO-D6) δ ppm 2.01 (s, 3 H) 4.27 (s, 2 H) 4.85 (s, 2 H) 6.67 (m, 1 H) 6.80 (m, 2 H) 7.03 (d, J=7.33 Hz, 1 H) 7.17 (t, J=7.83 Hz, 1 H) 7.24 (t, J=7.96 Hz, 1 H) 7.49 (d, J=8.59 Hz, 1 H) 7.54 (s, 1 H) 9.90 (s, 1 H).
ESI-MS: m/e=475 [M−CO$_2$]$^+$.

EXAMPLE 128

4-Bromo-3-carboxymethoxy-5-(3-cyclohexylaminophenyl)-thiophene-2-carboxylic acid The first step of Scheme 14: To a 1.5 mL DCE solution of 5-(3-amino-phenyl)-4-bromo-3-ethoxycarbonylmethoxy-thiophene-2-carboxylic acid methyl ester (41 mg, 0.1 mmole) was added cyclohexanone (13 µL, 0.12 mmole), acetic acid (10 µL, 0.15 mmole) and sodium triacetoxyborohydride (53 mg, 0.25 mmole). The reaction mixture was stirred at room temperature overnight. The reaction mixture was then diluted with CH$_2$Cl$_2$ and washed with saturated sodium bicarbonate solution and dried over MgSO$_4$. Filtration and evaporation gave the crude product which was then purified by chromatography on silica gel using a gradient of hexane/EtOAc (5 to 25%) as eluent. Pure fractions were combined and evaporated to give 35 mg (70%) 4-bromo-5-(3-cyclohexylamino-phenyl)-3-ethoxycarbonylmethoxy-thiophene-2-carboxylic acid methyl ester as a yellow oil.
¹H NMR (400 MHz, CHLOROFORM-D) δ ppm 1.21 (m, 3 H) 1.32 (m, 3 H) 1.39 (m, 2 H) 1.66 (m, 1 H) 1.77 (m, 2 H) 2.08 (dd, J=12.76, 3.16 Hz, 2 H) 3.28 (m, 1 H) 3.70 (s, 1 H) 3.87 (s, 3 H) 4.30 (q, J=7.07 Hz, 2 H) 4.90 (s, 2 H) 6.64 (dd, J=7.71, 1.89 Hz, 1 H) 6.85 (m, 1 H) 6.90 (m, 1 H) 7.21 (t, J=7.83 Hz, 1 H).

The second step of Scheme 14: 4-Bromo-5-(3-cyclohexylamino-phenyl)-3-ethoxycarbonylmethoxy-thiophene-2-carboxylic acid methyl ester (35 mg, 0.07 mmol) was dissolved in 1.5 mL of a 2:1 mixture of THF:H$_2$O and LiOH.H$_2$O (15 mg, 0.35 mmol) was added and the mixture stirred at room temperature overnight. The reaction mixture was then evaporated and the residue re-dissolved in 2-3 mL of H$_2$O. It was acidified dropwise with 1N HCl while stirring. A solid emerged that was filtered, washed with water, and vacuum oven-dried to give 26 mg (83%) of 4-bromo-3-carboxymethoxy-5-(3-cyclohexylamino-phenyl)-thiophene-2-carboxylic acid as a pale yellow solid.
¹H NMR (400 MHz, DMSO-D6) δ ppm 1.18 (m, 5 H) 1.34 (m, 2 H) 1.60 (m, 1 H) 1.73 (m, 2 H) 1.95 (m, 1 H) 4.88 (s, 2 H) 6.70 (m, 1 H) 6.77 (m, 1 H) 6.84 (s, 1 H) 7.19 (t, J=7.71 Hz, 1 H).
ESI-MS: m/e=452 [M−H]$^−$.

EXAMPLE 129

4-Bromo-3-carboxymethoxy-5-(3-cyclopentylaminophenyl)-thiophene-2-carboxylic acid The first step of Scheme 14: 4-Bromo-5-(3-cyclopentylamino-phenyl)-3-ethoxycarbonylmethoxy-thiophene-2-carboxylic acid methyl ester was obtained in 75% yield as a yellow glassy solid, following the procedure in the first step of Scheme 14 of Example 128.
¹H NMR (400 MHz, CHLOROFORM-D) δ ppm 1.32 (t, J=7.07 Hz, 3 H) 1.50 (m, 2 H) 1.69 (m, 4 H) 2.05 (m, 2 H) 3.81 (m, 1 H) 3.87 (s, 3 H) 4.30 (q, J=7.16 Hz, 2 H) 4.90 (s, 2 H) 6.65 (m, 1 H) 6.87 (m, 1 H) 6.93 (m, 1 H) 7.22 (t, J=7.96 Hz, 1 H).

The second step of Scheme 14: 4-Bromo-5-(3-cyclopentylamino-phenyl)-3-ethoxycarbonylmethoxy-thiophene-2-carboxylic acid methyl ester was hydrolyzed according to the procedure in the second step of Scheme 14 of Example 128 to give 4-bromo-3-carboxymethoxy-5-(3-cyclopentylaminophenyl)-thiophene-2-carboxylic acid in 79% yield as a pale yellow solid.
¹H NMR (400 MHz, DMSO-D6) δ ppm 1.47 (m, 2 H) 1.56 (m, 2 H) 1.67 (m, 2 H) 1.93 (m, 2 H) 3.71 (m, 1 H) 4.88 (s, 2 H) 6.67 (m, 1 H) 6.77 (d, J=1.26 Hz, 1 H) 6.82 (d, J=2.02 Hz, 1 H) 7.17 (m, 1 H).
ESI-MS: m/e=440[M+H]$^+$.

EXAMPLE 130

5-[3-(1-Acetyl-piperidin-4-ylamino)-phenyl]-4-bromo-3-carboxymethoxy-thiophene-2-carboxylic acid The first step of Scheme 14: 5-[3-(1-Acetyl-piperidin-4-ylamino)-phenyl]-4-bromo-3-ethoxycarbonylmethoxy-thiophene-2-carboxylic acid methyl ester was obtained in 66% yield as a yellow oil, following the procedure in the first step of Scheme 14 of Example 128.
¹H NMR (400 MHz, CHLOROFORM-D) δ ppm 1.32 (t, J=7.20 Hz, 2 H) 1.40 (m, 2 H) 2.17 (m, 6 H) 2.49 (dd, J=6.57, 2.27 Hz, 1 H) 2.88 (m, 1 H) 3.23 (m, 1 H) 3.55 (s, 1 H) 3.74 (m, 1 H) 3.83 (m, 1 H) 3.88 (s, 3 H) 4.30 (q, J=7.16 Hz, 1 H) 4.50 (m, 1 H) 4.91 (s, 2 H) 6.67 (m, 1 H) 6.88 (m, 1 H) 6.96 (m, 1 H) 7.24 (t, J=7.83 Hz, 1 H).

The second step of Scheme 14: 5-[3-(1-Acetyl-piperidin-4-ylamino)-phenyl]-4-bromo-3-ethoxycarbonylmethoxy-thiophene-2-carboxylic acid methyl ester was hydrolyzed according to the procedure in the second step of Scheme 14 of Example 128 to give 5-[3-(1-acetyl-piperidin-4-ylamino)-phenyl]-4-bromo-3-carboxymethoxy-thiophene-2-carboxylic acid in 51% yield as a yellow solid.
¹H NMR (400 MHz, DMSO-D6) δ ppm 1.25 (m, 2 H) 1.94 (m, 2 H) 2.00 (s, 3 H) 2.82 (m, 1 H) 3.18 (m, 2 H) 3.52 (s, 1 H) 3.78 (m, 1 H) 4.21 (m, 1 H) 4.84 (s, 2 H) 6.72 (m, 1 H) 6.77 (d, J=7.58 Hz, 1 H) 6.85 (s, 1 H) 7.19 (t, J=7.83 Hz, 1 H).
ESI-MS: m/e=497 [M+H]$^+$.

EXAMPLE 131

4-Bromo-3-carboxymethoxy-5-(3-cycloheptylaminophenyl)-thiophene-2-carboxylic acid The first step of Scheme 14: 4-Bromo-5-(3-cycloheptylamino-phenyl)-3-ethoxycarbonylmethoxy-thiophene-2-carboxylic acid methyl ester was obtained in 72% yield as a pale yellow glassy solid, following the procedure in the first step of Scheme 14 of Example 128.
¹H NMR (400 MHz, CHLOROFORM-D) δ ppm 1.32 (t, J=7.07 Hz, 3 H) 1.57 (m, 10 H) 2.03 (m, 2 H) 3.47 (m, 1 H) 3.76 (s, 1 H) 3.87 (s, 3 H) 4.30 (q, J=7.16 Hz, 2 H) 4.90 (s, 2 H) 6.60 (dd, J=8.21, 2.40 Hz, 1 H) 6.81 (t, J=1.89 Hz, 1 H) 6.90 (d, J=7.58 Hz, 1 H) 7.21 (t, J=7.96 Hz, 1 H).

The second step of Scheme 14: 4-Bromo-5-(3-cycloheptylamino-phenyl)-3-ethoxycarbonylmethoxy-thiophene-2-carboxylic acid methyl ester was hydrolyzed according to the procedure in the second step of Scheme 14 of Example 128 to give 4-bromo-3-carboxymethoxy-5-(3-cycloheptylaminophenyl)-thiophene-2-carboxylic acid in 71% yield as a pale yellow solid.
¹H NMR (400 MHz, DMSO-D6) δ ppm 1.53 (m, 10 H) 1.90 (t, J=6.82 Hz, 2 H) 4.88 (s, 2 H) 6.65 (dd, J=8.59, 2.27 Hz, 1 H) 6.77 (m, 2 H) 7.19 (t, J=7.83 Hz, 1 H).

EXAMPLE 132

5-[3-(Bicyclo[3.3.1]non-9-ylamino)-pheny]-4-bromo-3-carboxymethoxy-thiophene-2-carboxylic acid The first step of Scheme 14: 5-[3-(Bicyclo[3.3.1]non-9-ylamino)-phenyl]-4-bromo-3-ethoxycarbonylmethoxy-thiophene-2-carboxylic acid methyl ester was obtained in 76% yield as a yellow oil, following the procedure in the first step of Scheme 14 of Example 128.
$^1$H NMR (400 MHz, CHLOROFORM-D) δ ppm 1.32 (t, J=7.20 Hz, 3 H) 1.50 (m, 3 H) 1.81 (m, 8 H) 2.02 (m, 4 H) 3.39 (s, 1 H) 3.87 (s, 3 H) 4.11 (s, 1 H) 4.30 (q, J=7.07 Hz, 2 H) 4.90 (s, 2 H) 6.66 (m, 1 H) 6.88 (m, 1 H) 6.91 (m, 1 H) 7.21 (t, J=7.96 Hz, 1 H).

The second step of Scheme 14: 5-[3-(Bicyclo[3.3.1]non-9-ylamino)-phenyl]-4-bromo-3-ethoxycarbonylmethoxy-thiophene-2-carboxylic acid methyl ester was hydrolyzed according to the procedure in the second step of Scheme 14 of Example 128 to give 5-[3-(bicyclo[3.3.1]non-9-ylamino)-phenyl]-4-bromo-3-carboxymethoxy-thiophene-2-carboxylic acid in 59% yield as a pale yellow solid.
$^1$H NMR (400 MHz, DMSO-D6) δ ppm 1.46 (s, 6 H) 1.83 (s, 10 H) 3.29 (s, 1 H) 4.87 (s, 2 H) 6.77 (m, 2 H) 6.92 (s, 1 H) 7.18 (t, J=7.83 Hz, 1 H).
ESI-MS: m/e=494 [M+H]$^+$.

EXAMPLE 133

4-Bromo-3-carboxymethoxy-5-[3-(4-ethyl-cyclohexylamino)-phenyl]-thiophene-2-carboxylic acid The first step of Scheme 14: 4-Bromo-3-ethoxycarbonylmethoxy-5-[3-(4-ethyl-cyclohexylamino)-phenyl]-thiophene-2-carboxylic acid methyl ester was obtained in 65% as a yellow glassy solid, following the procedure in the first step of Scheme 14 of Example 128.
$^1$H NMR (400 MHz, CHLOROFORM-D) δ ppm 0.89 (m, 3 H) 1.18 (m, 5 H) 1.32 (t, J=7.20 Hz, 3 H) 1.64 (m, 3 H) 1.80 (m, 2 H) 2.16 (m, 1 H) 3.22 (s, 1 H) 3.60 (m, 1 H) 3.87 (s, 3 H) 4.30 (q, J=7.16 Hz, 2 H) 4.90 (s, 2 H) 6.64 (m, 1 H) 6.86 (m, 1 H) 6.90 (m, 1 H) 7.21 (m, 1 H).

The second step of Scheme 14: 4-Bromo-3-ethoxycarbonylmethoxy-5-[3-(4-ethyl-cyclohexylamino)-phenyl]-thiophene-2-carboxylic acid methyl ester was hydrolyzed according to the procedure in the second step of Scheme 14 of Example 128 to give 4-bromo-3-carboxymethoxy-5-[3-(4-ethyl-cyclohexylamino)-phenyl]-thiophene-2-carboxylic acid in 96% yield as a pale yellow solid.
$^1$H NMR (400 MHz, DMSO-D6) δ ppm 0.87 (t, J=6.95 Hz, 3 H) 1.14 (m, 3 H) 1.37 (m, 2 H) 1.50 (m, 2 H) 1.58 (m, 2 H) 1.66 (m, 2 H) 1.76 (m, 1 H) 2.01 (m, 1 H) 4.88 (s, 2 H) 6.74 (m, 2 H) 6.88 (s, 1 H) 7.18 (t, J=7.96 Hz, 1 H).
ESI-MS: m/e=482 [M+H]$^+$.

EXAMPLE 134

4-Bromo-3-carboxymethoxy-5-[3-cis(4-phenyl-cyclohexylamino)-phenyl]-thiophene-2-carboxylic acid The first step of Scheme 14: To a 1.5 mL DCE solution of 5-(3-amino-phenyl)-4-bromo-3-ethoxycarbonylmethoxy-thiophene-2-carboxylic acid methyl ester (41 mg, 0.1 mmole) was added 4-phenylcyclohexanone (13 μL, 0.12 mmole), acetic acid (10 μL, 0.15 mmole) and sodium triacetoxyborohydride (53 mg, 0.25 mmole). The reaction mixture was stirred at room temperature overnight. The reaction mixture was then diluted with $CH_2Cl_2$ and washed with saturated sodium bicarbonate solution and dried over $MgSO_4$. Filtration and evaporation gave the crude product which was then purified by chromatography on silica gel using a gradient of hexane/EtOAc (0 to 25%) as eluent. Pure fractions of two products were obtained. The less polar product fractions were evaporated to give 26 mg (45%) 4-bromo-3-ethoxycarbonylmethoxy-5-[3-cis(4-phenyl-cyclohexylamino)-phenyl]-thiophene-2-carboxylic acid methyl ester as a yellow oil.
$^1$H NMR (400 MHz, CHLOROFORM-D) δ ppm 1.32 (t, J=7.07 Hz, 3 H) 1.78 (m, 6 H) 2.04 (m, 2 H) 2.62 (dd, J=9.98, 3.66 Hz, 1 H) 3.77 (s, 1 H) 3.87 (s, 3 H) 4.04 (s, 1 H) 4.30 (q, J=7.24 Hz, 2 H) 4.90 (s, 2 H) 6.70 (dd, J=7.83, 2.02 Hz, 1 H) 6.91 (t, J=1.89 Hz, 1 H) 6.94 (d, J=7.58 Hz, 1 H) 7.25 (m, 6 H).

The second step of Scheme 14: 4-Bromo-3-ethoxycarbonylmethoxy-5-[3-cis(4-phenyl-cyclohexylamino)-phenyl]-thiophene-2-carboxylic acid methyl ester was hydrolyzed according to the procedure in the second step of Scheme 14 of Example 128 to give 4-bromo-3-carboxymethoxy-5-[3-cis(4-phenyl-cyclohexylamino)-phenyl]-thiophene-2-carboxylic acid in 96% yield as a pale yellow solid.
$^1$H NMR (400 MHz, DMSO-D6) δ ppm 1.60 (dd, J=11.37, 4.55 Hz, 2 H) 1.70 (m, 2 H) 1.87 (m, 4 H) 3.69 (s, 1 H) 4.88 (s, 2 H) 6.79 (m, 1 H) 6.95 (t, J=1.89 Hz, 1 H) 7.19 (m, 2 H) 7.30 (m, 5 H).
ESI-MS: m/e=530 [M+H]$^+$.

EXAMPLE 135

4-Bromo-3-carboxymethoxy-5-[3-trans(4-phenyl-cyclohexylamino)-phenyl]-thiophene-2-carboxylic acid The first step of Scheme 14: 4-Bromo-3-ethoxycarbonylmethoxy-5-[3-trans(4-phenyl-cyclohexylamino)-phenyl]-thiophene-2-carboxylic acid methyl ester was obtained from the more polar fractions of the chromatography described in Example 134 in 21% yield as a yellow oil.
$^1$H NMR (400 MHz, CHLOROFORM-D) δ ppm 1.30 (m, 5 H) 1.64 (m, 2 H) 2.00 (m, 2 H) 2.30 (m, 2 H) 2.57 (m, J=12.19, 12.19, 3.41, 3.28 Hz, 1 H) 3.36 (m, 1 H) 3.71 (s, 1 H) 3.88 (s, 3 H) 4.30 (q, J=7.24 Hz, 2 H) 4.90 (s, 2 H) 6.67 (dd, J=7.71, 1.89 Hz, 1 H) 6.89 (m, 1 H) 6.93 (d, J=7.58 Hz, 1 H) 7.22 (m, 4 H) 7.31 (m, 2 H).

The second step of Scheme 14: 4-Bromo-3-ethoxycarbonylmethoxy-5-[3-trans(4-phenyl-cyclohexylamino)-phenyl]-thiophene-2-carboxylic acid methyl ester was hydrolyzed according to the procedure in the second step of Scheme 14 of Example 128 to give 4-bromo-3-carboxymethoxy-5-[3-trans(4-phenyl-cyclohexylamino)-phenyl]-thiophene-2-carboxylic acid in 90% yield as a pale yellow solid.
$^1$H NMR (400 MHz, DMSO-D6) δ ppm 1.30 (m, 3 H) 1.62 (m, 2 H) 1.85 (d, J=13.89 Hz, 2 H) 2.12 (d, J=11.12 Hz, 2 H) 2.56 (m, 1 H) 4.88 (s, 2 H) 6.72 (d, J=9.60 Hz, 1 H) 6.77 (d, J=6.06 Hz, 1 H) 6.86 (s, 1 H) 7.18 (m, 2 H) 7.28 (m, 4 H).
ESI-MS: m/e=530 [M+H]$^+$.

EXAMPLE 136

4-Bromo-3-carboxymethoxy-5-[3-(1-cyclohexyl-ethylamino)-phenyl]-thiophene-2-carboxylic acid The first step of Scheme 14: 4-Bromo-5-[3-(1-cyclohexyl-ethylamino)-phenyl]-3-ethoxycarbonylmethoxy-thiophene-2-carboxylic acid methyl ester was obtained in 48% yield as a yellow glassy solid, following the procedure in the first step of Scheme 14 of Example 128.

¹H NMR (400 MHz, CHLOROFORM-D) δ ppm 1.06 (m, 2 H) 1.14 (d, J=6.32 Hz, 2 H) 1.23 (m, 4 H) 1.32 (m, 3 H) 1.48 (m, 2 H) 1.73 (m, 4 H) 3.34 (m, 1 H) 3.67 (s, 1 H) 3.87 (s, 3 H) 4.30 (q, J=7.07 Hz, 2 H) 4.90 (s, 2 H) 6.61 (m, 1 H) 6.83 (m, 1 H) 6.89 (m, 1 H) 7.20 (m, 1 H).

The second step of Scheme 14: 4-Bromo-5-[3-(1-cyclohexyl-ethylamino)-phenyl]-3-ethoxycarbonylmethoxy-thiophene-2-carboxylic acid methyl ester was hydrolyzed according to the procedure in the second step of Scheme 14 of Example 128 to give 4-bromo-3-carboxymethoxy-5-[3-(1-cyclohexyl-ethylamino)-phenyl]-thiophene-2-carboxylic acid in 73% yield as a pale yellow solid.

¹H NMR (400 MHz, DMSO-D6) δ ppm 1.01 (m, 2 H) 1.06 (d, J=6.32 Hz, 3 H) 1.17 (m, 2 H) 1.44 (m, 1 H) 1.61 (m, 1 H) 1.77 (m, 6 H) 3.27 (m, 1 H) 4.88 (s, 2 H) 6.67 (dd, J=8.34, 2.02 Hz, 1 H) 6.73 (d, J=7.83 Hz, 1 H) 6.82 (m, 1 H) 7.16 (t, J=7.83 Hz, 1 H).

ESI-MS: m/e=482 [M+H]⁺.

EXAMPLE 137

4-Bromo-3-carboxymethoxy-5-[3-(3,3,5,5-tetramethyl-cyclohexylamino)-phenyl]-thiophene-2-carboxylic acid The first step of Scheme 14: 4-Bromo-3-ethoxycarbonylmethoxy-5-[3-(3,3,5,5-tetramethyl-cyclohexylamino)-phenyl]-thiophene-2-carboxylic acid methyl ester was obtained in 56% yield as a pale yellow glassy solid, following the procedure in the first step of Scheme 14 of Example 128.

¹H NMR (400 MHz, CHLOROFORM-D) δ ppm 0.90 (m, 2 H) 0.94 (s, 6 H) 1.05 (m, 2 H) 1.12 (s, 6 H) 1.29 (s, 1 H) 1.32 (t, J=7.20 Hz, 3 H) 1.89 (d, J=11.87 Hz, 1 H) 3.61 (m, 2 H) 3.87 (s, 3 H) 4.30 (q, J=7.16 Hz, 2 H) 4.89 (s, 2 H) 6.63 (dd, J=7.07, 1.26 Hz, 1 H) 6.90 (m, 2 H) 7.21 (t, J=7.96 Hz, 1 H).

The second step of Scheme 14: 4-Bromo-3-ethoxycarbonylmethoxy-5-[3-(3,3,5,5-tetramethyl-cyclohexylamino)-phenyl]-thiophene-2-carboxylic acid methyl ester was hydrolyzed according to the procedure in the second step of Scheme 14 of Example 128 to give 4-bromo-3-carboxymethoxy-5-[3-(3,3,5,5-tetramethyl-cyclohexylamino)-phenyl]-thiophene-2-carboxylic acid in 66% yield as a pale yellow solid.

¹H NMR (400 MHz, DMSO-D6) δ ppm 0.91 (s, 6 H) 0.95 (m, 2 H) 1.09 (m, 7 H) 1.26 (m, 1 H) 1.75 (d, J=12.38 Hz, 2 H) 3.51 (m, 1 H) 4.87 (s, 2 H) 6.68 (dd, J=8.21, 1.64 Hz, 1 H) 6.76 (d, J=7.33 Hz, 1 H) 6.84 (s, 1 H) 7.18 (t, J=7.96 Hz, 1 H).

ESI-MS: m/e=510 [M+H]⁺.

EXAMPLE 138

5-[3-(Adamantan-2-ylamino)-phenyl]-4-bromo-3-carboxymethoxy-thiophene-2-carboxylic acid The first step of Scheme 14: 5-[3-(Adamantan-2-ylamino)-phenyl]-4-bromo-3-ethoxycarbonylmethoxy-thiophene-2-carboxylic acid methyl ester was obtained in 93% yield as a pale yellow solid, following the procedure in the first step of Scheme 14 of Example 128.

¹H NMR (400 MHz, CHLOROFORM-D) δ ppm 1.32 (t, J=7.20 Hz, 3 H) 1.57 (m, 5 H) 1.85 (m, 8 H) 2.06 (m, 4 H) 3.58 (s, 1 H) 3.87 (s, 3 H) 4.30 (q, J=7.16 Hz, 1 H) 4.90 (s, 1 H) 6.65 (m, 1 H) 6.87 (m, 1 H) 6.90 (d, J=7.58 Hz, 1 H) 7.21 (t, J=7.83 Hz, 1 H).

The second step of Scheme 14: 5-[3-(Adamantan-2-ylamino)-phenyl]-4-bromo-3-ethoxycarbonylmethoxy-thiophene-2-carboxylic acid methyl ester was hydrolyzed according to the procedure in the second step of Scheme 14 of Example 128 to give 5-[3-(adamantan-2-ylamino)-phenyl]-4-bromo-3-carboxymethoxy-thiophene-2-carboxylic acid in 55% yield as a pale yellow solid.

¹H NMR (400 MHz, CHLOROFORM-D) δ ppm 1.32 (t, J=7.20 Hz, 3 H) 1.57 (m, 5 H) 1.85 (m, 8 H) 2.06 (m, 4 H) 3.58 (s, 1 H) 3.87 (s, 3 H) 4.30 (q, J=7.16 Hz, 1 H) 4.90 (s, 1 H) 6.65 (m, 1 H) 6.87 (m, 1 H) 6.90 (d, J=7.58 Hz, 1 H) 7.21 (t, J=7.83 Hz, 1 H).

ESI-MS: m/e=506 [M+H]⁺.

EXAMPLE 139

4-Bromo-3-carboxymethoxy-5-[3-(tetrahydro-pyran-4-ylamino)-phenyl]-thiophene-2-carboxylic acid The first step of Scheme 14: 4-Bromo-3-tert-butoxycarbonylmethoxy-5-[3-(tetrahydro-pyran-4-ylamino)-phenyl]-thiophene-2-carboxylic acid methyl ester was obtained in 83% yield as a pale yellow glassy solid, following the procedure in the first step of Scheme 14 of Example 128.

¹H NMR (400 MHz, CHLOROFORM-D) δ ppm 1.51 (m, 13 H) 2.06 (m, 2 H) 3.53 (m, 3 H) 3.72 (s, 1 H) 3.87 (s, 3 H) 4.82 (s, 2 H) 6.66 (dd, J=7.83, 2.02 Hz, 1 H) 6.88 (m, 1 H) 6.95 (m, 1 H) 7.23 (t, J=7.96 Hz, 1 H).

The second step of Scheme 14: 4-Bromo-3-tert-butoxycarbonylmethoxy-5-[3-(tetrahydro-pyran-4-ylamino)-phenyl]-thiophene-2-carboxylic acid methyl ester was hydrolyzed according to the procedure in the second step of Scheme 14 of Example 128 to give 4-bromo-3-carboxymethoxy-5-[3-(tetrahydro-pyran-4-ylamino)-phenyl]-thiophene-2-carboxylic acid in 84% yield as a pale yellow solid.

¹H NMR (400 MHz, DMSO-D6) δ ppm 1.39 (m, 2 H) 1.90 (d, J=11.37 Hz, 2 H) 3.44 (m, 4 H) 3.86 (m, 2 H) 4.87 (s, 2 H) 6.72 (dd, J=8.34, 2.27 Hz, 1 H) 6.77 (d, J=7.58 Hz, 1 H) 6.85 (s, 1 H) 7.19 (t, J=7.96 Hz, 1 H).

ESI-MS: m/e=456 [M+H]⁺.

EXAMPLE 140

4-Bromo-3-carboxymethoxy-5-[3-(cyclohexylmethyl-amino)-phenyl]-thiophene-2-carboxylic acid The first step of Scheme 12: 4-Bromo-5-[3-(cyclohexylmethyl-amino)-phenyl]-3-ethoxycarbonylmethoxy-thiophene-2-carboxylic acid methyl ester was obtained in 69% yield as a pale yellow oil, following the procedure in the first step of Scheme 14 of Example 128.

¹H NMR (400 MHz, CHLOROFORM-D) δ ppm 0.99 (m, 2 H) 1.21 (m, 4 H) 1.32 (t, J=7.20 Hz, 3 H) 1.70 (m, 5 H) 2.98 (d, J=6.82 Hz, 2 H) 3.87 (s, 3 H) 4.30 (q, J=7.24 Hz, 2 H) 4.90 (s, 2 H) 6.65 (m, 1 H) 6.85 (m, 1 H) 6.93 (d, J=7.58 Hz, 1 H) 7.22 (t, J=7.83 Hz, 1 H).

The second step of Scheme 12: 4-Bromo-5-[3-(cyclohexylmethyl-amino)-phenyl]-3-ethoxycarbonylmethoxy-thiophene-2-carboxylic acid methyl ester was hydrolyzed according to the procedure in the second step of Scheme 14 of Example 128 to give 4-bromo-3-carboxymethoxy-5-[3-(cyclohexylmethyl-amino)-phenyl]-thiophene-2-carboxylic acid in 59% yield as a pale yellow solid.

¹H NMR (400 MHz, DMSO-D6) δ ppm 0.94 (m, 2 H) 1.20 (m, 4 H) 1.67 (m, 5 H) 2.87 (d, J=6.57 Hz, 2 H) 4.87 (s, 2 H) 6.66 (dd, J=8.21, 1.64 Hz, 1 H) 6.76 (d, J=7.58 Hz, 1 H) 6.81 (m, 1 H) 7.17 (t, J=7.96 Hz, 1 H).

ESI-MS: m/e=466 [M−H]⁻.

EXAMPLE 141

4-Bromo-3-carboxymethoxy-5-[3-(1-methanesulfonyl-piperidin-4-ylamino)-phenyl]-thiophene-2-carboxylic acid The first step of Scheme 15: To a 12 mL DCE solution of 5-(3-amino-phenyl)-4-bromo-3-tert-butoxycarbonylmethoxy-thiophene-2-carboxylic acid methyl ester (1.33 g, 3.0 mmole) was added tert-butyl-4-oxo-1-piperidinecarboxylate (897 mg, 4.5 mmole), acetic acid (0.25 mL, 4.5 mmole), and sodium triacetoxyborohydride (1.48 g, 7.0 mmole) and the resulting mixture was allowed to stir at room temperature overnight. The reaction mixture was then diluted with $CH_2Cl_2$ and washed twice with saturated sodium bicarbonate solution and dried over $MgSO_4$. Filtration and evaporation gave the crude product, which was purified by chromatography on silica gel using a gradient of hexane/EtOAc (5 to 35%) as eluent. Pure fractions were combined and evaporated to give 1.62 g (86%) of 4-[3-(3-bromo-4-tert-butoxycarbonylmethoxy-5-methoxycarbonyl-thiophen-2-yl)-phenylamino]-piperidine-1-carboxylic acid tert-butyl ester as a pale yellow foam.

¹H NMR (400 MHz, CHLOROFORM-D) δ ppm 1.37 (m, 2 H) 1.47 (s, 9 H) 1.51 (s, 9 H) 2.07 (m, 2 H) 2.94 (t, J=12.13 Hz, 2 H) 3.47 (m, 1 H) 3.69 (m, 1 H) 3.87 (s, 3 H) 4.06 (m, 2 H) 4.82 (s, 2 H) 6.65 (m, 1 H) 6.87 (m, 1 H) 6.94 (ddd, J=7.64, 1.58, 0.88 Hz, 1 H) 7.23 (t, J=7.96 Hz, 1 H).

The second step of Scheme 15: 4-[3-(3-Bromo-4-tert-butoxycarbonylmethoxy-5-methoxycarbonyl-thiophen-2-yl)-phenylamino]-piperidine-1-carboxylic acid tert-butyl ester (1.33 g, 2.1 mmole) was dissolved in a mixture of 10.5 mL 1N HCl in EtOAc (Prepared by bubbling dry HCl gas into dry EtOAc) and 2 mL MeOH and the reaction mixture was allowed to stir at room temperature overnight. The reaction mixture was then evaporated exhaustively to give 4-bromo-3-tert-butoxycarbonylmethoxy-5-[3-(piperidin-4-ylamino)-phenyl]-thiophene-2-carboxylic acid methyl ester hydrochloride in quantitative yield as a white solid.

¹H NMR (400 MHz, MeOD) δ ppm 1.46 (s, 9 H) 2.00 (m, 2 H) 2.26 (m, 2 H) 3.09 (td, J=12.95, 2.65 Hz, 1 H) 3.51 (m, 2 H) 3.84 (s, 3 H) 3.89 (m, 2 H) 4.82 (s, 2 H) 7.47 (m, 1 H) 7.61 (m, 2 H) 7.67 (m, 1 H).

The third step of Scheme 15: To a 1 mL pyridine solution of 4-bromo-3-tert-butoxycarbonylmethoxy-5-[3-(piperidin-4-ylamino)-phenyl]-thiophene-2-carboxylic acid methyl ester hydrochloride (50 mg, 0.1 mmole) was added methanesulfonyl chloride (9 μL, 0.12 mmole) and the reaction mixture was allowed to stir at room temperature overnight. 8 mL 2N HCl was added to the reaction mixture and extracted with EtOAc and the organic layer washed with saturated sodium bicarbonate solution, brine and dried over $MgSO_4$. Filtration and evaporation gave the crude product, which was purified by chromatography on silica gel using a gradient of hexane/EtOAc (20 to 60%) as eluent. Pure fractions were combined and evaporated to give 12 mg (21%) 4-bromo-3-ethoxycarbonylmethoxy-5-[3-(1-methanesulfonyl-piperidin-4-ylamino)-phenyl]-thiophene-2-carboxylic acid methyl ester as a pale yellow glassy solid.

¹H NMR (400 MHz, CHLOROFORM-D) δ ppm 1.32 (t, J=7.20 Hz, 3 H) 1.59 (m, 2 H) 2.20 (m, 2 H) 2.82 (s, 3 H) 2.92 (m, 2 H) 3.46 (dd, J=11.87, 8.34 Hz, 1 H) 3.78 (m, 2 H) 3.88 (s, 3 H) 4.30 (q, J=7.16 Hz, 2 H) 4.90 (s, 2 H) 6.66 (ddd, J=8.15, 2.46, 0.76 Hz, 1 H) 6.87 (m, 1 H) 6.97 (ddd, J=7.58, 1.64, 0.88 Hz, 1 H) 7.24 (t, J=7.96 Hz, 1 H).

The fourth step of Scheme 15: 4-Bromo-3-ethoxycarbonylmethoxy-5-[3-(1-methanesulfonyl-piperidin-4-ylamino)-phenyl]-thiophene-2-carboxylic acid methyl ester (12 mg, 0.021) was dissolved in 1.5 mL of a 2:1 mixture of THF:$H_2O$. LiOH.$H_2O$ (5 mg, 0.11 mmole) was added and the reaction mixture was stirred at room temperature overnight. The solvent was evaporated and re-dissolved in 2-3 mL water. The mixture was acidified dropwise with 1N HCl while stirring. A solid emerged that was filtered, washed with water, and vacuum-oven dried to give 6 mg (54%) of 4-bromo-3-carboxymethoxy-5-[3-(1-methanesulfonyl-piperidin-4-ylamino)-phenyl]-thiophene-2-carboxylic acid as a pale yellow solid.

¹H NMR (400 MHz, DMSO-D6) δ ppm 3.53 (d, J=11.37 Hz, 2 H) 4.87 (s, 2 H) 6.72 (dd, J=8.21, 1.64 Hz, 1 H) 6.79 (d, J=8.08 Hz, 1 H) 6.85 (s, 1 H) 7.20 (t, J=8.08 Hz, 1 H).

ESI-MS: m/e=533 [M+H]⁺.

EXAMPLE 142

5-[3-(1-Benzenesulfonyl-piperidin-4-ylamino)-phenyl-4-bromo-3-carboxymethoxy-thiophene-2-carboxylic acid The third step of Scheme 15: 5-[3-(1-Benzenesulfonyl-piperidin-4-ylamino)-phenyl]-4-bromo-3-tert-butoxycarbonylmethoxy-thiophene-2-carboxylic acid methyl ester was obtained in 55% yield as a colorless glassy residue, following the procedure in the third step of Scheme 15 of Example 141.

¹H NMR (400 MHz, CHLOROFORM-D) δ ppm 1.50 (s, 9 H) 1.56 (m, 2 H) 2.14 (m, 2 H) 2.54 (td, J=11.62, 2.53 Hz, 2 H) 3.28 (m, 1 H) 3.65 (s, 1 H) 3.74 (m, 2 H) 3.86 (s, 3 H) 4.80 (s, 2 H) 6.59 (dd, J=7.83, 2.02 Hz, 1 H) 6.78 (m, 1 H) 6.93 (d, J=7.58 Hz, 1 H) 7.19 (t, J=7.83 Hz, 1 H) 7.60 (m, 3 H) 7.78 (m, 2 H).

The fourth step of Scheme 15: 5-[3-(1-Benzenesulfonyl-piperidin-4-ylamino)-phenyl]-4-bromo-3-tert-butoxycarbonylmethoxy-thiophene-2-carboxylic acid methyl ester was hydrolyzed according to the procedure in the fourth step of Scheme 15 of Example 141 to give 5-[3-(1-benzenesulfonyl-piperidin-4-ylamino)-phenyl]-4-bromo-3-carboxymethoxy-thiophene-2-carboxylic acid in 82% yield as a pale yellow solid.

¹H NMR (400 MHz, DMSO-D6) δ ppm 1.44 (m, 2 H) 1.98 (m, 2 H) 3.56 (d, J=11.37 Hz, 2 H) 4.85 (s, 2 H) 6.66 (dd, J=7.71, 1.89 Hz, 1 H) 6.76 (m, 2 H) 7.15 (t, J=7.71 Hz, 1 H) 7.66 (t, J=7.07 Hz, 2 H) 7.75 (m, 3 H).

ESI-MS: m/e=595 [M+H]⁺.

EXAMPLE 143

4-Bromo-3-carboxymethoxy-5-[3-(1-phenylmethanesulfonyl-piperidin-4-ylamino)-phenyl]-thiophene-2-carboxylic acid The third step of Scheme 15: 4-Bromo-3-tert-butoxycarbonylmethoxy-5-[3-(piperidin-4-ylamino)-phenyl]-thiophene-2-carboxylic acid methyl ester hydrochloride (56 mg, 0.1 mmole) was dissolved in a vigorously stirred mixture of 0.5 mL $CH_2Cl_2$ and 0.5 mL saturated sodium bicarbonate solution. α-Toluenesulfonyl chloride (23 mg, 0.12 mmole) was then added and the biphasic mixture was stirred at room temperature for 3 hours. The reaction mixture was diluted with CH$_2$Cl$_2$, washed with saturated sodium bicarbonate solution, and dried over MgSO$_4$. Filtration and evaporation gave the crude product which was purified by chromatography on silica gel using a gradient of hexane/EtOAc (5 to 35%) as eluent. Pure fractions were combined and evaporated to give 47 mg (69%) 4-bromo-3-tert-butoxycarbonylmethoxy-5-[3-(1-phenylmethanesulfonyl-piperidin-4-ylamino)-phenyl]-thiophene-2-carboxylic acid methyl ester as a colorless glassy solid.

$^1$H NMR (400 MHz, CHLOROFORM-D) δ ppm 1.41 (m, 2 H) 1.51 (s, 9 H) 2.03 (m, 2 H) 2.78 (m, 2 H) 3.35 (m, 1 H) 3.62 (m, 2 H) 3.87 (s, 3 H) 4.24 (s, 2 H) 4.82 (s, 2 H) 6.61 (dd, J=7.83, 2.02 Hz, 1 H) 6.83 (m, 1 H) 6.94 (d, J=8.08 Hz, 1 H) 7.21 (t, J=7.83 Hz, 1 H) 7.40 (m, 5 H).

The fourth step of Scheme 15: 4-Bromo-3-tert-butoxycarbonylmethoxy-5-[3-(1-phenylmethanesulfonyl-piperidin-4-ylamino)-phenyl]-thiophene-2-carboxylic acid methyl ester was hydrolyzed according to the procedure in the fourth step of Scheme 15 of Example 141 to give 4-bromo-3-carboxymethoxy-5-[3-(1-phenylmethanesulfonyl-piperidin-4-ylamino)-phenyl]-thiophene-2-carboxylic acid in 88% yield as a pale yellow solid.

$^1$H NMR (400 MHz, DMSO-D6) δ ppm 1.36 (m, 2 H) 1.96 (m, 2 H) 2.92 (m, 2 H) 3.53 (m, 2 H) 4.40 (s, 2 H) 4.87 (s, 2 H) 6.71 (dd, J=8.08, 1.52 Hz, 1 H) 6.79 (d, J=7.58 Hz, 1 H) 6.84 (t, J=1.89 Hz, 1 H) 7.20 (t, J=7.83 Hz, 1 H) 7.40 (m, 5 H).

ESI-MS: m/e=609 [M+H]$^+$.

EXAMPLE 144

4-Bromo-3-carboxymethoxy-5-[3-(1-ethanesulfonyl-piperidin-4-ylamino)-phenyl]-thiophene-2-carboxylic acid The third step of Scheme 15: 4-Bromo-3-tert-butoxycarbonylmethoxy-5-[3-(1-ethanesulfonyl-piperidin-4-ylamino)-phenyl]-thiophene-2-carboxylic acid methyl ester was obtained in 71% yield as a pale yellow glassy solid, following the procedure in the third step of Scheme 15 of Example 143.

$^1$H NMR (400 MHz, CHLOROFORM-D) δ ppm 1.38 (t, J=7.45 Hz, 3 H) 1.51 (s, 9 H) 1.57 (m, 2 H) 2.18 (m, 2 H) 3.00 (m, 4 H) 3.46 (m, 1 H) 3.81 (m, 2 H) 3.87 (s, 3 H) 4.82 (s, 2 H) 6.66 (m, 1 H) 6.87 (m, 1 H) 6.96 (dd, J=6.69, 1.64 Hz, 1 H) 7.24 (t, J=7.96 Hz, 1 H).

The fourth step of Scheme 15: 4-Bromo-3-tert-butoxycarbonylmethoxy-5-[3-(1-ethanesulfonyl-piperidin-4-ylamino)-phenyl]-thiophene-2-carboxylic acid methyl ester was hydrolyzed according to the procedure in the fourth step of Scheme 15 of Example 141 to give 4-bromo-3-carboxymethoxy-5-[3-(1-ethanesulfonyl-piperidin-4-ylamino)-phenyl]-thiophene-2-carboxylic acid in 87% yield as a pale yellow solid.

$^1$H NMR (400 MHz, DMSO-D6) δ ppm 1.22 (t, J=7.33 Hz, 3 H) 1.41 (m, 2 H) 2.00 (d, J=9.85 Hz, 2 H) 3.03 (m, 4 H) 3.58 (d, J=12.38 Hz, 2 H) 4.87 (s, 2 H) 6.72 (dd, J=8.21, 1.89 Hz, 1 H) 6.79 (d, J=7.83 Hz, 1 H) 6.85 (t, J=1.89 Hz, 1 H) 7.20 (t, J=7.96 Hz, 1 H).

ESI-MS: m/e=547 [M+H]$^+$.

EXAMPLE 145

4-Bromo-3-carboxymethoxy-5-{3-[1-(propane-2-sulfonyl)-piperidin-4-ylamino]-phenyl}-thiophene-2-carboxylic acid The third step of Scheme 15: 4-Bromo-3-tert-butoxycarbonylmethoxy-5-{3-[1-(propane-2-sulfonyl)-piperidin-4-ylamino]-phenyl}-thiophene-2-carboxylic acid methyl ester was obtained in 59% yield as a colorless glassy solid, following the procedure in the third step of Scheme 15 of Example 143.

$^1$H NMR (400 MHz, CHLOROFORM-D) δ ppm 1.36 (d, J=7.07 Hz, 6 H) 1.51 (s, 9 H) 1.55 (m, 2 H) 2.15 (dd, J=13.26, 3.16 Hz, 2 H) 3.08 (m, 2 H) 3.20 (m, 1 H) 3.47 (m, 1 H) 3.84 (m, 2 H) 3.87 (s, 3 H) 4.82 (s, 2 H) 6.65 (m, 1 H) 6.87 (m, 1 H) 6.96 (ddd, J=7.58, 1.64, 0.88 Hz, 1 H) 7.23 (t, J=7.96 Hz, 1 H).

The fourth step of Scheme 15: 4-Bromo-3-tert-butoxycarbonylmethoxy-5-{3-[1-(propane-2-sulfonyl)-piperidin-4-ylamino]-phenyl}-thiophene-2-carboxylic acid methyl ester was hydrolyzed according to the procedure in the fourth step of Scheme 15 of Example 141 to give the tile compound in 69% yield as a pale yellow solid.

$^1$H NMR (400 MHz, DMSO-D6) δ ppm 1.23 (d, J=6.82 Hz, 6 H) 1.38 (m, 2 H) 1.97 (dd, J=13.39, 4.29 Hz, 2 H) 3.08 (m, 2 H) 3.49 (m, 1 H) 3.63 (m, 2 H) 4.87 (s, 2 H) 6.71 (dd, J=8.08, 2.02 Hz, 1 H) 6.78 (d, J=8.08 Hz, 1 H) 6.85 (t, J=2.02 Hz, 1 H) 7.20 (t, J=7.96 Hz, 1 H).

ESI-MS: m/e=561 [M+H]$^+$.

EXAMPLE 146

4-Bromo-5-{3-[1-(butane-1-sulfonyl)-piperidin-4-ylamino]-phenyl}-3-carboxymethoxy-thiophene-2-carboxylic acid The third step of Scheme 15: 4-Bromo-5-{3-[1-(butane-1-sulfonyl)-piperidin-4-ylamino]-phenyl}-3-tert-butoxycarbonylmethoxy-thiophene-2-carboxylic acid methyl ester was obtained in 65% yield as a colorless oil, following the procedure in the third step of Scheme 15 of Example 143.

$^1$H NMR (400 MHz, CHLOROFORM-D) δ ppm 1.46 (m, 5 H) 1.51 (s, 9 H) 1.57 (m, 2 H) 1.81 (m, 2 H) 2.18 (dd, J=13.52, 3.16 Hz, 2 H) 2.96 (m, 4 H) 3.46 (m, 1 H) 3.80 (m, 2 H) 3.87 (s, 3 H) 4.82 (s, 2 H) 6.66 (ddd, J=8.15, 2.46, 0.76 Hz, 1 H) 6.87 (m, 1 H) 6.96 (m, 1 H) 7.24 (t, J=7.96 Hz, 1 H).

The fourth step of Scheme 15: 4-Bromo-5-{3-[1-(butane-1-sulfonyl)-piperidin-4-ylamino]-phenyl}-3-tert-butoxycarbonylmethoxy-thiophene-2-carboxylic acid methyl ester was hydrolyzed according to the procedure in the fourth step of Scheme 15 of Example 141 to give 4-bromo-5-{3-[1-(butane-1-sulfonyl)-piperidin-4-ylamino]-phenyl}-3-carboxymethoxy-thiophene-2-carboxylic acid in 75% yield as a pale yellow solid.

$^1$H NMR (400 MHz, DMSO-D6) δ ppm 0.90 (t, J=7.33 Hz, 3 H) 1.41 (m, 4 H) 1.64 (m, 2 H) 2.00 (m, 2 H) 3.01 (m, 4 H) 3.44 (s, 1 H) 3.57 (m, 2 H) 4.87 (s, 2 H) 6.72 (dd, J=8.21, 2.15 Hz, 1 H) 6.79 (d, J=7.33 Hz, 1 H) 6.85 (m, 1 H) 7.20 (t, J=7.96 Hz, 1 H).

ESI-MS: m/e=575 [M+H]$^+$.

EXAMPLE 147

5-{3-[1-(3,5-Bis-trifluoromethyl-phenylmethane-sulfonyl)-piperidin-4-ylamino]-phenyl}-4-bromo-3-carboxymethoxy-thiophene-2-carboxylic acid The third step of Scheme 15: 5-{3-[1-(3,5-Bis-trifluoromethyl-phenylmethanesulfonyl)-piperidin-4-ylamino]-phenyl}-4-bromo-3-tert-butoxycarbonylmethoxy-thiophene-2-carboxylic acid methyl ester was obtained in 34% yield as a pale yellow foam, following the procedure in the third step of Scheme 15 of Example 143.

$^1$H NMR (400 MHz, CHLOROFORM-D) δ ppm 1.46 (m, 2 H) 1.51 (s, 9 H) 2.13 (dd, J=13.26, 3.16 Hz, 2 H) 2.94 (m, 2 H) 3.45 (m, 1 H) 3.69 (m, 3 H) 3.88 (s, 3 H) 4.29 (s, 2 H) 4.82 (s, 2 H) 6.64 (dd, J=8.21, 1.64 Hz, 1 H) 6.86 (m, 1 H) 6.97 (d, J=8.34 Hz, 1 H) 7.23 (t, J=7.96 Hz, 1 H) 7.88 (s, 2 H) 7.92 (s, 1 H).

The fourth step of Scheme 15: 5-{3-[1-(3,5-Bis-trifluoromethyl-phenylmethanesulfonyl)-piperidin-4-ylamino]-phenyl}-4-bromo-3-tert-butoxycarbonylmethoxy-thiophene-2-carboxylic acid methyl ester was hydrolyzed according to the procedure in the fourth step of Scheme 15 of Example 141 to give 5-{3-[1-(3,5-bis-trifluoromethyl-phenylmethanesulfonyl)-piperidin-4-ylamino]-phenyl}-4-bromo-3-carboxymethoxy-thiophene-2-carboxylic acid in 49% yield as a yellow solid.

$^1$H NMR (400 MHz, DMSO-D6) δ ppm 1.41 (m, 2 H) 2.01 (m, 2 H) 3.02 (m, 2 H) 3.46 (s, 1 H) 3.61 (m, 2 H) 4.72 (s, 2 H) 4.87 (s, 2 H) 6.73 (dd, J=8.34, 1.77 Hz, 1 H) 6.80 (d, J=8.34 Hz, 1 H) 6.86 (m, 1 H) 7.21 (t, J=7.83 Hz, 1 H) 8.15 (s, 3 H).

ESI-MS: m/e=745 [M+H]$^+$.

EXAMPLE 148

4-Bromo-3-carboxymethoxy-5-{3-[1-(propane-1-sulfonyl)-piperidin-4-ylamino]-phenyl}-thiophene-2-carboxylic acid The third step of Scheme 15: 4-Bromo-3-carboxymethoxy-5-{3-[1-(propane-1-sulfonyl)-piperidin-4-ylamino]-phenyl}-thiophene-2-carboxylic acid was prepared following the procedure in the third step of Example 3. 4-Bromo-3-tert-butoxycarbonylmethoxy-5-{3-[1-(propane-1-sulfonyl)-piperidin-4-ylamino]-phenyl}-thiophene-2-carboxylic acid methyl ester was obtained in 74% yield as a yellow oil, following the procedure in Example 143.

$^1$H NMR (400 MHz, CHLOROFORM-D) δ ppm 1.07 (t, J=7.45 Hz, 3 H) 1.51 (s, 9 H) 1.57 (m, 2 H) 1.87 (m, 2 H) 2.18 (dd, J=13.14, 3.28 Hz, 2 H) 2.91 (m, 2 H) 2.99 (m, 2 H) 3.46 (m, 1 H) 3.80 (m, 2 H) 3.88 (s, 3 H) 4.82 (s, 2 H) 6.87 (m, 1 H) 6.96 (m, 1 H) 7.24 (t, J=7.96 Hz, 1 H).

The fourth step of Scheme 15: 4-Bromo-3-tert-butoxycarbonylmethoxy-5-{3-[1-(propane-1-sulfonyl)-piperidin-4-ylamino]-phenyl}-thiophene-2-carboxylic acid methyl ester was hydrolyzed according to the procedure in the fourth step of Scheme 15 of Example 141 to give 4-bromo-3-carboxymethoxy-5-{3-[1-(propane-1-sulfonyl)-piperidin-4-ylamino]-phenyl}-thiophene-2-carboxylic acid in 79% yield as a pale yellow solid.

$^1$H NMR (400 MHz, DMSO-D6) δ ppm 0.99 (t, J=7.33 Hz, 3 H) 1.43 (m, 2 H) 1.69 (m, 2 H) 2.00 (m, 2 H) 3.00 (m, 4 H) 3.44 (m, 1 H) 3.57 (m, 2 H) 4.87 (s, 2 H) 6.72 (dd, J=8.59, 2.02 Hz, 1 H) 6.79 (m, 1 H) 6.85 (m, 1 H) 7.20 (m, 1 H).

ESI-MS: m/e=561 [M+H]$^+$.

EXAMPLE 149

4-Bromo-3-carboxymethoxy-5-{3-[1-(3-trifluoromethyl-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(3-trifluoromethyl-phenylmethanesulfonyl)-piperidin-4-ylamino]-phenyl}-thiophene-2-carboxylic acid methyl ester was obtained in 66% yield as a pale yellow oil, following the procedure in the third step of Scheme 15 of Example 143.

$^1$H NMR (400 MHz, CHLOROFORM-D) δ ppm 1.43 (m, 2 H) 1.51 (s, 9 H) 2.08 (m, 2 H) 2.86 (m, 2 H) 3.40 (m, 1 H) 3.66 (m, 3 H) 3.87 (s, 3 H) 4.26 (s, 2 H) 4.82 (s, 2 H) 6.62 (dd, J=8.21, 2.15 Hz, 1 H) 6.84 (t, J=1.77 Hz, 1 H) 6.95 (d, J=7.58 Hz, 1 H) 7.22 (t, J=7.96 Hz, 1 H) 7.54 (t, J=7.96 Hz, 1 H) 7.65 (m, 3 H).

The fourth step of Scheme 15: 4-Bromo-3-tert-butoxycarbonylmethoxy-5-{3-[1-(3-trifluoromethyl-phenylmethanesulfonyl)-piperidin-4-ylamino]-phenyl}-thiophene-2-carboxylic acid methyl ester was hydrolyzed according to the procedure in the fourth step of Scheme 15 of Example 141 to give 4-bromo-3-carboxymethoxy-5-{3-[1-(3-trifluoromethyl-phenylmethanesulfonyl)-piperidin-4-ylamino]-phenyl}-thiophene-2-carboxylic acid in 64% yield as a pale yellow solid.

$^1$H NMR (400 MHz, DMSO-D6) δ ppm 1.39 (m, 2 H) 1.98 (m, 2 H) 2.97 (m, 2 H) 3.56 (m, 2 H) 4.57 (s, 2 H) 4.87 (s, 2 H) 6.72 (dd, J=7.45, 1.64 Hz, 1 H) 6.79 (d, J=7.83 Hz, 1 H) 6.85 (s, 1 H) 7.20 (t, J=7.96 Hz, 1 H) 7.64 (t, J=7.96 Hz, 1 H) 7.74 (m, 2 H) 7.80 (s, 1 H).

ESI-MS: m/e=677 [M+H]$^+$.

EXAMPLE 150

4-Bromo-3-carboxymethoxy-5-{3-[1-(4-fluoro-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(4-fluoro-phenylmethanesulfonyl)-piperidin-4-ylamino]-phenyl}-thiophene-2-carboxylic acid methyl ester was obtained in 65% yield as a yellow oil, following the procedure in the third step of Scheme 15 of Example 143.

$^1$H NMR (400 MHz, CHLOROFORM-D) δ ppm 1.43 (m, 2 H) 1.51 (s, 9 H) 2.08 (m, 2 H) 2.81 (m, 2 H) 3.37 (m, 1 H) 3.64 (m, 3 H) 3.88 (s, 3 H) 4.19 (s, 2 H) 4.82 (s, 2 H) 6.62 (m, 1 H) 6.84 (m, 1 H) 6.95 (m, 1 H) 7.10 (m, 2 H) 7.22 (t, J=7.83 Hz, 1 H) 7.39 (m, 2 H).

The fourth step of Scheme 15: 4-Bromo-3-tert-butoxycarbonylmethoxy-5-{3-[1-(4-fluoro-phenylmethanesulfonyl)-piperidin-4-ylamino]-phenyl}-thiophene-2-carboxylic acid methyl ester was hydrolyzed according to the procedure in the fourth step of Scheme 15 of Example 141 to give 4-bromo-3-carboxymethoxy-5-{3-[1-(4-fluoro-phenylmethanesulfonyl)-piperidin-4-ylamino]-phenyl}-thiophene-2-carboxylic acid in 70% yield as a pale yellow solid.

ESI-MS: m/e=627 [M+H]$^+$.

EXAMPLE 151

4-Bromo-3-carboxymethoxy-5-{3-[1-(4-trifluoromethyl-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(4-trifluoromethyl-phenylmethanesulfonyl)-piperidin-4-ylamino]-phenyl}-thiophene-2-carboxylic acid methyl ester was obtained in 60% yield as a pale yellow solid, following the procedure in the third step of Scheme 15 of Example 143.

$^1$H NMR (400 MHz, CHLOROFORM-D) δ ppm 1.45 (m, 2 H) 1.51 (s, 9 H) 2.10 (dd, J=13.39, 3.28 Hz, 2 H) 2.85 (m, 2 H) 3.41 (m, 1 H) 3.69 (m, 3 H) 3.88 (s, 3 H) 4.25 (s, 2 H) 4.82 (s, 2 H) 6.63 (dd, J=7.71, 1.89 Hz, 1 H) 6.84 (m, 1 H) 6.95 (m, 1 H) 7.23 (t, J=7.96 Hz, 1 H) 7.54 (d, J=8.08 Hz, 2 H) 7.67 (d, J=8.08 Hz, 2 H).

The fourth step of Scheme 15: 4-Bromo-3-tert-butoxycarbonylmethoxy-5-{3-[1-(4-trifluoromethyl-phenylmethanesulfonyl)-piperidin-4-ylamino]-phenyl}-thiophene-2-carboxylic acid methyl ester was hydrolyzed according to the procedure in the fourth step Scheme 15 of Example 141 to give 4-bromo-3-carboxymethoxy-5-{3-[1-(4-trifluoromethyl-phenylmethanesulfonyl)-piperidin-4-ylamino]-phenyl}-thiophene-2-carboxylic acid in 71% yield as an off-white solid.

$^1$H NMR (400 MHz, DMSO-D6) δ ppm 1.38 (m, 2 H) 1.98 (m, 2 H) 2.98 (m, 2 H) 3.57 (m, 2 H) 4.55 (s, 2 H) 4.85 (s, 2 H) 6.71 (dd, J=8.08, 1.26 Hz, 1 H) 6.79 (d, J=7.33 Hz, 1 H) 6.85 (s, 1 H) 7.20 (t, J=7.96 Hz, 1 H) 7.65 (d, J=7.83 Hz, 2 H) 7.77 (d, J=8.08 Hz, 2 H).

ESI-MS: m/e=677 [M+H]$^+$.

EXAMPLE 152

4-Bromo-3-carboxymethoxy-5-{3-[1-(naphthalene-1-sulfonyl)-piperidin-4-ylamino]-phenyl}-thiophene-2-carboxylic acid The third step of Scheme 15: To a solution of 4-bromo-3-tert-butoxycarbonylmethoxy-5-[3-(piperidin-4-ylamino)-phenyl]-thiophene-2-carboxylic acid methyl ester (HCl salt, 54 mg, 0.0965 mmol) in DCM (2 mL) was added naphthalene-1-sulfonyl chloride (1.2 eq) and saturated aq. NaHCO$_3$ solution (2 mL). The resultant reaction mixture was stirred at room temperature vigorously overnight. The organic layer was separated and the aqueous layer was extracted with DCM. The combined organic layer was dried over MgSO$_4$, and concentrated under vacuum. The crude product was purified on CombiFlash column eluted with EtOAc/Hexanes to give 4-bromo-3-tert-butoxycarbonylmethoxy-5-{3-[1-(naphthalene-1-sulfonyl)-piperidin-4-ylamino]-phenyl}-thiophene-2-carboxylic acid methyl ester (48 mg, 67%).

$^1$H NMR (400 MHz, CHLOROFORM-D) δ ppm 1.51 (m, 2 H) 1.50 (m, 9 H) 2.10 (m, 2 H) 2.81 (m, 2 H) 3.33 (m, 1 H) 3.60 (d, J=7.83 Hz, 1 H) 3.82 (m, 1 H) 3.86 (s, 3 H) 4.79 (s, 3 H) 6.57 (dd, J=7.58, 2.27 Hz, 1 H) 6.77 (m, 1 H) 6.92 (m, 1 H) 7.18 (m, 1 H) 7.63 (m, 3 H) 7.95 (m, 1 H) 8.10 (d, J=8.08 Hz, 1 H) 8.24 (dd, J=7.33, 1.26 Hz, 1 H) 8.77 (d, J=8.84 Hz, 1 H).

The fourth step of Scheme 15: 4-Bromo-3-carbonylmethoxy-5-{3-[1-(naphthalene-1-sulfonyl)-piperidin-4-ylamino]-phenyl}-thiophene-2-carboxylic acid (38.8 mg, 96%), was prepare as a light yellow solid according to the procedure in the second step of Scheme 1 of Example 1 using 4-bromo-3-tert-butoxycarbonylmethoxy-5-{3-[1-(naphthalene-1-sulfonyl)-piperidin-4-ylamino]-phenyl}-thiophene-2-carboxylic acid methyl ester (45 mg, 0.0628 mmol) as the starting material.

$^1$H NMR (400 MHz, DMSO-D6) δ ppm 1.36 (m, 2 H) 1.95 (d, J=15.66 Hz, 2 H) 2.80 (t, J=12.63 Hz, 2 H) 3.68 (d, J=12.13 Hz, 2 H) 4.84 (s, 2 H) 5.85 (d, J=10.61 Hz, 1 H) 6.63 (d, J=2.78 Hz, 1 H) 6.76 (m, 2 H) 7.14 (m, 1 H) 7.72 (m, 3 H) 8.14 (m, 2 H) 8.30 (d, J=8.34 Hz, 1 H) 8.68 (d, J=8.59 Hz, 1 H).

EXAMPLE 153

4-Bromo-3-carboxymethoxy-5-{3-[1-(naphthalene-2-sulfonyl)-piperidin-4-ylamino]-phenyl}-thiophene-2-carboxylic acid The third step of Scheme 15: 4-Bromo-3-tert-butoxycarbonylmethoxy-5-{3-[1-(naphthalene-2-sulfonyl)-piperidin-4-ylamino]-phenyl}-thiophene-2-carboxylic acid methyl ester (61 mg, 86%) was prepared according to the procedure in the thirds step of Scheme 15 of Example 152, using 4-bromo-3-tert-butoxycarbonylmethoxy-5-[3-(piperidin-4-ylamino)-phenyl]-thiophene-2-carboxylic acid methyl ester (HCl Salt, 56 mg, 0.10 mmol) as the starting material.

$^1$H NMR (400 MHz, CHLOROFORM-D) δ ppm 1.49 (s, 9 H) 1.59 (m, 2 H) 2.15 (dd, J=13.39, 3.28 Hz, 2 H) 2.61 (m, 2 H) 3.26 (m, 1 H) 3.62 (d, J=7.83 Hz, 1 H) 3.81 (m, 2 H) 3.85 (s, 3 H) 4.78 (s, 2 H) 6.56 (m, 1 H) 6.75 (m, 1 H) 6.91 (dd, J=7.96, 1.39 Hz, 1 H) 7.18 (t, J=7.96 Hz, 1 H) 7.66 (m, 2 H) 7.78 (dd, J=8.59, 2.02 Hz, 1 H) 7.95 (m, 1 H) 8.00 (m, 1 H) 8.36 (d, J=1.77 Hz, 1 H).

The fourth step of Scheme 15: 4-Bromo-3-carbonylmethoxy-5-{3-[1-(naphthalene-2-sulfonyl)-piperidin-4-ylamino]-phenyl}-thiophene-2-carboxylic acid (50 mg, 89%), was prepare as a light yellow solid according to the procedure in the second step of Scheme 1 of Example 1 using 4-bromo-3-tert-butoxycarbonylmethoxy-5-{3-[1-(naphthalene-2-sulfonyl)-piperidin-4-ylamino]-phenyl}-thiophene-2-carboxylic acid methyl ester (45 mg, 0.0628 mmol) as the starting material.

$^1$H NMR (400 MHz, DMSO-D6) δ ppm 1.43 (m, 2 H) 1.98 (m, 2 H) 2.58 (t, J=12.38 Hz, 2 H) 3.61 (m, 3 H) 5.82 (m, 1 H) 6.62 (d, J=9.60 Hz, 1 H) 6.74 (m, J=2.27 Hz, 2 H) 7.12 (m, 1 H) 7.74 (m, 3 H) 8.09 (d, J=8.08 Hz, 1 H) 8.20 (m, 2 H) 8.45 (d, J=1.52 Hz, 1 H).

EXAMPLE 154

4-Bromo-3-carboxymethoxy-5-{3-[1-(2-nitro-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(2-nitro-phenylmethanesulfonyl)-piperidin-4-ylamino]-phenyl}-thiophene-2-carboxylic acid methyl ester (104 mg, 72%) was prepared according to the procedure in the third step of Scheme 15 of Example 152, using 4-bromo-3-tert-butoxycarbonylmethoxy-5-[3-(piperidin-4-ylamino)-phenyl]-thiophene-2-carboxylic acid methyl ester (HCl salt, 113 mg, 0.20 mmol) as the starting material.

$^1$H NMR (400 MHz, CHLOROFORM-D) δ ppm 1.47 (m, 2 H) 1.51 (s, 9 H) 2.08 (m, 2 H) 2.91 (m, 2 H) 3.43 (m, 1 H) 3.62 (m, 3 H) 3.88 (s, 3 H) 4.76 (s, 2 H) 4.82 (s, 2 H) 6.64 (dd, J=7.83, 2.02 Hz, 1 H) 6.85 (m, 1 H) 6.96 (m, 1 H) 7.23 (t, J=7.83 Hz, 1 H) 7.60 (m, 3 H) 8.04 (dd, J=8.21, 1.39 Hz, 1 H).

The fourth step of Scheme 15: 4-Bromo-3-carbonylmethoxy-5-{3-[1-(2-nitro-phenylmethanesulfonyl)-piperidin-4-ylamino]-phenyl}-thiophene-2-carboxylic acid (24 mg, 51%), was prepare as a light yellow solid according to the procedure in the second step of Scheme 1 of Example 1 using 4-bromo-3-tert-butoxycarbonylmethoxy-5-{3-[1-(2-nitro-phenylmethanesulfonyl)-piperidin-4-ylamino]-phenyl}-thiophene-2-carboxylic acid methyl ester (52 mg, 0.0717 mmol) as the starting material.

$^1$H NMR (400 MHz, DMSO-D6) δ ppm 1.40 (m, 2 H) 1.99 (dd, J=12.76, 3.16 Hz, 2 H) 3.00 (t, J=12.00 Hz, 2 H) 3.49 (m, 3 H) 4.87 (s, 2 H) 4.89 (s, 2 H) 5.96 (s, 1 H) 6.72 (dd, J=8.59, 1.52 Hz, 1 H) 6.79 (d, J=8.34 Hz, 1 H) 6.85 (t, J=1.89 Hz, 1 H) 7.20 (t, J=7.96 Hz, 1 H) 7.69 (m, 2 H) 7.79 (m, 1 H) 8.06 (dd, J=8.08, 1.26 Hz, 1 H).

EXAMPLE 155

4-Bromo-3-carboxymethoxy-5-{3-[1-(4-chloro-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(4-chloro-phenylmethanesulfonyl)-piperidin-4-ylamino]-phenyl}-thiophene-2-carboxylic acid methyl ester (108 mg, 77%) was prepared according to the procedure in the third step of Scheme 15 of Example 152, using 4-bromo-3-tert-butoxycarbonylmethoxy-5-[3-(piperidin-4-ylamino)-phenyl]-thiophene-2-carboxylic acid methyl ester (HCl salt, 110 mg, 0.197 mmol) as the starting material.

$^1$H NMR (400 MHz, CHLOROFORM-D) δ ppm 1.43 (m, 2 H) 1.51 (s, 9 H) 2.08 (dd, J=13.52, 2.91 Hz, 2 H) 2.82 (m, 2 H) 3.39 (m, 1 H) 3.65 (m, 3 H) 3.88 (s, 3 H) 4.18 (s, 2 H) 4.82 (s, 2 H) 6.63 (m, 1 H) 6.84 (m, 1 H) 6.95 (d, J=7.58 Hz, 1 H) 7.22 (t, J=7.83 Hz, 1 H) 7.37 (m, 4 H).

The fourth step of Scheme 15: 4-Bromo-3-carbonylmethoxy-5-{3-[1-(4-chloro-phenylmethanesulfonyl)-piperidin-4-ylamino]-phenyl}-thiophene-2-carboxylic acid (55 mg, 98%), was prepare as a yellow solid according to the procedure in the second step of Scheme 1 of Example 1 using 4-bromo-3-tert-butoxycarbonylmethoxy-5-{3-[1-(4-chloro-phenylmethanesulfonyl)-piperidin-4-ylamino]-phenyl}-thiophene-2-carboxylic acid methyl ester (62 mg, 0.087 mmol) as the starting material.

$^1$H NMR (400 MHz, DMSO-D6) δ ppm 1.36 (m, 2 H) 1.96 (d, J=13.89 Hz, 2 H) 2.93 (t, J=9.85 Hz, 2 H) 3.33 (s, 1 H) 3.53 (m, 2 H) 4.43 (s, 2 H) 4.87 (s, 2 H) 6.71 (dd, J=8.59, 2.02 Hz, 1 H) 6.79 (m, 1 H) 6.85 (m, 1 H) 7.20 (t, J=7.96 Hz, 1 H) 7.45 (d, J=2.53 Hz, 4 H).

EXAMPLE 156

4-Bromo-3-carboxymethoxy-5-{3-[1-(3,5-dichloro-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(3,5-dichloro-phenylmethanesulfonyl)-piperidin-4-ylamino]-phenyl}-thiophene-2-carboxylic acid methyl ester (121 mg, 82%) was prepared according to the procedure in the third step of Scheme 15 of Example 152, using 4-bromo-3-tert-butoxycarbonylmethoxy-5-[3-(piperidin-4-ylamino)-phenyl]-thiophene-2-carboxylic acid methyl ester (HCl salt, 110 mg, 0.197 mmol) as the starting material.

$^1$H NMR (400 MHz, CHLOROFORM-D) δ ppm 1.46 (m, 2 H) 1.51 (s, 9 H) 2.11 (m, 2 H) 2.91 (m, 2 H) 3.44 (m, 1 H) 3.67 (m, 3 H) 3.88 (s, 3 H) 4.13 (s, 2 H) 4.82 (s, 2 H) 6.64 (ddd, J=9.35, 1.26, 1.01 Hz, 1 H) 6.86 (m, 1 H) 6.96 (dd, J=6.69, 1.64 Hz, 1 H) 7.23 (t, J=7.96 Hz, 1 H) 7.31 (d, J=1.77 Hz, 2 H) 7.40 (t, J=1.77 Hz, 1 H).

The fourth step of Scheme 15: 4-Bromo-3-carbonylmethoxy-5-{3-[1-(3,5-dichloro-phenylmethanesulfonyl)-piperidin-4-ylamino]-phenyl}-thiophene-2-carboxylic acid (44 mg, 82%), was prepared as a yellow solid according to the procedure in the second step of Scheme 1 of Example 1 using 4-bromo-3-tert-butoxycarbonylmethoxy-5-{3-[1-(4-chloro-phenylmethanesulfonyl)-piperidin-4-ylamino]-phenyl}-thiophene-2-carboxylic acid methyl ester (60 mg, 0.08 mmol) as the starting material.

$^1$H NMR (400 MHz, DMSO-D6) δ ppm 1.40 (m, 2 H) 1.99 (m, 2 H) 2.99 (t, J=11.12 Hz, 2 H) 3.46 (m, 1 H) 3.55 (m, 3 H) 4.49 (s, 2 H) 4.88 (s, 2 H) 6.73 (dd, J=8.34, 2.78 Hz, 1 H) 6.80 (d, J=8.34 Hz, 1 H) 6.86 (m, 1 H) 7.20 (t, J=7.96 Hz, 1 H) 7.50 (d, J=2.02 Hz, 2 H) 7.64 (t, J=1.89 Hz, 1 H).

EXAMPLE 157

4-Bromo-3-carboxymethoxy-5-{3-[1-(3,4-dichloro-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(3,4-dichloro-phenylmethanesulfonyl)-piperidin-4-ylamino]-phenyl}-thiophene-2-carboxylic acid methyl ester (103 mg, 70%) was prepared according to the procedure in the third step of Scheme 15 of Example 152, using 4-bromo-3-tert-butoxycarbonylmethoxy-5-[3-(piperidin-4-ylamino)-phenyl]-thiophene-2-carboxylic acid methyl ester (HCl salt, 110 mg, 0.197 mmol) as the starting material.

$^1$H NMR (400 MHz, CHLOROFORM-D) δ ppm 1.45 (m, 2 H) 1.51 (s, 9 H) 2.11 (m, 2 H) 2.88 (m, 2 H) 3.42 (m, 1 H) 3.67 (ms, 3 H) 4.14 (s, 2 H) 4.82 (s, 2 H) 6.64 (m, 1 H) 6.85 (m, 1 H) 6.96 (dd, J=6.69, 1.64 Hz, 1 H) 7.25 (m, 2 H) 7.50 (m, 2 H).

The fourth step of Scheme 15: 4-Bromo-3-carbonylmethoxy-5-{3-[1-(3,4-dichloro-phenylmethanesulfonyl)-piperidin-4-ylamino]-phenyl}-thiophene-2-carboxylic acid (49 mg, 90%), was prepare as a yellow solid according to the procedure in the second step of Scheme 1 of Example 1 using 4-bromo-3-tert-butoxycarbonylmethoxy-5-{3-[1-(3,4-dichloro-phenylmethanesulfonyl)-piperidin-4-ylamino]-phenyl}-thiophene-2-carboxylic acid methyl ester (60 mg, 0.08 mmol) as the starting material.

$^1$H NMR (400 MHz, DMSO-D6) δ ppm 1.38 (m, 2 H) 1.97 (m, 2 H) 2.97 (m, 2 H) 3.55 (m, 3 H) 4.48 (s, 2 H) 4.88 (s, 2 H) 6.72 (m, 1 H) 6.79 (d, J=8.59 Hz, 1 H) 6.86 (s, 1 H) 7.21 (m, 1 H) 7.42 (d, J=10.61 Hz, 1 H) 7.68 (m, 2 H).

EXAMPLE 158

4-Bromo-3-carboxymethoxy-5-{3-[1-(3-nitro-phenylmethanesulfonyl)-piperidin-4-ylaminol]-phenyl}-thiophene-2-carboxylic acid The third step of Scheme 15: 4-Bromo-3-tert-butoxycarbonylmethoxy-5-{3-[1-(3-nitro-phenylmethanesulfonyl)-piperidin-4-ylamino]-phenyl}-thiophene-2-carboxylic acid methyl ester was prepared as a white solid (31 mg, 24%), following the procedure in the third step of Scheme 15 of Example 143.

$^1$H NMR (400 MHz, CHLOROFORM-D) δ ppm 1.51 (m, 11 H) 2.12 (d, J=12.38 Hz, 2 H) 2.92 (s, 2 H) 3.44 (m, 1 H) 3.68 (s, 2 H) 3.88 (s, 3 H) 4.12 (q, J=7.07 Hz, 2 H) 4.28 (s, 2 H) 4.82 (s, 2 H) 6.64 (d, J=7.58 Hz, 1 H) 6.85 (s, 1 H) 6.97 (d, J=7.83 Hz, 1 H) 7.24 (m, 1 H) 7.61 (dd, J=8.84, 7.83 Hz, 1 H) 7.79 (m, 1 H) 8.26 (m, 2 H).

The fourth step of Scheme 15: 4-Bromo-3-carboxymethoxy-5-{3-[1-(3-nitro-phenylmethanesulfonyl)-piperidin-4-ylamino]-phenyl}-thiophene-2-carboxylic acid was prepared as an orange solid (26 mg, 93%) according to the procedure in the fourth step of Scheme 15 of Example 141.

$^1$H NMR (400 MHz, DMSO-D6) δ ppm 1.39 (s, 2 H) 1.95 (d, J=32.08 Hz, 2 H) 2.98 (s, 2 H) 3.32 (s, 1 H) 3.56 (s, 2 H) 4.65 (s, 2 H) 4.86 (s, 2 H) 5.91 (s, 1 H) 6.71 (m, 1 H) 6.79 (s, 1 H) 6.85 (d, J=1.77 Hz, 1 H) 7.20 (m, 1 H) 7.71 (m, 1 H) 7.88 (m, 1 H) 8.24 (m, 1 H) 8.33 (s, 1 H).

EXAMPLE 159

4-Bromo-3-carboxymethoxy-5-{3-[1-(3-chloro-phenylmethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(3-chloro-phenylmethanesulfonyl)-piperidin-4-ylamino]-phenyl}-thiophene-2-carboxylic acid methyl ester was prepared as a light yellow solid (110 mg, 86%), following the procedure in the third step of Scheme 15 of Example 143.

$^1$H NMR (400 MHz, CHLOROFORM-D) δ ppm 1.45 (m, 2 H) 1.50 (d, J=10.11 Hz, 9 H) 1.55 (m, 4 H) 2.09 (m, 2 H) 2.85 (m, 2 H) 3.39 (s, 1 H) 3.64 (m, 2 H) 3.88 (s, 3 H) 4.82 (s, 2 H) 6.64 (d, J=2.02 Hz, 1 H) 6.85 (s, 1 H) 6.96 (d, J=7.83 Hz, 1 H) 7.34 (m, 6 H).

The fourth step of Scheme 15: 4-Bromo-3-carboxymethoxy-5-{3-[1-(3-chloro-phenylmethanesulfonyl)-piperidin-4-ylamino]-phenyl}-thiophene-2-carboxylic acid was prepared as a yellow solid (81 mg, 90%) according to the procedure in the fourth step of Scheme 15 of Example 141.

$^1$H NMR (400 MHz, DMSO-D6) δ ppm 1.39 (s, 2 H) 1.95 (d, J=31.83 Hz, 2 H) 2.96 (s, 1 H) 3.56 (s, 1 H) 4.45 (s, 2 H) 4.87 (s, 2 H) 6.71 (s, 1 H) 6.79 (m, 1 H) 6.85 (t, J=1.89 Hz, 1 H) 7.20 (t, J=7.83 Hz, 1 H) 7.40 (d, J=2.02 Hz, 1 H) 7.43 (m, 2 H) 7.50 (s, 1 H).

EXAMPLE 160

4-Bromo-3-carboxymethoxy-5-{3-[1-(2-phenylethanesulfonyl)-piperidin-4-ylamino]-phenyl}-thiophene-2-carboxylic acid The third step of Scheme 15: 4-Bromo-3-tert-butoxycarbonylmethoxy-5-{3-[1-(2-phenylethanesulfonyl)-piperidin-4-ylamino]-phenyl}-thiophene-2-carboxylic acid methyl ester was prepared as a yellow foam (87 mg, 70%) according to the procedure in the third step of Scheme 15 of Example 143.

$^1$H NMR (400 MHz, CHLOROFORM-D) δ ppm 1.50 (s, 9 H) 2.16 (dd, J=13.64, 2.78 Hz, 2 H) 2.97 (m, 2 H) 3.17 (m, 4 H) 3.44 (m, 1 H) 3.70 (s, 1 H) 3.79 (m, 2 H) 3.87 (s, 3 H) 4.81 (s, 2 H) 6.64 (dd, J=8.08, 1.52 Hz, 1 H) 6.86 (m, 1 H) 6.96 (d, J=7.58 Hz, 1 H) 7.24 (m, 4 H) 7.34 (m, 2 H).

The fourth step of Scheme 15: 4-Bromo-3-carboxymethoxy-5-{3-[1-(2-phenylethanesulfonyl)-piperidin-4-ylamino]-phenyl}-thiophene-2-carboxylic acid was prepared as a pale-yellow solid (62 mg, 77%) according to the procedure in the fourth step of Scheme 15 in Example 141.

$^1$H NMR (400 MHz, DMSO-D6) δ ppm 1.36-1.49 (s, 2 H) 1.94-2.04 (s, 2 H) 2.96-3.08 (m, 4 H) 3.30.3.38 (m, 2 H) 3.57-3.65 (s, 2 H) 4.86-4.90 (s, 2 H) 6.70-6.74 (dd, J=8.08, 2.02 Hz, 1 H) 6.78-6.82 (d, J=7.58 Hz, 1 H) 6.84-6.87 (m, J=2.02 Hz, 1 H) 7.17-7.27 (m, 2 H) 7.30-7.35 (m, J=4.55 Hz, 4 H).

EXAMPLE 161

4-Bromo-3-carboxymethoxy-5-[3-(1-o-tolyl-methanesulfonyl-piperidin-4-ylamino)-phenyl]-thiophene-2-carboxylic acid The third step of Scheme 15: To an oven-dried 25 mL round bottom flask under a nitrogen atmosphere was added 4-bromo-3-tert-butoxycarbonylmethoxy-5-[3-(piperidin-4-ylamino)-phenyl]-thiophene-2-carboxylic acid methyl ester (0.200 g, 0.38 mmol), o-tolyl-methanesulfonyl chloride (0.24 g, 1.14 mmol), 5 mL CH$_2$Cl$_2$, and 5 mL saturated aqueous sodium bicarbonate solution. The resulting mixture was allowed to stir for 12 hours. The mixture was then diluted with 30 mL CH$_2$Cl$_2$ and washed with three 25 mL portions of saturated aqueous sodium bicarbonate, three 25 mL portions water, and one 25 mL portion brine. The organic layer was dried over MgSO$_4$ and the solvent removed in vacuo to give 4-bromo-3-tert-butoxycarbonylmethoxy-5-[3-(1-o-tolyl-methanesulfonyl-piperidin-4-ylamino)-phenyl]-thiophene-2-carboxylic acid methyl ester as a yellow oil (0.096 g, 40%).

$^1$H NMR (400 MHz, CHLOROFORM-D) δ ppm 1.51 (s, 9 H) 2.09 (dd, J=12.88, 4.04 Hz, 2 H) 2.47 (s, 3 H) 2.89 (m, 2 H) 3.41 (m, 1 H) 3.67 (m, 4 H) 3.88 (s, 3 H) 4.28 (s, 2 H) 4.82 (s, 2 H) 6.63 (m, 1 H) 6.85 (m, 1 H) 6.95 (m, 1 H) 7.26 (m, 5 H).

The fourth step of Scheme 15: To a 25 mL round bottom flask was added 4-bromo-3-tert-butoxycarbonylmethoxy-5-[3-(1-o-tolylmethanesulfonyl-piperidin-4-ylamino)-phenyl]-thiophene-2-carboxylic acid methyl ester(0.096 g, 0.15 mmol) and 5 mL THF. To this mixture added a solution of lithium hydroxide hydrate (0.025 g, 0.60 mmol) in 3 mL water. This mixture was allowed to stir at room temperature for 16 hours. At this time 15 mL 1.2 N HCl was added, and a precipitate formed. The solids were collected by filtration and dried in vacuo to give 4-bromo-3-carboxymethoxy-5-[3-(1-o-tolylmethanesulfonyl-piperidin-4-ylamino)-phenyl]-thiophene-2-carboxylic acid as a white solid (0.046 g, 49%).

$^1$H NMR (400 MHz, d$_4$-methanol) δ ppm 1.41 (m, 2 H) 2.00 (m, 2 H) 2.35 (s, 3 H) 2.93 (t, J=11.12 Hz, 2 H) 3.38 (m, 1 H) 3.60 (d, J=12.88 Hz, 2 H) 4.27 (s, 2 H) 4.82 (s, 2 H) 6.65 (dd, J=8.84, 2.78 Hz, 1 H) 6.77 (dd, J=6.82, 1.52 Hz, 1 H) 6.83 (t, J=1.89 Hz, 1 H) 7.12 (m, 4 H) 7.25 (d, J=7.07 Hz, 1 H).

EXAMPLE 162

4-Bromo-3-carboxymethoxy-5-[3-(1-m-tolyl-methanesulfonyl-piperidin-4-ylamino)-phenyl]-thiophene-2-carboxylic acid The third step of Scheme 15: 4-Bromo-3-tert-butoxycarbonylmethoxy-5-[3-(1-m-tolylmethanesulfonyl-piperidin-4-ylamino)-phenyl]-thiophene-2-carboxylic acid methyl ester was prepared as a yellow oil (0.15 g, 64%) following the procedure in the third step of Scheme 15 of Example 161.

$^1$H NMR (400 MHz, CHLOROFORM-D) δ ppm 1.51 (s, 9 H) 2.05 (m, 2 H) 2.38 (s, 3 H) 2.80 (m, 2 H) 3.36 (t, J=9.09 Hz, 1 H) 3.63 (m, 4 H) 3.88 (s, 3 H) 4.20 (s, 2 H) 4.82 (s, 2 H) 6.62 (m, 1 H) 6.83 (m, 1 H) 6.95 (m, 1 H) 7.24 (m, 5 H).

The fourth step of Scheme 15: 4-Bromo-3-carboxymethoxy-5-[3-(1-m-tolylmethanesulfonyl-piperidin-4-ylamino)-phenyl]-thiophene-2-carboxylic acid was prepared as a white solid (0.100 g, 0.64%) according to the procedure in the fourth step of Scheme 15 of Example 161.

¹H NMR (400 MHz, d₄-methanol) δ ppm 1.21 (m, 1 H) 1.36 (m, 1 H) 1.94 (m, 2 H) 2.27 (s, 3 H) 2.81 (m, 2 H) 3.31 (t, J=3.79 Hz, 1 H) 3.54 (m, 2 H) 4.20 (s, 2 H) 4.82 (s, 2 H) 16.64 (dd, J=8.59, 3.03 Hz, 1 H) 6.77 (dd, J=7.07, 1.77 Hz, 1 H) 6.82 (m, 1 H) 7.13 (m, 5 H).

EXAMPLE 163

4-Bromo-3-carboxymethoxy-5-{3-[1-(2,6-dimethyl-phenylmethanesulfonyl)-piperidin-4-ylamino]-phenyl}-thiophene-2-carboxylic acid The third step of Scheme 15: To an oven-dried 25 mL round bottom flask under a nitrogen atmosphere was added 4-bromo-3-tert-butoxycarbonylmethoxy-5-[3-(piperidin-4-ylamino)-phenyl]-thiophene-2-carboxylic acid methyl ester (0.194 g, 0.35 mmol), 2,6-dimethylbenzylsulfonyl chloride (0.24 g, 1.14 mmol), 5 mL $CH_2Cl_2$, and 5 mL saturated aqueous sodium bicarbonate solution. The resulting mixture was allowed to stir for 12 hours. The mixture was then diluted with 30 mL $CH_2Cl_2$ and washed with three 25 mL portions of saturated aqueous sodium bicarbonate, three 25 mL portions water, and one 25 mL portion brine. The organic layer was dried over $MgSO_4$ and the solvent removed in vacuo to give 4-bromo-3-tert-butoxycarbonylmethoxy-5-{3-[1-(2,6-dimethyl-phenylmethanesulfonyl)-piperidin-4-ylamino]-phenyl}-thiophene-2-carboxylic acid methyl ester as a yellow oil (0.091 g, 34%).

¹H NMR (400 MHz, CHLOROFORM-D) δ ppm 1.52 (m, 9 H) 1.59 (m, 2 H) 2.47 (s, 6 H) 2.96 (m, 2 H) 3.45 (m, 1 H) 3.77 (m, 2 H) 3.88 (s, 3 H) 4.35 (s, 2 H) 4.82 (s, 2 H) 6.74 (d, J=8.08 Hz, 1 H) 6.97 (s, 1 H) 7.06 (m, J=12.88, 7.58 Hz, 3 H) 7.15 (m, 1 H) 7.26 (m, 1 H).

The fourth step of Scheme 15: To a 25 mL round bottom flask 4-bromo-3-tert-butoxycarbonylmethoxy-5-{3-[1-(2,6-dimethyl-phenylmethanesulfonyl)-piperidin-4-ylamino]-phenyl}-thiophene-2-carboxylic acid methyl ester (0.091 g, 0.15 mmol) and 5 mL THF were added. To this mixture was added a solution of lithium hydroxide hydrate (0.025 g, 0.60 mmol) in 3 mL water. This mixture was allowed to stir at room temperature for 16 hours. At this time 15 mL 1.2 N HCl was added, and a precipitate formed. The solids were collected by filtration and dried in vacuo to give 4-bromo-3-carboxymethoxy-5-{3-[1-(2,6-dimethyl-phenylmethanesulfonyl)-piperidin-4-ylamino]-phenyl}-thiophene-2-carboxylic acid as a white solid (0.043 g, 45%).

¹H NMR (400 MHz, MeOD) δ ppm 1.48 (m, 2 H) 2.06 (d, J=10.36 Hz, 2 H) 2.36 (s, 6 H) 3.04 (t, J=10.61 Hz, 2 H) 3.43 (m, J=10.23, 10.23 Hz, 1 H) 3.69 (m, J=12.63 Hz, 2 H) 4.34 (s, 2 H) 4.78 (s, 2 H) 6.68 (dd, J=8.21, 1.64 Hz, 1 H) 6.79 (d, J=8.08 Hz, 1 H) 6.85 (m, 1 H) 6.96 (m, J=7.33 Hz, 1 H) 7.02 (m, 1 H) 7.12 (t, J=7.83 Hz, 1 H).

EXAMPLE 164

4-Bromo-3-carboxymethoxy-5-{3-[1-(2-imidazol-1-yl-ethanesulfonyl)-piperidin-4-ylamino]-phenyl}-thiophene-2-carboxylic acid The third step of Scheme 15 of this example is a two-part reaction. In the first part, 4-bromo-3-tert-butoxycarbonyl-methoxy-5-[3-(piperidin-4-ylamino)-phenyl]-thiophene-2-carboxylic acid methyl ester hydrochloride (1.13 g, 2.0 mmole) was dissolved in 10 mL $CH_2Cl_2$ containing triethylamine (0.7 mL, 7.0 mmole). 2-chloroethanesulfonyl chloride (0.25 mL, 2.4 mmole) was added and the reaction mixture was allowed to stir at room temperature for 4 hours. The reaction mixture was diluted with $CH_2Cl_2$ and washed with dilute aqueous HCl. The aqueous phase was extracted with $CH_2Cl_2$ and the combined organic phases were washed with saturated sodium bicarbonate solution and dried ($MgSO_4$). Filtration and evaporation yielded the crude product which was then purified by flash chromatography (10 to 40% EtOAc/Hex as gradient). Pure fractions were combined and evaporated to give 212 mg (17%) 4-bromo-3-tert-butoxycarbonylmethoxy-5-[3-(1-ethenesulfonyl-piperidin-4-ylamino)-phenyl]-thiophene-2-carboxylic acid methyl ester as a pale yellow foam.

¹H NMR (400 MHz, CHLOROFORM-D) δ ppm 1.51 (s, 9 H) 1.59 (m, 2 H) 2.18 (dd, J=13.26, 3.41 Hz, 2 H) 2.85 (m, 2 H) 3.71 (m, 3 H) 3.87 (s, 3 H) 4.82 (s, 2 H) 6.06 (d, J=9.85 Hz, 1 H) 6.27 (d, J=16.67 Hz, 1 H) 6.46 (m, 1 H) 6.65 (m, 1 H) 6.86 (m, 1 H) 6.96 (dd, J=7.96, 1.39 Hz, 1 H) 7.23 (m, 1 H).

For the second part of the third step of Scheme 15: To a 1 mL suspension of 4-bromo-3-tert-butoxycarbonylmethoxy-5-[3-(1-ethenesulfonyl-piperidin-4-ylamino)-phenyl]-thiophene-2-carboxylic acid methyl ester (49 mg, $8.0 \times 10^{-5}$ mmole) was added imidazole (54 mg, 0.8 mmole) and the reaction mixture was allowed to stir at reflux overnight. The reaction mixture was cooled to room temperature and acidified to pH 6 with 1N HCl. A solid emerged that was filtered, washed with water and vacuum-oven dried. 42 mg (77%) 4-bromo-3-tert-butoxycarbonylmethoxy-5-{3-[1-(2-imidazol-1-yl-ethanesulfonyl)-piperidin-4-ylamino]-phenyl}-thiophene-2-carboxylic acid methyl ester was obtained as a pale yellow solid.

¹H NMR (400 MHz, DMSO-D6) δ ppm 1.37 (m, 2 H) 1.43 (s, 9 H) 1.99 (m, 2 H) 2.98 (m, 2 H) 3.57 (m, 5 H) 3.81 (s, 3 H) 4.36 (m, 2 H) 4.87 (s, 2 H) 5.94 (d, J=8.08 Hz, 1 H) 6.72 (dd, J=7.96, 1.89 Hz, 1 H) 6.79 (d, J=7.58 Hz, 1 H) 6.84 (s, 1 H) 6.91 (s, 1 H) 7.21 (t, J=7.83 Hz, 1 H) 7.29 (s, 1 H).

The fourth step of Scheme 15: 4-Bromo-3-tert-butoxycarbonylmethoxy-5-{3-[1-(2-imidazol-1-yl-ethanesulfonyl)-piperidin-4-ylamino]-phenyl}-thiophene-2-carboxylic acid methyl ester (42 mg, $6.1 \times 10^{-5}$ mmole) was dissolved in 1.5 mL of a 2:1 mixture of THF:$H_2O$ and LiOH.$H_2O$ (13 mg, 0.31 mmol) was added and the mixture stirred at room temperature overnight. The reaction mixture was then evaporated and the residue re-dissolved in 2-3 mL of $H_2O$. The residue was acidified dropwise with 1N HCl while stirring. A solid emerged that was filtered, washed with water, and vacuum oven-dried to give 26 mg (53%) of 4-bromo-3-carboxymethoxy-5-{3-[1-(2-imidazol-1-yl-ethanesulfonyl)-piperidin-4-ylamino]-phenyl}-thiophene-2-carboxylic acid as a pale yellow solid.

¹H NMR (400 MHz, DMSO-D6) δ ppm 1.41 (m, 2 H) 2.01 (m, 2 H) 3.00 (t, J=10.36 Hz, 3 H) 3.43 (s, 1 H) 3.57 (d, J=12.13 Hz, 2 H) 3.66 (t, J=6.95 Hz, 2 H) 4.46 (t, J=6.95 Hz, 2 H) 4.77 (s, 2 H) 6.70 (m, 1 H) 6.78 (d, J=7.58 Hz, 1 H) 6.82 (s, 1 H) 7.20 (m, 2 H) 7.51 (s, 1 H) 8.29 (s, 1 H).

ESI-MS: m/e=613 [M+H]⁺.

EXAMPLE 165

4-Bromo-3-carboxymethoxy-5-{3-[1-(2-pyrazol-1-yl-ethanesulfonyl)-piperidin-4-ylamino]-phenyl}-thiophene-2-carboxylic acid The first part of the third step of Scheme 15 was the same as that of Example 164. For the second part of the third step of Scheme 15 (2): To a 1 mL iprOH suspension of 4-bromo-3-tert-butoxycarbonylmethoxy-5-[3-(1-ethenesulfonyl-piperidin-4-ylamino)-phenyl]-thiophene-2-carboxylic acid methyl ester (31 mg, 0.05 mmole) was added potassium carbonate (20 mg, 0.15 mmole) and pyrazole (34 mg, 0.5 mmole) and the mixture was heated at reflux overnight. The reaction mixture was diluted with water and acidified to pH=4 with 1N HCl and extracted with EtOAc. Organic layer washed with water, brine, and dried (MgSO$_4$). Filtration and evaporation yielded the crude product which was then purified by flash chromatography (0% to 3% MeOH/CH$_2$Cl$_2$ as gradient). Pure fractions were combined and evaporated to give 32 mg of material that was still contaminated with unwanted pyrazole. This was purified by preparative thin layer chromatography (2% MeOH/CH$_2$Cl$_2$). 13 mg (38%) 4-bromo-3-tert-butoxycarbonylmethoxy-5-{3-[1-(2-pyrazol-1-yl-ethanesulfonyl)-piperidin-4-ylamino]-phenyl}-thiophene-2-carboxylic acid methyl ester was obtained as a pale yellow semisolid.

$^1$H NMR (400 MHz, CHLOROFORM-D) δ ppm 1.35 (d, J=6.32 Hz, 6 H) 1.51 (s, 9 H) 2.11 (m, 2 H) 2.87 (m, 2 H) 3.56 (m, 2 H) 3.67 (m, 3 H) 4.58 (t, J=6.82 Hz, 2 H) 4.80 (s, 2 H) 5.20 (m, 1 H) 6.28 (t, J=2.15 Hz, 1 H) 6.63 (dd, J=8.08, 2.53 Hz, 1 H) 6.85 (m, 1 H) 6.96 (d, J=7.58 Hz, 1 H) 7.23 (t, J=7.96 Hz, 1 H) 7.47 (d, J=2.53 Hz, 1 H) 7.57 (d, J=2.02 Hz, 1 H).

The fourth step of Scheme 15: 4-Bromo-3-tert-butoxycarbonylmethoxy-5-{3-[1-(2-pyrazol-1-yl-ethanesulfonyl)-piperidin-4-ylamino]-phenyl}-thiophene-2-carboxylic acid methyl ester was prepared as a pale yellow solid (77%) according to the procedure in the fourth step of Scheme 15 of Example 164.

$^1$H NMR (400 MHz, DMSO-D6) δ ppm 1.41 (m, 2 H) 1.98 (m, 2 H) 2.97 (m, 2 H) 3.57 (m, 5 H) 4.50 (m, 2 H) 4.87 (s, 2 H) 6.25 (m, 1 H) 6.70 (dd, J=8.21, 2.40 Hz, 1 H) 6.79 (d, J=7.33 Hz, 1 H) 6.84 (t, J=2.02 Hz, 1 H) 7.20 (t, J=7.83 Hz, 1 H) 7.49 (d, J=1.77 Hz, 1 H) 7.82 (d, J=2.27 Hz, 1 H).

ESI-MS: m/e=613 [M+H]$^+$.

EXAMPLE 166

4-Bromo-3-carboxymethoxy-5-{3-[1-(2-isopropoxy-ethanesulfonyl)-piperidin-4-ylamino]-phenyl}-thiophene-2-carboxylic acid 4-Bromo-3-tert-butoxycarbonylmethoxy-5-{3-[1-(2-isopropoxy-ethanesulfonyl)-piperidin-4-ylamino]-phenyl}-thiophene-2-carboxylic acid methyl ester was isolated as a side product in the second part of the third step of Scheme 15 of Example 165 and was subsequently hydrolyzed following the procedure in the fourth step of Scheme 15 of Example 164 to give 4-bromo-3-carboxymethoxy-5-{3-[1-(2-isopropoxy-ethanesulfonyl)-piperidin-4-ylamino]-phenyl}-thiophene-2-carboxylic acid.

$^1$H NMR (400 MHz, DMSO-D6) δ ppm 1.11 (d, J=6.32 Hz, 6 H) 1.41 (q, J=10.27 Hz, 2 H) 2.00 (d, J=11.62 Hz, 2 H) 3.28 (t, J=6.19 Hz, 2 H) 3.60 (m, 4 H) 3.69 (t, J=6.19 Hz, 2 H) 4.85 (s, 2 H) 6.71 (d, J=8.34 Hz, 1 H) 6.79 (d, J=7.83 Hz, 1 H) 6.85 (s, 1 H) 7.20 (t, J=7.83 Hz, 1 H).

ESI-MS: m/e=605 [M+H]$^+$.

EXAMPLE 167

5-{3-[1-(2-Amino-phenylmethanesulfonyl)-piperidin-4-ylamino]-phenyl}-4-bromo-3-carboxymethoxy-thiophene-2-carboxylic acid The third step of Scheme 15: 5-{3-[1-(2-Amino-phenyl-methanesulfonyl)-piperidin-4-ylamino]-phenyl}4-bromo-3-ethoxycarbonylmethoxy-thiophene-2-carboxylic acid methyl ester was obtained in 19% yield as a pale yellow foam, following the procedure in the third step of Scheme 15 of Example 152 with a subsequent Tin(II) chloride reduction.

$^1$H NMR (400 MHz, CHLOROFORM-D) δ ppm 1.3 (t, J=7.2 Hz, 3 H) 1.5 (m, 2 H) 2.1 (m, 2 H) 2.9 (m, 2 H) 3.4 (m, 1 H) 3.7 (m, 2 H) 3.9 (s, 3 H) 4.3 (m, 4 H) 4.9 (s, 2 H) 6.6 (m, 1 H) 6.8 (m, 2 H) 6.8 (m, 1 H) 6.9 (m, 1 H) 7.1 (m, 2 H) 7.2 (t, J=7.8 Hz, 1 H) 7.3 (s, 1 H).

The fourth step of Scheme 15: 5-{3-[1-(2-Amino-phenyl-methanesulfonyl)-piperidin-4-ylamino]-phenyl}4-bromo-3-carboxymethoxy-thiophene-2-carboxylic acid was hydrolyzed according to the procedure in the fourth step of Scheme 15 of Example 164 to give 5-{3-[1-(2-amino-phenylmethanesulfonyl)-piperidin-4-ylamino]-phenyl}-4-bromo-3-carboxymethoxy-thiophene-2-carboxylic acid in 36% yield as a pale brown solid.

$^1$H NMR (400 MHz, DMSO-D6) δ ppm 1.4 (m, 2 H) 1.8 (m, J=6.7, 6.7 Hz, 1 H) 2.0 (m, 2 H) 3.0 (m, 2 H) 3.6 (m, 2 H) 4.3 (s, 2 H) 4.9 (s, 2 H) 6.6 (m, 1 H) 6.8 (m, 3 H) 6.9 (m, 1 H) 7.1 (m, 1 H) 7.1 (dd, J=7.7, 1.6 Hz, 1 H) 7.2 (t, J=8.0 Hz, 1 H).

ESI-MS: m/e=623 [M+H]$^+$.

EXAMPLE 168

4-[3-(3-Bromo-5-carboxymethoxy-thiophen-2-yl)-phenylamino]-piperidine-1-carboxylic acid methyl ester The first step of Scheme 16: To a 1 mL pyridine solution of 4-bromo-3-ethoxycarbonylmethoxy-5-[3-(piperidin-4-ylamino)-phenyl]-thiophene-2-carboxylic acid methyl ester hydrochloride salt (60 mg, 0.1 mmole) was added methyl chloroformate (18 mL, 0.24 mmole) and the reaction mixture stirred at room temperature for 5 hours. 10 mL 2N HCl was added, and the mixture extracted with EtOAc. It was washed with saturated sodium bicarbonate solution, brine and dried over MgSO$_4$. Filtration and evaporation gave the crude product which was purified by chromatography on silica gel using a gradient of EtOAc/hexane (20 to 60%) as eluent. Pure fractions were combined and evaporated to give 15 mg (27%) 4-[3-(3-bromo-4-ethoxycarbonylmethoxy-5-methoxycarbonyl-thiophen-2-yl)-phenylamino]-piperidine-1-carboxylic acid methyl ester as a pale glassy solid.

$^1$H NMR (400 MHz, CHLOROFORM-D) δ ppm 1.32 (t, J=7.07 Hz, 3 H) 1.41 (m, 2 H) 2.09 (m, 2 H) 3.02 (m, 2 H) 3.48 (m, 1 H) 3.71 (s, 3 H) 3.87 (s, 3 H) 4.11 (m, 2 H) 4.30 (q, J=7.07 Hz, 2 H) 4.90 (s, 2 H) 6.66 (m, 1 H) 6.87 (m, 1 H) 6.95 (m, 1 H) 7.23 (t, J=7.83 Hz, 1 H).

The second step of Scheme 16: 4-[3-(3-Bromo-4-ethoxycarbonylmethoxy-5-methoxycarbonyl-thiophen-2-yl)-phenylamino]-piperidine-1-carboxylic acid methyl ester (15 mg, 0.027 mmole) was dissolved in 1.5 mL of a 2:1 mixture of THF:H$_2$O. LiOH.H$_2$O (6 mg, 0.14 mmole) was added and the reaction mixture was allowed to stir at room temperature overnight. The solvent was evaporated and re-dissolved in 2-3 mL water. The mixture was acidified dropwise with 1N HCl while stirring. A solid emerged that was filtered, washed with water, and vacuum-oven dried to give 10 mg (72%) of 4-[3-(3-bromo-5-carboxy-4-carboxymethoxy-thiophen-2-yl)-phenylamino]-piperidine-1-carboxylic acid methyl ester as a pale yellow solid.

$^1$H NMR (400 MHz, DMSO-D6) δ ppm 1.27 (m, 2 H) 1.92 (m, 2 H) 3.01 (m, 2 H) 3.46 (m, 1 H) 3.59 (s, 3 H) 3.91 (m, 2

H) 4.87 (s, 2 H) 6.71 (dd, J=8.21, 2.40 Hz, 1 H) 6.78 (d, J=7.58 Hz, 1 H) 6.85 (s, 1 H) 7.19 (t, J=7.83 Hz, 1 H).
ESI-MS: m/e=513 [M+H]$^+$.

EXAMPLE 169

5-[3-(1-Benzoyl-piperidin-4-ylamino)-phenyl]-4-bromo-3-carboxymethoxy-thiophene-2-carboxylic acid The first step of Scheme 16: 5-[3-(1-Benzoyl-piperidin-4-ylamino)-phenyl]-4-bromo-3-tert-butoxycarbonylmethoxy-thiophene-2-carboxylic acid methyl ester was obtained in 40% yield as a pale yellow foam, following the procedure in the first step of Scheme 16 of Example 168.
$^1$H NMR (400 MHz, CHLOROFORM-D) δ ppm 1.44 (m, 2 H) 1.50 (s, 9 H) 2.13 (m, 2 H) 3.10 (m, 2 H) 3.59 (m, 2 H) 3.87 (s, 3 H) 4.82 (s, 2 H) 6.67 (m, 1 H) 6.88 (m, 1 H) 6.96 (m, 1 H) 7.23 (t, J=7.83 Hz, 1 H) 7.45 (m, 5 H).

The second step of Scheme 16: 5-[3-(1-Benzoyl-piperidin-4-ylamino)-phenyl]-4-bromo-3-tert-butoxycarbonyl-methoxy-thiophene-2-carboxylic acid methyl ester was hydrolyzed according to the procedure in the second step of Scheme 16 of Example 168 to give 5-[3-(1-benzoyl-piperidin-4-ylamino)-phenyl]-4-bromo-3-carboxymethoxy-thiophene-2-carboxylic acid in 71% yield as a pale yellow solid.
$^1$H NMR (400 MHz, DMSO-D6) δ ppm 1.37 (m, 2 H) 1.97 (m, 2 H) 3.15 (m, 2 H) 3.58 (m, 2 H) 4.35 (m, 1 H) 4.87 (s, 2 H) 6.73 (dd, J=8.34, 2.27 Hz, 1 H) 6.78 (d, J=7.58 Hz, 1 H) 6.86 (s, 1 H) 7.20 (t, J=7.83 Hz, 1 H) 7.38 (m, 2 H) 7.45 (m, 3 H).
ESI-MS: m/e=559 [M+H]$^+$.

EXAMPLE 170

4-Bromo-3-carboxymethoxy-5-[3-(1-phenylacetyl-piperidin-4-ylamino)-phenyl]-thiophene-2-carboxylic acid The first step of Scheme 16: To a 1 mL DMF solution of 4-bromo-3-tert-butoxycarbonylmethoxy-5-[3-(piperidin-4-ylamino)-phenyl]-thiophene-2-carboxylic acid methyl ester hydrochloride (56 mg, 0.1 mmole) was added phenylacetic acid (20 mg, 0.15 mmole), HATU (46 mg, 0.12 mmole), and diisopropylethylamine (71 µL, 0.4 mmole) and the reaction mixture stirred at room temperature overnight. Water (15 mL) was then added, and the mixture was acidified with 1N HCl and extracted with EtOAc. It was then washed with saturated sodium bicarbonate solution, brine and dried over MgSO$_4$. Filtration and evaporation gave the crude product which was then purified by chromatography on silica gel using a gradient of EtOAc/hexane (20 to 60%) as eluent. Pure fractions were combined and evaporated to give 49 mg (76%) of 4-bromo-3-tert-butoxycarbonylmethoxy-5-[3-(1-phenylacetyl-piperi-din-4-ylamino)-phenyl]-thiophene-2-carboxylic acid methyl ester as a pale yellow foam.
$^1$H NMR (400 MHz, CHLOROFORM-D) δ ppm 1.10 (m, 1 H) 1.34 (m, 1 H) 1.50 (s, 9 H) 1.95 (s, 1 H) 2.06 (s, 1 H) 2.90 (m, 1 H) 3.14 (m, 1 H) 3.48 (m, 2 H) 3.76 (s, 2 H) 3.87 (s, 3 H) 4.52 (dd, J=13.26, 1.39 Hz, 1 H) 4.81 (s, 2 H) 6.61 (m, 1 H) 6.83 (m, 1 H) 6.94 (m, 1 H) 7.21 (m, 1 H) 7.25 (m, 3 H) 7.33 (m, 2 H).

The second step of Scheme 16: 4-Bromo-3-tert-butoxycarbonylmethoxy-5-[3-(1-phenylacetyl-piperidin-4-ylamino)-phenyl]-thiophene-2-carboxylic acid methyl ester was hydrolyzed according to the procedure in the second step of Scheme 16 of Example 168 to give 4-bromo-3-carboxymethoxy-5-[3-(1-phenylacetyl-piperidin-4-ylamino)-phenyl]-thiophene-2-carboxylic acid in 85% yield as a pale yellow solid.
$^1$H NMR (400 MHz, DMSO-D6) δ ppm 1.16 (m, 2 H) 1.89 (m, 1 H) 2.88 (m, 1 H) 3.18 (m, 1 H) 3.51 (m, 1 H) 3.72 (d, J=2.27 Hz, 1 H) 3.92 (d, J=17.68 Hz, 1 H) 4.24 (d, J=13.14 Hz, 1 H) 4.87 (s, 2 H) 6.70 (dd, J=7.96, 1.64 Hz, 1 H) 6.77 (d, J=6.32 Hz, 1 H) 6.84 (d, J=1.77 Hz, 1 H) 7.18 (m, 1 H) 7.24 (m, 3 H) 7.31 (m, 2 H).
ESI-MS: m/e=573 [M+H]$^+$.

EXAMPLE 171

5-{3-[3-Benzyl-1-(1-benzylcarbamoyl-piperidin-4-yl)-ureido]-phenyl}-4-bromo-3-carboxymethoxy-thiophene-2-carboxylic acid The first step of Scheme 16: To a 1 mL DMF solution of 4-bromo-3-ethoxycarbonylmethoxy-5-[3-(piperidin-4-ylamino)-phenyl]-thiophene-2-carboxylic acid methyl ester hydrochloride (65 mg, 0.11 mmole) was added diisopropyl-ethylamine (23 µL, 0.13 mmole) and benzyl isocyanate (34 µL, 0.27 mmole) and the reaction mixture was heated to 80° C. After 3 hours the reaction was cooled to room temperature, diluted with water and acidified with 1N HCl. The mixture was extracted with EtOAc and washed with saturated sodium bicarbonate solution, brine and dried over MgSO$_4$. Filtration and evaporation gave the crude product which was then purified by chromatography on silica gel using a gradient of EtOAc/hexane (30 to 100%) as eluent. Pure fractions were combined and evaporated to give 37 mg (44%) 5-{3-[3-benzyl-1-(1-benzylcarbamoyl-piperidin-4-yl)-ureido]-phenyl})-4-bromo-3-ethoxycarbonylmethoxy-thiophene-2-carboxylic acid methyl ester as a colorless glassy solid.
$^1$H NMR (400 MHz, MeOD) δ ppm 1.21 (m, 5 H) 1.76 (d, J=10.36 Hz, 2 H) 2.76 (t, J=12.25 Hz, 2 H) 3.20 (m, 1 H) 3.75 (s, 3 H) 3.97 (d, J=13.39 Hz, 2 H) 4.15 (m, 6 H) 4.49 (m, 1 H) 4.74 (s, 2 H) 4.81 (s, 2 H) 5.80 (t, J=6.06 Hz, 1 H) 6.83 (t, J=5.81 Hz, 1 H) 7.08 (m, 10 H) 7.22 (d, J=7.83 Hz, 1 H) 7.43 (t, J=1.77 Hz, 1 H) 7.49 (t, J=7.83 Hz, 1 H) 7.58 (m, 1 H).

The second step of Scheme 16: 5-{3-[3-Benzyl-1-(1-benzylcarbamoyl-piperidin-4-yl)-ureido]-phenyl}-4-bromo-3-ethoxycarbonylmethoxy-thiophene-2-carboxylic acid methyl was hydrolyzed according to the procedure in the second step of Scheme 16 of Example 168 to give 5-{3-[3-benzyl-1-(1-benzylcarbamoyl-piperidin-4-yl)-ureido]-phenyl}-4-bromo-3-carboxymethoxy-thiophene-2-carboxylic acid in 62% yield as an off-white solid.
$^1$H NMR (400 MHz, DMSO-D6) δ ppm 1.14 (m, 2 H) 1.76 (m, 2 H) 2.72 (m, 2 H) 4.01 (m, 2 H) 4.14 (d, J=5.56 Hz, 2 H) 4.18 (d, J=5.81 Hz, 2 H) 4.48 (m, 1 H) 4.89 (s, 1 H) 6.08 (t, J=5.43 Hz, 1 H) 6.98 (m, 1 H) 7.23 (m, 10 H) 7.48 (t, J=1.89 Hz, 1 H) 7.61 (t, J=7.83 Hz, 1 H) 7.71 (m, 1 H).
ESI-MS: m/e=721 [M+H]$^+$.

EXAMPLE 172

5-[3-(1-Benzylcarbamoyl-piperidin-4-ylamino)-pheny]-4-bromo-3-carboxymethoxy-thiophene-2 carboxylic acid The first step of Scheme 16: To a 1 mL DMF solution of 4-bromo-3-ethoxycarbonylmethoxy-5-[3-(piperidin-4-ylamino)-phenyl]-thiophene-2-carboxylic acid methyl ester (as a free base ~50 mg, 0.1 mmole) was added benzyl isocyanate (14 µL, 0.11 mmole) and the reaction mixture stirred at room temperature. After 3 hours the reaction was diluted with water and acidified with 1N HCl. The product was extracted with EtOAc and washed with saturated sodium bicarbonate solution, brine and dried over MgSO$_4$. Filtration and evaporation gave the crude product which was then purified by chromatography on silica gel using a gradient of EtOAc/hexane (20 to 100%) as eluent. Pure fractions were combined and evaporated to give 18 mg (29%) 5-[3-(1-benzylcarbamoyl-piperidin-4-ylamino)-phenyl]-4-bromo-3-ethoxycarbonylmethoxy-thiophene-2-carboxylic acid methyl ester as pale yellow glassy solid.

$^1$H NMR (400 MHz, CHLOROFORM-D) δ ppm 1.32 (t, J=7.07 Hz, 3 H) 1.42 (dd, J=13.64, 2.27 Hz, 2 H) 2.10 (m, 2 H) 3.01 (m, 2 H) 3.49 (m, 1 H) 3.74 (s, 1 H) 3.87 (s, 3 H) 3.94 (m, 2 H) 4.29 (q, J=7.07 Hz, 2 H) 4.43 (d, J=5.31 Hz, 2 H) 4.80 (t, J=5.31 Hz, 1 H) 4.90 (s, 2 H) 6.65 (m, 1 H) 6.87 (m, 1 H) 6.95 (d, J=8.34 Hz, 1 H) 7.23 (t, J=7.96 Hz, 1 H) 7.31 (m, 5 H).

The second step of Scheme 16: 5-[3-(1-Benzylcarbamoyl-piperidin-4-ylamino)-phenyl]-4-bromo-3-ethoxycarbonylmethoxy-thiophene-2-carboxylic acid methyl ester was hydrolyzed according to the procedure in the second step of Scheme 16 of Example 168 to give 5-[3-(1-benzylcarbamoyl-piperidin-4-ylamino)-phenyl]-4-bromo-3-carboxymethoxy-thiophene-2-carboxylic acid in 94% yield as an off-white solid.

$^1$H NMR (400 MHz, DMSO-D6) δ ppm 1.29 (m, 2 H) 1.90 (m, 2 H) 2.91 (m, 2 H) 3.47 (m, 1 H) 3.93 (dd, J=12.63, 1.52 Hz, 2 H) 4.24 (d, J=5.81 Hz, 2 H) 4.88 (s, 2 H) 6.72 (dd, J=8.21, 2.15 Hz, 1 H) 6.78 (d, J=8.59 Hz, 1 H) 6.85 (m, 1 H) 7.08 (t, J=6.32 Hz, 1 H) 7.24 (m, 5 H).

ESI-MS: m/e=588 [M+H]$^+$.

EXAMPLE 173

4-Bromo-3-carboxymethoxy-5-{3-[(1-methanesulfonyl-piperidin-4-ylmethyl)-amino]-phenyl}-thiophene-2-carboxylic acid Preparation of 4-formyl-piperidine-1-carboxylic acid tert-butyl ester: To a 25 mL CH$_2$Cl$_2$ solution of N-Boc-4-piperidinemethanol (1.08 g, 5.0 mmol) was added pyridinium chlorochromate (1.62 g, 7.5 mmole) and the resulting reaction mixture was stirred at room temperature for 4 hours. Ether (40 mL) was then added and the mixture was allowed to stir several minutes. The solution was filtered through a plug of celite and the filtrate was evaporated. The resulting brown oil was triturated with ether (20 mL). A solid emerged that was filtered and discarded. The filtrate was evaporated to give 955 mg (90%) 4-formyl-piperidine-1-carboxylic acid tert-butyl ester as a pale green oil.

$^1$H NMR (400 MHz, CHLOROFORM-D) δ ppm 1.46 (s, 9 H) 1.60 (m, 2 H) 1.91 (m, 2 H) 2.45 (m, 1 H) 2.91 (m, 2 H) 4.03 (m, 2 H) 9.66 (s, 1 H).

The first step of Scheme 17: To a 16 mL DCE solution of 5-(3-amino-phenyl)-4-bromo-3-tert-butoxycarbonylmethoxy-thiophene-2-carboxylic acid methyl ester (1.8 g, 4.0 mmole) was added 4-formyl-piperidine-1-carboxylic acid tert-butyl ester (947 mg, 4.4 mmole), and acetic acid (0.35 mL, 6.1 mmole). The reaction mixture was stirred 15 minutes and sodium triacetoxyborohydride (2.15 g, 10.2 mmoles) added, and the mixture was stirred at room temperature for 6 hours. It was diluted with CH$_2$Cl$_2$, washed twice with saturated sodium bicarbonate solution and dried over MgSO$_4$. Filtration and evaporation gave the crude product which was purified by chromatography on silica gel using a gradient of EtOAc/hexane (10 to 40%) as eluent. Pure fractions were combined and evaporated to give 1.81 g (71%) 4-{[3-(3-bromo-4-tert-butoxycarbonylmethoxy-5-methoxycarbonyl-thiophen-2-yl)-phenylamino]-methyl}-piperidine-1-carboxylic acid tert-butyl ester as a viscous yellow oil which solidified on standing.

$^1$H NMR (400 MHz, CHLOROFORM-D) δ ppm 1.20 (m, 2 H) 1.46 (s, 9 H) 1.51 (s, 9 H) 1.77 (m, 3 H) 2.70 (t, J=13.01 Hz, 2 H) 3.06 (d, J=6.32 Hz, 2 H) 3.87 (s, 3 H) 4.82 (s, 2 H) 6.65 (m, 1 H) 6.86 (m, 1 H) 6.95 (m, 1 H) 7.23 (t, J=7.83 Hz, 1 H).

The second step of Scheme 17: 4-{[3-(3-Bromo-4-tert-butoxycarbonylmethoxy-5-methoxycarbonyl-thiophen-2-yl)-phenylamino]-methyl}-piperidine-1-carboxylic acid tert-butyl ester (1.81 g, 2.8 mmole) was dissolved in a mixture of 14 mL 1N HCl in EtOAc (Prepared by bubbling dry HCl gas into dry EtOAc) and 3 mL MeOH. The reaction mixture was stirred at room temperature overnight. The reaction mixture was then evaporated exhaustively to give 4-{[3-(3-bromo-4-tert-butoxycarbonylmethoxy-5-methoxycarbonyl-thiophen-2-yl)-phenylamino]-methyl}-piperidine-1-carboxylic acid tert-butyl ester hydrochloride in quantitative yield as a white solid.

$^1$H NMR (400 MHz, MeOD) δ ppm 1.42 (s, 9 H) 1.49 (m, 2 H) 2.06 (m, 3 H) 2.96 (td, J=12.95, 2.65 Hz, 2 H) 3.30 (d, J=6.82 Hz, 2 H) 3.38 (m, 2 H) 3.79 (s, 3 H) 4.78 (s, 2 H) 7.34 (d, J=7.83 Hz, 1 H) 7.50 (m, 3 H).

The third step of Scheme 17: 4-{[3-(3-Bromo-4-tert-butoxycarbonylmethoxy-5-methoxycarbonyl-thiophen-2-yl)-phenylamino]-methyl}-piperidine-1-carboxylic acid tert-butyl ester hydrochloride (57 mg, 0.1 mmole) was dissolved in a vigorously stirred mixture of 0.5 mL CH$_2$Cl$_2$ and 0.5 mL saturated sodium bicarbonate solution. Methanesulfonyl chloride (10 μL, 0.12 mmole) was then added and the biphasic mixture was allowed to stir at room temperature for 2 hours. The reaction mixture was diluted with CH$_2$Cl$_2$ and washed with saturated sodium bicarbonate solution and dried over MgSO$_4$. Filtration and evaporation gave the crude product which was purified by chromatography on silica gel using a gradient of EtOAc/hexane (10 to 60%) as eluent. Evaporation of pure fractions gave 41 mg (66%) of 4-bromo-3-tert-butoxycarbonylmethoxy-5-{3-[(1-methanesulfonyl-piperidin-4-ylmethyl)-amino]-phenyl}-thiophene-2-carboxylic acid methyl ester as a pale yellow oil.

$^1$H NMR (400 MHz, CHLOROFORM-D) δ ppm 1.40 (m, 2 H) 1.51 (s, 9 H) 1.78 (m, 1 H) 1.93 (d, J=12.63 Hz, 1 H) 2.66 (td, J=12.00, 2.02 Hz, 1 H) 2.77 (s, 3 H) 3.11 (d, J=6.82 Hz, 2 H) 3.84 (s, 2 H) 3.87 (s, 3 H) 4.82 (s, 2 H) 6.65 (dd, J=8.21, 2.40 Hz, 1 H) 6.86 (m, 1 H) 6.96 (dd, J=7.58, 1.01 Hz, 1 H) 7.23 (t, J=7.96 Hz, 1 H).

The fourth step of Scheme 17: 4-Bromo-3-tert-butoxycarbonylmethoxy-5-{3-[(1-methanesulfonyl-piperidin-4-ylmethyl)-amino]-phenyl}-thiophene-2-carboxylic acid methyl ester (41 mg, 0.066 mmole) was dissolved in 1.5 mL of a 2:1 mixture of THF:H$_2$O. LiOH.H$_2$O (14 mg, 0.33 mmole) was added and the reaction mixture was allowed to stir at room temperature overnight. The solvent was evaporated and re-dissolved in 2-3 mL water. The mixture was acidified dropwise with 1N HCl while stirring. A solid emerged that was filtered, washed with water, and vacuum-oven dried to give 27 mg (75%) of 4-bromo-3-carboxymethoxy-5-{3-[(1-methanesulfonyl-piperidin-4-ylmethyl)-amino]-phenyl}-thiophene-2-carboxylic acid as a pale yellow solid.

$^1$H NMR (400 MHz, DMSO-D6) δ ppm 1.23 (m, 2 H) 1.70 (m, 1 H) 1.87 (m, 2 H) 2.68 (m, 2 H) 2.84 (s, 3 H) 2.98 (d, J=6.82 Hz, 2 H) 3.57 (d, J=11.62 Hz, 2 H) 4.88 (s, 2 H) 6.69 (dd, J=8.08, 1.77 Hz, 1 H) 6.78 (m, 1 H) 6.83 (t, J=1.89 Hz, 1 H) 7.19 (t, J=7.96 Hz, 1 H).

ESI-MS: m/e=546 [M+H]$^+$.

EXAMPLE 174

4-Bromo-3-carboxymethoxy-5-{3-[(1-ethanesulfonyl-piperidin-4-ylmethyl)-amino]-phenyl}-thiophene-2-carboxylic acid The third step of Scheme 17: 4-Bromo-3-tert-butoxycarbonylmethoxy-5-{3-[(1-ethanesulfonyl-piperidin-4-ylmethyl)-amino]-phenyl}-thiophene-2-carboxylic acid methyl ester was obtained in 75% yield as a colorless glassy solid, following the procedure in the third step of Scheme 17 of Example 173.

$^1$H NMR (400 MHz, CHLOROFORM-D) δ ppm 1.37 (m, 5 H) 1.51 (s, 9 H) 1.77 (m, 1 H) 1.89 (dd, J=12.76, 1.89 Hz, 2 H) 2.78 (td, J=12.25, 2.53 Hz, 2 H) 2.95 (q, J=7.33 Hz, 2 H) 3.10 (d, J=6.57 Hz, 2 H) 3.84 (s, 2 H) 3.87 (s, 3 H) 4.82 (s, 2 H) 6.65 (ddd, J=8.15, 2.46, 0.76 Hz, 1 H) 6.86 (m, 1 H) 6.96 (m, 1 H) 7.23 (t, J=7.96 Hz, 1 H).

The fourth step of Scheme 17: 4-Bromo-3-tert-butoxycarbonylmethoxy-5-{3-[(1-ethanesulfonyl-piperidin-4-ylmethyl)-amino]-phenyl}-thiophene-2-carboxylic acid methyl ester was hydrolyzed according to the procedure in the fourth step of Scheme 17 of Example 173 to give 4-bromo-3-carboxymethoxy-5-{3-[(1-ethanesulfonyl-piperidin-4-ylmethyl)-amino]-phenyl}-thiophene-2-carboxylic acid in 71% yield as a yellow solid.

$^1$H NMR (400 MHz, DMSO-D6) δ ppm 1.22 (m, 5 H) 1.72 (m, 1 H) 1.85 (m, 2 H) 2.78 (m, 2 H) 3.00 (m, 4 H) 3.61 (m, 2 H) 4.87 (s, 2 H) 6.69 (d, J=6.32 Hz, 1 H) 6.77 (d, J=7.07 Hz, 1 H) 6.83 (s, 1 H) 7.19 (t, J=8.34 Hz, 1 H).

ESI-MS: m/e=561 [M+H]$^+$.

EXAMPLE 175

5-{3-[(1-Benzenesulfonyl-piperidin-4-ylmethyl)-amino]-phenyl}-4-bromo-3-carboxymethoxy-thiophene-2-carboxylic acid The third step of Scheme 17: 5-{3-[(1-Benzenesulfonyl-piperidin-4-ylmethyl)-amino]-phenyl}4-bromo-3-tert-butoxycarbonylmethoxy-thiophene-2-carboxylic acid methyl ester was obtained in 60% yield as a pale yellow glassy solid, following the procedure in the third step of Scheme 17 of Example 173.

$^1$H NMR (400 MHz, CHLOROFORM-D) δ ppm 1.38 (m, 2 H) 1.50 (s, 9 H) 1.56 (m, 1 H) 1.85 (d, J=10.86 Hz, 2 H) 2.26 (td, J=11.94, 2.40 Hz, 2 H) 3.04 (d, J=6.57 Hz, 2 H) 3.83 (m, 2 H) 3.87 (s, 3 H) 4.81 (s, 2 H) 6.60 (m, 1 H) 6.80 (m, 1 H) 6.93 (dd, J=7.96, 1.39 Hz, 1 H) 7.20 (t, J=7.83 Hz, 1 H) 7.52 (m, 2 H) 7.59 (m, 1 H) 7.76 (m, 2 H).

The fourth step of Scheme 17: 5-{3-[(1-Benzenesulfonyl-piperidin-4-ylmethyl)-amino]-phenyl}-4-bromo-3-tert-butoxycarbonylmethoxy-thiophene-2-carboxylic acid methyl ester was hydrolyzed according to the procedure in the fourth step of Scheme 17 of Example 173 to give 5-{3-[(1-benzenesulfonyl-piperidin-4-ylmethyl)-amino]-phenyl}-4-bromo-3-carboxymethoxy-thiophene-2-carboxylic acid in 82% yield as a pale yellow solid.

$^1$H NMR (400 MHz, DMSO-D6) δ ppm 1.25 (m, 2 H) 1.52 (m, 1 H) 1.82 (m, 2 H) 2.21 (m, 2 H) 2.90 (d, J=6.06 Hz, 2 H) 3.67 (d, J=11.87 Hz, 2 H) 4.86 (s, 2 H) 6.64 (dd, J=7.96, 1.89 Hz, 1 H) 6.77 (m, 2 H) 7.15 (t, J=7.83 Hz, 1 H) 7.63 (m, 2 H) 7.71 (m, 3 H).

ESI-MS: m/e=609 [M+H]$^+$.

EXAMPLE 176

4-Bromo-3-carboxymethoxy-5-{3-[(1-phenyl-methanesulfonyl-piperidin-4-ylmethyl)-amino]-phenyl}-thiophene-2-carboxylic acid The third step of Scheme 17: 4-Bromo-3-tert-butoxycarbonylmethoxy-5-{3-[(1-phenylmethanesulfonyl-piperidin-4-ylmethyl)-amino]-phenyl}-thiophene-2-carboxylic acid methyl ester was obtained in 79% yield as a pale yellow foam, following the procedure in the third step of Scheme 17 of Example 173.

$^1$H NMR (400 MHz, CHLOROFORM-D) δ ppm 1.24 (m, 2 H) 1.51 (s, 9 H) 1.67 (m, 1 H) 1.76 (m, 2 H) 2.54 (td, J=12.32, 2.40 Hz, 2 H) 3.03 (d, J=6.82 Hz, 2 H) 3.69 (d, J=12.38 Hz, 2 H) 3.87 (s, 3 H) 4.21 (s, 2 H) 4.82 (s, 2 H) 6.62 (dd, J=7.83, 2.02 Hz, 1 H) 6.83 (m, 1 H) 6.94 (d, J=8.08 Hz, 1 H) 7.22 (t, J=7.83 Hz, 1 H) 7.38 (m, 5 H).

The fourth step of Scheme 17: 4-Bromo-3-tert-butoxycarbonylmethoxy-5-{3-[(1-phenylmethanesulfonyl-piperidin-4-ylmethyl)-amino]-phenyl}-thiophene-2-carboxylic acid methyl ester was hydrolyzed according to the procedure in the fourth step of Scheme 17 of Example 173 to give 4-bromo-3-carboxymethoxy-5-{3-[(1-phenylmethanesulfonyl-piperidin-4-ylmethyl)-amino]-phenyl}-thiophene-2-carboxylic acid in 75% yield as a pale yellow solid.

$^1$H NMR (400 MHz, DMSO-D6) δ ppm 1.14 (m, 2 H) 1.66 (m, 1 H) 1.79 (d, J=12.38 Hz, 2 H) 2.67 (m, 2 H) 2.94 (d, J=6.57 Hz, 2 H) 3.57 (d, J=12.38 Hz, 2 H) 4.38 (s, 2 H) 4.88 (s, 2 H) 6.68 (dd, J=8.97, 2.40 Hz, 1 H) 6.77 (d, J=6.82 Hz, 1 H) 6.81 (s, 1 H) 7.18 (t, J=7.96 Hz, 1 H) 7.39 (m, 5 H).

ESI-MS: m/e=623 [M+H]$^+$.

EXAMPLE 177

5-(3-{[1-(2-Amino-phenylmethanesulfonyl)-piperidin-4-ylmethyl]-amino}-phenyl)-4-bromo-3-carboxymethoxy-thiophene-2-carboxylic acid The third step of Scheme 17: 5-(3-{[1-(2-Amino-phenylmethanesulfonyl)-piperidin-4-ylmethyl]-amino}-phenyl)-4-bromo-3-methoxycarbonylmethoxy-thiophene-2-carboxylic acid methyl ester was obtained in 24% yield as a yellow foam, following the procedure in the third step of Scheme 17 of Example 173 with a subsequent Tin(II) chloride reduction.

$^1$H NMR (400 MHz, CHLOROFORM-D) δ ppm 1.31 (t, J=6.82 Hz, 2 H) 1.71 (m, 2 H) 1.81 (dd, J=13.14, 1.77 Hz, 2 H) 2.70 (m, 2 H) 3.06 (d, J=6.82 Hz, 2 H) 3.79 (m, 2 H) 3.84 (s, 3 H) 3.87 (s, 3 H) 4.25 (s, 2 H) 4.92 (s, 2 H) 6.64 (m, 1 H) 6.77 (m, 2 H) 6.84 (m, 1 H) 6.94 (m, 1 H) 7.07 (m, 1 H) 7.15 (td, J=7.71, 1.52 Hz, 1 H) 7.22 (t, J=7.96 Hz, 1 H).

The fourth step of Scheme 17: 5-(3-{[1-(2-Amino-phenylmethanesulfonyl)-piperidin-4-ylmethyl]-amino}-phenyl)-4-bromo-3-carboxymethoxy-thiophene-2-carboxylic acid was hydrolyzed according to the procedure in the fourth step of Scheme 17 of Example 173 to give 5-(3-{[1-(2-amino-phenylmethanesulfonyl)-piperidin-4-ylmethyl]-amino}-phenyl)-4-bromo-3-carboxymethoxy-thiophene-2-carboxylic acid in 66% yield as a yellow solid.

$^1$H NMR (400 MHz, DMSO-D6) δ ppm 1.3 (m, 1 H) 1.7 (m, 2 H) 1.8 (m, 2 H) 2.7 (m, 2 H) 2.9 (m, 2 H) 3.6 (m, 2 H)

4.3 (s, 2 H) 4.8 (s, 2 H) 6.6 (m, 1 H) 6.7 (m, 2 H) 6.8 (dd, J=7.2, 1.9 Hz, 1 H) 6.8 (d, J=2.5 Hz, 1 H) 7.0 (m, 1 H) 7.1 (dd, J=7.5, 1.6 Hz, 1 H) 7.2 (m, 1 H).

EXAMPLE 178

4-{[3-(3-Bromo-5-carboxy-4-carboxymethoxy-thiophen-2-yl)-phenylamino]-methyl}-piperidine-1-carboxylic acid methyl ester The first step of Scheme 18: To 1 mL $CH_2Cl_2$ was added 4-bromo-3-tert-butoxycarbonylmethoxy-5-[3-(piperidin-4-ylamino)-phenyl]-thiophene-2-carboxylic acid methyl ester hydrochloride (57 mg, 0.1 mmole) and diisopropylethylamine (45 µL, 0.25 mmole) followed by methyl chloroformate (9 µL, 0.11 mmole) and the reaction mixture was allowed to stir at room temperature overnight. The reaction mixture was diluted with $CH_2Cl_2$ and washed with dilute aqueous HCl, saturated sodium bicarbonate solution, and dried over $MgSO_4$. Filtration and evaporation gave the crude product, which was purified by chromatography on silica gel using a gradient of Hexane/EtOAc (0 to 40%) as eluent. Pure fractions were combined and evaporated to give 12 mg (20%) 4-{[3-(3-bromo-4-tert-butoxycarbonylmethoxy-5-methoxymethyl-thiophen-2-yl)-phenylamino]-methyl}-piperidine-1-carboxylic acid methyl ester as a pale yellow oil.

$^1$H NMR (400 MHz, CHLOROFORM-D) δ ppm 1.22 (m, 3 H) 1.51 (s, 9 H) 1.80 (m, 2 H) 2.76 (m, 2 H) 3.06 (d, J=6.32 Hz, 2 H) 3.69 (s, 3 H) 3.87 (s, 3 H) 4.82 (s, 2 H) 6.65 (m, 1 H) 6.86 (m, 1 H) 6.95 (m, 1 H) 7.23 (t, J=7.96 Hz, 1 H).

The second step of Scheme 18: 4-{[3-(3-Bromo-4-tert-butoxycarbonylmethoxy-5-methoxymethyl-thiophen-2-yl)-phenylamino]-methyl}-piperidine-1-carboxylic acid methyl ester (12 mg, 2.0×10$^{-5}$ mmole) was dissolved in 1.5 µL of a 2:1 mixture of THF:$H_2O$. $LiOH.H_2O$ (4 mg, 0.1 mmole) was added and the reaction mixture was allowed to stir at room temperature overnight. The solvent was evaporated and re-dissolved in 2-3 µL water. The mixture was acidified dropwise with 1N HCl while stirring. A solid emerged that was filtered, washed with water, and vacuum-oven dried to give 9 mg (85%) of 4-{[3-(3-bromo-5-carboxy-4-carboxymethoxy-thiophen-2-yl)-phenylamino]-methyl}-piperidine-1-carboxylic acid methyl ester as a pale yellow solid.

$^1$H NMR (400 MHz, DMSO-D6) δ ppm 1.08 (m, 2 H) 1.76 (m, 2 H) 2.77 (m, 1 H) 2.93 (t, J=5.81 Hz, 2 H) 3.58 (s, 3 H) 3.98 (d, J=10.11 Hz, 1 H) 4.85 (s, 2 H) 6.68 (m, 1 H) 6.77 (m, 1 H) 6.82 (d, J=2.02 Hz, 1 H) 7.18 (t, J=7.96 Hz, 1 H).

ESI-MS: m/e=483 [M−CO$_2$]$^+$.

EXAMPLE 179

4-Bromo-3-carboxymethoxy-5-{3-[(1-phenylcarbamoyl-piperidin-4-ylmethyl)-amino]-phenyl}-thiophene-2-carboxylic acid The first step of Scheme 18: To a 1 mL DMF solution was added 4-bromo-3-tert-butoxycarbonylmethoxy-5-[3-(piperidin-4-ylamino)-phenyl]-thiophene-2-carboxylic acid methyl ester hydrochloride (57 mg, 0.1 mmole) and diisopropylethylamine (27 µL, 0.15 mmole) followed by phenyl isocyanate (12 µL, 0.11 mmole) and the reaction mixture was allowed to stir 90 minutes at room temperature. The solution was diluted with water and extracted with EtOAc, washed with dilute aqueous HCl, saturated sodium bicarbonate solution, brine and dried over $MgSO_4$. Filtration and evaporation of the solvent gave the crude product which was purified by chromatography on silica gel using a gradient of Hexane/EtOAc (5 to 50%) as eluent. Pure fractions were combined and evaporated to give 41 mg (62%) 4-bromo-3-tert-butoxycarbonylmethoxy-5-{3-[(1-phenylcarbamoyl-piperidin-4-ylmethyl)-amino]-phenyl}-thiophene-2-carboxylic acid methyl ester as a pale yellow oil.

$^1$H NMR (400 MHz, CHLOROFORM-D) δ ppm 1.31 (m, 2 H) 1.51 (s, 9 H) 1.88 (m, 3 H) 2.89 (m, 2 H) 3.10 (d, J=6.06 Hz, 2 H) 3.87 (s, 3 H) 4.12 (m, 2 H) 4.82 (s, 2 H) 6.38 (s, 1 H) 6.66 (m, 1 H) 6.87 (m, 1 H) 6.96 (dd, J=6.69, 1.64 Hz, 1 H) 7.03 (m, 1 H) 7.24 (m, 1 H) 7.29 (m, 2 H) 7.35 (m, 2 H).

The second step of Scheme 18: 4-Bromo-3-tert-butoxycarbonylmethoxy-5-{3-[(1-phenylcarbamoyl-piperidin-4-ylmethyl)-amino]-phenyl}-thiophene-2-carboxylic acid methyl ester was hydrolyzed according to the procedure in the second step of Scheme 18 of Example 178 to give 4-bromo-3-carboxymethoxy-5-{3-[(1-phenylcarbamoyl-piperidin-4-ylmethyl)-amino]-phenyl}-thiophene-2-carboxylic acid in 90% yield as a pale yellow solid.

$^1$H NMR (400 MHz, DMSO-D6) δ ppm 1.16 (m, 2 H) 1.79 (m, 3 H) 2.77 (m, 2 H) 2.97 (d, J=5.81 Hz, 2 H) 4.15 (d, J=12.63 Hz, 2 H) 4.87 (s, 2 H) 6.70 (dd, J=8.72, 1.89 Hz, 1 H) 6.78 (d, J=7.58 Hz, 1 H) 6.84 (t, J=1.77 Hz, 1 H) 6.91 (t, J=7.33 Hz, 1 H) 7.20 (m, 3 H) 7.45 (dd, J=8.72, 1.14 Hz, 2 H) 8.44 (s, 1 H).

ESI-MS: m/e=588 [M+H]$^+$.

EXAMPLE 180

5-{3-[(1-Benzylcarbamoyl-piperidin-4-ylmethyl)-amino]-phenyl}-4-bromo-3-carboxymethoxy-thiophene-2-carboxylic acid The first step of Scheme 18: 5-{3-[(1-Benzylcarbamoyl-piperidin-4-ylmethyl)-amino]-phenyl}4-bromo-3-tert-butoxycarbonylmethoxy-thiophene-2-carboxylic acid methyl ester was obtained in 58% yield as a yellow oil, following the procedure in the first step of Scheme 18 of Example 179.

$^1$H NMR (400 MHz, CHLOROFORM-D) δ ppm 1.24 (m, 2 H) 1.50 (s, 9 H) 1.81 (m, 3 H) 2.79 (td, J=12.88, 2.27 Hz, 2 H) 3.07 (d, J=6.06 Hz, 2 H) 3.87 (s, 3 H) 4.00 (d, J=13.39 Hz, 2 H) 4.43 (d, J=5.56 Hz, 2 H) 4.76 (t, J=5.43 Hz, 1 H) 4.81 (s, 2 H) 6.65 (m, 1 H) 6.85 (m, 1 H) 6.94 (m, 1 H) 7.23 (m, 1 H) 7.30 (m, 5 H).

The second step of Scheme 18: 5-{3-[(1-Benzylcarbamoyl-piperidin-4-ylmethyl)-amino]-phenyl}4-bromo-3-tert-butoxycarbonylmethoxy-thiophene-2-carboxylic acid methyl ester was hydrolyzed according to the procedure in the second step of Scheme 18 of Example 178 to give 5-{3-[(1-benzylcarbamoyl-piperidin-4-ylmethyl)-amino]-phenyl}-4-bromo-3-carboxymethoxy-thiophene-2-carboxylic acid in 92% yield as a pale yellow solid.

$^1$H NMR (400 MHz, DMSO-D6) δ ppm 1.07 (m, 2 H) 1.73 (m, 3 H) 2.66 (m, 2 H) 2.94 (m, 2 H) 4.01 (m, 2 H) 4.23 (d, J=5.05 Hz, 2 H) 4.87 (s, 2 H) 6.68 (m, 1 H) 6.77 (d, J=6.82 Hz, 1 H) 6.83 (s, 1 H) 7.01 (t, J=6.44 Hz, 1 H) 7.24 (m, 6 H).

ESI-MS: m/e=602 [M+H]$^+$.

EXAMPLE 181

4-Bromo-3-carboxymethoxy-5-{3-[(1-cyclohexylcarbamoyl-piperidin-4-ylmethyl)-amino]-phenyl}-thiophene-2-carboxylic acid The first step of Scheme 18: (4-Bromo-5-{3-[(1-cyclohexylcarbamoyl-piperidin-4-ylmethyl)-amino]-phenyl}-2-methoxymethyl-thiophen-3-yloxy)-acetic acid tert-butyl ester was obtained in 69% yield as a pale yellow foam, following the procedure in the first step of Scheme 18 of Example 179.

$^1$H NMR (400 MHz, CHLOROFORM-D) δ ppm 1.36 (m, 3 H) 1.51 (m, 9 H) 1.61 (m, 2 H) 1.69 (m, 4 H) 1.80 (d, J=3.03 Hz, 3 H) 1.94 (m, 2 H) 2.75 (m, 2 H) 3.06 (d, J=6.32 Hz, 2 H) 3.64 (m, 1 H) 3.87 (s, 3 H) 3.96 (m, 3 H) 4.29 (m, 1 H) 4.82 (s, 2 H) 6.65 (m, 1 H) 6.86 (m, 1 H) 6.94 (dd, J=7.96, 1.39 Hz, 1 H) 7.23 (m, 1 H).

The second step of Scheme 18: (4-Bromo-5-{3-[(1-cyclohexylcarbamoyl-piperidin-4-ylmethyl)-amino]-phenyl}-2-methoxymethyl-thiophen-3-yloxy)-acetic acid tert-butyl ester was hydrolyzed according to the procedure in the second step of Scheme 18 of Example 178 to give 4-bromo-3-carboxymethoxy-5-{3-[(1-cyclohexylcarbamoyl-piperidin-4-ylmethyl)-amino)-phenyl}-thiophene-2-carboxylic acid in 89% yield as a pale yellow solid.

$^1$H NMR (400 MHz, DMSO-D6) δ ppm 1.04 (m, 3 H) 1.20 (m, 4 H) 1.56 (m, 1 H) 1.70 (m, 7 H) 2.58 (m, 2 H) 2.93 (m, 2 H) 3.98 (m, 2 H) 4.87 (s, 2 H) 6.05 (d, J=7.58 Hz, 1 H) 6.68 (dd, J=7.83, 1.77 Hz, 1 H) 6.77 (d, J=7.83 Hz, 1 H) 6.82 (t, J=1.89 Hz, 1 H) 7.18 (m, 1 H) 7.18 (m, 1 H).

ESI-MS: m/e=594 [M+H]$^+$.

EXAMPLE 182

4-Bromo-3-carboxymethoxy-5-(3-{[1-(4-methoxy-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(4-methoxy-phenylcarbamoyl)-piperidin-4-ylmethyl]-amino}-phenyl)-thiophene-2-carboxylic acid methyl ester was obtained in 62% yield as a yellow oil, following the procedure in the first step of Scheme 18 of Example 179.

$^1$H NMR (400 MHz, CHLOROFORM-D) δ ppm 1.28 (m, 2 H) 1.51 (s, 9 H) 1.87 (m, 3 H) 2.87 (td, J=12.82, 2.15 Hz, 2 H) 3.09 (d, J=5.81 Hz, 2 H) 3.78 (s, 3 H) 3.87 (s, 3 H) 3.95 (s, 1 H) 4.11 (m, 2 H) 4.82 (s, 2 H) 6.30 (s, 1 H) 6.66 (dd, J=7.83, 2.02 Hz, 1 H) 6.83 (d, J=8.84 Hz, 2 H) 6.87 (m, 1 H) 6.95 (d, J=7.58 Hz, 1 H) 7.24 (m, 3 H).

The second step of Scheme 18: 4-Bromo-3-tert-butoxycarbonylmethoxy-5-(3-{[1-(4-methoxy-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(4-methoxy-phenylcarbamoyl)-piperidin-4-ylmethyl]-amino}-phenyl)-thiophene-2-carboxylic acid in 82% yield as a pale yellow solid.

$^1$H NMR (400 MHz, DMSO-D6) δ ppm 1.13 (m, 2 H) 1.79 (m, 3 H) 2.75 (m, 2 H) 2.96 (m, 2 H) 3.70 (s, 3 H) 4.12 (m, 2 H) 4.88 (s, 2 H) 6.69 (m, 1 H) 6.80 (m, 4 H) 7.18 (d, J=7.58 Hz, 1 H) 7.33 (d, J=9.09 Hz, 2 H) 8.28 (s, 1 H).

ESI-MS: m/e=618 [M+H]$^+$.

EXAMPLE 183

4-Bromo-3-carboxymethoxy-5-(3-{[1-(4-cyano-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(4-cyano-phenylcarbamoyl)-piperidin-4-ylmethyl]-amino}-phenyl)-thiophene-2-carboxylic acid methyl ester was obtained in 50% yield as a yellow oil, following the procedure in the first step of Scheme 18 of Example 179.

$^1$H NMR (400 MHz, CHLOROFORM-D) δ ppm 1.29 (m, 2 H) 1.51 (s, 9 H) 1.90 (m, 3 H) 2.89 (m, 2 H) 3.10 (d, J=5.31 Hz, 2 H) 3.87 (s, 3 H) 3.96 (s, 1 H) 4.15 (d, J=12.88 Hz, 2 H) 4.82 (s, 2 H) 6.66 (dd, J=7.71, 1.89 Hz, 1 H) 6.85 (s, 1 H) 6.86 (m, 1 H) 6.95 (d, J=8.34 Hz, 1 H) 7.24 (t, J=7.83 Hz, 1 H) 7.53 (m, 4 H).

The second step of Scheme 18: 4-Bromo-3-tert-butoxycarbonylmethoxy-5-(3-{[1-(4-cyano-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(4-cyano-phenylcarbamoyl)-piperidin-4-ylmethyl]-amino}-phenyl)-thiophene-2-carboxylic acid in 82% yield as a pale yellow solid.

$^1$H NMR (400 MHz, DMSO-D6) δ ppm 1.15 (m, 2 H) 1.80 (m, 3 H) 2.81 (m, 2 H) 2.98 (m, 2 H) 4.15 (d, J=13.39 Hz, 2 H) 4.87 (s, 2 H) 6.70 (dd, J=7.96, 1.89 Hz, 1 H) 6.78 (d, J=7.58 Hz, 1 H) 6.84 (t, J=1.89 Hz, 1 H) 7.19 (t, J=7.96 Hz, 1 H) 7.66 (s, 4 H) 8.95 (s, 1 H).

ESI-MS: m/e=611 [M−H]$^−$.

EXAMPLE 184

4-Bromo-3-carboxymethoxy-5-{3-[(1-p-tolylcarbamoyl-piperidin-4-ylmethyl)-amino]-phenyl}-thiophene-2-carboxylic acid The first step of Scheme 18: 4-Bromo-3-tert-butoxycarbonylmethoxy-5-{3-[(1-p-tolylcarbamoyl-piperidin-4-ylmethyl)-amino]-phenyl}-thiophene-2-carboxylic acid methyl ester was obtained in 68% yield as a yellow oil, following the procedure in the first step of Scheme 18 of Example 179.

$^1$H NMR (400 MHz, CHLOROFORM-D) δ ppm 1.27 (m, 2 H) 1.50 (s, 9 H) 1.86 (m, 3 H) 2.29 (s, 3 H) 2.87 (m, 2 H) 3.08 (d, J=6.06 Hz, 2 H) 3.87 (s, 3 H) 3.97 (s, 1 H) 4.11 (m, 2 H) 4.82 (s, 2 H) 6.37 (s, 1 H) 6.65 (m, 1 H) 6.86 (m, 1 H) 6.95 (m, 1 H) 7.08 (d, J=7.83 Hz, 2 H) 7.23 (m, 3 H).

The second step of Scheme 18: 4-Bromo-3-tert-butoxycarbonylmethoxy-5-{3-[(1-p-tolylcarbamoyl-piperidin-4-ylmethyl)-amino]-phenyl}-thiophene-2-carboxylic acid methyl ester was hydrolyzed according to the procedure in the second step of Scheme 18 of Example 178 to give 4-bromo-3-carboxymethoxy-5-{3-[(1-p-tolylcarbamoyl-piperidin-4-ylmethyl)-amino]-phenyl}-thiophene-2-carboxylic acid in 90% yield as a pale yellow solid.

$^1$H NMR (400 MHz, DMSO-D6) δ ppm 1.14 (m, 2 H) 1.79 (m, 3 H) 2.22 (s, 3 H) 2.75 (m, 2 H) 2.97 (m, 2 H) 4.13 (d, J=12.63 Hz, 2 H) 4.87 (s, 2 H) 6.69 (dd, J=8.72, 1.64 Hz, 1 H) 6.77 (d, J=6.82 Hz, 1 H) 6.84 (m, 1 H) 7.02 (d, J=8.08 Hz, 2 H) 7.19 (t, J=7.83 Hz, 1 H) 7.32 (d, J=8.59 Hz, 2 H) 8.34 (s, 1 H).

ESI-MS: m/e=602 [M+H]$^+$.

EXAMPLE 185

4-Bromo-3-carboxymethoxy-5-(3-{[1-(3-methoxy-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(3-methoxy-phenylcarbamoyl)-piperidin-4-ylmethyl]-amino}-phenyl)-thiophene-2-carboxylic acid methyl ester was obtained in 70% yield as a yellow oil, following the procedure in the first step of Scheme 18 of Example 179.

$^1$H NMR (400 MHz, CHLOROFORM-D) δ ppm 1.28 (m, 2 H) 1.50 (s, 9 H) 1.86 (m, 3 H) 2.87 (m, 2 H) 3.08 (d, J=6.32 Hz, 2 H) 3.78 (s, 3 H) 3.87 (s, 3 H) 4.12 (m, 2 H) 4.82 (s, 2 H) 6.56 (s, 1 H) 6.58 (ddd, J=8.21, 2.53, 0.88 Hz, 1 H) 6.65 (dd, J=7.83, 2.02 Hz, 1 H) 6.84 (m, 1 H) 6.86 (m, 1 H) 6.95 (m, 1 H) 7.15 (m, 2 H) 7.23 (t, J=7.96 Hz, 1 H).

The second step of Scheme 18: 4-Bromo-3-tert-butoxycarbonylmethoxy-5-(3-{[1-(3-methoxy-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(3-methoxy-phenylcarbamoyl)-piperidin-4-ylmethyl]-amino}-phenyl)-thiophene-2-carboxylic acid in 91% yield as a pale yellow solid.

$^1$H NMR (400 MHz, DMSO-D6) δ ppm 1.14 (m, 2 H) 1.81 (m, 3 H) 2.76 (m, 2 H) 2.97 (d, J=5.31 Hz, 2 H) 3.70 (s, 3 H) 4.14 (d, J=12.63 Hz, 2 H) 4.87 (s, 2 H) 6.49 (ddd, J=7.89, 2.46, 1.01 Hz, 1 H) 6.70 (dd, J=7.96, 1.64 Hz, 1 H) 6.77 (d, J=8.34 Hz, 1 H) 6.84 (t, J=1.89 Hz, 1 H) 7.04 (m, 1 H) 7.10 (t, J=7.96 Hz, 1 H) 7.15 (t, J=2.15 Hz, 1 H) 7.19 (t, J=7.83 Hz, 1 H) 8.42 (s, 1 H).

ESI-MS: m/e=618 [M+H]$^+$.

EXAMPLE 186

4-Bromo-3-carboxymethoxy-5-(3-{[1-(2-methoxy-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(2-methoxy-phenylcarbamoyl)-piperidin-4-ylmethyl]-amino}-phenyl)-thiophene-2-carboxylic acid methyl ester was obtained in 56% yield as a yellow oil, following the procedure in the first step of Scheme 18 of Example 179.

$^1$H NMR (400 MHz, CHLOROFORM-D) δ ppm 1.33 (m, 2 H) 1.51 (s, 9 H) 1.87 (dd, J=11.37, 8.59 Hz, 3 H) 2.90 (m, 2 H) 3.10 (d, J=6.32 Hz, 2 H) 3.87 (s, 3 H) 3.88 (s, 3 H) 4.14 (d, J=13.14 Hz, 2 H) 4.82 (s, 2 H) 6.66 (m, 1 H) 6.86 (m, 2 H) 6.94 (m, 3 H) 7.13 (s, 1 H) 7.24 (t, J=7.96 Hz, 1 H) 8.14 (m, 1 H).

The second step of Scheme 18: 4-Bromo-3-tert-butoxycarbonylmethoxy-5-(3-{[1-(2-methoxy-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(2-methoxy-phenylcarbamoyl)-piperidin-4-ylmethyl]-amino}-phenyl)-thiophene-2-carboxylic acid as a pale yellow solid.

$^1$H NMR (400 MHz, DMSO-D6) δ ppm 1.16 (m, 2 H) 1.80 (m, 3 H) 2.81 (m, 2 H) 2.97 (d, J=5.81 Hz, 2 H) 3.80 (s, 3 H) 4.07 (d, J=13.39 Hz, 2 H) 4.87 (s, 2 H) 6.70 (m, 1 H) 6.77 (d, J=7.83 Hz, 1 H) 6.85 (m, 2 H) 6.98 (m, 2 H) 7.19 (t, J=7.83 Hz, 1 H) 7.57 (s, 1 H) 7.66 (d, J=7.58 Hz, 1 H).

ESI-MS: m/e=618 [M+H]$^+$.

EXAMPLE 187

4-Bromo-3-carboxymethoxy-5-(3-{[1-(3-chloro-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(3-chloro-phenylcarbamoyl)-piperidin-4-ylmethyl]-amino}-phenyl)-thiophene-2-carboxylic acid methyl ester was obtained in 63% yield as a yellow oil, following the procedure in the first step of Scheme 18 of Example 179.

$^1$H NMR (400 MHz, CHLOROFORM-D) δ ppm 1.28 (m, 2 H) 1.51 (s, 9 H) 1.88 (m, 3 H) 2.88 (m, 2 H) 3.09 (d, J=6.06 Hz, 2 H) 3.87 (s, 3 H) 4.12 (m, 2 H) 4.82 (s, 2 H) 6.50 (s, 1 H) 6.66 (m, 1 H) 6.86 (m, 1 H) 6.95 (dd, J=6.69, 1.64 Hz, 1 H) 6.99 (m, 1 H) 7.21 (m, 3 H) 7.47 (t, J=1.77 Hz, 1 H).

The second step of Scheme 18: 4-Bromo-3-tert-butoxycarbonylmethoxy-5-(3-{[1-(3-chloro-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(3-chloro-phenylcarbamoyl)-piperidin-4-ylmethyl]-amino}-phenyl)-thiophene-2-carboxylic acid in 82% yield as a pale yellow solid.

$^1$H NMR (400 MHz, DMSO-D6) δ ppm 1.15 (m, 2 H) 1.80 (m, 3 H) 2.78 (m, 2 H) 2.97 (d, J=6.06 Hz, 2 H) 4.14 (d, J=13.39 Hz, 2 H) 4.88 (s, 2 H) 6.70 (dd, J=8.21, 1.89 Hz, 1 H) 6.78 (d, J=8.08 Hz, 1 H) 6.84 (s, 1 H) 6.95 (dd, J=7.96, 2.15 Hz, 1 H) 7.21 (m, 2 H) 7.39 (dd, J=8.59, 1.52 Hz, 1 H) 7.65 (m, 1 H) 8.64 (s, 1 H).

ESI-MS: m/e=622 [M+H]$^+$.

EXAMPLE 188

4-Bromo-3-carboxymethoxy-5-(3-{[1-(2-chloro-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(2-chloro-phenylcarbamoyl)-piperidin-4-ylmethyl]-amino}-phenyl)-thiophene-2-carboxylic acid methyl ester was obtained in 56% yield as a yellow oil, following the procedure in the first step of Scheme 18 of Example 179.

$^1$H NMR (400 MHz, CHLOROFORM-D) δ ppm 1.33 (dd, J=12.25, 2.91 Hz, 2 H) 1.51 (s, 9 H) 1.91 (m, 3 H) 2.94 (m, 2 H) 3.10 (d, J=6.06 Hz, 2 H) 3.87 (s, 3 H) 4.15 (m, 2 H) 4.82 (s, 2 H) 6.66 (m, 1 H) 6.87 (m, 1 H) 6.94 (m, 2 H) 7.04 (s, 1 H) 7.23 (m, 2 H) 7.33 (dd, J=8.08, 1.52 Hz, 1 H) 8.18 (dd, J=8.34, 1.52 Hz, 1 H).

The second step of Scheme 18: 4-Bromo-3-tert-butoxycarbonylmethoxy-5-(3-{[1-(2-chloro-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(2-chloro-phenylcarbamoyl)-piperidin-4-ylmethyl]-amino}-phenyl)-thiophene-2-carboxylic acid in 88% yield as a pale yellow solid.

$^1$H NMR (400 MHz, DMSO-D6) δ ppm 1.16 (m, 2 H) 1.79 (m, 3 H) 2.82 (m, 2 H) 2.97 (d, J=6.82 Hz, 2 H) 4.11 (d, J=13.39 Hz, 2 H) 4.87 (s, 2 H) 6.70 (dd, J=8.21, 2.15 Hz, 1 H) 6.78 (d, J=7.58 Hz, 1 H) 6.84 (t, J=1.77 Hz, 1 H) 7.12 (td, J=7.64, 1.64 Hz, 1 H) 7.19 (t, J=7.83 Hz, 1 H) 7.27 (td, J=7.71, 1.52 Hz, 1 H) 7.43 (dd, J=7.96, 1.39 Hz, 1 H) 7.49 (dd, J=7.96, 1.39 Hz, 1 H) 8.10 (s, 1 H).

ESI-MS: m/e=622 [M+H]$^+$.

EXAMPLE 189

4-Bromo-3-carboxymethoxy-5-{3-[(1-m-tolylcarbamoyl-piperidin-4-ylmethyl)-amino]-phenyl}-thiophene-2-carboxylic acid The first step of Scheme 18: 4-Bromo-3-tert-butoxycarbonylmethoxy-5-{3-[(1-m-tolylcarbamoyl-piperidin-4-ylmethyl)-amino]-phenyl}-thiophene-2-carboxylic acid methyl ester was obtained in 51% yield as a yellow oil, following the procedure in the first step of Scheme 18 of Example 179.

$^1$H NMR (400 MHz, CHLOROFORM-D) δ ppm 1.29 (m, 2 H) 1.51 (s, 9 H) 1.87 (m, 3 H) 2.32 (s, 3 H) 2.88 (td, J=12.82, 2.15 Hz, 2 H) 3.09 (d, J=5.81 Hz, 2 H) 3.87 (s, 3 H) 3.95 (s, 1 H) 4.11 (m, 2 H) 4.82 (s, 2 H) 6.37 (s, 1 H) 6.66 (m, 1 H) 6.84 (d, J=7.33 Hz, 1 H) 6.87 (m, 1 H) 6.95 (dd, J=7.96, 1.39 Hz, 1 H) 7.11 (d, J=8.34 Hz, 1 H) 7.16 (m, 1 H) 7.23 (t, J=7.83 Hz, 2 H).

The second step of Scheme 18: 4-Bromo-3-tert-butoxycarbonylmethoxy-5-{3-[(1-m-tolylcarbamoyl-piperidin-4-ylmethyl)-amino]-phenyl}-thiophene-2-carboxylic acid methyl ester was hydrolyzed according to the procedure in the second step of Scheme 18 of Example 178 to give 4-bromo-3-carboxymethoxy-5-{3-[(1-m-tolylcarbamoyl-piperidin-4-ylmethyl)-amino]-phenyl}-thiophene-2-carboxylic acid in 94% yield as a pale yellow solid.

$^1$H NMR (400 MHz, DMSO-D6) δ ppm 1.13 (m, 2 H) 1.79 (m, 3 H) 2.24 (s, 3 H) 2.75 (m, 2 H) 2.97 (m, 2 H) 4.14 (dd, J=11.87, 4.04 Hz, 2 H) 4.87 (s, 2 H) 6.71 (m, 2 H) 6.77 (m, 1 H) 6.84 (s, 1 H) 7.09 (t, J=7.71 Hz, 1 H) 7.19 (t, J=7.83 Hz, 1 H) 7.24 (m, 1 H) 7.29 (s, 1 H) 8.36 (s, 1 H).

ESI-MS: m/e=602 [M+H]$^+$.

EXAMPLE 190

4-Bromo-3-carboxymethoxy-5-{3-[(1-o-tolylcarbamoyl-piperidin-4-ylmethyl)-amino]-phenyl}-thiophene-2-carboxylic acid The first step of Scheme 18: 4-Bromo-3-tert-butoxycarbonylmethoxy-5-{3-[(1-o-tolylcarbamoyl-piperidin-4-ylmethyl)-amino]-phenyl}-thiophene-2-carboxylic acid methyl ester was obtained in 41% yield as a yellow oil, following the procedure in the first step of Scheme 18 of Example 179.

$^1$H NMR (400 MHz, CHLOROFORM-D) δ ppm 1.33 (m, 2 H) 1.51 (s, 9 H) 1.88 (m, 3 H) 2.25 (s, 3 H) 2.91 (td, J=12.88, 2.02 Hz, 2 H) 3.10 (d, J=5.81 Hz, 2 H) 3.87 (s, 3 H) 3.95 (s, 1 H) 4.11 (d, J=13.14 Hz, 2 H) 4.82 (s, 2 H) 6.15 (s, 1 H) 6.66 (m, 1 H) 6.87 (m, 1 H) 6.96 (m, 1 H) 7.01 (td, J=7.45, 1.26 Hz, 1 H) 7.18 (m, 2 H) 7.24 (t, J=7.96 Hz, 1 H) 7.62 (d, J=8.08 Hz, 1 H).

The second step of Scheme 18: 4-Bromo-3-tert-butoxycarbonylmethoxy-5-{3-[(1-o-tolylcarbamoyl-piperidin-4-ylmethyl)-amino]-phenyl}-thiophene-2-carboxylic acid methyl ester was hydrolyzed according to the procedure in the second step of Scheme 18 of Example 178 to give 4-bromo-3-carboxymethoxy-5-{3-[(1-o-tolylcarbamoyl-piperidin-4-ylmethyl)-amino]-phenyl}-thiophene-2-carboxylic acid in 88% yield as a pale yellow solid.

$^1$H NMR (400 MHz, DMSO-D6) δ ppm 1.17 (m, 2 H) 1.78 (m, 3 H) 2.15 (s, 3 H) 2.78 (m, 2 H) 2.97 (d, J=6.06 Hz, 2 H) 4.11 (d, J=13.39 Hz, 2 H) 4.88 (s, 2 H) 6.70 (dd, J=8.21, 1.64 Hz, 1 H) 6.78 (d, J=8.34 Hz, 1 H) 6.84 (t, J=1.89 Hz, 1 H) 7.02 (td, J=7.26, 1.64 Hz, 1 H) 7.10 (m, 1 H) 7.18 (m, 3 H) 7.97 (s, 1 H).

ESI-MS: m/e=602 [M+H]$^+$.

EXAMPLE 191

4-Bromo-3-carboxymethoxy-5-(3-{[1-(2,6-dimethyl-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(2,6-dimethyl-phenylcarbamoyl)-piperidin-4-ylmethyl]-amino}-phenyl)-thiophene-2-carboxylic acid methyl ester was obtained in 69% yield as a pale yellow oil, following the procedure in the first step of Scheme 18 of Example 179.

$^1$H NMR (400 MHz, CHLOROFORM-D) δ ppm 1.30 (m, 3 H) 1.51 (s, 9 H) 1.86 (d, J=9.60 Hz, 2 H) 2.24 (s, 6 H) 2.90 (m, 2 H) 3.10 (d, J=6.32 Hz, 2 H) 3.87 (s, 3 H) 4.10 (m, 2 H) 4.82 (s, 2 H) 5.82 (s, 1 H) 6.66 (m, 1 H) 6.87 (m, 1 H) 6.96 (d, J=8.34 Hz, 1 H) 7.24 (m, 1 H).

The second step of Scheme 18: 4-Bromo-3-tert-butoxycarbonylmethoxy-5-(3-{[1-(2,6-dimethyl-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(2,6-dimethyl-phenylcarbamoyl)-piperidin-4-ylmethyl]-amino}-phenyl)-thiophene-2-carboxylic acid in 82% yield as a pale yellow solid.

$^1$H NMR (400 MHz, DMSO-D6) δ ppm 1.14 (m, 2 H) 1.80 (m, 3 H) 2.13 (s, 6 H) 2.79 (m, 2 H) 2.97 (d, J=6.06 Hz, 2 H) 4.12 (d, J=12.63 Hz, 2 H) 4.88 (s, 2 H) 6.70 (dd, J=8.34, 1.52 Hz, 1 H) 6.78 (d, J=7.58 Hz, 1 H) 6.84 (t, J=1.89 Hz, 1 H) 7.03 (m, 3 H) 7.19 (t, J=7.96 Hz, 1 H).

ESI-MS: m/e=616 [M+H]$^+$.

EXAMPLE 192

4-Bromo-3-carboxymethoxy-5-(3-{[1-(2-trifluoromethyl-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(2-trifluoromethyl-phenylcarbamoyl)-piperidin-4-ylmethyl]-amino}-phenyl)-thiophene-2-carboxylic acid methyl ester was obtained in 70% yield as a pale yellow oil, following the procedure in the first step of Scheme 18 of Example 179.

$^1$H NMR (400 MHz, CHLOROFORM-D) δ ppm 1.32 (m, 2 H) 1.51 (s, 9 H) 1.91 (m, 3 H) 2.93 (m, 2 H) 3.10 (d, J=6.32 Hz, 2 H) 3.87 (s, 3 H) 4.10 (d, J=13.39 Hz, 2 H) 4.82 (s, 2 H) 6.66 (m, 1 H) 6.83 (s, 1 H) 6.87 (m, 1 H) 6.96 (m, 1 H) 7.13 (t, J=7.71 Hz, 1 H) 7.24 (t, J=7.96 Hz, 1 H) 7.51 (t, J=7.83 Hz, 1 H) 7.56 (d, J=7.83 Hz, 1 H) 8.09 (d, J=8.34 Hz, 1 H).

The second step of Scheme 18: 4-Bromo-3-tert-butoxycarbonylmethoxy-5-(3-{[1-(2-trifluoromethyl-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(2-trifluoromethyl-phenylcarbamoyl)-piperidin-4-ylmethyl]-amino}-phenyl)-thiophene-2-carboxylic acid in 83% yield as a pale yellow solid.

$^1$H NMR (400 MHz, DMSO-D6) δ ppm 1.13 (m, 2 H) 1.80 (m, 2 H) 2.79 (m, 2 H) 2.96 (m, 2 H) 4.08 (m, 2 H) 4.85 (s, 2 H) 6.70 (m, 1 H) 6.78 (d, J=7.83 Hz, 1 H) 6.84 (m, 1 H) 7.19 (t, J=7.96 Hz, 1 H) 7.40 (m, 2 H) 7.62 (t, J=7.83 Hz, 1 H) 7.67 (d, J=7.83 Hz, 1 H) 8.13 (s, 1 H).

ESI-MS: m/e=656 [M+H]$^+$.

EXAMPLE 193

4-Bromo-3-carboxymethoxy-5-(3-{[1-(methyl-phenyl-carbamoyl)-piperidin-4-ylmethyl]-amino}-phenyl)-thiophene-2-carboxylic acid The first step of Scheme 18: To a 1 mL CH$_2$Cl$_2$ solution of 4-bromo-3-tert-butoxycarbonylmethoxy-5-[3-(piperidin-4-ylamino)-phenyl]-thiophene-2-carboxylic acid methyl ester hydrochloride (57 mg, 0.1 mmole) and triethylamine (35 µL, 0.25 mole) was added N-methyl-N-phenylcarbamoyl chloride (19 mg, 0.11 mmole) and the resulting mixture was allowed to stir at room temperature overnight. The reaction had not reached completion as judged by LC/MS analysis so additional N-methyl-N-phenylcarbamoyl chloride (15 mg) was added and the reaction allowed to continue for another 2 hours. The reaction mixture was then diluted with CH$_2$Cl$_2$ and washed with dilute aqueous HCl, saturated bicarbonate solution, and dried (MgSO$_4$). Filtration and evaporation yielded the crude product which was then purified by flash chromatography (20 to 60% EtOAc/Hex as gradient). Pure fractions were combined and evaporated to give 38 mg (57%) 4-bromo-3-tert-butoxycarbonylmethoxy-5-(3-{[1-(methyl-phenyl-carbamoyl)-piperidin-4-ylmethyl]-amino}-phenyl)-thiophene-2-carboxylic acid methyl ester as a yellow oil.

$^1$H NMR (400 MHz, CHLOROFORM-D) δ ppm 1.03 (dd, J=11.87, 3.79 Hz, 2 H) 1.50 (s, 9 H) 1.64 (m, 4 H) 2.98 (d, J=6.57 Hz, 2 H) 3.21 (s, 3 H) 3.86 (m, 3 H) 3.87 (s, 3 H) 4.81 (s, 2 H) 6.60 (m, 1 H) 6.80 (m, 1 H) 6.92 (m, 1 H) 7.10 (m, 3 H) 7.20 (t, J=7.83 Hz, 1 H) 7.32 (m, 2 H).

The second step of Scheme 18: 4-Bromo-3-tert-butoxycarbonylmethoxy-5-(3-{[1-(methyl-phenyl-carbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(methyl-phenyl-carbamoyl)-piperidin-4-ylmethyl]-amino}-phenyl)-thiophene-2-carboxylic acid in 76% yield as a pale yellow solid.

$^1$H NMR (400 MHz, DMSO-D6) δ ppm 0.94 (m, 2 H) 1.62 (m, 3 H) 2.56 (t, J=11.49 Hz, 2 H) 2.86 (d, J=6.32 Hz, 2 H) 3.07 (s, 3 H) 3.72 (d, J=12.88 Hz, 2 H) 4.87 (s, 2 H) 6.64 (dd, J=7.96, 1.89 Hz, 1 H) 6.75 (d, J=7.58 Hz, 1 H) 6.78 (t, J=1.89 Hz, 1 H) 7.08 (m, 3 H) 7.16 (m, 1 H) 7.34 (m, 2 H).

ESI-MS: m/e=602 [M+H]$^+$.

EXAMPLE 194

4-Bromo-3-carboxymethoxy-5-(3-{[1-(2-methylsulfanyl-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(2-methylsulfanyl-phenylcarbamoyl)-piperidin-4-ylmethyl]-amino}-phenyl)-thiophene-2-carboxylic acid methyl ester was obtained in 64% yield as a yellow oil, following the procedure in the first step of Scheme 18 of Example 179.

$^1$H NMR (400 MHz, CHLOROFORM-D) δ ppm 1.32 (m, 2 H) 1.51 (s, 9 H) 1.91 (m, 3 H) 2.36 (s, 3 H) 2.94 (m, 2 H) 3.10 (d, J=6.06 Hz, 2 H) 3.87 (s, 3 H) 4.19 (d, J=13.39 Hz, 2 H) 4.82 (s, 2 H) 6.66 (m, 1 H) 6.87 (m, 1 H) 6.97 (m, 2 H) 7.24 (m, 1 H) 7.28 (dd, J=7.20, 1.39 Hz, 1 H) 7.46 (dd, J=7.58, 1.52 Hz, 1 H) 7.87 (s, 1 H) 8.16 (dd, J=8.34, 1.52 Hz, 1 H).

The second step of Scheme 18: 4-Bromo-3-tert-butoxycarbonylmethoxy-5-(3-{[1-(methyl-phenyl-carbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(2-methylsulfanyl-phenylcarbamoyl)-piperidin-4-ylmethyl]-amino}-phenyl)-thiophene-2-carboxylic acid in 73% yield as a pale yellow solid.

$^1$H NMR (400 MHz, DMSO-D6) δ ppm 1.19 (m, 2 H) 1.79 (d, J=10.86 Hz, 3 H) 2.37 (s, 3 H) 2.81 (t, J=12.00 Hz, 2 H) 2.97 (d, J=5.31 Hz, 2 H) 4.09 (d, J=12.38 Hz, 2 H) 4.88 (s, 2 H) 6.70 (d, J=6.82 Hz, 1 H) 6.78 (d, J=7.07 Hz, 1 H) 6.85 (s, 1 H) 7.14 (m, 2 H) 7.20 (t, J=7.96 Hz, 1 H) 7.31 (m, 1 H) 7.36 (m, 1 H) 8.02 (s, 1 H)

ESI-MS: m/e=634 [M+H]$^+$.

EXAMPLE 195

4-Bromo-3-carboxymethoxy-5-(3-{[1-(2,3-dimethyl-phenylcarbamoyl)-piperidin-4-ylmethyl]-amino}-phenyl)-thiophene-2-carboxylic acid The first step of Scheme 18: 4-Bromo-3-tert-butoxycarbonylmethoxy-5-(3-{[1-(2,3-dimethyl-phenylcarbamoyl)-piperidin-4-ylmethyl]-amino}-phenyl)-thiophene-2-carboxylic acid methyl ester was obtained in 54% yield as a yellow oil, following the procedure in the first step Scheme 18 of Example 179.

$^1$H NMR (400 MHz, CHLOROFORM-D) δ ppm 1.31 (m, 2 H) 1.51 (s, 9 H) 1.87 (m, 3 H) 2.14 (s, 3 H) 2.29 (s, 3 H) 2.90 (m, 2 H) 3.10 (d, J=6.06 Hz, 2 H) 3.87 (s, 3 H) 4.11 (m, 2 H) 4.82 (s, 2 H) 6.11 (s, 1 H) 6.66 (m, 1 H) 6.87 (m, 1 H) 6.95 (m, 2 H) 7.07 (t, J=7.71 Hz, 1 H) 7.24 (m, 1 H) 7.30 (d, J=8.34 Hz, 1 H).

The second step of Scheme 18: 4-Bromo-3-tert-butoxycarbonylmethoxy-5-(3-{[1-(2,3-dimethyl-phenylcarbamoyl)-piperidin-4-ylmethyl]-amino}-phenyl)-thiophene-2-carboxylic acid methyl ester was hydrolyzed according to the procedure in the second step of Scheme 18 of Example 178 to give 4-bromo-3-carboxymethoxy-5-(3-{[1-(2,3-dimethyl-phenylcarbamoyl)-piperidin-4-ylmethyl]-amino}-phenyl)-thiophene-2-carboxylic acid in 84% yield as a pale yellow solid.

$^1$H NMR (400 MHz, DMSO-D6) δ ppm 1.17 (m, 2 H) 1.79 (d, J=11.87 Hz, 3 H) 2.02 (s, 3 H) 2.23 (s, 3 H) 2.77 (t, J=13.01 Hz, 2 H) 2.98 (m, 2 H) 4.12 (d, J=12.38 Hz, 2 H) 4.87 (s, 2 H) 6.71 (m, 1 H) 6.78 (m, 1 H) 6.85 (m, 1 H) 6.99 (m, 3 H) 7.19 (m, 1 H) 8.01 (s, 1 H).

ESI-MS: m/e=616 [M+H]$^+$.

EXAMPLE 196

4-{[3-(3-Bromo-5-carboxy-4-carboxymethoxy-thiophen-2-yl)-phenylamino]-methyl}-piperidine-1-carboxylic acid tert-butyl ester The second step of Scheme 18: 4-{[3-(3-bromo-4-tert-butoxycarbonylmethoxy-5-methoxycarbonyl-thiophen-2-yl)-phenylamino]-methyl}-piperidine-1-carboxylic acid tert-butyl ester (obtained as an intermediate in the second step of Scheme 17 of Example 178) was hydrolyzed according to the procedure in the second step of Scheme 18 of Example 178 to give 4-f{[3-(3-bromo-5-carboxy-4-carboxymethoxy-thiophen-2-yl)-phenylamino]-methyl}-piperidine-1-carboxylic acid tert-butyl ester in 76% yield as a pale yellow solid.

$^1$H NMR (400 MHz, DMSO-D6) δ ppm 1.05 (m, 2 H) 1.39 (s, 9 H) 1.74 (m, 3 H) 2.94 (d, J=6.32 Hz, 2 H) 3.94 (dd, J=8.59, 5.31 Hz, 2 H) 4.87 (s, 2 H) 6.68 (dd, J=7.96, 2.15 Hz, 1 H) 6.77 (d, J=7.58 Hz, 1 H) 6.82 (m, 1 H) 7.18 (t, J=7.96 Hz, 1 H).

ESI-MS: m/e=469 [M−tert-butylcarbonyl]$^+$.

EXAMPLE 197

4-Bromo-3-carboxymethoxy-5-(3-cyclohexyl-methoxy-phenyl)-thiophene-2-carboxylic acid The first step of Scheme 19: To a solution of 4-bromo-3-ethoxycarbonylmethoxy-5-(3-hydroxy-phenyl)-thiophene-2-carboxylic acid methyl ester in DMF was added bromomethyl-cyclohexane (21 μL) and $K_2CO_3$ (27.6 mg). The resultant suspension was stirred at room temperature, then heated to 80° C. until the disappearance of the starting material as monitored by TLC. The reaction mixture was cooled to room temperature and diluted with EtOAc, and filtered through a pad of Celite, rinsed with EtOAc. The solvent was removed, the crude product was purified on CombiFlash column eluting with hexane/EtOAc to give the desire product, 4-bromo-3-ethoxycarboxymethoxyl-5-3-cyclohexyl-methoxy-phenyl)-thiophene-2-carboxylic acid methyl ester (44 mg, 85%) as a colorless oil.

$^1$H NMR (400 MHz, CHLOROFORM-D) δ ppm 1.2 (m, 8 H) 1.8 (m, 6 H) 3.8 (d, J=6.3 Hz, 2 H) 3.9 (s, 3 H) 4.3 (q, J=7.1 Hz, 2 H) 4.9 (s, 2 H) 7.0 (m, 1 H) 7.2 (m, 2 H) 7.3 (m, 1 H).

The second step of Scheme 19: 4-bromo-3-carbonylmethoxy-5-(3-hydroxy-phenyl)-thiophene-2-carboxylic acid (32 mg, 83%) was prepared according to the procedure in the second step of Scheme 1 of Example 1, using 4-bromo-3-ethoxycarbonylmethoxy-5-(3-hydroxy-phenyl)-thiophene-2-carboxylic acid methyl ester (42 mg, 0.082 mmol) as the starting material.

$^1$H NMR (400 MHz, DMSO-D6) δ ppm 1.1 (m, 6 H) 1.7 (m, 5 H) 3.8 (d, J=6.3 Hz, 2 H) 4.9 (s, 2 H) 7.1 (m, 1 H) 7.2 (m, 2 H) 7.4 (m, 1 H).

EXAMPLE 198

5-[3-(3,5-Bis-trifluoromethyl-benzyloxy)-phenyl]-4-bromo-3-carboxymethoxy-thiophene-2 carboxylic acid The first step of Scheme 19: To 4-bromo-3-ethoxycarbonylmethoxy-5-(3-hydroxy-phenyl)-thiophene-2-carboxylic acid methyl ester was added 1-bromomethyl-3,5-bis-trifluoromethyl-benzene (2 eq.) and potassium carbonate (2 eq.) according to the procedure in the first step of Scheme 19 of Example 197 to give 30 mg (40%) of 5-[3-(3,5-bis-trifluoromethyl-benzyloxy)-phenyl]-4-bromo-3-ethoxycarbonylmethoxy-thiophene-2-carboxylic acid methyl ester.

$^1$H NMR (400 MHz, CHLOROFORM-D) δ ppm 1.5 (m, 9 H) 3.9 (m, 3 H) 4.8 (m, 2 H) 5.2 (m, 2 H) 7.1 (m, 1 H) 7.3 (m, 2 H) 7.4 (m, 1 H) 7.9 (s, 1 H) 7.9 (s, 2 H).

The second step of Scheme 19: 5-[3-(3,5-Bis-trifluoromethyl-benzyloxy)-phenyl]-4-bromo-3-carboxymethoxy-thiophene-2-carboxylic acid (5 mg, 19%) was prepared according to the procedure in the second step of Scheme 1 of Example 1.

$^1$H NMR (400 MHz, DMSO-D6) δ ppm 4.9 (m, 2 H) 5.4 (m, 2 H) 7.2 (m, 1 H) 7.3 (m, 1 H) 7.3 (m, 1 H) 7.5 (t, 1 H) 8.1 (m, 1 H) 8.2 (m, 2 H).

EXAMPLE 199

5-(3-Benzyloxy-phenol)-4-bromo-3-carboxymethoxy-thiophene-2-carboxylic acid

The first step of Scheme 19: To a 4 mL solution of 4-bromo-3-ethoxycarbonylmethoxy-5-(3-hydroxy-phenyl)-thiophene-2-carboxylic acid methyl ester (50 mg) in DMF was added benzylbromide (22 μL, 1.5 eq) and $K_2CO_3$ (33 mg, 2 eq). The resulting suspension was stirred at room temperature, then heated to 60° C. until the disappearance of the starting material as monitored by TLC. DMF was evaporated under reduced pressure. $CH_2Cl_2$ (20 mL) was added and the resulting organic solution was washed with water twice, brine once and then dried over anhydrous $Na_2SO_4$. The solvent was removed, the crude product was purified on CombiFlash column and eluted with hexane/EtOAc to give the desire product, 5-(3-benzyloxy-phenyl)-4-bromo-3-ethoxycarbonyl-methoxy-thiophene-2-carboxylic acid methyl ester (52 mg, 86% yield).

$^1$H NMR (400 MHz, CHLOROFORM-D) δ ppm 1.32 (t, J=7.20 Hz, 3 H) 3.87 (s, 3 H) 4.29 (q, J=7.24 Hz, 2 H) 4.91 (s, 2 H) 5.12 (s, 2 H) 7.06 (m, 1 H) 7.24 (m, 1 H) 7.29 (m, 1 H) 7.39 (m, 6 H).

The second step of Scheme 19: 5-(3-Benzyloxy-phenyl)-4-bromo-3-carboxymethoxy-thiophene-2-carboxylic acid was prepared following the procedure in the second step of Scheme 1 of Example 1. 5-(3-Benzyloxy-phenyl)-4-bromo-3-ethoxycarbonylmethoxy-thiophene-2-carboxylic acid methyl ester (52 mg) was hydrolyzed to give 49 mg (>99%) of 5-(3-benzyloxy-phenyl)-4-bromo-3-carboxymethoxy-thiophene-2-carboxylic acid as a white solid.

$^1$H NMR (400 MHz, DMSO-D6) δ ppm 4.86 (s, 2 H) 5.18 (s, 2 H) 7.16 (dd, J=7.96, 2.15 Hz, 1 H) 7.23 (dd, J=6.44, 1.39 Hz, 1 H) 7.28 (m, J=7.33 Hz, 1 H) 7.35 (m, 1 H) 7.44 (m, 5 H).

EXAMPLE 200

4-Bromo-3-carboxymethoxy-5-[3-(1-phenyl-ethoxy)-phenyl]-thiophene-2-carboxylic acid The first step of Scheme 19: 4-Bromo-3-ethoxycarbonylmethoxy-5-[3-(1-phenyl-ethoxy)-phenyl]-thiophene-2-carboxylic acid methyl ester was prepared according to the procedure in the first step of Scheme 19 of Example 199 as a white solid (38 mg, 62% yield).

$^1$H NMR (400 MHz, CHLOROFORM-D) δ ppm 1.30 (m, 3 H) 1.66 (d, J=6.32 Hz, 3 H) 3.86 (s, 3 H) 4.29 (q, J=7.16 Hz, 2 H) 4.88 (s, 2 H) 5.34 (q, J=6.57 Hz, 1 H) 6.94 (dd, J=8.34, 1.77 Hz, 1 H) 7.14 (m, 1 H) 7.19 (m, 1 H) 7.25 (m, 2 H) 7.36 (m, 4 H).

The second step of Scheme 19: 4-Bromo-3-carboxymethoxy-5-[3-(1-phenyl-ethoxy)-phenyl]-thiophene-2-carboxylic acid was prepared following the procedure in the second step of Scheme 1 of Example 1 as a white solid (27 mg, 77%), using 38 mg of 4-bromo-3-ethoxycarbonylmethoxy-5-[3-(1-phenyl-ethoxy)-phenyl]-thiophene-2-carboxylic acid methyl ester as the starting material.

$^1$H NMR (400 MHz, DMSO-D6) δ ppm 1.57 (d, J=6.32 Hz, 3 H) 4.82 (s, 2 H) 5.57 (q, J=6.48 Hz, 1 H) 7.04 (dd, J=8.08, 2.02 Hz, 1 H) 7.15 (m, 2 H) 7.26 (m, 1 H) 7.35 (m, 3 H) 7.43 (m, 2 H).

EXAMPLE 201

4-Bromo-5-[3-(1-carboxy-ethoxy)-phenyl]-3-carboxymethoxy-thiophene-2-carboxylic acid The first step of Scheme 19: 4-Bromo-5-[3-(1-carbamoyl-ethoxy)-phenyl]-3-ethoxycarbonylmethoxy-thiophene-2-carboxylic acid methyl ester was prepared according to the procedure in the first step of Scheme 19 of Example 199 (26 mg, 45% yield).

$^1$H NMR (400 MHz, CHLOROFORM-D) δ ppm 1.64 (d, J=6.82 Hz, 3 H) 3.88 (s, 3 H) 4.29 (q, J=7.16 Hz, 2 H) 4.73 (q, J=6.74 Hz, 1 H) 4.92 (s, 2 H) 5.64 (s, 1 H) 6.42 (s, 1 H) 7.00 (dd, J=7.83, 2.02 Hz, 1 H) 7.25 (m, 1 H) 7.30 (d, J=8.08 Hz, 1 H) 7.39 (t, J=7.96 Hz, 1 H).

The second step of Scheme 19: 4-Bromo-5-[3-(1-carboxy-ethoxy)-phenyl]-3-carboxymethoxy-thiophene-2-carboxylic acid was prepared following the procedure in the second step of Scheme 1 of Example 1 as a white solid (21 mg, 88% yield), using 38 mg of 4-bromo-5-[3-(1-carbamoyl-ethoxy)-phenyl]-3-ethoxycarbonylmethoxy-thiophene-2-carboxylic acid methyl ester as the starting material.

$^1$H NMR (400 MHz, DMSO-D6) δ ppm 1.53 (d, J=6.82 Hz, 3 H) 4.90 (m, 3 H) 7.01 (dd, J=8.08, 2.27 Hz, 1 H) 7.14 (m, 1 H) 7.24 (m, 1 H) 7.43 (t, J=8.08 Hz, 1 H).

EXAMPLE 202

4-Bromo-3-carboxymethoxy-5-[3-(naphthalen-2-ylmethoxy)-phenyl]-thiophene-2-carboxylic acid The first step of Scheme 19: 4-Bromo-3-ethoxycarbonylmethoxy-5-[3-(naphthalen-2-ylmethoxy)-phenyl]-thiophene-2-carboxylic acid methyl ester was prepared according to the procedure in the first step of Scheme 19 of Example 199 (27 mg, 40% yield).

$^1$H NMR (400 MHz, CHLOROFORM-D) δ ppm 1.31 (m, 3 H) 3.87 (s, 3 H) 4.29 (q, J=7.24 Hz, 2 H) 4.90 (s, 2 H) 5.28 (s, 2 H) 7.10 (m, 1 H) 7.25 (m, 1 H) 7.37 (m, 2 H) 7.51 (m, 3 H) 7.86 (m, 4 H).

The second step of Scheme 19: 4-Bromo-3-carboxymethoxy-5-[3-(naphthalen-2-ylmethoxy)-phenyl]-thiophene-2-carboxylic acid was prepared following the procedure in the second step of Scheme 1 of Example 1 as a white solid (16 mg, 64% yield), using 27 mg of 4-bromo-3-ethoxycarbonylmethoxy-5-[3-(naphthalen-2-ylmethoxy)-phenyl]-thiophene-2-carboxylic acid methyl ester as the starting material.

$^1$H NMR (400 MHz, DMSO-D6) δ ppm 4.81 (s, 2 H) 5.36 (s, 2 H) 7.21 (m, 2 H) 7.34 (m, 1 H) 7.45 (t, J=7.96 Hz, 1 H) 7.54 (dd, 2 H) 7.61 (dd, J=8.59, 1.52 Hz, 1 H) 7.95 (m, 4 H).

EXAMPLE 203

4-Bromo-3-carboxymethoxy-5-[3-(3-methyl-3,3a-dihydro-benzo[1,2,5]oxadiazol-5-ylmethoxy)-phenyl]-thiophene-2-carboxylic acid The first step of Scheme 19: 4-Bromo-3-ethoxycarbonylmethoxy-5-[3-(3-methyl-3,3a-dihydro-benzo[1,2,5]oxadiazol-5-ylmethoxy)-phenyl]-thiophene-2-carboxylic acid methyl ester was prepared according to the procedure in the first step of Scheme 19 of Example 199 (58 mg, 88% yield).

$^1$H NMR (400 MHz, CHLOROFORM-D) δ ppm 1.32 (t, J=7.07 Hz, 3 H) 3.88 (s, 3 H) 4.29 (q, J=7.07 Hz, 2 H) 4.92 (s, 2 H) 5.20 (d, J=1.26 Hz, 2 H) 7.08 (m, 1 H) 7.31 (m, 2 H) 7.45 (m, 2 H) 7.90 (m, 2 H).

The second step of Scheme 19: 4-Bromo-3-carboxymethoxy-5-[3-(3-methyl-3,3a-dihydro-benzo[1,2,5]oxadiazol-5-ylmethoxy)-phenyl]-thiophene-2-carboxylic acid was prepared following the procedure in the second step of Scheme 1 of Example 1 as a white solid (30 mg, 56% yield), using 58 mg of 4-bromo-3-ethoxycarbonylmethoxy-5-[3-(3-methyl-3,3a-dihydro-benzo[1,2,5]oxadiazol-5-ylmethoxy)-phenyl]-thiophene-2-carboxylic acid methyl ester as the starting material.

$^1$H NMR (400 MHz, DMSO-D6) δ ppm 4.88 (s, 2 H) 5.34 (d, J=13.14 Hz, 2 H) 7.25 (m, 2 H) 7.36 (m, 1 H) 7.49 (t, J=8.08 Hz, 1 H) 7.64 (m, 2 H) 8.11 (m, 2 H).

EXAMPLE 204

4-Bromo-5-[3-(3-carboxy-benzyloxy)-phenyl]-3-carboxymethoxy-thiophene-2-carboxylic acid The first step of Scheme 19: 4-Bromo-3-ethoxycarbonylmethoxy-5-[3-(3-methoxycarbonyl-benzyloxy)-phenyl]-thiophene-2-carboxylic acid methyl ester was prepared according to the procedure in the first step of Scheme 19 of Example 199 (49 mg, 72% yield).

$^1$H NMR (400 MHz, CHLOROFORM-D) δ ppm 1.32 (t, J=7.20 Hz, 3 H) 3.88 (s, 3 H) 3.93 (d, J=5.05 Hz, 3 H) 4.29 (q, J=7.24 Hz, 2 H) 4.91 (s, 2 H) 5.16 (s, 2 H) 7.05 (m, 1 H) 7.25 (d, J=9.35 Hz, 1 H) 7.30 (m, 1 H) 7.37 (t, J=7.96 Hz, 1 H) 7.48 (t, J=7.71 Hz, 1 H) 7.65 (d, J=7.58 Hz, 1 H) 8.01 (d, J=7.58 Hz, 1 H) 8.13 (s, 1 H).

The second step of Scheme 19: 4-Bromo-5-[3-(3-carboxy-benzyloxy)-phenyl]-3-carboxymethoxy-thiophene-2-carboxylic acid was prepared following the procedure in the second step of Scheme 1 of Example 1 as a white solid (34 mg, 80% yield), using 47 mg of 4-bromo-3-ethoxycarbonylmethoxy-5-[3-(3-methoxycarbonyl-benzyloxy)-phenyl]-thiophene-2-carboxylic acid methyl ester as the starting material.

$^1$H NMR (400 MHz, DMSO-D6) δ ppm 4.87 (s, 2 H) 5.27 (s, 2 H) 7.18 (m, J=8.21, 2.15 Hz, 1 H) 7.24 (d, J=7.83 Hz, 1 H) 7.30 (m, 1 H) 7.46 (t, J=7.96 Hz, 1 H) 7.54 (t, J=7.71 Hz, 1 H) 7.73 (d, J=7.58 Hz, 1 H) 7.91 (d, J=7.83 Hz, 1 H) 8.05 (s, 1 H).

EXAMPLE 205

4-Bromo-3-carboxymethoxy-5-[3-(3-trifluoromethoxy-benzyloxy)-phenyl]-thiophene-2-carboxylic acid The first step of Scheme 19: 4-Bromo-3-ethoxycarbonylmethoxy-5-[3-(3-trifluoromethoxy-benzyloxy)-phenyl]-thiophene-2-carboxylic acid methyl ester was prepared according to the procedure in the first step of Scheme 19 of Example 199 (60 mg, 85% yield).

$^1$H NMR (400 MHz, CHLOROFORM-D) δ ppm 1.32 (t, J=7.07 Hz, 3 H) 3.88 (s, 3 H) 4.29 (q, J=7.16 Hz, 2 H) 4.91 (s, 2 H) 5.13 (s, 2 H) 7.05 (m, 1 H) 7.19 (m, 1 H) 7.27 (m, 2 H) 7.32 (s, 1 H) 7.39 (m, 3 H).

The second step of Scheme 19: 4-Bromo-3-carboxymethoxy-5-[3-(3-trifluoromethoxy-benzyloxy)-phenyl]-thiophene-2-carboxylic acid was prepared following the procedure in the second step of Scheme 1 of Example 1 as a white solid (36 mg, 67% yield), using 58 mg of 4-bromo-3-ethoxycarbonylmethoxy-5-[3-(3-trifluoromethoxy-benzyloxy)-phenyl]-thiophene-2-carboxylic acid methyl ester as the starting material.

¹H NMR (400 MHz, DMSO-D6) δ ppm 4.87 (s, 2 H) 5.26 (s, 2 H) 7.18 (m, 1 H) 7.25 (d, J=7.58 Hz, 1 H) 7.29 (m, 1 H) 7.34 (m, 1 H) 7.52 (m, 4 H).

EXAMPLE 206

4-[3-(3-Bromo-5-carboxy-4-carboxymethoxy-thiophen-2-yl)-phenoxy]-piperidine-1-carboxylic acid tert-butyl ester The first step of Scheme 20: To a solution of 4-3-(4,4,5,5-tetramethyl-[1,3,2]dioxaborolan-2-yl)-phenol (441 mg, 2.0 mmol), 4-hydroxy-piperidine-1-carboxylic acid tert-butyl ester (603.8 mg, 3.0 mmol) and triphenylphosphine (788 mg, 3.0 mmol) in THF (5 mL) was added DIAD (0.59 mL, 3.0 mmol) dropwise at 0° C. The resulting solution was stirred at room temperature for 36 h. The solvent was removed and the crude product was purified on the CombiFlash column eluting with hexanes/EtOAc to give the desired compound, 4-[3-(4,4,5,5-tetramethyl-[1,3,2]dioxaborolan-2-yl)-phenoxy]-piperidine-1-carboxylic acid tert-butyl ester (635 mg, 79%) as a colorless crystalline solid.

¹H NMR (400 MHz, CHLOROFORM-D) δ ppm 1.33 (m, 12 H) 1.48 (m, 9 H) 1.75 (m, 2 H) 1.89 (m, 2 H) 3.37 (m, 2 H) 3.67 (m, 2 H) 4.53 (m, 1 H) 7.01 (m, 1 H) 7.29 (m, 1 H) 7.34 (d, J=2.78 Hz, 1 H) 7.40 (m, 1 H).

The second step of Scheme 20: 4-[3-(3-bromo-4-ethoxycarbonylmethoxy-5-methoxycarbonyl-thiophen-2-yl)-phenoxy]-piperidine-1-carboxylic acid tert-butyl ester (125 mg, 51%) was prepared according to the procedure in the second step of Scheme 3 of Example 13, using 4,5-dibromo-3-ethoxycarbonylmethoxy-thiophene-2-carboxylic acid methyl ester (211.5 mg, 0.53 mmol) and 4-[3-(4,4,5,5-tetramethyl-[1,3,2]dioxaborolan-2-yl)-phenoxy]-piperidine-1-carboxylic acid tert-butyl ester (165 mg, 0.41 mmol) as the starting materials.

¹H NMR (400 MHz, CHLOROFORM-D) δ ppm 1.5 (s, 9 H) 1.8 (m, 2 H) 2.0 (m, 2 H) 3.4 (m, 2 H) 3.7 (m, 2 H) 4.5 (m, 1 H) 6.9 (dd, J=7.7, 2.1 Hz, 1 H) 7.1 (m, 1 H) 7.2 (m, 1 H) 7.3 (t, J=8.0 Hz, 1 H).

The fifth step of Scheme 20: Hydrolysis of 4-[3-(3-bromo-4-ethoxycarbonylmethoxy-5-methoxycarbonyl-thiophen-2-yl)-phenoxy]-piperidine-1-carboxylic acid tert-butyl ester according to the procedure in the second step of Scheme 1 of Example 1 gave 4-[3-(3-bromo-5-carboxy-4-carboxymethoxy-thiophen-2-yl)-phenoxy]-piperidine-1-carboxylic acid tert-butyl ester (7.5 mg, 67%), as a white solid.

¹H NMR (400 MHz, DMSO-D6) δ ppm 1.4 (s, 9 H) 1.5 (m, 2 H) 1.9 (m, 2 H) 3.2 (m, 2 H) 3.7 (m, 2 H) 4.6 (m, 1 H) 4.9 (s, 2 H) 7.1 (m, 1 H) 7.2 (m, 1 H) 7.2 (m, 1 H) 7.4 (m, 1 H).

EXAMPLE 207

4-Bromo-3-carboxymethoxy-5-[3-(1-phenylcarbamoyl-piperidin-4-yloxy)-phenyl]-thiophene-2-carboxylic acid The first step of Scheme 20 and the second step of Scheme 20 are the same as that of Example 206.

The third step of Scheme 20: 4-Bromo-3-ethoxycarbonylmethoxy-5-[3-(piperidin-4-yloxy)-phenyl]-thiophene-2-carboxylic acid methyl ester (TFA salt) was obtained by treating 4-[3-(3-bromo-4-ethoxycarbonylmethoxy-5-methoxycarbonyl-thiophen-2-yl)-phenoxy]-piperidine-1-carboxylic acid tert-butyl ester (210 mg, 0.35 mmol) with TFA/CH₂Cl₂ (v/v 1:10) at room temperature overnight.

The fourth step of Scheme 20: To a solution of 4-bromo-3-ethoxycarbonylmethoxy-5-[3-(piperidin-4-yloxy)-phenyl]-thiophene-2-carboxylic acid methyl ester (TFA salt, 0.117 mmol) in DCM (2 mL) and pyridine (1 mL) was added phenyl isocyanate (0.036 mL, 0.33 mmol) at room temperature. The resultant reaction mixture was stirred at room temperate overnight. The solvent was removed, and the crude product was purified on CombiFlash column eluted with hexanes/EtOAc to give 4-bromo-3-ethoxycarbonylmethoxy-5-[3-(1-phenylcarbamoyl-piperidin-4-yloxy)-phenyl]-thiophene-2-carboxylic acid methyl ester (70 mg, 97%, 2 steps) as colorless oil.

¹H NMR (400 MHz, CHLOROFORM-D) δ ppm 1.3 (t, J=7.1 Hz, 3 H) 1.9 (m, 2 H) 2.0 (m, 2 H) 3.5 (m, 2 H) 3.7 (m, 2 H) 3.9 (s, 3 H) 4.3 (q, J=7.1 Hz, 2 H) 4.6 (m, 1 H) 4.9 (s, 2 H) 6.4 (s, 1 H) 7.0 (m, 2 H) 7.3 (m, 7 H).

The fifth step of Scheme 20: 4-Bromo-3-carboxymethoxy-5-[3-(1-phenylcarbamoyl-piperidin-4-yloxy)-phenyl]-thiophene-2-carboxylic acid (59 mg, 90%), was prepared as a white solid according to the procedure in the second step of Scheme 1 of Example 1, using 4-bromo-3-ethoxycarbonylmethoxy-5-[3-(1-phenylcarbamoyl-piperidin-4-yloxy)-phenyl]-thiophene-2-carboxylic acid methyl ester (70 mg, 0.113 mmol) as the starting material.

¹H NMR (400 MHz, DMSO-D6) δ ppm 1.6 (m, 2 H) 2.0 (m, 2 H) 3.3 (m, 2 H) 3.8 (m, 2 H) 4.7 (m, 1 H) 4.7 (s, 2 H) 6.9 (m, 1 H) 7.1 (dd, J=8.5, 1.6 Hz, 1 H) 7.2 (m, 4 H) 7.4 (m, 3 H) 8.5 (s, 1 H).

EXAMPLE 208

4-[3-(3-Bromo-5-carboxy-4-carboxymethoxy-thiophen-2-yl)-phenoxy]-piperidine-1-carboxylic acid phenyl ester The first step of Scheme 20, the second step of Scheme 20 and the third step of Scheme 20 are the same as that of Example 207.

The fourth step of Scheme 20: 4-[3-(3-Bromo-4-ethoxycarbonylmethoxy-5-methoxycarbonyl-thiophen-2-yl)-phenoxy]-piperidine-1-carboxylic acid phenyl ester (70 mg, 97%, 2 steps) was prepared as colorless oil according to the procedure in the first step of Scheme 4 of Example 23, using 4-bromo-3-ethoxycarbonylmethoxy-5-[3-(piperidin-4-yloxy)-phenyl]-thiophene-2-carboxylic acid methyl ester (TFA salt, 0.117 mmol) as the starting material.

¹H NMR (400 MHz, CHLOROFORM-D) δ ppm 1.3 (t, J=7.2 Hz, 3 H) 1.9 (m, 2 H) 2.1 (m, 2 H) 3.7 (m, 3 H) 3.9 (s, 3 H) 4.3 (q, J=7.1 Hz, 2 H) 4.6 (m, 1 H) 4.9 (s, 2 H) 7.0 (m, 1 H) 7.1 (m, 2 H) 7.2 (m, 3 H) 7.4 (m, 3 H).

The fifth step of Scheme 20: 4-[3-(3-Bromo-5-carboxy-4-carboxymethoxy-thiophen-2-yl)-phenoxy]-piperidine-1-carboxylic acid phenyl ester (43 mg, 71%), was prepared as a white solid according to the procedure in the second step of Scheme 1 of Example 1, using 4-[3-(3-bromo-4-ethoxycarbonylmethoxy-5-methoxycarbonyl-thiophen-2-yl)-phenoxy]-piperidine-1-carboxylic acid phenyl ester (65 mg, 0.105 mmol) as the starting material.

¹H NMR (400 MHz, DMSO-D6) δ ppm 1.7 (m, 2 H) 2.0 (m, 2 H) 3.5 (m, 2 H) 3.8 (m, 1 H) 3.9 (m, 1 H) 4.8 (m, 1 H) 4.8 (s, 2 H) 7.1 (m, 3 H) 7.2 (m, 2 H) 7.3 (m, 1 H) 7.4 (m, 3 H).

EXAMPLE 209

4-Bromo-3-carboxymethoxy-5-[3-(1-phenyl-methanesulfonyl-piperidin-4-yloxy-phenyl]-thiophene-2-carboxylic acid The first step of Scheme 20, the second step of Scheme 20 and the third step of Scheme 20 are the same as that of Example 207.

The fourth step of Scheme 20: 4-Bromo-3-ethoxycarbonylmethoxy-5-[3-(1-phenylmethanesulfonyl-piperidin-4-yloxy)-phenyl]-thiophene-2-carboxylic acid methyl ester (62 mg, 81%, 2 steps) was prepared as a colorless oil according to the procedure in the fourth step of Scheme 20 of Example 208, using 4-bromo-3-ethoxycarbonylmethoxy-5-[3-(piperidin-4-yloxy)-phenyl]-thiophene-2-carboxylic acid methyl ester (TFA salt, 0.117 mmol).

The fifth step of Scheme 20: 4-Bromo-3-carboxymethoxy-5-[3-(1-phenylmethanesulfonyl-piperidin-4-yloxy)-phenyl]-thiophene-2-carboxylic acid (43 mg, 57%), was prepared as a white solid according to the procedure in the second step of Scheme 1 of Example 1, using 4-bromo-3-ethoxycarbonyl-methoxy-5-[3-(1-phenylmethanesulfonyl-piperidin-4-yloxy)-phenyl]-thiophene-2-carboxylic acid methyl ester (60 mg, 0.092 mmol) as the starting material.

$^1$H NMR (400 MHz, DMSO-D6) δ ppm 1.7 (m, 2 H) 1.9 (m, 2 H) 3.1 (m, 2 H) 3.4 (m, 2 H) 4.4 (s, 2 H) 4.6 (m, 1 H) 4.8 (s, 2 H) 7.1 (m, 1 H) 7.2 (m, 2 H) 7.4 (m, 6 H).

EXAMPLE 210

4-[3-(3-Bromo-5-carboxy-4-carboxymethoxy-thiophen-2-yl)-phenoxymethyl]-piperidine-1-carboxylic acid tert-butyl ester The first step of Scheme 21: To a solution of 4-bromo-3-ethoxycarbonylmethoxy-5-(3-hydroxy-phenyl)-thiophene-2-carboxylic acid methyl ester in DMF (4 mL) was added 4-methanesulfonyloxy-piperidine-1-carboxylic acid tert-butyl ester (2 eq.). The mixture was stirred at 80° C. overnight. The residue was then washed with sodium bicarbonate, dried over magnesium sulfate, and then concentrated for purification on CombiFlash column eluted with Hexane/EtoAc to give 84 mg (39%) of 4-[3-(3-bromo-4-tert-butoxycarbonyl-methoxy-5-methoxycarbonyl-thiophen-2-yl)-phenoxymethyl]-piperidine-1-carboxylic acid tert-butyl ester.

$^1$H NMR (400 MHz, CHLOROFORM-D) δ ppm 1.3 (m, 2 H) 1.5 (s, 9 H) 1.5 (s, 9 H) 1.8 (m, 2 H) 2.0 (m, 1 H) 2.8 (t, J=12.3 Hz, 2 H) 3.8 (d, J=6.6 Hz, 2 H) 3.9 (s, 3 H) 4.8 (s, 2 H) 7.0 (dd, 1 H) 7.2 (t, 1 H) 7.2 (dt, J=8.3 Hz, 1 H) 7.3 (t, J=8.0 Hz, 1 H).

The fourth step of Scheme 21: 4-[3-(3-Bromo-4-tert-butoxycarbonylmethoxy-5-methoxycarbonyl-thiophen-2-yl)-phenoxymethyl]-piperidine-1-carboxylic acid tert-butyl ester was hydrolyzed with LiOH (6 eq.) in THF: H$_2$O (1:1). The reaction mixture was then stirred overnight. Solvents were evaporated, and to the residue were added water and 1N HCl to pH 2. The precipitate was filtered, washed with water, and dried, which yielded 60 mg (80%) of 4-[3-(3-bromo-5-carboxy-4-carboxymethoxy-thiophen-2-yl)-phenoxymethyl]-piperidine-1-carboxylic acid tert-butyl ester.

$^1$H NMR (400 MHz, DMSO-D6) δ ppm 1.2 (m, 4 H) 1.4 (m, 9 H) 1.8 (d, 2 H) 3.9 (d, 2 H) 4.6 (m, 1 H) 7.0 (m, 1 H) 7.2 (m, 2 H) 7.4 (t, 1 H).

EXAMPLE 211

4-Bromo-3-carboxymethoxy-5-[3-(1-methanesulfonyl-piperidin-4-ylmethoxy)-phenyl]-thiophene-2-carboxylic acid The second step of Scheme 21: 4-Bromo-3-ethoxycarbonylmethoxy-5-[3-(piperidin-4-ylmethoxy)-phenyl]-thiophene-2-carboxylic acid methyl ester TFA salt was obtained by treating 4-[3-(3-bromo-4-tert-butoxycarbonyl-methoxy-5-methoxycarbonyl-thiophen-2-yl)-phenoxymethyl]-piperidine-1-carboxylic acid tert-butyl ester with 30% TFA in DCM at room temperature.

The third step of Scheme 21: To a solution of 4-bromo-3-ethoxycarbonylmethoxy-5-[3-(piperidin-4-ylmethoxy)-phenyl]-thiophene-2-carboxylic acid methyl ester TFA salt (1 eq.) in DCM (2 mL) cooled in an ice bath was added mesyl chloride (1.5 eq.) and sodium bicarbonate (2 mL). The mixture was stirred overnight at room temperature. Purification by Combiflash column yielded 320 mg (91%) of the ester intermediate, 4-bromo-3-ethoxycarbonylmethoxy-5-[3-(1-methanesulfonyl-piperidin-4-ylmethoxy)-phenyl]-thiophene-2-carboxylic acid methyl ester.

$^1$H NMR (400 MHz, CHLOROFORM-D) δ ppm 1.3 (t, J=7.2 Hz, 3 H) 1.5 (m, 2 H) 2.0 (m, 3 H) 2.7 (td, J=12.1, 2.3 Hz, 2 H) 2.8 (m, J=3.0 Hz, 3 H) 3.9 (m, 7 H) 4.3 (q, J=7.2 Hz, 2 H) 4.9 (m, J=2.8 Hz, 2 H) 7.0 (m, 1 H) 7.2 (t, 1 H) 7.2 (m, 1 H) 7.4 (t, J=8.1 Hz, 1 H).

The fourth step of Scheme 21: 4-Bromo-3-ethoxycarbonylmethoxy-5-[3-(1-methanesulfonyl-piperidin-4-ylmethoxy)-phenyl]-thiophene-2-carboxylic acid methyl ester was hydrolyzed according to the procedure in the fourth step of Scheme 21 of Example 210 to give 179 mg (60%) of 4-bromo-3-carboxymethoxy-5-[3-(1-methanesulfonyl-piperidin-4-ylmethoxy)-phenyl]-thiophene-2-carboxylic acid.

$^1$H NMR (400 MHz, DMSO-D6) δ ppm 1.3 (dt, 2 H) 1.9 (d, 2 H) 2.9 (m, 3 H) 3.6 (d, 2 H) 3.9 (d, 2 H) 4.8 (m, 2 H) 7.1 (dd, 1 H) 7.4 (t, 1 H).

EXAMPLE 212

4-Bromo-3-carboxymethoxy-5-[3-(1-phenyl-methanesulfonyl-piperidin-4-ylmethoxy)-phenyl]-thiophene-2-carboxylic acid The third step of Scheme 21: 4-Bromo-3-ethoxycarbonyl-methoxy-5-[3-(1-phenylmethanesulfonyl-piperidin-4-yl-methoxy)-phenyl]-thiophene-2-carboxylic acid methyl ester (37 mg, 48%) was prepared following the procedure in the third step of Scheme 21 of Example 211, except that phenyl methanesulfonyl chloride was used as a starting material.

$^1$H NMR (400 MHz, CHLOROFORM-D) δ ppm 1.3 (t, 3 H) 1.4 (dd, 2 H) 1.9 (d, 2 H) 2.7 (td, 2 H) 3.7 (d, 2 H) 3.8 (m, 2 H) 3.9 (m, 3 H) 4.3 (q, 2 H) 4.8 (m, 2 H) 4.9 (m, 3 H) 7.0 (dd, 1 H) 7.2 (t, 1 H) 7.2 (d, J=7.8 Hz, 1 H) 7.4 (t, 1 H) 7.6 (m, 3 H) 8.0 (dd, J=8.1, 1.3 Hz, 1 H).

The fourth step of Scheme 21: 4-Bromo-3-ethoxycarbonylmethoxy-5-[3-(1-phenylmethanesulfonyl-piperidin-4-yl-methoxy)-phenyl]-thiophene-2-carboxylic acid methyl ester was hydrolyzed according to the procedure in the fourth step of Scheme 21 of Example 210 to afford 4-bromo-3-carboxymethoxy-5-[3-(1-phenylmethanesulfonyl-piperidin-4-ylmethoxy)-phenyl]-thiophene-2-carboxylic acid in 29% yield (10 mg).

¹H NMR (400 MHz, CHLOROFORM-D) δ ppm 1.3 (d, 2 H) 1.8 (m, 3 H) 2.6 (t, 2 H) 3.7 (d, 2 H) 3.8 (d, 2 H) 4.2 (m, 2 H) 5.0 (m, 2 H) 7.0 (d, 1 H) 7.1 (m, 2 H) 7.2 (d, 1 H) 7.4 (m, 6 H).

EXAMPLE 213

4-Bromo-3-carboxymethoxy-5-{3-[1-(toluene-4-sulfonyl)-piperidin-4-ylmethoxy]-phenyl}-thiophene-2-carboxylic acid The third step of Scheme 21: 4-Bromo-3-ethoxycarbonylmethoxy-5-{3-[1-(toluene-4-sulfonyl)-piperidin-4-ylmethoxy]-phenyl}-thiophene-2-carboxylic acid methyl ester (100 mg, 63%) was prepared following the procedure in the third step of Scheme 21 of Example 211.

¹H NMR (400 MHz, CHLOROFORM-D) δ ppm 1.3 (t, 3 H) 1.5 (m, 3 H) 1.9 (d, 2 H) 2.3 (td, 2 H) 2.4 (m, 3 H) 3.8 (d, 2 H) 3.9 (m, 3 H) 4.3 (q, 2 H) 4.9 (m, 2 H) 6.9 (m, 1 H) 7.1 (t, 1 H) 7.2 (m, 1 H) 7.3 (m, 3 H) 7.7 (m, 2 H).

The fourth step of Scheme 21: 4-Bromo-3-ethoxycarbonylmethoxy-5-{3-[1-(toluene-4-sulfonyl)-piperidin-4-ylmethoxy]-phenyl}-thiophene-2-carboxylic acid methyl ester was hydrolyzed according to the procedure in the fourth step of Scheme 21 of Example 210 to afford 4-bromo-3-carboxymethoxy-5-{3-[1-(toluene-4-sulfonyl)-piperidin-4-ylmethoxy]-phenyl}-thiophene-2-carboxylic acid in 79% yield (74 mg).

¹H NMR (400 MHz, DMSO-D6) δ ppm 1.9 (d, J=13.1 Hz, 2 H) 2.3 (td, J=11.9, 2.8 Hz, 2 H) 2.4 (s, 3 H) 3.7 (d, J=12.6 Hz, 2 H) 3.9 (d, J=5.8 Hz, 2 H) 4.8 (s, 2 H) 7.0 (dd, J=9.0, 2.9 Hz, 1 H) 7.1 (t, J=2.0 Hz, 1 H) 7.2 (dt, 1 H) 7.4 (t, 1 H) 7.4 (d, J=7.8 Hz, 2 H) 7.6 (d, J=8.3 Hz, 2 H).

EXAMPLE 214

5-[3-(1-Benzenesulfonyl-piperidin-4-ylmethoxy)-phenyl]-4-bromo-3-carboxymethoxy-thiophene-2-carboxylic acid The third step of Scheme 21: 5-[3-(1-Benzenesulfonyl-piperidin-4-ylmethoxy)-phenyl]-4-bromo-3-ethoxycarbonylmethoxy-thiophene-2-carboxylic acid methyl ester (105 mg, 26%) was prepared following the procedure in the third step of Scheme 21 of Example 211.

¹H NMR (400 MHz, CHLOROFORM-D) δ ppm 1.2 (t, 3 H) 1.4 (m, 2 H) 1.7 (m, 2 H) 1.8 (d, 2 H) 2.3 (td, J=12.0, 2.5 Hz, 2 H) 3.7 (d, J=6.3 Hz, 2 H) 3.8 (s, 3 H) 4.2 (q, J=7.2 Hz, 2 H) 4.8 (s, 2 H) 6.8 (m, 1 H) 7.1 (m, 1 H) 7.1 (m, 1 H) 7.3 (t, J=8.0 Hz, 1 H) 7.5 (m, 3 H) 7.7 (m, 2 H).

The fourth step of Scheme 21: 5-[3-(1-Benzenesulfonyl-piperidin-4-ylmethoxy)-phenyl]-4-bromo-3-ethoxycarbonylmethoxy-thiophene-2-carboxylic acid methyl ester was hydrolyzed according to the procedure in the fourth step of Scheme 21 of Example 210 to afford 5-[3-(1-benzenesulfonyl-piperidin-4-ylmethoxy)-phenyl]-4-bromo-3-carboxymethoxy-thiophene-2-carboxylic acid in 95% yield (117 mg).

¹H NMR (400 MHz, DMSO-D6) δ ppm 1.3 (d, 2 H) 1.8 (d, 2 H) 2.3 (td, J=12.5, 1.8 Hz, 2 H) 3.7 (d, J=12.1 Hz, 2 H) 3.9 (d, J=5.6 Hz, 2 H) 4.8 (dd, 2 H) 7.0 (dd, 1 H) 7.1 (m, 1 H) 7.2 (dt, 1 H) 7.4 (t, 1 H) 7.7 (m, 5 H).

EXAMPLE 215

4-[3-(3-Bromo-5-carboxy-4-carboxymethoxy-thiophen-2-yl)-phenoxymethyl]-piperidine-1-carboxylic acid phenyl ester The third step of Scheme 21: To a solution of 4-bromo-3-ethoxycarbonylmethoxy-5-[3-(piperidin-4-ylmethoxy)-phenyl]-thiophene-2-carboxylic acid methyl ester TFA salt (1 eq.) in DCM (2 mL) cooled in a dried ice bath (−78° C.) was added phenylchloroformate (3 eq.) and triethylamine (3 eq.). The mixture was stirred 1 h. Purification by Combiflash column yielded 57 mg (43%) of the ester intermediate, 4-[3-(3-bromo-4-ethoxycarbonylmethoxy-5-methoxycarbonyl-thiophen-2-yl)-phenoxymethyl]-piperidine-1-carboxylic acid phenyl ester.

¹H NMR (400 MHz, CHLOROFORM-D) δ ppm 1.3 (t, 3 H) 1.4 (m, 2 H) 3.9 (m, 3 H) 3.9 (d, 2 H) 4.3 (q, 2 H) 4.9 (m, 2 H) 7.0 (dd, 1 H) 7.1 (m, 2 H) 7.2 (m, 3 H) 7.4 (m, 3 H).

The fourth step of Scheme 21: 4-[3-(3-Bromo-4-ethoxycarbonylmethoxy-5-methoxycarbonyl-thiophen-2-yl)-phenoxymethyl]-piperidine-1-carboxylic acid phenyl ester was hydrolyzed according to the procedure in the fourth step of Scheme 21 of Example 210 to afford 4-[3-(3-bromo-5-carboxy-4-carboxymethoxy-thiophen-2-yl)-phenoxymethyl]-piperidine-1-carboxylic acid phenyl ester in 48% yield (26 mg).

¹H NMR (400 MHz, DMSO-D6) δ ppm 1.3 (d, 2 H) 1.9 (d, 2 H) 2.9 (d, 2 H) 4.0 (d, 2 H) 4.2 (d, 2 H) 4.9 (m, 2 H) 7.1 (m, 3 H) 7.2 (m, 2 H) 7.4 (m, 4 H).

EXAMPLE 216

4-[3-(3-Bromo-5-carboxy-4-carboxymethoxy-thiophen-2-yl)-phenoxethyl]-piperidine-1-carboxylic acid methyl ester The third step of Scheme 21: 4-[3-(3-Bromo-4-ethoxycarbonylmethoxy-5-methoxycarbonyl-thiophen-2-yl)-phenoxymethyl]-piperidine-1-carboxylic acid methyl ester (50% yield) was prepared following the procedure in the third step of Scheme 21 of Example 215.

¹H NMR (400 MHz, CHLOROFORM-D) δ ppm 1.3 (t, J=7.2 Hz, 3 H) 1.9 (m, 2 H) 2.0 (m, 1 H) 2.8 (t, J=12.9 Hz, 2 H) 3.7 (s, 3 H) 3.9 (d, J=6.3 Hz, 2 H) 3.9 (s, 3 H) 4.3 (q, J=7.2 Hz, 2 H) 4.9 (s, 2 H) 7.0 (m, 1 H) 7.2 (t, 1 H) 7.2 (m, 1 H) 7.4 (t, 1 H).

The fourth step of Scheme 21: 4-[3-(3-Bromo-4-ethoxycarbonylmethoxy-5-methoxycarbonyl-thiophen-2-yl)-phenoxymethyl]-piperidine-1-carboxylic acid methyl ester was hydrolyzed according to the procedure in the fourth step of Scheme 21 of Example 210 to afford 4-[3-(3-bromo-5-carboxy-4-carboxymethoxy-thiophen-2-yl)-phenoxymethyl]-piperidine-1-carboxylic acid methyl ester in 32% yield.

¹H NMR (400 MHz, DMSO-D6) δ ppm 1.2 (m, 3 H) 1.8 (d, 2 H) 2.8 (m, 2 H) 3.6 (s, 3 H) 3.9 (d, J=6.6 Hz, 2 H) 4.0 (s, 2 H) 4.8 (s, 2 H) 7.1 (dd, J=8.2, 2.1 Hz, 1 H) 7.2 (m, 2 H) 7.4 (t, J=8.1 Hz, 1 H).

EXAMPLE 217

4-Bromo-3-carboxymethoxy-5-[3-(1-ethylcarbamoyl-piperidin-4-ylmethoxy)-phenyl]-thiophene-2-carboxylic acid The third step of Scheme 21: To a solution of 4-bromo-3-ethoxycarbonylmethoxy-5-[3-(piperidin-4-ylmethoxy)-phenyl]-thiophene-2-carboxylic acid methyl ester TFA salt (1 eq.) in DCM (1 mL) cooled in a dried ice bath (−78° C.) was added ethyl isocyanate (3 eq.) and pyridine (1.5 mL). The mixture was stirred for 3 h. Purification by Combiflash column yielded the ester intermediate, 4-bromo-3-ethoxycarbonylmethoxy-5-[3-(1-ethylcarbamoyl-piperidin-4-ylmethoxy)-phenyl]-thiophene-2-carboxylic acid methyl ester, in 64%.

$^1$H NMR (400 MHz, CHLOROFORM-D) δ ppm 1.1 (t, 3 H) 1.3 (t, 3 H) 1.9 (m, 3 H) 2.0 (m, 1 H) 2.8 (td, 2 H) 3.3 (m, 2 H) 3.8 (d, 2 H) 3.9 (m, 3 H) 4.0 (m, 2 H) 4.3 (q, 2 H) 4.9 (m, 2 H) 7.0 (dd, 1 H) 7.2 (t, 1 H) 7.2 (m, 1 H) 7.4 (t, 1 H).

The fourth step of Scheme 21: 4-Bromo-3-ethoxycarbonylmethoxy-5-[3-(1-ethylcarbamoyl-piperidin-4-ylmethoxy)-phenyl]-thiophene-2-carboxylic acid methyl ester was hydrolyzed according to the procedure in the fourth step of Scheme 21 of Example 210 to afford 4-bromo-3-carboxymethoxy-5-[3-(1-ethylcarbamoyl-piperidin-4-ylmethoxy)-phenyl]-thiophene-2-carboxylic acid in 21% yield (15 mg).

$^1$H NMR (400 MHz, DMSO-D6) δ ppm 1.0 (t, 3 H) 1.2 (m, 2 H) 1.7 (d, 2 H) 2.7 (t, 2 H) 3.0 (q, 2 H) 3.9 (d, 2 H) 4.0 (d, 2 H) 4.8 (m, 2 H) 7.1 (dd, 1 H) 7.2 (m, 2 H) 7.4 (t, 1 H).

EXAMPLE 218

4-Bromo-3-carboxymethoxy-5-[3-(1-phenylcarbamoyl-piperidin-4-ylmethoxy)-phenyl]-thiophene-2-carboxylic acid The third step of Scheme 21: 4-Bromo-3-ethoxycarbonylmethoxy-5-[3-(1-phenylcarbamoyl-piperidin-4-ylmethoxy)-phenyl]-thiophene-2-carboxylic acid methyl ester (90% yield) was prepared according to the procedure in the third step of Scheme 21 of Example 217.

$^1$H NMR (400 MHz, CHLOROFORM-D) δ ppm 1.2 (t, J=7.2 Hz, 3 H) 1.4 (m, 2 H) 1.7 (m, 1 H) 1.8 (m, 2 H) 2.3 (td, J=12.0, 2.5 Hz, 2 H) 3.7 (d, J=6.3 Hz, 2 H) 3.8 (s, 3 H) 4.2 (q, J=7.3 Hz, 2 H) 4.8 (s, 2 H) 6.8 (dd, 1 H) 7.1 (t, 1 H) 7.1 (m, 1 H) 7.3 (t, J=8.0 Hz, 1 H) 7.5 (m, 3 H) 7.7 (m, 2 H).

The fourth step of Scheme 21: 4-Bromo-3-ethoxycarbonylmethoxy-5-[3-(1-phenylcarbamoyl-piperidin-4-ylmethoxy)-phenyl]-thiophene-2-carboxylic acid methyl ester was hydrolyzed according to the procedure in the fourth step of Scheme 21 of Example 210 to afford 4-bromo-3-carboxymethoxy-5-[3-(1-phenylcarbamoyl-piperidin-4-ylmethoxy)-phenyl]-thiophene-2-carboxylic acid in 75% yield.

$^1$H NMR (400 MHz, DMSO-D6) δ ppm 1.0 (d, 2 H) 2.0 (td, 2 H) 2.8 (m, 2 H) 3.0 (d, 2 H) 3.3 (d, 2 H) 4.5 (m, 2 H) 6.1 (m, 2 H) 6.3 (m, 4 H) 6.4 (m, 3 H).

EXAMPLE 219

4-Bromo-3-carboxymethoxy-5-{3-[1-(2-chloro-phenylcarbamoyl)-piperidin-4-ylmethoxyl-phenyl}-thiophene-2-carboxylic acid The third step of Scheme 21: 4-Bromo-5-{3-[1-(2-chloro-phenylcarbamoyl)-piperidin-4-ylmethoxy]-phenyl}-3-ethoxycarbonylmethoxy-thiophene-2-carboxylic acid methyl ester (56 mg, 41% yield) was prepared according to the procedure in the third step of Scheme 21 of Example 217.

$^1$H NMR (400 MHz, CHLOROFORM-D) δ ppm 1.3 (t, J=7.2 Hz, 3 H) 1.4 (m, 2 H) 2.0 (m, 2 H) 3.0 (td, J=12.9, 2.8 Hz, 2 H) 3.9 (s, 3 H) 3.9 (d, J=6.3 Hz, 2 H) 4.2 (m, 2 H) 4.3 (q, J=7.2 Hz, 2 H) 4.9 (s, 2 H) 7.0 (m, 2 H) 7.2 (m, 2 H) 7.3 (m, 2 H) 8.2 (dd, J=8.3, 1.5 Hz, 1 H).

The fourth step of Scheme 21: 4-Bromo-5-{3-[1-(2-chloro-phenylcarbamoyl)-piperidin-4-ylmethoxy]-phenyl}-3-ethoxycarbonylmethoxy-thiophene-2-carboxylic acid methyl ester was hydrolyzed according to the procedure in the fourth step of Scheme 21 of Example 210 to afford 17.6 mg (34%) of 4-bromo-3-carboxymethoxy-5-{3-[1-(2-chloro-phenylcarbamoyl)-piperidin-4-ylmethoxy]-phenyl}-thiophene-2-carboxylic acid.

$^1$H NMR (400 MHz, DMSO-D6) δ ppm 1.3 (m, 2 H) 1.8 (dd, 2 H) 2.9 (t, J=12.1 Hz, 2 H) 3.9 (d, J=6.3 Hz, 2 H) 4.1 (d, J=13.1 Hz, 2 H) 4.9 (s, 2 H) 7.1 (m, 2 H) 7.3 (m, 3 H) 7.5 (m, 3 H).

EXAMPLE 220

4-Bromo-3-carboxymethoxy-5-[3-(1-o-tolylcarbamoyl-piperidin-4-ylmethoxy)-phenyl]-thiophene-2-carboxylic acid The third step of Scheme 21: 4-Bromo-3-ethoxycarbonylmethoxy-5-[3-(1-o-tolylcarbamoyl-piperidin-4-ylmethoxy)-phenyl]-thiophene-2-carboxylic acid methyl ester (61 mg, 47% yield) was prepared according to the procedure in the third step of Scheme 21 of Example 217.

$^1$H NMR (400 MHz, CHLOROFORM-D) δ ppm 1.3 (t, J=7.2 Hz, 3 H) 1.4 (m, 2 H) 1.9 (m, 2 H) 2.1 (m, 1 H) 2.2 (s, 3 H) 2.9 (td, J=12.9, 2.5 Hz, 2 H) 3.9 (m, 5 H) 4.3 (q, J=7.2 Hz, 2 H) 4.9 (s, 2 H) 7.0 (m, 2 H) 7.2 (m, 4 H) 7.4 (t, J=8.1 Hz, 1 H) 7.6 (d, J=8.1 Hz, 1 H).

The fourth step of Scheme 21: 4-Bromo-3-ethoxycarbonylmethoxy-5-[3-(1-o-tolylcarbamoyl-piperidin-4-ylmethoxy)-phenyl]-thiophene-2-carboxylic acid methyl ester was hydrolyzed according to the procedure in the fourth step of Scheme 21 of Example 210 to afford 49 mg (85%) of 4-bromo-3-carboxymethoxy-5-[3-(1-o-tolylcarbamoyl-piperidin-4-ylmethoxy)-phenyl]-thiophene-2-carboxylic acid.

$^1$H NMR (400 MHz, DMSO-D6) δ ppm 1.3 (m, 2 H) 1.8 (m, 2 H) 2.2 (s, 3 H) 2.8 (t, J=13.1 Hz, 2 H) 3.9 (d, J=6.3 Hz, 2 H) 4.1 (d, J=14.1 Hz, 2 H) 4.9 (s, 2 H) 7.1 (m, 7 H) 7.4 (t, 1 H).

EXAMPLE 221

4-Bromo-3-carboxymethoxy-5-{3-[1-(2-methoxy-phenylcarbamoyl)-piperidin-4-ylmethoxy]-phenyl}-thiophene-2-carboxylic acid The third step of Scheme 21: 4-Bromo-3-ethoxycarbonylmethoxy-5-{3-[1-(2-methoxy-phenylcarbamoyl)-piperidin-4-ylmethoxy]-phenyl}-thiophene-2-carboxylic acid methyl ester (74 mg, 55%) was prepared according to the procedure in the third step of Scheme 21 of Example 217.

$^1$H NMR (400 MHz, CHLOROFORM-D) δ ppm 1.3 (t, J=7.2 Hz, 3 H) 1.4 (m, 2 H) 1.9 (m, 2 H) 3.0 (td, J=12.9, 2.5 Hz, 2 H) 3.9 (m, 8 H) 4.2 (d, J=13.1 Hz, 2 H) 4.3 (q, 2 H) 4.9 (s, 2 H) 6.9 (m, 1 H) 7.0 (m, 3 H) 7.2 (m, 2 H) 7.4 (t, J=8.1 Hz, 1 H) 8.2 (m, 1 H).

The fourth step of Scheme 21: 4-Bromo-3-ethoxycarbonylmethoxy-5-{3-[1-(2-methoxy-phenylcarbamoyl)-piperidin-4-ylmethoxy]-phenyl}-thiophene-2-carboxylic acid methyl ester was hydrolyzed according to the procedure in the fourth step of Scheme 21 of Example 210 to afford 56 mg (81%) of 4-bromo-3-carboxymethoxy-5-{3-[1-(2-methoxy-phenylcarbamoyl)-piperidin-4-ylmethoxy]-phenyl}-thiophene-2-carboxylic acid.

$^1$H NMR (400 MHz, DMSO-D6) δ ppm 1.2 (m, 2 H) 1.8 (dd, J=12.5, 1.9 Hz, 2 H) 2.9 (td, 2 H) 3.8 (s, 3 H) 3.9 (d, J=6.3

Hz, 2 H) 4.1 (d, J=12.1 Hz, 2 H) 4.9 (s, 2 H) 6.9 (m, 1 H) 7.0 (m, 2 H) 7.1 (dd, 1 H) 7.2 (m, 2 H) 7.4 (t, J=8.0 Hz, 1 H) 7.7 (dd, 1 H).

EXAMPLE 222

4-Bromo-3-carboxymethoxy-5-{3-[1-(2-isopropyl-phenylcarbamoyl)-piperidin-4-ylmethoxy]-phenyl}-thiophene-2-carboxylic acid The third step of Scheme 21: 4-Bromo-3-ethoxycarbonyl-methoxy-5-{3-[1-(2-isopropyl-phenylcarbamoyl)-piperidin-4-ylmethoxy]-phenyl}-thiophene-2-carboxylic acid methyl ester (72 mg, 53%) was prepared according to the procedure in the third step of Scheme 21 of Example 217.

$^1$H NMR (400 MHz, CHLOROFORM-D) δ ppm 1.3 (m, 6 H) 1.3 (t, J=7.1 Hz, 3 H) 1.4 (m, 2 H) 1.9 (m, 2 H) 2.1 (m, 1 H) 3.0 (m, 3 H) 3.9 (m, 5 H) 4.1 (m, 2 H) 4.3 (q, J=7.2 Hz, 2 H) 4.9 (s, 2 H) 7.0 (m, 1 H) 7.2 (m, 3 H) 7.2 (m, 2 H) 7.4 (t, 1 H) 7.5 (m, J=8.0, 1.4 Hz, 1 H).

The fourth step of Scheme 21: 4-Bromo-3-ethoxycarbonylmethoxy-5-{3-[1-(2-isopropyl-phenylcarbamoyl)-piperidin-4-ylmethoxy]-phenyl}-thiophene-2-carboxylic acid methyl ester was hydrolyzed according to the procedure in the fourth step of Scheme 21 of Example 210 to afford 15 mg (22%) of 4-bromo-3-carboxymethoxy-5-{3-[1-(2-isopropyl-phenylcarbamoyl)-piperidin-4-ylmethoxy]-phenyl}-thiophene-2-carboxylic acid.

$^1$H NMR (400 MHz, MeOD) δ ppm 1.1 (d, J=6.8 Hz, 6 H) 1.3 (dd, J=12.9, 3.5 Hz, 2 H) 1.8 (d, J=13.9 Hz, 2 H) 2.9 (td, J=12.7, 1.9 Hz, 2 H) 3.9 (d, J=6.1 Hz, 2 H) 4.1 (d, J=13.1 Hz, 2 H) 7.0 (dd, 1 H) 7.1 (m, 5 H) 7.2 (dd, J=7.5, 0.9 Hz, 1 H) 7.3 (t, J=8.1 Hz, 1 H).

EXAMPLE 223

4-Bromo-3-carboxymethoxy-5-{3-[1-(2-phenoxy-phenylcarbamoyl)-piperidin-4-ylmethoxy]-phenyl}-thiophene-2-carboxylic acid The third step of Scheme 21: 4-Bromo-3-ethoxycarbonyl-methoxy-5-{3-[1-(2-phenoxy-phenylcarbamoyl)-piperidin-4-ylmethoxy]-phenyl}-thiophene-2-carboxylic acid methyl ester (79 mg, 54%) was prepared according to the procedure in the third step of Scheme 21 of Example 217.

$^1$H NMR (400 MHz, CHLOROFORM-D) δ ppm 1.3 (t, 3 H) 1.9 (m, 2 H) 2.9 (td, J=12.9, 2.5 Hz, 2 H) 3.8 (d, J=6.3 Hz, 2 H) 3.9 (s, 3 H) 4.0 (m, 2 H) 4.3 (q, J=7.2 Hz, 2 H) 4.9 (s, 2 H) 6.9 (m, 6 H) 7.1 (m, 4 H) 7.3 (m, 3 H) 8.2 (dd, J=8.1, 1.5 Hz, 1 H).

The fourth step of Scheme 21: 4-Bromo-3-ethoxycarbon-ylmethoxy-5-{3-[1-(2-phenoxy-phenylcarbamoyl)-piperi-din-4-ylmethoxy]-phenyl}-thiophene-2-carboxylic acid methyl ester was hydrolyzed according to the procedure in the fourth step of Scheme 21 of Example 210 to afford 4 mg (5%) of 4-bromo-3-carboxymethoxy-5-{3-[1-(2-phenoxy-phenyl-carbamoyl)-piperidin-4-ylmethoxy]-phenyl}-thiophene-2-carboxylic acid.

$^1$H NMR (400 MHz, DMSO-D6) δ ppm 1.0 (dd, J=11.4, 3.8 Hz, 2 H) 1.7 (dd, J=12.9, 2.5 Hz, 2 H) 2.7 (td, J=12.4, 1.3 Hz, 2 H) 3.8 (d, J=6.3 Hz, 2 H) 4.0 (d, J=12.9 Hz, 2 H) 4.8 (s, 2 H) 6.9 (d, J=8.6 Hz, 2 H) 7.0 (dd, J=8.0, 1.6 Hz, 1 H) 7.1 (m, 7 H) 7.3 (t, 1 H) 7.4 (t, J=8.1 Hz, 1 H) 7.6 (dd, J=7.8, 1.8 Hz, 1 H).

EXAMPLE 224

4-Bromo-3-carboxymethoxy-5-{3-{1-(2,6-diethyl-phenylcarbamoyl)-piperidin-4-ylmethoxy]-phenyl}-thiophene-2-carboxylic acid The third step of Scheme 21: 4-Bromo-5-{3-[1-(2,6-di-ethyl-phenylcarbamoyl)-piperidin-4-ylmethoxy]-phenyl}-3-ethoxycarbonylmethoxy-thiophene-2-carboxylic acid methyl ester (75 mg, 53%) was prepared according to the procedure in the third step of Scheme 21 of Example 217.

$^1$H NMR (400 MHz, CHLOROFORM-D) δ ppm 1.2 (t, J=7.6 Hz, 6 H) 1.3 (t, J=7.2 Hz, 3 H) 1.4 (m, 2 H) 1.9 (m, J=10.4 Hz, 2 H) 2.1 (m, 1 H) 2.6 (q, J=7.6 Hz, 4 H) 3.0 (td, J=12.8, 2.4 Hz, 2 H) 3.9 (m, 5 H) 4.1 (m, 2 H) 4.3 (q, J=7.2 Hz, 2 H) 4.9 (s, 2 H) 7.0 (dd, J=8.0, 2.1 Hz, 1 H) 7.1 (m, J=7.1 Hz, 2 H) 7.2 (m, 2 H) 7.2 (m, J=7.6 Hz, 1 H) 7.4 (t, 1 H).

The fourth step of Scheme 21: 4-Bromo-5-{3-[1-(2,6-di-ethyl-phenylcarbamoyl)-piperidin-4-ylmethoxy]-phenyl}-3-ethoxycarbonylmethoxy-thiophene-2-carboxylic acid methyl ester was hydrolyzed according to the procedure in the fourth step of Scheme 21 of Example 210 to afford 18 mg (26%) of 4-bromo-3-carboxymethoxy-5-{3-[1-(2,6-diethyl-phenylcarbamoyl)-piperidin-4-ylmethoxy]-phenyl}-thiophene-2-carboxylic acid.

$^1$H NMR (400 MHz, DMSO-D6) δ ppm 1.1 (t, J=7.5 Hz, 6 H) 1.3 (dd, J=12.6, 2.5 Hz, 2 H) 1.8 (dd, J=12.8, 2.1 Hz, 2 H) 2.5 (q, 4 H) 3.9 (d, J=6.1 Hz, 2 H) 4.1 (d, J=13.4 Hz, 2 H) 7.1 (m, 4 H) 7.2 (m, 2 H) 7.4 (t, J=8.1 Hz, 1 H).

EXAMPLE 225

4-Bromo-3-carboxymethoxy-5-{3-[1-(2,4,6-trim-ethyl-phenylcarbamoyl)-piperidin-4-ylmethoxy]-phenyl}-thiophene-2-carboxylic acid The third step of Scheme 21: 4-Bromo-3-ethoxycarbonyl-methoxy-5-{3-[1-(2,4,6-trimethyl-phenylcarbamoyl)-pip-eridin-4-ylmethoxy]-phenyl}-thiophene-2-carboxylic acid methyl ester (64 mg, 47%) was prepared according to the procedure in the third step of Scheme 21 of Example 217.

$^1$H NMR (400 MHz, CHLOROFORM-D) δ ppm 1.3 (t, J=7.2 Hz, 3 H) 1.4 (m, 2 H) 1.9 (m, 2 H) 2.2 (s, 6 H) 2.2 (s, 3 H) 2.9 (td, J=12.9, 2.3 Hz, 2 H) 3.9 (m, 5 H) 4.3 (q, J=7.2 Hz, 2 H) 4.9 (s, 2 H) 6.9 (s, 2 H) 7.0 (dd, J=8.0, 2.1 Hz, 1 H) 7.2 (t, 1 H) 7.2 (m, 1 H) 7.4 (t, 1 H).

The fourth step of Scheme 21: 4-Bromo-3-ethoxycarbon-ylmethoxy-5-{3-[1-(2,4,6-trimethyl-phenylcarbamoyl)-pip-eridin-4-ylmethoxy]-phenyl}-thiophene-2-carboxylic acid methyl ester was hydrolyzed according to the procedure in the fourth step of Scheme 21 of Example 210 to afford 18.6 mg (31%) of 4-bromo-3-carboxymethoxy-5-{3-[1-(2,4,6-trim-ethyl-phenylcarbamoyl)-piperidin-4-ylmethoxy]-phenyl}-thiophene-2-carboxylic acid.

$^1$H NMR (400 MHz, MeOD) δ ppm 1.3 (td, J=12.4, 3.7 Hz, 2 H) 1.8 (dd, J=13.3, 2.1 Hz, 2 H) 2.1 (s, 6 H) 2.1 (s, 3 H) 2.9 (td, 2 H) 3.8 (d, J=6.1 Hz, 2 H) 4.1 (d, J=13.6 Hz, 2 H) 4.8 (s, 2 H) 6.8 (s, 2 H) 6.9 (dt, 1 H) 7.1 (m, J=7.2, 1.1 Hz, 2 H) 7.3 (t, J=8.2 Hz, 1 H).

EXAMPLE 226

4-Bromo-3-carboxymethoxy-5-{3-[1-(2-isopropyl-6-methyl-phenylcarbamoyl)-piperidin-4-ylmethoxy]-phenyl}-thiophene-2-carboxylic acid The third step of Scheme 21: 4-Bromo-3-ethoxycarbonylmethoxy-5-{3-[1-(2-isopropyl-6-methyl-phenylcarbamoyl)-piperidin-4-ylmethoxy]-phenyl}-thiophene-2-carboxylic acid methyl ester (75 mg, 54%) was prepared according to the procedure in the third step of Scheme 21 of Example 217.

$^1$H NMR (400 MHz, CHLOROFORM-D) δ ppm 1.2 (d, J=6.8 Hz, 6 H) 1.3 (t, J=7.2 Hz, 3 H) 1.4 (m, 2 H) 1.9 (m, 2 H) 2.2 (s, 3 H) 2.9 (m, 2 H) 3.2 (m, 1 H) 3.9 (m, 5 H) 4.2 (m, 2 H) 4.3 (q, J=7.2 Hz, 2 H) 4.9 (dd, 2 H) 7.0 (dd, 1 H) 7.0 (m, J=4.7, 4.7 Hz, 1 H) 7.1 (m, 2 H) 7.2 (t, 1 H) 7.2 (m, J=7.6 Hz, 1 H) 7.4 (t, J=8.0 Hz, 1 H).

The fourth step of Scheme 21: 4-Bromo-3-ethoxycarbonylmethoxy-5-{3-[1-(2-isopropyl-6-methyl-phenylcarbamoyl)-piperidin-4-ylmethoxy]-phenyl}-thiophene-2-carboxylic acid methyl ester was hydrolyzed according to the procedure in the fourth step of Scheme 21 of Example 210 to afford 8.3 mg (12%) of 4-bromo-3-carboxymethoxy-5-{3-[1-(2-isopropyl-6-methyl-phenylcarbamoyl)-piperidin-4-ylmethoxy]-phenyl}-thiophene-2-carboxylic acid.

$^1$H NMR (400 MHz, MeOD) δ ppm 1.1 (d, J=7.1. Hz, 6 H) 1.4 (td, 2 H) 1.8 (dd, J=12.9, 2.0 Hz, 2 H) 2.1 (s, 3 H) 2.9 (td, J=12.9, 2.1 Hz, 2 H) 3.1 (m, 2 H) 3.8 (d, J=6.1 Hz, 2 H) 4.1 (d, J=13.6 Hz, 2 H) 7.0 (m, 2 H) 7.1 (m, 2 H) 7.3 (t, J=7.8 Hz, 1 H).

EXAMPLE 227

4-Bromo-3-carboxymethoxy-5-{3-[1-(3-phenoxy-phenylcarbamoyl)-piperidin-4-ylmethoxy]-phenyl}-thiophene-2-carboxylic acid The third step of Scheme 21: 4-Bromo-3-ethoxycarbonylmethoxy-5-{3-[1-(3-phenoxy-phenylcarbamoyl)-piperidin-4-ylmethoxy]-phenyl}-thiophene-2-carboxylic acid methyl ester (79 mg, 54%) was prepared according to the procedure in the third step of Scheme 21 of Example 217.

$^1$H NMR (400 MHz, CHLOROFORM-D) δ ppm 1.3 (t, 3 H) 1.4 (m, 2 H) 1.9 (m, 2 H) 2.9 (m, 2 H) 3.8 (m, 5 H) 4.3 (q, 2 H) 4.9 (m, 2 H) 6.6 (m, 3 H) 7.3 (m, 10 H).

The fourth step of Scheme 21: 4-Bromo-3-ethoxycarbonylmethoxy-5-{3-[1-(3-phenoxy-phenylcarbamoyl)-piperidin-4-ylmethoxy]-phenyl}-thiophene-2-carboxylic acid methyl ester was hydrolyzed according to the procedure in the fourth step of Scheme 21 of Example 210 to afford 11.5 mg (16%) of 4-bromo-3-carboxymethoxy-5-{3-[1-(3-phenoxy-phenylcarbamoyl)-piperidin-4-ylmethoxy]-phenyl}-thiophene-2-carboxylic acid.

$^1$H NMR (400 MHz, MeOD) δ ppm 1.3 (dd, J=11.4, 4.0 Hz, 2 H) 1.8 (dt, J=13.7, 1.9 Hz, 2 H) 2.8 (tt, 2 H) 3.8 (d, J=6.3 Hz, 2 H) 4.1 (d, J=13.9 Hz, 2 H) 4.8 (s, 2 H) 6.5 (dt, 1 H) 7.0 (m, 6 H) 7.1 (m, 3 H) 7.3 (m, 3 H).

EXAMPLE 228

4-Bromo-3-carboxymethoxy-5-{3-[1-(2,6-dimethyl-phenylcarbamoyl)-piperidin-4-ylmethoxy]-phenyl}-thiophene-2-carboxylic acid The third step of Scheme 21: 4-Bromo-5-{3-[1-(2,6-dimethyl-phenylcarbamoyl)-piperidin-4-ylmethoxy]-phenyl}-3-ethoxycarbonylmethoxy-thiophene-2-carboxylic acid methyl ester (50 mg, 43%) was prepared according to the procedure in the third step of Scheme 21 of Example 217.

$^1$H NMR (400 MHz, CHLOROFORM-D) δ ppm 1.3 (t, J=7.2 Hz, 3 H) 1.4 (m, 3 H) 1.9 (dd, J=12.8, 2.1 Hz, 2 H) 2.2 (s, 6 H) 3.0 (td, J=12.9, 2.5 Hz, 2 H) 3.9 (m, 5 H) 4.2 (m, 2 H) 4.3 (q, J=7.1 Hz, 2 H) 4.9 (s, 2 H) 7.0 (dd, 1 H) 7.0 (s, 3 H) 7.2 (t, 1 H) 7.2 (m, J=8.3 Hz, 1 H) 7.4 (t, J=8.0 Hz, 1 H).

The fourth step of Scheme 21: 4-Bromo-5-{3-[1-(2,6-dimethyl-phenylcarbamoyl)-piperidin-4-ylmethoxy]-phenyl}-3-ethoxycarbonylmethoxy-thiophene-2-carboxylic acid methyl ester was hydrolyzed according to the procedure in the fourth step of Scheme 21 of Example 210 to afford 30 mg (64%) of 4-bromo-3-carboxymethoxy-5-{3-[1-(2,6-dimethyl-phenylcarbamoyl)-piperidin-4-ylmethoxy]-phenyl}-thiophene-2-carboxylic acid.

$^1$H NMR (400 MHz, DMSO-D6) δ ppm 1.3 (m, 3 H) 1.8 (dt, 2 H) 2.1 (s, 6 H) 2.8 (tt, 2 H) 3.9 (d, J=6.3 Hz, 2 H) 4.9 (s, 2 H) 7.1 (m, 4 H) 7.2 (m, 2 H) 7.4 (t, J=8.2 Hz, 1 H) 7.8 (s, 1 NH).

EXAMPLE 229

4-Bromo-3-carboxymethoxy-5-{3-[1-(4-methyl-2-nitro-phenylcarbamoyl)-piperidin-4-ylmethoxy]-phenyl}-thiophene-2-carboxylic acid The third step of Scheme 21: 4-Bromo-3-ethoxycarbonylmethoxy-5-{3-[1-(4-methyl-2-nitro-phenylcarbamoyl)-piperidin-4-ylmethoxy]-phenyl}-thiophene-2-carboxylic acid methyl ester (40 mg, 33%) was prepared according to the procedure in the third step of Scheme 21 of Example 217.

$^1$H NMR (400 MHz, CHLOROFORM-D) δ ppm 1.3 (t, J=7.1 Hz, 3 H) 1.4 (m, 2 H) 2.0 (dd, J=13.0, 2.4 Hz, 2 H) 2.1 (m, 1 H) 2.4 (s, 3 H) 3.0 (td, J=12.9, 2.3 Hz, 2 H) 3.9 (m, 5 H) 4.3 (m, 4 H) 4.9 (s, 2 H) 7.0 (m, 1 H) 7.2 (t, 1 H) 7.2 (m, 1 H) 7.4 (t, J=8.1 Hz, 1 H) 7.4 (dd, J=8.8, 2.0 Hz, 1 H) 8.0 (m, J=1.0 Hz, 1 H) 8.5 (d, J=8.6 Hz, 1 H).

The fourth step of Scheme 21: 4-Bromo-3-ethoxycarbonylmethoxy-5-{3-[1-(4-methyl-2-nitro-phenylcarbamoyl)-piperidin-4-ylmethoxy]-phenyl}-thiophene-2-carboxylic acid methyl ester was hydrolyzed according to the procedure in the fourth step of Scheme 21 of Example 210 to afford 15.4 mg (41%) of 4-bromo-3-carboxymethoxy-5-{3-[1-(4-methyl-2-nitro-phenylcarbamoyl)-piperidin-4-ylmethoxy]-phenyl}-thiophene-2-carboxylic acid.

$^1$H NMR (400 MHz, MeOD) δ ppm 1.4 (m, 2 H) 1.9 (m, 2 H) 2.1 (m, 1 H) 2.3 (m, 3 H) 3.0 (td, 2 H) 3.9 (d, 2 H) 4.1 (m, 2 H) 4.8 (s, 2 H) 7.0 (m, 1 H) 7.1 (m, 2 H) 7.3 (t, 1 H) 7.4 (dd, 1 H) 7.9 (m, 2 H).

EXAMPLE 230

4-Bromo-3-carboxymethoxy-5-{3-[1-(5-chloro-2-nitro-phenylcarbamoyl)-piperidin-4-ylmethoxy]-phenyl}-thiophene-2-carboxylic acid The third step of Scheme 21: 4-Bromo-5-{3-[1-(5-chloro-2-nitro-phenylcarbamoyl)-piperidin-4-ylmethoxy]-phenyl}-3-ethoxycarbonylmethoxy-thiophene-2-carboxylic acid methyl ester (20 mg, 16%) was prepared according to the procedure in the third step of Scheme 21 of Example 217.

$^1$H NMR (400 MHz, CHLOROFORM-D) δ ppm 1.3 (t, 3 H) 1.5 (m, 2 H) 2.0 (m, 2 H) 3.0 (m, 2 H) 3.9 (m, 5 H) 4.3 (m, 4 H) 4.8 (m, 2 H) 7.0 (m, 2 H) 7.2 (m, 3 H) 7.4 (t, 1 H) 8.2 (d, 1 H) 8.2 (dd, 1 H).

The fourth step of Scheme 21: 4-Bromo-5-{3-[1-(5-chloro-2-nitro-phenylcarbamoyl)-piperidin-4-ylmethoxy]- phenyl}-3-ethoxycarbonylmethoxy-thiophene-2-carboxylic acid methyl ester was hydrolyzed according to the procedure in the fourth step of Scheme 21 of Example 210 to afford 3 mg (16%) of 4-bromo-3-carboxymethoxy-5-{3-[1-(5-chloro-2-nitro-phenylcarbamoyl)-piperidin-4-ylmethoxy]-phenyl}-thiophene-2-carboxylic acid.

$^1$H NMR (400 MHz, DMSO-D6) δ ppm 1.5 (m, 2 H) 2.0 (m, 2 H) 3.0 (m, 2 H) 3.9 (d, 2 H) 4.3 (m, 4 H) 4.8 (m, 2 H) 6.9 (m, 2 H) 7.0 (m, 3 H) 7.2 (t, 1 H) 7.3 (d, 1 H) 7.5 (dd, 1 H).

EXAMPLE 231

4-Bromo-3-carboxymethoxy-5-{3-[1-(2-nitro-phenylcarbamoyl)-piperidin-4-ylmethoxy]-phenyl}-thiophene-2-carboxylic acid The third step of Scheme 21: 4-Bromo-3-ethoxycarbonylmethoxy-5-{3-[1-(2-nitro-phenylcarbamoyl)-piperidin-4-ylmethoxy]-phenyl}-thiophene-2-carboxylic acid methyl ester (40 mg, 34%) was prepared according to the procedure in the third step of Scheme 21 of Example 217.

$^1$H NMR (400 MHz, CHLOROFORM-D) δ ppm 1.3 (t, 3 H) 1.5 (m, 2 H) 2.0 (m, 2 H) 3.0 (m, 2 H) 3.9 (m, 5 H) 4.3 (m, 4 H) 4.8 (m, 2 H) 7.0 (m, 2 H) 7.2 (m, 4 H) 7.2 (t, 1 H) 7.9 (d, 1 H) 8.2 (dd, 1 H).

The fourth step of Scheme 21: 4-Bromo-3-ethoxycarbonylmethoxy-5-{3-[1-(2-nitro-phenylcarbamoyl)-piperidin-4-ylmethoxy]-phenyl}-thiophene-2-carboxylic acid methyl ester was hydrolyzed according to the procedure in the fourth step of Scheme 21 of Example 210 to afford 25 mg (67%) of 4-bromo-3-carboxymethoxy-5-{3-[1-(2-nitro-phenylcarbamoyl)-piperidin-4-ylmethoxy]-phenyl}-thiophene-2-carboxylic acid.

$^1$H NMR (400 MHz, DMSO-D6) δ ppm 1.3 (m, 2 H) 1.8 (m, 2 H) 2.9 (m, 2 H) 3.9 (d, 2 H) 4.1 (m, 2 H) 4.8 (m, 2 H) 7.1 (dd, 1 H) 7.2 (m, 3 H) 7.4 (t, 1 H) 7.7 (m, 2 H) 7.9 (dd, 1 H).

EXAMPLE 232

4-Bromo-3-carboxymethoxy-5-(3-phenylaminomethyl-phenyl)-thiophene-2-carboxylic acid The first step of Scheme 22: A microwave vessel was charged with 4,5-dibromo-3-ethoxycarbonylmethoxy-thiophene-2-carboxylic acid methyl ester (201 mg, 0.5 mmole), 3-formylbenzeneboronic acid (93 mg, 0.6 mmole), Pd(PPh$_3$)$_4$ (29 mg, 5 mol %), and potassium fluoride (87 mg, 1.5 mmole). The vessel was capped and flushed with argon. 2.5 mL THF was added and the vessel heated to 150° C. under microwave conditions for 20 minutes. The reaction mixture was then partition between ether and saturated sodium bicarbonate solution. The organic layer was washed with water, brine, and dried (MgSO$_4$). Filtration and evaporation yielded the crude product which was then purified by chromatography on silica gel using a gradient of hexane/EtOAc (5 to 35%) as eluent. Pure fractions were combined and evaporated to give 126 mg (59%) 4-bromo-3-ethoxycarbonylmethoxy-5-(3-formyl-phenyl)-thiophene-2-carboxylic acid methyl ester as a white solid.

$^1$H NMR (400 MHz, CHLOROFORM-D) δ ppm 1.33 (t, J=7.07 Hz, 3 H) 3.89 (s, 3 H) 4.30 (q, J=7.07 Hz, 2 H) 4.95 (s, 2 H) 7.65 (t, J=7.71 Hz, 1 H) 7.95 (m, 2 H) 8.17 (s, 1 H) 10.08 (s, 1 H).

The second step of Scheme 22: To a 1.5 mL DCE solution of 4-bromo-3-ethoxycarbonylmethoxy-5-(3-formyl-phenyl)-thiophene-2-carboxylic acid methyl ester (43 mg, 0.1 mmole) was added aniline (14 µL, 0.15 mmole), acetic acid (10 µL, 0.15 mmole) and sodium triacetoxyborohydride (32 mg, 0.15 mmole) and the reaction mixture stirred at room temperature overnight. The reaction mixture was diluted with CH$_2$Cl$_2$ and washed with saturated sodium bicarbonate solution and dried (MgSO$_4$). Filtration and evaporation yielded the crude product which was then purified by chromatography on silica gel using a gradient of hexane/EtOAc (5 to 35%) as eluent. Pure fractions were combined and evaporated to give 35 mg (69%) 4-bromo-3-ethoxycarbonylmethoxy-5-(3-phenylaminomethyl-phenyl)-thiophene-2-carboxylic acid methyl ester as a colorless oil.

$^1$H NMR (400 MHz, CHLOROFORM-D) δ ppm 1.31 (t, J=7.07 Hz, 3 H) 3.87 (s, 3 H) 4.29 (q, J=7.16 Hz, 2 H) 4.41 (s, 2 H) 4.90 (s, 2 H) 6.64 (dd, J=8.59, 1.01 Hz, 2 H) 6.73 (m, 1 H) 7.17 (m, 2 H) 7.44 (m, 2 H) 7.56 (dt, J=6.76, 1.93 Hz, 1 H) 7.67 (s, 1 H).

The fourth step of Scheme 22: 4-Bromo-3-ethoxycarbonylmethoxy-5-(3-phenylaminomethyl-phenyl)-thiophene-2-carboxylic acid methyl ester (35 mg, 6.9×10$^{-5}$ mmole) was dissolved in 1.5 mL of a 2:1 mixture of THF:H$_2$O and LiOH.H$_2$O (15 mg, 0.35 mmol) was added and the mixture stirred at room temperature overnight. The reaction mixture was then evaporated and the residue re-dissolved in 2-3 mL of H$_2$O. It was acidified dropwise with 1N HCl while stirring. A solid emerged that was filtered, washed with water, and vacuum oven-dried to give 29 mg (91%) of 4-bromo-3-carboxymethoxy-5-(3-phenylaminomethyl-phenyl)-thiophene-2-carboxylic acid as a white solid.

$^1$H NMR (400 MHz, DMSO-D6) δ ppm 4.34 (s, 2 H) 4.88 (s, 2 H) 6.51 (t, J=7.20 Hz, 1 H) 6.58 (d, J=7.58 Hz, 2 H) 7.04 (t, J=7.96 Hz, 2 H) 7.48 (m, 2 H) 7.54 (m, 1 H) 7.65 (s, 1 H).

SI-MS: m/e=461 [M−H]$^-$.

EXAMPLE 233

4-Bromo-3-carboxymethoxy-5-{3-[(3-trifluoromethyl-phenylamino)-methyl]-phenyl}-thiophene-2-carboxylic acid The second step of Scheme 22: To 4-bromo-3-ethoxycarbonylmethoxy-5-(3-formyl-phenyl)-thiophene-2-carboxylic acid methyl ester (43 mg, 0.1 mmol), 3-trifluoromethylaniline (16 µL, 0.13 mmol) and acetic acid (9 µL, 0.15 mmol) in 1,2-dichloroethane (1 mL) was added sodium triacetoxyborohydride (53 mg, 0.25 mmol). The reaction was stirred vigorously at room temperature for 3 hours and then diluted with dichloromethane (50 mL). The organic layer was washed with aqueous sodium bicarbonate (20 mL). The organic layer was dried over magnesium sulfate and filtered. The solvent was removed under reduced pressure. The material was purified by CombiFlash column chromatography eluting with a 20-60% ethyl acetate-hexane gradient to give 57 mg (99%) of 4-bromo-3-ethoxycarbonylmethoxy-5-{3-[(3-trifluoromethyl-phenylamino)-methyl]-phenyl}-thiophene-2-carboxylic acid methyl ester as a white solid.

$^1$H NMR (400 MHz, CHLOROFORM-D) δ ppm 1.32 (t, J=7.20 Hz, 3 H) 3.88 (s, 3 H) 4.12 (d, J=5.05 Hz, 1 H) 4.29 (q, J=7.24 Hz, 2 H) 4.35 (d, J=5.56 Hz, 2 H) 4.91 (s, 2 H) 6.30 (m, 1 H) 6.41 (m, 1 H) 6.95 (m, 1 H) 7.43 (m, 3 H) 7.57 (m, 1 H) 7.64 (s, 1 H).

The fourth step of Scheme 22: 4-Bromo-3-carboxymethoxy-5-{3-[(3-trifluoromethyl-phenylamino)-methyl]-phenyl}-thiophene-2-carboxylic acid was prepared following the procedure in the fourth step of Scheme 22 of Example 232 to give 41 mg (77%) of 4-bromo-3-carboxymethoxy-5-{3-[(3-trifluoromethyl-phenylamino)-methyl]-phenyl}-thiophene-2-carboxylic acid as a light yellow solid.

$^1$H NMR (400 MHz, DMSO-D6) δ ppm 4.33 (s, 2 H) 4.88 (s, 2 H) 6.38 (m, 1 H) 6.55 (m, 2 H) 7.09 (m, 1 H) 7.49 (m, 2 H) 7.56 (m, 1 H) 7.65 (s, 1 H).

EXAMPLE 234

4-Bromo-3-carboxymethoxy-5-{3-[(3,4-difluoro-phenylamino)-methyl]-phenyl}-thiophene-2-carboxylic acid The second step of Scheme 22: 4-Bromo-5-{3-[(3,4-difluoro-phenylamino)-methyl]-phenyl}-3-ethoxycarbonylmethoxy-thiophene-2-carboxylic acid methyl ester was prepared following the procedure in the second step of Scheme 22 of Example 233 to give 37 mg (62%) of off white solid.

$^1$H NMR R (400 MHz, CHLOROFORM-D) δ ppm 1.32 (t, J=7.20 Hz, 3 H) 3.88 (s, 3 H) 4.29 (q, J=7.24 Hz, 2 H) 4.32 (m, 1 H) 4.43 (d, J=5.56 Hz, 2 H) 4.91 (s, 2 H) 6.76 (dd, J=8.34, 2.27 Hz, 1 H) 6.86 (s, 1 H) 6.96 (d, J=7.58 Hz, 1 H) 7.26 (m, 1 H) 7.44 (m, 1 H) 7.58 (m, 1 H) 7.66 (s, 1 H).

The fourth step of Scheme 22: 4-Bromo-3-carboxymethoxy-5-{3-[(3,4-difluoro-phenylamino)-methyl]-phenyl}-thiophene-2-carboxylic acid was prepared following the procedure in the fourth step of Scheme 22 of Example 232 to give 33 mg (95%) of 4-bromo-3-carboxymethoxy-5-{3-[(3,4-difluoro-phenylamino)-methyl]-phenyl}-thiophene-2-carboxylic acid as a white solid.

$^1$H NMR (400 MHz, CD$_3$OD) δ ppm 4.44 (s, 2 H) 4.86 (s, 2 H) 6.82 (m, 3 H) 7.21 (t, J=7.83 Hz, 1 H) 7.49 (m, 3 H) 7.69 (s, 1 H).

EXAMPLE 235

4-Bromo-3-carboxymethoxy-5-(3-cyclohexylaminomethyl-phenyl)-thiophene-2-carboxylic acid The second step of Scheme 22: 4-Bromo-5-(3-cyclohexylaminomethyl-phenyl)-3-ethoxycarbonylmethoxy-thiophene-2-carboxylic acid methyl ester (37 mg, 99%) was prepared as an off white solid following the procedure in the second step of Scheme 22 of Example 233.

$^1$H NMR (400 MHz, CHLOROFORM-D) δ ppm 1.23 (m, 8 H) 1.32 (t, J=7.20 Hz, 3 H) 1.61 (d, J=13.89 Hz, 1 H) 1.73 (d, J=3.54 Hz, 2 H) 1.94 (d, J=13.39 Hz, 2 H) 2.51 (m, 1 H) 3.88 (m, 3 H) 4.30 (q, J=7.07 Hz, 2 H) 4.91 (s, 2 H) 7.42 (s, 1 H) 7.54 (m, 1 H) 7.62 (s, 1 H).

The fourth step of Scheme 22: 4-Bromo-3-carboxymethoxy-5-(3-cyclohexylaminomethyl-phenyl)-thiophene-2-carboxylic acid was prepared following the procedure in the fourth step of Scheme 22 of Example 232 to give 37 mg (86%) of 4-bromo-3-carboxymethoxy-5-(3-cyclohexylaminomethyl-phenyl)-thiophene-2-carboxylic acid as a white solid.

$^1$H NMR (400 MHz, DMSO-D6) δ ppm 1.21 (m, 5 H) 1.61 (d, J=16.93 Hz, 1 H) 1.80 (m, 2 H) 2.11 (m, 2 H) 3.01 (m, 1 H) 4.23 (s, 2 H) 4.65 (s, 2 H) 7.69 (m, 4 H).

EXAMPLE 236

4-Bromo-3-carboxymethoxy-5-{3-[(3-nitro-phenylamino)-methyl]-phenyl}-thiophene-2-carboxylic acid The second step of Scheme 22: 4-Bromo-3-ethoxycarbonylmethoxy-5-{3-[(3-nitro-phenylamino)-methyl]-phenyl}-thiophene-2-carboxylic acid methyl ester (36 mg, 66%) was prepared as an off white solid following the procedure in the second step of Scheme 22 of Example 233.

$^1$H NMR (400 MHz, CHLOROFORM-D) δ ppm 1.32 (t, J=7.20 Hz, 3 H) 3.88 (s, 3 H) 4.29 (q, J=7.07 Hz, 2 H) 4.47 (d, J=3.54 Hz, 2 H) 4.91 (s, 2 H) 6.90 (m, 1 H) 7.28 (m, 1 H) 7.45 (m, 3 H) 7.57 (m, 2 H) 7.66 (s, 1 H).

The fourth step of Scheme 22: 4-Bromo-3-carboxymethoxy-5-{3-[(3-nitro-phenylamino)-methyl]-phenyl}-thiophene-2-carboxylic acid was prepared following the procedure in the fourth step of Scheme 22 of Example 232 to give 33 mg (99%) of 4-bromo-3-carboxymethoxy-5-{3-[(3-nitro-phenylamino)-methyl]-phenyl}-thiophene-2-carboxylic acid as a bright yellow powder.

$^1$H NMR (400 MHz, DMSO-D6) δ ppm 4.45 (m, 2 H) 4.87 (s, 2 H) 7.03 (m, 1 H) 7.09 (m, 1 H) 7.34 (m, 1 H) 7.39 (t, J=2.15 Hz, 1 H) 7.50 (d, J=5.05 Hz, 2 H) 7.57 (s, 1 H) 7.67 (s, 1 H).

EXAMPLE 237

4-Bromo-5-{3-r(4-bromo-3-trifluoromethyl-phenylamino)-methyl]-phenyl}-3-carboxymethoxy-thiophene-2-carboxylic acid The second step of Scheme 22: 4-Bromo-5-{3-[(4-bromo-3-trifluoromethyl-phenylamino)-methyl]-phenyl}-3-ethoxycarbonylmethoxy-thiophene-2-carboxylic acid methyl ester (21 mg, 36%) was prepared following the procedure in the second step of Scheme 22 of Example 233.

$^1$H NMR (400 MHz, CHLOROFORM-D) δ ppm 1.32 (t, J=7.07 Hz, 3 H) 3.88 (s, 3 H) 4.29 (q, J=7.16 Hz, 2 H) 4.37 (m, 1 H) 4.41 (m, 2 H) 4.92 (s, 2 H) 6.60 (dd, J=8.59, 3.03 Hz, 1 H) 6.95 (d, J=3.03 Hz, 1 H) 7.43 (m, 3 H) 7.58 (d, J=7.58 Hz, 1 H) 7.64 (s, 1 H).

The fourth step of Scheme 22: The procedure in the fourth step of Scheme 22 of Example 232 afforded 18 mg (98%) of 4-bromo-5-{3-[(4-bromo-3-trifluoromethyl-phenylamino)-methyl]-phenyl}-3-carboxymethoxy-thiophene-2-carboxylic acid as an off white solid.

$^1$H NMR (400 MHz, DMSO-D6) δ ppm 4.41 (m, 2 H) 4.86 (s, 2 H) 6.74 (dd, J=8.84, 2.53 Hz, 1 H) 7.04 (d, J=2.53 Hz, 1 H) 7.49 (m, 3 H) 7.55 (m, 1 H) 7.64 (s, 1 H).

EXAMPLE 238

4-Bromo-3-carboxymethoxy-5-{3-[(3,5-difluoro-phenylamino)-methyl]-phenyl}-thiophene-2-carboxylic acid The second step of Scheme 22: 4-Bromo-5-{3-[(3,5-difluoro-phenylamino)-methyl]-phenyl}-3-ethoxycarbonylmethoxy-thiophene-2-carboxylic acid methyl ester (24 mg, 54%) was prepared as a white solid following the procedure in the second step of Scheme 22 of Example 233.

$^1$H NMR (400 MHz, CHLOROFORM-D) δ ppm 1.32 (m, 3 H) 3.88 (m, 3 H) 4.30 (m, 2 H) 4.38 (s, 2 H) 4.91 (m, 2 H) 6.15 (m, 3 H) 7.44 (m, 2 H) 7.58 (m, 1 H) 7.64 (d, J=1.26 Hz, 1 H).

The fourth step of Scheme 22: The procedure of the fourth step of Scheme 22 of Example 232 afforded give 32 mg (95%) of 4-bromo-3-carboxymethoxy-5-{3-[(3,5-difluoro-phenylamino)-methyl]-phenyl}-thiophene-2-carboxylic acid as an off white solid.

$^1$H NMR (400 MHz, Solvent) δ ppm 4.38 (s, 2 H) 4.87 (s, 2 H) 6.05 (m, 1 H) 6.15 (dd, J=10.48, 2.15 Hz, 2 H) 7.46 (m, 2 H) 7.54 (m, 1 H) 7.67 (s, 1 H).

EXAMPLE 239

4-Bromo-3-carboxymethoxy-5-{3-[(3-fluoro-4-methyl-phenylamino)-methyl]-phenyl}-thiophene-2-carboxylic acid The second step of Scheme 22: 4-Bromo-3-ethoxycarbonylmethoxy-5-{3-[(3-fluoro-4-methyl-phenylamino)-methyl]-phenyl}-thiophene-2-carboxylic acid methyl ester (37 mg) was prepared as an off white solid following the procedure in the second step of Scheme 22 of Example 233.

$^1$H NMR (400 MHz, CHLOROFORM-D) δ ppm 1.32 (t, J=7.07 Hz, 3 H) 2.14 (d, J=1.52 Hz, 3 H) 3.88 (s, 3 H) 4.10 (s, 1 H) 4.29 (q, J=7.07 Hz, 2 H) 4.37 (d, J=5.56 Hz, 2 H) 4.91 (s, 2 H) 6.33 (m, 2 H) 6.94 (t, J=8.72 Hz, 1 H) 7.43 (d, J=5.31 Hz, 2 H) 7.56 (m, 1 H) 7.65 (s, 1 H).

The fourth step of Scheme 22: The procedure of the fourth step of Scheme 22 of Example 232 afforded 33 mg (98%) of 4-bromo-3-carboxymethoxy-5-{3-[(3-fluoro-4-methyl-phenylamino)-methyl]-phenyl}-thiophene-2-carboxylic acid as a white solid.

$^1$H NMR (400 MHz, Solvent) δ ppm 4.36 (s, 2 H) 4.87 (m, 2 H) 6.32 (m, 2 H) 6.88 (s, 1 H) 7.45 (m, 2 H) 7.52 (d, J=6.82 Hz, 1 H) 7.67 (s, 1 H).

EXAMPLE 240

4-Bromo-3-carboxymethoxy-5-{3-[(4-chloro-3-trifluoromethyl-phenylamino)-methyl]-phenyl}-thiophene-2-carboxylic acid The second step of Scheme 22: 4-Bromo-5-{3-[(4-chloro-3-trifluoromethyl-phenylamino)-methyl]-phenyl}-3-ethoxycarbonylmethoxy-thiophene-2-carboxylic acid methyl ester (27 mg, 64%) was prepared as an off white solid following the procedure in the second step of Scheme 22 of Example 233.

$^1$H NMR (400 MHz, CHLOROFORM-D) δ ppm 1.32 (t, J=7.20 Hz, 3 H) 3.88 (s, 3 H) 4.29 (q, J=7.07 Hz, 2 H) 4.37 (d, J=5.05 Hz, 1 H) 4.41 (m, 2 H) 4.91 (s, 2 H) 6.67 (dd, J=8.46, 2.91 Hz, 1 H) 6.93 (d, J=2.78 Hz, 1 H) 7.25 (m, 1 H) 7.44 (m, 2 H) 7.58 (m, 1 H) 7.64 (s, 1 H).

The fourth step of Scheme 22: The procedure of the fourth step of Scheme 22 of Example 232 afforded 22 mg (99%) of 4-bromo-3-carboxymethoxy-5-{3-[(4-chloro-3-trifluoromethyl-phenylamino)-methyl]-phenyl}-thiophene-2-carboxylic acid as a white solid.

$^1$H NMR (400 MHz, Solvent) δ ppm 4.43 (s, 2 H) 4.87 (s, 2 H) 6.74 (dd, J=8.72, 2.91 Hz, 1 H) 6.96 (d, J=2.78 Hz, 1 H) 7.22 (d, J=8.59 Hz, 1 H) 7.46 (m, 2 H) 7.53 (m,

EXAMPLE 241

4-Bromo-3-carboxymethoxy-5-{3-[(4-methyl-3-nitro-phenylamino)-methyl]-phenyl}-thiophene-2-carboxylic acid The second step of Scheme 22: 4-Bromo-3-ethoxycarbonylmethoxy-5-{3-[(4-methyl-3-nitro-phenylamino)-methyl]-phenyl}-thiophene-2-carboxylic acid methyl ester (20 mg, 39%) was prepared as an off white solid following the procedure in the second step of Scheme 22 of Example 233.

$^1$H NMR (400 MHz, CHLOROFORM-D) δ ppm 1.32 (t, J=7.20 Hz, 3 H) 3.88 (s, 3 H) 4.29 (q, J=7.16 Hz, 3 H) 4.43 (d, J=5.81 Hz, 2 H) 4.91 (s, 2 H) 6.76 (dd, J=8.46, 2.65 Hz, 1 H) 7.10 (d, J=8.34 Hz, 1 H) 7.24 (d, J=2.53 Hz, 1 H) 7.44 (m, 2 H) 7.58 (m, 1 H) 7.65 (s, 1 H).

The fourth step of Scheme 22: 4-Bromo-3-carboxymethoxy-5-{3-[(4-methyl-3-nitro-phenylamino)-methyl]-phenyl}-thiophene-2-carboxylic acid was prepared following the procedure in the fourth step of Scheme 22 of Example 232 to give 15 mg (81%) of 4-bromo-3-carboxymethoxy-5-{3-[(4-methyl-3-nitro-phenylamino)-methyl]-phenyl}-thiophene-2-carboxylic acid as an orange solid.

$^1$H NMR (400 MHz, Solvent) δ ppm 2.36 (s, 3 H) 4.43 (s, 2 H) 4.87 (s, 2 H) 6.83 (dd, J=8.21, 2.40 Hz, 1 H) 7.09 (d, J=8.34 Hz, 1 H) 7.16 (d, J=2.53 Hz, 1 H) 7.46 (m, 2 H) 7.53 (m, 1 H) 7.68 (s, 1 H).

EXAMPLE 242

5-{3-[(Acetyl-cyclohexyl-amino)-methyl]-phenyl}-4-bromo-3-carboxymethoxy-thiophene-2-carboxylic acid The first step of Scheme 22: 4-Bromo-3-ethoxycarbonylmethoxy-5-(3-formyl-phenyl)-thiophene-2-carboxylic acid methyl ester (240 mg, 56%) was prepared according to the procedure in the first step of Scheme 22 of Example 232 using 4,5-dibromo-3-ethoxycarbonylmethoxy-thiophene-2-carboxylic acid methyl ester (400 mg, 1.0 mmol) and 3-formylphenyl boronic acid (225 mg, 1.5 mmol) as the starting materials.

$^1$H NMR (400 MHz, CHLOROFORM-D) δ ppm 1.3 (t, J=7.2 Hz, 3 H) 3.9 (s, 3 H) 4.3 (q, J=7.3 Hz, 2 H) 4.9 (t, 2 H) 7.7 (t, J=7.8 Hz, 1 H) 8.0 (m, 2 H) 8.2 (t, J=1.5 Hz, 1 H) 10.1 (s, 1 H).

The second step of Scheme 22: To a solution of 4-bromo-3-ethoxycarbonylmethoxy-5-(3-formyl-phenyl)-thiophene-2-carboxylic acid methyl ester (193 mg, 0.45 mmol) and cyclohexylamine (0.079 mL, 0.69 mmol) in DCE was added HOAc (0.04 mL, 0.69 mmol) at room temperature. The resultant mixture was stirred at the same temperature for 5 min, and NaBH(OAc)$_3$ (144 mg, 0.69 mmol) was added in one portion. After vigorously stirring for 3 h, the reaction mixture was quenched with aq. NaHCO$_3$ and extracted with DCM. The combined organic layer was dried over MgSO$_4$ and concentrated. The crude product was purified on CombiFlash column eluted with EtOAc to give 4-bromo-5-(3-cyclohexylaminomethyl-phenyl)-3-ethoxycarbonylmethoxy-thiophene-2-carboxylic acid methyl ester (195 mg, 85%) as a colorless oil.

$^1$H NMR (400 MHz, CHLOROFORM-D) δ ppm 1.2 (m, 5 H) 1.3 (t, J=7.1 Hz, 3 H) 1.6 (m, 1 H) 1.8 (m, 2 H) 2.0 (m, 2 H) 2.6 (m, 1 H) 3.9 (s, 3 H) 3.9 (s, 2 H) 4.3 (q, J=7.2 Hz, 2 H) 4.9 (s, 2 H) 7.4 (t, J=7.6 Hz, 1 H) 7.5 (m, 1 H) 7.6 (m, 1 H) 7.6 (t, J=1.5 Hz, 1 H).

In similar fashion, 4-bromo-3-tert-butoxycarbonylmethoxy-5-(3-cyclohexylaminomethyl-phenyl)-thiophene-2-carboxylic acid methyl ester (195 mg, 86%) was prepared from 4-bromo-3-tert-butoxycarbonylmethoxy-5-(3-formyl-phenyl)-thiophene-2-carboxylic acid methyl ester (190 mg, 0.42 mmol).

The third step of Scheme 22: 5-{3-[(Acetyl-cyclohexyl-amino)-methyl]-phenyl}-4-bromo-3-tert-butoxycarbonylmethoxy-thiophene-2-carboxylic acid methyl ester (121 mg, 94%, a mixture of two tautomers) was prepared as a colorless oil according to the procedure in the first step of Scheme 4 of Example 22 using 4-bromo-3-tert-butoxycarbonylmethoxy-5-(3-cyclohexylaminomethyl-phenyl)-thiophene-2-carboxylic acid methyl ester (125 mg, 0.23 mmol) as the starting material.

The fourth step of Scheme 22: 5-{3-[(Acetyl-cyclohexyl-amino)-methyl]-phenyl}-4-bromo-3-carboxymethoxy-thiophene-2-carboxylic acid (41 mg, 78%, a mixture of two tautomers at room temperature) was prepared as a white solid according to the procedure in the second step of Scheme 2 of Example 1, using 5-{3-[(acetyl-cyclohexyl-amino)-methyl]-phenyl}-4-bromo-3-tert-butoxycarbonylmethoxy-thiophene-2-carboxylic acid methyl ester (60 mg, 0.102 mmol) as the starting material.

EXAMPLE 243

4-Bromo-3-carboxymethoxy-5-{3-[(cyclohexyl-methanesulfonyl-amino)-methyl]-phenyl}-thiophene-2-carboxylic acid The third step of Scheme 22: 4-Bromo-5-{3-[(cyclohexyl-methanesulfonyl-amino)-methyl]-phenyl}-3-ethoxycarbonylmethoxy-thiophene-2-carboxylic acid methyl ester (56 mg, 86%) was prepared as a colorless oil according to the procedure in the first step of Scheme 5 of Example 36, using 4-bromo-3-ethoxycarbonylmethoxy-5-(3-cyclohexylaminomethyl-phenyl)-thiophene-2-carboxylic acid methyl ester (56.5 mg, 0.11 mmol) as the starting material.

$^1$H NMR (400 MHz, CHLOROFORM-D) δ ppm 1.4 (m, 8 H) 1.6 (m, 1 H) 1.8 (m, 4 H) 2.9 (s, 3 H) 3.7 (m, 1 H) 3.9 (s, 3 H) 4.3 (q, J=7.2 Hz, 2 H) 4.4 (s, 2 H) 4.9 (s, 2 H) 7.4 (t, J=7.7 Hz, 1 H) 7.5 (m, 2 H) 7.7 (s, 1 H).

The fourth step of Scheme 22: 4-Bromo-3-carboxymethoxy-5-{3-[(cyclohexyl-methanesulfonyl-amino)-methyl]-phenyl}-thiophene-2-carboxylic acid (40 mg, 78%) was prepared as a white solid according to the procedure in the second step of Scheme 1 of Example 1 using 4-bromo-5-{3-[(cyclohexyl-methanesulfonyl-amino)-methyl]-phenyl}-3-ethoxycarbonylmethoxy-thiophene-2-carboxylic acid methyl ester (55 mg, 0.093 mmol) as the starting material.

$^1$H NMR (400 MHz, DMSO-D6) δ ppm 1.4 (m, 10 H) 3.0 (s, 3 H) 3.6 (m, 1 H) 4.4 (s, 2 H) 4.9 (s, 2 H) 7.5 (m, 2 H) 7.6 (m, 1 H) 7.7 (d, J=1.8 Hz, 1 H).

EXAMPLE 244

4-Bromo-3-carboxymethoxy-5-{3-[(cyclohexyl-methoxycarbonyl-amino)-methyl]-phenyl}-thiophene-2-carboxylic acid The third step of Scheme 22: 4-Bromo-5-{3-[(cyclohexyl-methoxycarbonyl-amino)-methyl]-phenyl}-3-ethoxycarbonylmethoxy-thiophene-2-carboxylic acid methyl ester (23 mg, 37%) was prepared as a colorless oil according to the procedure in the first step of Scheme 5 of Example 36, using 4-bromo-3-ethoxycarbonylmethoxy-5-(3-cyclohexylaminomethyl-phenyl)-thiophene-2-carboxylic acid methyl ester (56.5 mg, 0.11 mmol) as the starting material.

$^1$H NMR (400 MHz, CHLOROFORM-D) δ ppm 1.0 (m, 1 H) 1.3 (m, 9 H) 1.6 (m, 1 H) 1.7 (m, 4 H) 3.7 (br, s, 3 H) 3.9 (s, 3 H) 4.3 (q, J=7.2 Hz, 2 H) 4.5 (br, s, 2 H) 4.9 (s, 2 H) 7.3 (m, 1 H) 7.4 (t, J=7.7 Hz, 1 H) 7.5 (m, 2 H)

The fourth step of Scheme 22: 4-Bromo-3-carboxymethoxy-5-{3-[(cyclohexyl-methoxycarbonyl-amino)-methyl]-phenyl}-thiophene-2-carboxylic acid (14 mg, 66%) was prepared as a white solid according to the procedure in the second step of Scheme 1 of Example 1, using 4-bromo-5-{3-[(cyclohexyl-methoxycarbonyl-amino)-methyl]-phenyl}-3-ethoxycarbonylmethoxy-thiophene-2-carboxylic acid methyl ester (23 mg, 0.04 mmol) as the starting material.

$^1$H NMR (400 MHz, MeOD) δ ppm 1.4 (m, 13 H) 3.7 (br, s, 3 H) 4.0 (m, 1 H) 4.9 (s, 2 H) 4.9 (s, 2 H) 7.4 (br, s, 1 H) 7.5 (t, J=7.7 Hz, 1 H) 7.6 (m, 1 H) 7.6 (br, s, 1 H).

EXAMPLE 245

4-Bromo-3-carboxymethoxy-5-[3-(1-cyclohexyl-3-ethyl-ureidomethyl)-phenyl]-thiophene-2-carboxylic acid The third step of Scheme 22: 4-Bromo-5-[3-(1-cyclohexyl-3-ethyl-ureidomethyl)-phenyl]-3-ethoxycarbonylmethoxy-thiophene-2-carboxylic acid methyl ester (22 mg, 34%) was prepared as a colorless oil according to the procedure in the first step of Scheme 5 of Example 36, using 4-bromo-3-ethoxycarbonylmethoxy-5-(3-cyclohexylaminomethyl-phenyl)-thiophene-2-carboxylic acid methyl ester (56.5 mg, 0.11 mmol) as the starting material.

$^1$H NMR (400 MHz, CHLOROFORM-D) δ ppm 1.0 (t, J=7.2 Hz, 3 H) 1.1 (m, 1 H) 1.3 (m, 8 H) 1.6 (m, 1 H) 1.8 (m, 4 H) 3.2 (m, 2 H) 3.9 (s, 3 H) 4.2 (m, 2 H) 4.3 (q, J=7.1 Hz, 2 H) 4.4 (s, 2 H) 4.9 (s, 2 H) 7.4 (d, J=8.1 Hz, 1 H) 7.4 (t, J=7.6 Hz, 1 H) 7.6 (m, 2 H).

The fourth step of Scheme 22: 4-Bromo-3-carboxymethoxy-5-[3-(1-cyclohexyl-3-ethyl-ureidomethyl)-phenyl]-thiophene-2-carboxylic acid (8 mg, 41%) was prepared as a white solid according to the procedure in the second step of Scheme 1 of Example 1, using 4-bromo-5-[3-(1-cyclohexyl-3-ethyl-ureidomethyl)-phenyl]-3-ethoxycarbonylmethoxy-thiophene-2-carboxylic acid methyl ester (22 mg, 0.036 mmol) as the starting material. $^1$H NMR (400 MHz, MeOD) δ ppm 1.1 (t, J=7.2 Hz, 3 H) 1.4 (m, 5 H) 1.7 (m, 5 H) 4.0 (m, 1 H) 4.5 (s, 2 H) 4.9 (s, 2 H) 7.4 (d, J=7.8 Hz, 1 H) 7.4 (t, J=7.7 Hz, 1 H) 7.5 (d, J=8.3 Hz, 1 H) 7.6 (s, 1 H).

EXAMPLE 246

5-(3-[Acetyl-(3,3,5,5-tetramethyl-cyclohexyl)-amino]-methyl}-phenyl)-4-bromo-3-carboxymethoxy-thiophene-2-carboxylic acid The second step of Scheme 22: 5-(3-{[Acetyl-(3,3,5,5-tetramethyl-cyclohexyl)-amino]-methyl}-phenyl)-4-bromo-3-ethoxycarbonylmethoxy-thiophene-2-carboxylic acid methyl ester (125 mg, 28%) was prepared according to the procedure in the first step of Scheme 14 of Example 137, using 4-bromo-3-ethoxycarbonylmethoxy-5-(3-formyl-phenyl)-thiophene-2-carboxylic acid methyl ester (350 mg, 0.818 mmol), 3,3,5,5-tetramethyl-cyclohexylamine (173 mg, 1.23 mmol), HOAc (0.072 mL, 1.23 mmol) and NaBH(OAc)$_3$ (260.7 mg, 1.23 mmol) as the starting materials.

$^1$H NMR (400 MHz, CHLOROFORM-D) δ ppm 0.9 (m, 1 H) 0.9 (s, 6 H) 1.0 (s, 6 H) 1.1 (d, J=13.9 Hz, 1 H) 1.2 (m, 2 H) 1.3 (t, J=7.2 Hz, 3 H) 1.7 (m, 2 H) 3.9 (s, 3 H) 3.9 (s, 2 H) 4.3 (q, J=7.2 Hz, 2 H) 4.9 (s, 2 H) 7.4 (m, 2 H) 7.5 (m, 1 H) 7.6 (m, 1 H).

The third step of Scheme 22: 5-(3-{[Acetyl-(3,3,5,5-tetramethyl-cyclohexyl)-amino]-methyl}-phenyl)-4-bromo-3-ethoxycarbonylmethoxy-thiophene-2-carboxylic acid methyl ester (41 mg, 93%, a mixture of two tautomers) was prepared as a colorless oil according to the procedure in the first step of Scheme 4 of Example 22, using 5-(3-{[acetyl-(3,3,5,5-tetramethyl-cyclohexyl)-amino]-methyl}-phenyl)-4-bromo-3-ethoxycarbonylmethoxy-thiophene-2-carboxylic acid methyl ester (40 mg, 0.072 mmol) as the starting material.

The fourth step of Scheme 22: 5-(3-{[Acetyl-(3,3,5,5-tetramethyl-cyclohexyl)-amino]-methyl}-phenyl)-4-bromo-3-carboxymethoxy-thiophene-2-carboxylic acid (31 mg, 83%, a mixture of two tautomers) was prepared as a white solid according to the procedure in the second step of Scheme 1 of Example 1, using 5-(3-{[acetyl-(3,3,5,5-tetramethyl-cyclohexyl)-amino]-methyl}-phenyl)-4-bromo-3-ethoxycarbonylmethoxy-thiophene-2-carboxylic acid methyl ester (40 mg, 0.066 mmol) as the starting material.

EXAMPLE 247

4-{Acetyl-[3-(3-bromo-5-carboxy-4-carboxymethoxy-thiophen-2-yl)-benzyl]-amino}-piperidine-1-carboxylic acid ethyl ester The second step of Scheme 22: 5-(3-{[Acetyl-(3,3,5,5-tetramethyl-cyclohexyl)-amino]-methyl}-phenyl)-4-bromo-3-ethoxycarbonylmethoxy-thiophene-2-carboxylic acid methyl ester (477 mg, 99%) was prepared according to the procedure in the second step of Scheme 22 of Example 242, using 4-bromo-3-ethoxycarbonylmethoxy-5-(3-formyl-phenyl)-thiophene-2-carboxylic acid methyl ester (350 mg, 0.818 mmol), 4-amino-piperidine-1-carboxylic acid ethyl ester (0.21 mL, 1.23 mmol), HOAc (0.072 mL, 1.23 mmol) and NaBH(OAc)$_3$ (260.7 mg, 1.23 mmol) as the starting materials.

$^1$H NMR (400 MHz, CHLOROFORM-D) δ ppm 1.3 (t, J=7.2 Hz, 3 H) 1.3 (t, J=7.2 Hz, 3 H) 1.4 (m, 2 H) 1.9 (m, 2 H) 2.8 (m, 3 H) 3.9 (s, 3 H) 3.9 (s, 2 H) 4.1 (m, 2 H) 4.1 (q, J=7.1 Hz, 2 H) 4.3 (q, J=7.1 Hz, 2 H) 4.9 (m, 2 H) 7.4 (m, 2 H) 7.6 (m, 1 H) 7.6 (s, 1 H).

The third step of Scheme 22: 4-{Acetyl-[3-(3-bromo-4-ethoxycarbonylmethoxy-5-methoxycarbonyl-thiophen-2-yl)-benzyl]-amino}-piperidine-1-carboxylic acid ethyl ester (210 mg, 98%, a mixture of two tautomers) was prepared as a colorless oil according to the procedure in the first step of Scheme 4 of Example 22, using 5-(3-{[acetyl-(3,3,5,5-tetramethyl-cyclohexyl)-amino]-methyl}-phenyl)-4-bromo-3-ethoxycarbonylmethoxy-thiophene-2-carboxylic acid methyl ester (200 mg, 0.342 mmol) as the starting material.

The fourth step of Scheme 22: 4-{Acetyl-[3-(3-bromo-5-carboxy-4-carboxymethoxy-thiophen-2-yl)-benzyl]-amino}-piperidine-1-carboxylic acid ethyl ester (62 mg, 83%, a mixture of two tautomers) was prepared as a white solid according to the procedure in the second step of Scheme 1 of Example 1, using 4-{acetyl-[3-(3-bromo-4-ethoxycarbonylmethoxy-5-methoxycarbonyl-thiophen-2-yl)-benzyl]-amino}-piperidine-1-carboxylic acid ethyl ester (80 mg, 0.128 mmol) as the starting material.

EXAMPLE 248

4-Bromo-3-carboxymethoxy-5-(4-methoxy-3-phenylaminomethyl-phenyl)-thiophene-2-carboxylic acid The first step of Scheme 23: 4-Bromo-3-ethoxycarbonylmethoxy-5-(3-formyl-4-methoxy-phenyl)-thiophene-2-carboxylic acid methyl ester (210 mg, 38%) was prepared according to the procedure in the first step of Scheme 22 of Example 232, using 4,5-dibromo-3-ethoxycarbonyl-methoxy-thiophene-2-carboxylic acid methyl ester (480 mg, 1.2 mmol) as the starting material.

$^1$H NMR (400 MHz, CHLOROFORM-D) δ ppm 1.32 (t, J=7.07 Hz, 3 H) 3.88 (s, 3 H) 4.01 (s, 3 H) 4.29 (q, J=7.16 Hz, 2 H) 4.92 (s, 2 H) 7.10 (d, J=8.84 Hz, 1 H) 7.90 (dd, J=8.59, 2.53 Hz, 1 H) 8.11 (d, J=2.53 Hz, 1 H) 8.11 (d, J=2.53 Hz, 1 H) 10.49 (s, 1 H).

The second step of Scheme 23: 4-Bromo-3-ethoxycarbonylmethoxy-5-(4-methoxy-3-phenylaminomethyl-phenyl)-thiophene-2-carboxylic acid methyl ester (53 mg, 99%) was prepared from 4-bromo-3-ethoxycarbonylmethoxy-5-(3-formyl-4-methoxy-phenyl)-thiophene-2-carboxylic acid methyl ester (50 mg, 0.11 mmol) and aniline (0.015 mL, 0.165 mmol) according to the procedure in the second step of Scheme 22 of Example 242.

$^1$H NMR (400 MHz, CHLOROFORM-D) δ ppm 1.31 (t, J=7.20 Hz, 3 H) 3.85 (s, 3 H) 3.92 (s, 3 H) 4.17 (s, 1 H) 4.28 (q, J=7.24 Hz, 2 H) 4.38 (s, 2 H) 4.87 (s, 2 H) 6.68 (m, 3 H) 6.95 (d, J=8.59 Hz, 1 H) 7.16 (m, 2 H) 7.54 (dd, J=8.46, 2.40 Hz, 1 H) 7.65 (d, J=2.27 Hz, 1 H).

The fourth step of Scheme 23: 4-Bromo-3-carboxymethoxy-5-(4-methoxy-3-phenylaminomethyl-phenyl)-thiophene-2-carboxylic acid (35 mg, 72%) was prepared as a yellow solid according to the procedure in the second step of Scheme 1 of Example 1, using 4-bromo-3-ethoxycarbonylmethoxy-5-(4-methoxy-3-phenylaminomethyl-phenyl)-thiophene-2-carboxylic acid methyl ester (53 mg, 0.1 mmol) as the starting material.

$^1$H NMR (400 MHz, DMSO-D6) δ ppm 3.91 (s, 3 H) 4.26 (s, 2 H) 4.71 (s, 2 H) 6.50 (t, J=7.20 Hz, 1 H) 6.55 (d, J=7.58 Hz, 2 H) 7.04 (dd, J=8.59, 7.33 Hz, 2 H) 7.14 (d, J=9.10 Hz, 1 H) 7.53 (m, 2 H).

EXAMPLE 249

5-{3-[(Acetyl-phenyl-amino)-methyl]-4-methoxy-phenyl}-4-bromo-3-carboxymethoxy-thiophene-2-carboxylic acid The first step of Scheme 23 and the second step of Scheme 23 are same as that of Example 248.

The third step of Scheme 23: 5-{3-[(Acetyl-phenyl-amino)-methyl]-4-methoxy-phenyl)}4-bromo-3-ethoxycarbonylmethoxy-thiophene-2-carboxylic acid methyl ester (55 mg, 100%) was prepared according to the procedure in the first step of Scheme 4 of Example 22, using 4-bromo-3-ethoxycarbonylmethoxy-5-(4-methoxy-3-phenylaminomethyl-phenyl)-thiophene-2-carboxylic acid methyl ester (50 mg, 0.0936 mmol) as the starting material.

$^1$H NMR (400 MHz, CHLOROFORM-D) δ ppm 1.32 (t, J=7.07 Hz, 3 H) 3.90 (s, 3 H) 4.30 (q, J=7.07 Hz, 2 H) 4.43 (q, J=8.59 Hz, 2 H) 4.94 (s, 2 H) 7.45 (m, 2 H) 7.82 (m, 2 H)

The fourth step of Scheme 23: 5-{3-[(Acetyl-phenyl-amino)-methyl]-4-methoxy-phenyl}-4-bromo-3-carboxymethoxy-thiophene-2-carboxylic acid (48 mg, 94%, a mixture o two tautomers) was prepared according to the procedure in the second step of Scheme 1 of Example 1, using 5-{3-[(acetyl-phenyl-amino)-methyl]-4-methoxy-phenyl}-4-bromo-3-ethoxycarbonylmethoxy-thiophene-2-carboxylic acid methyl ester (55 mg, 0.095 mmol) as the starting material.

¹H NMR (400 MHz, DMSO-D6) δ ppm 1.85 (s, 3 H) 3.72 (s, 3 H) 4.86 (s, 2 H) 4.88 (s, 2 H) 7.08 (m, 1 H) 7.28 (m, 3 H) 7.39 (m, 2 H) 7.53 (m, 2 H).

EXAMPLE 250

5-{3-[(3,5-Bis-trifluoromethyl-phenylamino)-methyl]-4-methoxy-phenyl}-4-bromo-3-carboxymethoxy-thiophene-2-carboxylic acid The second step of Scheme 23: 5-{3-[(3,5-Bis-trifluoromethyl-phenylamino)-methyl]-4-methoxy-phenyl}-4-bromo-3-ethoxycarbonylmethoxy-thiophene-2-carboxylic acid methyl ester (30 mg, 44%) was prepared from 4-bromo-3-ethoxycarbonylmethoxy-5-(3-formyl-4-methoxy-phenyl)-thiophene-2-carboxylic acid methyl ester (46 mg, 0.10 mmol) and 3,5-bis-trifluoromethyl-phenylamine (0.023 mL, 0.15 mmol) according to the procedure in the second step of Scheme 22 of Example 242.

¹H NMR (400 MHz, CHLOROFORM-D) δ ppm 1.31 (t, J=7.07 Hz, 3 H) 3.86 (s, 3 H) 3.94 (s, 3 H) 4.28 (q, J=7.16 Hz, 2 H) 4.43 (d, J=5.81 Hz, 2 H) 4.60 (t, J=6.06 Hz, 1 H) 4.89 (s, 2 H) 6.99 (m, 3 H) 7.15 (s, 1 H) 7.58 (m, 2 H)

The fourth step of Scheme 23: 5-{3-[(3,5-Bis-trifluoromethyl-phenylamino)-methyl]-4-methoxy-phenyl})-4-bromo-3-carboxymethoxy-thiophene-2-carboxylic acid (11 mg, 42%) was prepared as a white solid according to the procedure in the second step of Scheme 1 of Example 1, using 5-{3-[(3,5-bis-trifluoromethyl-phenylamino)-methyl]-4-methoxy-phenyl}-4-bromo-3-ethoxycarbonylmethoxy-thiophene-2-carboxylic acid methyl ester (28 mg, 0.042 mmol) as the starting material.

¹H NMR (400 MHz, Solvent) δ ppm 3.78 (s, 3 H) 4.25 (s, 2 H) 4.62 (s, 1 H) 6.82 (s, 1 H) 6.85 (s, 2 H) 6.94 (d, J=8.59 Hz, 1 H) 7.37 (dd, J=8.34, 2.27 Hz, 1 H) 7.43 (d, J=2.27 Hz, 1 H).

EXAMPLE 251

4-Bromo-3-carboxymethoxy-5-[3-(2-carboxy-vinyl)-4-methoxy-phenyl]-thiophene-2-carboxylic acid The first step of Scheme 24: To a solution of 4-bromo-3-ethoxycarbonylmethoxy-5-(3-formyl-4-methoxy-phenyl)-thiophene-2-carboxylic acid methyl ester (46 mg, 0.1 mmol) in toluene (2 mL) was added (triphenyl-λ⁵-phosphanylidene)-acetic acid tert-butyl ester (57 mg, 0.15 mmol). The resultant solution was stirred at 100° C. for 16 h. Solvent was removed under vacuum. The crude product was purified on CombiFlash column eluted with hexanes/EtOAc to give 4-bromo-5-[3-(2-tert-butoxycarbonyl-vinyl)-4-methoxy-phenyl]-3-ethoxycarbonylmethoxy-thiophene-2-carboxylic acid methyl ester (56 mg, 99+%) as a 4:1 E/Z mixture.

For the major product: 1H NMR (400 MHz, CHLOROFORM-D) δ ppm 1.32 (t, J=7.20 Hz, 3 H) 1.54 (s, 9 H) 3.88 (s, 3 H) 3.94 (s, 3 H) 4.30 (q, J=7.07 Hz, 2 H) 4.92 (s, 2 H) 6.48 (d, J=16.17 Hz, 1 H) 6.99 (d, J=8.84 Hz, 1 H) 7.65 (dd, J=8.59, 2.27 Hz, 1 H) 7.80 (d, J=2.53 Hz, 1 H) 7.90 (d, J=16.67 Hz, 1 H)

The second step of Scheme 24: 4-Bromo-3-carboxymethoxy-5-[3-(2-carboxy-vinyl)-4-methoxy-phenyl]-thiophene-2-carboxylic acid was prepared as a white solid according to the procedure in the second step of Scheme 1 of Example 1, using 4-bromo-5-[3-(2-tert-butoxycarbonyl-vinyl)-4-methoxy-phenyl]-3-ethoxycarbonylmethoxy-thiophene-2-carboxylic acid methyl ester as the starting material.

¹H NMR (400 MHz, DMSO-D6) δ ppm 3.94 (s, 3 H) 4.77 (s, 2 H) 6.59 (d, J=16.17 Hz, 1 H) 7.24 (d, J=8.59 Hz, 1 H) 7.68 (dd, J=8.72, 1.89 Hz, 1 H) 7.78 (d, J=15.92 Hz, 1 H) 7.92 (d, J=2.02 Hz, 1 H).

EXAMPLE 252

4-Bromo-3-carboxymethoxy-5-{4-methoxy-3-[2-(2,2,2-trifluoro-ethylcarbamoyl)-vinyl]-phenyl}-thiophene-2-carboxylic acid The first step of Scheme 25: To a solution of 4-bromo-3-ethoxycarbonylmethoxy-5-(3-formyl-4-methoxy-phenyl)-thiophene-2-carboxylic acid methyl ester (46 mg, 0.1 mmol) in pyridine (2 mL) was added malonic acid (20.8 mg, 0.2 mmol) and one drop of piperidine. The resultant solution was stirred at 150° C. for 30 min in microwave oven. The solvent was concentrated to 0.2 mL under vacuum. To this was added H₂O (2 mL) and 10% aqueous HCl (1 mL). The precipitate was collected by filtration and washed with H₂O, dried under vacuum to give 4-bromo-5-[3-(2-carboxy-vinyl)-4-methoxy-phenyl]-3-ethoxycarbonylmethoxy-thiophene-2-carboxylic acid methyl ester (46 mg, 92%) as a 4:1 E/Z mixture.

For the major product: 1H NMR (400 MHz, CHLOROFORM-D) δ ppm 1.33 (t, J=7.07 Hz, 3 H) 3.88 (s, 3 H) 3.97 (s, 3 H) 4.30 (q, J=7.16 Hz, 2 H) 4.93 (s, 2 H) 6.60 (d, J=16.17 Hz, 1 H) 7.02 (d, J=8.84 Hz, 1 H) 7.69 (dd, J=8.59, 2.27 Hz, 1 H) 7.84 (d, J=2.27 Hz, 1 H) 8.09 (d, J=16.17 Hz, 1 H).

The second step of Scheme 25: 4-Bromo-3-ethoxycarbonylmethoxy-5-{4-methoxy-3-[2-(2,2,2-trifluoro-ethylcarbamoyl)-vinyl]-phenyl}-thiophene-2-carboxylic acid methyl ester (36 mg, 67%) was prepared according to the procedure in the first step of Scheme 4 of Example 25, using 4-bromo-5-[3-(2-carboxy-vinyl)-4-methoxy-phenyl]-3-ethoxycarbonylmethoxy-thiophene-2-carboxylic acid methyl ester (46 mg, 0.092 mmol, E/Z=4/1) as the starting material.

For the major product: ¹H NMR (400 MHz, CHLOROFORM-D) δ ppm 1.32 (t, J=7.07 Hz, 3 H) 3.87 (d, J=4.29 Hz, 3 H) 3.95 (s, 3 H) 4.09 (m, 2 H) 4.30 (q, J=7.07 Hz, 2 H) 4.93 (s, 2 H) 6.59 (d, J=15.92 Hz, 1 H) 7.00 (d, J=8.59 Hz, 1 H) 7.65 (dd, J=8.72, 2.40 Hz, 1 H) 7.79 (d, J=2.53 Hz, 1 H) 7.97 (d, J=15.92 Hz, 1 H).

The third step of Scheme 25: 4-Bromo-3-carboxymethoxy-5-{4-methoxy-3-[2-(2,2,2-trifluoro-ethylcarbamoyl)-vinyl]-phenyl}-thiophene-2-carboxylic acid (23 mg, 71%) was prepared as a white solid according to the procedure in the second step of Scheme 1 of Example 1, using 4-bromo-3-ethoxycarbonylmethoxy-5-{4-methoxy-3-[2-(2,2,2-trifluoro-ethylcarbamoyl)-vinyl]-phenyl}-thiophene-2-carboxylic acid methyl ester (35 mg, 0.06 mmol) as the starting material.

¹H NMR (400 MHz, DMSO-D6) δ ppm 3.95 (s, 3 H) 4.05 (m, 2 H) 4.90 (s, 2 H) 6.84 (d, J=15.92 Hz, 1 H) 7.26 (d, J=8.84 Hz, 1 H) 7.71 (dd, J=8.59, 2.53 Hz, 1 H) 7.75 (d, J=15.92 Hz, 1 H) 7.86 (d, J=2.53 Hz, 1 H) 8.77 (m, 1 H).

EXAMPLE 253

5-(3,4-Bis-benzyloxy-phenyl)-4-bromo-3-(2-hydroxy-ethoxy)-thiophene-2-carboxylic acid The first step of Scheme 26: 5-Benzo[1,3]dioxol-5-yl-4-bromo-3-ethoxycarbonylmethoxy-thiophene-2-carboxylic acid methyl ester (180 mg, 68%) was prepared according to the procedure in the first step of Scheme 22 of Example 232, using 4,5-dibromo-3-ethoxycarbonylmethoxy-thiophene-2-carboxylic acid methyl ester (239 mg, 0.6 mmol), 3,4-methylenedioxyphenylboroni acid (149 mg, 0.9 mmol), Pd(PPh$_3$)$_4$ (69.3 mg, 0.06 mmol) and KF (140 mg, 2.4 mmol) in DME (6 mL).

$^1$H NMR (400 MHz, CHLOROFORM-D) δ ppm 1.32 (t, J=7.07 Hz, 3 H) 3.87 (s, 3 H) 4.29 (q, J=7.16 Hz, 2 H) 4.90 (s, 2 H) 6.04 (s, 2 H) 6.89 (d, J=7.83 Hz, 1 H) 7.15 (m, 2 H).

The second step of Scheme 26: To a solution of 5-benzo[1,3]dioxol-5-yl-4-bromo-3-ethoxycarbonylmethoxy-thiophene-2-carboxylic acid methyl ester (280 mg, 0.633 mmol) in DCM was added EtSH (0.23 mL, 3.17 mmol) and AlCl$_3$ (422.5 mg, 3.17 mmol) at −78° C. under N$_2$. The cooling bath was removed, and the resultant reaction mixture was stirred for 2 h before quenched with aqueous NaHCO$_3$, extracted with DCM. The combined organic layer was dried over MgSO$_4$. The solvent was removed under vacuum. The crude product was purified on CombiFlash column eluted with hexanes/EtOAc to give 4-bromo-5-(3,4-dihydroxy-phenyl)-3-ethoxycarbonylmethoxy-thiophene-2-carboxylic acid methyl ester (166 mg, 61%) as a colorless oil.

$^1$H NMR (400 MHz, CHLOROFORM-D) δ ppm 1.33 (t, J=7.20 Hz, 3 H) 3.84 (s, 3 H) 4.31 (q, J=7.24 Hz, 2 H) 4.87 (s, 3 H) 5.72 (s, 1 H) 5.98 (s, 1 H) 6.93 (d, J=8.34 Hz, 1 H) 7.10 (m, 1 H) 7.22 (d, J=2.02 Hz, 1 H).

The third step of Scheme 26: To a solution of 4-bromo-5-(3,4-dihydroxy-phenyl)-3-ethoxycarbonylmethoxy-thiophene-2-carboxylic acid methyl ester (160 mg, 0.37 mmol) in DMF was added BnBr (0.88 mL, 0.5 M in toluene) and K$_2$CO$_3$ (51 mg, 0.37 mmol) at 0° C. The temperature was slowly risen to room temperature during 2 h. The mixture was diluted with Et$_2$O, filtered through a pad of Celite. The solvent was removed under vacuum. The crude product was purified on CombiFlash column eluted with hexanes/EtOAc to give 5-(3,4-bis-benzyloxy-phenyl)-4-bromo-3-ethoxycarbonylmethoxy-thiophene-2-carboxylic acid methyl ester (45 mg, 20%).

$^1$H NMR (400 MHz, CHLOROFORM-D) δ ppm 1.31 (t, J=7.07 Hz, 3 H) 3.86 (s, 3 H) 4.29 (q, J=7.24 Hz, 2 H) 4.88 (s, 2 H) 5.22 (s, 4 H) 6.98 (d, J=8.59 Hz, 1 H) 7.17 (m, 1 H) 7.35 (m, 7 H) 7.46 (m, 4 H).

5-(3-benzyloxy-4-hydroxy-phenyl)-4-bromo-3-ethoxycarbonylmethoxy-thiophene-2-carboxylic acid methyl ester (12 mg, 6%).

$^1$H NMR (400 MHz, CHLOROFORM-D) δ ppm 1.32 (t, J=7.07 Hz, 3 H) 3.87 (s, 3 H) 4.29 (q, J=7.07 Hz, 2 H) 4.90 (s, 2 H) 5.16 (s, 2 H) 5.76 (s, 1 H) 6.99 (d, J=8.34 Hz, 1 H) 7.17 (m, 1 H) 7.30 (d, J=2.27 Hz, 1 H) 7.41 (m, 5 H).

5-(4-benzyloxy-4-hydroxy-phenyl)-4-bromo-3-ethoxycarbonylmethoxy-thiophene-2-carboxylic acid methyl ester (69 mg, 36%).

$^1$H NMR (400 MHz, CHLOROFORM-D) δ ppm 1.32 (t, J=7.20 Hz, 3 H) 3.87 (s, 3 H) 4.29 (q, J=7.07 Hz, 2 H) 4.90 (s, 2 H) 5.17 (s, 2 H) 7.01 (d, J=8.34 Hz, 1 H) 7.19 (dd, J=8.34, 2.02 Hz, 1 H) 7.30 (d, J=2.02 Hz, 1 H) 7.41 (m, 5 H).

The fourth step of Scheme 26: 5-(3,4-Bis-benzyloxy-phenyl)-4-bromo-3-(2-hydroxy-ethoxy)-thiophene-2-carboxylic acid (29 mg, 69%) was prepared as a white solid according to the procedure in the second step of Scheme 1 of Example 1, using 5-(3,4-bis-benzyloxy-phenyl)-4-bromo-3-ethoxycarbonylmethoxy-thiophene-2-carboxylic acid methyl ester (45 mg, 0.074 mmol) as the starting material.

$^1$H NMR (400 MHz, ACETONE-D6) δ ppm 5.06 (s, 2 H) 5.30 (s, 2 H) 5.32 (s, 2 H) 7.37 (m, 9 H) 7.57 (m, 4 H).

EXAMPLE 254

5-(3-Benzyloxy-4-hydroxy-phenyl)-4-bromo-3-(2-hydroxy-ethoxy-thiophene-2-carboxylic acid The first step of Scheme 26, the second step of Scheme 26 and the third step of Scheme 26 are identical to that of Example 253.

The fourth step of Scheme 26: 5-(3-Benzyloxy-4-hydroxy-phenyl)-4-bromo-3-(2-hydroxy-ethoxy)-thiophene-2-carboxylic acid (10.5 mg, 98%) was prepared as a white solid according to the procedure in the second step of Scheme 1 of Example 1, using 5-(3-benzyloxy-4-hydroxy-phenyl)-4-bromo-3-ethoxycarbonylmethoxy-thiophene-2-carboxylic acid methyl ester (12 mg, 0.023 mmol) as the starting material.

$^1$H NMR (400 MHz, ACETONE-D6) δ ppm 5.02 (s, 2 H) 5.30 (s, 2 H) 7.03 (d, J=8.34 Hz, 1 H) 7.23 (dd, J=8.34, 2.02 Hz, 1 H) 7.36 (m, 1 H) 7.42 (m, 3 H) 7.56 (m, 2 H).

EXAMPLE 255

5-(4-Benzyloxy-3-hydroxy-phenyl)-4-bromo-3-(2-hydroxy-ethoxy)-thiophene-2-carboxylic acid The first step of Scheme 26, the second step of Scheme 26 and the third step of Scheme 26 are identical to that of Example 253.

The fourth step of Scheme 26: 5-(4-Benzyloxy-4-hydroxy-phenyl)-4-bromo-3-(2-hydroxy-ethoxy)-thiophene-2-carboxylic acid (46 mg, 80%) was prepared as a white solid according to the procedure in the second step of Scheme 1 of Example 1, using 5-(4-benzyloxy-4-hydroxy-phenyl)-4-bromo-3-ethoxycarbonylmethoxy-thiophene-2-carboxylic acid methyl ester (64 mg, 0.123 mmol) as the starting material.

$^1$H NMR (400 MHz, ACETONE-D6) δ ppm 5.10 (s, 2 H) 5.31 (s, 2 H) 7.23 (m, 2 H) 7.32 (d, J=2.02 Hz, 1 H) 7.45 (m, 4 H) 7.60 (m, 2 H).

EXAMPLE 256

4,5-Dibromo-3-methoxycarbonylmethoxy-thiophene-2-carboxylic acid

The first step of Scheme 27: To a solution of 4,5-dibromo-3-carboxymethoxy-thiophene-2-carboxylic acid (132 mg) in MeOH (4 mL) was added a tiny drop of concentrated H$_2$SO$_4$ at 0° C. The resultant solution was stirred at room temperature for 3 h before saturated aqueous NaHCO3 (0.2 mL) was added. The mixture was concentrated under vacuum, diluted with EtOAc, washed with H$_2$O. The aqueous layer was back extracted with EtOAc. The combined organic layer was dried over MgSO$_4$. The solvent was removed under vacuum. The resultant product was triturated with hexanes/EtOAc to give 4,5-dibromo-3-methoxycarbonylmethoxy-thiophene-2-carboxylic acid as a white solid (134 mg, 98%).

$^1$H NMR (400 MHz, DMSO-D6) δ ppm 3.7 (s, 3 H) 5.0 (s, 2 H).

EXAMPLE 257

4-Bromo-3-methoxycarbonylmethoxy-5-phenyl-thiophene-2-carboxylic acid

The first step of Scheme 27: 4-Bromo-3-methoxycarbonylmethoxy-5-phenyl-thiophene-2-carboxylic acid (25.5 mg, 79%) was synthesized according to the procedure in the first step f Scheme 27 of Example 256 from 4-bromo-3-carboxymethoxy-5-phenyl-thiophene-2-carboxylic acid (31.1 mg).
$^1$H NMR (400 MHz, CHLOROFORM-D) δ ppm 3.9 (s, 3 H) 5.0 (s, 2 H) 7.5 (m, 3 H) 7.6 (m, 2 H).

EXAMPLE 258

4-Bromo-3-methoxycarbonylmethoxy-5-[3-(3,3,5,5-tetramethyl-cyclohexylamino)-phenyl]-thiophene-2-carboxylic acid The first step of Scheme 27: 4-Bromo-3-methoxycarbonylmethoxy-5-[3-(3,3,5,5-tetramethyl-cyclohexylamino)-phenyl]-thiophene-2-carboxylic acid (16 mg, 52%), was synthesized according to the procedure in the first step of Scheme 27 of Example 256 from 4-bromo-3-carboxymethoxy-5-[3-(3,3,5,5-tetramethyl-cyclohexylamino)-phenyl]-thiophene-2-carboxylic acid (30 mg).
$^1$H NMR (400 MHz, CHLOROFORM-D) δ ppm 0.9 (m, 2 H) 0.9 (s, 6 H) 1.1 (s, 6 H) 1.3 (m, 2 H) 1.9 (d, J=12.6 Hz, 2 H) 3.6 (m, 1 H) 3.9 (s, 3 H) 5.0 (s, 2 H) 6.6 (m, 1 H) 6.8 (m, 1 H) 6.9 (dd, J=8.5, 2.4 Hz, 1 H) 7.2 (m, 1 H).

EXAMPLE 259

4-Bromo-3-methoxycarbonylmethoxy-5-[3-(1-phenylmethanesulfonyl-piperidin-4-ylamino)-phenyl]-thiophene-2-carboxylic acid The first step of Scheme 27: 4-Bromo-3-methoxycarbonylmethoxy-5-[3-(1-phenylmethanesulfonyl-piperidin-4-ylamino)-phenyl]-thiophene-2-carboxylic acid (49 mg, 95%) was synthesized according to the procedure in the first step of Scheme 27 of Example 256 from 4-bromo-3-carboxymethoxy-5-[3-(1-phenylmethanesulfonyl-piperidin-4-ylamino)-phenyl]-thiophene-2-carboxylic acid (50.5 mg).
$^1$H NMR (400 MHz, MeOD) δ ppm 1.5 (m, 2 H) 2.0 (m, 2 H) 2.9 (m, 2 H) 3.4 (m, 1 H) 3.7 (m, 2 H) 3.8 (s, 3 H) 4.4 (s, 2 H) 4.9 (s, 2 H) 6.7 (m, 1 H) 6.9 (dd, J=7.5, 1.9 Hz, 1 H) 6.9 (d, J=2.5 Hz, 1 H) 7.2 (t, J=8.3 Hz, 1 H) 7.4 (m, 3 H) 7.5 (m, 2 H).

EXAMPLE 260

4-Bromo-3-carboxymethoxy-5-phenyl-thiophene-2-carboxylic acid methyl ester

The first step of Scheme 28: 4-Bromo-3-tert-butoxycarbonylmethoxy-5-phenyl-thiophene-2-carboxylic acid methyl ester (8 mg, 0.0188 mmol) was dissolved in DCM[TFA (v/v=10/1) and the solution was stirred at room temperature overnight. Solvent was removed under vacuum, and the crude product was triturated with Hexanes/EtOAc to give 5 mg (72%) of 4-bromo-3-carboxymethoxy-5-phenyl-thiophene-2-carboxylic acid methyl ester.
$^1$H NMR (400 MHz, CHLOROFORM-D) δ ppm 4.0 (s, 3 H) 4.9 (s, 2 H) 7.5 (m, 3 H) 7.6 (m, 2 H).

EXAMPLE 261

4-Bromo-3-carboxymethoxy-5-{3-[1-(2-nitro-phenylmethanesulfonyl)-piperidin-4-ylamino]-phenyl}-thiophene-2-carboxylic acid methyl ester The first step of Scheme 28: 4-Bromo-3-carbonylmethoxy-5-{3-[1-(2-nitro-phenylmethanesulfonyl)-piperidin-4-ylamino]-phenyl}-thiophene-2-carboxylic acid methyl ester (40 mg, 83%) was prepared according to the procedure in the first step of Scheme 28 of Example 261 using 4-bromo-3-tert-butoxycarbonylmethoxy-5-{3-[1-(2-nitro-phenylmethanesulfonyl)-piperidin-4-ylamino]-phenyl}-thiophene-2-carboxylic acid methyl ester (52 mg, 0.072 mmol) as the starting material.
$^1$H NMR (400 MHz, CHLOROFORM-D) δ ppm 1.75 (m, 2 H) 2.05 (d, J=13.64 Hz, 2 H) 2.78 (t, J=11.62 Hz, 2 H) 3.56 (m, 1 H) 3.70 (m, 2 H) 3.92 (s, 3 H) 4.76 (s, 2 H) 4.91 (s, 2 H) 7.41 (d, J=7.83 Hz, 1 H) 7.61 (m, 6 H) 8.01 (m, 1 H).

EXAMPLE 262

4-Bromo-3-carboxymethoxy-5-{3-[1-(4-chloro-phenylmethanesulfonyl)-piperidin-4-ylamino]-phenyl}-thiophene-2-carboxylic acid methyl ester The first step of Scheme 28: 4-Bromo-3-carbonylmethoxy-5-{3-[1-(4-chloro-phenylmethanesulfonyl)-piperidin-4-ylamino]-phenyl}-thiophene-2-carboxylic acid methyl ester (42 mg, 99%) was prepared according to the procedure in the first step of Scheme 28 of Example 261 using 4-bromo-3-tert-butoxycarbonylmethoxy-5-{3-[1-(4-chloro-phenylmethanesulfonyl)-piperidin-4-ylamino]-phenyl}-thiophene-2-carboxylic acid methyl ester (46 mg, 0.064 mmol) as the starting material.
$^1$H NMR (400 MHz, CHLOROFORM-D) δ ppm 1.69 (m, 2 H) 2.02 (m, 2 H) 2.70 (m, 2 H) 3.47 (m, 1 H) 3.69 (dd, J=11.49, 4.42 Hz, 2 H) 3.92 (s, 3 H) 4.18 (s, 2 H) 4.91 (s, 2 H) 7.32 (m, 5 H) 7.48 (m, 3 H).

EXAMPLE 263

4-Bromo-3-carboxymethoxy-5-{3-[1-(3,5-dichloro-phenylmethanesulfonyl)-piperidin-4-ylamino]-phenyl}-thiophene-2-carboxylic acid methyl ester The first step of Scheme 28: 4-Bromo-3-carbonylmethoxy-5-{3-[1-(3,5-dichloro-phenylmethanesulfonyl)-piperidin-4-ylamino]-phenyl}-thiophene-2-carboxylic acid methyl ester (33 mg, 60%) was prepared according to the procedure in the first step of Scheme 28 of Example 261 using 4-bromo-3-tert-butoxycarbonylmethoxy-5-{3-[1-(3,5-dichloro-phenylmethanesulfonyl)-piperidin-4-ylamino]-phenyl}-thiophene-2-carboxylic acid methyl ester (60 mg, 0.08 mmol) as the starting material.
$^1$H NMR (400 MHz, CHLOROFORM-D) δ ppm 1.55 (m, 2 H) 2.09 (m, 2 H) 2.87 (m, 2 H) 3.45 (m, 1 H) 3.70 (m, 2 H) 3.95 (s, 3 H) 4.13 (s, 2 H) 4.92 (s, 2 H) 6.85 (dd, J=9.09, 2.02 Hz, 1 H) 7.00 (t, J=2.27 Hz, 1 H) 7.10 (m, 1 H) 7.32 (m, 3 H) 7.40 (t, J=1.89 Hz, 1 H).

341

EXAMPLE 264

4-Bromo-3-carboxymethoxy-5-{3-[1-(3,4-dichloro-phenylmethanesulfonyl)-piperidin-4-ylamino]phenyl}-thiophene-2-carboxylic acid methyl ester The first step of Scheme 28: 4-Bromo-3-carbonylmethoxy-5-{3-[1-(3,4-dichloro-phenylmethanesulfonyl)-piperidin-4-ylamino]-phenyl}-thiophene-2-carboxylic acid methyl ester (29 mg, 78%) was prepared according to the procedure in the first step of Scheme 28 of Example 261 using 4-bromo-3-tert-butoxycarbonylmethoxy-5-{3-[1-(3,4-dichloro-phenyl-methanesulfonyl)-piperidin-4-ylamino]-phenyl}-thiophene-2-carboxylic acid methyl ester (40 mg, 0.053 mmol) as the starting material.

$^1$H NMR (400 MHz, CHLOROFORM-D) δ ppm 1.65 (m, 2 H) 2.07 (m, 2 H) 2.79 (m, 2 H) 3.47 (m, 1 H) 3.72 (m, 2 H) 3.94 (s, 3 H) 4.14 (s, 2 H) 4.91 (s, 2 H) 7.12 (m, 1 H) 7.23 (dd, J=8.34, 2.02 Hz, 1 H) 7.33 (m, 2 H) 7.42 (t, J=7.83 Hz, 1 H) 7.48 (m, 2 H).

EXAMPLE 265

4-Bromo-3-carboxymethoxy-5-(3-cyclohexyl-methoxy-phenyl)-thiophene-2-carboxylic acid methyl ester The first step of Scheme 28: 4-Bromo-3-carboxymethoxy-5-(3-cyclohexylmethoxy-phenyl)-thiophene-2-carboxylic acid methyl ester (10 mg, 44%) was prepared according to the procedure in the first step of Scheme 28 of Example 261.

$^1$H NMR (400 MHz, CHLOROFORM-D) δ ppm 1.1 (m, 6 H) 1.7 (m, 5 H) 3.7 (d, 2 H) 3.8 (m, 3 H) 4.9 (m, 2 H) 6.9 (m, 1 H) 7.0 (t, 1 H) 7.1 (d, 1 H) 7.3 (t, 1 H).

EXAMPLE 266

4-Bromo-3-carboxymethoxy-5-[3-(1-phenyl-methanesulfonyl-piperidin-4-ylamino)-phenyl]-thiophene-2-carboxylic acid methyl ester The first step of Scheme 28: 4-Bromo-3-tert-butoxycarbo-nylmethoxy-5-[3-(1-phenylmethanesulfonyl-piperidin-4-ylamino)-phenyl]-thiophene-2-carboxylic acid methyl ester (1.46 g, 2.15 mmol) was dissolved in 10 mL CH$_2$Cl$_2$ and 10 mL trifluoroacetic acid was added and the reaction mixture was allowed to stir 4 hours at room temperature. The solvent was evaporated and then 25 mL CH$_2$Cl$_2$ added and evaporated exhaustively. This process was repeated twice more and the resulting foam as vacuum-oven dried to give 1.4 g (100%) of 4-bromo-3-tert-butoxycarbonylmethoxy-5-[3-(1-phenyl-methanesulfonyl-piperidin-4-ylamino)-phenyl]-thiophene-2-carboxylic acid methyl ester as an off-white solid.

$^1$H NMR (400 MHz, DMSO-D6) δ ppm 1.37 (m, 2 H) 1.96 (m, 2 H) 2.92 (m, 2 H) 3.42 (m, 1 H) 3.54 (m, 2 H) 3.81 (s, 3 H) 4.40 (s, 2 H) 4.86 (s, 2 H) 6.75 (dd, J=8.34, 1.52 Hz, 1 H) 6.83 (d, J=7.58 Hz, 1 H) 6.89 (m, 1 H) 7.22 (t, J=7.83 Hz, 1 H) 7.39 (m, 5 H).

ESI-MS: m/e=623 [M+H]$^+$.

342

EXAMPLE 267

4-Bromo-3-carboxymethoxy-5-{3-[1-(3-trifluoromethyl-phenylmethanesulfonyl)-piperidin-4-ylamino]-phenyl}-thiophene-2-carboxylic acid methyl ester The first step of Scheme 28: 4-Bromo-3-carboxymethoxy-5-{3-[1-(3-trifluoromethyl-phenylmethanesulfonyl)-piperidin-4-ylamino]-phenyl}-thiophene-2-carboxylic acid methyl ester was prepared according to the procedure in the first step of Scheme 28 of Example 266 from 4-bromo-3-tert-butoxy-carbonylmethoxy-5-{3-[1-(3-trifluoromethyl-phenyl-methanesulfonyl)-piperidin-4-ylamino]-phenyl}-thiophene-2-carboxylic acid methyl ester in 80% yield as a pale yellow foam.

$^1$H NMR (400 MHz, DMSO-D6) δ ppm 1.38 (m, 2 H) 1.97 (m, 2 H) 2.97 (m, 2 H) 3.44 (m, 1 H) 3.58 (m, 2 H) 3.81 (s, 3 H) 4.57 (s, 2 H) 4.86 (s, 2 H) 6.74 (dd, J=8.21, 1.64 Hz, 1 H) 6.82 (d, J=7.07 Hz, 1 H) 6.88 (s, 1 H) 7.22 (t, J=7.96 Hz, 1 H) 7.65 (t, J=7.58 Hz, 1 H) 7.74 (m, 2 H) 7.80 (s, 1 H).

ESI-MS: m/e=691 [M+H]$^+$.

EXAMPLE 268

4-Bromo-3-carboxymethoxy-5-{3-[1-(4-fluoro-phenylmethanesulfonyl)-piperidin-4-ylamino]-phenyl}-thiophene-2-carboxylic acid methyl ester The first step of Scheme 28: 4-Bromo-3-carboxymethoxy-5-{3-[1-(4-fluoro-phenylmethanesulfonyl)-piperidin-4-ylamino]-phenyl}-thiophene-2-carboxylic acid methyl ester was prepared according to the procedure in the first step of Scheme 28 of Example 266 from 4-bromo-3-tert-butoxycar-bonylmethoxy-5-{3-[1-(4-fluoro-phenylmethanesulfonyl)-piperidin-4-ylamino]-phenyl}-thiophene-2-carboxylic acid methyl ester (For preparation see Scheme 6, Example 10) in 100% yield as a white foam.

$^1$H NMR (400 MHz, DMSO-D6) δ ppm 1.36 (m, 2 H) 1.95 (m, 2 H) 2.92 (m, 2 H) 3.42 (m, 1 H) 3.53 (m, 2 H) 3.81 (s, 3 H) 4.42 (s, 2 H) 4.86 (s, 2 H) 6.73 (dd, J=8.08, 2.27 Hz, 1 H) 6.81 (d, J=8.34 Hz, 1 H) 6.86 (t, J=1.77 Hz, 1 H) 7.22 (m, 3 H) 7.46 (m, 2 H).

ESI-MS: m/e=641 [M+H]$^+$.

EXAMPLE 269

4-Bromo-3-carboxymethoxy-5-{3-[1-(4-trifluoromethyl-phenylmethanesulfonyl)-piperidin-4-ylamino]-phenyl}-thiophene-2-carboxylic acid methyl ester The first step of Scheme 28: 4-Bromo-3-carboxymethoxy-5-{3-[1-(4-trifluoromethyl-phenylmethanesulfonyl)-piperidin-4-ylamino]-phenyl}-thiophene-2-carboxylic acid methyl ester was prepared according to the procedure in the first step of Scheme 28 of Example 266 from 4-bromo-3-tert-butoxy-carbonylmethoxy-5-{3-[1-(4-trifluoromethyl-phenyl-methanesulfonyl)-piperidin-4-ylamino]-phenyl}-thiophene-2-carboxylic acid methyl ester in 100% yield as a white foam.

$^1$H NMR (400 MHz, DMSO-D6) δ ppm 1.39 (m, 2 H) 1.98 (m, 2 H) 2.96 (m, 2 H) 3.44 (m, 1 H) 3.58 (m, 2 H) 3.81 (s, 3 H) 4.56 (s, 2 H) 4.86 (s, 2 H) 6.74 (dd, J=8.21, 1.64 Hz, 1 H)

6.82 (d, J=7.58 Hz, 1 H) 6.87 (s, 1 H) 7.22 (t, J=7.96 Hz, 1 H) 7.65 (d, J=8.08 Hz, 2 H) 7.77 (d, J=8.08 Hz, 2 H).
ESI-MS: m/e=691 [M+H]$^+$.

EXAMPLE 270

4,5-Dibromo-3-carboxymethoxy-thiophene-2-carboxylic acid methyl ester

The first step of Scheme 28: 4,5-Dibromo-3-carboxymethoxy-thiophene-2-carboxylic acid methyl ester (223.5 mg, 86%) was prepared as a white solid according to the procedure in the first step of Scheme 28 of Example 261, using 4,5-dibromo-3-tert-butoxycarbonylmethoxy-thiophene-2-carboxylic acid methyl ester (300 mg, 0.696 mmol) as the starting material.
$^1$H NMR (400 MHz, DMSO-D6) δ ppm 3.79 (s, 3 H) 4.88 (s, 2 H) 13.01 (s, 1 H).

EXAMPLE 271

4-Bromo-3-carboxymethoxy-5-[3-(3,3,5,5-tetramethyl-cyclohexylamino)-phenyl]-thiophene-2-carboxylic acid methyl ester The first step of Scheme 28: 4-Bromo-3-carboxymethoxy-5-[3-(3,3,5,5-tetramethyl-cyclohexylamino)-phenyl]-thiophene-2-carboxylic acid methyl ester was prepared according to the procedure in the first step of Scheme 28 of Example 266 from 4-Bromo-3-tert-butoxycarbonylmethoxy-5-[3-(3,3,5,5-tetramethyl-cyclohexylamino)-phenyl]-thiophene-2-carboxylic acid methyl ester in quantitative yield as an off-white foam.
$^1$H NMR (400 MHz, DMSO-D6) δ ppm 0.91 (s, 6 H) 0.97 (m, 2 H) 1.08 (s, 6 H) 1.26 (m, 2 H) 1.74 (d, J=12.63 Hz, 2 H) 3.54 (m, 1 H) 3.81 (s, 3 H) 4.86 (s, 2 H) 6.75 (m, 1 H) 6.82 (m, 1 H) 6.91 (s, 1 H) 7.22 (t, J=7.45 Hz, 1 H).
ESI-MS: m/e=524 [M+H]$^+$.

EXAMPLE 272

5-{3-[(Acetyl-cyclohexyl-amino)-methyl]-pheny}-4-bromo-3-carboxymethoxy-thiophene-2-carboxylic acid methyl ester The first step of Scheme 28: 5-{3-[(Acetyl-cyclohexyl-amino)-methyl]-phenyl})-4-bromo-3-carboxymethoxy-thiophene-2-carboxylic acid methyl ester (41 mg, 76%) was prepared as a white solid according to the procedure in the first step of Scheme 28 of Example 261, using 5-{3-[(acetyl-cyclohexyl-amino)-methyl]-phenyl}-4-bromo-3-tert-butoxycarbonylmethoxy-thiophene-2-carboxylic acid methyl ester (62 mg, 0.102 mmol) as the starting material.
$^1$H NMR (400 MHz, CHLOROFORM-D) for major tautomer: δ ppm 1.25-1.86 (m, 10 H) 2.37 (s, 3 H) 3.72 (m, 1 H) 3.95 (s, 3 H) 4.53 (m, 1 H) 4.67 (s, 2 H) 4.95 (s, 2 H) 7.32 (d, J=7.58 Hz, 1 H) 7.49 (m, 3 H); for minor tautomer: δ ppm 1.25-1.86 (m, 10 H) 2.17 (s, 3 H) 3.96 (s, 3 H) 4.53 (m, 1 H) 4.63 (s, 2 H) 4.95 (s, 2 H) 7.32 (d, J=7.58 Hz, 1 H) 7.49 (m, 3 H).

EXAMPLE 273

3-(Carboxymethyl-amino)-thiophene-2-carboxylic acid

The first step of Scheme 29: To a solution of 3-amino-thiophene-2-carboxylic acid methyl ester (786 mg, 5.0 mmol) in pyridine (5 mL) was added trifluoroacetic anhydride (1 mL). The resultant solution was stirred at room temperature for 1 h. Solvent was removed under vacuum. The crude product was purified on CombiFlash column eluted with hexanes/EtOAc to give 3-(2,2,2-trifluoro-acetylamino)-thiophene-2-carboxylic acid methyl ester (1.01 g, 80%) as a white solid.
$^1$H NMR (400 MHz, CHLOROFORM-D) δ ppm 3.9 (s, 2 H) 7.6 (d, J=5.6 Hz, 1 H) 8.1 (d, J=5.6 Hz, 1 H) 11.2 (br, s, 1 H).

The second step of Scheme 29: To a solution of 3-(2,2,2-trifluoro-acetylamino)-thiophene-2-carboxylic acid methyl ester (430 mg, 1.7 mmol) in DMF (4 mL) was added K$_2$CO$_3$ (419.2 mg, 3.4 mmol) and tert-butyl bromoacetate (0.29 mL, 2.04 mmol). The resultant mixture was stirred at room temperature overnight, diluted with Et$_2$O, filtered through a pad of Celite. The solvent was removed, the crude product was purified on CombiFlash column eluted with hexanes/EtOAc to give 3-[tert-butoxycarbonylmethyl-(2,2,2-trifluoro-acetyl)-amino]-thiophene-2-carboxylic acid methyl ester (622 mg, 96%) as a white solid.
$^1$H NMR (400 MHz, CHLOROFORM-D) δ ppm 1.5 (s, 9 H) 3.7 (d, J=17.2 Hz, 1 H) 3.9 (s, 3 H) 5.0 (d, J=17.4 Hz, 1 H) 7.3 (d, J=5.3 Hz, 1 H) 7.5 (d, J=5.1 Hz, 1 H).

The third step of Scheme 29: 3-(Carboxymethyl-amino)-thiophene-2-carboxylic acid (24 mg, 58%) was prepared as a gray solid according to the procedure in the second step of Scheme 1 of Example 1, using 3-[tert-butoxycarbonylmethyl-(2,2,2-trifluoro-acetyl)-amino]-thiophene-2-carboxylic acid methyl ester (75 mg, 0.2 mmol) as the starting material.
$^1$H NMR (400 MHz, DMSO-D6) δ ppm 3.7 (s, 3 H) 4.1 (d, J=5.8 Hz, 2 H) 6.8 (d, J=5.6 Hz, 1 H) 7.1 (t, J=6.8 Hz, 1 H) 7.7 (d, J=5.6 Hz, 1 H).

EXAMPLE 274

3-Carboxymethoxy-4-methyl-5-phenyl-thiophene-2-carboxylic acid

The first step of Scheme 30: To a 1000 mL round bottom flask was added NaH (60% by wt in oil; 12.5 g, 156 mmol). The powder was washed with anhydrous hexane (2×100 mL). The hexane was decanted from the flask before adding anhydrous THF. The suspension was cooled to −78° C. and treated with methylpropionate (15 mL, 156 mmol) added slowly through an addition funnel. The reaction was warmed to room temperature and treated with methyl formate (17 mL, 156 mmol). After 24 h, the mixture was poured into a stirred solution of 2N HCl (180 mL). The aqueous layer was extracted with Et$_2$O (3×200 mL). The organic layers were combined and dried over MgSO$_4$. The solution was filtered and concentrated under reduced pressure to give 5.6 g (31%) of 2-methyl-3-oxo-propionic acid methyl ester (5.6 g) as clear light yellow oil.
$^1$H NMR (400 MHz, CHLOROFORM-D) δ ppm 1.37 (d, J=7.33 Hz, 3 H) 2.92-2.88 (m, 1 H) 3.79 (s, 3 H) 9.79 (d, J=1.26 Hz, 1 H).

The second step of Scheme 30: Through a mixture of 2-methyl-3-oxo-propionic acid methyl ester (5.6 g, 48 mmol) and methylthioglycolate (8.6 mL, 97 mmol) at 10° C. was bubbled HCl (g) for 5 minutes. The solution was warmed slowly to room temperature and stirred at room temperature overnight. The reaction was diluted with EtOAc (300 mL) and washed with NaHCO$_3$ (2×100 mL) and brine (100 mL). The organic layer was dried over MgSO$_4$ and filtered. The solvent was removed under reduced pressure to give 3,3-bis-methoxycarbonylmethylsulfanyl-2-methyl-propionic acid methyl ester, which was used in the preparation of 3-hydroxy-4-methyl-thiophene-2-carboxylic acid methyl ester without further purification.

¹H NMR (400 MHz, CHLOROFORM-D) δ ppm 1.36 (d, J=6.82 Hz, 3 H) 2.90 (m, 1 H) 3.35 (d, J=2.53 Hz, 1 H) 3.38 (d, J=2.78 Hz, 1 H) 3.48 (d, J=4.29 Hz, 1 H) 3.52 (d, J=4.55 Hz, 1 H) 3.73 (s, 3 H) 3.74 (s, 6 H) 4.40 (d, J=7.83 Hz, 1 H).

The third step of Scheme 30: A flask containing 3,3-bis-methoxycarbonylmethylsulfanyl-2-methyl-propionic acid methyl ester was treated with 2N NaOMe (32 mL, 64 mmol) and stirred at room temperature. After 48 h, the reaction was complete as judged by TLC (35% EtOAc-Hexane, Rf=0.65). The solution was made acidic by slow addition of concentrated HCl (6 mL, 72 mmol). The solvents were removed under reduced pressure. The crude material was purified by combi-flash chromatography using a 35 g column. The product was eluted with a 7-35% EtOAc-Hexane, 2% acetic acid to provide 1.5 g of 3-hydroxy-4-methyl-thiophene-2-carboxylic acid methyl ester as a clear, viscous liquid in 42% yield (2 steps).

¹H NMR (400 MHz, CHLOROFORM-D) δ ppm 2.14 (s, 3 H) 3.89 (s, 3 H) 7.03 (s, 1 H) 9.64 (s, 1 H).

The fourth step of Scheme 30: A round bottom flask equipped with a distillation head was charged with 3-hydroxy-4-methyl-thiophene-2-carboxylic acid methyl ester (1.5 g, 8.7 mmol) and acetic acid (22 mL). The stirred reaction was treated with $Br_2$ (540 μL, 11 mmol) and then heated to 70° C. After 18 h of heating, the reaction was cooled to room temperature and the acetic acid was removed under reduced pressure to provide 5-bromo-3-hydroxy-4-methyl-thiophene-2-carboxylic acid methyl ester (2.19 g) as a light red solid in 99% yield.

¹H NMR (400 MHz, CHLOROFORM-D) δ ppm 2.08 (s, 3 H) 3.88 (s, 3 H).

The fifth step of Scheme 30: To a solution of 5-bromo-3-hydroxy-4-methyl-thiophene-2-carboxylic acid methyl ester (2.19 g, 8.7 mmol) and ethyl bromoacetate (1.2 mL, 10.5 mmol) was added $K_2CO_3$ (3.6 g, 26 mmol). The reaction was stirred vigorously at 45° C. After 4 hours, the reaction was diluted with ethyl acetate (350 mL) and washed with water (100 mL) and 5% LiCl (2×100 mL). The organic layer was dried over magnesium sulfate and filtered. The solvent was removed under reduced pressure and the material was purified by CombiFlash column chromatography eluting with a 5-50% ethyl acetate-hexane gradient to give 2.94 g (74%) of 5-bromo-3-ethoxycarbonylmethoxy-4-methyl-thiophene-2-carboxylic acid methyl ester as an orange solid.

¹H NMR (400 MHz, CHLOROFORM-D) δ ppm 1.29 (t, J=7.20 Hz, 3 H) 2.16 (m, 3 H) 3.83 (m, 3 H) 4.24 (q, J=7.16 Hz, 2 H) 4.89 (s, 2 H).

The sixth step of Scheme 30: 3-Ethoxycarbonylmethoxy-4-methyl-5-phenyl-thiophene-2-carboxylic acid methyl ester (63 mg, 95%) was prepared as a white solid following the procedure in the first step of Scheme 7 of Example 46.

¹H NMR (400 MHz, CHLOROFORM-D) δ ppm 1.30 (t, J=7.20 Hz, 3 H) 2.26 (s, 3 H) 3.86 (s, 3 H) 4.26 (q, J=7.16 Hz, 2 H) 4.92 (s, 2 H) 7.43 (m, 5 H).

The seventh step of Scheme 30: The procedure of the second step of Scheme 1 of Example 1 was followed to give 45 mg of 3-carboxymethoxy-4-methyl-5-phenyl-thiophene-2-carboxylic acid as an orange powder.

¹H NMR (400 MHz, d6-DMSO) δ ppm 2.17 (s, 3 H) 4.82 (s, 2 H) 5.49 (s, 1 H).

EXAMPLE 275

5-Bromo-3-carboxymethoxy-4-methyl-thiophene-2-carboxylic acid

The seventh step of Scheme 30: 5-Bromo-3-carboxymethoxy-4-methyl-thiophene-2-carboxylic acid was prepared from 5-bromo-3-ethoxycarbonylmethoxy-4-methyl-thiophene-2-carboxylic acid methyl ester and LiOH using the procedure in the second step of Scheme 1 of Example 1 to give 36 mg (98%) of 5-bromo-3-carboxymethoxy-4-methyl-thiophene-2-carboxylic acid as an orange solid.

ESI-MS: m/e=293.92 $[M-CO2]^-$.

EXAMPLE 276

3-Carboxymethoxy-4-methyl-thiophene-2-carboxylic acid

The seventh step of Scheme 30: 3-Carboxymethoxy-4-methyl-thiophene-2-carboxylic acid was prepared from 3-hydroxy-4-methyl-thiophene-2-carboxylic acid methyl ester following the procedure in the second step of Scheme 1 of Example 1 to give 11 mg (51%) of 3-carboxymethoxy-4-methyl-thiophene-2-carboxylic acid as a white solid.

¹H NMR (400 MHz, DMSO-D6) δ ppm 2.19 (s, 3 H) 4.87 (s, 2 H) 7.48 (m, 5 H).

EXAMPLE 277

3-Carboxymethoxy-4-methyl-5-styryl-thiophene-2-carboxylic acid

The sixth step of Scheme 30: A microwave tube containing 5-bromo-3-ethoxycarbonylmethoxy-4-methyl-thiophene-2-carboxylic acid methyl ester (55 mg, 0.16 mmol), styrene (23 μL, 0.20 mmol), HP(t-Bu)$_3$BF$_4$ (9 mg, 0.03 mmol) and Pd$_2$dba$_3$ (7 mg, 0.01 mmol) was degassed under argon. To the reaction mixture was added dioxane (1.0 mL) and dicyclohexyl-methyl-amine (41 μL). The reaction was heated at 150° C. for 25 minutes in the microwave. The crude material was filtered through a pad of silica gel and then purified by CombiFlash column chromatography to give 30 mg (52%) of 3-ethoxycarbonylmethoxy-4-methyl-5-styryl-thiophene-2-carboxylic acid methyl ester (1F) as a pale yellow solid.

¹H NMR (400 MHz, CHLOROFORM-D) δ ppm 1.28 (m, 3 H) 2.27 (s, 3 H) 3.84 (d, J=6.06 Hz, 3 H) 4.25 (q, J=7.07 Hz, 2 H) 4.88 (d, J=2.27 Hz, 2 H) 7.03 (d, J=16.17 Hz, 1 H) 7.20 (m, 1 H) 7.37 (m, J=7.45, 7.45 Hz, 3 H) 7.49 (m, 2 H).

The seventh step of Scheme 30: The procedure in the second step of Scheme 1 of Example 1 afforded 27 mg (98%) of 3-carboxymethoxy-4-methyl-5-styryl-thiophene-2-carboxylic acid as a yellow solid.

¹H NMR (400 MHz, CHLOROFORM-D) δ ppm 2.27 (d, 3 H) 4.88 (d, J=2.27 Hz, 2 H) 7.02 (d, J=15.92 Hz, 1 H) 7.20 (d, 1 H) 7.37 (m, 3 H) 7.49 (m, 2 H).

EXAMPLE 278

3-Carboxymethoxy-5-(4-hydroxy-phenyl)-4-methyl-thiophene-2-carboxylic acid

The sixth step of Scheme 30: 3-Ethoxycarbonylmethoxy-5-(4-hydroxy-phenyl)-4-methyl-thiophene-2-carboxylic acid methyl ester (41 mg, 53%) was prepared as a tan solid following the procedure in the first step of Scheme 7 of Example 46.

$^1$H NMR (400 MHz, CHLOROFORM-D) δ ppm 1.30 (t, J=7.07 Hz, 3 H) 2.23 (s, 3 H) 3.85 (s, 3 H) 4.26 (q, J=7.16 Hz, 2 H) 4.91 (s, 2 H) 6.90 (m, 2 H) 7.35 (m, 2 H).

The seventh step of Scheme 30: The procedure in the second step of Scheme 1 of Example 1 afforded 18 mg (49%) of 3-carboxymethoxy-5-(4-hydroxy-phenyl)-4-methyl-thiophene-2-carboxylic acid as a light brown solid.

$^1$H NMR (400 MHz, DMSO-D6) δ ppm 2.16 (m, 3 H) 4.85 (s, 2 H) 6.87 (m, 2 H) 7.33 (m, 2 H) 9.83 (s, 1 H).

EXAMPLE 279

3-Carboxymethoxy-4-methyl-5-[3-(pyridin-3-ylcarbamoyl)-phenyl]-thiophene-2-carboxylic acid The first step of Scheme 31: 5-(3-Amino-phenyl)-3-ethoxycarbonylmethoxy-4-methyl-thiophene-2-carboxylic acid methyl ester (350 mg, 82%) was prepared as a white solid following the procedure in the first step of Scheme 7 of Example 46.

$^1$H NMR (400 MHz, CHLOROFORM-D) δ ppm 1.30 (t, J=7.07 Hz, 3 H) 2.26 (s, 3 H) 3.76 (s, 2 H) 3.85 (s, 3 H) 4.26 (q, J=7.07 Hz, 2 H) 4.91 (s, 2 H) 6.70 (m, 1 H) 6.76 (m, J=1.89, 1.89 Hz, I H) 6.85 (m, 1 H) 7.21 (t, J=7.83 Hz, 1 H).

The second step of Scheme 31: To a solution of 5-(3-amino-phenyl)-3-ethoxycarbonylmethoxy-thiophene-2-carboxylic acid methyl ester (53 mg, 0.15 mmol), Nicotinic acid (28 mg, 0.23 mmol) and triethylamine (105 mL, 0.75 mL) in N,N-dimethylformamide (1.5 mL) was added O-(7-azabenzotriazol-1-yl)-N,N,N'N'-tetramethyluronium hexafluorophosphate (68 mg, 0.18 mmol). After 24 hours, the reaction was diluted with ethyl acetate (75 mL) and washed with water (25 mL). The organic layer was dried over magnesium sulfate and filtered. The solvent was removed under reduced pressure and the material was purified by CombiFlash column chromatography eluting with 5% methanol-dichloromethane to give 71 mg (99%) of 5-(3-benzoylamino-phenyl)-3-ethoxycarbonylmethoxy-thiophene-2-carboxylic acid methyl ester as a white solid.

$^1$H NMR (400 MHz, CHLOROFORM-D) δ ppm 1.31 (t, J=7.20 Hz, 3 H) 2.30 (s, 3 H) 3.85 (d, J=3.28 Hz, 3 H) 4.26 (q, J=7.07 Hz, 2 H) 4.92 (s, 2 H) 7.28 (m, 1 H) 7.45 (t, J=8.08 Hz, 2 H) 7.72 (d, J=8.08 Hz, 1 H) 7.83 (s, 1 H) 8.27 (d, J=9.85 Hz, 1 H) 8.46 (s, 1 H) 8.79 (dd, J=4.80, 1.52 Hz, 1 H) 9.15 (d, J=2.02 Hz, 1 H).

The third step of Scheme 31: The procedure of the second step of Scheme 31 of Example 1 afforded 25 mg (38%) of 3-carboxymethoxy-4-methyl-5-[3-(pyridin-3-ylcarbamoyl)-phenyl]-thiophene-2-carboxylic acid as an off-white solid.

$^1$H NMR (400 MHz, DMSO-D6) δ ppm 2.24 (s, 3 H) 4.85 (s, 2 H) 7.28 (d, J=8.08 Hz, 1 H) 7.50 (t, J=7.96 Hz, 1 H) 7.59 (dd, J=7.96, 4.93 Hz, 1 H) 7.85 (s, 1 H) 8.00 (d, J=1.77 Hz, 1 H) 8.32 (m, 1 H) 8.78 (dd, J=4.80, 1.52 Hz, 1 H) 10.59 (s, 1 H).

EXAMPLE 280

3-Carboxymethoxy-5-[4-(3-isopropyl-ureido)-phenyl]-4-methyl-thiophene-2-carboxylic acid The second step of Scheme 31: 3-Ethoxycarbonylmethoxy-5-[4-(3-isopropyl-ureido)-phenyl]-4-methyl-thiophene-2-carboxylic acid methyl ester (38 mg, 52%) was prepared as a white solid, following the procedure in the third step of Scheme 7 of Example 51.

$^1$H NMR (400 MHz, CHLOROFORM-D) δ ppm 1.18 (d, J=6.57 Hz, 6 H) 1.31 (t, J=7.20 Hz, 3 H) 2.18 (s, 3 H) 3.84 (s, 3 H) 4.00 (m, J=14.27, 6.69 Hz, 1 H) 4.27 (q, J=7.16 Hz, 2 H) 4.89 (s, 2 H) 5.03 (d, J=6.82 Hz, 1 H) 7.00 (s, 1 H) 7.34 (m, 4 H).

The third step of Scheme 31: The procedure in the second step of Scheme 1 of Example 1 afforded 30 mg (87%) of 3-carboxymethoxy-5-[4-(3-isopropyl-ureido)-phenyl]-4-methyl-thiophene-2-carboxylic acid as a white solid.

$^1$H NMR (400 MHz, DMSO-D6) δ ppm 1.05 (m, 6 H) 2.17 (s, 3 H) 3.76 (m, 1 H) 4.85 (s, 2 H) 6.07 (d, J=7.58 Hz, 1 H) 7.38 (m, 2 H) 7.49 (m, 2 H) 8.52 (s, 1 H).

EXAMPLE 281

5-(3-Carboxymethanesulfonylamino-phenyl)-3-carboxymethoxy-4-methyl-thiophene-2-carboxylic acid The second step of Scheme 31: To a solution of 5-(3-amino-phenyl)-3-ethoxycarbonylmethoxy-4-methyl-thiophene-2-carboxylic acid methyl ester (64 mg, 0.18 mmol) in pyridine (1 mL) was added 2,2,2-trifluoro-ethanesulfonyl chloride (20 µL, 0.18 mmol). After 4 hours, the reaction was diluted with ethyl acetate (75 mL) and washed with 1N HCl (25 mL) and brine (25 mL). The organic layer was dried over magnesium sulfate and filtered. The solvent was removed under reduced pressure and the material was purified by CombiFlash column chromatography to give 60 mg (67%) of 3-ethoxycarbonylmethoxy-4-methyl-5-[3-(2,2,2-trifluoroethanesulfonylamino)-phenyl]-thiophene-2-carboxylic acid methyl ester as a white solid.

$^1$H NMR (400 MHz, CHLOROFORM-D) δ ppm 1.31 (t, J=7.07 Hz, 3 H) 2.26 (s, 3 H) 3.86 (s, 2 H) 4.26 (q, J=7.07 Hz, 2 H) 4.92 (s, 2 H) 6.97 (s, 1 H) 7.26 (s, 1 H) 7.29 (m, 1 H) 7.35 (m, 2 H) 7.46 (t, J=8.08 Hz, 1 H).

The third step of Scheme 31: The procedure of the second step of Scheme 1 of Example 1 afforded 25 mg (46%) of 5-(3-carboxymethanesulfonylamino-phenyl)-3-carboxymethoxy-4-methyl-thiophene-2-carboxylic acid as a tan solid.

$^1$H NMR (400 MHz, DMSO-D6) δ ppm 2.20 (s, 2 H) 4.87 (s, 2 H) 5.76 (s, 2 H) 7.29 (dd, J=7.96, 1.89 Hz, 1 H) 7.37 (m, 1 H) 7.47 (m, 1 H).

EXAMPLE 282

5-(3-Benzylamino-phenyl)-3-carboxymethoxy-4-methyl-thiophene-2-carboxylic acid The first step of Scheme 32: 5-(3-Benzylamino-phenyl)-3-ethoxycarbonylmethoxy-4-methyl-thiophene-2-carboxylic acid methyl ester (36 mg, 55%) was prepared as a white solid, following the procedure in the second step of Scheme 22 of Example 233.

$^1$H NMR (400 MHz, CHLOROFORM-D) δ ppm 1.30 (t, J=7.07 Hz, 3 H) 2.18 (s, 3 H) 3.84 (s, 3 H) 4.26 (q, J=7.24 Hz, 2 H) 4.36 (s, 2 H) 4.71 (s, 1 H) 4.89 (s, 2 H) 6.67 (m, 2 H) 6.80 (dd, J=6.57, 1.52 Hz, 1 H) 7.22 (t, J=7.96 Hz, 1 H) 7.35 (m, 5 H).

The second step of Scheme 32: The procedure of the second step of Scheme 1 of Example 1 afforded 32 mg (98%) of 5-(3-Benzylamino-phenyl)-3-carboxymethoxy-4-methyl-thiophene-2-carboxylic acid as a light yellow solid.

$^1$H NMR (400 MHz, DMSO-D6) δ ppm 2.02 (d, J=26.53 Hz, 3 H) 4.83 (s, 2 H) 5.76 (s, 2 H) 6.55 (s, 1 H) 6.63 (m, 2 H) 7.14 (m, 1 H) 7.23 (t, J=7.07 Hz, 1 H) 7.35 (m, 4 H).

EXAMPLE 283

3-Carboxymethoxy-5-[3-(cyclohexylmethyl-amino)-phenyl]-4-methyl-thiophene-2-carboxylic acid The first step of Scheme 32: 5-[3-(Cyclohexylmethyl-amino)-phenyl]-3-ethoxycarbonylmethoxy-4-methyl-thiophene-2-carboxylic acid methyl ester (48 mg, 72%) was prepared as a white solid, following the procedure in the second step of Scheme 22 of Example 233.

$^1$H NMR (400 MHz, CHLOROFORM-D) δ ppm 0.99 (m, 2 H) 1.23 (m, 3 H) 1.30 (m, 3 H) 1.75 (m, 6 H) 2.26 (s, 3 H) 2.97 (d, J=6.57 Hz, 2 H) 3.83 (s, 1 H) 3.85 (s, 3 H) 4.26 (q, J=7.16 Hz, 2 H) 4.90 (s, 2 H) 6.62 (m, 2 H) 6.76 (m, 1 H) 7.20 (t, J=7.83 Hz, 1 H).

The second step of Scheme 32: The procedure in the second step of Scheme 1 of Example 1 afforded 25 mg (56%) of 3-carboxymethoxy-5-[3-(cyclohexylmethyl-amino)-phenyl]-4-methyl-thiophene-2-carboxylic acid as a light yellow solid.

$^1$H NMR (400 MHz, DMSO-D6) δ ppm 1.31 (m, 10 H) 2.18 (s, 3 H) 2.87 (d, J=6.82 Hz, 2 H) 4.85 (s, 2 H) 6.62 (m, 4 H) 7.15 (t, J=7.83 Hz, 1 H).

EXAMPLE 284

3-Carboxymethoxy-4-methyl-5-[3-(3-phenoxy-benzylamino)-phenyl]-thiophene-2-carboxylic acid The first step of Scheme 32: 3-Ethoxycarbonylmethoxy-4-methyl-5-[3-(3-phenoxy-benzylamino)-phenyl]-thiophene-2-carboxylic acid methyl ester (51 mg, 74%) was prepared as a white solid, following the procedure in the second step of Scheme 22 of Example 233.

$^1$H NMR (400 MHz, CHLOROFORM-D) δ ppm 1.30 (t, J=7.20 Hz, 3 H) 2.14 (s, 3 H) 3.85 (s, 3 H) 4.26 (q, J=7.16 Hz, 2 H) 4.36 (s, 2 H) 4.89 (s, 2 H) 7.16 (m, 14 H).

The second step of Scheme 32: The procedure of the second step of Scheme 1 of Example 1 afforded 35 mg (72%) of 3-carboxymethoxy-4-methyl-5-[3-(3-phenoxy-benzylamino)-phenyl]-thiophene-2-carboxylic acid as a light yellow solid.

$^1$H NMR (400 MHz, DMSO-D6) δ ppm 2.06 (s, 3 H) 4.31 (d, J=5.56 Hz, 2 H) 4.47 (s, 1 H) 4.83 (s, 2 H) 6.62 (m, 3 H) 6.86 (m, 1 H) 6.95 (m, 1 H) 7.02 (m, 1 H) 7.14 (m, J=15.79, 7.71 Hz, 3 H) 7.35 (m, 4 H).

EXAMPLE 285

5-[3-(3-Bromo-benzylamino)-phenyl]-3-carboxymethoxy-4-methyl-thiophene-2-carboxylic acid The first step of Scheme 32: 5-[3-(3-Bromo-benzylamino)-phenyl]-3-ethoxycarbonylmethoxy-4-methyl-thiophene-2-carboxylic acid methyl ester (37 mg, 55%) was prepared as a white solid, following the procedure in the second step of Scheme 22 of Example 233.

$^1$H NMR (400 MHz, CHLOROFORM-D) δ ppm 1.30 (t, J=7.07 Hz, 3 H) 2.12 (s, 3 H) 3.85 (s, 3 H) 4.26 (m, 2 H) 4.36 (s, 2 H) 4.69 (s, 1 H) 4.89 (s, 2 H) 7.35 (m, 8 H).

The second step of Scheme 32: The procedure of the second step of Scheme 1 of Example 1 afforded 23 mg (71%) of 5-[3-(3-Bromo-benzylamino)-phenyl]-3-carboxymethoxy-4-methyl-thiophene-2-carboxylic acid as a light yellow solid.

$^1$H NMR (400 MHz, DMSO-D6) δ ppm 2.06 (s, 3 H) 4.32 (d, J=5.31 Hz, 2 H) 4.83 (s, 2 H) 6.64 (m, 4 H) 7.15 (t, J=7.96 Hz, 1 H) 7.30 (t, J=7.71 Hz, 1 H) 7.42 (m, 2 H) 7.57 (d, J=1.77 Hz, 1 H).

EXAMPLE 286

3-Carboxyethoxy-4-methyl-5-[3-(3-trifluoromethyl-benzylamino)-phenyl]-thiophene-2-carboxylic acid The first step of Scheme 32: 3-Ethoxycarbonylmethoxy-4-methyl-5-[3-(3-trifluoromethyl-benzylamino)-phenyl]-thiophene-2-carboxylic acid methyl ester (27 mg, 41%) was prepared as an off white solid, following the procedure in the second step of Scheme 22 of Example 233.

$^1$H NMR (400 MHz, CHLOROFORM-D) δ ppm 1.30 (m, 3 H) 2.09 (s, 3 H) 3.85 (s, 3 H) 4.25 (m, 2 H) 4.46 (s, 2 H) 4.78 (s, 1 H) 4.89 (s, 2 H) 7.48 (m, 8 H).

The second step of Scheme 32: The procedure of the second step of Scheme 1 of Example 1 afforded 23 mg (99%) of 3-carboxymethoxy-4-methyl-5-[3-(3-trifluoromethyl-benzylamino)-phenyl]-thiophene-2-carboxylic acid as a light yellow solid.

$^1$H NMR (400 MHz, DMSO-D6) δ ppm 2.02 (s, 3 H) 4.42 (d, J=5.56 Hz, 2 H) 4.82 (s, 2 H) 6.65 (m, 4 H) 7.16 (t, J=7.83 Hz, 1 H) 7.58 (d, J=7.83 Hz, 2 H) 7.69 (m, J=7.07 Hz, 1 H) 7.73 (s, 1 H).

EXAMPLE 287

3-Carboxymethoxy-5-[3-(cycloheptylmethyl-amino)-phenyl]-4-methyl-thiophene-2-carboxylic acid The first step of Scheme 32: 5-[3-(Cycloheptylmethyl-amino)-phenyl]-3-ethoxycarbonylmethoxy-4-methyl-thiophene-2-carboxylic acid methyl ester was prepared as an off white solid, following the procedure in the second step of Scheme 22 of Example 233.

$^1$H NMR (400 MHz, CHLOROFORM-D) δ ppm 1.55 (m, 17 H) 1.94 (m, 2 H) 2.20 (s, 3 H) 2.42 (m, 4 H) 3.40 (m, 1 H) 3.78 (s, 3 H) 4.73 (s, 2 H) 6.49 (dd, J=8.08, 1.77 Hz, 1 H) 6.54 (s, 1 H) 6.68 (d, J=8.08 Hz, 1 H) 7.12 (t, J=7.83 Hz, 1 H).

The second step of Scheme 32: The procedure of the second step of Scheme 1 of Example 1 afforded 10 mg (75%) of 3-carboxymethoxy-5-[3-(cycloheptylmethyl-amino)-phenyl]-4-methyl-thiophene-2-carboxylic acid as a pale yellow solid.

¹H NMR (400 MHz, DMSO-D6) δ ppm 1.56 (m, 8 H) 1.70 (m, 2 H) 1.92 (m, 2 H) 2.20 (s, 3 H) 3.51 (m, 1 H) 3.97 (m, 1 H) 4.87 (s, 2 H) 6.96 (m, 4 H).

EXAMPLE 288

5-Benzofuran-2-yl-4-bromo-3-carboxymethoxy-thiophene-2-carboxylic acid

The second step of Scheme 3: 5-Benzofuran-2-yl-4-bromo-3-ethoxycarbonylmethoxy-thiophene-2-carboxylic acid methyl ester (21 mg, 39%) was prepared according to the procedure in the second step of Scheme 3 of Example 17.

¹H NMR (400 MHz, CHLOROFORM-D) δ ppm 1.31 (t, 3 H) 3.90 (s, 3 H) 4.29 (q, J=7.07 Hz, 2 H) 4.93 (s, 2 H) 7.28 (m, 1 H) 7.37 (m, 1 H) 7.51 (d, J=8.08 Hz, 1 H) 7.64 (d, J=7.58 Hz, 1 H) 7.69 (s, 1 H).

The third step of Scheme 3: The procedure of the second step of Scheme 1 of Example 1 afforded 17 mg (78%) of 5-benzofuran-2-yl-4-bromo-3-carboxymethoxy-thiophene-2-carboxylic acid.

¹H NMR (400 MHz, DMSO-D6) δ ppm 4.93 (s, 2 H) 7.34 (m, 1 H) 7.44 (m, 1 H) 7.69 (m, 1 H) 7.80 (m, 2 H).

EXAMPLE 289

4,5-Bis-benzofuran-2-yl-3-ethoxycarbonylmethoxy-thiophene-2-carboxylic acid methyl ester The second step of Scheme 3: 4,5-Bis-benzofuran-2-yl-3-ethoxycarbonylmethoxy-thiophene-2-carboxylic acid methyl ester (5 mg, 8%) was prepared as a side product according to the procedure in the second step of Scheme 3 of Example 288.

¹H NMR (400 MHz, CHLOROFORM-D) δ ppm 1.20 (t, J=7.20 Hz, 3 H) 3.92 (s, 3 H) 4.17 (q, J=7.16 Hz, 2 H) 4.83 (s, 2 H) 6.84 (d, J=1.01 Hz, 1 H) 7.22 (m, 2 H) 7.33 (m, 3 H) 7.49 (t, J=8.72 Hz, 3 H) 7.68 (m, 1 H).

EXAMPLE 290

5-Biphenyl-3-yl-4-bromo-3-carboxymethoxy-thiophene-2-carboxylic acid

The second step of Scheme 3: 5-Biphenyl-3-yl-4-bromo-3-ethoxycarbonylmethoxy-thiophene-2-carboxylic acid methyl ester (45 mg, 60%) was prepared as a white solid, following the procedure in the second step of Scheme 3 of Example 17.

¹H NMR (400 MHz, CHLOROFORM-D) δ ppm 1.31 (m, 3 H) 3.89 (s, 3 H) 4.28 (m, 2 H) 4.94 (s, 2 H) 7.49 (m, 8 H) 7.89 (t, J=1.64 Hz, 1 H).

The third step of Scheme 3: The procedure of the second step of Scheme 1 of Example 1 afforded 21 mg (51%) of 5-Biphenyl-3-yl-4-bromo-3-carboxymethoxy-thiophene-2-carboxylic acid as a white solid.

¹H NMR (400 MHz, DMSO-D6) δ ppm 4.91 (s, 2 H) 7.43 (m, 2 H) 7.51 (t, J=7.45 Hz, 3 H) 7.65 (m, 2 H) 7.74 (dd, J=8.34, 1.26 Hz, 1 H) 7.80 (m, 1 H) 7.93 (m, J=1.77 Hz, 1 H).

EXAMPLE 291

5-Benzo[1,3]dioxol-5-yl-4-bromo-3-carboxymethoxy-thiophene-2-carboxylic acid The second step of Scheme 3: 5-Benzo[1,3]dioxol-5-yl-4-bromo-3-ethoxycarbonylmethoxy-thiophene-2-carboxylic acid methyl ester 67 mg (99%) was prepared as an off white solid, following the procedure in the second step of Scheme 3 of Example 17.

¹H NMR (400 MHz, CHLOROFORM-D) δ ppm 1.32 (t, J=7.07 Hz, 3 H) 3.87 (s, 3 H) 4.29 (q, J=7.16 Hz, 2 H) 4.90 (s, 2 H) 6.04 (s, 2 H) 6.89 (d, J=7.83 Hz, 1 H) 7.14 (m, 1 H) 7.16 (d, J=1.52 Hz, 1 H).

The third step of Scheme 3: The procedure of the second step of Scheme 1 of Example 1 afforded 19 mg (32%) of 5-benzo[1,3]dioxol-5-yl-4-bromo-3-carboxymethoxy-thiophene-2-carboxylic acid as a white solid.

¹H NMR (400 MHz, DMSO-D6) δ ppm 4.84 (s, 2 H) 6.12 (s, 2 H) 7.06 (d, J=8.08 Hz, 1 H) 7.15 (m, 1 H) 7.22 (d, J=1.77 Hz, 1 H).

EXAMPLE 292

4-Bromo-3-carboxymethoxy-5-pyridin-4-yl-thiophene-2-carboxylic acid

The second step of Scheme 3: 4-Bromo-3-ethoxycarbonylmethoxy-5-pyridin-4-yl-thiophene-2-carboxylic acid methyl ester (71 mg, 36%) was prepared as a white solid, following the procedure in the second step of Scheme 3 of Example 17.

¹H NMR (400 MHz, CHLOROFORM-D) δ ppm 1.32 (t, J=7.20 Hz, 3 H) 3.90 (s, 3 H) 4.29 (q, J=7.16 Hz, 2 H) 4.95 (s, 2 H) 7.64 (d, J=6.06 Hz, 2 H) 8.74 (s, 2 H).

The third step of Scheme 3: The procedure in the second step of Scheme 1 of Example 1 afforded 33 mg (52%) of 4-Bromo-3-carboxymethoxy-5-pyridin-4-yl-thiophene-2-carboxylic acid as a white solid.

¹H NMR (400 MHz, DMSO-D6) δ ppm 4.91 (s, 2 H) 7.71 (m, 2 H) 8.73 (m, 2 H).

EXAMPLE 293

4-Bromo-3-carboxymethoxy-5-[3-(4-trifluoromethylphenylcarbamoyl)phenyl]-thiophene-2-carboxylic acid Scheme 8, steps 1-3: 4-Bromo-3-ethoxycarbonylmethoxy-5-[3-(4-trifluoromethyl-phenylcarbamoyl)-phenyl]-thiophene-2-carboxylic acid methyl ester was prepared following the procedures in Scheme 8, steps 1-3 of Example 53.

The fourth step of Scheme 8: The procedure of the second step of Scheme 1 of Example 1 afforded 28 mg (92%) of 4-bromo-3-carboxymethoxy-5-[3-(4-trifluoromethyl-phenylcarbamoyl)-phenyl]-thiophene-2-carboxylic acid as a white powder.

¹H NMR (400 MHz, DMSO-D6) δ ppm 4.90 (s, 2 H) 7.73 (m, 3 H) 7.92 (m, 1 H) 8.02 (d, J=8.34 Hz, 2 H) 8.09 (m, 1 H) 8.22 (t, J=1.64 Hz, 1 H) 10.71 (s, 1 H).

EXAMPLE 294

4-Bromo-3-carboxymethoxy-5-naphthalen-1-yl-thiophene-2-carboxylic acid

The second step of Scheme 3: 4-Bromo-3-tert-butoxycarbonylmethoxy-5-naphthalen-2-yl-thiophene-2-carboxylic acid methyl ester was synthesized according to the procedure in the second step of Scheme 3 of Example 9, using 4,5-dibromo-3-tert-butoxycarbonylmethoxyl-thiophene-2-carboxylic acid methyl ester as the starting material.

¹H NMR (400 MHz, CHLOROFORM-D) δ ppm 1.52 (s, 9 H) 3.90 (s, 3 H) 4.86 (s, 2 H) 7.55 (m, 2 H) 7.76 (dd, J=8.59, 1.77 Hz, 1 H) 7.90 (m, 3 H) 8.16 (d, J=1.52 Hz, 1 H).

The third step of Scheme 3: 4-Bromo-3-carboxymethoxy-5-naphthalen-2-yl-thiophene-2-carboxylic acid (41.5 mg, 99+%) was synthesized according to the procedure in the second step of Scheme 1 of Example 1, using 4-bromo-3-tert-butoxycarbonylmethoxy-5-naphthalen-2-yl-thiophene-2-carboxylic acid methyl ester (49 mg) and excess of LiOH.

¹H NMR (400 MHz, DMSO-D6) δ ppm 4.93 (m, 2 H) 7.62 (m, 2 H) 7.80 (dd, J=8.46, 1.89 Hz, 1 H) 8.00 (d, J=9.10 Hz, 1 H) 8.06 (t, J=7.71 Hz, 1 H) 8.28 (d, J=1.77 Hz, 1 H).

EXAMPLE 295

3-Bromo-4-carboxymethoxy-[2,3]-bithiophenyl-5-carboxylic acid

The second step of Scheme 3: 3-Bromo-4-tert-butoxycarbonylmethoxy-[2,3]-bithiophenyl-5-carboxylic acid methyl ester was synthesized according to the procedure in the second step of Scheme 3 of Example 9, using 5-dibromo-3-tert-butoxycarbonylmethoxyl-thiophene-2-carboxylic acid methyl ester as the starting material.

¹H NMR (400 MHz, CHLOROFORM-D) δ ppm 1.50 (s, 9 H) 3.87 (s, 3 H) 4.82 (s, 2 H) 7.41 (dd, J=5.18, 2.91 Hz, 1 H) 7.48 (m, 1 H) 7.91 (dd, J=2.91, 1.39 Hz, 1 H).

The third step of Scheme 3: 3-Bromo-4-carboxymethoxy-[2,3]-bithiophenyl-5-carboxylic acid (52.8 mg, 96%) was prepared according to the procedure in the second step of Scheme 1 of Example 1, using 3-bromo-4-tert-butoxycarbonylmethoxy-[2,3]-bithiophenyl-5-carboxylic acid methyl ester (65 mg, 0.15 mmol) and LiOH (excess) as starting materials.

¹H NMR (400 MHz, DMSO-D6) δ ppm 4.89 (s, 2 H) 7.54 (dd, J=5.05, 1.52 Hz, 1 H) 7.76 (dd, J=5.05, 3.03 Hz, 1 H) 8.14 (dd, J=2.91, 1.39 Hz, 1 H).

EXAMPLE 296

4-Bromo-3-carboxymethoxy-5-pyridin-3-yl-thiophene-2-carboxylic acid

The second step of Scheme 3: 4-Bromo-3-tert-butoxycarbonylmethoxy-5-pyridin-3-yl-thiophene-2-carboxylic acid methyl ester was prepared according to the procedure in the second step of Scheme 3 of Example 9, using 3-pyridylboronic acid as one of the coupling partners.

¹H NMR (400 MHz, CHLOROFORM-D) δ ppm 1.32 (t, J=7.20 Hz, 3 H) 3.90 (s, 3 H) 4.30 (q, J=7.07 Hz, 2 H) 4.95 (s, 2 H) 7.41 (ddd, J=8.02, 4.86, 0.76 Hz, 1 H) 8.00 (ddd, J=8.02, 2.34, 1.77 Hz, 1 H) 8.68 (dd, J=4.80, 1.77 Hz, 1 H) 8.89 (dd, J=2.53, 0.76 Hz, 1 H).

The third step of Scheme 3: 4-Bromo-3-carboxylmethoxy-5-pyridin-3-yl-thiophene-2-carboxylic acid (13.9 mg, 99%) was prepared as a white solid according to the procedure in the second step of Scheme 1 of Example 1 from 4-bromo-3-tert-butoxycarbonylmethoxy-5-pyridin-3-yl-thiophene-2-carboxylic acid methyl ester (15.5 mg).

¹H NMR (400 MHz, DMSO-D6) δ ppm 4.91 (s, 2 H) 7.58 (dd, J=7.45, 5.43 Hz, 1 H) 8.09 (m, 1 H) 8.69 (dd, J=5.05, 1.77 Hz, 1 H) 8.85 (d, J=2.27 Hz, 1 H).

EXAMPLE 297

3-Bromo-4-carboxymethoxy-2'-formyl-[2,3]-bithiophenyl-5-carboxylic acid

The second step of Scheme 3: 3-Bromo-4-ethoxycarbonylmethoxy-2'-formyl-[2,3]-bithiophenyl-5-carboxylic acid methyl ester was prepared according to the procedure in the first step of Scheme 7 of Example 46, using 2-formylthiophene-3-boronic acid as a coupling partner.

¹H NMR (400 MHz, CHLOROFORM-D) δ ppm 1.32 (t, J=7.07 Hz, 3 H) 3.90 (s, 3 H) 4.29 (q, J=7.24 Hz, 2 H) 4.97 (s, 2 H) 7.27 (d, J=1.01 Hz, 1 H) 7.80 (dd, J=5.05, 1.26 Hz, 1 H) 9.92 (d, J=1.26 Hz, 1 H).

The third step of Scheme 3: 3-Bromo-4-carboxymethoxy-2'-formyl-[2,3]-bithiophenyl-5-carboxylic acid (10 mg, 37%) was prepared according to the procedure in the second step of Scheme 1 of Example 1, using 3-Bromo-4-ethoxycarbonylmethoxy-2'-formyl-[2,3]-bithiophenyl-5-carboxylic acid methyl ester (30 mg, 0.07 mmol) and LiOH (excess) as starting materials.

¹H NMR (400 MHz, DMSO-D6) δ ppm 4.91 (s, 2 H) 7.43 (d, J=5.05 Hz, 1 H) 8.28 (dd, J=4.93, 1.14 Hz, 1 H) 9.83 (d, J=1.26 Hz, 1 H).

ESI-MS: m/e=345 [M−CO$_2$]⁻.

EXAMPLE 298

3-Bromo-4-carboxymethoxy-2'-(isobutylamino-methyl)-[2,3]-bithiophenyl-5-carboxylic acid The second step of Scheme 3: 3-Bromo-4-ethoxycarbonylmethoxy-2'-(isobutylamino-methyl)-[2,3]-bithiophenyl-5-carboxylic acid methyl ester was prepared according to the first step of Scheme 12 of Example 102 using 3-bromo-4-ethoxycarbonylmethoxy-2'-formyl-[2,3]-bithiophenyl-5-carboxylic acid methyl ester and isobutyl amine as starting materials. Crude product was purified by preparative thin-layer chromatography (40% EtOAc/Hex) to give the product in 35% yield.

¹H NMR (400 MHz, CHLOROFORM-D) δ ppm 0.89 (d, J=6.57 Hz, 6 H) 1.32 (t, J=7.20 Hz, 3 H) 1.71 (m, 1 H) 2.43 (d, J=6.57 Hz, 2 H) 3.87 (s, 2 H) 3.95 (s, 3 H) 4.30 (q, J=7.24 Hz, 2 H) 4.92 (s, 2 H) 7.06 (d, J=5.31 Hz, 1 H) 7.27 (m, 1 H).

The third step of Scheme 3: 3-Bromo-4-carboxymethoxy-2'-(isobutylamino-methyl)-[2,3]-bithiophenyl-5-carboxylic acid (10 mg, 64%) was prepared according to the procedure in the second step of Scheme 1 of Example 1, using 3-bromo-4-ethoxycarbonylmethoxy-2'-(isobutylamino-methyl)-[2,3]-bithiophenyl-5-carboxylic acid methyl ester (17 mg) and LiOH (excess) as starting materials.

¹H NMR (400 MHz, DMSO-D6) δ ppm 0.87 (d, J=6.82 Hz, 6 H) 1.84 (s, 1 H) 2.62 (d, J=6.82 Hz, 2 H) 4.32 (s, 2 H) 4.70 (s, 2 H) 7.19 (d, J=5.05 Hz, 1 H) 7.81 (d, J=5.05 Hz, 1 H).

ESI-MS: m/e=448 [M+H]⁺.

EXAMPLE 299

4-Bromo-3-carboxymethoxy-5-{3-[(5-phenylcarbamoyl-thiophen-2-ylmethyl)-amino]-phenyl}-thiophene-2-carboxylic acid The first step of Scheme 33: 4-Bromo-3-tert-butoxycarbonylmethoxy-5-{3-[(5-carboxythiophen-2-ylmethyl)-amino]-phenyl}-thiophene-2-carboxylic acid methyl ester (2.25 g, 97%) was prepared from 5-(3-amino-phenyl)-4-bromo-3-tert-butoxycarbonylmethoxy-thiophene-2-carboxylic acid methyl ester and 5-Formyl-thiophene-2-carboxylic acid 4 according to the procedure in the first step of Scheme 6 of Example 44.

$^1$H NMR (400 MHz, CHLOROFORM-D) δ ppm 1.48 (m, 9 H) 3.87 (s, 3 H) 4.60 (s, 2 H) 4.81 (s, 2 H) 6.73 (s, 1 H) 6.94 (m, 1 H) 7.02 (m, 1 H) 7.06 (d, J=3.79 Hz, 1 H) 7.25 (m, 1 H) 7.75 (d, J=3.79 Hz, 1 H).

The second step of Scheme 33: 4-Bromo-3-tert-butoxycarbonylmethoxy-5-{3-[(5-phenylcarbamoyl-thiophen-2-ylmethyl)-amino]-phenyl}-thiophene-2-carboxylic acid methyl ester (232 mg, 86%) was prepared from 4-bromo-3-tert-butoxycarbonylmethoxy-5-{3-[(5-carboxythiophen-2-ylmethyl)-amino]-phenyl}-thiophene-2-carboxylic acid methyl ester according to the procedure in the third step of Scheme 9 of Example 62.

$^1$H NMR (400 MHz, CHLOROFORM-D) δ ppm 1.49 (m, 9 H) 3.87 (s, 3 H) 4.41 (m, 1 H) 4.60 (d, J=5.31 Hz, 2 H) 4.80 (s, 2 H) 6.73 (dd, J=7.83, 2.02 Hz, 1 H) 6.95 (m, 1 H) 7.03 (m, 2 H) 7.14 (m, J=7.33 Hz, 1 H) 7.26 (m, 1 H) 7.35 (m, 1 H) 7.52 (d, J=3.79 Hz, 1 H) 7.59 (m, 1 H) 7.66 (s, 1 H) 8.02 (s, 1 H) 8.02 (s, 1 H).

The third step of Scheme 33: 4-Bromo-3-carboxymethoxy-5-{3-[(5-phenylcarbamoyl-thiophen-2-ylmethyl)-amino]-phenyl}-thiophene-2-carboxylic acid (127 mg, 77%) was prepared according to the procedure in the second step of Scheme 1 of Example 1.

$^1$H NMR (400 MHz, DMSO-D6) δ ppm 4.54 (s, 2 H) 4.86 (s, 2 H) 5.76 (s, 1 H) 6.76 (m, 2 H) 6.86 (m, J=7.07, 1.26 Hz, 1 H) 6.90 (t, J=1.89 Hz, 1 H) 7.09 (m, 1 H) 7.15 (d, J=3.79 Hz, 1 H) 7.22 (m, 1 H) 7.33 (m, 2 H) 7.69 (m, 2 H) 7.87 (d, J=3.79 Hz, 1 H) 10.12 (s, 1 H).

EXAMPLE 300

5-{3-[(5-Benzylcarbamoyl-thiophen-2-ylmethyl)-amino]-phenyl}-4-bromo-3-carboxymethoxy-thiophene-2-carboxylic acid The second step of Scheme 33: 5-{3-[(5-Benzylcarbamoyl-thiophen-2-ylmethyl)-amino]-phenyl}-4-bromo-3-tert-butoxycarbonylmethoxy-thiophene-2-carboxylic acid methyl ester (232 mg, 86%) was prepared according to the procedure in the third step of Scheme 9 of Example 62.

$^1$H NMR (400 MHz, CHLOROFORM-D) δ ppm 1.49 (m, 9 H) 3.87 (s, 3 H) 4.56 (s, 2 H) 4.60 (d, J=5.81 Hz, 2 H) 4.80 (s, 2 H) 6.21 (s, 1 H) 6.71 (m, 1 H) 6.93 (m, 1 H) 7.00 (m, 2 H) 7.31 (m, 7 H).

The third step of Scheme 33: 5-{3-[(5-Benzylcarbamoyl-thiophen-2-ylmethyl)-amino]-phenyl}-4-bromo-3-carboxymethoxy-thiophene-2-carboxylic acid (64 mg, 56%) was prepared according to the procedure in the second step of Scheme 1 of Example 1.

$^1$H NMR (400 MHz, DMSO-D6) δ ppm 4.41 (d, J=6.06 Hz, 2 H) 4.52 (m, 2 H) 4.86 (s, 2 H) 6.74 (dd, J=8.08, 1.01 Hz, 2 H) 6.84 (d, J=5.05 Hz, 1 H) 6.89 (m, 1 H) 7.07 (d, J=3.79 Hz, 1 H) 7.27 (m, 7 H) 7.65 (d, J=3.79 Hz, 1 H).

EXAMPLE 301

4-Bromo-3-carboxymethoxy-5-{3-[(5-cyclohexyl-carbamoyl-thiophen-2-ylmethyl)-amino]-phenyl}-thiophene-2-carboxylic acid The second step of Scheme 33: 4-Bromo-3-tert-butoxycarbonylmethoxy-5-{3-[(5-cyclohexylcarbamoyl-thiophen-2-ylmethyl)-amino]-phenyl}-thiophene-2-carboxylic acid methyl ester (208 mg, 77%) was prepared according to the procedure in the third step of Scheme 9 of Example 62.

$^1$H NMR (400 MHz, CHLOROFORM-D) δ ppm 1.34 (m, 6 H) 1.49 (m, 9 H) 1.72 (s, 2 H) 2.00 (m, 2 H) 2.21 (none, 1 H) 3.01 (s, 1 H) 3.88 (m, 3 H) 4.56 (s, 2 H) 4.81 (m, 2 H) 6.71 (m, 1 H) 6.94 (m, 1 H) 6.98 (m, J=3.79 Hz, 1 H) 7.01 (dd, J=6.44, 1.39 Hz, 1 H) 7.24 (m, 1 H) 7.35 (d, J=3.54 Hz, 1 H) 8.02 (s, 1 H).

The third step of Scheme 33: 4-Bromo-3-carboxymethoxy-5-{3-[(5-cyclohexylcarbamoyl-thiophen-2-ylmethyl)-amino]-phenyl}-thiophene-2-carboxylic acid (84 mg, 74%) was prepared according to the procedure in the second step of Scheme 1 of Example 1. 1H NMR (400 MHz, DMSO-D6) δ ppm 1.26 (m, 6 H) 1.70 (m, 4 H) 2.45 (m, 1 H) 4.48 (m, 2 H) 4.86 (s, 2 H) 6.72 (m, 2 H) 6.84 (m, J=9.35 Hz, 1 H) 6.88 (m, J=1.77, 1.77 Hz, 1 H) 7.04 (d, J=3.54 Hz, 1 H) 7.20 (m, 1 H) 7.61 (d, J=3.79 Hz, 1 H) 8.09 (d, J=7.83 Hz, 1 H).

EXAMPLE 302

4-Bromo-3-(carboxymethoxy)-5-[3-(piperidin-4-ylamino)phenyl]thiophene-2-carboxylic acid 4-Bromo-3-ethoxycarbonylmethoxy-5-[3-(piperidin-4-ylamino)-phenyl]-thiophene-2-carboxylic acid methyl ester HCl salt was dissolved in 2 mL THF, followed by addition of 1 mL 1N LiOH. The mixture was stirred at 35° C. for 5 hours. THF was evaporated under reduced pressure. 1N HCl was then added drop wise until a white precipitate was formed. 4-Bromo-3-(carboxymethoxy)-5-[3-(piperidin-4-ylamino)phenyl]thiophene-2-carboxylic acid was obtained as a white solid (46 mg, 49% yield).

$^1$H NMR (400 MHz, DMSO-D6) δ ppm 1.58 (m, 2 H) 2.05 (m, 2 H) 3.03 (m, 2 H) 3.38 (m, 2 H) 3.57 (m, 1 H) 4.77 (s, 2 H) 6.03 (d, J=7.58 Hz, 1 H) 6.72 (dd, J=8.08, 1.77 Hz, 1 H) 6.80 (d, J=7.58 Hz, 1 H) 6.84 (s, 1 H) 7.20 (t, J=7.96 Hz, 1 H) 8.45 (s, 1 H) 8.60 (s, 1 H).

EXAMPLE 303

({4-Bromo-2-(methoxycarbonyl)-5-[3-(piperidin-4-ylamino)phenyl]thien-3-yl}oxy)acetic acid 4-Bromo-3-tert-butoxycarbonylmethoxy-5-[3-(piperidin-4-ylamino)-phenyl]-thiophene-2-carboxylic acid methyl ester HCl salt was treated with 20% TFA in CH$_2$Cl$_2$. ({4-bromo-2-(methoxycarbonyl)-5-[3-(piperidin-4-ylamino) phenyl]thien-3-yl}oxy)acetic acid was obtained as a light yellow solid (165 mg, 95% yield).

$^1$H NMR (400 MHz, DMSO-D6) δ ppm 1.57 (m, 2 H) 2.07 (m, 2 H) 3.03 (m, 2 H) 3.33 (m, 2 H) 3.57 (m, 1 H) 3.81 (s, 3 H) 4.86 (s, 2 H) 6.75 (dd, J=8.21, 1.64 Hz, 1 H) 6.82 (d, J=7.58 Hz, 1 H) 6.87 (d, J=1.77 Hz, 1 H) 7.23 (t, J=7.96 Hz, 1 H) 8.42 (s, 1 H) 8.58 (s, 1 H).

EXAMPLE 304

Methyl 4-bromo-3-(2-ethoxy-2-oxoethoxy)-5-(3-{[1-(5-nitropyridin-2-yl)piperidin-4-yl]amino}phenyl) thiophene-2-carboxylate 4-Bromo-3-tert-butoxycarbonylmethoxy-5-[3-(piperidin-4-ylamino)-phenyl]-thiophene-2-carboxylic acid methyl ester HCl salt (100 mg, 0.193 mmol), 2-chloro-5-nitro-pyridine (61 mg, 0.386 mmol) and Et3N (107 mL, 0.772 mmol)

were dissolved in 2 mL EtOH. The mixture was heated at 120° C. in Personal Chemistry microwave for 40 minutes. Solvents were evaporated and the crude product was purified by column chromatography. Methyl 4-bromo-3-(2-ethoxy-2-oxoethoxy)-5-(3-{[1-(5-nitropyridin-2-yl)piperidin-4-yl]amino}phenyl)thiophene-2-carboxylate was obtained as a yellow solid (96 mg, 80% yield).

$^1$H NMR (400 MHz, CHLOROFORM-D) δ ppm 1.31 (m, 3 H) 1.51 (m, 2 H) 2.24 (m, 2 H) 3.29 (m, 2 H) 3.70 (m, 2 H) 3.87 (m, 3 H) 3.88 (s, 3 H) 4.29 (q, J=7.24 Hz, 2 H) 4.46 (d, J=13.64 Hz, 2 H) 4.91 (s, 2 H) 6.61 (d, J=9.60 Hz, 1 H) 6.69 (dd, J=7.71, 1.89 Hz, 1 H) 6.91 (m, 1 H) 6.97 (d, J=7.58 Hz, 1 H) 7.26 (m, 2 H) 8.20 (dd, J=9.47, 2.91 Hz, 1 H) 9.04 (d, J=2.27 Hz, 1 H).

HRMS: calcd for $C_{26}H_{27}BrN_4O_7S$, 618.0784; found (ESI-FTMS), 619.0856.

EXAMPLE 305

4-Bromo-3-(carboxymethoxy)-5-(3-{[1-(5-nitropyridin-2-yl)piperidin-4-yl]amino}phenyl)thiophene-2-carboxylic acid Methyl 4-bromo-3-(2-ethoxy-2-oxoethoxy)-5-(3-{[1-(5-nitropyridin-2-yl)piperidin-4-yl]amino}phenyl)thiophene-2-carboxylate (75 mg, 0.12 mmol)) was hydrolyzed by LiOH to provide 4-bromo-3-(carboxymethoxy)-5-(3-{[1-(5-nitropyridin-2-yl)piperidin-4-yl]amino}phenyl)thiophene-2-carboxylic acid as a yellow solid (52 mg, 75% yield).

$^1$H NMR (400 MHz, DMSO-D6) δ ppm 1.39 (m, J=10.86 Hz, 2 H) 2.04 (m, 2 H) 3.34 (m, 2 H) 3.67 (m, 1 H) 4.41 (m, J=4.04 Hz, 2 H) 4.41 (d, 2 H) 4.88 (s, 2 H) 6.75 (dd, J=8.34, 1.77 Hz, 1 H) 6.80 (d, J=7.83 Hz, 1 H) 6.88 (s, 1 H) 6.99 (d, J=9.85 Hz, 1 H) 7.21 (t, J=7.83 Hz, 1 H) 8.21 (dd, J=9.60, 2.78 Hz, 1 H) 8.97 (d, J=2.78 Hz, 1 H).

HRMS: calcd for $C_{23}H_{21}BrN_4O_7S$, 576.0314; found (ESI-FTMS), 577.0388.

EXAMPLE 306

5-[3-({1-[5-(Acetylamino)pyridin-2-yl]piperidin-4-yl}amino)phenyl]-4-bromo-3-(carboxymethoxy)thiophene-2-carboxylic acid Methyl 4-bromo-3-(2-ethoxy-2-oxoethoxy)-5-(3-{[1-(5-nitropyridin-2-yl)piperidin-4-yl]amino}phenyl)thiophene-2-carboxylate (56 mg, 0.09 mmol)) was dissolved in 4 mL EtOH/THF (1:1) followed by addition of Pd/C (15 mg). The solution was purged with hydrogen 5 times and then stirred under a hydrogen balloon at room temperature for 16 hours. The mixture was filtered through a plug of celite and the filtrate was collected. Evaporation of the solvent gave 42 mg (78% yield) of 5-[3-(5'-amino-3,4,5,6-tetrahydro-2H-[1,2']bipyridinyl-4-ylamino)-phenyl]-4-bromo-3-ethoxycarbonylmethoxy-thiophene-2-carboxylic acid methyl ester.

5-[3-(5'-Amino-3,4,5,6-tetrahydro-2H-[1,2']bipyridinyl-4-ylamino)-phenyl]-4-bromo-3-ethoxycarbonylmethoxy-thiophene-2-carboxylic acid methyl ester (42 mg, 0.071 mmol) was dissolved in 2 mL $CH_2Cl_2$. Acetic anhydride (14 μL, 0.142 mmol) and $Et_3N$ (20 μL, 0.142 mmol) were then added. The mixture was stirred at room temperature overnight. Solvent was evaporated and the crude products were purified by column chromatography. 5-[3-(5'-Acetylamino-3,4,5,6-tetrahydro-2H-[1,2']bipyridinyl-4-ylamino)-phenyl]-4-bromo-3-ethoxycarbonylmethoxy-thiophene-2-carboxylic acid methyl ester was obtained as a red/purple solid (48 mg, >95% yield).

5-[3-(5'-Acetylamino-3,4,5,6-tetrahydro-2H-[1,2']bipyridinyl-4-ylamino)-phenyl]-4-bromo-3-ethoxycarbonylmethoxy-thiophene-2-carboxylic acid methyl ester (40 mg, 0.063 mmol) was hydrolyzed by LiOH to give 5-[3-({1-[5-(acetylamino)pyridin-2-yl]piperidin-4-yl}amino)phenyl]-4-bromo-3-(carboxymethoxy)thiophene-2-carboxylic acid as an off white solid (15 mg, 40% yield).

$^1$H NMR (400 MHz, DMSO-D6) δ ppm 1.35 (m, 2 H) 1.63 (m, 1 H) 1.95 (m, 1 H) 2.00 (s, 3 H) 3.01 (m, 2 H) 3.53 (m, 1 H) 4.13 (m, 2 H) 4.87 (s, 2 H) 6.72 (dd, 1 H) 6.78 (d, 1 H) 7.20 (t, J=7.96 Hz, 1 H) 7.71 (m, 2 H) 8.25 (d, J=2.53 Hz, 1 H) 9.77 (s, 1 H).

HRMS: calcd for $C_{25}H_{25}BrN_4O_6S$, 588.0678; found (ESI-FTMS), 589.0745.

EXAMPLE 307

4-Bromo-3-(carboxymethoxy)-5-(3-{[1-(5-{[(methylamino)carbonyl]amino}pyridin-2-yl)piperidin-4-yl]amino}phenyl)thiophene-2-carboxylic acid 4-Bromo-3-ethoxycarbonylmethoxy-5-{3-[5'-(3-methyl-ureido)-3,4,5,6-tetrahydro-2H-[1,2']bipyridinyl-4-ylamino]-phenyl}-thiophene-2-carboxylic acid methyl ester was prepared following procedure similar to that of Example 306. It was then hydrolyzed by LiOH to give 4-bromo-3-(carboxymethoxy)-5-(3-{[1-(5-{[(methylamino)carbonyl]amino}pyridin-2-yl)piperidin-4-yl]amino}phenyl)thiophene-2-carboxylic acid as an off white solid (15 mg, 36% yield).

$^1$H NMR (400 MHz, DMSO-D6) δ ppm 1.38 (m, 2 H) 1.98 (m, J=8.59 Hz, 2 H) 2.62 (d, J=4.55 Hz, 3 H) 2.98 (t, J=11.37 Hz, 2 H) 3.51 (s, 1 H) 4.07 (m, 2 H) 4.86 (s, 2 H) 5.95 (d, 1 H) 5.86 (m, 1 H) 5.95 (d, J=4.55 Hz, 1 H) 6.72 (dd, J=8.21, 1.64 Hz, 1 H) 6.77 (d, J=7.58 Hz, 1 H) 6.84 (m, 3 H) 7.19 (t, J=7.96 Hz, 1 H) 7.62 (m, 1 H) 8.08 (d, J=2.53 Hz, 1 H) 8.20 (s, 1 H).

HRMS: calcd for $C_{25}H_{26}BrN_5O_6S$, 603.0787; found (ESI-FTMS), 604.087.

EXAMPLE 308

4-Bromo-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid 4-Bromo-3-ethoxycarbonylmethoxy-5-(3-{3-methyl-1-[5'-(3-methyl-ureido)-3,4,5,6-tetrahydro-2H-[1,2']bipyridinyl-4-yl]-ureido}-phenyl)-thiophene-2-carboxylic acid methyl ester (96 mg, 0.136 mmol) was hydrolyzed by LiOH to give 4-bromo-3-(carboxymethoxy)-5-(3-{[(methylamino)carbonyl][1-(5-{[(methylamino)carbonyl]amino}pyridin-2-yl)piperidin-4-yl]amino}phenyl)thiophene-2-carboxylic acid as an off white solid (11 mg, 13% yield).

$^1$H NMR (400 MHz, DMSO-D6) δ ppm 1.25 (m, 2 H) 1.82 (d, 2 H) 2.59 (d, J=4.29 Hz, 3 H) 2.77 (t, 2 H) 3.22 (none, 39 H) 4.20 (d, 2 H) 4.48 (m, 1 H) 4.87 (s, 2 H) 5.38 (s, 1 H) 5.92 (s, 1 H) 6.74 (d, 1 H) 7.26 (d, 1 H) 7.41 (s, 1 H) 7.55 (s, 3 H) 7.99 (s, 1 H) 8.15 (s, 1 H).

HRMS: calcd for $C_{27}H_{29}BrN_6O_7S$, 660.1002; found (ESI-FTMS), 661.1077.

EXAMPLE 309

4-Bromo-3-(carboxymethoxy)-5-{3-[(1-{5-[(methylsulfonyl)amino]pyridin-2-yl}piperidin-4-yl)amino]phenyl}thiophene-2-carboxylic acid 4-Bromo-3-ethoxycarbonylmethoxy-5-[3-(5'-methanesulfonylamino-3,4,5,6-tetrahydro-2H-[1,2']bipyridinyl-4-ylamino)-phenyl]-thiophene-2-carboxylic acid methyl ester (36 mg, 0.048 mmol) was hydrolyzed by LiOH to give 4-bromo-3-(carboxymethoxy)-5-{3-[(1-{5-[(methylsulfonyl)amino]pyridin-2-yl}piperidin-4-yl)amino]phenyl}thiophene-2-carboxylic acid as a light yellow solid (19 mg, 62% yield).

$^1$H NMR (400 MHz, DMSO-D6) δ ppm 1.35 (m, 2 H) 1.99 (m, 2 H) 2.89 (s, 3 H) 3.04 (t, J=11.12 Hz, 2 H) 3.52 (m, J=15.16 Hz, 1 H) 4.15 (m, 2 H) 4.84 (s, 2 H) 5.87 (s, 1 H) 6.72 (dd, J=7.96, 1.64 Hz, 1 H) 6.77 (d, J=7.58 Hz, 1 H) 6.87 (m, 3 H) 7.19 (t, J=7.96 Hz, 1 H) 7.40 (dd, J=8.97, 2.65 Hz, 1 H) 7.99 (d, J=2.53 Hz, 1 H) 9.21 (s, 1 H).

HRMS: calcd for $C_{24}H_{25}BrN_4O_7S_2$, 624.0348; found (ESI-FTMS), 625.043.

EXAMPLE 310

3-(Carboxymethoxy)-5-phenylthiophene-2-carboxylic acid

4-Bromo-3-tert-butoxycarbonylmethoxy-5-phenyl-thiophene-2-carboxylic acid methyl ester (150 mg, 0.35 mmol) and Pd(PPh$_3$)$_4$ (40 mg, 0.035 mmol) were dissolved in 3 mL CH$_3$CN. The mixture was purged with nitrogen gas followed by addition of NaBH(OAc)$_3$ (298 mg, 1.4 mmol). The mixture was heated at 120° C. in Personal Chemistry microwave for 30 minutes. The solution was passed through a plug of celite and the crude products were purified by column chromatography. 3-tert-butoxycarbonylmethoxy-5-phenyl-thiophene-2-carboxylic acid methyl ester was obtained as a light yellow glassy solid (85 mg, 70% yield).

3-tert-Butoxycarbonylmethoxy-5-phenyl-thiophene-2-carboxylic acid methyl ester (20 mg, 0.057 mmol) was hydrolyzed by LiOH to give 3-(carboxymethoxy)-5-phenylthiophene-2-carboxylic acid as an off white solid (11 mg, 67% yield).

$^1$H NMR (400 MHz, DMSO-D6) δ ppm 4.88 (s, 2 H) 7.44 (m, 4 H) 7.72 (m, 2 H).

HRMS: calcd for $C_{13}H_{10}O_5S$, 278.0249; found (ESI-FTMS), 579.0399.

EXAMPLE 311

Methyl 5-(3-{[1-(benzylsulfonyl)piperidin-4-yl]amino}phenyl)-4-bromo-3-{2-[(2-methylphenyl)amino]-2-oxoethoxy}thiophene-2-carboxylate 4-Bromo-3-carboxymethoxy-5-[3-(1-phenylmethanesulfonyl-piperidin-4-ylamino)-phenyl]-thiophene-2-carboxylic acid methyl ester (1 eq), o-tolylamine (1.2 eq), benzotriazol-1-yloxyl-tris(dimethylamino)phosphonium hexafluorophosphate (1.2 eq) and diisopropylethylamine (2.0 eq) were dissolved in 5 mL of DMF. The mixture was stirred at room temperature for 16 hours. Water was then added. A light yellow precipitate was formed and collected by filtration. The solid was washed with water three times and the crude product was purified by column chromatography. Methyl 5-(3-{[1-(benzylsulfonyl)piperidin-4-yl]amino}phenyl)-4-bromo-3-{2-[(2-methylphenyl)amino]-2-oxoethoxy}thiophene-2-carboxylate was obtained as a yellow solid (220 mg, 52% yield).

$^1$H NMR (400 MHz, CHLOROFORM-D) δ ppm 1.42 (m, 2 H) 2.03 (m, 2 H) 2.38 (s, 3 H) 2.78 (m, 2 H) 3.36 (m, 1 H) 3.63 (m, 2 H) 3.87 (s, 3 H) 4.23 (s, 2 H) 4.89 (s, 2 H) 6.64 (dd, J=7.83, 2.02 Hz, 1 H) 6.80 (d, J=1.77 Hz, 1 H) 6.93 (d, J=7.58 Hz, 1 H) 7.12 (t, J=7.33 Hz, 1 H) 7.24 (m, 3 H) 7.40 (m, 5 H) 7.91 (d, J=7.83 Hz, 1 H) 9.21 (s, 1 H).

HRMS: calcd for $C_{33}H_{34}BrN_3O_6S_2$, 711.1072; found (ESI-FTMS), 712.1144.

EXAMPLE 312

5-(3-{[1-(Benzylsulfonyl)piperidin-4-yl][(ethylamino)carbonyl]amino}phenyl)-4-bromo-3-(carboxymethoxy)thiophene-2-carboxylic acid 4-Bromo-3-tert-butoxycarbonylmethoxy-5-{3-[3-ethyl-1-(1-phenylmethanesulfonyl-piperidin-4-yl)-ureido]-phenyl}-thiophene-2-carboxylic acid methyl ester was hydrolyzed by LiOH to give 5-(3-{[1-(benzylsulfonyl)piperidin-4-yl][(ethylamino)carbonyl]amino}phenyl)-4-bromo-3-(carboxymethoxy)thiophene-2-carboxylic acid as an off white solid (206 mg, 95% yield).

$^1$H NMR (400 MHz, DMSO-D6) δ ppm 0.91 (t, J=7.07 Hz, 3 H) 1.12 (m, 2 H) 1.76 (m, 2 H) 2.76 (m, 2 H) 2.98 (dd, J=13.26, 6.44 Hz, 2 H) 3.12 (m, 1 H) 3.52 (d, 3 H) 3.52 (d, J=12.63 Hz, 2 H) 4.34 (s, 2 H) 4.88 (s, 2 H) 5.46 (t, J=5.68 Hz, 1 H) 7.29 (m, 6 H) 7.41 (t, J=1.89 Hz, 1 H) 7.61 (t, J=7.83 Hz, 1 H) 7.71 (d, J=8.34 Hz, 1 H).

HRMS: calcd for $C_{28}H_{30}BrN_3O_8S_2$, 679.0658; found (ESI-FTMS), 680.0743.

EXAMPLE 313

4,5-Dibromo-3-[carboxy(fluoro)methoxy]thiophene-2-carboxylic acid 4,5-dibromo-3-(tert-butoxycarbonyl-fluoro-methoxy)-thiophene-2-carboxylic acid methyl ester was hydrolyzed by LiOH to give 4,5-dibromo-3-[carboxy(fluoro)methoxy]thiophene-2-carboxylic acid as an off white solid (240 mg, 40% yield).

$^1$H NMR (400 MHz, DMSO-D6) δ ppm 6.25 (d, J=57.10 Hz, 1 H).

HRMS: calcd for C7H$_3$Br2FO$_5$S, 375.8052; found (ESI-FTMS), 374.7972.

EXAMPLE 314

{[5-Phenyl-2-(2H-tetrazol-5-yl)thien-3-yl]oxy}acetic acid 3-tert-Butoxycarbonylmethoxy-5-phenyl-thiophene-2-carboxylic acid methyl ester (85 mg, 0.24 mmol) was treated with 5 mL 20% TFA in CH$_2$Cl$_2$ for 2 hours at room temperature. Solvents were evaporated under reduced pressure. To the resulting solid, 5 mL of NH4OH (30% by weight in water) was added and the mixture was stirred at room temperature overnight. 1N HCl was then added slowly until pH3. A white precipitate was formed and collected by filtration, which yielded (2-carbamoyl-5-phenyl-thiophen-3-yloxy)-acetic acid (44 mg, 65% yield). The resulting compound was then esterified in MeOH catalyzed by sulfuric acid to provide (2-carbamoyl-5-phenyl-thiophen-3-yloxy)-acetic acid methyl ester as an off white solid (44 mg, 95% yield).

(2-Carbamoyl-5-phenyl-thiophen-3-yloxy)-acetic acid methyl ester (44 mg, 0.15 mmol) and cyanuric chloride (42 mg, 1.5 eq) were dissolved in 4 mL DMF. The mixture was stirred at room temperature for 4 hours. Water was added and the mixture was stirred for 20 minutes. A white precipitate was formed and collected by filtration. The solid was washed with water twice and dried in vacuum oven to give (2-cyano-5-phenyl-thiophen-3-yloxy)-acetic acid methyl ester (35 mg, 85% yield).

(2-Cyano-5-phenyl-thiophen-3-yloxy)-acetic acid methyl ester (35 mg, 0.128 mmol), sodium azide (25 mg, 3.0 eq) and Et3N.HCl (53 mg, 3.0 eq) were dissolved in 3 mL toluene and stirred at 100° C. for 16 hours. Ethyl acetate (20 mL) was then added and the organic layer was washed with water twice, brine once and dried over anhydrous Na2SO4. Evaporation of solvents yielded an off white solid which was hydrolyzed with LiOH to give {[5-phenyl-2-(2H-tetrazol-5-yl)thien-3-yl]oxy}acetic acid (29 mg, 75% yield).

$^1$H NMR (400 MHz, DMSO-D6) δ ppm 4.98 (s, 2 H) 7.42 (m, 1 H) 7.48 (m, 2 H) 7.72 (s, 1 H) 7.76 (m, 2 H).

HRMS: calcd for $C_{13}H_{10}N_4O_3S$, 302.0474; found (ESI-FTMS), 303.055.

EXAMPLE 315

{[5-[3-({[1-(Anilinocarbonyl)piperidin-4-yl]methyl}amino)phenyl]-4-bromo-2-(methoxycarbonyl)thien-3-yl]oxy}acetic acid 4-Bromo-3-tert-butoxycarbonylmethoxy-5-{3-[(1-phenylcarbamoyl-piperidin-4-ylmethyl)-amino]-phenyl}-thiophene-2-carboxylic acid methyl ester (320 mg, 0.485 mmol) was hydrolyzed in 20% TFA in $CH_2Cl_2$ to give {[5-[3-({[1-(anilinocarbonyl)piperidin-4-yl]methyl}amino)phenyl]-4-bromo-2-(methoxycarbonyl)thien-3-yl]oxy}acetic acid as a light yellow solid (253 mg, 86% yield).

$^1$H NMR (400 MHz, CHLOROFORM-D) δ ppm 1.29 (m, 2 H) 1.85 (d, J=10.36 Hz, 3 H) 1.85 (d, 2 H) 2.87 (t, J=12.13 Hz, 2 H) 3.07 (d, J=6.06 Hz, 2 H) 3.90 (s, 3 H) 4.12 (d, J=13.14 Hz, 2 H) 4.88 (s, 2 H) 6.61 (s, 1 H) 6.68 (d, J=8.08 Hz, 1 H) 6.81 (s, 1 H) 6.91 (d, J=7.58 Hz, 1 H) 7.01 (t, J=7.20 Hz, 1 H) 7.26 (t, J=7.71 Hz, 3 H) 7.33 (m, 2 H).

HRMS: calcd for $C_{27}H_{28}BrN_3O_6S$, 601.0882; found (ESI-FTMS), 602.0966.

EXAMPLE 316

5-(3-{{[1-(Anilinocarbonyl)piperidin-4-yl]methyl}[(ethylamino)carbonyl]amino}phenyl)-4-bromo-3-(carboxymethoxy)thiophene-2-carboxylic acid 4-Bromo-3-tert-butoxycarbonylmethoxy-5-{3-[3-ethyl-1-(1-phenylcarbamoyl-piperidin-4-ylmethyl)-ureido]-phenyl}-thiophene-2-carboxylic acid methyl ester (42 mg, 0.057 mmol) was hydrolyzed by LiOH to give 5-(3-{{[1-(anilinocarbonyl)piperidin-4-yl]methyl}[(ethylamino)carbonyl]amino}phenyl)-4-bromo-3-(carboxymethoxy)thiophene-2-carboxylic acid as a white solid (26 mg, 68% yield).

$^1$H NMR (400 MHz, DMSO-D6) δ ppm 0.90 (t, J=7.07 Hz, 3 H) 1.28 (m, 2 H) 1.58 (m, 2 H) 2.62 (m, 2 H) 2.97 (m, 2 H) 3.53 (m, 2 H) 3.99 (m, 2 H) 4.07 (m, 1 H) 4.82 (s, 2 H) 5.93 (s, 1 H) 6.83 (s, 1 H) 7.13 (t, J=7.83 Hz, 2 H) 7.34 (dd, J=12.51, 7.45 Hz, 3 H) 7.48 (d, J=7.83 Hz, 2 H) 7.63 (m, 1 H) 8.33 (s, 1 H).

HRMS: calcd for $C_{29}H_{31}BrN_4O_7S$, 658.1097; found (ESI-FTMS), 659.1166;

Anal. Calcd for $C_{29}H_{31}BrN_4O_7S$: C, 52.81; H, 4.74; N, 8.49. Found: C, 51.85; H, 4.27; N, 8.01.

EXAMPLE 317

4-Bromo-3-(carboxymethoxy)-5-{3-[(1-{[2-(trifluoromethoxy)phenyl]sulfonyl}piperidin-4-yl)amino]phenyl}thiophene-2-carboxylic acid 4-Bromo-3-tert-butoxycarbonylmethoxy-5-{3-[1-(2-trifluoromethyl-benzenesulfonyl)-piperidin-4-ylamino]-phenyl}-thiophene-2-carboxylic acid methyl ester (119 mg, 0.16 mmol) was hydrolyzed by LiOH to give 4-bromo-3-(carboxymethoxy)-5-{3-[(1-{[2-(trifluoromethoxy)phenyl]sulfonyl}piperidin-4-yl)amino]phenyl}thiophene-2-carboxylic acid as an off white solid (88 mg, 81% yield).

$^1$H NMR (400 MHz, DMSO-D6) δ ppm 1.21 (m, 2 H) 1.81 (d, J=13.39 Hz, 2 H) 2.68 (m, 2 H) 3.45 (d, J=12.63 Hz, 2 H) 4.69 (s, 2 H) 6.51 (dd, J=8.21, 1.64 Hz, 1 H) 6.60 (d, J=7.58 Hz, 1 H) 6.64 (s, 1 H) 7.00 (t, J=7.96 Hz, 1 H) 7.45 (m, 2 H) 7.67 (m, 1 H) 7.78 (dd, J=7.83, 1.52 Hz, 1 H).

EXAMPLE 318

4-Bromo-3-(carboxymethoxy)-5-[3-({1-[(5-chloro-2-methoxyphenyl)sulfonyl]piperidin-4-yl}amino)phenyl]thiophene-2-carboxylic acid 4-Bromo-3-tert-butoxycarbonylmethoxy-5-{3-[1-(5-chloro-2-methoxy-benzenesulfonyl)-piperidin-4-ylamino]-phenyl}-thiophene-2-carboxylic acid methyl ester (134 mg, 0.18 mmol) was hydrolyzed by LiOH to give 4-bromo-3-(carboxymethoxy)-5-[3-({1-[(5-chloro-2-methoxyphenyl)sulfonyl]piperidin-4-yl}amino)phenyl]thiophene-2-carboxylic acid as an off white solid (96 mg, 79% yield).

$^1$H NMR (400 MHz, DMSO-D6) δ ppm 1.45 (m, 2 H) 2.03 (m, 2 H) 2.96 (t, 2 H) 3.71 H) 4.00 (s, 3 H) 4.95 (s, 2 H) 6.79 (d, 1 H) 6.85 (m, 1 H) 6.90 (s, 1 H) 7.26 (t, J=7.96 Hz, 1 H) 7.41 (d, J=8.59 Hz, 1 H) 7.79 (m, 2 H).

EXAMPLE 319

4-Bromo-3-(carboxymethoxy)-5-[3-({1-[(3,5-dichloro-2-hydroxyphenyl)sulfonyl]piperidin-4-yl}amino)phenyl]thiophene-2-carboxylic acid 4-Bromo-3-tert-butoxycarbonylmethoxy-5-{3-[1-(3,5-dichloro-2-hydroxy-benzenesulfonyl)-piperidin-4-ylamino]-phenyl}-thiophene-2-carboxylic acid methyl ester (70 mg, 0.09 mmol) was hydrolyzed by LiOH to give 4-bromo-3-(carboxymethoxy)-5-[3-({1-[(3,5-dichloro-2-hydroxyphenyl)sulfonyl]piperidin-4-yl}amino)phenyl]thiophene-2-carboxylic acid as an off white solid (44 mg, 68% yield).

$^1$H NMR (400 MHz, DMSO-D6) δ ppm 1.47 (s, 2 H) 2.04 (d, J=13.64 Hz, 2 H) 2.98 (s, 2 H) 3.73 (d, J=12.63 Hz, 2 H) 4.93 (s, 2 H) 6.75 (s, 1 H) 6.83 (d, J=7.33 Hz, 1 H) 6.88 (s, 1 H) 7.24 (t, J=7.96 Hz, 1 H) 7.68 (d, J=2.78 Hz, 1 H) 7.95 (d, J=2.78 Hz, 1 H) 10.88 (s, 1 H).

EXAMPLE 320

Propyl 4-bromo-3-(2-tert-butoxy-2-oxoethoxy)-5-{3-[(3,3,5,5-tetramethylcyclohexyl)amino]phenyl}thiophene-2-carboxylate 4,5-Dibromo-3-hydroxy-thiophene-2-carboxylic acid methyl ester (1.5 g, 4.74 mmol) and Ti(OiPr)4 in 4 mL 1-propanol was heated at 180° C. in personal chemistry microwave for 2 hours. Solvent was evaporated and the crude products were purified by column chromatography. 4,5-Dibromo-3-hydroxy-thiophene-2-carboxylic acid propyl ester (1.0 g, 61%) was obtained as a white solid.

4,5-Dibromo-3-hydroxy-thiophene-2-carboxylic acid propyl ester (1.0 g, 2.9 mmol) was alkylated with bromo-acetic acid tert-butyl ester to give 4,5-dibromo-3-tert-butoxycarbonylmethoxy-thiophene-2-carboxylic acid propyl ester (1.35 g, 95%) as a light yellow oil.

Suzuki coupling reaction of 4,5-dibromo-3-tert-butoxycarbonylmethoxy-thiophene-2-carboxylic acid propyl ester (1.32 g, 2.88 mmol) and 3-aminophenylboronic acid provided 5-(3-amino-phenyl)-4-bromo-3-tert-butoxycarbonylmethoxy-thiophene-2-carboxylic acid propyl ester (962 mg, 90% yield) as a light yellow oil.

Reductive amination reaction of 5-(3-amino-phenyl)-4-bromo-3-tert-butoxycarbonylmethoxy-thiophene-2-carboxylic acid propyl ester (960 mg, 2.04 mmol) and 3,3,5,5-tetramethyl-cyclohexanone yielded 4-bromo-3-tert-butoxycarbonylmethoxy-5-[3-(3,3,5,5-tetramethyl-cyclohexylamino)-phenyl]-thiophene-2-carboxylic acid propyl ester (401 mg, 41%) as a light yellow oil.

$^1$H NMR (400 MHz, CHLOROFORM-D) δ ppm 0.94 (s, 6 H) 1.00 (t, J=7.45 Hz, 3 H) 1.12 (s, 6 H) 1.30 (m, 1 H) 1.49 (d, J=4.80 Hz, 9 H) 1.55 (s, 2 H) 1.75 (m, 2 H) 1.89 (d, J=12.13 Hz, 2 H) 3.60 (m, 2 H) 4.24 (t, J=6.69 Hz, 2 H) 4.81 (s, 2 H) 6.62 (m, 1 H) 6.91 (m, 2 H) 7.21 (t, J=7.83 Hz, 1 H).

HRMS: calcd for $C_{30}H_{42}BrNO_5S$, 607.1967; found (ESI-FTMS), 304.6056.

EXAMPLE 321

[(4-Bromo-2-(propoxycarbonyl)-5-{3-[(3,3,5,5-tetramethylcyclohexyl)amino]phenyl}thien-3-yl)oxy]acetic acid 4-Bromo-3-tert-butoxycarbonylmethoxy-5-[3-(3,3,5,5-tetramethyl-cyclohexylamino)-phenyl]-thiophene-2-carboxylic acid propyl ester (401 mg, 0.658 mmol) was hydrolyzed by 20% TFA in $CH_2Cl_2$ to give [(4-bromo-2-(propoxycarbonyl)-5-{3-[(3,3,5,5-tetramethylcyclohexyl)amino]phenyl}thien-3-yl)oxy]acetic acid as a light yellow solid (338 mg, 93% yield).

$^1$H NMR (400 MHz, DMSO-D6) δ ppm 0.76 (m, 9 H) 0.91 (s, 6 H) 1.09 (m, 1 H) 1.49 (m, 2 H) 1.56 (m, 2 H) 3.34 (m, 1 H) 4.01 (t, J=6.44 Hz, 2 H) 4.67 (s, 2 H) 5.54 (d, J=1.01 Hz, 1 H) 6.50 (dd, J=8.21, 1.64 Hz, 1 H) 6.60 (d, J=7.58 Hz, 1 H) 6.66 (d, J=1.77 Hz, 1 H) 7.00 (t, J=7.83 Hz, 1 H).

HRMS: calcd for $C_{26}H_{34}BrNO_5S$, 551.1341; found (ESI-FTMS), 1103.274.

HRMS: calcd for $C_{26}H_{34}BrNO_5S$, 551.1341; found (ESI-FTMS), 552.1427.

EXAMPLE 322

4-Bromo-3-carboxymethoxy-5-{3-[1-(2-trifluoromethyl-phenylmethanesulfonyl)-piperidin-4-ylamino]-phenyl}-thiophene-2-carboxylic acid For the first step of Scheme 38, 4-bromo-3-tert-butoxycarbonylmethoxy-5-{3-[1-(2-trifluoromethyl-phenylmethanesulfonyl)-piperidin-4-ylamino]-phenyl}-thiophene-2-carboxylic acid methyl ester was obtained in 71% yield as a light yellow solid following the procedures in the third step of Scheme 15 (Example 141).

$^1$H NMR (400 MHz, CHLOROFORM-D) δ ppm 1.45 (m, 2 H) 1.51 (s, 9 H) 2.09 (dd, J=13.26, 3.16 Hz, 2 H) 2.89 (m, 2 H) 3.42 (m, 1 H) 3.69 (m, 3 H) 3.87 (s, 3 H) 4.42 (s, 2 H) 4.82 (s, 2 H) 6.63 (dd, J=8.08, 1.52 Hz, 1 H) 6.84 (m, 1 H) 6.95 (dd, J=9.35, 1.01 Hz, 1 H) 7.22 (t, J=7.96 Hz, 1 H) 7.49 (t, J=7.71 Hz, 1 H) 7.60 (t, J=7.58 Hz, 1 H) 7.73 (d, J=7.83 Hz, 1 H) 7.84 (d, J=7.83 Hz, 1 H).

For the second step of Scheme 38: To a solution of 4-bromo-3-tert-butoxycarbonylmethoxy-5-{3-[1-(2-trifluoromethyl-phenylmethanesulfonyl)-piperidin-4-ylamino]-phenyl}-thiophene-2-carboxylic acid methyl ester (410 mg, 0.548 mmol) in DCM (50 mL) was added TFA (5 mL). The resultant solution was stirred at room temperature for 6 hours. DCM was removed under vacuum and water (150 mL) was added. The product, 4-bromo-3-carboxymethoxy-5-{3-[1-(2-trifluoromethyl-phenylmethanesulfonyl)-piperidin-4-ylamino]-phenyl}-thiophene-2-carboxylic acid methyl ester (347 mg, 90%) was collected by filtration (washed with water and dried in vacuum oven at 50° C.) as a pale yellow solid.

$^1$H NMR (400 MHz, Acetone) δ ppm 1.81 (m, 2 H) 2.42 (m, 2 H) 3.41 (m, 2 H) 3.88 (m, 1 H) 4.01 (m, 2 H) 4.12 (d, J=2.78 Hz, 3 H) 4.77 (s, 2 H) 5.24 (s, 1 H) 7.06 (dd, J=8.59, 2.78 Hz, 1 H) 7.14 (dd, J=7.96, 1.14 Hz, 1 H) 7.23 (m, 1 H) 7.49 (t, J=7.83 Hz, 1 H) 7.84 (m, 1 H) 7.95 (t, J=7.83 Hz, 1 H) 8.04 (m, 2 H).

ESI-FTMS: m/e=691.0389 [M+H]$^+$.

Anal. Calcd for $C_{27}H_{26}BrF_3N_2O_7S_2$: C, 46.89; H, 3.79; Br, 11.55; F, 8.24; N, 4.05; O, 16.20; S, 9.27. Found: C, 46.89; H, 3.55; N, 3.95.

4-Bromo-3-carboxymethoxy-5-{3-[1-(2-trifluoromethyl-phenylmethanesulfonyl)-piperidin-4-ylamino]-phenyl}-thiophene-2-carboxylic acid methyl ester was hydrolyzed according to the procedure of the fourth step of Scheme 15 of example 141 to give 4-bromo-3-carboxymethoxy-5-{3-[1-(2-trifluoromethyl-phenylmethanesulfonyl)-piperidin-4-ylamino]-phenyl}-thiophene-2-carboxylic acid in 96% yield as a light yellow solid.

$^1$H NMR (400 MHz, DMSO-D6) δ ppm 1.45 (m, 2 H) 2.02 (m, 2 H) 3.08 (m, 2 H) 3.55 (m, 3 H) 4.53 (s, 2 H) 4.88 (s, 2 H) 6.74 (d, J=8.59 Hz, 1 H) 6.81 (d, J=8.08 Hz, 1 H) 6.88 (s, 1 H) 7.22 (t, J=7.96 Hz, 1 H) 7.60 (m, 1 H) 7.72 (m, 2 H) 7.80 (d, J=8.08 Hz, 1 H).

ESI-FTMS: m/e=677.0242 [M+H]$^+$.

EXAMPLE 323

4-Bromo-3-carboxymethoxy-5-[3-(indan-2-ylamino)-phenyl]-thiophene-2-carboxylic acid The first step of Scheme 38: 4-bromo-3-tert-butoxycarbonylmethoxy-5-[3-(indan-2-ylamino)-phenyl]-thiophene-2-carboxylic acid methyl ester was prepared in 81% yield as a yellow oil, according to the first step of Scheme 15 of Example 141.

¹H NMR (400 MHz, CHLOROFORM-D) δ ppm 1.50 (s, 9 H) 2.92 (dd, J=15.92, 4.29 Hz, 2 H) 3.39 (dd, J=16.17, 6.82 Hz, 2 H) 3.87 (s, 3 H) 4.37 (m, 1 H) 4.82 (s, 2 H) 6.68 (m, 1 H) 6.92 (m, 1 H) 6.97 (m, 1 H) 7.22 (m, 5 H).

4-Bromo-3-carboxymethoxy-5-[3-(indan-2-ylamino)-phenyl]-thiophene-2-carboxylic acid methyl ester was prepared in 65% yield as a gray solid according to the procedure of the second step of Scheme 38 from 4-bromo-3-tert-butoxycarbonylmethoxy-5-[3-(indan-2-ylamino)-phenyl]-thiophene-2-carboxylic acid methyl ester.

¹H NMR (400 MHz, DMSO-D6) δ ppm 2.84 (dd, J=15.92, 5.05 Hz, 2 H) 3.32 (dd, J=16.17, 7.07 Hz, 2 H) 3.81 (s, 3 H) 4.25 (m, 1 H) 4.86 (s, 2 H) 6.76 (m, 1 H) 6.83 (m, 1 H) 6.90 (t, J=2.02 Hz, 1 H) 7.15 (m, 2 H) 7.24 (m, 3 H).

For the third step of Scheme 38, 4-bromo-3-carboxymethoxy-5-[3-(indan-2-ylamino)-phenyl]-thiophene-2-carboxylic acid methyl ester was hydrolyzed according to the fourth step of Scheme 15 of example 141 to give 4-bromo-3-carboxymethoxy-5-[3-(indan-2-ylamino)-phenyl]-thiophene-2-carboxylic acid in 45% yield as a dark yellow solid.

¹H NMR (400 MHz, DMSO-D6) δ ppm 2.83 (dd, J=15.92, 5.05 Hz, 2 H) 3.32 (dd, J=15.79, 6.95 Hz, 2 H) 4.25 (m, 1 H) 4.62 (s, 2 H) 6.21 (d, J=6.82 Hz, 1 H) 6.70 (dd, J=7.45, 2.40 Hz, 1 H) 6.78 (m, 1 H) 6.85 (t, J=1.89 Hz, 1 H) 7.19 (m, 5 H).

ESI-FTMS: m/e=488.0156 [M+H]⁺.

EXAMPLE 324

3-[3-(3-Bromo-5-carboxy-4-carboxymethoxy-thiophen-2-yl)-phenylamino]-8-aza-bicyclo[3.2.1]octane-8-carboxylic acid ethyl ester For the first step of Scheme 38, 3-[3-(3-bromo-4-tert-butoxycarbonylmethoxy-5-methoxycarbonyl-thiophen-2-yl)-phenylamino]-8-aza-bicyclo[3.2.1]octane-8-carboxylic acid ethyl ester was prepared in 87% yield as a yellow oil, according to the first step of Scheme 15 of Example 141.

¹H NMR (400 MHz, CHLOROFORM-D) δ ppm 1.51 (s, 9 H) 1.82 (d, J=14.40 Hz, 2 H) 2.05 (m, 6 H) 3.73 (t, J=6.06 Hz, 1 H) 3.87 (s, 3 H) 4.32 (m, 2 H) 4.81 (s, 2 H) 6.60 (m, 1 H) 6.80 (m, 1 H) 6.97 (dd, J=6.69, 1.64 Hz, 1 H) 7.24 (t, J=7.83 Hz, 1 H).

For the second step of Scheme 38, 3-[3-(3-bromo-4-carboxymethoxy-5-methoxycarbonyl-thiophen-2-yl)-phenylamino]-8-aza-bicyclo[3.2.1]octane-8-carboxylic acid ethyl ester was prepared in 82% yield as a gray solid according to the second step of Scheme 38 of Example 322 from 3-[3-(3-bromo-4-tert-butoxycarbonylmethoxy-5-methoxycarbonyl-thiophen-2-yl)-phenylamino]-8-aza-bicyclo[3.2.1]octane-8-carboxylic acid ethyl ester.

¹H NMR (400 MHz, DMSO-D6) δ ppm 1.19 (t, J=7.07 Hz, 3 H) 1.83 (m, 2 H) 2.09 (m, 4 H) 3.38 (m, 2 H) 3.57 (m, 1 H) 3.81 (s, 3 H) 4.05 (q, J=6.99 Hz, 2 H) 4.13 (m, 2 H) 4.86 (s, 2 H) 6.00 (d, J=2.02 Hz, 1 H) 6.69 (m, 1 H) 6.83 (m, 2 H) 7.21 (t, J=7.96 Hz, 1 H).

For the third step of Scheme 38, 3-[3-(3-bromo-4-tert-butoxycarbonylmethoxy-5-methoxycarbonyl-thiophen-2-yl)-phenylamino]-8-aza-bicyclo[3.2.1]octane-8-carboxylic acid ethyl ester was hydrolyzed according to the fourth step of Scheme 15 of example 141 to give 3-[3-(3-bromo-5-carboxy-4-carboxymethoxy-thiophen-2-yl)-phenylamino]-8-aza-bicyclo[3.2.1]octane-8-carboxylic acid ethyl ester in 85% yield as a yellow solid.

¹H NMR (400 MHz, DMSO-D6) δ ppm 1.19 (t, J=7.07 Hz, 3 H) 1.76 (m, 2 H) 1.87 (m, 2 H) 2.09 (m, 4 H) 3.58 (m, 1 H) 4.05 (m, 2 H) 4.13 (s, 2 H) 4.88 (s, 2 H) 6.00 (s, 1 H) 6.68 (m, 1 H) 6.81 (m, 2 H) 7.21 (t, J=8.21 Hz, 1 H).

ESI-FTMS: m/e=553.0653 [M+H]⁺.

EXAMPLE 325

4-Bromo-3-carboxymethoxy-5-[3-(8-phenylmethanesulfonyl-8-aza-bicyclo[3.2.1]oct-3-ylamino)-phenyl]-thiophene-2-carboxylic acid For the first step of Scheme 38, 4-bromo-3-tert-butoxycarbonylmethoxy-5-[3-(8-phenylmethanesulfonyl-8-aza-bicyclo[3.2.1]oct-3-ylamino)-phenyl]-thiophene-2-carboxylic acid methyl ester was prepared in 8% yield as a light yellow oil, according to the first step of Scheme 15 of Example 141.

For the second step of Scheme 38, 4-bromo-3-carboxymethoxy-5-[3-(8-phenylmethanesulfonyl-8-aza-bicyclo[3.2.1]oct-3-ylamino)-phenyl]-thiophene-2-carboxylic acid methyl ester was prepared in 95% yield as a light yellow solid according to the second step of Scheme 38 of Example 322 from 4-bromo-3-tert-butoxycarbonylmethoxy-5-[3-(8-phenylmethanesulfonyl-8-aza-bicyclo[3.2.1]oct-3-ylamino)-phenyl]-thiophene-2-carboxylic acid methyl ester.

¹H NMR (400 MHz, Acetone) δ ppm 2.03 (m, 4 H) 2.29 (m, 4 H) 3.81 (t, J=5.05 Hz, 1 H) 3.99 (s, 3 H) 4.16 (m, 2 H) 4.47 (s, 2 H) 5.12 (s, 2 H) 6.85 (dd, J=8.34, 2.27 Hz, 1 H) 7.02 (m, 2 H) 7.36 (m, 1 H) 7.51 (m, 3 H) 7.62 (m, 2 H).

For the third step of Scheme 38, 4-bromo-3-carboxymethoxy-5-[3-(8-phenylmethanesulfonyl-8-aza-bicyclo[3.2.1]oct-3-ylamino)-phenyl]-thiophene-2-carboxylic acid methyl ester was hydrolyzed according to the fourth step of Scheme 15 of Example 141 to give 4-bromo-3-carboxymethoxy-5-[3-(8-phenylmethanesulfonyl-8-aza-bicyclo[3.2.1]oct-3-ylamino)-phenyl]-thiophene-2-carboxylic acid in 80% yield as a light yellow solid.

¹H NMR (400 MHz, DMSO-D6) δ ppm 1.82 (m, 4 H) 2.07 (m, 4 H) 3.54 (m, 1 H) 4.01 (m, 2 H) 4.40 (s, 2 H) 4.88 (s, 2 H) 6.65 (dd, J=8.46, 2.65 Hz, 1 H) 6.80 (m, 2 H) 7.21 (m, 1 H) 7.40 (m, 5 H).

ESI-FTMS: m/e=652.0787 [M+NH4]+

EXAMPLE 326

5-(1-Benzyl-1H-pyrazol-4-yl)-4-bromo-3-carboxymethoxy-thiophene-2-carboxylic acid; compound with methane 5-(1-Benzyl-1H-pyrazol-4-yl)-4-bromo-3-carboxymethoxy-thiophene-2-carboxylic acid; compound with methane (62 mg) was synthesized from 5-(1-benzyl-1H-pyrazol-4-yl)-4-bromo-3-tert-butoxycarbonylmethoxy-thiophene-2-carboxylic acid methyl ester (80 mg, 0.158 mmol) in 87% yield as a white solid.

¹H NMR (400 MHz, DMSO-D6) δ ppm 4.88 (s, 2 H) 5.41 (s, 2 H) 7.33 (m, 5 H) 8.00 (d, J=1.01 Hz, 1 H) 8.56 (d, J=1.01 Hz, 1 H).

ESI-FTMS: m/e=436.9787 [M+H]⁺.

EXAMPLE 327

5-{3-[1-(2-Acetylamino-phenylmethanesulfonyl)-piperidin-4-ylamino]-phenyl}-4-bromo-3-carboxymethoxy-thiophene-2-carboxylic acid The first step of Scheme 39: To a solution of 4-bromo-3-methoxycarbonylmethoxy-5-{3-[1-(2-nitro-phenylmethanesulfonyl)-piperidin-4-ylamino]-phenyl}-thiophene-2-carboxylic acid methyl ester (558 mg, 0.82 mmol) in DCM (10 mL) was added pyridine (2 mL) then TFAA (1 mL). The resultant mixture was stirred at room temperature for 4 hours. The solvent was removed and the crude product was purified on CombiFlash column eluted with hexanes/ethyl acetate to give 4-bromo-3-methoxycarbonylmethoxy-5-{3-[[1-(2-nitro-phenylmethanesulfonyl)-piperidin-4-yl]-(2,2,2-trifluoro-acetyl)-amino]-phenyl}-thiophene-2-carboxylic acid methyl ester (635 mg, 100%) as a light yellow solid.

$^1$H NMR (400 MHz, CHLOROFORM-D) δ ppm 1.23 (m, 2 H) 1.68 (m, 2 H) 2.61 (m, 2 H) 3.47 (m, 2 H) 3.63 (s, 3 H) 3.68 (s, 3 H) 4.43 (m, 1 H) 4.50 (m, J=1.52 Hz, 2 H) 4.73 (s, 2 H) 6.99 (d, J=8.08 Hz, 1 H) 7.27 (s, 1 H) 7.33 (m, 3 H) 7.42 (m, 1 H) 7.52 (m, 1 H) 7.79 (m, 1 H).

The second step of Scheme 39: To a solution of 4-bromo-3-methoxycarbonylmethoxy-5-{3-[[1-(2-nitro-phenylmethanesulfonyl)-piperidin-4-yl]-(2,2,2-trifluoro-acetyl)-amino]-phenyl}-thiophene-2-carboxylic acid methyl ester (635 mg, 0.82 mmol) in EtOAc (80 mL) was purged with argon and added Pd/C (100 mg) at room temperature. The reaction mixture was stirred under a hydrogen balloon over night. MeOH (30 mL) was added and the reaction was allowed to stir for additional 2 hours before filtered through a pad of Celite. The crude product was purified on CombiFlash column eluted with 20-80% EtOAc/hexanes to give 5-{3-[[1-(2-amino-phenylmethanesulfonyl)-piperidin-4-yl]-(2,2,2-trifluoro-acetyl)-amino]-phenyl}-4-bromo-3-methoxycarbonylmethoxy-thiophene-2-carboxylic acid methyl ester (305 mg, 50%) and 5-{3-[[1-(2-amino-phenylmethanesulfonyl)-piperidin-4-yl]-(2,2,2-trifluoro-acetyl)-amino]-phenyl}-3-methoxycarbonylmethoxy-thiophene-2-carboxylic acid methyl ester (272 mg, 50%). Both are light yellow solid.

For 5-{3-[[1-(2-amino-phenylmethanesulfonyl)-piperidin-4-yl]-(2,2,2-trifluoro-acetyl)-amino]-phenyl)}-4-bromo-3-methoxycarbonylmethoxy-thiophene-2-carboxylic acid methyl ester: $^1$H NMR (400 MHz, CHLOROFORM-D) δ ppm 1.26 (m, 2 H) 1.71 (m, 2 H) 2.67 (m, 2 H) 3.64 (m, 2 H) 3.66 (s, 3 H) 3.71 (s, 3 H) 4.16 (s, 2 H) 4.44 (m, 1 H) 4.76 (s, 2 H) 6.73 (t, J=7.58 Hz, 1 H) 6.84 (d, J=7.58 Hz, 1 H) 6.91 (dd, J=7.71, 1.39 Hz, 1 H) 7.04 (m, 2 H) 7.30 (s, 1 H) 7.36 (m, 1 H) 7.56 (m, 1 H).

For 5-{3-[[1-(2-amino-phenylmethanesulfonyl)-piperidin-4-yl]-(2,2,2-trifluoro-acetyl)-amino]-phenyl}-3-methoxycarbonylmethoxy-thiophene-2-carboxylic acid methyl ester: $^1$H NMR (400 MHz, CHLOROFORM-D) δ ppm 1.43 (m, 2 H) 1.88 (d, J=12.63 Hz, 2 H) 2.84 (m, 2 H) 3.80 (d, J=1.52 Hz, 2 H) 3.83 (s, 3 H) 3.90 (s, 3 H) 4.30 (s, 2 H) 4.61 (m, 1 H) 4.87 (s, 2 H) 6.85 (m, 1 H) 6.90 (d, J=8.08 Hz, 1 H) 7.00 (s, 1 H) 7.07 (dd, J=7.71, 1.39 Hz, 1 H) 7.13 (d, J=7.58 Hz, 1 H) 7.20 (m, 1 H) 7.30 (s, 1 H) 7.51 (t, J=7.96 Hz, 1 H) 7.70 (d, J=8.59 Hz, 1 H).

For the third step of Scheme 39: To a solution of 5-{3-[[1-(2-amino-phenylmethanesulfonyl)-piperidin-4-yl]-(2,2,2-trifluoro-acetyl)-amino]-phenyl}-4-bromo-3-methoxycarbonylmethoxy-thiophene-2-carboxylic acid methyl ester (100 mg, 0.133 mmol) in DCM (3 mL) was added pyridine (1 mL) and acetic anhydride (42 □L, 0.45 mmol). The resultant mixture was stirred at room temperature over night. The solvent was removed and the crude product was purified on CombiFlash column eluted with EtOAc/Hexanes to give 5-{3-[[1-(2-acetylamino-phenylmethanesulfonyl)-piperidin-4-yl]-(2,2,2-trifluoro-acetyl)-amino]-phenyl}-4-bromo-3-methoxycarbonylmethoxy-thiophene-2-carboxylic acid methyl ester (101 mg, 96%) as a light yellow solid.

$^1$H NMR (400 MHz, CHLOROFORM-D) δ ppm 1.33 (m, 2 H) 1.80 (d, J=8.84 Hz, 2 H) 2.70 (m, 2 H) 3.65 (m, 2 H) 3.76 (s, 3 H) 3.82 (s, 3 H) 4.18 (s, 2 H) 4.52 (m, 1 H) 4.88 (s, 2 H) 7.08 (m, 3 H) 7.32 (m, 1 H) 7.40 (s, 1 H) 7.47 (t, J=7.96 Hz, 1 H) 7.67 (m, 1 H) 7.73 (d, J=8.08 Hz, 1 H) 8.51 (s, 1 H).

For the fourth step of Scheme 39: To a solution of 5-{3-[[1-(2-acetylamino-phenylmethanesulfonyl)-piperidin-4-yl]-(2,2,2-trifluoro-acetyl)-amino]-phenyl}-4-bromo-3-methoxycarbonylmethoxy-thiophene-2-carboxylic acid methyl ester (95 mg, 0.12 mmol) in THF (3 mL) and water (3 mL) was added LiOH (2.0 M, 0.6 mL). The reaction mixture was stirred at room temperature overnight, then 50° C. for 1 h before concentrated and acidified with 10% aq. HCl. 5-{3-[1-(2-Acetylamino-phenylmethanesulfonyl)-piperidin-4-ylamino]-phenyl}-4-bromo-3-carboxymethoxy-thiophene-2-carboxylic acid (67 mg, 84%) was collected by filtration, washed with water and dried under vacuum oven.

$^1$H NMR (400 MHz, DMSO-D6) δ ppm 1.37 (m, 2 H) 1.94 (m, 2 H) 2.89 (m, 2 H) 3.40 (m, 1 H) 3.50 (d, J=8.08 Hz, 2 H) 4.50 (s, 2 H) 4.88 (s, 2 H) 6.74 (m, 1 H) 6.83 (d, J=7.58 Hz, 1 H) 6.88 (d, J=1.01 Hz, 1 H) 7.21 (m, 2 H) 7.34 (t, J=7.96 Hz, 1 H) 7.43 (dd, J=7.83, 1.52 Hz, 1 H) 7.50 (d, J=7.58 Hz, 1 H) 9.44 (s, 1 H).

ESI-FTMS: m/e=664.0423 [M−H]−

EXAMPLE 328

5-{3-[1-(2-Acetylamino-phenylmethanesulfonyl)-piperidin-4-ylamino]-phenyl}-3-carboxymethoxy-thiophene-2-carboxylic acid 5-{3-[1-(2-Acetylamino-phenylmethanesulfonyl)-piperidin-4-ylamino]-phenyl}-3-carboxymethoxy-thiophene-2-carboxylic acid was prepared in 86% yield as a light yellow solid, according to the fourth step of Scheme 39 of Example 327 from 5-{3-[[1-(2-acetylamino-phenylmethanesulfonyl)-piperidin-4-yl]-(2,2,2-trifluoro-acetyl)-amino]-phenyl}-3-methoxycarbonylmethoxy-thiophene-2-carboxylic acid methyl ester.

$^1$H NMR (400 MHz, DMSO-D6) δ ppm 1.35 (m, 2 H) 1.92 (m, 2 H) 2.09 (s, 3 H) 2.90 (m, 2 H) 3.41 (m, 1 H) 3.49 (m, 1 H) 4.51 (s, 1 H) 4.89 (s, 1 H) 6.63 (d, J=10.61 Hz, 1 H) 6.87 (m, 2 H) 7.18 (m, 2 H) 7.30 (s, 1 H) 7.35 (m, 1 H) 7.44 (m, 1 H) 7.51 (d, J=7.58 Hz, 1 H) 9.46 (s, 1 H).

EXAMPLE 329

4-Bromo-3-carboxymethoxy-5-{3-[1-(2-methanesulfonylamino-phenylmethanesulfonyl)-piperidin-4-ylamino]-phenyl}-thiophene-2-carboxylic acid 4-Bromo-3-carboxymethoxy-5-{3-[1-(2-methanesulfonylamino-phenylmethanesulfonyl)-piperidin-4-ylamino]-phenyl}-thiophene-2-carboxylic acid was prepared in 70% yield as a light yellow solid, according to the fourth step of Scheme 39 of Example 327 from 5-{3-[[1-(2-acetylamino-phenylmethanesulfonyl)-piperidin-4-yl]-(2,2,2-trifluoro-acetyl)-amino]-phenyl}-3-methoxycarbonylmethoxy-thiophene-2-carboxylic acid methyl ester.

$^1$H NMR (400 MHz, DMSO-D6) δ ppm 1.37 (m, 2 H) 1.97 (dd, J=12.88, 3.28 Hz, 2 H) 2.95 (t, J=12.63 Hz, 2 H) 3.02 (s, 1 H) 3.53 (m, 3 H) 4.60 (s, 2 H) 4.88 (s, 2 H) 6.72 (d, J=8.34 Hz, 1 H) 6.81 (d, J=7.33 Hz, 1 H) 6.86 (s, 1 H) 7.21 (t, J=7.83 Hz, 1 H) 7.30 (m, 1 H) 7.42 (m, 2 H) 7.51 (dd, J=7.71, 1.39 Hz, 1 H) 9.15 (s, 1 H).

ESI-FTMS: m/e=700.0084 [M−H]−.

EXAMPLE 330

3-Carboxymethoxy-5-{3-[1-(2-methanesulfony-lamino-phenylmethanesulfonyl)-piperidin-4-ylamino]-phenyl}-thiophene-2-carboxylic acid 3-Carboxymethoxy-5-{3-[1-(2-methanesulfonylamino-phenylmethanesulfonyl)-piperidin-4-ylamino]-phenyl}-thiophene-2-carboxylic acid was prepared in 40% yield as a light yellow solid, according to the fourth step of Scheme 39 of Example 327 from 3-tert-butoxycarbonylmethoxy-5-{3-[[1-(2-methanesulfonylamino-phenylmethanesulfonyl)-piperidin-4-yl]-(2,2,2-trifluoro-acetyl)-amino]-phenyl}-thiophene-2-carboxylic acid methyl ester.

$^1$H NMR (400 MHz, Acetone) δ ppm 1.37 (m, 2 H) 1.93 (m, 2 H) 2.95 (m, 2 H) 2.96 (s, 3 H) 3.47 (m, 1 H) 3.56 (m, 2 H) 4.47 (s, 2 H) 4.84 (s, 2 H) 6.57 (dd, J=8.34, 2.53 Hz, 1 H) 6.81 (dd, J=8.84, 2.02 Hz, 2 H) 7.03 (t, J=8.21 Hz, 1 H) 7.17 (m, 1 H) 7.22 (s, 1 H) 7.30 (m, 1 H) 7.45 (dd, J=16.55, 6.69 Hz, 2 H) 7.98 (s, 1 H).

EXAMPLE 331

4-Bromo-3-carboxymethoxy-5-(3-{1-[2-(3-ethyl-ureido)-phenylmethanesulfonyl]-piperidin-4-ylamino}-phenyl)-thiophene-2-carboxylic acid 4-Bromo-3-carboxymethoxy-5-(3-{1-[2-(3-ethyl-ureido)-phenylmethanesulfonyl]-piperidin-4-ylamino}-phenyl)-thiophene-2-carboxylic acid was prepared in 95% yield as a light yellow solid, according to the fourth step of Scheme 39 of Example 327 from 4-bromo-5-{3-[{1-[2-(3-ethyl-ureido)-phenylmethanesulfonyl]-piperidin-4-yl}-(2,2,2-trifluoro-acetyl)-amino]-phenyl}-3-methoxycarbonylmethoxy-thiophene-2-carboxylic acid methyl ester.

$^1$H NMR (400 MHz, DMSO-D6) δ ppm 1.05 (t, J=7.20 Hz, 3 H) 1.35 (m, 2 H) 1.93 (m, 2 H) 2.91 (t, J=10.86 Hz, 2 H) 3.11 (m, 2 H) 3.50 (m, 3 H) 4.42 (s, 2 H) 4.88 (s, 2 H) 6.62 (t, J=4.93 Hz, 1 H) 6.70 (dd, J=7.71, 2.15 Hz, 1 H) 6.78 (m, 1 H) 6.83 (d, J=2.02 Hz, 1 H) 7.04 (m, 1 H) 7.20 (t, J=7.83 Hz, 1 H) 7.27 (dd, J=15.66, 1.52 Hz, 1 H) 7.35 (dd, J=7.83, 1.52 Hz, 1 H) 7.70 (d, J=8.34 Hz, 1 H) 7.76 (s, 1 H).

ESI-FTMS: m/e=693.071 [M−H]$^-$.

EXAMPLE 332

3-Carboxymethoxy-5-(3-{1-[2-(3-ethyl-ureido)-phenylmethanesulfonyl]-piperidin-4-ylamino}-phenyl)-thiophene-2-carboxylic acid 3-Carboxymethoxy-5-(3-{1-[2-(3-ethyl-ureido)-phenylmethanesulfonyl]-piperidin-4-ylamino}-phenyl)-thiophene-2-carboxylic acid was prepared in 76% yield as a light yellow solid, according to the fourth step of Scheme 39 of Example 327 from 5-{3-[{1-[2-(3-ethyl-ureido)-phenylmethanesulfonyl]-piperidin-4-yl}-(2,2,2-trifluoro-acetyl)-amino]-phenyl}-3-methoxycarbonylmethoxy-thiophene-2-carboxylic acid methyl ester.

$^1$H NMR (400 MHz, DMSO-D6) 3 ppm 1.06 (t, J=7.20 Hz, 3 H) 1.34 (m, 2 H) 1.89 (m, 2 H) 2.93 (t, J=10.61 Hz, 2 H) 3.12 (m, 2 H) 3.50 (m, 3 H) 4.42 (s, 2 H) 4.89 (s, 2 H) 5.77 (s, 1 H) 6.62 (m, 1 H) 6.86 (m, 1 H) 7.05 (m, 1 H) 7.15 (t, J=7.83 Hz, 1 H) 7.28 (m, 1 H) 7.31 (s, 1 H) 7.36 (dd, J=7.71, 1.39 Hz, 1 H) 7.71 (m, 1 H) 7.79 (s, 1 H).

ESI-FTMS: m/e=617.1726 [M+H]$^+$.

EXAMPLE 333

4-Bromo-3-carboxymethoxy-5-{3-[1-(2-chloromethanesulfonylamino-phenylmethanesulfonyl)-piperidin-4-ylamino]-phenyl}-thiophene-2-carboxylic acid 4-Bromo-3-carboxymethoxy-5-{3-[1-(2-chloromethanesulfonylamino-phenylmethanesulfonyl)-piperidin-4-ylamino]-phenyl}-thiophene-2-carboxylic acid was prepared in 95% yield as a light yellow solid, according to the fourth step of Scheme 39 of Example 327 from 4-bromo-3-tert-butoxycarbonylmethoxy-5-{3-[[1-(2-chloromethanesulfonylamino-phenylmethanesulfonyl)-piperidin-4-yl]-(2,2,2-trifluoro-acetyl)-amino]-phenyl}-thiophene-2-carboxylic acid methyl ester.

$^1$H NMR (400 MHz, DMSO-D6) δ ppm 1.41 (m, 2 H) 1.98 (d, J=10.61 Hz, 2 H) 2.95 (t, J=10.86 Hz, 1 H) 3.47 (m, 1 H) 3.58 (m, 2 H) 4.59 (s, 2 H) 4.88 (s, 2 H) 5.03 (s, 2 H) 6.78 (d, J=7.07 Hz, 1 H) 6.87 (d, J=6.82 Hz, 1 H) 6.92 (s, 1 H) 7.24 (t, J=7.96 Hz, 1 H) 7.35 (m, 1 H) 7.42 (d, J=3.79 Hz, 2 H) 7.55 (d, J=7.58 Hz, 1 H) 9.76 (s, 1 H).

ESI-FTMS: m/e=617.1726 [[M+H]$^+$.

EXAMPLE 334

5-{3-[(Acetyl-isopropyl-amino)-methyl]-phenyl}-4-bromo-3-carboxymethoxy-thiophene-2-carboxylic acid The first step of Scheme 40: To a solution of 4-bromo-3-tert-butoxycarbonylmethoxy-5-(3-formyl-phenyl)-thiophene-2-carboxylic acid methyl ester (118 mg, 0.25 mmol) in DCE was added isopropylamine (25 □L, 0.3 mmol) and HOAc (18 □L, 0.3 mmol) then NaBH(OAc)$_3$ (79.3 mg, 0.375 mmol). The reaction mixture was stirred at room temperature overnight, followed by addition of Et3N (278 □L, 2.0 mmol) and Ac2O (118 □L, 1.25 mmol). The resultant mixture was stirred for additional 4 hours before loaded to a CombiFlash column, eluted with EtOAc/hexanes to give 5-{3-[(acetyl-isopropyl-amino)-methyl]-phenyl}-4-bromo-3-tert-butoxycarbonylmethoxy-thiophene-2-carboxylic acid methyl ester (102 mg, 76%, a 1:1 mixture of tautomers) as a light yellow oil.

$^1$H NMR (400 MHz, CHLOROFORM-D) δ ppm 1.12 (d, J=6.82 Hz, 3 H) 1.18 (d, J=6.57 Hz, 3 H) 2.05 (s, 1.5 H) 2.26 (s, 1.5 H) 3.88 (s, 1.5 H) 3.88 (s, 1.5 H) 4.16 (m, 0.5 H) 4.53 (s, 1 H) 4.59 (s, 1 H) 4.82 (s, 1 H) 4.84 (s, 1 H) 4.90 (m, 0.5 H) 7.42 (m, 4 H)

The second step of Scheme 40: To a solution of 5-{3-[(acetyl-isopropyl-amino)-methyl]-phenyl}4-bromo-3-tert-butoxycarbonylmethoxy-thiophene-2-carboxylic acid methyl ester (102 mg, 0.188 mmol) in DCM (4 mL) was added TFA (1 mL). The resultant reaction mixture was stirred at room temperature overnight. The solvent was removed to give 5-{3-[(acetyl-isopropyl-amino)-methyl]-phenyl}-4-bromo-3-carboxymethoxy-thiophene-2-carboxylic acid methyl ester (85 mg, 93%, a 1.1:1 mixture of tautomers) as a light yellow oil.

For the major tautomer: $^1$H NMR (400 MHz, MeOD) δ ppm 1.51 (d, J=6.82 Hz, 6 H) 2.58 (s, 3 H) 4.18 (s, 3 H) 4.62 (m, 1 H) 4.94 (s, 2 H) 5.19 (s, 2 H) 7.66 (m, 4 H).

The third step of Scheme 40: 5-{3-[(Acetyl-isopropyl-amino)-methyl]-phenyl}-4-bromo-3-carboxymethoxy-thiophene-2-carboxylic acid methyl ester was hydrolyzed according to fourth step of Scheme 39 of Example 327 to give 5-{3-[(acetyl-isopropyl-amino)-methyl]-phenyl}-4-bromo-3-carboxymethoxy-thiophene-2-carboxylic acid in 78% (a 1.4:1 mixture of tautomers) yield as a white sticky solid.

For the major tautomer: $^1$H NMR (400 MHz, DMSO-D6) δ ppm 1.11 (d, J=6.57 Hz, 6 H) 2.16 (s, 3 H) 4.19 (m, 1 H) 4.51 (s, 2 H) 4.89 (s, 2 H) 7.48 (m, 4 H).

EXAMPLE 335

5-{3-[(Acetyl-isobutyl-amino)-methyl]-phenyl}-4-bromo-3-carboxymethoxy-thiophene-2-carboxylic acid The third step of Scheme 40: 5-{3-[(Acetyl-isobutyl-amino)-methyl]-phenyl}-4-bromo-3-carboxymethoxy-thiophene-2-carboxylic acid methyl ester was hydrolyzed according to the fourth step of Scheme 39 of Example 327 to give 5-{3-[(acetyl-isobutyl-amino)-methyl]-phenyl}-4-bromo-3-carboxymethoxy-thiophene-2-carboxylic acid in 74% yield (a 1.4:1 mixture of tautomers) as a white sticky solid.

For the major tautomer: $^1$H NMR (400 MHz, DMSO-D6) δ ppm 0.87 (d, J=6.82 Hz, 6 H) 1.95 (m, 1 H) 2.10 (s, 3 H) 3.11 (d, J=7.33 Hz, 2 H) 4.58 (s, 2 H) 4.89 (s, 2 H) 7.48 (m, 4 H).

EXAMPLE 336

5-{3-[(Acetyl-cyclohexylmethyl-amino)-methyl]-phenyl}-bromo-3-carboxymethoxy-thiophene-2-carboxylic acid The third step of Scheme 40: 5-{3-[(Acetyl-cyclohexylmethyl-amino)-methyl]-phenyl}-4-bromo-3-carboxymethoxy-thiophene-2-carboxylic acid methyl ester was hydrolyzed according to the fourth step of Scheme 39 of Example 327 to give 5-{3-[(acetyl-cyclohexylmethyl-amino)-methyl]-phenyl}4-bromo-3-carboxymethoxy-thiophene-2-carboxylic acid in 78% yield (a ~1.3:1 mixture of tautomers) as a white solid.

For the major tautomer: $^1$H NMR (400 MHz, DMSO-D6) δ ppm 0.90 (m, 2 H) 1.13 (m, 3 H) 1.62 (m, 6 H) 2.09 (s, 3 H) 3.13 (d, J=6.57 Hz, 2 H) 4.57 (s, 2 H) 4.84 (s, 2 H) 7.47 (m, 4 H).

EXAMPLE 337

5-{3-[(Acetyl-p-tolyl-amino)-methyl]-phenyl}-4-bromo-3-carboxymethoxy-thiophene-2-carboxylic acid The third step of Scheme 40: 5-{3-[(Acetyl-p-tolyl-amino)-methyl]-phenyl}4-bromo-3-carboxymethoxy-thiophene-2-carboxylic acid methyl ester was hydrolyzed according to the fourth step of Scheme 39 of Example 327 to give 5-{3-[(acetyl-p-tolyl-amino)-methyl]-phenyl}-4-bromo-3-carboxymethoxy-thiophene-2-carboxylic acid in 75% yield as a white solid.

$^1$H NMR (400 MHz, DMSO-D6) δ ppm 1.83 (s, 3 H) 2.28 (s, 3 H) 4.88 (s, 2 H) 4.90 (s, 2 H) 7.10 (d, J=8.08 Hz, 2 H) 7.19 (d, J=8.08 Hz, 2 H) 7.31 (d, J=7.58 Hz, 1 H) 7.44 (m, 2 H) 7.53 (d, J=8.08 Hz, 1 H).

EXAMPLE 338

5-(3-{[Acetyl-(4-tert-butyl-phenyl)-amino]-methyl}-phenyl)-4-bromo-3-carboxymethoxy-thiophene-2-carboxylic acid The third step of Scheme 40: 5-(3-{[Acetyl-(4-tert-butyl-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-tert-butyl-phenyl)-amino]-methyl}-phenyl)-4-bromo-3-carboxymethoxy-thiophene-2-carboxylic acid in 87% yield as a white solid.

$^1$H NMR (400 MHz, DMSO-D6) δ ppm 1.26 (s, 9 H) 1.84 (s, 3 H) 4.67 (s, 2 H) 4.90 (s, 2 H) 7.15 (m, 2 H) 7.32 (d, J=7.58 Hz, 1 H) 7.42 (m, 4 H) 7.49 (m, 2 H).

EXAMPLE 339

5-(3-{[Acetyl-(4-trifluoromethyl-phenyl)-amino]-methyl}-phenyl)-4-bromo-3-carboxymethoxy-thiophene-2-carboxylic acid The third step of Scheme 40: 5-(3-{[Acetyl-(4-trifluoromethyl-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-trifluoromethyl-phenyl)-amino]-methyl}-phenyl)-4-bromo-3-carboxymethoxy-thiophene-2-carboxylic acid in 39% yield as a white solid.

$^1$H NMR (400 MHz, MeOD) δ ppm 1.93 (s, 3 H) 4.88 (s, 2 H) 5.03 (s, 2 H) 7.38 (m, 4 H) 7.54 (m, 2 H) 7.71 (d, J=8.34 Hz, 2 H).

EXAMPLE 340

5-{3-[(Acetyl-phenyl-amino)-methyl]-phenyl}-4-bromo-3-carboxymethoxy-thiophene-2-carboxylic acid The third step of Scheme 40: 5-{3-[(Acetyl-phenyl-amino)-methyl]-phenyl}-4-bromo-3-carboxymethoxy-thiophene-2-carboxylic acid methyl ester was hydrolyzed according to the fourth step of Scheme 39 of Example 327 to give 5-{3-[(acetyl-phenyl-amino)-methyl]-phenyl}-4-bromo-3-carboxymethoxy-thiophene-2-carboxylic acid in 74% yield as a white solid.

$^1$H NMR (400 MHz, DMSO-D6) δ ppm 1.85 (s, 3 H) 4.83 (s, 2 H) 4.93 (s, 2 H) 7.24 (m, 2 H) 7.32 (d, J=7.07 Hz, 2 H) 7.45 (m, 5 H).

EXAMPLE 341

5-{3-[(Acetyl-cyclopropyl-amino)-methyl]-phenyl}-4-bromo-3-carboxymethoxy-thiophene-2-carboxylic acid The third step of Scheme 40: 5-{3-[(Acetyl-cyclopropyl-amino)-methyl]-phenyl}-4-bromo-3-carboxymethoxy-thiophene-2-carboxylic acid methyl ester was hydrolyzed according to the fourth step of Scheme 39 of Example 327 to give 5-{3-[(acetyl-cyclopropyl-amino)-methyl]-phenyl}-4-bromo-3-carboxymethoxy-thiophene-2-carboxylic acid in 75% yield as a white solid.

$^1$H NMR (400 MHz, MeOD) δ ppm 1.19 (m, 4 H) 2.61 (s, 3 H) 3.06 (m, 1 H) 4.98 (s, 2 H) 5.20 (s, 2 H) 7.67 (d, J=7.83 Hz, 1 H) 7.75 (t, J=7.58 Hz, 1 H) 7.85 (d, J=9.35 Hz, 2 H).

EXAMPLE 342

5-(3-{[Acetyl-(4-bromo-phenyl)-amino]-methyl}-phenyl)-4-bromo-3-carboxymethoxy-thiophene-2-carboxylic acid The third step of Scheme 40: 5-(3-{[Acetyl-(4-bromo-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-bromo-phenyl)-amino]-methyl}-phenyl)-4-bromo-3-carboxymethoxy-thiophene-2-carboxylic acid in 87% yield as a white solid.

$^1$H NMR (400 MHz, DMSO-D6) δ ppm 1.87 (s, 3 H) 4.87 (s, 2 H) 4.93 (s, 2 H) 7.21 (m, 2 H) 7.32 (d, J=7.58 Hz, 1 H) 7.45 (m, 2 H) 7.52 (m, 1 H) 7.58 (d, J=8.59 Hz, 2 H).

EXAMPLE 343

5-{3-[(Acetyl-biphenyl-4-yl-amino)-methyl]-phenyl}-4-bromo-3-carboxymethoxy-thiophene-2-carboxylic acid The third step of Scheme 40: 5-{3-[(Acetyl-biphenyl-4-yl-amino)-methyl]-phenyl}-4-bromo-3-carboxymethoxy-thiophene-2-carboxylic acid methyl ester was hydrolyzed according to the fourth step of Scheme 39 of Example 327 to give 5-{3-[(acetyl-biphenyl-4-yl-amino)-methyl]-phenyl}-4-bromo-3-carboxymethoxy-thiophene-2-carboxylic acid in 93% yield as a white solid.

$^1$H NMR (400 MHz, DMSO-D6) δ ppm 1.92 (s, 3 H) 4.73 (s, 2 H) 4.98 (s, 2 H) 7.35 (m, 4 H) 7.47 (m, 5 H) 7.68 (m, 4 H).

EXAMPLE 344

5-(3-{[Acetyl-(4-phenoxy-phenyl)-amino]-methyl}-phenyl)-4-bromo-3-carboxymethoxy-thiophene-2-carboxylic acid The third step of Scheme 40: 5-(3-{[Acetyl-(4-phenoxy-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-phenoxy-phenyl)-amino]-methyl}-phenyl)-4-bromo-3-carboxymethoxy-thiophene-2-carboxylic acid in 88% yield as a white solid.

$^1$H NMR (400 MHz, DMSO-D6) δ ppm 1.86 (s, 3 H) 4.85 (s, 2 H) 4.91 (s, 2 H) 7.00 (m, 4 H) 7.20 (m, 3 H) 7.44 (m, 6 H).

EXAMPLE 345

5-{3-[(Acetyl-benzyl-amino)-methyl]-phenyl}-4-bromo-3-carboxymethoxy-thiophene-2-carboxylic acid The third step of Scheme 40: 5-{3-[(Acetyl-benzyl-amino)-methyl]-phenyl})-4-bromo-3-carboxymethoxy-thiophene-2-carboxylic acid methyl ester was hydrolyzed according to the fourth step of Scheme 39 of Example 327 to give 5-{3-[(acetyl-benzyl-amino)-methyl]-phenyl}4-bromo-3-carboxymethoxy-thiophene-2-carboxylic acid in 74% yield (a ~1.2:1 mixture of tautomers) as a white solid.

For the major tautomer: $^1$H NMR (400 MHz, DMSO-D6) δ ppm 2.12 (s, 3 H) 4.56 (s, 2 H) 4.58 (s, 2 H) 4.89 (s, 2 H) 7.40 (m, 9 H).

EXAMPLE 346

5-(3-{[Acetyl-(4-methoxy-benzyl)-amino]-methyl}-phenyl)-4-bromo-3-carboxymethoxy-thiophene-2-carboxylic acid The third step of Scheme 40: 5-(3-{[Acetyl-(4-methoxy-benzyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-methoxy-benzyl)-amino]-methyl}-phenyl)-4-bromo-3-carboxymethoxy-thiophene-2-carboxylic acid in 94% (a ~1.2:1 mixture of tautomers) yield as a white solid.

For the major tautomer: $^1$H NMR (400 MHz, DMSO-D6) δ ppm 2.14 (s, 2 H) 3.74 (s, 3 H) 4.49 (s, 2 H) 4.52 (s, 2 H) 4.89 (s, 2 H) 6.92 (m, 2 H) 7.16 (t, J=8.46 Hz, 2 H) 7.46 (m, 4 H).

EXAMPLE 347

5-{3-[(Acetyl-biphenyl-4-ylmethyl-amino)-methyl]-phenyl}-4-bromo-3-carboxymethoxy-thiophene-2-carboxylic acid The third step of Scheme 40: 5-{3-[(Acetyl-biphenyl-4-ylmethyl-amino)-methyl]-phenyl}-4-bromo-3-carboxymethoxy-thiophene-2-carboxylic acid methyl ester was hydrolyzed according to the fourth step of Scheme 39 of Example 327 to give 5-{3-[(acetyl-biphenyl-4-ylmethyl-amino)-methyl]-phenyl}4-bromo-3-carboxymethoxy-thiophene-2-carboxylic acid in 79% yield (a ~1.1:1 mixture of tautomers) as a white solid.

For the major tautomer: $^1$H NMR (400 MHz, DMSO-D6) δ ppm 2.16 (s, 3 H) 4.60 (s, 2 H) 4.63 (s, 2 H) 4.89 (s, 2 H) 7.49 (m, 13 H).

EXAMPLE 348

5-(3-{[Acetyl-(4-chloro-phenyl)-amino]-methyl}-phenyl)-4-bromo-3-carboxymethoxy-thiophene-2-carboxylic acid The third step of Scheme 40: 5-(3-{[Acetyl-(4-chloro-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-chloro-phenyl)-amino]-methyl}-phenyl)-4-bromo-3-carboxymethoxy-thiophene-2-carboxylic acid in 71% (a ~1:1 mixture of tautomers) yield as a white sticky solid.

$^1$H NMR (400 MHz, DMSO-D6) δ ppm 2.11 (s, 3 H) 2.12 (s, 3 H) 4.51 (s, 2 H) 4.55 (s, 2 H) 4.58 (s, 2 H) 4.63 (s, 2 H) 4.89 (s, 2 H) 4.90 (s, 2 H) 7.41 (m, 16 H).

EXAMPLE 349

5-(3-{[Acetyl-(4-trifluoromethyl-phenyl)-amino]-methyl}-phenyl)-4-bromo-3-carboxymethoxy-thiophene-2-carboxylic acid The third step of Scheme 40: 5-(3-{[Acetyl-(4-trifluoromethyl-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(4-trifluoromethyl-phenyl)-amino]-methyl}-phenyl)-4-bromo-3-carboxymethoxy-thiophene-2-carboxylic acid in 98% yield (a ~1:1 mixture of tautomers) as a white solid.

$^1$H NMR (400 MHz, DMSO-D6) δ ppm 2.10 (s, 3 H) 2.15 (s, 3 H) 4.59 (s, 2 H) 4.61 (s, 2 H) 4.67 (s, 2 H) 4.70 (s, 2 H) 4.89 (s, 4 H) 7.36 (m, 2 H) 7.49 (m, 10 H) 7.65 (d, J=8.08 Hz, 2 H) 7.72 (d, J=8.08 Hz, 2 H).

EXAMPLE 350

5-(3-{[Acetyl-(3,5-bis-trifluoromethyl-phenyl)-amino]-methyl}-phenyl)-4-bromo-3-carboxymethoxy-thiophene-2-carboxylic acid The third step of Scheme 40: 5-(3-{[Acetyl-(3,5-bis-trifluoromethyl-phenyl)-amino]-methyl}-phenyl)-4-bromo-3-carboxymethoxy-thiophene-2-carboxylic acid methyl ester was hydrolyzed according to the fourth step of Scheme 39 of Example 327 to give 5-(3-{[acetyl-(3,5-bis-trifluoromethyl-phenyl)-amino]-methyl}-phenyl)-4-bromo-3-carboxymethoxy-thiophene-2-carboxylic acid in 97% (a ~1.7:1 mixture of tautomers) yield as a white solid.

For the major tautomer: $^1$H NMR (400 MHz, DMSO-D6) δ ppm 2.18 (s, 3 H) 4.72 (s, 2 H) 4.77 (s, 2 H) 4.88 (s, 2 H) 7.45 (m, 4 H) 7.78 (s, 1 H) 7.85 (s, 1 H) 7.90 (s, 1 H).

EXAMPLE 351

5-[3-({Acetyl-[2-(4-chloro-phenyl)-ethyl]-amino}-methyl)-phenyl]-4-bromo-3-carboxymethoxy-thiophene-2-carboxylic acid The third step of Scheme 40: 5-[3-({Acetyl-[2-(4-chloro-phenyl)-ethyl]-amino}-methyl)-phenyl]-4-bromo-3-carboxymethoxy-thiophene-2-carboxylic acid methyl ester was hydrolyzed according to the fourth step of Scheme 39 of Example 327 to give 5-[3-({acetyl-[2-(4-chloro-phenyl)-ethyl]-amino}-methyl)-phenyl]-4-bromo-3-carboxymethoxy-thiophene-2-carboxylic acid in 82% yield (a ~1.5:1 mixture of tautomers) as a white solid.

For the major tautomer: $^1$H NMR (400 MHz, DMSO-D6) δ ppm 1.96 (s, 3 H) 2.84 (t, J=7.33 Hz, 2 H) 3.47 (t, J=6.95 Hz, 2 H) 4.60 (s, 2 H) 4.87 (s, 2 H) 7.40 (m, 8 H).

EXAMPLE 352

4-Bromo-3-carboxymethoxy-5-[3-(1,3-diisopropyl-ureido)-phenyl]-thiophene-2-carboxylic acid The first step of Scheme 41: To a solution of 5-(3-amino-phenyl)-4-bromo-3-tert-butoxycarbonylmethoxy-thiophene-2-carboxylic acid methyl ester (177 mg, 0.4 mmol) in DCE (3 mL) was added acetone (32.4 μL, 0.44 mmol), HOAc (28.3 μL, 0.48 mmol) and NaBH(OAc)$_3$ (127.2 mg, 0.6 mmol). The resultant mixture was stirred at room temperature overnight. Pyridine (3 mL) and isopropylisocyanate (146 μL, 2.0 mmol) were added subsequently. The reaction mixture was stirred for additional 6 hours before filtered through a pad of SiO$_2$ column and concentrated. The crude product was purified on CombiFlash column eluted with hexanes/EtOAc to give 4-bromo-3-tert-butoxycarbonylmethoxy-5-[3-(1,3-diisopropyl-ureido)-phenyl]-thiophene-2-carboxylic acid methyl ester (150 mg, 66%) as a light yellow oil.

$^1$H NMR (400 MHz, CHLOROFORM-D) δ ppm 1.02 (d, J=6.32 Hz, 6 H) 1.09 (d, J=6.82 Hz, 6 H) 3.69 (d, J=7.83 Hz, 1 H) 3.89 (s, 3 H) 3.96 (m, 1 H) 4.86 (s, 2 H) 4.92 (m, 1 H) 7.24 (m, 1 H) 7.52 (m, 2 H) 7.65 (m, 1 H).

The second step of Scheme 41: 4-Bromo-3-tert-butoxycarbonylmethoxy-5-[3-(1,3-diisopropyl-ureido)-phenyl]-thiophene-2-carboxylic acid methyl ester was hydrolyzed according to the fourth step of Scheme 15 of Example 141 to give 4-bromo-3-carboxymethoxy-5-[3-(1,3-diisopropyl-ureido)-phenyl]-thiophene-2-carboxylic acid in 78% yield as a white solid.

$^1$H NMR (400 MHz, DMSO-D6) δ ppm 0.96 (d, J=6.57 Hz, 6 H) 1.00 (d, J=6.82 Hz, 6 H) 3.78 (m, 1 H) 4.64 (m, 1 H) 4.91 (d, J=7.83 Hz, 1 H) 4.90 (s, 2 H) 7.26 (m, 1 H) 7.43 (t, J=1.77 Hz, 1 H) 7.59 (t, J=7.83 Hz, 1 H) 7.67 (m, 1 H).

EXAMPLE 353

4-Bromo-3-carboxymethoxy-5-{3-[1-(2,2-dimethyl-propyl)-3-isopropyl-ureido]-phenyl}-thiophene-2-carboxylic acid The second step of Scheme 41: 4-Bromo-3-tert-butoxycarbonylmethoxy-5-{3-[1-(2,2-dimethyl-propyl)-3-isopropyl-ureido]-phenyl}-thiophene-2-carboxylic acid methyl ester was hydrolyzed according to the fourth step of Scheme 15 of Example 141 to give 4-bromo-3-carboxymethoxy-5-{3-[1-(2,2-dimethyl-propyl)-3-isopropyl-ureido]-phenyl}-thiophene-2-carboxylic acid in 75% yield as a white solid.

$^1$H NMR (400 MHz, DMSO-D6) δ ppm 0.77 (s, 9 H) 1.01 (d, J=6.57 Hz, 6 H) 3.79 (m, 1 H) 4.88 (s, 2 H) 5.51 (d, J=7.83 Hz, 1 H) 7.47 (m, 3 H) 7.58 (t, J=1.64 Hz, 1 H).

EXAMPLE 354

4-Bromo-3-carboxymethoxy-5-[3-(1-isobutyl-3-isopropyl-ureido)-phenyl]-thiophene-2-carboxylic acid The second step of Scheme 41: 4-Bromo-3-tert-butoxycarbonylmethoxy-5-[3-(1-isobutyl-3-isopropyl-ureido)-phenyl]-thiophene-2-carboxylic acid methyl ester was hydrolyzed according to the fourth step of Scheme 15 of Example 141 to give 4-bromo-3-carboxymethoxy-5-[3-(1-isobutyl-3-isopropyl-ureido)-phenyl]-thiophene-2-carboxylic acid in 74% yield as a white solid.

$^1$H NMR (400 MHz, DMSO-D6) δ ppm 0.83 (d, J=6.57 Hz, 6 H) 1.02 (d, J=6.57 Hz, 6 H) 1.67 (m, 1 H) 3.50 (d, J=7.33 Hz, 2 H) 3.80 (m, 1 H) 4.89 (s, 2 H) 5.62 (d, J=7.83 Hz, 1 H) 7.36 (m, 1 H) 7.52 (m, 3 H).

EXAMPLE 355

5-[3-(1-Benzyl-3-isopropyl-ureido)-phenyl]-4-bromo-3-carboxymethoxy-thiophene-2-carboxylic acid The second step of Scheme 41: 4-Bromo-3-tert-butoxycarbonylmethoxy-5-[3-(1-benzyl-3-isopropyl-ureido)-phenyl]- thiophene-2-carboxylic acid methyl ester was hydrolyzed according to the fourth step of Scheme 15 of Example 141 to give 5-[3-(1-Benzyl-3-isopropyl-ureido)-phenyl]-4-bromo-3-carboxymethoxy-thiophene-2-carboxylic acid in 58% yield as a white solid.

$^1$H NMR (400 MHz, DMSO-D6) δ ppm 1.05 (d, J=6.57 Hz, 6 H) 3.86 (m, 1 H) 4.86 (s, 2 H) 4.91 (s, 2 H) 6.02 (d, J=8.08 Hz, 1 H) 7.26 (m, 6 H) 7.44 (m, 3 H).

EXAMPLE 356

4-Bromo-3-carboxymethoxy-5-{3-[3-isopropyl-1-(4-trifluoromethyl-benzyl)-ureido]-phenyl}-thiophene-2-carboxylic acid The second step of Scheme 41: 4-Bromo-3-tert-butoxycarbonylmethoxy-5-{3-[3-isopropyl-1-(4-trifluoromethyl-benzyl)-ureido]-phenyl}-thiophene-2-carboxylic acid methyl ester was hydrolyzed according to the fourth step of Scheme 15 of Example 141 to give 4-Bromo-3-carboxymethoxy-5-{3-[3-isopropyl-1-(4-trifluoromethyl-benzyl)-ureido]-phenyl}-thiophene-2-carboxylic acid in 70% yield as a white solid.

$^1$H NMR (400 MHz, DMSO-D6) δ ppm 1.05 (d, J=6.57 Hz, 6 H) 3.86 (m, 1 H) 4.87 (s, 2 H) 4.99 (s, 2 H) 6.10 (d, J=7.83 Hz, 1 H) 7.32 (m, 1 H) 7.47 (m, 5 H) 7.67 (d, J=8.34 Hz, 2 H).

EXAMPLE 357

4-Bromo-5-{3-[1-(4-tert-butyl-benzyl)-3-isopropyl-ureido]-phenyl}-3-carboxymethoxy-thiophene-2-carboxylic acid The second step of Scheme 41: 4-Bromo-3-tert-butoxycarbonylmethoxy-5-{3-[1-(4-tert-butyl-benzyl)-3-isopropyl-ureido]-phenyl}-thiophene-2-carboxylic acid methyl ester was hydrolyzed according to the fourth step of Scheme 15 of Example 141 to give 4-bromo-5-{3-[1-(4-tert-butyl-benzyl)-3-isopropyl-ureido]-phenyl}-3-carboxymethoxy-thiophene-2-carboxylic acid in 76% yield as a white solid.

$^1$H NMR (400 MHz, DMSO-D6) δ ppm 1.04 (d, J=6.57 Hz, 6 H) 1.24 (s, 9 H) 3.86 (m, 1 H) 4.85 (s, 2 H) 4.86 (s, 2 H) 5.99 (d, J=7.83 Hz, 1 H) 7.14 (d, J=8.34 Hz, 2 H) 7.31 (m, 3 H) 7.44 (m, 3 H).

EXAMPLE 358

5-[3-(Acetyl-cyclohexylmethyl-amino)-phenyl]-4-bromo-3-carboxymethoxy-thiophene-2-carboxylic acid The first step of Scheme 42: To a solution of 4-bromo-3-tert-butoxycarbonylmethoxy-5-[3-(cyclohexylmethyl-amino)-phenyl]-thiophene-2-carboxylic acid methyl ester (107 mg, 0.2 mmol) in DCM (3 mL) was added AcCl (42.6 mL, 0.6 mmol) at −30° C., TEA (139 mL, 1.0 mmol) and DMAP (5 mg). The temperature was allowed to rise to room temperature and the resultant mixture was stirred for 4 hour before concentrated and purified on CombiFlash column eluted with hexanes/EtOAc to give 5-[3-(acetyl-cyclohexylmethyl-amino)-phenyl]-4-bromo-3-tert-butoxycarbonylmethoxy-thiophene-2-carboxylic acid methyl ester (58 mg, 50%) as a light yellow oil.

$^1$H NMR (400 MHz, CHLOROFORM-D) δ ppm 1.02 (m, 2 H) 1.24 (m, 3 H) 1.51 (s, 9 H) 1.64 (m, 6 H) 1.90 (s, 3 H) 3.62 (d, J=7.58 Hz, 2 H) 3.89 (s, 3 H) 4.86 (s, 2 H) 7.26 (m, 1 H) 7.52 (m, 2 H) 7.59 (m, 1 H).

The second step of Scheme 42: 5-[3-(Acetyl-cyclohexylmethyl-amino)-phenyl]-4-bromo-3-tert-butoxycarbonylmethoxy-thiophene-2-carboxylic acid methyl ester was hydrolyzed according to the fourth step of Scheme 15 of Example 141 to give 5-[3-(acetyl-cyclohexylmethyl-amino)-phenyl]-4-bromo-3-carboxymethoxy-thiophene-2-carboxylic acid in 82% yield as a white solid.

$^1$H NMR (400 MHz, DMSO-D6) δ ppm 0.90 (m, 2 H) 1.09 (m, 3 H) 1.40 (m, 1 H) 1.62 (m, 5 H) 1.81 (s, 3 H) 3.56 (d, J=7.33 Hz, 2 H) 4.90 (s, 2 H) 4.90 (s, 2 H) 7.46 (m, 1 H) 7.59 (m, 3 H).

EXAMPLE 359

4-Bromo-3-carboxymethoxy-5-{3-[cyclohexylmethyl-(3-methyl-butyryl)-amino]-phenyl}-thiophene-2-carboxylic acid The second step of Scheme 41: 4-Bromo-3-tert-butoxycarbonylmethoxy-5-{3-[cyclohexylmethyl-(3-methyl-butyryl)-amino]-phenyl}-thiophene-2-carboxylic acid methyl ester was hydrolyzed according to the fourth step of Scheme 15 of Example 141 to give 4-bromo-3-carboxymethoxy-5-{3-[cyclohexylmethyl-(3-methyl-butyryl)-amino]-phenyl}-thiophene-2-carboxylic acid in 56% yield as a white solid.

$^1$H NMR (400 MHz, DMSO-D6) δ ppm 0.78 (d, J=4.80 Hz, 6 H) 0.92 (m, 2 H) 1.10 (m, 3 H) 1.40 (m, 1 H) 1.62 (m, 5 H) 1.97 (m, 1 H) 1.94 (s, 3 H) 3.57 (d, J=7.33 Hz, 2 H) 4.90 (s, 2 H) 7.41 (d, J=7.07 Hz, 1 H) 7.61 (m, 3 H).

EXAMPLE 360

4-Bromo-3-carboxymethoxy-5-[3-(cyclohexanecarbonyl-cyclohexylmethyl-amino)-phenyl]-thiophene-2-carboxylic acid The second step of Scheme 41: 4-Bromo-3-tert-butoxycarbonylmethoxy-5-[3-(cyclohexanecarbonyl-cyclohexylmethyl-amino)-phenyl]-thiophene-2-carboxylic acid methyl ester was hydrolyzed according to the fourth step of Scheme 15 of Example 141 to give 4-bromo-3-carboxymethoxy-5-[3-(cyclohexanecarbonyl-cyclohexylmethyl-amino)-phenyl]-thiophene-2-carboxylic acid in 74% yield as a white solid.

$^1$H NMR (400 MHz, DMSO-D6) δ ppm 0.89 (m, 4 H) 1.10 (m, 4 H) 1.34 (m, 4 H) 1.56 (m, 9 H) 2.12 (m, 1 H) 3.52 (d, J=7.07 Hz, 2 H) 4.90 (s, 2 H) 7.44 (m, 1 H) 7.57 (s, 1 H) 7.63 (m, 2 H).

EXAMPLE 361

4-Bromo-3-carboxymethoxy-5-[3-(cyclohexylmethyl-isobutyryl-amino)-phenyl]-thiophene-2-carboxylic acid The second step of Scheme 41: 4-Bromo-3-tert-butoxycarbonylmethoxy-5-[3-(cyclohexylmethyl-isobutyryl-amino)-phenyl]-thiophene-2-carboxylic acid methyl ester was hydrolyzed according to the fourth step of Scheme 15 of Example 141 to give 4-bromo-3-carboxymethoxy-5-[3-(cyclohexylmethyl-isobutyryl-amino)-phenyl]-thiophene-2-carboxylic acid in 61% yield as a white solid.

¹H NMR (400 MHz, DMSO-D6) δ ppm 0.93 (m, 8 H) 1.11 (m, 3 H) 1.40 (m, 1 H) 1.61 (m, 5 H) 2.42 (m, 1 H) 3.54 (d, J=7.33 Hz, 2 H) 4.91 (s, 2 H) 7.45 (d, J=6.82 Hz, 1 H) 7.62 (m, 3 H).

EXAMPLE 362

4-Bromo-3-carboxymethoxy-5-[3-(cyclohexylmethyl-methoxycarbonyl-amino)-phenyl]-thiophene-2-carboxylic acid The second step of Scheme 41: 4-Bromo-3-tert-butoxycarbonylmethoxy-5-[3-(cyclohexylmethyl-methoxycarbonyl-amino)-phenyl]-thiophene-2-carboxylic acid methyl ester was hydrolyzed according to the fourth step of Scheme 15 of Example 141 to give 4-bromo-3-carboxymethoxy-5-[3-(cyclohexylmethyl-methoxycarbonyl-amino)-phenyl]-thiophene-2-carboxylic acid in 95% yield as a white solid.

¹H NMR (400 MHz, DMSO-D6) δ ppm 0.89 (m, 2 H) 1.08 (m, 3 H) 1.43 (m, 1 H) 1.61 (m, 5 H) 3.57 (d, J=7.33 Hz, 2 H) 3.59 (s, 3 H) 4.86 (s, 2 H) 7.41 (m, 1 H) 7.52 (m, 2 H) 7.57 (s, 1 H).

EXAMPLE 363

3-Carboxymethoxy-5-[3-(cyclohexylmethyl-methoxycarbonyl-amino)-phenyl]-4-methyl-thiophene-2-carboxylic acid The second step of Scheme 41: 3-tert-Butoxycarbonylmethoxy-5-[3-(cyclohexylmethyl-methoxycarbonyl-amino)-phenyl]-4-methyl-thiophene-2-carboxylic acid methyl ester was hydrolyzed according to the fourth step of Scheme 15 of Example 141 to give 3-carboxymethoxy-5-[3-(cyclohexylmethyl-methoxycarbonyl-amino)-phenyl]-4-methyl-thiophene-2-carboxylic acid in 87% yield as a white solid.

¹H NMR (400 MHz, DMSO-D6) δ ppm 0.88 (m, 2 H) 1.09 (m, 3 H) 1.42 (m, 1 H) 1.61 (m, 5 H) 2.20 (s, 3 H) 3.56 (d, J=7.33 Hz, 2 H) 3.59 (s, 3 H) 7.37 (m, 3 H) 7.50 (t, J=7.83 Hz, 1 H).

EXAMPLE 364

3-Carboxymethoxy-5-[3-(cyclohexylmethyl-isopropoxycarbonyl-amino)-phenyl]-4-methyl-thiophene-2-carboxylic acid The second step of Scheme 41: 3-tert-Butoxycarbonylmethoxy-5-[3-(cyclohexylmethyl-isopropoxycarbonyl-amino)-phenyl]-4-methyl-thiophene-2-carboxylic acid methyl ester was hydrolyzed according to the fourth step of Scheme 15 of Example 141 to give 3-carboxymethoxy-5-[3-(cyclohexylmethyl-isopropoxycarbonyl-amino)-phenyl]-4-methyl-thiophene-2-carboxylic acid in 95% yield as a white solid.

¹H NMR (400 MHz, DMSO-D6) δ ppm 0.90 (m, 2 H) 1.08 (m, 3 H) 1.16 (d, J=6.06 Hz, 6 H) 1.39 (m, 1 H) 1.59 (m, 5 H) 2.20 (s, 3 H) 3.57 (d, J=7.33 Hz, 2 H) 4.83 (m, 1 H) 4.87 (s, 2 H) 7.35 (m, 3 H) 7.49 (t, J=7.83 Hz, 1 H).

EXAMPLE 365

5-[3-(Bis-cyclohexylmethyl-amino)-phenyl]-3-carboxymethoxy-4-methyl-thiophene-2-carboxylic acid The second step of Scheme 41: 5-[3-(Bis-cyclohexylmethyl-amino)-phenyl]-3-tert-butoxycarbonylmethoxy-4-methyl-thiophene-2-carboxylic acid methyl ester was hydrolyzed according to the fourth step of Scheme 15 of Example 141 to give 5-[3-(Bis-cyclohexylmethyl-amino)-phenyl]-3-carboxymethoxy-4-methyl-thiophene-2-carboxylic acid in 95% yield as a white solid.

¹H NMR (400 MHz, DMSO-D6) δ ppm 0.96 (m, 4 H) 1.13 (m, 6 H) 1.67 (m, 12 H) 3.20 (d, J=6.82 Hz, 4 H) 4.88 (s, 2 H) 6.75 (m, 2 H) 6.85 (s, 1 H) 7.25 (m, 1 H).

EXAMPLE 366

4-Bromo-3-carboxymethoxy-5-[3-(1-cyclohexylmethyl-3-phenyl-ureido)-phenyl]-thiophene-2-carboxylic acid The first step of Scheme 43: To a 1 mL CH₂Cl₂ solution of 4-bromo-3-tert-butoxycarbonylmethoxy-5-[3-(cyclohexylmethyl-amino)-phenyl]-thiophene-2-carboxylic acid methyl ester (60 mg, 0.11 mmole) was added an isocyanate (in this case, phenyl isocyanate, 36 μL, 0.33 mmole) and the reaction mixture was allowed to stir at room temperature overnight. Polystyrene-bound Trisamine (Argonaut Laboratories—250 mg of 4.11 mmol/g) was added and the suspension stirred for 2 hours. The mixture was then filtered and evaporated to give 4-bromo-3-tert-butoxycarbonylmethoxy-5-[3-(1-cyclohexylmethyl-3-phenyl-ureido)-phenyl]-thiophene-2-carboxylic acid methyl ester as a yellow oil.

¹H NMR (400 MHz, CHLOROFORM-D) δ ppm 0.97-1.08 (m, 2 H) 1.12-1.28 (m, 4 H) 1.50 (s, 9 H) 1.62-1.81 (m, 5 H) 3.66 (d, J=7.33 Hz, 2 H) 3.89 (s, 3 H) 4.85 (s, 2 H) 6.21 (s, 1 H) 6.95-7.01 (m, 1 H) 7.19-7.25 (m, 2 H) 7.27-7.32 (m, 2 H) 7.38-7.42 (m, 1 H) 7.57 (t, J=7.71 Hz, 1 H) 7.60-7.64 (m, 1 H) 7.70 (t, J=1.89 Hz, 1 H).

The second step of Scheme 43: 4-Bromo-3-tert-butoxycarbonylmethoxy-5-[3-(1-cyclohexylmethyl-3-phenyl-ureido)-phenyl]-thiophene-2-carboxylic acid methyl ester (64 mg, 0.11 mmol) was dissolved in 1 mL THF and 1.0N LiOH.H₂O was added (440 μL, 0.44 mmol) and stirred at room temperature for 3 hours. The reaction mixture was evaporated, diluted with water, and acidified with 1N HCl. Filtration gave 38 mg (59% over two steps) as an off-white solid.

¹H NMR (400 MHz, DMSO-D6) δ ppm 0.89-1.03 (m, 2 H) 1.04-1.18 (m, 3 H) 1.45-1.74 (m, 6 H) 3.62 (d, J=7.33 Hz, 2 H) 4.88 (s, 2 H) 6.93 (t, J=7.33 Hz, 1 H) 7.21 (t, J=7.96 Hz, 2 H) 7.36-7.47 (m, 3 H) 7.50-7.65 (m, 3 H) 8.17 (s, 1 H).

ESI-MS: m/e=587 [M+H]⁺.

EXAMPLE 367

5-[3-(3-Benzyl-1-cyclohexylmethyl-ureido)-nhenvl]-4-bromo-3-carboxymethoxy-thiophene-2-carboxylic acid The first step of Scheme 43: 5-[3-(3-Benzyl-1-cyclohexylmethyl-ureido)-phenyl]-4-bromo-3-tert-butoxycarbonylmethoxy-thiophene-2-carboxylic acid methyl ester was obtained as a yellow oil, following the general procedure in the first step of Scheme 43 of Example 366.

¹H NMR (400 MHz, CHLOROFORM-D) δ ppm 0.94-1.05 (m, 2 H) 1.12-1.21 (m, 4 H) 1.50 (s, 9 H) 1.64-1.78 (m, 5 H)

3.62 (d, J=7.33 Hz, 2 H) 3.89 (s, 3 H) 4.40 (d, J=5.81 Hz, 2 H) 4.61 (t, J=5.68 Hz, 1 H) 4.84 (s, 2 H) 7.19-7.24 (m, 4 H) 7.27-7.34 (m, 2 H) 7.46-7.54 (m, 2 H) 7.59 (t, J=1.64 Hz, 1 H).

The second step of Scheme 43: 5-[3-(3-Benzyl-1-cyclohexylmethyl-ureido)-phenyl]-4-bromo-3-tert-butoxycarbonylmethoxy-thiophene-2-carboxylic acid methyl ester was hydrolyzed as in the second step of Example 366 to give 45 mg (68% over two steps) of 5-[3-(3-Benzyl-1-cyclohexylmethyl-ureido)-phenyl]-4-bromo-3-carboxymethoxy-thiophene-2-carboxylic acid as an off-white solid.

$^1$H NMR (400 MHz, DMSO-D6) δ ppm 0.83-0.97 (m, 2 H) 1.04-1.15 (m, 4 H) 1.38-1.49 (m, 1 H) 1.53-1.71 (m, 4 H) 3.53 (d, J=7.33 Hz, 2 H) 4.20 (d, J=6.32 Hz, 2 H) 4.90 (s, 2 H) 6.49 (t, J=5.94 Hz, 1 H) 7.15-7.24 (m, 3 H) 7.24-7.30 (m, 2 H) 7.37-7.42 (m, 1 H) 7.53-7.58 (m, 3 H).

ESI-MS: m/e=601 [M+H]$^+$.

EXAMPLE 368

4-Bromo-3-carboxymethoxy-5-{3-[1-cyclohexylmethyl-3-(4-ethyl-phenyl)-ureido]-phenyl}-thiophene-2-carboxylic acid The first step of Scheme 43: 4-Bromo-3-tert-butoxycarbonylmethoxy-5-{3-[1-cyclohexylmethyl-3-(4-ethyl-phenyl)-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.95-1.09 (m, 6 H) 1.17 (t, J=7.71 Hz, 3 H) 1.50 (s, 9 H) 1.59 (dd, J=7.20, 3.66 Hz, 1 H) 1.68-1.80 (m, 4 H) 2.56 (q, J=7.58 Hz, 2 H) 3.65 (d, J=7.33 Hz, 2 H) 3.89 (s, 3 H) 4.85 (s, 2 H) 6.16 (s, 1 H) 7.03-7.08 (m, 2H) 7.18-7.22 (m, 2 H) 7.39 (dt, J=7.58, 1.77 Hz, 1 H) 7.56 (t, J=7.71 Hz, 1 H) 7.61 (dt, J=7.83, 1.64 Hz, 1 H) 7.69 (t, J=1.64 Hz, 1 H).

The second step of Scheme 43: 4-Bromo-3-tert-butoxycarbonylmethoxy-5-{3-[1-cyclohexylmethyl-3-(4-ethyl-phenyl)-ureido]-phenyl}-thiophene-2-carboxylic acid methyl ester was hydrolyzed as in the second step of Scheme 43 of Example 366 to give 50 mg (74% over two steps) of 4-bromo-3-carboxymethoxy-5-{3-[1-cyclohexylmethyl-3-(4-ethyl-phenyl)-ureido]-phenyl}-thiophene-2-carboxylic acid as an off-white solid.

$^1$H NMR (400 MHz, DMSO-D6) δ ppm 0.89-1.02 (m, 2 H) 1.07-1.18 (m, 7 H) 1.47-1.74 (m, 6 H) 3.61 (d, J=7.33 Hz, 2 H) 4.88 (s, 2 H) 7.04 (d, J=8.59 Hz, 2 H) 7.29 (d, J=8.59 Hz, 2 H) 7.40-7.45 (m, 1 H) 7.50-7.59 (m, 2 H) 7.61 (s, 1 H).

ESI-MS: m/e=615 [M+H]$^+$.

EXAMPLE 369

4-Bromo-3-carboxymethoxy-5-{3-[1-cyclohexylmethyl-3-(4-ethoxy-phenyl)-ureido]-phenyl}-thiophene-2-carboxylic acid The first step of Scheme 43: 4-Bromo-3-tert-butoxycarbonylmethoxy-5-{3-[1-cyclohexylmethyl-3-(4-ethoxy-phenyl)-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.95-1.07 (m, 2 H) 1.11-1.22 (m, 4 H) 1.37 (t, J=7.07 Hz, 3 H) 1.50 (s, 9 H) 1.55-1.62 (m, 1 H) 1.66-1.81 (m, 4 H) 3.65 (d, J=7.33 Hz, 2 H) 3.89 (s, 3 H) 3.97 (q, J=6.99 Hz, 2 H) 4.85 (s, 2 H) 6.08 (s, 1 H) 6.76-6.80 (m, 2 H) 7.16-7.21 (m, 2 H) 7.40 (dt, J=7.58, 1.77 Hz, 1 H) 7.56 (t, J=7.71 Hz, 1 H) 7.59-7.62 (m, 1 H) 7.68-7.70 (m, 1 H).

The second step of Scheme 43: 4-Bromo-3-tert-butoxycarbonylmethoxy-5-{3-[1-cyclohexylmethyl-3-(4-ethoxy-phenyl)-ureido]-phenyl}-thiophene-2-carboxylic acid methyl ester was hydrolyzed as in the second step of Scheme 43 of Example 366 to give 49 mg (71% over two steps) of 4-bromo-3-carboxymethoxy-5-{3-[1-cyclohexylmethyl-3-(4-ethoxy-phenyl)-ureido]-phenyl}-thiophene-2-carboxylic acid as an off-white solid.

$^1$H NMR (400 MHz, DMSO-D6) δ ppm 0.89-1.01 (m, 2 H) 1.05-1.17 (m, 4 H) 1.44-1.74 (m, 5 H) 3.60 (d, J=7.58 Hz, 2 H) 3.95 (q, J=6.91 Hz, 2 H) 4.88 (s, 2 H) 6.78 (d, J=9.09 Hz, 2 H) 7.26 (d, J=9.09 Hz, 2 H) 7.40-7.45 (m, 1 H) 7.49-7.59 (m, 2 H) 7.60 (s, 1 H) 7.99 (s, 1 H).

ESI-MS: m/e=631 [M+H]$^+$.

EXAMPLE 370

4-Bromo-3-carboxymethoxy-5-{3-[1-cyclohexylmethyl-3-(4-phenoxy-phenyl)-ureido]-phenyl}-thiophene-2-carboxylic acid The first step of Scheme 43: 4-Bromo-3-tert-butoxycarbonylmethoxy-5-{3-[1-cyclohexylmethyl-3-(4-phenoxy-phenyl)-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.98-1.08 (m, 2 H) 1.13-1.23 (m, 4 H) 1.50 (s, 9 H) 1.54-1.61 (m, 1 H) 1.67-1.80 (m, 4 H) 3.66 (d, J=7.33 Hz, 2 H) 3.89 (s, 3 H) 4.86 (s, 2 H) 6.18 (s, 1 H) 6.89-6.96 (m, 4 H) 7.01-7.07 (m, 1 H) 7.25-7.32 (m, 4 H) 7.39-7.43 (m, 1 H) 7.55-7.64 (m, 2 H) 7.71 (t, J=1.77 Hz, 1 H).

The second step of Scheme 43: 4-Bromo-3-tert-butoxycarbonylmethoxy-5-{3-[1-cyclohexylmethyl-3-(4-phenoxy-phenyl)-ureido]-phenyl}-thiophene-2-carboxylic acid methyl ester was hydrolyzed as in the second step of Scheme 43 of Example 366 to give 50 mg (67% over two steps) of 4-bromo-3-carboxymethoxy-5-{3-[1-cyclohexylmethyl-3-(4-phenoxy-phenyl)-ureido]-phenyl}-thiophene-2-carboxylic acid as an off-white solid.

$^1$H NMR (400 MHz, DMSO-D6) δ ppm 0.90-1.03 (m, 2 H) 1.06-1.17 (m, 4 H) 1.46-1.75 (m, 5 H) 3.62 (d, J=7.33 Hz, 2 H) 4.89 (s, 2 H) 6.88-6.96 (m, 4 H) 7.04-7.10 (m, 1 H) 7.30-7.38 (m, 2 H) 7.39-7.47 (m, 3 H) 7.51-7.60 (m, 2 H) 7.61-7.64 (m, 1 H)

ESI-MS: m/e=679 [M+H]$^+$.

EXAMPLE 371

4-Bromo-3-carboxymethoxy-5-{3-[3-(2-cyano-phenyl)-1-cyclohexylmethyl-ureido]-phenyl}-thiophene-2-carboxylic acid The first step of Scheme 43: 4-Bromo-3-tert-butoxycarbonylmethoxy-5-{3-[3-(2-cyano-phenyl)-1-cyclohexylmethyl-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 1.01-1.11 (m, 2 H) 1.16-1.28 (m, 4 H) 1.50 (s, 9 H) 1.60-1.68 (m, 1 H) 1.69-1.83 (m, 4 H) 3.68 (d, J=7.58 Hz, 2 H) 3.88 (s, 3 H) 4.83 (s, 2 H) 6.86 (s, 1 H) 6.99-7.04 (m, 1 H) 7.40 (dd, J=7.83, 1.01 Hz, 1 H) 7.43-7.47 (m, 1 H) 7.48-7.55 (m, 1 H) 7.64 (t, J=8.08 Hz, 1 H) 7.67-7.73 (m, 2 H) 8.32 (d, J=8.59 Hz, 1 H).

The second step of Scheme 43: 4-Bromo-3-tert-butoxycarbonylmethoxy-5-{3-[3-(2-cyano-phenyl)-1-cyclohexylmethyl-ureido]-phenyl}-thiophene-2-carboxylic acid methyl ester was hydrolyzed as in the second step of Scheme 43 of Example 366 to give 33 mg (49% over two steps) of 4-bromo-3-carboxymethoxy-5-{3-[3-(2-cyano-phenyl)-1-cyclohexylmethyl-ureido]-phenyl}-thiophene-2-carboxylic acid as an off-white solid.

$^1$H NMR (400 MHz, DMSO-D6) δ ppm 0.90-1.02 (m, 2 H) 1.07-1.17 (m, 4 H) 1.46-1.54 (m, 1 H) 1.60-1.69 (m, 2 H) 1.70-1.78 (m, 2 H) 3.64 (d, J=7.07 Hz, 2 H) 4.89 (s, 2 H) 7.19-7.26 (m, 1 H) 7.48 (d, J=8.08 Hz, 1 H) 7.51-7.58 (m, 1 H) 7.57-7.66 (m, 3 H) 7.68-7.76 (m, 2 H) 8.31 (s, 1 H).

ESI-MS: m/e=612 [M+H]$^+$.

EXAMPLE 372

4-Bromo-3-carboxymethoxy-5-[3-(1-cyclohexylmethyl-3-thiophen-3-yl-ureido)-phenyl]-thiophene-2-carboxylic acid The first step of Scheme 43: 4-Bromo-3-tert-butoxycarbonylmethoxy-5-[3-(1-cyclohexylmethyl-3-thiophen-3-yl-ureido)-phenyl]-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.97-1.07 (m, 2 H) 1.12-1.23 (m, 4 H) 1.50 (s, 9 H) 1.54-1.61 (m, 1 H) 1.67-1.79 (m, 4 H) 3.65 (d, J=7.33 Hz, 2 H) 3.89 (s, 3 H) 4.85 (s, 2 H) 6.46 (s, 1 H) 6.79 (dd, J=5.18, 1.39 Hz, 1 H) 7.13 (dd, J=5.05, 3.28 Hz, 1 H) 7.27-7.28 (m, 1 H) 7.39 (dt, J=7.58, 1.89 Hz, 1 H) 7.57 (t, J=7.83 Hz, 1 H) 7.60-7.63 (m, 1 H) 7.69 (t, J=1.64 Hz, 1 H).

The second step of Scheme 43: 4-Bromo-3-tert-butoxycarbonylmethoxy-5-[3-(1-cyclohexylmethyl-3-thiophen-3-yl-ureido)-phenyl]-thiophene-2-carboxylic acid methyl ester was hydrolyzed as in the second step of Scheme 43 of Example 366 to give 42 mg (64% over two steps) of 4-bromo-3-carboxymethoxy-5-[3-(1-cyclohexylmethyl-3-thiophen-3-yl-ureido)-phenyl]-thiophene-2-carboxylic acid as an off-white solid.

$^1$H NMR (400 MHz, DMSO-D6) δ ppm 0.88-1.02 (m, 2 H) 1.04-1.19 (m, 4 H) 1.44-1.54 (m, 1 H) 1.54-1.74 (m, 4 H) 3.61 (d, J=7.33 Hz, 2 H) 4.89 (s, 2 H) 7.09 (d, J=5.31 Hz, 1 H) 7.26 (d, J=3.03 Hz, 1 H) 7.32 (dd, J=4.93, 3.41 Hz, 1 H) 7.42 (d, J=7.33 Hz, 1 H) 7.52-7.63 (m, 3 H) 8.56 (s, 1 H).

ESI-MS: m/e=593 [M+H]$^+$.

EXAMPLE 373

4-Bromo-3-carboxymethoxy-5-{3-[1-cyclohexylmethyl-3-(3,5-dimethyl-isoxazol-4-yl)-ureido]-phenyl}-thiophene-2-carboxylic acid The first step of Scheme 43: 4-Bromo-3-tert-butoxycarbonylmethoxy-5-{3-[1-cyclohexylmethyl-3-(3,5-dimethyl-isoxazol-4-yl)-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.98-1.08 (m, 2 H) 1.12-1.23 (m, 4 H) 1.51 (s, 9 H) 1.52-1.59 (m, 1 H) 1.69-1.78 (m, 4 H) 2.14 (s, 3 H) 2.27 (s, 3 H) 3.63 (d, J=7.33 Hz, 2 H) 3.90 (s, 3 H) 4.87 (s, 2 H) 5.29 (s, 1 H) 7.42 (dt, J=7.83, 1.64 Hz, 1 H) 7.59 (t, J=7.83 Hz, 1 H) 7.65 (dt, J=7.77, 1.42 Hz, 1 H) 7.70 (t, J=1.89 Hz, 1 H).

The second step of Scheme 43: 4-Bromo-3-tert-butoxycarbonylmethoxy-5-{3-[1-cyclohexylmethyl-3-(3,5-dimethyl-isoxazol-4-yl)-ureido]-phenyl}-thiophene-2-carboxylic acid methyl ester was hydrolyzed as in the second step of Scheme 43 of Example 366 to give 49 mg (73% over two steps) of 4-bromo-3-carboxymethoxy-5-{3-[1-cyclohexylmethyl-3-(3,5-dimethyl-isoxazol-4-yl)-ureido]-phenyl}-thiophene-2-carboxylic acid as an off-white solid.

$^1$H NMR (400 MHz, DMSO-D6) δ ppm 0.88-1.02 (m, 2 H) 1.04-1.18 (m, 4 H) 1.40-1.52 (m, 1 H) 1.54-1.73 (m, 4 H) 2.05 (s, 3 H) 2.19 (s, 3 H) 3.58 (d, J=7.33 Hz, 2 H) 4.91 (s, 2 H) 7.44-7.53 (m, 2 H) 7.56-7.63 (m, 2 H) 7.66 (s, 1 H).

ESI-MS: m/e=606 [M+H]$^+$.

EXAMPLE 374

4-Bromo-3-carboxymethoxy-5-{3-[1-cyclohexylmethyl-3-(5-methyl-3-phenyl-isoxazol-4-yl)-ureido]-phenyl}-thiophene-2-carboxylic acid The first step of Scheme 43: 4-Bromo-3-tert-butoxycarbonylmethoxy-5-{3-[1-cyclohexylmethyl-3-(5-methyl-3-phenyl-isoxazol-4-yl)-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.98-1.07 (m, 2 H) 1.13-1.23 (m, 4 H) 1.51 (s, 9 H) 1.63-1.67 (m, 1 H) 1.69-1.77 (m, 4 H) 2.41 (s, 3 H) 3.63 (d, J=7.33 Hz, 2 H) 3.90 (s, 3 H) 4.86 (s, 2 H) 5.37 (s, 1 H) 7.30-7.34 (m, 1 H) 7.36-7.41 (m, 3 H) 7.52 (t, J=7.83 Hz, 1 H) 7.55-7.60 (m, 3 H) 7.59-7.64 (m, 1 H).

The second step of Scheme 43: 4-Bromo-3-tert-butoxycarbonylmethoxy-5-{3-[1-cyclohexylmethyl-3-(5-methyl-3-phenyl-isoxazol-4-yl)-ureido]-phenyl}-thiophene-2-carboxylic acid methyl ester was hydrolyzed as in the second step of Scheme 43 of Example 366 to give 48 mg (65% over two steps) of 4-bromo-3-carboxymethoxy-5-{3-[1-cyclohexylmethyl-3-(5-methyl-3-phenyl-isoxazol-4-yl)-ureido]-phenyl}-thiophene-2-carboxylic acid as an off-white solid.

$^1$H NMR (400 MHz, DMSO-D6) δ ppm 0.83-0.95 (m, 2 H) 1.04-1.15 (m, 4 H) 1.39-1.47 (m, 1 H) 1.55-1.69 (m, 4 H) 2.28 (s, 3 H) 3.54 (d, J=7.07 Hz, 2 H) 4.91 (s, 2 H) 7.40-7.48 (m, 3 H) 7.54 (s, 1 H) 7.58-7.63 (m, 3 H) 7.67 (dd, J=7.71, 1.64 Hz, 2 H).

ESI-MS: m/e=668 [M+H]$^+$.

EXAMPLE 375

4-Bromo-3-carboxymethoxy-5-{3-[3-(4-carboxyphenyl)-1-cyclohexylmethyl-ureido]-phenyl}-thiophene-2-carboxylic acid The first step of Scheme 43: 4-Bromo-3-tert-butoxycarbonylmethoxy-5-{3-[3-(4-carboxy-phenyl)-1-cyclohexylmethyl-ureido]-phenyl}-thiophene-2-carboxylic acid methyl ester was obtained as a yellow oil, following the general procedure in the first step of Scheme 43 of Example 366.

$^1$H NMR (400 MHz, CHLOROFORM-D) δ ppm 0.98-1.08 (m, 2 H) 1.14-1.23 (m, 4 H) 1.37 (t, J=7.07 Hz, 3 H) 1.50 (s, 9 H) 1.56-1.63 (m, 1 H) 1.68-1.80 (m, 4 H) 3.66 (d, J=7.33 Hz, 2 H) 3.89 (s, 3 H) 4.33 (q, J=7.07 Hz, 2 H) 4.85 (s, 2 H) 6.43 (s, 1 H) 7.35-7.42 (m, 3 H) 7.57-7.66 (m, 2 H) 7.70 (t, J=1.64 Hz, 1 H) 7.88-7.94 (m, 2 H).

The second step of Scheme 43: 4-Bromo-3-tert-butoxycarbonylmethoxy-5-{3-[3-(4-carboxy-phenyl)-1-cyclohexylmethyl-ureido]-phenyl}-thiophene-2-carboxylic acid methyl ester was hydrolyzed as in the second step of Scheme 43 of Example 366, (except using 550 μL of 1N LiOH) to give 29 mg (42% over two steps) of 4-bromo-3-carboxymethoxy-5-

{3-[3-(4-carboxy-phenyl)-1-cyclohexylmethyl-ureido]-phenyl}-thiophene-2-carboxylic acid as an off-white solid.

¹H NMR (400 MHz, DMSO-D6) δ ppm 0.90-1.02 (m, 2 H) 1.05-1.17 (m, 4 H) 1.45-1.74 (m, 5 H) 3.64 (d, J=7.07 Hz, 2 H) 4.88 (s, 2 H) 7.42-7.48 (m, 1 H) 7.50-7.60 (m, 4 H) 7.63 (s, 1 H) 7.79 (d, J=8.59 Hz, 2 H) 8.54 (s, 1 H).

ESI-MS: m/e=631 [M+H]⁺.

EXAMPLE 376

4-Bromo-3-carboxymethoxy-5-[3-(1-cyclohexylmethyl-3-ethyl-ureido)-phenyl]-thiophene-2-carboxylic acid The first step of Scheme 43: 4-Bromo-3-tert-butoxycarbonylmethoxy-5-[3-(1-cyclohexylmethyl-3-ethyl-ureido)-phenyl]-thiophene-2-carboxylic acid methyl ester was obtained as a yellow oil, following the general procedure in the first step of Scheme 43 of Example 366.

Mixture of rotamers: ¹H NMR (400 MHz, CHLOROFORM-D) δ ppm 1.04 (t, J=7.20 Hz, 3 H) 1.18 (m, 4 H) 1.51 (s, 9 H) 1.69 (m, 2 H) 3.27 (m, 3 H) 3.58 (d, J=7.33 Hz, 2 H) 3.89 (s, 3 H) 4.23 (t, J=5.43 Hz, 1 H) 4.86 (s, 2 H) 7.31 (dt, J=7.64, 1.74 Hz, 2 H) 7.51 (t, J=7.71 Hz, 1 H) 7.55 (m, 1 H) 7.59 (t, J=1.77 Hz, 2 H).

The second step of Scheme 43: 4-Bromo-3-tert-butoxycarbonylmethoxy-5-[3-(1-cyclohexylmethyl-3-ethyl-ureido)-phenyl]-thiophene-2-carboxylic acid methyl ester was hydrolyzed as in the second step of Scheme 43 of Example 366 to give 16 mg (27% over two steps) of 4-bromo-3-carboxymethoxy-5-[3-(1-cyclohexylmethyl-3-ethyl-ureido)-phenyl]-thiophene-2-carboxylic acid as an off-white solid.

¹H NMR (400 MHz, MeOD) δ ppm 0.94 (m, 2 H) 1.04 (t, J=7.07 Hz, 3 H) 1.20 (m, 4 H) 1.70 (m, 6 H) 3.14 (q, J=7.16 Hz, 2 H) 3.57 (d, J=7.33 Hz, 2 H) 4.91 (s, 2 H) 7.37 (dt, J=7.01, 2.05 Hz, 1 H) 7.59 (m, 3 H).

ESI-MS: m/e=539 [M+H]⁺.

EXAMPLE 377

3-Carboxymethoxy-5-[3-(1-cyclohexylmethyl-3-isopropyl-ureido)-phenyl]-4-methyl-thiophene-2-carboxylic acid The first step of Scheme 44: To 4-methyl-3-tert-butoxycarbonylmethoxy-5-[3-(cyclohexylmethyl-amino)-phenyl]-thiophene-2-carboxylic acid methyl ester (50 mg, 0.11 mmole) was added isopropyl isocyanate (0.5 mL, large excess) and the reaction mixture was allowed to stir at room temperature overnight. The reaction mixture was evaporated to give 3-tert-butoxycarbonylmethoxy-5-[3-(1-cyclohexylmethyl-3-isopropyl-ureido)-phenyl]-4-methyl-thiophene-2-carboxylic acid methyl ester as a yellow oil.

¹H NMR (400 MHz, CHLOROFORM-D) δ ppm 0.93-1.01 (m, 2 H) 1.05 (d, J=6.06 Hz, 6 H) 1.12-1.20 (m, 4 H) 1.49 (s, 9 H) 1.59-1.64 (m, 1 H) 1.66-1.74 (m, 4 H) 2.28 (s, 3 H) 3.56 (d, J=7.33 Hz, 2 H) 3.87 (s, 3 H) 3.93-4.02 (m, 1 H) 4.84 (s, 2 H) 7.15-7.20 (m, 1 H) 7.32 (t, J=1.77 Hz, 1 H) 7.40 (ddd, J=8.08, 1.39, 1.14 Hz, 1 H) 7.49 (t, J=7.83 Hz, 1 H).

The second step of Scheme 44: 3-tert-Butoxycarbonylmethoxy-5-[3-(1-cyclohexylmethyl-3-isopropyl-ureido)-phenyl]-4-methyl-thiophene-2-carboxylic acid methyl ester (54 mg, 0.11 mmol) was dissolved in 1 mL THF and 1N LiOH.H₂O was added (440 μL, 0.44 mmol) and stirred at room temperature overnight. The reaction mixture was then diluted with water and extracted with hexane. The aqueous layer was removed and acidified to pH 2 with 1N HCl. The mixture was extracted with EtOAc and the organic layer was washed with brine and dried (MgSO₄). Filtration and evaporation gave 43 mg (80%) 3-carboxymethoxy-5-[3-(1-cyclohexylmethyl-3-isopropyl-ureido)-phenyl]-4-methyl-thiophene-2-carboxylic acid as a white foam.

¹H NMR (400 MHz, DMSO-D6) δ ppm 0.88-0.99 (m, 2 H) 1.06 (d, J=6.57 Hz, 6 H) 1.08-1.18 (m, 4 H) 1.39-1.46 (m, 1 H) 1.58-1.71 (m, 4 H) 2.26 (s, 3 H) 3.55 (d, J=7.33 Hz, 2 H) 3.79-3.89 (m, 1 H) 4.91 (s, 2 H) 5.62 (d, J=8.08 Hz, 1 H) 7.31-7.37 (m, 2 H) 7.37-7.41 (m, 1 H) 7.55 (t, J=7.71 Hz, 1 H).

ESI-MS: m/e=489 [M+H]⁺.

EXAMPLE 378

3-Carboxymethoxy-5-[3-(1-cyclohexyl-3-isopropyl-ureido)-phenyl]-4-methyl-thiophene-2-carboxyl acid The first step of Scheme 44: 3-tert-Butoxycarbonylmethoxy-5-[3-(1-cyclohexyl-3-isopropyl-ureido)-phenyl]-4-methyl-thiophene-2-carboxylic acid methyl ester was obtained as a yellow oil, following the general procedure in the second step of Scheme 44 of Example 377.

¹H NMR (400 MHz, CHLOROFORM-D) δ ppm 1.01 (d, J=6.57 Hz, 6 H) 1.03-1.08 (m, 4 H) 1.33-1.44 (m, 2 H) 1.49 (s, 9 H) 1.68-1.77 (m, 2 H) 1.84-1.92 (m, 2 H) 2.28 (s, 3 H) 3.62 (d, J=7.58 Hz, 1 H) 3.87 (s, 3 H) 3.90-3.99 (m, 1 H) 4.42-4.52 (m, 1 H) 4.83 (s, 2 H) 7.13-7.20 (m, 1 H) 7.23-7.27 (m, 2 H) 7.48-7.50 (m, 1 H).

The second step of Scheme 44: 3-tert-Butoxycarbonylmethoxy-5-[3-(1-cyclohexyl-3-isopropyl-ureido)-phenyl]-4-methyl-thiophene-2-carboxylic acid methyl ester was hydrolyzed as in Step 2B of Example 12 to give 49 mg (88% over two steps) of 3-carboxymethoxy-5-[3-(1-cyclohexyl-3-isopropyl-ureido)-phenyl]-4-methyl-thiophene-2-carboxylic acid as a white foam.

¹H NMR (400 MHz, DMSO-D6) δ ppm 0.98-1.07 (m, 2 H) 1.12 (d, J=6.57 Hz, 6 H) 1.38-1.52 (m, 2 H) 1.63-1.71 (m, 2 H) 1.80-1.88 (m, 2 H) 1.90-1.98 (m, 2 H) 2.38 (s, 3 H) 3.90-4.01 (m, 1 H) 4.34-4.44 (m, 1 H) 5.00 (s, 1 H) 5.02 (s, 2 H) 7.33-7.37 (m, 2 H) 7.64-7.74 (m, 2 H).

ESI-MS: m/e=475 [M+H]⁺.

EXAMPLE 379

3-Carboxymethoxy-5-[3-(1-cyclohexylmethyl-3-phenyl-ureido)-phenyl]-4-methyl-thiophene-2-carboxylic acid The first step of Scheme 44: To a 1 mL CH₂Cl₂ solution of 4-methyl-3-tert-butoxycarbonylmethoxy-5-[3-(cyclohexylmethyl-amino)-phenyl]-thiophene-2-carboxylic acid methyl ester (50 mg, 0.11 mmole) was added phenyl isocyanate (36 μL, 0.33 mmole) and the reaction mixture was allowed to stir at room temperature overnight. Polystyrene-bound Trisamine (Argonaut Laboratories—250 mg of 4.11 mmol/g) was added and the suspension stirred for 2 hours. The mixture was then filtered and evaporated to give 3-tert-butoxycarbonylmethoxy-5-[3-(1-cyclohexylmethyl-3-phenyl-ureido)-phenyl]-4-methyl-thiophene-2-carboxylic acid methyl ester as a yellow oil.

¹H NMR (400 MHz, CHLOROFORM-D) δ ppm 0.97-1.08 (m, 2 H) 1.12-1.23 (m, 4 H) 1.49 (s, 9 H) 1.53-1.61 (m, 1 H) 1.68-1.81 (m, 4 H) 2.30 (s, 3 H) 3.65 (d, J=7.33 Hz, 2 H) 3.87 (s, 3 H) 4.83 (s, 2 H) 6.17 (s, 1 H) 6.99 (t, J=7.20 Hz, 1 H) 7.20-7.30 (m, 4 H) 7.35 (d, J=7.83 Hz, 1 H) 7.43 (s, 1 H) 7.46-7.51 (m, 1 H) 7.56 (t, J=7.83 Hz, 1 H).

The second step of Scheme 44: 3-tert-Butoxycarbonyl-methoxy-5-[3-(1-cyclohexylmethyl-3-phenyl-ureido)-phenyl]-4-methyl-thiophene-2-carboxylic acid methyl ester was hydrolyzed as in Step 2B of Example 12 to give 33 mg (57% over two steps) of 3-carboxymethoxy-5-[3-(1-cyclohexylmethyl-3-phenyl-ureido)-phenyl]-4-methyl-thiophene-2-carboxylic acid as a white foam.

$^1$H NMR (400 MHz, DMSO-D6) δ ppm 1.05-1.15 (m, 2 H) 1.42-1.51 (m, 1 H) 1.62-1.74 (m, 4 H) 2.19 (s, 3 H) 3.61 (d, J=7.33 Hz, 2 H) 4.86 (s, 2 H) 6.90-6.96 (m, 1 H) 7.17-7.24 (m, 2 H) 7.35-7.43 (m, 5 H) 7.51-7.57 (m, 1 H) 8.1 (s, 1 H).

ESI-MS: m/e=523 [M+H]$^+$.

EXAMPLE 380

5-[3-(3-Benzyl-1-cyclohexylmethyl-ureido)-phenyl]-3-carboxymethoxy-4-methyl-thiophene-2-carboxylic acid The first step of Scheme 44: 5-[3-(3-Benzyl-1-cyclohexylmethyl-ureido)-phenyl]-3-tert-butoxycarbonylmethoxy-4-methyl-thiophene-2-carboxylic acid methyl ester was obtained as a yellow oil, following the general procedure in the first step of Scheme 44 of Example 379.

$^1$H NMR (400 MHz, CHLOROFORM-D) δ ppm 0.95-1.06 (m, 2 H) 1.13-1.21 (m, 4 H) 1.49 (s, 9 H) 1.50-1.56 (m, 1 H) 1.67-1.78 (m, 4 H) 2.23 (s, 3 H) 3.60 (d, J=7.33 Hz, 2 H) 3.87 (s, 3 H) 4.39 (d, J=5.81 Hz, 2 H) 4.55 (t, J=5.81 Hz, 1 H) 4.83 (s, 2 H) 7.19-7.24 (m, 3 H) 7.24-7.31 (m, 3 H) 7.33-7.36 (m, 1 H) 7.37-7.41 (m, 1 H) 7.47 (t, J=7.83 Hz, 1 H).

The second step of Scheme 44: 5-[3-(3-Benzyl-1-cyclohexylmethyl-ureido)-phenyl]-3-tert-butoxycarbonyl-methoxy-4-methyl-thiophene-2-carboxylic acid methyl ester was hydrolyzed as in the second step of Scheme 44 of Example 377 to give 16 mg (27% over two steps) of 5-[3-(3-Benzyl-1-cyclohexylmethyl-ureido)-phenyl]-3-carboxymethoxy-4-methyl-thiophene-2-carboxylic acid as a white foam.

$^1$H NMR (400 MHz, DMSO-D6) δ ppm 0.95-1.07 (m, 2 H) 1.15-1.25 (m, 4 H) 1.50-1.56 (m, 1 H) 1.67-1.80 (m, 4 H) 2.31 (s, 3 H) 3.64 (d, J=7.33 Hz, 2 H) 4.31 (d, J=5.56 Hz, 2 H) 4.98 (s, 2 H) 6.57 (t, J=5.81 Hz, 1 H) 7.27-7.36 (m, 3 H) 7.36-7.42 (m, 2 H) 7.43-7.47 (m, 2 H) 7.51 (d, J=8.34 Hz, 1 H) 7.65 (t, J=7.71 Hz).

ESI-MS: m/e=537 [M+H]$^+$.

EXAMPLE 381

5-[3-(3-Benzyl-1-cyclohexyl-ureido)-phenyl]-3-carboxymethoxy-4-methyl-thiophene-2-carboxylic acid The first step of Scheme 44: 5-[3-(3-Benzyl-1-cyclohexyl-ureido)-phenyl]-3-tert-butoxycarbonylmethoxy-4-methyl-thiophene-2-carboxylic acid methyl ester was obtained as a yellow oil following the general procedure in the first step of Scheme 44 of Example 379, except using double the amount of reagents.

$^1$H NMR (400 MHz, CHLOROFORM-D) δ ppm 0.99-1.12 (m, 2 H) 1.33-1.46 (m, 2 H) 1.49 (s, 9 H) 1.54-1.62 (m, 1 H) 1.74 (d, J=13.64 Hz, 3 H) 1.91 (d, J=11.37 Hz, 2 H) 2.24 (s, 3 H) 3.87 (s, 3 H) 4.24 (t, J=5.81 Hz, 1 H) 4.37 (d, J=5.81 Hz, 2 H) 4.51 (tt, J=12.13, 3.54 Hz, 1 H) 4.83 (s, 2 H) 7.16-7.23 (m, 4 H) 7.24-7.30 (m, 3 H) 7.46-7.49 (m, 2 H).

The second step of Scheme 44: 5-[3-(3-Benzyl-1-cyclohexyl-ureido)-phenyl]-3-tert-butoxycarbonylmethoxy-4-methyl-thiophene-2-carboxylic acid methyl ester was hydrolyzed as in the second step of Scheme 44 of Example 377 to give 26 mg (45% over two steps) of 5-[3-(3-Benzyl-1-cyclohexyl-ureido)-phenyl]-3-carboxymethoxy-4-methyl-thiophene-2-carboxylic acid as a white foam.

$^1$H NMR (400 MHz, DMSO-D6) δ ppm 0.89-1.09 (m, 4 H) 1.27-1.40 (m, 3 H) 1.53-1.61 (m, 1 H) 1.71-1.79 (m, 2 H) 1.87 (dd, J=9.35, 4.55 Hz, 2 H) 2.27 (s, 3 H) 4.23 (d, J=5.81 Hz, 2 H) 4.26-4.36 (m, 1 H) 4.92 (s, 2 H) 6.03 (t, J=6.06 Hz, 1 H) 7.19-7.26 (m, 3 H) 7.28-7.36 (m, 4 H) 7.55-7.66 (m, 2 H).

ESI-MS: m/e=523 [M+H]$^+$.

EXAMPLE 382

3-Carboxymethoxy-5-[3-(1-cyclohexylmethyl-3-phenethyl-ureido)-phenyl]-4-methyl-thiophene-2-carboxylic acid The first step of Scheme 44: 3-tert-Butoxycarbonyl-methoxy-5-[3-(1-cyclohexylmethyl-3-phenethyl-ureido)-phenyl]-4-methyl-thiophene-2-carboxylic acid methyl ester was obtained as a yellow oil following the general procedure in the first step of Scheme 44 of Example 379, except using double the amount of reagents.

$^1$H NMR (400 MHz, CHLOROFORM-D) δ ppm 0.94-1.02 (m, 2 H) 1.11-1.20 (m, 4 H) 1.49 (s, 9 H) 1.62-1.65 (m, 1 H) 1.66-1.74 (m, 4 H) 2.24 (s, 3 H) 2.74 (t, J=6.82 Hz, 2 H) 3.39-3.45 (m, 2 H) 3.55 (d, J=7.33 Hz, 2 H) 3.88 (s, 3 H) 4.16 (t, J=5.81 Hz, 1 H) 4.84 (s, 2 H) 7.03-7.06 (m, 2 H) 7.08-7.13 (m, 2 H) 7.14-7.17 (m, 2 H) 7.18-7.21 (m, 1 H) 7.36 (dt, J=7.77, 1.55 Hz, 1 H) 7.41 (t, J=7.58 Hz, 1 H).

The second step of Scheme 44: 3-tert-Butoxycarbonyl-methoxy-5-[3-(1-cyclohexylmethyl-3-phenethyl-ureido)-phenyl]-4-methyl-thiophene-2-carboxylic acid methyl ester was hydrolyzed as in the second step of Scheme 44 of Example 377 to give 32 mg (53% over two steps) of 3-carboxymethoxy-5-[3-(1-cyclohexylmethyl-3-phenethyl-ureido)-phenyl]-4-methyl-thiophene-2-carboxylic acid as a white foam.

$^1$H NMR (400 MHz, DMSO-D6) δ ppm 0.58-0.69 (m, 2 H) 0.79-0.91 (m, 4 H) 1.09-1.18 (m, 1 H) 1.30-1.44 (m, 4 H) 1.96 (s, 3 H) 2.44 (t, J=7.20 Hz, 2 H) 2.95-3.03 (m, 2 H) 3.25 (d, J=7.07 Hz, 2 H) 4.65 (s, 2 H) 5.52 (t, J=5.68 Hz, 1 H) 6.87-6.93 (m, 3 H) 6.95-7.02 (m, 4 H) 7.14 (d, J=7.58 Hz, 1 H) 7.26 (t, J=7.71 Hz, 1 H).

ESI-MS: m/e=551 [M+H]$^+$.

EXAMPLE 383

3-Carboxymethoxy-5-[3-(1-cyclohexylmethyl-3-phenethyl-ureido)-phenyl]-4-methyl-thiophene-2-carboxylic acid The first step of Scheme 44: 3-tert-Butoxycarbonyl-methoxy-5-[3-(1-cyclohexylmethyl-3-phenethyl-ureido)-phenyl]-4-methyl-thiophene-2-carboxylic acid methyl ester was obtained as a yellow oil following the general procedure in the first step of Scheme 44 of Example 379, except using double the amount of reagents.

$^1$H NMR (400 MHz, CHLOROFORM-D) δ ppm 0.87-1.08 (m, 4 H) 1.34-1.44 (m, 2 H) 1.49 (s, 9 H) 1.73 (d, J=13.14 Hz, 2 H) 1.87 (d, J=11.12 Hz, 2 H) 2.25 (s, 3 H) 2.71 (t, J=6.82 Hz, 2 H) 3.35-3.43 (m, 2 H) 3.83 (t, J=5.68 Hz, 1 H) 3.88 (s, 3 H) 4.47 (tt, J=12.13, 3.54 Hz, 1 H) 4.84 (s, 2 H) 6.99-7.06 (m, 3 H) 7.06-7.12 (m, 1 H) 7.12-7.18 (m, 3 H) 7.40 (t, J=7.71 Hz, 1 H) 7.43-7.46 (m, 1 H).

The second step of Scheme 44: 3-tert-Butoxycarbonyl-methoxy-5-[3-(1-cyclohexylmethyl-3-phenethyl-ureido)-phenyl]-4-methyl-thiophene-2-carboxylic acid methyl ester was hydrolyzed as in the second step of Scheme 44 of Example 377 to give 40 mg (68% over two steps) of 3-carboxymethoxy-5-[3-(1-cyclohexylmethyl-3-phenethyl-ureido)-phenyl]-4-methyl-thiophene-2-carboxylic acid as a white foam.

$^1$H NMR (400 MHz, DMSO-D6) δ ppm 0.78-0.92 (m, 2 H) 1.16-1.27 (m, 3 H) 1.43-1.50 (m, 1 H) 1.60-1.68 (m, 2 H) 1.69-1.76 (m, 2 H) 2.16 (s, 3 H) 2.58 (t, J=7.33 Hz, 2 H) 3.09-3.16 (m, 2 H) 4.15-4.23 (m, 1 H) 4.83 (s, 2 H) 5.13 (t, J=5.81 Hz, 1 H) 7.01-7.10 (m, 5 H) 7.12-7.18 (m, 2 H) 7.43-7.49 (m, 2 H).

ESI-MS: m/e=537 [M+H]$^+$.

EXAMPLE 384

4-Bromo-3-isopropoxycarbonylmethoxy-5-[3-(1-phenylmethanesulfonyl-piperidin-4-ylamino)-phenyl]-thiophene-2-carboxylic acid The first step of Scheme 45: 4-Bromo-3-carboxymethoxy-5-[3-(1-phenylmethanesulfonyl-piperidin-4-ylamino)-phenyl]-thiophene-2-carboxylic acid (150 mg, 0.25 mmole) was dissolved in a mixture of 3 mL isopropyl alcohol and 0.3 mL DMF. A drop of concentrated $H_2SO_4$ was added and heated to 60° C. overnight. The reaction mixture was then evaporated and the residue partitioned between water and EtOAc. The organic layer was washed with aqueous sodium bicarbonate solution, 5% aqueous LiCl, brine, and dried (MgSO$_4$). Evaporation gave 115 mg (71%) of 4-bromo-3-isopropoxycarbonylmethoxy-5-[3-(1-phenylmethanesulfonyl-piperidin-4-ylamino)-phenyl]-thiophene-2-carboxylic acid as a pale yellow foam.

$^1$H NMR (400 MHz, DMSO-D6) δ ppm 1.18 (d, J=6.32 Hz, 6 H) 1.30-1.42 (m, 2 H) 1.92-2.00 (m, 2 H) 2.87-2.96 (m, 2 H) 3.50-3.58 (m, 2 H) 4.40 (s, 2 H) 4.89-5.00 (m, 1 H) 5.25 (s, 2 H) 5.82 (d, J=7.07 Hz, 1 H) 6.64 (dd, J=8.08, 1.52 Hz, 1 H) 6.74 (d, J=8.08 Hz, 1 H) 6.80 (t, J=1.89 Hz, 1 H) 7.15 (t, J=7.96 Hz, 1 H) 7.34-7.45 (m, 5 H)

ESI-MS: m/e=651 [M+H]$^+$.

EXAMPLE 385

4-Bromo-3-isobutoxycarbonylmethoxy-5-[3-(1-phenylmethanesulfonyl-piperidin-4-ylamino)-phenyl]-thiophene-2-carboxylic acid 4-Bromo-3-isobutoxycarbonylmethoxy-5-[3-(1-phenylmethanesulfonyl-piperidin-4-ylamino)-phenyl]-thiophene-2-carboxylic acid was prepared as described in the general procedure of Scheme 45 of Example 384 in 75% yield as a yellow foam.

$^1$H NMR (400 MHz, DMSO-D6) δ ppm 0.85 (d, J=6.57 Hz, 6 H) 1.29-1.42 (m, 2 H) 1.82-1.91 (m, 1 H) 1.91-1.98 (m, 2 H) 2.87-2.97 (m, 2 H) 3.50-3.58 (m, 2 H) 3.87 (d, J=6.82 Hz, 2 H) 4.40 (s, 2 H) 5.37 (s, 2 H) 5.80 (d, J=8.08 Hz, 1 H) 6.60-6.65 (m, 1 H) 6.73 (d, J=7.58 Hz, 1 H) 6.77-6.80 (m, 1 H) 7.14 (t, J=7.96 Hz, 1 H) 7.35-7.45 (m, 5 H)

ESI-MS: m/e=665 [M+H]$^+$.

EXAMPLE 386

4-Bromo-5-[3-(1-phenylmethanesulfonyl-piperidin-4-ylamino)-phenyl]-3-propoxycarbonylmethoxy-thiophene-2-carboxylic acid 4-Bromo-5-[3-(1-phenylmethanesulfonyl-piperidin-4-ylamino)-phenyl]-3-propoxycarbonylmethoxy-thiophene-2-carboxylic acid was prepared as described in the general procedure of Scheme 45 of Example 384 in 88% yield as a yellow foam.

$^1$H NMR (400 MHz, DMSO-D6) δ ppm 0.86 (t, J=7.45 Hz, 3 H) 1.31-1.41 (m, 2 H) 1.55-1.64 (m, 2 H) 1.91-1.98 (m, 2 H) 2.87-2.96 (m, 2 H) 3.50-3.58 (m, 2 H) 4.04 (t, J=6.57 Hz, 2 H) 4.40 (s, 2 H) 5.26 (s, 2 H) 5.83 (d, J=7.33 Hz, 1 H) 6.63-6.67 (m, 1 H) 6.73-6.76 (m, 1 H) 6.79-6.81 (m, 1 H) 7.16 (t, J=7.83 Hz, 1 H) 7.35-7.44 (m, 5 H).

ESI-MS: m/e=651 [M+H]$^+$.

EXAMPLE 387

4-Bromo-3-cyclolpropylmethoxycarbonylmethoxy-5-[3-(1-phenylmethanesulfonyl-piperidin-4-ylamino)-phenyl]-thiophene-2-carboxylic acid 4-Bromo-3-cyclopropylmethoxycarbonylmethoxy-5-[3-(1-phenylmethanesulfonyl-piperidin-4-ylamino)-phenyl]-thiophene-2-carboxylic acid was prepared as described in the first step of Scheme 45 of Example 384. The product was also co-evaporated 3 times with toluene and lyophilized to remove residual cyclopropylmethanol.

$^1$H NMR (400 MHz, DMSO-D6) δ ppm 0.26 (m, 2 H) 0.50 (m, 2 H) 1.08 (m, 1 H) 1.36 (m, 2 H) 1.96 (d, J=10.86 Hz, 2 H) 2.92 (t, J=10.74 Hz, 2 H) 3.54 (d, J=12.13 Hz, 2 H) 3.93 (d, J=7.07 Hz, 2 H) 4.40 (s, 2 H) 5.30 (s, 2 H) 5.80 (d, J=7.58 Hz, 1 H) 6.63 (dd, J=8.08, 1.77 Hz, 1 H) 6.74 (d, J=7.33 Hz, 1 H) 6.80 (s, 1 H) 7.15 (t, J=7.83 Hz, 1 H) 7.39 (m, 5 H).

ESI-MS: m/e=663 [M+H]$^+$.

EXAMPLE 388

3-Benzyloxycarbonylmethoxy-4-bromo-5-[3-(1-phenylmethanesulfonyl-piperidin-4-ylamino)-phenyl]-thiophene-2-carboxylic acid The first step of Scheme 45: 4-Bromo-3-carboxymethoxy-5-[3-(1-phenylmethanesulfonyl-piperidin-4-ylamino)-phenyl]-thiophene-2-carboxylic acid (305 mg, 0.5 mmole) was dissolved in a mixture of 2.5 mL $CH_2Cl_2$ and 125 μL DMF. EDCI (115 mg, 0.6 mmole) was added along with DMAP (6 mg, 10 mol %) and the reaction mixture was stirred for 6 hours. The reaction was evaporated and the residue portioned between EtOAc and water. The residue was washed with 5% aqueous LiCl, sodium bicarbonate, brine and dried (MgSO$_4$). Evaporation yielded the crude product which was triturated with 5 mL ether. 3-Benzyloxycarbonylmethoxy-4-bromo-5-[3-(1-phenylmethanesulfonyl-piperidin-4-ylamino)-phenyl]-thiophene-2-carboxylic acid (170 mg, 48%) was obtained as a pale yellow solid.

$^1$H NMR (400 MHz, DMSO-D6) δ ppm 1.31-1.41 (m, 2 H) 1.91-1.99 (m, 2 H) 2.86-2.98 (m, 2 H) 3.49-3.58 (m, 2 H) 4.40 (s, 2 H) 5.18 (s, 2 H) 5.23 (s, 2 H) 5.86 (d, J=7.58 Hz, 1 H) 6.67 (dd, J=8.59, 2.02 Hz, 1 H) 6.75 (d, J=7.07 Hz, 1 H) 6.81 (t, J=2.02 Hz, 1 H) 7.17 (t, J=8.08 Hz, 1 H) 7.30-7.45 (m, 10 H).

ESI-MS: m/e=699 [M+H]$^+$.

EXAMPLE 389

4-Bromo-3-cyclohexylmethoxycarbonylmethoxy-5-[3-(1-phenylmethanesulfonyl-piperidin-4-ylamino)-phenyl]-thiophene-2-carboxylic acid The first step of Scheme 45: 4-Bromo-3-carboxymethoxy-5-[3-(1-phenylmethanesulfonyl-piperidin-4-ylamino)-phenyl]-thiophene-2-carboxylic acid (305 mg, 0.5 mmole) was dissolved in a mixture of 2.5 mL CH$_2$Cl$_2$ and 125 µL DMF. DCC (112 mg, 0.55 mmole) was added along with DMAP (6 mg, 10 mol %) and the reaction mixture was stirred overnight. The reaction was then diluted with CH$_2$Cl$_2$ and filtered through celite and evaporated. The residue was triturated with EtOAc and the filtrate was washed with water, saturated sodium bicarbonate, brine, and dried (MgSO$_4$). Filtration and evaporation gave the crude product which was purified by chromatography on silica gel using a gradient of hexane/EtOAc containing 0.2% HOAc (25 to 100%) as eluent. Pure fractions were combined and evaporated to give 130 mg (37%) of 4-bromo-3-cyclohexylmethoxycarbonylmethoxy-5-[3-(1-phenylmethanesulfonyl-piperidin-4-ylamino)-phenyl]-thiophene-2-carboxylic acid as a pale yellow foam.

$^1$H NMR (400 MHz, DMSO-D6) δ ppm 0.88-0.98 (m, 2 H) 1.11-1.23 (m, 4 H) 1.31-1.42 (m, 2 H) 1.56-1.69 (m, 5 H) 1.91-1.99 (m, 2 H) 2.87-2.96 (m, 2 H) 3.50-3.58 (m, 2 H) 3.94 (d, J=6.32 Hz, 2 H) 4.40 (s, 2 H) 5.03 (s, 2 H) 5.88-5.93 (m, 1 H) 6.71 (dd, J=8.46, 2.40 Hz, 1 H) 6.78 (d, J=8.59 Hz, 1 H) 6.84 (t, J=2.15 Hz, 1 H) 7.17-7.23 (m, 1 H) 7.34-7.45 (m, 5 H).

ESI-MS: m/e=705 [M+H]$^+$.

EXAMPLE 390

4-Bromo-3-cyclohexyloxycarbonylmethoxy-5-[3-(1-phenylmethanesulfonyl-piperidin-4-ylamino)-phenyl]-thiophene-2-carboxylic acid 4-Bromo-3-cyclohexyloxycarbonylmethoxy-5-[3-(1-phenylmethanesulfonyl-piperidin-4-ylamino)-phenyl]-thiophene-2-carboxylic acid was prepared as described in the first step of Scheme 45 of Example 389 in 34% yield as a pale yellow foam.

$^1$H NMR (400 MHz, DMSO-D6) δ ppm 1.26-1.42 (m, 8 H) 1.57-1.66 (m, 2 H) 1.72-1.80 (m, 2 H) 1.89-1.98 (m, 2 H) 2.86-2.96 (m, 2 H) 3.50-3.58 (m, 2 H) 4.40 (s, 2 H) 4.69-4.77 (m, 1 H) 5.17-5.25 (m, 1 H) 5.84 (d, J=9.09 Hz, 1 H) 6.63-6.68 (m, 1 H) 6.75 (d, J=8.34 Hz, 1 H) 6.80 (s, 1 H) 7.16 (t, J=7.83 Hz, 1 H) 7.34-7.45 (m, 5 H).

ESI-MS: m/e=691 [M+H]$^+$.

EXAMPLE 391

4-Bromo-3-carboxymethoxy-5-{3-[1-(2,3-dichloro-phenylmethanesulfonyl)-piperidin-4-ylamino]-phenyl}-thiophene-2-carboxylic acid The third step of Scheme 15: 4-Bromo-5-{3-[1-(2,3-dichloro-phenylmethanesulfonyl)-piperidin-4-ylamino]-phenyl}-3-ethoxycarbonylmethoxy-thiophene-2-carboxylic acid methyl ester was obtained in 25% yield as pale yellow foam, following the procedure in the third step of Scheme 15 of Example 141.

$^1$H NMR (400 MHz, CHLOROFORM-D) δ ppm 1.25 (t, J=7.07 Hz, 3 H) 1.33-1.46 (m, 2 H) 2.01 (dd, J=13.39, 3.28 Hz, 2 H) 2.79-2.89 (m, 2 H) 3.31-3.42 (m, 2 H) 3.57 (ddd, J=13.01, 3.28, 3.16 Hz, 2 H) 3.80 (s, 3 H) 4.23 (q, J=7.07 Hz, 2 H) 4.42 (s, 2 H) 4.83 (s, 2H) 6.59 (d, J=7.58 Hz, 1 H) 6.79 (s, 1 H) 6.89 (d, J=7.58 Hz, 1 H) 7.12-7.23 (m, 3 H) 7.40-7.49 (m, 2 H).

The fourth step of Scheme 15: 4-Bromo-5-{3-[1-(2,3-dichloro-phenylmethanesulfonyl)-piperidin-4-ylamino]-phenyl}-3-ethoxycarbonylmethoxy-thiophene-2-carboxylic acid methyl ester was hydrolyzed according to the procedure in the fourth step of Scheme 15 of Example 141 to give 4-bromo-3-carboxymethoxy-5-{3-[1-(2,3-dichloro-phenyl-methanesulfonyl)-piperidin-4-ylamino]-phenyl}-thiophene-2-carboxylic acid in 88% yield as a pale yellow solid.

$^1$H NMR (400 MHz, DMSO-D6) δ ppm 1.41 (m, 2 H) 1.76 (m, 1 H) 2.02 (m, 2 H) 3.05 (m, 2 H) 3.60 (m, 2 H) 4.62 (s, 2 H) 4.88 (s, 2 H) 6.73 (dd, J=8.21, 1.64 Hz, 1 H) 6.80 (d, J=7.58 Hz, 1 H) 6.86 (t, J=1.89 Hz, 1 H) 7.21 (t, J=7.83 Hz, 1 H) 7.42 (t, J=7.83 Hz, 1 H) 7.53 (m, 1 H) 7.67 (dd, J=8.08, 1.52 Hz, 1 H).

ESI-MS: m/e=676 [M+H]$^+$.

EXAMPLE 392

4-Bromo-5-{3-[1-(2,3-dichloro-phenylmethanesulfonyl)-piperidin-4-ylamino]-phenyl}-3-methoxycarbonylmethoxy-thiophene-2-carboxylic acid 4-Bromo-5-{3-[1-(2,3-dichloro-phenylmethanesulfonyl)-piperidin-4-ylamino]-phenyl}-3-methoxycarbonylmethoxy-thiophene-2-carboxylic acid was obtained in 89% yield as an off-white solid following the procedure in the first step of Scheme 27 of Example 256, using 4-bromo-3-carboxymethoxy-5-{3-[1-(2,3-dichloro-phenylmethanesulfonyl)-piperidin-4-ylamino]-phenyl}-thiophene-2-carboxylic acid as the starting material.

$^1$H NMR (400 MHz, DMSO-D6) δ ppm 1.40 (m, 2 H) 2.01 (d, J=11.12 Hz, 2 H) 3.05 (t, J=10.99 Hz, 2 H) 3.47 (m, 1 H) 3.58 (d, J=11.87 Hz, 2 H) 3.70 (s, 3 H) 4.62 (s, 2 H) 4.97 (m, 2 H) 6.75 (d, J=9.85 Hz, 1 H) 6.82 (d, J=7.58 Hz, 1 H) 6.88 (s, 1 H) 7.22 (t, J=7.96 Hz, 1 H) 7.42 (t, J=7.96 Hz, 1 H) 7.53 (d, J=6.32 Hz, 1 H) 7.68 (dd, J=7.96, 1.39 Hz, 1 H).

ESI-MS: m/e=691 [M+H]$^+$.

EXAMPLE 393

4-Bromo-3-carboxymethoxy-5-{3-[1-(2,3-dichloro-phenylmethanesulfonyl)-piperidin-4-ylamino]-phenyl}-thiophene-2-carboxylic acid methyl ester 4-Bromo-3-carboxymethoxy-5-{3-[1-(2,3-dichloro-phenylmethanesulfonyl)-piperidin-4-ylamino]-phenyl}-thiophene-2-carboxylic acid methyl ester was prepared in 96% yield according to the procedure in the first step of Scheme 28 of Example 261 using 4-bromo-3-tert-butoxycarbonylmethoxy-5-{3-[1-(2,3-dichloro-phenylmethanesulfonyl)-piperidin-4-ylamino]-phenyl}-thiophene-2-carboxylic acid methyl ester as the starting material.

$^1$H NMR (400 MHz, DMSO-D6) δ ppm 1.41 (m, 2 H) 2.01 (m, 2 H) 3.06 (m, 2 H) 3.48 (m, 1 H) 3.59 (m, 2 H) 3.81 (s, 3 H) 4.63 (s, 2 H) 4.86 (s, 2 H) 6.75 (dd, J=8.21, 1.39 Hz, 1 H) 6.82 (d, J=7.58 Hz, 1 H) 6.88 (t, J=1.89 Hz, 1 H) 7.22 (m, 1 H) 7.42 (t, J=7.83 Hz, 1 H) 7.53 (m, 1 H) 7.68 (dd, J=7.96, 1.64 Hz, 1 H)

ESI-MS: m/e=691 [M+H]$^+$.

EXAMPLE 394

[4-Bromo-5-(3-cyclohexylamino-phenyl)-2-(2H-tetrazol-5-yl)-thiophen-3-yloxyl-acetic acid The first step of Scheme 46: 4,5-Dibromo-3-carboxymethoxy-thiophene-2-carboxylic acid methyl ester (16.1 g, 43 mmole) was suspended in 150 mL water and 100 mL (excess) aqueous ammonia was added. A highly viscous suspension results that was stirred at room temperature for one hour. The reaction mixture was cooled in an ice bath, diluted with water, and acidified slowly with concentrated HCl (the neutralization was very exothermic). The resulting suspension was filtered and suction-dried overnight. The wet cake was transferred to a flask and azeotroped twice with toluene. 14.75 g (95%) (4,5-dibromo-2-carbamoyl-thiophen-3-yloxy)-acetic acid was obtained as a tan solid. This was suspended in 200 mL EtOH and 2 mL concentrated sulfuric acid was added and heated at reflux overnight. Upon cooling to room temperature, a crystalline solid emerged. The suspension was cooled in an ice bath, filtered, and washed with cold EtOH to give 13.68 (86%) (4,5-dibromo-2-carbamoyl-thiophen-3-yloxy)-acetic acid ethyl ester as an off-white crystalline solid.

$^1$H NMR (400 MHz, DMSO-D6) δ ppm 1.23 (t, J=7.07 Hz, 3 H) 4.20 (q, J=7.07 Hz, 2 H) 4.95-5.06 (m, 2 H) 7.80 (s, 1 H) 7.99 (s, 1 H).

The second step of Scheme 46: (4,5-Dibromo-2-carbamoyl-thiophen-3-yloxy)-acetic acid ethyl ester (7.74 g, 20.0 mmole) was dissolved in 80 mL dry DMF and cyanuric chloride (3.87 g, 21.0 mmole) was added and stirred at room temperature for 5 hours. The reaction mixture was diluted with 250 mL water and extracted with ether (3×150 mL). The combined organic phases were washed with saturated sodium bicarbonate, brine, and dried (MgSO$_4$). Filtration and evaporation gave 6.62 g (90%) (4,5-dibromo-2-cyano-thiophen-3-yloxy)-acetic acid ethyl ester as a yellow oil that solidified upon standing.

$^1$H NMR (400 MHz, CHLOROFORM-D) δ ppm 1.33 (t, J=7.07 Hz, 3 H) 4.32 (q, J=7.16 Hz, 2 H) 5.07 (s, 2 H).

The third step of Scheme 46: In a 75 mL pressure vessel (4,5-dibromo-2-cyano-thiophen-3-yloxy)-acetic acid ethyl ester (1.11 g, 3.0 mmole) was dissolved in 15 mL THF and 3-aminophenylboronic acid monohydrate (511 mg, 3.3 mmole) was added followed by potassium fluoride (523 mg, 9.0 mmole) and Pd(PPh$_3$)$_4$ (69 mg, 2 mol %). Argon was bubbled through the solution for several minutes and then capped and heated to 100° C. overnight. The reaction mixture was then cooled to room temperature and diluted with ether. Washed with dilute sodium hydroxide, water, brine, and dried (MgSO$_4$). Filtration and evaporation gave a yellow solid that was triturated with 50 mL 1:1 hexane:ether. 815 mg (71%) [5-(3-amino-phenyl)-4-bromo-2-cyano-thiophen-3-yloxy]-acetic acid ethyl ester was obtained as a yellow solid.

$^1$H NMR (400 MHz, CHLOROFORM-D) δ ppm 1.35 (t, J=7.20 Hz, 3 H) 3.82 (s, 2 H) 4.34 (q, J=7.24 Hz, 2 H) 5.10 (s, 2 H) 6.77 (dt, J=8.08, 1.26 Hz, 1 H) 6.90 (t, J=1.89 Hz, 1 H) 6.98 (dt, J=7.64, 1.36 Hz, 1 H) 7.24 (t, J=7.96 Hz, 1 H).

The fourth step of Scheme 46: To a 1.5 mL DCE solution of [5-(3-amino-phenyl)-4-bromo-2-cyano-thiophen-3-yloxy]-acetic acid ethyl ester (95 mg, 0.25 mmole) was added cyclohexanone (39 µL, 0.38 mmole), acetic acid (23 µL, 0.38 mmole) and sodium triacetoxyborohydride (265 mg, 1.25 mmole). The reaction mixture was stirred at room temperature for 5 hours then diluted with CH$_2$Cl$_2$ and then washed with dilute NaOH and dried (MgSO$_4$). Filtration and evaporation yielded the crude product which was purified by chromatography on silica gel using a gradient of hexane/EtOAc (0 to 15%) as eluent. Pure fractions were combined and evaporated to give 83 mg (71%) [4-bromo-2-cyano-5-(3-cyclohexylamino-phenyl)-thiophen-3-yloxy]-acetic acid ethyl ester as a yellow oil.

$^1$H NMR (400 MHz, CHLOROFORM-D) δ ppm 1.11-1.25 (m, 4 H) 1.28 (t, J=7.07 Hz, 3 H) 1.47-1.62 (m, 2 H) 1.65-1.75 (m, 2 H) 1.98-2.06 (m, 2 H) 3.14-3.25 (m, 1 H) 4.27 (q, J=7.24 Hz, 2 H) 5.02-5.04 (m, 2 H) 6.79-6.90 (m, 1 H) 6.93-7.06 (m, 2 H) 7.18-7.26 (m, 1 H).

The fifth step of Scheme 46: To a 1.5 mL toluene solution of [4-bromo-2-cyano-5-(3-cyclohexylamino-phenyl)-thiophen-3-yloxy]-acetic acid ethyl ester (83 mg, 0.18 mmole) was added sodium azide (58 mg, 0.9 mmole) and triethylamine hydrochloride (123 mg, 0.9 mmole). The suspension was heated to 100° C. for 4 hours. The reaction mixture was then cooled to room temperature, diluted with EtOAc and the organic phase washed with dilute HCl, brine, and dried (MgSO$_4$). Filtration and evaporation gave the crude product which was purified by preparative thin layer chromatography (3% MeOH/CH$_2$Cl$_2$ +0.1% HOAc). 46 mg (50%) of [4-bromo-5-(3-cyclohexylamino-phenyl)-2-(2H-tetrazol-5-yl)-thiophen-3-yloxy]-acetic acid ethyl ester was obtained as a pale yellow glass.

$^1$H NMR (400 MHz, CHLOROFORM-D) δ ppm 1.06-1.22 (m, 4 H) 1.26-1.36 (m, 4 H) 1.56-1.64 (m, 1 H) 1.66-1.76 (m, 2 H) 1.98-2.06 (m, 2 H) 3.17-3.27 (m, 1 H) 4.34 (q, J=7.16 Hz, 2 H) 5.01 (s, 2 H) 6.59 (dd, J=7.71, 1.89 Hz, 1 H) 6.71-6.75 (m, 1 H) 6.81-6.86 (m, 1 H) 7.16 (t, J=7.83 Hz, 1 H).

The sixth step of Scheme 46: [4-Bromo-5-(3-cyclohexylamino-phenyl)-2-(2H-tetrazol-5-yl)-thiophen-3-yloxy]-acetic acid ethyl ester (46 mg, 0.09 mmole) was dissolved in 1.5 mL 2:1 THF:water and LiOH monohydrate (19 mg, 0.45 mmole) was added and stirred at room temperature for 4 hours. The solvent was evaporated and the residue dissolved in 4 mL water and acidified dropwise with 1N HCl. A solid emerged that was filtered, washed with water, and vacuum oven dried to give 39 mg (90%) of [4-bromo-5-(3-cyclohexylamino-phenyl)-2-(2H-tetrazol-5-yl)-thiophen-3-yloxy]-acetic acid as a pale yellow solid.

$^1$H NMR (400 MHz, DMSO-D6) δ ppm 1.11-1.25 (m, 3 H) 1.28-1.41 (m, 2 H) 1.56-1.64 (m, 1 H) 1.68-1.77 (m, 2 H) 1.94 (s, 2 H) 3.18-3.27 (m, 1 H) 4.87 (s, 2 H) 6.68 (dd, J=8.21, 1.89 Hz, 1 H) 6.78 (d, J=8.08 Hz, 1 H) 6.85 (t, J=1.89 Hz, 1 H) 7.19 (t, J=7.96 Hz, 1 H).

ESI-MS: m/e=476 [M−H]−.

EXAMPLE 395

[4-Bromo-5-[3-(cyclohexylmethyl-amino)-phenyl]-2-(2H-tetrazol-5-yl)-thiophen-3-yloxy]-acetic acid The fourth step of Scheme 46: {4-Bromo-2-cyano-5-[3-(cyclohexylmethyl-amino)-phenyl]-thiophen-3-yloxy}-acetic acid ethyl ester was obtained in 85% yield as a yellow oil, following the general procedure in Example 394.

$^1$H NMR (400 MHz, CHLOROFORM-D) δ ppm 0.93-1.06 (m, 2 H) 1.14-1.31 (m, 4 H) 1.34 (t, J=7.07 Hz, 3 H) 1.57-1.65 (m, 1 H) 1.66-1.79 (m, 2 H) 1.79-1.87 (m, 2 H) 2.98 (d, J=6.82 Hz, 2 H) 3.91 (s, 1 H) 4.34 (q, J=7.07 Hz, 2 H) 5.09 (s, 2 H) 6.64-6.69 (m, 1 H) 6.77-6.80 (m, 1 H) 6.85-6.89 (m, 1 H) 7.20-7.25 (m, 1 H).

The fifth step of Scheme 46: [4-Bromo-5-[3-(cyclohexylmethyl-amino)-phenyl]-2-(2H-tetrazol-5-yl)-thiophen-3-yloxy]-acetic acid ethyl ester was obtained in 47% yield as a yellow glass, following the procedure in Example 394.

$^1$H NMR (400 MHz, CHLOROFORM-D) δ ppm 0.88-0.99 (m, 2 H) 1.08-1.26 (m, 4 H) 1.31 (t, J=7.20 Hz, 3 H) 1.50-1.73 (m, 4 H) 1.73-1.81 (m, 2 H) 2.93 (d, J=6.57 Hz, 2 H) 4.35 (q, J=7.07 Hz, 2 H) 5.01 (s, 2 H) 6.64 (dd, J=8.21, 1.64 Hz, 1 H) 6.77 (s, 1 H) 6.88 (d, J=8.08 Hz, 1 H) 7.18 (t, J=7.83 Hz, 1 H).

The sixth step of Scheme 46: [4-Bromo-5-[3-(cyclohexylmethyl-amino)-phenyl]-2-(2H-tetrazol-5-yl)-thiophen-3-yloxy]-acetic acid was prepared in 100% yield as a pale yellow solid following the procedure Example 394.

$^1$H NMR (400 MHz, DMSO-D6) δ ppm 0.90-1.02 (m, 2 H) 1.15-1.27 (m, 4 H) 1.53-1.61 (m, 1 H) 1.66-1.75 (m, 2 H) 1.78-1.85 (m, 2 H) 2.89 (d, J=6.57 Hz, 2 H) 4.92 (s, 2 H) 6.68

(dd, J=8.08, 1.77 Hz, 1 H) 6.79 (d, J=8.34 Hz, 1 H) 6.83 (t, J=2.02 Hz, 1 H) 7.20 (t, J=7.83 Hz, 1 H).
ESI-MS: m/e=490 [M–H]–.

EXAMPLE 396

[4-Bromo-5-[3-(3,3,5,5-tetramethyl-cyclohexylamino)-phenyl]-2-(2H-tetrazol-5-yl)-thiophen-3-yloxy]-acetic acid The fourth step of Scheme 46: {4-Bromo-2-cyano-5-[3-(3,3,5,5-tetramethyl-cyclohexylamino)-phenyl]-thiophen-3-yloxy}-acetic acid ethyl ester was obtained in 77% yield as a yellow oil, following the procedure in Example 394.

$^1$H NMR (400 MHz, CHLOROFORM-D) δ ppm 0.88-0.97 (m, 9 H) 1.12 (s, 6 H) 1.28-1.31 (m, J=1.89, 1.89 Hz, 1 H) 1.34 (t, J=7.07 Hz, 3 H) 1.88 (d, J=13.14 Hz, 2 H) 3.55-3.64 (m, 1 H) 4.34 (q, J=7.07 Hz, 2 H) 5.09 (s, 2 H) 6.63-6.67 (m, 1 H) 6.81-6.83 (m, 1 H) 6.84-6.88 (m, 1 H) 7.22 (t, J=7.83 Hz, 1 H).

The fifth step of Scheme 46: [4-Bromo-5-[3-(3,3,5,5-tetramethyl-cyclohexylamino)-phenyl]-2-(2H-tetrazol-5-yl)-thiophen-3-yloxy]-acetic acid ethyl ester was obtained in 29% yield as a yellow film, following the procedure Example 394.

$^1$H NMR (400 MHz, CHLOROFORM-D) δ ppm 0.82-0.91 (m, 8 H) 1.06 (s, 6 H) 1.16-1.28 (m, 3 H) 1.31 (t, J=7.07 Hz, 3 H) 1.82 (d, J=12.13 Hz, 2 H) 3.50-3.60 (m, 1 H) 4.35 (q, J=7.33 Hz, 2 H) 5.01 (s, 2 H) 6.59 (dd, J=8.21, 2.15 Hz, 1 H) 6.76 (t, J=1.89 Hz, 1 H) 6.84 (d, J=7.83 Hz, 1 H) 7.15-7.20 (m, 1 H).

The sixth step of Scheme 46: [4-Bromo-5-[3-(3,3,5,5-tetramethyl-cyclohexylamino)-phenyl]-2-(2H-tetrazol-5-yl)-thiophen-3-yloxy]-acetic acid was prepared in 78% yield as a pale yellow solid following the procedure Example 394.

$^1$H NMR (400 MHz, DMSO-D6) δ ppm 0.92 (s, 7 H) 0.94-1.00 (m, 2 H) 1.10 (s, 6 H) 1.23-1.30 (m, 1 H) 1.76 (d, J=13.39 Hz, 2 H) 3.49-3.59 (m, 1 H) 4.91 (s, 2 H) 6.70 (dd, J=7.96, 1.89 Hz, 1 H) 6.81 (d, J=8.34 Hz, 1 H) 6.88 (s, 1 H) 7.22 (t, J=7.83 Hz, 1 H).
ESI-MS: m/e=532 [M–H]–.

EXAMPLE 397

Tetrazole/acid: [5-{3-[Acetyl-(3,3,5,5-tetramethyl-cyclohexyl)-amino]-phenyl}-4-bromo-2-(2H-tetrazol-5-yl)-thiophen-3-yloxy]-acetic acid The fourth step of Scheme 46, part 2: {4-Bromo-2-cyano-5-[3-(3,3,5,5-tetramethyl-cyclohexylamino)-phenyl]-thiophen-3-yloxy}-acetic acid ethyl ester, as prepared in Example 396 was subjected to the following acylation conditions: {4-Bromo-2-cyano-5-[3-(3,3,5,5-tetramethyl-cyclohexylamino)-phenyl]-thiophen-3-yloxy}-acetic acid ethyl ester (100 mg, 0.19 mmole) was dissolved in 1.5 m]L CH$_2$Cl$_2$ and triethylamine (69 μL, 0.96 mmole) was added followed by acetyl chloride (66 μL, 0.48 mmole) and stirred at room temperature 30 minutes. The reaction mixture was diluted with CH$_2$Cl$_2$ and washed with 1N HCl, saturated sodium bicarbonate and dried (MgSO$_4$). Filtration and evaporation gave 94 mg (88%) of (5-{3-[acetyl-(3,3,5,5-tetramethyl-cyclohexyl)-amino]-phenyl}4-bromo-2-cyano-thiophen-3-yloxy)-acetic acid ethyl ester as a colorless oil.

$^1$H NMR (400 MHz, CHLOROFORM-D) δ ppm 0.78 (s, 3 H) 0.82 (d, 1 H) 1.06 (s, 6 H) 1.12 (d, J=13.89 Hz, 2 H) 1.28 (t, J=7.20 Hz, 3 H) 1.50 (d, J=11.87 Hz, 2 H) 1.71 (q, 3 H) 4.27 (q, J=7.24 Hz, 2 H) 5.00 (m, 1 H) 5.05 (s, 2 H) 7.14 (m, 1 H) 7.37 (s, 1 H) 7.48 (m, 2 H)

The fifth step of Scheme 46: [5-{3-[Acetyl-(3,3,5,5-tetramethyl-cyclohexyl)-amino]-phenyl}-4-bromo-2-(2H-tetrazol-5-yl)-thiophen-3-yloxy]-acetic acid ethyl ester was obtained in 73% yield as a white solid, following the procedure in Example 394, except the crude product was triturated with ether instead of being subjected to preparative thin layer chromatography.

$^1$H NMR (400 MHz, DMSO-D6) δ ppm 0.83 (s, 6 H) 0.88 (s, 2 H) 1.07 (s, 6 H) 1.09 (s, 2 H) 1.13 (t, J=7.20 Hz, 3 H) 1.56 (m, 2 H) 1.67 (s, 3 H) 4.10 (q, J=7.16 Hz, 2 H) 5.00 (s, 2 H) 7.37 (m, 1 H) 7.57 (s, 1 H) 7.63 (t, J=7.45 Hz, 1 H) 7.70 (m, 1 H).

The sixth step of Scheme 46: tetrazole/acid: [5-{3-[Acetyl-(3,3,5,5-tetramethyl-cyclohexyl)-amino]-phenyl}-4-bromo-2-(2H-tetrazol-5-yl)-thiophen-3-yloxy]-acetic acid was prepared in 78% yield as a white solid following the procedure Example 394.

$^1$H NMR (400 MHz, DMSO-D6) δ ppm 0.83 (s, 7 H) 0.88 (s, 2 H) 1.07 (s, 6 H) 1.15 (m, 1 H) 1.56 (d, J=10.86 Hz, 2 H) 1.68 (s, 3 H) 4.92 (s, 2 H) 4.98 (m, 1 H) 7.37 (d, J=7.58 Hz, 1 H) 7.57 (s, 1 H) 7.63 (t, J=7.71 Hz, 1 H) 7.71 (m, 1 H).
ESI-MS: m/e=574 [M–H]–.

EXAMPLE 398

[4-Bromo-5-[3-(1-phenylmethanesulfonyl-piperidin-4-ylamino)-phenyl]-2-(2H-tetrazol-5-yl)-thiophen-3-yloxyl-acetic acid The first step of Scheme 47: 4-[3-(3-Bromo-5-cyano-4-ethoxycarbonylmethoxy-thiophen-2-yl)-phenylamino]-piperidine-1-carboxylic acid tert-butyl ester was prepared as in the fourth step of Scheme 46, Example 394 in 56% yield as a pale yellow solid.

$^1$H NMR (400 MHz, CHLOROFORM-D) δ ppm 1.34 (t, J=7.07 Hz, 3 H) 1.37 (m, 2 H) 1.47 (s, 9 H) 2.06 (m, 2 H) 2.94 (t, J=12.00 Hz, 2 H) 3.45 (m, 1 H) 4.33 (q, J=7.24 Hz, 2 H) 5.10 (s, 2 H) 6.67 (m, 1 H) 6.81 (m, 1 H) 6.88 (m, 1 H) 7.24 (m, 1 H).

The second step of Scheme 47: To a 2 mL CH$_2$Cl$_2$ solution of 4-[3-(3-bromo-5-cyano-4-ethoxycarbonylmethoxy-thiophen-2-yl)-phenylamino]-piperidine-1-carboxylic acid tert-butyl ester (114 mg, 0.2 mmole) was added trifluoroacetic acid (1 mL, excess) and the mixture stirred at room temperature for 1 hour. The solvent was evaporated and then co-evaporated twice with CH$_2$Cl$_2$. {4-Bromo-2-cyano-5-[3-(piperidin-4-ylamino)-phenyl]-thiophen-3-yloxy}-acetic acid ethyl ester; trifluoroacetic acid salt was obtained in quantitative yield as a colorless oil.

$^1$H NMR (400 MHz, MeOD) δ ppm 1.23 (t, J=7.16 Hz, 3 H) 1.64 (m, 2 H) 2.17 (m, 2 H) 3.07 (m, 2 H) 3.37 (m, 2 H) 3.59 (m, 1 H) 4.22 (q, J=7.16 Hz, 2 H) 5.09 (s, 2 H) 6.74 (m, 1 H) 6.81 (m, 1 H) 6.86 (m, 1 H) 7.17 (t, J=7.96 Hz, 1 H).

The third step of Scheme 47: To a 2 mL CH$_2$Cl$_2$ solution of {4-bromo-2-cyano-5-[3-(piperidin-4-ylamino)-phenyl]-thiophen-3-yloxy}-acetic acid ethyl ester; trifluoroacetic acid salt (116 mg, 0.2 mmole) was added triethylamine (168 μL, 1.2 mmole) followed by phenyl-methanesulfonyl chloride (114 mg, 0.6 mmole) and the reaction mixture stirred at room temperature overnight. The reaction was then diluted with CH$_2$Cl$_2$ and washed with dilute HCl, saturated sodium bicarbonate solution, and dried (MgSO$_4$). Filtration and evaporation yielded the crude product which was purified by chromatography on silica gel using a gradient of hexane/EtOAc (15 to 50%) as eluent. Pure fractions were combined and evaporated to give 101 mg (82%) of {4-bromo-2-cyano-5-[3-

(1-phenylmethanesulfonyl-piperidin-4-ylamino)-phenyl]-thiophen-3-yloxy}-acetic acid ethyl ester as a pale yellow foam.

¹H NMR (400 MHz, CHLOROFORM-D) Mix of chair & boat isomers: δ ppm 1.35 (m, 6 H) 1.42 (m, 2 H) 1.61 (m, 1 H) 1.80 (m, 2 H) 2.03 (m, 2 H) 2.64 (m, 1 H) 2.77 (m, 1 H) 3.33 (m, 1 H) 3.66 (m, 4 H) 4.19 (s, 2 H) 4.24 (s, 2 H) 4.34 (m, 2 H) 4.57 (m, 1 H) 5.10 (s, 2 H) 5.11 (s, 2 H) 6.64 (m, 1 H) 6.76 (m, 1 H) 6.89 (d, J=8.34 Hz, 1 H) 7.22 (m, 3 H) 7.34 (m, 5 H) 7.40 (m, 5 H) 7.54 (m, 1 H) 7.67 (m, 1 H).

The fourth step of Scheme 47: {4-Bromo-2-cyano-5-[3-(1-phenylmethanesulfonyl-piperidin-4-ylamino)-phenyl]-thiophen-3-yloxy}-acetic acid ethyl (78 mg, 0.13 mmole) was suspended in isopropyl alcohol/H₂O (4:1) and NaN₃ (9 mg, 0.14 mmole) was added followed by ZnBr₂ (28 mg, 0.13 mmole). The mixture was heated at 90° C. for 40 hours and then cooled to room temperature and partitioned between EtOAc and dilute NaOH. The aqueous layer was removed and acidified with two drops of concentrated HCl. A gelatinous solid emerged, which was extracted with EtOAc. The organic layer was washed with brine and dried (MgSO₄). Filtration and evaporation yielded the crude product which was purified by preparative HPLC to give (10 mg, 12%) of [4-bromo-5-[3-(1-phenylmethanesulfonyl-piperidin-4-ylamino)-phenyl]-2-(2H-tetrazol-5-yl)-thiophen-3-yloxy]-acetic acid as a pale yellow solid.

¹H NMR (400 MHz, MeOD) δ ppm 1.19 (t, J=7.20 Hz, 9 H) 1.38 (m, 2 H) 1.97 (m, 2 H) 2.84 (m, 1 H) 3.05 (q, J=7.24 Hz, 6 H) 3.57 (dd, J=9.98, 3.16 Hz, 2 H) 4.27 (s, 2 H) 4.58 (s, 2 H) 6.63 (m, 1 H) 6.82 (m, 1 H) 6.87 (s, 1 H) 7.12 (t, J=8.08 Hz, 1 H) 7.31 (m, 3 H) 7.38 (m, 2 H).

ESI-MS: m/e=633 [M+H]⁺.

EXAMPLE 399

4-Bromo-3-carboxymethoxy-5-[3-(1-phenyl-methanesulfonyl-piperidin-4-ylamino)-phenyl]-thiophene-2-carboxylic acid methyl ester, ethanolamine salt Scheme 48: To a 3 mL EtOH solution of 4-bromo-3-carboxymethoxy-5-[3-(1-phenylmethanesulfonyl-piperidin-4-ylamino)-phenyl]-thiophene-2-carboxylic acid methyl ester (300 mg, 0.48 mmole) was added ethanolamine (32 μL, 0.53 mmole). A solid emerged and the suspension was stirred at room temperature overnight. The reaction mixture was filtered, washed with minimal EtOH and dried to give 280 mg (85%) of 4-bromo-3-carboxymethoxy-5-[3-(1-phenylmethanesulfonyl-piperidin-4-ylamino)-phenyl]-thiophene-2-carboxylic acid methyl ester, ethanolamine salt as an off-white solid.

¹H NMR (400 MHz, DMSO-D6) δ ppm 1.30-1.43 (m, 2 H) 1.91-2.00 (m, 2 H) 2.80 (t, J=5.31 Hz, 2 H) 2.93 (t, J=10.48 Hz, 2 H) 3.39-3.48 (m, 1 H) 3.49-3.59 (m, 4 H) 3.78 (s, 3 H) 4.40 (s, 2 H) 4.51 (s, 2 H) 5.89 (d, J=8.34 Hz, 1 H) 6.70 (dd, J=8.59, 1.77 Hz, 1 H) 6.79 (d, J=7.33 Hz, 1 H) 6.85 (s, 1 H) 7.19 (t, J=7.83 Hz, 1 H) 7.33-7.45 (m, 5 H).

EXAMPLE 400

4-Bromo-3-carboxymethoxy-5-[3-(1-phenyl-methanesulfonyl-piperidin-4-ylamino)-phenyl]-thiophene-2-carboxylic acid methyl ester choline salt Scheme 48: 4-Bromo-3-carboxymethoxy-5-[3-(1-phenyl-methanesulfonyl-piperidin-4-ylamino)-phenyl]-thiophene-2-carboxylic acid methyl ester, choline salt was prepared as described in Example 399 in 46% yield as an off-white solid.

¹H NMR (400 MHz, DMSO-D6) δ ppm 1.31-1.42 (m, 2 H) 1.92-2.00 (m, 2 H) 2.89-2.97 (m, 2 H) 3.11 (s, 9 H) 3.38-3.42 (m, 2 H) 3.50-3.58 (m, 2 H) 3.77 (s, 3 H) 3.81-3.87 (m, 2 H) 4.40 (s, 2 H) 4.42 (s, 2 H) 5.88 (d, J=8.08 Hz, 1 H) 6.70 (dd, J=8.72, 1.89 Hz, 1 H) 6.79 (d, J=7.83 Hz, 1 H) 6.86 (s, 1 H) 7.19 (t, J=7.96 Hz, 1 H) 7.35-7.45 (m, 5 H).

EXAMPLE 401

4-Bromo-3-carboxymethoxy-5-[3-(1-phenyl-methanesulfonyl-piperidin-4-ylamino)-phenyl]-thiophene-2-carboxylic acid methyl ester, sodium salt Scheme 48: To a 3 mL MeOH solution of 4-bromo-3-carboxymethoxy-5-[3-(1-phenylmethanesulfonyl-piperidin-4-ylamino)-phenyl]-thiophene-2-carboxylic acid methyl ester (300 mg, 0.48 mmole) was added NaHCO₃ (480 μL of 1.0M aqueous solution, 0.48 mmole) and the reaction mixture was stirred at room temperature for 2 hours then evaporated. The resulting solid was triturated with EtOAc and filtered to give 4-bromo-3-carboxymethoxy-5-[3-(1-phenylmethanesulfonyl-piperidin-4-ylamino)-phenyl]-thiophene-2-carboxylic acid methyl ester, sodium salt in 90% yield as a yellow solid.

¹H NMR (400 MHz, DMSO-D6) δ ppm 1.30-1.42 (m, 2 H) 1.91-2.00 (m, 2 H) 2.88-2.97 (m, 2 H) 3.37-3.45 (m, 1 H) 3.49-3.58 (m, 2 H) 3.78 (s, 3 H) 4.40 (s, 2 H) 4.43 (s, 2 H) 5.89 (d, J=7.83 Hz, 1 H) 6.70 (dd, J=8.34, 1.77 Hz, 1 H) 6.79 (d, J=7.58 Hz, 1 H) 6.85 (t, J=1.89 Hz, 1 H) 7.19 (t, J=7.83 Hz, 1 H) 7.34-7.45 (m, 5 H).

EXAMPLE 402

{[2-[(Benzyloxycarbonyl]-5-(3-{[1-(benzylsulfonyl) piperidin-4-yl]amino}phenyl)-4-bromothien-3-yl] oxy}acetic acid The first step of Scheme 49: SOCl₂ (0.9 mL) was added to 2-allyloxycarbonylmethoxy-3-bromo-4-[3-(1-phenyl-methanesulfonyl-piperidin-4-ylamino)-phenyl]-cyclopenta-1,3-dienecarboxylic acid (800 mg, 1.23 mmol) in DCE (10 mL) and heated at 60° C. for 1 hr. The solvent and excess SOCl₂ was then removed by rotary evaporation. The material was split into four equal portions after adding DCE (20 mL). One 5 mL portion was stirred with benzyl alcohol (70 μl) and triethylamine (200 μl) for approx 16 hr. The solvent was removed and the crude material was purified by silica chromatography (5% to 50% EtOAc in Hexane) yielding 100 mg (44%) of 3-allyloxycarbonylmethoxy-4-bromo-5-[3-(1-phenylmethanesulfonyl-piperidin-4-ylamino)-phenyl)-thiophene-2-carboxylic acid benzyl ester.

The first step of Scheme 49. (Ph₃P)₄Pd (7.8 mg) was added to a solution of 3-allyloxycarbonylmethoxy-4-bromo-5-[3-(1-phenylmethanesulfonyl-piperidin-4-ylamino)-phenyl]-thiophene-2-carboxylic acid benzyl ester (100 mg. 0.135 mmol) in THF (5 mL) with 4 equivalents of morpholine. After the starting material was consumed (TLC) the solvent was removed and the crude material was purified on silica gel eluting with 10% MeOH in EtOAc with 1% AcOH. {[2-[(benzyloxy)carbonyl]-5-(3-{[1-(benzylsulfonyl)piperidin-4-yl]amino}phenyl)-4-bromothien-3-yl]oxy}acetic acid was isolated as a yellow solid after lyopholization in acetonitrile/water (77 mg, 82%).

¹H NMR (400 MHz, CHLOROFORM-D) δ ppm 1.41 (m, 2 H) 2.03 (m, 2 H) 2.77 (t, J=13.14 Hz, 2 H) 3.41-3.28 (m, 1 H) 3.62 (d, J=16.17 Hz, 2 H) 4.24 (s, 2 H) 4.91 (s, 2 H) 5.38 (s, 2 H) 6.63 (d, J=9.85 Hz, 1 H) 6.74 (s, 1 H) 6.90 (d, J=8.34 Hz, 1 H) 7.23 (t, J=7.96 Hz, 1 H) 7.41 (m, J=40.17 Hz, 5 H).

MS (ESI-FTMS) m/z 699.0829 (CALC'D); MS (ESI-FTMS) m/z 699.0837 ([M+H]¹⁺); HRMS: calcd for $C_{32}H_{31}BrN_2O_7S_2$, 698.0756; found (ESI-FTMS), 699.0837.

EXAMPLE 403

[(5-(3-{[1-(Benzylsulfonyl)piperidin-4-yl]amino}phenyl)-4-bromo-2-{[(2-nitrobenzyl)oxy]carbonyl}thien-3-yl)oxy]acetic acid The first step of Scheme 49: Potassium carbonate (43 mg) was added to a solution of 2-allyloxycarbonylmethoxy-3-bromo-4-[3-(1-phenylmethanesulfonyl-piperidin-4-ylamino)-phenyl]-cyclopenta-1,3-dienecarboxylic acid (157 mg, 0.24 mmol) and 2-nitrobenzylbromide (78 mg, 0.36 mmol) in DMF (2 mL) and stirred for 2 hr at 60° C. After sitting at room temperature for 16 hr, EtOAc was added and the organics were washed with water three times, dried over MgSO₄, filtered and rotary evaporated. The crude material was purified on silica gel eluting with a gradient of 10% to 50% EtOAc in hexanes. 3-Allyloxycarbonylmethoxy-4-bromo-5-[3-(1-phenylmethanesulfonyl-piperidin-4-ylamino)-phenyl]-thiophene-2-carboxylic acid 2-nitro-benzyl ester (150 mg, 79%) was isolated as a yellow film.

¹H NMR (400 MHz, CHLOROFORM-D) δ ppm 1.41 (m, 2 H) 2.04 (m, J=12.51, 3.66 Hz, 3 H) 2.78 (m, 2 H) 3.36 (m, 1 H) 3.62 (m, 2 H) 4.24 (s, 2 H) 4.70 (dt, J=5.87, 1.36 Hz, 2 H) 4.95 (s, 2 H) 5.26 (dq, J=10.36, 1.26 Hz, 1 H) 5.34 (dq, J=17.18, 1.43 Hz, 1 H) 5.74 (s, 2 H) 5.92 (m, 1 H) 6.63 (ddd, J=8.21, 2.40, 0.76 Hz, 1 H) 6.83 (m, 1 H) 6.96 (ddd, J=7.71, 1.64, 1.01 Hz, 1 H) 7.23 (t, J=7.83 Hz, 1 H) 7.40 (m, 5 H) 7.52 (m, 1 H) 7.68 (m, 2 H) 8.15 (d, J=7.83 Hz, 1 H).

The second step of Scheme 49: Using a procedure similar to the second step of Scheme 49 of Example 402, 3-allyloxycarbonylmethoxy-4-bromo-5-[3-(1-phenylmethanesulfonyl-piperidin-4-ylamino)-phenyl]-thiophene-2-carboxylic acid 2-nitro-benzyl ester (150 mg, 0.19 mmol) was heated for 5 min at 100° C. in the microwave. Work-up and purification by reverse phase HPLC gave [(5-(3-{[1-(benzylsulfonyl)piperidin-4-yl]amino}phenyl)-4-bromo-2-{[(2-nitrobenzyl)oxy]carbonyl}thien-3-yl)oxy]acetic acid (41 mg, 29%) as a yellow solid.

¹H NMR (400 MHz, DMSO-D6) δ ppm 1.35 (m, 2 H) 1.95 (d, J=14.91 Hz, 1 H) 2.92 (m, J=11.62, 11.62 Hz, 2 H) 3.41 (s, 1 H) 3.53 (d, J=11.87 Hz, 2 H) 4.40 (s, 2 H) 4.85 (s, 2 H) 5.66 (s, 2 H) 5.93 (d, J=7.58 Hz, 1 H) 6.73 (d, J=7.33 Hz, 1 H) 6.81 (d, J=7.58 Hz, 1 H) 6.86 (t, J=1.89 Hz, 1 H) 7.21 (t, J=7.83 Hz, 1 H) 7.40 (m, 5 H) 7.66 (m, 1 H) 7.77 (dd, J=8.08, 1.52 Hz, 1 H) 7.82 (m, 1 H) 8.16 (dd, J=8.21, 1.14 Hz, 1 H).

HRMS: calcd for $C_{32}H_{30}BrN_3O_9S_2$, 743.0607; found (ESI-FTMS), 744.0694.

EXAMPLE 404

[(5-(3-{[1-(Benzylsulfonyl)piperidin-4-yl]amino}phenyl)-4-bromo-2-{[(2-nitrobenzyl)oxy]carbonyl}thien-3-yl)oxy]acetic acid The second part of the first step of Scheme 49: Following Example 403, 3-methoxybromobenzene (35 µl) and 2-allyloxycarbonylmethoxy-3-bromo-4-[3-(1-phenylmethanesulfonyl-piperidin-4-ylamino)-phenyl]-cyclopenta-1,3-dienecarboxylic acid (153 mg, 0.24 mmol) were heated to 100° C. in the microwave for 5 min. Work-up and purification yielded 135 mg (75%) of 3-allyloxycarbonylmethoxy-4-bromo-5-[3-(1-phenylmethanesulfonyl-piperidin-4-ylamino)-phenyl]-thiophene-2-carboxylic acid 3-methoxy-benzyl ester.

The second step of Scheme 49: The second step in Example 402 was followed using 3-allyloxycarbonylmethoxy-4-bromo-5-[3-(1-phenylmethanesulfonyl-piperidin-4-ylamino)-phenyl]-thiophene-2-carboxylic acid 3-methoxy-benzyl ester (135 mg, 0.18 mmol). Work up and purification by reversed phase HPLC yielded [(5-(3-{[1-(benzylsulfonyl)piperidin-4-yl]amino}phenyl)-4-bromo-2-{[(2-nitrobenzyl)oxy]carbonyl}thien-3-yl)oxy]acetic acid (54 mg, 42%) as a yellow solid.

¹H NMR (400 MHz, DMSO-D6) δ ppm 1.35 (m, 2 H) 1.94 (d, J=10.61 Hz, 2 H) 2.91 (m, 2 H) 3.40 (br s, 1 H) 3.53 (d, J=12.13 Hz, 2 H) 3.76 (s, 3 H) 4.40 (s, 2 H) 4.84 (s, 2 H) 5.28 (s, 2 H) 5.91 (d, J=8.08 Hz, 1 H) 6.71 (dd, J=7.96, 1.89 Hz, 1 H) 6.80 (d, J=7.58 Hz, 1 H) 6.86 (t, J=1.89 Hz, 1 H) 6.92 (m, 1 H) 7.00 (m, 2 H) 7.20 (t, J=7.96 Hz, 1 H) 7.31 (t, J=7.96 Hz, 1 H) 7.39 (m, 5 H).

HRMS: calcd for $C_{33}H_{33}BrN_2O_8S_2$, 728.0862; found (ESI-FTMS), 751.0758.

EXAMPLE 405

({5-(3-{[1-(Benzylsulfonyl)piperidin-4-yl]amino}phenyl)-4-bromo-2-[(pyridin-3-ylmethoxy)carbonyl]thien-3-yl}oxy)acetic acid Following the second part of the first step of Scheme 49 in Example 404 using 3-bromomethyl-pyridinium chloride (88 mg, 0.35 mmol) and 2-allyloxycarbonylmethoxy-3-bromo-4-[3-(1-phenylmethanesulfonyl-piperidin-4-ylamino)-phenyl]-cyclopenta-1,3-dienecarboxylic acid (189 mg, 0.29 mmol), 3-allyloxycarbonylmethoxy-4-bromo-5-[3-(1-phenylmethanesulfonyl-piperidin-4-ylamino)-phenyl]-thiophene-2-carboxylic acid pyridin-3-ylmethyl ester (108 mg, 50%) was isolated.

The second step of Scheme 49: Following the second step of Example 403, 3-allyloxycarbonylmethoxy-4-bromo-5-[3-(1-phenylmethanesulfonyl-piperidin-4-ylamino)-phenyl]-thiophene-2-carboxylic acid pyridin-3-ylmethyl ester was used. Work-up and purification yielded ({5-(3-{[1-(benzylsulfonyl)piperidin-4-yl]amino}phenyl)-4-bromo-2-[(pyridin-3-ylmethoxy)carbonyl]thien-3-yl}oxy)acetic acid as a yellow solid (82 mg, 84%).

¹H NMR (400 MHz, DMSO-D6) δ ppm 1.35 (app q, J=10.53 Hz, 2 H) 1.94 (m, 2 H) 2.91 (app t, J=10.74 Hz, 3 H) 3.32 (br s, 1 H) 3.53 (m, 2 H) 4.40 (s, 2 H) 4.77 (s, 2 H) 5.35 (s, 2 H) 5.91 (d, J=8.08 Hz, 1 H) 6.71 (dd, J=8.21, 1.89 Hz, 1 H) 6.80 (d, J=7.58 Hz, 1 H) 6.85 (t, J=1.77 Hz, 1 H) 7.19 (t; J=7.96 Hz, 1 H) 7.40 (m, 5 H) 7.87 (m, 1 H) 8.57 (dd, J=4.80, 1.52 Hz, 1 H) 8.67 (d, J=2.02 Hz, 1 H).

HRMS: calcd for $C_{31}H_{30}BrN_3O_7S_2$, 699.0709; found (ESI-FTMS), 700.0773.

EXAMPLE 406

({5-(3-{[1-(Benzylsulfonyl)piperidin-4-yl]amino}phenyl)-4-bromo-2-[(cyclohexylmethoxy)carbonyl]thien-3-yl}oxy)acetic acid The first part of the first step of Scheme 49: Following Example 402, SOCl₂ (0.9 mL) was added to 2-allyloxycarbonylmethoxy-3-bromo-4-[3-(1-phenylmethanesulfonyl-piperidin-4-ylamino)-phenyl]-cyclopenta-1,3-dienecarboxylic acid (800 mg, 1.23 mmol) in DCE (10 mL) and heated at 60° C. for 1 hr. The solvent and excess SOCl$_2$ was then removed by rotary evaporation. The material was split into four equal portions after adding DCE (20 mL). One 5 mL portion was stirred with cyclohexyl-methanol (80 µl) and triethylamine (200 µl). Work up and purification yielded 28 mg (12%) of 3-allyloxycarbonylmethoxy-4-bromo-5-[3-(1-phenyl-methanesulfonyl-piperidin-4-ylamino)-phenyl]-thiophene-2-carboxylic acid cyclohexylmethyl ester.

The second step of Scheme 49: Following Example 402, 3-allyloxycarbonylmethoxy-4-bromo-5-[3-(1-phenyl-methanesulfonyl-piperidin-4-ylamino)-phenyl]-thiophene-2-carboxylic acid cyclohexylmethyl ester (113 mg, 0.15 mmol) was used. Work up and purification yielded 72 mg (67%) of ({5-(3-{[1-(benzylsulfonyl)piperidin-4-yl]amino}phenyl)-4-bromo-2-[(cyclohexylmethoxy)carbonyl]thien-3-yl}oxy)acetic acid as a yellow solid.

$^1$H NMR (400 MHz, CHLOROFORM-D) δ ppm 1.03 (m, 2 H) 1.23 (m, 3 H) 1.41 (m, 2 H) 1.72 (m, 6 H) 2.03 (d, J=11.37 Hz, 2 H) 2.78 (m, 2 H) 3.36 (m, 1 H) 3.63 (d, J=12.88 Hz, 2 H) 4.15 (d, J=6.06 Hz, 2 H) 4.24 (s, 2 H) 4.90 (s, 2 H) 6.64 (dd, J=8.08, 2.02 Hz, 1 H) 6.77 (s, 1 H) 6.90 (d, J=7.58 Hz, 1 H) 7.23 (t, J=7.96 Hz, 1 H) 7.40 (m, 5 H).

HRMS: calcd for C$_{32}$H$_{37}$BrN$_2$O$_7$S$_2$, 704.1226; found (ESI-FTMS), 705.1312.

EXAMPLE 407

{[5-(3-{[1-(Benzylsulfonyl)piperidin-4-yl]amino}phenyl)-4-bromo-2-(isobutoxycarbonyl)thien-3-yl]oxy}acetic acid The second part of the first step of Scheme 49: Example 403 was followed, using 1-iodo-2-methylpropane (34 µL, 0.30 mmol) and 2-allyloxycarbonylmethoxy-3-bromo-4-[3-(1-phenylmethanesulfonyl-piperidin-4-ylamino)-phenyl]-cyclopenta-1,3-dienecarboxylic acid (96 mg, 0.15 mmol). Work up yielded 3-allyloxycarbonylmethoxy-4-bromo-5-[3-(1-phenylmethanesulfonyl-piperidin-4-ylamino)-phenyl]-thiophene-2-carboxylic acid isobutyl ester (99 mg, 93%) as a yellow film.

The second step of Scheme 49: Using a procedure similar to the second step of Example 402, 3-allyloxycarbonyl-methoxy-4-bromo-5-[3-(1-phenylmethanesulfonyl-piperidin-4-ylamino)-phenyl]-thiophene-2-carboxylic acid isobutyl ester (141 mg, 0.20 mmol) was used. Work up and purification yielded {[5-(3-{[1-(benzylsulfonyl)piperidin-4-yl]amino}phenyl)-4-bromo-2-(isobutoxycarbonyl)thien-3-yl]oxy}acetic acid (123 mg, 92%) as a yellow solid.

$^1$H NMR (400 MHz, DMSO-D6) δ ppm 0.94 (d, J=6.57 Hz, 6 H) 1.35 (m, 2 H) 1.96 (m, 3 H) 2.92 (t, J=11.75 Hz, 2 H) 3.53 (d, J=12.38 Hz, 2 H) 4.02 (d, J=6.57 Hz, 2 H) 4.40 (s, 2 H) 4.68 (s, 2 H) 5.91 (d, J=7.83 Hz, 1 H) 6.71 (dd, J=8.08, 1.77 Hz, 1 H) 6.80 (d, J=7.58 Hz, 1 H) 6.86 (t, J=2.02 Hz, 1 H) 7.20 (t, J=7.83 Hz, 1 H) 7.40 (m, 5 H).

HRMS: calcd for C$_{29}$H$_{33}$BrN$_2$O$_7$S$_2$, 664.0913; found (ESI-FTMS), 765.0354.

EXAMPLE 408

5-[3-(Benzyloxycarbonyl-cyclohexyl-amino)-phenyl]-4-bromo-3-carboxymethoxy-thiophene-2-carboxylic acid The first step of Scheme 50 (Reductive Amination): To a solution of 5-(3-amino-phenyl)-4-bromo-3-tert-butoxycarbonylmethoxy-thiophene-2-carboxylic acid methyl ester (3.0 g, 7.9 mmol) in DCE (30 mL) was added cyclohexanone (0.9 mL, 8.7 mmol), and NaBH$_3$(OAc)$_3$ (2.9 g, 13.8 mmol). HOAc (0.56 mL, 9.5 mmol) was then added drop-wise and the solution was allowed to stir at ambient temperature for two hours after which the reaction was judged complete by TLC. The solution was filtered through silica gel, concentrated in vacuo and purified via normal phase SiO$_2$ chromatography using a 5% to 20% ethyl acetate/hexanes gradient, affording 4-bromo-3-tert-butoxycarbonylmethoxy-5-[3-(cyclohexyl-amino)-phenyl]-thiophene-2-carboxylic acid methyl ester as a viscous yellow oil.

The second step of Scheme 50 (Carbamate Formation): To a solution of 4-bromo-3-tert-butoxycarbonylmethoxy-5-[3-(cyclohexyl-amino)-phenyl]-thiophene-2-carboxylic acid methyl ester (90 mg, 0.17 mol) in DCM (2 mL) was added pyridine (0.5 mL). The mixture was then cooled to −78° C. after which benzyl chloroformate (0.12 mL, 0.86 mmol) was added dropwise. The reaction was allowed to stir and warm to ambient temperature over one hour after which it was judged complete by TLC. The reaction was quenched with excess aqueous NaHCO$_3$, and extracted twice into DCM. The organic layers were combined, washed with brine, dried with MgSO$_4$, and concentrated in vacuo affording 79 mg of 5-[3-(Benzyloxycarbonyl-cyclohexyl-amino)-phenyl]-4-bromo-3-tert-butoxycarbonylmethoxy-thiophene-2-carboxylic acid methyl ester as a viscous clear oil; (70.6% Yield).

$^1$H NMR (400 MHz, CHLOROFORM-D) δ ppm 0.86-1.01 (m, 2 H) 1.13-1.27 (m, 3 H) 1.30-1.43 (m, 2 H) 1.49-1.52 (s, 9 H) 1.75 (d, 2 H) 1.92 (d, 2 H) 3.89 (d, 3 H) 4.16-4.25 (m, 1 H) 4.82-4.85 (m, 2 H) 5.09-5.13 (m, 2 H) 7.15-7.20 (m, J=6.82 Hz, 3 H) 7.23-7.31 (m, 3 H) 7.42 (s, 1 H) 7.45 (t, 1 H) 7.60 (m, 1 H).

LCMS: m/e=679.2 [M+Na]+.

The third step of Scheme 50 (Hydrolysis): To a solution of 5-[3-(Benzyloxycarbonyl-cyclohexyl-amino)-phenyl]-4-bromo-3-tert-butoxycarbonylmethoxy-thiophene-2-carboxylic acid methyl ester (79 mg, 0.12 mmol) in THF/H$_2$O (1 mL each) was added aqueous 2.0 M LiOH (0.3 mL). The mixture was allowed to stir at ambient temperature for a 16 hour period after which the reaction was judged complete by LCMS. THF was removed in vacuo and the remaining aqueous layer was acidified to pH 1 with 10% HCl, precipitating a white solid which was decanted, rinsed twice with deionized H$_2$O, and dried in vacuo at 50° C., affording 69 mg of 5-[3-(Benzyloxycarbonyl-cyclohexyl-amino)-phenyl]-4-bromo-3-carboxymethoxy-thiophene-2-carboxylic acid as a white solid; (96% Yield).

$^1$H NMR (400 MHz, DMSO-D6) δ ppm 0.82-0.97 (m, 1 H) 1.06-1.19 (m, 2 H) 1.22-1.36 (m, 2 H) 1.47-1.56 (m, 1 H) 1.67-1.74 (m, 2 H) 1.84-1.92 (m, 2 H) 4.01-4.14 (m, 1 H) 4.90 (s, 2 H) 5.06 (s, 2 H) 7.18 (d, J=6.82 Hz, 2 H) 7.24-7.34 (m, 4 H) 7.43-7.47 (m, 1 H) 7.55 (t, J=7.96 Hz, 1 H) 7.59-7.67 (m, 1 H).

LCMS: m/e=587.9 [+H]$^+$.

EXAMPLE 409

4-Bromo-3-carboxymethoxy-5-{3-(cyclohexyl-propoxycarbonyl-amino)-phenyl]-thiophene-2-carboxylic acid The first step of Scheme 50 (Reductive Amination): Synthesis of 4-bromo-3-tert-butoxycarbonylmethoxy-5-[3-(cyclohexyl-amino)-phenyl]-thiophene-2-carboxylic acid methyl ester according to the procedure in Example 408.

The second step of Scheme 50 (Carbamate Formation): Addition of propyl chloroformate (0.11 mL, 0.86 mmol) to 4-bromo-3-tert-butoxycarbonylmethoxy-5-[3-(cyclohexyl-amino)-phenyl]-thiophene-2-carboxylic acid methyl ester (90 mg, 0.17 mmol) according to the second step of Example 409, afforded 86 mg of 4-bromo-3-tert-butoxycarbonyl-methoxy-5-[3-(cyclohexyl-propoxycarbonyl-amino)-phenyl]-thiophene-2-carboxylic acid methyl ester; (82.7% Yield).

$^1$H NMR (400 MHz, CHLOROFORM-D) δ ppm 0.76-0.83 (m, 3 H) 0.92-1.01 (m, 1 H) 1.14-1.28 (m, 3 H) 1.31-1.43 (m, 2 H) 1.50-1.53 (m, 9 H) 1.72-1.80 (m, 2 H) 1.87-1.95 (m, 2 H) 3.88-3.90 (m, 3 H) 4.00 (t, J=6.57 Hz, 2 H) 4.13-4.22 (m, 1 H) 4.83-4.84 (m, 2 H) 7.16 (ddd, J=7.83, 2.02, 1.01 Hz, 1 H) 7.41-7.46 (m, 2 H) 7.58 (ddd, J=7.83, 1.64, 1.14 Hz, 1 H).

LCMS: m/e=631.2 [M+Na]$^+$.

The third step of Scheme 50 (Hydrolysis): Hydrolysis of 4-bromo-3-tert-butoxycarbonylmethoxy-5-[3-(cyclohexyl-propoxycarbonyl-amino)-phenyl]-thiophene-2-carboxylic acid methyl ester (86 mg, 0.14 mmol) according to the third step of Scheme 50, Example 408, afforded 78 mg of 4-bromo-3-carboxymethoxy-5-[3-(cyclohexyl-propoxycarbonyl-amino)-phenyl]-thiophene-2-carboxylic acid; (quantitative yield).

$^1$H NMR (400 MHz, DMSO-D6) δ ppm 0.74 (t, J=7.33 Hz, 3 H) 0.84-0.97 (m, 1 H) 1.05-1.17 (m, 2 H) 1.23-1.36 (m, 2 H) 1.41-1.49 (m, 2 H) 1.49-1.56 (m, 1 H) 1.68-1.76 (m, 2 H) 1.83-1.90 (m, 2 H) 3.92 (t, J=6.44 Hz, 2 H) 4.00-4.07 (m, 1 H) 4.90 (s, 2 H) 7.28 (ddd, J=7.83, 2.02, 1.26 Hz, 1 H) 7.42-7.44 (m, 1 H) 7.54 (t, J=7.83 Hz, 1 H) 7.63 (ddd, J=7.83, 1.64, 1.14 Hz, 1 H).

LCMS: m/e=539.9 [M+H]$^+$.

EXAMPLE 410

4-Bromo-3-carboxymethoxy-5-[3-(cyclohexyl-isopropoxycarbonyl-amino)-phenyl]-thiophene-2-carboxylic acid The first step of Scheme 50 (Reductive Amination): Synthesis of 4-bromo-3-tert-butoxycarbonylmethoxy-5-[3-(cyclohexyl-amino)-phenyl]-thiophene-2-carboxylic acid methyl ester according to the procedure in Example 408.

The second step of Scheme 50 (Carbamate Formation): Addition of 1M isopropyl chloroformate in toluene (0.86 mL, 0.86 mmol) to 4-bromo-3-tert-butoxycarbonylmethoxy-5-[3-(cyclohexyl-amino)-phenyl]-thiophene-2-carboxylic acid methyl ester (90 mg, 0.17 mmol) according to the second step of Example 408, afforded 80 mg of 4-bromo-3-tert-butoxycarbonylmethoxy-5-[3-(cyclohexyl-isopropoxycarbonyl-amino)-phenyl]-thiophene-2-carboxylic acid methyl ester; (76.5% Yield).

$^1$H NMR (400 MHz, CHLOROFORM-D) δ ppm 0.91-1.01 (m, 1 H) 1.15 (d, J=6.32 Hz, 6 H) 1.17-1.28 (m, 3 H) 1.30-1.43 (m, 3 H) 1.51 (s, 9 H) 1.72-1.79 (m, 3 H) 1.86-1.94 (m, 2 H) 3.88 (s, 3 H) 4.11-4.20 (m, 1 H) 4.83 (s, 2 H) 4.90-4.94 (m, 1 H) 7.15 (ddd, J=7.96, 1.89, 1.01 Hz, 1 H) 7.40-7.45 (m, 2 H) 7.57 (ddd, J=7.71, 1.77, 1.14 Hz, 1 H).

LCMS: m/e=631.2 [M+Na]$^+$.

The third step of Scheme 50 (Hydrolysis): Hydrolysis of 4-bromo-3-tert-butoxycarbonylmethoxy-5-[3-(cyclohexyl-isopropoxycarbonyl-amino)-phenyl]-thiophene-2-carboxylic acid methyl ester (80 mg, 0.13 mmol) according to the third step of Scheme 50, Example 408, afforded 69 mg of 4-bromo-3-carboxymethoxy-5-[3-(cyclohexyl-isopropoxycarbonyl-amino)-phenyl]-thiophene-2-carboxylic acid (98% yield).

$^1$H NMR (400 MHz, DMSO-D6) δ ppm 0.87-0.96 (m, 1 H) 1.09 (d, J=6.06 Hz, 6 H) 1.11-1.17 (m, 1 H) 1.22-1.35 (m, 2 H) 1.49-1.56 (m, 1 H) 1.67-1.75 (m, 2 H) 1.81-1.89 (m, 2 H) 3.97-4.06 (m, 1 H) 4.75-4.82 (m, 1 H) 4.90 (s, 2 H) 7.26 (ddd, J=7.83, 2.02, 1.26 Hz, 1 H) 7.39-7.42 (m, 1 H) 7.54 (t, J=7.83 Hz, 1 H) 7.59-7.66 (m, 1 H).

LCMS: m/e=540.1 [M+H]$^+$.

EXAMPLE 411

4-Bromo-3-carboethoxy-5-[3-(cyclohexylphenoxy-carbonyl-amino)-phenyl]-thiophene-2-carboxylic acid The first step of Scheme 50 (Reductive Amination): Synthesis of 4-bromo-3-tert-butoxycarbonylmethoxy-5-[3-(cyclohexyl-amino)-phenyl]-thiophene-2-carboxylic acid methyl ester according to the procedure in Example 408.

The second step of Scheme 50 (Carbamate Formation): Addition of phenyl chloroformate (0.11 mL, 0.86 mmol) to 4-bromo-3-tert-butoxycarbonylmethoxy-5-[3-(cyclohexyl-amino)-phenyl]-thiophene-2-carboxylic acid methyl ester (90 mg, 0.17 mmol) according to the second step of Scheme 50, Example 408, afforded 70 mg of 4-bromo-3-tert-butoxycarbonylmethoxy-5-[3-(cyclohexyl-phenoxycarbonyl-amino)-phenyl]-thiophene-2-carboxylic acid methyl ester; (63.8% Yield).

$^1$H NMR (400 MHz, CHLOROFORM-D) δ ppm 0.95-1.04 (m, J=12.88 Hz, 1 H) 1.25-1.43 (m, 5 H) 1.51 (s, 9 H) 1.76-1.83 (m, 2 H) 1.98-2.04 (m, 2 H) 3.89 (s, 3 H) 4.22-4.31 (m, 1 H) 4.84 (s, 2 H) 7.03-7.08 (m, 2 H) 7.12-7.17 (m, Hz, 1 H) 7.28-7.33 (m, 3 H) 7.48 (t, J=7.83 Hz, 1 H) 7.57-7.59 (m, 1 H) 7.62 (ddd, J=7.77, 1.71, 1.14 Hz, 1 H).

LCMS: m/e=665.8 [N+Na]+.

The third step of Scheme 50 (Hydrolysis): Hydrolysis of 4-bromo-3-tert-butoxycarbonylmethoxy-5-[3-(cyclohexyl-phenoxycarbonyl-amino)-phenyl]-thiophene-2-carboxylic acid methyl ester (70 mg, 0.11 mmol) according to the third step of Scheme 50, Example 408, afforded 38 mg of 4-bromo-3-carboxymethoxy-5-[3-(cyclohexyl-phenoxycarbonyl-amino)-phenyl]-thiophene-2-carboxylic acid (60% yield).

$^1$H NMR (400 MHz, DMSO-D6) δ ppm 0.87-1.01 (m, 1 H) 1.11-1.25 (m, 2 H) 1.26-1.40 (m, 2 H) 1.48-1.59 (m, 1 H) 1.70-1.80 (m, 2 H) 1.93-2.05 (m, 2 H) 4.07-4.18 (m, 1 H) 4.88-4.93 (m, 2 H) 7.04-7.11 (m, 2 H) 7.19 (t, J=7.33 Hz, 1 H) 7.35 (t, J=7.83 Hz, 2 H) 7.48 (d, J=7.58 Hz, 1 H) 7.60 (t, J=7.83 Hz, 1 H) 7.63-7.70 (m, 2 H).

LCMS: m/e=573.9 [M+H]$^+$.

EXAMPLE 412

5-[3-(Benzyloxycarbonyl-cyclohexymethyl-amino)-phenyl]-4-bromo-3-carboxymethoxy-thiophene-2-carboxylic acid The first step of Scheme 51 (Reductive Animation): To a solution of 5-(3-amino-phenyl)-4-bromo-3-tert-butoxycarbonylmethoxy-thiophene-2-carboxylic acid methyl ester (5.0 g, 13.2 mmol) in DCE (50 mL) was added cyclohexane carboxaldehyde (1.6 mL, 13.0 mmol), and NaBH$_3$ (OAc)$_3$ (4.9 g, 23.1 mmol). HOAc (0.94 mL, 15.9 mmol) was then added dropwise and the solution was allowed to stir at ambient temperature for two hours after which the reaction was judged complete by TLC. The solution was filtered through silica gel, concentrated in vacuo and purified via normal phase SiO$_2$ chromatography using a 5% to 20% ethyl acetate/hexanes gradient, affording 4-bromo-3-tert-butoxycarbonylmethoxy-5-[3-(cyclohexylmethyl-amino)-phenyl]-thiophene-2-carboxylic acid methyl ester as a viscous yellow oil.

The second step of Scheme 51 (Carbamate Formation): Addition of benzyl chloroformate (0.13 mL, 0.93 mmol) to 4-bromo-3-tert-butoxycarbonylmethoxy-5-[3-(cyclohexylmethyl-amino)-phenyl]-thiophene-2-carboxylic acid methyl ester (100 mg, 0.19 mmol) according to the second step of Example 408, afforded 77 mg of 5-[3-(Benzyloxycarbonyl-cyclohexylmethyl-amino)-phenyl]-4-bromo-3-tert-butoxycarbonylmethoxy-thiophene-2-carboxylic acid methyl ester; (60.2% Yield).

$^1$H NMR (400 MHz, CHLOROFORM-D) δ ppm 0.90-1.01 (m, 2 H) 1.09-1.19 (m, 3 H) 1.49-1.52 (m, 9 H) 1.62-1.64 (m, 1 H) 1.65-1.73 (m, 4 H) 3.60 (d, 2 H) 3.87-3.90 (m, 3 H) 4.82-4.85 (m, 2 H) 5.14-5.17 (m, 2 H) 7.27-7.34 (m, 6 H) 7.43 (t, J=7.83 Hz, 1 H) 7.50 (m, 1 H) 7.54 (s, 1 H).

LCMS: m/e=693.2 [M+Na]+.

The third step of Scheme 51 (Hydrolysis): Hydrolysis of 5-[3-(Benzyloxycarbonyl-cyclohexylmethyl-amino)-phenyl]-4-bromo-3-tert-butoxycarbonylmethoxy-thiophene-2-carboxylic acid methyl ester (77 mg, 0.12 mmol) according to the third step of Example 408, afforded 54 mg of 5-[3-(Benzyloxycarbonyl-cyclohexylmethyl-amino)-phenyl]-4-bromo-3-carboxymethoxy-thiophene-2-carboxylic acid; (90% yield).

$^1$H NMR (400 MHz, CHLOROFORM-D) δ ppm 0.88-1.02 (m, 3 H) 1.08-1.20 (m, 3 H) 1.49-1.59 (m, 1 H) 1.59-1.66 (m, 1 H) 1.65-1.76 (m, 5 H) 3.61 (d, 2 H) 4.88-4.95 (m, 3 H) 5.16-5.23 (m, 2 H) 7.28-7.38 (m, 6 H) 7.45-7.49 (m, 2 H) 7.55 (s, 1 H).

LCMS: m/e=601.9 [M+H]$^+$.

EXAMPLE 413

4-Bromo-3-carboxymethoxy-5-[3-(cyclohexylmethyl-isopropoxycarbonyl-amino)-phenyl]-thiophene-2-carboxylic acid The first step of Scheme 51 (Reductive Amination): Synthesis of 4-bromo-3-tert-butoxycarbonylmethoxy-5-[3-(cyclohexylmethyl-amino)-phenyl]-thiophene-2-carboxylic acid methyl ester according to the procedure in Example 408.

The second step of Scheme 51 (Carbamate Formation): Addition of 1M isopropyl chloroformate in toluene (0.93 mL, 0.93 mmol) to 4-bromo-3-tert-butoxycarbonylmethoxy-5-[3-(cyclohexylmethyl-amino)-phenyl]-thiophene-2-carboxylic acid methyl ester (100 mg, 0.19 mmol) according to the second step of Scheme 51, Example 408, afforded 63 mg of 4-bromo-3-tert-butoxycarbonylmethoxy-5-[3-(cyclohexylmethyl-isopropoxycarbonyl-amino)-phenyl]-thiophene-2-carboxylic acid methyl ester; (53.1% Yield).

$^1$H NMR (400 MHz, CHLOROFORM-D) δ ppm 0.92-1.01 (m, 2 H) 1.10-1.19 (m, 3 H) 1.22 (d, 6 H) 1.49-1.52 (s, 9 H) 1.69 (d, 4 H) 3.56-3.61 (m, 2 H) 3.87-3.90 (m, 3 H) 4.82-4.85 (m, 2 H) 4.93-5.00 (m, 1 H) 7.29 (d, J=7.83 Hz, 1 H) 7.42 (t, J=7.83 Hz, 1 H) 7.48 (m, 1 H) 7.54 (s, 1 H).

LCMS: m/e=645.2 [M+Na]+

Hydrolysis of 4-bromo-3-tert-butoxycarbonylmethoxy-5-[3-(cyclohexylmethyl-isopropoxycarbonyl-amino)-phenyl]-thiophene-2-carboxylic acid methyl ester (63 mg, 0.10 mmol) according to the third step of Scheme 51, Example 408, afforded 34 mg of 4-bromo-3-carboxymethoxy-5-[3-(cyclohexyl-isopropoxycarbonyl-amino)-phenyl]-thiophene-2-carboxylic acid (61% yield).

$^1$H NMR (400 MHz, CHLOROFORM-D) δ ppm 0.91-1.03 (m, 2 H) 1.13-1.21 (m, 2 H) 1.29 (d, 6 H) 1.51-1.58 (m, 1 H) 1.62-1.67 (m, 1 H) 1.72 (d, 4 H) 3.59 (d, 2 H) 4.88-4.92 (m, 2 H) 4.98-5.06 (m, 1 H) 7.33 (d, J=7.58 Hz, 1 H) 7.42 (d, 1 H) 7.48 (t, J=7.83 Hz, 1 H) 7.59 (s, 1 H).

LCMS: m/e=577.9 [M+Na]$^+$.

EXAMPLE 414

4-Bromo-3-carboxymethoxy-5-[3-(cyclohexylmethyl-propoxycarbonyl-amino)-phenyl]-thiophene-2-carboxylic acid The first step of Scheme 51 (Reductive Amination): Synthesis of 4-bromo-3-tert-butoxycarbonylmethoxy-5-[3-(cyclohexylmethyl-amino)-phenyl]-thiophene-2-carboxylic acid methyl ester according to the procedure in Example 408.

The second step of Scheme 51 (Carbamate Formation): Addition of propyl chloroformate (0.10 mL, 0.93 mmol) to 4-bromo-3-tert-butoxycarbonylmethoxy-5-[3-(cyclohexylmethyl-amino)-phenyl]-thiophene-2-carboxylic acid methyl ester (100 mg, 0.19 mmol) according to the second step of Scheme 51, Example 408, afforded 53 mg of 4-bromo-3-tert-butoxycarbonylmethoxy-5-[3-(cyclohexylmethyl-propoxycarbonyl-amino)-phenyl]-thiophene-2-carboxylic acid methyl ester; (44.2% Yield).

$^1$H NMR (400 MHz, CHLOROFORM-D) δ ppm 0.83-0.91 (m, 3 H) 0.92-1.01 (m, 2 H) 1.11-1.20 (m, 3 H) 1.49-1.53 (s, 9 H) 1.56-1.65 (m, 3 H) 1.65-1.75 (m, 5 H) 3.59 (d, 2 H) 3.86-3.90 (m, 3 H) 4.06 (t, 2 H) 4.82-4.85 (m, 2 H) 7.29 (d, J=7.83 Hz, 1 H) 7.43 (t, J=7.83 Hz, 1 H) 7.49 (m, 1 H) 7.55 (s, 1 H).

LCMS: m/e=645.2 [M+Na]+.

Hydrolysis of 4-bromo-3-tert-butoxycarbonylmethoxy-5-[3-(cyclohexylmethyl-propoxycarbonyl-amino)-phenyl]-thiophene-2-carboxylic acid methyl ester (53 mg, 0.09 mmol) according to the third step of Scheme 51, Example 408, afforded 37 mg of 4-bromo-3-carboxymethoxy-5-[3-(cyclohexyl-propoxycarbonyl-amino)-phenyl]-thiophene-2-carboxylic acid (78% yield).

$^1$H NMR (400 MHz, DMSO-D6) δ ppm 0.81 (t, 3 H) 0.86-0.96 (m, 2 H) 1.05-1.15 (m, 3 H) 1.40-1.47 (m, 1 H) 1.48-1.58 (m, 3 H) 1.60-1.70 (m, 4 H) 3.98 (t, 2 H) 4.88-4.92 (m, 2 H) 7.39-7.45 (m, 1 H) 7.51-7.55 (m, 2 H) 7.57 (s, 1 H).

LCMS: m/e=553.9 [M+H]$^+$.

EXAMPLE 415

4-Bromo-3-carboxymethoxy-5-[3-(cyclohexylmethyl-phenoxycarbonyl-amino)-phenyl]-thiophene-2-carboxylic acid The first step of Scheme 51 (Reductive Amination): Synthesis of 4-bromo-3-tert-butoxycarbonylmethoxy-5-[3-(cyclohexylmethyl-amino)-phenyl]-thiophene-2-carboxylic acid methyl ester according to the procedure in Example 408.

The second step of Scheme 51 (Carbamate Formation): Addition of phenyl chloroformate (0.12 mL, 0.93 mmol) to 4-bromo-3-tert-butoxycarbonylmethoxy-5-[3-(cyclohexylmethyl-amino)-phenyl]-thiophene-2-carboxylic acid methyl ester (100 mg, 0.19 mmol) according to the second step of Scheme 51, Example 408, afforded 95 mg of 4-bromo-3-tert-butoxycarbonylmethoxy-5-[3-(cyclohexylmethyl-phenoxycarbonyl-amino)-phenyl]-thiophene-2-carboxylic acid methyl ester; (75.7% Yield).

$^1$H NMR (400 MHz, CHLOROFORM-D) δ ppm 1.02 (m, 2 H) 1.20 (m, 3 H) 1.50 (s, 9 H) 1.60-1.68 (m, J=8.08 Hz, 2 H) 1.69-1.82 (m, 4 H) 3.70 (s, 2 H) 3.88 (s, 3 H) 4.84 (s, 2 H)

7.07-7.14 (m, 2 H) 7.14-7.21 (m, 1 H) 7.29-7.37 (m, 2 H) 7.38-7.44 (m, 1 H) 7.48 (t, J=7.83 Hz, 1 H) 7.51-7.56 (m, 1 H) 7.66-7.70 (m, 1 H).

LCMS: m/e=680.0 [M+Na]+.

Hydrolysis of 4-bromo-3-tert-butoxycarbonylmethoxy-5-[3-(cyclohexylmethyl-phenoxycarbonyl-amino)-phenyl]-thiophene-2-carboxylic acid methyl ester (95 mg, 0.15 mmol) according to the third step of Scheme 51, Example 408, afforded 81 mg of 4-bromo-3-carboxymethoxy-5-[3-(cyclohexyl-phenoxycarbonyl-amino)-phenyl]-thiophene-2-carboxylic acid (78% yield).

$^1$H NMR (400 MHz, DMSO-D6) δ ppm 0.90-1.04 (m, 2 H) 1.09-1.18 (m, 3 H) 1.47-1.55 (m, 1 H) 1.56-1.61 (m, 1 H) 1.62-1.70 (m, 2 H) 1.71-1.79 (m, 2 H) 3.63-3.73 (m, 2 H) 4.90 (s, 2 H) 7.13 (d, J=7.83 Hz, 2 H) 7.22 (t, J=7.33 Hz, 1 H) 7.34-7.41 (m, 2 H) 7.56-7.62 (m, 3 H) 7.76 (s, 1 H).

LCMS: m/e=587.9 [M+H]$^+$.

EXAMPLE 416

5-[3-(Benzoyl-cyclohexylmethyl-amino)-phenyl]-4-bromo-3-carboxymethoxy-thiophene-2-carboxylic acid The first step of Scheme 51 (Reductive Amination): Synthesis of 4-bromo-3-tert-butoxycarbonylmethoxy-5-[3-(cyclohexylmethyl-amino)-phenyl]-thiophene-2-carboxylic acid methyl ester according to the procedure in Example 408.

The second step of Scheme 51 (Amide Formation): Addition of benzoyl chloride (0.03 mL, 0.28 mmol) to 4-bromo-3-tert-butoxycarbonylmethoxy-5-[3-(cyclohexylmethyl-amino)-phenyl]-thiophene-2-carboxylic acid methyl ester (100 mg, 0.19 mmol) according to the second step of Scheme 51, Example 408, afforded 90 mg of 5-[3-(Benzoyl-cyclohexylmethyl-amino)-phenyl]-4-bromo-3-tert-butoxycarbonylmethoxy-thiophene-2-carboxylic acid methyl ester; (75.2% Yield).

$^1$H NMR (400 MHz, CHLOROFORM-D) δ ppm 0.86-0.90 (m, 1 H) 1.04-1.12 (m, 1 H) 1.14-1.20 (m, 2 H) 1.25-1.30 (m, 1 H) 1.48-1.52 (s, 9 H) 1.69-1.80 (m, 5 H) 3.85 (d, J=7.07 Hz, 2 H) 3.87 (s, 3 H) 4.81 (s, 2 H) 7.11-7.38 (m, 4 H) 7.45-7.51 (m, 2 H) 7.59-7.65 (m, 1 H) 8.09-8.14 (m, 2 H).

LCMS: m/e=642.0 [M+H]$^+$.

Hydrolysis of 5-[3-(Benzoyl-cyclohexylmethyl-amino)-phenyl]-4-bromo-3-tert-butoxycarbonylmethoxy-thiophene-2-carboxylic acid methyl ester (90 mg, 0.14 mmol) according to the third step of Scheme 51, Example 408, afforded 61 mg of 5-[3-(Benzoyl-cyclohexylmethyl-amino)-phenyl]-4-bromo-3-carboxymethoxy-thiophene-2-carboxylic acid; (76.4% yield).

$^1$H NMR (400 MHz, DMSO-D6) δ ppm 0.87-0.93 (m, 1 H) 0.98-1.09 (m, 2 H) 1.12-1.19 (m, 3 H) 1.26-1.33 (m, 1 H) 1.54-1.65 (m, 2 H) 1.66-1.79 (m, 2 H) 3.83 (d, J=7.58 Hz, 2 H) 4.87-4.91 (s, 2 H) 7.23-7.33 (m, 5 H) 7.34-7.39 (m, 1 H) 7.42-7.47 (m, 3 H).

LCMS: m/e=571.9 [M+H]$^+$.

EXAMPLE 417

4-Bromo-3-carboxymethoxy-5-[3-(cyclohexylmethyl-phenylacetyl-amino)-phenyl]-thiophene-2-carboxylic acid The first step of Scheme 51 (Reductive Amination): Synthesis of 4-bromo-3-tert-butoxycarbonylmethoxy-5-[3-(cyclohexylmethyl-amino)-phenyl]-thiophene-2-carboxylic acid methyl ester according to the procedure in Example 408.

The second step of Scheme 51 (Amide Formation): Addition of phenyl acetyl chloride (0.04 mL, 0.28 mmol) to 4-bromo-3-tert-butoxycarbonylmethoxy-5-[3-(cyclohexylmethyl-amino)-phenyl]-thiophene-2-carboxylic acid methyl ester (100 mg, 0.19 mmol) according to the second step of Scheme 51, Example 408, with the exception of substitution of NaHCO$_3$ (100 mg, 1.9 mmol) for pyridine, afforded 75 mg of 4-bromo-3-tert-butoxycarbonylmethoxy-5-[3-(cyclohexylmethyl-phenylacetyl-amino)-phenyl]-thiophene-2-carboxylic acid methyl ester; (61.3% Yield).

$^1$H NMR (400 MHz, CHLOROFORM-D) δ ppm 1.11-1.19 (m, 2 H) 1.48-1.54 (s, 9 H) 1.59-1.64 (m, 2 H) 1.64-1.72 (m, 3 H) 3.50 (s, 2 H) 3.61 (d, J=7.33 Hz, 2 H) 3.90 (s, 3 H) 4.85 (s, 2 H) 7.00 (d, J=7.07 Hz, 2 H) 7.10-7.23 (m, 4 H) 7.39 (s, 1 H) 7.45 (t, J=7.83 Hz, 1 H) 7.59 (d, J=8.08 Hz, 1 H).

LCMS: m/e=656.0 [M+H]$^+$.

Hydrolysis of 4-bromo-3-tert-butoxycarbonylmethoxy-5-[3-(cyclohexylmethyl-phenylacetyl-amino)-phenyl]-thiophene-2-carboxylic acid methyl ester (75 mg, 0.11 mmol) according to the third step of Scheme 51, Example 408, afforded 62 mg of 4-bromo-3-carboxymethoxy-5-[3-(cyclohexylmethyl-phenylacetyl-amino)-phenyl]-thiophene-2-carboxylic acid; (96.4% yield).

$^1$H NMR (400 MHz, DMSO-D6) δ ppm 0.78-0.94 (m, 2 H) 1.00-1.13 (m, 3 H) 1.32-1.43 (m, 1 H) 1.49-1.56 (m, 1 H) 1.56-1.66 (m, 4 H) 3.36-3.44 (m, 2 H) 3.55 (d, J=7.07, 6.06 Hz, 2 H) 4.86 (s, 2 H) 6.88-6.99 (m, 2 H) 7.08-7.21 (m, 3 H) 7.38 (d, J=7.83 Hz, 1 H) 7.45-7.48 (m, 1 H) 7.52-7.64 (m, 2 H).

LCMS: m/e=585.9 [M+H]$^+$.

EXAMPLE 418

4-Bromo-3-carboxymethoxy-5-{3-[cyclohexylmethyl-(4-methyl-pentanoyl)-amino]-phenyl}-thiophene-2-carboxylic acid methyl ester The first step of Scheme 51 (Reductive Amination): Synthesis of 4-bromo-3-tert-butoxycarbonylmethoxy-5-[3-(cyclohexylmethyl-amino)-phenyl]-thiophene-2-carboxylic acid methyl ester according to the procedure in Example 408.

The second step of Scheme 51 (Amide Formation): Addition of isovaleryl chloride (0.45 mL, 3.72 mmol) to 4-bromo-3-tert-butoxycarbonylmethoxy-5-[3-(cyclohexylmethyl-amino)-phenyl]-thiophene-2-carboxylic acid methyl ester (1.0 g, 1.9 mmol) according to the second step of Scheme 51, Example 408, afforded 980 mg of 4-bromo-3-tert-butoxycarbonylmethoxy-5-{3-[cyclohexylmethyl-(4-methyl-pentanoyl)-amino]-phenyl}-thiophene-2-carboxylic acid methyl ester; (85% Yield).

$^1$H NMR (400 MHz, CHLOROFORM-D) δ ppm 0.85 (d, J=6.82 Hz, 6 H) 0.95-1.07 (m, 3 H) 1.10-1.20 (m, 3 H) 1.51 (s, 9 H) 1.64-1.74 (n, 4 H) 1.94-2.00 (m, 2 H) 2.09-2.19 (n, 1 H) 3.62 (d, J=7.58 Hz, 2 H) 3.89 (s, 3 H) 4.86 (s, 2 H) 7.22 (d, J=6.82 Hz, 1 H) 7.48-7.51 (m, 2 H) 7.59 (d, 1 H).

LCMS: m/e=621.9 [M+H]$^+$.

The third step of Scheme 51 (Deprotection): A solution of 4-bromo-3-tert-butoxycarbonylmethoxy-5-{3-[cyclohexylmethyl-(4-methyl-pentanoyl)-amino]-phenyl}-thiophene-2-carboxylic acid methyl ester (980 mg, 1.6 mmol) in DCM (20 mL) was cooled to 0° C. Trifluoroacetic acid (5 mL) was then added drop-wise and the reaction was allowed to stir for four hours, after which the reaction was judged complete by TLC. The contents of the flask were concentrated in vacuo and the resulting crude product was recrystallized from a 5% ethyl acetate/hexanes mixture, affording 680 mg of 4-bromo- 3-carboxymethoxy-5-{3-[cyclohexylmethyl-(4-methyl-pentanoyl)-amino]-phenyl}-thiophene-2-carboxylic acid methyl ester; (75.9% yield).

$^1$H NMR (400 MHz, DMSO-D6) δ ppm 0.65 (d, J=5.31 Hz, 6 H) 0.72-0.85 (m, J=10.86 Hz, 2 H) 0.94-1.03 (m, 3 H) 1.24-1.33 (m, 1 H) 1.41-1.48 (m, 1 H) 1.48-1.56 (m, 4 H) 1.78-1.86 (m, 3 H) 3.44 (d, J=7.58 Hz, 2 H) 3.70 (s, 3 H) 4.76 (s, 2 H) 7.30 (d, 1 H) 7.43-7.54 (m, 3 H).

LCMS: m/e=566.9 [M+H]$^+$.

EXAMPLE 419

4-Bromo-3-carboxymethoxy-5-{3-[1-(3-chloro-phenylmethanesulfonyl)-piperidin-4-ylamino]-phenyl}-thiophene-2-carboxylic acid methyl ester Scheme 52: To a solution of 4-bromo-3-tert-butoxycarbonylmethoxy-5-[3-(piperidin-4-ylamino)-phenyl]-thiophene-2-carboxylic acid methyl ester hydrochloride (300 mg, 0.53 mmol) in dichloromethane-NaHCO$_3$ aq. (4 mL, 1:1) was added (3-chloro-phenyl)-methanesulfonyl chloride (206 mg, 1.1 mmol). The reaction was stirred vigorously for 24 hours. The solution was diluted with ethyl acetate (100 mL) and washed with brine (50 mL). The organic layer was dried over magnesium sulfate and then filtered. The solvent was removed under reduced pressure and purified by column chromatography eluting with a 15-30% ethyl acetate-hexane gradient. The material was dissolved in dichloromethane (2 mL) and treated with trifluoroacetic acid (0.5 mL). After 2 hours, the solvents were removed under vacuum to afford 174 mg (94%) of 4-bromo-3-carboxymethoxy-5-{3-[1-(3-chloro-phenylmethanesulfonyl)-piperidin-4-ylamino]-phenyl}-thiophene-2-carboxylic acid methyl ester as a light brown solid.

$^1$H NMR (400 MHz, MeOD) δ ppm 1.44 (m, 2 H) 1.85 (m, 2 H) 2.72 (m, 2 H) 3.41 (m, 1 H) 3.56 (d, J=13.14 Hz, 2 H) 3.70 (d, J=4.04 Hz, 3 H) 4.19 (s, 2 H) 5.32 (s, 2 H) 6.95 (m, 1 H) 7.14 (m, 2 H) 7.21 (m, 3 H) 7.31 (d, J=3.03 Hz, 2 H).

HRMS: calcd for C$_{26}$H$_{26}$BrClN$_2$O$_7$S$_2$, 656.0053; found (ESI-FTMS), 657.0142.

EXAMPLE 420

4-Bromo-3-carboxymethoxy-5-{3-[1-(3-fluoro-phenylmethanesulfonyl)-piperidin-4-ylamino]-phenyl}-thiophene-2-carboxylic acid methyl ester Scheme 52: 4-Bromo-3-carboxymethoxy-5-{3-[1-(3-fluoro-phenylmethanesulfonyl)-piperidin-4-ylamino]-phenyl}-thiophene-2-carboxylic acid methyl ester was prepared according to the procedure in Example 419 to afford 142 mg (42%) of a pale yellow solid.

$^1$H NMR (400 MHz, DMSO-D6) δ ppm 1.35 (m, 2 H) 1.95 (m, 2 H) 2.94 (s, 2 H) 3.43 (m, 1 H) 3.53 (m, 2 H) 3.81 (s, 3 H) 4.46 (s, 2 H) 4.85 (s, 2 H) 5.92 (m, J=7.58 Hz, 1 H) 6.72 (m, 1 H) 6.79 (d, J=8.59 Hz, 1 H) 6.86 (s, 1 H) 7.23 (m, 4 H) 7.45 (m, 1 H).

HRMS: calcd for C$_{26}$H$_{26}$BrFN$_2$O$_7$S$_2$, 640.0349; found (ESI-FTMS), 641.0423.

EXAMPLE 421

4-Bromo-3-carboxymethoxy-5-{3-[1-(2-chloro-phenylmethanesulfonyl)-piperidin-4-ylamino]-phenyl}-thiophene-2-carboxylic acid Scheme 53: 4-Bromo-5-{3-[1-(2-chloro-phenylmethanesulfonyl)-piperidin-4-ylamino]-phenyl}-3-ethoxycarbonylmethoxy-thiophene-2-carboxylic acid methyl ester was prepared according to the procedure in the first step of Scheme 52, Example 419. The material was dissolved in THF (2 mL) and treated with 1N sodium hydroxide (720 µL, 0.72 mmol). The reaction was stirred vigorously for 24 hours. The tetrahydrofuran was removed under reduced pressure and the resulting aqueous layer was acidified with 1N hydrochloric acid (720 µL, 0.72 mmol) added slowly. 4-Bromo-3-carboxymethoxy-5-{3-[1-(2-chloro-phenylmethanesulfonyl)-piperidin-4-ylamino]-phenyl}-thiophene-2-carboxylic acid was isolated by filtration to yield 116 mg (98%; two steps) of a pale yellow solid.

$^1$H NMR (400 MHz, DMSO-D6) δ ppm 1.41 (s, 2 H) 2.00 (m, 2 H) 3.03 (s, 2 H) 3.45 (m, 1 H) 3.55 (s, 2 H) 4.54 (s, 2 H) 4.88 (m, 2 H) 5.94 (m, 1 H) 6.72 (m, 1 H) 6.80 (m, 1 H) 6.85 (m, 1 H) 7.20 (m, 1 H) 7.40 (m, 2 H) 7.54 (m, 2 H).

HRMS: calcd for C$_{25}$H$_{24}$BrClN$_2$O$_7$S$_2$, 641.9897; found (ESI-FTMS), 642.9968.

EXAMPLE 422

4-Bromo-5-{3-[1-(2-chloro-phenylmethanesulfonyl)-piperidin-4-ylamino]-phenyl}-3-methoxycarbonylmethoxy-thiophene-2-carboxylic acid The second step of Scheme 53: To a solution of 4-bromo-3-carboxymethoxy-5-{3-[1-(2-chloro-phenylmethanesulfonyl)-piperidin-4-ylamino]-phenyl}-thiophene-2-carboxylic acid in methanol-N,N-dimethylformamide (4 mL; 3:1) was added concentrated sulfuric acid (2 drops). After several hours, the reaction was diluted with ethyl acetate (100 mL) and washed with water (3×25 mL) and brine (30 mL). The organic layer was dried over magnesium sulfate and filtered to afford 103 mg (92%) of 4-bromo-5-{3-[1-(2-chloro-phenylmethanesulfonyl)-piperidin-4-ylamino]-phenyl}-3-methoxycarbonylmethoxy-thiophene-2-carboxylic acid as a yellow solid.

$^1$H NMR (400 MHz, DMSO-D6) δ ppm 1.42 (m, 2 H) 2.01 (m, 2 H) 3.03 (s, 2 H) 3.45 (s, 2 H) 3.55 (s, 2 H) 3.70 (s, 3 H) 4.54 (s, 2 H) 4.97 (s, 2 H) 5.95 (m, 1 H) 6.73 (d, J=7.58 Hz, 1 H) 6.80 (m, 1 H) 6.85 (m, J=1.89, 1.89 Hz, 1 H) 7.20 (m, 1 H) 7.40 (m, 2 H) 7.54 (m, 2 H).

HRMS: calcd for C$_{26}$H$_{26}$BrClN$_2$O$_7$S$_2$, 656.0053; found (ESI-FTMS), 657.0136.

EXAMPLE 423

3-Carboxymethoxy-5-{3-[1-(3-fluoro-phenylmethanesulfonyl)-piperidin-4-ylamino]-phenyl}-4-methyl-thiophene-2-carboxylic acid methyl ester The first step of Scheme 54: 3-tert-Butoxycarbonylmethoxy-5-{3-[1-(3-fluoro-phenylmethanesulfonyl)-piperidin-4-ylamino]-phenyl}-4-methyl-thiophene-2-carboxylic acid methyl ester was prepared following the procedure in the first step of Scheme 52, Example 419.

The second step of Scheme 54: 3-Carboxymethoxy-5-{3-[1-(3-fluoro-phenylmethanesulfonyl)-piperidin-4-ylamino]-phenyl}-4-methyl-thiophene-2-carboxylic acid methyl ester was prepared following the procedure in the second step of Scheme 52, Example 419 to provide 167 mg (55%; 2 steps) of a pale yellow solid.

$^1$H NMR (400 MHz, MeOD) δ ppm 1.31 (m, J=21.22 Hz, 2 H) 1.85 (m, 2 H) 2.05 (s, 3 H) 2.77 (m, 2 H) 3.32 (m, 1 H) 3.52 (m, 2 H) 3.67 (s, 3 H) 4.19 (s, 2 H) 4.70 (m, 2 H) 6.68 (d, J=18.19 Hz, 3 H) 6.94 (m, J=7.83 Hz, 1 H) 7.09 (m, 3 H) 7.24 (m, 1 H).

HRMS: calcd for $C_{27}H_{29}FN_2O_7S_2$, 576.1400; found (ESI-FTMS), 577.1468.

EXAMPLE 424

3-Carboxymethoxy-4-methyl-5-[3-(1-phenyl-methanesulfonyl-piperidin-4-ylamino)-phenyl]-thiophene-2-carboxylic acid methyl ester The first step of Scheme 54: 3-tert-Butoxycarbonyl-methoxy-4-methyl-5-[3-(1-phenylmethanesulfonyl-piperidin-4-ylamino)-phenyl]-thiophene-2-carboxylic acid methyl ester was prepared according to the procedure in the first step of Scheme 52, Example 419.

The second step of Scheme 54: 3-Carboxymethoxy-4-methyl-5-[3-(1-phenylmethanesulfonyl-piperidin-4-ylamino)-phenyl]-thiophene-2-carboxylic acid methyl ester was prepared following the procedure in the second step of Scheme 52, Example 419 to give 143 mg (83%; 2 steps) of a pale yellow solid.

$^1$H NMR (400 MHz, DMSO-D6) δ ppm 1.37 (m, 2 H) 1.93 (m, 2 H) 2.20 (s, 3 H) 2.93 (m, 2 H) 3.38 (m, J=7.07 Hz, 1 H) 3.54 (m, 2 H) 3.78 (s, 3 H) 4.40 (s, 2 H) 4.84 (s, 2 H) 6.70 (m, 3 H) 7.20 (t, J=7.71 Hz, 1 H) 7.40 (m, 5 H).

HRMS: calcd for $C_{27}H_{30}N_2O_7S_2$, 558.1494; found (ESI-FTMS), 559.1576.

EXAMPLE 425

3-Carboxymethoxy-4-methyl-5-{3-[1-(2-trifluorom-ethyl-phenylmethanesulfonyl)-piperidin-4-ylamino]-phenyl}-thiophene-2-carboxylic acid methyl ester The first step of Scheme 54: 3-tert-Butoxycarbonyl-methoxy-4-methyl-5-{3-[1-(2-trifluoromethyl-phenyl-methanesulfonyl)-piperidin-4-ylamino]-phenyl}-thiophene-2-carboxylic acid methyl ester was prepared according to the procedure in the first step of Scheme 52, Example 419.

The second step of Scheme 54: 3-Carboxymethoxy-4-methyl-5-{3-[1-(2-trifluoromethyl-phenylmethanesulfonyl)-piperidin-4-ylamino]-phenyl}-thiophene-2-carboxylic acid methyl ester was prepared according to the procedure in the second step of Scheme 52, Example 419, to give 86 mg of a white solid.

$^1$H NMR (400 MHz, DMSO-D6) δ ppm 1.44 (s, 2 H) 1.99 (m, 2 H) 2.20 (s, 3 H) 3.10 (m, 2 H) 3.49 (m, 1 H) 3.58 (m, 2 H) 3.78 (s, 3 H) 4.53 (s, 2 H) 4.84 (s, 2 H) 6.70 (m, 3 H) 7.20 (t, J=7.83 Hz, 1 H) 7.61 (m, 1 H) 7.71 (m, 2 H) 7.80 (d, J=8.08 Hz, 1 H).

HRMS: calcd for $C_{28}H_{29}F3N_2O_7S_2$, 626.1368; found (ESI-FTMS), 314.0764.

EXAMPLE 426

3-Carboxymethoxy-4-methyl-5-[3-(1-phenyl-methanesulfonyl-piperidin-4-ylamino)-phenyl]-thiophene-2-carboxylic acid The first step of Scheme 54: 3-tert-Butoxycarbonyl-methoxy-4-methyl-5-[3-(1-phenylmethanesulfonyl-piperidin-4-ylamino)-phenyl]-thiophene-2-carboxylic acid methyl ester was prepared following the procedure in the first step of Scheme 53, Example 419 to yield a beige solid.

Hydrolysis of 3-tert-butoxycarbonylmethoxy-4-methyl-5-[3-(1-phenylmethanesulfonyl-piperidin-4-ylamino)-phenyl]-thiophene-2-carboxylic acid methyl ester following the procedure in the first step of Scheme 52, Example 419, provided 96 mg (71%) of 3-carboxymethoxy-4-methyl-5-[3-(1-phenylmethanesulfonyl-piperidin-4-ylamino)-phenyl]-thiophene-2-carboxylic acid as a pale beige solid.

$^1$H NMR (400 MHz, DMSO-D6) δ ppm 1.36 (m, 2 H) 1.91 (m, 2 H) 2.18 (s, 3 H) 2.92 (s, 2 H) 3.42 (m, 1 H) 3.56 (m, 2 H) 4.40 (s, 2 H) 4.86 (s, 2 H) 6.69 (s, 2 H) 7.18 (m, 1 H) 7.40 (m, 6 H).

HRMS: calcd for $C_{26}H_{28}N_2O_7S_2$, 544.1338; found (ESI-FTMS), 545.1423.

EXAMPLE 427

3-Methoxycarbonylmethoxy-4-methyl-5-[3-(1-phe-nylmethanesulfonyl-piperidin-4-ylamino)-phenyl]-thiophene-2-carboxylic acid 3-Methoxycarbonylmethoxy-4-methyl-5-[3-(1-phenyl-methanesulfonyl-piperidin-4-ylamino)-phenyl]-thiophene-2-carboxylic acid was prepared from 3-carboxymethoxy-4-methyl-5-[3-(1-phenylmethanesulfonyl-piperidin-4-ylamino)-phenyl]-thiophene-2-carboxylic acid following the procedure outlined in the second step of Scheme 53, Example 422, to give 142 mg (79%) of a pale yellow solid.

$^1$H NMR (400 MHz, MeOD) δ ppm 1.82 (m, 2 H) 2.26 (m, 2 H) 2.49 (s, 3 H) 3.08 (m, 2 H) 3.83 (d, J=4.04 Hz, 1 H) 3.94 (m, 2 H) 4.03 (s, 3 H) 4.60 (s, 2 H) 5.21 (s, 1 H) 5.74 (s, 2 H) 7.37 (m, 1 H) 7.43 (m, 1 H) 7.51 (m, 1 H) 7.67 (m, 6 H).

HRMS: calcd for $C_{27}H_{30}N_2O_7S_2$, 558.1494; found (ESI-FTMS), 559.1579.

EXAMPLE 428

3-Carboxymethoxy-4-methyl-5-[3-(3,3,5,5-tetram-ethyl-cyclohexylamino)-phenyl]-thiophene-2-car-boxylic acid methyl ester]

3-Methoxycarbonylmethoxy-4-methyl-5-[3-(3,3,5,5-tet-ramethyl-cyclohexylamino)-phenyl]-thiophene-2-carboxy-lic acid was prepared from 3-carboxymethoxy-4-methyl-5-[3-(3,3,5,5-tetramethyl-cyclohexylamino)-phenyl]-thiophene-2-carboxylic acid according to the procedure outlined in the second step of Scheme 54, Example 424, to yield 2.82 g (97%) of a white solid.

$^1$H NMR (400 MHz, DMSO-D6) δ ppm 0.91 (s, 6 H) 0.97 (m, 2 H) 1.08 (m, 1 H) 1.07 (s, 6 H) 1.27 (d, J=13.90 Hz, 1 H) 1.71 (m, 2 H) 2.21 (s, 3 H) 3.57 (m, 1 H) 3.78 (s, 3 H) 4.84 (s, 2 H) 6.76 (m, 3 H) 7.23 (t, J=7.96 Hz, 1 H).

HRMS: calcd for $C_{25}H_{33}NO_5S$, 459.2079; found (ESI-FTMS), 460.217.

EXAMPLE 429

4,5-Dibromo-3-(1-carboxy-ethoxy)-thiophene-2-carboxylic acid

The first step of Scheme 55: To a solution of 4,5-dibromo-3-hydroxy-thiophene-2-carboxylic acid methyl ester (2.0 g, 6.3 mmol) and 2-bromo-propionic acid tert-butyl ester (1.2 mL, 6.9 mmol) in DMF (18 mL) was added potassium carbonate (1.3 g, 9.5 mmol). The reaction was heated to 50° C. for 24 hours. The solution was cooled and diluted with ethyl acetate (250 mL). The organic layer was washed with 5% lithium chloride (100 mL) and brine (100 mL). The solution was dried over magnesium sulfate and filtered. The solvent was removed under reduced pressure to give 2.69 g (96%) of 4,5-dibromo-3-(1-tert-butoxycarbonyl-ethoxy)-thiophene-2-carboxylic acid methyl ester as a viscous oil.

$^1$H NMR (400 MHz, CHLOROFORM-D) δ ppm 1.43 (s, 9 H) 1.60 (d, J=6.57 Hz, 3 H) 3.84 (s, 3 H) 5.20 (q, J=6.82 Hz, 1 H).

HRMS: calcd for $C_{13}H_{16}Br2O_5S$, 441.9085; found (ESI-FTMS), 464.8963.

The second step of Scheme 55: A solution of 4,5-dibromo-3-(1-tert-butoxycarbonyl-ethoxy)-thiophene-2-carboxylic acid methyl ester (273 mg, 0.61 mmol) was dissolved in tetrahydrofuran (5 mL) and treated with 1N sodium hydroxide (3 mL). The reaction was stirred vigorously at 55° C. for three hours. The tetrahydrofuran was removed under reduced pressure and 1N hydrochloric acid (3 mL) was added dropwise. 4,5-Dibromo-3-(1-carboxy-ethoxy)-thiophene-2-carboxylic acid was filtered and dried in the vacuum oven to afford 222 mg (98%) of a white solid.

$^1$H NMR (400 MHz, DMSO-D6) δ ppm 1.48 (d, J=6.82 Hz, 3 H) 5.16 (m, 1 H).

HRMS: calcd for C8H6Br2O5S, 371.8303; found (ESI-FTMS), 372.8378.

EXAMPLE 430

[4,5-Dibromo-2-(5-methyl-[1,2,4]oxadiazol-3-yl)-thiophen-3-yloxy]-acetic acid

The first step of Scheme 56: To a solution of 4,5-dibromo-3-carboxymethoxy-thiophene-2-carboxylic acid methyl ester (6.0 g, 14.0 mmol) in MeOH (100 mL) was bubbled ammonia gas. The reaction was sealed and stirred for 24 hours. The solid material was filtered and dried to constant weight in the vacuum oven to afford 4.64 g (98%) of 4,5-dibromo-2-carbamoyl-thiophen-3-yloxy)-acetic acid as a pale gray solid.

$^1$H NMR (400 MHz, DMSO-D6) δ ppm 4.31 (s, 2 H) 7.42 (s, 1 H) 10.46 (s, 1 H).

The second step of Scheme 56: To a solution of 4,5-dibromo-2-carbamoyl-thiophen-3-yloxy)-acetic acid in methanol (55 mL) was added concentrated sulfuric acid (0.5 mL). The reaction was stirred for 24 and then made basic by the addition of aqueous sodium bicarbonate. The reaction was evaporated and the residue dissolved in ethyl acetate (250 mL) and washed with water (100 mL). The organic layer was dried over magnesium sulfate and filtered to yield 777 mg (28%) of (4,5-dibromo-2-carbamoyl-thiophen-3-yloxy)-acetic acid methyl ester.

$^1$H NMR (400 MHz, MeOD) δ ppm 3.72 (s, 3 H) 4.92 (s, 2 H).

The third step of Scheme 56: A solution of (4,5-dibromo-2-carbamoyl-thiophen-3-yloxy)-acetic acid methyl ester (500 mg, 1.54 mmol) and cyanuric chloride (422 mg, 2.31 mmol) in N,N-dimethylformamide (15 mL) were stirred for 24 hours. The reaction was diluted with ethyl acetate (150 mL) and water (60 mL). The contents were stirred vigorously for 5 minutes until the mixture was clear. The layers were separated and the aqueous layer was extracted with ethyl acetate (50 mL). The organic layers were combined and dried over magnesium sulfate. The solution was filtered and then concentrated. The residue was diluted with ethyl acetate (10 mL) and then filtered through a plug of silica gel eluting with ethyl acetate. The solvent was removed under reduced pressure to give 386 mg (78%) of (4,5-dibromo-2-cyano-thiophen-3-yloxy)-acetic acid methyl ester as a white solid.

$^1$H NMR (400 MHz, CHLOROFORM-D) δ ppm 3.86 (s, 3 H) 5.08 (s, 2 H).

The fourth step of Scheme 56: A solution of (4,5-dibromo-2-cyano-thiophen-3-yloxy)-acetic acid methyl ester in tetrahydrofuran was cooled to 0° C. and potassium hydroxide (1N, 840 mL, 0.84 mmol) was added dropwise. After 2 hrs the reaction was acidified by the addition of 1N hydrochloric acid (1 mL). The reaction mixture was diluted with ethyl acetate (80 mL) and washed with water (30 mL). The organic layer was dried over magnesium sulfate and filtered. The solvent was removed under reduced pressure to give 76 mg (80%) of (4,5-dibromo-2-cyano-thiophen-3-yloxy)-acetic acid as a light orange solid.

$^1$H NMR (400 MHz, MeOD) δ ppm 5.04 (s, 2 H).

The fifth step of Scheme 56: A flask containing (4,5-dibromo-2-cyano-thiophen-3-yloxy)-acetic acid hydroxylamine hydrochloride and potassium carbonate in ethanol-water (5:1; 2.2 mL) was heated at reflux for several hours. The reaction was cooled, and the solvents were removed under reduced pressure to give [4,5-dibromo-2-(N-hydroxycarbamimidoyl)-thiophen-3-yloxy]-acetic acid as a pale yellow solid.

$^1$H NMR (400 MHz, DMSO-D6) δ ppm 4.81 (s, 2 H)

The sixth step of Scheme 56: A solution of [4,5-dibromo-2-(N-hydroxycarbamimidoyl)-thiophen-3-yloxy]-acetic acid in acetic anhydride was heated to 120° C. for 2 hours. The reaction was cooled and diluted with 30 mL of 1N NaOH and 20 mL of water and stirred vigorously for five to ten minutes. The layers were separated and the organic layer dried over magnesium sulfate and filtered. The solvent was removed under reduced pressure to give 37 mg (42%) of [4,5-dibromo-2-(5-methyl-[1,2,4]oxadiazol-3-yl)-thiophen-3-yloxy]-acetic acid as a pale orange solid.

$^1$H NMR (400 MHz, DMSO-D6) δ ppm 2.64 (m, 3 H) 4.80 (m, 2 H).

HRMS: calcd for C9H6Br2N$_2$O$_4$S, 395.8415; found (ESI-FTMS), 418.8306.

EXAMPLE 431

[4,5-Dibromo-2-(5-ethyl-[1,2,4]oxadiazol-3-yl)-thiophen-3-yloxy]-acetic acid

[4,5-Dibromo-2-(5-ethyl-[1,2,4]oxadiazol-3-yl)-thiophen-3-yloxy]-acetic acid was prepared from propargyl chloride and [4,5-dibromo-2-(N-hydroxycarbamimidoyl)-thiophen-3-yloxy]-acetic acid following the procedure in the sixth step of Scheme 56, Example 430 to give 20 mg (26%) of a white solid.

$^1$H NMR (400 MHz, MeOD) δ ppm 1.20 (t, J=7.71 Hz, 3 H) 2.76 (m, J=7.71, 7.71 Hz, 2 H) 4.57 (s, 2 H).

HRMS: calcd for $C_{10}H8Br2N_2O_4S$, 409.8571; found (ESI-FTMS), 410.8644.

EXAMPLE 432

[4,5-Dibromo-2-(5-isopropyl-[1,2,4]oxadiazol-3-yl)-thiophen-3-yloxy]-acetic acid

[4,5-Dibromo-2-(5-isopropyl-[1,2,4]oxadiazol-3-yl)-thiophen-3-yloxy]-acetic acid was prepared from isobutyryl chloride and [4,5-dibromo-2-(N-hydroxycarbamimidoyl)-thiophen-3-yloxy]-acetic acid following the procedure in the sixth step of Scheme 56, Example 430 to give 17 mg (35%) of a white solid.

$^1$H NMR (400 MHz, MeOD) δ ppm 1.33 (m, 6 H) 1.78 (m, 1 H) 4.71 (m, 2 H)

HRMS: calcd for $C_{11}H_{10}Br2N_2O_4S$, 423.8728; found (ESI-FTMS), 424.8808.

EXAMPLE 433

[4-Bromo-5-[3-(1-phenylmethanesulfonyl-piperidin-4-ylamino)-phenyl]-2-(1H-tetrazol-5-yl)-thiophen-3-yloxy]-acetic acid The first step of Scheme 57: A mixture of (4,5-dibromo-2-cyano-thiophen-3-yloxy)-acetic acid ethyl ester (6.0 g, 16.3 mmol), potassium fluoride (2.84 g, 48.9 mmol), Pd(PPh$_3$)$_4$ (381 mg, 0.33 mmol) and 3-aminophenylboronic acid (2.77 g, 17.9 mmol) in a sealed tube was degassed with nitrogen. The solids were suspended in tetrahydrofuran (85 mL), the tube was sealed and the reaction was heated to 100 degrees for 24 hours. The contents were cooled and the material was filtered through a silica gel plug eluting with ethyl acetate. The crude material was purified by column chromatography eluting with 25-50% ethyl acetate-hexane to give 4.56 g (74%) of [5-(3-amino-phenyl)-4-bromo-2-cyano-thiophen-3-yloxy]-acetic acid ethyl ester as a yellow powder.

$^1$H NMR (400 MHz, CHLOROFORM-D) δ ppm 1.34 (t, J=7.20 Hz, 3 H) 3.82 (s, 2 H) 4.34 (q, J=7.24 Hz, 2 H) 5.10 (s, 2 H) 6.77 (ddd, J=8.08, 2.40, 0.88 Hz, 1 H) 6.90 (t, J=1.89 Hz, 1 H) 6.98 (ddd, J=7.58, 1.77, 1.01 Hz, 1 H) 7.24 (t, J=7.96 Hz, 1 H).

The second step of Scheme 57: To a mixture of [5-(3-amino-phenyl)-4-bromo-2-cyano-thiophen-3-yloxy]-acetic acid ethyl ester (316 mg, 0.83 mmol), 1-phenylmethanesulfonyl-piperidin-4-one (209 mg, 0.83 mmol) and acetic acid (72 μL, 1.3 mmol) in 1,2-dichloroethane (10 mL) was added sodium triacetoxyborohydride (439 mg, 2.1 mmol). The reaction was stirred for 24 hours and then diluted with ethyl acetate (75 mL). The organic layer was washed with water (50 mL) and dried over magnesium sulfate. The product was filtered and the organic solvent was removed under reduced pressure. The crude material was taken into the next step without further purification.

$^1$H NMR (400 MHz, CHLOROFORM-D) δ ppm 1.35 (m, J=7.07, 7.07 Hz, 3 H) 1.43 (m, 2 H) 2.03 (m, J=11.12 Hz, 2 H) 2.77 (m, 2 H) 3.33 (s, 1 H) 3.63 (d, J=13.39 Hz, 2 H) 4.24 (s, 2 H) 4.34 (q, J=7.07 Hz, 2 H) 5.10 (s, 2 H) 6.64 (ddd, J=8.21, 2.40, 1.01 Hz, 1 H) 6.76 (m, 1 H) 6.89 (m, 1 H) 7.23 (t, J=7.83 Hz, 1 H) 7.41 (m, 5 H).

The third step of Scheme 57: To a solution of {4-bromo-2-cyano-5-[3-(1-phenylmethanesulfonyl-piperidin-4-ylamino)-phenyl]-thiophen-3-yloxy}-acetic acid ethyl ester (432 mg, 0.70 mmol) and zinc bromide (79 mg, 0.35 mmol) in DME-H$_2$O (6 mL; 1:1) was added sodium azide (91 mg, 1.4 mmol). The reaction was heated to reflux for 48 hours and then cooled to room temperature. The solution was diluted with ethyl acetate 150 mL) and washed with 1N HCl (30 mL) and brine (30 mL). The organic layer was dried over magnesium sulfate and filtered. The solvent was removed under reduced pressure to give [4-bromo-5-[3-(1-phenylmethanesulfonyl-piperidin-4-ylamino)-phenyl]-2-(1H-tetrazol-5-yl)-thiophen-3-yloxy]-acetic acid.

$^1$H NMR (400 MHz, DMSO-D6) δ ppm 1.38 (m, 2 H) 1.95 (m, 2 H) 2.91 (m, 2 H) 3.42 (m, I H) 3.54 (m, J=12.38 Hz, 2 H) 4.40 (s, 2 H) 4.85 (s, 2 H) 5.92 (s, 1 H) 6.71 (m, J=8.21, 1.39 Hz, 1 H) 6.82 (m, J=8.34 Hz, 1 H) 6.87 (m, J=1.77 Hz, 1 H) 7.21 (m, 1 H) 7.40 (m, 5 H).

HRMS: calcd for $C_{25}H_{25}BrN_6O_5S_2$, 632.0511; found (ESI-FTMS), 633.0589.

EXAMPLE 434

[4-Bromo-5-[3-(1-phenylmethanesulfonyl-piperidin-4-ylamino)-phenyl]-2-(1H-tetrazol-5-yl)-thiophen-3-yloxy]-acetic acid isopropyl ester The fourth step of Scheme 57: [4-Bromo-5-[3-(1-phenyl-methanesulfonyl-piperidin-4-ylamino)-phenyl]-2-(1H-tetrazol-5-yl)-thiophen-3-yloxy]-acetic acid (51 mg, 0.08 mmol) was dissolved in 0.3 mL of DMF. To the solution was added isopropanol (1.5 mL) and 1 drop of concentrated sulfuric acid. The reaction was heated to 75 degrees for 24 hours and then cooled to room temperature. The solution was made basic by the addition of solid sodium bicarbonate. The solvent was removed under reduced pressure and the material was purified by preparative HPLC to afford 15 mg (29%) of [4-bromo-5-[3-(1-phenylmethanesulfonyl-piperidin-4-ylamino)-phenyl]-2-(1H-tetrazol-5-yl)-thiophen-3-yloxy]-acetic acid isopropyl ester as a tan solid.

$^1$H NMR (400 MHz, MeOD) δ ppm 1.21 (d, J=6.32 Hz, 6 H) 1.50 (m, 2 H) 2.01 (m, 2 H) 2.88 (m, 2 H) 3.48 (m, J=3.79 Hz, 1 H) 3.66 (m, J=12.63 Hz, 2 H) 4.34 (s, 2 H) 5.09 (m, 1 H) 5.07 (m, 2 H) 6.92 (m, 1 H) 7.08 (m, 2 H) 7.33 (t, J=8.08 Hz, 1 H) 7.41 (m, 5 H).

HRMS: calcd for $C_{28}H_{31}BrN_6O_5S_2$, 674.0981; found (ESI-FTMS), 675.1052.

EXAMPLE 435

[4-Bromo-5-[3-(1-phenylmethanesulfonyl-piperidin-4-ylamino)-phenyl]-2-(1H-tetrazol-5-yl)-thiophen-3-yloxy]-acetic acid methyl ester The fourth step of Scheme 57: [4-Bromo-5-[3-(1-phenyl-methanesulfonyl-piperidin-4-ylamino)-phenyl]-2-(1H-tetrazol-5-yl)-thiophen-3-yloxy]-acetic acid methyl ester was prepared from [4-bromo-5-[3-(1-phenylmethanesulfonyl-piperidin-4-ylamino)-phenyl]-2-(1H-tetrazol-5-yl)-thiophen-3-yloxy]-acetic acid and methanol following the procedure shown in Example 434 to yield 38 mg (39%) of [4-bromo-5-[3-(1-phenylmethanesulfonyl-piperidin-4-ylamino)-phenyl]-2-(1H-tetrazol-5-yl)-thiophen-3-yloxy]-acetic acid methyl ester as a tan solid.

$^1$H NMR (400 MHz, CHLOROFORM-D) δ ppm 1.43 (dd, J=13.52, 3.41 Hz, 2 H) 2.04 (m, 2 H) 2.79 (m, 2 H) 3.36 (s, 1 H) 3.64 (m, 2 H) 3.96 (s, 3 H) 4.25 (s, 2 H) 5.09 (s, 2 H) 6.64 (dd, J=7.83, 2.02 Hz, 1 H) 6.76 (m, 1 H) 6.97 (d, J=8.34 Hz, 1 H) 7.25 (m, 1 H) 7.41 (m, 5 H).

HRMS: calcd for C$_{26}$H$_{27}$BrN$_6$O$_5$S$_2$, 646.0668; found (ESI-FTMS), 647.0742.

EXAMPLE 436

4,5-Dibromo-3-(isobutylcarbamoyl-methoxy)-thiophene-2-carboxylic acid methyl ester Scheme 58: To a solution of 4,5-dibromo-3-carboxymethoxy-thiophene-2-carboxylic acid methyl ester (120 mg, 0.32 mmol) and PS-carbodiimide (0.3 g) in dichloromethane (2.1 mL) was added isobutylamine (25 µL, 0.25 mmol). The reaction was stirred gently for 24 hours. The solid phase resin was removed by filtration and the solvent was removed under reduced pressure to give 112 mg (82%) of 4,5-dibromo-3-(isobutylcarbamoyl-methoxy)-thiophene-2-carboxylic acid methyl ester as a white solid.

$^1$H NMR (400 MHz, CHLOROFORM-D) δ ppm 0.98 (d, J=6.57 Hz, 6 H) 1.89 (m, 1 H) 3.20 (m, 2 H) 3.86 (s, 3 H) 4.73 (s, 2 H).

HRMS: calcd for C$_{12}$H$_{15}$Br2NO$_4$S, 426.9089; found (ESI-FTMS), 427.9164.

EXAMPLE 437

4,5-Dibromo-3-(2-oxo-2-pyrrolidin-1-yl-ethoxy)-thiophene-2-carboxylic acid methyl ester 4,5-Dibromo-3-(2-oxo-2-pyrrolidin-1-yl-ethoxy)-thiophene-2-carboxylic acid methyl ester was prepared according to the procedure shown in Scheme 58, Example 436 to give 125 mg (91%) of a pale beige solid.

$^1$H NMR (400 MHz, CHLOROFORM-D) δ ppm 1.88 (d, J=7.07 Hz, 2 H) 1.99 (m, 2 H) 3.53 (m, 4 H) 3.84 (s, 3 H) 4.94 (s, 2 H).

HRMS: calcd for C$_{12}$H$_{15}$Br2NO$_4$S, 426.9089; found (ESI-FTMS), 427.9164.

EXAMPLE 438

4,5-Dibromo-3-[(2-hydroxy-1-methyl-ethylcarbamoyl)-methoxy]-thiophene-2-carboxylic acid methyl ester Scheme 58: 4,5-Dibromo-3-[(2-hydroxy-1-methyl-ethylcarbamoyl)-methoxy]-thiophene-2-carboxylic acid methyl ester was prepared according to the procedure shown in Scheme 58, Example 436 to give 121 mg (88%) of a white solid.

$^1$H NMR (400 MHz, CHLOROFORM-D) δ ppm 1.28 (d, J=6.82 Hz, 3 H) 3.61 (dd, J=11.37, 6.32 Hz, 1 H) 3.76 (dd, J=11.37, 3.54 Hz, 1 H) 3.87 (s, 3 H) 4.18 (dd, J=7.20, 3.66 Hz, 1 H) 4.73 (m, 2 H) 7.94 (m, 1 H).

HRMS: calcd for C$_{11}$H$_{13}$Br2NO$_5$S, 428.8881; found (ESI-FTMS), 429.8958.

EXAMPLE 439

4,5-Dibromo-3-[(2-tert-butoxycarbonylamino-ethyl-carbamoyl)-methoxy]-thiophene-2-carboxylic acid methyl ester Scheme 58: 4,5-Dibromo-3-[(2-tert-butoxycarbonylamino-ethylcarbamoyl)-methoxy]-thiophene-2-carboxylic acid methyl ester was prepared according to the procedure shown in Scheme 58, Example 436 to give 133 mg (81%) of a pale beige solid.

$^1$H NMR (400 MHz, CHLOROFORM-D) δ ppm 1.46 (m, 9 H) 3.37 (s, 2 H) 3.49 (s, 2 H) 3.89 (s, 3 H) 4.72 (s, 2 H) 5.26 (m, 1 H).

HRMS: calcd for C$_{15}$H$_{20}$Br2N$_2$O$_6$S, 513.9409; found (ESI-FTMS), 514.9498.

EXAMPLE 440

4,5-Dibromo-3-(tert-butylcarbamoyl-methoxy)-thiophene-2-carboxylic acid methyl ester Scheme 58: 4,5-Dibromo-3-(tert-butylcarbamoyl-methoxy)-thiophene-2-carboxylic acid methyl ester was prepared according to the procedure shown in Scheme 58, Example 436 to give 103 mg (75%) of a white solid.

$^1$H NMR (400 MHz, CHLOROFORM-D) δ ppm 1.44 (s, 9 H) 3.87 (s, 3 H) 4.59 (s, 2 H) 7.42 (s, 1 H).

HRMS: calcd for C$_{12}$H$_{15}$Br2NO$_4$S, 426.9089; found (ESI-FTMS), 427.9165.

EXAMPLE 441

4-[2-(4,5-Dibromo-2-methoxycarbonyl-thiophen-3-yloxy)-acetyl]piperazine-1-carboxylic acid tert-butyl ester Scheme 58: 4-[2-(4,5-Dibromo-2-methoxycarbonyl-thiophen-3-yloxy)-acetyl]-piperazine 1-carboxylic acid tert-butyl ester was prepared according to the procedure shown in Scheme 58, Example 436 to give 117 mg (67%) of a white solid.

$^1$H NMR (400 MHz, CHLOROFORM-D) δ ppm 1.51 (m, J=24.00 Hz, 9 H) 3.47 (m, 4 H) 3.62 (s, 4 H) 3.85 (s, 3 H) 4.95 (s, 2 H).

HRMS: calcd for C$_{17}$H$_{22}$Br2N$_2$O$_6$S, 539.9565; found (ESI-FTMS), 540.9646.

EXAMPLE 442

4,5-Dibromo-3-[(2-hydroxy-1-methyl-ethylcarbamoyl)-methoxy]-thiophene-2-carboxylic acid methyl ester Scheme 58: 4,5-Dibromo-3-[(2-hydroxy-1-methyl-ethylcarbamoyl)-methoxy]-thiophene-2-carboxylic acid methyl ester was prepared according to the procedure shown in Scheme 58, Example 436 to give 111 mg (80%) of a white solid.

$^1$H NMR (400 MHz, CHLOROFORM-D) δ ppm 1.28 (d, J=7.07 Hz, 3 H) 2.84 (d, 1 H) 3.61 (dd, J=11.37, 6.32 Hz, 1 H) 3.76 (dd, J=11.49, 3.41 Hz, 1 H) 3.87 (s, 3 H) 4.17 (m, 1 H) 4.73 (m, 2 H) 7.96 (m, 1 H).

HRMS: calcd for C$_{11}$H$_{13}$Br2NO$_5$S, 428.8881; found (ESI-FTMS), 429.8961.

EXAMPLE 443

4,5-Dibromo-3-[2-(2-carbamoyl-pyrrolidin-1-yl)-2-oxo-ethoxy]-thiophene-2-carboxylic acid methyl ester Scheme 58: 4,5-Dibromo-3-[2-(2-carbamoyl-pyrrolidin-1-yl)-2-oxo-ethoxy]-thiophene-2-carboxylic acid methyl ester was prepared according to the procedure shown in Scheme 58, Example 436 to give 91 mg (61%) of a white solid.

¹H NMR (400 MHz, CHLOROFORM-D) δ ppm 2.00 (m, 3 H) 2.45 (m, 1 H) 3.54 (m, 1 H) 3.66 (m, 1 H) 3.84 (m, 3 H) 4.67 (dd, J=8.21, 2.15 Hz, 1 H) 4.99 (m, 2 H) 5.29 (s, 1 H) 7.00 (s, 1 H).

HRMS: calcd for $C_{13}H_{14}Br2N_2O_5S$, 467.8990; found (ESI-FTMS), 468.907.

EXAMPLE 444

3-[(2-Amino-ethylcarbamoyl)-methoxy]-4,5-dibromo-thiophene-2-carboxylic acid methyl ester Scheme 58: 3-[(2-Amino-ethylcarbamoyl)-methoxy]-4,5-dibromo-thiophene-2-carboxylic acid methyl ester was prepared according to the procedure shown in Scheme 58, Example 436 to give 133 mg of a white solid.

¹H NMR (400 MHz, DMSO-D6) δ ppm 2.93 (m, 2 H) 3.42 (q, J=6.23 Hz, 2 H) 3.81 (s, 3 H) 4.66 (s, 2 H) 7.83 (s, 2 H) 8.31 (s, 1 H).

HRMS: calcd for $C_{10}H_{12}Br_2N_2O_4S \cdot HCl$, 449.8651; found (ESI-FTMS), 414.8974.

EXAMPLE 445

3-{[2-(4-Hydroxy-phenyl)-1-methoxycarbonyl-ethylcarbamoyl]-methoxy}-4-methyl-5-[3-(3,3,5,5-tetramethyl-cyclohexyl)-phenyl]-thiophene-2-carboxylic acid methyl ester Scheme 59: A solution of 3-carboxymethoxy-4-methyl-5-[3-(3,3,5,5-tetramethyl-cyclohexyl)-phenyl]-thiophene-2-carboxylic acid methyl ester (250 mg, 0.34 mmol), PS-carbodiimide (0.52 g, 0.68 mmol), PS-DIEA (99 mg, 0.37 mmol) and 2-amino-3-(4-hydroxy-phenyl)-propionic acid methyl ester hydrochloride (79 mg, 0.34) in dichloromethane (4 mL) was stirred for 24 hours. The reaction was filtered and the solid phase resin was washed with dichloromethane (~5 mL). The organic solvents were removed under reduced pressure to yield the desired product. Purification by silica gel chromatography eluting with a 30-50% ethyl acetate-hexane gradient afforded 137 mg (57%) of 3-{[2-(4-Hydroxy-phenyl)-1-methoxycarbonyl-ethylcarbamoyl]-methoxy}-4-methyl-5-[3-(3,3,5,5-tetramethyl-cyclohexyl)-phenyl]-thiophene-2-carboxylic acid methyl ester as a yellow solid.

¹H NMR (400 MHz, CHLOROFORM-D) δ ppm 0.94 (m, 2 H) 0.94 (s, 6 H) 1.11 (m, J=11.37 Hz, 1 H) 1.12 (s, 6 H) 1.31 (d, J=14.40 Hz, 1 H) 1.87 (m, 2 H) 3.14 (dd, J=18.19, 6.32 Hz, 2 H) 3.60 (m, 1 H) 3.72 (s, 3 H) 3.85 (s, 3 H) 4.75 (s, 2 H) 4.93 (m, 1 H) 6.65 (m, 1 H) 6.72 (m, 2 H) 6.84 (m, 1 H) 6.88 (m, J=7.96, 1.39 Hz, 1 H) 7.07 (m, 2 H) 7.22 (t, J=7.83 Hz, 1 H).

HRMS: calcd for $C_{34}H_{41}BrN_2O_7S$, 700.1818; found (ESI-FTMS), 701.1886.

EXAMPLE 446

1-(2-{2-Methoxycarbonyl-4-methyl-5-[3-(3,3,5,5-tetramethyl-cyclohexyl)-phenyl]-thiophen-3-yloxy}-acetyl)-pyrrolidine-2-carboxylic acid methyl ester Scheme 59: 1-(2-{2-Methoxycarbonyl-4-methyl-5-[3-(3,3,5,5-tetramethyl-cyclohexyl)-phenyl]-thiophen-3-yloxy}-acetyl)-pyrrolidine-2-carboxylic acid methyl ester was prepared following the procedure in Scheme 59, Example 445 to afford 103 mg (48%) as a yellow solid.

¹H NMR (400 MHz, CHLOROFORM-D) δ ppm 0.91 (m, 2 H) 0.94 (s, 6 H) 1.10 (m, J=11.37 Hz, 1 H) 1.12 (s, 6 H) 1.30 (m, 1 H) 1.89 (m, J=12.13 Hz, 2 H) 2.07 (m, 2 H) 2.23 (m, 2 H) 3.60 (m, 2 H) 3.74 (s, 3 H) 3.80 (m, 1 H) 3.87 (s, 3 H) 4.58 (m, J=8.34, 3.79 Hz, 1 H) 4.91 (m, 2 H) 6.63 (dd, J=8.59, 2.02 Hz, 1 H) 6.89 (m, 2 H) 7.21 (t, J=7.83 Hz, 1 H).

HRMS: calcd for $C_{30}H_{39}BrN_2O_6S$, 634.1712; found (ESI-FTMS), 635.1809.

EXAMPLE 447

4-Methyl-3-(2-oxo-2-pyrrolidin-1-yl-ethoxy)-5-[3-(3,3,5,5-tetramethyl-cyclohexyl)-phenyl]-thiophene-2-carboxylic acid methyl ester Scheme 59: 4-Methyl-3-(2-oxo-2-pyrrolidin-1-yl-ethoxy)-5-[3-(3,3,5,5-tetramethyl-cyclohexyl)-phenyl]-thiophene-2-carboxylic acid methyl ester was prepared following the procedure in Scheme 59, Example 445 to afford 83 mg (76%) as a yellow solid.

¹H NMR (400 MHz, CHLOROFORM-D) δ ppm 0.91 (d, J=19.20 Hz, 3 H) 0.94 (s, 6 H) 1.10 (d, J=11.87 Hz, 3 H) 1.12 (s, 6 H) 1.30 (d, J=14.40 Hz, 1 H) 1.88 (m, 2 H) 1.99 (m, 2 H) 3.56 (t, J=6.95 Hz, 2 H) 3.62 (t, J=6.82 Hz, 2 H) 3.87 (s, 3 H) 4.89 (s, 2 H) 6.63 (m, 1 H) 6.90 (m, 2 H) 7.21 (t, J=7.83 Hz, 1 H).

HRMS: calcd for $C_{28}H_{37}BrN_2O_4S$, 576.1657; found (ESI-FTMS), 289.0921.

EXAMPLE 448

3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester Scheme 59: 3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester was prepared following the procedure in Scheme 59, Example 445 to afford 36 mg (33%) as a yellow solid.

¹H NMR (400 MHz, CHLOROFORM-D) δ ppm 0.94 (s, 2 H) 0.94 (s, 6 H) 1.09 (m, 2 H) 1.12 (s, 6 H) 1.29 (d, J=6.82 Hz, 3 H) 1.88 (d, J=13.64 Hz, 2 H) 2.98 (s, 1 H) 3.60 (s, 2 H) 3.77 (m, 1 H) 3.88 (s, 3 H) 4.20 (m, 1 H) 4.78 (m, 2 H) 6.65 (m, 1 H) 6.85 (m, 2 H) 7.23 (t, J=7.83 Hz, 1 H).

HRMS: calcd for $C_{27}H_{37}BrN_2O_5S$, 580.1607; found (ESI-FTMS), 581.1702.

EXAMPLE 449

3-[(1-Methoxycarbonyl-2-methyl-propylcarbamoyl)-methoxy]-4-methyl-5-[3-(3,3,5,5-tetramethyl-cyclohexyl)-phenyl]-thiophene-2-carboxylic acid methyl ester Scheme 59: 3-[(1-Methoxycarbonyl-2-methyl-propylcarbamoyl)-methoxy]-4-methyl-5-[3-(3,3,5,5-tetramethyl-cyclohexyl)-phenyl]-thiophene-2-carboxylic acid methyl ester was prepared following the procedure in Scheme 59, Example 445 to afford 132 mg (68%) as a yellow solid.

¹H NMR (400 MHz, CHLOROFORM-D) δ ppm 0.94 (m, 2 H) 0.94 (s, 6 H) 1.02 (d, J=2.02 Hz, 3 H) 1.03 (d, J=2.02 Hz, 3 H) 1.12 (m, 1 H) 1.12 (s, 6 H) 1.31 (m, 1 H) 1.87 (m, 2 H) 2.29 (m, 1 H) 3.63 (m, 1 H) 3.76 (s, 3 H) 3.89 (s, 3 H) 4.64 (dd, J=8.97, 5.43 Hz, 1 H) 4.81 (s, 2 H) 6.64 (m, 1 H) 6.85 (m, 1 H) 6.89 (m, J=7.58, 1.01 Hz, 1 H) 7.22 (t, J=7.83 Hz, 1 H) 8.02 (d, J=8.84 Hz, 1 H).

HRMS: calcd for $C_{30}H_{41}BrN_2O_6S$, 636.1869; found (ESI-FTMS), 637.195.

EXAMPLE 450

3-[(1-Methoxycarbonyl-3-methyl-butylcarbamoyl)-methoxy]-4-methyl-5-[3-(3,3,5,5-tetramethyl-cyclohexyl)-phenyl]-thiophene-2-carboxylic acid methyl ester Scheme 59: 3-[(1-Methoxycarbonyl-3-methyl-butylcarbamoyl)-methoxy]-4-methyl-5-[3-(3,3,5,5-tetramethyl-cyclohexyl)-phenyl]-thiophene-2-carboxylic acid methyl ester was prepared following the procedure in Scheme 59, Example 445 to afford 178 mg (89%) as a yellow solid.

$^1$H NMR (400 MHz, CHLOROFORM-D) δ ppm 0.94 (s, 2 H) 0.94 (s, 6 H) 0.97 (d, J=3.03 Hz, 3 H) 0.99 (d, J=3.03 Hz, 3 H) 1.11 (m, J=11.37 Hz, 1 H) 1.12 (s, 6 H) 1.31 (m, 1 H) 1.75 (m, 2 H) 1.89 (d, J=12.63 Hz, 2 H) 3.60 (m, 1 H) 3.75 (s, 3 H) 3.88 (s, 3 H) 4.71 (m, 1 H) 4.82 (d, J=1.52 Hz, 2 H) 6.65 (m, 1 H) 6.84 (m, 1 H) 6.88 (m, 1 H) 7.22 (t, J=7.83 Hz, 1 H) 8.21 (d, J=8.59 Hz, 1 H).

HRMS: calcd for $C_{31}H_{43}BrN_2O_6S$, 650.2025; found (ESI-FTMS), 651.2106.

EXAMPLE 451

3-[(1-Methoxycarbonyl-2-phenyl-ethylcarbamoyl)-methoxy]-4-methyl-5-[3-(3,3,5,5-tetramethyl-cyclohexyl)-phenyl]-thiophene-2-carboxylic acid methyl ester Scheme 59: 3-[(1-Methoxycarbonyl-2-phenyl-ethylcarbamoyl)-methoxy]-4-methyl-5-[3-(3,3,5,5-tetramethyl-cyclohexyl)-phenyl]-thiophene-2-carboxylic acid methyl ester was prepared following the procedure in Scheme 59, Example 445 to afford 188 mg (81%) as a yellow solid.

$^1$H NMR (400 MHz, CHLOROFORM-D) δ ppm 0.94 (d, J=7.07 Hz, 2 H) 0.94 (s, 6 H) 1.11 (d, J=11.12 Hz, 1 H) 1.13 (s, 6 H) 1.30 (m, 1 H) 1.87 (s, 2 H) 3.22 (m, 2 H) 3.61 (m, 1 H) 3.72 (s, 3 H) 3.84 (s, 3 H) 4.75 (s, 2 H) 4.97 (m, 1 H) 6.64 (m, 1 H) 6.83 (m, 1 H) 6.87 (m, 1 H) 7.26 (m, 5 H) 8.11 (d, J=8.08 Hz, 1 H).

HRMS: calcd for $C_{34}H_{41}BrN_2O_6S$, 684.1869; found (ESI-FTMS), 685.1947.

EXAMPLE 452

3-[2-(2-Carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester Scheme 59: 3-[2-(2-Carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester was prepared following the procedure in Scheme 59, Example 445 to afford 78 mg (66%) as a yellow solid.

$^1$H NMR (400 MHz, DMSO-D6) δ ppm 0.94 (m, 2 H) 0.91 (s, 6 H) 1.08 (m, 1 H) 1.09 (s, 6 H) 1.26 (m, 1 H) 1.75 (d, J=11.37 Hz, 2 H) 1.87 (m, 2 H) 2.01 (m, 2 H) 3.49 (m, 2 H) 3.81 (dd, 3 H) 4.22 (dd, J=8.72, 2.91 Hz, 2 H) 4.99 (m, J=49.77, 14.15 Hz, 2 H) 5.71 (d, J=7.58 Hz, 2 H) 6.68 (dd, J=7.71, 2.65 Hz, 1 H) 6.75 (m, J=9.35 Hz, 1 H) 6.85 (t, J=1.64 Hz, 1 H) 6.95 (s, 1 H) 7.18 (t, J=7.96 Hz, 1 H) 7.28 (s, 1 H).

HRMS: calcd for $C_{29}H_{38}BrN_3O_5S$, 619.1716; found (ESI-FTMS), 620.1794.

EXAMPLE 453

3-[(2-tert-Butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester Scheme 59: 3-[(2-tert-Butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester was prepared following the procedure in Scheme 59, Example 453 to afford 120 mg (95%) as a yellow solid.

$^1$H NMR (400 MHz, CHLOROFORM-D) δ ppm 0.94 (m, J=5.56 Hz, 2 H) 0.94 (s, 6 H) 1.12 (m, 1 H) 1.12 (s, 6 H) 1.31 (m, 1 H) 1.44 (s, 9 H) 1.87 (s, 2 H) 3.39 (s, 2 H) 3.51 (s, 2 H) 3.62 (m, 1 H) 3.91 (s, 3 H) 4.78 (s, 2 H) 5.37 (s, 1 H) 6.65 (m, 1 H) 6.84 (m, 1 H) 6.87 (m, 1 H) 7.23 (m, 1 H) 8.27 (s, 1 H).

EXAMPLE 454

4-(2-{2-Methoxycarbonyl-4-methyl-5-[3-(3,3,5,5-tetramethyl-cyclohexyl)-phenyl]-thiophen-3-yloxy}-acetyl)-piperazine-1-carboxylic acid tert-butyl ester Scheme 59: 4-(2-{2-Methoxycarbonyl-4-methyl-5-[3-(3,3,5,5-tetramethyl-cyclohexyl)-phenyl]-thiophen-3-yloxy}-acetyl)-piperazine-1-carboxylic acid tert-butyl ester was prepared following the procedure in Scheme 59, Example 445 to afford 121 mg (92%) as a yellow solid.

$^1$H NMR (400 MHz, CHLOROFORM-D) δ ppm 0.93 (m, 2 H) 0.94 (s, 6 H) 1.11 (d, J=11.37 Hz, 1 H) 1.12 (s, 6 H) 1.30 (m, 1 H) 1.48 (s, 9 H) 1.87 (s, 2 H) 3.64 (m, 9 H) 3.87 (s, 3 H) 4.92 (s, 2 H) 6.63 (m, 1 H) 6.88 (m, 2 H) 7.21 (t, J=7.83 Hz, 1 H).

EXAMPLE 455

3-[(2-Amino-ethylcarbamoyl)-methoxy]-4-methyl-5-[3-(3,3,5,5-tetramethyl-cyclohexyl)-phenyl]-thiophene-2-carboxylic acid methyl ester Scheme 60: To 3-[(2-tert-Butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester in dichloromethane was added HCl in dioxane (excess). The solvent was removed under reduced pressure to give 63 mg (82%) of 3-[(2-amino-ethylcarbamoyl)-methoxy]-4-methyl-5-[3-(3,3,5,5-tetramethyl-cyclohexyl)-phenyl]-thiophene-2-carboxylic acid methyl ester as a white solid.

$^1$H NMR (400 MHz, DMSO-D6) δ ppm 0.91 (s, 6 H) 0.99 (s, 2 H) 1.09 (m, 1 H) 1.08 (s, 6 H) 1.24 (m, J=5.05 Hz, 1 H) 1.73 (m, 2 H) 3.13 (d, J=18.95 Hz, 4 H) 3.53 (m, J=6.82 Hz, 1 H) 3.82 (m, 3 H) 5.05 (m, 2 H) 6.74 (m, 1 H) 6.81 (m, 1 H) 6.89 (m, 1 H) 7.22 (m, 1 H) 9.10 (m, 1 H).

HRMS: calcd for $C_{26}H_{36}BrN_3O_4S$. 2.00 HCl, 637.1143; found (ESI-FTMS), 566.1681.

EXAMPLE 456

4-Methyl-3-(2-oxo-2-piperazin-1-yl-ethoxy)-5-[3-(3,3,5,5-tetramethyl-cyclohexyl)-phenyl]-thiophene-2-carboxylic acid methyl ester Scheme 60: 4-Methyl-3-(2-oxo-2-piperazin-1-yl-ethoxy)-5-[3-(3,3,5,5-tetramethyl-cyclohexyl)-phenyl]-thiophene-2-carboxylic acid methyl ester was prepared following the procedure in Scheme 60, Example 455 to afford 57 mg (78%) as a white solid.

¹H NMR (400 MHz, DMSO-D6) δ ppm 0.91 (s, 6 H) 1.00 (m, 2 H) 1.08 (m, 6 H) 1.25 (m, 2 H) 1.73 (m, 2 H) 2.94 (m, J=6.06 Hz, 4 H) 3.44 (m, 4 H) 3.57 (m, 1 H) 3.83 (s, 2 H) 4.67 (s, 2 H) 6.87 (s, 3 H) 7.26 (m, 1 H) 7.88 (s, 2 H) 8.35 (m, 1 H).

HRMS: calcd for $C_{28}H_{38}BrN_3O_4S \cdot 2.00$ HCl, 663.1300; found (ESI-FTMS), 592.1835.

EXAMPLE 457

4-Bromo-5-[3-(1-phenylmethanesulfonyl-piperidin-4-yl)-phenyl]-3-(piperidin-4-yloxycarbonyl-methoxy)-thiophene-2-carboxylic acid methyl ester The first step of Scheme 61: To 4-bromo-3-carboxymethoxy-5-[3-(1-phenylmethanesulfonyl-piperidin-4-yl)-phenyl]-thiophene-2-carboxylic acid methyl ester (956 mg, 1.5 mmol), HATU (570 mg, 1.5 mmol), diisopropylethylamine (392 μL, 2.3 mmol) in dimethylformamide (7.5 mL) was added 4-hydroxy-piperidine-1-carboxylic acid tert-butyl ester (403 mg, 2.0 mmol). After four days, the reaction was diluted with ethyl acetate (250 mL) and washed with water (3×100 mL), saturated sodium bicarbonate (100 mL), 5% citric acid (100 mL) and brine (100 mL). The organic layer was dried over magnesium sulfate and filtered. The solvent was removed and the material was purified by column chromatography eluting with 45% ethyl acetate-hexane to give 523 mg (43%) of 4-(2-{4-bromo-2-methoxycarbonyl-5-[3-(1-phenylmethanesulfonyl-piperidin-4-yl)-phenyl]-thiophen-3-yloxy}-acetoxy)-piperidine-1-carboxylic acid tert-butyl ester as a pale yellow solid.

¹H NMR (400 MHz, CHLOROFORM-D) δ ppm 1.39 (m, 2 H) 1.46 (s, 9 H) 1.68 (s, 2 H) 1.89 (s, 2 H) 2.05 (m, 2 H) 2.79 (m, 2 H) 3.24 (m, 2 H) 3.37 (m, 2 H) 3.63 (s, 4 H) 3.87 (d, 3 H) 4.24 (s, 2 H) 4.95 (s, 2 H) 5.09 (d, J=4.29 Hz, 1 H) 6.62 (m, 1 H) 6.82 (m, 1 H) 6.94 (d, J=6.57 Hz, 1 H) 7.22 (t, J=7.96 Hz, 1 H) 7.40 (m, 5 H).

HRMS: calcd for $C_{36}H_{44}BrN_3O_9S_2$, 805.1702; found (ESI-FTMS), 806.1774.

The second step of Scheme 61: A solution of 4-(2-{4-bromo-2-methoxycarbonyl-5-[3-(1-phenylmethanesulfonyl-piperidin-4-yl)-phenyl]-thiophen-3-yloxy}-acetoxy)-piperidine-1-carboxylic acid tert-butyl ester (500 mg, 0.62 mmol) in TFA-$CH_2Cl_2$ (15 mL; 1:6.5) was stirred for 3 hours. The solvents were removed under reduced pressure. The material was dissolved in dichloromethane (200 mL) and washed with water (100 mL). The organic layer was dried over magnesium sulfate and filtered. The solvent was removed under reduced pressure to give 376 mg (74%) of 4-bromo-5-[3-(1-phenyl-methanesulfonyl-piperidin-4-yl)-phenyl]-3-(piperidin-4-yloxycarbonylmethoxy)-thiophene-2-carboxylic acid methyl ester as a yellow solid.

¹H NMR (400 MHz, DMSO-D6) δ ppm 1.37 (m, 2 H) 1.80 (m, 2 H) 2.02 (m, 4 H) 2.92 (m, 2 H) 3.14 (m, 4 H) 3.38 (m, J=7.07 Hz, 2 H) 3.52 (m, 2 H) 3.81 (s, 3 H) 4.40 (s, 2 H) 5.01 (s, 2 H) 5.05 (m, 1 H) 5.92 (d, J=7.83 Hz, 1 H) 6.73 (m, J=8.08 Hz, 1 H) 6.80 (m, 1 H) 6.84 (m, J=1.77, 1.77 Hz, 1 H) 7.21 (m, 1 H) 7.40 (m, 5 H) 8.39 (s, 1 H).

HRMS: calcd for $C_{31}H_{36}BrN_3O_7S_2 \cdot C2HF3O_2$, 819.1107; found (ESI-FTMS), 706.1239.

EXAMPLE 458

4-Bromo-3-methoxycarbonylmethoxy-5-[3-(1-phenylmethanesulfonyl-piperidin-4-yl)-phenyl]-thiophene-2-carboxylic acid 2,2-dimethyl-propionyloxymethyl ester Scheme 62: A solution of 4-bromo-3-methoxycarbonyl-methoxy-5-[3-(1-phenylmethanesulfonyl-piperidin-4-yl)-phenyl]-thiophene-2-carboxylic acid (22 mg, 0.04 mmol) and triethylamine (25 μL, 0.18 mmol) in DMF (250 μL) was cooled to 0° C. The reaction was treated with 2,2-dimethyl-propionic acid iodomethyl ester (10 mg, 0.4 mmol) and warmed slowly to room temperature. The solution was diluted with ethyl acetate (50 mL) and washed with brine (25 mL). The organic layer was dried over magnesium sulfate and filtered. The solvent was removed under reduced pressure and the material was purified by combi-flash chromatography eluting with 5-30% ethyl acetate-hexane to give 14 mg (54%) of 4-bromo-3-methoxycarbonylmethoxy-5-[3-(1-phenyl-methanesulfonyl-piperidin-4-yl)-phenyl]-thiophene-2-carboxylic acid 2,2-dimethyl-propionyloxymethyl ester as a white solid.

¹H NMR (400 MHz, CHLOROFORM-D) δ ppm 1.23 (m, 9 H) 1.43 (s, 2 H) 2.07 (m, 2 H) 2.79 (m, 2 H) 3.36 (m, 1 H) 3.63 (m, 2 H) 3.84 (s, 3 H) 4.24 (s, 2 H) 4.91 (s, 2 H) 5.30 (s, 1 H) 5.93 (s, 2 H) 6.62 (m, 1 H) 6.81 (m, 1 H) 6.96 (m, J=1.77 Hz, 1 H) 7.22 (t, J=7.96 Hz, 1 H) 7.40 (m, 5 H).

HRMS: calcd for $C_{32}H_{37}BrN_2O_9S_2$, 736.1124; found (ESI-FTMS), 737.1204.

EXAMPLE 459

4-Bromo-3-isopropoxycarbonylmethoxy-5-[3-(1-phenylmethanesulfonyl-piperidin-4-yl)-phenyl]-thiophene-2-carboxylic acid 2,2-dimethyl-propionyloxymethyl ester Scheme 62: 4-bromo-3-isopropoxycarbonylmethoxy-5-[3-(1-phenylmethanesulfonyl-piperidin-4-yl)-phenyl]-thiophene-2-carboxylic acid 2,2-dimethyl-propionyloxymethyl ester was prepared following the procedure in Scheme 62, Example 458 to afford 110 mg (53%) of a pale yellow solid.

¹H NMR (400 MHz, CHLOROFORM-D) δ ppm 1.23 (s, 9 H) 1.28 (d, J=2.53 Hz, 3 H) 1.30 (s, 3 H) 1.42 (s, 2 H) 2.05 (s, 2 H) 2.80 (m, 2 H) 3.36 (s, 1 H) 3.61 (s, 2 H) 4.24 (s, 2 H) 4.90 (s, 2 H) 5.16 (m, 1 H) 5.93 (s, 2 H) 6.62 (m, 1 H) 6.82 (m, 1 H) 6.96 (s, 1 H) 7.22 (m, 1 H) 7.40 (m, 5 H).

HRMS: calcd for $C_{34}H_{41}BrN_2O_9S_2$, 764.1437; found (ESI-FTMS), 765.1517.

EXAMPLE 460

4-Bromo-3-isopropoxycarbonylmethoxy-5-[3-(1-phenylmethanesulfonyl-piperidin-4-yl)-phenyl]-thiophene-2-carboxylic acid acetoxymethyl ester Scheme 62: 4-Bromo-3-isopropoxycarbonylmethoxy-5-[3-(1-phenylmethanesulfonyl-piperidin-4-yl)-phenyl]-thiophene-2-carboxylic acid acetoxymethyl ester was prepared following the procedure in Scheme 62, Example 458 to afford 142 mg (62%) of a yellow solid.

¹H NMR (400 MHz, CHLOROFORM-D) δ ppm 1.28 (d, J=4.80 Hz, 3 H) 1.31 (s, 3 H) 1.42 (s, 2 H) 2.05 (s, 2 H) 2.16 (m, 3 H) 2.78 (m, 2 H) 3.35 (s, 1 H) 3.64 (s, 2 H) 4.24 (s, 2 H)

4.90 (s, 2 H) 5.17 (m, 1 H) 5.91 (s, 2 H) 6.62 (dd, J=7.33, 2.27 Hz, 1 H) 6.82 (m, 1 H) 6.95 (d, J=8.34 Hz, 1 H) 7.22 (t, J=7.96 Hz, 1 H) 7.41 (m, 5 H).

HRMS: calcd for $C_{31}H_{35}BrN_2O_9S_2$, 722.0967; found (ESI-FTMS), 723.105.

EXAMPLE 461

4,5-Dibromo-3-methoxycarbonylmethoxy-thiophene-2-carboxylic acid 2,2-dimethyl-propionyloxymethyl ester Scheme 62: 4,5-Dibromo-3-methoxycarbonylmethoxy-thiophene-2-carboxylic acid 2,2-dimethyl-propionyloxymethyl ester was prepared from 4,5-dibromo-3-methoxycarbonylmethoxy-thiophene-2-carboxylic acid following the procedure in Scheme 62, Example 458 to afford 123 mg (97%) of a yellow solid.

$^1$H NMR (400 MHz, CHLOROFORM-D) δ ppm 1.22 (s, 9 H) 3.81 (s, 3 H) 4.91 (s, 2 H) 5.89 (s, 2 H).

EXAMPLE 462

[5-Bromo-4-methyl-2-(1H-tetrazol-5-yl)-thiophen-3-yloxy]-acetic acid

The first step of Scheme 63: (5-bromo-2-carbamoyl-4-methyl-thiophen-3-yloxy)-acetic acid was prepared according to the procedure in the first step of Scheme 56, Example 430, to yield a light gray solid in 78% yield.

$^1$H NMR (400 MHz, DMSO-D6) δ ppm 2.12 (s, 3 H) 4.81 (s, 2 H) 7.72 (s, 1 H) 7.95 (s, 1 H) 13.40 (m, 1 H).

The second step of Scheme 63: The procedure in the second step of Scheme 56, Example 430 was followed to provide 3.48 g (89%) of (5-bromo-2-carbamoyl-4-methyl-thiophen-3-yloxy)-acetic acid as a light brown solid.

$^1$H NMR (400 MHz, CHLOROFORM-D) δ ppm 2.16 (s, 3 H) 3.85 (s, 2 H) 4.65 (s, 2 H) 5.64 (s, 1 H) 7.93 (s, 1 H).

The third step of Scheme 63: The procedure in the third step of Scheme 56, Example 430 was used to provide 3.27 g (89%) of (5-bromo-2-cyano-4-methyl-thiophen-3-yloxy)-acetic acid methyl ester.

$^1$H NMR (400 MHz, CHLOROFORM-D) δ ppm 2.10 (s, 3 H) 3.85 (s, 3 H) 5.05 (s, 2 H).

The fifth step of Scheme 63: Using the procedure in the third step of Scheme 57, Example 433, 109 mg (88%) of [5-bromo-4-methyl-2-(1H-tetrazol-5-yl)-thiophen-3-yloxy]-acetic acid was prepared as a white solid.

$^1$H NMR (400 MHz, MeOD) δ ppm 2.15 (m, 3 H) 4.80 (s, 2 H).

HRMS: calcd for $C_8H_7BrN_4O_3S$, 317.9422; found (ESI-FTMS), 318.94949.

EXAMPLE 463

[4-Methyl-5-phenyl-2-(1H-tetrazol-5-yl)-thiophen-3-yloxy]-acetic acid

The fourth step of Scheme 63: The procedure in the first step of Scheme 57, Example 433, was used to generate 152 mg (85%) of (2-cyano-4-methyl-5-phenyl-thiophen-3-yloxy)-acetic acid methyl ester as a white solid.

$^1$H NMR (400 MHz, CHLOROFORM-D) δ ppm 2.18 (s, 3 H) 3.86 (s, 3 H) 5.10 (s, 2 H) 7.43 (m, 5 H).

The fifth step of Scheme 63: Using the procedure in the third step of Scheme 57, Example 433, 29 mg (21%) of [4-methyl-5-phenyl-2-(1H-tetrazol-5-yl)-thiophen-3-yloxy]-acetic acid was prepared as a white solid.

$^1$H NMR (400 MHz, MeOD) δ ppm 2.22 (m, 3 H) 4.87 (m, 2 H) 7.38 (m, 5 H).

HRMS: calcd for $C_{14}H_{12}N_4O_3S$, 316.0630; found (ESI-FTMS), 317.07.

EXAMPLE 464

[5-Bromo-4-methyl-2-(2-methyl-2H-tetrazol-5-yl)-thiophen-3-yloxy]-acetic acid

The sixth step of Scheme 63: To a solution of [5-bromo-4-methyl-2-(1H-tetrazol-5-yl)-thiophen-3-yloxy]-acetic acid and potassium carbonate in dimethylformamide was added methyliodide. After 2 hours the reaction was diluted with ethyl acetate and washed with 5% aqueous lithium chloride. The organic layer was dried over magnesium sulfate and filtered. The solvent was removed under reduced pressure and the material was purified by preparative HPLC to give 23 mg (66%) of [5-bromo-4-methyl-2-(2-methyl-2H-tetrazol-5-yl)-thiophen-3-yloxy]-acetic acid methyl ester as a white solid.

$^1$H NMR (400 MHz, MeOD) δ ppm 2.14 (s, 3 H) 3.71 (s, 3 H) 4.34 (s, 3 H) 4.79 (s, 2 H).

The seventh step of Scheme 63: The procedure in the fourth step of Scheme 56, Example 430 was used to prepare 17 mg (81%) of [5-bromo-4-methyl-2-(2-methyl-2H-tetrazol-5-yl)-thiophen-3-yloxy]-acetic acid as a white powder.

$^1$H NMR (400 MHz, MeOD) δ ppm 2.09 (m, 3 H) 4.29 (m, 3 H) 4.67 (m, 2 H).

HRMS: calcd for C9H9BrN$_4$O$_3$S, 331.9579; found (ESI-FTMS), 332.9653.

EXAMPLE 465

3-Carboxymethoxy-5-{3-[1-(3-chloro-benzenesulfonyl)-piperidin-4-ylamino]-pheny}-4-methyl-thiophene-2-carboxylic acid The first step of Scheme 64: 3-tert-Butoxycarbonylmethoxy-5-{3-[1-(3-chloro-benzenesulfonyl)-piperidin-4-ylamino]-phenyl}-4-methyl-thiophene-2-carboxylic acid methyl ester was prepared following the procedure in the first step of Scheme 52, Example 419, to give 79 mg (57%) of a yellow solid.

$^1$H NMR (400 MHz, CHLOROFORM-D) δ ppm 1.48 (s, 9 H) 1.55 (m, 2 H) 2.15 (m, J=13.52, 3.16 Hz, 2 H) 2.23 (s, 3 H) 2.60 (m, 2 H) 3.30 (m, 1 H) 3.72 (m, 2 H) 3.85 (s, 3 H) 4.79 (t, 2 H) 6.56 (m, 2 H) 6.78 (dd, J=6.69, 1.64 Hz, 1 H) 7.19 (t, J=7.83 Hz, 1 H) 7.51 (m, 1 H) 7.60 (ddd, J=8.02, 2.08, 1.01 Hz, 1 H) 7.67 (m, 1 H) 7.77 (t, J=1.89 Hz, 1 H).

HRMS: calcd for $C_{25}H_{25}ClN_2O_7S_2$, 564.0792; found (ESI-FTMS), 565.08651.

The second step of Scheme 64: 3-Carboxymethoxy-5-{3-[1-(3-chloro-benzenesulfonyl)-piperidin-4-ylamino]-phenyl}-4-methyl-thiophene-2-carboxylic acid was prepared following the procedure in the first step of Scheme 53, Example 421 to give 50 mg (40%) of a beige solid.

$^1$H NMR (400 MHz, DMSO-D6) δ ppm 1.41 (m, J=4.55 Hz, 3 H) 1.76 (m, 1 H) 1.95 (s, 2 H) 2.15 (s, 3 H) 2.60 (m, 2 H) 3.35 (m, 1 H) 4.84 (s, 2 H) 5.83 (m, 1 H) 6.62 (m, 3 H) 7.13 (t, J=7.96 Hz, 1 H) 7.74 (m, 3 H) 7.83 (m, 1 H).

EXAMPLE 466

3-Carboxymethoxy-5-{3-[1-(2-chloro-benzenesulfonyl)-piperidin-4-ylamino]-phenyl}-4-methyl-thiophene-2-carboxylic acid The first step of Scheme 64: 5-{3-[1-(2-Chloro-benzenesulfonyl)-piperidin-4-ylamino]-phenyl}-3-methoxycarbonylmethoxy-4-methyl-thiophene-2-carboxylic acid tert-butyl ester was prepared following the procedure in the first step of Scheme 52, Example 419, to give 112 mg (80%) of a tan solid.

$^1$H NMR (400 MHz, CHLOROFORM-D) δ ppm 1.49 (m, 9 H) 1.56 (m, 2 H) 2.13 (m, 2 H) 2.24 (s, 3 H) 2.98 (m, 2 H) 3.43 (m, 1 H) 3.62 (m, 1 H) 3.85 (m, 2 H) 3.85 (m, 3 H) 4.79 (d, 2 H) 6.58 (m, 1 H) 6.62 (m, 1 H) 6.79 (m, J=7.58 Hz, 1 H) 7.20 (t, J=7.83 Hz, 1 H) 7.41 (ddd, J=8.21, 6.69, 1.52 Hz, 1 H) 7.50 (m, J=7.58, 7.58, 1.52 Hz, 1 H) 7.53 (d, J=1.52 Hz, 1 H) 8.08 (dd, J=7.71, 1.89 Hz, 1 H).

The second step of Scheme 64: Step B: 3-Carboxymethoxy-5-{3-[1-(2-chloro-benzenesulfonyl)-piperidin-4-ylamino]-phenyl}-4-methyl-thiophene-2-carboxylic acid was prepared following the procedure in the first step of Scheme 53, Example 421 to give 53 mg (43%) of a beige solid.

$^1$H NMR (400 MHz, DMSO-D6) δ ppm 1.41 (d, J=5.31 Hz, 2 H) 1.94 (s, 2 H) 2.17 (m, 3 H) 2.96 (s, 2 H) 3.65 (s, 2 H) 4.85 (s, 2 H) 5.87 (t, 1 H) 6.39 (none, 1 H) 6.63 (m, J=6.95, 6.95 Hz, 2 H) 6.68 (s, 1 H) 7.15 (t, J=7.83 Hz, 1 H) 7.58 (m, 1 H) 7.70 (m, 2 H) 7.99 (dd, J=7.83, 1.52 Hz, 1 H).

HRMS: calcd for $C_{25}H_{25}ClN_2O_7S_2$, 564.0792; found (ESI-FTMS), 565.08653.

EXAMPLE 467

3-Carboxymethoxy-4-methyl-5-{3-[1-(2-nitro-benzenesulfonyl)-piperidin-4-ylamino]-phenyl}-thiophene-2-carboxylic acid The first step of Scheme 64: 3-tert-Butoxycarbonylmethoxy-4-methyl-5-{3-[1-(2-nitro-benzenesulfonyl)-piperidin-4-ylamino]-phenyl}-thiophene-2-carboxylic acid methyl ester was prepared following the procedure in the first step of Scheme 52, Example 419, to give 71 mg (50%) of a tan solid.

$^1$H NMR (400 MHz, CHLOROFORM-D) δ ppm 1.49 (s, 9 H) 1.52-1.63 (m, 2 H) 2.11-2.20 (m, 2 H) 2.24 (s, 3 H) 2.94-3.06 (m, 2 H) 3.40-3.47 (m, 1 H) 3.60-3.68 (m, 1 H) 3.78-3.88 (m, 2 H) 3.85 (s, 3 H) 4.79 (s, 2 H) 6.55-6.63 (m, 2 H) 6.77-6.82 (m, 1 H) 7.21 (t, J=7.83 Hz, 1 H) 7.61-7.66 (m, 1 H) 7.67-7.78 (m, 2 H) 7.99-8.04 (m, 1 H).

The second step of Scheme 64: The procedure in the first step of Scheme 53, Example 421 was followed to give 51 mg (40%) of 3-carboxymethoxy-4-methyl-5-{3-[1-(2-nitro-benzenesulfonyl)-piperidin-4-ylamino]-phenyl}-thiophene-2-carboxylic acid as a yellow solid.

$^1$H NMR (400 MHz, DMSO-D6) δ ppm 1.42 (m, 2 H) 1.99 (m, 2 H) 2.16 (s, 3 H) 2.96 (d, J=9.85 Hz, 2 H) 3.47 (s, 1 H) 3.64 (s, 2 H) 4.84 (s, 2 H) 5.83 (m, 1 H) 6.63 (m, 2 H) 6.66 (m, J=1.77 Hz, 1 H) 7.15 (m, J=7.96, 7.96 Hz, 1 H) 7.87 (dt, J=7.58, 1.52 Hz, 1 H) 7.92 (dt, J=7.64, 1.64 Hz, 1 H) 8.01 (m, 2 H).

HRMS: calcd for $C_{25}H_{25}N_3O_9S_2$, 575.1032; found (ESI-FTMS), 576.1107.

EXAMPLE 468

3-Carboxymethoxy-5-{3-[1-(4-methoxy-benzenesulfonyl)-piperidin-4-ylamino]-phenyl}-4-methyl-thiophene-2-carboxylic acid The first step of Scheme 64: 3-tert-Butoxycarbonylmethoxy-4-methyl-5-{3-[1-(2-nitro-benzenesulfonyl)-piperidin-4-ylamino]-phenyl}-thiophene-2-carboxylic acid methyl ester was prepared following the procedure in the first step of Scheme 52, Example 419, to give 130 mg (69%) of a beige solid.

$^1$H NMR (400 MHz, CHLOROFORM-D) δ ppm 1.48 (s, 9 H) 1.57 (m, 2 H) 2.13 (m, 2 H) 2.23 (s, 3 H) 2.51 (m, 2 H) 3.26 (s, 1 H) 3.61 (m, 1 H) 3.71 (m, 2 H) 3.84 (s, 2 H) 3.89 (s, 2 H) 4.79 (s, 2 H) 6.55 (m, 2 H) 6.77 (m, J=8.34, 1.52 Hz, 1 H) 7.02 (d, J=8.84 Hz, 2 H) 7.18 (t, J=7.83 Hz, 1 H) 7.18 (t, J=7.83 Hz, 1 H) 7.72 (t, J=9.09 Hz, 2 H).

The second step of Scheme 64: The procedure in the first step of Scheme 53, Example 421 was followed to give 77 mg (62%) of 3-carboxymethoxy-5-{3-[1-(4-methoxy-benzenesulfonyl)-piperidin-4-ylamino]-phenyll}4-methyl-thiophene-2-carboxylic acid as a beige solid.

$^1$H NMR (400 MHz, DMSO-D6) δ ppm 1.41 (m, 2 H) 1.97 (m, 2 H) 2.15 (s, 3 H) 2.50 (m, 2 H) 3.30 (m, J=9.09 Hz, 1 H) 3.54 (m, 2 H) 3.86 (s, 3 H) 4.84 (s, 2 H) 6.61 (m, J=9.09 Hz, 3 H) 7.13 (t, J=7.71 Hz, 1 H) 7.17 (d, J=9.09 Hz, 2 H) 7.69 (d, J=8.84 Hz, 2 H) 7.68 (none, 1 H).

HRMS: calcd for $C_{26}H_{28}N_2O_8S_2$, 560.1287; found (ESI-FTMS), 561.1364.

EXAMPLE 469

3-Carboxymethoxy-4-methyl-5-{3-[1-(4-nitro-benzenesulfonyl)-piperidin-4-ylamino]-phenyl}-thiophene-2-carboxylic acid The first step of Scheme 64: 3-tert-Butoxycarbonylmethoxy-4-methyl-5-{3-[1-(4-nitro-benzenesulfonyl)-piperidin-4-ylamino]-phenyl}-thiophene-2-carboxylic acid methyl ester was prepared following the procedure in the first step of Scheme 52, Example 419, to give 179 mg (92%) of a beige solid.

$^1$H NMR (400 MHz, CHLOROFORM-D) δ ppm 1.48 (s, 9 H) 1.58 (m, 2 H) 2.18 (m, 2 H) 2.23 (s, 3 H) 2.62 (m, 2 H) 3.30 (m, 1 H) 3.78 (m, 3 H) 3.84 (s, 3 H) 4.79 (s, 2 H) 6.56 (m, 2 H) 6.79 (m, 1 H) 7.19 (t, J=7.83 Hz, 1 H) 7.97 (d, J=8.84 Hz, 2 H) 8.41 (d, J=9.09 Hz, 2 H).

The second step of Scheme 64: The procedure in the first step of Scheme 53, Example 421 was followed to give 120 mg (69%) of 3-carboxymethoxy-4-methyl-5-{3-[1-(4-nitro-benzenesulfonyl)-piperidin-4-ylamino]-phenyl}-thiophene-2-carboxylic acid as a beige solid.

$^1$H NMR (400 MHz, DMSO-D6) δ ppm 1.40 (m, 2 H) 1.98 (m, 2 H) 2.14 (s, 3 H) 2.67 (m, 2 H) 3.32 (m, 1 H) 3.59 (m, J=4.04 Hz, 2 H) 4.84 (s, 2 H) 6.60 (m, J=11.12 Hz, 3 H) 7.13 (t, J=8.08 Hz, 1 H) 8.04 (d, J=9.09 Hz, 2 H) 8.46 (d, J=8.84 Hz, 2 H).

HRMS: calcd for $C_{25}H_{25}N_3O_9S_2$, 575.1032; found (ESI-FTMS), 598.0935.

EXAMPLE 470

5-{3-[1-(4-Carboxy-benzenesulfonyl)-piperidin-4-ylamino]-phenyl}-3-carboxymethoxy-4-methyl-thiophene-2-carboxylic acid The first step of Scheme 64: 3-tert-Butoxycarbonyl-methoxy-5-{3-[1-(4-carboxy-benzenesulfonyl)-piperidin-4-ylamino]-phenyl}-4-methyl-thiophene-2-carboxylic acid methyl ester was prepared following the procedure in the first step of Scheme 52, Example 419 to give 150 mg (79%) of a beige solid.

$^1$H NMR (400 MHz, CHLOROFORM-D) δ ppm 1.49 (s, 9 H) 1.58 (m, 2 H) 2.15 (m, 2 H) 2.23 (s, 3 H) 2.60 (m, 2 H) 3.31 (s, 1 H) 3.62 (m, 1 H) 3.75 (m, 2 H) 3.85 (s, 3 H) 4.79 (s, 2 H) 6.56 (m, 2 H) 6.79 (m, J=7.58 Hz, 1 H) 7.19 (t, J=7.83 Hz, 1 H) 7.88 (m, 4 H).

The second step of Scheme 64: The procedure in the first step of Scheme 53, Example 421 was followed to give 114 mg (68%) of 5-{3-[1-(4-carboxy-benzenesulfonyl)-piperidin-4-ylamino]-phenyl}-3-carboxymethoxy-4-methyl-thiophene-2-carboxylic acid as a beige solid.

$^1$H NMR (400 MHz, DMSO-D6) δ ppm 1.40 (s, 2 H) 1.95 (m, 2 H) 2.14 (s, 3 H) 2.51 (m, 2 H) 3.34 (m, 1 H) 3.57 (m, 2 H) 4.84 (s, 2 H) 5.78 (s, 1 H) 6.61 (t, 3 H) 7.12 (t, J=7.83 Hz, 1 H) 7.88 (d, J=8.84 Hz, 2 H) 8.18 (d, J=8.84 Hz, 2 H).

EXAMPLE 471

3-Carboxymethoxy-5-{3-[1-(2-cyano-benzenesulfonyl)-piperidin-4-ylamino]-phenyl}-4-methyl-thiophene-2-carboxylic acid The first step of Scheme 64: 3-tert-Butoxycarbonyl-methoxy-5-{3-[1-(2-cyano-benzenesulfonyl)-piperidin-4-ylamino]-phenyl})4-methyl-thiophene-2-carboxylic acid methyl ester was prepared following the procedure in the first step of Scheme 52, Example 419 to give 85 mg (49%) of a beige solid.

$^1$H NMR (400 MHz, CHLOROFORM-D) δ ppm 1.49 (s, 9 H) 1.57 (m, 2 H) 2.16 (m, 1 H) 2.24 (s, 3 H) 2.91 (s, 2 H) 3.61 (m, J=3.03 Hz, 1 H) 3.87 (m, 2 H) 3.87 (m, 2 H) 3.85 (s, 3 H) 4.79 (s, 2 H) 6.58 (m, 2 H) 6.79 (m, J=7.20, 2.15 Hz, 1 H) 7.20 (m, J=7.83, 7.83 Hz, 1 H) 7.72 (m, J=7.52, 7.52, 1.39 Hz, 1 H) 7.78 (m, 1 H) 7.90 (dd, J=7.71, 1.39 Hz, 1 H) 8.08 (dd, J=8.08, 1.26 Hz, 1 H).

The second step of Scheme 64: The procedure in the first step of Scheme 53, Example 421 was followed to give 120 mg (80%) of 3-carboxymethoxy-5-{3-[1-(2-cyano-benzenesulfonyl)-piperidin-4-ylamino]-phenyl})-4-methyl-thiophene-2-carboxylic acid as a beige solid.

$^1$H NMR (400 MHz, DMSO-D6) δ ppm 1.40 (m, 2 H) 1.96 (s, 2 H) 2.15 (s, 3 H) 2.84 (s, 2 H) 3.43 (m, 1 H) 3.65 (m, 2 H) 4.84 (s, 2 H) 5.82 (d, J=9.09 Hz, 1 H) 6.61 (m, J=8.34 Hz, 2 H) 6.65 (s, 1 H) 7.14 (t, J=7.96 Hz, 1 H) 7.91 (m, 1 H) 7.98 (m, 1 H) 8.04 (m, J=7.33 Hz, 1 H) 8.19 (dd, J=7.45, 1.14 Hz, 1 H).

EXAMPLE 472

3-Carboxymethoxy-4-methyl-5-{3-[1-(4-trifluoromethyl-benzenesulfonyl)-piperidin-4-ylamino]-phenyl}-thiophene-2-carboxylic acid The first step of Scheme 64: 3-tert-Butoxycarbonyl-methoxy-4-methyl-5-{3-[1-(4-trifluoromethyl-benzenesulfonyl)-piperidin-4-ylamino]-phenyl}-thiophene-2-carboxylic acid methyl ester was prepared following the procedure in the first step of Scheme 52, Example 419 to give 103 mg (55%) of a beige solid.

$^1$H NMR (400 MHz, CHLOROFORM-D) δ ppm 1.48 (s, 9 H) 1.57 (m, 2 H) 2.15 (m, 2 H) 2.23 (s, 3 H) 2.59 (m, 2 H) 3.30 (m, 1 H) 3.58 (m, J=8.84 Hz, 1 H) 3.80 (m, 2 H) 3.84 (s, 3 H) 4.79 (s, 2 H) 6.55 (m, 2 H) 6.78 (t, 1 H) 7.19 (t, J=7.96 Hz, 1 H) 7.88 (m, 4 H).

The second step of Scheme 64: The procedure in the first step of Scheme 53, Example 421 was followed to give 127 mg (76%) of 3-carboxymethoxy-4-methyl-5-{3-[1-(4-trifluoromethyl-benzenesulfonyl)-piperidin-4-ylamino]-phenyl}-thiophene-2-carboxylic acid as a beige solid.

$^1$H NMR (400 MHz, DMSO-D6) δ ppm 1.40 (m, 2 H) 1.96 (s, 2 H) 2.14 (s, 3 H) 2.59 (m, 2 H) 3.32 (m, 1 H) 3.58 (m, 2 H) 4.81 (s, 2 H) 5.77 (d, J=7.58 Hz, 1 H) 6.61 (m, 3 H) 7.12 (t, J=7.96 Hz, 1 H) 7.98 (d, J=8.08 Hz, 2 H) 8.05 (d, 2 H).

HRMS: calcd for $C_{26}H_{25}F3N_2O_7S_2$, 598.1055; found (ESI-FTMS), 599.1129.

EXAMPLE 473

4-Bromo-3-carboxymethoxy-5-[3-(1-cyclohexyl-3-methyl-ureido)-phenyl]-thiophene-2-carboxylic acid The first step of Scheme 65: 4,5-Dibromo-3-tert-butoxy-carbonylmethoxy-thiophene-2-carboxylic acid methyl ester (23.67 g, 87%) was prepared as follows: To a solution of 4,5-dibromo-3-hydroxy-thiophene-2-carboxylic acid methyl ester (20.0 g, 63.11 mmol) in DMF (200 mL) was added tert-butyl bromoacetate (9.32 mL, 63.11 mmol) and $K_2CO_3$ (17.45 g, 126.22 mmol). The resultant reaction mixture was stirred at room temperature overnight, and then filtered through a celite bed. DMF was mostly removed under reduced pressure, residue diluted with EtOAc and washed with $H_2O$, then saturated brine (aq.). Organic layer was dried over $MgSO_4$, solvent was removed under vacuum and the crude product was used in the next step without further purification.

$^1$H NMR (400 MHz, CHLOROFORM-D) δ ppm 1.49 (s, 9 H) 3.85 (s, 3 H) 4.82 (s, 2 H).

The second step of Scheme 65: 5-(3-Amino-phenyl)-4-bromo-3-tert-butoxycarbonylmethoxy-thiophene-2-carboxylic acid methyl ester (7.32 g, 63%) was prepared as follows: A reaction flask was charged with 4,5-dibromo-3-tert-butoxycarbonylmethoxy-thiophene-2-carboxylic acid methyl ester (11.24 g, 26.13 mmol), 3-aminobenzene boronic acid monohydrate (4.45 g, 28.74 mmol), tetrakis (triphenylphosphine) palladium (0) (1.5 g, 1.31 mmol), and KF (4.55 g, 78.39 mmol). Under a nitrogen atmosphere, THF (230 mL) was introduced, and the reaction mixture was refluxed for 6 h. Then an additional amount of tetrakis (triphenylphosphine) palladium(0) (1.5 g, 1.31 mmol) was added and allowed to reflux overnight. Solvent was removed under reduced pressure, and the residue was partitioned between ether and $NaHCO_3$. The organic layer was washed with saturated brine, dried over $MgSO_4$, and the solvents evaporated under reduced pressure. The crude material was purified by silica gel chromatography using a gradient of EtOAc/Hexane (10 to 15%) as eluent. Pure fractions were collected and evaporation of solvent gave 5-(3-amino-phenyl)-4-bromo-3-tert-butoxycarbonylmethoxy-thiophene-2-carboxylic acid methyl ester as a white solid.

$^1$H NMR (400 MHz, CHLOROFORM-D) δppm 1.50 (s, 9 H) 3.79 (s, 2 H) 3.87 (s, 3 H) 4.81 (s, 2 H) 6.74 (d, J=7.83 Hz, 1 H) 6.97 (s, 1 H) 7.03 (d, J=7.83 Hz, 1 H) 7.22 (t, J=7.83 Hz, 1 H).

The third step of Scheme 65: 4-Bromo-3-tert-butoxycarbonylmethoxy-5-(3-cyclohexylamino-phenyl)-thiophene-2-carboxylic acid methyl ester (2.6 g, 54.8%) was prepared as follows: To a solution of 5-(3-amino-phenyl)-4-bromo-3-tert-butoxycarbonylmethoxy-thiophene-2-carboxylic acid methyl ester (4 g, 9.043 mmol), and Cyclohexanone (1.13 mL, 10.85 mmol) in DCE (50 mL), was added NaBH(OAc)$_3$ (5.75 g, 27.13 mmol), and HOAc (1.55 mL, 27.13 mmol) at room temperature. After vigorously stirring overnight, the reaction mixture was quenched with aq. NaHCO$_3$, extracted with DCM. The organic layer was dried over MgSO$_4$ and concentrated. The crude product was purified on Biotage column, eluting with 5% EtOAc/Hexanes, then lyophilized overnight to give 4-bromo-3-tert-butoxycarbonylmethoxy-5-(3-cyclohexylamino-phenyl)-thiophene-2-carboxylic acid methyl ester as yellow gummy solid.

$^1$H NMR (400 MHz, CHLOROFORM-D) δppm 1.21 (m, 2 H) 1.39 (m, 2 H) 1.51 (s, 9 H) 1.56 (s, 1 H) 1.65 (m, 1 H) 1.77 (m, 2 H) 2.09 (d, J=12.88 Hz, 2 H) 3.28 (m, 1 H) 3.69 (s, 1 H) 3.87 (s, 3 H) 4.81 (s, 2 H) 6.63 (d, J=8.34 Hz, 1 H) 6.85 (m, 1 H) 6.90 (d, J=9.35 Hz, 1 H) 7.20 (t, J=7.83 Hz, 1 H).

The fourth step of Scheme 65: 4-Bromo-3-tert-butoxycarbonylmethoxy-5-[3-(1-cyclohexyl-3-methyl-ureido)-phenyl]-thiophene-2-carboxylic acid methyl ester (119 mg, 76%) was prepared as follows: To a microwave tube previously purged with Argon, was charged 4-bromo-3-tert-butoxycarbonylmethoxy-5-(3-cyclohexylamino-phenyl)-thiophene-2-carboxylic acid methyl ester (141 mg, 0.267 mmol), methylisocyanate (500 mg, 8.76 mmol), and Et$_3$N (31 μL). The reaction mixture was stirred for 5 days at room temperature. Solvent was evaporated and crude product was purified by silica gel chromatography using first 40% EtOAc/Hexane then 10% EtOAc/DCM as eluent, to afford 4-bromo-3-tert-butoxycarbonylmethoxy-5-[3-(1-cyclohexyl-3-methyl-ureido)-phenyl]-thiophene-2-carboxylic acid methyl ester as a pale yellow gummy solid.

$^1$H NMR (400 MHz, CHLOROFORM-D) δppm 0.91 (m, 2 H) 1.06 (m, 2 H) 1.40 (m, 2 H) 1.51 (s, 9 H) 1.73 (d, J=12.88 Hz, 2 H) 1.89 (d, J=12.63 Hz, 2 H) 2.04 (s, 3 H) 3.89 (s, 3 H) 4.12 (q, J=7.24 Hz, 1 H) 4.48 (m, 1 H) 4.85 (s, 2 H) 7.23 (d, J=7.83 Hz, 1 H) 7.51 (m, 2 H) 7.66 (d, J=9.60 Hz, 1 H)

The fifth step of Scheme 65: 4-Bromo-3-carboxymethoxy-5-[3-(1-cyclohexyl-3-methyl-ureido)-phenyl]-thiophene-2-carboxylic acid (48.7 mg, 46.5%) was prepared as follows: To a solution of 4-bromo-3-tert-butoxycarbonylmethoxy-5-[3-(1-cyclohexyl-3-methyl-ureido)-phenyl]-thiophene-2-carboxylic acid methyl ester (119 mg, 0.2046 mmol) in THF (3 mL)/H$_2$O (1.5 mL) was added 5 equivalent of 1N LiOH (1.023 mL, 1.023 mmol). The resultant reaction mixture was stirred at room temperature overnight, and concentrated under vacuum to remove THF. The aqueous solution was acidified with 2N aqueous HCl solution to pH ~3. The precipitate was collected by filtration, washed with H$_2$O, and dried under vacuum to give 4-bromo-3-carboxymethoxy-5-[3-(1-cyclohexyl-3-methyl-ureido)-phenyl]-thiophene-2-carboxylic acid as off white solid.

$^1$H NMR (400 MHz, DMSO-D6) δppm 0.86 (d, J=12.88 Hz, 1 H) 0.98 (m, 2 H) 1.29 (q, 2 H) 1.51 (d, J=12.13 Hz, 1 H) 1.73 (m, 4 H) 2.50 (s, 3 H) 4.23 (m, 1 H) 4.90 (s, 2 H) 5.28 (d, J=4.55 Hz, 1 H) 7.25 (d, J=7.83 Hz, 1 H) 7.42 (t, J=1.77 Hz, 1 H) 7.57 (t, J=7.83 Hz, 1 H) 7.68 (d, J=7.83 Hz, 1 H).

EXAMPLE 474

5-[3-(3-Benzyl-1-cyclohexyl-ureido)-phenyl]-4-bromo-3-carboxymethoxy-thiophene-2-carboxylic acid The fourth step of Scheme 65: 5-[3-(3-Benzyl-1-cyclohexyl-ureido)-phenyl]-4-bromo-3-tert-butoxycarbonylmethoxy-thiophene-2-carboxylic acid methyl ester (123 mg, 65%) was prepared as off white solid according to procedure of the fourth step of Scheme 65 in Example 473, using 4-bromo-3-tert-butoxycarbonylmethoxy-5-(3-cyclohexylamino-phenyl)-thiophene-2-carboxylic acid methyl ester (150 mg, 0.286 mmol), and Benzylisocyanate (500 μL, 4.048 mmol) as starting materials, and Et3N (48 μL, 0.3432 mmol) as base. This reaction was performed in the absence of solvent.

$^1$H NMR (400 MHz, CHLOROFORM-D) δ ppm 0.92 (m, 2 H) 1.08 (m, 2 H) 1.41 (m, 2 H) 1.50 (s, 9 H) 1.74 (d, J=13.14 Hz, 2 H) 1.92 (d, J=10.86 Hz, 2 H) 3.89 (s, 3 H) 4.26 (t, J=5.81 Hz, 1 H) 4.38 (d, J=5.81 Hz, 2 H) 4.52 (m, 1 H) 4.84 (s, 2 H) 7.23 (m, 6 H) 7.49 (m, 2 H) 7.62 (d, J=4.80 Hz, 1 H).

The fifth step of Scheme 65: 5-[3-(3-Benzyl-1-cyclohexyl-ureido)-phenyl]-4-bromo-3-carboxymethoxy-thiophene-2-carboxylic acid (54.8 mg, 50%) was prepared according to procedure in the fifth step of Scheme 65 of Example 473, using 5-[3-(3-Benzyl-1-cyclohexyl-ureido)-phenyl]-4-bromo-3-tert-butoxycarbonylmethoxy-thiophene-2-carboxylic acid methyl ester (123.0 mg, 0.187 mmol) and 1N LiOH (935 μL, 0.935 mmol) as starting materials. 5-[3-(3-Benzyl-1-cyclohexyl-ureido)-phenyl]-4-bromo-3-carboxymethoxy-thiophene-2-carboxylic acid was obtained as off white solid.

$^1$H NMR (400 MHz, DMSO-D6) δppm 0.87 (d, J=11.37 Hz, 1 H) 1.01 (m, 2 H) 1.27 (m, 2 H) 1.51 (d, J=10.36 Hz, 1 H) 1.70 (d, J=15.66 Hz, 2 H) 1.80 (d, J=11.12 Hz, 2 H) 4.17 (d, J=5.81 Hz, 2 H) 4.24 (m, 1 H) 4.90 (s, 2 H) 5.97 (t, J=5.94 Hz, 1 H) 7.17 (m, 3 H) 7.27 (m, 3 H) 7.46 (t, J=1.89 Hz, 1 H) 7.59 (t, J=7.83 Hz, 1 H) 7.69 (d, J=6.57 Hz, 1 H).

EXAMPLE 475

4-Bromo-3-tert-butoxycarbonylmethoxy-5-[3-(3,3,5,5-tetramethyl-cyclohexylamino)-phenyl]-thiophene-2-carboxylic acid methyl ester The first step of Scheme 66: 4-Bromo-3-tert-butoxycarbonylmethoxy-5-[3-(3,3,5,5-tetramethyl-cyclohexylamino)-phenyl]-thiophene-2-carboxylic acid methyl ester (1.89 g, 48%) was synthesized as a yellow solid according to procedure in the third step of Scheme 65 of Example 473, using 5-(3-amino-phenyl)-4-bromo-3-tert-butoxycarbonylmethoxy-thiophene-2-carboxylic acid methyl ester (3 g, 6.782 mmol), 3,3,5,5 tetramethyl cyclohexanone (1.41 mL, 8.1384 mmol), NaBH(OAc)$_3$ (2.156 g, 10.173 mmol), HOAc (582 μL) as starting materials and DCE (40 mL) as solvent. Purification was achieved using gradient elution using 5-15% EtOAc/Hexanes as eluent.

$^1$H NMR (400 MHz, CHLOROFORM-D) δ ppm 0.94 (s, 8 H) 1.12 (s, 8 H) 1.30 (m, 1 H) 1.50 (s, 9 H) 1.89 (d, J=12.63 Hz, 2 H) 3.57 (s, 1 H) 3.87 (s, 3 H) 4.81 (s, 2 H) 6.63 (dd, J=7.33, 2.53 Hz, 1 H) 6.90 (m, 2 H) 7.21 (t, J=7.71 Hz, 1 H).

HRMS: calcd for C$_{28}$H$_{38}$BrNO$_5$S, 579.1654; found (ESI-FTMS), 580.1719; Anal. Calcd for C$_{28}$H$_{38}$BrNO$_5$S: C, 57.93; H, 6.60; N, 2.41. Found: C, 57.84; H, 6.53; N, 2.25.

EXAMPLE 476

4-Bromo-3-carboxymethoxy-5-{3-[3-methyl-1-(3,3,5,5-tetramethyl-cyclohexyl)-ureido]-phenyl}-thiophene-2-carboxylic acid The first step of Scheme 67: 4-Bromo-3-tert-butoxycarbonylmethoxy-5-{3-[3-methyl-1-(3,3,5,5-tetramethyl-cyclohexyl)-ureido]-phenyl}-thiophene-2-carboxylic acid methyl ester (150 mg, 85%) was synthesized as a colorless gummy solid according procedures in the fourth step of Scheme 65 of Example 473 using 4-bromo-3-tert-butoxycarbonylmethoxy-5-[3-(3,3,5,5-tetramethyl-cyclohexylamino)-phenyl]-thiophene-2-carboxylic acid methyl ester (160 mg, 0.276 mmol) and methylisocyanate (500 mg, 8.76 mmol) as starting materials, triethylamine (46 µL, 0.3312 mmol) as base and DCM (4 mL) as solvent. After stirring at room temperature for 6 days solvent evaporation gave crude product. The latest was purified by Column Chromatography using 40% EtOAc/Hexanes as eluent to yield 4-bromo-3-tert-butoxycarbonylmethoxy-5-{3-[3-methyl-1-(3,3,5,5-tetramethyl-cyclohexyl)-ureido]-phenyl}-thiophene-2-carboxylic acid methyl ester.
$^1$H NMR (400 MHz, CHLOROFORM-D) δ ppm 0.84 (s, 6 H) 0.89 (s, 2 H) 1.13 (s, 6 H) 1.17 (d, J=13.64 Hz, 2 H) 1.50 (s, 9 H) 1.62 (d, J=12.38 Hz, 2 H) 2.73 (d, J=4.80 Hz, 3 H) 3.83 (d, J=4.55 Hz, 1 H) 3.89 (s, 3 H) 4.85 (s, 2 H) 4.93 (m, 1 H) 7.22 (d, J=6.57 Hz, 1 H) 7.52 (m, 2 H) 7.63 (m, 1 H).

The second step of Scheme 67: 4-Bromo-3-carboxymethoxy-5-{3-[3-methyl-1-(3,3,5,5-tetramethyl-cyclohexyl)-ureido]-phenyl}-thiophene-2-carboxylic acid (51.2 mg, 79%) was prepared as a white solid according procedures in the fifth step of Scheme 65 of Example 473, using 4-bromo-3-tert-butoxycarbonylmethoxy-5-{3-[3-methyl-1-(3,3,5,5-tetramethyl-cyclohexyl)-ureido]-phenyl}-thiophene-2-carboxylic acid methyl ester (73 mg, 0.115 mmol), 1 N LiOH (aq) (575 µL, 0.575 mmol), as starting materials and THF (2 mL)/H$_2$O (1 mL) as solvent.
$^1$H NMR (400 MHz, DMSO-D6) δ ppm 0.79 (s, 1 H) 0.81 (s, 6 H) 0.84 (d, J=5.56 Hz, 2 H) 1.06 (s, 6 H) 1.13 (d, J=16.17 Hz, 1 H) 1.53 (d, J=10.61 Hz, 2 H) 2.50 (s, 3 H) 4.76 (m, 1 H) 4.90 (s, 2 H) 5.22 (d, J=4.29 Hz, 1 H) 7.24 (d, J=10.36 Hz, 1 H) 7.43 (t, J=1.77 Hz, 1 H) 7.58 (t, J=7.71 Hz, 1 H) 7.66 (d, J=6.82 Hz, 1 H).
HRMS: calcd for C$_{25}$H$_{31}$BrN$_2$O$_6$S, 566.1086; found (ESI-FTMS), 567.1161

EXAMPLE 477

4-Bromo-3-carboxymethoxy-5-{3-[3-ethyl-1-(3,3,5,5-tetramethyl-cyclohexyl)-ureido]-phenyl}-thiophene-2-carboxylic acid The first step of Scheme 67: 4-Bromo-3-tert-butoxycarbonylmethoxy-5-{3-[3-ethyl-1-(3,3,5,5-tetramethyl-cyclohexyl)-ureido]-phenyl}-thiophene-2-carboxylic acid methyl ester (96.4 mg, 83.8%) was prepared as follows: 4-Bromo-3-tert-butoxycarbonylmethoxy-5-[3-(3,3,5,5-tetramethyl-cyclohexylamino)-phenyl]-thiophene-2-carboxylic acid methyl ester (103 mg, 0.178 mmol) in DCM (0.5 mL) was added with ethyl isocyanate (282 mL, 3.56 mmol) then Et3N (29.7 µL, 0.2136 mmol) and stirred at room temperature for 5 days. Solvent was removed under reduced pressure, then crude product was purified by column chromatography using 30% EtOAc/Hexanes as eluent to yield pure 4-bromo-3-tert-butoxycarbonylmethoxy-5-{3-[3-ethyl-1-(3,3,5,5-tetramethyl-cyclohexyl)-ureido]-phenyl}-thiophene-2-carboxylic acid methyl ester as off white solid.
$^1$H NMR (400 MHz, CHLOROFORM-D) δ ppm 1.07 (m, 19 H) 1.50 (s, 9 H) 1.62 (d, J=11.12 Hz, 2 H) 3.20 (q, J=7.07 Hz, 2 H) 3.83 (t, J=5.56 Hz, 1 H) 3.89 (s, 3 H) 4.86 (s, 2 H) 4.92 (d, 1 H) 7.22 (d, J=9.85 Hz, 1 H) 7.52 (m, 2 H) 7.62 (d, J=8.34 Hz, 1 H).

The second step of Scheme 67: 4-Bromo-3-carboxymethoxy-5-{3-[3-ethyl-1-(3,3,5,5-tetramethyl-cyclohexyl)-ureido]-phenyl}-thiophene-2-carboxylic acid (46.4 mg, 54%) was prepared as a white solid according to procedures in the fifth step of Example 473 of Scheme 65, using 4-bromo-3-tert-butoxycarbonylmethoxy-5-{3-[3-ethyl-1-(3,3,5,5-tetramethyl-cyclohexyl)-ureido]-phenyl}-thiophene-2-carboxylic acid methyl ester (96 mg, 0.147 mmol), 1 N LiOH (aq.) (735 µL, 0.735 mmol) as starting materials and THF (2 mL)/H$_2$O (1 mL) as solvent.
$^1$H NMR (400 MHz, DMSO-D6) δ ppm 0.96 (m, 19 H) 1.53 (d, J=12.13 Hz, 2 H) 2.98 (m, 2 H) 4.75 (m, 1 H) 4.89 (s, 2 H) 5.25 (t, J=5.68 Hz, 1 H) 7.23 (d, J=8.59 Hz, 1 H) 7.43 (t, J=1.77 Hz, 1 H) 7.58 (t, J=7.83 Hz, 1 H) 7.67 (m, 1 H).

EXAMPLE 478

4-Bromo-3-carboxymethoxy-5-{3-[3-methyl-1-(3,3,5,5-tetramethyl-cyclohexyl)-ureido]-phenyl}-thiophene-2-carboxylic acid methyl ester The first step of Scheme 68: Step 4A [L25575-61-1]: 4-Bromo-3-carboxymethoxy-5-{3-[3-methyl-1-(3,3,5,5-tetramethyl-cyclohexyl)-ureido]-phenyl}-thiophene-2-carboxylic acid methyl ester (90.1 mg, 75.7%) was prepared as follows: 4-Bromo-3-tert-butoxycarbonylmethoxy-5-{3-[3-methyl-1-(3,3,5,5-tetramethyl-cyclohexyl)-ureido]-phenyl}-thiophene-2-carboxylic acid methyl ester (131 mg, 0.205 mmol) was dissolved in DCM (4 mL). TFA (2 mL) was added to it at 0° C., and it was stirred room temperature for 4 hr. Solvent was then removed under reduced pressure, TFA chased with DCM then Hexanes. Residual solvent was removed under high vacuum and compound was lyophilized overnight to yield 4-bromo-3-carboxymethoxy-5-{3-[3-methyl-1-(3,3,5,5-tetramethyl-cyclohexyl)-ureido]-phenyl}-thiophene-2-carboxylic acid methyl ester as white solid.
$^1$H NMR (400 MHz, CHLOROFORM-D) 3 ppm 1.09 (m, 16 H) 1.62 (d, J=9.85 Hz, 2 H) 2.74 (s, 3 H) 3.97 (s, 4 H) 4.90 (t, J=3.16 Hz, 1 H) 4.93 (d,2 H) 7.29 (d, J=7.83 Hz, 1 H) 7.48 (t, J=1.77 Hz, 1 H) 7.58 (t, J=7.71 Hz, 1 H) 7.64 (m, 1 H).
HRMS: calcd for C$_{26}$H$_{33}$BrN$_2$O$_6$S, 580.1243; found (ESI-FTMS), 581.1313.

EXAMPLE 479

4-Bromo-3-ethoxycarbonylmethoxy-5-[3-(piperidin-4-ylamino)-phenyl]-thiophene-2-carboxylic acid methyl ester hydrochloride The first step of Scheme 69: 4,5-Dibromo-3-ethoxycarbonylmethoxy-thiophene-2-carboxylic acid methyl ester (33.3 g, 66%) was prepared as follows: To a solution of 4,5-dibromo-3-hydroxy-thiophene-2-carboxylic acid methyl ester (40 g, 126.2 mmol) in DMF (400 mL) was added K$_2$CO$_3$ (34.88 g, 252.4 mmol) followed by ethylbromoacetate (14 mL, 126.2 mmol). The resultant reaction mixture was stirred at room temperature overnight, and then filtered through a celite bed. DMF was mostly removed under reduced pressure, residue diluted with EtOAc and washed with H$_2$O, then saturated brine (aq.). Organic layer was dried over MgSO$_4$. During solvent evaporation solid precipitated. It was filtered off, EtOAc chased with Hexanes and DCM to yield 4,5-dibromo-3-ethoxycarbonylmethoxy-thiophene-2-carboxylic acid methyl ester as white solid.

$^1$H NMR (400 MHz, CHLOROFORM-D) δppm 1.30 (t, J=7.07 Hz, 3 H) 3.85 (s, 3 H) 4.27 (q, J=7.16 Hz, 2 H) 4.90 (s, 2 H).

The second step of Scheme 69: 5-(3-Amino-phenyl)-4-bromo-3-ethoxycarbonylmethoxy-thiophene-2-carboxylic acid methyl ester (7 g, 42.0%) was prepared as follows: A reaction flask was charged with 4,5-dibromo-3-ethoxycarbonylmethoxy-thiophene-2-carboxylic acid methyl ester (16.6 g, 41.29 mmol), 3-aminobenzene boronic acid monohydrate (7.04 g, 45.42 mmol), tetrakis (triphenylphosphine) palladium(0) (2.38 g, 2.0645 mmol) and KF (7.2 g, 123.87 mmol). Under nitrogen atmosphere, THF (275 mL) was introduced, and the reaction mixture was refluxed for 4.5 h. Then to it was added an additional amount of tetrakis (triphenylphosphine) palladium(0) (2.38 g, 2.0645 mmol), and was allowed to reflux overnight. Solvent was removed under reduced pressure, and the residue was partitioned between ether and NaHCO$_3$. The organic layer was washed with saturated brine and dried over MgSO$_4$. Solvents were evaporated under reduced pressure. The crude material was purified by triturating three times with EtOAc/Hexanes (1:1). Additional product was obtained from the combined filtrates. The concentrated filtrates were triturated with (1:5 EtOAc/Hexanes). Decantation and further trituration with 1:1 EtOAc/Hexanes yielded pure 5-(3-amino-phenyl)-4-bromo-3-ethoxycarbonylmethoxy-thiophene-2-carboxylic acid methyl ester as white solid.

$^1$H NMR (400 MHz, CHLOROFORM-D) δ ppm 1.32 (d, J=14.15 Hz, 3 H) 3.80 (s, 1 H) 3.87 (s, 3 H) 4.30 (q, J=7.07 Hz, 2 H) 4.90 (s, 2 H) 6.75 (m, 1 H) 6.97 (m, 1 H) 7.03 (m, 1 H) 7.23 (t, J=8.08 Hz, 1 H).

The third step of Scheme 69: 4-[3-(3-Bromo-4-ethoxycarbonylmethoxy-5-methoxycarbonyl-thiophen-2-yl)-phenylamino]-piperidine-1-carboxylic acid tert-butyl ester (2.785 g, 33%) was prepared as follows: To a 55 mL DCE solution of 5-(3-amino-phenyl)-4-bromo-3-ethoxycarbonylmethoxy-thiophene-2-carboxylic acid methyl ester (5.76 g, 13.90 mmol) was added tert-butyl-4-oxo-1-piperidinecarboxylate (3.323 g, 16.68 mmol), acetic acid (1.25 mL, 20.85 mmol), and sodium triacetoxyborohydride (4.42 g, 20.85 mmol) and the resulting mixture was allowed to stir at room temperature overnight. The reaction mixture was then diluted with CH$_2$Cl$_2$ and washed twice with saturated sodium bicarbonate solution and dried over MgSO$_4$. Filtration and evaporation gave the crude product that was triturated with ether (80 mL) and hexanes (180 mL). A gummy solid was removed by decantation. The solid precipitated during solvent evaporation of the supernatant was filtered off to yield desired 4-[3-(3-bromo-4-ethoxycarbonylmethoxy-5-methoxycarbonyl-thiophen-2-yl)-phenylamino]-piperidine-1-carboxylic acid tert-butyl ester as off white solid.

$^1$H NMR (400 MHz, CHLOROFORM-D) δ ppm 1.31 (m, 5 H) 1.47 (s, 9 H) 2.04 (s, 2 H) 2.94 (m, 2 H) 3.45 (s, 1 H) 3.68 (d, J=10.11 Hz, 1 H) 3.87 (s, 3 H) 4.07 (s, 2 H) 4.30 (m, 2 H) 4.90 (d, 2 H) 6.66 (d, J=8.34 Hz, 1 H) 6.87 (d, J=2.02 Hz, 1 H) 6.95 (d, J=6.57 Hz, 1 H) 7.22 (d, J=7.83 Hz, 1 H).

The fourth step of Scheme 69: 4-Bromo-3-ethoxycarbonylmethoxy-5-[3-(piperidin-4-ylamino)-phenyl]-thiophene-2-carboxylic acid methyl ester hydrochloride (2.413 g, 76%) was prepared as follows: 4-[3-(3-Bromo-4-ethoxycarbonylmethoxy-5-methoxycarbonyl-thiophen-2-yl)-phenylamino]-piperidine-1-carboxylic acid tert-butyl ester (3.56 g, 5.958 mmol) was dissolved in a mixture of 30 mL 1N HCl in EtOAc (Prepared by bubbling dry HCl gas into dry EtOAc) and 6 mL MeOH and the reaction mixture was allowed to stir at room temperature overnight. The reaction mixture was then evaporated exhaustively to give 4-bromo-3-ethoxycarbonylmethoxy-5-[3-(piperidin-4-ylamino)-phenyl]-thiophene-2-carboxylic acid methyl ester hydrochloride as off white solid.

$^1$H NMR (400 MHz, MeOD) δ ppm 1.47 (t, J=7.07 Hz, 3 H) 2.07 (m, 2 H) 2.45 (d, J=11.62 Hz, 2 H) 3.31 (t, J=11.24 Hz, 2 H) 3.69 (s, 2 H) 3.97 (s, 1 H) 4.04 (s, 3 H) 4.43 (q, J=7.07 Hz, 2 H) 5.11 (s, 2 H) 7.41 (d, J=9.60 Hz, 1 H) 7.57 (m, 2 H) 7.67 (t, J=7.96 Hz, 1 H).

EXAMPLE 480

4-Bromo-3-carboxymethoxy-5-{3-[1-(4-trifluoromethyl-pyrimidin-2-yl)-piperidin-4-ylamino]-phenyl}-thiophene-2-carboxylic acid The first step of Scheme 70: 4-[3-(3-bromo-4-tert-butoxycarbonylmethoxy-5-methoxycarbonyl-thiophen-2-yl)-phenylamino]-piperidine-1-carboxylic acid tert-butyl ester (6.1565, 87%) was prepared according to procedure in the third step of Scheme 65 of Example 473, using 5-(3-aminophenyl)-4-bromo-3-tert-butoxycarbonylmethoxy-thiophene-2-carboxylic acid methyl ester (5.017 g, 11.34 mmol), 4-oxo-piperidine-1-carboxylic acid tert-butyl ester (2.71 g, 13.61 mmol), NaBH(OAc)$_3$, (3.6 g, 17.01 mmol), HOAc (1.0 mL, 17.01 mmol) as starting materials and DCE (45 mL) as solvent. 4-[3-(3-Bromo-4-tert-butoxycarbonylmethoxy-5-methoxycarbonyl-thiophen-2-yl)-phenylamino]-piperidine-1-carboxylic acid tert-butyl ester was obtained as off white solid.

$^1$H NMR (400 MHz, CHLOROFORM-D) δ ppm 1.35 (m, 2 H) 1.47 (s, 9 H) 1.51 (s, 9 H) 1.56 (s, 1 H) 2.07 (d, J=14.15 Hz, 2 H) 2.94 (m, 2 H) 3.46 (dd, J=13.90, 7.07 Hz, 1 H) 3.68 (d, J=8.34 Hz, 1 H) 3.88 (s, 3 H) 4.07 (s, 1 H) 4.82 (s, 2 H) 6.66 (d, J=9.09 Hz, 1 H) 6.87 (m, 1 H) 6.94 (d, J=5.81 Hz, 1 H) 7.23 (t, J=7.96 Hz, 1 H).

The second step of Scheme 70: 4-Bromo-3-tert-butoxycarbonylmethoxy-5-[3-(piperidin-4-ylamino)-phenyl]-thiophene-2-carboxylic acid methyl ester hydrochloride (7.99 g, 100%) was prepared in quantitative yield using 4-[3-(3-bromo-4-tert-butoxycarbonylmethoxy-5-methoxycarbonyl-thiophen-2-yl)-phenylamino]-piperidine-1-carboxylic acid tert-butyl ester (8.65 g, 13.83 mmol) as starting material and 1N HCl in EtOAc (69.15 mL, 69.15 mmol) and MeOH (13.83 mL) as solvent.

$^1$H NMR (400 MHz, DMSO-D6) δ ppm 1.43 (s, 9 H) 1.63 (d, J=10.86 Hz, 2 H) 2.06 (d, J=13.90 Hz, 2 H) 2.99 (m, 2 H) 3.29 (d, J=13.39 Hz, 2 H) 3.60 (m, 1 H) 3.81 (s, 3 H) 4.88 (s, 2 H) 6.81 (d, J=9.60 Hz, 1 H) 6.87 (d, J=7.07 Hz, 1 H) 6.93 (s, 1 H) 7.25 (t, J=7.83 Hz, 1 H) 8.82 (s, 1 H) 8.96 (m, 1 H).

The third step of Scheme 70: 4-Bromo-3-tert-butoxycarbonylmethoxy-5-{3-[1-(4-trifluoromethyl-pyrimidin-2-yl)-piperidin-4-ylamino]-phenyl}-thiophene-2-carboxylic acid methyl ester (105 mg, 87%) was prepared as follows: 4-Bromo-3-tert-butoxycarbonylmethoxy-5-[3-(piperidin-4-ylamino)-phenyl]-thiophene-2-carboxylic acid methyl ester hydrochloride (101 mg, 0.180 mmol) and 2-chloro-4-trifluoromethyl-pyrimidine (33.0 mg, 0.180 mmol) were mixed in EtOH (500 μL), added with Et3N (63 μL, 0.45 mmol) and exposed to microwave irradiation for 10 min. at 100° C. An additional amount of 2-chloro-4-trifluoromethyl-pyrimidine (44 mg, 0.240 mmol) and Et$_3$N (63 μL, 0.45 mmol) was introduced to the reaction mixture then the reaction mixture was exposed to microwave irradiation for an additional 20 min at 100° C. The crude material obtained upon solvent evaporation was purified by column chromatography using gradient elution (0-1% MeOH/DCM). 4-Bromo-3-tert-butoxycarbonylmethoxy-5-{3-[1-(4-trifluoromethyl-pyrimidin-2-yl)-piperidin-4-ylamino]-phenyl}-thiophene-2-carboxylic acid methyl ester was obtained as yellow solid.

$^1$H NMR (400 MHz, CHLOROFORM-D) δ ppm 1.45 (m, 2 H) 1.51 (s, 9 H) 2.20 (d, J=15.66 Hz, 2 H) 3.22 (m, 2 H) 3.62 (s, 1 H) 3.72 (d, J=6.82 Hz, 1 H) 3.88 (s, 3 H) 4.72 (m, 2 H) 4.82 (s, 2 H) 6.69 (d, J=8.08 Hz, 1 H) 6.75 (d, J=4.80 Hz, 1 H) 6.91 (d, J=2.02 Hz, 1 H) 6.96 (d, J=6.57 Hz, 1 H) 7.24 (d, J=7.83 Hz, 1 H) 8.49 (d, J=4.55 Hz, 1 H).

The fourth step of Scheme 70: 4-Bromo-3-carboxymethoxy-5-{3-[1-(4-trifluoromethyl-pyrimidin-2-yl)-piperidin-4-ylamino]-phenyl}-thiophene-2-carboxylic acid (70.4 mg, 84%) was prepared according to procedure in the fifth step of Scheme 65 of Example 473, using 4-bromo-3-tert-butoxycarbonylmethoxy-5-{3-[1-(4-trifluoromethyl-pyrimidin-2-yl)-piperidin-4-ylamino]-phenyl}-thiophene-2-carboxylic acid methyl ester (93.5 mg, 0.140 mmol) and 1N LiOH (aq.) (700 µL, 0.70 mmol) as starting materials and THF (3 mL)/H$_2$O (1.5 mL) as solvent. 4-Bromo-3-carboxymethoxy-5-{3-[1-(4-trifluoromethyl-pyrimidin-2-yl)-piperidin-4-ylamino]-phenyl}-thiophene-2-carboxylic acid was obtained as a yellow solid.

$^1$H NMR (400 MHz, DMSO-D6) 3 ppm 0.88 (s, 1 H) 1.33 (m, 3 H) 2.03 (d, J=9.35 Hz, 2 H) 3.63 (s, 1 H) 4.52 (d, J=13.90 Hz, 2 H) 4.88 (s, 2 H) 6.77 (dd, J=18.44, 7.58 Hz, 2 H) 6.89 (s, 1 H) 7.00 (d, J=4.80 Hz, 1 H) 7.21 (m, 1 H) 8.68 (d, J=5.05 Hz, 1 H).

EXAMPLE 481

4-Bromo-3-carboxymethoxy-5-[3-(1-pyrimidin-2-yl-piperidin-4-ylamino)-phenyl]-thiophene-2-carboxylic acid The third step of Scheme 70: 4-Bromo-3-ethoxycarbonylmethoxy-5-[3-(1-pyrimidin-2-yl-piperidin-4-ylamino)-phenyl]-thiophene-2-carboxylic acid methyl ester (38 mg, 35%), was prepared according to procedure in the third step of Scheme 70 of Example 480, using 4-bromo-3-ethoxycarbonylmethoxy-5-[3-(piperidin-4-ylamino)-phenyl]-thiophene-2-carboxylic acid methyl ester (101 mg, 0.189 mmol), 2-chloro-pyrimidine (21.66 mg, 0.189 mmol) as starting materials, Et3N (66 µL, 0.475 mmol) as base and EtOH (1 mL) as solvent.

$^1$H NMR (400 MHz, CHLOROFORM-D) δ ppm 1.33 (m, 3 H) 1.45 (m, 2 H) 2.18 (d, J=13.39 Hz, 2 H) 3.17 (t, J=11.49 Hz, 2 H) 3.60 (s, 1 H) 3.72 (s, 1 H) 3.88 (s, 3 H) 4.30 (q, J=7.24 Hz, 2 H) 4.68 (d, J=13.64 Hz, 2 H) 4.90 (s, 2 H) 6.48 (t, J=4.80 Hz, 1 H) 6.69 (d, J=6.57 Hz, 1 H) 6.91 (m, 1 H) 6.95 (d, J=10.11 Hz, 1 H) 7.23 (d, J=7.83 Hz, 1 H) 8.31 (d, J=4.80 Hz, 2 H).

The fourth step of Scheme 70: 4-Bromo-3-carboxymethoxy-5-[3-(1-pyrimidin-2-yl-piperidin-4-ylamino)-phenyl]-thiophene-2-carboxylic acid (27.2 mg, 77%) was prepared according to procedure in the fifth step of Scheme 65 of Example 473, using 4-bromo-3-ethoxycarbonylmethoxy-5-[3-(1-pyrimidin-2-yl-piperidin-4-ylamino)-phenyl]-thiophene-2-carboxylic acid methyl ester (38 mg, 0.066 mmol) and 1N LiOH (330 µL, 0.33 mmol) as starting materials and THF (2 mL)/H$_2$O (1 mL) as solvent. 4-Bromo-3-carboxymethoxy-5-[3-(1-pyrimidin-2-yl-piperidin-4-ylamino)-phenyl]-thiophene-2-carboxylic acid was obtained as light yellow solid.

$^1$H NMR (400 MHz, DMSO-D6) 3 ppm 1.32 (m, 2 H) 1.99 (d, J=12.63 Hz, 2 H) 3.16 (m, 2 H) 3.59 (t, J=9.85 Hz, 2 H) 4.52 (s, 1 H) 4.55 (s, 1 H) 4.88 (s, 2 H) 6.60 (t, J=4.67 Hz, 1 H) 6.77 (dd, J=19.45, 7.07 Hz, 2 H) 6.88 (s, 1 H) 7.21 (t, J=7.96 Hz, 1 H) 8.35 (d, J=4.80 Hz, 2 H).

EXAMPLE 482

4-Bromo-3-carboxymethoxy-5-[3-(5'-trifluoromethyl-3,4,5,6-tetrahydro-2H-[1,2']bipyridinyl-4-ylamino)-phenyl]-thiophene-2-carboxylic acid The third step of Scheme 70: 4-Bromo-3-tert-butoxycarbonylmethoxy-5-[3-(5'-trifluoromethyl-3,4,5,6-tetrahydro-2H-[1,2']bipyridinyl-4-ylamino)-phenyl]-thiophene-2-carboxylic acid methyl ester (50 mg, 42%) was obtained according the procedure in the third step of Scheme 70 of Example 480, using 4-bromo-3-tert-butoxycarbonylmethoxy-5-[3-(piperidin-4-ylamino)-phenyl]-thiophene-2-carboxylic acid methyl ester (100 mg, 0.178 mmol), 2-chloro-5-trifluoromethyl-pyridine (32.32 mg, 0.178 mmol) as starting materials, Et$_3$N (62 µL, 0.445 mmol) as base and EtOH (1 mL) as solvent.

$^1$H NMR (400 MHz, CHLOROFORM-D) δ ppm 1.49 (t, J=1.64 Hz, 2 H) 1.51 (s, 9 H) 2.20 (d, J=10.11 Hz, 2 H) 3.17 (m, 2 H) 3.62 (s, 1 H) 3.71 (s, 1 H) 3.88 (s, 3 H) 4.35 (d, J=13.39 Hz, 2 H) 4.82 (s, 2 H) 6.68 (d, J=8.59 Hz, 2 H) 6.93 (m, 2 H) 7.24 (d, J=8.08 Hz, 1 H) 7.62 (s, 1 H) 8.40 (s, 1 H).

The fourth step of Scheme 70: 4-Bromo-3-carboxymethoxy-5-[3-(5'-trifluoromethyl-3,4,5,6-tetrahydro-2H-[1,2']bipyridinyl-4-ylamino)-phenyl]-thiophene-2-carboxylic acid (31.6 mg, 75.7%) was prepared according to the procedure in the fifth step of Scheme 65, Example 473, using 4-bromo-3-tert-butoxycarbonylmethoxy-5-[3-(5'-trifluoromethyl-3,4,5,6-tetrahydro-2H-[1,2']bipyridinyl-4-ylamino)-phenyl]-thiophene-2-carboxylic acid methyl ester (46.6 mg, 0.0817 mmol) and 1N NaOH (408 µL, 0.4085 mmol) as starting materials and THF (2 mL)/H$_2$O (1 mL) as solvent. 4-Bromo-3-carboxymethoxy-5-[3-(5'-trifluoromethyl-3,4,5,6-tetrahydro-2H-[1,2']bipyridinyl-4-ylamino)-phenyl]-thiophene-2-carboxylic acid was obtained as a yellow solid.

$^1$H NMR (400 MHz, DMSO-D6) δ ppm 1.35 (m, 4 H) 2.01 (d, J=6.32 Hz, 2 H) 3.19 (m, 2 H) 4.34 (d, J=11.12 Hz, 2 H) 4.88 (s, 2 H) 6.77 (dd, J=20.46, 8.08 Hz, 2 H) 6.89 (s, 1 H) 7.00 (d, J=6.82 Hz, 1 H) 7.21 (t, J=7.96 Hz, 1 H) 7.78 (d, J=8.84 Hz, 1 H) 8.41 (s, 1 H).

EXAMPLE 483

4-Bromo-3-ethoxycarbonylmethoxy-5-[3-(1-phenylmethanesulfonyl-piperidin-4-ylamino)-phenyl]-thiophene-2-carboxylic acid ethyl ester The first step of Scheme 71: 4-Bromo-3-ethoxycarbonylmethoxy-5-[3-(1-phenylmethanesulfonyl-piperidin-4-ylamino)-phenyl]-thiophene-2-carboxylic acid methyl ester (1.59 g, 65%) was obtained as follows: To a vigorously stirring suspension of 4-bromo-3-ethoxycarbonylmethoxy-5-[3-(piperidin-4-ylamino)-phenyl]-thiophene-2-carboxylic acid methyl ester hydrochloride (2 g, 3.746 mmol) in DCM (21 mL) and aqueous saturated NaHCO$_3$ (21 mL) was added phenyl-methanesulfonyl chloride (0.786 g, 4.12 mmol). The biphasic reaction mixture was allowed to stir for 1.5 h at room temperature, then diluted with DCM and washed with NaHCO$_3$. The organic layer was dried over MgSO$_4$, solvent was removed under vacuum and crude product was purified by DCM/EtOAc/Hexanes trituration to yield a pale yellow solid.

$^1$H NMR showed 85% C3 ethyl ester along with 15% C3 methyl ester. It was hydrolyzed as it is.

The second step of Scheme 71: 4-Bromo-3-carboxymethoxy-5-[3-(1-phenylmethanesulfonyl-piperidin-4-ylamino)-phenyl]-thiophene-2-carboxylic acid (1.40 g, 95%) was prepared according procedure the fifth step of Scheme 65, using 4-bromo-3-ethoxycarbonylmethoxy-5-[3-(1-phenylmethanesulfonyl-piperidin-4-ylamino)-phenyl]-thiophene-2-carboxylic acid methyl ester (1.59 g, 2.44 mmol) and 1N LiOH (12.2 mL, 12.2 mmol) as starting materials and THF (24.4 mL) as solvent. 4-Bromo-3-carboxymethoxy-5-[3-(1-phenylmethanesulfonyl-piperidin-4-ylamino)-phenyl]-thiophene-2-carboxylic acid was obtained as a yellow solid.

$^1$H NMR (400 MHz, DMSO-D6) δ ppm 1.35 (m, 2 H) 1.95 (d, J=10.11 Hz, 2 H) 2.51 (s, 1 H) 2.92 (m, 2 H) 3.54 (d, J=9.85 Hz, 2 H) 4.40 (s, 2 H) 4.87 (s, 2 H) 5.91 (s, 1 H) 6.77 (m, 3 H) 7.20 (m, 1 H) 7.39 (m, 5 H).

The third step of Scheme 71: 4-Bromo-3-ethoxycarbonylmethoxy-5-[3-(1-phenylmethanesulfonyl-piperidin-4-ylamino)-phenyl]-thiophene-2-carboxylic acid ethyl ester (253.2 mg, 46%) was prepared as follows: 4-Bromo-3-carboxymethoxy-5-[3-(1-phenylmethanesulfonyl-piperidin-4-ylamino)-phenyl]-thiophene-2-carboxylic acid (505 mg, 0.828 mmol) was combined with DMF (25 mL), K$_2$CO$_3$ (powder) (2.29 g, 16.56 mmol) and EtI (236 µL, 3.312 mmol) and stirred at room temperature for three days. It was then filtered off, solvent was removed under vacuum and the residue was purified by column chromatography using 40% EtOAc/Hexanes as eluent and lyophilized to yield 4-bromo-3-ethoxycarbonylmethoxy-5-[3-(1-phenylmethanesulfonyl-piperidin-4-ylamino)-phenyl]-thiophene-2-carboxylic acid ethyl ester as yellow solid.

$^1$H NMR (400 MHz, CHLOROFORM-D) δ ppm 1.34 (m, 7 H) 2.04 (m, 2 H) 2.78 (t, J=10.74 Hz, 2 H) 3.36 (s, 1 H) 3.63 (d, J=9.09 Hz, 3 H) 4.24 (s, 2 H) 4.32 (m, 4 H) 4.90 (s, 2 H) 6.61 (d, J=8.08 Hz, 1 H) 6.83 (m, 1 H) 6.95 (d, J=10.11 Hz, 1 H) 7.22 (t, J=7.96 Hz, 1 H) 7.41 (s, 5 H).

HRMS: calcd for C$_{29}$H$_{33}$BrN$_2$O$_7$S$_2$, 664.0913; found (ESI-FTMS), 665.0991.

EXAMPLE 484

4-Bromo-5-[3-(1-phenylmethanesulfonyl-piperidin-4-ylamino)-phenyl]-3-(o-tolylcarbamoyl-methoxy)-thiophene-2-carboxylic acid Scheme 72: 4-Bromo-5-[3-(1-phenylmethanesulfonyl-piperidin-4-ylamino)-phenyl]-3-(o-tolylcarbamoyl-methoxy)-thiophene-2-carboxylic acid (4.4 mg, 4.1%) was prepared as follows: 4-Bromo-3-carboxymethoxy-5-[3-(1-phenylmethanesulfonyl-piperidin-4-ylamino)-phenyl]-thiophene-2-carboxylic acid (93 mg, 0.153 mmol) was added with DMF (2 mL), DIEA (32 µL, 0.1836 mmol) and BOP reagent (81.2 mg, 0.1836 mmol) and stirred at room temperature for 1 h. Then o-tolylamine (16.4 µL, 0.153 mmol) was added and stirred overnight. The reaction mixture was poured into cold water; the precipitate was filtered off, washed with water and purified by preparative HPLC. 4-Bromo-5-[3-(1-phenylmethanesulfonyl-piperidin-4-ylamino)-phenyl]-3-(o-tolylcarbamoyl-methoxy)-thiophene-2-carboxylic acid was obtained as off white solid.

$^1$H NMR (400 MHz, DMSO-D6) δ ppm 1.37 (d, J=12.88 Hz, 2 H) 1.96 (d, J=12.13 Hz, 2 H) 2.27 (s, 3 H) 2.92 (t, J=9.73 Hz, 2 H) 3.41 (s, 1 H) 3.54 (m, 2 H) 4.40 (s, 2 H) 4.83 (s, 2 H) 5.87 (s, 1 H) 6.76 (m, 3 H) 7.18 (m, 4 H) 7.39 (m, 5 H) 7.51 (d, J=7.33 Hz, 1 H) 8.14 (s, 1 H).

EXAMPLE 485

{4-Bromo-2-hydroxymethyl-5-[3-(1-phenylmethanesulfonyl-piperidin-4-ylamino)-phenyl]-thiophen-3-yloxy}-acetic acid {4-Bromo-2-hydroxymethyl-5-[3-(1-phenylmethanesulfonyl-piperidin-4-ylamino)-phenyl]-thiophen-3-yloxy}-acetic acid was synthesized according to the following procedure: 4-bromo-3-carboxymethoxy-5-[3-(1-phenylmethanesulfonyl-piperidin-4-ylamino)-phenyl]-thiophene-2-carboxylic acid methyl ester (400 mg) was dissolved in ethanol (20 mL). To the solution was added excess sodium borohydride (0.6 g). Stirring the mixture at room temperature overnight gave two products. The products were separated by column chromatrography on silica gel using ethylacetate/hexane as eluent. One was the target compound, {4-bromo-2-hydroxymethyl-5-[3-(1-phenylmethanesulfonyl-piperidin-4-ylamino)-phenyl]-thiophen-3-yloxy}-acetic acid (100 mg, yield 30%).

$^1$H NMR (400 MHz, MeOD) δ ppm 1.53 (m, 2 H) 2.00 (m, 2 H) 2.83 (m, 2 H) 3.52 (m, 1 H) 3.68 (m, J=12.88 Hz, 2 H) 4.34 (s, 2 H) 4.69 (s, 2 H) 4.80 (s, 2 H) 7.02 (d, 1 H) 7.24 (m, 2 H) 7.40 (m, 6 H).

The other compound was 3-carboxymethoxy-5-[3-(1-phenylmethanesulfonyl-piperidin-4-ylamino)-phenyl]-thiophene-2-carboxylic acid methyl ester (30 mg).

EXAMPLE 486

3-Carboxymethoxy-5-[3-(1-phenylmethanesulfonyl-piperidin-4-ylamino)-phenyl]-thiophene-2-carboxylic acid 3-Carboxymethoxy-5-[3-(1-phenylmethanesulfonyl-piperidin-4-ylamino)-phenyl]-thiophene-2-carboxylic acid was prepared as a white solid (11 mg, yield 58%) according to procedure in the second step of Scheme 2, using 3-carboxymethoxy-5-[3-(1-phenylmethanesulfonyl-piperidin-4-ylamino)-phenyl]-thiophene-2-carboxylic acid methyl ester (20 mg) as the starting material.

$^1$H NMR (400 MHz, MeOD) δ ppm 1.55 (m, 2 H) 2.03 (m, 2 H) 2.84 (m, 2 H) 3.57 (m, 1 H) 3.69 (d, J=12.63 Hz, 2 H) 4.35 (s, 2 H) 4.89 (s, 2 H) 7.01 (d, J=7.33 Hz, 1 H) 7.26 (s, 2 H) 7.40 (m, 7 H).

EXAMPLE 487

4-Bromo-3-carboxymethoxy-5-(3-{1-[3-(3-ethyl-ureido)-phenylmethanesulfonyl]-piperidin-4-ylamino}-phenyl)-thiophene-2-carboxylic acid To a solution of 4-bromo-3-methoxycarbonylmethoxy-5-{3-[1-(3-nitro-phenylmethanesulfonyl)-piperidin-4-ylamino]-phenyl}-thiophene-2-carboxylic acid ethyl ester (1.21 g, 1.74 mmol) and pyridine (3.4 mmol) in methylene chloride (25 mL) was added with trifluoroacetic anhydride (0.37 mL, 1.5 equiv.) at 0° C. The mixture was stirred at room temperature for 2 h before being quenched with aqueous sodium bicarbonate solution. The product was extracted with ethyl acetate and washed with aqueous ammonium chloride solution and brine, dried over sodium sulfate. Removal of the solvent gave 4-bromo-3-methoxycarbonylmethoxy-5-{3-[[1-(3-nitro-phenylmethanesulfonyl)-piperidin-4-yl]-(2,2,2-trifluoro-acetyl)-amino]-phenyl}-thiophene-2-carboxylic acid ethyl ester (1.25 g, yield 91%).

4-Bromo-3-methoxycarbonylmethoxy-5-{3-[[1-(3-nitro-phenylmethanesulfonyl)-piperidin-4-yl]-(2,2,2-trifluoro-acetyl)-amino]-phenyl}-thiophene-2-carboxylic acid ethyl ester (0.26 g, 0.33 mmol) was dissolved into ethyl acetate (5 mL). 10% palladium on carbon was added and the mixture was subjected to hydrogen overnight. After filtration and removal of the solvent, 5-{3-[[1-(3-amino-phenylmethanesulfonyl)-piperidin-4-yl]-(2,2,2-trifluoro-acetyl)-amino]-phenyl}-4-bromo-3-methoxycarbonylmethoxy-thiophene-2-carboxylic acid ethyl ester (0.25 g, yield 99%) was obtained.

5-{3-[[1-(3-Amino-phenylmethanesulfonyl)-piperidin-4-yl]-(2,2,2-trifluoro-acetyl)-amino]-phenyl}4-bromo-3-methoxycarbonylmethoxy-thiophene-2-carboxylic acid ethyl ester (60 mg, 0.078 mmol) was dissolved into methylene chloride (2 mL). The solution was added with ethyl isocyanate and stirred at room temperature overnight. Solvent was removed under reduced pressure. The crude product was purified with HPLC, and then hydrolyzed according to procedure the second step of Scheme 2 to give 4-bromo-3-carboxymethoxy-5-(3-{1-[3-(3-ethyl-ureido)-phenylmethanesulfonyl]-piperidin-4-ylamino}-phenyl)-thiophene-2-carboxylic acid (49 mg, yield 91%).

$^1$H NMR (400 MHz, MeOD) δ ppm 1.24 (t, J=7.20 Hz, 3 H) 1.74 (m, 2 H) 2.00 (m, 2 H) 3.03 (m, 2 H) 3.33 (q, J=7.33 Hz, 2 H) 3.85 (m, J=6.69 Hz, 3 H) 4.47 (s, 2 H) 5.05 (s, 2 H) 7.24 (d, J=8.59 Hz, 1 H) 7.31 (d, J=6.82 Hz, 1 H) 7.41 (t, J=7.83 Hz, 2 H) 7.63 (m, 3 H) 7.75 (s, 1 H).

EXAMPLE 488

[2-(2-{4-Bromo-2-methoxycarbonyl-5-[3-(1-phenyl-methanesulfonyl-piperidin-4-ylamino)-phenyl]-thiophen-3-yloxy}-acetoxy)-ethyl]-trimethyl-ammonium chloride

[2-(2-{4-Bromo-2-methoxycarbonyl-5-[3-(1-phenyl-methanesulfonyl-piperidin-4-ylamino)-phenyl]-thiophen-3-yloxy}-acetoxy)-ethyl]-trimethyl-ammonium chloride was synthesized according to the procedure set forth in Example 489.

$^1$H NMR (400 MHz, MeOD) δ ppm 1.47 (m, 2 H) 2.00 (m, J=6.06 Hz, 2 H) 2.91 (t, 2 H) 3.20 (m, 2 H) 3.25 (s, 9 H) 3.40 (m, 1 H) 3.60 (m, 2 H) 3.80 (m, 2 H) 3.85 (s, 3 H) 4.34 (s, 2 H) 4.98 (s, 2 H) 6.74 (dd, J=2.27 Hz, 1 H) 6.86 (m, 2 H) 7.20 (t, J=7.96 Hz, 1 H) 7.41 (m, 4 H).

EXAMPLE 489

4-Bromo-3-cyclohexylcarbamoylmethoxy-5-[3-(1-phenylmethanesulfonyl-piperidin-4-ylamino)-phenyl]-thiophene-2-carboxylic acid methyl ester

[2-(2-{4-Bromo-2-methoxycarbonyl-5-[3-(1-phenyl-methanesulfonyl-piperidin-4-ylamino)-phenyl]-thiophen-3-yloxy}-acetoxy)-ethyl]-trimethyl-ammonium chloride (Example 488) and 4-bromo-3-cyclohexylcarbamoylmethoxy-5-[3-(1-phenylmethanesulfonyl-piperidin-4-ylamino)-phenyl]-thiophene-2-carboxylic acid methyl ester (Example 489) were synthesized according to the following procedures: 4-Bromo-3-carboxymethoxy-5-[3-(1-phenylmethanesulfonyl-piperidin-4-ylamino)-phenyl]-thiophene-2-carboxylic acid methyl ester (500 mg, 0.8 mmol) was dissolved in anhydrous acetonitrile and 1,3-dicyclohexylcarbodiimide (0.19 g, 1.2 equiv.) was added. The solution was stirred at room temperature for 10 min before the addition of choline chloride (0.22 g, 2.0 equiv.). The temperature was raised to 60° C. and the reaction was allowed to proceed for 4 h until the disappearance of the starting material. Solvent was removed under reduced pressure. The crude product was purified with HPLC to give [2-(2-{4-bromo-2-methoxycarbonyl-5-[3-(1-phenyl-methanesulfonyl-piperidin-4-ylamino)-phenyl]-thiophen-3-yloxy}-acetoxy)-ethyl]-trimethyl-ammonium chloride (92 mg, yield 16%), and 4-bromo-3-cyclohexylcarbamoyl-methoxy-5-[3-(1-phenylmethanesulfonyl-piperidin-4-ylamino)-phenyl]-thiophene-2-carboxylic acid methyl ester (120 mg, yield 23%).

$^1$H NMR (400 MHz, CHLOROFORM-D) δ ppm 1.37 (m, 6 H) 1.82 (m, 6 H) 2.02 (m, J=8.59 Hz, 4 H) 2.79 (m, 2 H) 3.62 (m, 2 H) 3.84 (s, 3 H) 4.24 (s, 2 H) 4.88 (s, 2 H) 6.62 (dd, J=7.96 Hz, 1 H) 6.81 (m, 1 H) 6.92 (d, J=7.83 Hz, 1 H) 7.22 (t, J=7.96 Hz, 1 H) 7.41 (m, 5 H).

EXAMPLE 490

(4,5-Dibromo-2-hydroxymethyl-thiophen-3-yloxy)-acetic acid (4,5-Dibromo-2-hydroxymethyl-thiophen-3-yloxy)-acetic acid was synthesized according to the following procedure: 4,5-Dibromo-3-carboxymethoxy-thiophene-2-carboxylic acid methyl ester (45 mg, 0.12 mmol) was dissolved into ethanol (2 mL). To the solution was added excess amount of sodium borohydride (0.1 g). The mixture was stirred at room temperature for 0.5 h. The solvent was removed under reduced pressure and the crude product was purified by HPLC to afford (4,5-dibromo-2-hydroxymethyl-thiophen-3-yloxy)-acetic acid (40 mg, yield 96%).

$^1$H NMR (400 MHz, CHLOROFORM-D) δ ppm 3.73 (d, J=7.07 Hz, 2 H) 4.79 (m, J=2.78 Hz, 2 H).

EXAMPLE 491

5-[3-(Acetyl-cyclohexyl-amino)-phenyl]-4-bromo-3-carboxymethoxy-thiophene-2-carboxylic acid 5-[3-(Acetyl-cyclohexyl-amino)-phenyl]-4-bromo-3-carboxymethoxy-thiophene-2-carboxylic acid was prepared according to the procedure of Example 492.

$^1$H NMR (400 MHz, MeOD) δ ppm 1.20 (m, 10 H) 1.79 (s, 3 H) 2.03 (m, 1 H) 4.54 (m, 1 H) 4.91 (s, 2 H) 6.82 (d, J=10.36 Hz, 1 H) 7.33 (d, J=8.84 Hz, 1 H) 7.55 (s, 1 H) 7.61 (t, J=7.96 Hz, 1 H).

EXAMPLE 492

5-[3-(Acetyl-cyclohexyl-amino)-phenyl]-4-bromo-3-carboxymethoxy-thiophene-2-carboxylic acid methyl ester The first step of Scheme 73: 4-Bromo-3-tert-butoxycarbonylmethoxy-5-(3-cyclohexylamino-phenyl)-thiophene-2-carboxylic acid methyl ester (40 mg, 0.076 mmol) was dissolved in methylene chloride (1 mL). To the solution was added Hunig's base (2.0 equiv.) and acetyl chloride (1.2equiv.). The mixture was stirred at room temperature for 0.5 h.

5-[3-(Acetyl-cyclohexyl-amino)-phenyl]-4-bromo-3-tert-butoxycarbonylmethoxy-thiophene-2-carboxylic acid methyl ester (39 mg) was obtained as a light yellow solid.

The second step of Scheme 73: 5-[3-(Acetyl-cyclohexyl-amino)-phenyl]-4-bromo-3-carboxymethoxy-thiophene-2-carboxylic acid (Example 491) and 5-[3-(acetyl-cyclohexyl-amino)-phenyl]-4-bromo-3-carboxymethoxy-thiophene-2-carboxylic acid methyl ester (Example 492) were prepared following the procedure in the second step of Example 1. Solvent was removed under reduced pressure. HPLC purification gave 5-[3-(acetyl-cyclohexyl-amino)-phenyl]-4-bromo-3-carboxymethoxy-thiophene-2-carboxylic acid (6 mg) as a white solid, and 5-[3-(acetyl-cyclohexyl-amino)-phenyl]-4-bromo-3-carboxymethoxy-thiophene-2-carboxylic acid methyl ester (3 mg) as a white solid.

$^1$H NMR (400 MHz, MeOD) δ ppm 0.97 (m, J=13.14 Hz, 1 H) 1.14 (m, 2 H) 1.39 (m, 2 H) 1.59 (m, 1 H) 1.79 (m, 2 H) 1.79 (s, 3 H) 1.89 (m, 2 H) 3.79 (s, 3 H) 4.55 (m, 1 H) 4.96 (s, 2 H) 7.33 (d, J=7.33 Hz, 1 H) 7.55 (s, 1 H) 7.61 (t, J=7.83 Hz, 1 H) 7.70 (d, 1 H).

EXAMPLE 493

5-[3-(Benzoyl-cyclohexyl-amino)-phenyl]-4-bromo-3-carboxymethoxy-thiophene-2-carboxylic acid 5-[3-(Benzoyl-cyclohexyl-amino)-phenyl]-4-bromo-3-carboxymethoxy-thiophene-2-carboxylic acid (10 mg), was synthesized as a white solid according to Scheme 73.

$^1$H NMR (400 MHz, MeOD) δ ppm 1.03 (m, J=12.38 Hz, 1 H) 1.33 (m, 4 H) 1.46 (m, 1 H) 1.62 (m, 1 H) 1.84 (d, J=14.91 Hz, 2 H) 2.03 (s, 2 H) 4.87 (s, 2 H) 7.24 (m, 6 H) 7.40 (m, 3 H).

EXAMPLE 494

5-[3-(Benzoyl-cyclohexyl-amino)-phenyl]-4-bromo-3-carboxymethoxy-thiophene-2-carboxylic acid methyl ester 5-[3-(Benzoyl-cyclohexyl-amino)-phenyl]-4-bromo-3-carboxymethoxy-thiophene-2-carboxylic acid methyl ester (15 mg), was synthesized as a white solid according to Scheme 73.

$^1$H NMR (400 MHz, MeOD) δ ppm 1.05 (m, 1 H) 1.31 (m, J=12.63 Hz, 2 H) 1.46 (m, 1 H) 1.63 (m, 1 H) 1.82 (m, 2 H) 2.04 (m, 2 H) 3.78 (s, 3 H) 4.93 (s, 2 H) 7.27 (m, 6 H) 7.40 (m, J=10.11 Hz, 3 H).

EXAMPLE 495

4-Bromo-3-carboxymethoxy-5-{3-[cyclohexyl-(3-phenyl-acryloyl)-amino]-phenyl}-thiophene-2-carboxylic acid methyl ester 4-Bromo-3-carboxymethoxy-5-{3-[cyclohexyl-(3-phenyl-acryloyl)-amino]-phenyl}-thiophene-2-carboxylic acid methyl ester (5 mg), was synthesized as a white solid according to Scheme 73.

$^1$H NMR (400 MHz, MeOD) δ ppm 1.04 (m, 1 H) 1.24 (m, 3 H) 1.44 (s, 2 H) 1.62 (m, 1 H) 1.81 (m, 4 H) 3.77 (s, 3 H) 4.94 (s, 2 H) 6.20 (d, J=15.66 Hz, 1 H) 7.29 (m, 5 H) 7.37 (d, J=8.84 Hz, 1 H) 7.56 (m, 2 H) 7.65 (t, J=7.83 Hz, 1 H) 7.73 (d, 1 H).

EXAMPLE 496

4-Bromo-3-carboxymethoxy-5-[3-(cyclohexanecarbonyl-cyclohexyl-amino)-phenyl]-thiophene-2-carboxylic acid methyl ester 4-Bromo-3-carboxymethoxy-5-[3-(cyclohexanecarbonyl-cyclohexyl-amino)-phenyl]-thiophene-2-carboxylic acid methyl ester (7 mg), was synthesized as a white solid according to Scheme 73.

$^1$H NMR (400 MHz, MeOD) δ ppm 0.94 (m, 4 H) 1.11 (m, 3 H) 1.54 (m, 14 H) 3.79 (s, 3 H) 4.51 (m, 1 H) 4.97 (s, 2 H) 7.32 (d, J=1.01 Hz, 1 H) 7.50 (d, J=1.52 Hz, 1 H) 7.62 (t, J=7.71 Hz, 1 H) 7.70 (m, 1 H).

EXAMPLE 497

5-{3-[Benzoyl-(3,3,5,5-tetramethyl-cyclohexyl)-amino]-phenyl}-4-bromo-3-carboxymethoxy-thiophene-2-carboxylic acid 5-{3-[Benzoyl-(3,3,5,5-tetramethyl-cyclohexyl)-amino]-phenyl}-4-bromo-3-carboxymethoxy-thiophene-2-carboxylic acid (51 mg), was synthesized as a white solid according to Scheme 73.

$^1$H NMR (400 MHz, MeOD) δ ppm 0.90 (s, 12 H) 1.12 (m, 4 H) 1.76 (m, 3 H) 4.89 (s, 2 H) 7.31 (m, 9 H)

EXAMPLE 498

4-Bromo-3-carboxymethoxy-5-[3-(1-phenyl-methanesulfonyl-piperidin-4-ylamino)-phenyl]-thiophene-2-carboxylic acid methyl ester (Hydrochloride Salt)

4-Bromo-3-carboxymethoxy-5-[3-(1-phenylmethanesulfonyl-piperidin-4-ylamino)-phenyl]-thiophene-2-carboxylic acid methyl ester (Hydrochloride Salt) (265 mg) was prepared by treating 4-bromo-3-tert-butoxycarbonyl-methoxy-5-[3-(1-phenylmethanesulfonyl-piperidin-4-ylamino)-phenyl]-thiophene-2-carboxylic acid methyl ester with 4 mL of 4M solution of HCl in dioxane for 4 h.

$^1$H NMR (400 MHz, DMSO-D6) δ ppm 1.40 (m, 2 H) 1.95 (d, J=9.85 Hz, 2 H) 2.91 (m, 2 H) 3.43 (m, 1 H) 3.55 (d, J=12.88 Hz, 2 H) 3.81 (s, 3 H) 4.40 (s, 2 H) 4.86 (s, 2 H) 6.83 (d, J=7.58 Hz, 1 H) 6.90 (d, J=8.08 Hz, 1 H) 6.90 (d, 2 H) 6.97 (s, 1 H) 7.26 (t, J=7.83 Hz, 1 H) 7.39 (m, 5 H).

EXAMPLE 499

4-Bromo-3-[(carbamoylmethyl-carbamoyl)-methoxy]-5-[3-(3,3,5,5-tetramethyl-cyclohexylamino)-phenyl]-thiophene-2-carboxylic acid methyl ester Scheme 74: To a methylene chloride suspension of PS-DIC resin (0.41 g, 0.54 mmol) was added 4-bromo-3-carboxymethoxy-5-[3-(3,3,5,5-tetramethyl-cyclohexylamino)-phenyl]-thiophene-2-carboxylic acid methyl ester (0.215 g, 0.41 mmol). The heterogeneous mixture was stirred for 5 minutes. Hydrochloride salt of glycinamide (0.035 g, 0.322 mmol) was added to the above reaction mixture followed by the addition of PS-DIEA resin (0.100 g, 0.39 mmol). The resulting mixture was stirred overnight at room temperature. The resin was filtered off and the methylene chloride was evaporated using Genevac. The final product 4-bromo-3-[(carbamoylmethyl-carbamoyl)-methoxy]-5-[3-(3,3,5,5-tetramethyl-cyclohexylamino)-phenyl]-thiophene-2-carboxylic acid methyl ester was obtained through reverse phase HPLC purification (21 mg, 11%).

$^1$H NMR (400 MHz, CHLOROFORM-D) δ ppm 0.92 (d, J=12 Hz, 1 H) 0.94 (s, 6 H) 0.96 (d, J=12 Hz, 1 H) 1.10 (d, J=8 Hz, 1 H) 1.11 (s, 6 H) 1.31 (d, J=13.64 Hz, 1 H) 1.88 (d, J=12.13 Hz, 2 H) 3.62 (m, 1 H) 3.88 (s, 3 H) 4.12 (d, J=6.06 Hz, 2 H) 4.79 (s, 2 H) 5.64 (s, 1 H) 6.57 (s, 1 H) 6.68 (d, J=9.09 Hz, 1 H) 6.87 (s, 1 H) 6.90 (d, J=7.58 Hz, 1 H) 7.23 (d, J=8.08 Hz, 1 H) 8.30 (t, J=8.08 Hz, 1 H).

EXAMPLE 500

4-Bromo-3-[(1-carbamoyl-ethylcarbamoyl)-methoxy]-5-[3-(3,3,5,5-tetramethyl-cyclohexylamino)-phenyl]-thiophene-2-carboxylic acid methyl ester Scheme 74: 4-Bromo-3-[(1-carbamoyl-ethylcarbamoyl)-methoxy]-5-[3-(3,3,5,5-tetramethyl-cyclohexylamino)-phenyl]-thiophene-2-carboxylic acid methyl ester was prepared (18.5 mg, 11%) according to the procedure in Example 499.

$^1$H NMR (400 MHz, CHLOROFORM-D) δ ppm 0.92 (d, J=12 Hz, 1 H) 0.94 (s, 6 H) 0.96 (d, J=12 Hz, 1 H) 1.11 (d, J=8 Hz, 1 H) 1.12 (s, 6 H) 1.31 (m, 1 H) 1.53 (d, J=7.33 Hz, 3 H) 1.88 (d, J=12.88 Hz, 2 H) 3.61 (m, 1 H) 3.88 (s, 3 H) 4.63 (m, 1 H) 4.79 (dd, 2 H, J=12 Hz) 5.76 (s, 1 H) 6.65 (s, 1 H) 6.68 (dd, J=1.77 Hz, 2 H) 6.88 (t, J=2.02 Hz, 1 H) 6.90 (d, 1 H) 7.23 (d, J=7.83 Hz, 1 H) 8.22 (d, J=7.83 Hz, 1 H).

EXAMPLE 501

4-Bromo-3-[(ethoxycarbonylmethyl-carbamoyl)-methoxy]-5-[3-(3,3,5,5-tetramethyl-cyclohexylamino)-phenol-thiophene-2-carboxylic acid methyl ester Scheme 74: 4-Bromo-3-[(ethoxycarbonylmethyl-carbamoyl)-methoxy]-5-[3-(3,3,5,5-tetramethyl-cyclohexylamino)-phenyl]-thiophene-2-carboxylic acid methyl ester was prepared (66.5 mg, 44%) according to the procedure Example 499.

$^1$H NMR (400 MHz, CHLOROFORM-D) δ ppm 0.92 (d, J=12 Hz, 1 H) 0.94 (s, 6 H) 0.96 (d, J=12 Hz, 1 H) 1.10 (d, J=8 Hz, 1 H) 1.11 (s, 6 H) 1.30 (t, J=7.07 Hz, 3 H) 1.31 (d, J=8 Hz, 1 H) 1.88 (d, J=12.63 Hz, 2 H) 3.61 (m, 1 H) 3.89 (s, 3 H) 4.17 (d, J=5.56 Hz, 2 H) 4.24 (q, J=7.24 Hz, 2 H) 4.81 (s, 2 H) 6.69 (dd, J=1.52 Hz, 1 H) 6.90 (s, 1 H) 6.92 (d, J=7.58 Hz, 1 H) 7.24 (t, J=7.96 Hz, 1 H) 8.24 (t, J=5.94 Hz, 1 H).

EXAMPLE 502

4-Bromo-3-r(1-ethoxycarbonyl-ethylcarbamoyl)-methoxy]-5-[3-(3,3,5,5-tetramethyl-cyclohexylamino)-phenyl]-thiophene-2-carboxylic acid methyl ester Scheme 74: 4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester was prepared (85.2 mg, 53%) according to the procedure in Example 499.

$^1$H NMR (400 MHz, CHLOROFORM-D) δ ppm 0.91 (d, J=12 Hz, 1 H) 0.94 (s, 6 H) 0.95 (d, J=12 Hz, 1 H) 1.09 (d, J=8 Hz, 1 H) 1.12 (s, 6 H) 1.29 (t, J=7.07 Hz, 3 H) 1.33 (t, J=1.77 Hz, 1 H) 1.53 (d, J=7.07 Hz, 3 H) 1.89 (d, J=12.38 Hz, 2 H) 3.61 (m, 1 H) 3.88 (s, 3 H) 4.22 (q, J=7.07 Hz, 2 H) 4.68 (m, 1 H) 4.80 (s, 2 H) 6.65 (dd, J=2.02 Hz, 1 H) 6.85 (t, J=1.77 Hz, 1 H) 6.88 (d, J=7.83 Hz, 1 H) 7.22 (t, J=7.83 Hz, 1 H) 8.26 (d, J=7.58 Hz, 1 H).

EXAMPLE 503

4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester Scheme 74: 4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester was prepared (85.2 mg, 21%) according to the procedure in Example 499.

$^1$H NMR (400 MHz, CHLOROFORM-D) δ ppm 0.92 (d, J=12 Hz, 1 H) 0.94 (s, 6 H) 0.96 (d, J=12 Hz, 1 H) 1.11 (d, J=8 Hz, 1 H) 1.12 (s, 6 H) 1.29 (t, J=7.07 Hz, 3 H) 1.33 (m, 1 H) 1.53 (d, J=7.33 Hz, 2 H) 1.88 (d, J=12.88 Hz, 2 H) 3.62 (m, 1 H) 3.89 (s, 3 H) 4.22 (q, J=7.07 Hz, 2 H) 4.69 (m, 1 H) 4.80 (s, 2 H) 6.69 (dd, J=1.39 Hz, 1 H) 6.89 (t, 1 H) 6.92 (d, J=7.58 Hz, 1 H) 7.23 (t, J=7.83 Hz, 1 H) 8.28 (d, J=7.83 Hz, 1 H).

EXAMPLE 504

3-1 [(Benzylcarbamoyl-methyl)-carbamoyl]-methoxy}-4-bromo-5-[3-(3,3,5,5-tetramethylcyclohexylamino)-phenyl]-thiophene-2-carboxylic acid methyl ester Scheme 74: 3-{[(Benzylcarbamoyl-methyl)-carbamoyl]-methoxy}-4-bromo-5-[3-(3,3,5,5-tetramethylcyclohexylamino)-phenyl]-thiophene-2-carboxylic acid methyl ester was prepared (121 mg, 67%) according to the procedure in Example 499 using 4-bromo-3-carboxymethoxy-5-[3-(3,3,5,5-tetramethyl-cyclohexylamino)-phenyl]-thiophene-2-carboxylic acid methyl ester as the starting material.

$^1$H NMR (400 MHz, CHLOROFORM-D) δ ppm 0.92 (d, J=12 Hz, 1 H) 0.94 (s, 6 H) 0.96 (d, J=12 Hz, 1 H) 1.11 (d, J=8 Hz, 1 H) 1.12 (s, 6 H) 1.33 (t, J=1.77 Hz, 1 H) 1.88 (d, J=13.64 Hz, 2 H) 2.00 (s, 1 H) 3.61 (m, 1 H) 3.68 (s, 3 H) 4.17 (d, 2 H) 4.52 (d, J=6.06 Hz, 2 H) 4.76 (s, 2 H) 6.66 (dd, J=2.02 Hz, 1 H) 6.85 (t, J=2.02 Hz, 1 H) 6.88 (d, J=7.83 Hz, 1 H) 6.99 (t, 1 H) 7.28 (m, 6 H) 8.21 (t, J=6.32 Hz, 1 H).

EXAMPLE 505

4-Bromo-3-carboxymethoxy-5-{3-[1-(3-methanesulfonylamino-phenylmethanesulfonyl)-piperidin-4-ylamino]-phenyl}-thiophene-2-carboxylic acid The first step of Scheme 75: 4-Bromo-3-ethoxycarbonylmethoxy-5-{3-[1-(3-nitro-phenylmethanesulfonyl)-piperidin-4-ylamino]-phenyl}-thiophene-2-carboxylic acid methyl ester was obtained in 71% yield following the procedure in the third step of Scheme 15 of Example 143.

The second step of Scheme 75: To a 0.194 mL pyridine solution of 4-bromo-3-ethoxycarbonylmethoxy-5-{3-[1-(3-nitro-phenylmethanesulfonyl)-piperidin-4-ylamino]-phenyl}-thiophene-2-carboxylic acid methyl ester (1.13 g, 1.6 mmol) was added trifluoroaceticanhydride (0.409 g, 1.95 mmol) and the reaction mixture was allowed to stir at room temperature overnight. 8 mL 2N HCl was added to the reaction mixture and extracted with EtOAc and the organic layer washed with saturated sodium bicarbonate solution, brine and dried over MgSO$_4$. Filtration and evaporation gave 1.26 g (99%) of 4-bromo-3-ethoxycarbonylmethoxy-5-{3-[[1-(3-nitro-phenylmethanesulfonyl)-piperidin-4-yl]-(2,2,2-trifluoro-acetyl)-amino]-phenyl}-thiophene-2-carboxylic acid methyl ester.

The third step of Scheme 75: 4-Bromo-3-ethoxycarbonyl-methoxy-5-{3-[[1-(3-nitro-phenylmethanesulfonyl)-piperidin-4-yl]-(2,2,2-trifluoro-acetyl)-amino]-phenyl}-thiophene-2-carboxylic acid methyl ester (1.27 g, 1.6 mmol) was reduced using hydrogen gas over 10% palladium on carbon in methanol for 5 h to afford 5-{3-[[1-(3-amino-phenylmethanesulfonyl)-piperidin-4-yl]-(2,2,2-trifluoro-acetyl)-amino]-phenyl}-4-bromo-3-ethoxycarbonyl-methoxy-thiophene-2-carboxylic acid methyl ester in 79% yield.

The fourth step of Scheme 75: 4-Bromo-3-ethoxycarbonylmethoxy-5-{3-[[1-(3-methanesulfonylamino-phenyl-methanesulfonyl)-piperidin-4-yl]-(2,2,2-trifluoro-acetyl)-amino]-phenyl}-thiophene-2-carboxylic acid methyl ester (83%) and 5-{3-[[1-(3-acetylamino-phenylmethanesulfonyl)-piperidin-4-yl]o-(2,2,2-trifluoro-acetyl)-amino]-phenyl}4-bromo-3-ethoxycarbonylmethoxy-thiophene-2-carboxylic acid methyl ester (74%) were prepared from 5-{3-[[1-(3-amino-phenylmethanesulfonyl)-piperidin-4-yl]-(2,2,2-trifluoro-acetyl)-amino]-phenyl)-4-bromo-3-ethoxycarbonylmethoxy-thiophene-2-carboxylic acid methyl ester following the procedure in the third step of Scheme 15 of Example 143.

The fifth step of Scheme 75: 4-Bromo-3-ethoxycarbonyl-methoxy-5-{3-[[1-(3-methanesulfonylamino-phenyl-methanesulfonyl)-piperidin-4-yl]-(2,2,2-trifluoro-acetyl)-amino]-phenyl}-thiophene-2-carboxylic acid methyl ester was hydrolyzed according to the procedure in the fourth step of Scheme 15 of Example 141 to give 4-bromo-3-carboxymethoxy-5-{3-[1-(3-methanesulfonylamino-phenyl-methanesulfonyl)-piperidin-4-ylamino]-phenyl}-thiophene-2-carboxylic acid in 27% yield as a pale yellow solid.

$^1$H NMR (400 MHz, MeOD) δ ppm 1.57 (m, 2 H) 2.05 (m, 2 H) 2.91 (t, J=12.25 Hz, 2 H) 3.02 (s, 3 H) 3.59 (m, 1 H) 3.72 (d, J=12.63 Hz, 2 H) 4.39 (s, 2 H) 4.94 (s, 2 H) 7.12 (m, 1 H) 7.25 (m, 2 H) 7.32 (m, 2 H) 7.39 (m, 2 H) 7.46 (m, 1 H).

EXAMPLE 506

5-{3-[1-(3-Acetylamino-phenylmethanesulfonyl)-piperidin-4-ylamino]-phenyl}-4-bromo-3-carboxymethoxy-thiophene-2-carboxylic acid The fifth step of Scheme 75: 5-{3-[[1-(3-Acetylamino-phenylmethanesulfonyl)-piperidin-4-yl]-(2,2,2-trifluoro-acetyl)-amino]-phenyl}-4-bromo-3-ethoxycarbonyl-methoxy-thiophene-2-carboxylic acid methyl ester was hydrolyzed according to the procedure in the fourth step of Scheme 15 of Example 141 to give 5-{3-[1-(3-acetylamino-phenylmethanesulfonyl)-piperidin-4-ylamino]-phenyl}-4-bromo-3-carboxymethoxy-thiophene-2-carboxylic acid in 39% yield as a off white solid.

$^1$H NMR (400 MHz, MeOD) δ ppm 1.73 (m, 2 H) 2.10 (d, J=13.64 Hz, 2 H) 2.26 (s, 3 H) 2.99 (t, J=12.25 Hz, 2 H) 3.75 (m, 1 H) 3.81 (d, J=13.64 Hz, 2 H) 4.47 (s, 2 H) 5.04 (s, 2 H) 7.31 (m, 1 H) 7.46 (m, 3 H) 7.67 (m, 3 H) 7.89 (s, 1 H).

EXAMPLE 507

{[4-Bromo-5-(3-methoxyphenyl)-2-(morpholin-4-ylcarbonyl)thien-3-yl]oxy}acetic acid The first step of Scheme 76: A solution of 4,5-dibromo-3-methoxycarbonylmethoxy-thiophene-2-carboxylic acid (5.10 g, 14 mmol) and thionyl chloride (5 mL, 5 eq) in toluene (100 mL) was heated at 90° C. for 16 h. Evaporation provided (4,5-dibromo-2-chlorocarbonyl-thiophen-3-yloxy)-acetic acid methyl ester (5.23 g, 100%).

$^1$H NMR (400 MHz, CHLOROFORM-D) δ ppm 3.81 (s, 3 H) 4.89 (s, 2 H).

The second step of Scheme 76: A solution of (4,5-dibromo-2-chlorocarbonyl-thiophen-3-yloxy)-acetic acid methyl ester (1.0 g, 2.5 mmol), morpholine (0.67 mL, 3 eq), and 4,4-dimethylaminopyridine (50 mg) in THF (20 mL) was stirred at room temperature for 16 h. The solution was diluted with ethyl acetate, washed with 10% aq. HCl, water and brine, dried, evaporated and flash chromatographed (40% ethyl acetate/hexanes) to provide [4,5-dibromo-2-(morpholine-4-carbonyl)-thiophen-3-yloxy]-acetic acid methyl ester (0.95 g, 85%).

$^1$H NMR (400 MHz, CHLOROFORM-D) δ ppm 3.60-3.76 (m, 8 H) 3.78 (s, 3 H) 4.68 (s, 2 H).

The third step of Scheme 76: A solution of [4,5-dibromo-2-(morpholine-4-carbonyl)-thiophen-3-yloxy]-acetic acid methyl ester (200 mg, 0.5 mmol), KF (79 mg, 3 eq), Pd(Ph$_3$P)$_4$ (52 mg, 0.1 eq), 3-methoxyphenylboronic acid (89 mg, 1.3 eq.) dissolved in DME (2 mL) and water (1 mL) was heated in a microwave reactor at 130° C. for 20 min. The reaction was diluted with ethyl acetate, washed with water and brine, dried, filtered, evaporated and chromatographed (60% ethyl acetate/hexanes) to provide [4-bromo-5-(3-methoxyphenyl)-2-(morpholine-4-carbonyl)-thiophen-3-yloxy]-acetic acid methyl ester (89 mg).

$^1$H NMR (400 MHz, CHLOROFORM-D) δ ppm 3.65-3.79 (m, 8 H) 3.80 (s, 3 H) 3.85 (s, 3 H) 4.72 (s, 2 H) 6.97 (dd, J=8.34, 2.53 Hz, 1 H) 7.14-7.21 (m, 2 H) 7.36 (t, J=7.96 Hz, 1 H).

The fourth step of Scheme 76: A solution of [4-bromo-5-(3-methoxy-phenyl)-2-(morpholine-4-carbonyl)-thiophen-3-yloxy]-acetic acid methyl ester and lithium hydroxide (8 mg, 1 eq) in THF (1 mL), MeOH, (1 mL), and water (0.5 mL) was stirred at room temperature for 1 h. The solution was acidified with Amberlyst 15 resin, filtered and evaporated to provide [4-bromo-5-(3-methoxy-phenyl)-2-(morpholine-4-carbonyl)-thiophen-3-yloxy]-acetic acid (89 mg, 43%, 2 steps).

$^1$H NMR (400 MHz, CHLOROFORM-D) δ ppm 3.76 (s, 8 H) 3.86 (s, 3 H) 4.85 (s, 2 H) 6.96-7.01 (m, 1 H) 7.13-7.19 (m, 2 H) 7.37 (t, 1 H).

EXAMPLE 508

{[5-(1,3-Benzodioxol-5-yl)-4-bromo-2-(morpholin-4-ylcarbonyl)thien-3-yl]oxy}acetic acid The third step of Scheme 76: [5-Benzo[1,3]dioxol-5-yl-4-bromo-2-(morpholine-4-carbonyl)-thiophen-3-yloxy]-acetic acid methyl ester (55 mg, 25%) was synthesized according to the procedures in the third step of Scheme 76 of Example 507, using [4,5-dibromo-2-(morpholine-4-carbonyl)-thiophen-3-yloxy]-acetic acid methyl ester (200 mg, 0.45 mmol) and 3,4-methylenedioxy-benzeneboronic acid (97 mg, 1.3 eq).

$^1$H NMR (400 MHz, CHLOROFORM-D) δ ppm 3.65-3.78 (m, 8 H) 3.79 (s, 3 H) 4.71 (s, 2 H) 6.03 (s, 2 H) 6.88 (d, J=8.08 Hz, 1 H) 7.05-7.12 (m, 2 H).

The fourth step of Scheme 76: [5-Benzo[1,3]dioxol-5-yl-4-bromo-2-(morpholine-4-carbonyl)-thiophen-3-yloxy]-acetic acid ester (38 mg) was synthesized according to the procedures in the fourth step of Scheme 76 of Example 507, using [5-benzo[1,3]dioxol-5-yl-4-bromo-2-(morpholine-4-carbonyl)-thiophen-3-yloxy]-acetic acid methyl ester as a starting material to provide {[5-(1,3-benzodioxol-5-yl)-4-bromo-2-(morpholin-4-ylcarbonyl)thien-3-yl]oxy}acetic acid.

$^1$H NMR (400 MHz, CHLOROFORM-D) δ ppm 3.76 (s, 8 H) 4.84 (s, 2 H) 6.04 (s, 2 H) 6.89 (d, J=7.58 Hz, 1 H) 7.05-7.11 (m, 1 H).

EXAMPLE 509

{[3-Bromo-5-(morpholin-4-ylcarbonyl)-2,3'-bithien-4-yl]oxy}acetic acid

[3-Bromo-5-(morpholine-4-carbonyl)-[2,3]-bithiophenyl-4-yloxy]-acetic acid methyl ester (108 mg, 53%) was synthesized according to the procedures in the third step of Scheme 76 of Example 507, using [4,5-dibromo-2-(morpholine-4-carbonyl)-thiophen-3-yloxy]-acetic acid methyl ester (200 mg, 0.45 mmol) and thiophene-3-boronic acid (75 mg, 1.3 eq).

$^1$H NMR (400 MHz, CHLOROFORM-D) δ ppm 3.66-3.78 (m, 8 H) 3.79 (s, 3 H) 4.71 (s, 2 H) 7.39-7.44 (m, 2 H) 7.78 (dd, J=2.65, 1.64 Hz, 1 H).

[3-Bromo-5-(morpholine-4-carbonyl)-[2,3]-bithiophenyl-4-yloxy]-acetic acid (99 mg, 95%) was synthesized according to the procedures in the fourth step of Scheme 76 of Example 507, using [3-bromo-5-(morpholine-4-carbonyl)-[2,3]-bithiophenyl-4-yloxy]-acetic acid methyl ester.

$^1$H NMR (400 MHz, CHLOROFORM-D) δ ppm 3.71-3.81 (m, 8 H) 4.83 (s, 2 H) 7.25-7.30 (m, 1 H) 7.39-7.45 (m, 2 H) 7.79 (dd, J=2.78, 1.52 Hz, 1 H).

EXAMPLE 510

{[4-Bromo-2-(morpholin-4-ylcarbonyl)-5-phenylthien-3-yl]oxy}acetic acid

The third step of Scheme 76: [4-Bromo-2-(morpholine-4-carbonyl)-5-phenyl-thiophen-3-yloxy]-acetic acid methyl (106 mg, 43%) ester was synthesized according to the procedures in Example 507, using [4,5-dibromo-2-(morpholine-4-carbonyl)-thiophen-3-yloxy]-acetic acid methyl ester (250 mg, 0.56 mmol) benzeneboronic acid (90 mg, 1.3 eq) Pd(Ph$_3$P)$_4$ (65 mg, 0.1 eq), and KF (98 mg, 3 eq).

$^1$H NMR (400 MHz, CHLOROFORM-D) δ ppm 3.67-3.79 (m, 8 H) 3.80 (s, 3 H) 4.72 (s, 2 H) 7.41-7.49 (m, 3 H) 7.59-7.64 (m, 2 H).

The fourth step of Scheme 76: [4-Bromo-2-(morpholine-4-carbonyl)-5-phenyl-thiophen-3-yloxy]-acetic acid (100 mg, 100%) was synthesized according to the procedures in Example 507, using [4-bromo-2-(morpholine-4-carbonyl)-5-phenyl-thiophen-3-yloxy]-acetic acid methyl ester.

$^1$H NMR (400 MHz, CHLOROFORM-D) δ ppm 3.73-3.82 (m, 8 H) 4.85 (s, 2 H) 7.43-7.50 (m, 3 H) 7.57-7.63 (m, 2 H).

EXAMPLE 511

[(4,5-Dibromo-2-{[(2-hydroxy-1,1-dimethylethyl)amino]carbonyl}thien-3-yl)oxy]acetic acid The second step of Scheme 76: [4,5-Dibromo-2-(2-hydroxy-1,1-dimethyl-ethylcarbamoyl)-thiophen-3-yloxy]-acetic acid methyl ester (228 mg, 39%) was synthesized according to the procedures in Example 507, using (4,5-dibromo-2-chlorocarbonyl-thiophen-3-yloxy)-acetic acid methyl ester (500 mg, 1.3 mmol), pyridine (320 µL), and 2-amino-2-methyl-1-propanol (188 µL, 1.5 eq) in dichloromethane (5 mL).

$^1$H NMR (400 MHz, CHLOROFORM-D) δ ppm 1.41 (s, 6 H) 3.67 (d, J=6.06 Hz, 2 H) 3.84 (s, 3 H) 4.38-4.46 (m, 1 H) 4.90 (s, 2 H) 7.90 (s, 1 H).

The fourth step of Scheme 76: [4,5-Dibromo-2-(2-hydroxy-1,1-dimethyl-ethylcarbamoyl)-thiophen-3-yloxy]-acetic acid methyl ester (100 mg, 100%) was synthesized according to the procedures in Example 507, using [4,5-dibromo-2-(2-hydroxy-1,1-dimethyl-ethylcarbamoyl)-thiophen-3-yloxy]-acetic acid.

$^1$H NMR (400 MHz, DMSO-D6) δ ppm 1.29 (s, 6 H) 3.33 (bs, 1 H) 3.48 (s, 2 H) 4.89 (s, 2 H) 7.81 (s, 1 H).

EXAMPLE 512

({4,5-Dibromo-2-[(dimethylamino)carbonyl]thien-3-yl}oxy)acetic acid

The second step of Scheme 76: (4,5-Dibromo-2-dimethylcarbamoyl-thiophen-3-yloxy)-acetic acid methyl ester (102 mg, 100%) was synthesized according to the procedures in Example 507, using (4,5-dibromo-2-chlorocarbonyl-thiophen-3-yloxy)-acetic acid methyl ester (100 mg, 0.25 mmol) and dimethylamine (5 eq).

$^1$H NMR (400 MHz, CHLOROFORM-D) δ ppm 3.09 (s, 6 H) 3.77 (s, 3 H) 4.65 (s, 2 H).

The fourth step of Scheme 76: (4,5-Dibromo-2-dimethylcarbamoyl-thiophen-3-yloxy)-acetic acid (40 mg, 41%) was synthesized according to the procedures in Example 507, using (4,5-dibromo-2-dimethylcarbamoyl-thiophen-3-yloxy)-acetic acid methyl ester (102 mg, 0.25 mmol).

$^1$H NMR (400 MHz, CHLOROFORM-D) δ ppm 3.15 (s, 6 H) 4.79 (s, 2 H).

EXAMPLE 513

({4,5-Dibromo-2-[(diethylamino)carbony]thien-3-yl}oxy)acetic acid

The second step of Scheme 76: (4,5-Dibromo-2-diethylcarbamoyl-thiophen-3-yloxy)-acetic acid methyl ester (114 mg, 100%) was synthesized according to the procedures in Example 507, using (4,5-dibromo-2-chlorocarbonyl-thiophen-3-yloxy)-acetic acid methyl ester (100 mg, 0.25 mmol) and diethylamine (5 eq).

$^1$H NMR (400 MHz, CHLOROFORM-D) δ ppm 1.19 (t, J=7.20 Hz, 6 H) 3.46 (d, J=7.07 Hz, 4 H) 3.77 (s, 3 H) 4.69 (s, 2 H).

The fourth step of Scheme 76: (4,5-Dibromo-2-diethylcarbamoyl-thiophen-3-yloxy)-acetic acid (15 mg, 14%) was synthesized according to the procedures in Example 507, using (4,5-dibromo-2-diethylcarbamoyl-thiophen-3-yloxy)-acetic acid methyl ester (114 mg, 0.26 mmol).

$^1$H NMR (400 MHz, CHLOROFORM-D) δ ppm 1.25 (t, J=7.07 Hz, 6 H) 3.52 (q, J=7.07 Hz, 4 H) 4.86 (s, 2 H).

EXAMPLE 514

({4,5-Dibromo-2-[(1,3-thiazol-2-ylamino)carbonyl]thien-3-yl}oxy)acetic acid

The second step of Scheme 76: [4,5-Dibromo-2-(thiazol-2-ylcarbamoyl)-thiophen-3-yloxy]-acetic acid methyl ester (94 mg, 40%) was synthesized according to the procedures in Example 507, using (4,5-dibromo-2-chlorocarbonyl-thiophen-3-yloxy)-acetic acid methyl ester (200 mg, 0.51 mmol) and 2-aminothiazole (61 mg, 1.2 eq).

¹H NMR (400 MHz, CHLOROFORM-D) δ ppm 3.93 (s, 3 H) 5.07 (s, 2 H) 7.02 (d, J=3.54 Hz, 1 H) 7.57 (d, J=3.54 Hz, 1 H) 11.40 (s, 1 H).

The fourth step of Scheme 76: [4,5-Dibromo-2-(thiazol-2-ylcarbamoyl)-thiophen-3-yloxy]-acetic acid (30 mg, 33%) was synthesized according to the procedures in Example 507, using [4,5-dibromo-2-(thiazol-2-ylcarbamoyl)-thiophen-3-yloxy]-acetic acid methyl ester (90 mg, 0.26 mmol).

¹H NMR (400 MHz, DMSO-D6) δ ppm 5.09 (s, 1 H) 7.25 (d, J=3.79 Hz, 1 H) 7.52 (d, J=3.79 Hz, 1 H).

EXAMPLE 515

[4,5-Dibromo-2-(2H-pyrazol-3-ylcarbamoyl)-thiophen-3-yloxyl-acetic acid

The second step of Scheme 76: [4,5-Dibromo-2-(2H-pyrazol-3-ylcarbamoyl)-thiophen-3-yloxy]-acetic acid methyl ester (107 mg, 49%) was synthesized according to the procedures in Example 507, using (4,5-dibromo-2-chlorocarbonyl-thiophen-3-yloxy)-acetic acid methyl ester (200 mg, 0.51 mmol) and 3-aminopyrazole (64 mg, 1.5 eq).

¹H NMR (400 MHz, CHLOROFORM-D) δ ppm 3.83 (s, 3 H) 4.10 (bs, 2 H) 4.84 (s, 2 H) 5.97 (d, J=3.03 Hz, 1 H) 8.12 (d, J=3.03 Hz, 1 H).

The fourth step of Scheme 76: [4,5-Dibromo-2-(2H-pyrazol-3-ylcarbamoyl)-thiophen-3-yloxy]-acetic acid (7 mg, 7%) was synthesized according to the procedures in Example 507, using [4,5-dibromo-2-(2H-pyrazol-3-ylcarbamoyl)-thiophen-3-yloxy]-acetic acid methyl ester (107 mg, 0.24 mmol).

¹H NMR (400 MHz, DMSO-D6) δ ppm 5.01 (s, 2 H) 5.76 (s, 2 H) 6.51 (s, 1 H) 7.64 (s, 1 H) 10.78 (s, 1 H).

EXAMPLE 516

{[4,5-Dibromo-2-(morpholin-4-ylcarbonyl)thien-3-yl]oxy}acetic acid

The fourth step of Scheme 76: [4,5-Dibromo-2-(morpholine-4-carbonyl)-thiophen-3-yloxy]-acetic acid (117 mg, 94%) was synthesized according to the procedures in Example 507, using [4,5-dibromo-2-(morpholine-4-carbonyl)-thiophen-3-yloxy]-acetic acid methyl ester (129 mg, 0.29 mmol) and barium hydroxide octahydrate (183 mg, 2 eq).

¹H NMR (400 MHz, DMSO-D6) δ ppm 3.49 (s, 4 H) 3.60 (m, 4 H) 4.69 (s, 2 H).

EXAMPLE 517

[(4,5-Dibromo-2-{[(2R,6S)-2,6-dimethylmorpholin-4-yl]carbonyl}thien-3-yl)oxy]acetic acid The second step of Scheme 76: [4,5-Dibromo-2-(2,6-dimethyl-morpholine-4-carbonyl)-thiophen-3-yloxy]-acetic acid methyl ester (148 mg, 62%) was synthesized according to the procedures in Example 507, using (4,5-dibromo-2-chlorocarbonyl-thiophen-3-yloxy)-acetic acid methyl ester (200 mg, 0.51 mmol) and cis-2,6-dimethylmorpholine (176 mg, 3 eq).

¹H NMR (400 MHz, CHLOROFORM-D) δ ppm 1.21 (d, J=6.32 Hz, 6 H) 2.74 (bs, 2 H) 3.63 (m, 2 H) 3.77 (s, 3 H) 4.67 (s, 2 H).

The fourth step of Scheme 76: [4,5-Dibromo-2-(2,6-dimethylmorpholine-4-carbonyl)-thiophen-3-yloxy]-acetic acid (136 mg, 96%) was synthesized according to the procedures in Example 507, using [4,5-dibromo-2-(2,6-dimethyl-morpholine-4-carbonyl)-thiophen-3-yloxy]-acetic acid methyl ester (148 mg, 0.31 mmol) and barium hydroxide octahydrate (198 mg, 2 eq) as starting materials to provide [(4,5-Dibromo-2-{[(2R,6S)-2,6-dimethylmorpholin-4-yl]carbonyl}thien-3-yl)oxy]acetic acid.

¹H NMR (400 MHz, DMSO-D6) δ ppm 1.08 (d, J=6.06 Hz, 6 H) 3.34 (m, 2 H) 3.54 (m, 2 H) 4.69 (s, 2 H).

EXAMPLE 518

{[4,5-Dibromo-2-(thiomorpholin-4-ylcarbonyl)thien-3-yl]oxy}acetic acid

The second step of Scheme 76: [4,5-Dibromo-2-(thiomorpholine-4-carbonyl)-thiophen-3-yloxy]-acetic acid methyl ester (145 mg, 63%) was synthesized according to the procedures in Example 507, using (4,5-dibromo-2-chlorocarbonyl-thiophen-3-yloxy)-acetic acid methyl ester (200 mg, 0.51 mmol) and thiamorpholine (158 mg, 3 eq).

¹H NMR (400 MHz, CHLOROFORM-D) δ ppm 2.71 (m, 4 H) 3.78 (d, J=1.26 Hz, 3 H) 3.88 (s, 4 H) 4.67 (s, 2 H).

The fourth step of Scheme 76: [4,5-Dibromo-2-(thiomorpholine-4-carbonyl)-thiophen-3-yloxy]-acetic acid (136 mg, 33%) was synthesized according to the procedures in Example 507, using [4,5-dibromo-2-(thiomorpholine-4-carbonyl)-thiophen-3-yloxy]-acetic acid methyl ester (148 mg, 0.31 mmol) and barium hydroxide octahydrate (199 mg, 2 eq).

¹H NMR (400 MHz, DMSO-D6) δ ppm 2.66 (m, 4 H) 3.72 (s, 4 H) 4.68 (s, 2 H).

EXAMPLE 519

(4,5-Dibromo-2-phenylcarbamoylthiophen-3-yloxy)-acetic acid

The second step of Scheme 76: (4,5-Dibromo-2-phenylcarbamoylthiophen-3-yloxy)-acetic acid methyl ester (206 mg, 73%) was synthesized according to the procedures in the first step of Example 511, using (4,5-dibromo-2-chlorocarbonylthiophen-3-yloxy)-acetic acid methyl ester (250 mg, 0.64 mmol) and aniline (150 μL, 3 eq).

¹H NMR (400 MHz, CHLOROFORM-D) δ ppm 3.86 (s, 3 H) 4.98 (s, 2 H) 7.14 (m, 1 H) 7.36 (m, 2 H) 7.81 (m, 2 H).

The fourth step of Scheme 76: (4,5-Dibromo-2-phenylcarbamoylthiophen-3-yloxy)-acetic acid (195 mg, 99%) was synthesized according to the procedures in Example 507, using (4,5-Dibromo-2-phenylcarbamoylthiophen-3-yloxy)-acetic acid methyl ester (200 mg, 0.45 mmol) and barium hydroxide octahydrate (84 mg, 0.6 eq).

¹H NMR (400 MHz, DMSO-D6) δ ppm 3.34 (bs, 1 H) 5.09 (s, 2 H) 7.14 (m, 1 H) 7.37 (m, 2 H) 7.76 (m, 2 H) 10.36 (s, 1 H).

EXAMPLE 520

{[4,5-Dibromo-2-(piperidin-1-ylcarbonyl)thien-3-yl]oxy}acetic acid

The second step of Scheme 76: [4,5-Dibromo-2-(piperidine-1-carbonyl)-thiophen-3-yloxy]-acetic acid methyl ester (200 mg, 72%) was synthesized according to the procedures in Example 507, using (4,5-dibromo-2-chlorocarbonylthiophen-3-yloxy)-acetic acid methyl ester (250 mg, 0.64 mmol) and piperidine (315 mg, 5 eq).

¹H NMR (400 MHz, DMSO-D6) δ ppm 1.51 (m, 6 H) 3.44 (s, 4 H) 4.67 (s, 2 H).

The fourth step of Scheme 76: [4,5-Dibromo-2-(piperidine-1-carbonyl)-thiophen-3-yloxy]-acetic acid (89 mg, 46%) was synthesized according to the procedures in Example 507, using [4,5-dibromo-2-(piperidine-1-carbonyl)-thiophen-3-yloxy]-acetic acid methyl ester (200 mg, 0.45 mmol) and barium hydroxide octahydrate (84 mg, 0.6 eq) as starting materials to provide {[4,5-dibromo-2-(piperidin-1-ylcarbonyl)thien-3-yl]oxy}acetic acid.

¹H NMR (400 MHz, DMSO-D6) δ ppm 1.51 (m, 6 H) 3.44 (bs, 4 H) 4.67 (s, 2 H).

EXAMPLE 521

{[4,5-Dibromo-2-(4,4-dimethyl-4,5-dihydro-1,3-oxazol-2-yl)thien-3-yl]oxy}acetic acid The first step of Scheme 77: A solution of [4,5-dibromo-2-(2-hydroxy-1,1-dimethyl-ethylcarbamoyl)-thiophen-3-yloxy]-acetic acid methyl ester (150 mg, 0.34 mmol), pyridine (136 µL, 5 eq), DMAP (4 mg, 0.1 eq), and trifluoromethanesulfonic anhydride (85 L, 1.5 eq) in dichloroethane was stirred at 80° C. for 2 h. The reaction was quenched with water, diluted with ethyl acetate, washed with 10% aq. HCl, water, and brine, dried, filtered, evaporated, and flash chromatographed (20% ethyl acetate/hexanes) to provide [4,5-dibromo-2(4,4-dimethyl-4,5-dihydro-oxazol-2-yl)-thiophen-3-yloxy]-acetic acid methyl ester (95 mg, 65%).

¹H NMR (400 MHz, CHLOROFORM-D) δ ppm 1.34 (s, 6 H) 3.81 (s, 3 H) 4.05 (s, 2 H) 4.89 (s, 2 H).

The fourth step of Scheme 76: [4,5-Dibromo-2-(4,4-dimethyl-4,5-dihydro-oxazol-2-yl)-thiophen-3-yloxy]-acetic acid (62 mg, 68%) was synthesized according to the procedures in Example 507, using [4,5-dibromo-2-(4,4-dimethyl-4,5-dihydro-oxazol-2-yl)-thiophen-3-yloxy]-acetic acid methyl ester as a starting material to provide {[4,5-dibromo-2-(4,4-dimethyl-4,5-dihydro-1,3-oxazol-2-yl)thien-3-yl]oxy}acetic acid.

¹H NMR (400 MHz, DMSO-D6) δ ppm 1.27 (s, 6 H) 4.10 (s, 2 H) 4.94 (s, 2 H).

EXAMPLE 522

{[5-(3-{[1-(Benzylsulfonyl)piperidin-4-yl]amino}phenyl)-4-bromo-2-(morpholin-4-ylcarbonyl)thien-3-yl]oxy}acetic acid The third step of Scheme 76: [5-(3-Aminophenyl)-4-bromo-2-(morpholine-4-carbonyl)-thiophen-3-yloxy]-acetic acid methyl ester (55 mg, 61%) was synthesized according to the procedures in Example 507, using [4,5-dibromo-2-(morpholine-4-carbonyl)-thiophen-3-yloxy]-acetic acid methyl ester (875 mg, 2 mmol), Pd(Ph₃P)₄ (114 mg, 5 mol %), KF (573 mg, 5 eq), and 3-aminobenzeneboronic acid (367 mg, 1.2 eq) in THF (30 mL).

¹H NMR (400 MHz, CHLOROFORM-D) δ ppm 3.66-3.78 (m, 9 H) 3.79 (s, 3 H) 4.71 (s, 2 H) 6.71-6.75 (m, 1 H) 6.91 (t, J=1.9 Hz, 1 H) 6.97-7.01 (m, 1 H) 7.22 (t, J=8.1 Hz, 1 H).

The first step of Scheme 78: A solution of [5-(3-aminophenyl)-4-bromo-2-(morpholine-4-carbonyl)-thiophen-3-yloxy]-acetic acid methyl ester (250 mg, 0.55 mmol), N-(tert-butoxycarbonyl)-4-piperidone (165 mg, 1.5 eq), acetic acid (50 µL), and sodium triacetoxyborohydride (350 mg, 3 eq) in dichloroethane was stirred at room temperature for 18 h. The reaction was quenched with 10% aq. sodium bicarbonate, diluted with ethyl acetate, washed with water and brine, dried, filtered, evaporated and flash chromatographed (60% ethyl acetate/hexanes) to provide 4-{3-[3-bromo-4-methoxycarbonylmethoxy-5-(morpholine-4-carbonyl)-thiophen-2-yl]-phenylamino}-piperidine-1-carboxylic acid tert-butyl ester ((226 mg, 64%).

¹H NMR (400 MHz, CHLOROFORM-D) δ ppm 1.46 (d, J=3.8 Hz, 9 H) 2.02-2.11 (m, 2 H) 2.87-3.08 (m, 2 H) 3.40-3.51 (m, 1 H) 3.63-3.78 (m, 8 H) 3.80 (s, 3 H) 4.01-4.13 (m, 1 H) 4.71 (s, 2 H) 6.61-6.66 (m, J=7.3, 2.5 Hz, 1 H) 6.79-6.83 (m, 1 H) 6.91 (t, J=8.0, 1.4 Hz, 1 H) 7.23 (t, J=7.8 Hz, 1 H).

The second step of Scheme 78, part 1: A solution of 4-{3-[3-bromo-4-methoxycarbonylmethoxy-5-(morpholine-4-carbonyl)-thiophen-2-yl]-phenylamino}-piperidine-1-carboxylic acid tert-butyl ester (220 mg, 0.35 mmol) and trifluoroacetic acid (1 mL) in dichloromethane (4 mL) was stirred at room temperature for 90 min. Evaporation provided crude {4-bromo-2-(morpholine-4-carbonyl)-5-[3-(piperidin-4-ylamino)-phenyl]-thiophen-3-yloxy}-acetic acid methyl ester that was used without further purification.

The second step of Scheme 78, part 2: A solution of {4-bromo-2-(morpholine-4-carbonyl)-5-[3-(piperidin-4-ylamino)-phenyl]-thiophen-3-yloxy}-acetic acid methyl ester (0.35 mmol) and α-toluenesulfonyl chloride (132 mg, 2 eq) was stirred in a biphasic mixture of saturated aq. sodium bicarbonate (10 mL) and dichloromethane (10 mL) for 4 h at room temperature. The organic layer was washed with water and brine, dried, evaporated and flash chromatographed (60-75% ethyl acetate/hexanes) to provide {4-bromo-2-(morpholine-4-carbonyl)-5-[3-(1-phenylmethanesulfonyl-piperidin-4-ylamino)-phenyl]-thiophen-3-yloxy}-acetic acid methyl ester (170 mg, 70%, 2 steps).

¹H NMR (400 MHz, CHLOROFORM-D) δ ppm 1.33-1.47 (m, 2 H) 1.98-2.08 (m, 2 H) 2.77 (t, J=10.7 Hz, 2 H) 3.58-3.66 (m, 3 H) 3.66-3.74 (m, 4 H) 3.74-3.79 (m, 4 H) 3.80 (s, 3 H) 4.24 (s, 2 H) 4.71 (s, 2 H) 6.60 (dd, J=7.7, 2.1 Hz, 1 H) 6.74-6.77 (m, 1 H) 6.92 (d, J=8.3 Hz, 1 H) 7.22 (t, J=8.0 Hz, 1 H) 7.36-7.46 (m, 5 H).

The third step of Scheme 78: {4-Bromo-2-(morpholine-4-carbonyl)-5-[3-(1-phenylmethanesulfonyl-piperidin-4-ylamino)-phenyl]-thiophen-3-yloxy}-acetic acid (93 mg, 60%) was synthesized according to the procedures in the fourth step of Scheme 76 of Example 507, using {4-bromo-2-(morpholine-4-carbonyl)-5-[3-(1-phenylmethanesulfonyl-piperidin-4-ylamino)-phenyl]-thiophen-3-yloxy}-acetic acid methyl ester (162 mg, 0.23 mmol) and barium hydroxide octahydrate (59 mg, 0.8 eq).

¹H NMR (400 MHz, DMSO-D6) δ ppm 1.31-1.43 (m, 1 H) 1.91-1.99 (m, 2 H) 2.85-2.97 (m, 2 H) 3.27-3.41 (m, 5 H) 3.49-3.59 (m, 5 H) 3.59-3.67 (m, 4 H) 4.40 (s, 2 H) 4.71 (s, 2 H) 6.67-6.71 (m, 1 H) 6.75 (d, J=7.58 Hz, 1 H) 6.81 (t, J=2.02 Hz, 1 H) 7.15-7.22 (m, 1 H) 7.35-7.46 (m, 5 H).

EXAMPLE 523

[(4-Bromo-2-(morpholin-4-ylcarbonyl)-5-{3-[(3,3,5,5-tetramethylcyclohexyl)amino]phenyl}thien-3-yl)oxy]acetic acid The first step of Scheme 78: {4-Bromo-2-(morpholine-4-carbonyl)-5-[3-(3,3,5,5-tetramethyl-cyclohexylamino)-phenyl]-thiophen-3-yloxy}-acetic acid methyl ester (125 mg, 32%) was synthesized according to the procedures in Example 522, using [5-(3-aminophenyl)-4-bromo-2-(morpholine-4-carbonyl)-thiophen-3-yloxy]-acetic acid methyl ester (294 mg, 0.65 mmol), acetic acid (60 µL), and sodium triacetoxyborohydride (411 mg, 3 eq) in dichloroethane (10 mL).

¹H NMR (400 MHz, CHLOROFORM-D) δ ppm 0.87-0.97 (m, 2 H) 0.94 (s, 6 H) 1.12 (s, 6 H) 1.27-1.34 (m, 2 H) 1.89 (d, J=11.9 Hz, 2 H) 3.55-3.66 (m, 2 H) 3.66-3.78 (m, 8 H) 3.79 (s, 3 H) 4.71 (s, 2 H) 6:59-6.64 (m, 1 H) 6.82-6.85 (m, 1 H) 6.87 (dd, J=7.6, 1.0 Hz, 1 H) 7.21 (t, J=7.8 Hz, 1 H).

The first step of Scheme 76: {4-Bromo-2-(morpholine-4-carbonyl)-5-[3-(3,3,5,5-tetramethyl-cyclohexylamino)-phenyl]-thiophen-3-yloxy}-acetic acid (63 mg, 52%) was synthesized according to the procedures in Example 507, using {4-bromo-2-(morpholine-4-carbonyl)-5-[3-(3,3,5,5-tetramethyl-cyclohexylamino)-phenyl]-thiophen-3-yloxy}-acetic acid methyl ester (125 mg, 0.21 mmol) and barium hydroxide octahydrate (67 mg, 1.0 eq).

¹H NMR (400 MHz, CHLOROFORM-D) δ ppm 0.89-0.97 (m, 3 H) 0.94 (s, 6 H) 1.12 (s, 6 H) 1.25-1.35 (m, 2 H) 1.87 (d, J=11.6 Hz, 2 H) 3.56-3.66 (m, J=3.4, 3.4 Hz, 1 H) 3.76 (s, 8 H) 4.86 (s, 2 H) 6.64 (dd, J=8.2, 2.1 Hz, 1 H) 6.82 (t, J=2.0 Hz, 1 H) 6.86 (d, J=7.6 Hz, 1 H) 7.22 (t, J=8.0 Hz, 1 H).

EXAMPLE 524

4-Bromo-5-(3-[1-(butylsulfonyl)piperidin-4-yl] amino}phenyl)-3-(2-methoxy-2-oxoethoxy) thiophene-2-carboxylic acid 5-(3-Amino-phenyl)-4-bromo-3-tert-butoxycarbonylmethoxy-thiophene-2-carboxylic acid methyl ester (5.62 g, 55%) was synthesized according to the procedures in the third step of Scheme 76 of Example 507, using 4,5-dibromo-3-tert-butoxycarbonylmethoxy-thiophene-2-carboxylic acid methyl ester (10.0 g, 23 mmol), 3-aminobenzeneboronic acid (4.3 g, 1.2 eq), Pd(Ph₃P)₄ (806 mg, 3 mol %), and KF (6.7 g, 5 eq) in THF (300 mL).

¹H NMR (400 MHz, CHLOROFORM-D) δ ppm 1.50 (s, 9 H) 3.81 (s, 2 H) 3.87 (s, 3 H) 4.81 (s, 2 H) 6.72-6.76 (m, 1 H) 6.93-6.98 (m, 1 H) 7.00-7.05 (m, 1 H) 7.22 (t, J=7.8 Hz, 1 H)

The first step of Scheme 80: 4-[3-(3-Bromo-5-methoxycarbonyl-4-methoxycarbonylmethoxy-thiophen-2-yl)-phenylamino]-piperidine-1-carboxylic acid tert-butyl ester (5.34 g, 67%) was synthesized according to the procedures in Example 522, using 5-(3-aminophenyl)-4-bromo-3-tert-butoxycarbonylmethoxy-thiophene-2-carboxylic acid methyl ester (5.6 g, 12.7 mmol), N-(tert-butoxycarbonyl)-4-piperidone (3.8 g, 1.5 eq), acetic acid (1.1 mL), and sodium triacetoxyborohydride (9.4 g, 3.5 eq) in dichloroethane (200 mL).

¹H NMR (400 MHz, CHLOROFORM-D) δ ppm 1.47 (s, 9 H) 1.50-1.52 (m, 9 H) 2.03-2.11 (m, 2 H) 2.44 (t, J=6.2 Hz, 2 H) 2.94 (s, 2 H) 3.46 (s, 1 H) 3.71 (q, J=6.7 Hz, 2 H) 3.87 (s, 3 H) 4.82 (s, 2 H) 6.86-6.88 (m, 1 H) 6.93-6.96 (m, 1 H) 7.23 (t, J=7.9 Hz, 1 H).

Crude 4-[3-(3-bromo-5-carboxy-4-carboxymethoxy-thiophen-2-yl)-phenylamino]-piperidine-1-carboxylic acid tert-butyl ester (1.0 g) was synthesized according to the procedures in the fourth step of Scheme 76 of Example 507, using 4-[3-(3-bromo-5-methoxycarbonyl-4-methoxycarbonylmethoxy-thiophen-2-yl)-phenylamino]-piperidine-1-carboxylic acid tert-butyl ester (1.0 g, 1.6 mmol) and lithium hydroxide (100 mg, 1.5 eq).

¹H NMR (400 MHz, DMSO-D6) δ ppm 1.20-1.32 (m, 2 H) 1.40 (s, 9 H) 1.86-1.94 (m, 2 H) 2.35 (t, J=6.3 Hz, 1 H) 3.39-3.50 (m, 1 H) 3.61 (t, J=6.2 Hz, 1 H) 3.87 (d, J=12.6 Hz, 2 H) 4.87 (s, 2 H) 6.71 (t, J=8.0, 1.9 Hz, 1 H) 6.75-6.80 (m, 1 H) 6.85 (t, J=1.9 Hz, 1 H) 7.19 (t, J=7.9 Hz 1H).

A solution of 4-[3-(3-Bromo-5-carboxy-4-carboxymethoxy-thiophen-2-yl)-phenylamino]-piperidine-1-carboxylic acid tert-butyl ester (1.0 g, 1.6 mmol) and trimethylsilydiazomethane (2.4 mL, 2 M soln, 3 eq) in CH₃CN (20 mL) and methanol (4 mL) was stirred at room temperature for 3 h. The solution was quenched with acetic acid, evaporated, and flash chromatographed (30% ethyl acetate/hexanes) to provide 4-[3-(3-bromo-5-methoxycarbonyl-4-methoxycarbonylmethoxy-thiophen-2-yl)-phenylamino]-piperidine-1-carboxylic acid tert-butyl ester (761 mg, 82%, 2 steps).

¹H NMR (400 MHz, CHLOROFORM-D) δ ppm 1.31 (s, 2 H) 1.47 (s, 9 H) 2.04-2.10 (n, 3 H) 2.94 (s, 2 H) 3.41-3.52 (m, 1 H) 3.84 (s, 3 H) 3.87 (s, 3 H) 4.00-4.12 (m, 2 H) 4.91 (s, 2 H) 6.66 (dd, J=7.8, 2.0 Hz, 1 H) 6.86-6.88 (m, 1 H) 6.93-6.97 (m, 1 H) 7.23 (t, J=8.0 Hz, 1 H).

Crude 4-bromo-3-methoxycarbonylmethoxy-5-[3-(piperidin-4-ylamino)-phenyl]-thiophene-2-carboxylic acid methyl ester (1.3 mmol) was synthesized according to the procedures in the second step of Scheme 78 of Example 522, using trifluoroacetic acid (1 mL) in dichloromethane (10 mL).

¹H NMR (400 MHz; DMSO-D6) δ ppm 1.46-1.59 (m, 2 H) 2.04 (dd, J=13.6, 2.8 Hz, 2 H) 2.90-3.01 (m, 2 H) 3.23-3.41 (m, 4 H) 3.72 (s, 3 H) 3.81 (s, 3 H) 4.96 (s, 2 H) 6.05 (d, J=7.8 Hz, 1 H) 6.74 (dd, J=8.1, 2.3 Hz, 1 H) 6.81 (d, J=7.6 Hz, 1 H) 6.84-6.88 (m, 1 H) 7.22 (t, J=7.8 Hz, 1 H).

4-Bromo-5-{3-[1-(butane-1-sulfonyl)-piperidin-4-ylamino]-phenyl}-3-methoxycarbonylmethoxy-thiophene-2-carboxylic acid methyl ester (151 mg, 61%) was synthesized according to the procedures in Example 522, using 4-bromo-3-methoxycarbonylmethoxy-5-[3-(piperidin-4-ylamino)-phenyl]-thiophene-2-carboxylic acid methyl ester (200 mg, 0.41 mmol) and 1-butanesulfonyl chloride (107 μL, 2 eq).

¹H NMR (400 MHz, CHLOROFORM-D) δ ppm 0.96 (t, J=7.3 Hz, 3 H) 1.40-1.62 (m, 4 H) 1.76-1.86 (m, 2 H) 2.14-2.22 (m, 2 H) 2.90-3.04 (m, 4 H) 3.39-3.52 (m, 1 H) 3.76-3.83 (m, 2 H) 3.84 (s, 3 H) 3.88 (s, 3 H) 4.91 (s, 2 H) 6.66 (dd, J=7.7, 1.9 Hz, 1 H) 6.85-6.89 (m, 1 H) 6.96 (d, J=8.3 Hz, 1 H) 7.24 (t, J=8.0 Hz, 1 H).

Crude 4-bromo-5-{3-[1-(butane-1-sulfonyl)-piperidin-4-ylamino]-phenyl}-3-carboxymethoxy-thiophene-2-carboxylic acid (151 mg, 61%) was synthesized according to the procedures in the fourth step of Scheme 76, Example 507 using 4-bromo-5-{3-[1-(butane-1-sulfonyl)-piperidin-4-ylamino]-phenyl}-3-methoxycarbonylmethoxy-thiophene-2-carboxylic acid methyl ester (200 mg, 0.41 mmol) and lithium hydroxide (32 mg, 3 eq).

A solution of 4-bromo-5-{3-[1-(butane-1-sulfonyl)-piperidin-4-ylamino]-phenyl}-3-carboxymethoxy-thiophene-2-carboxylic acid (151 mg, 0.25 mmol) and conc. sulfuric acid (1 drop) in methanol (30 mL) was stirred at room temperature for 48 h. The solution was diluted with ethyl acetate, washed with water and brine, dried, and evaporated to provide 4-bromo-5-{3-[1-(butane-1-sulfonyl)-piperidin-4-ylamino]-phenyl}-3-methoxycarbonylmethoxythiophene-2-carboxylic acid (122 mg, 82%).

¹H NMR (400 MHz, CHLOROFORM-D) δ ppm 0.96 (t, J=7.3 Hz, 3 H) 1.41-1.50 (m, 2 H) 1.51-1.63 (m, 2 H) 1.75-1.86 (m, 2 H) 2.12-2.22 (m, 2 H) 2.91-3.04 (m, 4 H) 3.40-3.51 (m, 1 H) 3.80 (d, J=12.9 Hz, 2 H) 3.87 (s, 3 H) 4.98 (s, 2 H) 6.69 (dd, J=8.1, 1.8 Hz, 1 H) 6.83 (t, J=1.9 Hz, 1 H) 6.96 (d, J=7.8 Hz, 1 H) 7.25 (t, J=7.8 Hz, 1 H).

EXAMPLE 525

4-Bromo-5-(3-{[1-(ethylsulfonyl)piperidin-4-yl]amino}phenyl)-3-(2-methoxy-2-oxoethoxy)thiophene-2-carboxylic acid 4-Bromo-5-[3-(1-ethanesulfonyl-piperidin-4-ylamino)-phenyl]-3-methoxycarbonylmethoxy-thiophene-2-carboxylic acid methyl ester (133 mg, 56%) was synthesized according to the procedures in the second step of Scheme 78 of Example 522 using 4-bromo-3-methoxy-carbonylmethoxy-5-[3-(piperidin-4-ylamino)-phenyl]-thiophene-2-carboxylic acid methyl ester (200 mg, 0.41 mmol) and ethanesulfonyl chloride (78 µL, 2 eq).

$^1$H NMR (400 MHz, CHLOROFORM-D) δ ppm 1.39 (t, J=7.5 Hz, 3 H) 1.49-1.62 (m, 2 H) 2.18 (dd, J=13.3, 3.7 Hz, 2 H) 2.94-3.06 (m, 4 H) 3.42-3.52 (m, J=3.9, 3.9 Hz, 1 H) 3.77-3.83 (m, 2 H) 3.84 (s, 3 H) 3.88 (s, 3 H) 4.91 (s, 2 H) 6.63-6.69 (m, 1 H) 6.85-6.89 (m, 1 H) 6.96 (dd, J=8.0, 1.4 Hz, 1 H) 7.24 (t, J=8.0 Hz, 1 H).

Crude 4-bromo-3-carboxymethoxy-5-[3-(1-ethanesulfonyl-piperidin-4-ylamino)-phenyl]-thiophene-2-carboxylic acid (0.23 mmol) was synthesized according to the procedures in the fourth step of Scheme 76 of Example 507 using 4-bromo-5-[3-(1-ethanesulfonyl-piperidin-4-ylamino)-phenyl]-3-methoxycarbonylmethoxy-thiophene-2-carboxylic acid methyl ester (133 mg, 0.23 mmol) and lithium hydroxide (29 mg, 3 eq).

4-Bromo-5-[3-(1-ethanesulfonyl-piperidin-4-ylamino)-phenyl]-3-methoxycarbonylmethoxy-thiophene-2-carboxylic acid (113 mg, 87%, 2 steps) was synthesized according to the procedures in the final steps of Scheme 80, Example 524 using crude 4-bromo-3-carboxymethoxy-5-[3-(1-ethanesulfonyl-piperidin-4-ylamino)-phenyl]-thiophene-2-carboxylic acid (0.23 mmol).

$^1$H NMR (400 MHz, CHLOROFORM-D) δ ppm 1.35-1.44 (m, 4 H) 1.50-1.65 (m, 2 H) 2.17 (dd, J=12.8, 3.4 Hz, 2 H) 2.95-3.06 (m, 4 H) 3.47 (s, 1 H) 3.77-3.85 (m, 2 H) 3.87 (s, 3 H) 4.99 (s, 2 H) 6.69 (dd, J=8.0, 1.9 Hz, 1 H) 6.83 (d, J=2.0 Hz, 1 H) 6.96 (d, J=8.3 Hz, 1 H) 7.25 (t, J=7.8 Hz, 1 H).

EXAMPLE 526

4-Bromo-5-(3-{[1-(isopropylsulfonyl)piperidin-4-yl]amino}phenyl)-3-(2-methoxy-2-oxoethoxy)thiophene-2-carboxylic acid 4-Bromo-3-methoxycarbonylmethoxy-5-{3-[1-(propane-2-sulfonyl)-piperidin-4-ylamino]-phenyl}-thiophene-2-carboxylic acid methyl ester (115 mg, 48%) was synthesized according to the procedures in the second step of Scheme 78, Example 522 using 4-bromo-3-methoxycarbonylmethoxy-5-[3-(piperidin-4-ylamino)-phenyl]-thiophene-2-carboxylic acid methyl ester (200 mg, 0.41 mmol) and isopropylsulfonyl chloride (93 µL, 2 eq).

$^1$H NMR (400 MHz, CHLOROFORM-D) δ ppm 1.35 (s, 3 H) 1.37 (s, 3 H) 1.47-1.64 (m, 2 H) 2.15 (dd, J=13.4, 3.0 Hz, 2 H) 3.03-3.13 (m, 2 H) 3.16-3.24 (m, 1 H) 3.43-3.53 (m, 1 H) 3.80-3.87 (m, 2 H) 3.84 (s, 3 H) 3.88 (s, 3 H) 4.91 (s, 2 H) 6.66 (dd, J=7.7, 1.9 Hz, 1 H) 6.86-6.88 (m, 1 H) 6.93-6.98 (m, 1 H) 7.24 (t, J=8.0 Hz, 1 H).

Crude 4-bromo-3-carboxymethoxy-5-{3-[1-(propane-2-sulfonyl)-piperidin-4-ylamino]-phenyl}-thiophene-2-carboxylic acid (0.20 mmol) was synthesized according to the procedures in the fourth step of Scheme 76, Example 507 using 4-bromo-3-methoxycarbonylmethoxy-5-{3-[1-(propane-2-sulfonyl)-piperidin-4-ylamino]-phenyl}-thiophene-2-carboxylic acid methyl ester (115 mg, 0.20 mmol) and lithium hydroxide ((25 mg, 3 eq).

4-Bromo-3-methoxycarbonylmethoxy-5-{3-[1-(propane-2-sulfonyl)-piperidin-4-ylamino]-phenyl}-thiophene-2-carboxylic acid (100 mg, 89%, 2 steps) was synthesized according to the procedures in the final steps of Scheme 80, Example 524 using 4-bromo-3-carboxymethoxy-5-{3-[1-(propane-2-sulfonyl)-piperidin-4-ylamino]-phenyl}-thiophene-2-carboxylic acid (0.20 mmol).

$^1$H NMR (400 MHz, CHLOROFORM-D) δ ppm 1.23-1.29 (m, 1 H) 1.35 (s, 3 H) 1.37 (s, 3 H) 1.47-1.60 (m, 2 H) 2.15 (dd, J=12.9, 2.5 Hz, 2 H) 3.04-3.12 (m, 2 H) 3.16-3.25 (m, 1 H) 3.43-3.52 (m, 1 H) 3.81-3.87 (m, 2 H) 3.88 (s, 3 H) 5.00 (s, 2 H) 6.68 (dd, J=7.8, 2.0 Hz, 1 H) 6.81 (t, J=1.8 Hz, 1 H) 6.95 (d, J=8.1 Hz, 1 H) 7.25 (t, J=8.0 Hz, 1 H).

EXAMPLE 527

5-{3-[Acetyl(3,3,5,5-tetramethylcyclohexyl)amino]phenyl}-4-bromo-3-(2-methoxy-2-oxoethoxy)thiophene-2-carboxylic acid Scheme 81: 5-{3-[Acetyl-(3,3,5,5-tetramethylcyclohexyl)amino]phenyl}-4-bromo-3-methoxycarbonylmethoxy-thiophene-2-carboxylic acid (8 mg, 78%) was synthesized according to the procedures in the final steps of Scheme 80, Example 524 using 5-{3-[acetyl-(3,3,5,5-tetramethyl-cyclohexyl)-amino]-phenyl}-4-bromo-3-carboxymethoxy-thiophene-2-carboxylic acid (10 mg, 0.02 mmol).

$^1$H NMR (400 MHz, CHLOROFORM-D) δ ppm 0.85 (s, 7 H) 0.86-0.93 (m, 2 H) 1.11-1.15 (m, 6 H) 1.16-1.30 (m, 1 H) 1.57 (d, J=11.1 Hz, 2 H) 1.80 (s, 3 H) 3.86 (s, 3 H) 5.01 (s, 2 H) 5.09 (t, J=12.0 Hz, 1 H) 7.20 (d, J=7.8 Hz, 1 H) 7.46 (t, J=1.8 Hz, 1 H) 7.52 (t, J=7.8 Hz, 1 H) 7.56-7.63 (m, 1 H).

EXAMPLE 528

[4-Bromo-5-[3-(cyclohexylamino)phenyl]-2-(methoxycarbonyl)thien-3-yl]oxyacetic acid The first step of Scheme 82: 4-Bromo-5-(3-cyclohexylamino-phenyl)-3-methoxycarbonylmethoxy-thiophene-2-carboxylic acid methyl ester (2.3 g, 100%) was synthesized according to the procedures in the first step of Example 522 using 5-(3-amino-phenyl)-4-bromo-3-methoxycarbonyl-methoxy-thiophene-2-carboxylic acid methyl ester (2.0 g, 4.5 mmol) and cyclohexanone (704 µL).

$^1$H NMR (400 MHz, CHLOROFORM-D) δ ppm 1.13-1.31 (m, 4 H) 1.32-1.46 (m, 2 H) 1.62-1.71 (m, 1 H) 1.72-1.82 (m, 2 H) 2.05-2.13 (m, 2 H) 3.66-3.74 (m, 1 H) 3.84 (s, 3 H) 3.87 (s, 3 H) 4.90 (s, 2 H) 6.64 (dd, J=7.83, 2.02 Hz, 1 H) 6.83-6.86 (m, 1 H) 6.88-6.93 (m, 1 H) 7.21 (t, J=7.96 Hz, 1 H).

The second step of Scheme 82: 4-Bromo-3-carboxymethoxy-5-(3-cyclohexylamino-phenyl)-thiophene-2-carboxylic acid (4.5 mmol) was synthesized according to the procedures in the fourth step of Scheme 76, Example 507 using 4-bromo-5-(3-cyclohexylamino-phenyl)-3-methoxycarbonylmethoxy-thiophene-2-carboxylic acid methyl ester (4.5 mmol) and potassium hydroxide (294 mg, 4 eq).

$^1$H NMR (400 MHz, DMSO-D6) δ ppm 1.11-1.26 (m, 4 H) 1.27-1.40 (m, 2 H) 1.59 (d, J=12.63 Hz, 1 H) 1.67-1.77 (m, J=9.35, 3.54 Hz, 1 H) 1.89-1.98 (m, 2 H) 3.16-3.27 (m, 1 H) 4.88 (s, 2 H) 6.66-6.90 (m, 3 H) 7.19 (t, J=7.96 Hz, 1 H).

The third step of Scheme 82: 3-Allyloxycarbonylmethoxy-4-bromo-5-(3-cyclohexylamino-phenyl)-thiophene-2-carboxylic acid (1.94 g, 93%) was synthesized according to the procedures in the final steps of Scheme 80, Example 524 using 4-bromo-3-carboxymethoxy-5-(3-cyclohexylamino-phenyl)-thiophene-2-carboxylic acid (1.90 g, 4.2 mmol) and allyl alcohol (50 mL).

¹H NMR (400 MHz, DMSO-D6) δ ppm 1.10-1.25 (m, 3 H) 1.27-1.40 (m, 2 H) 1.55-1.64 (m, 1 H) 1.67-1.77 (m, 2 H) 1.94 (dd, J=12.63, 2.78 Hz, 2 H) 3.16-3.26 (m, 1 H) 3.33 (s, 1 H) 4.63-4.69 (m, 2 H) 5.02 (s, 2 H) 5.20-5.26 (m, 1 H) 5.29-5.38 (m, 1 H) 5.87-6.00 (m, 1 H) 6.67 (dd, J=7.96, 1.89 Hz, 1 H) 6.74 (d, J=7.58 Hz, 1 H) 6.81 (t, J=2.02 Hz, 1 H) 7.13-7.22 (m, 1 H).

The fourth step of Scheme 82: 3-Allyloxycarbonyl-methoxy-4-bromo-5-(3-cyclohexylamino-phenyl)-thiophene-2-carboxylic acid methyl ester (506 mg, 50%) was synthesized according to the procedures in Example 524 using 3-allyloxycarbonylmethoxy-4-bromo-5-(3-cyclohexy-lamino-phenyl)-thiophene-2-carboxylic acid (1 g, 2 mmol).

¹H NMR (400 MHz, CHLOROFORM-D) δ ppm 1.12-1.30 (m, 3 H) 1.32-1.45 (m, 2 H) 1.66 (dd, J=8.72, 3.92 Hz, 1 H) 1.72-1.82 (m, 2 H) 2.08 (dd, J=12.88, 3.28 Hz, 2 H) 3.22-3.35 (m, J=3.54 Hz, 1 H) 3.70 (s, 1 H) 3.87 (s, 3 H) 4.71-4.76 (m, 2 H) 4.93 (s, 2 H) 5.25-5.31 (m, 1 H) 5.33-5.40 (m, 1 H) 5.90-6.02 (m, 1 H) 6.61-6.67 (m, 1 H) 6.85 (t, J=2.02 Hz, 1 H) 6.90 (dd, J=7.96, 1.39 Hz, 1 H) 7.21 (t, J=7.83 Hz, 1 H).

The fifth step of Scheme 82: A solution of 3-allyloxycar-bonylmethoxy-4-bromo-5-(3-cyclohexylamino-phenyl)-thiophene-2-carboxylic acid methyl ester (250 mg, 1 mmol), morpholine (0.21 mL, 5 eq) and Pd(Ph₃P)₄ (25 mg, 5 mol %) in THF (6 mL) was heated in a microwave reactor at 100° C. for 15 min. The solution was evaporated and flash chromatographed (20% MeOH/ethyl acetate) to provide 4-bromo-3-carboxymethoxy-5-(3-cyclohexylamino-phenyl)-thiophene-2-carboxylic acid methyl ester (190 mg, 41%).

¹H NMR (400 MHz, DMSO-D6) δ ppm 1.09-1.25 (m, 3 H) 1.27-1.42 (m, 2 H) 1.54-1.64 (m, 1 H) 1.66-1.78 (m, J=12.88 Hz, 2 H) 1.88-1.99 (m, J=8.34 Hz, 2 H) 3.80 (s, 3 H) 4.75 (s, 2 H) 5.78 (s, 1 H) 6.74 (d, J=7.33 Hz, 1 H) 6.82 (t, J=1.89 Hz, 1 H) 7.17 (dd, 1 H).

EXAMPLE 529

{[5-(3-{[1-(Benzylsulfonyl)piperidin-4-yl]amino}phenyl)-4-bromo-2-(ethoxycarbonyl)thien-3-yl]oxy}acetic acid The first step of Scheme 83: 3-Allyloxycarbonylmethoxy-4-bromo-5-[3-(1-phenylmethanesulfonyl-piperidin-4-ylamino)-phenyl]-thiophene-2-carboxylic acid (2.2 g, 100%) was synthesized according to the procedures in the final steps of Scheme 80 Example 524 using 4-bromo-3-carboxymethoxy-5-[3-(1-phenylmethanesulfonyl-piperidin-4-ylamino)-phenyl]-thiophene-2-carboxylic acid (3.4 mmol) and allyl alcohol (40 mL).

¹H NMR (400 MHz, CHLOROFORM-D) δ ppm 1.44 (d, J=4.3 Hz, 2 H) 1.99-2.08 (m, 2 H) 2.72-2.83 (m, 2 H) 3.29-3.41 (m, 1 H) 3.59-3.67 (m, 2 H) 4.25 (s, 2 H) 4.74-4.79 (m, 2 H) 5.02 (s, 2 H) 5.32 (dd, J=10.4, 1.3 Hz, 1 H) 5.36-5.43 (m, 1 H) 5.90-6.01 (m, 1 H) 6.66 (dd, J=7.8, 2.0 Hz, 1 H) 6.77-6.81 (m, 1 H) 6.96 (d, J=8.3 Hz, 1 H) 7.23 (d, J=7.8 Hz, 1 H) 7.37-7.45 (m, 5 H).

The second step of Scheme 83: 3-Allyloxycarbonyl-methoxy-4-bromo-5-[3-(1-phenylmethane-sulfonyl-piperi-din-4-ylamino)-phenyl]-thiophene-2-carboxylic acid ethyl ester (86 mg, 53%) was synthesized according to the procedures in the first step of Scheme 76, Example 507 using 3-allyloxycarbonylmethoxy-4-bromo-5-[3-(1-phenyl-methanesulfonyl-piperidin-4-ylamino)-phenyl]-thiophene-2-carboxylic acid (160 mg, 0.24 mmol) and thionyl chloride (1 mL), followed by reacting the resulting acid chloride with EtOH (1 mL), TEA (337 μL), in dichloromethane (1 mL). The solvents were evaporated, the residue was dissolved in ethyl acetate, washed, dried, filtered, and evaporated to provide 3-allyloxycarbonylmethoxy-4-bromo-5-[3-(1-phenyl-methane-sulfonyl-piperidin-4-ylamino)-phenyl]-thiophene-2-carboxylic acid ethyl ester.

¹H NMR (400 MHz, CHLOROFORM-D) δ ppm 1.36 (t, J=7.2 Hz, 3 H) 1.38-1.47 (m, 2 H) 1.59 (s, 1 H) 1.99-2.08 (m, 2 H) 2.73-2.83 (m, 2 H) 3.30-3.41 (m, 1 H) 3.62 (d, J=13.1 Hz, 2 H) 4.24 (s, 2 H) 4.34 (q, J=7.1 Hz, 2 H) 4.71-4.76 (m, 2 H) 4.94 (s, 2 H) 5.25-5.30 (m, 1 H) 5.33-5.41 (m, 1 H) 5.90-6.02 (m, 1 H) 6.59-6.63 (m, 1 H) 6.82-6.84 (m, 1 H) 6.93-6.97 (m, 1 H) 7.22 (t, J=7.8 Hz, 1 H) 7.38-7.44 (m, 5 H).

The third step of Scheme 83: 4-Bromo-3-carboxymethoxy-5-[3-(1-phenylmethanesulfonyl-piperidin-4-ylamino)-phenyl]-thiophene-2-carboxylic acid ethyl ester (67 mg, 83%) was synthesized according to the procedures in the fifth step of Scheme 82, Example 528 using 3-allyloxy-carbonylmethoxy-4-bromo-5-[3-(1-phenylmethanesulfonyl-piperidin-4-ylamino)-phenyl]-thiophene-2-carboxylic acid ethyl ester (86 mg, 0.13 mmol), morpholine (44 μL, 5 eq) and Pd(Ph₃P)₄ (7 mg, 5 mol %) in THF (2 mL).

¹H NMR (400 MHz, DMSO-D6) δ ppm 1.27 (t, J=7.1 Hz, 3 H) 1.30-1.43 (m, 2 H) 1.95 (dd, J=12.5, 2.9 Hz, 2 H) 2.87-2.97 (m, 2 H) 3.52 (s, 2 H) 4.26 (q, J=7.1 Hz, 2 H) 4.40 (s, 2 H) 4.67 (s, 2 H) 5.91 (d, J=7.8 Hz, 1 H) 6.68-6.74 (m, J=8.6, 2.0 Hz, 1 H) 6.81 (s, 1 H) 6.86 (s, 1 H) 7.19 (t, J=8.0 Hz, 1 H) 7.34-7.46 (m, 5 H).

EXAMPLE 530

{[5-(3-{[1-(Benzylsulfonylpiperidin-4-yl]amino}phenyl)-4-bromo-2-(isopropoxycarbonyl)thien-3 yl]oxy}acetic acid The second step of Scheme 83: A solution of 3-allyloxy-carbonylmethoxy-4-bromo-5-[3-(1-phenylmethanesulfonyl-piperidin-4-ylamino)-phenyl]-thiophene-2-carboxylic acid (200 mg, 0.31 mmol), EDCI (177 mg, 3 eq), isopropanol (118 μL) in DMF (2 mL) and catalytic DMAP were heated in a microwave reactor at 100° C. for 15 min. The reaction was diluted with ethyl acetate, washed with water and brine, dried, filtered, evaporated, and flash chromatographed (40% ethyl acetate/hexanes) to provide 3-allyloxycarbonylmethoxy-4-bromo-5-[3-(1-phenylmethanesulfonyl-piperidin-4-ylamino)-phenyl]-thiophene-2-carboxylic acid isopropyl ester (85 mg, 40%).

¹H NMR (400 MHz, CHLOROFORM-D) δ ppm 1.34 (s, 3 H) 1.35 (s, 3 H) 1.99-2.08 (m, 2 H) 2.73-2.83 (m, 2 H) 3.35 (s, 1 H) 3.55-3.70 (m, 3 H) 4.24 (s, 2 H) 4.71-4.77 (m, 2 H) 4.93 (s, 2 H) 5.16-5.24 (m, 1 H) 5.25-5.31 (m, 1 H) 5.33-5.41 (m, 1 H) 5.89-6.03 (m, 1 H) 6.61 (dd, J=7.8, 2.0 Hz, 1 H) 6.81-6.85 (m, 1 H) 6.95 (d, J=7.6 Hz, 1 H) 7.21 (t, J=8.0 Hz, 1 H) 7.36-7.46 (m, 5 H).

The third step of Scheme 83: 4-Bromo-3-carboxymethoxy-5-[3-(1-phenylmethanesulfonyl-piperidin-4-ylamino)-phenyl]-thiophene-2-carboxylic acid isopropyl ester (48 mg, 24%, 2 steps) was synthesized according to the procedures in the fifth step of Scheme 82, Example 528 using 3-allyloxycarbonylmethoxy-4-bromo-5-[3-(1-phenyl-methanesulfonyl-piperidin-4-ylamino)-phenyl]-thiophene-2-carboxylic acid isopropyl ester (85 mg, 0.12 mmol) morpholine (44 μL, 5 eq) and Pd(Ph₃P)₄ (7 mg, 5 mol %) in THF (2 mL).

¹H NMR (400 MHz, DMSO-D6) δ ppm 1.27 (s, 3 H) 1.29 (s, 3 H) 1.95 (d, J=10.1 Hz, 2 H) 2.92 (t, J=10.6 Hz, 2 H)

3.21-3.47 (m, 5 H) 3.53 (d, J=12.4 Hz, 2 H) 4.40 (s, 1 H) 4.59 (s, 2 H) 5.02-5.12 (m, 1 H) 5.89 (d, J=8.1 Hz, 1 H) 6.70 (dd, J=8.1, 1.8 Hz, 1 H) 6.79 (d, J=7.6 Hz, 1 H) 6.86 (s, 1 H) 7.19 (t, J=8.0 Hz, 1 H) 7.35-7.47 (m, 5 H).

EXAMPLE 531

({5-(3-{[1-(Benzylsulfonyl)piperidin-4-yl]amino}phenyl)-4-bromo-2-[(cyclohexyloxy)carbonyl]thien-3-yl}oxy)acetic acid The second step of Scheme 83: Crude 3-allyloxycarbonylmethoxy-4-bromo-5-[3-(1-phenylmethanesulfonyl-piperidin-4-ylamino)-phenyl]-thiophene-2-carboxylic acid cyclohexyl ester (0.31 mmol) was synthesized according to the procedures in Example 530 using 3-allyloxycarbonylmethoxy-4-bromo-5-[3-(1-phenylmethanesulfonyl-piperidin-4-ylamino)-phenyl]-thiophene-2-carboxylic acid (200 mg, 0.31 mmol), EDCI (177 mg, 3 eq), cyclohexanol (93 mg, 3 eq), and catalytic DMAP in DMF (2 mL).

The third step of Scheme 83: 4-Bromo-3-carboxymethoxy-5-[3-(1-phenylmethanesulfonyl-piperidin-4-ylamino)-phenyl]-thiophene-2-carboxylic acid cyclohexyl ester (49 mg, 30%) was synthesized according to the procedures in Example 528 using 3-allyloxycarbonylmethoxy-4-bromo-5-[3-(1-phenylmethanesulfonyl-piperidin-4-ylamino)-phenyl]-thiophene-2-carboxylic acid cyclohexyl ester (174 mg, 0.24 mmol), morpholine (104 µL, 5 eq) and Pd(Ph$_3$P)$_4$ (14 mg, 5 mol %) in THF (3 mL).

$^1$H NMR (400 MHz, DMSO-D6) δ ppm 1.43 (d, J=47.0 Hz, 9 H) 1.63-1.75 (m, 2 H) 1.95 (dd, J=12.4, 2.8 Hz, 1 H) 2.86-2.98 (m, 2 H) 3.52 (d, J=11.6 Hz, 2 H) 4.40 (s, 2 H) 4.53 (s, 1 H) 4.81-4.92 (m, 1 H) 5.89 (d, J=8.1 Hz, 1 H) 6.70 (dd, J=8.8, 2.3 Hz, 1 H) 6.79 (d, J=7.6 Hz, 1 H) 6.86 (t, J=1.9 Hz, 1 H) 7.19 (t, J=8.0 Hz, 1 H) 7.33-7.46 (m, 5 H).

EXAMPLE 532

{[4-Bromo-2-(Ethoxycarbonyl)-5-(3-{[1-(phenylsulfonyl)piperidin-4-yl]amino}phenyl)thien-3-yl]oxy}acetic acid 5-[3-(1-Benzenesulfonyl-piperidin-4-ylamino)-phenyl]-4-bromo-3-tert-butoxycarbonylmethoxy-thiophene-2-carboxylic acid ethyl ester (1.33 g, 59%) was synthesized according to the procedures in Scheme 78, Example 522 using 1-benzene-sulfonylpiperidin-4-one (1.1 g, 1.4 eq), sodium triacetoxyborohydride (2.1 g, 3 eq), and acetic acid (0.3 mL) in dichloroethane (20 mL).

$^1$H NMR (400 MHz, CHLOROFORM-D) δ ppm 1.36 (t, J=7.07 Hz, 3 H) 1.50 (s, 9 H) 2.15 (d, J=11.37 Hz, 2 H) 2.55 (t, J=11.49 Hz, 2 H) 3.21-3.35 (m, 1 H) 3.63 (d, J=6.57 Hz, 1 H) 3.70-3.80 (m, 2 H) 4.33 (q, J=6.99 Hz, 2 H) 4.79 (s, 2 H) 6.58 (dd, J=8.21, 2.15 Hz, 1 H) 6.79 (d, J=1.52 Hz, 1 H) 6.93 (d, J=7.58 Hz, 1 H) 7.19 (t, J=7.96 Hz, 1 H) 7.52-7.68 (m, 3 H) 7.76-7.82 (m, 2 H).

5-[3-(1-Benzenesulfonyl-piperidin-4-ylamino)-phenyl]-4-bromo-3-carboxymethoxy-thiophene-2-carboxylic acid ethyl ester (1.05 g, 86%) was synthesized according to the procedures in the third step of Scheme 78, Example 522 using 5-[3-(1-benzenesulfonyl-piperidin-4-ylamino)-phenyl]-4-bromo-3-tert-butoxycarbonylmethoxy-thiophene-2-carboxylic acid ethyl ester (1.33 g, 1.95 mmol) and trifluoroacetic acid (1 mL) in dichloromethane (5 mL).

$^1$H NMR (400 MHz, CHLOROFORM-D) δ ppm 1.39 (t, J=7.20 Hz, 3 H) 1.53-1.65 (m, 2 H) 2.11-2.18 (m, 4 H) 2.49-2.59 (m, 2 H) 3.74-3.80 (m, 2 H) 4.41 (q, J=7.16 Hz, 2 H) 4.89 (s, 2 H) 6.63 (dd, J=7.83, 2.02 Hz, 1 H) 6.75 (t, J=2.02 Hz, 1 H) 6.88-6.92 (m, 1 H) 7.22 (t, 1 H) 7.53-7.67 (m, 3 H) 7.80 (t, J=7.22 Hz, 1 H).

EXAMPLE 533

[4-Bromo-2-(methoxycarbonyl)-5-(3-{[1-(phenylsulfonyl)piperidin-4-yl]amino}phenyl)thien-3-yl]oxy-acetic acid The first step of Scheme 84: 4-[3-(3-Bromo-4-tert-butoxycarbonylmethoxy-5-methoxycarbonyl-thiophen-2-yl)-phenylamino]-piperidine-1-carboxylic acid tert-butyl ester (2.69 g, 96%) was synthesized according to the procedures in the first step of Scheme 78, Example 522 using 5-(3-aminophenyl)-4-bromo-3-tert-butoxycarbonylmethoxy-thiophene-2-carboxylic acid methyl ester (2.0 g, 4.5 mmol), N-(tert-butoxycarbonyl)-4-piperidone (1.3 g, 1.5 eq), acetic acid (400 µL), and sodium triacetoxyborohydride (3.2 g, 3.5 eq) in dichloroethane (50 mL).

$^1$H NMR (400 MHz, CHLOROFORM-D) δ ppm 1.47 (s, 9 H) 1.51 (s, 9 H) 2.03-2.12 (m, 2 H) 2.44 (t, J=6.19 Hz, 1 H) 2.88-3.01 (m, 2 H) 3.46 (s, 1 H) 3.66-3.75 (m, 2 H) 3.87 (s, 3 H) 4.82 (s, 2 H) 6.63-6.68 (m, 1 H) 6.86-6.89 (m, 1 H) 6.92-6.97 (m, 1 H) 7.23 (t, J=7.96 Hz, 1 H).

The second step of Scheme 84: A solution of 4-[3-(3-bromo-4-tert-butoxycarbonylmethoxy-5-methoxycarbonylthiophen-2-yl)-phenylamino]-piperidine-1-carboxylic acid tert-butyl ester (2.6 g, 4.2 mmol) in methanol (10 mL), ethyl acetate (10 mL), and ethyl acetate (10 mL) containing 0.77 g of HCl (gas) was stirred at room temperature for 6 h. Filtration and drying of the white precipitate provided crude 4-bromo-3-tert-butoxycarbonyl-methoxy-5-[3-(piperidin-4-ylamino)-phenyl]-thiophene-2-carboxylic acid methyl ester hydrochloride (2.55 g, 100%).

The third step of Scheme 84: 5-[3-(1-Benzenesulfonyl-piperidin-4-ylamino)-phenyl]-4-bromo-3-tert-butoxycarbonylmethoxy-thiophene-2-carboxylic acid methyl ester (265 mg, 44%) was synthesized according to the procedures in the second step of Scheme 78, Example 522 using 4-bromo-3-tert-butoxycarbonyl-methoxy-5-[3-(piperidin-4-ylamino)-phenyl]-thiophene-2-carboxylic acid methyl ester hydrochloride (500 mg, 0.9 mmol) benzenesulfonyl chloride (340 µL. 2 eq) in dichloromethane (10 mL) and satd. aqueous sodium bicarbonate (10 mL).

$^1$H NMR (400 MHz, CHLOROFORM-D) δ ppm 1.48-1.52 (m, 9 H) 2.10-2.20 (m, 2 H) 2.48-2.59 (m, 3 H) 3.27 (s, 1 H) 3.41 (t, J=6.19 Hz, 1 H) 3.61-3.67 (m, 1 H) 3.69-3.79 (m, 2 H) 3.87 (s, 3 H) 4.80 (s, 2 H) 6.59 (dd, J=7.83, 2.02 Hz, 1 H) 6.78 (t, J=2.02 Hz, 1 H) 6.93 (d, J=7.83 Hz, 1 H) 7.20 (t, J=7.96 Hz, 1 H) 7.53-7.60 (m, 2 H) 7.60-7.67 (m, 1 H) 7.76-7.83 (m, 2 H).

The fourth step of Scheme 84: 5-[3-(1-Benzenesulfonyl-piperidin-4-ylamino)-phenyl]-4-bromo-3-carboxymethoxy-thiophene-2-carboxylic acid methyl ester (268 mg, 100 mg) was synthesized according to procedures in the third step of Scheme 78, Example 522 using 5-[3-(1-benzenesulfonyl-piperidin-4-ylamino)-phenyl]-4-bromo-3-tert-butoxycarbonylmethoxy-thiophene-2-carboxylic acid methyl ester (250 mg, 0.38 mmol) and trifluoroacetic acid (2 mL) in dichloromethane (5 mL).

$^1$H NMR (400 MHz, DMSO-D6) δ ppm 1.44 (s, 2 H) 1.98 (d, J=10.86 Hz, 2 H) 2.41 (t, J=6.19 Hz, 1 H) 3.31 (t, J=6.32 Hz, 2 H) 3.57 (d, J=11.87 Hz, 2 H) 3.80 (s, 3 H) 4.84 (s, 2 H)

6.69 (dd, J=8.21, 1.89 Hz, 1 H) 6.75-6.83 (m, 2 H) 7.17 (t, 1 H) 7.62-7.71 (m, 2 H) 7.71-7.83 (m, 4 H).

EXAMPLE 534

[(4-Bromo-2-(ethoxycarbonyl)-5-{3-[(3,3,5,5-tetramethylcyclohexyl)amino]phenyl}thien-3-yl)oxy] acetic acid The first step of Scheme 85: 5-(3-Amino-phenyl)-4-bromo-3-tert-butoxycarbonylmethoxy-thiophene-2-carboxylic acid ethyl ester (3.38 g, 66%) was synthesized according to the procedures in the third step of Scheme 76, Example 507 using 4,5-dibromo-3-tert-butoxycarbonylmethoxy-thiophene-2-carboxylic acid ethyl ester (5.0 g, 11 mmol), KF (1.96 g, 3 eq), Pd(Ph$_3$P)$_4$ (0.26 g, 2 mol %), and 3-aminobenzeneboronic acid (2.1 g, 1.2 eq) in THF (100 mL) and water (30 mL).

$^1$H NMR(400 MHz, CHLOROFORM-D) δ ppm 1.36 (t, J=7.20 Hz, 3 H), 1.49-1.53 (m, 9 H), 3.79 (bs, 2 H), 4.34 (q, J=7.07 Hz, 2 H), 4.81 (s, 2 H), 6.74 (dd, J=8.08, 2.27 Hz, 1 H), 6.95-6.98 (m, 1 H), 7.03 (d, J=7.58 Hz, 1 H), 7.22 (t, J=7.83 Hz, 1 H).

The second step of Scheme 85: 4-Bromo-3-tert-butoxycarbonylmethoxy-5-[3-(3,3,5,5-tetramethyl-cyclohexylamino)-phenyl]-thiophene-2-carboxylic acid ethyl ester (1.64 g, 84%) was synthesized according to the procedures in the first step of Scheme 78, Example 522 using 5-(3-aminophenyl)-4-bromo-3-tert-butoxycarbonylmethoxythiophene-2-carboxylic acid ethyl ester (1.5 g, 3.3 mmol), 3,3,5,5-tetramethylcyclohexanone (0.85 mL, 1.5 eq), acetic acid (300 µL), and sodium triacetoxyborohydride (2.1 g, 3 eq).

$^1$H NMR (400 MHz, CHLOROFORM-D) δ ppm 0.94 (s, 6 H) 1.05 (s, 4 H) 1.12 (s, 6 H) 1.36 (t, J=7.20 Hz, 3 H) 1.50 (s, 9 H) 1.89 (d, J=12.13 Hz, 2 H) 3.57 (m, 2 H) 4.34 (q, J=7.07 Hz, 2 H) 4.80 (s, 2 H) 6.63 (m, 1 H) 6.90 (m, 2 H) 7.21 (t, J=8.21 Hz, 1 H).

The third step of Scheme 85: 4-Bromo-3-carboxymethoxy-5-[3-(3,3,5,5-tetramethyl-cyclohexylamino)-phenyl]-thiophene-2-carboxylic acid ethyl ester (1.19 g, 80%) was synthesized according to the procedures in the third step of Scheme 78, Example 522 using 4-bromo-3-tert-butoxycarbonylmethoxy-5-[3-(3,3,5,5-tetramethyl-cyclohexylamino)-phenyl]thiophene-2-carboxylic acid ethyl ester (1.64 g, 2.8 mmol) and trifluoroacetic acid (3 mL) in dichloromethane (10 mL).

$^1$H NMR (400 MHz, CHLOROFORM-D) δ ppm 0.94 (s, 6 H) 0.92-1.01 (m, 2 H) 1.11 (s, 6 H) 1.08-1.15 (m, 1 H) 1.27-1.35 (m, 1 H) 1.39 (t, J=7.20 Hz, 3 H) 1.84-1.91 (m, 2 H) 3.56-3.66 (m, 1 H) 4.41 (q, J=7.24 Hz, 2 H) 4.91 (s, 2 H) 6.74 (d, J=8.08 Hz, 1 H) 6.88-6.99 (m, 2 H) 7.23-7.26 (m, 1 H) 7.23-7.26 (m, J=7.83 Hz, 1 H).

EXAMPLE 535

{[4,5-Dibromo-2-(methoxyacetyl)thien-3-yl] oxy}acetic acid

The first step of Scheme 86: A solution of (4,5-dibromo-2-chlorocarbonylthiophen-3-yloxy)-acetic acid methyl ester (1.0 g, 2.5 mmol), tris(trimethylsiloxy)ethylene (1.48 g, 2 eq), and tin (IV) chloride (3 drops from µL syringe) in dichloroethane (3 mL) was stirred at room temperature for 16 h. The reaction was quenched with dioxane (1 mL) and 10% aq. HCl (1 mL), heated at 80° C. for 10 min, cooled, diluted with ethyl acetate, washed with water, aq. sodium bicarbonate, brine, dried, filtered, evaporated, and flash chromatographed (30-40% ethyl acetate/hexanes) to provide [4,5-dibromo-2-(2-hydroxy-acetyl)-thiophen-3-yloxy]-acetic acid methyl ester (619 mg, 64%).

$^1$H NMR (400 MHz, CHLOROFORM-D) δ ppm 3.82 (s, 3 H) 4.82 (s, 2 H) 4.97 (s, 2 H).

The second step of Scheme 86: A solution of [4,5-dibromo-2-(2-hydroxyacetyl)-thiophen-3-yloxy]-acetic acid methyl ester (300 mg, 0.78 mmol), silver (I) oxide (0.36 g, 2 eq), and iodomethane (2 mL, excess) in dichloromethane (3 mL) was stirred at room temperature 60 h. The solution was filtered, evaporated, and flash chromatographed (30% ethyl acetate/hexanes) to provide [4,5-dibromo-2-(2-methoxyacetyl) thiophen-3-yloxy]-acetic acid methyl ester (200 mg, 65%).

$^1$H NMR (400 MHz, CHLOROFORM-D) δ ppm 3.49 (s, 3 H) 3.82 (s, 3 H) 4.63 (s, 2 H) 4.92 (s, 2 H).

The third step of Scheme 86: [4,5-Dibromo-2-(2-methoxyacetyl)-thiophen-3-yloxy]-acetic acid (29 mg, 60%) was synthesized according to the procedures in the first step of Scheme 76, Example 507 using [4,5-dibromo-2-(2-methoxyacetyl)-thiophen-3-yloxy]-acetic acid methyl ester (50 mg, 0.13 mmol), and lithium hydroxide (5.2 mg, 1 eq).

$^1$H NMR (400 MHz, CHLOROFORM-D) δ ppm 3.50 (s, 3 H) 4.42 (s, 2 H) 4.92 (s, 2 H).

EXAMPLE 536

4-bromo-3-(carboxymethoxy)-5-(3-(1-cyclohexyl-3-phenylureido)phenol)thiophene-2-carboxylic acid (Step 1A in Scheme 90): To a 2000 mL round bottom flask as added methyl 4,5-dibromo-3-hydroxythiophene-2-carboxylate (50.0 g, 0.16 mol), tert-butyl bromoacetate (28 mL, 0.19 mol), potassium carbonate (43.6 g, 0.32 mol) and 500 mL DMF. The resulting mixture was allowed to stir for 2 days at room temperature. The resulting suspension was filtered through Celite, and concentrated in vacuo. The residue was redissolved into 750 mL ethyl acetate, and washed three times with 500 mL water, and one time with 500 mL brine. The organic layer was dried over magnesium sulfate, and the solvent removed to give methyl 4,5-dibromo-3-(2-tert-butoxy-2-oxoethoxy)thiophene-2-carboxylate 1B as a tan solid (67.5 g, 99%). This product was carried on without further purification. 1H NMR (400 MHz, CHLOROFORM-D) δ ppm 1.49 (s, 9 H) 3.85 (s, 3 H) 4.82 (s, 2 H)

(Step 1B in Scheme 90): To a 2-necked 1 L round bottomed flask equipped with a condenser and under a nitrogen atmosphere was added methyl 4,5-dibromo-3-(2-tert-butoxy-2-oxoethoxy)thiophene-2-carboxylate (15.0 g, 34.8 mmol), meta-aminophenylboronic acid (5.66 g, 36.5 mmol) potassium fluoride (6.06 g, 0.104 mol) and 500 mL THF. Nitrogen gas was bubbled through the resulting mixture for 0.5 h, at which point tetrakis(triphenylphosphine)palladium (2.0 g, 1.7 mmol) was added. This mixture was refluxed for 16 h. The solvent was then removed in vacuo, and the residue was partitioned between 500 mL water and 500 mL ether. The layers were separated, and the organic layer was washed three times with 250 mL water and one time with 250 mL brine. The organic layer was dried over magnesium sulfate and the solvent removed. The crude product was purified by silica gel chromatography (Biotage Flash 75, 25% ethyl acetate/hexanes) to give methyl 5-(3-aminophenyl)-4-bromo-3-(2-tert-butoxy-2-oxoethoxy)thiophene-2-carboxylate 1C as a white solid (6.23 g, 41%). 1H NMR (400 MHz, CHLOROFORM-D) δ ppm 1.50 (s, 9 H) 3.87 (s, 3 H) 4.81 (s, 2 H) 6.69-6.79 (m, 1 H) 6.96 (t, J=1.77 Hz, 1 H) 7.02 (dd, J=6.44, 1.39 Hz, 1 H) 7.22 (t, J=7.96 Hz, 1 H).

(Step 1C in Scheme 90): To a 1000 mL round bottom flask under nitrogen was added methyl 5-(3-aminophenyl)-4-bromo-3-(2-tert-butoxy-2-oxoethoxy)thiophene-2-carboxylate (15.0 g, 33.9 mmol), cyclohexanone (4.2 mL, 40.7 mmol), sodium triacetoxyborohydride (18.0 g, 85 mmol), acetic acid (4.9 mL, 85 mmol) and 500 mL dichloroethane. The resulting mixture was allowed to stir 16 h at room temperature. The mixture was then washed with water, and the solvent removed. The resulting oil was purified by silica gel chromatography (Biotage Flash 75, 10% ethyl acetate/hexanes) to give methyl 4-bromo-3-(2-tert-butoxy-2-oxoethoxy)-5-(3-(cyclohexylamino)phenyl)thiophene-2-carboxylate 1D (9.14 g, 51%) as a yellow oil. A small amount of methyl 4-bromo-3-(3-tert-butoxy-3-oxopropyl)-5-(3-(ethylamino)phenyl)thiophene-2-carboxylate 1E was isolated as a side product. 1H NMR (400 MHz, CHLOROFORM-D) δ ppm 1.09-1.30 (m, 3 H) 1.31-1.45 (m, 2 H) 1.50 (s, 9 H) 1.59-1.69 (m, 1 H) 1.70-1.87 (m, 2 H) 1.97-2.16 (m, 2 H) 3.09-3.38 (m, 1 H) 3.86 (s, 3 H) 4.81 (s, 2 H) 6.57-6.67 (m, 1 H) 6.83-6.87 (m, 1 H) 6.89 (d, J=7.58 Hz, 1 H) 7.19 (t, J=7.83 Hz, 1 H).

(Step 1D in Scheme 90): To a Genevac reaction tube was added methyl 4-bromo-3-(3-tert-butoxy-3-oxopropyl)-5-(3-(ethylamino)phenyl)thiophene-2-carboxylate (0.100 g, 0.19 mmol), phenyl isocyanate (0.068 g, 0.57 mmol and 10 mL methylene chloride. This mixture was allowed to stir for 72 hours at room temperature. To the resulting mixture was added 500 mg of trisamine-PS resin (Argonaut Technologies). This was allowed to stir an additional 12 hours. The solids were removed by filtration and the solvent removed by rotovap to give methyl 4-bromo-3-(2-tert-butoxy-2-oxoethoxy)-5-(3-(1-cyclohexyl-3-phenylureido)phenyl)thiophene-2-carboxylate as an off-white solid in >95% purity as determined by analytical reverse-phase HPLC with a mass spectrometer detector. This residue was carried on directly to the subsequent step without further characterization.

(Step 1F in Scheme 90): To a small vial was added methyl 4-bromo-3-(2-tert-butoxy-2-oxoethoxy)-5-(3-(1-cyclohexyl-3-phenylureido)phenyl)thiophene-2-carboxylate (0.19 mmol) and 4 mL THF. To this solution was added a solution of lithium hydroxide hydrate (0.040 g, 0.80 mmol) in 3 mL water, followed by 0.5 mL methanol. This solution was allowed to stir at room temperature overnight. 1.2 N HCl was then added until a precipitate formed. This suspension was then diluted into 25 mL water, and extracted with 25 mL ethyl acetate. The organic layer was dried over magnesium sulfate. The solids were removed by filtration and the solvent removed in vacuo to give 4-bromo-3-(carboxymethoxy)-5-(3-(1-cyclohexyl-3-phenylureido)phenyl)thiophene-2-carboxylic acid as a white solid (0.059 g, 54%). 1H NMR (400 MHz, DMSO-D6) δ ppm 0.78-0.98 (m, J=13.14 Hz, 1 H) 1.09 (dd, J=12.51, 3.16 Hz, 2 H) 1.22-1.44 (m, J=13.14 Hz, 2 H) 1.46-1.62 (m, 1 H) 1.71 (s, 2 H) 1.80-1.94 (m, 2 H) 4.24-4.36 (m, 1 H) 4.74-5.05 (m, 2 H) 6.85-6.99 (m, 1 H) 7.11-7.25 (m, 2 H) 7.28-7.40 (m, 2 H) 7.46 (s, 1 H) 7.54 (t, J=1.77 Hz, 1 H) 7.61 (t, J=7.83 Hz, 1 H) 7.66-7.75 (m, 1 H). Calc'd 573.0686. Found 573.0688. expl.-calc'd 0.19 mmu.

EXAMPLE 537

4-bromo-3-(carboxymethoxy)-5-(3-(1-cyclohexyl-3-isopropylureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-isopropylureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-isopropylureido) phenyl)thiophene-2-carboxylic acid as a white solid (0.022 g, 21%).

1H NMR (400 MHz, DMSO-D6) δ ppm 0.96 (d, J=6.57 Hz, 6 H) 1.00-1.05 (m, 1 H) 1.24 (s, 4 H) 1.45-1.56 (m, 1 H) 1.62-1.73 (m, 2 H) 1.73-1.83 (m, 2 H) 3.69-3.88 (m, 1 H) 4.12-4.31 (m, 1 H) 4.90 (s, 2 H) 7.25 (dd, J=7.33, 2.53 Hz, 1 H) 7.41 (t, J=1.77 Hz, 1 H) 7.58 (t, J=7.83 Hz, 1 H) 7.62-7.70 (m, 1 H). Calc'd 539.0846. Found 539.0852. expl.-calc'd 0.59 mmu.

EXAMPLE 538

4-bromo-3-(carboxymethoxy)-5-(3-(1-cyclohexyl-3-phenethylureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-phenethylureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-phenethylureido)phenyl)thiophene-2-carboxylic acid as a white solid (0.074 g, 65%).

1H NMR (400 MHz, DMSO-D6) δ ppm 0.75-0.92 (m, 1 H) 0.91-1.06 (m, 2 H) 1.18-1.36 (m, 2 H) 1.43-1.56 (m, 1 H) 1.64-1.73 (m, 2 H) 1.73-1.84 (m, 2 H) 2.56-2.70 (m, 2 H) 3.11-3.23 (m, 2 H) 4.15-4.31 (m, 1 H) 4.91 (s, 2 H) 7.03-7.15 (m, 3 H) 7.15-7.25 (m, J=7.20, 7.20 Hz, 3 H) 7.34 (t, J=1.77 Hz, 1 H) 7.54 (t, J=7.83 Hz, 1 H) 7.62-7.71 (m, 1 H). Calc'd 601.1003. Found 601.1009. expl.-calc'd 0.63 mmu.

EXAMPLE 539

4-bromo-3-(carboxymethoxy)-5-(3-(1-cyclohexyl-3-propylureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-propylureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-propylureido) phenyl)thiophene-2-carboxylic acid as a white solid (0.036 g, 35%). 1H NMR (400 MHz, DMSO-D6) δ ppm 0.74 (t, J=7.20 Hz, 3 H) 0.81-0.92 (m, 1 H) 0.92-1.05 (m, 2 H) 1.19-1.38 (m, 4 H) 1.44-1.56 (m, 1 H) 1.62-1.73 (m, 2 H) 1.73-1.84 (m, 2 H) 2.92 (q, 2 H) 4.17-4.31 (m, 1 H) 4.90 (s, 2 H) 7.15-7.30 (m, 1 H) 7.41 (s, 1 H) 7.53-7.63 (m, J=7.83 Hz, 1 H) 7.62-7.71 (m, 1 H). Calc'd 539.0831. Found 539.0846. expl.-calc'd 1.46 mmu.

EXAMPLE 540

4-bromo-3-(carboxymethoxy)-5-(3-(1-cyclohexyl-3-(4-ethoxyphenyl)ureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-(4-ethoxyphenyl)ureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-(4-ethoxyphenyl)ureido)phenyl)thiophene-2-carboxylic acid as a white solid (0.083 g, 71%). 1H NMR (400 MHz, DMSO-D6) δ ppm 0.89 (d, J=7.58 Hz, 1 H) 1.07 (d, J=11.12 Hz, 4 H) 1.28 (t, J=6.95 Hz, 3 H) 1.48-1.59 (m, 1 H) 1.64-1.78 (m, 2 H) 1.80-1.90 (m, 2 H) 3.94 (q, J=6.91 Hz, 2 H) 4.22-4.35 (m, 1 H) 4.89 (s, 2 H) 6.70-6.79 (m, 2 H) 7.14-7.24 (m, 2 H) 7.32-7.37 (m, 1 H) 7.52 (t, J=1.89 Hz, 1 H) 7.60 (t, J=7.83 Hz, 1 H) 7.66-7.73 (m, 1 H). Calc'd 617.0952. Found 617.0952. expl.-calc'd 0.05 mmu.

EXAMPLE 541

4-bromo-3-(carboxymethoxy)-5-(3-(1-cyclohexyl-3-(4-phenoxyphenyl)ureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-(4-phenoxyphenyl)ureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-(4-phenoxyphenyl)ureido)phenyl)thiophene-2-carboxylic acid as a white solid (0.085 g, 67%). 1H NMR (400 MHz, DMSO-D6) δ ppm 0.81-0.97 (m, 1 H) 1.01-1.16 (m, 2 H) 1.21-1.40 (m, 2 H) 1.48-1.60 (m, 1 H) 1.66-1.78 (m, 2 H) 1.80-1.93 (m, 2 H) 4.24-4.37 (m, 1 H) 4.89 (s, 2 H) 6.84-6.96 (m, 3 H) 7.02-7.12 (m, 1 H) 7.27-7.44 (m, 5 H) 7.53 (d, J=1.01 Hz, 2 H) 7.61 (t, J=7.83 Hz, 1 H) 7.67-7.74 (m, 1 H). Calc'd 665.0945. Found 665.0952. expl.-calc'd 0.73 mmu.

EXAMPLE 542

5-(3-(3-(5-bromo-2-methoxyphenethyl)-1-cyclohexylureido)phenyl)-4-bromo-3-(carboxymethoxy)thiophene-2-carboxylic acid See example 536, Step 1D in Scheme 90. Gave methyl 5-(3-(3-(5-bromo-2-methoxyphenethyl)-1-cyclohexylureido)phenyl)-4-bromo-3-(2-tert-butoxy-2-oxoethoxy)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 5-(3-(3-(5-bromo-2-methoxyphenethyl)-1-cyclohexylureido)phenyl)-4-bromo-3-(carboxymethoxy)thiophene-2-carboxylic acid as a white solid (0.050 g, 37%). 1H NMR (400 MHz, DMSO-D6) δ ppm 0.76-0.90 (m, 1 H) 0.91-1.06 (m, 2 H) 1.16-1.38 (m, 2 H) 1.42-1.56 (m, 1 H) 1.62-1.73 (m, 2 H) 1.72-1.83 (m, 2 H) 2.62 (t, J=6.57 Hz, 2 H) 3.16 (d, J=6.06 Hz, 2 H) 3.69 (s, 3 H) 4.09-4.29 (m, 1 H) 4.90 (s, 2 H) 6.84 (d, J=8.84 Hz, 1 H) 7.14 (d, J=2.53 Hz, 1 H) 7.16-7.21 (m, 1 H) 7.28 (dd, J=8.72, 2.65 Hz, 1 H) 7.34 (t, J=1.89 Hz, 1 H) 7.55 (t, J=7.83 Hz, 1 H) 7.62-7.70 (m, 1 H).

EXAMPLE 543

4-bromo-3-(carboxymethoxy)-5-(3-(1-cyclohexyl-3-(2-(thiophen-3-yl)ethyl)ureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-(2-(thiophen-3-yl)ethyl)ureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-(2-(thiophen-3-yl)ethyl)ureido)phenyl)thiophene-2-carboxylic acid as a white solid (0.057 g, 49%). 1H NMR (400 MHz, DMSO-D6) δ ppm 0.80-0.91 (m, 1 H) 0.92-1.07 (m, 2 H) 1.20-1.37 (m, 2 H) 1.45-1.56 (m, 1 H) 1.63-1.74 (m, 2 H) 1.74-1.84 (m, 2 H) 2.80-2.92 (m, 2 H) 3.12-3.24 (m, 2 H) 4.17-4.30 (m, 1 H) 4.91 (s, 2 H) 6.76 (dd, J=3.41, 1.14 Hz, 1 H) 6.86 (dd, J=5.05, 3.28 Hz, 1 H) 7.11-7.27 (m, 2 H) 7.38 (t, J=1.77 Hz, 1 H) 7.56 (t, J=7.83 Hz, 1 H) 7.63-7.71 (m, 1 H). Calc'd 607.0561. Found 607.0567. expl.-calc'd 0.63 mmu.

EXAMPLE 544

4-bromo-3-(carboxymethoxy)-5-(3-(1-cyclohexyl-3-(3,5-dimethylisoxazol-4-yl)ureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-(3,5-dimethylisoxazol-4-yl)ureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-(3,5-dimethylisoxazol-4-yl)ureido)phenyl)thiophene-2-carboxylic acid as a white solid (0.057 g, 51%). 1H NMR (400 MHz, DMSO-D6) δ ppm 0.81-0.94 (m, 1 H) 0.97-1.13 (m, 2 H) 1.22-1.40 (m, 2 H) 1.46-1.57 (m, 1 H) 1.63-1.76 (m, 2 H) 1.80-1.89 (m, J=1.77 Hz, 2 H) 2.02 (s, 3 H) 2.16 (s, 3 H) 4.17-4.30 (m, J=3.54 Hz, 1 H) 4.90 (s, 2 H) 6.96 (s, 1 H) 7.32-7.42 (m, 1 H) 7.54 (t, J=1.89 Hz, 1 H) 7.62 (t, J=7.83 Hz, 1 H) 7.67-7.75 (m, 1 H). Calc'd 592.0745. Found 592.0748. expl.-calc'd 0.32 mmu.

EXAMPLE 545

4-bromo-5-(3-(3-(2-carboxyethyl)-1-cyclohexylureido)phenyl)-3-(carboxymethoxy)thiophene-2-carboxylic acid See example 536, Step 1D in Scheme 90. Gave 3-(3-(3-bromo-4-(2-tert-butoxy-2-oxoethoxy)-5-(methoxycarbonyl)thiophen-2-yl)phenyl)-3-cyclohexylureido)propanoic acid as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-5-(3-(3-(2-carboxyethyl)-1-cyclohexylureido)phenyl)-3-(carboxymethoxy)thiophene-2-carboxylic acid as a white solid (0.057 g, 53%). 1H NMR (400 MHz, DMSO-D6) δ ppm 0.77-0.92 (m, 1 H) 0.91-1.08 (m, 2 H) 1.29 (dd, J=10.23, 3.16 Hz, 2 H) 1.45-1.57 (m, 1 H) 1.63-1.73 (m, 2 H) 1.73-1.84 (m, 2 H) 2.31 (t, J=6.95 Hz, 2 H) 3.17 (q, 2 H) 4.14-4.32 (m, 1 H) 4.90 (s, 2 H) 5.34 (t, J=5.68 Hz, 1 H) 7.20-7.29 (m, 1 H) 7.43 (t, J=1.77 Hz, 1 H) 7.57 (t, J=7.83 Hz, 1 H) 7.65-7.71 (m, 1 H). Calc'd 569.0581. Found 569.0588. expl.-calc'd 0.70 mmu.

EXAMPLE 546

4-bromo-3-(carboxymethoxy)-5-(3-(3-(4-carboxyphenyl)-1-cyclohexylureido)phenyl)thiophene-2-carboxylic acid See example 536, Step 1D in Scheme 90. Gave 4-(3-(3-(3-bromo-4-(2-tert-butoxy-2-oxoethoxy)-5-(methoxycarbonyl)thiophen-2-yl)phenyl)-3-cyclohexylureido)benzoic acid as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(3-(4-carboxyphenyl)-1-cyclohexylureido)phenyl)thiophene-2-carboxylic acid as a white solid (0.081 g, 69%). 1H NMR (400 MHz, DMSO-D6) δ ppm 0.92-1.08 (m, 1 H) 1.09-1.21 (m, 3 H) 1.21-1.38 (m, 4 H) 1.39-1.48 (m, 2 H) 1.48-1.58 (m, 1 H) 1.62-1.73 (m, 2 H) 1.72-1.86 (m, 2 H) 2.14 (t, J=7.33 Hz, 2 H) 2.93 (q, J=6.74 Hz, 2 H) 4.13-4.31 (m, 1 H) 4.90 (s, 2 H) 5.31 (t, J=5.68 Hz, 1 H) 7.20-7.26 (m, 1 H) 7.41 (t, J=1.89 Hz, 1 H) 7.57 (t, J=7.96 Hz, 1 H) 7.63-7.70 (m, 1 H). Calc'd 617.0579. Found 617.0588. expl.-calc'd 0.95 mmu.

EXAMPLE 547

4-bromo-3-(carboxymethoxy)-5-(3-(3-(3-carboxypropyl)-1-cyclohexylureido)phenyl)thiophene-2-carboxylic acid See example 536, Step 1D in Scheme 90. Gave 4-(3-(3-(3-bromo-4-(2-tert-butoxy-2-oxoethoxy)-5-(methoxycarbonyl)thiophen-2-yl)phenyl)-3-cyclohexylureido)butanoic acid as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(3-(3-carboxypropyl)-1-cyclohexylureido)phenyl)thiophene-2-carboxylic acid as a white solid (0.062 g, 56%). 1H NMR (400 MHz, DMSO-D6) δ ppm 0.77-0.91 (m, 1 H) 0.92-1.10 (m, J=12.13 Hz, 2 H) 1.21-1.38 (m, 2 H) 1.41-1.61 (m, 3 H) 1.62-1.74 (m, 2 H) 1.74-1.84 (m, 2 H) 2.06-2.17 (m, 2 H) 2.97 (q, J=6.48 Hz, 2 H) 4.14-4.29 (m, 1 H) 4.90 (s, 2 H) 5.42 (t, J=5.43 Hz, 1 H) 7.25 (dd, J=7.83, 1.01 Hz, 1 H) 7.42 (t, J=1.89 Hz, 1 H) 7.57 (t, J=7.83 Hz, 1 H) 7.64-7.71 (m, 1 H). Calc'd 583.0744. Found 583.0757. expl.-calc'd 1.34 mmu.

EXAMPLE 548

4-bromo-3-(carboxymethoxy)-5-(3-(3-(5-carboxypentyl)-1-cyclohexylureido)phenyl)thiophene-2-carboxylic acid See example 536, Step 1D in Scheme 90. Gave 6-(3-(3-(3-bromo-4-(2-tert-butoxy-2-oxoethoxy)-5-(methoxycarbonyl)thiophen-2-yl)phenyl)-3-cyclohexylureido)hexanoic acid as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(3-(5-carboxypentyl)-1-cyclohexylureido)phenyl)thiophene-2-carboxylic acid as a white solid (0.060 g, 52%). 1H NMR (400 MHz, DMSO-D6) δ ppm 0.91-1.06 (m, 1 H) 1.06-1.23 (m, J=7.07, 7.07 Hz, 4 H) 1.20-1.37 (m, 4 H) 1.39-1.48 (m, 2 H) 1.47-1.56 (m, 1 H) 1.62-1.74 (m, 2 H) 1.72-1.85 (m, 2 H) 2.14 (t, J=7.33 Hz, 2 H) 2.85-3.00 (m, 2 H) 4.15-4.33 (m, 1 H) 4.90 (s, 2 H) 5.31 (t, 1 H) 7.20-7.27 (m, 1 H) 7.41 (t, J=1.77 Hz, 1 H) 7.57 (t, J=7.83 Hz, 1 H) 7.67 (d, J=8.34 Hz, 1 H). Calc'd 611.1046. Found 611.1057. expl.-calc'd 1.10 mmu.

EXAMPLE 549

4-bromo-3-(carboxymethoxy)-5-(3-(1-cyclohexyl-3-(thiophen-3-yl)ureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-(thiophen-3-yl)ureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-(thiophen-3-yl)ureido)phenyl)thiophene-2-carboxylic acid as a white solid (0.076 g, 69%). 1H NMR (400 MHz, DMSO-D6) δ ppm 0.81-0.97 (m, 1 H) 0.98-1.13 (m, 2 H) 1.24-1.41 (m, 2 H) 1.47-1.60 (m, 1 H) 1.64-1.77 (m, 2 H) 1.79-1.90 (m, 2 H) 4.24-4.38 (m, 1 H) 4.89 (s, 2 H) 7.07 (dd, J=5.05, 1.26 Hz, 1 H) 7.23 (dd, J=3.28, 1.26 Hz, 1 H) 7.28 (dd, J=5.18, 3.16 Hz, 1 H) 7.31-7.37 (m, 1 H) 7.51 (t, J=1.77 Hz, 1 H) 7.61 (t, J=7.83 Hz, 1 H) 7.68-7.76 (m, 1 H) 7.93 (s, 1 H). Calc'd 579.0254. Found 579.0263. expl.-calc'd 0.95 mmu.

EXAMPLE 550

4-bromo-3-(carboxymethoxy)-5-(3-(1-cyclohexyl-3-(3-methyl-5-phenylisoxazol-4-yl)ureido)phenyl)thiophene-2-carboxylic acid See example 536, Step 1D in Scheme 90. Gave methyl 4-bromo-3-(2-tert-butoxy-2-oxoethoxy)-5-(3-(1-cyclohexyl-3-(3-methyl-5-phenylisoxazol-4-yl)ureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-cyclohexyl-3-(3-methyl-5-phenylisoxazol-4-yl)ureido)phenyl)thiophene-2-carboxylic acid as a white solid (0.048 g, 39%). 1H NMR (400 MHz, DMSO-D6) δ ppm 0.77-0.95 (m, 1 H) 0.95-1.10 (m, 2 H) 1.19-1.35 (m, 2 H) 1.51 (d, J=8.08 Hz, 1 H) 1.69 (d, J=13.64 Hz, 2 H) 1.80 (d, J=15.16 Hz, 2 H) 2.26 (s, 3 H) 4.14-4.27 (m, 1 H) 4.92 (s, 2 H) 7.11 (s, 1 H) 7.31-7.37 (m, 1 H) 7.41-7.48 (m, 3 H) 7.51 (t, J=1.89 Hz, 1 H) 7.59-7.69 (m, 3 H) 7.69-7.75 (m, 1 H).

EXAMPLE 551

4-bromo-5-(3-(1-cyclohexyl-3-methylureidophenyl)-3-(2-ethoxy-2-oxoethoxy)thiophene-2-carboxylic acid 4-bromo-3-(carboxymethoxy)-5-(3-(1-cyclohexyl-3-methylureido)phenyl)thiophene-2-carboxylic acid (0.173 g, 0.34 mmol) was dissolved in ethanol. A few drops of sulfuric acid were added. The resulting mixture was allowed to stir at room temperature for 16 hours. It was then diluted into 50 mL water and extracted three times with 25 mL ethyl acetate. The combined organic layers were then washed with water and brine, dried over magnesium sulfate, filtered and evaporated to give 4-bromo-5-(3-(1-cyclohexyl-3-methylureido)phenyl)-3-(2-ethoxy-2-oxoethoxy)thiophene-2-carboxylic acid (0.091 g, 50%). 1H NMR (400 MHz, MeOD) δppm 1.15-1.35 (m, 1 H) 1.35-1.52 (m, 2 H) 1.61 (t, J=7.07 Hz, 3 H) 1.66-1.81 (m, 2 H) 1.85-1.96 (m, 1 H) 2.02-2.14 (m, 2 H) 2.15-2.25 (m, 2 H) 2.96 (s, 3 H) 4.57 (q, J=7.24 Hz, 2 H) 4.61-4.74 (m, 1 H) 5.24-5.32 (m, 1 H) 7.55-7.66 (m, 1 H) 7.83 (t, J=1.77 Hz, 1 H) 7.91 (t, J=7.83 Hz, 1 H) 7.97-8.06 (m, 1 H). Calc'd 539.0842. Found 539.0846. expl.-calc'd 0.45 mmu.

Scheme 91

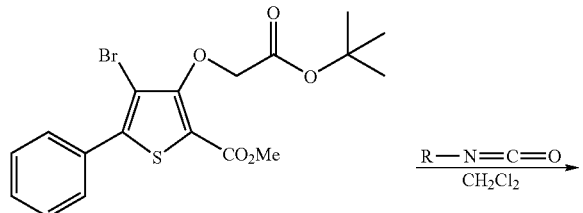

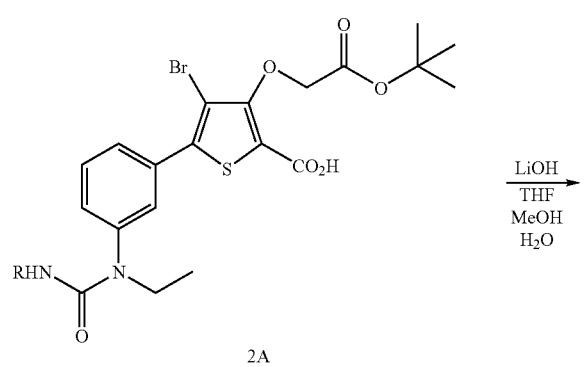

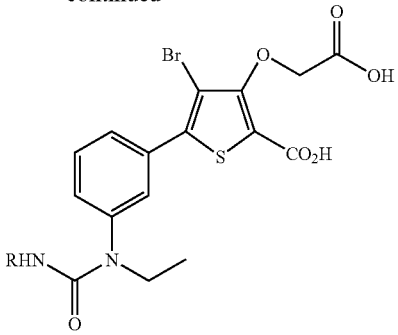

EXAMPLE 552

5-(3-(3-benzyl-1-ethylureido)phenyl)-4-bromo-3-(carboxymethoxy)thiophene-2-carboxylic acid See example 536, Step 1D in Scheme 90. Gave methyl 5-(3-(3-benzyl-1-ethylureido)phenyl)-4-bromo-3-(2-tert-butoxy-2-oxoethoxy)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 5-(3-(3-benzyl-1-ethylureido)phenyl)-4-bromo-3-(carboxymethoxy)thiophene-2-carboxylic acid as a white solid (0.041 g, 59%). 1H NMR (400 MHz, DMSO-D6) δ ppm 1.05 (t, 3 H) 3.68 (q, J=7.07 Hz, 2 H) 4.22 (d, J=5.81 Hz, 2 H) 4.90 (s, 2 H) 6.58 (t, J=6.19 Hz, 1 H) 7.10-7.33 (m, 4 H) 7.34-7.43 (m, 1 H) 7.49-7.62 (m, 3 H). Calc'd 533.0376. Found 533.0381. expl.-calc'd 0.47 mmu.

EXAMPLE 553

4-bromo-3-(carboxymethoxy)-5-(3-(1-ethyl-3-isopropylureido)phenyl)thiophene-2-carboxylic acid See example 536, Step 1D in Scheme 90. Gave methyl 4-bromo-3-(2-tert-butoxy-2-oxoethoxy)-5-(3-(1-ethyl-3-isopropylureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-ethyl-3-isopropylureido)phenyl)thiophene-2-carboxylic acid as a white solid (0.058 g, 28%). 1H NMR (400 MHz, DMSO-D6) δ ppm 0.98-1.08 (m, 9 H) 3.66 (q, J=6.99 Hz, 2 H) 3.75-3.89 (m, 1 H) 4.89 (s, 2 H) 5.72 (d, J=7.83 Hz, 1 H) 7.30-7.39 (m, 1 H) 7.44-7.64 (m, 3 H). Calc'd 485.0376. Found 485.0377. expl.-calc'd 0.04 mmu.

EXAMPLE 554

4-bromo-3-(carboxymethoxy)-5-(3-(1-ethyl-3-phenylureido)phenyl)thiophene-2-carboxylic acid See example 536, Step 1D in Scheme 90. Gave methyl 4-bromo-3-(2-tert-butoxy-2-oxoethoxy)-5-(3-(1-ethyl-3- phenylureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(1-ethyl-3-phenylureido)phenyl) thiophene-2-carboxylic acid as a white solid (0.081 g, 36%). 1H NMR (400 MHz, DMSO-D6) δ ppm 1.11 (t, J=6.95 Hz, 3 H) 3.76 (q, J=6.82 Hz, 2 H) 4.88 (s, 2 H) 6.94 (t, J=7.45 Hz, 1 H) 7.21 (t, J=7.71 Hz, 2 H) 7.42 (d, J=8.34 Hz, 3 H) 7.51-7.64 (m, 4 H) 8.24 (s, 1 H). Calc'd 519.0220. Found 519.0225. expl.-calc'd 0.48 mmu.

EXAMPLE 555

4-bromo-3-(carboxymethoxy)-5-(3-(3-cyclohexyl-1-ethylureido)phenyl)thiophene-2-carboxylic acid See example 536, Step 1D in Scheme 90. Gave methyl 4-bromo-3-(2-tert-butoxy-2-oxoethoxy)-5-(3-(3-cyclohexyl-1-ethylureido)phenyl)thiophene-2-carboxylate as an off-white solid in >95% purity as determined by analytical reverse-phase HPLC with a mass spectrometer detector. This residue was carried on directly to the subsequent step without further characterization.

See example 536, Step 1F in Scheme 90. Gave 4-bromo-3-(carboxymethoxy)-5-(3-(3-cyclohexyl-1-ethylureido)phenyl)thiophene-2-carboxylic acid as a white solid (0.096 g, 42%). 1H NMR (400 MHz, DMSO-D6) δ ppm 1.03 (t, J=6.95 Hz, 3 H) 1.09-1.31 (m, 5 H) 1.48-1.57 (m, 1 H) 1.58-1.67 (m, 2 H) 1.67-1.77 (m, 2 H) 3.39-3.53 (m, 1 H) 3.66 (q, J=6.99 Hz, 2 H) 4.89 (s, 2 H) 5.66 (d, J=8.34 Hz, 1 . H) 7.31-7.39 (m, 1 H) 7.48-7.58 (m, 3 H). Calc'd 525.0690. Found 525.0701. expl.-calc'd 1.12 mmu.

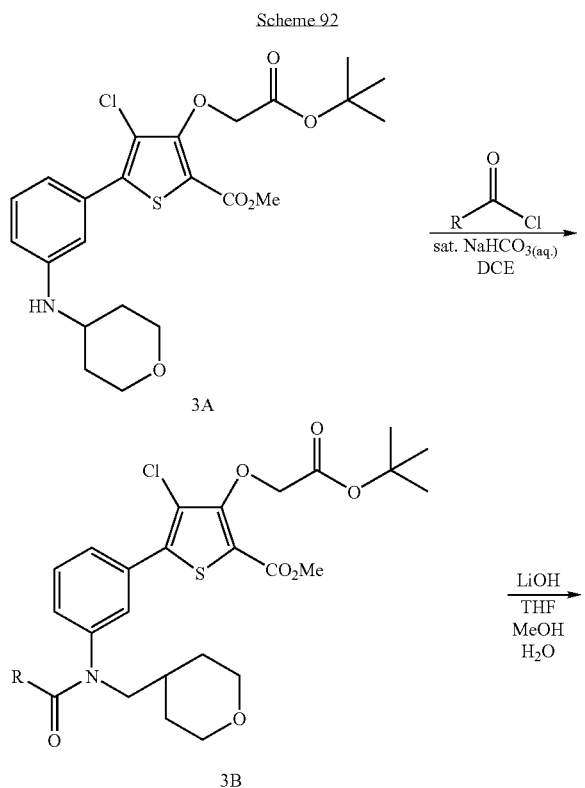

Scheme 92

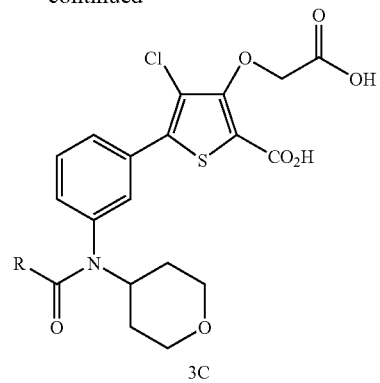

EXAMPLE 556

3-(carboxymethoxy)-4-chloro-5-(3-(3,4-difluoro-N-(tetrahydro-2H-pyran-4-yl)benzamido)phenyl) thiophene-2-carboxylic acid (Step 3A in Scheme 92): To a 50 mL round bottom flask under nitrogen was added methyl 3-(2-tert-butoxy-2-oxoethoxy)-4-chloro-5-(3-(tetrahydro-2H-pyran-4-ylamino)phenyl)thiophene-2-carboxylate (0.060 g, 0.12 mmol), 3,4 difluorobenzoyl chloride (0.016 mL, 0.13 mmol), 10 ml dichloroethane and 10 mL saturated aqueous sodium bicarbonate. This mixture was allowed to stir at room temperature for 16 hours, at which point the layers were separated and the organic layer washed with water. The organic layer was then dried over magnesium sulfate, filtered and concentrated to give methyl 3-(2-tert-butoxy-2-oxoethoxy)-4-chloro-5-(3-(3,4-difluoro-N-(tetrahydro-2H-pyran-4-yl)benzamido)phenyl)thiophene-2-carboxylate as a yellow oil. This product was carried on to the subsequent step without further purification or characterization.

See example 536, Step 1F in Scheme 90. Gave 3-(carboxymethoxy)-4-chloro-5-(3-(3,4-difluoro-N-(tetrahydro-2H-pyran-4-yl)benzamido)phenyl)thiophene-2-carboxylic acid as a white solid (0.009 g, 14%). 1H NMR (400 MHz, DMSO-D6) δ ppm 1.39-1.52 (m, 2 H) 1.73-1.95 (m, 2 H) 3.38-3.48 (m, 2 H) 3.83-3.96 (m, 2 H) 4.70-4.78 (m, 1 H) 4.90 (s, 2 H) 7.09-7.18 (m, 1 H) 7.24-7.32 (m, 1 H) 7.32-7.39 (m, 1 H) 7.43-7.50 (m, 4 H) 7.50-7.56 (m, 1 H). Calc'd 552.069. Found 552.0701. expl.-calc'd 1.08 mmu.

EXAMPLE 557

3-(carboxymethoxy)-4-chloro-5-(3-(3-fluoro-N-(tetrahydro-2H-pyran-4-yl)benzamido)phenyl) thiophene-2-carboxylic acid See example 556, Step 3A in Scheme 92. Gave methyl 3-(2-tert-butoxy-2-oxoethoxy)-4-chloro-5-(3-(3-fluoro-N-(tetrahydro-2H-pyran-4-yl)benzamido)phenyl)thiophene-2-carboxylate as a yellow oil. This product was carried on to the subsequent step without further purification or characterization.

See example 536, Step 1F in Scheme 90. Gave 3-(carboxymethoxy)-4-chloro-5-(3-(3-fluoro-N-(tetrahydro-2H-pyran-4-yl)benzamido)phenyl)thiophene-2-carboxylic acid as a white solid (0.019 g, 30%). 1H NMR (400 MHz, DMSO-D6) δ ppm 1.30-1.53 (m, J=33.35 Hz, 2 H) 1.82-1.94 (m, 2 H) 3.38-3.53 (m, 2 H) 3.83-3.93 (m, 2 H) 4.77-4.89 (m, 1 H) 4.91 (s, 2 H) 6.93-7.06 (m, 2 H) 7.16-7.26 (m, 1 H) 7.27-7.37 (m, 2 H) 7.38-7.46 (m, 2 H) 7.48-7.54 (m, 1 H). Calc'd 534.0784. Found 534.0801. expl.-calc'd 1.68 mmu.

EXAMPLE 558

3-(carboxymethoxy)-4-chloro-5-(3-(3-fluoro-N-(tetrahydro-2H-pyran-4-yl)benzamido)phenyl)thiophene-2-carboxylic acid See example 556, Step 3A in Scheme 92. Gave methyl 3-(2-tert-butoxy-2-oxoethoxy)-4-chloro-5-(3-(3-fluoro-N-(tetrahydro-2H-pyran-4-yl)benzamido)phenyl)thiophene-2-carboxylate as a yellow oil. This product was carried on to the subsequent step without further purification or characterization.

See example 536, Step 1F in Scheme 90. Gave 3-(carboxymethoxy)-4-chloro-5-(3-(3-fluoro-N-(tetrahydro-2H-pyran-4-yl)benzamido)phenyl)thiophene-2-carboxylic acid as a white solid (0.012 g, 19%). 1H NMR (400 MHz, DMSO-D6) δ ppm 1.32-1.53 (m, 2 H) 1.80-1.93 (m, 2 H) 3.37-3.53 (m, 2 H) 3.69-3.96 (m, 2 H) 4.72-4.81 (m, 1 H) 4.86 (s, 2 H) 7.00-7.17 (m, 3 H) 7.20-7.26 (m, 1 H) 7.31-7.36 (m, 1 H) 7.40-7.54 (m, 3 H). Calc'd 534.0784. Found 534.0805. expl.-calc'd 2.10 mmu.

EXAMPLE 559

3-(carboxymethoxy)-4-chloro-5-(3-(4-fluoro-N-(tetrahydro-2H-pyran-4-yl)benzamido)phenyl)thiophene-2-carboxylic acid See example 556, Step 3A in Scheme 92. Gave methyl 3-(2-tert-butoxy-2-oxoethoxy)-4-chloro-5-(3-(4-fluoro-N-(tetrahydro-2H-pyran-4-yl)benzamido)phenyl)thiophene-2-carboxylate as a yellow oil. This product was carried on to the subsequent step without further purification or characterization.

See example 536, Step 1F in Scheme 90. Gave 3-(carboxymethoxy)-4-chloro-5-(3-(4-fluoro-N-(tetrahydro-2H-pyran-4-yl)benzamido)phenyl)thiophene-2-carboxylic acid as a white solid (0.009 g, 14%). 1H NMR (400 MHz, DMSO-D6) δ ppm 1.36-1.57 (m, 2 H) 1.78-1.95 (m, 2 H) 3.37-3.49 (m, 2 H) 3.76-3.96 (m, 2 H) 4.73-4.78 (m, 1 H) 4.90 (s, 2 H) 7.03 (t, J=8.84 Hz, 2 H) 7.26-7.40 (m, 3 H) 7.39-7.60 (m, 3 H). Calc'd 534.0784. Found 534.0795. expl.-calc'd 1.13 mmu.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:
1. A compound of formula (I),

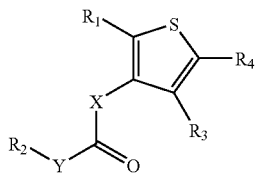

wherein $R_1$ is $C(O)OR_5$, $C(O)R_5$, or $C(O)NR_5R_6$;

$R_2$ is $R_5$;

X is —O—$C_{1-3}$alkylene, —$NR_8$—$C_{1-3}$alkylene, —S—$C_{1-3}$alkylene, —SO—$C_{1-3}$alkylene-, —$SO_2$—$C_{1-3}$alkylene, —$C_{1-4}$alkylene, —$C_{2-4}$alkenylene, —$C_{2-4}$ alkynylene-; wherein any of the alkylene, alkenylene or alkynylene groups is optionally substituted with one or more halogen, oxo, imido, CN, $OCF_3$, OH, $NH_2$, $NO_2$, or Q;

Y is absent, —O—, or —$NR_6$—;

$R_3$ is H, halogen, CN, $CFR_3$, $OCF_3$, $C_{1-3}$alkyl, $C_{3-4}$cycloalkyl, $C_{1-3}$alkoxy, or aryl;

$R_4$ is A-B-E-D, where A is arylene or heteroarylene, each A being optionally substituted with one or more of $C_{1-6}$alkyl, $C_{2-6}$alkenyl, $C_{2-6}$alkynyl, halogen, CN, $OCF_3$, OH, $NH_2$, CHO, $NO_2$, or Q; where any of the alkyl, alkenyl or alkynyl is optionally substituted with one or more halogen, oxo, CN, $OCF_3$, OH, $NH_2$, $NO_2$, $N_3$, or Q;

B is absent or —$NR_5$—, —$NR_7$—, —$N(R_5)CH_2$—, —$N(R_9)$—, —$N(R_9)C(O)$—, —$N(R_9)C(O)C(R_{11})(R_{12})$—, $N(R_9)C(O)C(O)$—, —$N(R_9)C(O)N(R_{10})$—, —$N(R_9)SO_2$—, —$N(R_9)SO_2C(R_{10})(R_{11})$—, —$N(R_9)(R_{10})C(R_{11})(R_{12})$—, —$N(R_9)C(R_{11})(R_{12})C(R_{13})(R_{14})$—, —O—, —O—$C(R_{11})(R_{12})$, —O—$C(R_{11})(R_{12})C(R_{13})(R_{14})$—, —$C(R_{11})(R_{12})$—O—, —$C(R_{11})(R_{12})$—O—$C(R_{13})(R_{14})$—, —$C(R_{11})(R_{12})N(R_9)$—, —$C(R_{11})(R_{12})N(R_9C(R_{13})(R_{14})$—, —$C(R_{11})(R_{12})S$—, —$C(R_{11})(R_{12})SC(R_{13})(R_{14})$—, or —$C(R_{11})(R_{12})SO_2C(R_{13})(R_{14})$—;

E is absent or $C_{3-12}$cycloalkylene, 3- to 12-membered heterocycdiyl, arylene, $C_{1-12}$alkylene, $C_{2-12}$alkenylene, or $C_{2-12}$alkynylene, where each E is optionally substituted with one or more $C_{1-3}$alkyl, $C_{1-3}$alkoxy, halogen, CN, OH, $NH_2$, or $NO_2$;

D is one or more H, halogen, OH, $NH_2$, CHO, CN, $NO_2$, $CF_3$, or Q;

each Q, independently, is —$R_5$, —$R_7$, —$OR_5$, —$OR_7$, —$NR_5R_6$, —$NR_5R_7$, —$N^+R_5R_6R_8$, $S(O)_nR_5$, or —$S(O)_nR_7$, where n is 0, 1, or 2;

each $R_5$, $R_6$, and $R_8$, independently, is H, $C_{1-12}$alkyl, $C_{2-12}$alkenyl, $C_{2-12}$alkynyl, $C_{3-12}$cycloalkyl, $C_{1-12}$alkoxy$C_{1-12}$alkyl, cycloalkyl$C_{1-6}$alkyl, 3- to 8-membered heterocycyl, heterocycyl$C_{1-6}$alkyl, aryl, aryl$C_{1-6}$alkyl, aryl$C_{2-6}$alkenyl, or aryl$C_{2-6}$alkynyl, where each $R_5$, $R_6$, and $R_8$ is optionally substituted with one or more $R_9$, —$OR_9$, —$OC(O)OR_9$, —$C(O)R_9$, —$C(O)OR_9$, —$C(O)NR_9R_{10}$, —$SR_9$, —$S(O)R_9$, —$S(O)_2R_9$, —$NR_9R_{10}$, —$N^+R_9R_{10}R_{11}$, —$NR_9C(O)R_{10}$, —$NC(O)NR_9R_{10}$, —$NR_9S(O)_2R_{10}$, oxo, halogen, CN, $OCF_3$, $CF_3$, OH, or $NO_2$;

$R_7$ is —$C(O)R_5$, —$C(O)OR_5$, —$C(O)NR_5R_6$, —$S(O)_2R_5$, —$S(O)R_5$, or —$S(O)_2NR_5R_6$; and each $R_9$, $R_{10}$, $R_{11}$, $R_{12}$, $R_{13}$ and $R_{14}$ is, independently, H, $C_{1-12}$alkyl, $C_{2-12}$alkenyl, $C_{2-12}$alkynyl, $C_{3-12}$cycloalkyl, aryl, or aryl$C_{1-12}$alkyl; where any of the alkyl, alkenyl, alkynyl, cycloalkyl, aryl, or arylalkyl, groups is optionally substituted with one or more halogen, oxo, CN, $OCF_3$, OH, $NH_2$, or $NO_2$; or a salt thereof.

2. The compound of claim 1, wherein $R_1$ is $C(O)OR_5$.
3. The compound of claim 1, wherein $R_1$ is $C(O)OH$.
4. The compound of claim 1, wherein $R_1$ is $C(O)OCH_3$.
5. The compound of claim 1, wherein $R_1$ is $C(O)OCH_2CH_3$.
6. The compound of claim 1, wherein $R_1$ is $C(O)OCH_2CH_2CH_3$.
7. The compound of claim 1, wherein $R_1$ is $C(O)OCH(CH_3)CH_3$.
8. The compound of claim 1, wherein $R_1$ is $C(O)OCH_2CH(CH_3)CH_3$.
9. The compound of claim 1, wherein $R_1$ is benzyl ester.
10. The compound of claim 1, wherein $R_1$ is $C(O)NR_5R_6$.
11. The compound of claim 1, wherein $R_1$ is $C(O)NH_2$.
12. The compound of claim 1, wherein $R_2$ is H.
13. The compound of claim 1, wherein $R_2$ is $CH_3$.
14. The compound of claim 1, wherein $R_2$ is $CH_2CH_3$.
15. The compound of claim 1, wherein $R_2$ is $CH(CH_3)CH_3$.
16. The compound of claim 1, wherein X is —O—$C_{1-3}$alkylene-.
17. The compound of claim 1, wherein X is —O—$CH_2$—.
18. The compound of claim 1, wherein X is —O—CH($CH_3$)—.
19. The compound of claim 1, wherein X is —O—CHF—.
20. The compound of claim 1, wherein X is —N—$C_{1-3}$alkylene-.
21. The compound of claim 1, wherein X is —N—$CH_2$—.
22. The compound of claim 1, wherein X is —N—CHF—.
23. The compound of claim 1, wherein Y is O.
24. The compound of claim 1, wherein $R_3$ is H, halogen, CN, $CF_3$, $OCF_3$, $C_{1-3}$alkyl, $C_{3-4}$cycloalkyl, or $C_{1-3}$alkoxy.
25. The compound of claim 1, wherein $R_3$ is halogen.
26. The compound of claim 1, wherein $R_3$ is fluorine.
27. The compound of claim 1, wherein $R_3$ is bromine.
28. The compound of claim 1, wherein $R_3$ is chlorine.
29. The compound of claim 1, wherein $R_3$ is H.
30. The compound of claim 1, wherein $R_3$ is $C_{1-3}$alkyl and is optionally substituted with one or more halogen, oxo, imido, CN, $OCF_3$, OH, $NH_2$, $NO_2$, or Q.
31. The compound of claim 1, wherein $R_3$ is $CH_3$.
32. The compound of claim 1, wherein $R_3$ is $CF_3$.
33. The compound of claim 1, wherein A is a 6-membered aryl group and B-E-D is connected to A in a meta (C-3 or C-5) position relative to the connection between A and thiophene.
34. The compound of claim 1, wherein A is a 5-membered heteroaryl group and B-E-D is connected to A at the C-3 or C-4 position relative to the connection between A and thiophene.
35. The compound of claim 1, wherein A is aryl optionally substituted with one or more $C_{1-6}$alkyl, $C_{2-6}$alkenyl, $C_{2-6}$alkynyl, halogen, CN, $OCF_3$, OH, $NH_2$, CHO, $NO_2$, Q, or B; where alkyl, alkenyl or alkynyl is optionally substituted with one or more halogen, oxo, CN, $OCF_3$, OH, $NH_2$, $NO_2$, $N_3$, Q, or B.
36. The compound of claim 1, wherein A is phenyl optionally substituted with one or more $C_{1-6}$alkyl, $C_{2-6}$alkenyl, $C_{2-6}$alkynyl, halogen, CN, $OCF_3$, OH, $NH_2$, CHO, $NO_2$, Q, or B; where alkyl, alkenyl or alkynyl is optionally substituted with one or more halogen, oxo, CN, $OCF_3$, OH, $NH_2$, $NO_2$, $N_3$, Q, or B.
37. The compound of claim 1, wherein A is phenyl and is substituted with $NR_5R_6$ or $NR_5R_7$.
38. The compound of claim 1, wherein A is phenyl and is substituted with $NR_5R_7$, where $R_7$ is $C(O)R_5$, $C(O)OR_5$, $C(O)NR_5R_6$, or $S(O)_2R_5$.
39. The compound of claim 1, wherein A is phenyl.
40. The compound of claim 1, wherein A is naphthyl.

41. The compound of claim 1, wherein A is thiophene, indole, benzofuran, or pyridine.
42. The compound of claim 1, wherein B is —$NR_7$—, $NR_5$—, —$NR_5CH_2$—, $NR_7CH_2$—, —O—, —O—$C(R_{11})(R_{12})$—, or —$C(R_{11})(R_{12})$—O—.
43. The compound of claim 1, wherein B is —NH—, —$NHCH_2$—, —$NHC(O)CH_2$—, —$NHC(O)$—, —O—, —$CH_2$—O—, or —O—$CH_2$—.
44. The compound of claim 1, wherein B is —$N(C(O)R_5)$—, —$N(C(O)OR_5)$—, or —$N(C(O)NHR_5)$—.
45. The compound of claim 1, wherein E is cyclopentdiyl, cyclohexdiyl, cycloheptdiyl, piperidindiyl, piperazindiyl, pyrrolidindiyl, tetrahydrofurandiyl, morpholindiyl, phenylene, pyridindiyl, pyrimidindiyl, thiophendiyl, furandiyl, imidazoldiyl, pyrroldiyl, benzimidazoldiyl, tetrahydrothiopyrandiyl, or tetrahydropyrandiyl, where E is optionally substituted with one or more $C_{1-3}$alkyl, $C_{1-3}$alkoxy, halogen, CN, OH, $NH_2$, or $NO_2$.
46. The compound of claim 1, wherein E is piperidindiyl optionally substituted with one or more $C_{1-3}$alkyl, $C_{1-3}$alkoxy, halogen, CN, OH, $NH_2$, or $NO_2$.
47. The compound of claim 1, wherein D is —$SO_2R_5$, —$C(O)R_5$, —$OC(O)NR_5R_6$, —$OR_5$, —$C(O)OR_5$, pyrimidinyl or pyridinyl.
48. The compound of claim 1, wherein $R_1$ is $C(O)OH$, X is —$OCH_2$—, Y is O, and $R_2$ is H.
49. The compound of claim 1, wherein $R_1$ is $C(O)OH$, X is —$OCH_2$—, Y is O, $R_2$ is H, and $R_3$ is Br.
50. A pharmaceutical composition comprising a compound of formula (I), or a pharmaceutically acceptable salt or prodrug thereof, and a pharmaceutically acceptable excipient or carrier, the compound of formula (I) being:

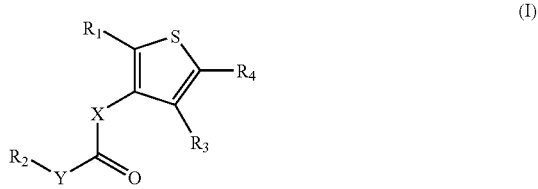

(I)

wherein $R_1$ is $C(O)OR_5$, $C(O)R_5$, or $C(O)NR_5R_6$;

$R_2$ is $R_5$;

X is —O—$C_{1-3}$alkylene, —$NR_8$—$C_{1-3}$alkylene, —S—$C_{1-3}$alkylene, —SO—$C_{1-3}$alkylene-, —$SO_2$—$C_{1-3}$alkylene, —$C_{1-4}$alkylene, —$C_{2-4}$alkenylene, —$C_{2-4}$ alkynylene-; wherein any of the alkylene, alkenylene or alkynylene groups is optionally substituted with one or more halogen, oxo, imido, CN, $OCF_3$, OH, $NH_2$, $NO_2$, or Q;

Y is absent, —O—, or —$NR_6$—;

$R_3$ is H, halogen, CN, $CF_3$, $OCF_3$, alkyl, $C_{3-4}$cycloalkyl, alkoxy, or aryl;

$R_4$ is A-B-E-D, where A is arylene or heteroarylene, each A being optionally substituted with one or more of $C_{1-6}$alkyl, $C_{2-6}$alkenyl, $C_{2-6}$alkynyl, halogen, CN, $OCF_3$, OH, $NH_2$, CHO, $NO_2$, or Q; where any of the alkyl, alkenyl or alkynyl is optionally substituted with one or more halogen, oxo, CN, $OCF_3$, OH, $NH_2$, $NO_2$, $N_3$, or Q;

B is absent or —$NR_5$—, —$NR_7$—, —$N(R_5)CH_2$—, —$N(R_9)$—, —$N(R_9)C(O)$—, —$N(R_9)C(O)C(R_{11})(R_{12})$—, $N(R_9)C(O)C(O)$—, —$N(R_9)C(O)N(R_{10})$—, —$N(R_9)SO_2$—, —$N(R_9)SO_2C(R_{10})(R_{11})$—, —$N(R_9)(R_{10})C(R_{11})(R_{12})$—, —$N(R_9)C(R_{11})(R_{12})C(R_{13})$ $(R_{14})$—, —O—, —O—C$(R_{11})(R_{12})$, —O—C$(R_{11})(R_{12})$C$(R_{13})(R_{14})$—, —C$(R_{11})(R_{12})$—O—, —C$(R_{11})(R_{12})$—O—C$(R_{13})(R_{14})$—, —C$(R_{11})(R_{12})$N$(R_9)$—, —C$(R_{11})(R_{12})$N$(R_9)$C$(R_{13})(R_{14})$—, —C$(R_{11})(R_{12})$S—, —C$(R_{11})(R_{12})$SC$(R_{13})(R_{14})$—, or —C$(R_{11})(R_{12})$SO$_2$C$(R_{13})(R_{14})$—;

E is absent or C$_{3-12}$cycloalkylene, 3- to 12-membered heterocycdiyl, arylene, C$_{1-12}$alkylene, C$_{2-12}$alkenylene, or C$_{2-12}$alkynylene, where each E is optionally substituted with one or more C$_{1-3}$alkyl, C$_{1-3}$alkoxy, halogen, CN, OH, NH$_2$, or NO$_2$;

D is one or more H, halogen, OH, NH$_2$, CHO, CN, NO$_2$, CF$_3$, or Q;

each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, where n is 0, 1, or 2;

each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxyC$_{1-12}$alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$;

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

51. A method of treating type I or type II diabetes comprising administering to a mammal a therapeutically effective amount of a compound of formula (I) or a pharmaceutically acceptable salt or prodrug thereof, the compound of formula (I) being:

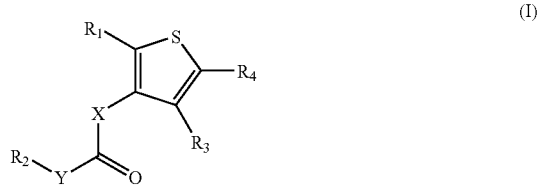

(I)

wherein R$_1$ is C(O)OR$_5$, C(O)R$_5$, or C(O)NR$_5$R$_6$;

R$_2$ is R$_5$;

X is —O—C$_{1-3}$alkylene, —NR$_8$—C$_{1-3}$alkylene, —S—C$_{1-3}$alkylene, —SO—alkylene-, —SO$_2$—C$_{1-3}$alkylene, —C$_{1-4}$alkylene, —C$_{2-4}$alkenylene, —C$_{2-4}$alkynylene-; wherein any of the alkylene, alkenylene or alkynylene groups is optionally substituted with one or more halogen, oxo, imido, CN, OCF$_3$, OH, NH$_2$, NO$_2$, or Q;

Y is absent, —O—, or —NR$_6$—;

R$_3$ is H, halogen, CN, CF$_3$, OCF$_3$, C$_{1-3}$alkyl, C$_{3-4}$cycloalkyl, C$_{1-3}$alkoxy, or aryl;

R$_4$ is A-B-E-D, where A is arylene or heteroarylene, each A being optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q; where any of the alkyl, alkenyl or alkynyl is optionally substituted with one or more halogen, oxo, CN, OCF$_3$, OH, NH$_2$, NO$_2$, N$_3$, or Q;

B is absent or —NR$_5$—, —NR$_7$—, —N(R$_5$)CH$_2$—, —N(R$_9$)—, —N(R$_9$)C(O)—, —N(R$_9$)C(O)C(R$_{11}$)(R$_{12}$)—, —N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—;

E is absent or C$_{3-12}$cycloalkylene, 3- to 12-membered heterocycdiyl, arylene, C$_{1-12}$alkylene, C$_{2-12}$alkenylene, or C$_{2-12}$alkynylene, where each E is optionally substituted with one or more C$_{1-3}$alkyl, C$_{1-3}$alkoxy, halogen, CN, OH, NH$_2$, or NO$_2$;

D is one or more H, halogen, OH, NH$_2$, CHO, CN, NO$_2$, CF$_3$, or Q;

each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, where n is 0, 1, or 2;

each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxyC$_{1-12}$alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$;

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$.

52. A method of synthesizing a compound of formula (I) for the inhibition of a PTPase wherein said method comprises a step of alkylating a compound of formula (II) to form a compound of formula (III), the compound of formula (I) being:

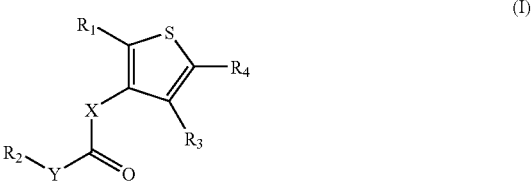

(I)

wherein R$_1$ is C(O)OR$_5$, C(O)R$_5$, or C(O)NR$_5$R$_6$;

R$_2$ is R$_5$;

X is —O—C$_{1-3}$alkylene, —NR$_8$—C$_{1-3}$alkylene, —S—C$_{1-3}$alkylene, —SO—C$_{1-3}$alkylene-, —SO$_2$—C$_{1-3}$alkylene, —C$_{1-4}$alkylene, —C$_{2-4}$alkenylene, —C$_{2-4}$ alkynylene-; wherein any of the alkylene, alkenylene or alkynylene groups is optionally substituted with one or more halogen, oxo, imido, CN, OCF$_3$, OH, NH$_2$, NO$_2$, or Q;

Y is absent, —O—, or —NR$_6$—;

R$_3$ is H, halogen, CN, CF$_3$, OCF$_3$, C$_{1-3}$alkyl, C$_{3-4}$cycloalkyl, C$_{1-3}$alkoxy, or aryl;

R$_4$ is A-B-E-D, where A arylene or heteroarylene, each A being optionally substituted with one or more of C$_{1-6}$alkyl, C$_{2-6}$alkenyl, C$_{2-6}$alkynyl, halogen, CN, OCF$_3$, OH, NH$_2$, CHO, NO$_2$, or Q; where any of the alkyl, alkenyl or alkynyl is optionally substituted with one or more halogen, oxo, CN, OCF$_3$, OH, NH$_2$, NO$_2$, N$_3$, or Q;

B is absent or —NR$_5$—, —NR$_7$—, —N(R$_5$)CH$_2$—, —N(R$_9$)—, —N(R$_9$)C(O)—, —N(R$_9$)C(O)C(R$_{11}$)(R$_{12}$)—, N(R$_9$)C(O)C(O)—, —N(R$_9$)C(O)N(R$_{10}$)—, —N(R$_9$)SO$_2$—, —N(R$_9$)SO$_2$C(R$_{10}$)(R$_{11}$)—, —N(R$_9$)(R$_{10}$)C(R$_{11}$)(R$_{12}$)—, —N(R$_9$)C(R$_{11}$)(R$_{12}$)C(R$_{13}$)(R$_{14}$)—, —O—, —O—C(R$_{11}$)(R$_{12}$), —O—C(R$_{11}$)(R$_{12}$)C(R$_{13}$)(R$_{14}$)—, —C(R$_{11}$)(R$_{12}$)—O—, —C(R$_{11}$)(R$_{12}$)—O—C(R$_{13}$)(R$_{14}$)—, —C(R$_{11}$)(R$_{12}$)N(R$_9$)—, —C(R$_{11}$)(R$_{12}$)N(R$_9$)C(R$_{13}$)(R$_{14}$)—, —C(R$_{11}$)(R$_{12}$)S—, —C(R$_{11}$)(R$_{12}$)SC(R$_{13}$)(R$_{14}$)—, or —C(R$_{11}$)(R$_{12}$)SO$_2$C(R$_{13}$)(R$_{14}$)—;

E is absent or C$_{3-12}$cycloalkylene, 3- to 12-membered heterocycdiyl, arylene, C$_{1-12}$alkylene, C$_{2-12}$alkenylene, or C$_{2-12}$alkynylene, where each E is optionally substituted with one or more C$_{1-3}$alkyl, C$_{1-3}$alkoxy, halogen, CN, OH, NH$_2$, or NO$_2$;

D is one or more H, halogen, OH, NH$_2$, CHO, CN, NO$_2$, CF$_3$, or Q;

each Q, independently, is —R$_5$, —R$_7$, —OR$_5$, —OR$_7$, —NR$_5$R$_6$, —NR$_5$R$_7$, —N$^+$R$_5$R$_6$R$_8$, S(O)$_n$R$_5$, or —S(O)$_n$R$_7$, where n is 0, 1, or 2;

each R$_5$, R$_6$, and R$_8$, independently, is H, C$_{1-12}$alkyl, C$_{2-12}$alkenyl, C$_{2-12}$alkynyl, C$_{3-12}$cycloalkyl, C$_{1-12}$alkoxyC$_{1-12}$alkyl, cycloalkylC$_{1-6}$alkyl, 3- to 8-membered heterocycyl, heterocycylC$_{1-6}$alkyl, aryl, arylC$_{1-6}$ alkyl, arylC$_{2-6}$ alkenyl, or arylC$_{2-6}$ alkynyl, where each R$_5$, R$_6$, and R$_8$ is optionally substituted with one or more R$_9$, —OR$_9$, —OC(O)OR$_9$, —C(O)R$_9$, —C(O)OR$_9$, —C(O)NR$_9$R$_{10}$, —SR$_9$, —S(O)R$_9$, —S(O)$_2$R$_9$, —NR$_9$R$_{10}$, —N$^+$R$_9$R$_{10}$R$_{11}$, —NR$_9$C(O)R$_{10}$, —NC(O)NR$_9$R$_{10}$, —NR$_9$S(O)$_2$R$_{10}$, oxo, halogen, CN, OCF$_3$, CF$_3$, OH, or NO$_2$;

R$_7$ is —C(O)R$_5$, —C(O)OR$_5$, —C(O)NR$_5$R$_6$, —S(O)$_2$R$_5$, —S(O)R$_5$, or —S(O)$_2$NR$_5$R$_6$; and each R$_9$, R$_{10}$, R$_{11}$, R$_{12}$, R$_{13}$ and R$_{14}$ is, independently, H, C$_{1-12}$alkyl, C$_{2-12}$alkenyl, C$_{2-12}$alkynyl, C$_{3-12}$cycloalkyl, aryl, or arylC$_{1-12}$alkyl; where any of the alkyl, alkenyl, alkynyl, cycloalkyl, aryl, or arylalkyl groups is optionally substituted with one or more halogen, oxo, CN, OCF$_3$, OH, NH$_2$, or NO$_2$;

wherein the compound of formula (II) is:

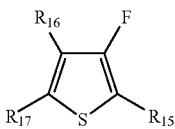

wherein R$_{15}$ is as defined for R$_1$, R$_{16}$ is as defined for R$_3$, and R$_{17}$ is as defined for R$_4$ in the compound of formula (I); and F is OH, NH$_2$, or S(O)$_2$CF$_3$;

and wherein the compound of formula (III) is defined as the compound of formula (II) except that F has been alkylated to form O(C$_{1-3}$alkyl)C(O)YR$_2$; NR$_5$ (C$_{1-3}$alkyl)C(O)YR$_2$, —S(C$_{1-3}$alkyl)C(O)YR$_2$, SO(C$_{1-3}$alkyl)C(O)YR$_2$, or SO$_2$ (C$_{1-3}$alkyl)C(O)YR$_2$, where Y, R$_2$, and R$_5$ are as defined for the compound of formula (I).

53. The method of claim 52, wherein said step of alkylating a compound of formula (II) comprises contacting the compound of formula (II) with ZCHC(O)OC$_{1-6}$alkyl, wherein Z is a halogen.

54. The compound according to claim 1 selected from:
4-Bromo-3-carboxymethoxy-5-phenyl-thiophene-2-carboxylic acid;
5-(4-Amino-phenyl)-4-bromo-3-carboxymethoxy-thiophene-2-carboxylic acid;
4-Bromo-3-carboxymethoxy-5-(4-dimethylamino-phenyl)-thiophene-2-carboxylic acid;
5-(3-Amino-phenyl)-4-bromo-3-carboxymethoxy-thiophene-2-carboxylic acid;
4-Bromo-3-carboxymethoxy-5-naphthalen-2-yl-thiophene-2-carboxylic acid;
4-Bromo-3-carboxymethoxy-5-(4-hydroxy-phenyl)-thiophene-2-carboxylic acid;
4-Bromo-3-carboxymethoxy-5-(4-methoxy-phenyl)-thiophene-2-carboxylic acid;
3-Carboxymethoxy-5-(4-trifluoromethoxy-phenyl)-thiophene-2-carboxylic acid;
4-Bromo-3-carboxymethoxy-5-(4-hydroxymethyl-phenyl)-thiophene-2-carboxylic acid;
4-Bromo-3-carboxymethoxy-5-(3-hydroxy-phenyl)-thiophene-2-carboxylic acid;
3-Ethoxycarbonylmethoxy-4,5-bis-(3-hydroxy-phenyl)-thiophene-2-carboxylic acid methyl ester;
4-Bromo-3-carboxymethoxy-5-(3-methoxy-phenyl)-thiophene-2-carboxylic acid;
4-Bromo-3-carboxymethoxy-5-(4-fluoro-phenyl)-thiophene-2-carboxylic acid;
3-Carboxymethoxy-5-o-tolyl-thiophene-2-carboxylic acid;
5-(4-Acetylamino-phenyl)-4-bromo-3-carboxymethoxy-thiophene-2-carboxylic acid;
5-(4-Benzoylamino-phenyl)-4-bromo-3-carboxymethoxy-thiophene-2-carboxylic acid;
4-Bromo-3-carboxymethoxy-5-{4-[(pyridine-3-carbonyl)-amino]-phenyl}-thiophene-2-carboxylic acid;
4-Bromo-3-carboxymethoxy-5-{4-[(furan-3-carbonyl)-amino]-phenyl}-thiophene-2-carboxylic acid;
4-Bromo-3-carboxymethoxy-5-{4-[(furan-2--carbonyl)-amino]-phenyl}-thiophene-2-carboxylic acid;
4-[4-(3-Bromo-5-carboxy-4-carboxymethoxy-thiophen-2-yl)-phenylcarbamoyl]-piperidine-1-carboxylic acid tert-butyl ester;
3-[4-(3-Bromo-5-carboxy-4-carboxymethoxy-thiophen-2-yl)-phenylcarbamoyl]-piperidine-1-carboxylic acid tert-butyl ester;
4-Bromo-3-carboxymethoxy-5-(4-methoxycarbonylamino-phenyl)-thiophene-2-carboxylic acid;
4-Bromo-3-carboxymethoxy-5-[4-(3-isopropyl-ureido)-phenyl]-thiophene-2-carboxylic acid;
5-[4-(2-Benzyloxy-acetylamino)-phenyl]-4-bromo-3-carboxymethoxy-thiophene-2-carboxylic acid;
4-Bromo-5-[4-(2-tert-butoxycarbonylamino-acetylamino)-phenyl]-3-carboxymethoxy-thiophene-2-carboxylic acid;
5-[4-(2-Amino-acetylamino)-pheny]-4-bromo-3-carboxymethoxy-thiophene-2-carboxylic acid;

4-Bromo-3-carboxymethoxy-5-[4-(oxalyl-amino)-phenyl]-thiophene-2-carboxylic acid;
4-Bromo-5-[4-(2-carboxy-acetylamino)-phenyl]-3-carboxymethoxy-thiophene-2-carboxylic acid;
4-Bromo-3-carboxymethoxy-5-(4-methanesulfonylamino-phenyl)-thiophene-2-carboxylic acid;
5-(4-Benzenesulfonylamino-phenyl)-4-bromo-3-carboxymethoxy-thiophene-2-carboxylic acid;
4-Bromo-3-carboxymethoxy-5-[4-(4-trifluoromethyl-benzenesulfonylamino)-phenyl]-thiophene-2-carboxylic acid;
4-Bromo-3-carboxymethoxy-5-{4-[methyl-(4-trifluoromethyl-benzenesulfonyl)-amino]-phenyl}-thiophene-2-carboxylic acid;
4-Bromo-3-carboxymethoxy-5-[4-(3-trifluoromethyl-benzenesulfonylamino)-phenyl]-thiophene-2-carboxylic acid;
4-Bromo-3-carboxymethoxy-5-[4-(2-trifluoromethyl-benzenesulfonylamino)-phenyl]-thiophene-2-carboxylic acid;
4-Bromo-3-carboxymethoxy-5-[4-(2,6-dichloro-benzenesulfonylamino)-phenyl]-thiophene-2-carboxylic acid;
4-Bromo-3-carboxymethoxy-5-[4-(2,6-difluoro-benzenesulfonylamino)-phenyl]-thiophene-2-carboxylic acid;
4-Bromo-3-carboxymethoxy-5-[4-(3,3,5,5-tetramethyl-cyclohexylamino)-phenyl]-thiophene-2-carboxylic acid;
3-Carboxymethoxy-5-[4-(3,3,5,5-tetramethyl-cyclohexylamino)-phenyl]-thiophene-2-carboxylic acid;
5-[4-(Benzenesulfonylamino-methyl)-phenyl]-4-bromo-3-carboxymethoxy-thiophene-2-carboxylic acid;
4-Bromo-5-[4-(tert-butoxycarbonylamino-methyl)-phenyl]-3-carboxymethoxy-thiophene-2-carboxylic acid;
4-Bromo-3-carboxymethoxy-5-[4-(ethanesulfonylamino-methyl)-phenyl]-thiophene-2-carboxylic acid;
5-[4-(Acetylamino-methyl)-phenyl]-4-bromo-3-carboxymethoxy-thiophene-2-carboxylic acid;
4-Bromo-3-carboxymethoxy-5-[4-(ethoxycarbonylamino-methyl)-phenyl]-thiophene-2-carboxylic acid;
4-Bromo-3-carboxymethoxy-5-[4-(3-isopropyl-ureidomethyl)-phenyl]-thiophene-2-carboxylic acid;
5-(4-Aminomethyl-phenyl)-4-bromo-3-carboxymethoxy-thiophene-2-carboxylic acid trifluoroacetic acid;
4-Bromo-3-carboxymethoxy-5-(4-phenylcarbamoyl-phenyl)-thiophene-2-carboxylic acid;
4-Bromo-3-carboxymethoxy-5-(4-formyl-phenyl)-thiophene-2-carboxyfic acid;
4-Bromo-3-carboxymethoxy-5-(4-isopropylcarbamoyl-phenyl)-thiophene-2-carboxylic acid;
4-Bromo-5-[4-(1-carbamoyl-ethylcarbamoyl)-phenyl]-3-carboxymethoxy-thiophene-2-carboxylic acid;
4-Bromo-3-carboxymethoxy-5-[4-(4-trifluoromethyl-phenylcarbamoyl)-phenyl]-thiophene-2-carboxylic acid;
4-Bromo-3-carboxymethoxy-5-(3-propionylamino-phenyl)-thiophene-2-carboxylic acid;
4-Bromo-5-(3-butyrylamino-phenyl)-3-carboxymethoxy-thiophene-2-carboxylic acid;
4-Bromo-3-carboxymethoxy-5-[3-(cyclohexanecarbonyl-amino)-phenyl]-thiophene-2-carboxylic acid;
4-Bromo-3-carboxymethoxy-5-(3-hexanoylamino-phenyl)-thiophene-2-carboxylic acid;
4-Bromo-3-carboxymethoxy-5-[3-(cyclopentanecarbonyl-amino)-phenyl]-thiophene-2-carboxylic acid;
4-[3-(3-Bromo-5-carboxy-4-carboxymethoxy-thiophen-2-yl)-phenylcarbamoyl]-piperdine-1-carboxylic acid tert-butyl ester;
3-[3-(3-Bromo-5-carboxy-4-carboxymethoxy-thiophen-2-yl)-phenylcarbamoyl]-piperdine-1-carboxylic acid tert-butyl ester;
4-Bromo-3-carboxymethoxy-5-[3-(3,3,3-trifiuoro-propionyiamino)-phenyi]-thiophene-2-carboxyiic acid;
5-(3-Benzoylamino-phenyl)-4-bromo-3-carboxymethoxy-thiophene-2-carboxylic acid;
4-Bromo-3-carboxymethoxy-5-{3-[(furan-2-carbonyl)-amino]-phenyl}-thiophene-2-carboxyiic acid;
4-Bromo-3-carboxymethoxy-5-{3-[(furan-3-carbonyl)-amino]-phenyl}-thiophene-2carboxylic acid;
4-Bromo-3-carboxymethoxy-5-[3-[(2-trifluoromethyl-benzoylamino)-phenyl]-thiophene-2carboxylic acid;
4-Bromo-3-carboxymethoxy-5-[3-(2-fluoro-benzoylamino)-phenyl]-thiophene-2-carboxylic acid;
4-Bromo-3-carboxymethoxy-5-[3-(3-fluoro-benzoylamino)-phenyl]-thiophene-2-carboxylic acid;
4-Bromo-3-carboxymethoxy-5-{3-[(pyridine-3-carbonyl)-amino]-phenyl}-thiophene-2-carboxylic acid;
4-Bromo-3-carboxymethoxy-5-[3-(4,4,4-trifluoro-butyrylamino)-phenyl]-thiophene-2carboxylic acid;
4-Bromo-3-carboxymethoxy-5-{3-[(2-hydroxy-pyridine-3-carbonyl)-amino]-phenyl}-thiophene-2-carboxylic acid;
4-Bromo-3-carboxymethoxy-5-{3-[(pyridine-4-carbonyl)-amino]-phenyl}-thiophene-2-carboxylic acid;
4-Bromo-3-carboxymethoxy-5-{3-[(quinoline-3-carbonyl)-amino]-phenyl}-thiophene-2-carboxytic acid;
4-Bromo-3-carboxymethoxy-5-{3-[(pyridine-2-carbonyl)-amino]-phenyl}-thiophene-2-carboxytic acid;
4-Bromo-3-carboxymethoxy-5-{3-[(1-oxy-pyridine-3-carbonyl)-amino]-phenyl}-thiophene-2-carboxylic acid;
4-Bromo-3-carboxymethoxy-5-[3-[(2-pyridin-2-yl-acetylamino)-phenyl]-thiophene-2-carboxylic acid;
4-Bromo-3-carboxymethoxy-5-[3-[(2-pyridin-3-yl-acetylamino)-phenyl]-thiophene-2-carboxylic acid;
4-Bromo-3-carboxymethoxy-5-{3-[(pyrazine-2-carbonyl)-amino]-phenyl}-thiophene-2-carboxytic acid;
4-Bromo-3-carboxymethoxy-5-[3-(2-pyridin-4-yl-acetylamino)-phenyl]-thiophene-2-carboxylic acid;
4-Bromo-3-carboxymethoxy-5-{3-[(piperidine-4-carbonyl)-amino]-phenyl}-thiophene-2-carboxylic acid;
4-Bromo-3-carboxymethoxy-5-[3-(cyclohexanecarbonyl-amino)-phenyl]-thiophene-2-carboxylic acid;
5-(3-Acetylamino-phenyl)-4-bromo-3-carboxymethoxy-thiophene-2-carboxylic acid;
4-Bromo-3-carboxymethoxy-5-(3-isobutyrylamino-phenyl)-thiophene-2-carboxylic acid;
4-Bromo-3-carboxymethoxy-5-[3-(2,2,2-trifluoro-ethanesulfonylamino)-phenyl]-thiophene-2-carboxylic acid;
5-(3-Benzenesulfonylamino-phenyl)-4-bromo-3-carboxymethoxy-thiophene-2-carboxylic acid;
4-Bromo-3-carboxymethoxy-5-(3-ethanesulfonylamino-phenyl)-thiophene-2-carboxylic acid;
4-Bromo-3-carboxymethoxy-5-(3-phenylmethanesulfonylamino-phenyl)-thiophene-2-carboxylic acid;
4-Bromo-3-carboxymethoxy-5-[3-(4-trifluoromethyl-benzenesulfonylamino)-phenyl]-thiophene-2-carboxylic acid;
4-Bromo-3-carboxymethoxy-5-[3-(4-trifluoromethoxy-benzenesulfonylamino)-phenyl]-thiophene-2-carboxylic acid;

4-Bromo-3-carboxymethoxy-5-[3-(3-trifluoromethyl-benzenesulfonylamino)-phenyl]-thiophene-2-carboxylic acid;
4-Bromo-3-carboxymethoxy-5-[3-(2-trifluoromethyl-benzenesulfonylamino)-phenyl]-thiophene-2-carboxylic acid;
4-Bromo-3-carboxymethoxy-5-[3-(2-cyano-benzenesulfonylamino)-phenyl]-thiophene-2-carboxylic acid;
4-Bromo-3-carboxymethoxy-5-[3-(4-methoxy-benzenesulfonylamino)-phenyl]-thiophene-2-carboxylic acid;
4Bromo-3-carboxymethoxy-5-[3-(4-cyano-benzenesulfonylamino)-phenyl]-thiophene-2-carboxylic acid;
4-Bromo-3-carboxymethoxy-5-[3-(4-fluoro-benzenesulfonylamino)-phenyl]-thiophene-2-carboxylic acid;
4-Bromo-3-carboxymethoxy-5-(3-methoxycarbonylamino-phenyl)-thiophene-2-carboxylic acid; or a pharmaceutically acceptable salt thereof.

55. The compound according to claim 1 selected from:
4-Bromo-3-carboxymethoxy-5-[3-(3-isopropyl-ureido)-phenyl]-thiophene-2-carboxylic acid;
4-Bromo-3-carboxymethoxy-5-[3-(3,3-diethyl-ureido)-phenyl]-thiophene-2-carboxylic acid;
5-(3-Benzylamino-phenyl)-4-bromo-3-carboxymethoxy-thiophene-2-carboxylic acid;
4-Bromo-3-carboxymethoxy-5-(3-(3-trifluoromethyl-benzylamino)-phenyl]-thiophene-2-carboxylic acid;
4-Bromo-3-carboxymethoxy-5-[3-(2-trifluoromethyl-benzylamino)-phenyl]-thiophene-2-carboxylic acid;
4-Bromo-3-carboxymethoxy-5-[3-(2-fluoro-benzylamino)-phenyl]-thiophene-2-carboxylic acid;
4-Bromo-3-carboxymethoxy-5-{3-[(furan-2-ylmethyl)-amino]-phenyl}-thiophene-2-carboxylic acid;
4-Bromo-3-carboxymethoxy-5-{3-[(furan-3-ylmethyl)-amino]-phenyl}-thiophene-2-carboxylic acid;
4-Bromo-3-carboxymethoxy-5-[3-(3-fluoro-benzylamino)-phenyl]-thiophene-2-carboxylic acid;
4-Bromo-3-carboxymethoxy-5-[3-(3-cyano-benzylamino)-phenyl]-thiophene-2-carboxylic acid;
4-Bromo-3-carboxymethoxy-5-{3-[(pyridin-3-ylmethyl)-amino]-phenyl}-thiophene-2carboxylic acid;
4-Bromo-3-carboxymethoxy-5-[3-(4-fluoro-benzylamino)-phenyl]-thiophene-2-carboxylic acid;
4-Bromo-3-carboxymethoxy-5-[3-(4-trifluoromethyl-benzylamino)-phenyl]-thiophene-2-carboxylic acid;
4-Bromo-3-carboxymethoxy-5-[3-(4-methoxy-benzylamino)-phenyl]-thiophene-2-carboxylic acid;
5-[3-(4-Benzyloxy-benzylamino)-phenyl]-4-bromo-3-carboxymethoxy-thiophene-2-carboxylic acid;
4-Bromo-3-carboxymethoxy-5-[3-(4-phenoxy-benzylamino)-phenyl]-thiophene-2-carboxylic acid;
4-Bromo-3-carboxymethoxy-5-{3-[(naphthalen-2-ylmethyl)-amino]-phenyl}-thiophene-2-carboxylic acid;
4-Bromo-5-[3-(3-carboxy-benzylamino)-phenyl]-3-carboxymethoxy-thiophene-2-carboxylic acid;
4-Bromo-3-carboxymethoxy-5-[3-(3-trifluoromethoxy-benzylamino)-phenyl]-thiophene-2-carboxylic acid;
4-Bromo-3-carboxymethoxy-5-[3-(2-trifluoromethoxy-benzylamino)-phenyl]-thiophene-2-carboxylic acid;
4-Bromo-3-carboxymethoxy-5-[3-(2-hydroxy-benzylamino)-phenyl]-thiophene-2-carboxylic acid;
4-Bromo-3-carboxymethoxy-5-[3-(4-methyl-benzylamino)-phenyl]-thiophene-2-carboxylic acid;
4-Bromo-3-carboxymethoxy-5-[3-(4-chloro-benzylamino)-phenyl]-thiophene-2-carboxylic acid;
4-Bromo-3-carboxymethoxy-5-[3-(4-isopropyl-benzylamino)-phenyl]-thiophene-2carboxylic acid;
4-Bromo-3-carboxymethoxy--5-[3-(3-nitro-benzylamino)-phenyl]-thiophene-2-carboxylic acid;
4-Bromo-3-carboxymethoxy--5-[3-(3-methanesulfonylamino-benzylamino)-phenyl]-thiophene-2-carboxylic acid;
5-[3-(3-Amino-benzylamino)-phenyl]-4-bromo-3-carboxymethoxy-thiophene-2-carboxylic acid;
5-[3-(3-Acetylamino-benzylamino)-phenyl]-4-bromo-3-carboxymethoxy-thiophene-2-carboxylic acid;
4-Bromo-3-carboxymethoxy-5-(3-cyclohexylamino-phenyl)-thiophene-2-carboxylic acid;
4-Bromo-3-carboxymethoxy-5-(3-cyclopentylamino-phenyl)-thiophene-2-carboxylic acid;
5-[3-(1-Acetyl-piperdin-4-ylamino)-phenyl]-4-bromo-3-carboxymethoxy-thiophene-2-carboxylic acid;
4-Bromo-3-carboxymethoxy-5-(3-cycloheptylamino-phenyl)-thiophene-2-carboxylic acid;
5-[3-(Bicyclo[3.3.1]non-9-ylamino)-phenyl]-4-bromo-3-carboxymethoxy-thiophene-2-carboxylic acid;
4-Bromo-3-carboxymethoxy-5-[3-(4-ethyl-cyclohexylamino)-phenyl]-thiophene-2-carboxylic acid;
4-Bromo-3-carboxymethoxy-5-[3-cis(4-phenyi-cyclohexylamino)-phenyl]-thiophene-2-carboxylic acid;
4-Bromo-3-carboxymethoxy-5-[3-trans(4-phenyl-cyclohexylamino)-phenyl]-thiophene-2-carboxylic acid;
4-Bromo-3-carboxymethoxy-5-[3-(1-cyclohexyl-ethylamino)-phenyl]-thiophene-2-carboxylic acid;
4-Bromo-3-carboxymethoxy-5-[3-(3,3,5,5-tetramethyl-cyclohexylamino)-phenyl]-thiophene-2-carboxylic acid;
5-[3-(Adamantan-2-ylamino)-phenyl]-4-bromo-3-carboxymethoxy-thiophene-2-carboxylic acid;
4-Bromo-3-carboxymethoxy-5-[3-(tetrahydro-pyran-4-ylamino)-phenyl]-thiophene-2-carboxylic acid;
4-Bromo-3-carboxymethoxy-5-[3-(cyclohexylmethylamino)-phenyl]-thiophene-2-carboxylic acid;
4-Bromo-3-carboxymethoxy-5-[3-(1-methanesulfonyl-piperidin-4-ylamino)-phenyl]-thiophene-2-carboxylic acid;
5-[3-(1-Benzenesulfonyl-piperidin-4-ylamino)-phenyl]-4-bromo-3-carboxymethoxy-thiophene-2-carboxylic acid;
4-Bromo-3-carboxymethoxy-5-[3-(1-phenylmethanesulfonyl-piperidin-4-ylamino)-phenyl]-thiophene-2-carboxylic acid;
4-Bromo-3-carboxymethoxy-5-[3-(1-ethanesulfonyl-piperidin-4-ylamino)-phenyl]-thiophene-2-carboxylic acid;
4-Bromo-3-carboxymethoxy-5-{3-[1-(propane-2-sulfonyl)-piperidin-4-ylamino]-phenyl}-thiophene-2-carboxylic acid;
4-Bromo-5-{3-[1-(butane-1-sulfonyl)-piperidin-4-ylamino]-phenyl}-3-carboxymethoxy-thiophene-2-carboxylic acid;
5-{3-[1-(3,5-Bis-trifluoromethyl-phenylmethanesulfonyl)-piperidin-4-ylamino]-phenyl}-4-bromo-3-carboxymethoxy-thiophene-2-carboxylic acid;
4-Bromo-3-carboxymethoxy-5-{3-[1-(propane-1-sulfonyl)-piperidin-4-ylamino]-phenyl}-thiophene-2-carboxylic acid;
4-Bromo-3-carboxymethoxy-5-{3-[1-(3-trifluoromethyl-phenylmethanesulfonyl)-piperidin-4-ylamino]-phenyl}-thiophene-2-carboxylic acid;
4-Bromo-3-carboxymethoxy-5-{3-[1-(4-fluoro-phenylmethanesulfonyl)-piperidin-4-ylamino]-phenyl}-thiophene-2-carboxylic acid;

4-Bromo-3-carboxymethoxy-5-{3-[1-(4-trifluoromethyl-phenylmethanesulfonyl)piperidin-4-ylamino]-phenyl}-thiophene-2-carboxylic acid;

4-Bromo-3-carboxymethoxy-5-{3-[1-(naphthalene-1-sulfonyl)-piperidin-4-ylamino]-phenyl}-thiophene-2-carboxylic acid;

4-Bromo-3-carboxymethoxy-5-{3-[1-(naphthalene-2-sulfonyl)-piperidin-4-ylamino]-phenyl}-thiophene-2-carboxylic acid;

4-Bromo-3-carboxymethoxy-5-{3-[1-(2-nitro-phenylmethanesulfonyl)-piperidin-4-ylamino]-phenyl}-thiophene-2-carboxylic acid;

4-Bromo-3-carboxymethoxy-5-{3-[1-(4-chloro-phenylmethanesulfonyl)-piperidin-4-ylamino]-phenyl}-thiophene-2-carboxylic acid;

4-Bromo-3-carboxymethoxy-5-{3-[1-(3,5-dichloro-phenylmethanesulfonyl)-piperidin-4-ylamino]-phenyl}-thiophene-2-carboxylic acid;

4-Bromo-3-carboxymethoxy-5-{3-[1-(3,4-dichloro-phenylmethanesulfonyl)-piperidin-4-ylamino]-phenyl}-thiophene-2-carboxylic acid;

4-Bromo-3-carboxymethoxy-5-{3-[1-(3-nitro-phenylmethanesulfonyl)-piperidin-4-ylamino]-phenyl}-thiophene-2-carboxylic acid;

4-Bromo-3-carboxymethoxy-5-{3-[1-(3-chloro-phenylmethanesulfonyl)-piperidin-4-ylamino]-phenyl}-thiophene-2-carboxylic acid;

4-Bromo-3-carboxymethoxy-5-{3-[1-(2-phenyl-ethanesulfonyl)-piperidin-4-ylamino]-phenyl}-thiophene-2-carboxylic acid;

4-Bromo-3-carboxymethoxy-5-[3(1-o-tolylmethanesulfonyl-piperidin-4-ylamino)-phenyl]-thiophene-2-carboxylic acid;

4-Bromo-3-carboxymethoxy-5-[3-(1-m-tolylmethanesulfonyl-piperidin-4-ylamino)-phenyl]-thiophene-2-carboxylic acid;

4-Bromo-3-carboxymethoxy-5-{3-[1-(2,6-dimethyl-phenylmethanesulfonyl)-piperidin-4-ylamino]-phenyl}-thiophene-2carboxylic acid;

4-Bromo-3-carboxymethoxy-5-{3-[1-(2-imidazol-1-yl-ethanesulfonyl)-piperidin-4-ylamino]-phenyl}-thiophene-2-carboxylic acid;

4-Bromo-3-carboxymethoxy-5-{3-[1-(2-pyrazol-1-yl-ethanesulfonyl)-piperidin-4-ylamino]-phenyl}-thiophene-2-carboxylic acid;

4-Bromo-3-carboxymethoxy-5-{3-[1-(2-isopropoxy-ethanesulfonyl)-piperidin-4-ylamino]-phenyl}-thiophene-2-carboxylic acid;

5-{3-[1-(2-Amino-phenylmethanesulfonyl)-piperidin-4-ylamino]-phenyl}-bromo-3-carboxymethoxy-thiophene-2-carboxylic acid;

4-[3-(3-Bromo-5-carboxy-4-carboxymethoxy-thiophen-2-yl)-phenylamino]-piperidine-1-carboxylic acid methyl ester;

5-[3-(1-Benzoyl-piperidin-4-ylamino)-phenyl]-4-bromo-3-carboxymethoxy-thiophene-2-carboxylic acid;

4-Bromo-3-carboxymethoxy-5-[3-(1-phenylacetyl-piperidin-4-ylamino)-phenyl]-thiophene-2-carboxylic acid;

5-{3-[3-Benzyl-1-(1-benzylcarbamoyl-piperidin-4-yl)-ureido]-phenyl}-4-bromo-3-carboxymethoxy-thiophene-2-carboxylic acid;

5-[3-(1-Benzylcarbamoyl-piperidin-4-ylamino)-phenyl]-4-bromo-3-carboxymethoxy-thiophene-2-carboxylic acid;

4-Bromo-3-carboxymethoxy-5-{3-[(1-methanesulfony[-piperidin-4-ylmethyl)-amino]-phenyl}-thiophene-2-carboxylic acid;

4-Bromo-3-carboxymethoxy-5-{3-[(1-ethanesulfonyl-piperidin-4-ylmethyl)-amino]-phenyl}-thiophene-2-carboxylic acid;

5-{3-[(1-Benzenesulfonyl-piperidin-4-ylmethyl)-amino]-phenyl}-4-bromo-3-carboxymethoxy-thiophene-2-carboxylic acid;

4-Bromo-3-carboxymethoxy-5-{3-[(1-phenylmethanesulfonyl-piperidin-4-ylmethyl)-amino]-phenyl}-thiophene-2-carboxylic acid;

5-(3-{[1-(2-Amino-phenylmethanesulfonyl)-piperidin-4-ylmethyl]-amino}-Phenyl)-4-bromo-3-carboxymethoxy-th iophene-2-carboxylic acid;

4-{[3-(3-Bromo-5-carboxy-4-carboxymethoxy-thiophen-2-yl)-phenylamino]-methyl}-piperidine-1-carboxylic acid methyl ester;

4-Bromo-3-carboxymethoxy-5-{3-[(1-phenylcarbamoyl-piperidin-4-ylmethyl)-amino]-phenyl}-thiophene-2-carboxylic acid;

5-{3-[(1-Benzylcarbamoyl-piperidin-4-ylmethyl)-amino]-phenyl}-4-bromo-3-carboxymethoxy-thiophene-2-carboxylic acid;

4-Bromo-3-carboxymethoxy-5-{3-[(1-cyclohexylcarbamoyl-piperidin-4-ylmethyl)-amino]-phenyl}-thiophene-2-carboxylic acid;

4-Bromo-3-carboxymethoxy-5-(3-{[1-(4-methoxy-phenylcarbamoyl)-piperidin-4-ylmethyl]-amino}-phenyi)-thiophene-2-carboxylic acid;

or a pharmaceutically acceptable salt thereof.

56. The compound according to claim 1 selected from:

4-Bromo-3-carboxymethoxy-5-(3-{[1(4-cyano-phenylcarbamoyl)-piperidin-4-ylmethyl]amino}-phenyl)-thiophene-2-carboxylic acid;

4-Bromo-3-carboxymethoxy-5-{3-[(1-p-tolylcarbamoyl-piperidin-4-ylmethyl)-amino]-phenyl}-thiophene-2-carboxylic acid;

4-Bromo-3-carboxymethoxy-5-(3-{[1-(3-methoxy-phenylcarbamoyl)-piperidin-4-ylmethyl]-amino}-phenyl)-thiophene-2-carboxylic acid;

4-Bromo-3-carboxymethoxy-5-(3-{[1-(2-methoxy-phenylcarbamoyl)-piperidin-4-ylmethyl]-amino}-phenyl)-thiophene-2-carboxylic acid;

4-Bromo-3-carboxymethoxy-5-(3-{[1-(3-chloro-phenylcarbamoyl)-piperidin-4-ylmethyl]-amino}-phenyl)-thiophene-2-carboxylic acid;

4-Bromo-3-carboxymethoxy-5-(3-{[1-(2-chloro-phenylcarbamoyl)-piperidin-4-ylmethyl]amino}-phenyl)-thiophene-2-carboxylic acid;

4-Bromo-3-carboxymethoxy-5-{3-[(1-m-tolylcarbamoyl-piperidin-4-ylmethyl)amino]-phenyl}-thiophene-2-carboxylic acid;

4-Bromo-3-carboxymethoxy-5-{3[(1-o-tolylcarbamoyl-piperidin-4-ylmethyl)-amino]-phenyl}-thiophene-2-carboxylic acid;

4-Bromo-3-carboxymethoxy-5-(3-{[1-(2,6-dimethyl-phenylcarbamoyl)-piperidin-4-ylmethyl]-amino}-phenyl)-thiophene-2-carboxylic acid;

4-Bromo-3-carboxymethoxy-5-(3-{[1-(2-trifluoromethyl-phenylcarbamoyl)-piperidin-4-ylmethyl]-amino}-phenyl)-thiophene-2-carboxylic acid;

4-Bromo-3-carboxymethoxy-5-(3-{[1-(methyl-phenylcarbamoyl)-piperidin-4-ylmethyl]amino}-phenyl)-thiophene-2-carboxylic acid;

4-Bromo-3-carboxymethoxy-5-(3-{[1-(2-methylsulfanyl-phenylcarbamoyl)-piperidin-4-ylmethyl]-amino}-phenyl)-thiophene-2-carboxylic acid;

4-Bromo-3-carboxymethoxy-5-(3-{[1-(2,3-dimethyl-phenylcarbamoyl)-piperidin-4-ylmethyl]-amino}-phenyl)-thiophene-2carboxylic acid;

4-{[3-(3-Bromo-5-carboxy-4-carboxymethoxy-thiophen-2-yl)-phenylamino]-methyl{-piperidine-1-carboxylic acid tert-butyl ester;

4-Bromo-3-carboxymethoxy-5-(3-cyclohexylmethoxy-phenyl)-thiophene-2-carboxylic acid;

5-[3-(3,5-Bis-trifluoromethyl-benzyloxy)-phenyl]-4-bromo-3-carboxymethoxy-thiophene-2-carboxylic acid;

5-(3-Benzyloxy-phenyl)-4-bromo-3-carboxymethoxy-thiophene-2-carboxylic acid;

4-Bromo-3-carboxymethoxy-5-[3-(1-phenyl-ethoxy)-phenyl]-thiophene-2-carboxylic acid;

4-Bromo-5-[3-(1-carboxy-ethoxy)-phenyl]-3-carboxymethoxy-thiophene-2-carboxylic acid;

4-Bromo-3-carboxymethoxy-5-[3-(naphthalen-2-ylmethoxy)-phenyl]-thiophene-2-carboxylic acid;

4-Bromo-3-carboxymethoxy-5-[3-(3-methyl-3,3a-dihydro-benzo[1,2,5]oxadiazol-5-ylmethoxy)-phenyl]-thiophene-2-carboxylic acid;

4-Bromo-3-carboxymethoxy-5-[3-(3-trifluoromethoxy-benzyloxy)-phenyl]-thiophene-2-carboxylic acid;

4-[3-(3-Bromo-5-carboxy-4-carboxymethoxy-thiopen-2-yl)-phenoxy]-piperdine-1-carboxylic acid tert-butyl ester;

4-Bromo-3-carboxymethoxy-5-[3-(1-phenylcarbamoyl-piperidin-4-yloxy)-phenyl]-thiophene-2-carboxylic acid;

4-[3-(3-Bromo-5-carboxy-4-carboxymethoxy-thiopen-2-yl)-phenoxy]-piperdine-1-carboxylic acid phenyl ester;

4-Bromo-3-carboxynlethoxy-5-[3-(1-phenylmethanesulfonyl-piperidin-4-yloxy)-phenyl]-thiophene-2-carboxylic acid;

4-[3-(3-Bromo-5-carboxy-4-carboxymethoxy-thiopen-2-yl)-phenoxymethyl]-piperdine-1carboxylic acid tert-butyl ester;

4-Bromo-3-carboxymethoxy-5-[3-(1-methanesulfonyl-piperidin-4ylmethoxy)-phenyl]-thiophene-2-carboxylic acid;

4-Bromo-3-carboxymethoxy-5-[3-(1-phenylmethanesulfonyl-piperidin-4-ylmethoxy)-phenyl]-thiophene-2-carboxylic acid;

4-Bromo-3-carboxymethoxy-5-{3-[1-(toluene-4-sulfonyl)-piperidin-4-ylmethoxy]-phenyl}-thiophene-2-carboxylic acid;

5-[3-(1-Benzenesulfonyl-piperidin-4-ylmethoxy)-phenyl]-4-bromo-3-carboxymethoxy-thiophene-2-carboxylic acid;

4-[3-(3-Bromo-5-carboxy-4-carboxymethoxy-thiopen-2-yl)-phenoxymethyl]-piperdine-1-carboxylic acid phenyl ester;

4-[3-(3-Bromo-5-carboxy-4-carboxymethoxy-thiopen-2-yl)-phenoxymethyl]-piperdine-1-carboxylic acid methyl ester;

4-Bromo-3-carboxynlethoxy-5-[3-(1-ethylcarbamoyl-piperidin-4-ylmethoxy)-phenyl]-thiophene-2-carboxylic acid;

4-Bromo-3-carboxymethoxy-5-[3-(1-phenylcarbamoyl-piperidin-4-ylmethoxy)-phenyl]-thiophene-2-carboxylic acid;

4-Bromo-3-carboxymethoxy-5-{3-[1-(2-chloro-phenylcarbamoyl)-piperidin-4-ylmethoxy]-phenyl}-thiophene-2-carboxylic acid;

4-Bromo-3-carboxymethoxy-5-[3-(1-o-tolylcarbamoyl-piperidin-4-ylmethoxy)-phenyl]-thiophene-2-carboxylic acid;

4-Bromo-3-carboxymethoxy-5-{3-[1-(2-methoxy-phenylcarbamoyl)-piperidin-4-ylmethoxyl-phenyl}-thiophene-2-carboxylic acid;

4-Bromo-3-carboxymethoxy-5-{3-[1-(2-isopropyl-phenylcarbamoyl)-piperidin-4-ylmethoxyj-phenyl}-thiophene-2-carboxylic acid;

4-Bromo-3-carboxymethoxy-5-{3-[1-(2-phenoxy-phenylcarbamoyl)-piperidin-4-ylmethoxy]-phenyl}-thiophene-2-carboxylic acid;

4-Bromo-3-carboxymethoxy-5-{3-[1-(2,6-diethyl-phenylcarbamoyl)-piperidin-4-ylmethoxy]-phenyl}-thiophene-2-carboxylic acid;

4-Bromo-3-carboxymethoxy-5-{3-[1-(2,4,6-trimethyl-phenylcarbamoyl)-piperidin-4-ylmethoxy]-phenyl}-thiophene-2-carboxylic acid;

4-Bromo-3-carboxymethoxy-5-{3-[1-(2-isopropyl-6-methyl-phenylcarbamoyl)-piperidin-4-ylmethoxy]-phenyl}-thiophene-2-carboxyiic acid;

4-Bromo-3-carboxymethoxy-5-{3-[1-(3-phenoxy-phenylcarbamoyl)-piperidin-4-ylmethoxy]-phenyl}-thiophene-2-carboxylic acid;

4-Bromo-3-carboxymethoxy-5-{3-[1-(2,6-dimethyl-phenylcarbamoyl)-piperidin-4-ylmethoxy]-phenyl}-thiophene-2-carboxylic acid;

4-Bromo-3-carboxymethoxy-5-{3-[1-(4-methyl-2-nitro-phenylcarbamoyl)-piperidin-4-ylmethoxy]-phenyl}-thiophene-2-carboxylic acid;

4-Bromo-3-carboxymethoxy-5-{3-[1-(5-chloro-2-nitro-phenylcarbamoyl)-piperidin-4-ylmethoxy]-phenyl}-thiophene-2-carboxylic acid;

4-Bromo-3-carboxymethoxy-5-{3-[1-(2-nitro-phenylcarbamoyl)-piperidin-4-ylmethoxy]-phenyl}-thiophene-2-carboxylic acid;

4-Bromo-3-carboxymethoxy-5-(3-phenylaminomethyl-phenyl)-thiophene-2-carboxylic acid;

4-Bromo-3-carboxymethoxy-5-{3-[(3-trifluoromethyi-phenylamino)-methyl]-phenyl}-thiophene-2-carboxylic acid;

4-Bromo-3-carboxymethoxy-5-{3-[(3,4-difluoro-phenylamino)-methyl]-phenyl}-thiophene-2-carboxylic acid;

4-Bromo-3-carboxymethoxy-5-(3-cyclohexylaminomethyl-phenyl)-thiophene-2-carboxylic acid;

4-Bromo-3-carboxymethoxy-5-{3[(3-nitro-phenylamino)-methyl]-phenyl}-thiophene-2-carboxylic acid;

4-Bromo-5-{3-[(4-bromo-3-trifluoromethyl-phenylamino)-methyl]-phenyl}-3-carboxymethoxy-thiophene-2-carboxylic acid;

4-Bromo-3-carboxymethoxy-5-{3-[(3,5-difluoro-phenylamino)-methyl]-phenyl}-thiophene-2-carboxylic acid;

4-Bromo-3-carboxymethoxy-5-{3-[(3-fluoro-4-methyl-phenylamino)-methyl]-phenyl}-thiophene-2-carboxylic acid;

4-Bromo-3-carboxymethoxy-5-{3-[(4-chloro-3-trifluoromethyl-phenylamino)-methyl]-phenyl}-thiophene-2-carboxylic acid;

4-Bromo-3-carboxymethoxy-5-{3-[(4-methyl-3-nitro-phenylamino)-methyl]-phenyl}thiophene-2-carboxylic acid;

5-{3-[(Acetyl-cyclohexyl-amino)methyl]-phenyl}-4-bromo-3-carboxymethoxy-thiophene-2-carboxylic acid;

4-Bromo-3-carboxymethoxy-5-{3-[(cyclohexyl-methanesulfonyl-amino)-methyl]-phenyl}-thiophene-2-carboxylic acid;
4-Bromo-3-carboxymethoxy-5-{3-[(cyclohexyl-methoxycarbonyl-amino)-methyl]-phenyl}-thiophene-2-carboxylic acid;
4-Bromo-3-carboxymethoxy-5-[3-(1-cyclohexyl-3-ethyl-ureidomethyl)-phenyl]-thiophene-2-carboxylic acid;
5-(3-{[Acetyl-(3,3,5,5-tetramethyl-cyclohexyl)-amino]-methyl}phenyl)-4-bromo-3-carboxymethoxy-thiophene-2-carboxylic acid;
4-{Acetyl-[3-(3-bromo-5-carboxy-4-carboxymethoxy-thiophen-2-yl)-benzyl]-amino}-piperidine-1-carboxylic acid ethyl ester;
4-Bromo-3-carboxymethoxy-5-(4-methoxy-3-phenylaminomethyl-phenyl)-thiophene-2-carboxylic acid;
5-{3-[(Acetyl-phenyl-amino)-methyl]-4-methoxy-phenyl}-4-bromo-3-carboxymethoxy-thiophene-2-carboxylic acid;
5-{3-[(3,5-Bis-trifluoromethyl-phenylamino)-methyl]-4-methoxy-phenyl}-4-bromo-3-carboxymethoxthiophene-2-carboxylic acid;
4-Bromo-3-carboxymethoxy-5-[3-(2-carboxy-vinyl)-4-methoxy-phenyl]-thiophene-2-carboxylic acid;
4-Bromo-3-carboxymethoxy-5-{4-methoxy-3-[2-(2,2,2-trifluoro-ethylcarbamoyl)-vinyl]-phenyl}-thiophene-2-carboxylic acid;
4-Bromo-3-methoxycarbonylmethoxy-5-phenyl-thiophene-2-carboxylic acid;
4-Bromo-3-methoxycarbonylmethoxy-5-[3-(3,3,5,5-tetramethyl-cyclohexylamino)-phenyl]-thiophene-2-carboxylic acid;
4-Bromo-3-methoxycarbonylmethoxy-5-[3-(1-phenyl-methanesulfonyl-piperidin-4-ylamino)-phenyl]-thiophene-2-carboxylic acid;
4-Bromo-3-carboxymethoxy-5-phenyl-thiophene-2-carboxylic acid methyl ester;
4-Bromo-3-carboxymethoxy-5-{3-[1-(2-nitro-phenyl-methanesulfonyl)-piperidin-4-ylamino]-phenyl}-thiophene-2carboxylic acid methyl ester;
4-Bromo-3-carboxymethoxy-5-{3-[1-(4-chloro-phenyl-methanesulfonyl)-piperidin-4-ylamino]-phenyl}-thiophene-2-carboxylic acid methyl ester;
4-Bromo-3-carboxymethoxy-5-{3-[1-(3,5-dichloro-phenylmethanesulfonyl)-piperidin-4-ylamino]-phenyl}-thiophene-2-carboxylic acid methyl ester;
4-Bromo-3-carboxymethoxy-5-{3-[1-(3,4-dichloro-phenylmethanesulfonyl)-piperidin-4-ylamino]-phenyl}-thiophene-2-carboxylic acid methyl ester;
4-Bromo-3-carboxymethoxy-5-(3-cyclohexylmethoxy-phenyl)-thiophene-2-carboxylic acid methyl ester;
4-Bromo-3-carboxymethoxy-5-[3-(1-phenylmethanesulfonyl-piperidin-4-ylamino)-phenyl]-thiophene-2-carboxylic acid methyl ester;
4-Bromo-3-carboxymethoxy-5-{3-[1-(3-trifluoromethyl-phenylmethanesulfonyl)-piperidin-4-ylamino]-phenyl}-thiophene-2-carboxylic acid methyl ester;
4-Brorno-3-carboxymethoxy-5-{3-[1-(4-fluoro-phenyl-methanesulfonyl)-piperidin-4-ylamino]-phenyl}-thiophene-2-carboxylic acid methyl ester;
4-Bromo-3-carboxymethoxy-5-{3-[1-(4-trifluoromethyl-phenylmethanesulfonyl)-piperidin-4-ylamino]-phenyl}-thiophene-2-carboxylic acid methyl ester;

or a pharmaceutically acceptable salt thereof.

57. The compound according to claim 1 selected from:
4-Bromo-3-carboxymethoxy-5-[3-(3,3,5,5-tetramethyl-cyclohexylamino)phenyl]-thiophene-2-carboxylic acid methyl ester;
5-{3-[(Acetyl-cyclohexyl-amino)-methyl]-phenyl}-4-bromo-3-carboxymethoxy-thiophene-2-carboxylic acid methyl ester;
3-Carboxymethoxy-4-methyl-5-phenyl-thiophene-2-carboxylic acid;
3-Carboxymethoxy-5-(4-hydroxy-phenyl)-4-methyl-thiophene-2-carboxylic acid;
3-Carboxymethoxy-4-methyl-5-[3-(pyridin-3-ylcarbamoyl)-phenyl]-thiophene-2-carboxylic acid;
3-Carboxymethoxy-5-[4-(3-isopropy-ureido)-phenyl]-4-methyl-thiophene-2-carboxylic acid;
5-(3-carboxymethanesulfonylamino-phenyl)-3-carboxymethoxy-4-methyl-thiophene-2-carboxylic acid;
5-(3-Benzaylamino-phenyl)-3-carboxymethoxy-4-methyl-thiophene-2-carboxylic acid;
3-Carboxymethoxy-5-[3-(cyclohexylmethyl-amino)-phenyl]-4-methyl-thiophene-2-carboxylic acid;
3-Carboxymethoxy-4-methyl-5-[3-(3phenoxy-benzylamino)-phenyl]-thiophene-2-carboxylic acid;
5-[3-(3-Bromo-benzylamino)-phenyl]-3-carboxymethoxy-4-methyl-thiophene-2-carboxylic acid;
3-Carboxymethoxy-4-methyl-5-[3-(3-trifluoromethyl-benzylamino)-phenyl]-thiophene-2-carboxylic acid;
3-Carboxymethoxy-5-[3-(cycloheptylmethyl-amino)-phenyl]-4-methyl-thiophene-2-carboxylic acid;
5-Benzofuran-2-yl-4-bromo-3-carboxymethoxy-thiophene-2-carboxylic acid; p1 4,5-Bis-benzofuran-2-yl-3-ethoxyycarbonylmethoxy-thiophene-2-carboxylic acid methyl ester;
5-Biphenyl-3-yl-4-bromo-3-carboxymethoxy-thiophene-2-carboxylic acid;
5-Benzo[1,3]dioxol-5-yl-4-bromo-3-carboxymethoxy-thiophene-2-carboxylic acid;
4Bromo-3-carboxymethoxy-5-pyridin-4-yl-thiophene-2-carboxylic acid;
4Bromo-3-carboxymethoxy-5-[3-(4-trifluoromethyl-phenylcarbamoyl)-phenyl]-thiophene-2-carboxylic acid;
4Bromo-3-carboxymethoxy-5-naphthalen-1-yl-thiophen-2-carboxylic acid;
3-Bromo-4-carboxymethoxy-[2,3]-bithiophenyl-5-carboxylic acid;
4-Bromo-3-carboxymethoxy-5-pyridin-3-ylthiophene-2-carboxylic acid,
3-Bromo-4-carboxymethoxy-2'-formyl-[2,3]-bithiophenyl-5-carboxylic acid;
3-Bromo-4-carboxymethoxy-2'-(isobutylamino-methyl)-[2,3]-bithiophenyl-5-carboxylic acid;
4Bromo-3-carboxymethoxy-5-{3-[(5-phenylcarbamoyl-thiophen-2-2-ylmethyl)-amino]-phenyl}-thiophene-2-carboxylic acid;
5-{3-[(5-Benzylcarbamoyl-thiophen-2-ylmethyl)-amino]-phenyl}-4-bromo-3-carboxymethoxy-thiophene-2-carboxylic acid;
4Bromo-3-carboxymethoxy-5-{3-[(5-cyclohexylcarbamoyl-thiophen-2-ylmethyl)-amino]-phenyl}-thiophene-2-carboxylic acid;
4-Bromo-3-(carboxymethoxy)-5-[3-(piperidin-4-ylamino)phenyl]thiophene-2-carboxylic acid;
({4-Bromo-2-(methoxycarbonyl)-5-[3-(piperidin-4-ylamino)phenyl]thien-3-yl}oxy)acetic acid;
Methyl 4-bromo-3-(2-ethoxy-2-oxoethoxy)-5-(3-{[1-(5-nitropyridin-2-yl)piperidin-4yl]amino}phenyl)thiophene-2-carboxylate;

4-Bromo-3-(carboxymethoxy)-5-(3-{[1-(5-nitropyridin-2-yl)piperidin-4-yl]amino}phenyl)thiophene-2-carboxylic acid;

5-[3-({1-[5-(Acetylamino)pyridin-2-yl]piperidin-4-yl}amino)pheny]-4-bromo-3-(carboxymethoxy)thiophene-2-carboxylic acid;

4-Bromo-3-(carboxymethoxy)-5-(3-{[1-(5-{[(methylamino)carbonyl]amino}pyridin-2-yl)piperidin-4-yl]amino}phenyl)thiophene-2-carboxylic acid;

4-Bromo-3-(carboxymethoxy)-5-(3-{[(methylamino)carbonyl][1-(5{[(methylamino)carbonyl]amino}pyridin-2-yl)piperidin-4-yllamino}phenyl)thiophene-2carboxylic acid;

4-Bromo-3-(carboxymethoxy)-5-{3-[1-{5-[(methylsulfonyl)amino]pyridin-2-yl}piperidin-4-yl)amino]phenyl}thiophene-2-carboxylic acid;

3-(Carboxymethoxy)-5-phenylthiophene-2-carboxylic acid;

Methyl 5-(3-{[1-(benzylsulfonyl)piperidin-4-yl]amino}phenyl)-4-bromo-3-{2-[(2-methylphenyl)amino]-2-oxoethoxy}thiophene-2-carboxylate;

5-(3-{[1-(Benzylsulfonyl)piperidin-4-yl][(ethylamino)carbonyl]amino}phenyl)-4-bromo3-(carboxymethoxy)thiophene-2-carboxylic acid;

{5-[3-({[1-(Anilinocarbonyl)piperidin-4-yl]methyl}amino)phenyl]-4-bromo-2-(methoxycarbonyl)thien-3-yl]oxy}acetic acid;

5-(3-{{[1-(Anilinocarbonyl)pipendin-4-yl]methyl}[(ethylamino)carbonyl]amino}phenyl)-4-bromo-3-(carboxymethoxy)thiophene-2-carboxylic acid;

4-Bromo-3-(carboxymethoxy)-5-{3-[(1-{[2-(trifluoromethoxy)phenyl]sulfonyl}piperidin-4-yl)amino]phenyl}thiophene-2-carboxylic acid;

4-Bromo-3-(carboxymethoxy)-5-[3-({1-[(5-chloro-2-methoxyphenyl)sulfonyl]piperidin-4-yl}amino)phenyl]thiophene-2-carboxylic acid;

4-Bromo-3-(carboxymethoxy)-5-[3-({1-[(3,5-dichloro-2-hydroxyphenyl)sulfonyl]piperidin-4-yl}amino)phenyl]thiophene-2-carboxylic acid;

Propyl 4-bromo-3-(2-tert-butoxy-2-oxoethoxy)-5-{3-[(3,3,5,5-tetramethylcyclohexyl)amino]phenyl}thiophene-2-carboxylate;

[(4-Bromo-2-(propoxycarbonyl)-5-{3-[(3,3,5,5-tetramethylcyclohexyl)amino]phenyl}thien-3-yl)oxy]acetic acid;

4-Bromo-3-carboxymethoxy-5-{3-[1-(2-trifluoromethyl-phenylmethanesulfonyl)-piperidin-4-ylamino]-phenyl}-thiophene-2-carboxylic acid;

4-Bromo-3-carboxymethoxy-5-{3-(indan-2-ylamino)-phenyl]-thiophene-2-carboxylic acid;

3-[3-(3-Bromo-5-carboxy-4-carboxymethoxy-thiophen-2-yl)-phenylamino]-8-aza-bicyclo[3.2.1]octane-8-carboxylic acid ethyl ester;

4-Bromo-3-carboxymethoxy-5-[3-(8-phenylmethanesulfonyl-8-aza-bicyclo[3.2.1]oct-3-ylamino)-phenyl]-thiophene-2-carboxylic acid;

5-(1-Benzyl-1H-pyrazol-4-yl)-4-bromo-3-carboxymethoxy-thiophene-2-carboxylic acid;

5-{3-[1-(2-Acetylamino-phenylmethanesulfonyl)-piperidin-4-ylamino]-phenyl}-4-bromo-3-carboxymethoxy-thiophene-2-carboxylic acid;

5-{3-[1-(2-Acetylamino-phenylmethanesulfonyl)-piperidin-4-ylamino]-phenyl}-3-carboxymethoxy-thiophene-2-carboxylic acid;

4-Bromo-3-carboxymethoxy-5-{3-[1-(2-methanesulfonylamino-phenylmethanesulfonyl)-piperidin-4-ylamino]-phenyl}-thiophene-2-carboxylic acid;

3-Carboxymethoxy-5-{3-[1-(2-methanesulfonylamino-phenylmethanesulfonyl)-piperidin-4-ylamino]-phenyl}-thiophene-2-carboxylic acid;

4-Bromo-3-carboxymethoxy-5-(3-{1-[2-(3-ethyl-ureido)-phenylmethanesulfonyl]-piperdin-4-ylamino}-phenyl)-thiophene-2-carboxylic acid;

3-Carboxymethoxy-5-(3-{1-[2-(3-ethyl-ureido)-phenylmethanesulfonyl]-piperdin-4-ylamino}-phenyl)-thiophene-2-carboxylic acid;

4-Bromo-3-carboxymethoxy-5-{3-[1-(2-chloromethanesulfonylamino-phenylmethanesulfonyl)-piperidin-4-ylamino]-phenyl}-thiophene-2-carboxylic acid;

5-{3-[(Acetyl-isopropyl-amino)-methyl]-phenyl}-4-bromo-3-carboxymethoxy-thiophene-2-carboxylic acid;

5-{3-[(Acetyl-cyclohexylmethyl-amino)-methyl]-phenyl}-4-bromo-3-carboxymethoxy-thiophene-2-carboxylic acid;

5-{3-[(Acetyl-p-tolyl-amino)-methyl]-phenyl}-4-bromo-3-carboxymethoxy-thiophene-2-carboxylic acid;

5-(3-{[Acetyl-(4-tert-butyl-phenyl)-amino]-methyl}-phenyl)-4-bromo-3-carboxymethoxy-thiophene-2-carboxylic acid;

5-(3-{[Acetyl-(4-trifluoromethyl-phenyl)-amino]-methyl}-phenyl)-4-bromo-3-carboxymethoxy-thiophene-2-carboxylic acid;

5-{3-[(Acetyl-phenyl-amino)-methyl]-phenyl}-4-bromo-3-carboxymethoxy-thiophene-2-carboxylic acid;

5-{3-[(Acetyl-cyclopropyl-amino)-methyl]-phenyl}-4-bromo-3-carboxymethoxy-thiophene-2-carboxylic acid;

5-(3-{[Acetyl-(4-bromo-phenyl)-amino]-methyl{-phenyl)-4-bromo-3-carboxymethoxy-thiophene-2-carboxylic acid;

5-{3-[(Acetyl-biphenyl-4-yl-amino)-methyl]-phenyl}-4-bromo-3-carboxymethoxy-thiophene-2-carboxylic acid;

5-(3-{[Acetyl-(4-phenoxy-phenyl)-amino]-methyl}-phenyl)-4-bromo-3-carboxymethoxy-thiophene-2-carboxylic acid;

5-{3-[(Acetyl-benzyl-amino)-methyl]-phenyl}-4-bromo-3-carboxymethoxy-thiophene-2-carboxylic acid;

5-(3-{[Acetyl-(4-methoxy-benzyl)-amino]-methyl}-phenyl)-4-bromo-3-carboxymethoxy-thiophene-2-carboxylic acid;

5-{3-[(Acetyl-biphenyl-4-ylmethyl-amino)-methyl]-phenyl}-4-bromo-3-carboxymethoxy-thiophene-2-carboxylic acid;

5-(3-{[Acetyl-(4-chloro-phenyl)-amino]-methyl}-phenyl)-4-bromo-3-carboxymethoxy-thiophene-2-carboxylic acid;

5-(3-{[Acetyl-(4-trifluoromethyl-phenyl)-amino]-methyl}-phenyl)-4-bromo-3-carboxymethoxy-thiophene-2-carboxylic acid;

5-(3-{[Acetyl-(3,5-bis-trifluoromethyl-phenyl)-amino]-methyl}-phenyl)-4-bromo-3-carboxymethoxy-thiophene-2-carboxylic acid;

5-[3-({Acetyl-[2-(4-chloro-phenyl)-ethyl]-amino}-methyl)-phenyl]-4-bromo-3-carboxymethoxy-thiophene-2-carboxylic acid;

4-Bromo-3-carboxymethoxy-5-[3-(1,3-diisopropyl-ureido)-phenyl]-thiophene-2-carboxylic acid;

4-Bromo-3-carboxymethoxy-5-{3-[1-(2,2-dimethyl-propyl)-3-isopropyl-ureido]-phenyl}-thiophene-2-carboxylic acid;

4-Bromo-3-carboxymethoxy-5-[3-(1-isobutyl-3-isopropyl-ureido)-phenyl]-thiophene-2-carboxylic acid;

5-[3-(1-Benzyl-3-isopropyl-ureido)-phenyl]-4-bromo-3-carboxymethoxy-thiophene-2carboxylic acid;
4-Bromo-3-carboxymethoxy-5-{3-[3-isopropyl-1-(4-trifluoromethyl-benzyl)-ureido]-phenyl}-thiophene-2-carboxylic acid;
4-Bromo-5-{3-[1-(4-tert-butyl-benzyl)-3-isopropyl-ureido]-phenyl}-3-carboxymethoxy-thiophene-2-carboxylic acid;
5-[3-(Acetyl-cyclohexylmethyl-amino)-phenyl]-4-bromo-3-carboxymethoxy-thiophene-2-carboxylic acid;
4-Bromo-3-carboxymethoxy-5-{3-[cyclohexylmethyl-(3-methyl-butyryl)-amino]-phenyl}-thiophene-2-carboxylic acid;
4-Bromo-3-carboxymethoxy-5-[3-(cyclohexanecarbonyl-cyclohexylmethyl-amino)-phenyl]-thiophene-2-carboxylic acid;
4-Bromo-3-carboxymethoxy-5-[3-(cyclohexylmethyl-isobutyryl-amino)-phenyl]-thiophene-2-carboxylic acid;
4-Bromo-3-carboxymethoxy-5-[3-(cyclohexylmethyl-methoxycarbonyl-amino)-phenyl]-thiophene-2-carboxylic acid;
3-Carboxymethoxy-5-[3-(cyclohexylmethyl-methoxycarbonyl-amino)-phenyl]-4-methyl-thiophene-2-carboxylic acid;
3-Carboxymethoxy-5-[3-(cyclohexylmethyl-isopropoxycarbonyl-amino)-phenyl]-4-methyl-thiophene-2-carboxylic acid;
or a pharmaceutically acceptable salt thereof.

58. The compound according to claim 1 selected from:
5-[3-(Bis-cyclohexylmethyl-amino)-phenyl]-3-carboxymethoxy-4-methyl-thiophene-2-carboxylic acid;
4-Bromo-3-carboxymethoxy-5-[3-(1-cyclohexylmethyl-3-phenyl-ureido)-phenyl]-thiophene-2-carboxylic acid;
5-[3-(3-Benzyl-1-cyclohexylmethyl-ureido)-phenylj-4-bromo-3-carboxymethoxy-thiophene-2-carboxylic acid;
4-Bromo-3-carboxymethoxy-5-{3-[1-cyclohexylmethyl-3-(4-ethyl-phenyl)-ureido]-phenyl}-thiophene-2-carboxylic acid;
4-Bromo-3-carboxymethoxy-5-{3-[1-cyclohexylmethyl-3-(4-ethoxy-phenyl)-ureido]phenyl}-thiophene-2-carboxylic acid;
4-Bromo-3-carboxymethoxy-5-{3-[1-cyclohexylmethyl-3-(4-phenoxy-phenyl)-ureido]-phenyl}-thiophene-2-carboxylic acid;
4-Bromo-3-carboxymethoxy-5-{3-[3-(2-cyano-phenyl)-1-cyclohexylmethyl-ureido]-phenyl}-thiophene-2-carboxylic acid;
4-Bromo-3-carboxymethoxy-5-[3-(1-cyclohexylmethyl-3-thiophen-3-yl-ureido)-phenyl]-thiophene-2-carboxylic acid;
4-Bromo-3-carboxymethoxy-5-{3-[1-cyclohexylmethyl-3-(3,5-dimethyl-isoxazol-4-yl)-ureidol-phenyl}-thiophene-2-carboxylic acid;
4-Bromo-3-carboxymethoxy-5-{3-[1-cyclohexylmethyl-3-(5-methyl-3-phenyl-isoxazol-4-yl)-ureido]-phenyl}-thiophene-2-carboxylic acid;
4-Bromo-3-carboxymethoxy-5-{3-[3-(4-carboxy-phenyl)-1-cyclohexylmethyl-ureido]-phenyl}-thiophene-2-carboxylic acid;
4-Bromo-3-carboxymethoxy-5-[3-(1-cyclohexylmethyl-3-ethyl-ureido)-phenyl]-thiophene-2-carboxylic acid;
3-Carboxymethoxy-5-[3-(1-cyclohexylmethyl-3-isopropyl-ureido)phenyl]-4-methyl-thiophene-2-carboxylic acid;
3-Carboxymethoxy-5-[3-(1-cyclohexyl-3-isopropyl-ureido)-phenyl]-4-methyl-thiophene-2-carboxylic acid;
3-Carboxymethoxy-5-[3-(1-cyclohexylmethyl-3-phenyl]-ureido)phenyl]-4-methyl-thiophene-2-carboxylic acid;
5-[3-(3-Benzyl-1-cyclohexylmethyl-ureido)-phenyl]-3-carboxymethoxy-4-methyl-thiophene-2-carboxylic acid;
5-[3-(3-Benzyl-1-cyclohexyl-ureido)-pheny]-3-carboxymethoxy-4-methyl-thiophene-2-carboxylic acid;
3-Carboxymethoxy-5-[3-(1-cyclohexylmethyl-3-phenethyl]-ureido)-phenyl]-4-methyl-thiophene-2-carboxylic acid;
3-Carboxymethoxy-5-[3-(1-cyclohexylmethyl-3-phenethyl]-ureido)-phenyl]-4-methyl-thiophene-2-carboxylic acid;
4-Bromo-3-isopropoxycarbonyimethoxy-5-[3-(1-phenyl-methanesulfonyl-piperidin-4-ylamino)-phenyl]-thiophene-2-carboxylic acid;
4-Bromo-3-isobutoxycarbonyimethoxy-5-[3-(1-phenyl-methanesulfonyl-piperidin-4-ylamino)-phenyl]-thiophene-2-carboxylic acid;
4-Bromo-5-[3-(1-phenylmethanesulfonyl-piperidin-4-ylamino)-phenyl]-3-propoxycarbonylmethoxy-thiophene-2-carboxylic acid;
4-Bromo-3-cyclopropylmethoxycarbonylmethoxy-5-[3-(1-phenylmethanesulfonyl-piperidin-4-ylamino)-phenyl]-thiophene-2-carboxylic acid;
3-Benzyloxycarbonylmethoxy-4-bromo-5-[3-(1-phenyl-methanesulfonyl-piperidin-4-ylamino)-phenyl]-thiophene-2-carboxylic acid;
4-Bromo-3-cyclohexylmethoxycarbonylmethoxy-5-[3-(1-phenylmethanesulfonyl-piperidin-4-ylamino)-phenyl]-thiophene-2-carboxylic acid;
4-Bromo-3-cyclohexyloxycarbonylmethoxy-5-[3-(1-phenylmethanesulfonyl-piperidin-4-ylamino)-phenyl]-thiophene-2-carboxylic acid;
4-Bromo-3-carboxymethoxy-5-{3-[1-(2,3-dichloro-phenylmethanesulfonyl)-piperidin-4-ylamino]-phenyl}-thiophene-2-carboxylic acid;
4-Bromo-5-{3-[1-(2,3-dichloro-phenylmethanesulfonyl)-piperidin-4-ylamino]-phenyl}-3-methoxycarbonylmethoxy-thiophene-2-carboxylic acid;
4-Bromo-3-carboxymethoxy-5-{3-[1-(2,3-dichloro-phenylmethanesulfonyl)-piperidin-4-ylamino]-phenyl}-thiophene-2-carboxylic acid methyl ester;
4-Bromo-3-carboxymethoxy-5-[3-(1-phenylmethane-sulfonyl-piperidin-4-ylamino)-phenyl]-thiophene-2-carboxylic acid methyl ester, ethanolamine salt;
4-Bromo-3-carboxymethoxy-5-[3-(1-phenylmethane-sulfonyl-piperidin-4-ylamino)-phenyl]-thiophene-2-carboxylic acid methyl ester, choline salt;
4-Bromo-3-carboxymethoxy-5-[3-(1-phenylmethane-sulfonyl-piperidin-4-ylamino)-phenyl]thiophene-2-carboxylic acid methyl ester, sodium salt;
{[2-[(Benzyloxy)carbonyl]-5-(3-{[1-(benzylsulfonyl)piperidin-4-yl]amino}phenyl)-4-bromothien-3-yl]oxy}acetic acid;
[(5-(3-{[1-(Benzylsulfonyl)piperidin-4-yl]amino}phenyl)-4-bromo-2-{[(2-nitrobenzyl)oxy]carbonyl}thien-3-yl)oxy]acetic acid;
[(5-(3-{[1-(Benzylsulfonyl)piperidin-4-yl]amino}phenyl)-4-bromo-2-{[(2-nitrobenzyl)oxy]carbonyl}thien-3yl)oxy]acetic acid;
({5-(3-{[1-(Benzylsulfonyl)piperidin-4-yl]amino}phenyl)-bromo-2-[(pyridin-3-ylmethoxy)carbonyl]thien-3-yl}oxy)acetic acid;

({5-(3-{[1-(Benzylsulfonyl)piperidin-4-yl]
amino}phenyl)-4-bromo-2-[(cyclohexylmethoxy)carbonyl]thien-3-yl}oxy)acetic acid;
{[5-(3-{[1-(Benzylsulfonyl)piperidin-4-yl]
amino}phenyl)-4-bromo-2-(isobutoxycarbonyl)thien-3-yl]oxy}acetic acid;
5-[3-(Benzyloxycarbonyl-cyclohexyl-amino)-phenyl]-4-bromo-3-carboxymethoxy-thiophene-2-carboxylic acid;
4-Bromo-3-carboxymethoxy-5-[3-(cyclohexyl-propoxycarbonyl-amino)-phenyl]-thiophene-2-carboxylic acid;
4-Bromo-3-carboxymethoxy-5-[3-(cyclohexyl-isopropoxycarbonyl-amino)-phenyl]-thiophene-2-carboxylic acid;
4-Bromo-3-carboxymethoxy-5-[3-(cyclohexyl-phenoxycarbonyl-amino)-phenyl]-thiophene-2-carboxylic acid;
5-[3-(Benzyloxycarbonyl-cyclohexylmethyl-amino)-phenyl]-4-bromo-3-carboxymethoxy-thiophene-2-carboxylic acid;
4-Bromo-3-carboxymethoxy-5-[3-(cyclohexylmethyl-isopropoxycarbonyl-amino)-phenyl]-thiophene-2-carboxylic acid;
4-Bromo-3-carboxymethoxy-5-[3-(cyclohexylmethyl-propoxycarbonyl-amino)-phenyl]-thiophene-2-carboxylic acid;
4-Bromo-3-carboxymethoxy-5-[3-(cyclohexylmethyl-phenoxycarbonyl-amino)-phenyl]-thiophene-2-carboxylic acid;
5-[3-(Benzoyl-cyclohexylmethyl-amino)-phenyl]-4-bromo-3-carboxymethoxy-thiophene-2-carboxylic acid;
4-Bromo-3-carboxymethoxy-5-[3-(cyclohexylmethyl-phenylacetyl-amino)-phenyl]-thiophene-2-carboxylic acid;
4-Bromo-3-carboxymethoxy-5-{3-(cyclohexylmethyl-(4-methyl-pentaoyl)-amino]phenyl}-thiophene-2-carboxylic acid methyl ester;
4-Bromo-3-carboxymethoxy-5-{3-[1-(3-chloro-phenylmethanesulfonyl)-piperidin-4-ylamino]-phenyl}-thiophene-2-carboxylic acid methyl ester;
4-Bromo-3-carboxymethoxy-5-{3-[1-(3-fluoro-phenylmethanesulfonyl)-piperidin-4-ylamino]-phenyl}-thiophene-2-carboxylic acid methyl ester;
4-Bromo-3-carboxymethoxy-5-{3-[1-(2-chloro-phenylmethanesulfonyl)-piperidin-4-ylamino]-phenyl}-thiophene-2-carboxylic acid;
4-Bromo-5-{3-[1-(2-chloro-phenylmethanesulfonyl)-piperidin-4-ylamino]-phenyl}-3-methoxycarbonylmethoxy-thiophene-2-carboxylic acid;
3-Carboxymethoxy-5-{3-[1-(3-fluoro-phenylmethanesulfonyl)-piperidin-4-ylamino]-phenyl}-4-methyl-thiophene-2-carboxylic acid methyl ester;
3-Carboxymethoxy-4-methyl-5-[3-(1-phenylmethanesulfonyl-piperidin-4-ylamino)-phenyl]-thiophene-2-carboxylic acid methyl ester;
3-Carboxymethoxy-4-methyl-5-{3-[1-(2-trifluoromethyl-phenylmethanesulfonyl)-piperidin-4-ylamino]-phenyl}-thiophene-2-carboxylic acid methyl ester;
3-Carboxymethoxy-4-methyl-5-[3-(1-phenylmethanesulfonyl-piperidin-4-ylamino)-phenyl]-thiophene-2-carboxylic acid;
3-Methoxycarbonylmethoxy-4-methyl-5-[3-(1-phenylmethanesulfonyl-pipendin-4-ylamino)-phenyl]-thiophene-2-carboxylic acid;
3-Carboxymethoxy-4-methyl-5-[3-(3,3,5,5-tetramethyl-cyclohexylamino)-phenyl]-thiophene-2-carboxylic acid methyl ester];
3-{[2-(4-Hydroxy-phenyl)-1-methoxycarbonyl-ethylcarbamoyl]-methoxy}-4-methyl-5-[3-(3,3,5,5-tetramethyl-cyclohexyl)-phenyl]-thiophene-2-carboxylic acid methyl ester;
1-(2-{2-Methoxycarbonyl-4-methyl-5-[3-(3,3 5,5-tetramethyl-cyclohexyl)-phenyl]-thiophen-3-yloxy}-acetyl)-pyrrolidine-2-carboxylic acid methyl ester;
4-Methyl-3-(2-oxo-2-pyrrolidin-1-yl-ethoxy)-5-[3-(3,3,5,5-tetramethyl-cyclohexyl)-phenyl]thiophene-2-carboxylic acid methyl ester;
3-(4-Hydroxy-3-methyl-2-oxo-butoxy)-4-methyl-5-[3-(3,3,5,5-tetramethyl-cyclohexyl)-phenyl]-thiophene-2-carboxylic acid methyl ester;
3-[(1-Methoxycarbonyl-2-methyl-propylcarbamoyl)-methoxy]-4-methyl-5-[3-(3,5,5-tetramethyl-cyclohexyl)-phenyl]-thiophene-2-carboxylic acid methyl ester;
3-[(1-Methoxycarbonyl-2-methyl-butylcarbamoyl)-methoxy]-4-methyl-5-[3-(3,5,5-tetramethyl-cyclohexyl)-phenyl]-thiophene-2-carboxylic acid methyl ester;
3-[(1-Methoxycarbonyl-2-phenyl-ethylcarbamoyl)-methoxy]-4-methyl-5-[3-(3,3,5,5-tetramethyl-cyclohexyl)-phenyl-thiophene-2-carboxylic acid methyl ester;
3-[2-(2-Carbamoyl-pyrrolidin-1-yl)-2-oxo-ethoxy]-4-methyl-5-[3-(3,3,5,5-tetramethyl-cyclohexyl)-phenyl]-thiophene-2-carboxylic acid methyl ester;
3-[(2-tert-Butoxycarbonylamino-ethylcarbamoyl)-methoxy]-4-methyl-5-[3-(3,3,5,5-tetramethyl-cyclohexyl)-phenyl]-thiophene-2-carboxylic acid methyl ester;
4-(2-{2-Methoxycarbonyl-4-methyl-5-[3-(3,3,5,5-tetramethyl-cyclohexyl)-phenyl]-thiophen-3-yloxy}-acetyl)-piperazine-1-carboxylic acid tert-butyl ester;
3-[(Amino-ethylcarbamoyl)-methoxy]-4-methyl-5-[3-(3,3,5,5-tetramethyl-cyclohexyl)-phenyl]-thiophene-2-carboxylic acid methyl ester;
4-Methyl-3-(2-oxo-2-piperazin-1-yl-ethoxy)-5-[3-(3,3,5,5-tetramethyl-cyclohexyl)-phenyl]thiophene-2-carboxylic acid methyl ester;
4-Bromo-5-[3-(1-phenylmethanesulfonyl-piperidin-4-yl)-phenyl]-3-(piperidin-4-yloxycarbonylmethoxy)-thiophene-2-carboxylic acid methyl ester;
4-Bromo-3-methoxycarbonylmethoxy-5-[3-(1-phenylmethanesulfonyl-piperidin-4yl)-phenyl]-thiophene-2-carboxylic acid 2,2-dimethyl-propionyloxymethyl ester;
4-Bromo-3-isopropoxycarbonylmethoxy-5-[3-(1-phenylmethanesulfonyl-piperidin-4-yl)-phenyl]-thiophene-2-carboxylic acid 2,2-dimethyl-propionyloxymethyl ester;
4-Bromo-3-isopropoxycarbonylmethoxy-5-[3-(1-phenylmethanesulfonyl-piperidin-4-yl)-phenyl]-thiophene-2-carboxyliC acid acetoxymethyl ester;
3-Carboxymethoxy-5-{3-[1-(3-chloro-benzenesulfonyl)-piperidin-4-ylamino]-phenyl}-4-methyl-thiophene-2-carboxylic acid;
3-Carboxymethoxy-5-{3-[1-(2-chloro-benzenesulfonyl)-piperidin-4-ylamino]-phenyl}-4-methyl-thiophene-2-carboxylic acid;
3-Carboxymethoxy-4-methyl-5-{3-[1-(2-nitro-benzenesulfonyl)-piperidin-4-ylamino]-phenyl}-thiophene-2-carboxylic acid;
3-Carboxymethoxy-5-{3-[1-(4-methoxy-benzenesulfonyl)-piperidin-4-ylamino]-phenyl}-4-methyl-thiophene-2-carboxylic acid;
3-Carboxymethoxy-4-methyl-5-{3-[1-(4-nitro-benzenesulfonyl)-piperidin-4-ylamino]-phenyl}-thiophene-2-carboxylic acid;

or a pharmaceutically acceptable salt thereof.

59. The compound according to claim 1 selected from:
5-{3-[1-(4-Carboxy-benzenesulfonyl)-piperidin-4-ylamino]-phenyl}-3-carboxymethoxy-4-methyl-thiophene-2-carboxylic acid;
3-Carboxymethoxy-5-{3-[1-(2-cyano-benzenesulfonyl)-piperidin-4-ylamino]-phenyl}-4-methyl-thiophene-2-carboxylic acid;
3-Carboxymethoxy-4-methyl-5-{3-[1-(4-trifluoromethyl-benzenesulfonyl)-piperidin-4-ylamino]-phenyt}-thiophene-2-carboxylic acid;
4-Bromo-3-carboxymethoxy-5-[3-(1-cyclohexyl-3-methyl-ureido)-phenyl]-thiophene-2-carboxylic acid;
5-[3-(3-Benzyl-1-cyclohexyl-ureido)-phenyl]-4-bromo-3-carboxymethoxy-thiophene-2-carboxylic acid;
4-Bromo-3-tert-butoxycarbonylmethoxy-5-[3-(3,3,5,5-tetramethyl-cyclohexylamino)-phenyl]-thiophene-2-carboxylic acid methyl ester;
4-Bromo-3-carboxymethoxy-5-{3-[3-methyl-1-(3,3,5,5-tetramethyl-cyclohexyl )-ureido]-phenyl}-thiophene-2-carboxylic acid;
4-Bromo-3-carboxymethoxy-5-{3-[3-ethyl-1-(3,3,5,5-tetramethyl-cyclohexyl)-ureido]-phenyl}-thiophene-2-carboxylic acid;
4-Bromo-3-carboxymethoxy-5-{3-[3-methyl-1-(3,3,5,5-tetramethyl-cyclohexyl)-ureido]-phenyl}-thiophene-2-carboxylic acid methyl ester;
4-Bromo-3-ethoxycarboxymethoxy-5-[3-(piperidin-4-ylamino)-phenyl]-thiophene-2-carboxylic acid methyl ester hydrochloride;
4Bromo-3-carboxymethoxy-5-{3-[1-(4-trifluoromethyl-pyrimidin-2-yl)-piperidin-4-ylamino]-phenyl}-thiophene-2-carboxylic acid;
4-Bromo-3-carboxymethoxy-5-[3-(1-pyrimidin-2-yl-piperidin-4-ylamino)-phenyl]-thiophene-2-carboxylic acid;
4-Bromo-3-carboxymethoxy-5-[3-(5'-trifluoromethyl-3,4,5,6-tetrahydro-2H-[1,2']biphenyl-4-ylamino)-phenyl]-thiophene-2-carboxylic acid;
4-Bromo-3-ethoxycarbonylmethoxy-5-[3-(1-phenyl-methanesulfonyl-piperidin-4-ylamino)-phenyl]-thiophene-2-carboxylic acid ethyl ester;
4-Bromo-5-[3-(1-phenylmethanesulfonyl-piperidin-4-ylamino)-phenyl]-3-(o-tolylcarbamoyl-methoxy)-thiophene-2-carboxylic acid;
3-Carboxymethoxy-5-[3-(1-phenylmethanesulfonyl-piperidin-4-ylamino)-phenyl]-thiophene-2-carboxylic acid;
4-Bromo-3-carboxymethoxy-5-(3-{1-[3-(3-ethyl-ureido)-phenylmethanesulfonyl]-piperidin-4-ylamino}-phenyl)-thiophene-2-carboxylic acid;
[2-(2-{4-Bromo-2-methoxycarbonyl-5-[3-(1-phenyl-methanesulfonyl-piperidin-4-ylamino)-phenyl]thiophene-3-yloxy}-acetoxy-ethyl]-trimethyl-ammonium chloride;
4-Bromo-3-cyclohexylcarbanoylmethoxy-5-[3-(1-phenylmethanesulfonyl-piperidin-4-ylamino)-phenyl]-thiophene-2-carboxylic acid methyl ester;
5-[3-(Acetyl-cyclohexyl-amino)-phenyl]-4-bromo-3-carboxymethoxy-thiophene-2-carboxylic acid;
5-[3-(Acetyl-cyclohexyl-amino)-phenyl]-4-bromo-3-carboxymethoxy-thiophene-2carboxylic acid methyl ester;
5-[3-(Benzoyl-cyclohexyl-amino)-phenyl]-4-bromo-3-carboxymethoxy-thiophene-2carboxylic acid;
5-[3-(Benzoyl-cyclohexyl-amino)-phenyl]-4-bromo-3-carboxymethoxy-thiophene-2carboxylic acid methyl ester;
4-Bromo-3-carboxymethoxy-5-{3-[cyclohexyl-(3-phenyl-acryloyl)-amino]-phenyl}-thiophene-2-carboxylic acid methyl ester;
4-Bromo-3-carboxymethoxy-5-[3-(cyclohexanecarbonyl-cyclohexyl-amino)-phenyl]-thiophene-2-carboxylic acid methyl ester;
5-{3-[Benzoyl-(3,3,5,5-tetramethyl-cyclohexyl)-amino]-phenyl}-4-bromo-3-carboxymethoxy-thiophene-2-carboxylic acid;
4-Bromo-3-carboxymethoxy-5-[3-(1-phenylmethane-sulfonyl-piperidin-4-ylamino)-phenyl]-thiophene-2-carboxylic acid methyl ester;
4-Bromo-3-[(carbamoylmethyl-carbamoyl)-methoxy]-5-[3-(3,3,5,5-tetramethyl-cyclohexylamino)-phenyl]-thiophene-2-carboxylic acid methyl ester;
4-Bromo-3-[(1-carbamoyl-ethylcarbamoyl)-methoxy]-5-[3-(3,3,5,5-tetramethyl-cyclohexylamino)-phenyl]-thiophene-2-carboxylic acid methyl ester;
4-Bromo-3-[(ethoxycarbonylmethyl-carbamoyl)-methoxy]-5-[3-(3,3,5,5-tetramethyl-cyclohexylamino)-phenyl]-thiophene-2-carboxylic acid methyl ester;
4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester;
4-Bromo-3-[(1-ethoxycarbonyl-ethylcarbamoyl)-methoxy]-5-[3-(3,3,5,5-tetramethyl-cyclohexylamino)-phenyl]-thiophene-2-carboxylic acid methyl ester;
3-{[(Benzylcarbamoyl-methyl)-carbamoyl]-methoxy}-4-bromo-5-[3-(3,3,5,5-tetramethylcyclohexylamino)-phenyl]-thiophene-2-carboxylic acid methyl ester;
4-Bromo-3-carboxymethoxy-5-{3-[1-(3-methanesulfonylamino-phenylmethanesulfonyl)-piperidin-4-ylamino]-phenyl}-thiophene-2-carboxylic acid;
5-{3-[1-(3-Acetylamino-phenylmethansulfonyl)-piperidin-4-ylamino]-phenyl}-4-bromo-3-carboxymethoxy-thiophene-2-carboxylic acid;
4-Bromo-5-(3-{[1-(butylsulfonyl)piperidin-4-yl]amino}phenyl)-3-(2-methoxy-2-oxoethoxy)thiophene-2-carboxylic acid;
4-Bromo-5-(3-{[1-(ethylsulfonyl)piperidin-4-yl]aminQ}phenyl)-3-(2-methoxy-2-oxoethoxy)thiophene-2-carboxylic acid;
4-Bromo-5-(3-{[1-(isopropylsulfonyl)piperidin-4-yl]amino}phenyl)-3-(2-methoxy-2-oxoethoxy)thiophene-2-carboxylic acid;
5-{3-[Acetyl(3,3,5,5-tetramethylcyclohexyl)amino]phenyl}-4-bromo-3-(2-methoxy-2-oxoethoxy)thiophene-2-carboxylic acid;
[4-Bromo-5-[3-cyclohexylamino)phenyl]-2-(methoxycarbonyl)thien-3-yl]oxyacetic acid;
{[5-(3-{[1-(Benzylsulfonyl)piperidin-4-yl]amino}phenyl)-4-bromo-2-(ethoxycarbonyl)thien-3-yl]oxy}acetic acid;
{[5-(3-{[1-(Benzylsulfonyl)piperidin-4-yl]amino}phenyl)-4-bromo-2-(isopropoxycarbonyl)thien-3-yl]oxy}acetic acid;
({5-(3-{[1-(Benzylsulfonyl)piperidin-4-yl]amino}phenyl)-4-bromo-2-[(cyclohexyloxy)carbonyl]thien-3-yl}oxy)acetic acid;
{[4-Bromo-2-(Ethoxycarbonyl)-5-(3-{[1-(phenylsulfonyl)piperidin-4-yl]amino}phenyl)thien-3-yl]oxy}acetic acid;
[4-Bromo-2-(methoxycarbonyl)-5-(3-{[1-(phenylsulfonyl)piperidin-4-yl]amino}phenyl)thien-3-yl]oxyacetic acid;

[(4-Bromo-2-(ethoxycarbonyl)-5-{3-[(3,3 5,5-tetramethylcyclohexyl)amino]phenyl}thien-3-yl)oxy]acetic acid;
4-bromo-3-(carboxymethoxy)-5-(3-(1-cyclohexyl-3-phenylureido)phenyl)thiophene-2-carboxylic acid;
4-bromo-3-(carboxymethoxy)-5-(3-(1-cyclohexyl-3-isopropylureido)phenyl)thiophene-2-carboxylic acid;
4-bromo-3-(carboxymethoxy)-5-(3-(1-cyclohexyl-3-phenethylureido)phenyl)thiophene-2-carboxylic acid;
4-bromo-3-(carboxymethoxy)-5-(3-(1-cyclohexyl-3-propylureido)phenyl)thiophene-2-carboxylic acid;
4-bromo-3-(carboxymethoxy)-5-(3-(1-cyclohexyl-3-(4-ethoxyphenyl)ureido)phenyl)thiophene-2-carboxylic acid;
4-bromo-3-(carboxymethoxy)-5-(3-(1-cyctohexyl-3-(4-phenoxyphenyl)ureido)phenyl)thiophene-2-carboxylic acid;
5-(3-(3-(5-bromo-2-methoxyphenethyl)-1-cyclohexylureido)phenyl)-4-bromo-3-(carboxymethoxy)thiophene-2-carboxylic acid;
4-bromo-3-(carboxymethoxy)-5-(3-(1-cyclohexyl-3-(2-(thiophen-3-yl)ethyl)ureido)phenyDthiophene-2-carboxylic acid;
4-bromo-3-(carboxymethoxy)-5-(3-(1-cyclohexyl-3-(3,5-dimethylisoxazol-4-yl)ureido)phenyl)thiophene-2-carboxylic acid;
4-bromo-5-(3-(3-(2-carboxyethyl)-1-cyclohexylureido)phenyl)-3-(carboxymethoxy)thiophene-2-carboxylic acid;
4-bromo-3-(carboxymethoxy)-5-(3-(3-(4-carboxyphenyl)-1-cyclohexylureido)phenyl)thiophene-2-carboxylic acid;
4-bromo-3-(carboxymethoxy)-5-(3-(3-(3-carboxypropyl)-1-cyclohexylureido)phenyl)thiophene-2-carboxylic acid;
4-bromo-3-(carboxymethoxy)-5-(3-(3-(5-carboxypentyl)-1-cyclohexylureido)phenyl)thiophene-2carboxylic acid;
4-bromo-3-(carboxymethoxy)-5-(3-(1-cyclohexyl-3-(thiophen-3-yl)ureido)phenyl)thiophene-2-carboxylic acid;
4-bromo-3-(carboxymethoxy)-5-(3-(1-cyclohexyl-3-(3-methyl-5-phenylisoxazol-4-yl)ureido)phenyl)thiophene-2-carboxylic acid;
4-bromo-5-(3-(1-cyclohexyl-3-methylureido)phenyl)-3-(2-ethoxy-2-oxoethoxy)thiophene-2-carboxylic acid;
5-(3-(3-benzyl-1-benzyl-1-ethylureido)phenyl)-4-bromo-3(carboxymethoxy)thiophene-2-carboxylic acid;
4-bromo-3-(carboxymethoxy)-5-(3-(1-ethyl-3-isopropylureido)phenyl)thiophene-2-carboxylic acid;
4-bromo-3-(carboxymethoxy)-5-(3-(1-ethyl-3-phenylureido)phenyl)thiophene-2-carboxylic acid;
4-bromo-3-(carboxymethoxy)-5-(3-(3-cyclohexyl-1-ethylureido)phenyl)thiophene-2-carboxylic acid;
3-(carboxymethoxy)-4-chloro-5-(3-(3,4-difluoro-N-(tetrahydro-2H-pyran-4-yl)benzamido)phenyl)thiophene-2-carboxylic acid;
3-(carboxymethoxy)-4-chloro-5-(3-(3-fluoro-N-(tetrahydro-2H-pyran-4-yl)benzamido)phenyl)thiophene-2-carboxylic acid;
3-(carboxymethoxy)-4-chloro-5-(3-(3-fluoro-N-(tetrahydro-2H-pyran-4-yl)benzamido)phenyl)thiophene-2-carboxylic acid;
3-(carboxymethoxy)-4-chloro-5-(3-(4-fluoro-N-(tetrahydro-2H-pyran-4-yl)benzamido)phenyl)thiophene-2-carboxylic acid;

or a pharmaceutically acceptable salt thereof.

\* \* \* \* \*